US011168093B2

(12) United States Patent
Armbrust et al.

(10) Patent No.: US 11,168,093 B2
(45) Date of Patent: Nov. 9, 2021

(54) THIENOPYRIDINE INHIBITORS OF RIPK2

(71) Applicant: Celgene Corporation, Cambridge, MA (US)

(72) Inventors: Kurt Armbrust, Cambridge, MA (US); Fedor Romanov Michailidis, Ain (FR); Karin Irmgard Worm, Jackson, NJ (US); John Michael Ellis, Needham, MA (US)

(73) Assignee: Celgene Corporation, Summit, NJ (US)

( * ) Notice: Subject to any disclaimer, the term of this patent is extended or adjusted under 35 U.S.C. 154(b) by 9 days.

(21) Appl. No.: 16/722,034

(22) Filed: Dec. 20, 2019

(65) Prior Publication Data
US 2020/0199148 A1 Jun. 25, 2020

Related U.S. Application Data

(60) Provisional application No. 62/783,742, filed on Dec. 21, 2018.

(51) Int. Cl.
C07D 495/00 (2006.01)
C07D 519/00 (2006.01)
C07D 495/04 (2006.01)

(52) U.S. Cl.
CPC ......... C07D 495/04 (2013.01); C07D 519/00 (2013.01)

(58) Field of Classification Search
CPC .......................... C07D 495/04; C07D 519/00
See application file for complete search history.

(56) References Cited

U.S. PATENT DOCUMENTS

| | | | |
|---|---|---|---|
| 4,659,717 A | 4/1987 | Wikel | |
| 5,686,457 A | 11/1997 | Traxler et al. | |
| 5,714,495 A | 2/1998 | Viaud et al. | |
| 6,096,749 A | 8/2000 | Traxler et al. | |
| 6,465,449 B1 | 10/2002 | Kath et al. | |
| 6,867,201 B2 | 3/2005 | Kath et al. | |
| 8,278,312 B2 | 10/2012 | Klein et al. | |
| 8,796,320 B2 | 8/2014 | Asai et al. | |
| 8,859,581 B2 | 10/2014 | Heinrich et al. | |
| 8,957,102 B2 | 2/2015 | Kim et al. | |
| 9,022,836 B2 | 5/2015 | Bened et al. | |
| 9,249,140 B2 | 2/2016 | Heinrich et al. | |
| 9,499,534 B2 * | 11/2016 | Arrington | A61K 31/5377 |
| 9,550,792 B2 | 1/2017 | Lu et al. | |
| 9,893,297 B2 | 2/2018 | Martynova et al. | |
| 2004/0176598 A1 | 9/2004 | Dugar | |
| 2005/0288299 A1 | 12/2005 | Mavunkel et al. | |
| 2006/0183758 A1 | 8/2006 | Beard et al. | |
| 2007/0082880 A1 | 4/2007 | Boschelli et al. | |
| 2012/0065219 A1 | 3/2012 | Ji et al. | |
| 2013/0096136 A1 | 4/2013 | Hata et al. | |
| 2013/0302248 A1 | 11/2013 | Gangadharmath et al. | |
| 2013/0317045 A1 | 11/2013 | Hadd et al. | |
| 2017/0010630 A1 | 1/2017 | Hu et al. | |
| 2017/0349562 A1 | 12/2017 | Hegde | |
| 2019/0002460 A1 | 1/2019 | Whitehead et al. | |
| 2019/0157567 A1 | 5/2019 | Kim et al. | |

FOREIGN PATENT DOCUMENTS

| | | |
|---|---|---|
| CN | 102399233 A | 4/2012 |
| CN | 103833753 A | 6/2014 |
| CN | 104119331 A | 10/2014 |
| CN | 103626783 B | 6/2016 |
| CN | 105712998 A | 6/2016 |
| CN | 107151240 A | 9/2017 |
| DE | 4208535 A1 | 9/1992 |
| EP | 1724268 A1 | 11/2006 |
| JP | 2005-194198 A | 7/2005 |
| JP | 4166296 B2 | 10/2008 |
| JP | 2008/308448 A | 12/2008 |
| JP | 2012/142510 A | 7/2012 |
| JP | 2013/093431 A | 5/2013 |
| JP | 5741373 B2 | 7/2015 |
| JP | 2015/167236 A | 9/2015 |
| JP | 2016/124825 A | 7/2016 |
| JP | 6070756 B2 | 2/2017 |
| KR | 2010-0123172 A | 11/2010 |
| KR | 2012-0119932 A | 11/2012 |
| KR | 2015-0131700 A | 11/2015 |
| WO | WO-97/02266 A1 | 1/1997 |
| WO | WO-97/039000 A1 | 10/1997 |
| WO | WO-98/07726 A1 | 2/1998 |
| WO | WO-99/21617 A2 | 5/1999 |
| WO | WO-99/24440 A1 | 5/1999 |
| WO | WO-99/62908 A2 | 12/1999 |

(Continued)

OTHER PUBLICATIONS

Caballero, et al., "Docking and quantitative structure-activity relationship studies for 3-fluoro-4-(pyrrolo[2,1-f][1,2,4]triazin-4-yloxy)aniline, 3-fluoro-4-(1H-pyrrolo[2,3-b]pyridin-4-yloxy)aniline, and 4-(4-amino-2-fluorophenoxy)-2-pyridinylamine derivatives as c-Met kinase inhibitors," *J. of Computer-Aided Molecular Design*, 25(4): 349-369 (2011).

Cai, et al., "Discovery of orally active pyrrolopyridine- and aminopyridine-based Met kinase inhibitors," *Bioorganic & Med. Chem. Letters*, 18(11):3224-3229 (2008).

Heinrich, et al., "Fragment-Based Discovery of New Highly Substituted 1H-Pyrrolo[2,3-b]- and 3H-Imidazolo[4,5-b]-Pyridines as Focal Adhesion Kinase Inhibitors," *J. of Med. Chem.*, 56(3): 1160-1170 (2013).

Xiang, et al., "Topomer CoMFA and Virtual Screening Studies of Azaindole Class Renin Inhibitors," *Combinatorial Chemistry & High Throughput Screening*, 17(5): 4588-472 (2014).

CAS Registry No. 1026177-90-1, Benzoic acid, 3-[[[4-[4-(6-benzothiazolylamino)-1H-pyrrolo[2,3-b]pyridin-2-yl]-3,6-dihydro-1(2H)-pyridinyl]carbonyl]amino].

(Continued)

*Primary Examiner* — Kamal A Saeed

(74) *Attorney, Agent, or Firm* — Choate, Hall & Stewart LLP; Kristen C. Buteau; Michael A. Shinall

(57) ABSTRACT

The present invention provides compounds, pharmaceutically acceptable compositions thereof, and methods of using the same.

17 Claims, No Drawings

(56) References Cited

FOREIGN PATENT DOCUMENTS

| | | |
|---|---|---|
| WO | WO-2000/075145 A1 | 12/2000 |
| WO | WO-2001/047922 A2 | 7/2001 |
| WO | WO-2001/062233 A2 | 8/2001 |
| WO | WO-2002/051849 A1 | 7/2002 |
| WO | WO-03/000690 A1 | 1/2003 |
| WO | WO-2003/000194 A2 | 1/2003 |
| WO | WO-2003/000688 A1 | 1/2003 |
| WO | WO-2003/013541 A1 | 2/2003 |
| WO | WO-2003/040114 A1 | 5/2003 |
| WO | WO-2004/012736 A1 | 2/2004 |
| WO | WO-2004/063155 A1 | 7/2004 |
| WO | WO-2004/082638 A2 | 9/2004 |
| WO | WO-2004/093812 A2 | 11/2004 |
| WO | WO-2004/099205 A1 | 11/2004 |
| WO | WO-2005/019216 A1 | 3/2005 |
| WO | WO-2005/067546 A2 | 7/2005 |
| WO | WO-2005/080377 A1 | 9/2005 |
| WO | WO-2005/081960 A2 | 9/2005 |
| WO | WO-2005/117890 A2 | 12/2005 |
| WO | WO-2005/121125 A1 | 12/2005 |
| WO | WO-2006/004636 A2 | 1/2006 |
| WO | WO-2006/004833 A2 | 1/2006 |
| WO | WO-2006/004884 A2 | 1/2006 |
| WO | WO-2006/009755 A2 | 1/2006 |
| WO | WO-2006/010264 A1 | 2/2006 |
| WO | WO-2006/010423 A2 | 2/2006 |
| WO | WO-2006/014325 A2 | 2/2006 |
| WO | WO-2006/017443 A2 | 2/2006 |
| WO | WO-2006/030031 A1 | 3/2006 |
| WO | WO-2006/043145 A1 | 4/2006 |
| WO | WO-2006/044933 A2 | 4/2006 |
| WO | WO-2006/055760 A1 | 5/2006 |
| WO | WO-2006/069080 A2 | 6/2006 |
| WO | WO-2006/092430 A1 | 9/2006 |
| WO | WO-2006/107784 A1 | 10/2006 |
| WO | WO-2006/114180 A1 | 11/2006 |
| WO | WO-2006/124874 A2 | 11/2006 |
| WO | WO-2006/135630 A1 | 12/2006 |
| WO | WO-2006/135639 A1 | 12/2006 |
| WO | WO-2007/01120 A1 | 1/2007 |
| WO | WO-2007/028145 A2 | 3/2007 |
| WO | WO-2007/035428 A1 | 3/2007 |
| WO | WO-2007/038519 A1 | 4/2007 |
| WO | WO-2007/054831 A2 | 5/2007 |
| WO | WO-2007/064861 A2 | 6/2007 |
| WO | WO-2007/067537 A1 | 6/2007 |
| WO | WO-2007/107005 A1 | 9/2007 |
| WO | WO-2007/120726 A2 | 10/2007 |
| WO | WO-2007/149427 A2 | 12/2007 |
| WO | WO-2008/008539 A2 | 1/2008 |
| WO | WO-2008/011560 A2 | 1/2008 |
| WO | WO-2008/019124 A1 | 2/2008 |
| WO | WO-2008/021364 A2 | 2/2008 |
| WO | WO-2008/041053 A2 | 4/2008 |
| WO | WO-2008/049855 A2 | 5/2008 |
| WO | WO-2008/058402 A1 | 5/2008 |
| WO | WO-2008/086053 A1 | 7/2008 |
| WO | WO-2008/089307 A2 | 7/2008 |
| WO | WO-2008/089310 A2 | 7/2008 |
| WO | WO-2008/104077 A1 | 9/2008 |
| WO | WO-2008/125207 A1 | 10/2008 |
| WO | WO-2008/135232 A1 | 11/2008 |
| WO | WO-2008/155017 A1 | 12/2008 |
| WO | WO-2009/017701 A2 | 2/2009 |
| WO | WO-2009/027732 A1 | 3/2009 |
| WO | WO-2009/049731 A1 | 4/2009 |
| WO | WO-2009/091374 A2 | 7/2009 |
| WO | WO-2009/142732 A2 | 11/2009 |
| WO | WO-2010/003133 A2 | 1/2010 |
| WO | WO-2010/007114 A2 | 1/2010 |
| WO | WO-2010/007116 A2 | 1/2010 |
| WO | WO-2010/020000 A1 | 2/2010 |
| WO | WO-2010/021686 A1 | 2/2010 |
| WO | WO-2010/021934 A2 | 2/2010 |
| WO | WO-2010/030757 A2 | 3/2010 |
| WO | WO-2010/036629 A2 | 4/2010 |
| WO | WO-2010/044543 A2 | 4/2010 |
| WO | WO-2010/045095 A1 | 4/2010 |
| WO | WO-2010/052569 A2 | 5/2010 |
| WO | WO-2010/054285 A2 | 5/2010 |
| WO | WO-2010/061903 A1 | 6/2010 |
| WO | WO-2010/075287 A2 | 7/2010 |
| WO | WO-2010/104306 A2 | 9/2010 |
| WO | WO-2010/0107765 A1 | 9/2010 |
| WO | WO-2010/107768 A1 | 9/2010 |
| WO | WO-2010/117935 A1 | 10/2010 |
| WO | WO-2011/031628 A1 | 3/2011 |
| WO | WO-2011/047129 A1 | 4/2011 |
| WO | WO-2011/047432 A1 | 4/2011 |
| WO | WO-2011/050323 A1 | 4/2011 |
| WO | WO-2011/055115 A1 | 5/2011 |
| WO | WO-2011/081205 A1 | 7/2011 |
| WO | WO-2011/100614 A1 | 8/2011 |
| WO | WO-2011/123751 A2 | 10/2011 |
| WO | WO-2011/146401 A1 | 11/2011 |
| WO | WO-2011/149827 A1 | 12/2011 |
| WO | WO-2011/159297 A1 | 12/2011 |
| WO | WO-2012/013633 A1 | 2/2012 |
| WO | WO-2012/016630 A1 | 2/2012 |
| WO | WO-2012/024670 A2 | 2/2012 |
| WO | WO-2012/028335 A2 | 3/2012 |
| WO | WO-2012/037141 A1 | 3/2012 |
| WO | WO-2012/048058 A2 | 4/2012 |
| WO | WO-2012/066578 A2 | 5/2012 |
| WO | WO-2012/101043 A1 | 8/2012 |
| WO | WO-2012/106343 A2 | 8/2012 |
| WO | WO-2012/107465 A1 | 8/2012 |
| WO | WO-2012/130829 A1 | 10/2012 |
| WO | WO-2012/154888 A1 | 11/2012 |
| WO | WO-2012/156756 A2 | 11/2012 |
| WO | WO-2013/026516 A1 | 2/2013 |
| WO | WO-2013/033981 A1 | 3/2013 |
| WO | WO-2013/072694 A1 | 5/2013 |
| WO | WO-2013/078254 A1 | 5/2013 |
| WO | WO-2013/083991 A1 | 6/2013 |
| WO | WO-2013/085339 A2 | 6/2013 |
| WO | WO-2013/106535 A1 | 7/2013 |
| WO | WO-2013/163244 A1 | 10/2013 |
| WO | WO-2013/165898 A2 | 11/2013 |
| WO | WO-2014/027814 A1 | 2/2014 |
| WO | WO-2014/055586 A1 | 4/2014 |
| WO | WO-2014/055587 A1 | 4/2014 |
| WO | WO-2014/059185 A1 | 4/2014 |
| WO | WO-2014/065498 A1 | 5/2014 |
| WO | WO-2014/079803 A1 | 5/2014 |
| WO | WO-2014/089280 A1 | 6/2014 |
| WO | WO-2014/108053 A1 | 7/2014 |
| WO | WO-2014/113407 A2 | 7/2014 |
| WO | WO-2014/164543 A1 | 10/2014 |
| WO | WO-2014/179785 A1 | 11/2014 |
| WO | WO-2014/179786 A1 | 11/2014 |
| WO | WO-2014/193647 A2 | 12/2014 |
| WO | WO-2014/194201 A2 | 12/2014 |
| WO | WO-2014/194242 A2 | 12/2014 |
| WO | WO-2014/194245 A2 | 12/2014 |
| WO | WO-2014/207260 A1 | 12/2014 |
| WO | WO-2015/042497 A2 | 3/2015 |
| WO | WO-2015/054572 A1 | 4/2015 |
| WO | WO-2015/055770 A1 | 4/2015 |
| WO | WO-2015/089327 A1 | 6/2015 |
| WO | WO-2015/171833 A1 | 11/2015 |
| WO | WO-2015/190718 A1 | 12/2015 |
| WO | WO-2016/022446 A1 | 2/2016 |
| WO | WO-2016/033445 A1 | 3/2016 |
| WO | WO-2016/040330 A1 | 3/2016 |
| WO | WO-2016/064102 A1 | 4/2016 |
| WO | WO-2016/064445 A1 | 4/2016 |
| WO | WO-2016/097918 A1 | 6/2016 |
| WO | WO-2016/115360 A1 | 7/2016 |
| WO | WO-2016/142327 A1 | 9/2016 |
| WO | WO-2016/200401 A1 | 12/2016 |
| WO | WO-2016/205942 A1 | 12/2016 |
| WO | WO-2017/001311 A1 | 1/2017 |

(56) References Cited

FOREIGN PATENT DOCUMENTS

| WO | WO-2017/008777 A1 | 1/2017 |
| WO | WO-2017/008826 A1 | 1/2017 |
| WO | WO-2017/012308 A1 | 1/2017 |
| WO | WO-2017/097871 A1 | 6/2017 |
| WO | WO-2017/112768 A1 | 6/2017 |
| WO | WO-2017/133664 A1 | 8/2017 |
| WO | WO-2017/142947 A1 | 8/2017 |
| WO | WO-2017/144341 A1 | 8/2017 |
| WO | WO-2017/153601 A1 | 9/2017 |
| WO | WO-2018/039495 A1 | 3/2018 |
| WO | WO-2018/213219 A1 | 11/2018 |
| WO | WO-2020/132384 A1 | 6/2020 |

OTHER PUBLICATIONS

CAS Registry No. 1026432-81-4, 1(2H)-Pyridinecarboxylic acid, 3,6-dihydro-4-[4-[[2-methoxy-3-(3-thienyl)phenyl]amino]-1H-pyrrolo[2,3-b]pyridin-2-yl]-, 1,1-dimethylethyl ester.

CAS Registry No. 1026907-58-3, 1(2H)-Pyridinecarboxamide, 4-[4-(6-benzothiazolylamino)-1H-pyrrolo[2,3-b]pyridin-2-yl]-3,6-dihydro-N-(2-methoxyphenyl).

CAS Registry No. 1347514-63-9, Ethanone, 1-[4-[[4-[4-[(3a,7a-dihydro-1H-indazol-5-yl)amino]-1H-pyrrolo[2,3-b]pyridin-2-yl]-3,6-dihydro-1(2H)-pyridinyl]carbonyl]-1-piperidinyl].

CAS Registry No. 1347876-08-7, 1(2H)-Pyridinecarboxylic acid, 3,6-dihydro-4-(1H-indol-5-ylamino)-1H-pyrrolo[2,3-b]pyridin-2-yl]-,1,1-dimethylethyl ester.

CAS Registry No. 1348062-42-9, Ethanone, 1-[4-[4-[(3a,7a-dihydro-1H-indazol-5-yl)amino]-1H-pyrrolo[2,3-b]pyridin-2-yl]-3,6-dihydro-1(2H)-pyridinyl]-2-methoxy.

CAS Registry No. 1348321-43-6, 1H-Indazol-5-amine, 2,3-dihydro-N-[2-[1,2,3,6-tetrahydro-1-(methylsulfonyl)-4-pyridinyl]-1H-pyrrolo[2,3-b]pyridin-4-yl].

CAS Registry No. 1348454-21-6, 1(2H)-Pyridinecarboxylic acid, 4-[4-[(2,3-dihydro-1-methyl-1H-indazol-5-yl)amino]-1H-pyrrolo[2,3-b]pyridin-2-yl]-3,6-dihydro-, 1,1-dimethylethyl ester.

CAS Registry No. 1349102-91-5, Methanone, [4-[4-[(3a,7a-dihydro-1H-indazol-5-yl)amino]-1H-pyrrolo[2,3-b]pyridin-2-yl]-3,6-dihydro-1(2H)-pyridinyl]-4-morpholinyl.

CAS Registry No. 1349377-12-3, 1(2H)-Pyridinecarboxylic acid, 4-[4-[(3a,7a-dihydro-3-methyl-1H-indazol-5-yl)amino]-1H-pyrrolo[2,3-b]pyridin-2-yl]-3,6-dihydro-, 1,1-dimethylethyl ester.

CAS Registry No. 1350147-96-4, Ethanone, 1-[4-[4-[(2,3-dihydro-1H-indazol-5-yl)amino]-1H-pyrrolo[2,3-b]pyridin-2-yl]-3,6-dihydro-1(2H)-pyridinyl]-2-(3-pyridinyl).

CAS Registry No. 1350165-73-9, 1-Propanone, 1-[4-[4-[(3a,7a-dihydro-1H-indazol-5-yl)amino]-1H-pyrrolo[2,3-b]pyridin-2-yl]-3,6-dihydro-1(2H)-pyridinyl]-3-(1-piperidinyl).

International Search Report for PCT/US19/67724, 4 pages (dated Feb. 27, 2020).

Li, Y. et al., Exploring the structure requirement for PKCq inhibitory activity of pyridinecarbonitrile derivatives: an in silico analysis, J. of Molecular Graphics and Modeling, 34:76-88 (2012).

Silarki, O. et al., Receptor Guided 3D-QSAR Analysis of Thieno[2,3-b]Pyridine-5-Carbonitril Inhibitors of Protein Kinase C Theta, Combinatorial Chem. & High Throuput Screening, 16(9):731-738 (2013).

Written Opinion for PCT/US19/67724, 6 pages (dated Feb. 27, 2020).

Wu, B. et al., Second generation 4-(4-methyl-1H-indol-5-ylamino)-2-phenylthieno[2,3-b]pyridine-5-carbonitrile PKCq inhibitors, Bioorganic & Med. Chem. Letters, 19(3):766-769 (2009).

\* cited by examiner

THIENOPYRIDINE INHIBITORS OF RIPK2

CROSS-REFERENCE TO RELATED APPLICATIONS

The present application claims priority to U.S. Provisional Application No. 62/783,742, filed Dec. 21, 2018, the entirety of which is hereby incorporated by reference.

BACKGROUND

Receptor interacting protein kinase 2 (RIPK2) is associated with promoting infiltration of immune cells into the central nervous system. Nachbur, et al., *Nature Communications*, 6:6442 (2015). In particular, RIPK2 mediates pro-inflammatory signaling from nucleotide-binding oligomerization domain containing proteins 1 and 2 (NOD1 and NOD2), and is implicated in numerous autoinflammatory disorders. Canning, et al., *Chemistry and Biology*, 22(9): 1174-1184 (17 Sep. 2015). Autoinflammatory disorders, such as inflammatory bowel disease (IBD), can be debilitating and sometimes lead to life-threatening complications. In 2011, studies showed that approximately 1.6 million Americans suffered from IBD. Accordingly, inhibition of RIPK2 is useful for treating certain diseases and disorders associated with autoinflammatory disorders.

SUMMARY

The present application provides technologies useful for inhibiting RIPK2. In some embodiments, provided technologies are useful for, among other things, treating and/or preventing inflammatory disorders such as inflammatory bowel disease.

In some embodiments, the present application provides compounds having a structure as set forth in Formula I:

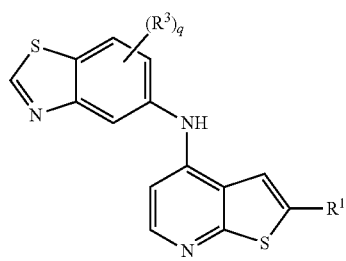

I or a pharmaceutically acceptable salt thereof,
wherein:
$R^1$ is a 4- to 7-membered monocyclic saturated or partially unsaturated heterocyclic ring having 1 to 3 heteroatoms independently selected from nitrogen, oxygen, and sulfur; a 9- to 10-membered bicyclic heterocyclic ring having 1 to 3 heteroatoms independently selected from nitrogen, oxygen, and sulfur; or a 7- to 11-membered spirocyclic fused heterocyclic ring having 1 to 3 heteroatoms independently selected from nitrogen, oxygen, and sulfur, and wherein $R^1$ is substituted with $(R^2)_p$;
each $R^2$ is independently halogen, optionally substituted $C_{1-6}$ aliphatic, —OR, —N(R)$_2$, —C(O)R, —C(O)OR, —SO$_2$R, or an optionally substituted 3- to 7-membered saturated heterocyclic ring having 1 to 2 heteroatoms independently selected from nitrogen, oxygen, and sulfur;
each R is independently hydrogen, optionally substituted $C_{1-6}$ aliphatic, or an optionally substituted 4- to 6-membered saturated heterocyclic ring having 1 to 3 heteroatoms independently selected from nitrogen, oxygen, and sulfur; or
two R groups on a nitrogen atom, together with the atoms to which they are attached, form a 4- to 6-membered heterocyclic ring having 1 or 2 additional heteroatoms independently selected from nitrogen, oxygen, or sulfur;
each $R^3$ is independently halogen, CN, —N(R)$_2$, —OR, or optionally substituted $C_{1-6}$ aliphatic;
p is 0-4; and
q is 0-4.

In some embodiments, the present application provides compounds having a structure as set forth in Formula I':

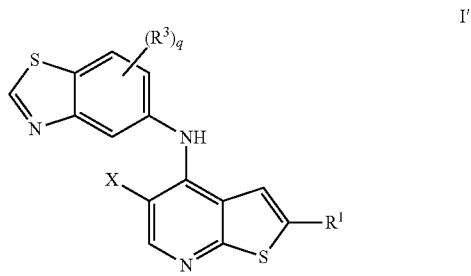

I' or a pharmaceutically acceptable salt thereof,
wherein:
$R^1$ is a 4- to 7-membered monocyclic saturated or partially unsaturated heterocyclic ring having 1 to 3 heteroatoms independently selected from nitrogen, oxygen, and sulfur; a 9- to 10-membered bicyclic heterocyclic ring having 1 to 3 heteroatoms independently selected from nitrogen, oxygen, and sulfur; or a 7- to 11-membered spirocyclic fused heterocyclic ring having 1 to 3 heteroatoms independently selected from nitrogen, oxygen, and sulfur, and wherein $R^1$ is substituted with $(R^2)_p$;
each $R^2$ is independently halogen, optionally substituted $C_{1-6}$ aliphatic, —OR, —N(R)$_2$, —C(O)R, —C(O)OR, —SO$_2$R, or an optionally substituted 3- to 7-membered saturated heterocyclic ring having 1 to 2 heteroatoms independently selected from nitrogen, oxygen, and sulfur;
each R is independently hydrogen, optionally substituted $C_{1-6}$ aliphatic, or an optionally substituted 4- to 6-membered saturated heterocyclic ring having 1 to 3 heteroatoms independently selected from nitrogen, oxygen, and sulfur; or
two R groups on a nitrogen atom, together with the atoms to which they are attached, form a 4- to 6-membered heterocyclic ring having 1 or 2 additional heteroatoms independently selected from nitrogen, oxygen, or sulfur;
each $R^3$ is independently halogen, CN, —N(R)$_2$, —OR, or optionally substituted $C_{1-6}$ aliphatic;
X is hydrogen or halogen;
p is 0-4; and
q is 0-4.

Definitions

Aliphatic: The term "aliphatic" refers to a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "cycloaliphatic"), that has a single point of attachment to the rest of the molecule. Unless otherwise specified, aliphatic groups contain 1-12 aliphatic carbon atoms. In some embodiments, aliphatic groups contain 1-6 aliphatic carbon atoms (e.g., $C_{1-6}$). In some embodiments, aliphatic groups contain 1-5 aliphatic carbon atoms (e.g., $C_{1-5}$). In other embodiments, aliphatic groups contain 1-4 aliphatic carbon atoms (e.g., $C_{1-4}$). In still other embodiments, aliphatic groups contain 1-3 aliphatic carbon atoms (e.g., $C_{1-3}$), and in yet other embodiments, aliphatic groups contain 1-2 aliphatic carbon atoms (e.g., $C_{1-2}$). In some embodiments, "cycloaliphatic" refers to a monocyclic $C_{3-8}$ hydrocarbon or a bicyclic $C_{7-10}$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof. A preferred aliphatic group is $C_{1-6}$ alkyl.

Alkyl: The term "alkyl", used alone or as part of a larger moiety, refers to a saturated, optionally substituted straight or branched chain or cyclic hydrocarbon group having (unless otherwise specified) 1-12, 1-10, 1-8, 1-6, 1-4, 1-3, or 1-2 carbon atoms (e.g., $C_{1-12}$, $C_{1-10}$, $C_{1-8}$, $C_{1-6}$, $C_{1-4}$, $C_{1-3}$, or $C_{1-2}$). Exemplary alkyl groups include methyl, ethyl, propyl, butyl, pentyl, hexyl, and heptyl. The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

Alkylene: The term "alkylene" refers to a bivalent alkyl group. In some embodiments, "alkylene" is a bivalent straight or branched alkyl group. In some embodiments, an "alkylene chain" is a polymethylene group, i.e., $-(CH_2)_n-$, wherein n is a positive integer, e.g., from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3- to 7-membered ring. The substituents can be on the same or different atoms.

Alkenyl: The term "alkenyl", used alone or as part of a larger moiety, refers to an optionally substituted straight or branched chain or cyclic hydrocarbon group having at least one double bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkenyl groups include ethenyl, propenyl, butenyl, pentenyl, hexenyl, and heptenyl. The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

Alkynyl: The term "alkynyl", used alone or as part of a larger moiety, refers to an optionally substituted straight or branched chain hydrocarbon group having at least one triple bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkynyl groups include ethynyl, propynyl, butynyl, pentynyl, hexynyl, and heptynyl.

Aryl: The term "aryl" refers to monocyclic and bicyclic ring systems having a total of five to fourteen ring members (e.g., $C_{5-14}$), wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Unless otherwise specified, "aryl" groups are hydrocarbons.

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid; peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example, nucleic acids or proteins extracted from a sample or obtained by subjecting a primary sample to techniques such as amplification or reverse transcription of mRNA, isolation and/or purification of certain components, etc.

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen or therapeutic regimen: Those skilled in the art will appreciate that the terms "dosing regimen" and "therapeutic regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Excipient: As used herein, the term "excipient" refers to a non-therapeutic agent that may be included in a pharmaceutical composition, for example, to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Heteroaryl: The terms "heteroaryl" and "heteroar-", used alone or as part of a larger moiety, e.g., "heteroaralkyl", or "heteroaralkoxy", refer to monocyclic or bicyclic ring groups having 5 to 10 ring atoms (e.g., 5- to 6-membered monocyclic heteroaryl or 9- to 10-membered bicyclic heteroaryl); having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, imidazo[1,2-a]pyrimidinyl, imidazo[1,2-a]pyridinyl, thienopyrimidinyl, triazolopyridinyl, and benzoisoxazolyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring (i.e., a bicyclic heteroaryl ring having 1 to 3 heteroatoms). Non-limiting examples include indolyl, isoindolyl, benzothienyl, benzofuranyl, dibenzofuranyl, indazolyl, benzimidazolyl, benzothiazolyl, benzothiadiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, and benzoisoxazolyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

Heteroatom: The term "heteroatom" as used herein refers to nitrogen, oxygen, or sulfur, and includes any oxidized form of nitrogen or sulfur, and any quaternized form of a basic nitrogen.

Heterocycle: As used herein, the terms "heterocycle", "heterocyclyl", "heterocyclic radical", and "heterocyclic ring" are used interchangeably and refer to a stable 3- to 8-membered monocyclic or 7- to 10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. A bicyclic heterocyclic ring also includes groups in which the heterocyclic ring is fused to one or more aryl rings. Exemplary bicyclic heterocyclic groups include indolinyl, isoindolinyl, benzodioxolyl, 1,3-dihydroisobenzofuranyl, 2,3-dihydrobenzofuranyl, tetrahydroquinolinyl, and

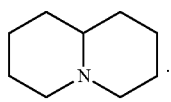

A bicyclic heterocyclic ring can also be a spirocyclic ring system (e.g., 7- to 11-membered spirocyclic fused heterocyclic ring having, in addition to carbon atoms, one or more heteroatoms as defined above (e.g., one, two, three or four heteroatoms)). Exemplary spirocyclic fused heterocyclic ring systems include

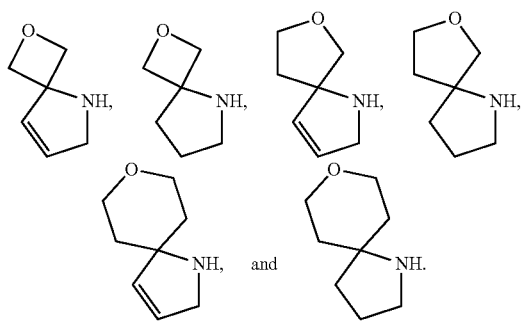

Inhibitory agent: As used herein, the term "inhibitory agent" refers to an entity, condition, or event whose presence, level, or degree correlates with decreased level or activity of a target. In some embodiments, an inhibitory agent may act directly (in which case it exerts its influence directly upon its target, for example, by binding to the target); in some embodiments, an inhibitory agent may act indirectly (in which case it exerts its influence by interacting with and/or otherwise altering a regulator of the target, so that level and/or activity of the target is reduced). In some embodiments, an inhibitory agent is one whose presence or level correlates with a target level or activity that is reduced relative to a particular reference level or activity (e.g., that observed under appropriate reference conditions, such as presence of a known inhibitory agent, or absence of the inhibitory agent in question, etc.).

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intra-arterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially Unsaturated: As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

Patient or subject: As used herein, the term "patient" or "subject" refers to any organism to which a provided composition is or may be administered, e.g., for experimental, diagnostic, prophylactic, cosmetic, and/or therapeutic purposes. Typical patients or subjects include animals (e.g., mammals such as mice, rats, rabbits, non-human primates, and/or humans). In some embodiments, a patient is a human. In some embodiments, a patient or a subject is suffering from or susceptible to one or more disorders or conditions. In some embodiments, a patient or subject displays one or more symptoms of a disorder or condition. In some embodiments, a patient or subject has been diagnosed with one or more disorders or conditions. In some embodiments, a patient or a subject is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, the active agent is present in unit dose amount appropriate for administration in a therapeutic or dosing regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Prevent or prevention: As used herein, the terms "prevent" or "prevention", when used in connection with the occurrence of a disease, disorder, and/or condition, refer to reducing the risk of developing the disease, disorder and/or condition and/or to delaying onset of one or more characteristics or symptoms of the disease, disorder or condition. Prevention may be considered complete when onset of a disease, disorder or condition has been delayed for a pre-defined period of time.

Specific: The term "specific", when used herein with reference to an agent having an activity, is understood by those skilled in the art to mean that the agent discriminates between potential target entities or states. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments, specificity is evaluated relative to that of a reference non-specific binding agent. In some embodiments, the agent or entity does not detectably bind to the competing alternative target under conditions of binding to its target entity. In some embodiments, a binding agent binds with higher on-rate, lower off-rate, increased affinity, decreased dissociation, and/or increased stability to its target entity as compared with the competing alternative target(s).

Substituted or optionally substituted: As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

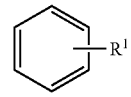

refers to at least

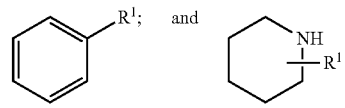

refers to at least

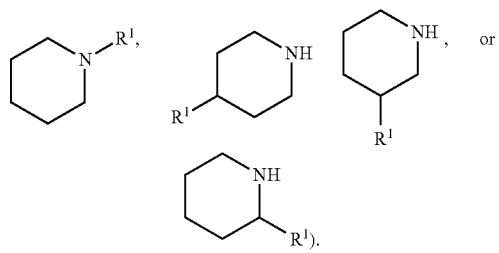

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes provided herein. Groups described as being "substituted" preferably have between 1 and 4 substituents, more preferably 1 or 2 substituents. Groups described as being "optionally substituted" may be unsubstituted or be "substituted" as described above.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5- to 6-membered heteroaryl ring), or a 3- to 6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$, —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 3- to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O ("oxo"), =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR', —NH$_2$, —NHR$^\bullet$, —NR$^\bullet$$_2$, or NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 3- to 6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 3- to 6-membered saturated, partially unsaturated, or aryl ring having 0-4 heteroatoms independently selected from nitrogen, oxygen, or sulfur.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Treat: As used herein, the terms "treat," "treatment," or "treating" refer to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example, for the purpose of decreasing the risk of developing pathology associated with the disease, disorder, and/or condition.

The bond designated as ⩬, as used herein, refers to a bond that, in some embodiments, is a single (e.g., saturated) bond, and in some embodiments, is a double (e.g., unsaturated) bond. For example, the following structure:

is intended to encompass both

The symbol ⁓, as used herein, refers to a point of attachment between two atoms.

The invention provides the compounds of Formula I or Formula I', or a pharmaceutically acceptable salt thereof, in the form of a solvate. The solvent may be water, in which case the solvate is termed a hydrate. Alternatively, the solvent may be an organic solvent. Thus, compounds of the present invention may exist as a hydrate, including a monohydrate, dihydrate, hemihydrate, sesquihydrate, trihydrate, tetrahydrate and the like.

It is understood by one skilled in the art that this invention also includes any compound provided herein that may be enriched at any or all atoms above naturally occurring isotopic ratios with one or more isotopes such as, but not limited to, deuterium ($^2$H or D).

The compounds of the invention, or their pharmaceutically acceptable salts, may contain chiral centers, which, unless specified otherwise, may be either of the (R) or (S) configuration, or which may comprise a mixture thereof. Accordingly, the present application includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present application.

DETAILED DESCRIPTION

RIPK2 Inhibition and Associated Disorders

Autoinflammatory disorders are diseases characterized by systemic and organic-specific inflammation due to abnormalities in the innate immune system. These abnormalities are associated with numerous inflammatory disorders such as inflammatory bowel disease (including Crohn's disease and ulcerative colitis), sarcoidosis, inflammatory arthritis, peritonitis, multiple sclerosis, rheumatoid arthritis, and Wegener's granulomatosis. These disorders affect millions of people.

NOD1 and NOD 2 (nucleotide-binding oligomerization domains 1 and 2) are among the most prominent members of the NLR (NOD-LRR) family, which represent important components of the mammalian innate immune system, serving as intracellular receptors for pathogens and for endogenous molecules elaborated by tissue injury. Correa, et al., *Biosci. Rep.*, 32:597-608 (2012). Heredity polymorphisms in the genes encoding NOD1 and NOD2 have been associated with inflammatory disorders. Once activated, NOD signaling leads to activation of NF-κB and MAP kinases, resulting in the transcription of pro-inflammatory kinases and the induction of autophagy. Nachbur, et al., *Nature Communication*, 6:6442 (2015).

Receptor-interacting protein kinase 2 (RIPK2) mediates pro-inflammatory signaling from NOD1 and NOD2. Canning, et al., *Chemistry & Biology*, 22(9):1174-1184 (17 Sep. 2015). In particular, RIPK2 is critical for NF-κB activation and cytokine production. Researchers have shown that inhibition of RIPK2 resolves abnormal inflammation states such as intestinal inflammation. Salla, et al., *J. Pharmacol. Exp. Ther.*, 365:354-367 (May 2018). Given these promising results, inhibitors of RIPK2 have potential to act as therapeutic agents, for example, to reduce or resolve inflammation for inflammatory disorders such as inflammatory bowel disease (including Crohn's disease and ulcerative colitis), sarcoidosis, inflammatory arthritis, peritonitis, multiple sclerosis, rheumatoid arthritis, and Wegener's granulomatosis.

Accordingly, the present application provides certain compounds and/or compositions that act as RIPK2 inhibitory agents, and technologies relating thereto.

Compounds

In some embodiments, the present application provides a compound of Formula I:

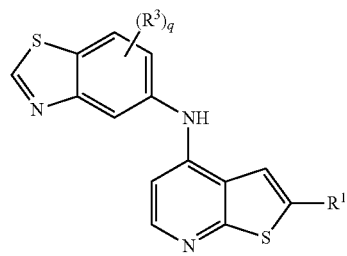

or a pharmaceutically acceptable salt thereof, wherein
$R^1$ is a 4- to 7-membered monocyclic saturated or partially unsaturated heterocyclic ring having 1 to 3 heteroatoms independently selected from nitrogen, oxygen, and sulfur; a 9- to 10-membered bicyclic heterocyclic ring having 1 to 3 heteroatoms independently selected from nitrogen, oxygen, and sulfur; or a 7- to 11-membered spirocyclic fused heterocyclic ring having 1 to 3 heteroatoms independently selected from nitrogen, oxygen, and sulfur, and wherein $R^1$ is substituted with $(R^2)_p$;

each $R^2$ is independently halogen, optionally substituted $C_{1-6}$ aliphatic, —OR, —N(R)$_2$, —C(O)R, —C(O)OR, —SO$_2$R, or an optionally substituted 3- to 7-membered saturated heterocyclic ring having 1 to 2 heteroatoms independently selected from nitrogen, oxygen, and sulfur;

each R is independently hydrogen, optionally substituted $C_{1-6}$ aliphatic, or an optionally substituted 4- to 6-membered saturated heterocyclic ring having 1 to 3 heteroatoms independently selected from nitrogen, oxygen, and sulfur; or two R groups on a nitrogen atom, together with the atoms to which they are attached, form a 4- to 6-membered heterocyclic ring having 1 or 2 additional heteroatoms independently selected from nitrogen, oxygen, or sulfur;

each $R^3$ is independently halogen, —CN, —N(R)$_2$, —OR, or optionally substituted $C_{1-6}$ aliphatic;

p is 0-4; and q is 0-4.

In some embodiments, the present application provides compounds having a structure as set forth in Formula I':

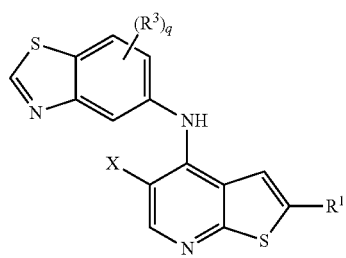

I' or a pharmaceutically acceptable salt thereof,
wherein:

$R^1$ is a 4- to 7-membered monocyclic saturated or partially unsaturated heterocyclic ring having 1 to 3 heteroatoms independently selected from nitrogen, oxygen, and sulfur; a 9- to 10-membered bicyclic heterocyclic ring having 1 to 3 heteroatoms independently selected from nitrogen, oxygen, and sulfur; or a 7- to 11-membered spirocyclic fused heterocyclic ring having 1 to 3 heteroatoms independently selected from nitrogen, oxygen, and sulfur, and wherein $R^1$ is substituted with $(R^2)_p$;

each $R^2$ is independently halogen, optionally substituted $C_{1-6}$ aliphatic, —OR, —N(R)$_2$, —C(O)R, —C(O)OR, —SO$_2$R, or an optionally substituted 3- to 7-membered saturated heterocyclic ring having 1 to 2 heteroatoms independently selected from nitrogen, oxygen, and sulfur;

each R is independently hydrogen, optionally substituted $C_{1-6}$ aliphatic, or an optionally substituted 4- to 6-membered saturated heterocyclic ring having 1 to 3 heteroatoms independently selected from nitrogen, oxygen, and sulfur; or two R groups on a nitrogen atom, together with the atoms to which they are attached, form a 4- to 6-membered heterocyclic ring having 1 or 2 additional heteroatoms independently selected from nitrogen, oxygen, or sulfur;

each $R^3$ is independently halogen, CN, —N(R)$_2$, —OR, or optionally substituted $C_{1-6}$ aliphatic;

X is hydrogen or halogen;

p is 0-4; and q is 0-4.

As defined generally above, $R^1$ is a 4- to 7-membered monocyclic saturated or partially unsaturated heterocyclic ring having 1 to 3 heteroatoms independently selected from nitrogen, oxygen, and sulfur; a 9- to 10-membered bicyclic heterocyclic ring having 1 to 3 heteroatoms independently selected from nitrogen, oxygen, and sulfur; or a 7- to 11-membered spirocyclic fused heterocyclic ring having 1 to 3 heteroatoms independently selected from nitrogen, oxygen, and sulfur, and wherein $R^1$ is substituted with $(R^2)_p$.

In some embodiments, $R^1$ is a 4- to 7-membered monocyclic saturated or partially unsaturated heterocyclic ring having 1 to 3 heteroatoms independently selected from nitrogen, oxygen, and sulfur. In some such embodiments, $R^1$ is substituted with 0, 1, 2, 3, or 4 $R^2$ groups.

In some embodiments, $R^1$ is a 4-membered monocyclic saturated heterocyclic ring having 1 heteroatom selected from nitrogen, oxygen, and sulfur. In some such embodiments, $R^1$ is substituted with 0, 1, 2, 3, or 4 $R^2$ groups.

In some embodiments, $R^1$ is a 5-membered monocyclic saturated heterocyclic ring having 1 heteroatom selected from nitrogen, oxygen, and sulfur. In some such embodiments, $R^1$ is substituted with 0, 1, 2, 3, or 4 $R^2$ groups.

In some embodiments, $R^1$ is a 6-membered monocyclic saturated heterocyclic ring having 1 to 2 heteroatoms independently selected from nitrogen, oxygen, and sulfur. In some such embodiments, $R^1$ is substituted with 0, 1, 2, 3, or 4 $R^2$ groups.

In some embodiments, $R^1$ is a 5-membered monocyclic partially unsaturated heterocyclic ring having 1 heteroatom selected from nitrogen, oxygen, and sulfur. In some such embodiments, $R^1$ is substituted with 0, 1, 2, 3, or 4 $R^2$ groups.

In some embodiments, $R^1$ is a 6-membered monocyclic partially unsaturated heterocyclic ring having 1 to 2 heteroatoms independently selected from nitrogen, oxygen, and sulfur. In some such embodiments, $R^1$ is substituted with 0, 1, 2, 3, or 4 $R^2$ groups.

In some embodiments, $R^1$ is piperidinyl substituted with 0, 1, 2, 3, or 4 $R^2$ groups. In some embodiments, $R^1$ is partially unsaturated piperdinyl substituted with 0, 1, 2, 3, or 4 $R^2$ groups. In some embodiments, $R^1$ is 1,2,3,6-tetrahydropyridinyl. In some such embodiments, $R^1$ is substituted with 0, 1, 2, 3, or 4 $R^2$ groups. In some embodiments, $R^1$ is 1,2,3,6-tetrahydropyridinyl substituted with 1 or 2 $R^2$ groups.

In some embodiments, $R^1$ is a 7-membered monocyclic saturated heterocyclic ring having 1 to 2 heteroatoms independently selected from nitrogen, oxygen, and sulfur. In some such embodiments, $R^1$ is substituted with 0, 1, 2, 3, or 4 $R^2$ groups.

In some embodiments, $R^1$ is a 7-membered monocyclic partially unsaturated heterocyclic ring having 1 to 2 heteroatoms independently selected from nitrogen, oxygen, and sulfur. In some such embodiments, $R^1$ is substituted with 0, 1, 2, 3, or 4 $R^2$ groups.

In some embodiments, $R^1$ is azepanyl or 2,3,4,7-tetrahydro-1H-azepinyl. In some such embodiments, $R^1$ is substituted with 0, 1, 2, 3, or 4 $R^2$ groups. In some such embodiments, $R^1$ is 2,3,6,7-tetrahydro-1H-azepinyl. In some such embodiments, $R^1$ is substituted with 0, 1, 2, 3, or 4 $R^2$ groups.

In some embodiments, R¹ is
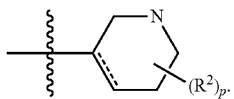
In some embodiments, R¹ is
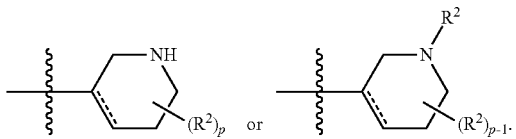
In some embodiments, R¹ is
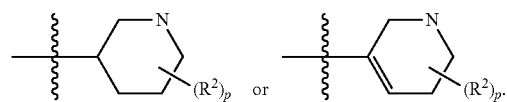
In some embodiments, R¹ is
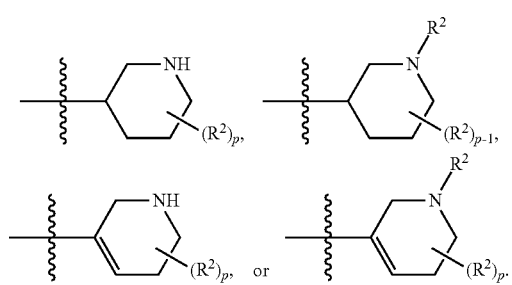
In some embodiments, R¹ is
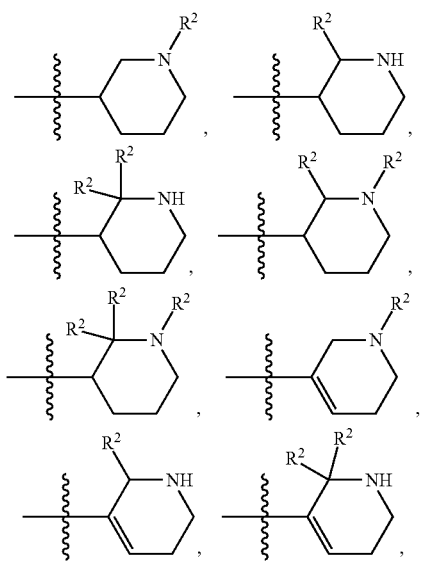
-continued
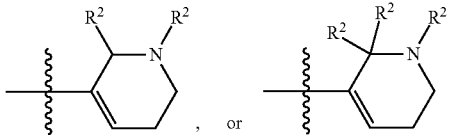
, or
In some embodiments, R¹ is
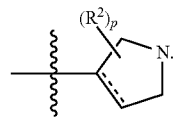
In some embodiments, R¹ is
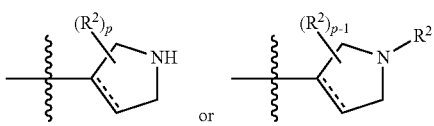
or
In some embodiments, R¹ is
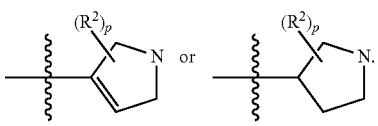
In some embodiments, R¹ is
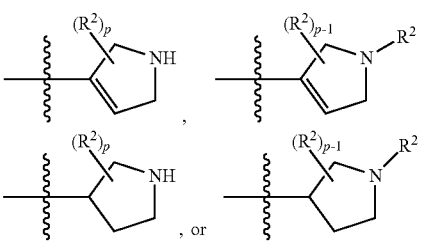
, or
In some embodiments, R¹ is
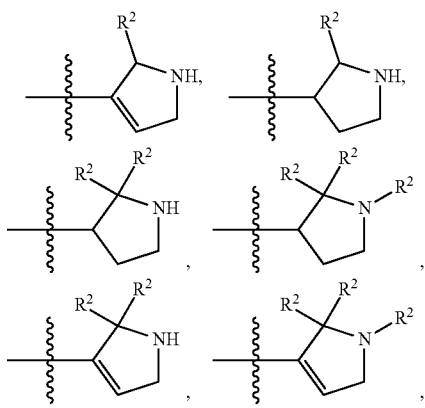

-continued
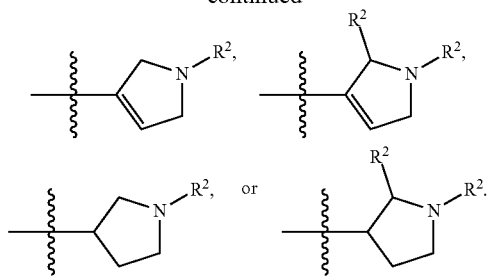
In some embodiments, $R^1$ is
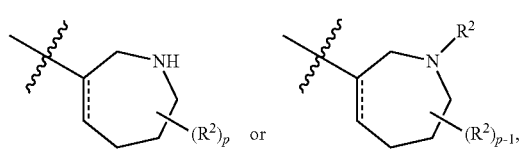
In some embodiments, $R^1$ is
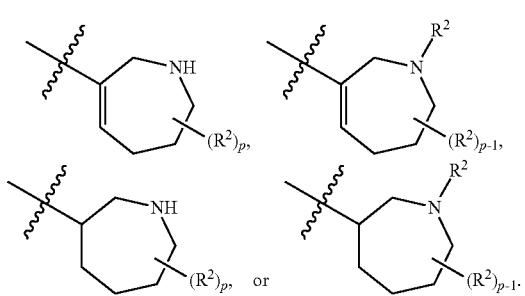
In some embodiments, $R^1$ is
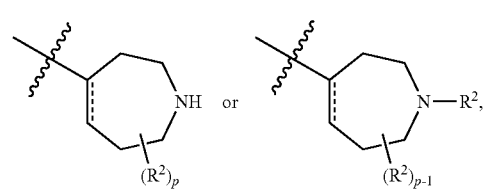
In some embodiments, $R^1$ is
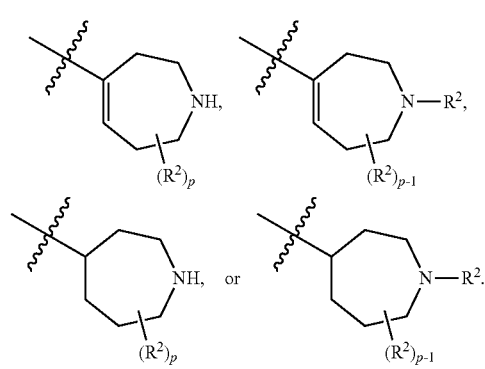
In some embodiments, $R^1$ is
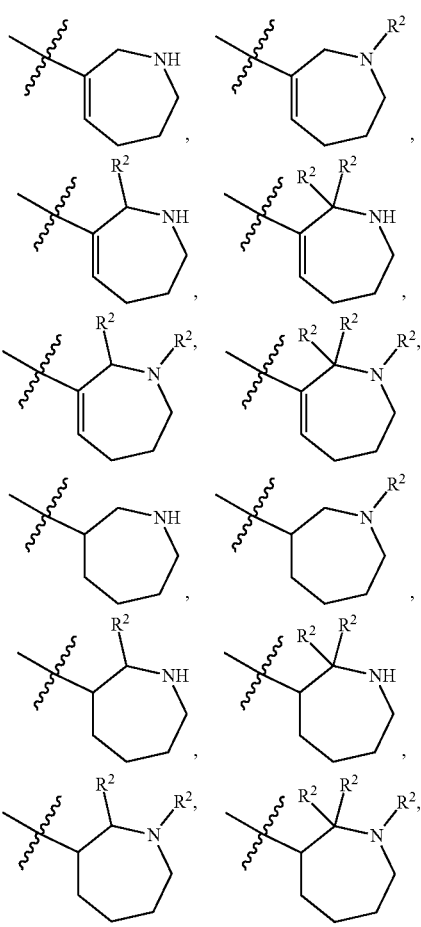
In some embodiments, $R^1$ is
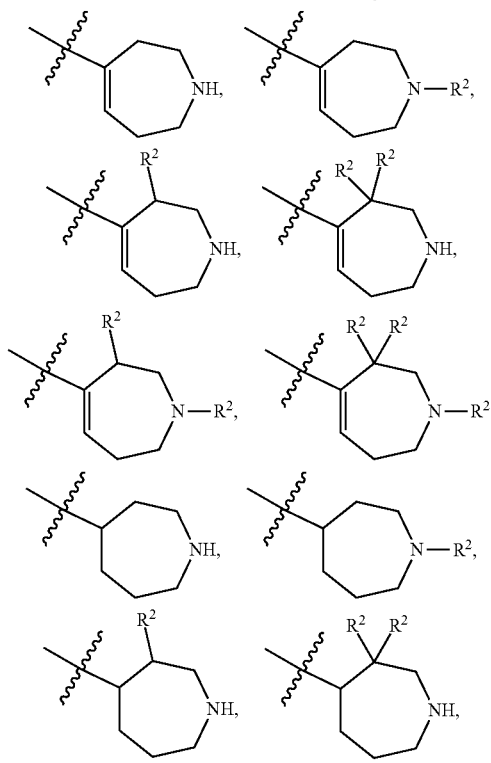

-continued

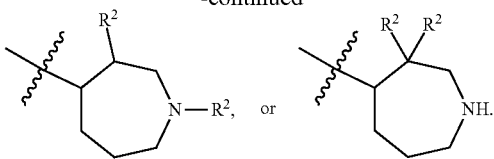

In some embodiments, $R^1$ is a 9- to 10-membered bicyclic heterocyclic ring having 1 to 3 heteroatoms independently selected from nitrogen, oxygen, and sulfur. In some such embodiments, $R^1$ is substituted with 0, 1, 2, 3, or 4 $R^2$ groups. In some embodiments, $R^1$ is a 10-membered bicyclic heterocyclic ring having 1 to 3 heteroatoms independently selected from nitrogen, oxygen, and sulfur. In some such embodiments, $R^1$ is substituted with 0, 1, 2, 3, or 4 $R^2$ groups. In some embodiments, $R^1$ is a 10-membered bicyclic heterocyclic ring having 1 heteroatom selected from nitrogen, oxygen, and sulfur. In some such embodiments, $R^1$ is substituted with 0, 1, 2, 3, or 4 $R^2$ groups.

In some embodiments, $R^1$ is

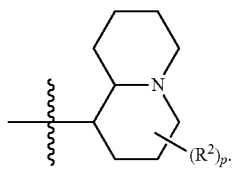

In some embodiments, $R^1$ is

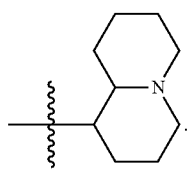 [SMILES: *C1CCCN2CCCCC12]

In some embodiments, $R^1$ is a 7- to 11-membered spirocyclic fused heterocyclic ring having 1 to 3 heteroatoms independently selected from nitrogen, oxygen, and sulfur. In some such embodiments, $R^1$ is substituted with 0, 1, 2, 3, or 4 $R^2$ groups. In some embodiments, $R^1$ is a 7-membered spirocyclic fused heterocyclic ring having 1 to 3 heteroatoms independently selected from nitrogen, oxygen, and sulfur. In some such embodiments, $R^1$ is substituted with 0, 1, 2, 3, or 4 $R^2$ groups.

In some embodiments, $R^1$ is an 8-membered spirocyclic fused heterocyclic ring having 1 to 3 heteroatoms independently selected from nitrogen, oxygen, and sulfur. In some such embodiments, $R^1$ is substituted with 0, 1, 2, 3, or 4 $R^2$ groups.

In some embodiments, $R^1$ is a 9-membered spirocyclic fused heterocyclic ring having 1 to 3 heteroatoms independently selected from nitrogen, oxygen, and sulfur. In some such embodiments, $R^1$ is substituted with 0, 1, 2, 3, or 4 $R^2$ groups.

In some embodiments, $R^1$ is a 10-membered spirocyclic fused heterocyclic ring having 1 to 3 heteroatoms independently selected from nitrogen, oxygen, and sulfur. In some such embodiments, $R^1$ is substituted with 0, 1, 2, 3, or 4 $R^2$ groups.

In some embodiments, $R^1$ is an 11-membered spirocyclic fused heterocyclic ring having 1 to 3 heteroatoms independently selected from nitrogen, oxygen, and sulfur. In some such embodiments, $R^1$ is substituted with 0, 1, 2, 3, or 4 $R^2$ groups.

In some embodiments, $R^1$ is

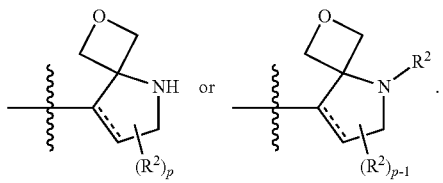

In some embodiments, $R^1$ is

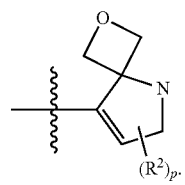

In some embodiments, $R^1$ is

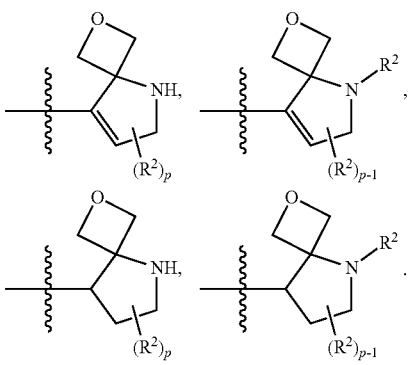

In some embodiments, $R^1$ is

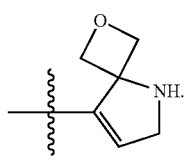 [SMILES: *C1=CCNC12COC2]

In some embodiments, $R^1$ is

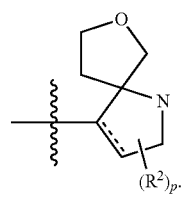

In some embodiments, $R^1$ is
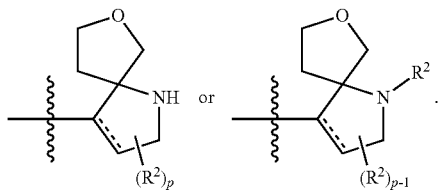
In some embodiments, $R^1$ is
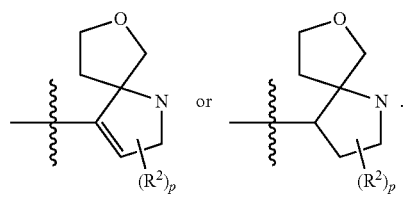
In some embodiments, $R^1$ is
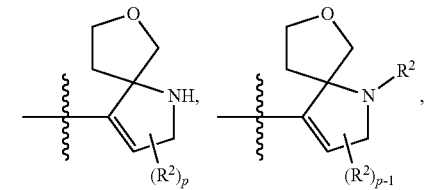
In some embodiments, $R^1$ is
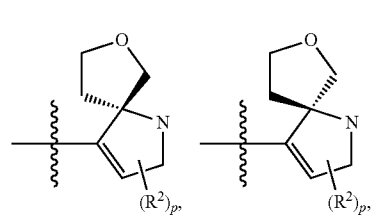
In some embodiments, $R^1$ is
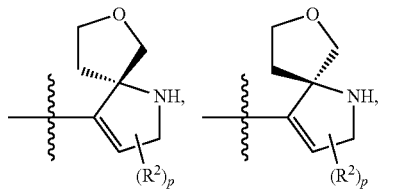
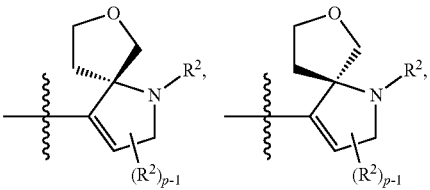
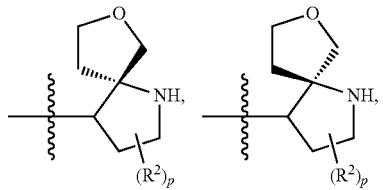
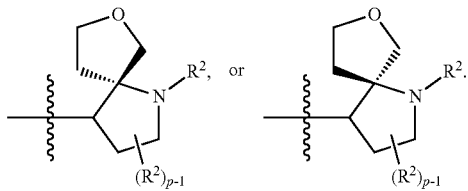
In some embodiments, $R^1$ is
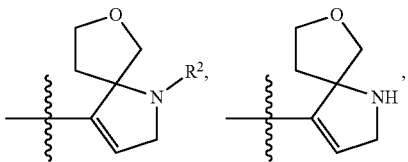
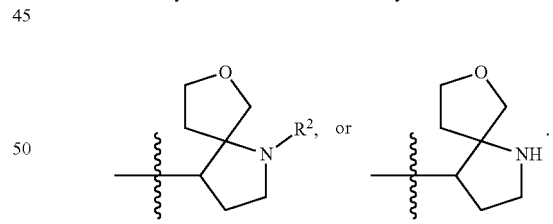
In some embodiments, $R^1$ is
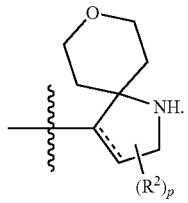

In some embodiments, R¹ is

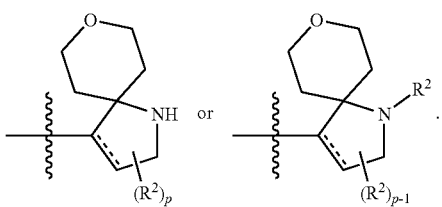

In some embodiments, R¹ is

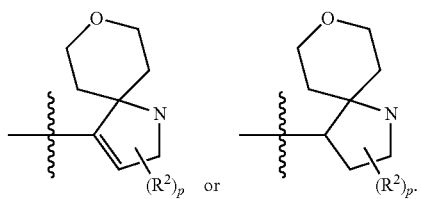

In some embodiments, R¹ is

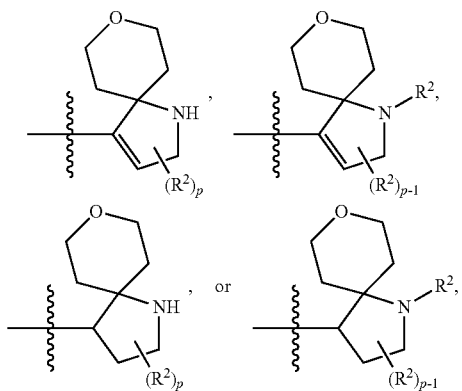

In some embodiments, R¹ is

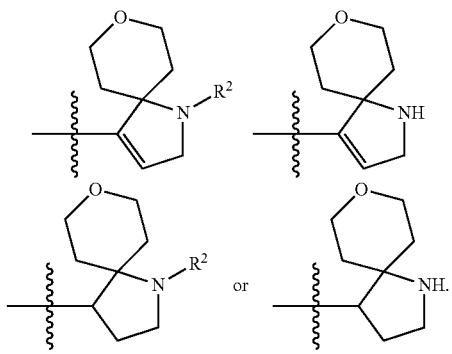

As defined generally above, each R² is independently optionally substituted $C_{1-6}$ aliphatic, —OR, —N(R)$_2$, —C(O)R, —C(O)OR, —SO$_2$R, or an optionally substituted 3- to 7-membered saturated heterocyclic ring having 1 to 2 heteroatoms independently selected from nitrogen, oxygen, and sulfur.

In some embodiments, a substituent on an optionally substituted carbon atom of an optionally substituted R² group is selected from: oxo, halogen, —(CH$_2$)$_{0-4}$R°, —(CH$_2$)$_{0-4}$OR°, and —(CH$_2$)$_{0-4}$N(R°)$_2$; wherein R° is hydrogen, $C_{1-6}$ aliphatic or a 3- to 6-membered saturated, partially unsaturated, or aryl ring having 0-4 heteroatoms independently selected from nitrogen, oxygen, or sulfur.

In some embodiments, a substituent on an optionally substituted carbon atom of an optionally substituted R² group is selected from: oxo, halogen, —(CH$_2$)$_{0-4}$OR°, and —(CH$_2$)$_{0-4}$N(R°)$_2$; wherein R° is hydrogen or $C_{1-6}$ aliphatic.

In some embodiments, R² is optionally substituted $C_{1-6}$ aliphatic. In some embodiments, R² is $C_{1-6}$ aliphatic optionally substituted with a group selected from halogen, —(CH$_2$)$_{0-4}$OR°, or —(CH$_2$)$_{0-4}$N(R°)$_2$. In some such embodiments, R° is hydrogen or $C_{1-6}$ aliphatic optionally substituted with —OR* wherein R* is $C_{1-4}$ aliphatic. In some embodiments, R² is $C_{1-4}$ aliphatic optionally substituted with a group selected from halogen, —(CH$_2$)$_{0-4}$OR°, or —(CH$_2$)$_{0-4}$N(R°)$_2$. In some embodiments, R² is $C_{1-4}$ alkyl optionally substituted with a group selected from halogen, —(CH$_2$)$_{0-4}$OR°, or —(CH$_2$)$_{0-4}$N(R°)$_2$. In some embodiments, R² is $C_{1-2}$ alkyl optionally substituted with a group selected from halogen, —(CH$_2$)$_{0-4}$OR°, or —(CH$_2$)$_{0-4}$N(R°)$_2$. In some embodiments, R² is $C_{1-2}$ alkyl optionally substituted with a group selected from halogen, —OR°, or —N(R°)$_2$. In some embodiments, R² is $C_{1-2}$ alkyl optionally substituted with halogen. In some embodiments, R² is selected from —CH$_2$CH$_2$F, —CH$_2$CHF$_2$, and —CH$_2$CF$_3$.

In some embodiments, R² is $C_{1-3}$ alkyl substituted with —OR° or —N(R°)$_2$. In some such embodiments, R° is hydrogen. In some embodiments, R² is —CH$_2$CH$_2$OH. In some embodiments, R² is —CH$_2$CH$_2$NH$_2$ or —CH$_2$CH$_2$CH$_2$NH$_2$. In some embodiments, R² is $C_{1-2}$ alkyl substituted with —OR° or —N(R°)$_2$, wherein R° is $C_{1-4}$ aliphatic. In some embodiments, R² is $C_{1-2}$ alkyl substituted with —OR° or —N(R°)$_2$, wherein R° is $C_{1-2}$ aliphatic. In some embodiments, R² is $C_{1-2}$ alkyl substituted with —OR°, wherein R° is —CH$_3$ or —CH$_2$CH$_3$. In some embodiments, R² is —CH$_2$CH$_2$OCH$_3$ or —CH$_2$CH$_2$OCH$_2$CH$_3$.

In some embodiments, R² is $C_{1-6}$ alkyl. In some embodiments, R² is methyl. In some embodiments, R² is ethyl. In some embodiments, R² is isopropyl.

In some embodiments, R² is —OR. In some embodiments, R² is —OR, wherein R is $C_{1-4}$ aliphatic. In some embodiments, R² is —OR, wherein R is $C_{1-2}$ aliphatic. In some embodiments, R² is —OCH$_3$.

In some embodiments, R² is —N(R)$_2$. In some embodiments, R² is —N(R)$_2$, wherein each R is independently hydrogen or $C_{1-4}$ aliphatic. In some embodiments, R² is —N(R)$_2$, wherein each R is independently hydrogen or $C_{1-2}$ aliphatic. In some embodiments, R² is —N(R)$_2$, wherein each R is independently hydrogen or $C_{1-2}$ alkyl. In some embodiments, R²—NH$_2$. In some embodiments, R² is —N(CH$_3$)$_2$. In some embodiments, R² is —NH(CH$_3$).

In some embodiments, R² is —C(O)R. In some embodiments, R² is —C(O)R, wherein R is optionally substituted $C_{1-6}$ aliphatic. In some embodiments, R² is —C(O)R, wherein R is $C_{1-4}$ aliphatic optionally substituted with —(CH$_2$)$_{0-4}$OR°, wherein R° is $C_{1-4}$ aliphatic. In some embodiments, R² is —C(O)R, wherein R is optionally substituted $C_{1-4}$ aliphatic. In some embodiments, R² is —C(O)R, wherein R is optionally substituted $C_{1-2}$ aliphatic. In some embodiments, R² is —C(O)R, wherein R is optionally substituted $C_{1-2}$ alkyl. In some embodiments, R² is —C(O)R, wherein R is methyl (e.g., R² is —C(O)CH$_3$).

In some embodiments, $R^2$ is —C(O)R, wherein R is $C_{1-6}$ aliphatic optionally substituted with —(CH$_2$)$_{0-4}$OR°, wherein R° is $C_{1-4}$ aliphatic. In some embodiments, $R^2$ is —C(O)R, wherein R is $C_{1-4}$ aliphatic optionally substituted with —(CH$_2$)$_{0-4}$OR°, wherein R° is $C_{1-2}$ aliphatic. In some embodiments, $R^2$ is —C(O)R, wherein R is $C_{1-4}$ aliphatic optionally substituted with —(CH$_2$)$_{0-4}$OR°, wherein R° is $C_{1-4}$ alkyl. In some embodiments, $R^2$ is —C(O)R, wherein R is $C_{1-4}$ aliphatic optionally substituted with —(CH$_2$)$_{0-4}$OR°, wherein R° is methyl. In some embodiments, $R^2$ is —C(O)CH$_2$OCH$_3$.

In some embodiments, $R^2$ is —C(O)OR. In some embodiments, $R^2$ is —C(O)OR, wherein R is $C_{1-6}$ aliphatic. In some embodiments, $R^2$ is —C(O)OR, wherein R is $C_{1-4}$ aliphatic. In some embodiments, $R^2$ is —C(O)OR, wherein R is $C_{1-4}$ alkyl. In some embodiments, $R^2$ is —C(O)OR, wherein R is methyl. In some embodiments, $R^2$ is —C(O)OR, wherein R is ethyl. In some embodiments, $R^2$ is —C(O)OR, wherein R is propyl. In some embodiments, $R^2$ is —C(O)OR, wherein R is isopropyl. In some embodiments, $R^2$ is —C(O)OR, wherein R is butyl. In some embodiments, $R^2$ is —C(O)OR, wherein R is t-butyl (i.e., $R^2$ is —C(O)OC(CH$_3$)$_3$).

In some embodiments, $R^2$ is —SO$_2$R. In some embodiments, $R^2$ is —SO$_2$R, wherein R is $C_{1-4}$ aliphatic. In some embodiments, $R^2$ is —SO$_2$R, wherein R is $C_{1-2}$ aliphatic. In some embodiments, $R^2$ is —SO$_2$CH$_3$.

In some embodiments, $R^2$ is a 3- to 7-membered saturated heterocyclic ring having 1 to 2 heteroatoms independently selected from nitrogen, oxygen, and sulfur. In some embodiments, $R^2$ is a 3-membered saturated heterocyclic ring having 1 heteroatom selected from nitrogen, oxygen, and sulfur. In some embodiments, $R^2$ is a 4-membered saturated heterocyclic ring having 1 heteroatom selected from nitrogen, oxygen, and sulfur. In some such embodiments, $R^2$ is oxetanyl. In some embodiments, $R^2$ is a 3- to 7-membered saturated heterocyclic ring having 1 to 2 heteroatoms independently selected from nitrogen, oxygen, and sulfur. In some embodiments, $R^2$ is a 5-membered saturated heterocyclic ring having 1 heteroatom selected from nitrogen, oxygen, and sulfur. In some embodiments, $R^2$ is a 6-membered saturated heterocyclic ring having 1 to 2 heteroatoms independently selected from nitrogen, oxygen, and sulfur. In some embodiments, $R^2$ is a 6-membered saturated heterocyclic ring having 1 to 2 heteroatoms independently selected from nitrogen, oxygen, and sulfur.

As described generally above, each R is independently hydrogen, optionally substituted $C_{1-6}$ aliphatic, or an optionally substituted 4- to 6-membered saturated heterocyclic ring having 1 to 3 heteroatoms independently selected from nitrogen, oxygen, and sulfur; or two R groups on a nitrogen atom, together with the atoms to which they are attached, form a 4- to 6-membered heterocyclic ring having 1 or 2 additional heteroatoms independently selected from nitrogen, oxygen, or sulfur.

In some embodiments, a substituent on an optionally substituted carbon atom of an optionally substituted R group is selected from: oxo, halogen, —(CH$_2$)$_{0-4}$R°, —(CH$_2$)$_{0-4}$OR°, and —(CH$_2$)$_{0-4}$N(R°)$_2$; wherein R° is hydrogen, $C_{1-6}$ aliphatic or a 3- to 6-membered saturated, partially unsaturated, or aryl ring having 0-4 heteroatoms independently selected from nitrogen, oxygen, or sulfur.

In some embodiments, a substituent on an optionally substituted carbon atom of an optionally substituted R group is selected from: oxo, halogen, —(CH$_2$)$_{0-4}$OR° and —(CH$_2$)$_{0-4}$N(R°)$_2$; wherein R° is hydrogen or $C_{1-6}$ aliphatic.

In some embodiments, R is hydrogen.

In some embodiments, R is an optionally substituted $C_{1-6}$ aliphatic. In some embodiments, R is an optionally substituted $C_{1-4}$ aliphatic. In some embodiments, R is an optionally substituted $C_{1-2}$ aliphatic. In some embodiments, R is an optionally substituted $C_{1-2}$ alkyl. In some embodiments, R is methyl. In some embodiments, R is ethyl. In some embodiments, R is propyl. In some embodiments, R is isopropyl. In some embodiments, R is butyl. In some embodiments, R is t-butyl. In some embodiments, R is a $C_{1-6}$ aliphatic optionally substituted with a group selected from halogen, —(CH$_2$)$_{0-4}$OR°, or —(CH$_2$)$_{0-4}$N(R°)$_2$. In some such embodiments, R° is hydrogen or $C_{1-6}$ aliphatic optionally substituted with —OR* wherein R* is $C_{1-4}$ aliphatic.

In some embodiments, R is $C_{1-4}$ aliphatic optionally substituted with a group selected from halogen, —(CH$_2$)$_{0-4}$OR°, or —(CH$_2$)$_{0-4}$N(R°)$_2$. In some such embodiments, R° is hydrogen or $C_{1-6}$ aliphatic optionally substituted with —OR' wherein R' is $C_{1-4}$ aliphatic. In some embodiments, R is $C_{1-2}$ aliphatic optionally substituted with a group selected from halogen, —(CH$_2$)$_{0-4}$OR°, or —(CH$_2$)$_{0-4}$N(R°)$_2$. In some such embodiments, R° is hydrogen or $C_{1-6}$ aliphatic optionally substituted with —OR* wherein R* is $C_{1-4}$ aliphatic. In some embodiments, R is $C_{1-2}$ alkyl optionally substituted with a group selected from halogen, —(CH$_2$)$_{0-4}$OR°, or —(CH$_2$)$_{0-4}$N(R°)$_2$. In some such embodiments, R° is hydrogen or $C_{1-6}$ aliphatic optionally substituted with —OR* wherein R* is $C_{1-4}$ aliphatic.

In some embodiments, R is $C_{1-6}$ aliphatic optionally substituted with a group selected from halogen, —OR°, or —N(R°)$_2$. In some such embodiments, R° is hydrogen or $C_{1-6}$ aliphatic optionally substituted with —OR* wherein R* is $C_{1-4}$ aliphatic. In some embodiments, R is $C_{1-4}$ aliphatic optionally substituted with a group selected from halogen, —OR°, or —N(R°)$_2$. In some such embodiments, R° is hydrogen or $C_{1-6}$ aliphatic optionally substituted with —OR$^●$ wherein R$^●$ is $C_{1-4}$ aliphatic. In some embodiments, R is $C_{1-2}$ aliphatic optionally substituted with a group selected from halogen, —OR°, or —N(R°)$_2$. In some such embodiments, R° is hydrogen or $C_{1-6}$ aliphatic optionally substituted with —OR' wherein R' is $C_{1-4}$ aliphatic. In some embodiments, R is $C_{1-2}$ alkyl optionally substituted with a group selected from halogen, —OR°, or —N(R°)$_2$. In some such embodiments, R° is hydrogen or $C_{1-6}$ aliphatic optionally substituted with —OR$^●$ wherein R$^●$ is $C_{1-4}$ aliphatic.

In some embodiments, R is an optionally substituted 4- to 6-membered saturated heterocyclic ring having 1 to 3 heteroatoms independently selected from nitrogen, oxygen, and sulfur. In some embodiments, R is an optionally substituted 4-membered saturated heterocyclic ring having 1 heteroatom selected from nitrogen, oxygen, and sulfur. In some embodiments, R is an optionally substituted 5-membered saturated heterocyclic ring having 1 heteroatom selected from nitrogen, oxygen, and sulfur. In some embodiments, R is an optionally substituted 6-membered saturated heterocyclic ring having 1 or 2 additional heteroatoms independently selected from nitrogen, oxygen, and sulfur.

In some embodiments, two R groups on a nitrogen atom, together with the atoms to which they are attached, form a 4- to 6-membered heterocyclic ring having 1 or 2 additional heteroatoms independently selected from nitrogen, oxygen, or sulfur. In some embodiments, two R groups on a nitrogen atom, together with the atoms to which they are attached, form a 4-membered heterocyclic ring. In some embodiments, two R groups on a nitrogen atom, together with the atoms to which they are attached, form a 5-membered heterocyclic ring. In some embodiments, two R groups on a nitrogen atom, together with the atoms to which they are attached, form a 6-membered heterocyclic ring having 0 or 1 additional heteroatom selected from nitrogen, oxygen, and sulfur.

In some embodiments, $R^1$ is piperidinyl and $R^2$ is methyl. In some embodiments, $R^1$ is piperidinyl, p is 1, and each $R^2$ is methyl. In some embodiments, $R^1$ is

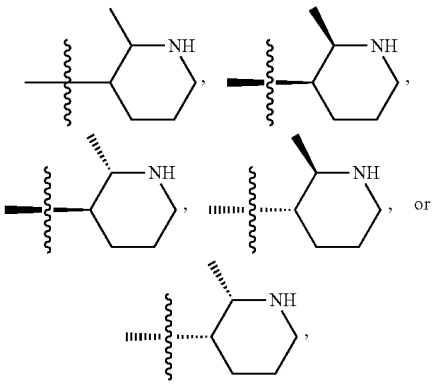

In some embodiments, $R^1$ is

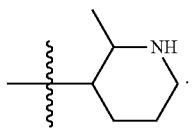 [SMILES: *C1CCCNC1C]

In some embodiments, $R^1$ is

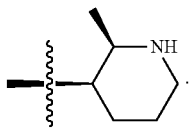

In some embodiments, $R^1$ is

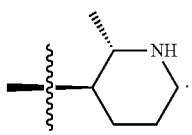

In some embodiments, $R^1$ is

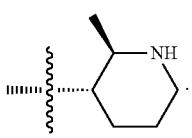

In some embodiments, $R^1$ is

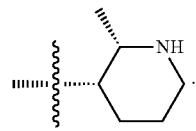

In some embodiments, $R^1$ is selected from:

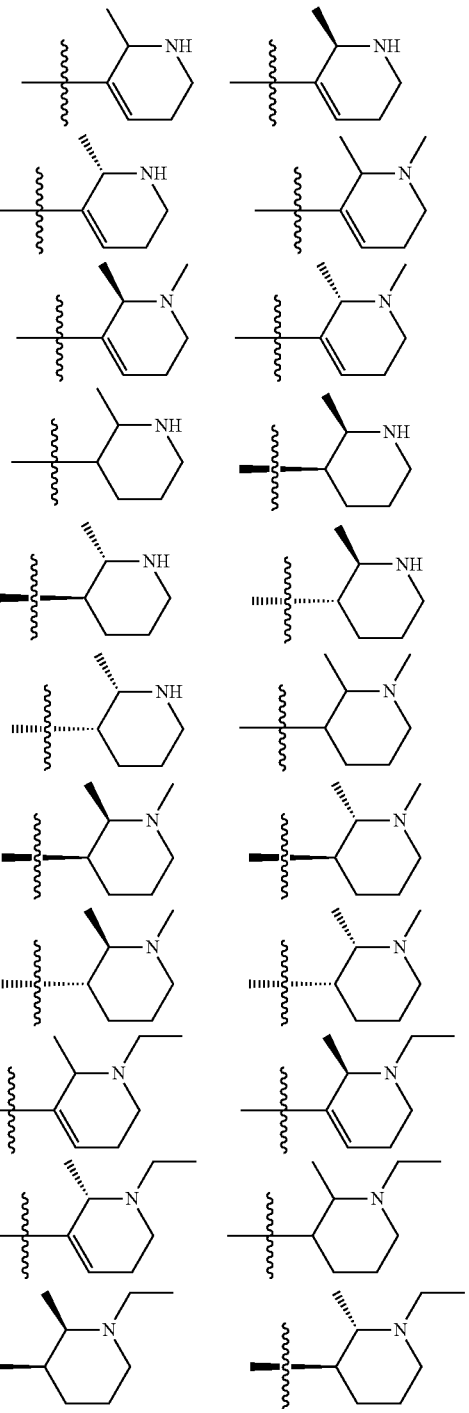

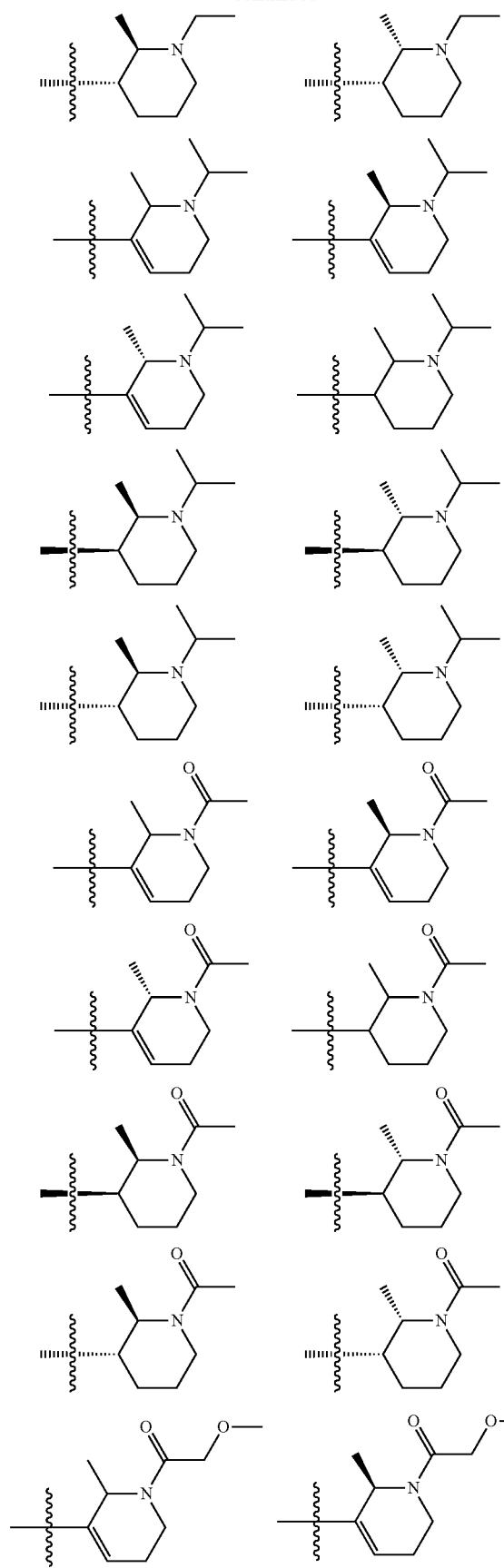
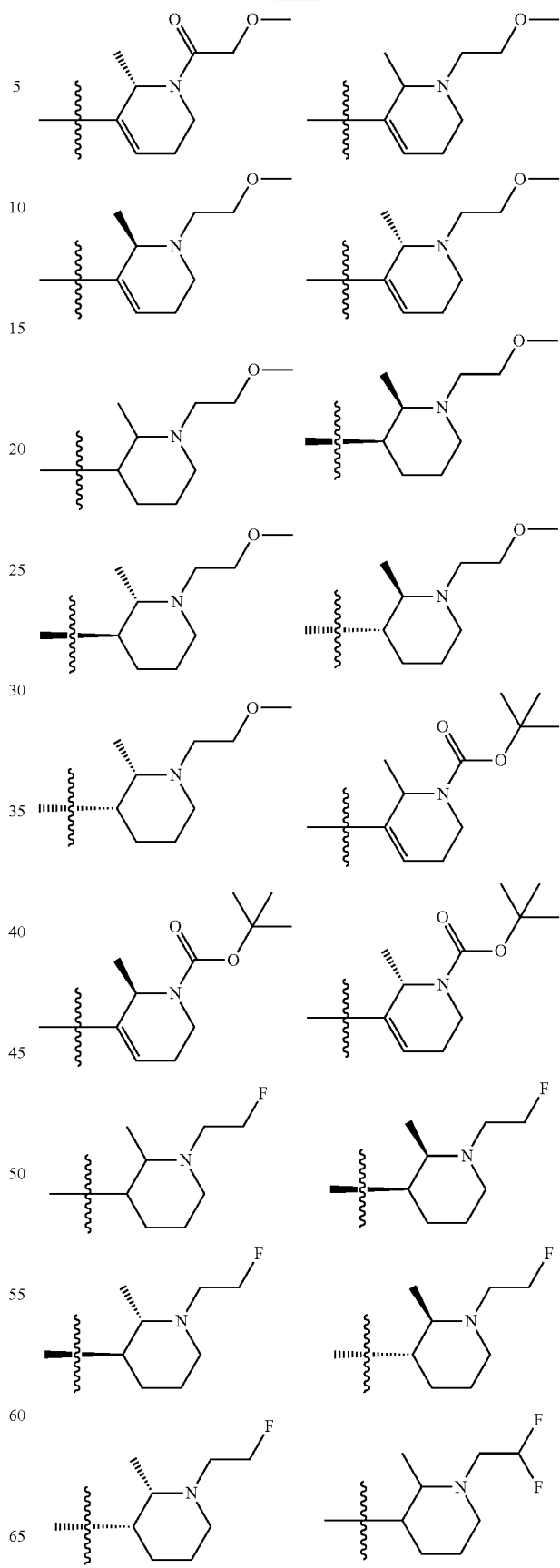

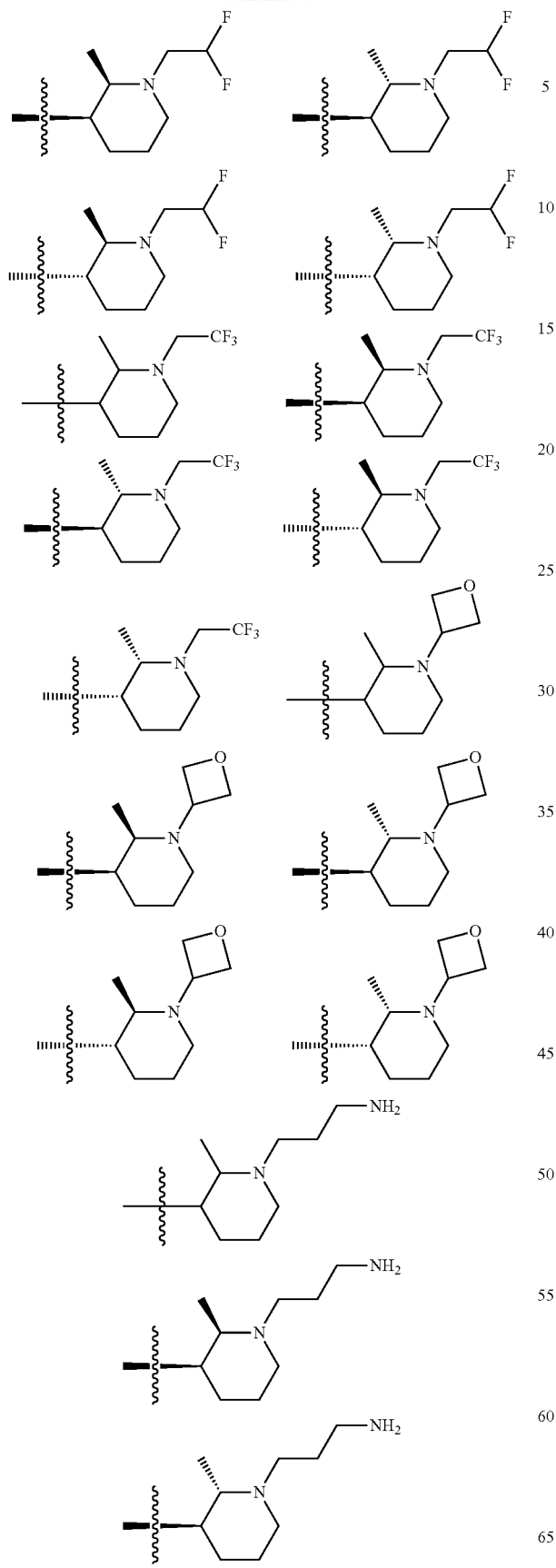
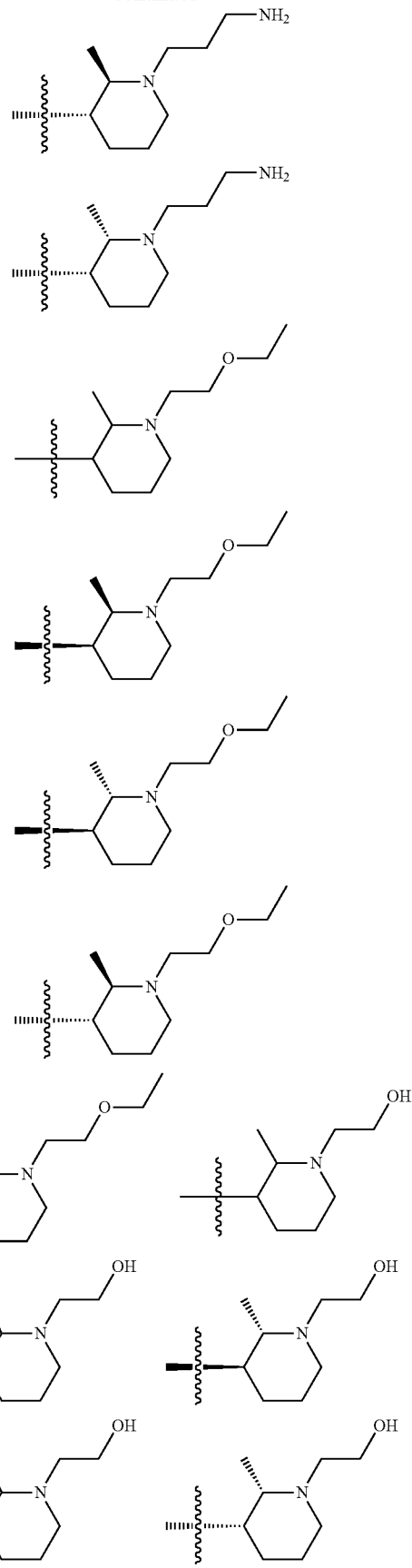

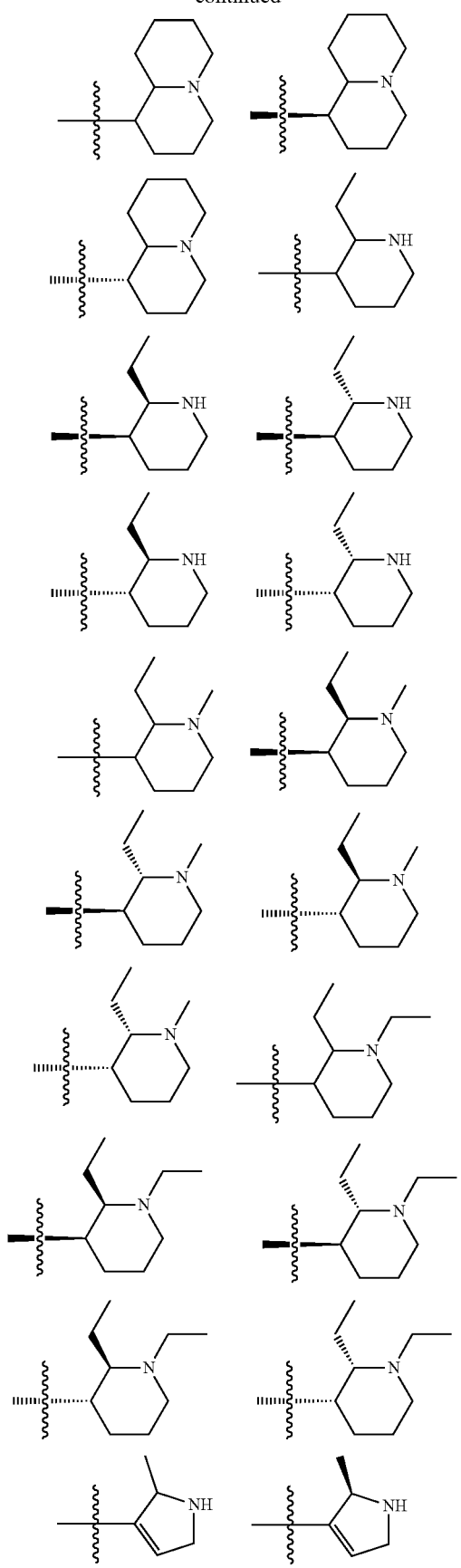
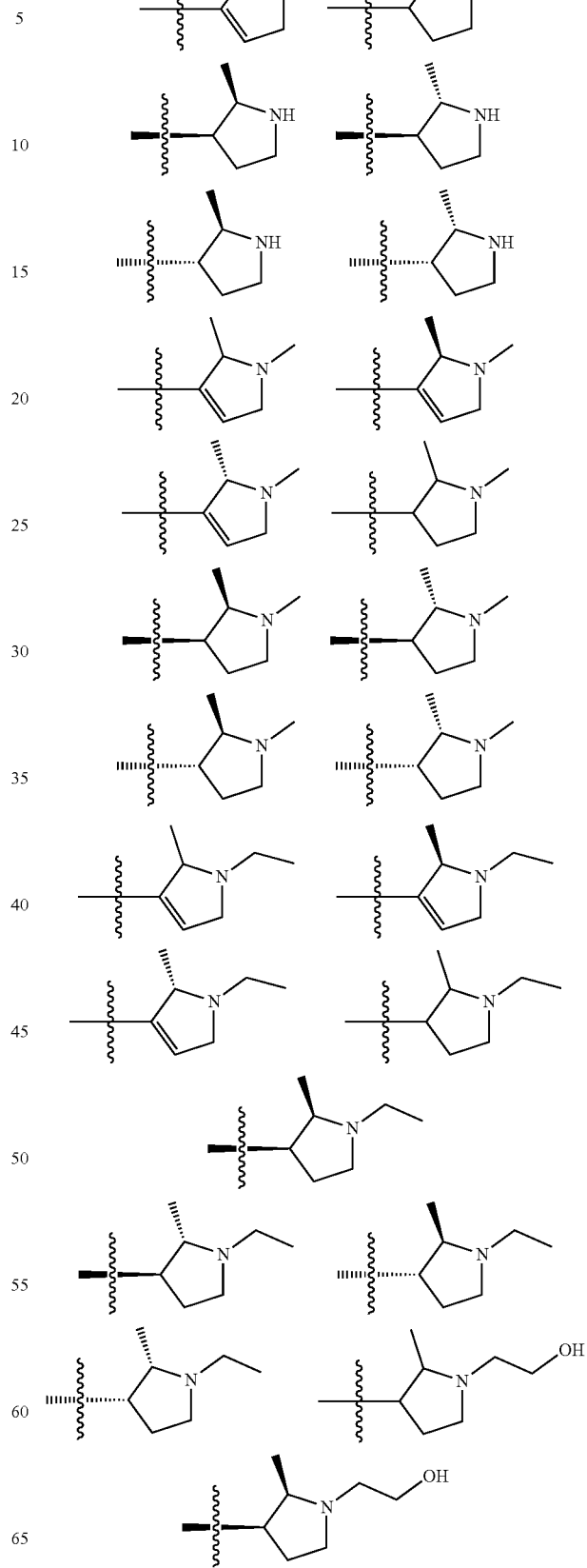

-continued
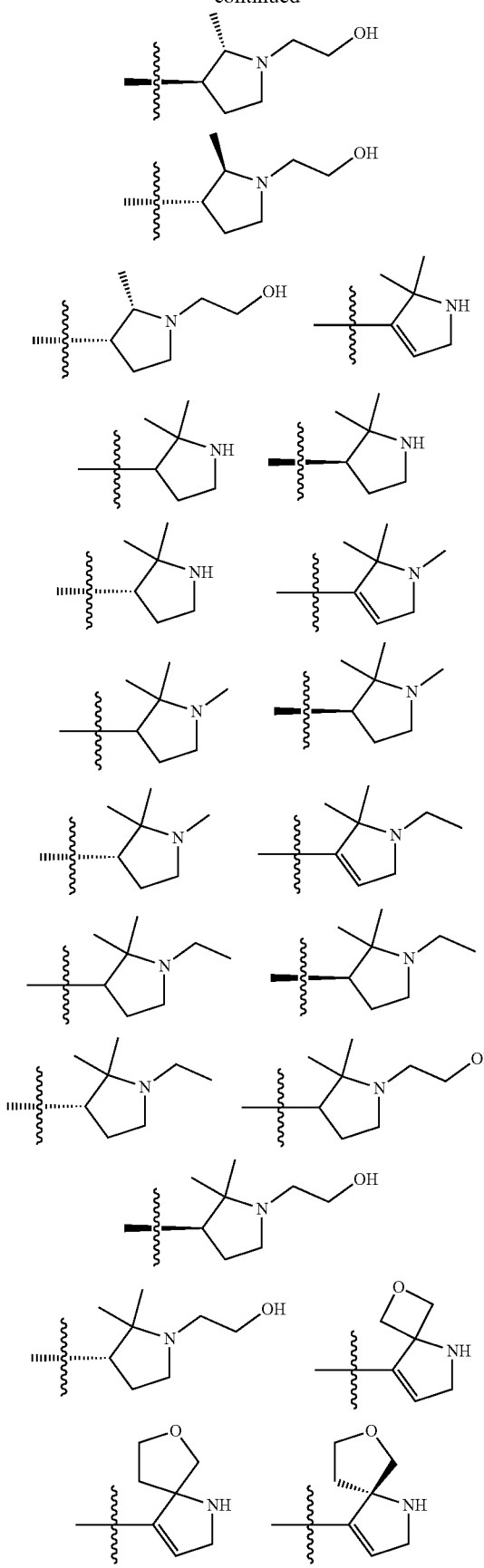
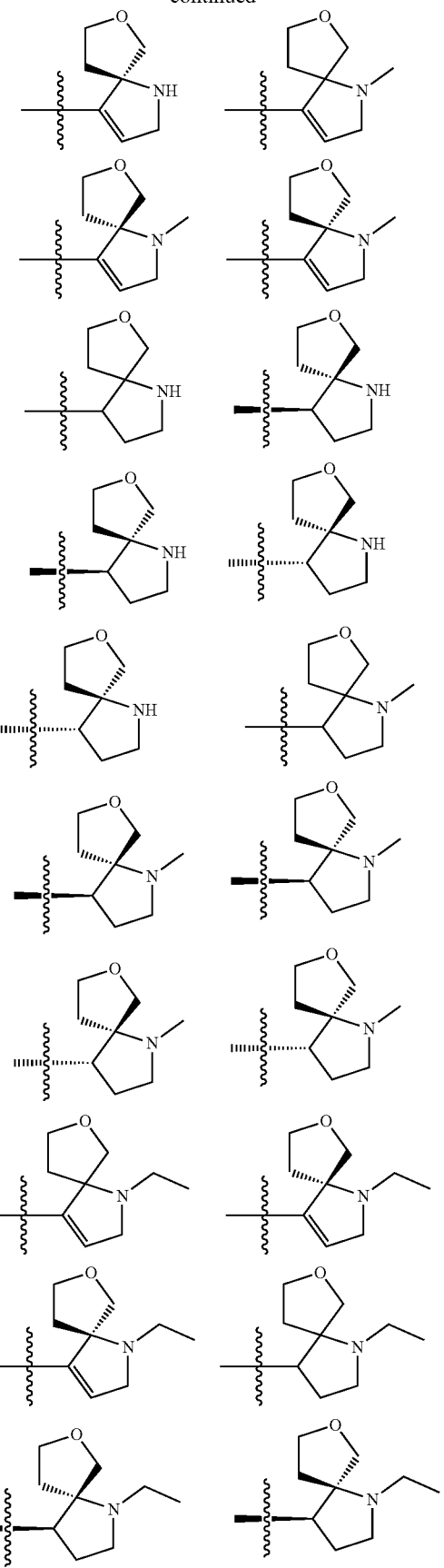

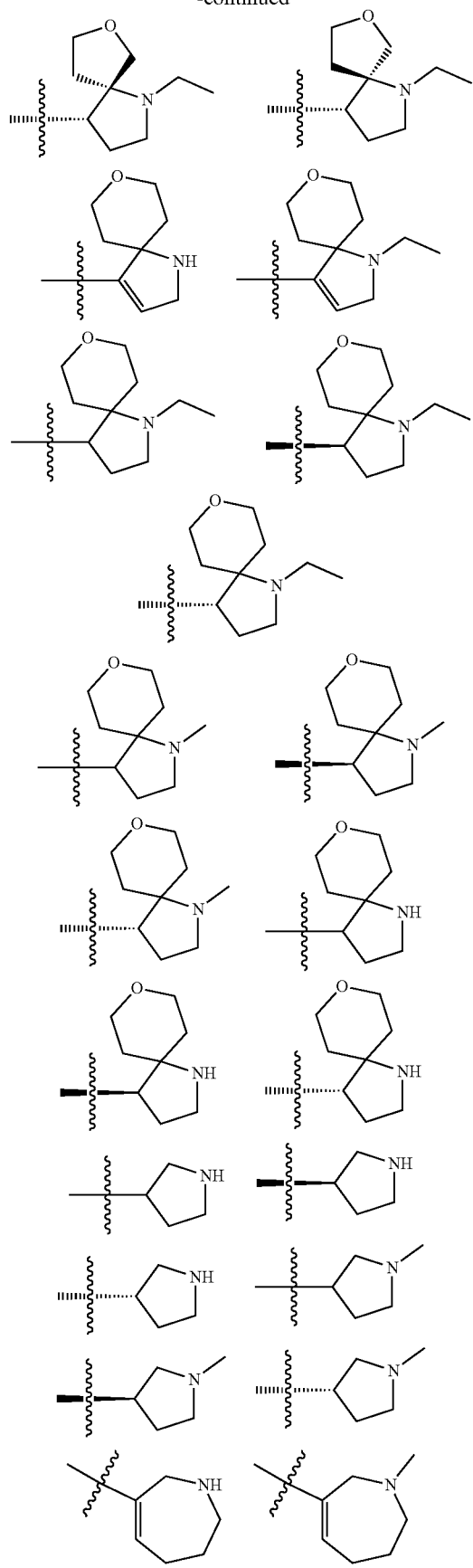
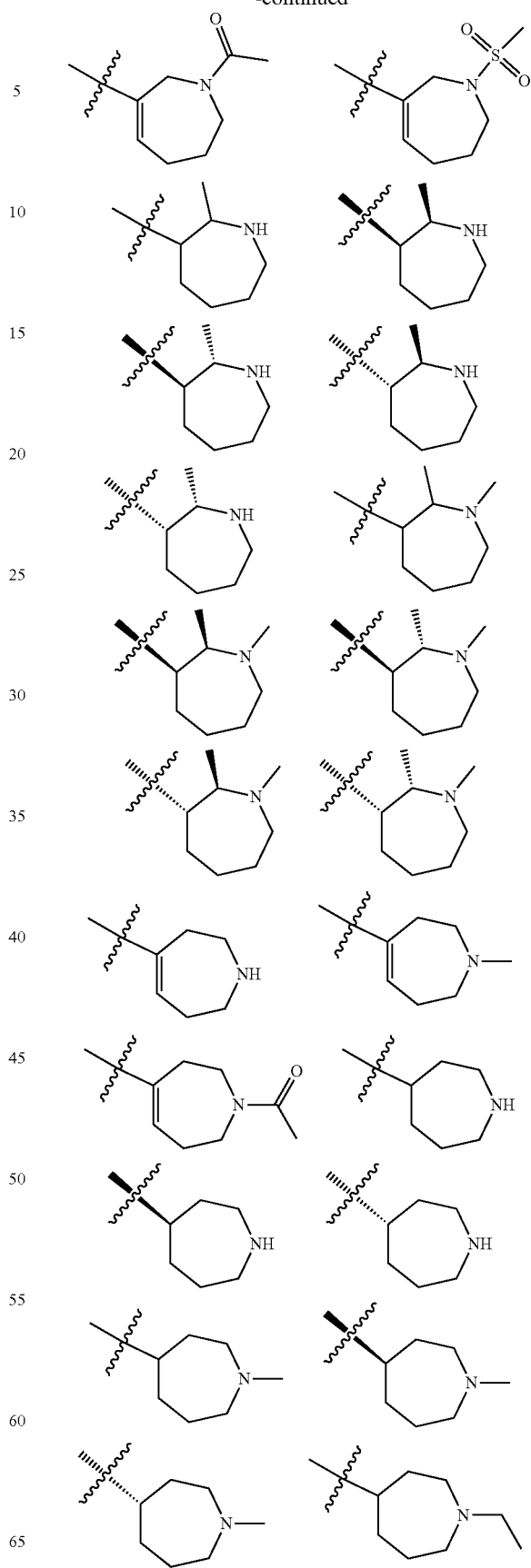

-continued

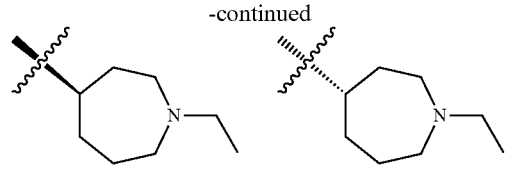

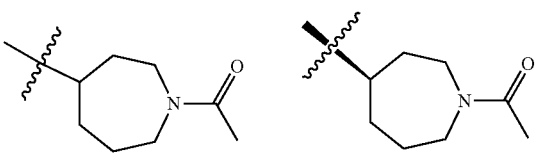

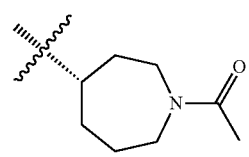

In some embodiments, each $R^3$ is independently halogen, —CN, —N(R)$_2$, —OR, or optionally substituted $C_{1-6}$ aliphatic.

In some embodiments, a substituent on an optionally substituted carbon atom of an optionally substituted $R^3$ group is selected from: oxo, halogen, —(CH$_2$)$_{0-4}$R°, —(CH$_2$)$_{0-4}$OR°, and —(CH$_2$)$_{0-4}$N(R°)$_2$; wherein R° is hydrogen, $C_{1-6}$ aliphatic or a 3- to 6-membered saturated, partially unsaturated, or aryl ring having 0-4 heteroatoms independently selected from nitrogen, oxygen, or sulfur.

In some embodiments, a substituent on an optionally substituted carbon atom of an optionally substituted $R^3$ group is selected from: halogen, —(CH$_2$)$_{0-4}$R°, —(CH$_2$)$_{0-4}$OR°, and —(CH$_2$)$_{0-4}$N(R°)$_2$; wherein R° is hydrogen, $C_{1-6}$ aliphatic, or a 3- to 6-membered saturated, partially unsaturated, or aryl ring having 0-4 heteroatoms independently selected from nitrogen, oxygen, or sulfur.

In some embodiments, $R^3$ is halogen. In some embodiments, $R^3$ is selected from bromo, chloro, or fluoro. In some embodiments, $R^3$ is bromo. In some embodiments, $R^3$ is chloro. In some embodiments $R^3$ is fluoro. In some embodiments, $R^3$ is optionally substituted $C_{1-6}$ aliphatic. In some embodiments, $R^3$ is optionally substituted $C_{1-4}$ aliphatic. In some embodiments, $R^3$ is optionally substituted $C_{1-2}$ aliphatic. In some embodiments, $R^3$ is optionally substituted $C_{1-2}$ alkyl. In some embodiments, $R^3$ is methyl.

As defined generally above, p is 0-4. In some embodiments, p is 0, 1, 2, 3, or 4. In some embodiments, p is 0. In some embodiments, p is 1. In some embodiments, p is 2. In some embodiments, p is 3. In some embodiments, p is 4.

As defined generally above, q is 0-4. In some embodiments, q is 0, 1, 2, 3, or 4. In some embodiments, q is 0. In some embodiments, q is 1. In some embodiments, q is 2. In some embodiments, q is 3. In some embodiments, q is 4.

As defined generally above, X is hydrogen or halogen. In some embodiments, X is hydrogen. In some embodiments, X is halogen. In some such embodiments, X is fluoro or chloro. In some embodiments, X is fluoro.

In some embodiments, the present application provides compounds of Formula II:

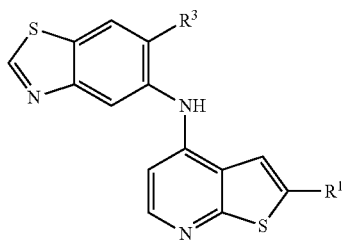

II or a pharmaceutically acceptable salt thereof, wherein each of $R^1$ and $R^3$ is as defined above and described herein.

In some embodiments, the present application provides compounds of Formula II':

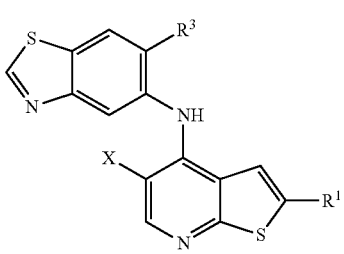

II' or a pharmaceutically acceptable salt thereof, wherein each of $R^1$, $R^3$, and X is as defined above and described herein.

In some embodiments, the present application provides compounds of Formula III:

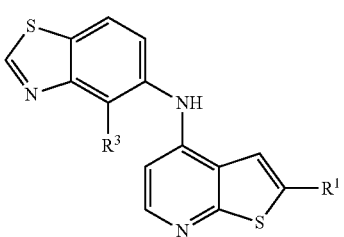

III or a pharmaceutically acceptable salt thereof, wherein each of $R^1$ and $R^3$ is as defined above and described herein.

In some embodiments, the present application provides compounds of Formula III':

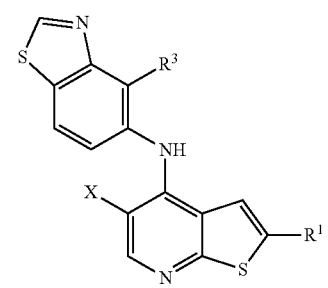

III' or a pharmaceutically acceptable salt thereof, wherein each of $R^1$, $R^3$, and X is as defined above and described herein.

In some embodiments, the present application provides compounds of Formula IV:

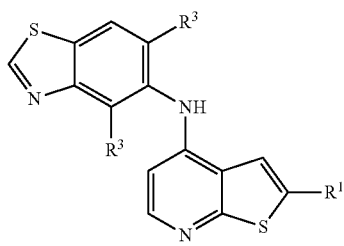

IV or a pharmaceutically acceptable salt thereof, wherein each of $R^1$ and $R^3$ is as defined above and described herein.

In some embodiments, the present application provides compounds of Formula IV':

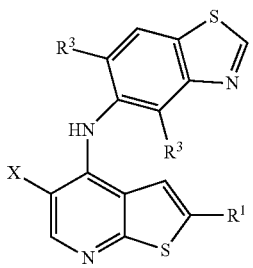

IV' or a pharmaceutically acceptable salt thereof, wherein each of $R^1$, $R^3$, and X is as defined above and described herein.

It is to be understood that the above embodiments may be combined together, as if each and every combination were specifically and individually listed.

In some embodiments, the compound of Formula I or Formula I' is selected from:

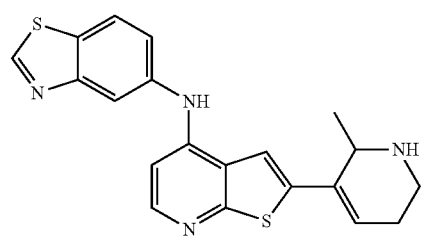

I-1

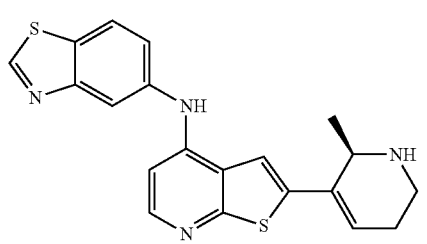

I-1-i

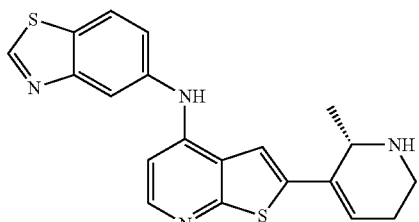

I-1-ii

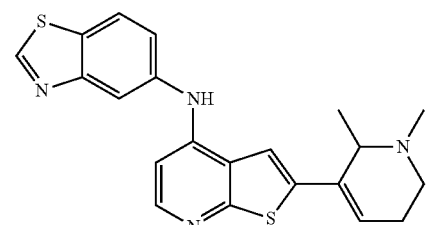

I-2

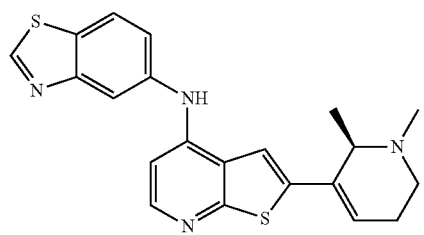

I-2-i

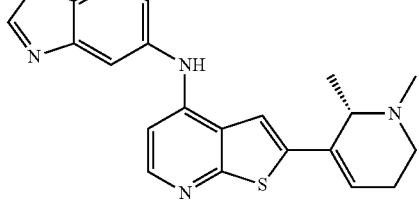

I-2-ii

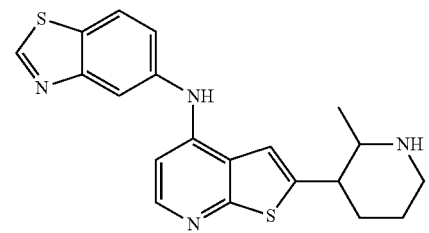

I-3

I-3-i

I-3-ii
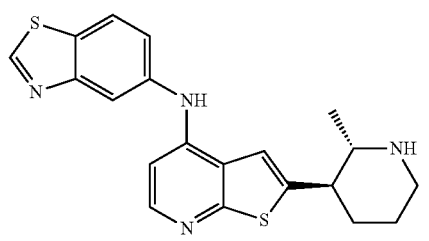
I-3-iii
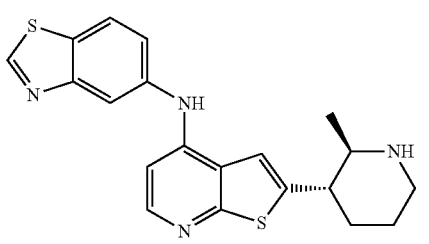
I-3-iv
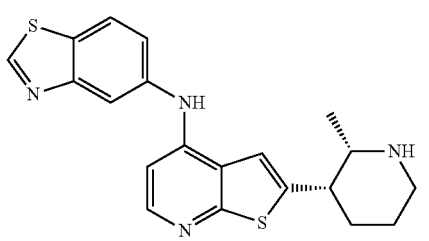
I-4
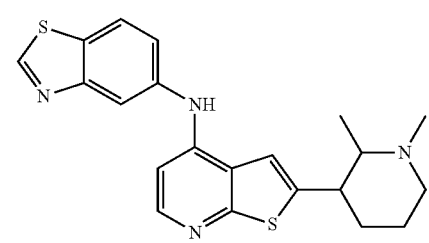
I-4-i
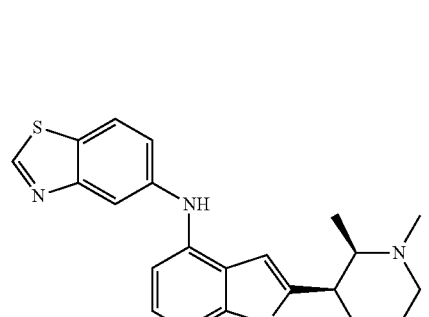
I-4-ii
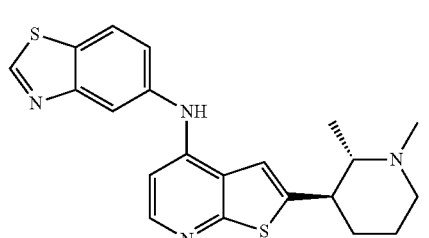
I-4-iii
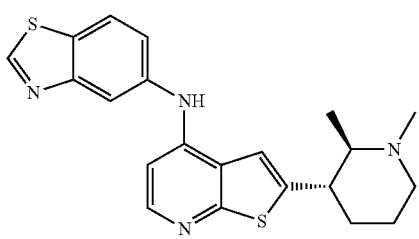
I-4-iv
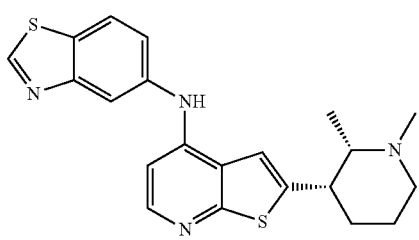
I-5
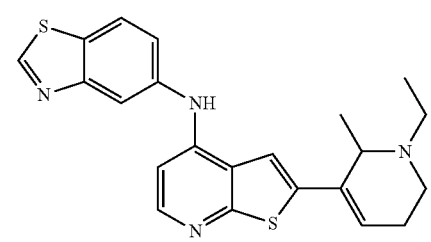
I-5-i
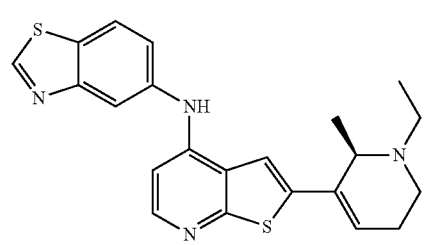
I-5-ii
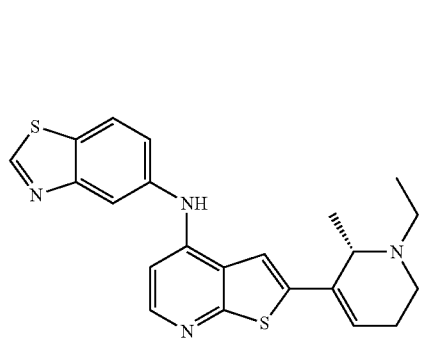
I-6
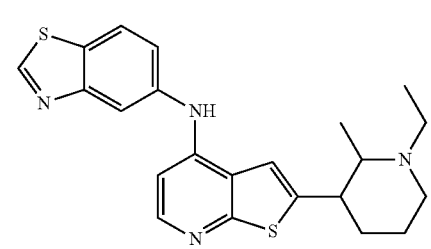

-continued
I-6-i
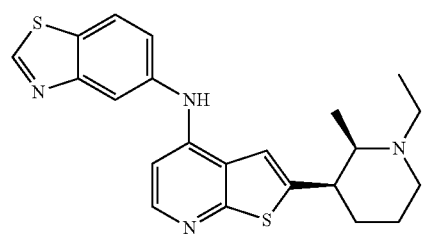
I-6-ii
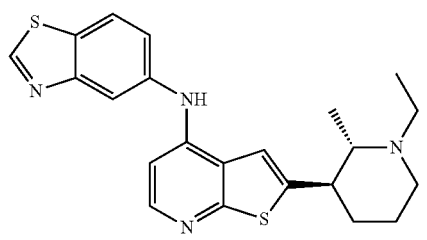
I-6-iii
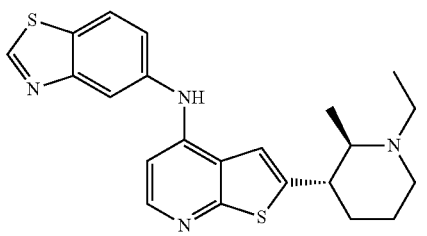
I-6-iv
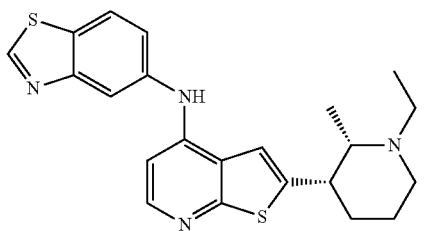
I-7
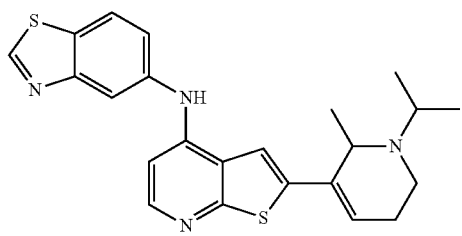
I-7-i
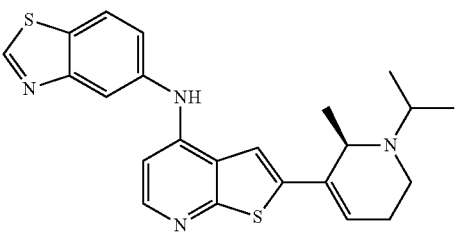
-continued
I-7-ii
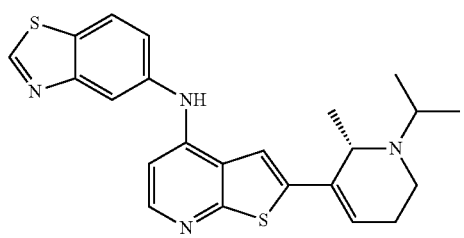
I-8
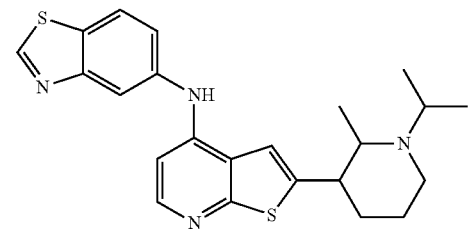
I-8-i
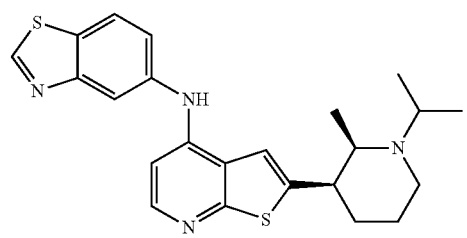
I-8-ii
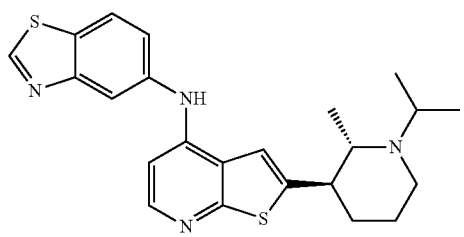
I-8-iii
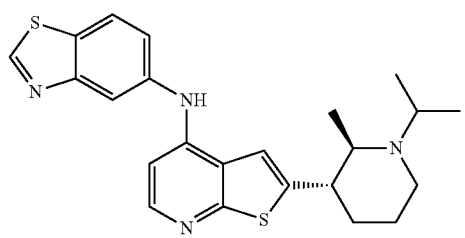
I-8-iv
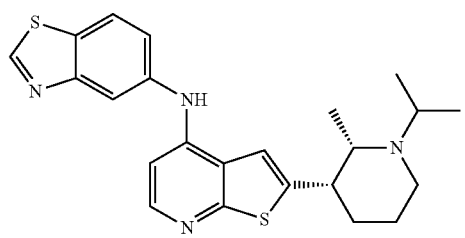

I-9
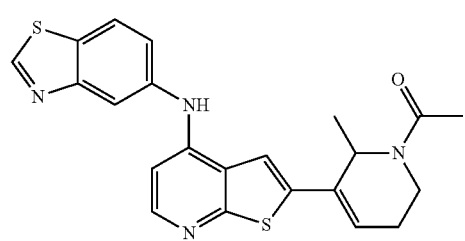
I-9-i
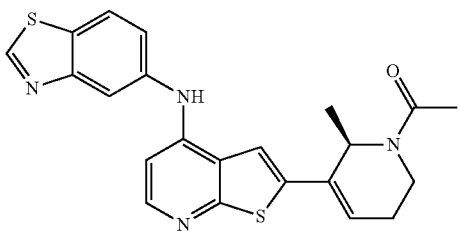
I-9-ii
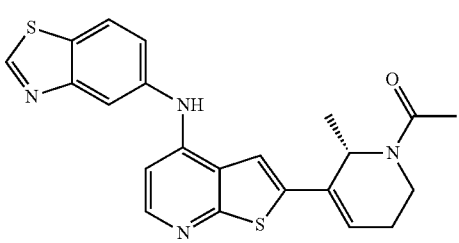
I-10
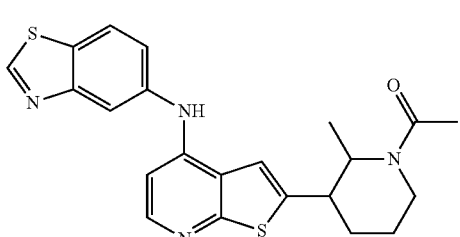
I-10-i
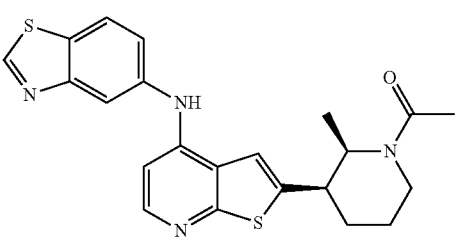
I-10-ii
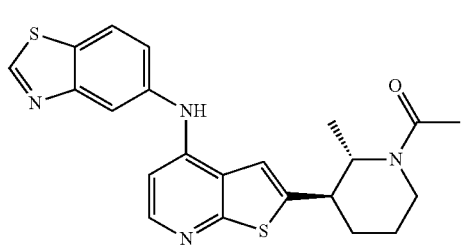
I-10-iii
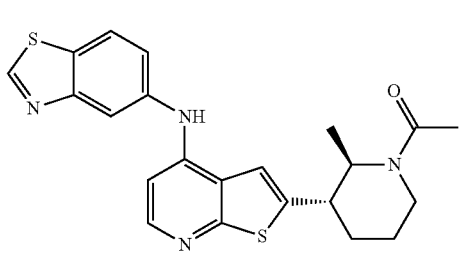
I-10-iv
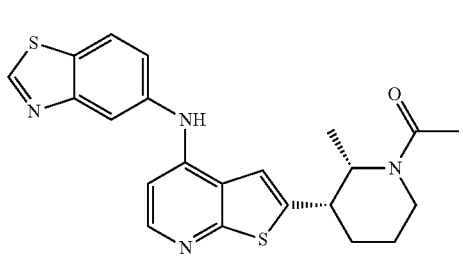
I-11
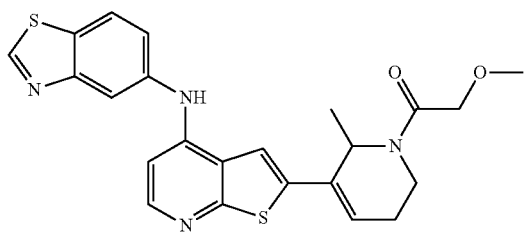
I-11-i
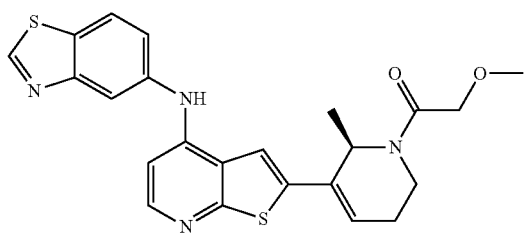
I-11-ii
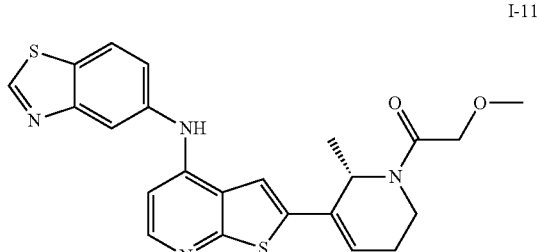
I-12
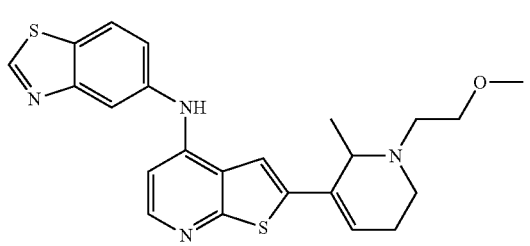

I-12-i
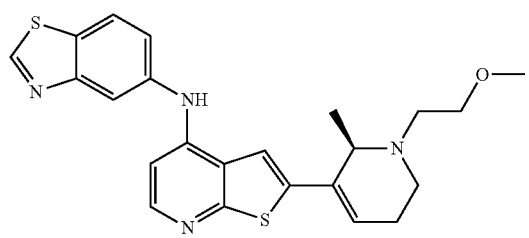
I-12-ii
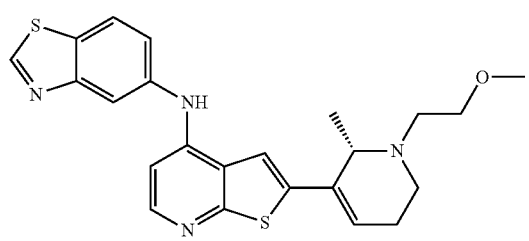
I-13
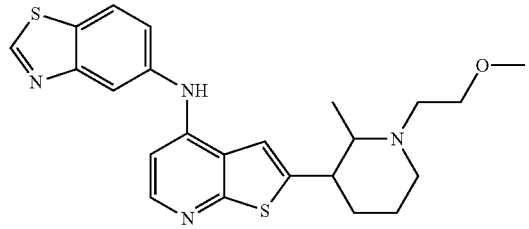
I-13-i
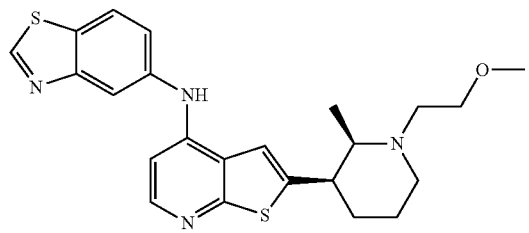
I-13-ii
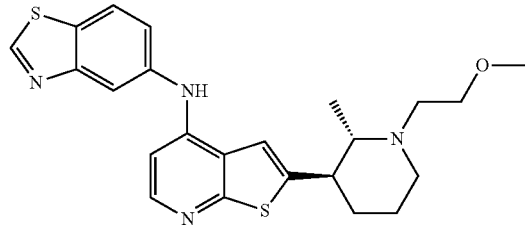
I-13-iii
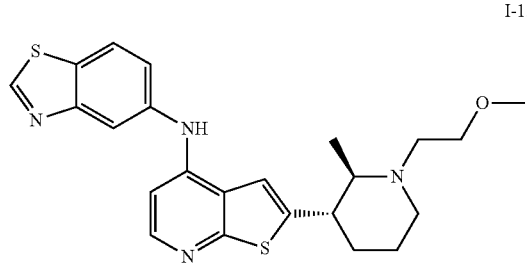
I-13-iv
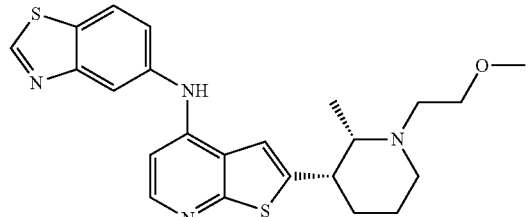
I-14
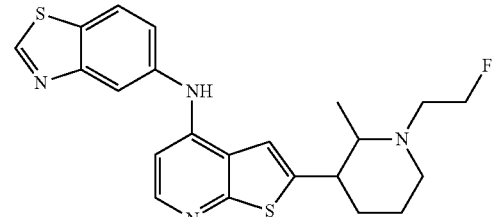
I-14-i
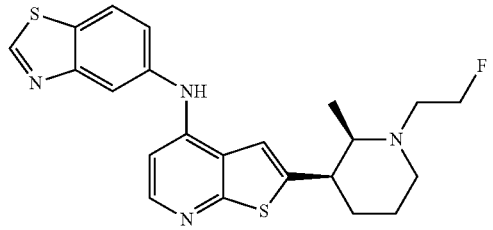
I-14-ii
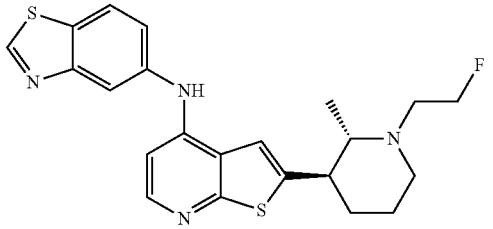
I-14-iii
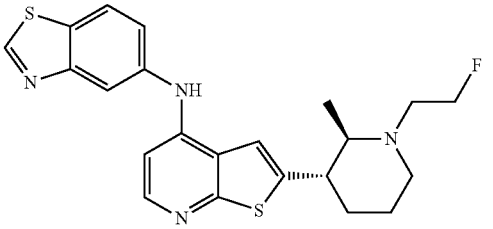
I-14-iv
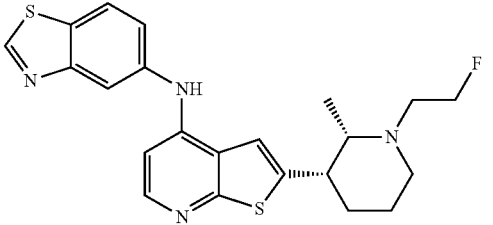

I-15
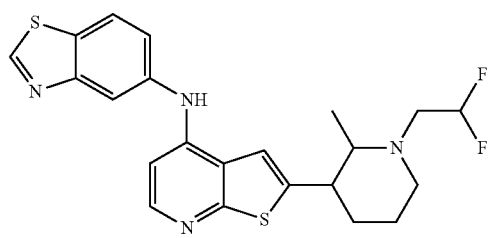
I-15-i
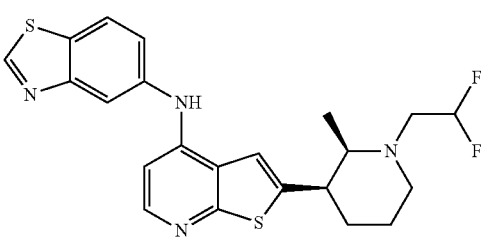
I-15-ii
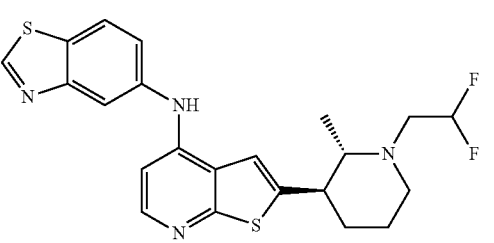
I-15-iii
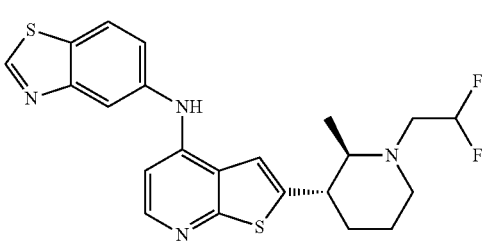
I-15-iv
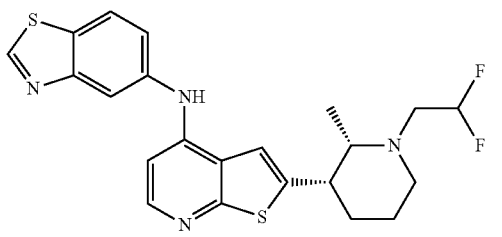
I-16
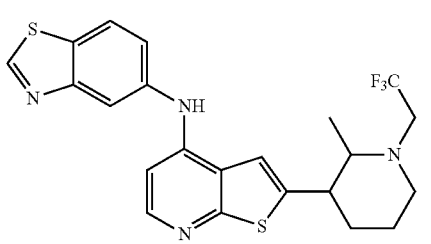
I-16-i
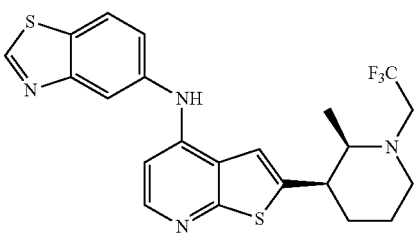
I-16-ii
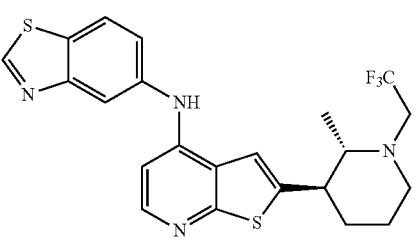
I-16-iii
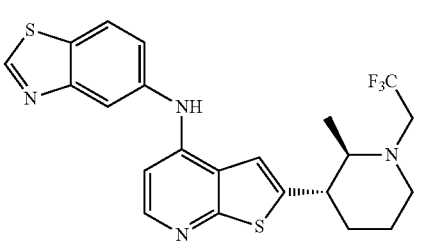
I-16-iv
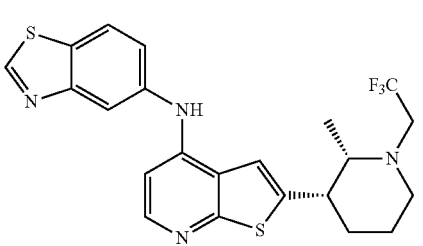
I-17
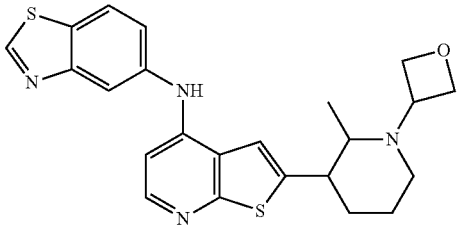
I-17-i
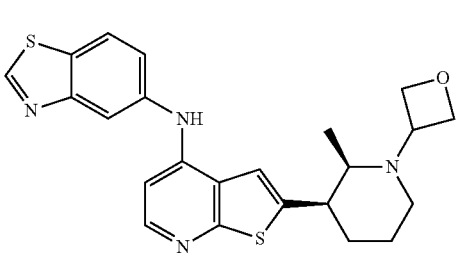

I-17-ii
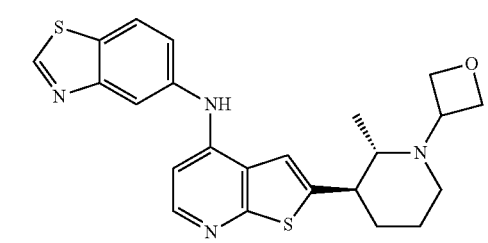
I-17-iii
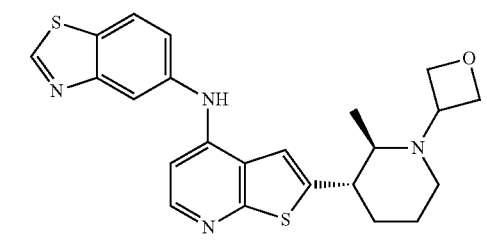
I-17-iv
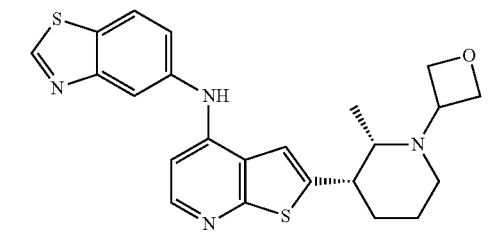
I-18
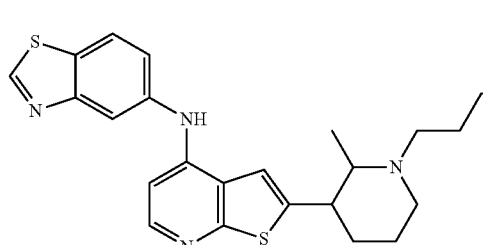
I-18-i
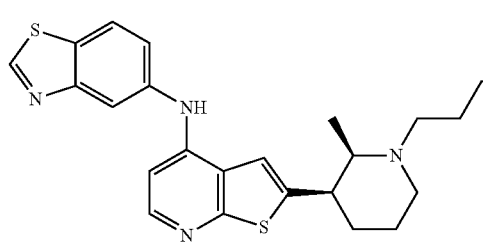
I-18-ii
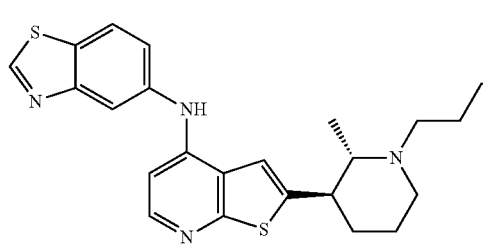
I-18-iii
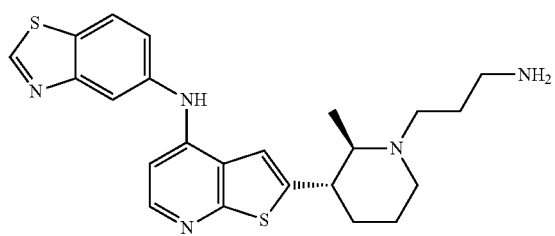
I-18-iv
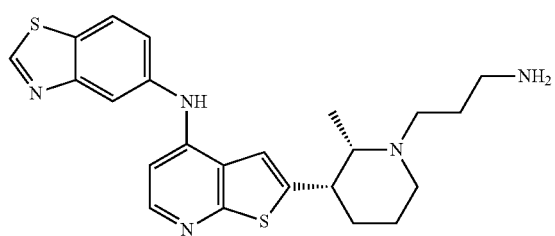
I-19
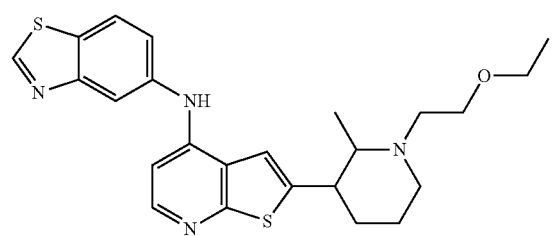
I-19-i
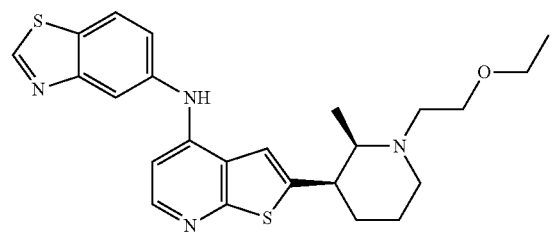
I-19-ii
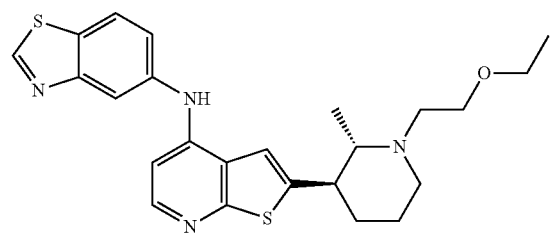
I-19-iii
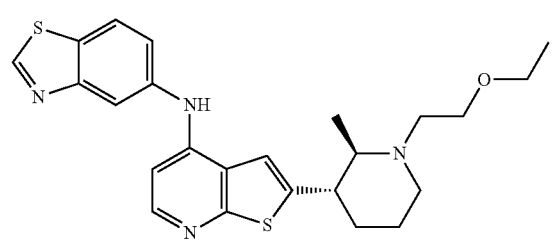

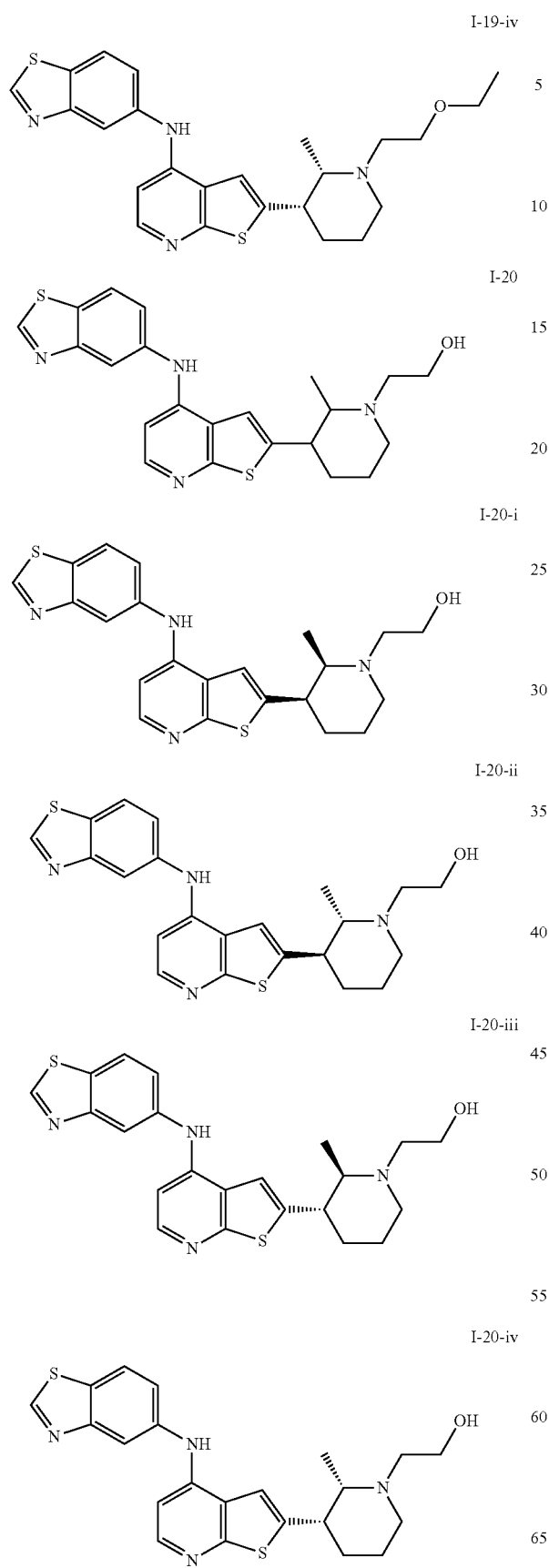
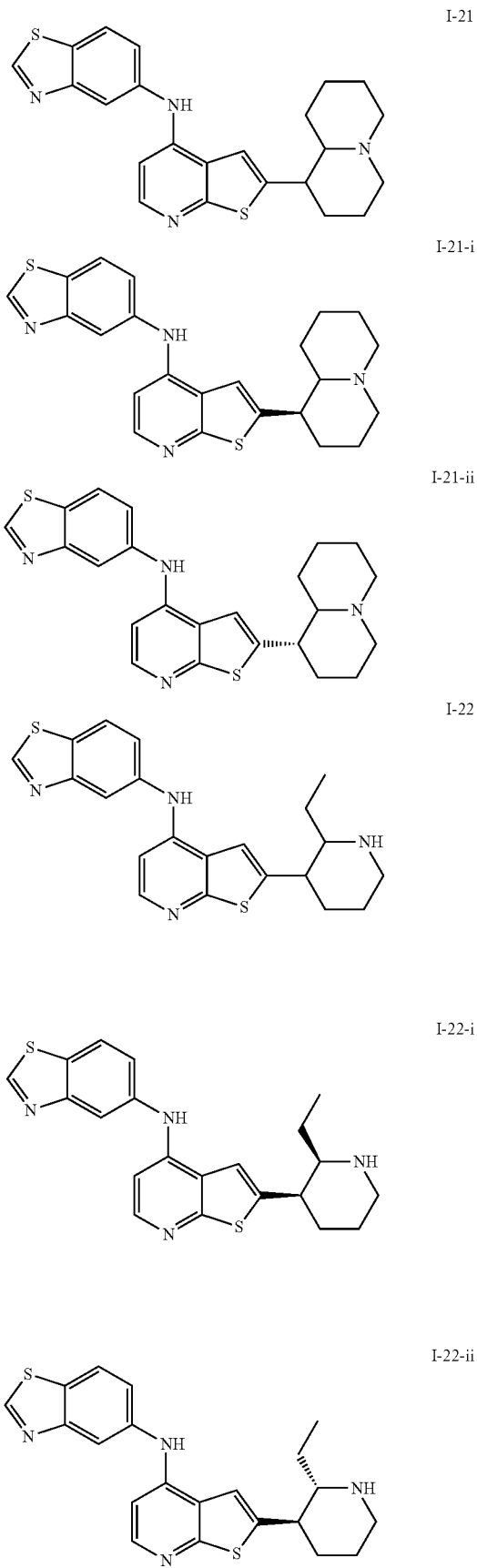

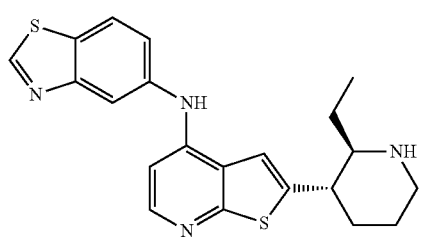
I-22-iii
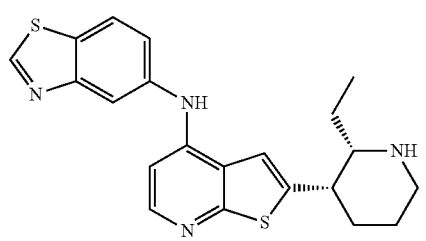
I-22-iv
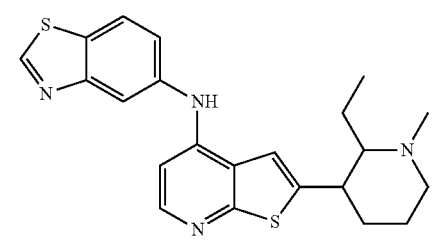
I-23
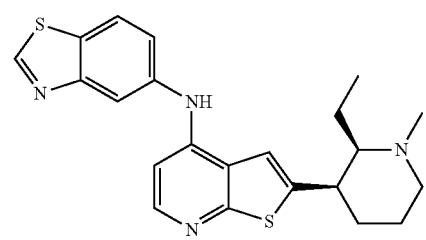
I-23-i
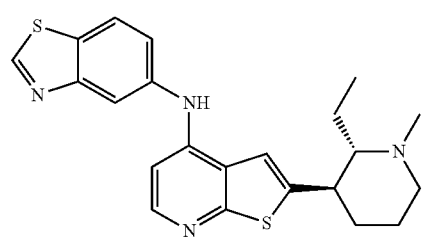
I-23-ii
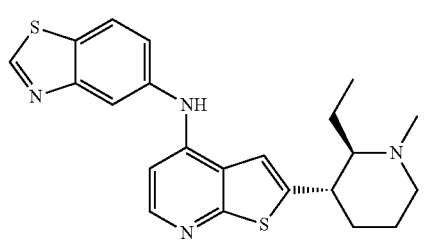
I-23-iii
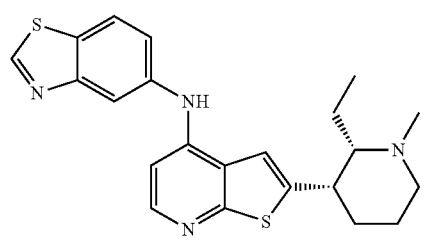
I-23-iv
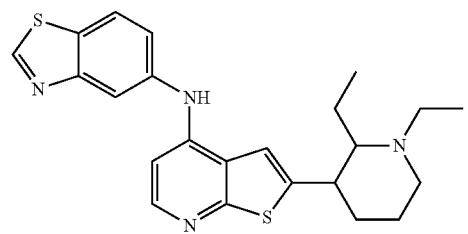
I-24
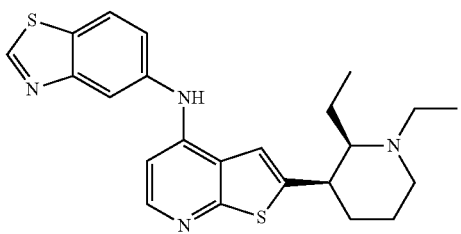
I-24-i
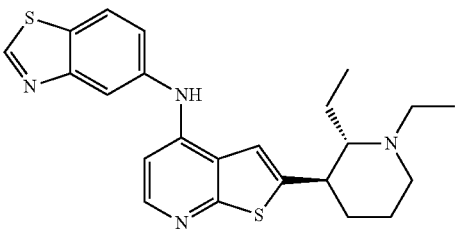
I-24-ii
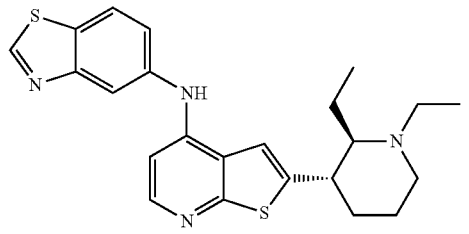
I-24-iii
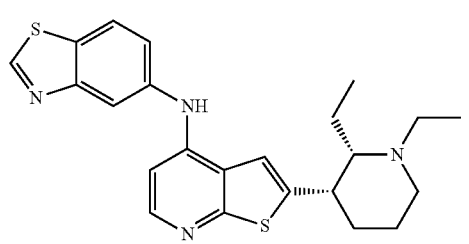
I-24-iv

-continued

I-25, I-25-i, I-25-ii, I-26, I-26-i, I-26-ii, I-26-iii, I-26-iv, I-27, I-27-i, I-27-ii, I-28

I-28-i
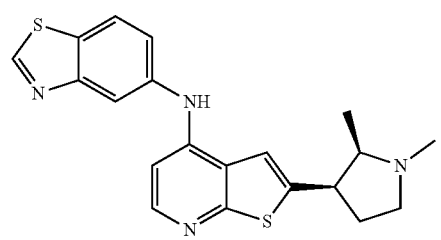
I-28-ii
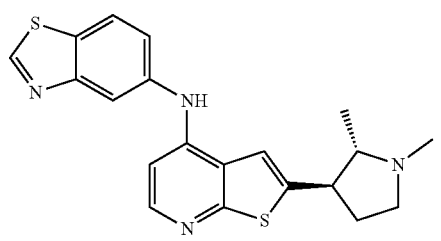
I-28-iii
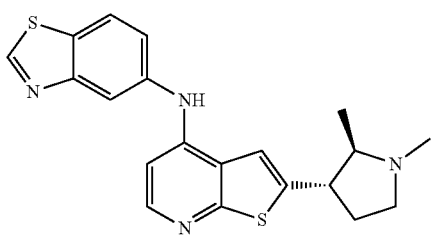
I-28-iv
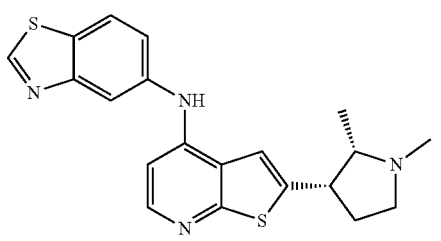
I-29
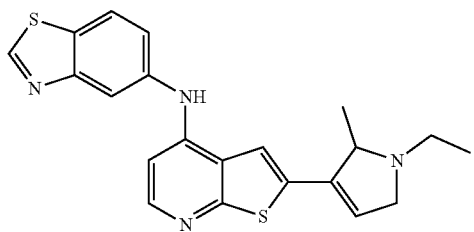
I-29-i
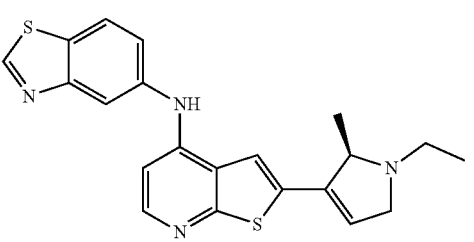
I-29-ii
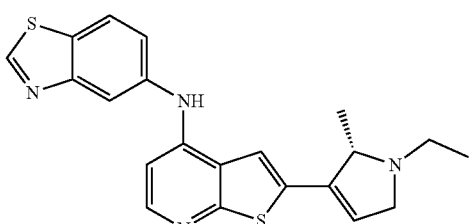
I-30
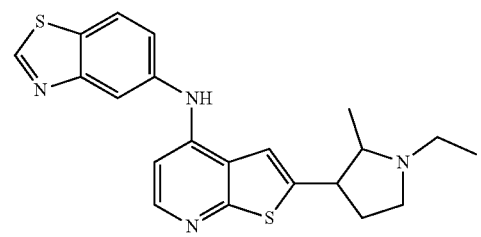
I-30-i
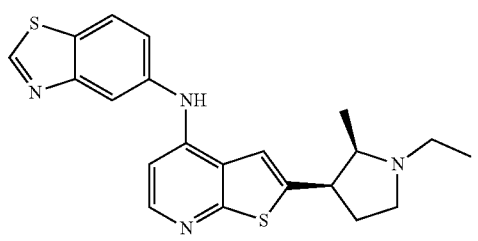
I-30-ii
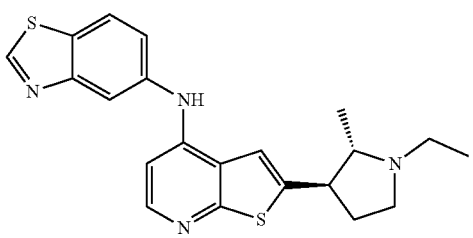
I-30-iii
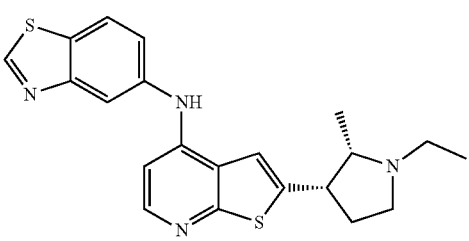
I-30-iv I-31
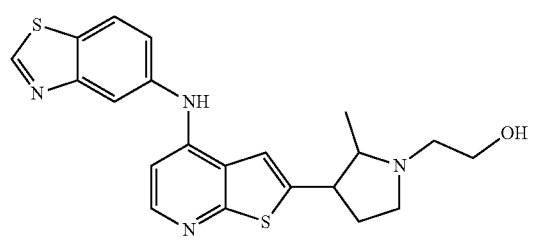
I-31-i
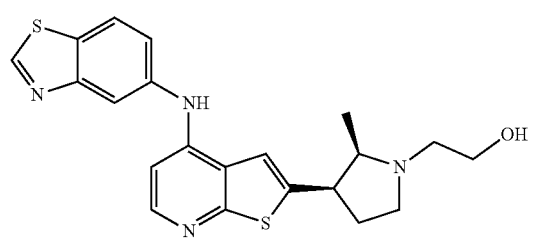
I-31-ii
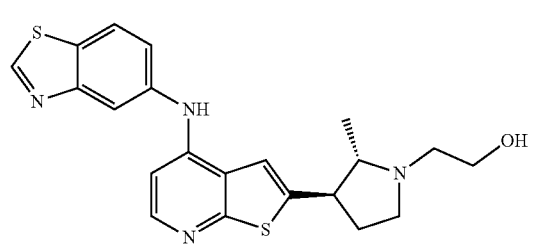
I-31-iii
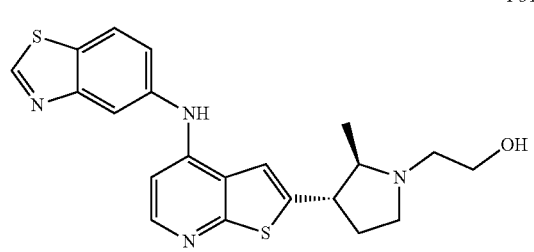
I-31-iv
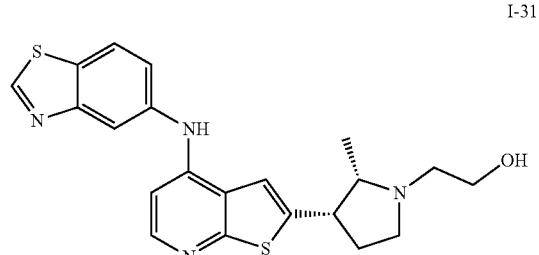
I-32
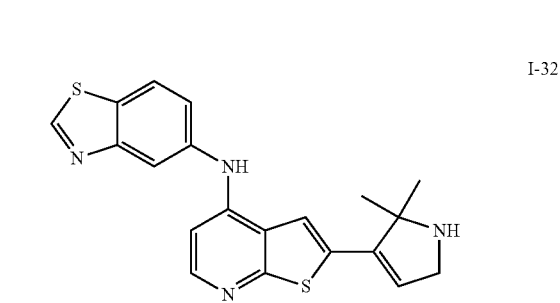
I-33
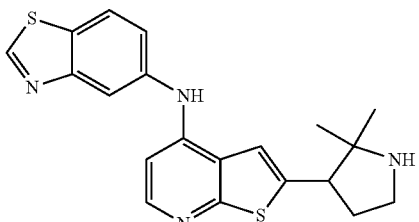
I-33-i
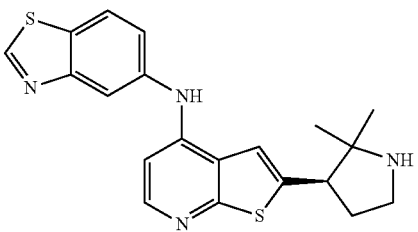
I-33-ii
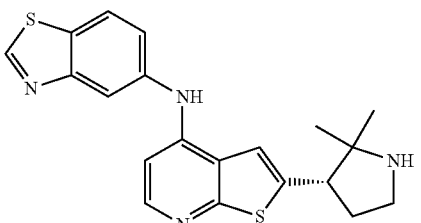
I-34
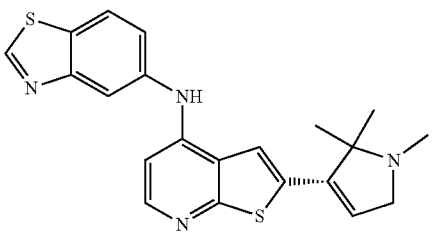
I-35
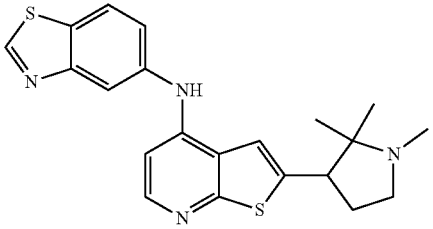
I-35-i
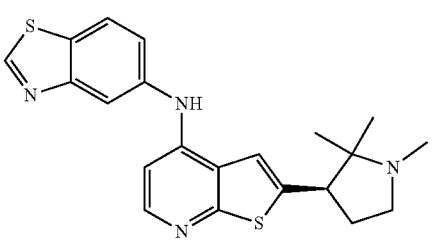

I-35-ii
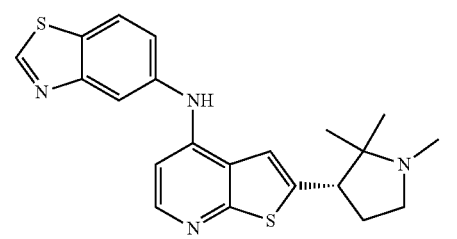
I-36
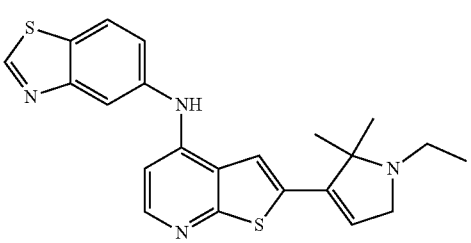
I-37
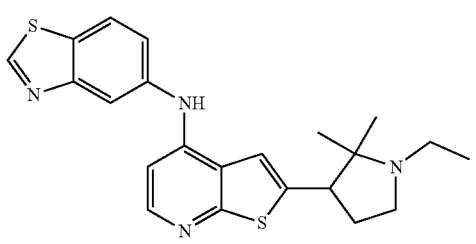
I-37-i
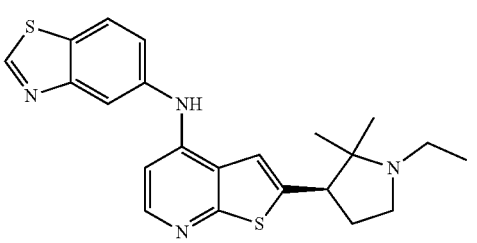
I-37-ii
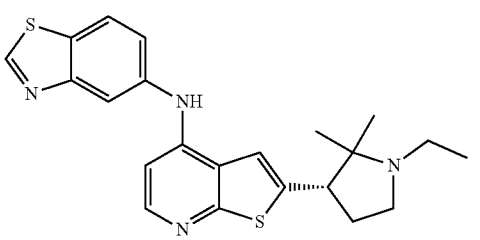
I-38
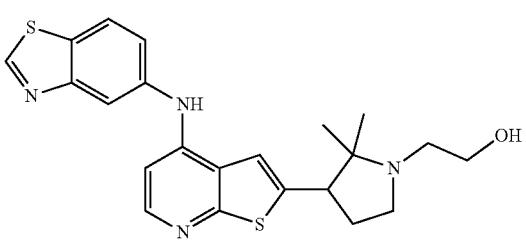
I-38-i
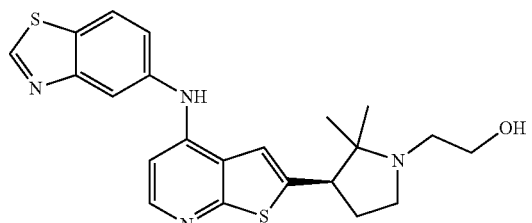
I-38-ii
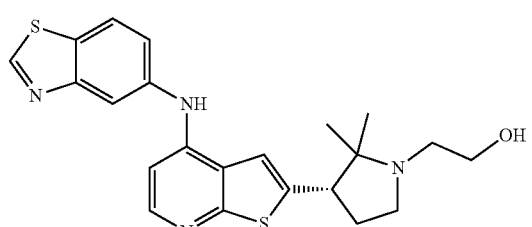
I-39
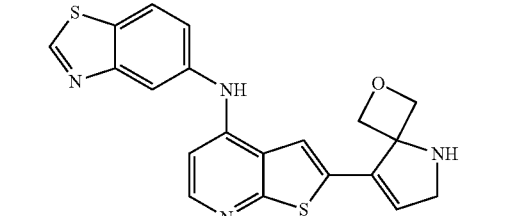
I-40
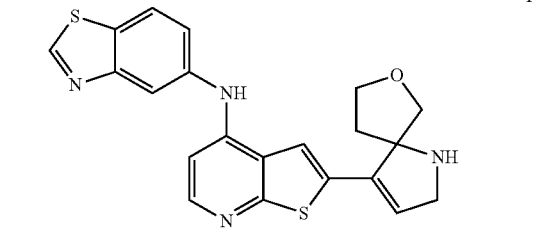
I-40-i
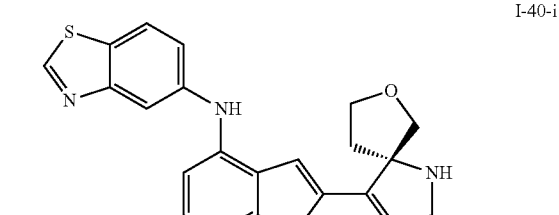
I-40-ii -continued
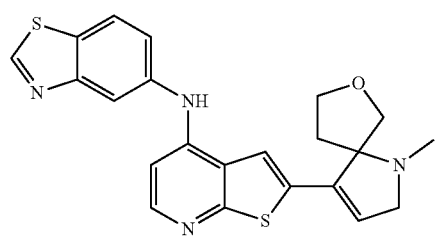
I-41
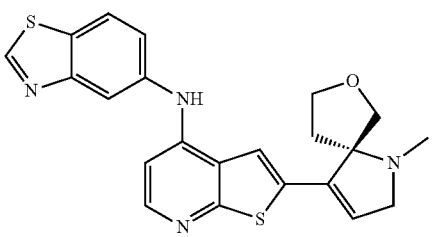
I-41-i
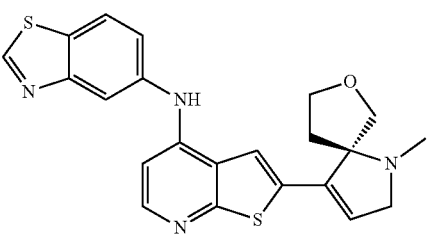
I-41-ii
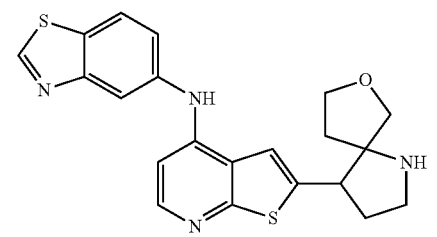
I-42
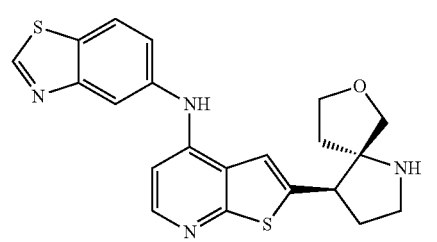
I-42-i
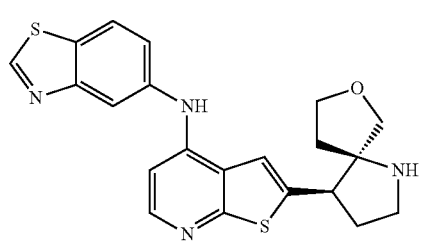
I-42-ii
-continued
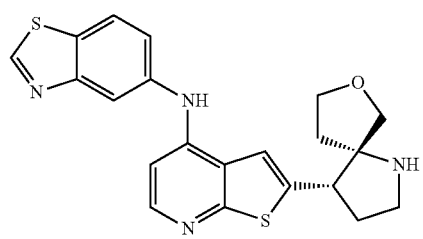
I-42-iii
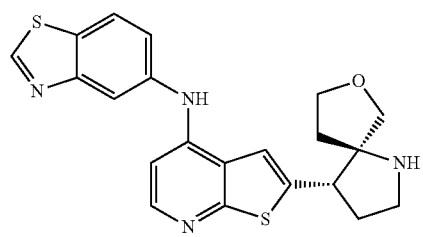
I-42-iv
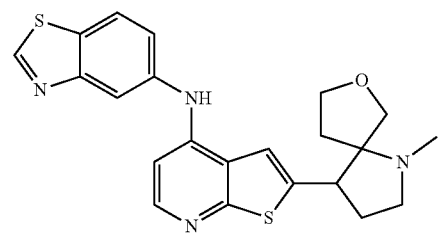
I-43
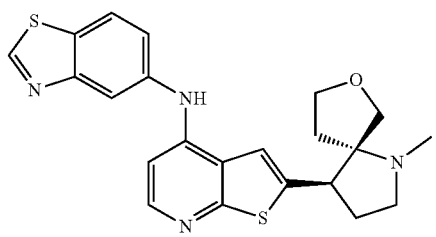
I-43-i
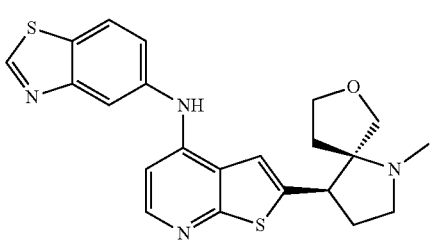
I-43-ii
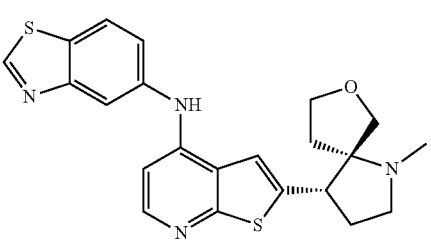
I-43-iii -continued
I-43-iv
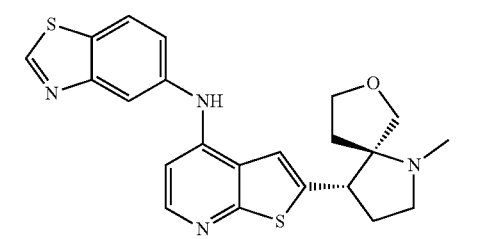
I-44
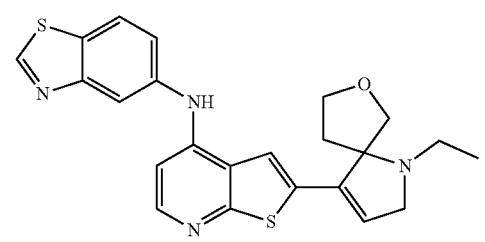
I-44-i
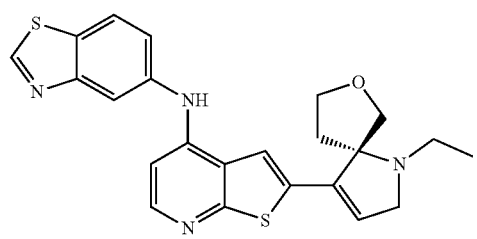
I-44-ii
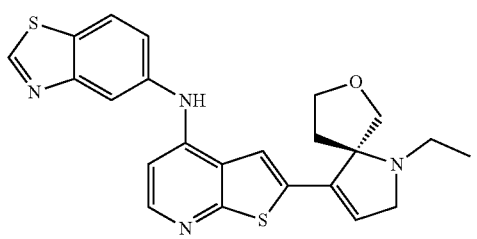
I-45
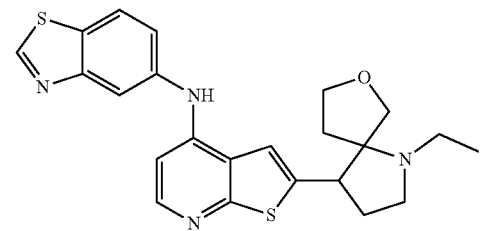
I-45-i
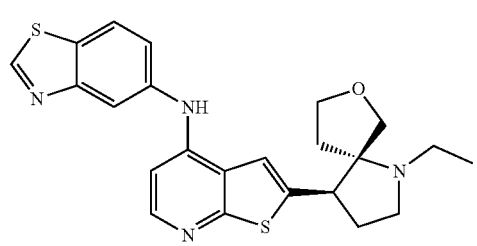
-continued
I-45-ii
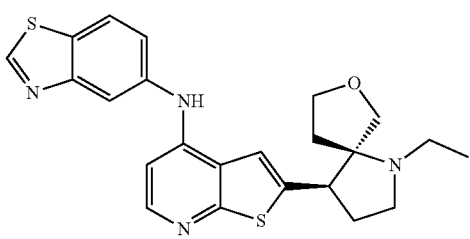
I-45-iii
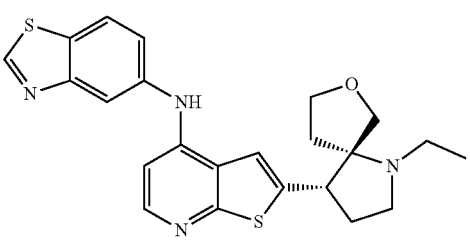
I-45-iv
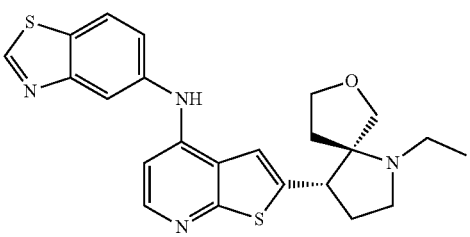
I-46
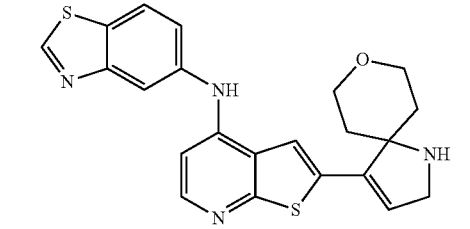
I-47
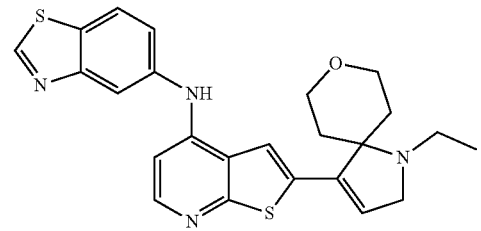
I-48
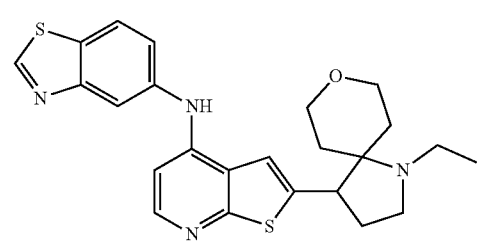

I-48-i
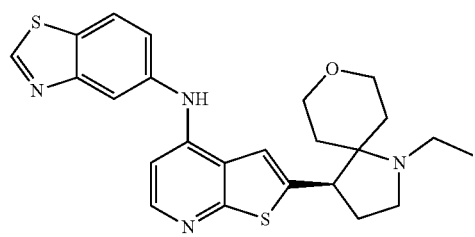
I-48-ii
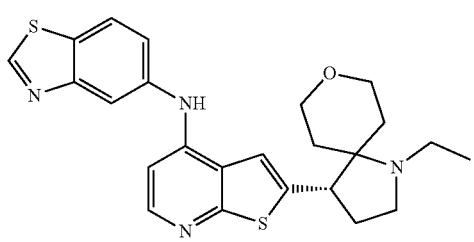
I-49
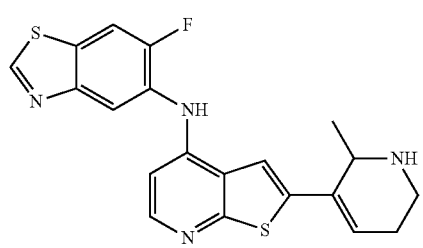
I-49-i
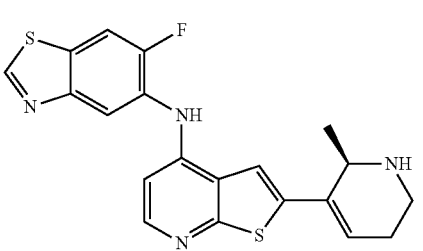
I-49-ii
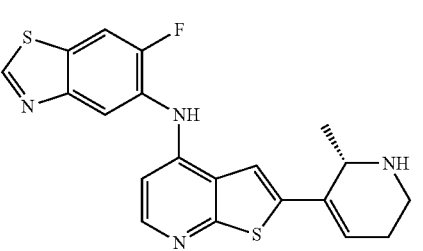
I-50
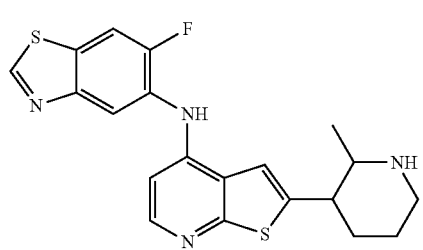
I-50-i
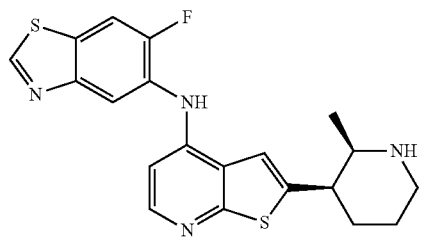
I-50-ii
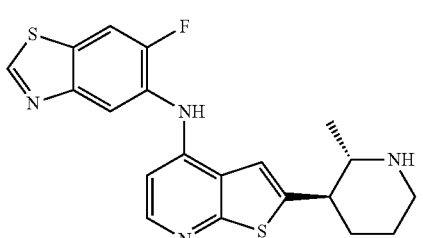
I-50-iii
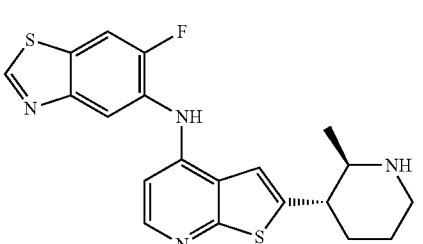
I-50-iv
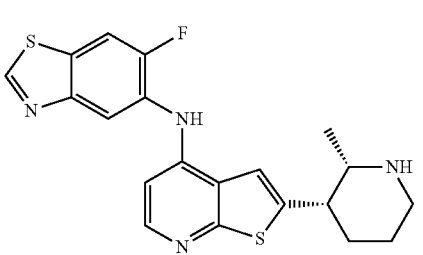
I-51
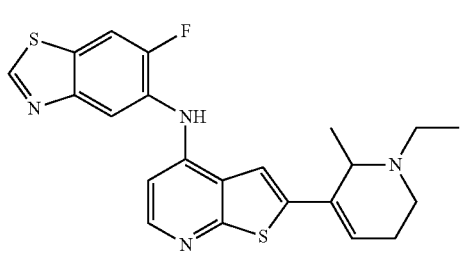
I-51-i
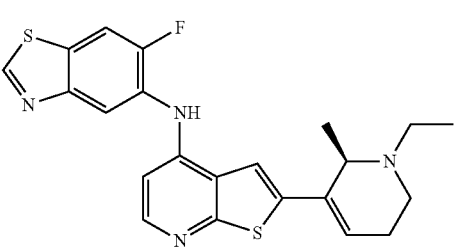

I-51-ii
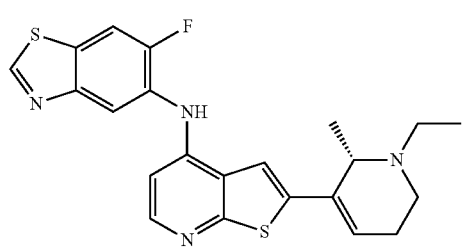
I-52
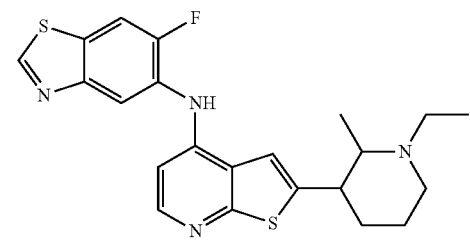
I-52-i
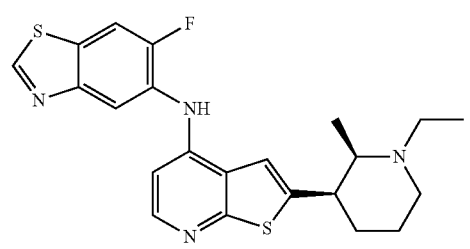
I-52-ii
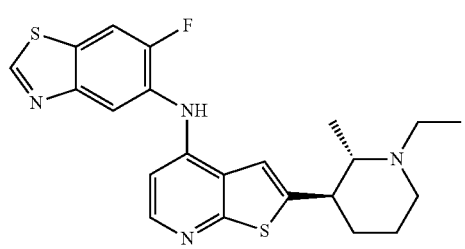
I-52-iii
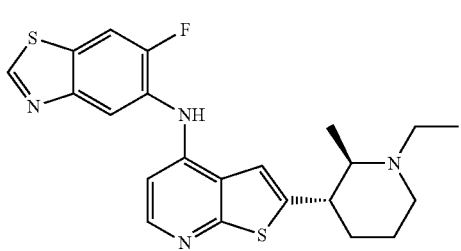
I-52-iv
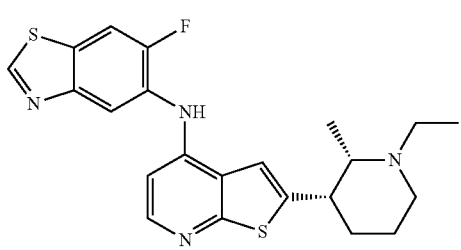
I-53
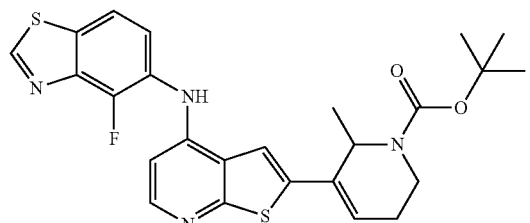
I-53-i
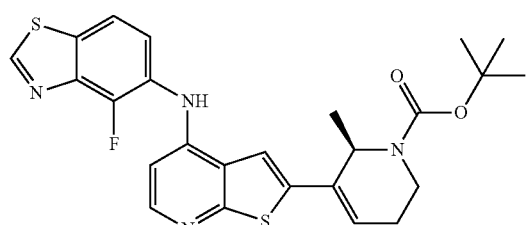
I-53-ii
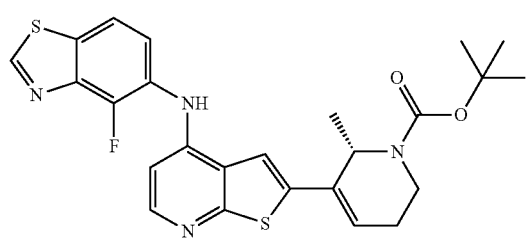
I-54
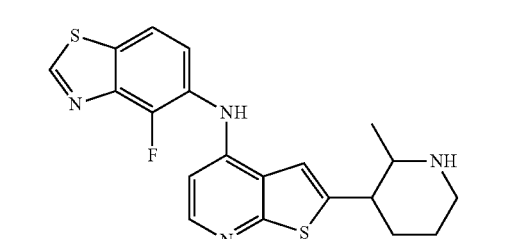
I-54-i
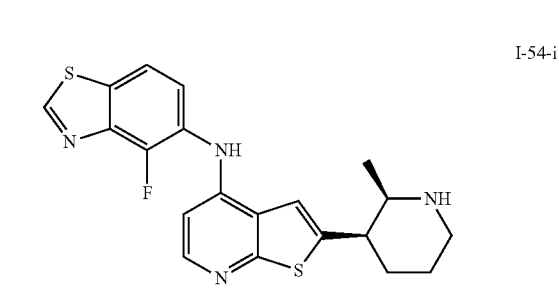
I-54-ii
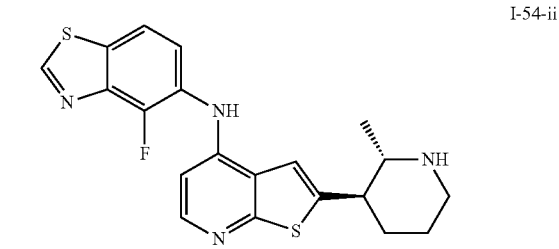

-continued
I-54-iii
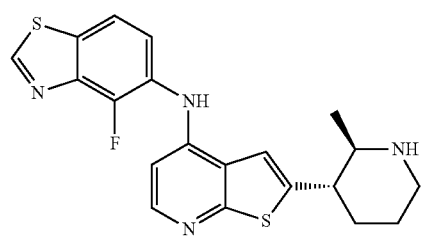
I-54-iv
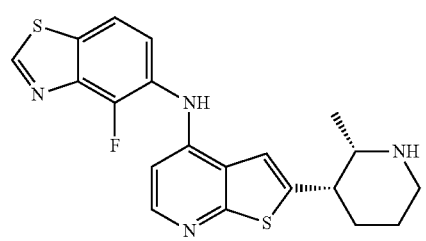
I-55
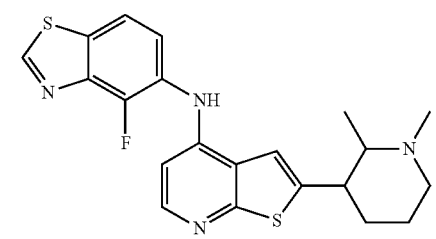
I-55-i
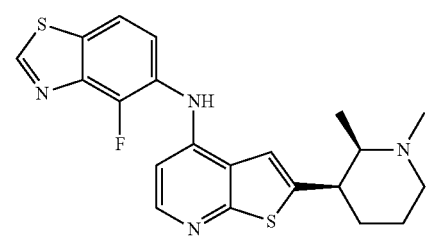
I-55-ii
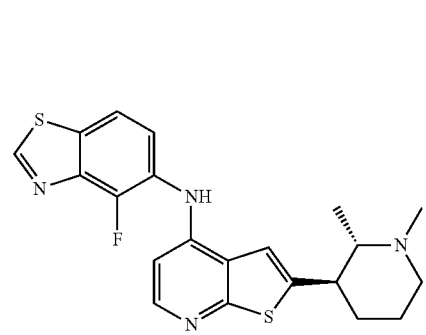
I-55-iii
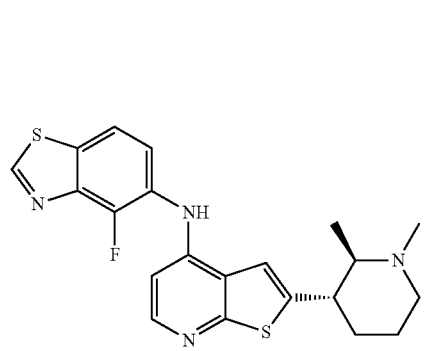
-continued
I-55-iv
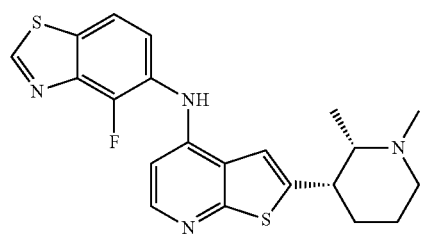
I-56
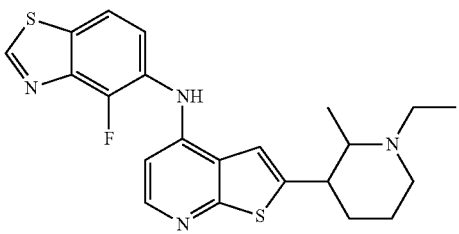
I-56-i
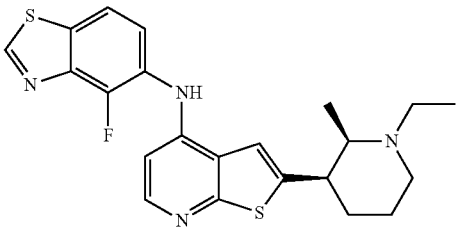
I-56-ii
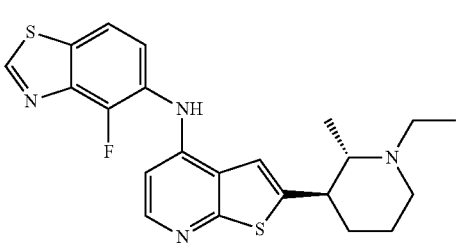
I-56-iii
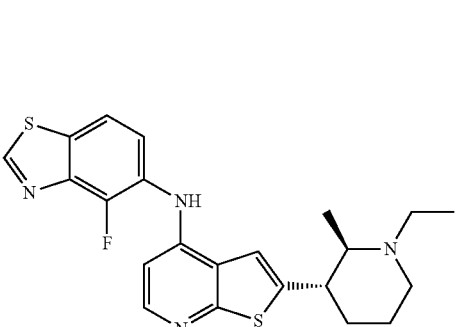
I-56-iv
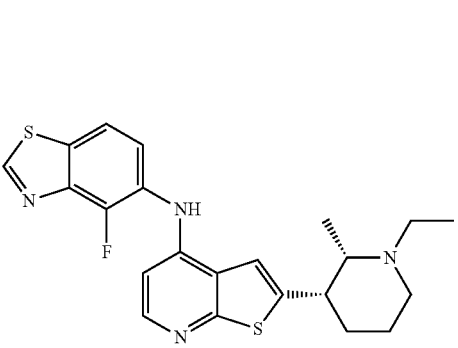

I-57
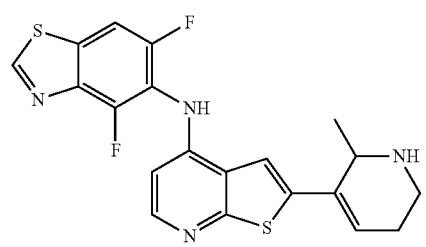
I-57-i
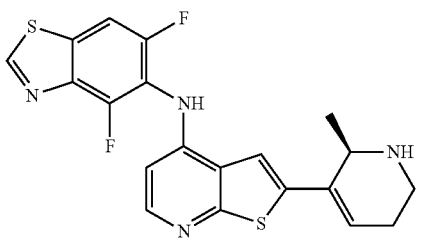
I-57-ii
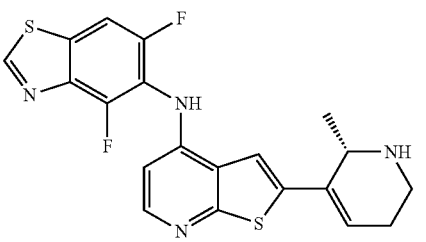
I-58
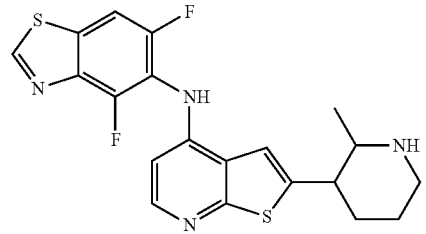
I-58-i
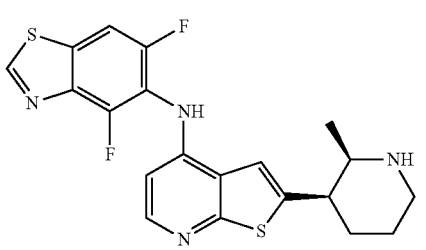
I-58-ii
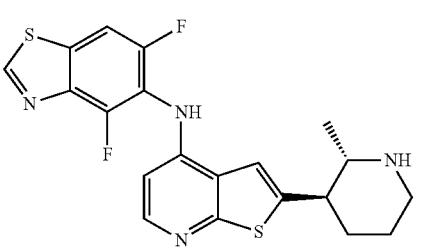
I-58-iii
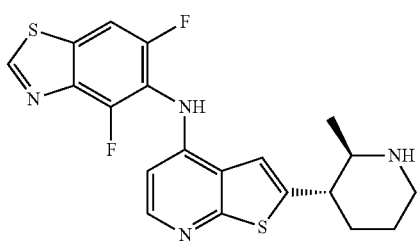
I-58-iv
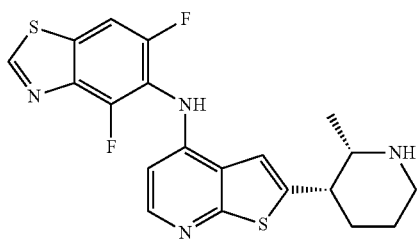
I-59
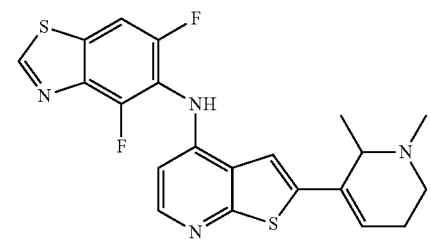
I-59-i
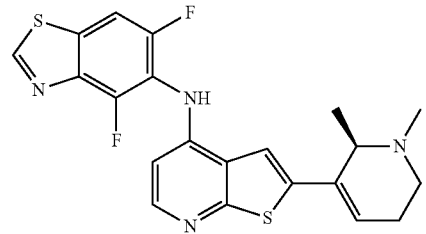
I-59-ii
I-60
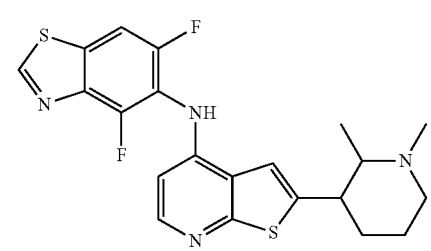

-continued
I-60-i
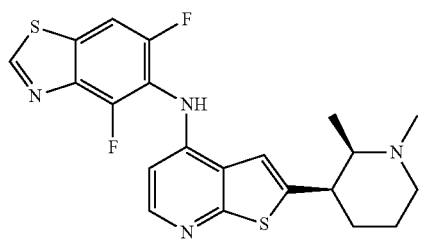
I-60-ii
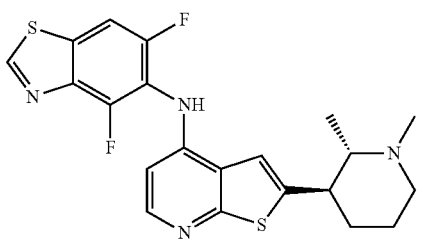
I-60-iii
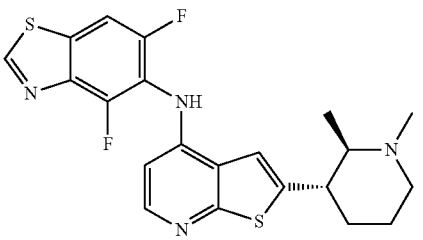
I-60-iv
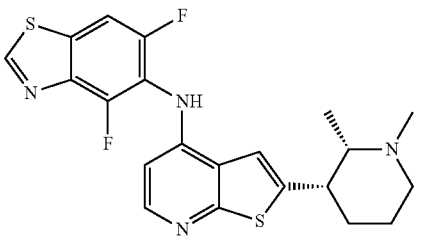
I-61
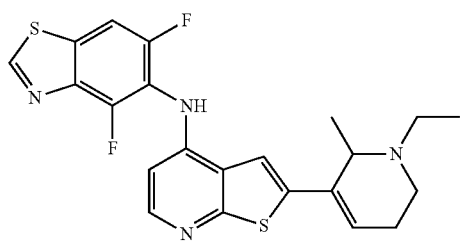
I-61-i
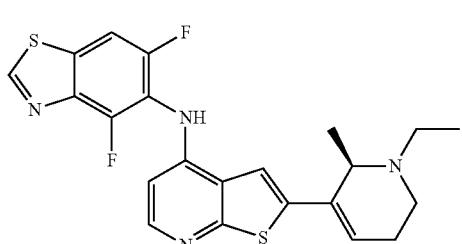
I-61-ii
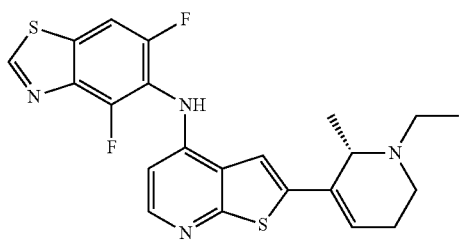
I-62
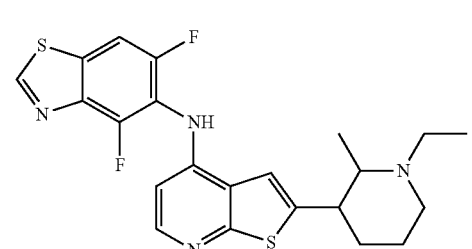
I-62-i
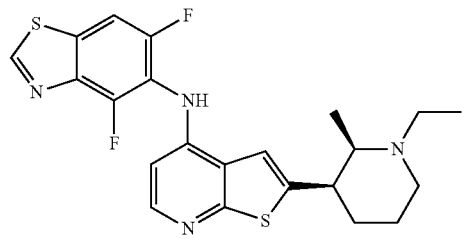
I-62-ii
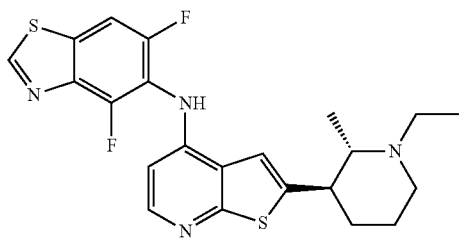
I-62-iii
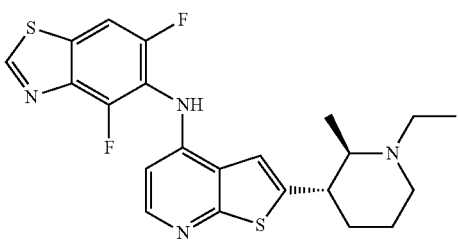
I-62-iv
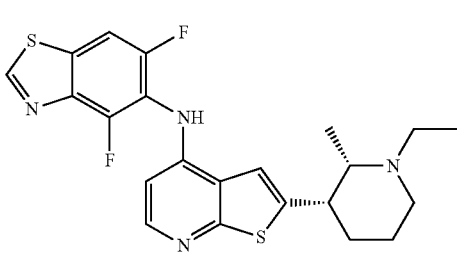

I-63
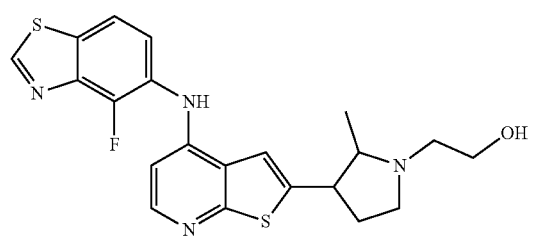
I-63-i
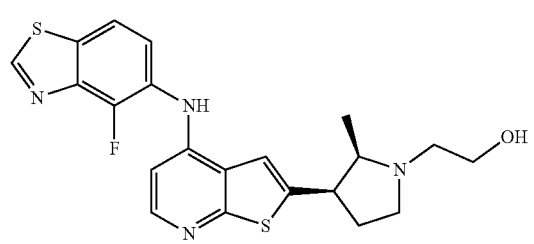
I-63-ii
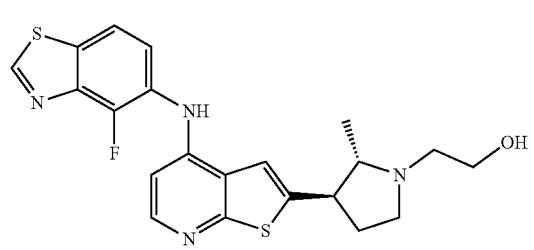
I-63-iii
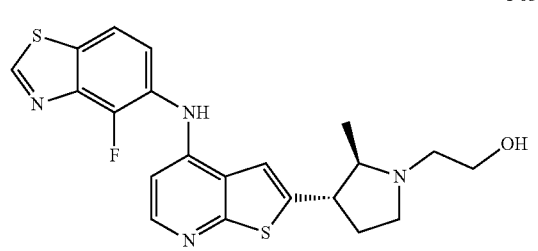
I-63-iv
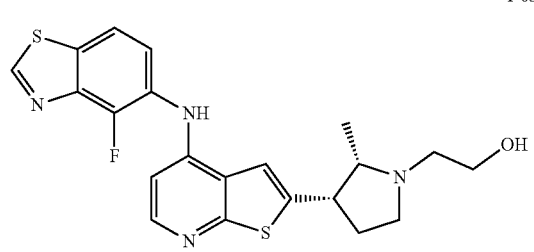
I-64
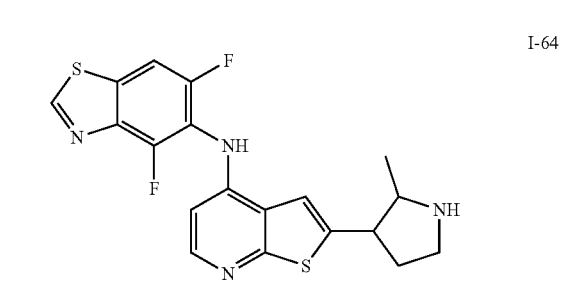
I-64-i
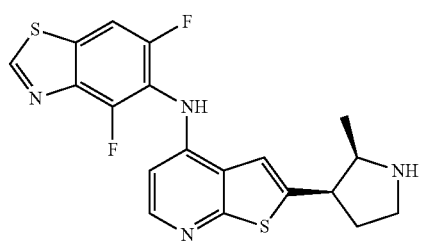
I-64-ii
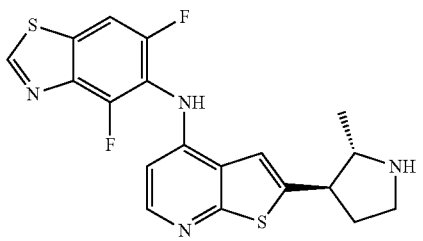
I-64-iii
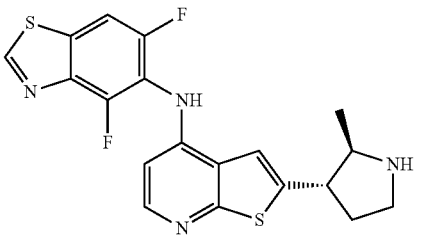
I-64-iv
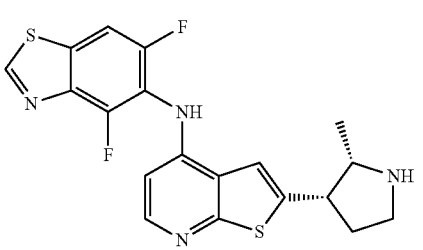
I-65
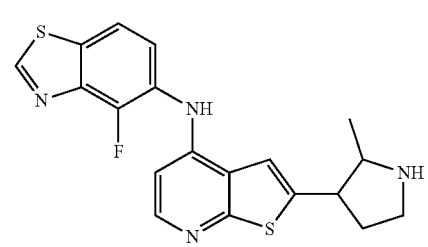
I-65-i
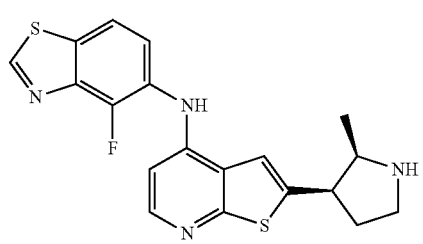

I-65-ii
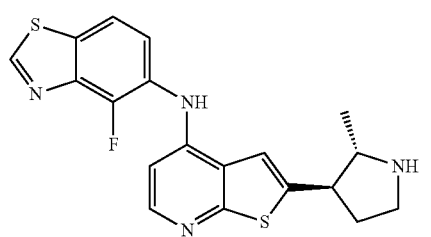
I-65-iii
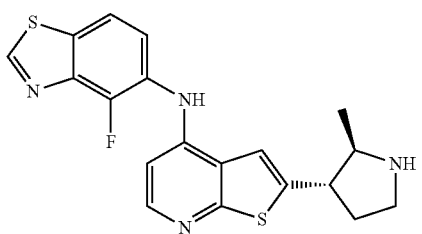
I-65-iv
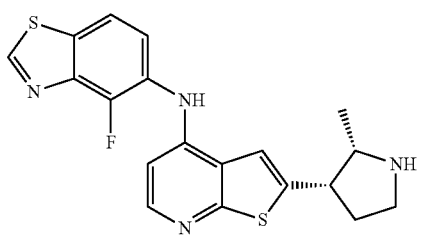
I-66
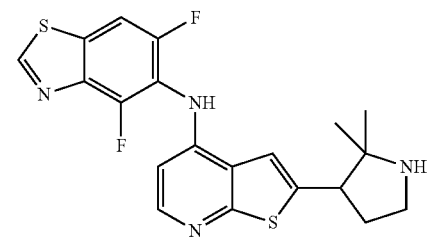
I-66-i
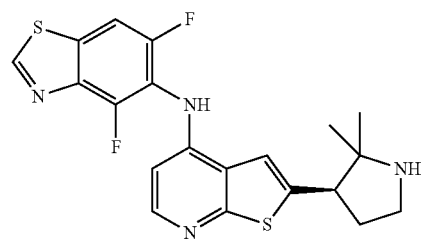
I-66-ii
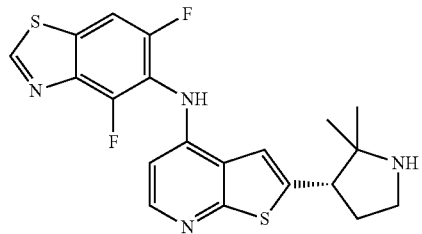
I-67
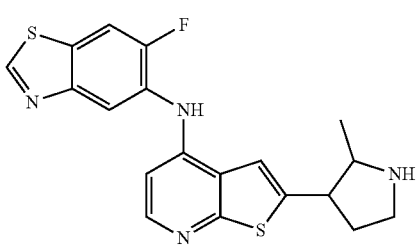
I-67-i
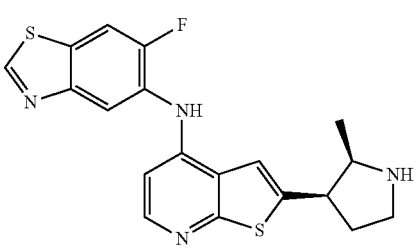
I-67-ii
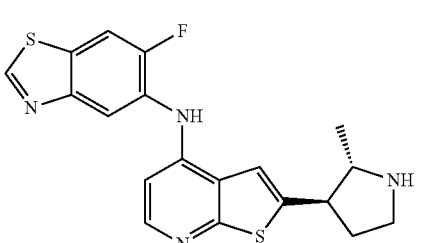
I-67-iii
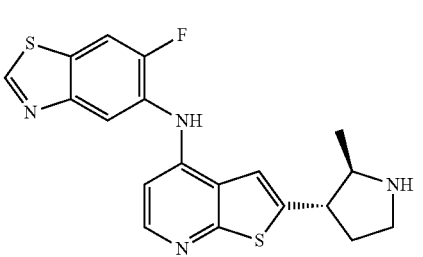
I-67-iv
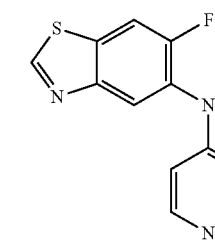
I-68
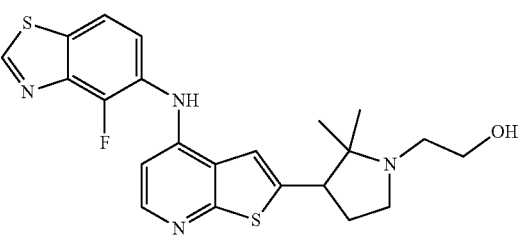

I-68-i
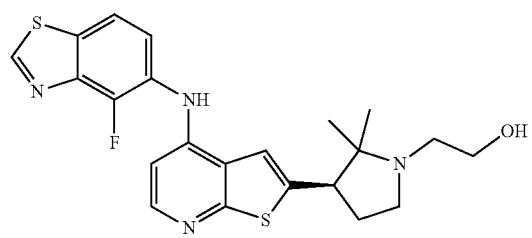
I-68-ii
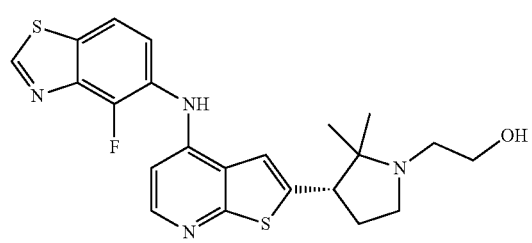
I-69
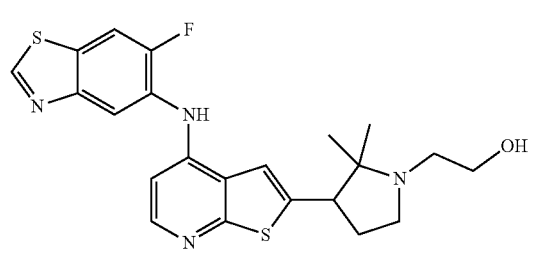
I-69-i
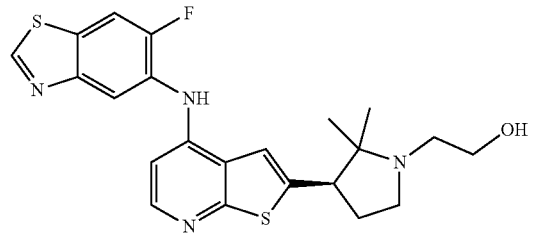
I-69-ii
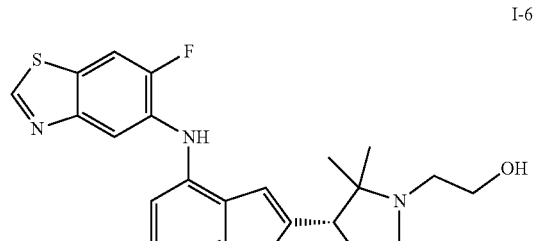
I-70
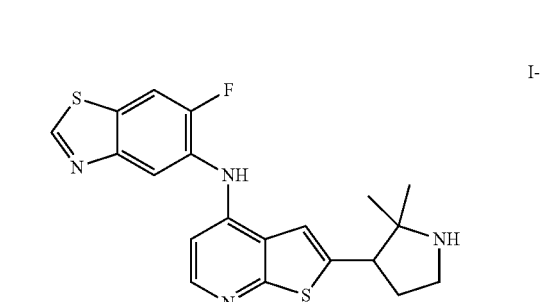
I-70-i
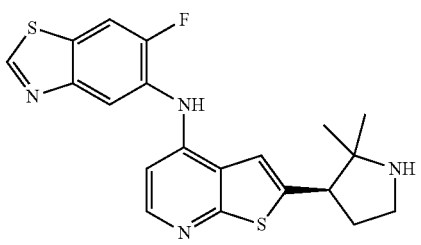
I-70-ii
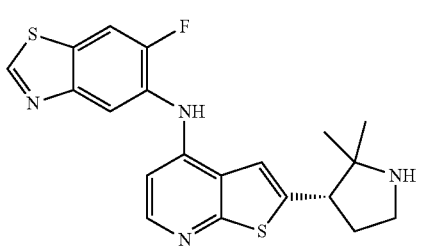
I-71
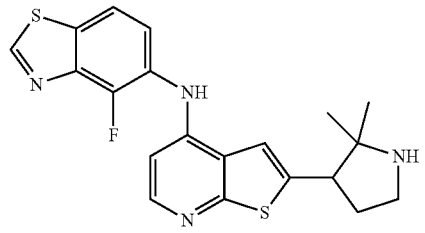
I-71-i
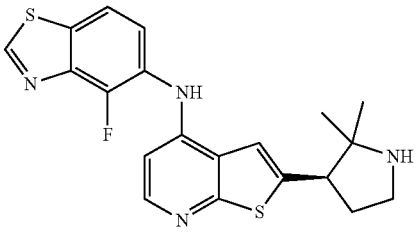
I-71-ii
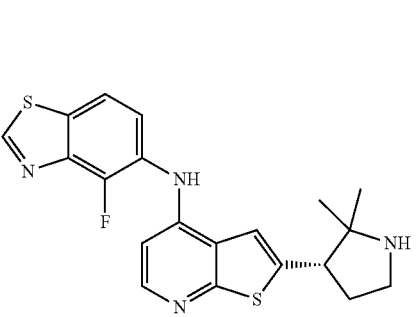
I-72
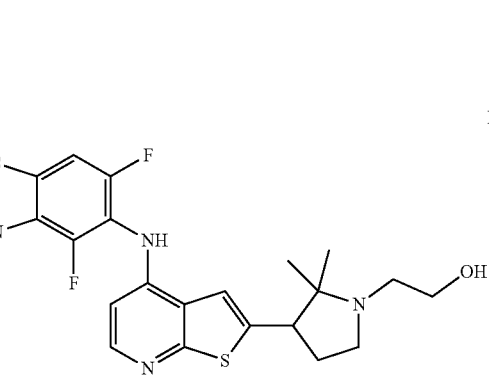

I-72-i
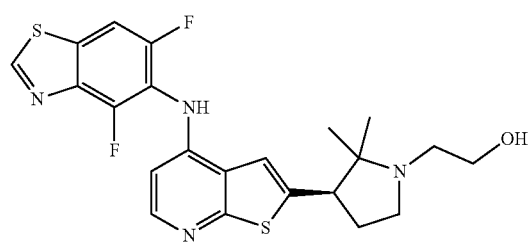
I-72-ii
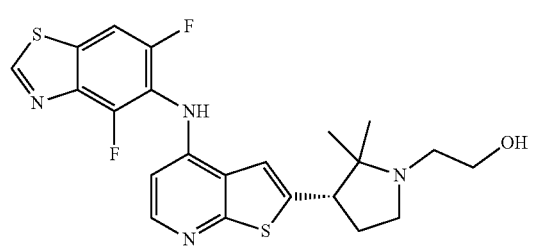
I-73
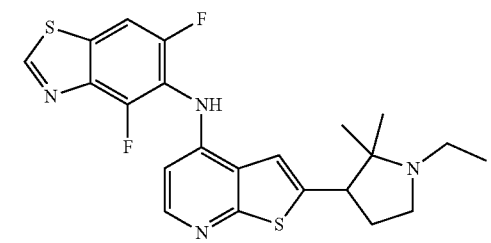
I-73-i
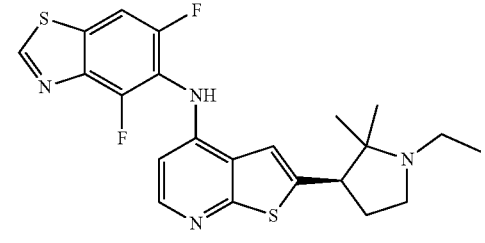
I-73-ii
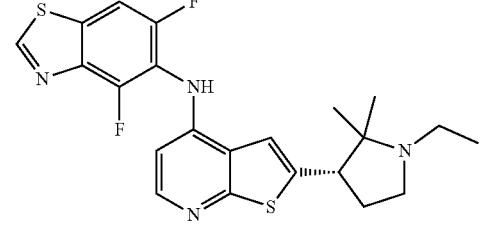
I-74
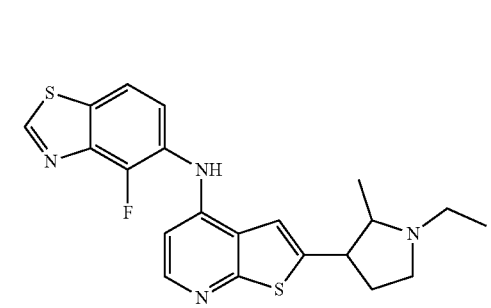
I-74-i
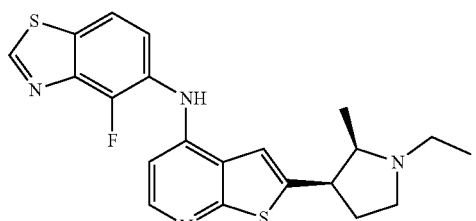
I-74-ii
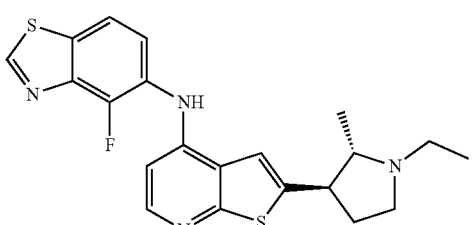
I-74-iii
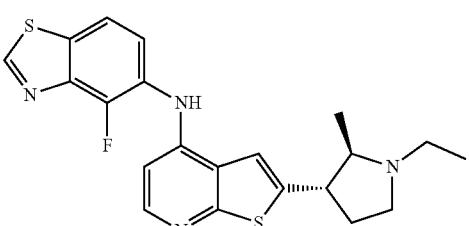
I-74-iv
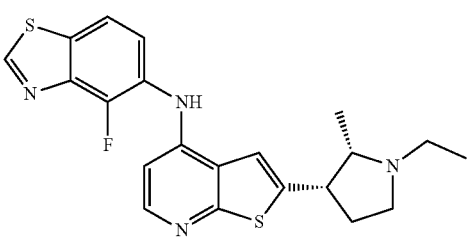
I-75
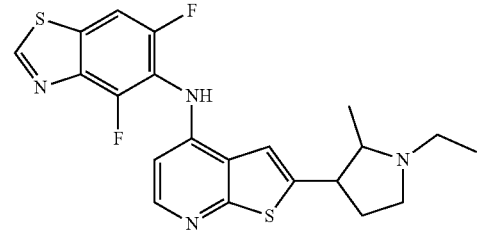
I-75-i
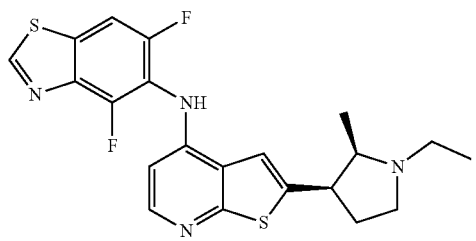

I-75-ii
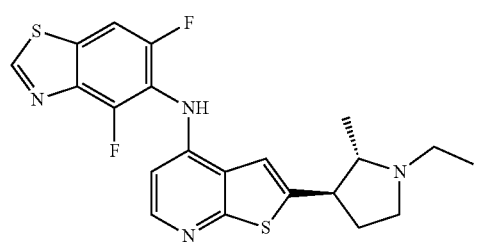
I-75-iii
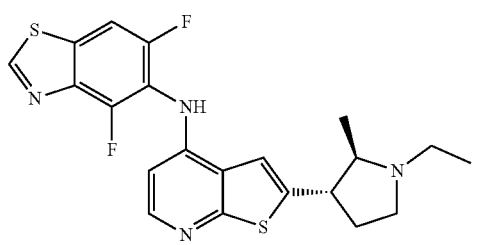
I-75-iv
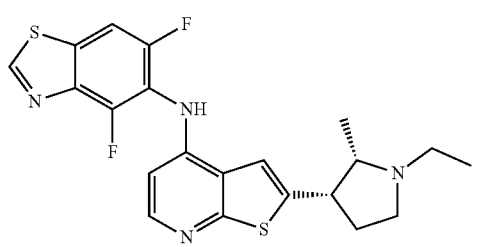
I-76
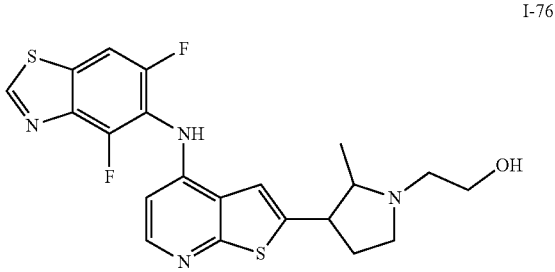
I-76-i
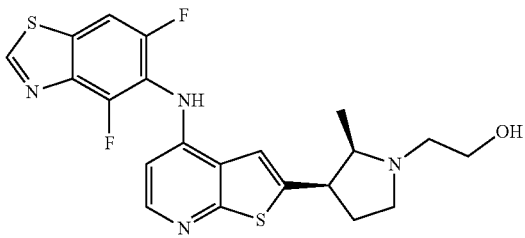
I-76-ii
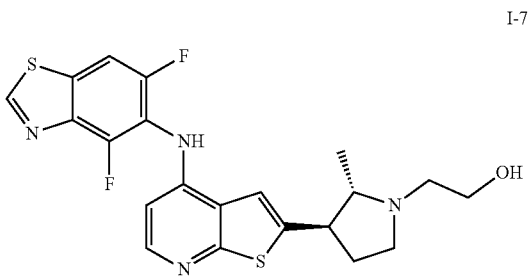
I-76-iii
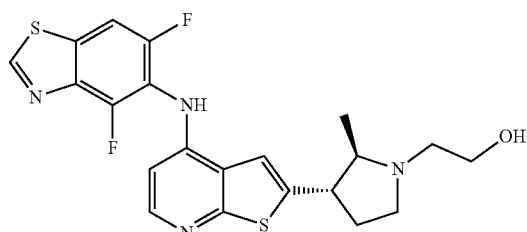
I-76-iv
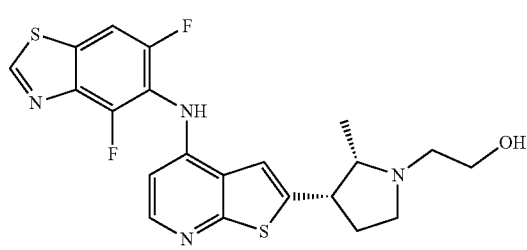
I-77
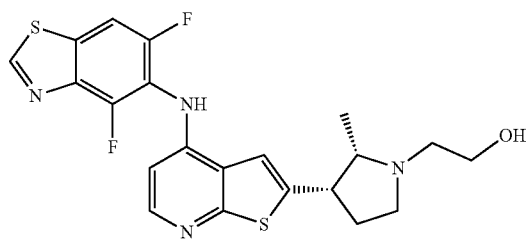
I-77-i
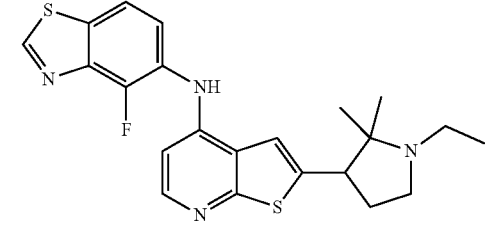
I-77-ii
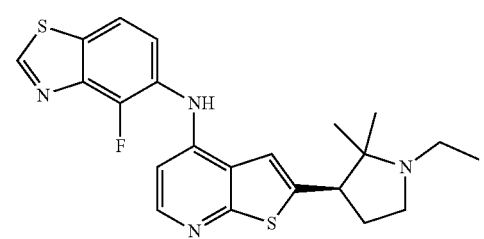
I-78
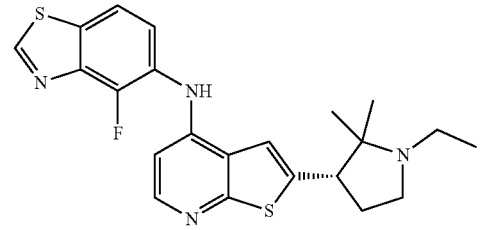

I-78-i
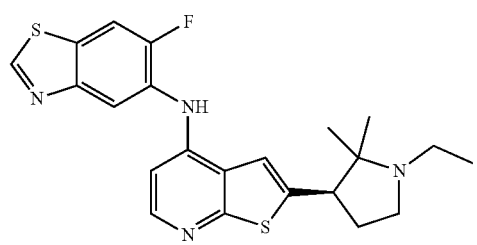
I-78-ii
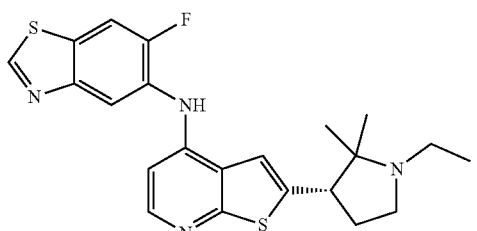
I-79
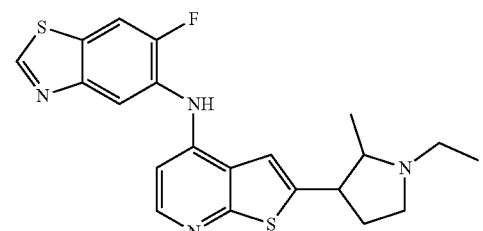
I-79-i
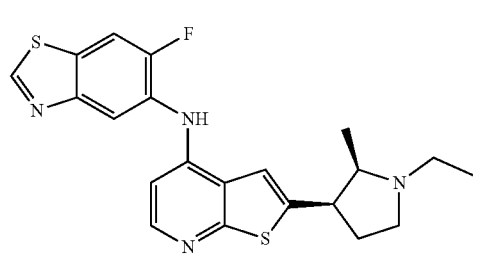
I-79-ii
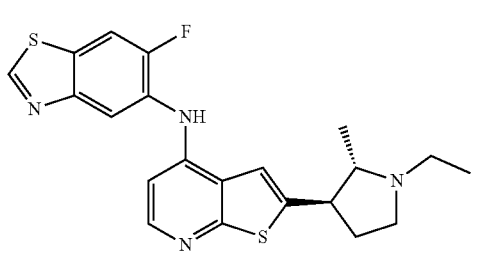
I-79-iii
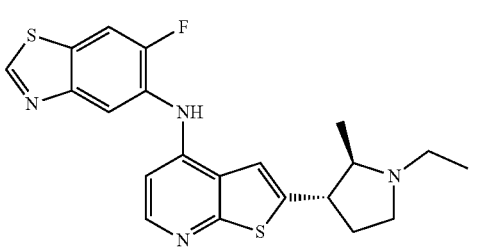
I-79-iv
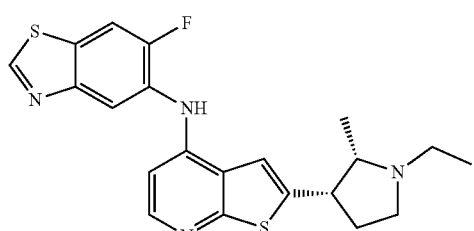
I-80
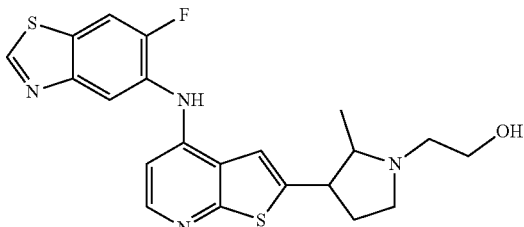
I-80-i
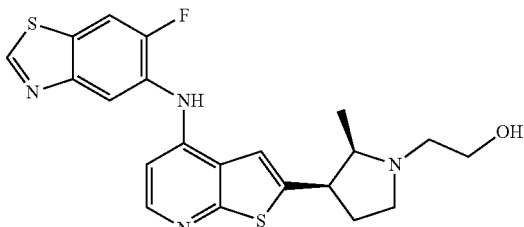
I-80-ii
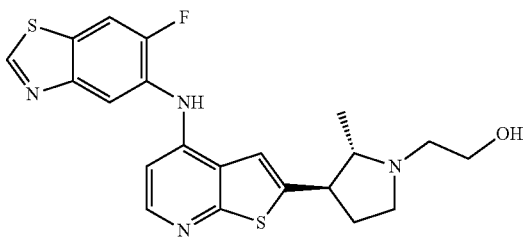
I-80-iii
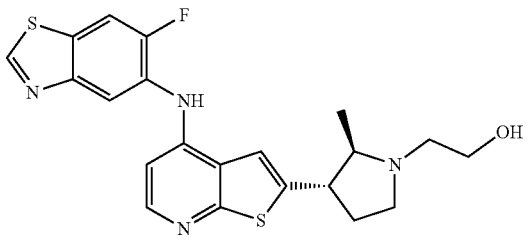
I-80-iv
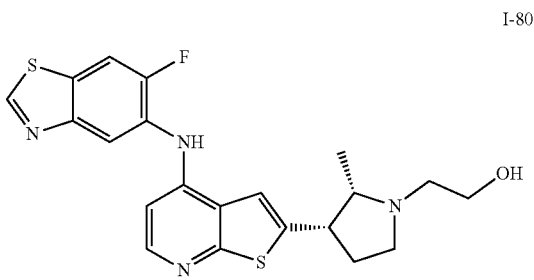

I-81 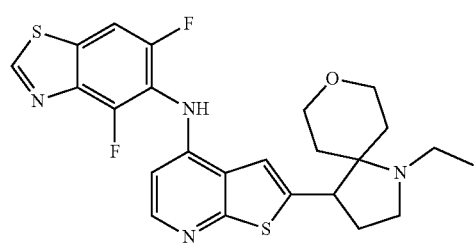
I-81-i 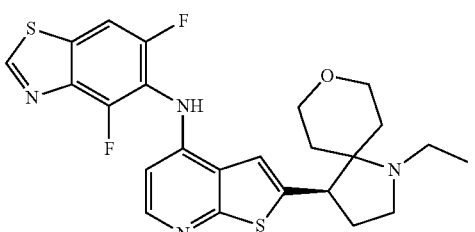
I-81-ii 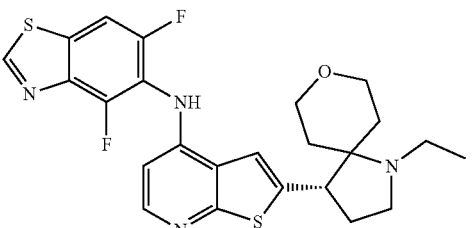
I-82 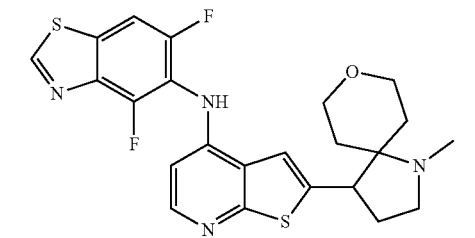
I-82-i 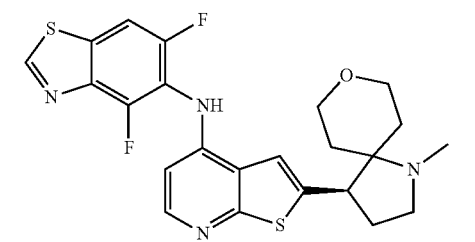
I-82-ii 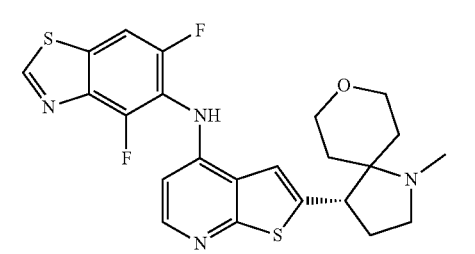
I-83 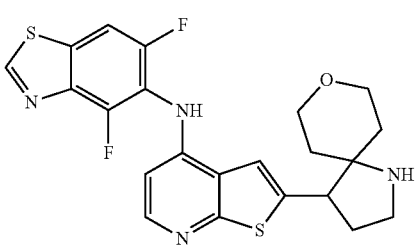
I-83-i 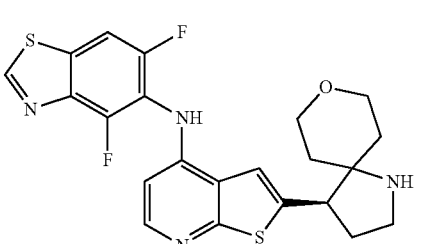
I-83-ii 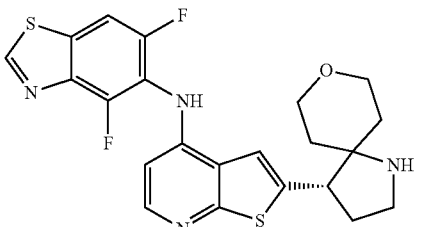
I-84 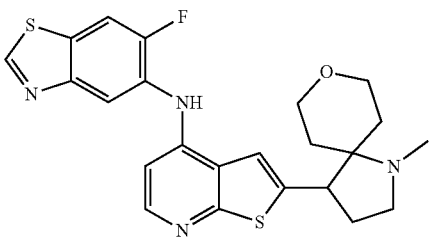
I-84-i 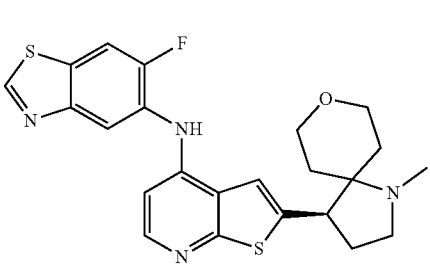
I-84-ii 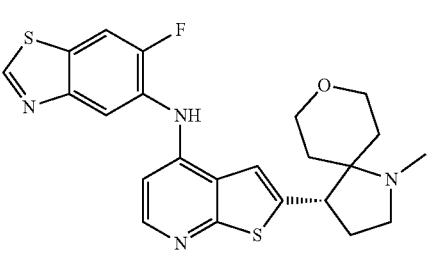

I-85
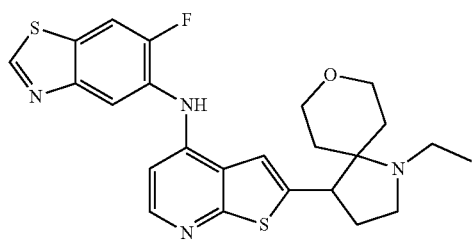
I-85-i
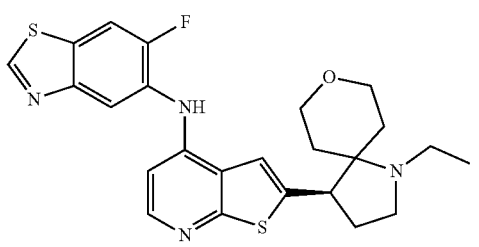
I-85-ii
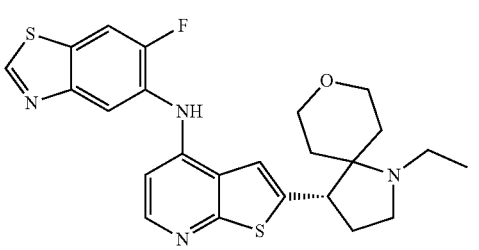
I-86
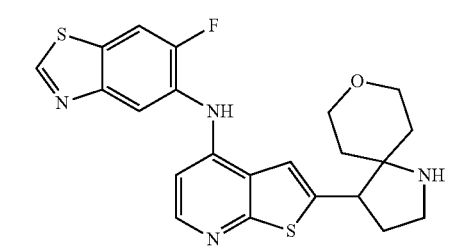
I-86-i
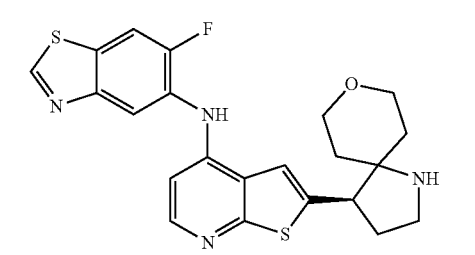
I-86-ii
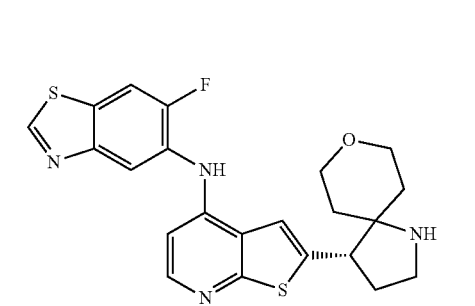
I-87
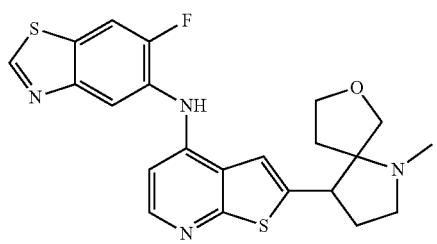
I-87-i
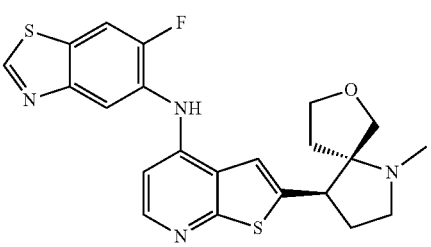
I-87-ii
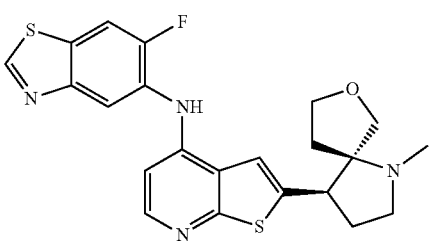
I-87-iii
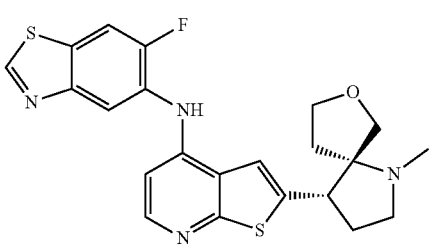
I-87-iv
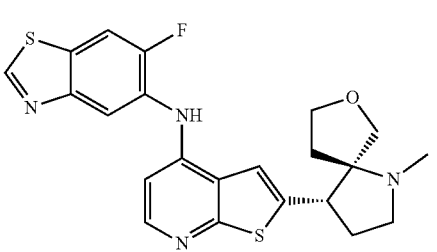
I-88
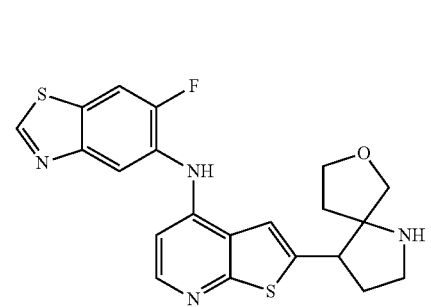

I-88-i
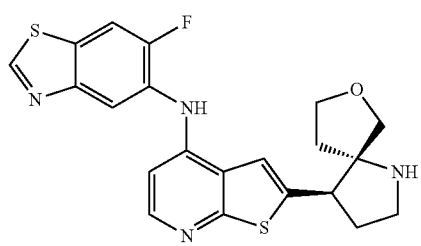
I-88-ii
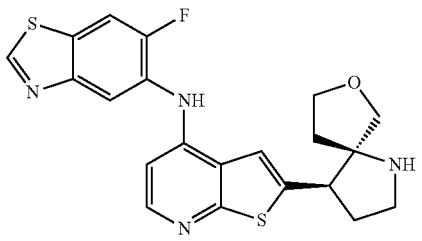
I-88-iii
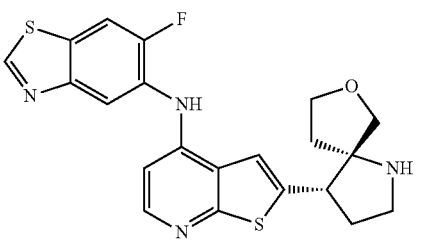
I-88-iv
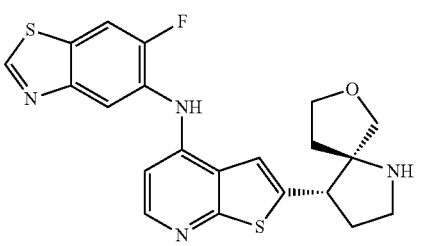
I-89
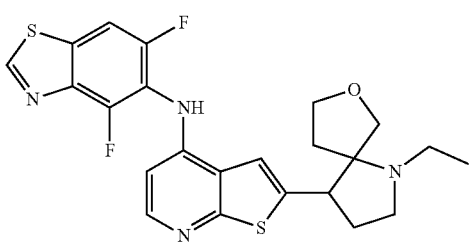
I-89-i
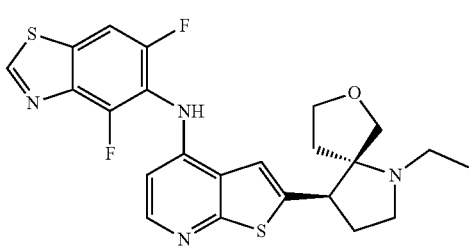
I-89-ii
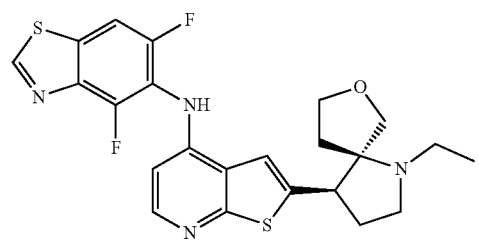
I-89-iii
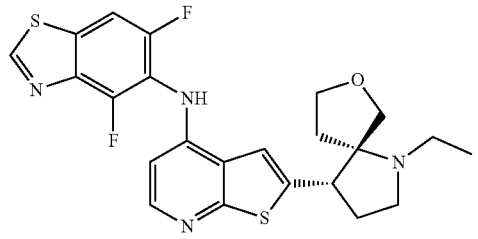
I-89-iv
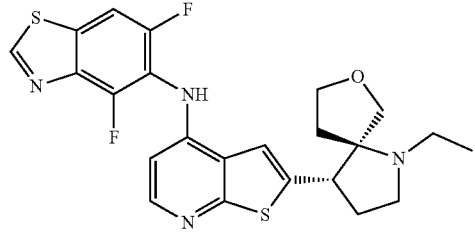
I-90
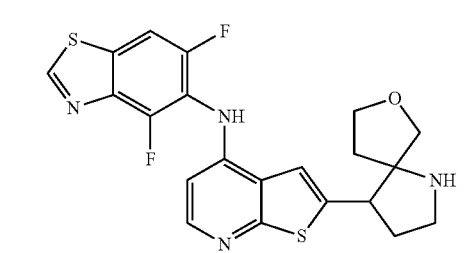
I-90-i
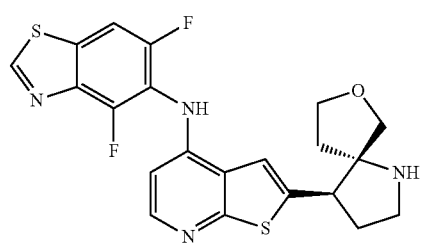
I-90-ii
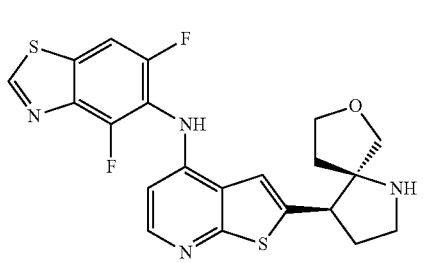

I-90-iii
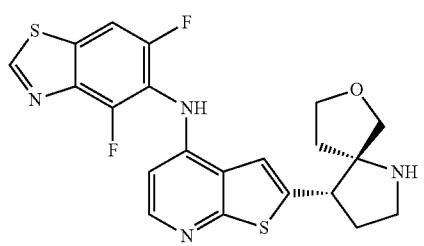
I-90-iv
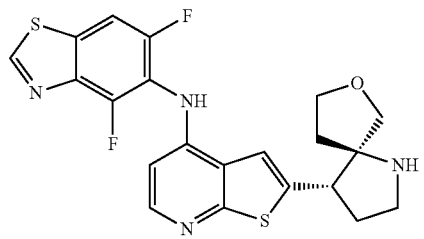
I-91
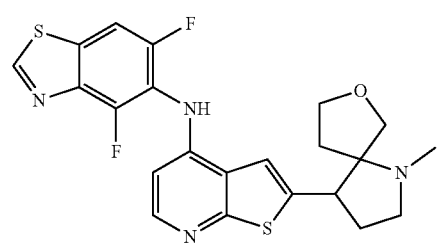
I-91-i
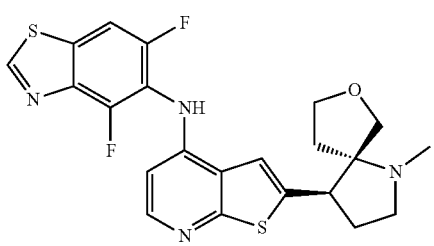
I-91-ii
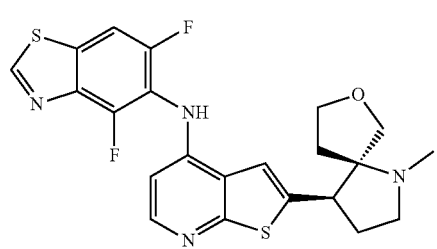
I-91-iii
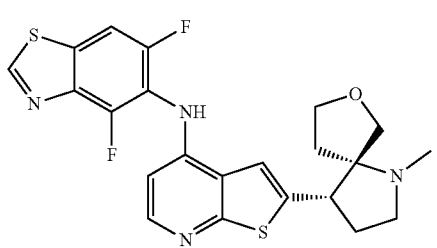
I-91-iv
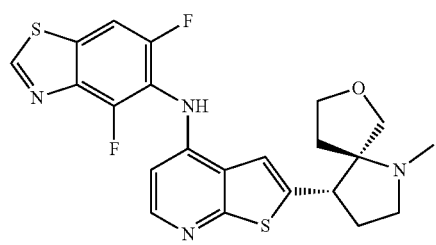
I-92
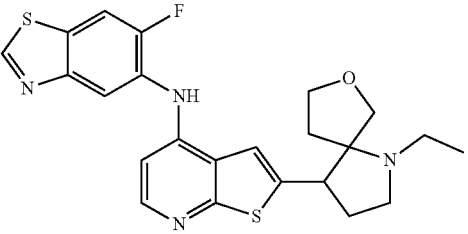
I-92-i
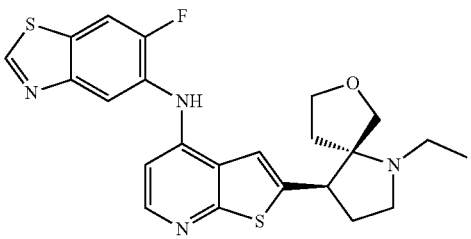
I-92-ii
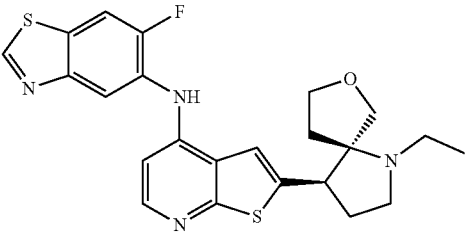
I-92-iii
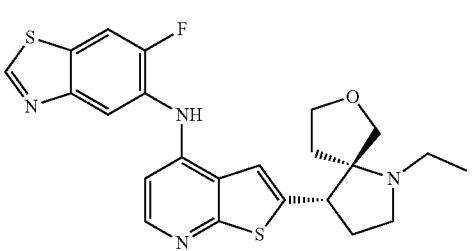
I-92-iv
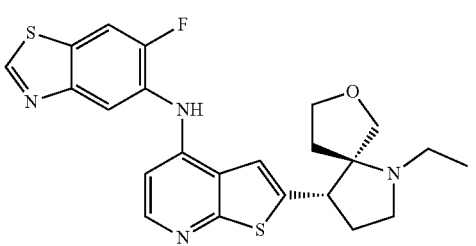

I-93
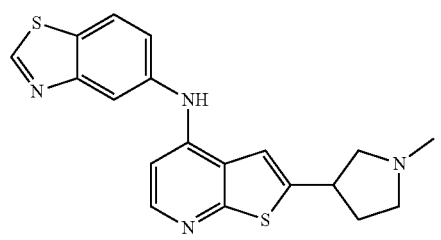
I-93-i
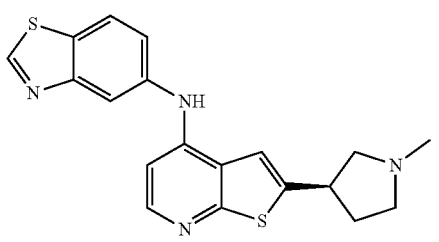
I-93-ii
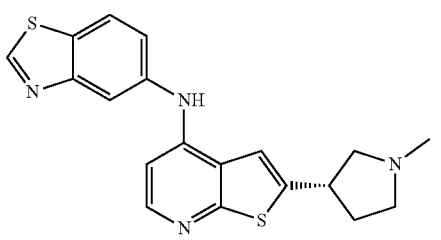
I-94
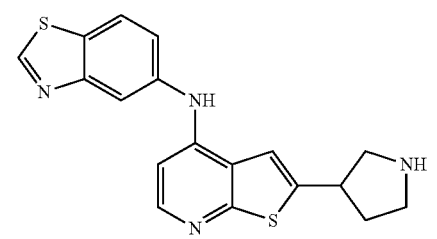
I-94-i
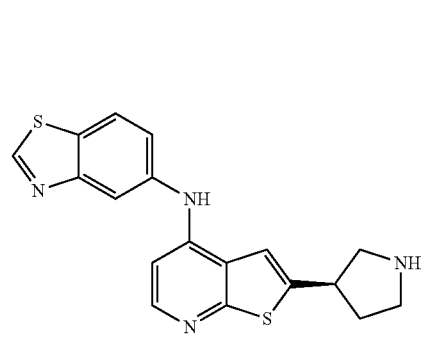
I-94-ii

I-95
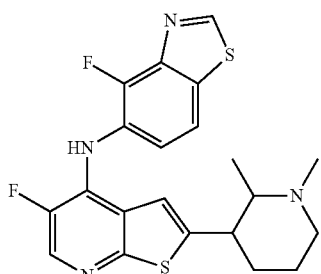
I-95-i
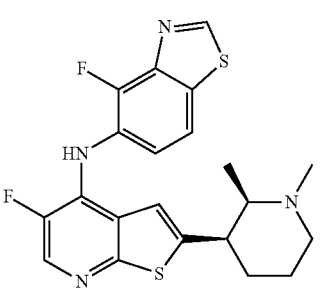
I-95-ii
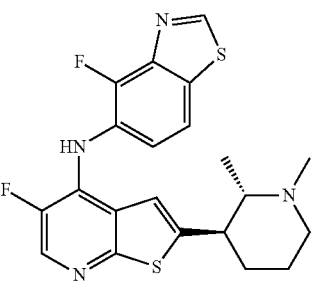
I-95-iii
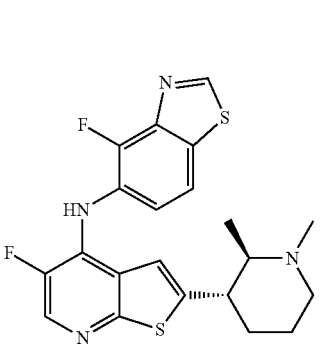
I-95-iv
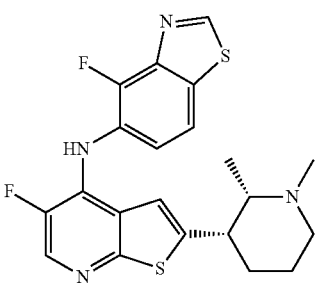

| | |
|---|---|
| I-96 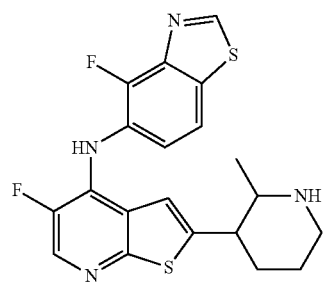 | I-97 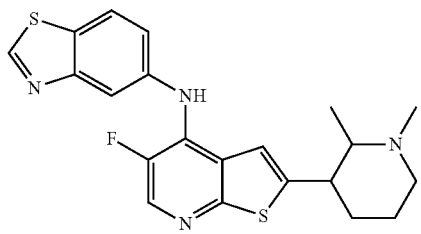 |
| I-96-i 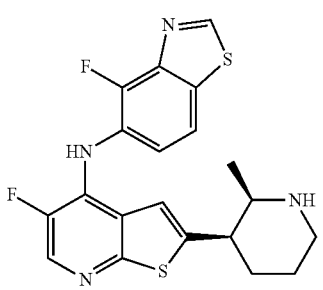 | I-97-i 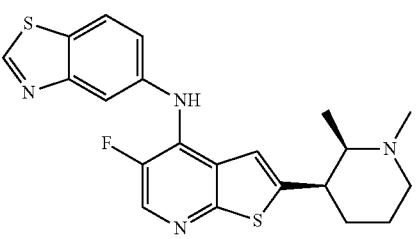 |
| I-96-ii 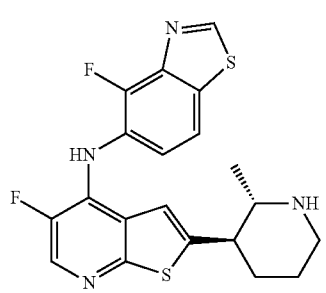 | I-97-ii 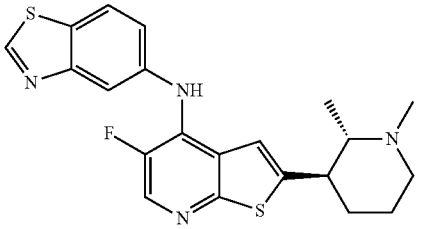 |
| I-96-iii 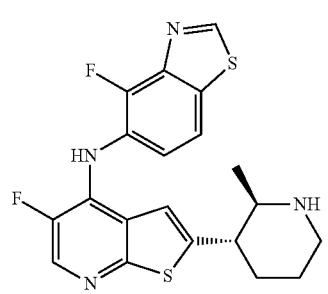 | I-97-iii 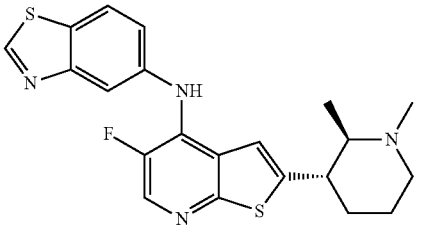 |
| I-96-iv 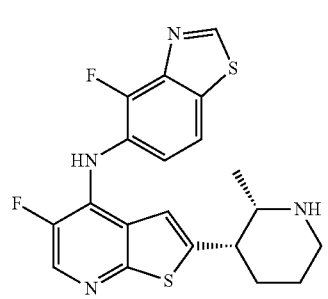 | I-97-iv 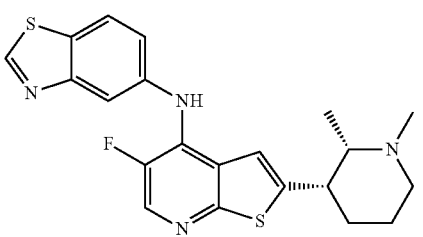 |
| | I-98 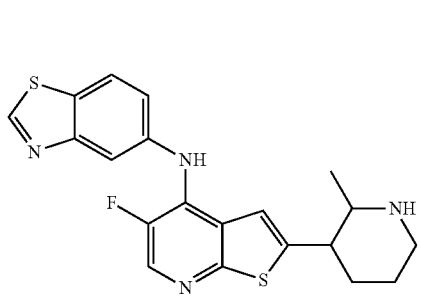 |

I-98-i
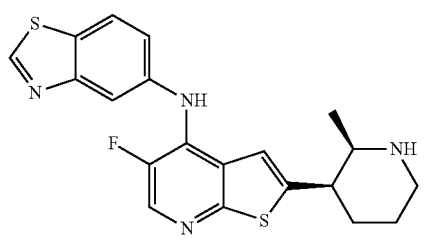
I-98-ii
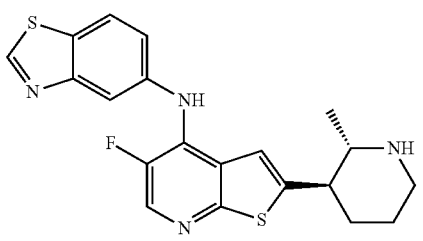
I-98-iii
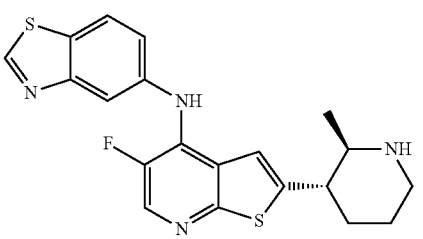
I-98-iv
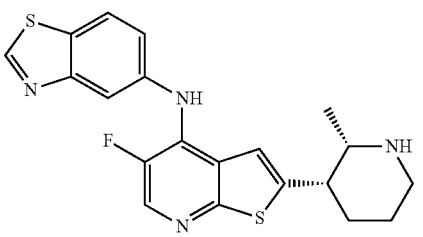
I-99
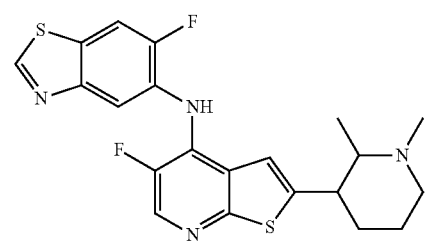
I-99-i
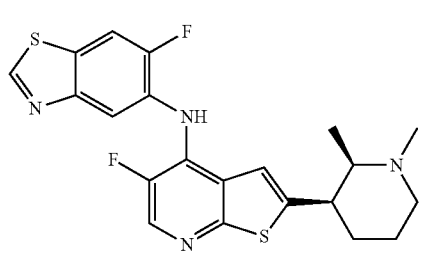
I-99-ii
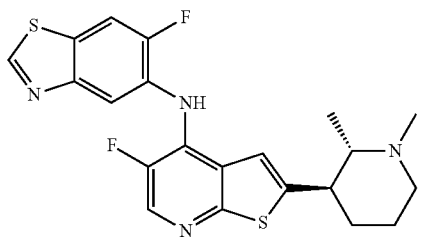
I-99-iii
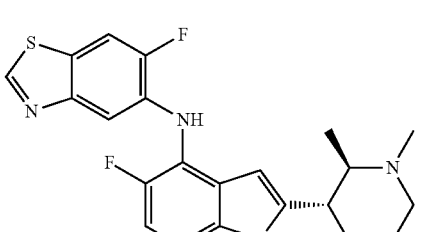
I-99-iv
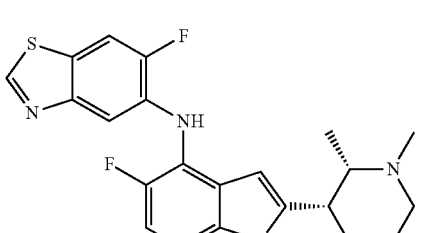
I-100
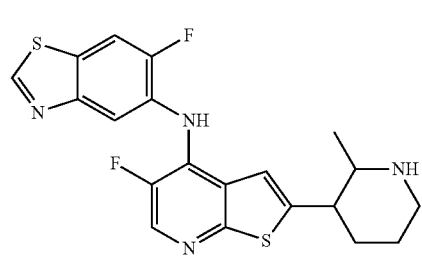
I-100-i
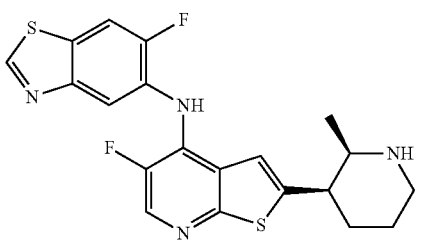
I-100-ii
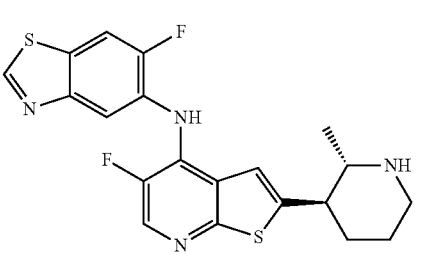

I-100-iii
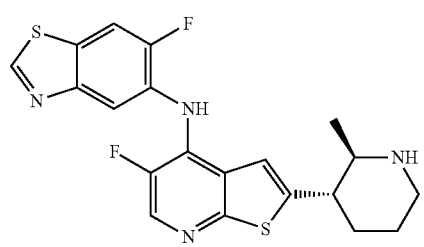
I-100-iv
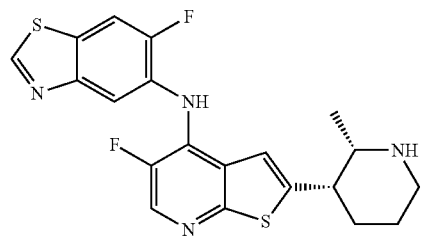
I-101
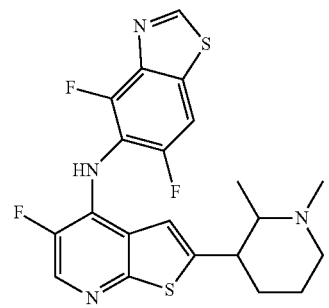
I-101-i
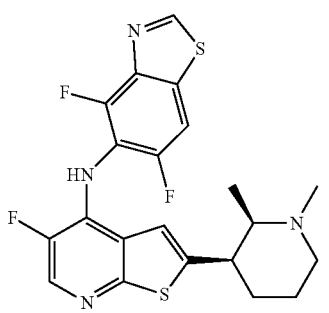
I-101-ii
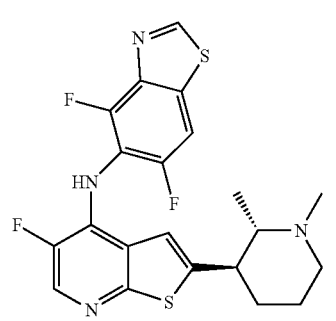
I-101-iii
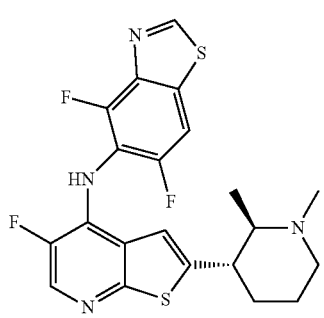
I-101-iv
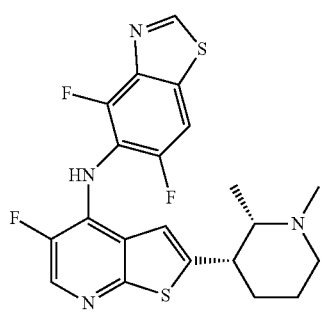
I-102
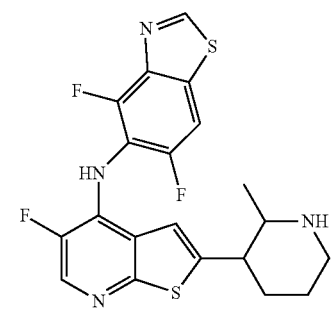
I-102-i
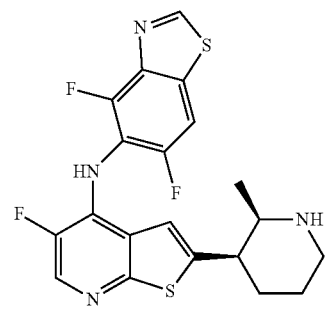
I-102-ii
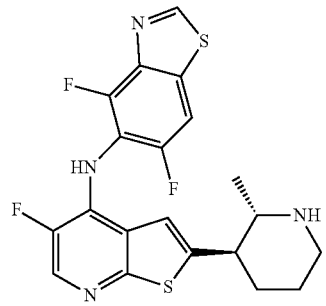

-continued
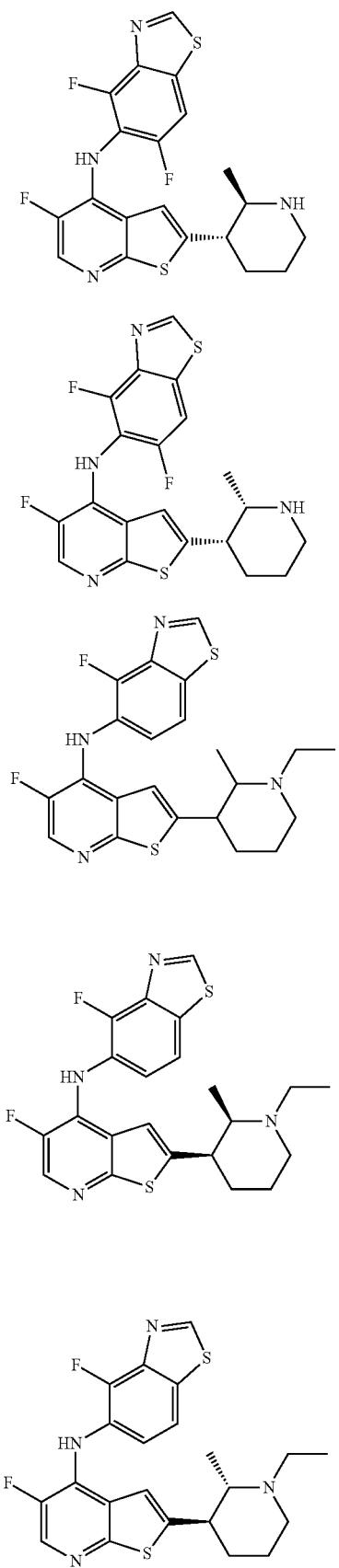
I-102-iii
I-102-iv
I-103
I-103-i
I-103-ii
-continued
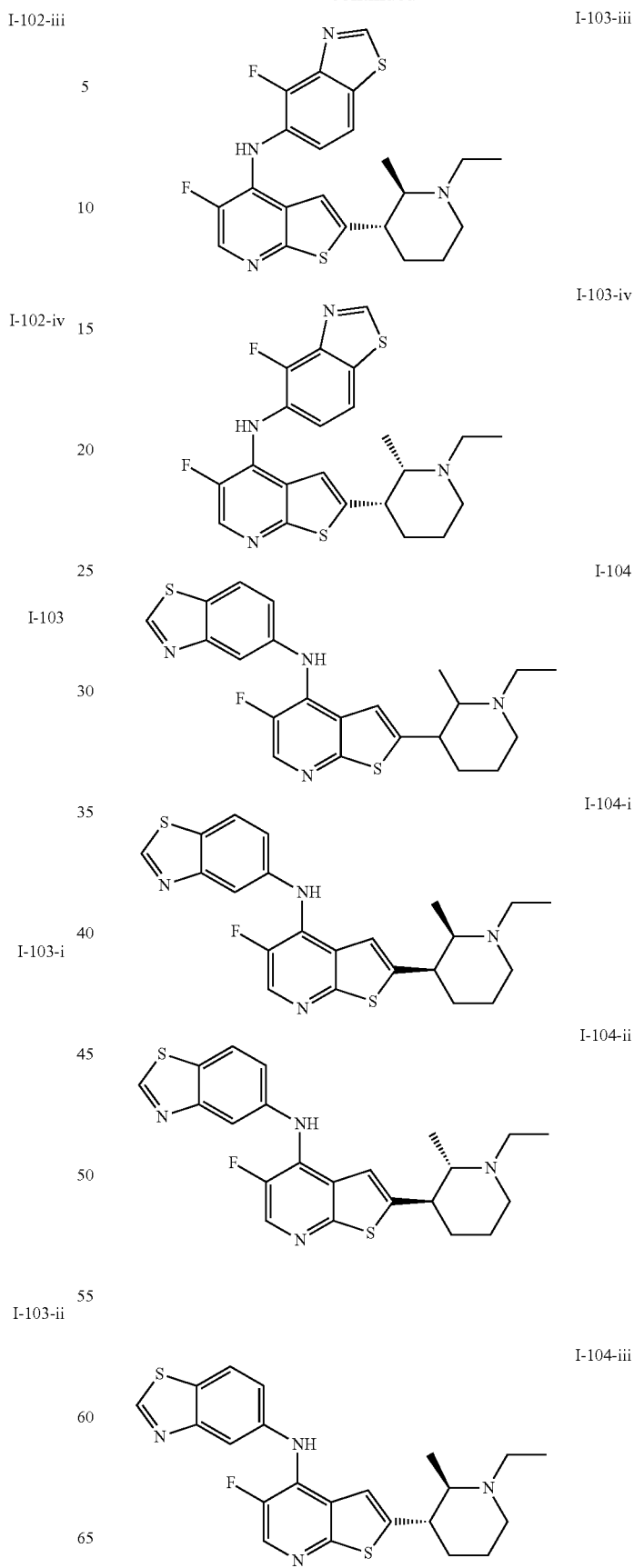
I-103-iii
I-103-iv
I-104
I-104-i
I-104-ii
I-104-iii

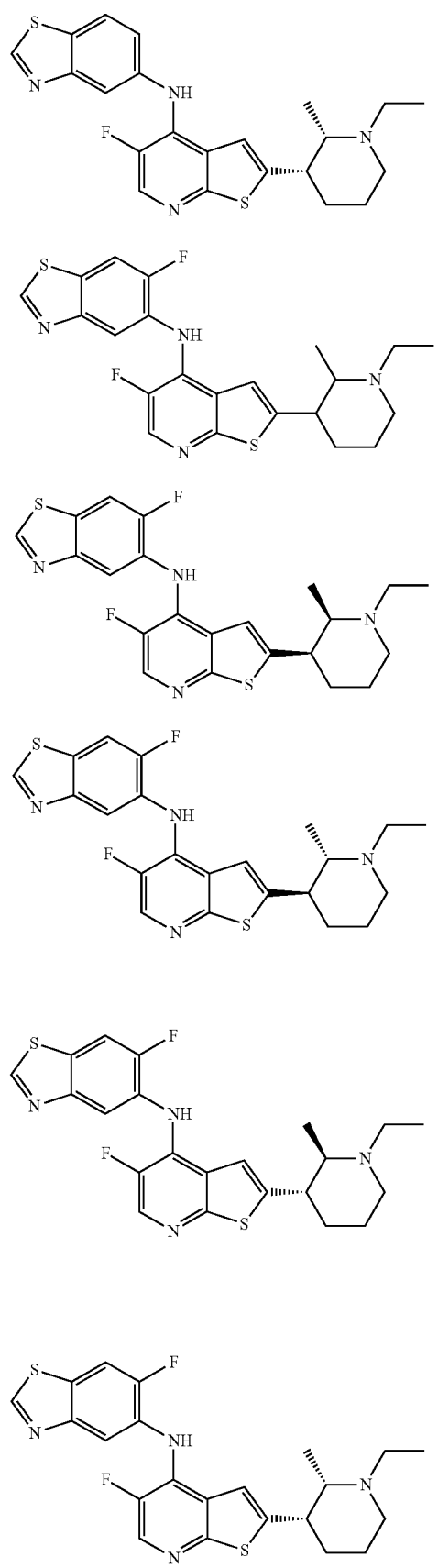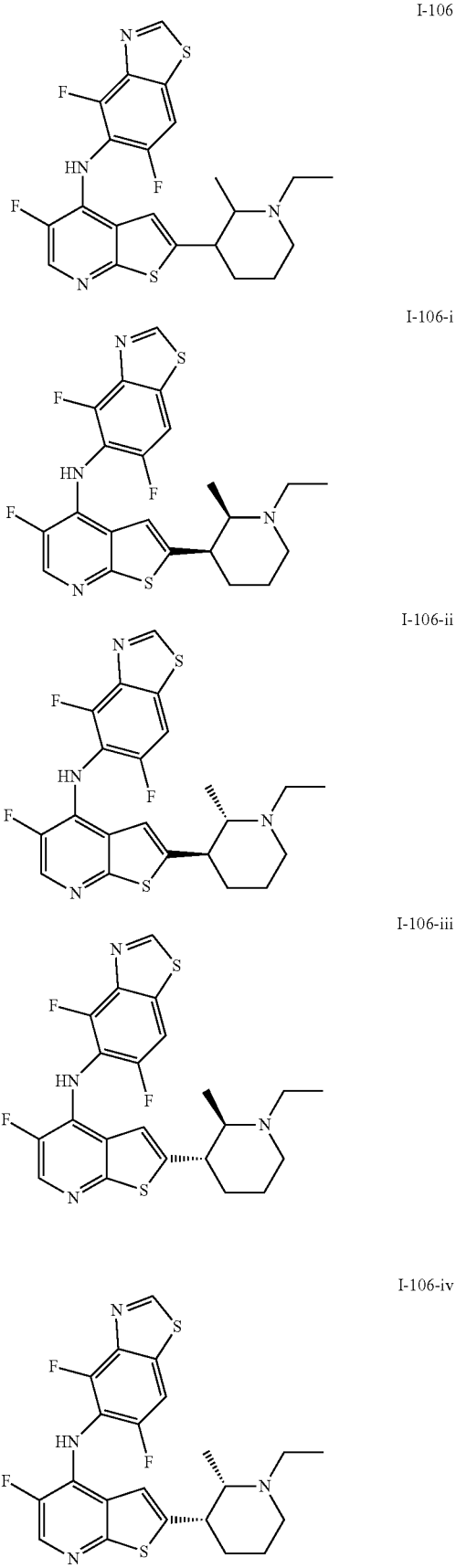

I-107
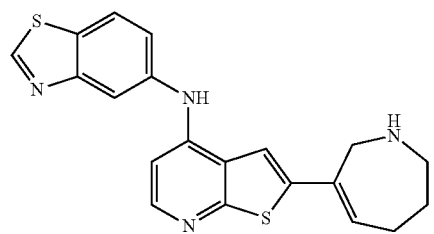
I-108
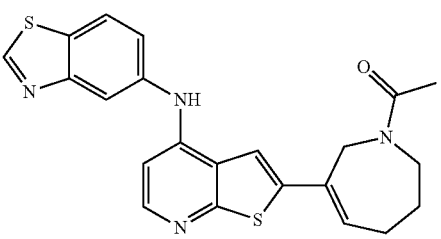
I-109
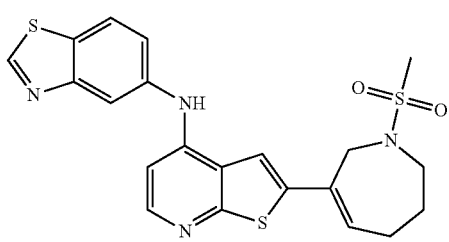
I-110
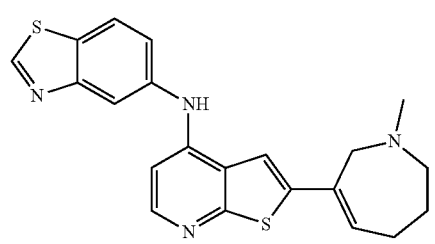
I-111
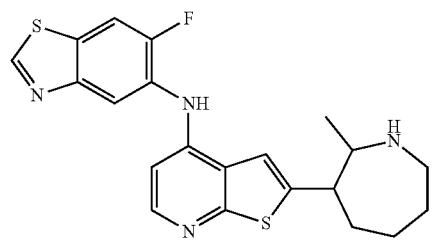
I-111-i
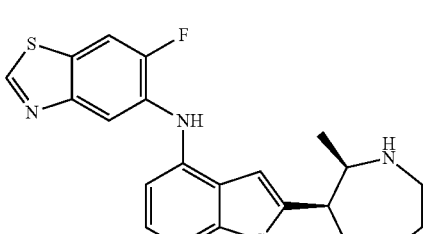
I-111-ii
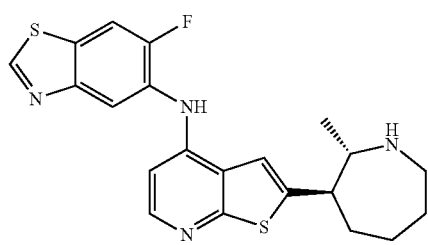
I-111-iii
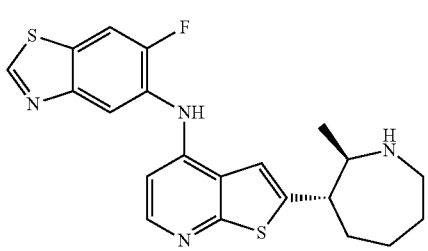
I-111-iv
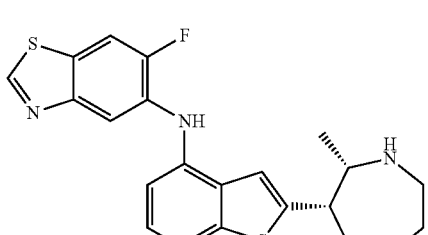
I-112
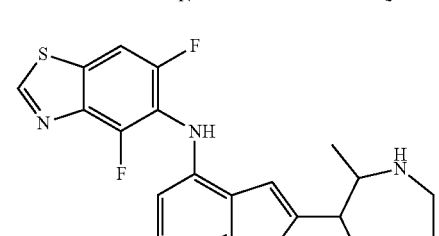
I-112-i
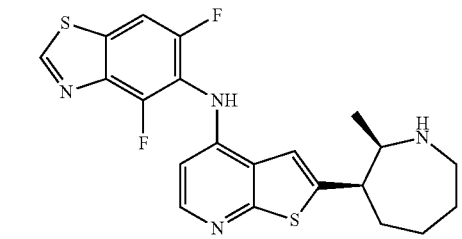
I-112-ii
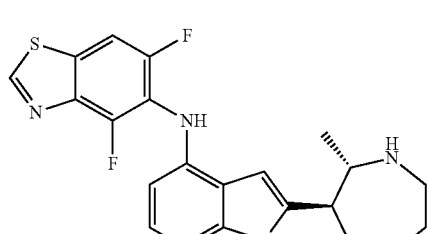

117
-continued
I-112-iii
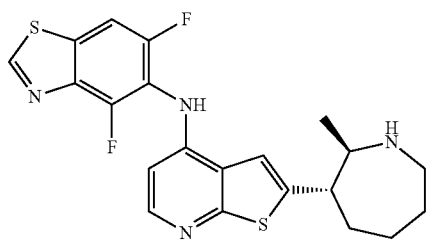
I-112-iv
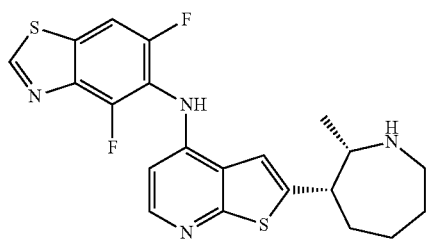
I-113
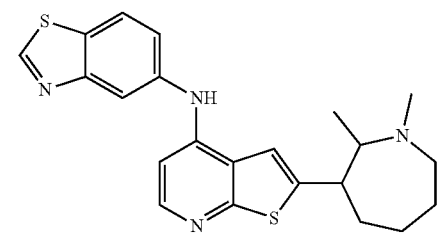
I-113-i
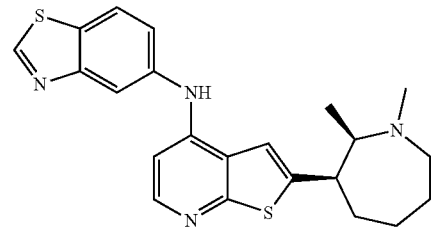
I-113-ii
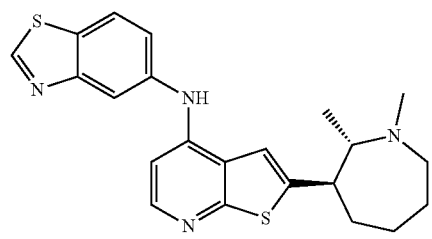
I-113-iii
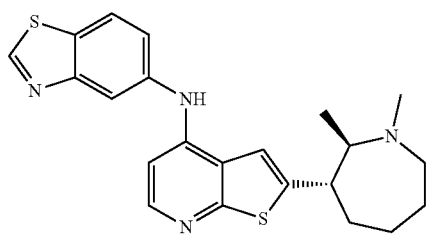
118
-continued
I-113-iv
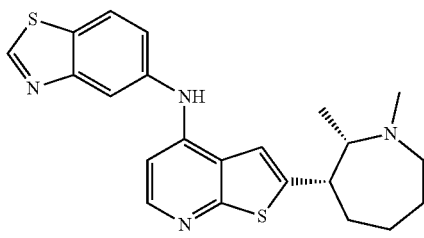
I-114
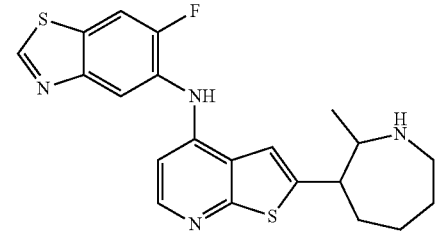
I-114-i
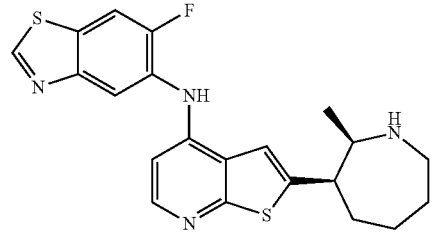
I-114-ii
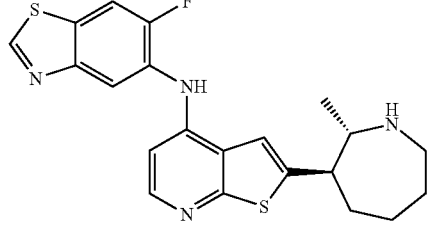
I-114-iii
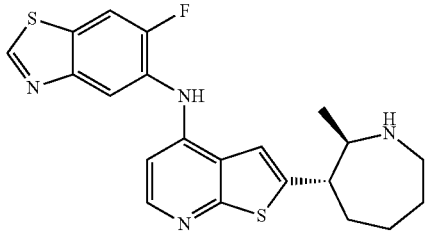
I-114-iv
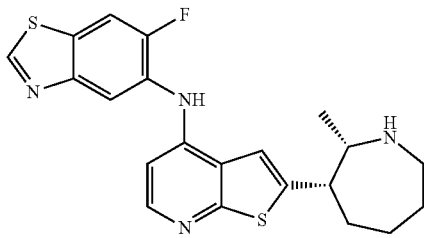

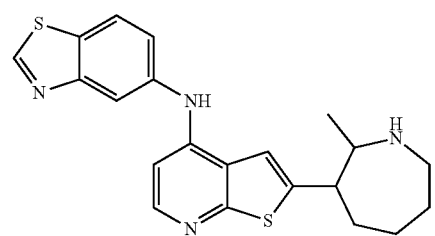
I-115
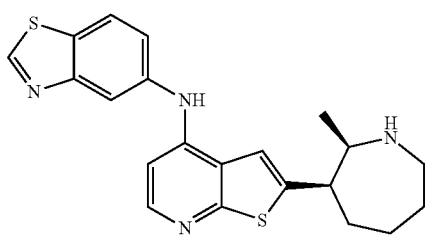
I-115-i
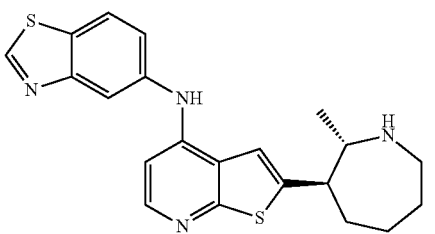
I-115-ii
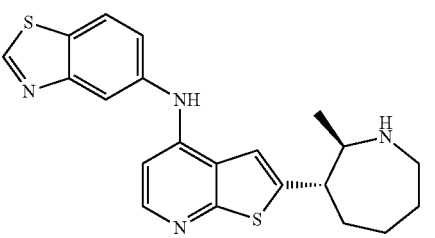
I-115-iii
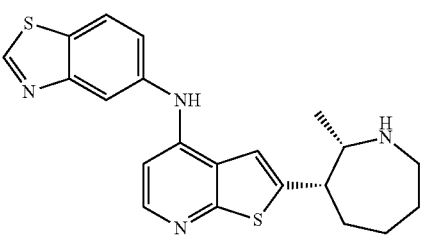
I-115-iv
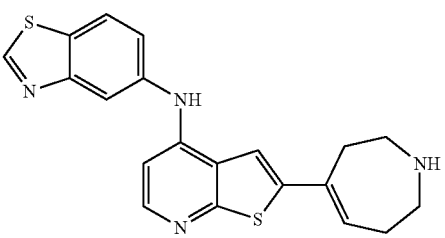
I-116
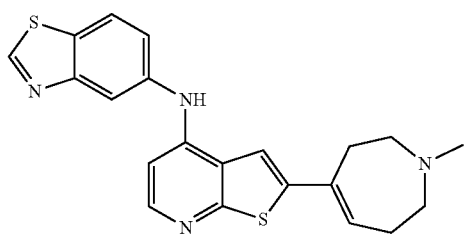
I-117
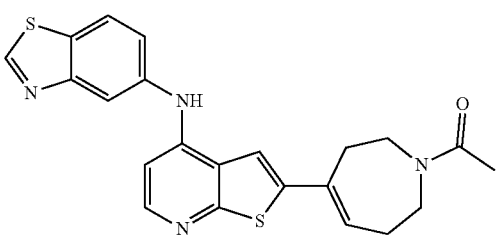
I-118
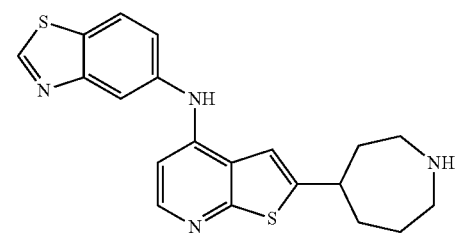
I-119
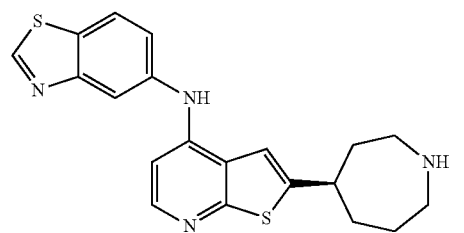
I-119-i
I-119-ii
I-120

-continued

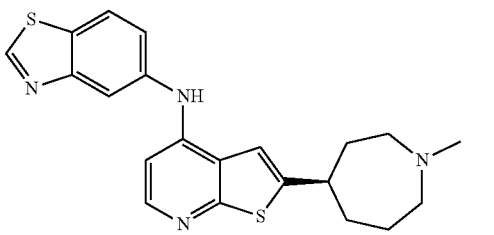
I-120-i

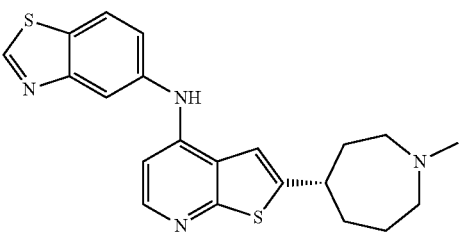
I-120-ii

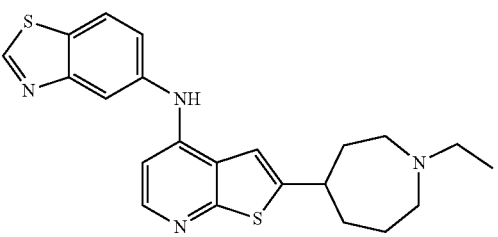
I-121

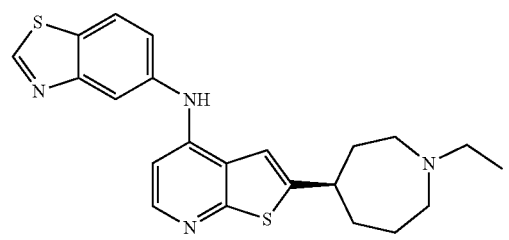
I-121-i

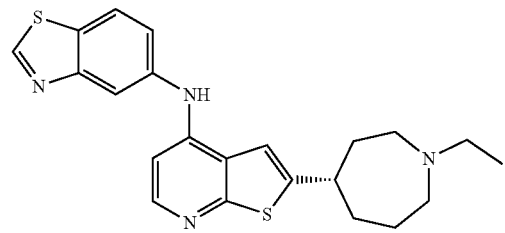
I-121-ii

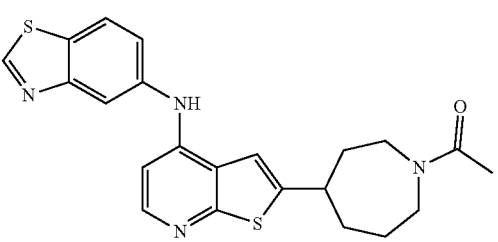
I-122

-continued

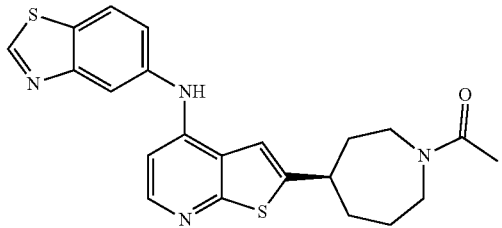
I-122-i

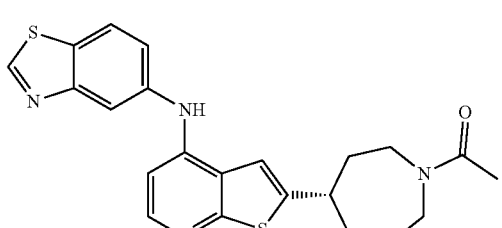
I-122-ii or a pharmaceutically acceptable salt thereof.

In some embodiments, the compound of Formula I or Formula I' is:

N-(2-(2-methyl-1,2,5,6-tetrahydropyridin-3-yl)thieno[2,3-b]pyridin-4-yl)benzo[d]thiazol-5-amine (I-1)

(R)—N-(2-(2-methyl-1,2,5,6-tetrahydropyridin-3-yl)thieno[2,3-b]pyridin-4-yl)benzo[d]thiazol-5-amine (I-1-i)

(S)—N-(2-(2-methyl-1,2,5,6-tetrahydropyridin-3-yl)thieno[2,3-b]pyridin-4-yl)benzo[d]thiazol-5-amine (I-1-ii)

N-(2-(1,2-dimethyl-1,2,5,6-tetrahydropyridin-3-yl)thieno[2,3-b]pyridin-4-yl)benzo[d]thiazol-5-amine (I-2)

(R)—N-(2-(1,2-dimethyl-1,2,5,6-tetrahydropyridin-3-yl)thieno[2,3-b]pyridin-4-yl)benzo[d]thiazol-5-amine (I-2-i)

(S)—N-(2-(1,2-dimethyl-1,2,5,6-tetrahydropyridin-3-yl)thieno[2,3-b]pyridin-4-yl)benzo[d]thiazol-5-amine (I-2-ii)

N-(2-(2-methylpiperidin-3-yl)thieno[2,3-b]pyridin-4-yl)benzo[d]thiazol-5-amine (I-3)

N-(2-((2R,3R)-2-methylpiperidin-3-yl)thieno[2,3-b]pyridin-4-yl)benzo[d]thiazol-5-amine (I-3-i)

N-(2-((2S,3R)-2-methylpiperidin-3-yl)thieno[2,3-b]pyridin-4-yl)benzo[d]thiazol-5-amine (I-3-ii)

N-(2-((2R,3S)-2-methylpiperidin-3-yl)thieno[2,3-b]pyridin-4-yl)benzo[d]thiazol-5-amine (I-3-iii)

N-(2-((2S,3S)-2-methylpiperidin-3-yl)thieno[2,3-b]pyridin-4-yl)benzo[d]thiazol-5-amine (I-3-iv)

N-(2-(1,2-dimethylpiperidin-3-yl)thieno[2,3-b]pyridin-4-yl)benzo[d]thiazol-5-amine (I-4)

N-(2-((2R,3R)-1,2-dimethylpiperidin-3-yl)thieno[2,3-b]pyridin-4-yl)benzo[d]thiazol-5-amine (I-4-i)

N-(2-((2S,3R)-1,2-dimethylpiperidin-3-yl)thieno[2,3-b]pyridin-4-yl)benzo[d]thiazol-5-amine (I-4-ii)

N-(2-((2R,3S)-1,2-dimethylpiperidin-3-yl)thieno[2,3-b]pyridin-4-yl)benzo[d]thiazol-5-amine (I-4-iii)

N-(2-((2S,3S)-1,2-dimethylpiperidin-3-yl)thieno[2,3-b]pyridin-4-yl)benzo[d]thiazol-5-amine (I-4-iv)

N-(2-(1-ethyl-2-methyl-1,2,5,6-tetrahydropyridin-3-yl)thieno[2,3-b]pyridin-4-yl)benzo[d]thiazol-5-amine (I-5)

(R)—N-(2-(1-ethyl-2-methyl-1,2,5,6-tetrahydropyridin-3-yl)thieno[2,3b]pyridin-4-yl)benzo[d]thiazol-5-amine (I-5-i)

(S)—N-(2-(1-ethyl-2-methyl-1,2,5,6-tetrahydropyridin-3-yl)thieno[2,3-b]pyridin-4-yl)benzo[d]thiazol-5-amine (I-5-ii)

N-(2-(1-ethyl-2-methylpiperidin-3-yl)thieno[2,3-b]pyridin-4-yl)benzo[d]thiazol-5-amine (I-6)

N-(2-((2R,3R)-1-ethyl-2-methylpiperidin-3-yl)thieno[2,3-b]pyridin-4-yl)benzo[d]thiazol-5-amine (I-6-i)

N-(2-((2S,3R)-1-ethyl-2-methylpiperidin-3-yl)thieno[2,3-b]pyridin-4-yl)benzo[d]thiazol-5-amine (I-6-ii)

N-(2-((2R,3S)-1-ethyl-2-methylpiperidin-3-yl)thieno[2,3-b]pyridin-4-yl)benzo[d]thiazol-5-amine (I-6-iii)

N-(2-((2S,3S)-1-ethyl-2-methylpiperidin-3-yl)thieno[2,3-b]pyridin-4-yl)benzo[d]thiazol-5-amine (I-6-iv)

N-(2-(1-isopropyl-2-methyl-1,2,5,6-tetrahydropyridin-3-yl)thieno[2,3-b]pyridin-4-yl)benzo[d]thiazol-5-amine (I-7)

(R)—N-(2-(1-isopropyl-2-methyl-1,2,5,6-tetrahydropyridin-3-yl)thieno[2,3-b]pyridin-4-yl)benzo[d]thiazol-5-amine (I-7-i)

(S)—N-(2-(1-isopropyl-2-methyl-1,2,5,6-tetrahydropyridin-3-yl)thieno[2,3-b]pyridin-4-yl)benzo[d]thiazol-5-amine (I-7-ii)

N-(2-(1-isopropyl-2-methylpiperidin-3-yl)thieno[2,3-b]pyridin-4-yl)benzo[d]thiazol-5-amine (I-8)

N-(2-((2R,3R)-1-isopropyl-2-methylpiperidin-3-yl)thieno[2,3-b]pyridin-4-yl)benzo[d]thiazol-5-amine (I-8-i)

N-(2-((2S,3R)-1-isopropyl-2-methylpiperidin-3-yl)thieno[2,3-b]pyridin-4-yl)benzo[d]thiazol-5-amine (I-8-ii)

N-(2-((2R,3S)-1-isopropyl-2-methylpiperidin-3-yl)thieno[2,3-b]pyridin-4-yl)benzo[d]thiazol-5-amine (I-8-iii)

N-(2-((2S,3S)-1-isopropyl-2-methylpiperidin-3-yl)thieno[2,3-b]pyridin-4-yl)benzo[d]thiazol-5-amine (I-8-iv)

1-(5-(4-(benzo[d]thiazol-5-ylamino)thieno[2,3-b]pyridin-2-yl)-6-methyl-3,6-dihydropyridin-1(2H)-yl)ethan-1-one (I-9)

(R)-1-(5-(4-(benzo[d]thiazol-5-ylamino)thieno[2,3-b]pyridin-2-yl)-6-methyl-3,6-dihydropyridin-1(2H)-yl)ethan-1-one (I-9-i)

(S)-1-(5-(4-(benzo[d]thiazol-5-ylamino)thieno[2,3-b]pyridin-2-yl)-6-methyl-3,6-dihydropyridin-1(2H)-yl)ethan-1-one (I-9-ii)

1-(3-(4-(benzo[d]thiazol-5-ylamino)thieno[2,3-b]pyridin-2-yl)-2-methylpiperidin-1-yl)ethan-1-one (I-10)

1-((2R,3R)-3-(4-(benzo[d]thiazol-5-ylamino)thieno[2,3-b]pyridin-2-yl)-2-methylpiperidin-1-yl)ethan-1-one (I-10-i)

1-((2S,3R)-3-(4-(benzo[d]thiazol-5-ylamino)thieno[2,3-b]pyridin-2-yl)-2-methylpiperidin-1-yl)ethan-1-one (I-10-ii)

1-((2R,3S)-3-(4-(benzo[d]thiazol-5-ylamino)thieno[2,3-b]pyridin-2-yl)-2-methylpiperidin-1-yl)ethan-1-one (I-10-iii)

1-((2S,3S)-3-(4-(benzo[d]thiazol-5-ylamino)thieno[2,3-b]pyridin-2-yl)-2-methylpiperidin-1-yl)ethan-1-one (I-10-iv)

1-(5-(4-(benzo[d]thiazol-5-ylamino)thieno[2,3-b]pyridin-2-yl)-6-methyl-3,6-dihydropyridin-1(2H)-yl)-2-methoxyethan-1-one (I-11)

(R)-1-(5-(4-(benzo[d]thiazol-5-ylamino)thieno[2,3-b]pyridin-2-yl)-6-methyl-3,6-dihydropyridin-1(2H)-yl)-2-methoxyethan-1-one (I-11-i)

(S)-1-(5-(4-(benzo[d]thiazol-5-ylamino)thieno[2,3-b]pyridin-2-yl)-6-methyl-3,6-dihydropyridin-1(2H)-yl)-2-methoxyethan-1-one (I-11-ii)

N-(2-(1-(2-methoxyethyl)-2-methyl-1,2,5,6-tetrahydropyridin-3-yl)thieno[2,3-b]pyridin-4-yl)benzo[d]thiazol-5-amine (I-12)

(R)—N-(2-(1-(2-methoxyethyl)-2-methyl-1,2,5,6-tetrahydropyridin-3-yl)thieno[2,3-b]pyridin-4-yl)benzo[d]thiazol-5-amine (I-12-i)

(S)—N-(2-(1-(2-methoxyethyl)-2-methyl-1,2,5,6-tetrahydropyridin-3-yl)thieno[2,3-b]pyridin-4-yl)benzo[d]thiazol-5-amine (I-12-ii)

N-(2-(1-(2-methoxyethyl)-2-methylpiperidin-3-yl)thieno[2,3-b]pyridin-4-yl)benzo[d]thiazol-5-amine (I-13)

N-(2-((2R,3R)-1-(2-methoxyethyl)-2-methylpiperidin-3-yl)thieno[2,3-b]pyridin-4-yl)benzo[d]thiazol-5-amine (I-13-i)

N-(2-((2S,3R)-1-(2-methoxyethyl)-2-methylpiperidin-3-yl)thieno[2,3-b]pyridin-4-yl)benzo[d]thiazol-5-amine (I-13-ii)

N-(2-((2R,3S)-1-(2-methoxyethyl)-2-methylpiperidin-3-yl)thieno[2,3-b]pyridin-4-yl)benzo[d]thiazol-5-amine (I-13-iii)

N-(2-((2S,3S)-1-(2-methoxyethyl)-2-methylpiperidin-3-yl)thieno[2,3-b]pyridin-4-yl)benzo[d]thiazol-5-amine (I-13-iv)

N-(2-(1-(2-fluoroethyl)-2-methylpiperidin-3-yl)thieno[2,3-b]pyridin-4-yl)benzo[d]thiazol-5-amine (I-14)

N-(2-((2R,3R)-1-(2-fluoroethyl)-2-methylpiperidin-3-yl)thieno[2,3-b]pyridin-4-yl)benzo[d]thiazol-5-amine (I-14-i)

N-(2-((2S,3R)-1-(2-fluoroethyl)-2-methylpiperidin-3-yl)thieno[2,3-b]pyridin-4-yl)benzo[d]thiazol-5-amine (I-14-ii)

N-(2-((2R,3S)-1-(2-fluoroethyl)-2-methylpiperidin-3-yl)thieno[2,3-b]pyridin-4-yl)benzo[d]thiazol-5-amine (I-14-iii)

N-(2-((2S,3S)-1-(2-fluoroethyl)-2-methylpiperidin-3-yl)thieno[2,3-b]pyridin-4-yl)benzo[d]thiazol-5-amine (I-14-iv)

N-(2-(1-(2,2-difluoroethyl)-2-methylpiperidin-3-yl)thieno[2,3-b]pyridin-4-yl)benzo[d]thiazol-5-amine (I-15)

N-(2-((2R,3R)-1-(2,2-difluoroethyl)-2-methylpiperidin-3-yl)thieno[2,3-b]pyridin-4-yl)benzo[d]thiazol-5-amine (I-15-i)

N-(2-((2S,3R)-1-(2,2-difluoroethyl)-2-methylpiperidin-3-yl)thieno[2,3-b]pyridin-4-yl)benzo[d]thiazol-5-amine (I-15-ii)

N-(2-((2R,3S)-1-(2,2-difluoroethyl)-2-methylpiperidin-3-yl)thieno[2,3-b]pyridin-4-yl)benzo[d]thiazol-5-amine (I-15-iii)

N-(2-((2S,3S)-1-(2,2-difluoroethyl)-2-methylpiperidin-3-yl)thieno[2,3-b]pyridin-4-yl)benzo[d]thiazol-5-amine (I-15-iv)

N-(2-(2-methyl-1-(2,2,2-trifluoroethyl)piperidin-3-yl)thieno[2,3-b]pyridin-4-yl)benzo[d]thiazol-5-amine (I-16)

N-(2-((2R,3R)-2-methyl-1-(2,2,2-trifluoroethyl)piperidin-3-yl)thieno[2,3-b]pyridin-4-yl)benzo[d]thiazol-5-amine (I-16-i)

N-(2-((2S,3R)-2-methyl-1-(2,2,2-trifluoroethyl)piperidin-3-yl)thieno[2,3-b]pyridin-4-yl)benzo[d]thiazol-5-amine (I-16-ii)

N-(2-((2R,3S)-2-methyl-1-(2,2,2-trifluoroethyl)piperidin-3-yl)thieno[2,3-b]pyridin-4-yl)benzo[d]thiazol-5-amine (I-16-iii)

N-(2-((2S,3S)-2-methyl-1-(2,2,2-trifluoroethyl)piperidin-3-yl)thieno[2,3-b]pyridin-4-yl)benzo[d]thiazol-5-amine (I-16-iv)

N-(2-(2-methyl-1-(oxetan-3-yl)piperidin-3-yl)thieno[2,3-b]pyridin-4-yl)benzo[d]thiazol-5-amine (I-17)

N-(2-((2R,3R)-2-methyl-1-(oxetan-3-yl)piperidin-3-yl)thieno[2,3-b]pyridin-4-yl)benzo[d]thiazol-5-amine (I-17-i)

N-(2-((2S,3R)-2-methyl-1-(oxetan-3-yl)piperidin-3-yl)thieno[2,3-b]pyridin-4-yl)benzo[d]thiazol-5-amine (I-17-ii)

N-(2-((2R,3S)-2-methyl-1-(oxetan-3-yl)piperidin-3-yl)thieno[2,3-b]pyridin-4-yl)benzo[d]thiazol-5-amine (I-17-iii)

N-(2-((2S,3S)-2-methyl-1-(oxetan-3-yl)piperidin-3-yl)thieno[2,3-b]pyridin-4-yl)benzo[d]thiazol-5-amine (I-17-iv)

N-(2-(1-(3-aminopropyl)-2-methylpiperidin-3-yl)thieno[2,3-b]pyridin-4-yl)benzo[d]thiazol-5-amine (I-18)

N-(2-((2R,3R)-1-(3-aminopropyl)-2-methylpiperidin-3-yl)thieno[2,3-b]pyridin-4-yl)benzo[d]thiazol-5-amine (I-18-i)

N-(2-((2S,3R)-1-(3-aminopropyl)-2-methylpiperidin-3-yl)thieno[2,3-b]pyridin-4-yl)benzo[d]thiazol-5-amine (I-18-ii)

N-(2-((2R,3S)-1-(3-aminopropyl)-2-methylpiperidin-3-yl)thieno[2,3-b]pyridin-4-yl)benzo[d]thiazol-5-amine (I-18-iii)

N-(2-((2S,3S)-1-(3-aminopropyl)-2-methylpiperidin-3-yl)thieno[2,3-b]pyridin-4-yl)benzo[d]thiazol-5-amine (I-18-iv)

N-(2-(1-(2-ethoxyethyl)-2-methylpiperidin-3-yl)thieno[2,3-b]pyridin-4-yl)benzo[d]thiazol-5-amine (I-19)

N-(2-((2R,3R)-1-(2-ethoxyethyl)-2-methylpiperidin-3-yl)thieno[2,3-b]pyridin-4-yl)benzo[d]thiazol-5-amine (I-19-i)

N-(2-((2S,3R)-1-(2-ethoxyethyl)-2-methylpiperidin-3-yl)thieno[2,3-b]pyridin-4-yl)benzo[d]thiazol-5-amine (I-19-ii)

N-(2-((2R,3S)-1-(2-ethoxyethyl)-2-methylpiperidin-3-yl)thieno[2,3-b]pyridin-4-yl)benzo[d]thiazol-5-amine (I-19-iii)

N-(2-((2S,3S)-1-(2-ethoxyethyl)-2-methylpiperidin-3-yl)thieno[2,3-b]pyridin-4-yl)benzo[d]thiazol-5-amine (I-19-iv)

2-(3-(4-(benzo[d]thiazol-5-ylamino)thieno[2,3-b]pyridin-2-yl)-2-methylpiperidin-1-yl)ethan-1-ol (I-20)

2-((2R,3R)-3-(4-(benzo[d]thiazol-5-ylamino)thieno[2,3-b]pyridin-2-yl)-2-methylpiperidin-1-yl)ethan-1-ol (I-20-i)

2-((2S,3R)-3-(4-(benzo[d]thiazol-5-ylamino)thieno[2,3-b]pyridin-2-yl)-2-methylpiperidin-1-yl)ethan-1-ol (I-20-ii)

2-((2R,3S)-3-(4-(benzo[d]thiazol-5-ylamino)thieno[2,3-b]pyridin-2-yl)-2-methylpiperidin-1-yl)ethan-1-ol (I-20-iii)

2-((2S,3S)-3-(4-(benzo[d]thiazol-5-ylamino)thieno[2,3-b]pyridin-2-yl)-2-methylpiperidin-1-yl)ethan-1-ol (I-20-iv)

N-(2-(octahydro-2H-quinolizin-1-yl)thieno[2,3-b]pyridin-4-yl)benzo[d]thiazol-5-amine (I-21)

N-(2-((1R)-octahydro-2H-quinolizin-1-yl)thieno[2,3-b]pyridin-4-yl)benzo[d]thiazol-5-amine (I-21-i)

N-(2-((1S)-octahydro-2H-quinolizin-1-yl)thieno[2,3-b]pyridin-4-yl)benzo[d]thiazol-5-amine (I-21-ii)

N-(2-(2-ethylpiperidin-3-yl)thieno[2,3-b]pyridin-4-yl)benzo[d]thiazol-5-amine (I-22)

N-(2-((2R,3R)-2-ethylpiperidin-3-yl)thieno[2,3-b]pyridin-4-yl)benzo[d]thiazol-5-amine (I-22-i)

N-((2-((2S,3R)-2-ethylpiperidin-3-yl)thieno[2,3-b]pyridin-4-yl)benzo[d]thiazol-5-amine (I-22-ii)

N-(2-((2R,3S)-2-ethylpiperidin-3-yl)thieno[2,3-b]pyridin-4-yl)benzo[d]thiazol-5-amine (I-22-iii)

N-(2-((2S,3S)-2-ethylpiperidin-3-yl)thieno[2,3-b]pyridin-4-yl)benzo[d]thiazol-5-amine (I-22-iv)

N-(2-(2-ethyl-1-methylpiperidin-3-yl)thieno[2,3-b]pyridin-4-yl)benzo[d]thiazol-5-amine (I-23)

N-(2-((2R,3R)-2-ethyl-1-methylpiperidin-3-yl)thieno[2,3-b]pyridin-4-yl)benzo[d]thiazol-5-amine (I-23-i)

N-((2-((2S,3R)-2-ethyl-1-methylpiperidin-3-yl)thieno[2,3-b]pyridin-4-yl)benzo[d]thiazol-5-amine (I-23-ii)

N-(2-((2R,3S)-2-ethyl-1-methylpiperidin-3-yl)thieno[2,3-b]pyridin-4-yl)benzo[d]thiazol-5-amine (I-23-iii)

N-(2-((2S,3S)-2-ethyl-1-methylpiperidin-3-yl)thieno[2,3-b]pyridin-4-yl)benzo[d]thiazol-5-amine (I-23-iv)

N-(2-(1,2-diethylpiperidin-3-yl)thieno[2,3-b]pyridin-4-yl)benzo[d]thiazol-5-amine (I-24)

N-(2-((2R,3R)-1,2-diethylpiperidin-3-yl)thieno[2,3-b]pyridin-4-yl)benzo[d]thiazol-5-amine (I-24-i)

N-(2-((2S,3R)-1,2-diethylpiperidin-3-yl)thieno[2,3-b]pyridin-4-yl)benzo[d]thiazol-5-amine (I-24-ii)

N-(2-((2R,3S)-1,2-diethylpiperidin-3-yl)thieno[2,3-b]pyridin-4-yl)benzo[d]thiazol-5-amine (I-24-iii)

N-(2-((2S,3S)-1,2-diethylpiperidin-3-yl)thieno[2,3-b]pyridin-4-yl)benzo[d]thiazol-5-amine (I-24-iv)

N-(2-(2-methyl-2,5-dihydro-1H-pyrrol-3-yl)thieno[2,3-b]pyridin-4-yl)benzo[d]thiazol-5-amine (I-25)

(R)—N-(2-(2-methyl-2,5-dihydro-1H-pyrrol-3-yl)thieno[2,3-b]pyridin-4-yl)benzo[d]thiazol-5-amine (I-25-i)

(S)—N-(2-(2-methyl-2,5-dihydro-1H-pyrrol-3-yl)thieno[2,3-b]pyridin-4-yl)benzo[d]thiazol-5-amine (I-25-ii)

N-(2-(2-methylpyrrolidin-3-yl)thieno[2,3-b]pyridin-4-yl)benzo[d]thiazol-5-amine (I-26)

N-(2-((2R,3R)-2-methylpyrrolidin-3-yl)thieno[2,3-b]pyridin-4-yl)benzo[d]thiazol-5-amine (I-26-i)

N-(2-((2S,3R)-2-methylpyrrolidin-3-yl)thieno[2,3-b]pyridin-4-yl)benzo[d]thiazol-5-amine (I-26-ii)

N-(2-((2R,3S)-2-methylpyrrolidin-3-yl)thieno[2,3-b]pyridin-4-yl)benzo[d]thiazol-5-amine (I-26-iii)

N-(2-((2S,3S)-2-methylpyrrolidin-3-yl)thieno[2,3-b]pyridin-4-yl)benzo[d]thiazol-5-amine (I-26-iv)

N-(2-(1,2-dimethyl-2,5-dihydro-1H-pyrrol-3-yl)thieno[2,3-b]pyridin-4-yl)benzo[d]thiazol-5-amine (I-27)

(R)—N-(2-(1,2-dimethyl-2,5-dihydro-1H-pyrrol-3-yl)thieno[2,3-b]pyridin-4-yl)benzo[d]thiazol-5-amine (I-27-i)

(S)—N-(2-(1,2-dimethyl-2,5-dihydro-1H-pyrrol-3-yl)thieno[2,3-b]pyridin-4-yl)benzo[d]thiazol-5-amine (I-27-ii)

N-(2-(1,2-dimethylpyrrolidin-3-yl)thieno[2,3-b]pyridin-4-yl)benzo[d]thiazol-5-amine (I-28)

N-(2-((2R,3R)-1,2-dimethylpyrrolidin-3-yl)thieno[2,3-b]pyridin-4-yl)benzo[d]thiazol-5-amine (I-28-i)

N-(2-((2S,3R)-1,2-dimethylpyrrolidin-3-yl)thieno[2,3-b]pyridin-4-yl)benzo[d]thiazol-5-amine (I-28-ii)

N-(2-((2R,3S)-1,2-dimethylpyrrolidin-3-yl)thieno[2,3-b]pyridin-4-yl)benzo[d]thiazol-5-amine (I-28-iii)

N-(2-((2S,3S)-1,2-dimethylpyrrolidin-3-yl)thieno[2,3-b]pyridin-4-yl)benzo[d]thiazol-5-amine (I-28-iv)

N-(2-(1-ethyl-2-methyl-2,5-dihydro-1H-pyrrol-3-yl)thieno[2,3-b]pyridin-4-yl)benzo[d]thiazol-5-amine (I-29)

(R)—N-(2-(1-ethyl-2-methyl-2,5-dihydro-1H-pyrrol-3-yl)thieno[2,3-b]pyridin-4-yl)benzo[d]thiazol-5-amine (I-29-i)

(S)—N-(2-(1-ethyl-2-methyl-2,5-dihydro-1H-pyrrol-3-yl)thieno[2,3-b]pyridin-4-yl)benzo[d]thiazol-5-amine (I-29-ii)

N-(2-(1-ethyl-2-methylpyrrolidin-3-yl)thieno[2,3-b]pyridin-4-yl)benzo[d]thiazol-5-amine (I-29)

N-(2-((2R,3R)-1-ethyl-2-methylpyrrolidin-3-yl)thieno[2,3-b]pyridin-4-yl)benzo[d]thiazol-5-amine (I-30-i)

N-(2-((2S,3R)-1-ethyl-2-methylpyrrolidin-3-yl)thieno[2,3-b]pyridin-4-yl)benzo[d]thiazol-5-amine (I-30-ii)

N-(2-((2R,3S)-1-ethyl-2-methylpyrrolidin-3-yl)thieno[2,3-b]pyridin-4-yl)benzo[d]thiazol-5-amine (I-30-iii)

N-(2-((2S,3S)-1-ethyl-2-methylpyrrolidin-3-yl)thieno[2,3-b]pyridin-4-yl)benzo[d]thiazol-5-amine (I-30-iv)

2-(3-(4-(benzo[d]thiazol-5-ylamino)thieno[2,3-b]pyridin-2-yl)-2-methylpyrrolidin-1-yl)ethan-1-ol (I-31)
2-((2R,3R)-3-(4-(benzo[d]thiazol-5-ylamino)thieno[2,3-b]pyridin-2-yl)-2-methylpyrrolidin-1-yl)ethan-1-ol (I-31-i)
2-((2S,3R)-3-(4-(benzo[d]thiazol-5-ylamino)thieno[2,3-b]pyridin-2-yl)-2-methylpyrrolidin-1-yl)ethan-1-ol (I-31-ii)
2-((2R,3S)-3-(4-(benzo[d]thiazol-5-ylamino)thieno[2,3-b]pyridin-2-yl)-2-methylpyrrolidin-1-yl)ethan-1-ol (I-31-iii)
2-((2S,3S)-3-(4-(benzo[d]thiazol-5-ylamino)thieno[2,3-b]pyridin-2-yl)-2-methylpyrrolidin-1-yl)ethan-1-ol (I-31-iv)
N-(2-(2,2-dimethyl-2,5-dihydro-1H-pyrrol-3-yl)thieno[2,3-b]pyridin-4-yl)benzo[d]thiazol-5-amine (I-32)
N-(2-(2,2-dimethylpyrrolidin-3-yl)thieno[2,3-b]pyridin-4-yl)benzo[d]thiazol-5-amine (I-33)
(R)—N-(2-(2,2-dimethylpyrrolidin-3-yl)thieno[2,3-b]pyridin-4-yl)benzo[d]thiazol-5-amine (I-33-i)
(S)—N-(2-(2,2-dimethylpyrrolidin-3-yl)thieno[2,3-b]pyridin-4-yl)benzo[d]thiazol-5-amine (I-33-ii)
N-(2-(1,2,2-trimethyl-2,5-dihydro-1H-pyrrol-3-yl)thieno[2,3-b]pyridin-4-yl)benzo[d]thiazol-5-amine (I-34)
N-(2-(1,2,2-trimethylpyrrolidin-3-yl)thieno[2,3-b]pyridin-4-yl)benzo[d]thiazol-5-amine (I-35)
(R)—N-(2-(1,2,2-trimethylpyrrolidin-3-yl)thieno[2,3-b]pyridin-4-yl)benzo[d]thiazol-5-amine (I-35-i)
(S)—N-(2-(1,2,2-trimethylpyrrolidin-3-yl)thieno[2,3-b]pyridin-4-yl)benzo[d]thiazol-5-amine (I-35-ii)
N-(2-(1-ethyl-2,2-dimethyl-2,5-dihydro-1H-pyrrol-3-yl)thieno[2,3-b]pyridin-4-yl)benzo[d]thiazol-5-amine (I-36)
N-(2-(1-ethyl-2,2-dimethylpyrrolidin-3-yl)thieno[2,3-b]pyridin-4-yl)benzo[d]thiazol-5-amine (I-37)
(R)—N-(2-(1-ethyl-2,2-dimethylpyrrolidin-3-yl)thieno[2,3-b]pyridin-4-yl)benzo[d]thiazol-5-amine (I-37-i)
(S)—N-(2-(1-ethyl-2,2-dimethylpyrrolidin-3-yl)thieno[2,3-b]pyridin-4-yl)benzo[d]thiazol-5-amine (I-37-ii)
2-(3-(4-(benzo[d]thiazol-5-ylamino)thieno[2,3-b]pyridin-2-yl)-2,2-dimethylpyrrolidin-1-yl)ethan-1-ol (I-38)
(R)-2-(3-(4-(benzo[d]thiazol-5-ylamino)thieno[2,3-b]pyridin-2-yl)-2,2-dimethylpyrrolidin-1-yl)ethan-1-ol (I-38-i)
(S)-2-(3-(4-(benzo[d]thiazol-5-ylamino)thieno[2,3-b]pyridin-2-yl)-2,2-dimethylpyrrolidin-1-yl)ethan-1-ol (I-38-ii)
N-(2-(2-oxa-5-azaspiro[3.4]oct-7-en-8-yl)thieno[2,3-b]pyridin-4-yl)benzo[d]thiazol-5-amine (I-39)
N-(2-(7-oxa-1-azaspiro[4.4]non-3-en-4-yl)thieno[2,3-b]pyridin-4-yl)benzo[d]thiazol-5-amine (I-40)
(S)—N-(2-(7-oxa-1-azaspiro[4.4]non-3-en-4-yl)thieno[2,3-b]pyridin-4-yl)benzo[d]thiazol-5-amine (I-40-i)
(R)—N-(2-(7-oxa-1-azaspiro[4.4]non-3-en-4-yl)thieno[2,3-b]pyridin-4-yl)benzo[d]thiazol-5-amine (I-40-ii)
N-(2-(1-methyl-7-oxa-1-azaspiro[4.4]non-3-en-4-yl)thieno[2,3-b]pyridin-4-yl)benzo[d]thiazol-5-amine (I-41)
(S)—N-(2-(1-methyl-7-oxa-1-azaspiro[4.4]non-3-en-4-yl)thieno[2,3-b]pyridin-4-yl)benzo[d]thiazol-5-amine (I-41-i)
(R)—N-(2-(1-methyl-7-oxa-1-azaspiro[4.4]non-3-en-4-yl)thieno[2,3-b]pyridin-4-yl)benzo[d]thiazol-5-amine (I-41-ii)
N-(2-(7-oxa-1-azaspiro[4.4]nonan-4-yl)thieno[2,3-b]pyridin-4-yl)benzo[d]thiazol-5-amine (I-42)
N-(2-((4R,5S)-7-oxa-1-azaspiro[4.4]nonan-4-yl)thieno[2,3-b]pyridin-4-yl)benzo[d]thiazol-5-amine (I-42-i)
N-(2-((4R,5R)-7-oxa-1-azaspiro[4.4]nonan-4-yl)thieno[2,3-b]pyridin-4-yl)benzo[d]thiazol-5-amine (I-42-ii)
N-(2-((4S,5S)-7-oxa-1-azaspiro[4.4]nonan-4-yl)thieno[2,3-b]pyridin-4-yl)benzo[d]thiazol-5-amine (I-42-iii)
N-(2-((4S,5R)-7-oxa-1-azaspiro[4.4]nonan-4-yl)thieno[2,3-b]pyridin-4-yl)benzo[d]thiazol-5-amine (I-42-iv)
N-(2-(1-methyl-7-oxa-1-azaspiro[4.4]nonan-4-yl)thieno[2,3-b]pyridin-4-yl)benzo[d]thiazol-5-amine (I-43)
N-(2-((4R,5S)-1-methyl-7-oxa-1-azaspiro[4.4]nonan-4-yl)thieno[2,3-b]pyridin-4-yl)benzo[d]thiazol-5-amine (I-43-i)
N-(2-((4R,5R)-1-methyl-7-oxa-1-azaspiro[4.4]nonan-4-yl)thieno[2,3-b]pyridin-4-yl)benzo[d]thiazol-5-amine (I-43-ii)
N-(2-((4S,5S)-1-methyl-7-oxa-1-azaspiro[4.4]nonan-4-yl)thieno[2,3-b]pyridin-4-yl)benzo[d]thiazol-5-amine (I-43-iii)
N-(2-((4S,5R)-1-methyl-7-oxa-1-azaspiro[4.4]nonan-4-yl)thieno[2,3-b]pyridin-4-yl)benzo[d]thiazol-5-amine (I-43-iv)
N-(2-(1-ethyl-7-oxa-1-azaspiro[4.4]non-3-en-4-yl)thieno[2,3-b]pyridin-4-yl)benzo[d]thiazol-5-amine (I-44)
(S)—N-(2-(1-ethyl-7-oxa-1-azaspiro[4.4]non-3-en-4-yl)thieno[2,3-b]pyridin-4-yl)benzo[d]thiazol-5-amine (I-44-i)
(R)—N-(2-(1-ethyl-7-oxa-1-azaspiro[4.4]non-3-en-4-yl)thieno[2,3-b]pyridin-4-yl)benzo[d]thiazol-5-amine (I-44-ii)
N-(2-(1-ethyl-7-oxa-1-azaspiro[4.4]nonan-4-yl)thieno[2,3-b]pyridin-4-yl)benzo[d]thiazol-5-amine (I-45)
N-(2-((4R,5S)-1-ethyl-7-oxa-1-azaspiro[4.4]nonan-4-yl)thieno[2,3-b]pyridin-4-yl)benzo[d]thiazol-5-amine (I-45-i)
N-(2-((4R,5R)-1-ethyl-7-oxa-1-azaspiro[4.4]nonan-4-yl)thieno[2,3-b]pyridin-4-yl)benzo[d]thiazol-5-amine (I-45-ii)
N-(2-((4S,5S)-1-ethyl-7-oxa-1-azaspiro[4.4]nonan-4-yl)thieno[2,3-b]pyridin-4-yl)benzo[d]thiazol-5-amine (I-45-iii)
N-(2-((4S,5R)-1-ethyl-7-oxa-1-azaspiro[4.4]nonan-4-yl)thieno[2,3-b]pyridin-4-yl)benzo[d]thiazol-5-amine (I-45-iv)
N-(2-(8-oxa-1-azaspiro[4.5]dec-3-en-4-yl)thieno[2,3-b]pyridin-4-yl)benzo[d]thiazol-5-amine (I-46)
N-(2-(1-ethyl-8-oxa-1-azaspiro[4.5]dec-3-en-4-yl)thieno[2,3-b]pyridin-4-yl)benzo[d]thiazol-5-amine (I-47)
N-(2-(1-ethyl-8-oxa-1-azaspiro[4.5]decan-4-yl)thieno[2,3-b]pyridin-4-yl)benzo[d]thiazol-5-amine (I-48)
(R)—N-(2-(1-ethyl-8-oxa-1-azaspiro[4.5]decan-4-yl)thieno[2,3-b]pyridin-4-yl)benzo[d]thiazol-5-amine (I-48-i)
(S)—N-(2-(1-ethyl-8-oxa-1-azaspiro[4.5]decan-4-yl)thieno[2,3-b]pyridin-4-yl)benzo[d]thiazol-5-amine (I-48-ii)
6-fluoro-N-(2-(2-methyl-1,2,5,6-tetrahydropyridin-3-yl)thieno[2,3-b]pyridin-4-yl)benzo[d]thiazol-5-amine (I-49)
(R)-6-fluoro-N-(2-(2-methyl-1,2,5,6-tetrahydropyridin-3-yl)thieno[2,3-b]pyridin-4-yl)benzo[d]thiazol-5-amine (I-49-i)
(S)-6-fluoro-N-(2-(2-methyl-1,2,5,6-tetrahydropyridin-3-yl)thieno[2,3-b]pyridin-4-yl)benzo[d]thiazol-5-amine (I-49-ii)
6-fluoro-N-(2-(2-methylpiperidin-3-yl)thieno[2,3-b]pyridin-4-yl)benzo[d]thiazol-5-amine (I-50)
6-fluoro-N-(2-((2R,3R)-2-methylpiperidin-3-yl)thieno[2,3-b]pyridin-4-yl)benzo[d]thiazol-5-amine (I-50-i)
6-fluoro-N-(2-((2S,3R)-2-methylpiperidin-3-yl)thieno[2,3-b]pyridin-4-yl)benzo[d]thiazol-5-amine (I-50-ii)
6-fluoro-N-(2-((2R,3S)-2-methylpiperidin-3-yl)thieno[2,3-b]pyridin-4-yl)benzo[d]thiazol-5-amine (I-50-iii)
6-fluoro-N-(2-((2S,3S)-2-methylpiperidin-3-yl)thieno[2,3-b]pyridin-4-yl)benzo[d]thiazol-5-amine (I-50-iv)

N-(2-(1-ethyl-2-methyl-1,2,5,6-tetrahydropyridin-3-yl)
thieno[2,3-b]pyridin-4-yl)-6-fluorobenzo[d]thiazol-5-
amine (I-51)

(R)—N-(2-(1-ethyl-2-methyl-1,2,5,6-tetrahydropyridin-3-
yl)thieno[2,3-b]pyridin-4-yl)-6-fluorobenzo[d]thiazol-5-
amine (I-51-i)

(S)—N-(2-(1-ethyl-2-methyl-1,2,5,6-tetrahydropyridin-3-
yl)thieno[2,3-b]pyridin-4-yl)-6-fluorobenzo[d]thiazol-5-
amine (I-51-ii)

N-(2-(1-ethyl-2-methylpiperidin-3-yl)thieno[2,3-b]pyridin-
4-yl)-6-fluorobenzo[d]thiazol-5-amine (I-52)

N-(2-((2R,3R)-1-ethyl-2-methylpiperidin-3-yl)thieno[2,3-
b]pyridin-4-yl)-6-fluorobenzo[d]thiazol-5-amine (I-52-i)

N-(2-((2S,3R)-1-ethyl-2-methylpiperidin-3-yl)thieno[2,3-b]
pyridin-4-yl)-6-fluorobenzo[d]thiazol-5-amine (I-52-ii)

N-(2-((2R,3S)-1-ethyl-2-methylpiperidin-3-yl)thieno[2,3-b]
pyridin-4-yl)-6-fluorobenzo[d]thiazol-5-amine (I-52-iii)

N-(2-((2S,3S)-1-ethyl-2-methylpiperidin-3-yl)thieno[2,3-b]
pyridin-4-yl)-6-fluorobenzo[d]thiazol-5-amine (I-52-iv)

tert-butyl 5-(4-((4-fluorobenzo[d]thiazol-5-yl)amino)thieno
[2,3-b]pyridin-2-yl)-6-methyl-3,6-dihydropyridine-1
(2H)-carboxylate (I-53)

tert-butyl (R)-5-(4-((4-fluorobenzo[d]thiazol-5-yl)amino)
thieno[2,3-b]pyridin-2-yl)-6-methyl-3,6-dihydropyri-
dine-1(2H)-carboxylate (I-53-i)

tert-butyl (S)-5-(4-((4-fluorobenzo[d]thiazol-5-yl)amino)
thieno[2,3-b]pyridin-2-yl)-6-methyl-3,6-dihydropyri-
dine-1(2H)-carboxylate (I-53-ii)

4-fluoro-N-(2-(2-methylpiperidin-3-yl)thieno[2,3-b]pyri-
din-4-yl)benzo[d]thiazol-5-amine (I-54)

4-fluoro-N-(2-((2R,3R)-2-methylpiperidin-3-yl)thieno[2,3-
b]pyridin-4-yl)benzo[d]thiazol-5-amine (I-54-i)

4-fluoro-N-(2-((2S,3R)-2-methylpiperidin-3-yl)thieno[2,3-
b]pyridin-4-yl)benzo[d]thiazol-5-amine (I-54-ii)

4-fluoro-N-(2-((2R,3S)-2-methylpiperidin-3-yl)thieno[2,3-
b]pyridin-4-yl)benzo[d]thiazol-5-amine (I-54-iii)

4-fluoro-N-(2-((2S,3S)-2-methylpiperidin-3-yl)thieno[2,3-
b]pyridin-4-yl)benzo[d]thiazol-5-amine (I-54-iv)

N-(2-(1,2-dimethylpiperidin-3-yl)thieno[2,3-b]pyridin-4-
yl)-4-fluorobenzo[d]thiazol-5-amine (I-55)

N-(2-((2R,3R)-1,2-dimethylpiperidin-3-yl)thieno[2,3-b]
pyridin-4-yl)-4-fluorobenzo[d]thiazol-5-amine (I-55-i)

N-((2S,3R)-1,2-dimethylpiperidin-3-yl)thieno[2,3-b]
pyridin-4-yl)-4-fluorobenzo[d]thiazol-5-amine (I-55-ii)

N-(2-((2R,3S)-1,2-dimethylpiperidin-3-yl)thieno[2,3-b]
pyridin-4-yl)-4-fluorobenzo[d]thiazol-5-amine (I-55-iii)

N-(2-((2S,3S)-1,2-dimethylpiperidin-3-yl)thieno[2,3-b]
pyridin-4-yl)-4-fluorobenzo[d]thiazol-5-amine (I-55-iv)

N-(2-(1-ethyl-2-methylpiperidin-3-yl)thieno[2,3-b]pyridin-
4-yl)-4-fluorobenzo[d]thiazol-5-amine (I-56)

N-(2-((2R,3R)-1-ethyl-2-methylpiperidin-3-yl)thieno[2,3-
b]pyridin-4-yl)-4-fluorobenzo[d]thiazol-5-amine (I-56-i)

N-(2-((2S,3R)-1-ethyl-2-methylpiperidin-3-yl)thieno[2,3-b]
pyridin-4-yl)-4-fluorobenzo[d]thiazol-5-amine (I-56-ii)

N-(2-((2R,3S)-1-ethyl-2-methylpiperidin-3-yl)thieno[2,3-b]
pyridin-4-yl)-4-fluorobenzo[d]thiazol-5-amine (I-56-iii)

N-(2-((2S,3S)-1-ethyl-2-methylpiperidin-3-yl)thieno[2,3-b]
pyridin-4-yl)-4-fluorobenzo[d]thiazol-5-amine (I-56-iv)

4,6-difluoro-N-(2-(2-methyl-1,2,5,6-tetrahydropyridin-3-yl)
thieno[2,3-b]pyridin-4-yl)benzo[d]thiazol-5-amine (I-57)

(R)-4,6-difluoro-N-(2-(2-methyl-1,2,5,6-tetrahydropyridin-
3-yl)thieno[2,3-b]pyridin-4-yl)benzo[d]thiazol-5-amine
(I-57-i)

(S)-4,6-difluoro-N-(2-(2-methyl-1,2,5,6-tetrahydropyridin-
3-yl)thieno[2,3-b]pyridin-4-yl)benzo[d]thiazol-5-amine
(I-57-ii)

4,6-difluoro-N-(2-(2-methylpiperidin-3-yl)thieno[2,3-b]
pyridin-4-yl)benzo[d]thiazol-5-amine (I-58)

4,6-difluoro-N-(2-((2R,3R)-2-methylpiperidin-3-yl)thieno
[2,3-b]pyridin-4-yl)benzo[d]thiazol-5-amine (I-58-i)

4,6-difluoro-N-(2-((2S,3R)-2-methylpiperidin-3-yl)thieno
[2,3-b]pyridin-4-yl)benzo[d]thiazol-5-amine (I-58-ii)

4,6-difluoro-N-(2-((2R,3S)-2-methylpiperidin-3-yl)thieno
[2,3-b]pyridin-4-yl)benzo[d]thiazol-5-amine (I-58-iii)

4,6-difluoro-N-(2-((2S,3S)-2-methylpiperidin-3-yl)thieno
[2,3-b]pyridin-4-yl)benzo[d]thiazol-5-amine (I-58-iv)

N-(2-(1,2-dimethyl-1,2,5,6-tetrahydropyridin-3-yl)thieno[2,
3-b]pyridin-4-yl)-4,6-difluorobenzo[d]thiazol-5-amine
(I-59)

(R)—N-(2-(1,2-dimethyl-1,2,5,6-tetrahydropyridin-3-yl)
thieno[2,3-b]pyridin-4-yl)-4,6-difluorobenzo[d]thiazol-5-
amine (I-59-i)

(S)—N-(2-(1,2-dimethyl-1,2,5,6-tetrahydropyridin-3-yl)
thieno[2,3-b]pyridin-4-yl)-4,6-difluorobenzo[d]thiazol-5-
amine (I-59-ii)

N-(2-(1,2-dimethylpiperidin-3-yl)thieno[2,3-b]pyridin-4-
yl)-4,6-difluorobenzo[d]thiazol-5-amine (I-60)

N-(2-((2R,3R)-1,2-dimethylpiperidin-3-yl)thieno[2,3-b]
pyridin-4-yl)-4,6-difluorobenzo[d]thiazol-5-amine (I-60-
i)

N-(2-((2R,3S)-1,2-dimethylpiperidin-3-yl)thieno[2,3-b]
pyridin-4-yl)-4,6-difluorobenzo[d]thiazol-5-amine (I-60-
ii)

N-(2-((2S,3R)-1,2-dimethylpiperidin-3-yl)thieno[2,3-b]
pyridin-4-yl)-4,6-difluorobenzo[d]thiazol-5-amine (I-60-
iii)

N-(2-((2S,3S)-1,2-dimethylpiperidin-3-yl)thieno[2,3-b]
pyridin-4-yl)-4,6-difluorobenzo[d]thiazol-5-amine (I-60-
iv)

N-(2-(1-ethyl-2-methyl-1,2,5,6-tetrahydropyridin-3-yl)
thieno[2,3-b]pyridin-4-yl)-4,6-difluorobenzo[d]thiazol-5-
amine (I-61)

(R)—N-(2-(1-ethyl-2-methyl-1,2,5,6-tetrahydropyridin-3-
yl)thieno[2,3-b]pyridin-4-yl)-4,6-difluorobenzo[d]thi-
azol-5-amine (I-61-i)

(S)—N-(2-(1-ethyl-2-methyl-1,2,5,6-tetrahydropyridin-3-
yl)thieno[2,3-b]pyridin-4-yl)-4,6-difluorobenzo[d]thi-
azol-5-amine (I-61-ii)

N-(2-(1-ethyl-2-methylpiperidin-3-yl)thieno[2,3-b]pyridin-
4-yl)-4,6-difluorobenzo[d]thiazol-5-amine (I-62)

N-(2-((2R,3R)-1-ethyl-2-methylpiperidin-3-yl)thieno[2,3-
b]pyridin-4-yl)-4,6-difluorobenzo[d]thiazol-5-amine
(I-62-i)

N-(2-((2S,3R)-1-ethyl-2-methylpiperidin-3-yl)thieno[2,3-b]
pyridin-4-yl)-4,6-difluorobenzo[d]thiazol-5-amine (I-62-
ii)

N-(2-((2R,3S)-1-ethyl-2-methylpiperidin-3-yl)thieno[2,3-b]
pyridin-4-yl)-4,6-difluorobenzo[d]thiazol-5-amine (I-62-
iii)

N-(2-((2S,3S)-1-ethyl-2-methylpiperidin-3-yl)thieno[2,3-b]
pyridin-4-yl)-4,6-difluorobenzo[d]thiazol-5-amine (I-62-
iv)

2-(3-(4-((4-fluorobenzo[d]thiazol-5-yl)amino)thieno[2,3-b]
pyridin-2-yl)-2-methylpyrrolidin-1-yl)ethan-1-ol (I-63)

2-((2R,3R)-3-(4-((4-fluorobenzo[d]thiazol-5-yl)amino)
thieno[2,3-b]pyridin-2-yl)-2-methylpyrrolidin-1-yl)
ethan-1-ol (I-63-i)

2-((2S,3R)-3-(4-((4-fluorobenzo[d]thiazol-5-yl)amino)
thieno[2,3-b]pyridin-2-yl)-2-methylpyrrolidin-1-yl)
ethan-1-ol (I-63-ii)

2-((2R,3S)-3-(4-((4-fluorobenzo[d]thiazol-5-yl)amino)
thieno[2,3-b]pyridin-2-yl)-2-methylpyrrolidin-1-yl)
ethan-1-ol (I-63-iii)

2-((2S,3S)-3-(4-((4-fluorobenzo[d]thiazol-5-yl)amino) thieno[2,3-b]pyridin-2-yl)-2-methylpyrrolidin-1-yl) ethan-1-ol (I-63-iv)
4,6-difluoro-N-(2-(2-methylpyrrolidin-3-yl)thieno[2,3-b] pyridin-4-yl)benzo[d]thiazol-5-amine (I-64)
4,6-difluoro-N-(2-((2R,3R)-2-methylpyrrolidin-3-yl)thieno [2,3-b]pyridin-4-yl)benzo[d]thiazol-5-amine (I-64-i)
4,6-difluoro-N-(2-((2S,3R)-2-methylpyrrolidin-3-yl)thieno [2,3-b]pyridin-4-yl)benzo[d]thiazol-5-amine (I-64-ii)
4,6-difluoro-N-(2-((2R,3S)-2-methylpyrrolidin-3-yl)thieno [2,3-b]pyridin-4-yl)benzo[d]thiazol-5-amine (I-64-iii)
4,6-difluoro-N-(2-((2S,3S)-2-methylpyrrolidin-3-yl)thieno [2,3-b]pyridin-4-yl)benzo[d]thiazol-5-amine (I-64-iv)
4-fluoro-N-(2-(2-methylpyrrolidin-3-yl)thieno[2,3-b]pyridin-4-yl)benzo[d]thiazol-5-amine (I-65)
4-fluoro-N-(2-((2R,3R)-2-methylpyrrolidin-3-yl)thieno[2,3-b]pyridin-4-yl)benzo[d]thiazol-5-amine (I-65-i)
4-fluoro-N-(2-((2S,3R)-2-methylpyrrolidin-3-yl)thieno[2,3-b]pyridin-4-yl)benzo[d]thiazol-5-amine (I-65-ii)
4-fluoro-N-(2-((2R,3S)-2-methylpyrrolidin-3-yl)thieno[2,3-b]pyridin-4-yl)benzo[d]thiazol-5-amine (I-65-iii)
4-fluoro-N-(2-((2S,3S)-2-methylpyrrolidin-3-yl)thieno[2,3-b]pyridin-4-yl)benzo[d]thiazol-5-amine (I-65-iv)
N-(2-(2,2-dimethylpyrrolidin-3-yl)thieno[2,3-b]pyridin-4-yl)-4,6-difluorobenzo[d]thiazol-5-amine (I-66)
(R)—N-(2-(2,2-dimethylpyrrolidin-3-yl)thieno[2,3-b]pyridin-4-yl)-4,6-difluorobenzo[d]thiazol-5-amine (I-66-i)
(S)—N-(2-(2,2-dimethylpyrrolidin-3-yl)thieno[2,3-b]pyridin-4-yl)-4,6-difluorobenzo[d]thiazol-5-amine (I-66-ii)
6-fluoro-N-(2-(2-methylpyrrolidin-3-yl)thieno[2,3-b]pyridin-4-yl)benzo[d]thiazol-5-amine (I-67)
6-fluoro-N-(2-((2R,3R)-2-methylpyrrolidin-3-yl)thieno[2,3-b]pyridin-4-yl)benzo[d]thiazol-5-amine (I-67-i)
6-fluoro-N-(2-((2S,3R)-2-methylpyrrolidin-3-yl)thieno[2,3-b]pyridin-4-yl)benzo[d]thiazol-5-amine (I-67-ii)
6-fluoro-N-(2-((2R,3S)-2-methylpyrrolidin-3-yl)thieno[2,3-b]pyridin-4-yl)benzo[d]thiazol-5-amine (I-67-iii)
6-fluoro-N-(2-((2S,3S)-2-methylpyrrolidin-3-yl)thieno[2,3-b]pyridin-4-yl)benzo[d]thiazol-5-amine (I-67-iv)
2-(3-(4-((4-fluorobenzo[d]thiazol-5-yl)amino)thieno[2,3-b]pyridin-2-yl)-2,2-dimethylpyrrolidin-1-yl)ethan-1-ol (I-68)
(R)-2-(3-(4-((4-fluorobenzo[d]thiazol-5-yl)amino)thieno[2,3-b]pyridin-2-yl)-2,2-dimethylpyrrolidin-1-yl)ethan-1-ol (I-68-i)
(S)-2-(3-(4-((4-fluorobenzo[d]thiazol-5-yl)amino)thieno[2,3-b]pyridin-2-yl)-2,2-dimethylpyrrolidin-1-yl)ethan-1-ol (I-68-ii)
2-(3-(4-((6-fluorobenzo[d]thiazol-5-yl)amino)thieno[2,3-b]pyridin-2-yl)-2,2-dimethylpyrrolidin-1-yl)ethan-1-ol (I-69)
(R)-2-(3-(4-((6-fluorobenzo[d]thiazol-5-yl)amino)thieno[2,3-b]pyridin-2-yl)-2,2-dimethylpyrrolidin-1-yl)ethan-1-ol (I-69-i)
(S)-2-(3-(4-((6-fluorobenzo[d]thiazol-5-yl)amino)thieno[2,3-b]pyridin-2-yl)-2,2-dimethylpyrrolidin-1-yl)ethan-1-ol (I-69-ii)
N-(2-(2,2-dimethylpyrrolidin-3-yl)thieno[2,3-b]pyridin-4-yl)-6-fluorobenzo[d]thiazol-5-amine (I-70)
(R)—N-(2-(2,2-dimethylpyrrolidin-3-yl)thieno[2,3-b]pyridin-4-yl)-6-fluorobenzo[d]thiazol-5-amine (I-70-i)
(S)—N-(2-(2,2-dimethylpyrrolidin-3-yl)thieno[2,3-b]pyridin-4-yl)-6-fluorobenzo[d]thiazol-5-amine (I-70-ii)
N-(2-(2,2-dimethylpyrrolidin-3-yl)thieno[2,3-b]pyridin-4-yl)-4-fluorobenzo[d]thiazol-5-amine (I-71)
(R)—N-(2-(2,2-dimethylpyrrolidin-3-yl)thieno[2,3-b]pyridin-4-yl)-4-fluorobenzo[d]thiazol-5-amine (I-71-i)
(S)—N-(2-(2,2-dimethylpyrrolidin-3-yl)thieno[2,3-b]pyridin-4-yl)-4-fluorobenzo[d]thiazol-5-amine (I-71-ii)
2-(3-(4-((4,6-difluorobenzo[d]thiazol-5-yl)amino)thieno[2,3-b]pyridin-2-yl)-2,2-dimethylpyrrolidin-1-yl)ethan-1-ol (I-72)
(R)-2-(3-(4-((4,6-difluorobenzo[d]thiazol-5-yl)amino) thieno[2,3-b]pyridin-2-yl)-2,2-dimethylpyrrolidin-1-yl) ethan-1-ol (I-72-i)
(S)-2-(3-(4-((4,6-difluorobenzo[d]thiazol-5-yl)amino) thieno[2,3-b]pyridin-2-yl)-2,2-dimethylpyrrolidin-1-yl) ethan-1-ol (I-72-ii)
N-(2-(1-ethyl-2,2-dimethylpyrrolidin-3-yl)thieno[2,3-b] pyridin-4-yl)-4,6-difluorobenzo[d]thiazol-5-amine (I-73)
(R)—N-(2-(1-ethyl-2,2-dimethylpyrrolidin-3-yl)thieno[2,3-b]pyridin-4-yl)-4,6-difluorobenzo[d]thiazol-5-amine (I-73-i)
(S)—N-(2-(1-ethyl-2,2-dimethylpyrrolidin-3-yl)thieno[2,3-b]pyridin-4-yl)-4,6-difluorobenzo[d]thiazol-5-amine (I-73-ii)
N-(2-(1-ethyl-2-methylpyrrolidin-3-yl)thieno[2,3-b]pyridin-4-yl)-4-fluorobenzo[d]thiazol-5-amine (I-74)
N-(2-((2R,3R)-1-ethyl-2-methylpyrrolidin-3-yl)thieno[2,3-b]pyridin-4-yl)-4-fluorobenzo[d]thiazol-5-amine (I-74-i)
N-(2-((2S,3R)-1-ethyl-2-methylpyrrolidin-3-yl)thieno[2,3-b]pyridin-4-yl)-4-fluorobenzo[d]thiazol-5-amine (I-74-ii)
N-(2-((2R,3S)-1-ethyl-2-methylpyrrolidin-3-yl)thieno[2,3-b]pyridin-4-yl)-4-fluorobenzo[d]thiazol-5-amine (I-74-iii)
N-(2-((2S,3S)-1-ethyl-2-methylpyrrolidin-3-yl)thieno[2,3-b]pyridin-4-yl)-4-fluorobenzo[d]thiazol-5-amine (I-74-iv)
N-(2-(1-ethyl-2-methylpyrrolidin-3-yl)thieno[2,3-b]pyridin-4-yl)-4,6-difluorobenzo[d]thiazol-5-amine (I-75)
N-(2-((2R,3R)-1-ethyl-2-methylpyrrolidin-3-yl)thieno[2,3-b]pyridin-4-yl)-4,6-difluorobenzo[d]thiazol-5-amine (I-75-i)
N-(2-((2S,3R)-1-ethyl-2-methylpyrrolidin-3-yl)thieno[2,3-b]pyridin-4-yl)-4,6-difluorobenzo[d]thiazol-5-amine (I-75-ii)
N-(2-((2R,3S)-1-ethyl-2-methylpyrrolidin-3-yl)thieno[2,3-b]pyridin-4-yl)-4,6-difluorobenzo[d]thiazol-5-amine (I-75-iii)
N-(2-((2S,3S)-1-ethyl-2-methylpyrrolidin-3-yl)thieno[2,3-b]pyridin-4-yl)-4,6-difluorobenzo[d]thiazol-5-amine (I-75-iv)
2-(3-(4-((4,6-difluorobenzo[d]thiazol-5-yl)amino)thieno[2,3-b]pyridin-2-yl)-2-methylpyrrolidin-1-yl)ethan-1-ol (I-76)
2-((2R,3R)-3-(4-((4,6-difluorobenzo[d]thiazol-5-yl)amino) thieno[2,3-b]pyridin-2-yl)-2-methylpyrrolidin-1-yl) ethan-1-ol (I-76-i)
2-((2S,3R)-3-(4-((4,6-difluorobenzo[d]thiazol-5-yl)amino) thieno[2,3-b]pyridin-2-yl)-2-methylpyrrolidin-1-yl) ethan-1-ol (I-76-ii)
2-((2R,3S)-3-(4-((4,6-difluorobenzo[d]thiazol-5-yl)amino) thieno[2,3-b]pyridin-2-yl)-2-methylpyrrolidin-1-yl) ethan-1-ol (I-76-iii)
2-((2S,3S)-3-(4-((4,6-difluorobenzo[d]thiazol-5-yl)amino) thieno[2,3-b]pyridin-2-yl)-2-methylpyrrolidin-1-yl) ethan-1-ol (I-76-iv)
N-(2-(1-ethyl-2,2-dimethylpyrrolidin-3-yl)thieno[2,3-b] pyridin-4-yl)-4-fluorobenzo[d]thiazol-5-amine (I-77)
(R)—N-(2-(1-ethyl-2,2-dimethylpyrrolidin-3-yl)thieno[2,3-b]pyridin-4-yl)-4-fluorobenzo[d]thiazol-5-amine (I-77-i)
(S)—N-(2-(1-ethyl-2,2-dimethylpyrrolidin-3-yl)thieno[2,3-b]pyridin-4-yl)-4-fluorobenzo[d]thiazol-5-amine (I-77-ii)

N-(2-(1-ethyl-2,2-dimethylpyrrolidin-3-yl)thieno[2,3-b]pyridin-4-yl)-6-fluorobenzo[d]thiazol-5-amine (I-78)
(R)—N-(2-(1-ethyl-2,2-dimethylpyrrolidin-3-yl)thieno[2,3-b]pyridin-4-yl)-6-fluorobenzo[d]thiazol-5-amine (I-78-i)
(S)—N-(2-(1-ethyl-2,2-dimethylpyrrolidin-3-yl)thieno[2,3-b]pyridin-4-yl)-6-fluorobenzo[d]thiazol-5-amine (I-78-ii)
N-(2-(1-ethyl-2-methylpyrrolidin-3-yl)thieno[2,3-b]pyridin-4-yl)-6-fluorobenzo[d]thiazol-5-amine (I-79)
N-(2-((2R,3R)-1-ethyl-2-methylpyrrolidin-3-yl)thieno[2,3-b]pyridin-4-yl)-6-fluorobenzo[d]thiazol-5-amine (I-79-i)
N-(2-((2S,3R)-1-ethyl-2-methylpyrrolidin-3-yl)thieno[2,3-b]pyridin-4-yl)-6-fluorobenzo[d]thiazol-5-amine (I-79-ii)
N-(2-((2R,3S)-1-ethyl-2-methylpyrrolidin-3-yl)thieno[2,3-b]pyridin-4-yl)-6-fluorobenzo[d]thiazol-5-amine (I-79-iii)
N-(2-((2S,3S)-1-ethyl-2-methylpyrrolidin-3-yl)thieno[2,3-b]pyridin-4-yl)-6-fluorobenzo[d]thiazol-5-amine (I-79-iv)
2-(3-(4-((6-fluorobenzo[d]thiazol-5-yl)amino)thieno[2,3-b]pyridin-2-yl)-2-methylpyrrolidin-1-yl)ethan-1-ol (I-80)
2-((2R,3R)-3-(4-((6-fluorobenzo[d]thiazol-5-yl)amino)thieno[2,3-b]pyridin-2-yl)-2-methylpyrrolidin-1-yl)ethan-1-ol (I-80-i)
2-((2S,3R)-3-(4-((6-fluorobenzo[d]thiazol-5-yl)amino)thieno[2,3-b]pyridin-2-yl)-2-methylpyrrolidin-1-yl)ethan-1-ol (I-80-ii)
2-((2R,3S)-3-(4-((6-fluorobenzo[d]thiazol-5-yl)amino)thieno[2,3-b]pyridin-2-yl)-2-methylpyrrolidin-1-yl)ethan-1-ol (I-80-iii)
2-((2S,3S)-3-(4-((6-fluorobenzo[d]thiazol-5-yl)amino)thieno[2,3-b]pyridin-2-yl)-2-methylpyrrolidin-1-yl)ethan-1-ol (I-80-iv)
N-(2-(1-ethyl-8-oxa-1-azaspiro[4.5]decan-4-yl)thieno[2,3-b]pyridin-4-yl)-4,6-difluorobenzo[d]thiazol-5-amine (I-81)
(R)—N-(2-(1-ethyl-8-oxa-1-azaspiro[4.5]decan-4-yl)thieno[2,3-b]pyridin-4-yl)-4,6-difluorobenzo[d]thiazol-5-amine (I-81-i)
(S)—N-(2-(1-ethyl-8-oxa-1-azaspiro[4.5]decan-4-yl)thieno[2,3-b]pyridin-4-yl)-4,6-difluorobenzo[d]thiazol-5-amine (I-81-ii)
4,6-difluoro-N-(2-(1-methyl-8-oxa-1-azaspiro[4.5]decan-4-yl)thieno[2,3-b]pyridin-4-yl)benzo[d]thiazol-5-amine (I-82)
(R)-4,6-difluoro-N-(2-(1-methyl-8-oxa-1-azaspiro[4.5]decan-4-yl)thieno[2,3-b]pyridin-4-yl)benzo[d]thiazol-5-amine (I-82-i)
(S)-4,6-difluoro-N-(2-(1-methyl-8-oxa-1-azaspiro[4.5]decan-4-yl)thieno[2,3-b]pyridin-4-yl)benzo[d]thiazol-5-amine (I-82-ii)
N-(2-(8-oxa-1-azaspiro[4.5]decan-4-yl)thieno[2,3-b]pyridin-4-yl)-4,6-difluorobenzo[d]thiazol-5-amine (I-83)
(R)—N-(2-(8-oxa-1-azaspiro[4.5]decan-4-yl)thieno[2,3-b]pyridin-4-yl)-4,6-difluorobenzo[d]thiazol-5-amine (I-83-i)
(S)—N-(2-(8-oxa-1-azaspiro[4.5]decan-4-yl)thieno[2,3-b]pyridin-4-yl)-4,6-difluorobenzo[d]thiazol-5-amine (I-83-ii)
6-fluoro-N-(2-(1-methyl-8-oxa-1-azaspiro[4.5]decan-4-yl)thieno[2,3-b]pyridin-4-yl)benzo[d]thiazol-5-amine (I-84)
(R)-6-fluoro-N-(2-(1-methyl-8-oxa-1-azaspiro[4.5]decan-4-yl)thieno[2,3-b]pyridin-4-yl)benzo[d]thiazol-5-amine (I-84-i)
(S)-6-fluoro-N-(2-(1-methyl-8-oxa-1-azaspiro[4.5]decan-4-yl)thieno[2,3-b]pyridin-4-yl)benzo[d]thiazol-5-amine (I-84-ii)
N-(2-(1-ethyl-8-oxa-1-azaspiro[4.5]decan-4-yl)thieno[2,3-b]pyridin-4-yl)-6-fluorobenzo[d]thiazol-5-amine (I-85)
(R)—N-(2-(1-ethyl-8-oxa-1-azaspiro[4.5]decan-4-yl)thieno[2,3-b]pyridin-4-yl)-6-fluorobenzo[d]thiazol-5-amine (I-85-i)
(S)—N-(2-(1-ethyl-8-oxa-1-azaspiro[4.5]decan-4-yl)thieno[2,3-b]pyridin-4-yl)-6-fluorobenzo[d]thiazol-5-amine (I-85-ii)
N-(2-(8-oxa-1-azaspiro[4.5]decan-4-yl)thieno[2,3-b]pyridin-4-yl)-6-fluorobenzo[d]thiazol-5-amine (I-86)
(R)—N-(2-(8-oxa-1-azaspiro[4.5]decan-4-yl)thieno[2,3-b]pyridin-4-yl)-6-fluorobenzo[d]thiazol-5-amine (I-86-i)
(S)—N-(2-(8-oxa-1-azaspiro[4.5]decan-4-yl)thieno[2,3-b]pyridin-4-yl)-6-fluorobenzo[d]thiazol-5-amine (I-86-ii)
6-fluoro-N-(2-(1-methyl-7-oxa-1-azaspiro[4.4]nonan-4-yl)thieno[2,3-b]pyridin-4-yl)benzo[d]thiazol-5-amine (I-87)
6-fluoro-N-(2-((4R,5S)-1-methyl-7-oxa-1-azaspiro[4.4]nonan-4-yl)thieno[2,3-b]pyridin-4-yl)benzo[d]thiazol-5-amine (I-87-i)
6-fluoro-N-(2-((4R,5R)-1-methyl-7-oxa-1-azaspiro[4.4]nonan-4-yl)thieno[2,3-b]pyridin-4-yl)benzo[d]thiazol-5-amine (I-87-ii)
6-fluoro-N-(2-((4S,5R)-1-methyl-7-oxa-1-azaspiro[4.4]nonan-4-yl)thieno[2,3-b]pyridin-4-yl)benzo[d]thiazol-5-amine (I-87-iii)
6-fluoro-N-(2-((4S,5S)-1-methyl-7-oxa-1-azaspiro[4.4]nonan-4-yl)thieno[2,3-b]pyridin-4-yl)benzo[d]thiazol-5-amine (I-87-iv)
N-(2-(7-oxa-1-azaspiro[4.4]nonan-4-yl)thieno[2,3-b]pyridin-4-yl)-6-fluorobenzo[d]thiazol-5-amine (I-88)
N-(2-((4R,5S)-7-oxa-1-azaspiro[4.4]nonan-4-yl)thieno[2,3-b]pyridin-4-yl)-6-fluorobenzo[d]thiazol-5-amine (I-88-i)
N-(2-((4R,5R)-7-oxa-1-azaspiro[4.4]nonan-4-yl)thieno[2,3-b]pyridin-4-yl)-6-fluorobenzo[d]thiazol-5-amine (I-88-ii)
N-(2-((4S,5R)-7-oxa-1-azaspiro[4.4]nonan-4-yl)thieno[2,3-b]pyridin-4-yl)-6-fluorobenzo[d]thiazol-5-amine (I-88-iii)
N-(2-((4S,5S)-7-oxa-1-azaspiro[4.4]nonan-4-yl)thieno[2,3-b]pyridin-4-yl)-6-fluorobenzo[d]thiazol-5-amine (I-88-iv)
N-(2-(1-ethyl-7-oxa-1-azaspiro[4.4]nonan-4-yl)thieno[2,3-b]pyridin-4-yl)-4,6-difluorobenzo[d]thiazol-5-amine (I-89)
N-(2-((4R,5S)-1-ethyl-7-oxa-1-azaspiro[4.4]nonan-4-yl)thieno[2,3-b]pyridin-4-yl)-4,6-difluorobenzo[d]thiazol-5-amine (I-89-i)
N-(2-((4R,5R)-1-ethyl-7-oxa-1-azaspiro[4.4]nonan-4-yl)thieno[2,3-b]pyridin-4-yl)-4,6-difluorobenzo[d]thiazol-5-amine (I-89-ii)
N-(2-((4S,5S)-1-ethyl-7-oxa-1-azaspiro[4.4]nonan-4-yl)thieno[2,3-b]pyridin-4-yl)-4,6-difluorobenzo[d]thiazol-5-amine (I-89-iii)
N-(2-((4S,5R)-1-ethyl-7-oxa-1-azaspiro[4.4]nonan-4-yl)thieno[2,3-b]pyridin-4-yl)-4,6-difluorobenzo[d]thiazol-5-amine (I-89-iv)
N-(2-(7-oxa-1-azaspiro[4.4]nonan-4-yl)thieno[2,3-b]pyridin-4-yl)-4,6-difluorobenzo[d]thiazol-5-amine (I-90)
N-(2-((4R,5S)-7-oxa-1-azaspiro[4.4]nonan-4-yl)thieno[2,3-b]pyridin-4-yl)-4,6-difluorobenzo[d]thiazol-5-amine (I-90-i)
N-(2-((4R,5R)-7-oxa-1-azaspiro[4.4]nonan-4-yl)thieno[2,3-b]pyridin-4-yl)-4,6-difluorobenzo[d]thiazol-5-amine (I-90-ii)
N-(2-((4S,5S)-7-oxa-1-azaspiro[4.4]nonan-4-yl)thieno[2,3-b]pyridin-4-yl)-4,6-difluorobenzo[d]thiazol-5-amine (I-90-iii)

N-(2-((4S,5R)-7-oxa-1-azaspiro[4.4]nonan-4-yl)thieno[2,3-b]pyridin-4-yl)-4,6-difluorobenzo[d]thiazol-5-amine (I-90-iv)

4,6-difluoro-N-(2-(1-methyl-7-oxa-1-azaspiro[4.4]nonan-4-yl)thieno[2,3-b]pyridin-4-yl)benzo[d]thiazol-5-amine (I-91)

4,6-difluoro-N-(2-((4R,5S)-1-methyl-7-oxa-1-azaspiro[4.4]nonan-4-yl)thieno[2,3-b]pyridin-4-yl)benzo[d]thiazol-5-amine (I-91-i)

4,6-difluoro-N-(2-((4R,5R)-1-methyl-7-oxa-1-azaspiro[4.4]nonan-4-yl)thieno[2,3-b]pyridin-4-yl)benzo[d]thiazol-5-amine (I-91-ii)

4,6-difluoro-N-(2-((4S,5S)-1-methyl-7-oxa-1-azaspiro[4.4]nonan-4-yl)thieno[2,3-b]pyridin-4-yl)benzo[d]thiazol-5-amine (I-91-iii)

4,6-difluoro-N-(2-((4S,5R)-1-methyl-7-oxa-1-azaspiro[4.4]nonan-4-yl)thieno[2,3-b]pyridin-4-yl)benzo[d]thiazol-5-amine (I-91-iv)

N-(2-(1-ethyl-7-oxa-1-azaspiro[4.4]nonan-4-yl)thieno[2,3-b]pyridin-4-yl)-6-fluorobenzo[d]thiazol-5-amine (I-92)

N-(2-((4R,5S)-1-ethyl-7-oxa-1-azaspiro[4.4]nonan-4-yl)thieno[2,3-b]pyridin-4-yl)-6-fluorobenzo[d]thiazol-5-amine (I-92-i)

N-(2-((4R,5R)-1-ethyl-7-oxa-1-azaspiro[4.4]nonan-4-yl)thieno[2,3-b]pyridin-4-yl)-6-fluorobenzo[d]thiazol-5-amine (I-92-ii)

N-(2-((4S,5S)-1-ethyl-7-oxa-1-azaspiro[4.4]nonan-4-yl)thieno[2,3-b]pyridin-4-yl)-6-fluorobenzo[d]thiazol-5-amine (I-92-iii)

N-(2-((4S,5R)-1-ethyl-7-oxa-1-azaspiro[4.4]nonan-4-yl)thieno[2,3-b]pyridin-4-yl)-6-fluorobenzo[d]thiazol-5-amine (I-92-iv)

N-(2-(1-methylpyrrolidin-3-yl)thieno[2,3-b]pyridin-4-yl)benzo[d]thiazol-5-amine (I-93)

(R)—N-(2-(1-methylpyrrolidin-3-yl)thieno[2,3-b]pyridin-4-yl)benzo[d]thiazol-5-amine (I-93-i)

(S)—N-(2-(1-methylpyrrolidin-3-yl)thieno[2,3-b]pyridin-4-yl)benzo[d]thiazol-5-amine (I-93-ii)

N-(2-(pyrrolidin-3-yl)thieno[2,3-b]pyridin-4-yl)benzo[d]thiazol-5-amine (I-94)

(R)—N-(2-(pyrrolidin-3-yl)thieno[2,3-b]pyridin-4-yl)benzo[d]thiazol-5-amine (I-94-i)

(S)—N-(2-(pyrrolidin-3-yl)thieno[2,3-b]pyridin-4-yl)benzo[d]thiazol-5-amine (I-94-ii)

N-(2-(1,2-dimethylpiperidin-3-yl)-5-fluorothieno[2,3-b]pyridin-4-yl)-4-fluorobenzo[d]thiazol-5-amine (I-95)

N-(2-((2R,3R)-1,2-dimethylpiperidin-3-yl)-5-fluorothieno[2,3-b]pyridin-4-yl)-4-fluorobenzo[d]thiazol-5-amine (I-95-i)

N-(2-((2S,3R)-1,2-dimethylpiperidin-3-yl)-5-fluorothieno[2,3-b]pyridin-4-yl)-4-fluorobenzo[d]thiazol-5-amine (I-95-ii)

N-(2-((2R,3S)-1,2-dimethylpiperidin-3-yl)-5-fluorothieno[2,3-b]pyridin-4-yl)-4-fluorobenzo[d]thiazol-5-amine (I-95-iii)

N-(2-((2S,3S)-1,2-dimethylpiperidin-3-yl)-5-fluorothieno[2,3-b]pyridin-4-yl)-4-fluorobenzo[d]thiazol-5-amine (I-95-iv)

4-fluoro-N-(5-fluoro-2-(2-methylpiperidin-3-yl)thieno[2,3-b]pyridin-4-yl)benzo[d]thiazol-5-amine (I-96)

4-fluoro-N-(5-fluoro-2-((2R,3R)-2-methylpiperidin-3-yl)thieno[2,3-b]pyridin-4-yl)benzo[d]thiazol-5-amine (I-96-i)

4-fluoro-N-(5-fluoro-2-((2S,3R)-2-methylpiperidin-3-yl)thieno[2,3-b]pyridin-4-yl)benzo[d]thiazol-5-amine (I-96-ii)

4-fluoro-N-(5-fluoro-2-((2R,3S)-2-methylpiperidin-3-yl)thieno[2,3-b]pyridin-4-yl)benzo[d]thiazol-5-amine (I-96-iii)

4-fluoro-N-(5-fluoro-2-((2S,3S)-2-methylpiperidin-3-yl)thieno[2,3-b]pyridin-4-yl)benzo[d]thiazol-5-amine (I-96-iv)

N-(2-(1,2-dimethylpiperidin-3-yl)-5-fluorothieno[2,3-b]pyridin-4-yl)benzo[d]thiazol-5-amine (I-97)

N-(2-((2R,3R)-1,2-dimethylpiperidin-3-yl)-5-fluorothieno[2,3-b]pyridin-4-yl)benzo[d]thiazol-5-amine (I-97-i)

N-((2-((2S,3R)-1,2-dimethylpiperidin-3-yl)-5-fluorothieno[2,3-b]pyridin-4-yl)benzo[d]thiazol-5-amine (I-97-ii)

N-(2-((2R,3S)-1,2-dimethylpiperidin-3-yl)-5-fluorothieno[2,3-b]pyridin-4-yl)benzo[d]thiazol-5-amine (I-97-iii)

N-(2-((2S,3S)-1,2-dimethylpiperidin-3-yl)-5-fluorothieno[2,3-b]pyridin-4-yl)benzo[d]thiazol-5-amine (I-97-iv)

N-(5-fluoro-2-(2-methylpiperidin-3-yl)thieno[2,3-b]pyridin-4-yl)benzo[d]thiazol-5-amine (I-98)

N-(5-fluoro-2-((2R,3R)-2-methylpiperidin-3-yl)thieno[2,3-b]pyridin-4-yl)benzo[d]thiazol-5-amine (I-98-i)

N-(5-fluoro-2-((2S,3R)-2-methylpiperidin-3-yl)thieno[2,3-b]pyridin-4-yl)benzo[d]thiazol-5-amine (I-98-ii)

N-(5-fluoro-2-((2R,3S)-2-methylpiperidin-3-yl)thieno[2,3-b]pyridin-4-yl)benzo[d]thiazol-5-amine (I-98-iii)

N-(5-fluoro-2-((2S,3S)-2-methylpiperidin-3-yl)thieno[2,3-b]pyridin-4-yl)benzo[d]thiazol-5-amine (I-98-iv)

N-(2-(1,2-dimethylpiperidin-3-yl)-5-fluorothieno[2,3-b]pyridin-4-yl)-6-fluorobenzo[d]thiazol-5-amine (I-99)

N-(2-((2R,3R)-1,2-dimethylpiperidin-3-yl)-5-fluorothieno[2,3-b]pyridin-4-yl)-6-fluorobenzo[d]thiazol-5-amine (I-99-i)

N-(2-((2S,3R)-1,2-dimethylpiperidin-3-yl)-5-fluorothieno[2,3-b]pyridin-4-yl)-6-fluorobenzo[d]thiazol-5-amine (I-99-ii)

N-(2-((2R,3S)-1,2-dimethylpiperidin-3-yl)-5-fluorothieno[2,3-b]pyridin-4-yl)-6-fluorobenzo[d]thiazol-5-amine (I-99-iii)

N-(2-((2S,3S)-1,2-dimethylpiperidin-3-yl)-5-fluorothieno[2,3-b]pyridin-4-yl)-6-fluorobenzo[d]thiazol-5-amine (I-99-iv)

6-fluoro-N-(5-fluoro-2-(2-methylpiperidin-3-yl)thieno[2,3-b]pyridin-4-yl)benzo[d]thiazol-5-amine (I-100)

6-fluoro-N-(5-fluoro-2-((2R,3R)-2-methylpiperidin-3-yl)thieno[2,3-b]pyridin-4-yl)benzo[d]thiazol-5-amine (I-100-i)

6-fluoro-N-(5-fluoro-2-((2S,3R)-2-methylpiperidin-3-yl)thieno[2,3-b]pyridin-4-yl)benzo[d]thiazol-5-amine (I-100-ii)

6-fluoro-N-(5-fluoro-2-((2R,3S)-2-methylpiperidin-3-yl)thieno[2,3-b]pyridin-4-yl)benzo[d]thiazol-5-amine (I-100-iii)

6-fluoro-N-(5-fluoro-2-((2S,3S)-2-methylpiperidin-3-yl)thieno[2,3-b]pyridin-4-yl)benzo[d]thiazol-5-amine (I-100-iv)

N-(2-(1,2-dimethylpiperidin-3-yl)-5-fluorothieno[2,3-b]pyridin-4-yl)-4,6-difluorobenzo[d]thiazol-5-amine (I-101)

N-(2-((2R,3R)-1,2-dimethylpiperidin-3-yl)-5-fluorothieno[2,3-b]pyridin-4-yl)-4,6-difluorobenzo[d]thiazol-5-amine (I-101-i)

N-(2-((2S,3R)-1,2-dimethylpiperidin-3-yl)-5-fluorothieno[2,3-b]pyridin-4-yl)-4,6-difluorobenzo[d]thiazol-5-amine (I-101-ii)

N-(2-((2R,3S)-1,2-dimethylpiperidin-3-yl)-5-fluorothieno[2,3-b]pyridin-4-yl)-4,6-difluorobenzo[d]thiazol-5-amine (I-101-iii)

N-(2-((2S,3S)-1,2-dimethylpiperidin-3-yl)-5-fluorothieno[2,3b]pyridin-4-yl)-4,6-difluorobenzo[d]thiazol-5-amine (I-101-iv)

4,6-difluoro-N-(5-fluoro-2-(2-methylpiperidin-3-yl)thieno[2,3-b]pyridin-4-yl)benzo[d]thiazol-5-amine (I-102)

4,6-difluoro-N-(5-fluoro-2-((2R,3R)-2-methylpiperidin-3-yl)thieno[2,3b]pyridin-4-yl)benzo[d]thiazol-5-amine (I-102-i)

4,6-difluoro-N-(5-fluoro-2-((2S,3R)-2-methylpiperidin-3-yl)thieno[2,3b]pyridin-4-yl)benzo[d]thiazol-5-amine (I-102-ii)

4,6-difluoro-N-(5-fluoro-2-((2R,3S)-2-methylpiperidin-3-yl)thieno[2,3-b]pyridin-4-yl)benzo[d]thiazol-5-amine (I-102-iii)

4,6-difluoro-N-(5-fluoro-2-((2S,3S)-2-methylpiperidin-3-yl)thieno[2,3-b]pyridin-4-yl)benzo[d]thiazol-5-amine (I-102-iv)

N-(2-(1-ethyl-2-methylpiperidin-3-yl)-5-fluorothieno[2,3-b]pyridin-4-yl)-4-fluorobenzo[d]thiazol-5-amine (I-103)

N-(2-((2R,3R)-1-ethyl-2-methylpiperidin-3-yl)-5-fluorothieno[2,3-b]pyridin-4-yl)-4-fluorobenzo[d]thiazol-5-amine (I-103-i)

N-(2-((2S,3R)-1-ethyl-2-methylpiperidin-3-yl)-5-fluorothieno[2,3-b]pyridin-4-yl)-4-fluorobenzo[d]thiazol-5-amine (I-103-ii)

N-(2-((2R,3S)-1-ethyl-2-methylpiperidin-3-yl)-5-fluorothieno[2,3-b]pyridin-4-yl)-4-fluorobenzo[d]thiazol-5-amine (I-103-iii)

N-(2-((2S,3S)-1-ethyl-2-methylpiperidin-3-yl)-5-fluorothieno[2,3-b]pyridin-4-yl)-4-fluorobenzo[d]thiazol-5-amine (I-103-iv)

N-(2-(1-ethyl-2-methylpiperidin-3-yl)-5-fluorothieno[2,3-b]pyridin-4-yl)benzo[d]thiazol-5-amine (I-104)

N-(2-((2R,3R)-1-ethyl-2-methylpiperidin-3-yl)-5-fluorothieno[2,3-b]pyridin-4-yl)benzo[d]thiazol-5-amine (I-104-i)

N-(2-((2S,3R)-1-ethyl-2-methylpiperidin-3-yl)-5-fluorothieno[2,3-b]pyridin-4-yl)benzo[d]thiazol-5-amine (I-104-ii)

N-(2-((2R,3S)-1-ethyl-2-methylpiperidin-3-yl)-5-fluorothieno[2,3-b]pyridin-4-yl)benzo[d]thiazol-5-amine (I-104-iii)

N-(2-((2S,3S)-1-ethyl-2-methylpiperidin-3-yl)-5-fluorothieno[2,3-b]pyridin-4-yl)benzo[d]thiazol-5-amine (I-104-iv)

N-(2-(1-ethyl-2-methylpiperidin-3-yl)-5-fluorothieno[2,3-b]pyridin-4-yl)-6-fluorobenzo[d]thiazol-5-amine (I-105)

N-(2-((2R,3R)-1-ethyl-2-methylpiperidin-3-yl)-5-fluorothieno[2,3-b]pyridin-4-yl)-6-fluorobenzo[d]thiazol-5-amine (I-105-i)

N-(2-((2S,3R)-1-ethyl-2-methylpiperidin-3-yl)-5-fluorothieno[2,3-b]pyridin-4-yl)-6-fluorobenzo[d]thiazol-5-amine (I-105-ii)

N-(2-((2R,3S)-1-ethyl-2-methylpiperidin-3-yl)-5-fluorothieno[2,3-b]pyridin-4-yl)-6-fluorobenzo[d]thiazol-5-amine (I-105-iii)

N-(2-((2S,3S)-1-ethyl-2-methylpiperidin-3-yl)-5-fluorothieno[2,3-b]pyridin-4-yl)-6-fluorobenzo[d]thiazol-5-amine (I-105-iv)

N-(2-(1-ethyl-2-methylpiperidin-3-yl)-5-fluorothieno[2,3-b]pyridin-4-yl)-4,6-difluorobenzo[d]thiazol-5-amine (I-106)

N-(2-((2R,3R)-1-ethyl-2-methylpiperidin-3-yl)-5-fluorothieno[2,3-b]pyridin-4-yl)-4,6-difluorobenzo[d]thiazol-5-amine (I-106-i)

N-(2-((2S,3R)-1-ethyl-2-methylpiperidin-3-yl)-5-fluorothieno[2,3-b]pyridin-4-yl)-4,6-difluorobenzo[d]thiazol-5-amine (I-106-ii)

N-(2-((2R,3S)-1-ethyl-2-methylpiperidin-3-yl)-5-fluorothieno[2,3-b]pyridin-4-yl)-4,6-difluorobenzo[d]thiazol-5-amine (I-106-iii)

N-(2-((2S,3S)-1-ethyl-2-methylpiperidin-3-yl)-5-fluorothieno[2,3-b]pyridin-4-yl)-4,6-difluorobenzo[d]thiazol-5-amine (I-106-iv)

N-(2-(2,5,6,7-tetrahydro-1H-azepin-3-yl)thieno[2,3-b]pyridin-4-yl)benzo[d]thiazol-5-amine (I-107)

1-(6-(4-(benzo[d]thiazol-5-ylamino)thieno[2,3-b]pyridin-2-yl)-2,3,4,7-tetrahydro-1H-azepin-1-yl)ethan-1-one (I-108)

N-(2-(1-(methylsulfonyl)-2,5,6,7-tetrahydro-1H-azepin-3-yl)thieno[2,3-b]pyridin-4-yl)benzo[d]thiazol-5-amine (I-109)

N-(2-(1-methyl-2,5,6,7-tetrahydro-1H-azepin-3-yl)thieno[2,3-b]pyridin-4-yl)benzo[d]thiazol-5-amine (I-110)

6-fluoro-N-(2-(2-methylazepan-3-yl)thieno[2,3-b]pyridin-4-yl)benzo[d]thiazol-5-amine (I-111)

6-fluoro-N-(2-((2R,3R)-2-methylazepan-3-yl)thieno[2,3-b]pyridin-4-yl)benzo[d]thiazol-5-amine (I-1114)

6-fluoro-N-(2-((2S,3R)-2-methylazepan-3-yl)thieno[2,3-b]pyridin-4-yl)benzo[d]thiazol-5-amine (I-111-ii)

6-fluoro-N-(2-((2R,3S)-2-methylazepan-3-yl)thieno[2,3-b]pyridin-4-yl)benzo[d]thiazol-5-amine (I-111-iii)

6-fluoro-N-(2-((2S,3S)-2-methylazepan-3-yl)thieno[2,3-b]pyridin-4-yl)benzo[d]thiazol-5-amine (I-111-iv)

4,6-difluoro-N-(2-(2-methylazepan-3-yl)thieno[2,3-b]pyridin-4-yl)benzo[d]thiazol-5-amine (I-112)

4,6-difluoro-N-(2-((2R,3R)-2-methylazepan-3-yl)thieno[2,3-b]pyridin-4-yl)benzo[d]thiazol-5-amine (I-112-ii)

4,6-difluoro-N-(2-((2S,3R)-2-methylazepan-3-yl)thieno[2,3-b]pyridin-4-yl)benzo[d]thiazol-5-amine (I-112-ii)

4,6-difluoro-N-(2-((2R,3S)-2-methylazepan-3-yl)thieno[2,3-b]pyridin-4-yl)benzo[d]thiazol-5-amine (I-112-iii)

4,6-difluoro-N-(2-((2S,3S)-2-methylazepan-3-yl)thieno[2,3-b]pyridin-4-yl)benzo[d]thiazol-5-amine (I-112-iv)

N-(2-(1,2-dimethylazepan-3-yl)thieno[2,3-b]pyridin-4-yl)benzo[d]thiazol-5-amine (I-113)

N-(2-((2R,3R)-1,2-dimethylazepan-3-yl)thieno[2,3-b]pyridin-4-yl)benzo[d]thiazol-5-amine (I-113-i)

N-(2-((2S,3R)-1,2-dimethylazepan-3-yl)thieno[2,3-b]pyridin-4-yl)benzo[d]thiazol-5-amine (I-113-ii)

N-(2-((2R,3S)-1,2-dimethylazepan-3-yl)thieno[2,3-b]pyridin-4-yl)benzo[d]thiazol-5-amine (I-113-iii)

N-(2-((2S,3S)-1,2-dimethylazepan-3-yl)thieno[2,3-b]pyridin-4-yl)benzo[d]thiazol-5-amine (I-113-iv)

6-fluoro-N-(2-(2-methylazepan-3-yl)thieno[2,3-b]pyridin-4-yl)benzo[d]thiazol-5-amine (I-114)

6-fluoro-N-(2-((2R,3R)-2-methylazepan-3-yl)thieno[2,3-b]pyridin-4-yl)benzo[d]thiazol-5-amine (I-1144)

6-fluoro-N-(2-((2S,3R)-2-methylazepan-3-yl)thieno[2,3-b]pyridin-4-yl)benzo[d]thiazol-5-amine (I-114-ii)

6-fluoro-N-(2-((2R,3S)-2-methylazepan-3-yl)thieno[2,3-b]pyridin-4-yl)benzo[d]thiazol-5-amine (I-114-iii)

6-fluoro-N-(2-((2S,3S)-2-methylazepan-3-yl)thieno[2,3-b]pyridin-4-yl)benzo[d]thiazol-5-amine (I-114-iv)

N-(2-(2-methylazepan-3-yl)thieno[2,3-b]pyridin-4-yl)benzo[d]thiazol-5-amine (I-115)

N-(2-((2R,3R)-2-methylazepan-3-yl)thieno[2,3-b]pyridin-4-yl)benzo[d]thiazol-5-amine (I-115-i)

N-(2-((2S,3R)-2-methylazepan-3-yl)thieno[2,3-b]pyridin-4-yl)benzo[d]thiazol-5-amine (I-115-ii)

N-(2-((2R,3S)-2-methylazepan-3-yl)thieno[2,3-b]pyridin-4-yl)benzo[d]thiazol-5-amine (I-115-iii)

N-(2-((2S,3S)-2-methylazepan-3-yl)thieno[2,3-b]pyridin-4-yl)benzo[d]thiazol-5-amine (I-115-iv)
N-(2-(2,3,6,7-tetrahydro-1H-azepin-4-yl)thieno[2,3-b]pyridin-4-yl)benzo[d]thiazol-5-amine (I-116)
N-(2-(1-methyl-2,3,6,7-tetrahydro-1H-azepin-4-yl)thieno[2,3-b]pyridin-4-yl)benzo[d]thiazol-5-amine (I-117)
1-(4-(4-(benzo[d]thiazol-5-ylamino)thieno[2,3-b]pyridin-2-yl)-2,3,6,7-tetrahydro-1H-azepin-1-yl)ethan-1-one (I-118)
N-(2-(azepan-4-yl)thieno[2,3-b]pyridin-4-yl)benzo[d]thiazol-5-amine (I-119)
(R)—N-(2-(azepan-4-yl)thieno[2,3-b]pyridin-4-yl)benzo[d]thiazol-5-amine (I-119-i)
(S)—N-(2-(azepan-4-yl)thieno[2,3-b]pyridin-4-yl)benzo[d]thiazol-5-amine (I-119-ii)
N-(2-(1-methylazepan-4-yl)thieno[2,3-b]pyridin-4-yl)benzo[d]thiazol-5-amine (I-120)
(R)—N-(2-(1-methylazepan-4-yl)thieno[2,3-b]pyridin-4-yl)benzo[d]thiazol-5-amine (I-120-i)
(S)—N-(2-(1-methylazepan-4-yl)thieno[2,3-b]pyridin-4-yl)benzo[d]thiazol-5-amine (I-120-ii)
N-(2-(1-ethylazepan-4-yl)thieno[2,3-b]pyridin-4-yl)benzo[d]thiazol-5-amine (I-121)
(R)—N-(2-(1-ethylazepan-4-yl)thieno[2,3-b]pyridin-4-yl)benzo[d]thiazol-5-amine (I-121-i)
(S)—N-(2-(1-ethylazepan-4-yl)thieno[2,3-b]pyridin-4-yl)benzo[d]thiazol-5-amine (I-121-ii)
1-(4-(4-(benzo[d]thiazol-5-ylamino)thieno[2,3-b]pyridin-2-yl)azepan-1-yl)ethan-1-one (I-122)
(R)-1-(4-(4-(benzo[d]thiazol-5-ylamino)thieno[2,3-b]pyridin-2-yl)azepan-1-yl)ethan-1-one (I-122-i)
(S)-1-(4-(4-(benzo[d]thiazol-5-ylamino)thieno[2,3-b]pyridin-2-yl)azepan-1-yl)ethan-1-one (I-122-ii).

In some embodiments, the compound of Formula I is:

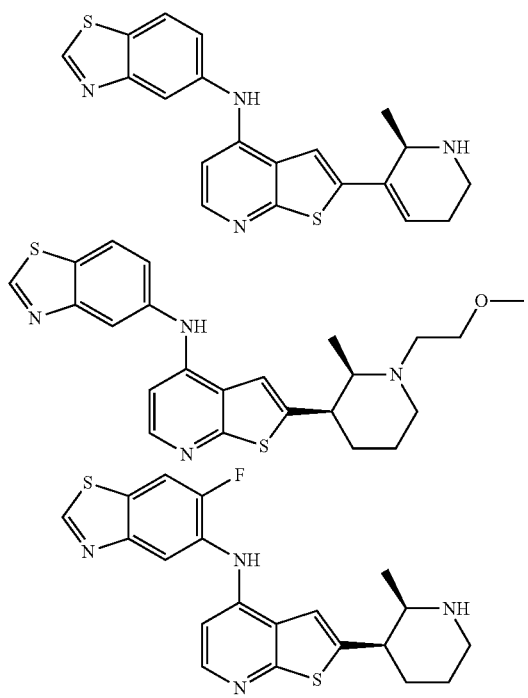

In some embodiments, the compound of Formula I is:

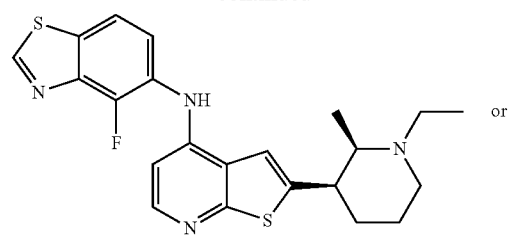 or

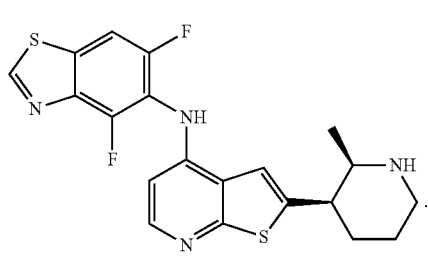

In some embodiments, the compound of Formula I is:

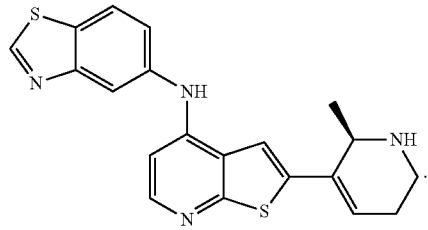 [SMILES: C[C@H]1NCCC=C1c1cc2c(Nc3ccc4scnc4c3)ccnc2s1]

In some embodiments, the compound of Formula I is:

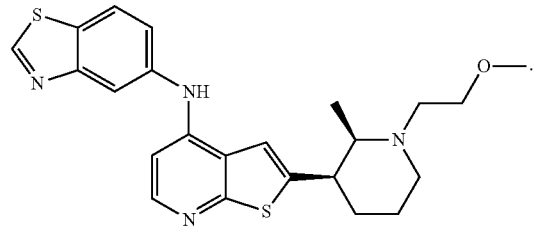 [SMILES: COCCN1CCC[C@@H](c2cc3c(Nc4ccc5scnc5c4)ccnc3s2)[C@H]1C]

In some embodiments, the compound of Formula I is:

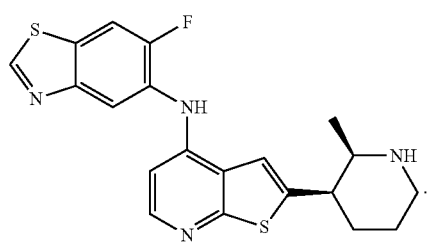 [SMILES: C[C@H]1NCCC[C@H]1c1cc2c(Nc3cc4ncsc4cc3F)ccnc2s1]

In some embodiments, the compound of Formula I is:

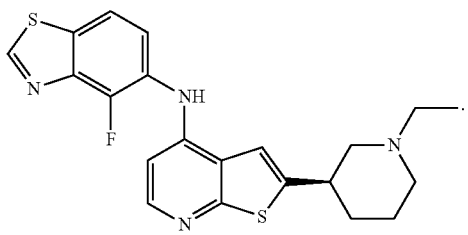 [SMILES: CCN1CCC[C@@H](c2cc3c(Nc4ccc5scnc5c4F)ccnc3s2)C1]

In some embodiments, the compound of Formula I is:

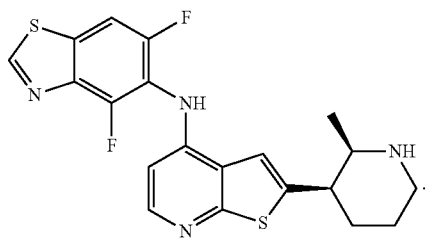 [SMILES: C[C@H]1NCCC[C@H]1c1cc2c(Nc3c(F)cc4scnc4c3F)ccnc2s1]

or a pharmaceutically acceptable salt thereof.

Synthetic Processes

In some embodiments, compounds of formula I an formula I' are prepared according to Scheme I:

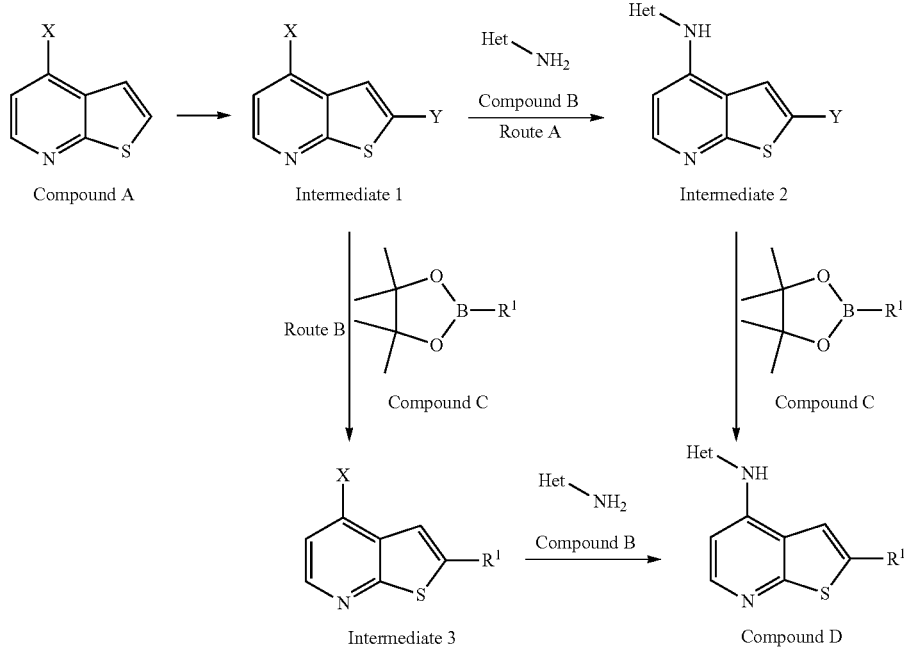

wherein X and Y are leaving groups (e.g., halogen, including bromo, chloro, and iodo), and can be the same or different, and "Het" is an 9-membered heteroaryl substituted by $(R^3)_q$, wherein $R^1$, $R^3$ and q are as defined above and described herein.

Accordingly, in some embodiments, X and Y are each halogen. In some embodiments, X is selected from bromo, chloro, and iodo. In some embodiments, X is bromo. In some embodiments, X is chloro. In some embodiments, X is iodo. In some embodiments, Y is selected from bromo, chloro, and iodo. In some embodiments, Y is bromo. In some embodiments, Y is chloro. In some embodiments, Y is iodo. In some embodiments, X is chloro and Y is iodo. In some embodiments, "Het" is benzothiazolyl substituted with 0-4 $R^3$ groups. In some embodiments, "Het" is benzothiazoyl substituted with 1 $R^3$ group. In some embodiments, "Het" is benzothiazolyl substituted with 2 $R^3$ groups. In some embodiments, "Het" is benzothiazolyl substituted with 3 $R^3$ groups. In some embodiments, "Het" is benzothiazolyl substituted with 4 $R^3$ groups. In some embodiments, $R^3$ is halogen. In some embodiments, each $R^3$ is independently selected from bromo, chloro, of fluoro. In some embodiments, $R^3$ is bromo. In some embodiments, $R^3$ is chloro. In some embodiments, $R^3$ is fluoro. In some embodiments, "Het" is:

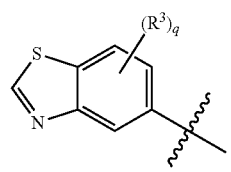

In some embodiments, "Het" is:

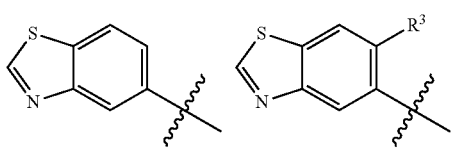

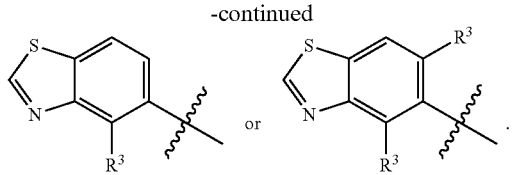

In some embodiments, "Het" is:

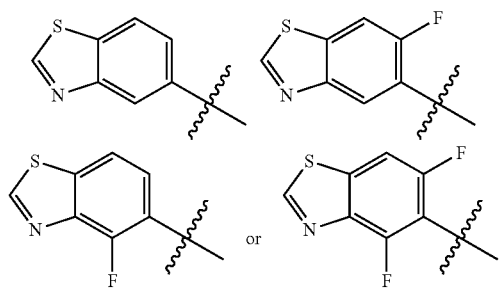

In some embodiments, Compound D is prepared by contacting Intermediate 3 with Compound B in the presence of a first palladium catalyst and a first base. In some embodiments, the first palladium catalyst is Pd(OAc)$_2$. In some embodiments, the first base is Cs$_2$CO$_3$. In some embodiments, Compound B is selected from:

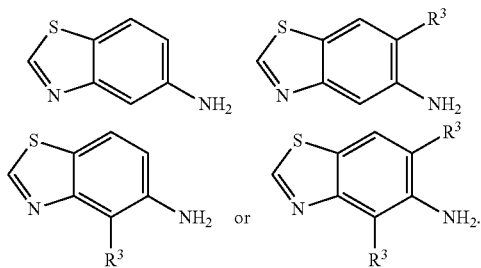

wherein R$^3$ is halogen. In some embodiments, each R$^3$ is independently selected from bromo, chloro, of fluoro. In some embodiments, R$^3$ is bromo. In some embodiments, R$^3$ is chloro. In some embodiments, R$^3$ is fluoro. In some embodiments, Compound B is:

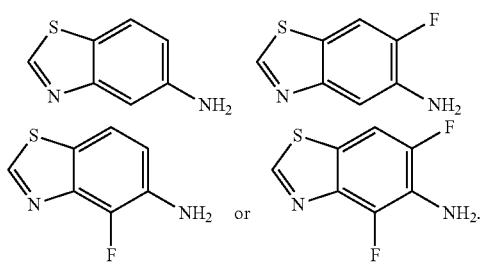

In some embodiments, Intermediate 3 is prepared by contacting Intermediate 1 with Compound C in the presence of a second palladium catalyst and a second base, wherein R$^1$ is as defined above and described herein. In some embodiments, the second palladium catalyst is Pd(dppf)Cl$_2$. In some embodiments, the second base is t-BuONa.

In some embodiments, Intermediate 1 is prepared by reacting Compound A with X$_2$ in the presence of a third base. In some embodiments, the third base is lithium diisopropylamide. In some embodiments, X$_2$ is I$_2$.

In some embodiments, Compound D is prepared by contacting Intermediate 2 with Compound C in the presence of a fourth palladium catalyst and a fourth base, wherein R$^1$ is as defined above and described herein. In some embodiments, the fourth palladium catalyst is Pd$_2$(dba)$_3$. In some embodiments, the fourth base is KOH.

In some embodiments, Intermediate 2 is prepared by contacting Intermediate 1 with Compound B in the presence of an acid. In some embodiments, the acid is p-TsOH. In some embodiments, Compound B is selected from:

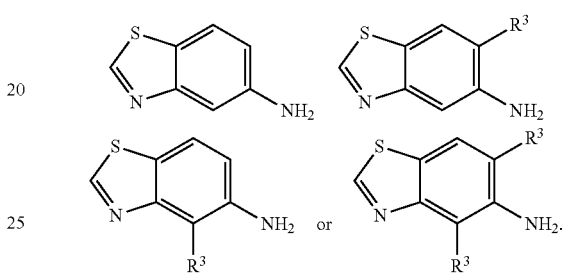

wherein R$^3$ is halogen. In some embodiments, each R$^3$ is independently selected from bromo, chloro, of fluoro. In some embodiments, R$^3$ is bromo. In some embodiments, R$^3$ is chloro. In some embodiments, R$^3$ is fluoro. In some embodiments, Compound B is:

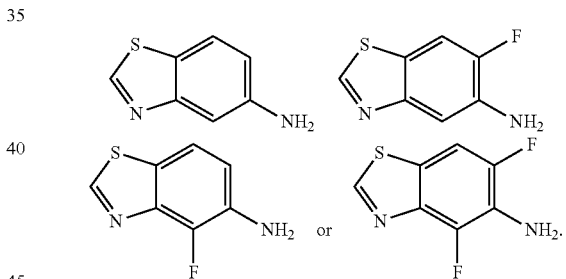

Compositions

In some embodiments, compounds reported herein may be provided in a composition (e.g., in combination) with one or more other components.

In some embodiments, the present application provides compositions that comprise and/or deliver compounds reported herein (e.g., compounds of formula I, I', II, II', III, III', IV, and/or IV'), or an active metabolite thereof, e.g., when contacted with or otherwise administered to a system or environment e.g., which system or environment may include RIPK2 activity; in some embodiments, administration of such a composition to the system or environment achieves inhibition of RIPK2 activity as described herein.

In some embodiments, a provided composition as described herein may be a pharmaceutical composition in that it comprises an active agent (e.g., a compound of formula I, I', II, II', III, III', IV, and/or IV') and one or more pharmaceutically acceptable excipients; in some such embodiments, a provided pharmaceutical composition comprises and/or delivers a compound reported herein (e.g., a compound of formula I, I', II, II', III, III', IV, and/or IV'), or an active metabolite thereof to a relevant system or environment (e.g., to a subject in need thereof) as described herein.

In some embodiments, one or more compounds reported herein (e.g., a compound of formula I, I', II, II', III, III', IV, and/or IV') is provided and/or utilized in a pharmaceutically acceptable salt form.

Among other things, the present application provides compositions comprising a compound reported herein (e.g., a compound of formula I, I', II, II', III, III', IV, and/or IV'), or a pharmaceutically acceptable salt or derivative thereof, and a pharmaceutically acceptable carrier, adjuvant, or vehicle. The amount of compound in provided compositions is such that is effective to measurably inhibit RIPK2 in a biological sample or in a patient. In certain embodiments, a provided compound or composition is formulated for administration to a patient in need of such composition. The compounds and compositions, according to the methods of the present application, may be administered using any amount and any route of administration effective for treating or lessening the severity of any disease or disorder described herein. Provided compounds are preferably formulated in dosage unit form for ease of administration and uniformity of dosage. The expression "dosage unit form" as used herein refers to a physically discrete unit of agent appropriate for the patient to be treated. It will be understood, however, that the total daily usage of the provided compounds and compositions will be decided by the attending physician within the scope of sound medical judgment. The specific effective dose level for any particular patient or organism will vary from subject to subject, depending on a variety of factors, including the disorder being treated and the severity of the disorder; the activity of the specific compound employed; the specific composition employed and its route of administration; the species, age, body weight, sex and diet of the patient; the general condition of the subject; the time of administration; the rate of excretion of the specific compound employed; the duration of the treatment; drugs used in combination or coincidental with the specific compound employed, and the like.

Provided compositions may be administered orally, parenterally, by inhalation or nasal spray, topically (e.g., as by powders, ointments, or drops), rectally, buccally, intravaginally, intraperitoneally, intracisternally or via an implanted reservoir, depending on the severity of the condition being treated. Preferably, the compositions are administered orally, intraperitoneally or intravenously. In certain embodiments, provided compounds are administered orally or parenterally at dosage levels of about 0.01 mg/kg to about 50 mg/kg, of subject body weight per day, one or more times a day, to obtain the desired therapeutic effect.

The term "parenteral" as used herein includes subcutaneous, intravenous, intramuscular, intra-articular, intra-synovial, intrasternal, intrathecal, intrahepatic, intralesional and intracranial injection or infusion techniques. Sterile injectable forms of provided compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Pharmaceutically acceptable compositions described herein may be orally administered in any orally acceptable dosage form including, but not limited to, capsules, tablets, aqueous suspensions or solutions. In such solid dosage forms the active compound may be admixed with at least one inert diluent such as sucrose, lactose or starch. Such dosage forms may also comprise, as is normal practice, additional substances other than inert diluents, e.g., lubricants and other tableting aids such a magnesium stearate and microcrystalline cellulose. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents. The active compounds can also be in micro-encapsulated form with one or more excipients as noted above.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings (i.e. buffering agents) and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions described herein may be administered in the form of suppositories for rectal or vaginal administration. These can be prepared by mixing the compounds of the present application with suitable non-irritating excipients or carriers that are solid at room temperature but liquid at body (e.g. rectal or vaginal) temperature and therefore will melt in the rectum or vaginal cavity to release the active compound. Such materials include cocoa butter, a suppository wax (e.g., beeswax) and polyethylene glycols.

Pharmaceutically acceptable compositions described herein may also be administered topically, especially when the target of treatment includes areas or organs readily accessible by topical application, including diseases of the eye, the skin, or the lower intestinal tract. Topical application for the lower intestinal tract can be effected in a rectal suppository formulation (see above) or in a suitable enema formulation.

Dosage forms for topical or transdermal administration of a provided compound include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and eye drops are also contemplated as being within the scope of this application. Additionally, the present application contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For topical applications, provided pharmaceutically acceptable compositions may be formulated in a suitable ointment containing the active component suspended or dissolved in one or more carriers. Carriers for topical administration of compounds of this application include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this application may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this application are formulated for oral administration.

Applications and Uses

The present application provides a variety of uses and applications for compounds and/or compositions as described herein, for example in light of their activities and/or characteristics as described herein. In some embodiments, such uses may include therapeutic and/or diagnostic uses. Alternatively, in some embodiments such uses may include research, production, and/or other technological uses.

In one aspect, the present application provides methods comprising administering one of more compounds of the present application (e.g., a compound of formula I, I', II, II', III, III', IV, and/or IV') to a subject, e.g., to treat, prevent, or reduce the risk of developing a disorder associated with NOD1, NOD2, and/or RIPK2 (e.g., an inflammatory or autoinflammatory disorder). Accordingly, in some embodiments, the compounds of the present application (e.g., a compound of formula I, I', II, II', III, III', IV, and/or IV') are inhibitors of RIPK2.

In some embodiments, the present application relates to a method of inhibiting RIPK2 in a subject comprising administering to the subject a provided compound, or a composition comprising said compound.

Inhibition of enzymes in a biological sample is useful for a variety of purposes that are known to one of skill in the art.

Examples of such purposes include, but are not limited to biological assays, gene expression studies, and biological target identification.

In some embodiments, the present application relates to a method of treating an inflammatory disorder, an autoimmune disorder, or a disorder associated with NOD1, NOD2, and/or RIPK2 in a biological sample comprising the step of contacting said biological sample with a compound or composition reported herein (e.g., a compound of formula I, I', II, II', III, III', IV, and/or IV').

In some embodiments, one or more compounds and/or compositions as described herein are useful, for example, as a method for treating a disorder mediated by RIPK2 comprising administering to a subject a compound or composition described herein. In some embodiments, the disorder is an inflammatory disorder, an autoimmune disorder, or a disorder associated with NOD1, NOD2, and/or RIPK2. In some embodiments, the disorder is an inflammatory disorder. In some embodiments, the inflammatory disorder is selected from inflammatory bowel disease, sarcoidosis, inflammatory arthritis, Crohn's disease, peritonitis, multiple sclerosis, rheumatoid arthritis, and Wegener's granulomatosis. In some embodiments, the inflammatory disorder is inflammatory bowel disease. In some embodiments, the inflammatory disorder is sarcoidosis. In some embodiments, the inflammatory disorder is inflammatory arthritis. In some embodiments, the inflammatory disorder is Crohn's disease. In some embodiments, the inflammatory disorder is peritonitis. In some embodiments, the inflammatory disorder is multiple sclerosis. In some embodiments, the inflammatory disorder is rheumatoid arthritis. In some embodiments, the inflammatory disorder is Wegener's granulomatosis.

In some embodiments, one or more compounds and/or compositions as described herein are useful in medicine.

In some embodiments, the present application relates to a use of a compound and/or composition described herein for inhibiting RIPK2 in a patient.

In some embodiments, the present application relates to a use of a compound and/or composition described herein for treating a disorder mediated by RIPK2. In some embodiments, the disorder mediated by RIPK2 is an inflammatory disorder, an autoimmune disorder, or a disorder associated with NOD1 and/or NOD2 receptors. In some embodiments, the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

In some embodiments, the present application relates to use of a compound and/or composition described herein for use in the manufacture of a medicament for inhibiting RIPK2.

In some embodiments, the present application relates to use of a compound and/or composition described herein for use in the manufacture of a medicament for treating a disorder mediated by RIPK2. In some embodiments, the disorder mediated by RIPK2 is an inflammatory disorder, an autoimmune disorder, or a disorder associated with NOD1 and/or NOD2 receptors. In some embodiments, the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

In some embodiments, the present application relates to a compound or composition described herein for use in treating a disorder mediated by RIPK2. In some embodiments, the disorder mediated by RIPK2 is an inflammatory disorder, an autoimmune disorder, or a disorder associated with NOD1 and/or NOD2 receptors. In some embodiments, the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

In some embodiments, the present application relates to a compound or composition described herein for use in treating an inflammatory disorder, an autoimmune disorder, or a disorder associated with NOD1 and/or NOD2 receptors. In some embodiments, the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

EXEMPLARY EMBODIMENTS

The embodiments presented below are examples of compounds, compositions, methods, and uses described in the present application.

Embodiment 1. A compound of formula (I)

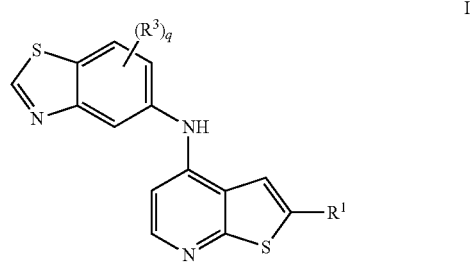

or a pharmaceutically acceptable salt thereof,
wherein
$R^1$ a 4- to 7-membered monocyclic saturated or partially unsaturated heterocyclic ring having 1 to 3 heteroatoms independently selected from nitrogen, oxygen, and sulfur; a 9- to 10-membered bicyclic heterocyclic ring having 1 to 3 heteroatoms independently selected from nitrogen, oxygen, and sulfur; or a 7- to 11-membered spirocyclic fused heterocyclic ring having 1 to 3 heteroatoms independently selected from nitrogen, oxygen, and sulfur, and wherein $R^1$ is substituted with $(R^2)_p$;
each $R^2$ is independently halogen, optionally substituted $C_{1-6}$ aliphatic, —OR, —N(R)$_2$, —C(O)R, —C(O)OR, —SO$_2$R, or an optionally substituted 3- to 7-membered saturated heterocyclic ring having 1 to 2 heteroatoms independently selected from nitrogen, oxygen, and sulfur;
each R is independently hydrogen, optionally substituted $C_{1-6}$ aliphatic, or an optionally substituted 4- to 6-membered saturated heterocyclic ring having 1 to 3 heteroatoms independently selected from nitrogen, oxygen, and sulfur; or
two R groups on a nitrogen atom, together with the atoms to which they are attached, form a 4- to 6-membered heterocyclic ring having 1 or 2 additional heteroatoms independently selected from nitrogen, oxygen, or sulfur;
each $R^3$ is independently halogen, CN, —N(R)$_2$, —OR, or optionally substituted $C_{1-6}$ aliphatic;
p is 0-4; and
q is 0-4.

Embodiment 2. The compound of Embodiment 1, wherein $R^1$ is a 4- to 7-membered monocyclic saturated or partially unsaturated heterocyclic ring having 1 to 3 heteroatoms independently selected from nitrogen, oxygen, and sulfur, wherein $R^1$ is substituted with $(R^2)_p$.

Embodiment 3. The compound of Embodiments 1 or 2, wherein $R^1$ is

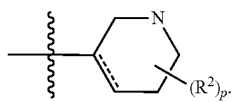

Embodiment 4. The compound of any one of Embodiments 1-3, wherein $R^1$ is

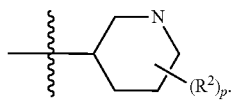

Embodiment 5. The compound of any one of Embodiments 1-3, wherein $R^1$ is

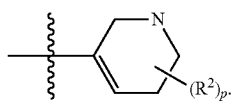

Embodiment 6. The compound of any one of Embodiments 1-4, wherein $R^1$ is

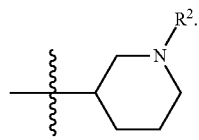

Embodiment 7. The compound of any one of Embodiments 1-4, wherein $R^1$ is

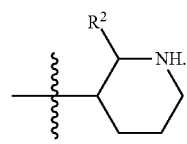

Embodiment 8. The compound of any one of Embodiments 1-4, wherein $R^1$ is

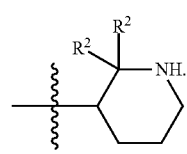

Embodiment 9. The compound of any one of Embodiments 1-4, wherein $R^1$ is

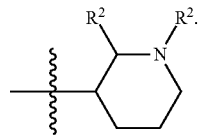

Embodiment 10. The compound of any one of Embodiments 1-4, wherein $R^1$ is

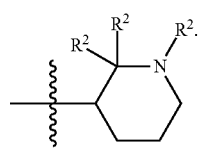

Embodiment 11. The compound of any one of Embodiments 1-3 or 5, wherein $R^1$ is

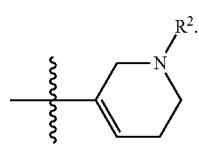

Embodiment 12. The compound of any one of Embodiments 1-3 or 5, wherein $R^1$ is

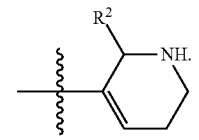

Embodiment 13. The compound of any one of Embodiments 1-3 or 5, wherein $R^1$ is

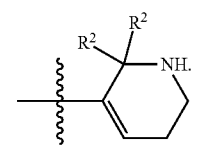

Embodiment 14. The compound of any one of Embodiments 1-3 or 5, wherein $R^1$ is

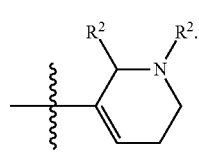

Embodiment 15. The compound of any one of Embodiments 1-3 or 5, wherein R¹ is

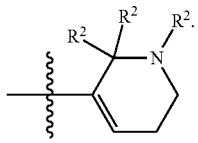

Embodiment 16. The compound of Embodiments 1 or 2, wherein R¹ is

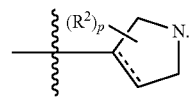

Embodiment 17. The compound of any one of Embodiments 1-2 or 16, wherein R¹ is

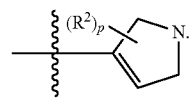

Embodiment 18. The compound of any one of Embodiments 1-2 or 16-17, wherein R¹ is

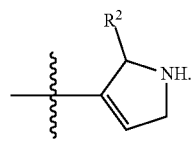

Embodiment 19. The compound of any one of Embodiments 1-2 or 16-17, wherein R¹ is

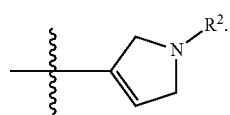

Embodiment 20. The compound of any one of Embodiments 1-2 or 16-17, wherein R¹ is

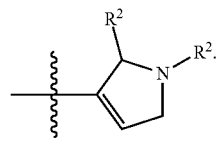

Embodiment 21. The compound of any one of Embodiments 1-2 or 16-17, wherein R¹ is

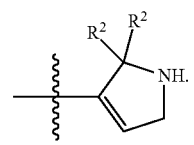

Embodiment 22. The compound of any one of Embodiments 1-2 or 16-17, wherein R¹ is

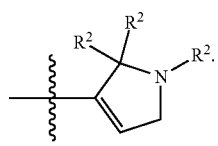

Embodiment 23. The compound of any one of Embodiments 1-2 or 16, wherein R¹ is

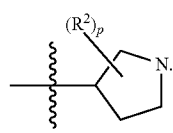

Embodiment 24. The compound of any one of Embodiments 1-2, 16, or 23, wherein R¹ is

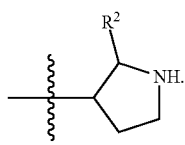

Embodiment 25. The compound of any one of Embodiments 1-2, 16, or 23, wherein R¹ is

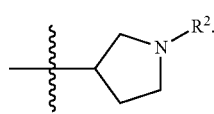

Embodiment 26. The compound of any one of Embodiments 1-2, 16, or 23, wherein R¹ is

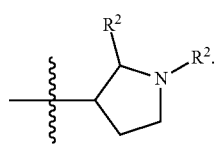

Embodiment 27. The compound of any one of Embodiments 1-2, 16, or 23, wherein R¹ is

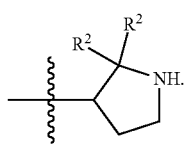

Embodiment 28. The compound of any one of Embodiments 1-2, 16, or 23, wherein $R^1$ is

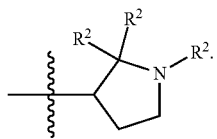

Embodiment 29. The compound of any one of Embodiments 1-28, wherein $R^2$ is optionally substituted $C_{1-6}$ aliphatic.

Embodiment 30. The compound of any one of Embodiments 1-3, 7, or 29, wherein $R^1$ is

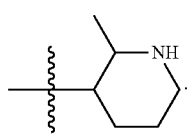 [SMILES: *C1CCCNC1C]

Embodiment 31. The compound of any one of Embodiments 1-3, 7, 29, or 30, wherein $R^1$ is

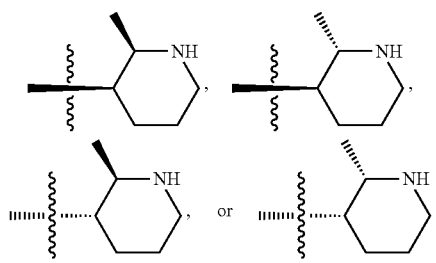

Embodiment 32. The compound of Embodiment 1, wherein $R^1$ is selected from

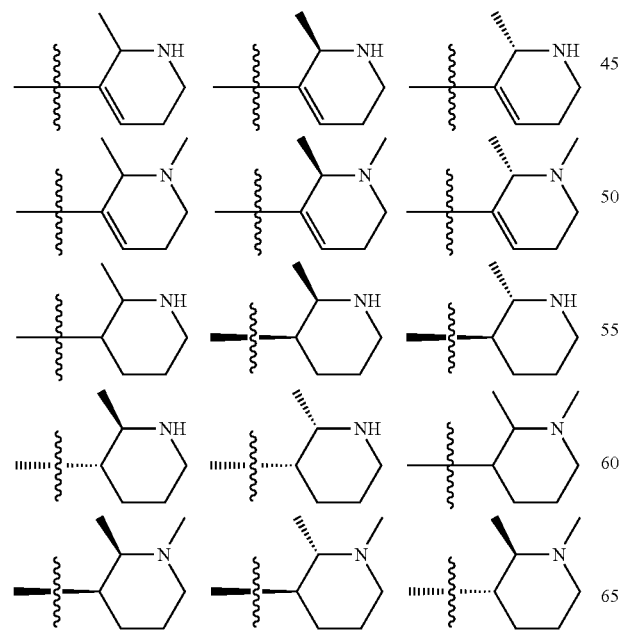

-continued

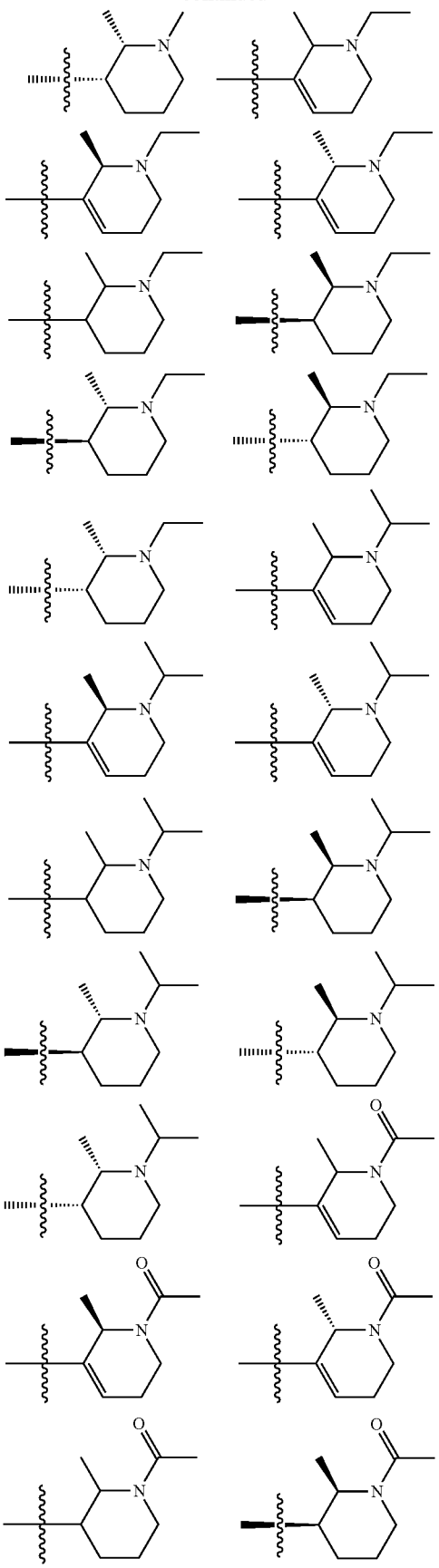

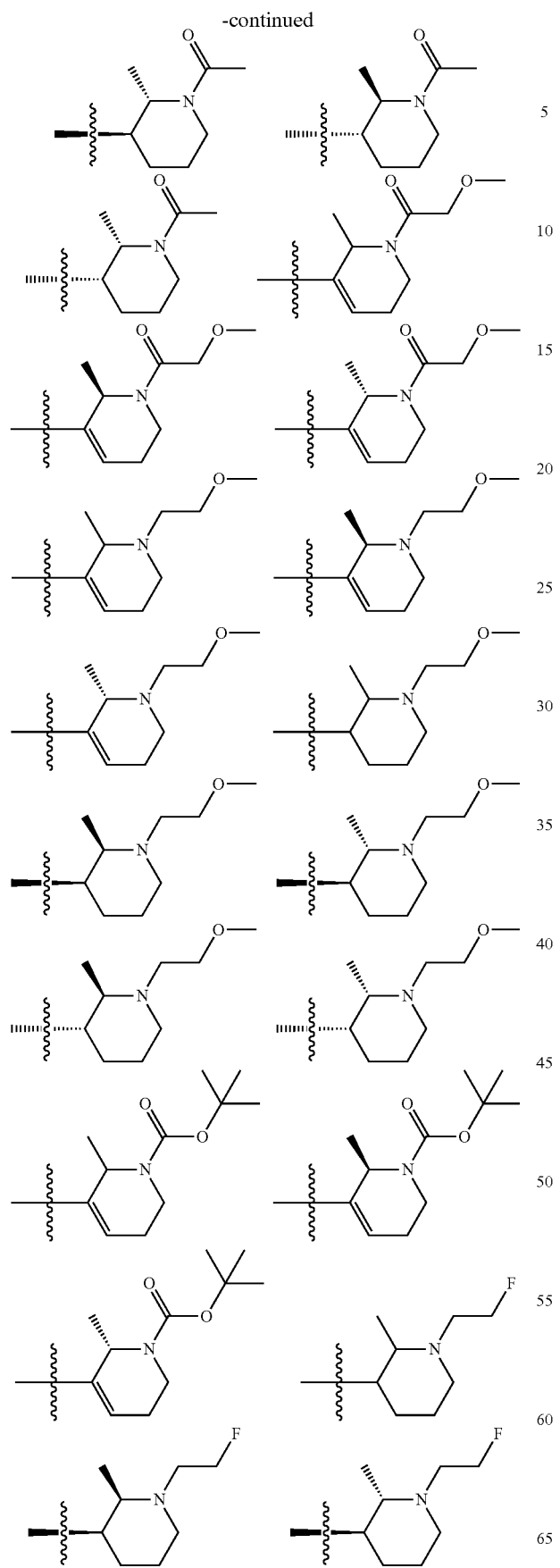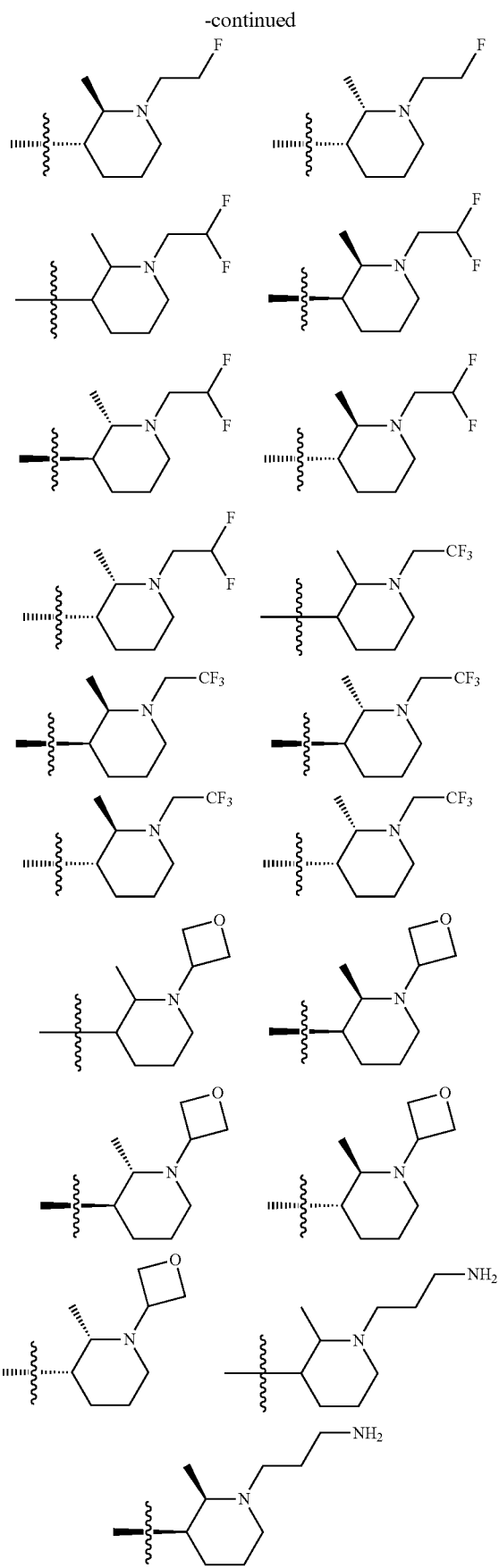

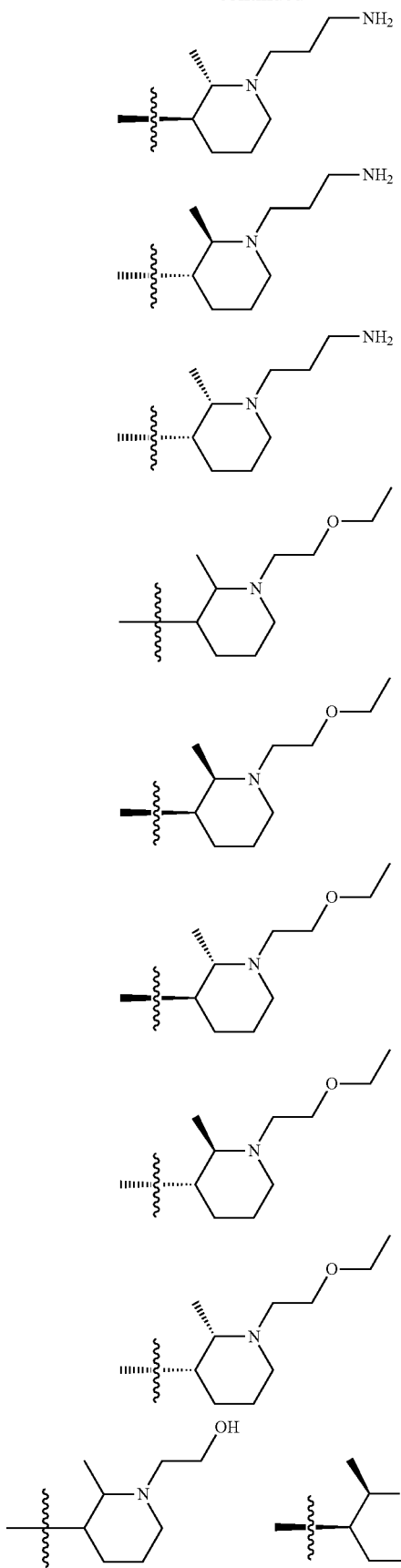
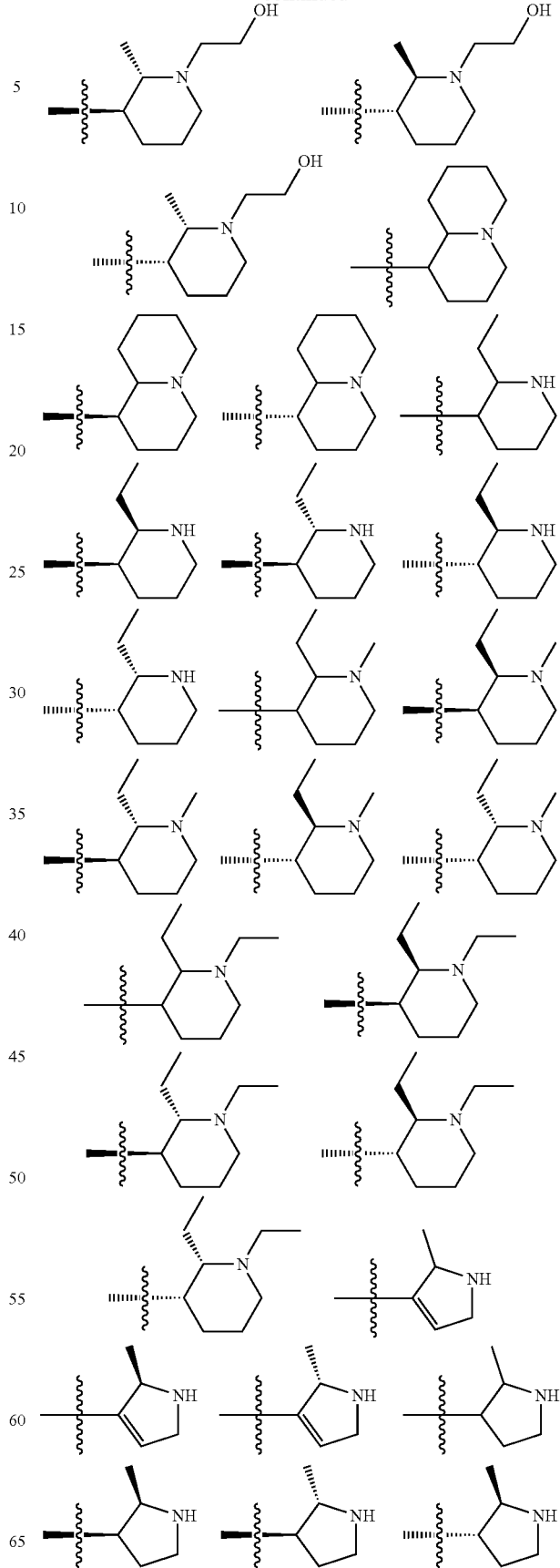

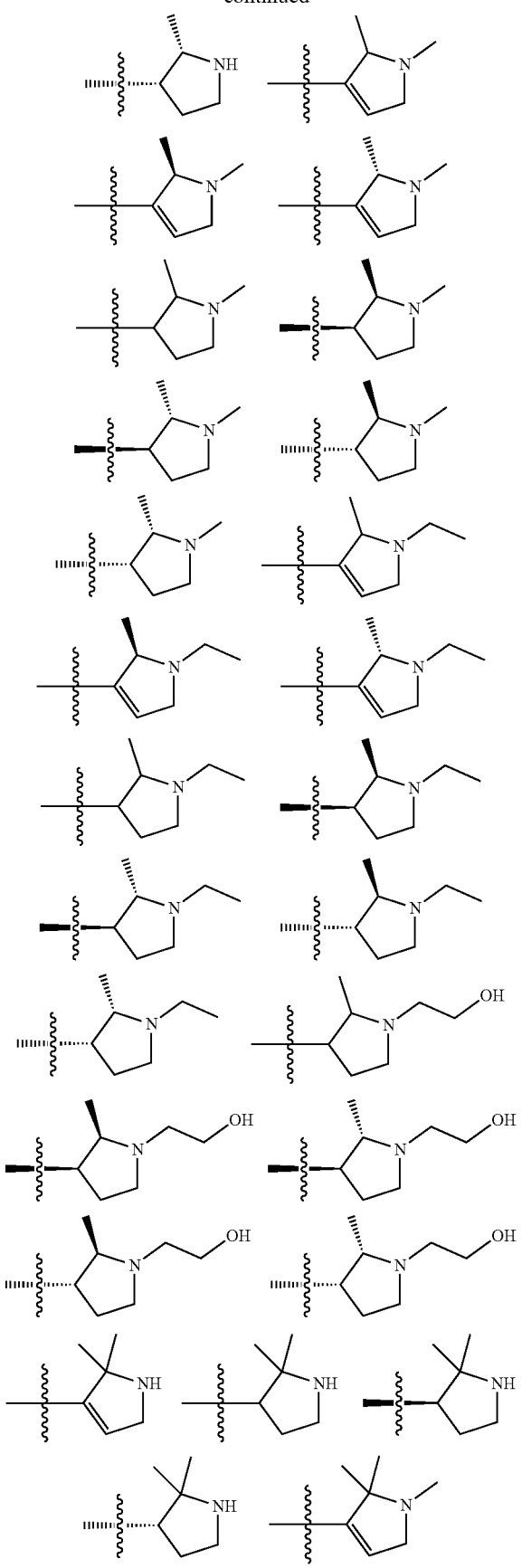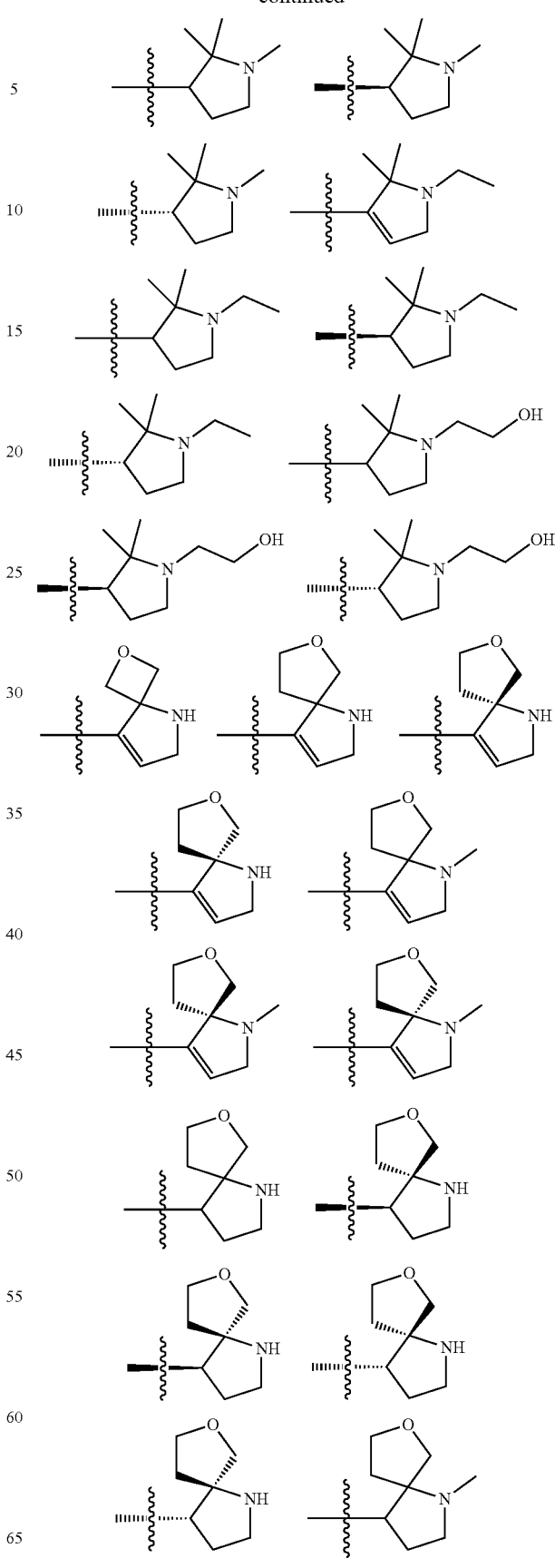

-continued

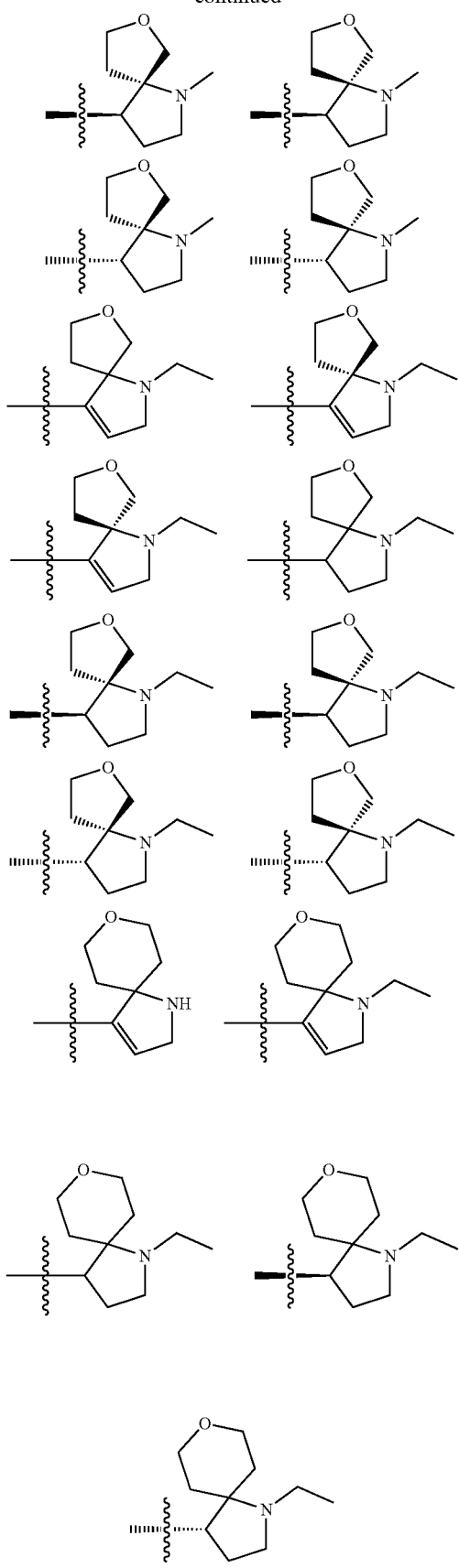

Embodiment 33. The compound of any of Embodiments 1-32, wherein the compound is of Formula II:

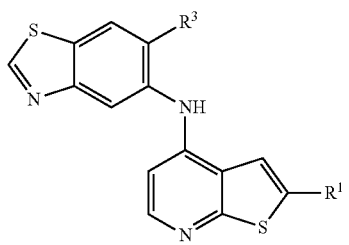

II or a pharmaceutically acceptable salt thereof.

Embodiment 34. The compound of any of Embodiments 1-32, wherein the compound is of Formula III:

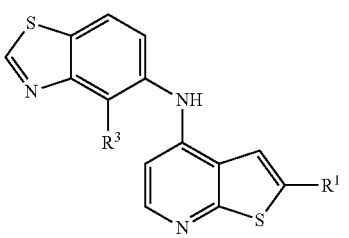

III or a pharmaceutically acceptable salt thereof.

Embodiment 35. The compound of any of Embodiments 1-32, wherein the compound is of Formula IV:

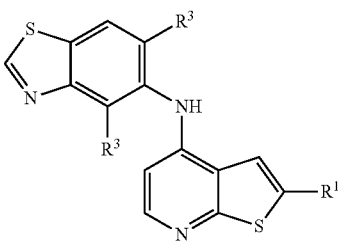

IV or a pharmaceutically acceptable salt thereof.

Embodiment 36. The compound of Embodiment 1, wherein the compound is selected from:

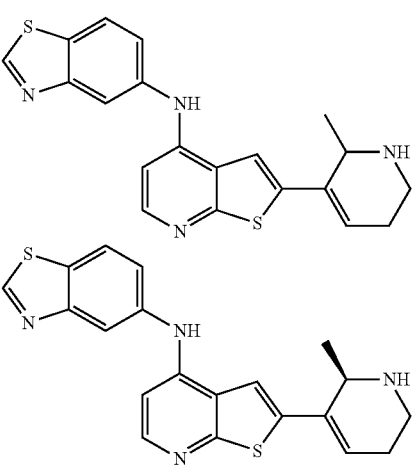

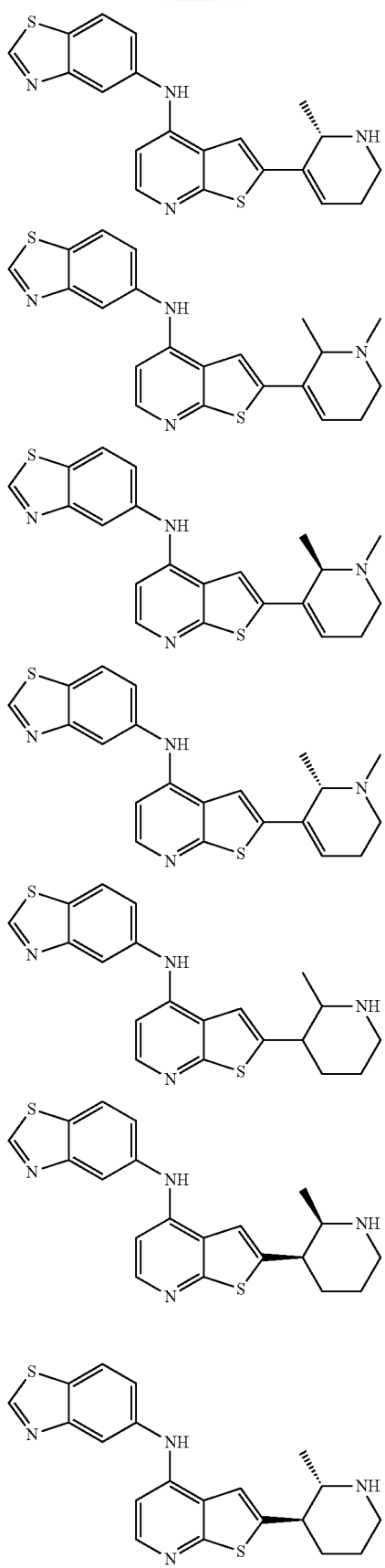
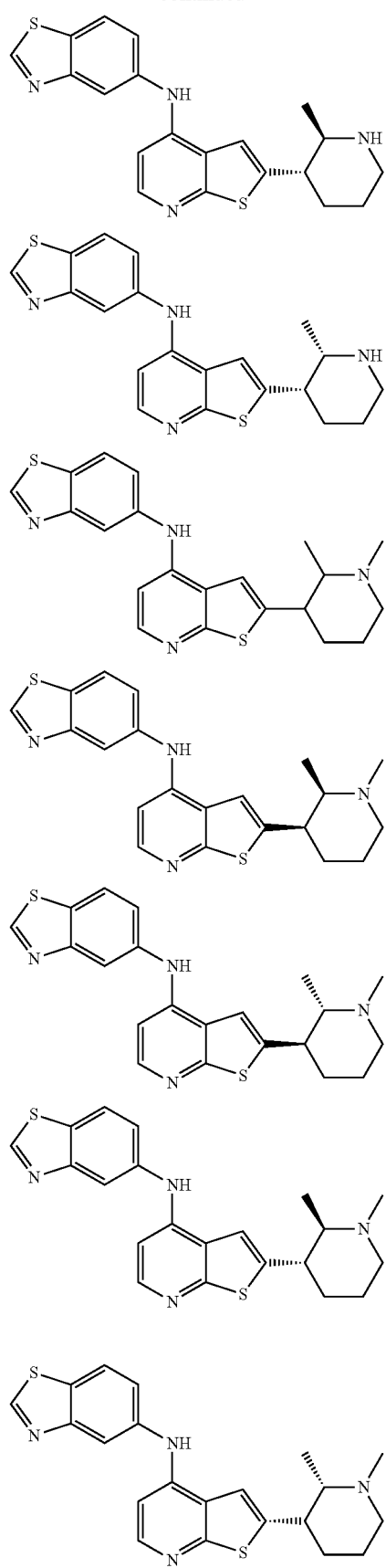

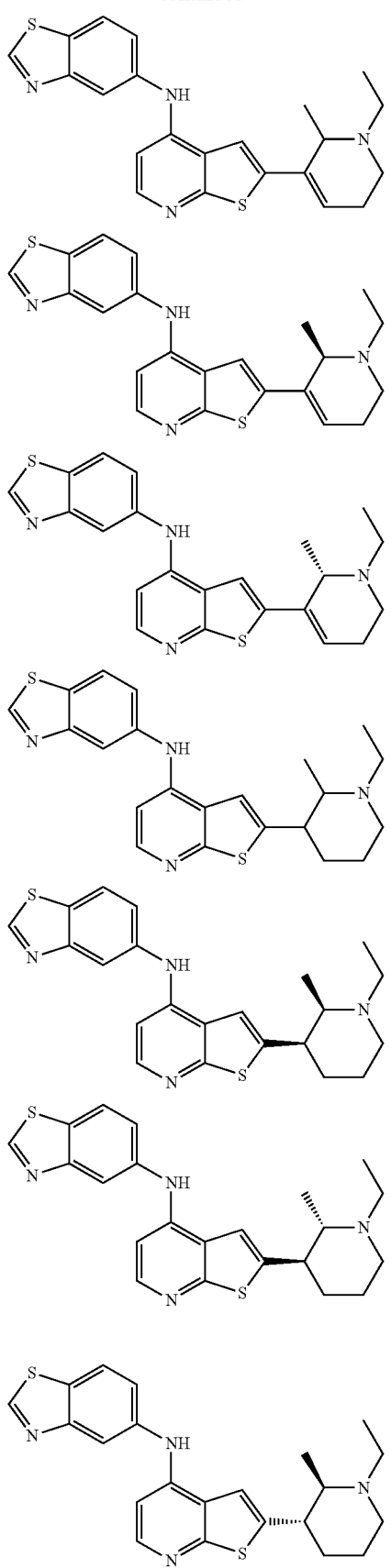
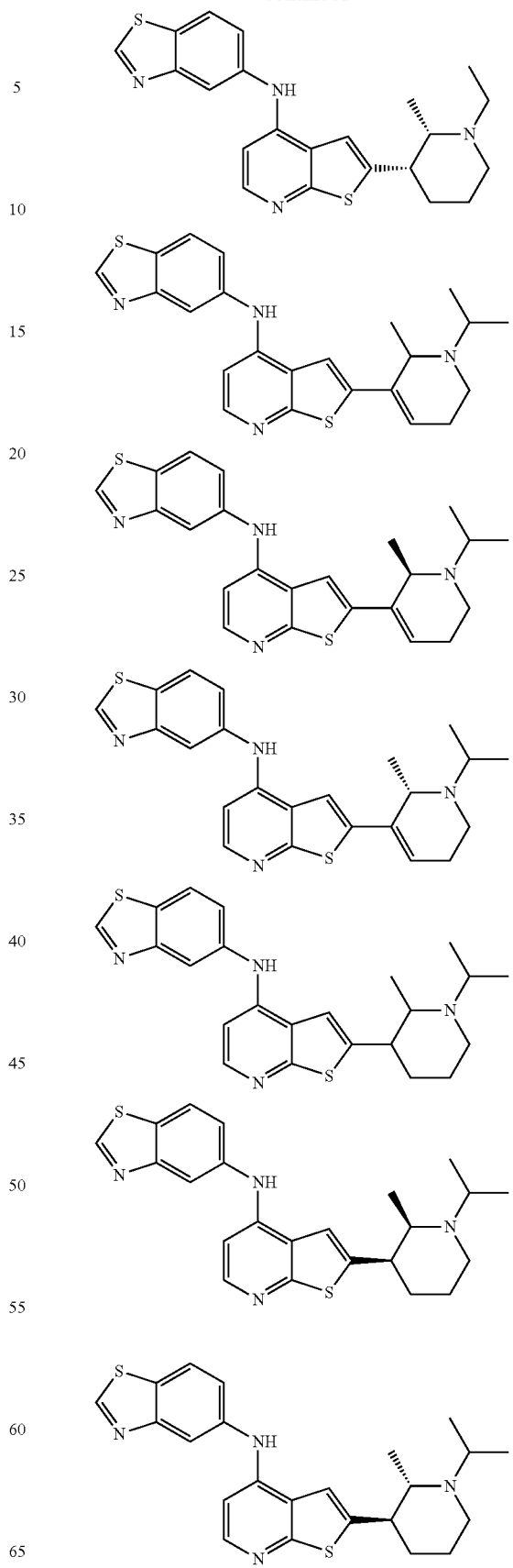

169
-continued
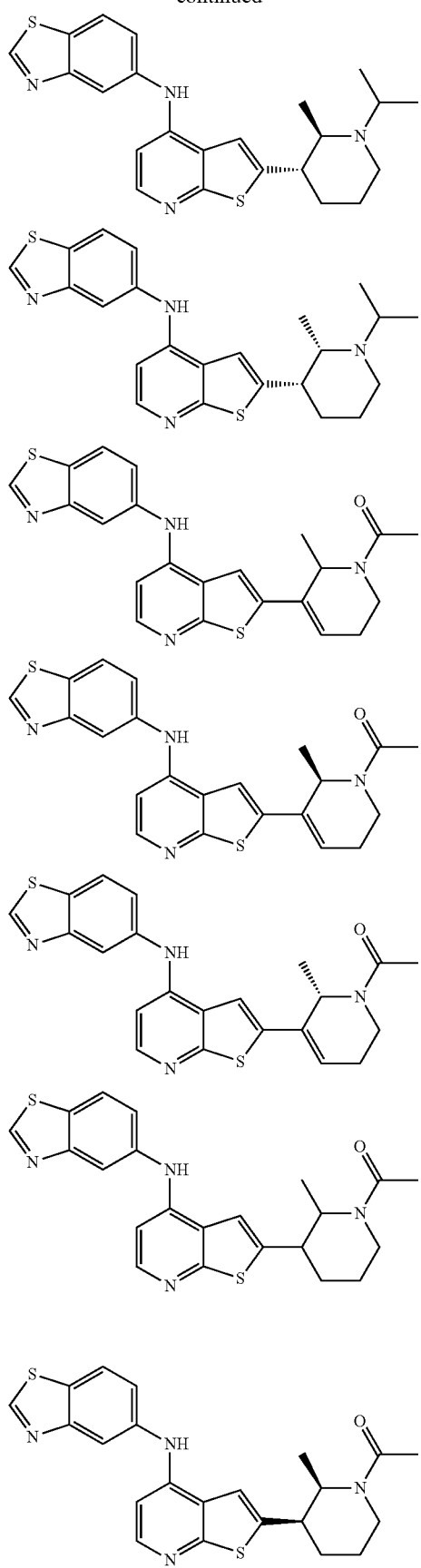
170
-continued
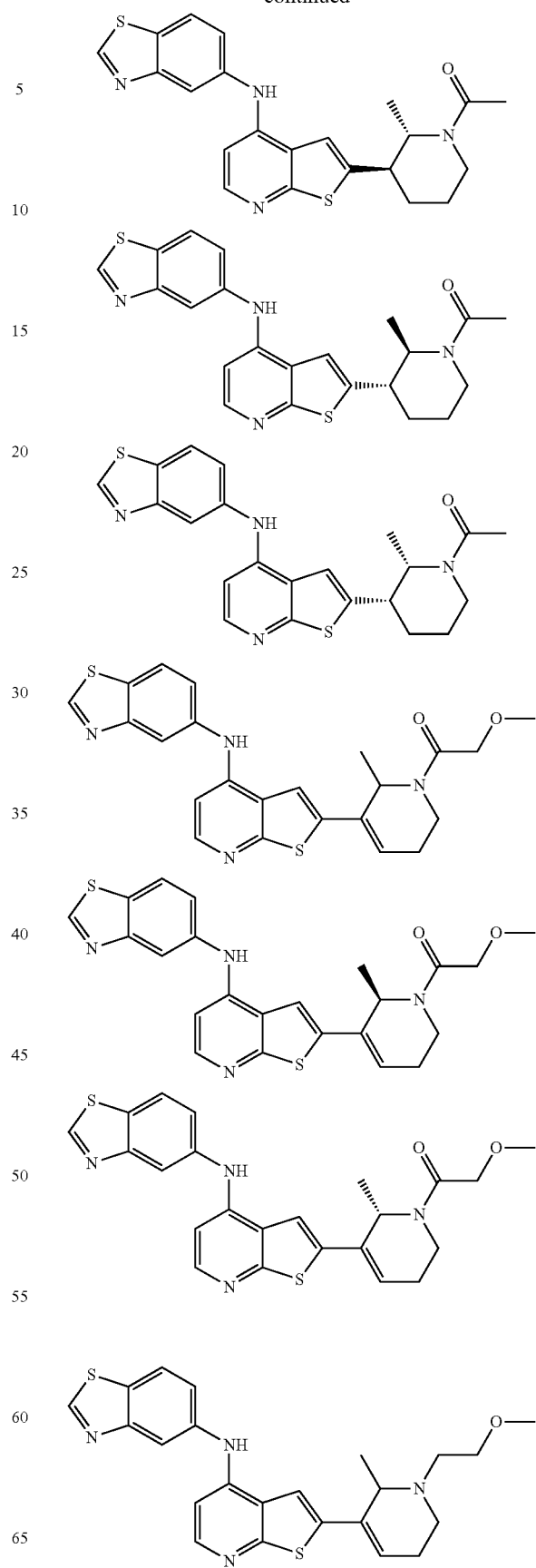

171
-continued
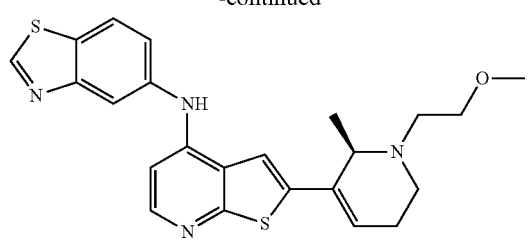
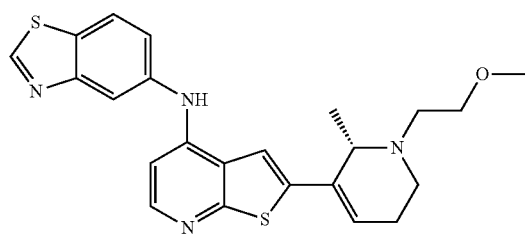
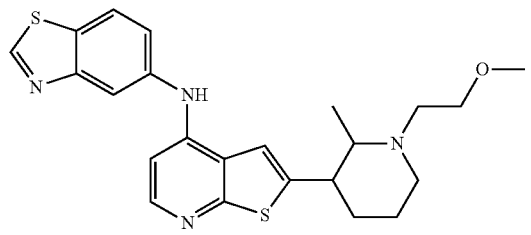
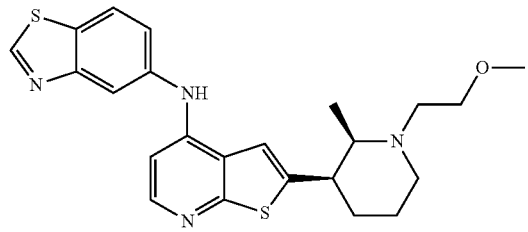
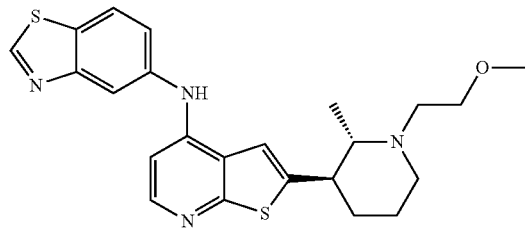
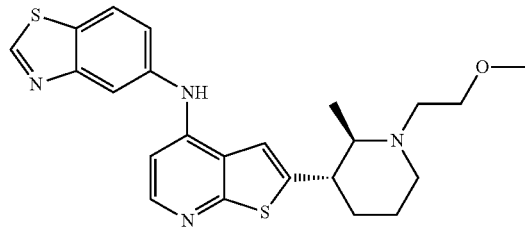
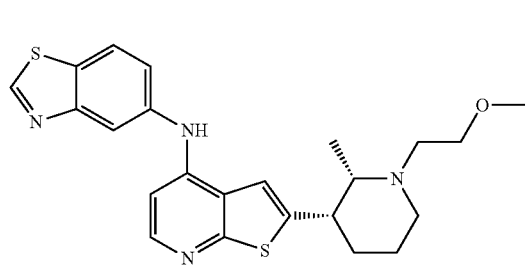
172
-continued
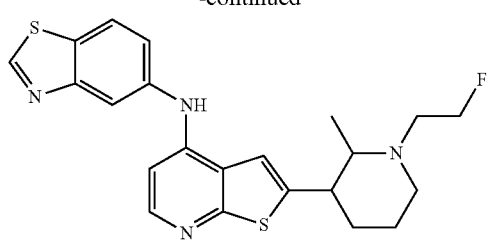
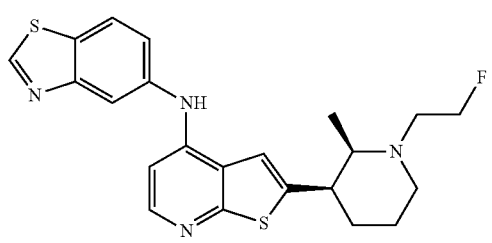
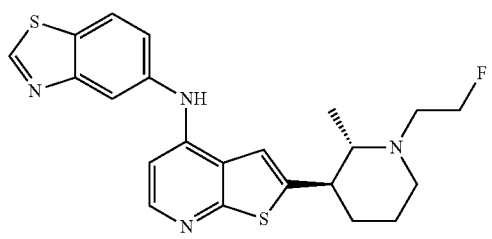
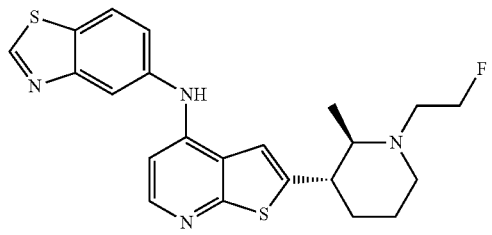
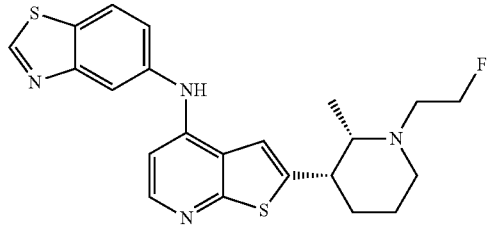
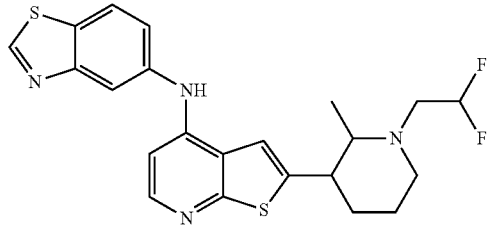
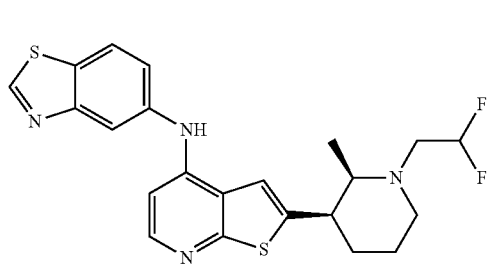

173
-continued
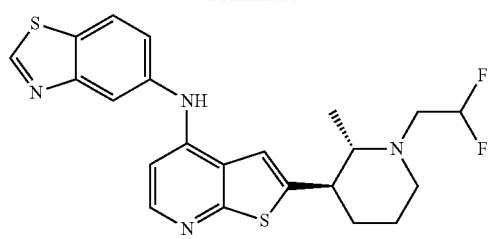
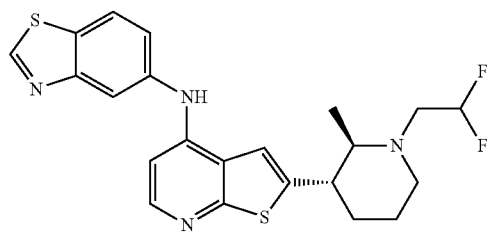
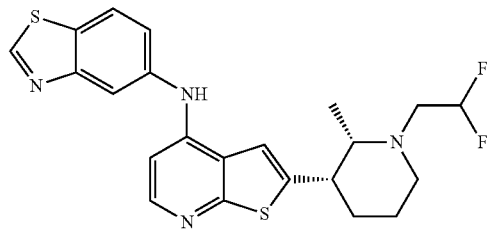
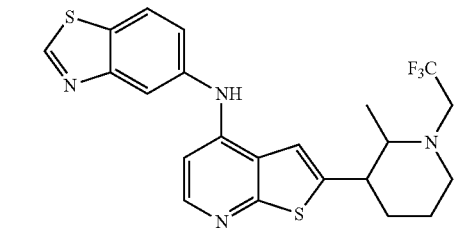
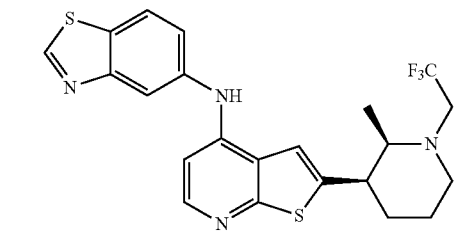
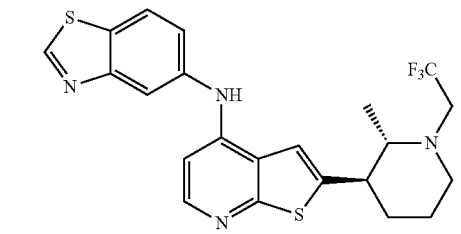
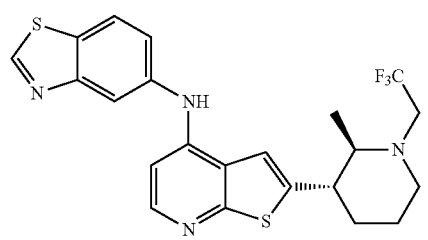
174
-continued
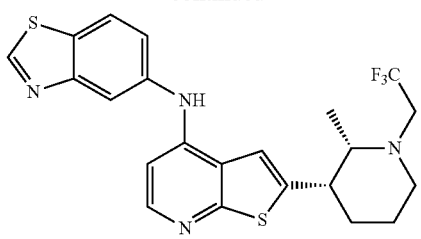
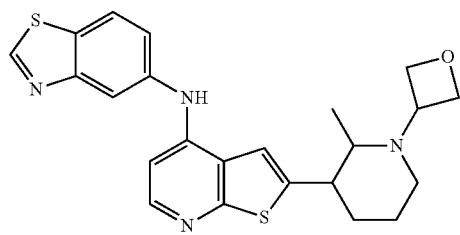
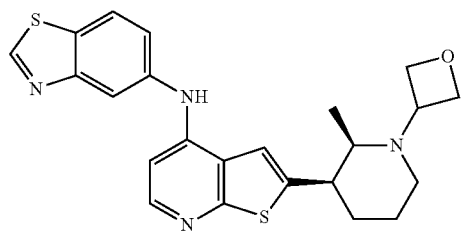
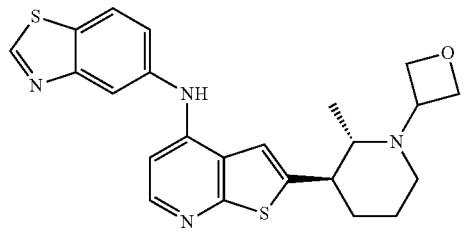
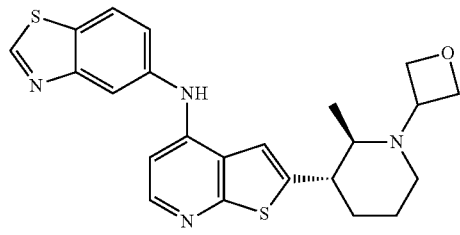
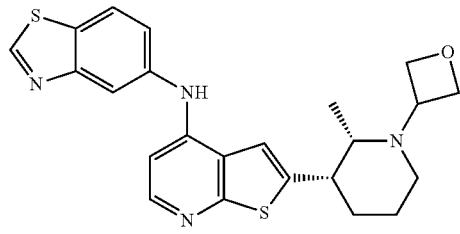
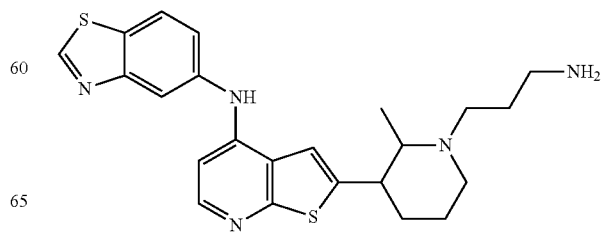

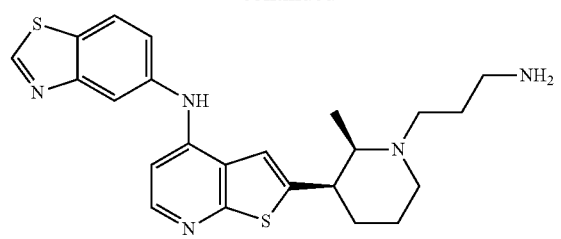
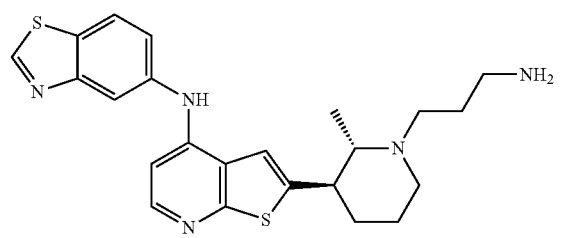
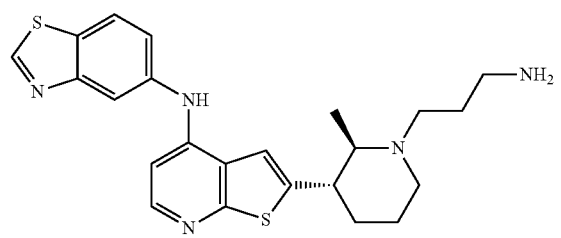
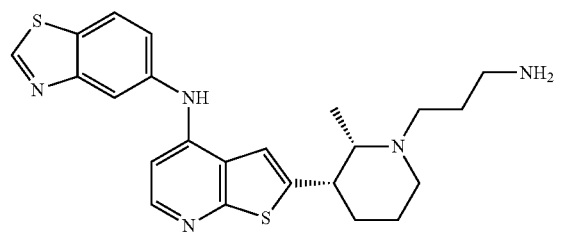
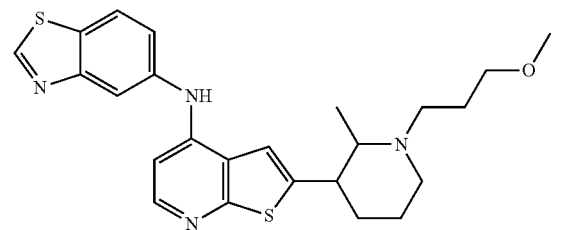
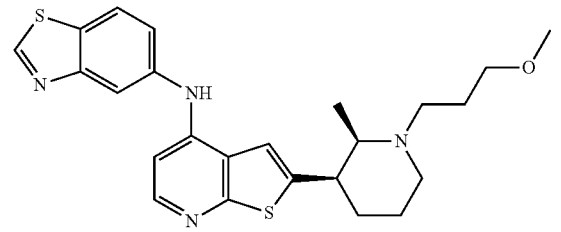
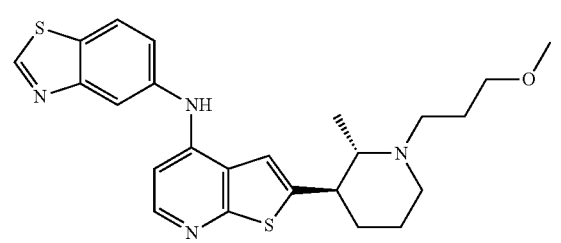
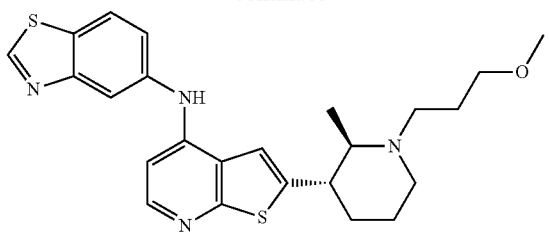
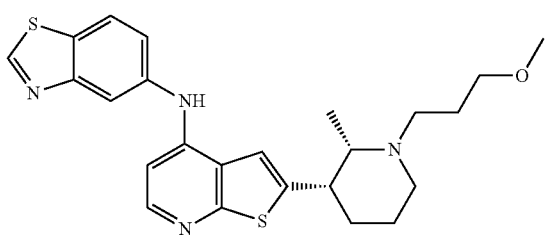
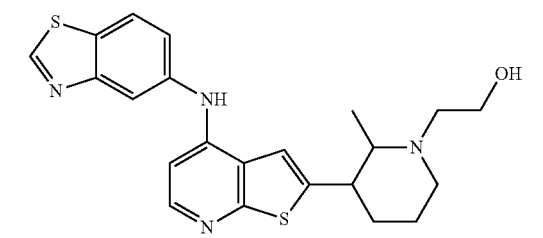
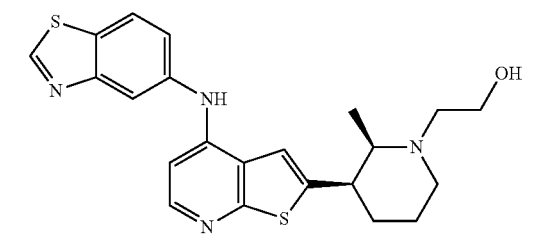
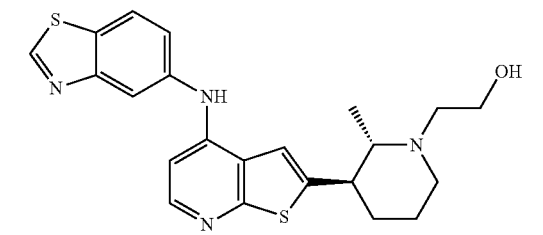
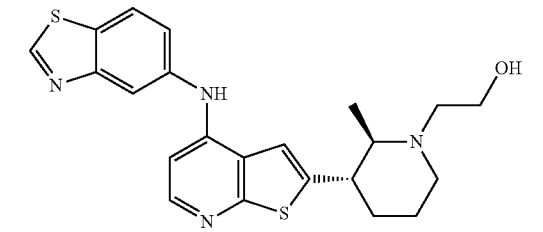
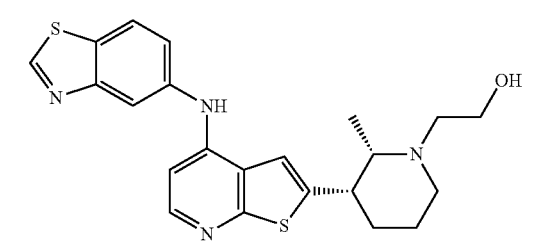

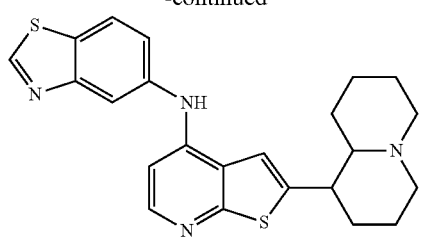
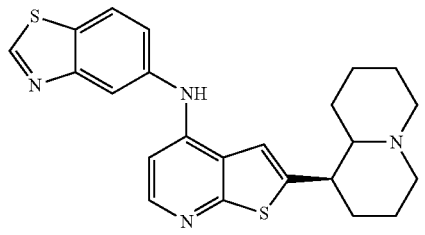
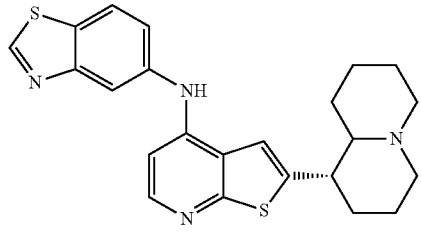
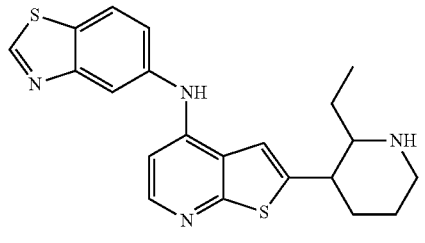
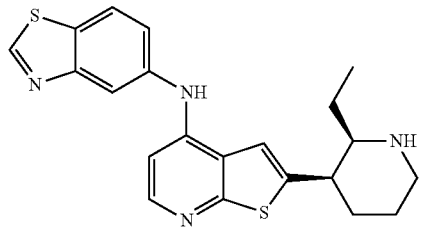
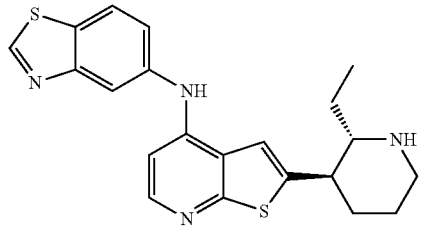
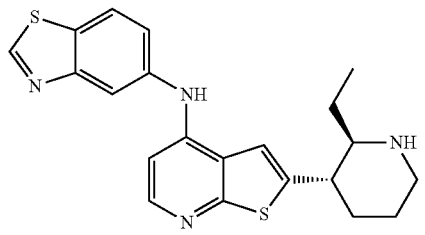
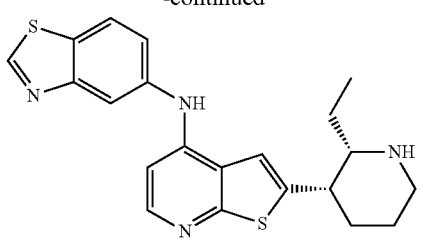
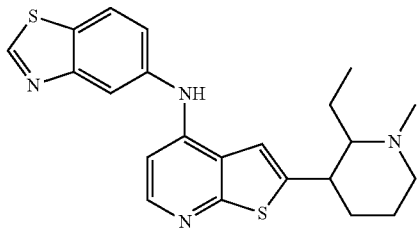
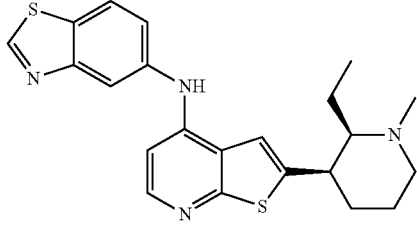
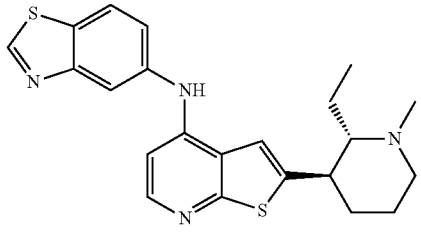
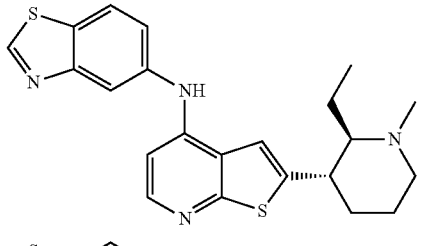
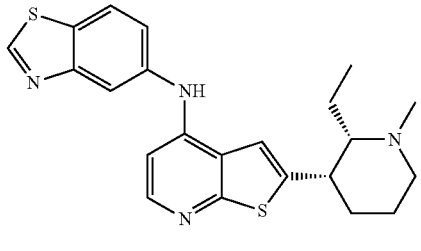
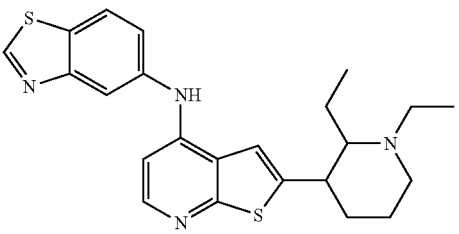

-continued
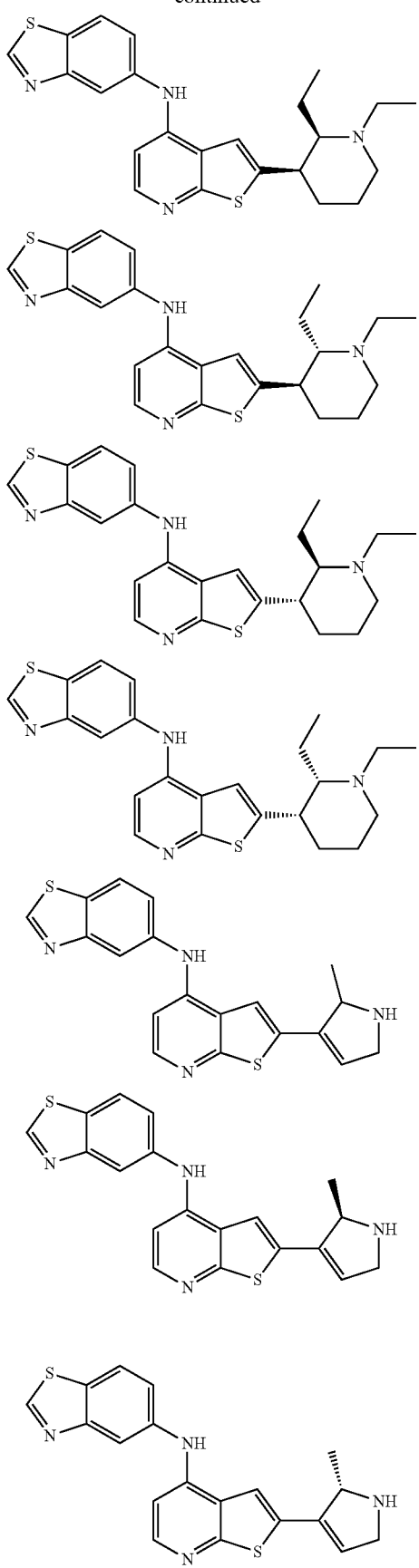
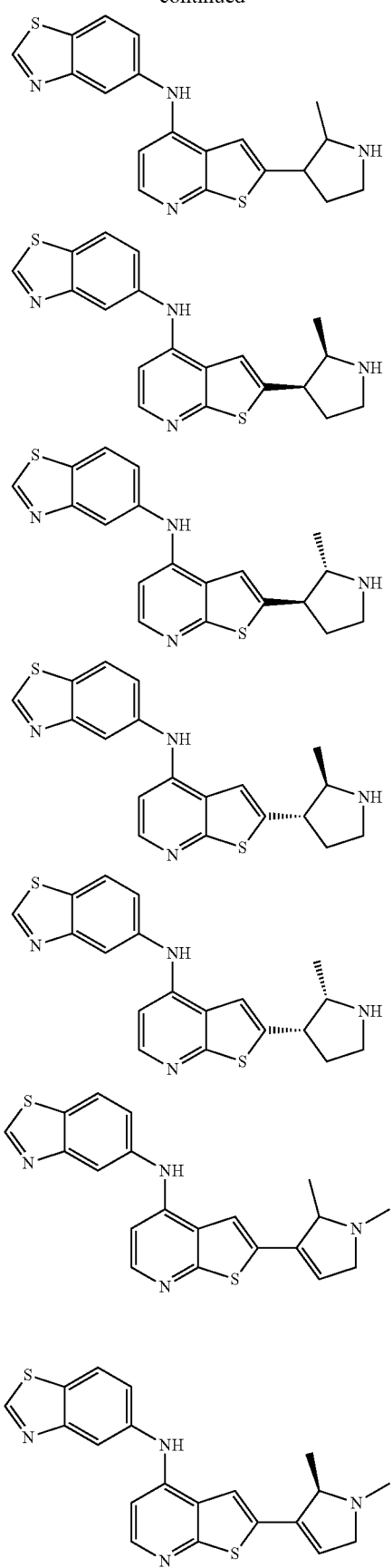

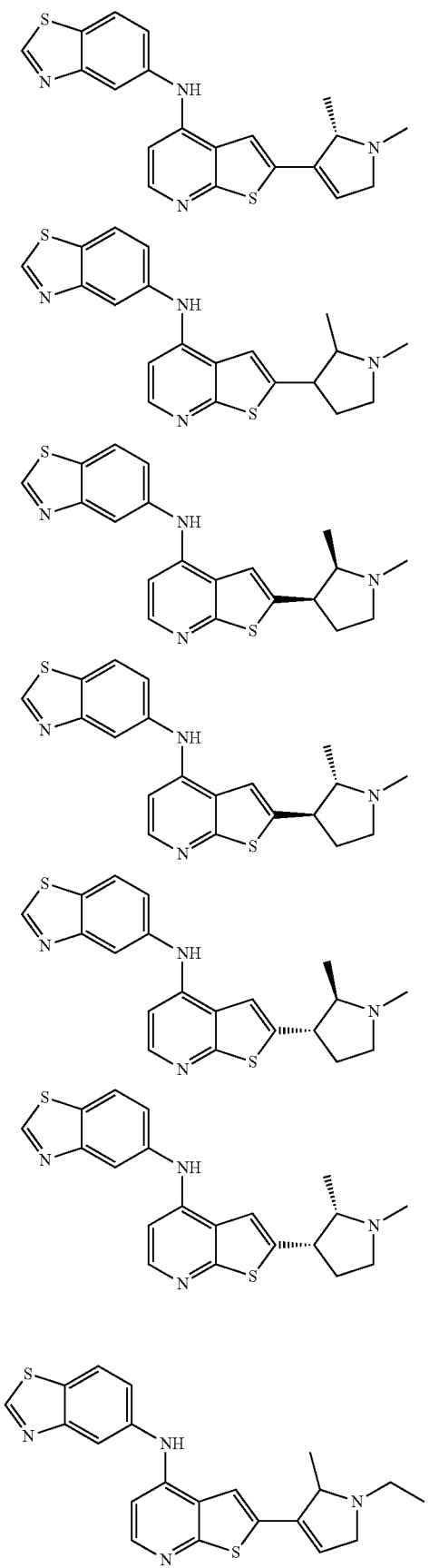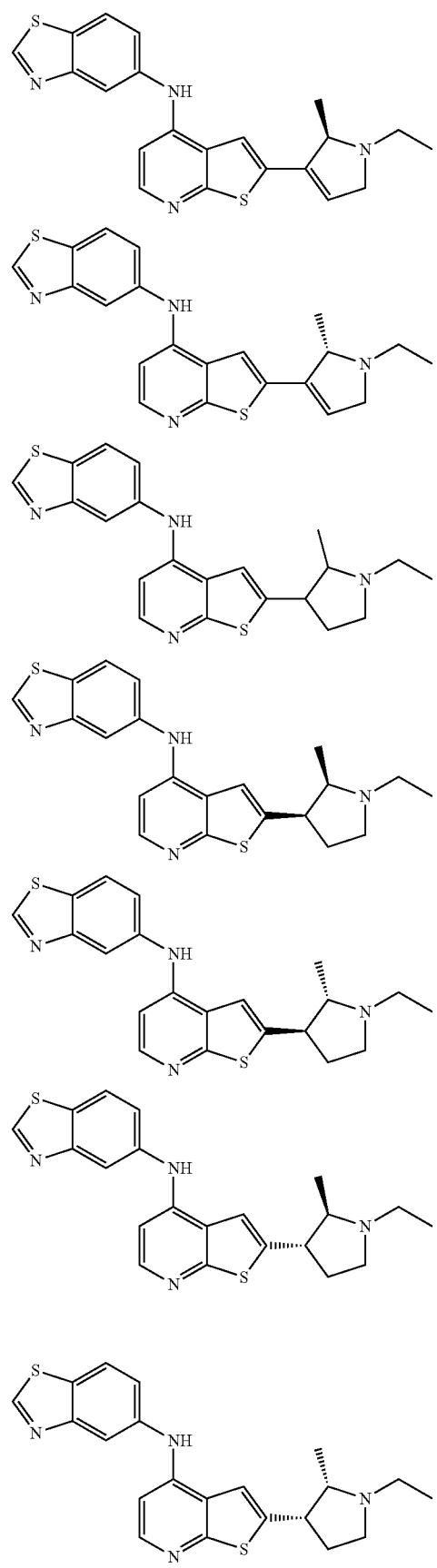

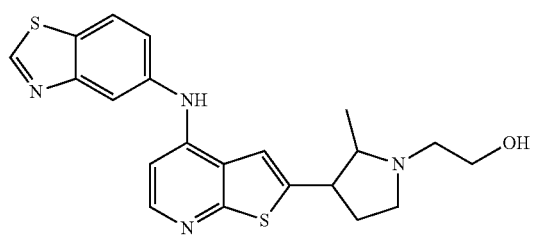
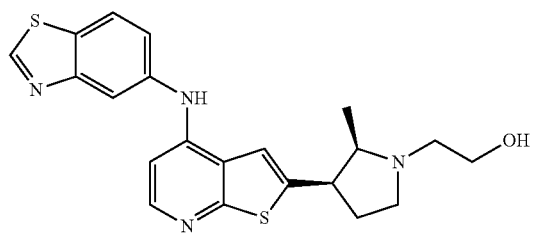
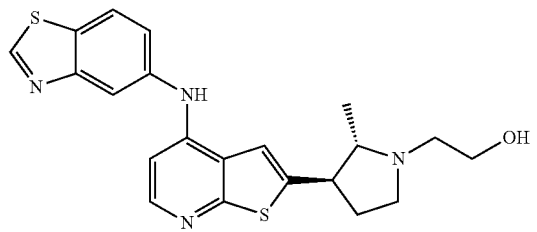
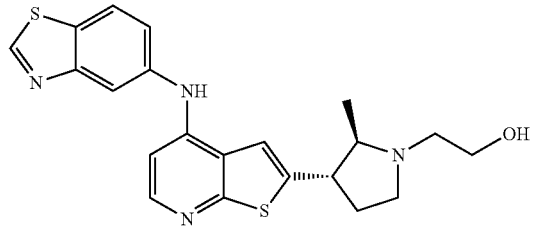
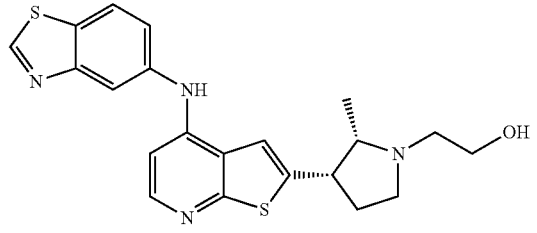
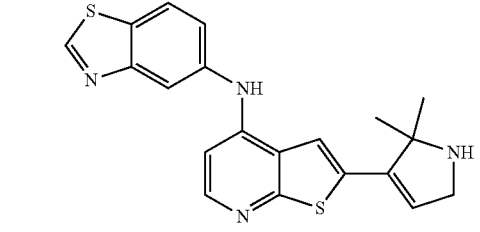
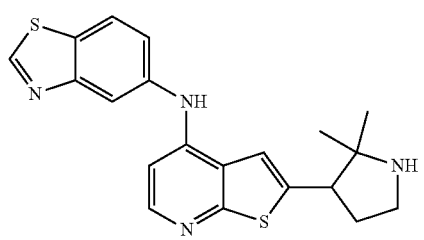
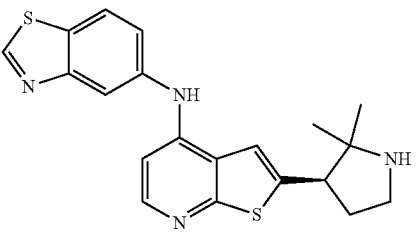
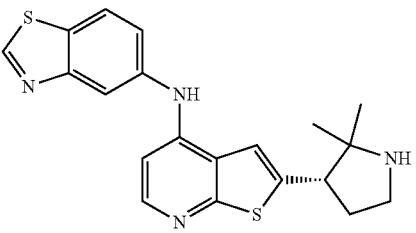
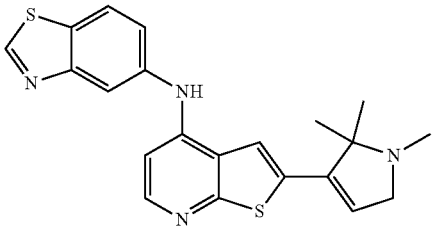
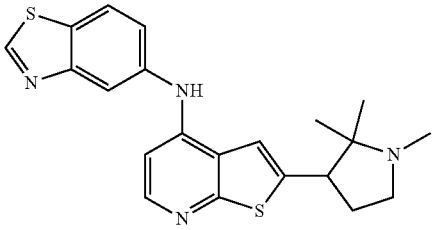
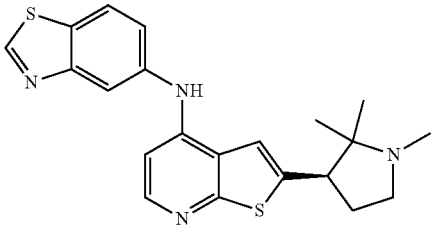
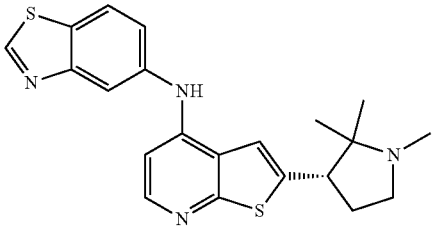
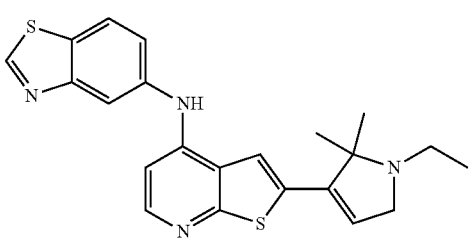

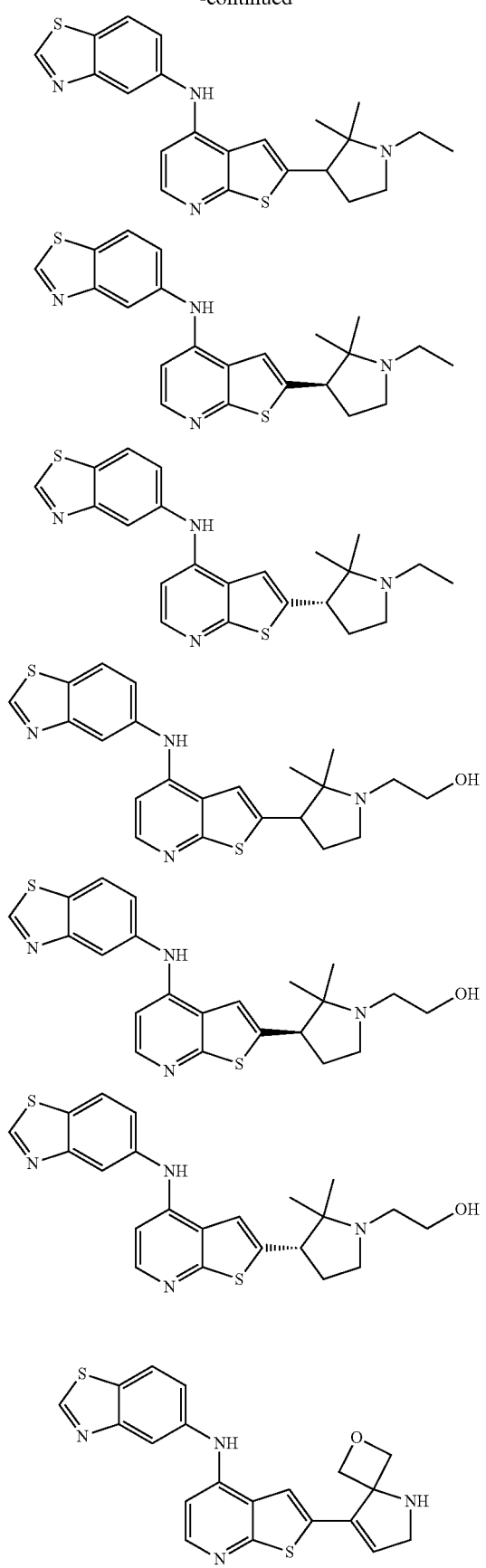
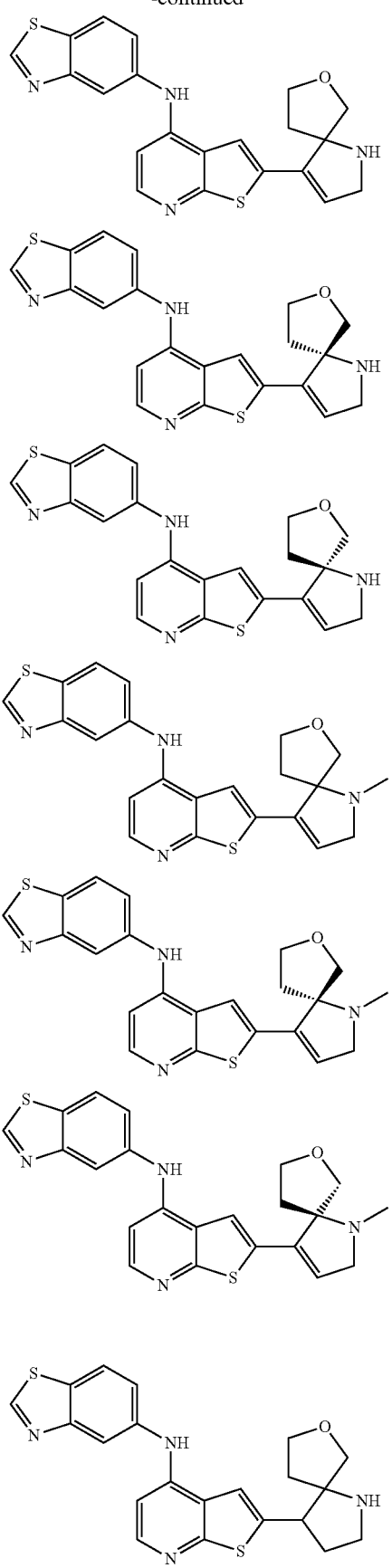

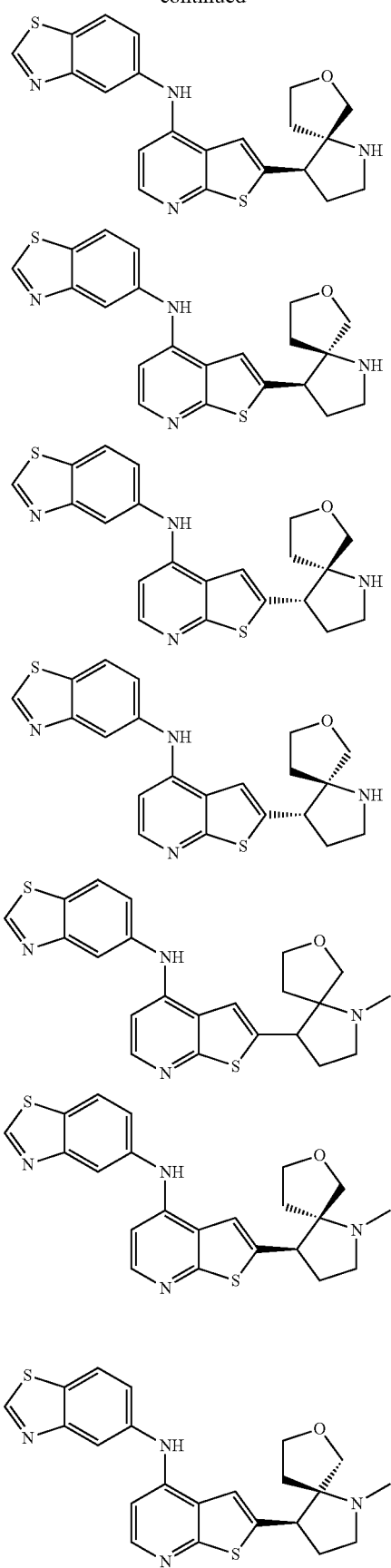
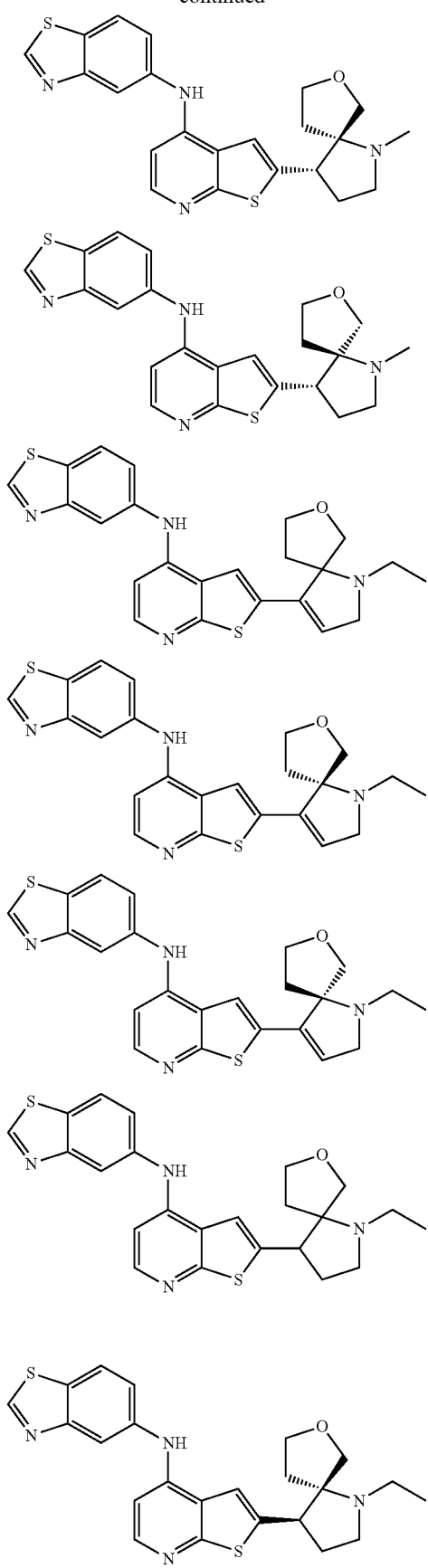

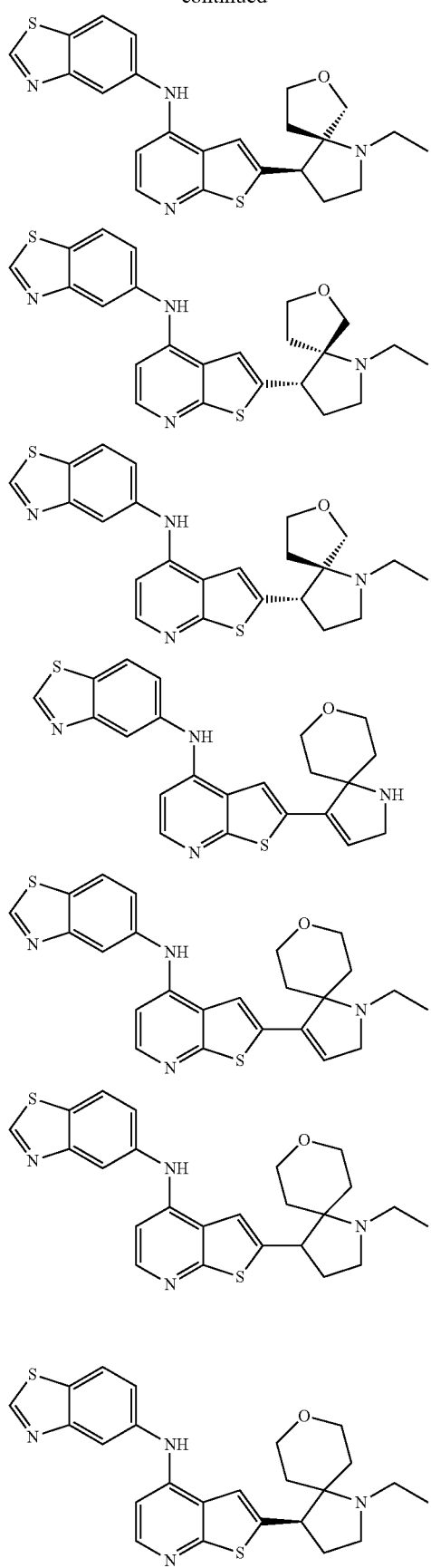
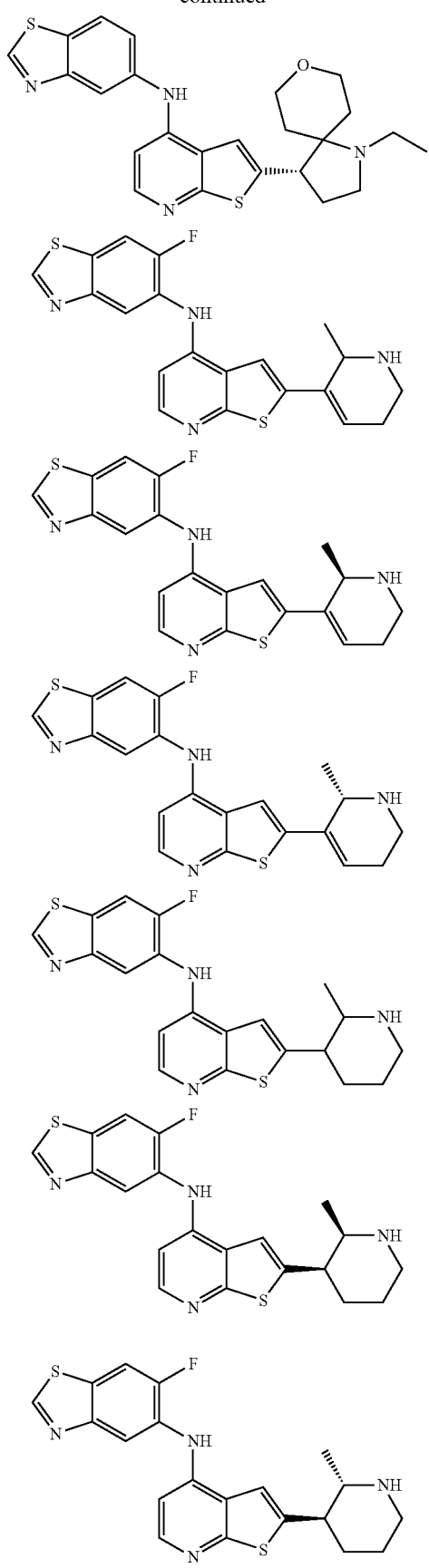

191
-continued
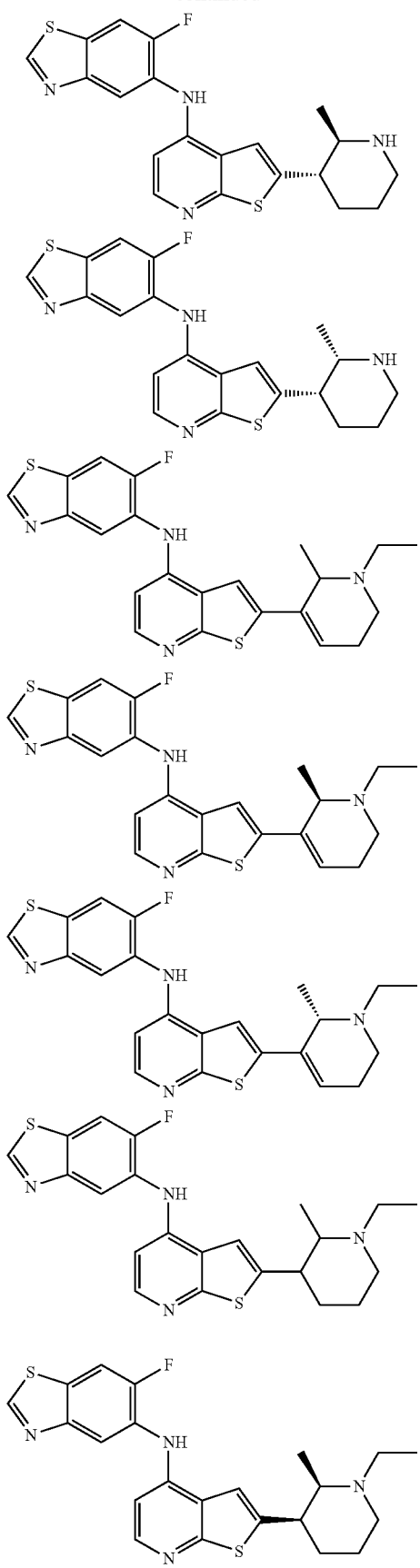
192
-continued
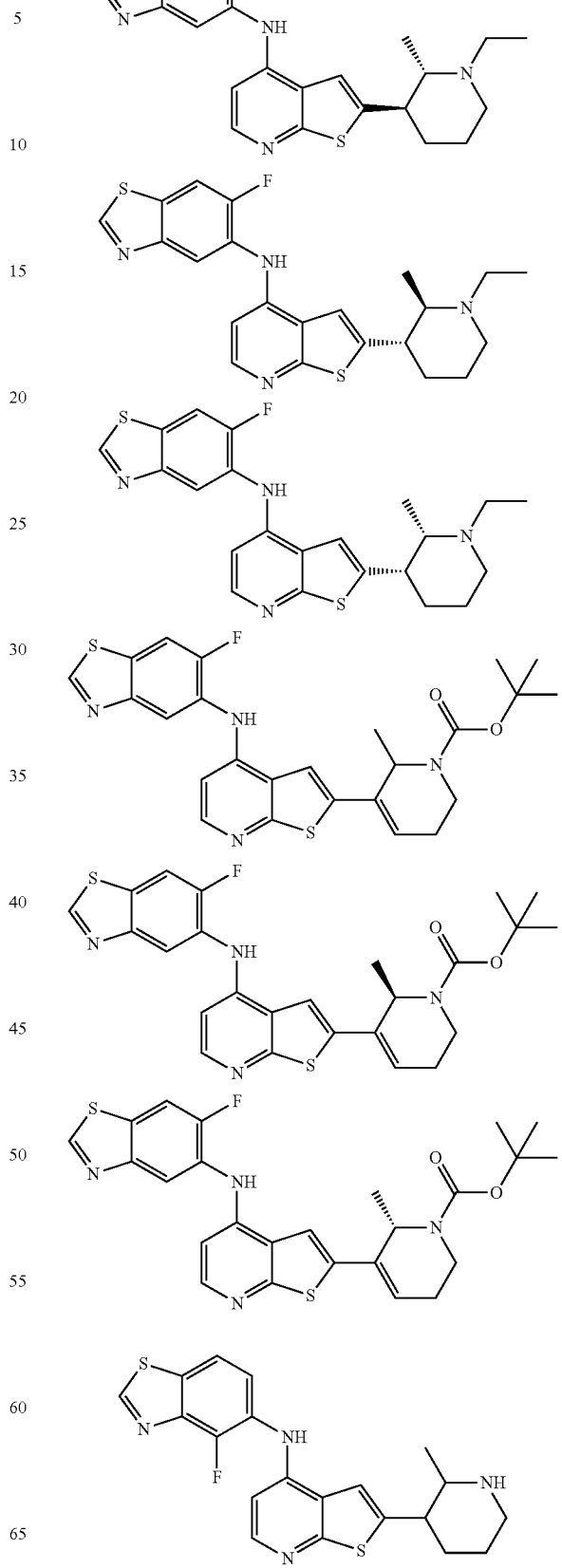

-continued
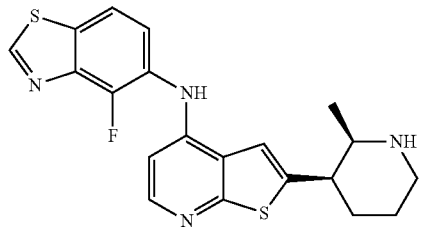
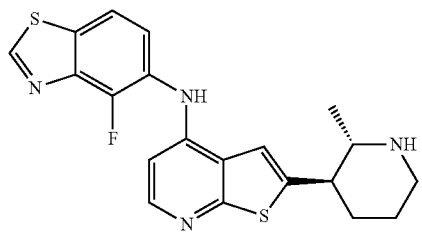
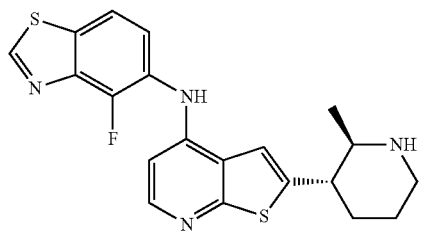
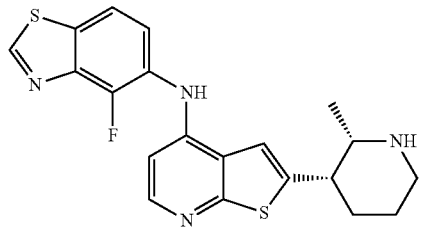
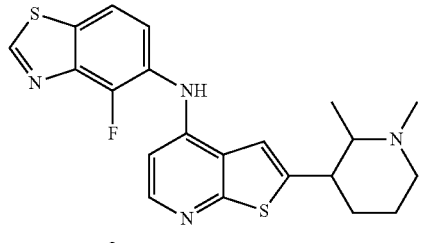
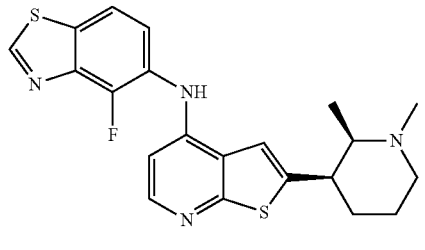
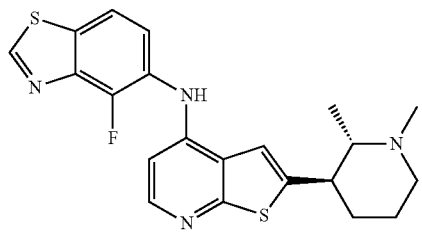
-continued
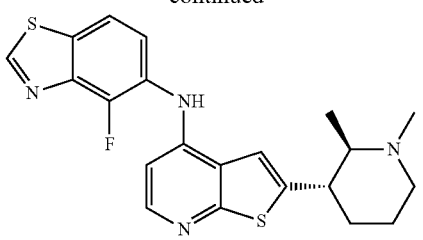
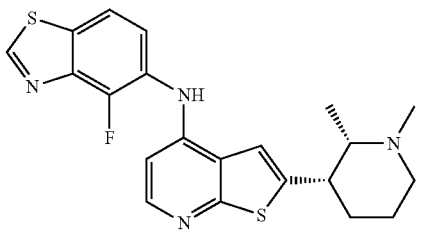
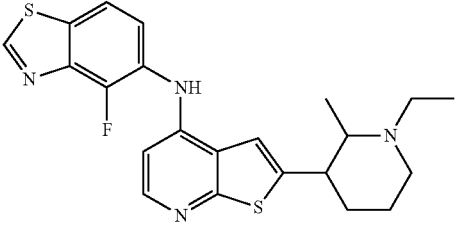
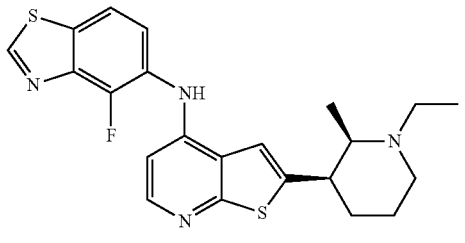
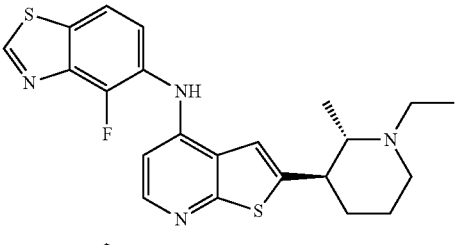
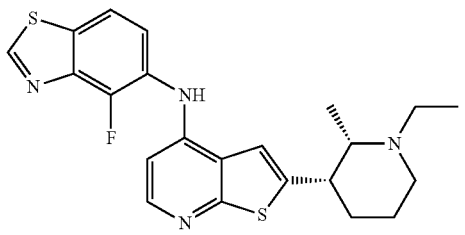

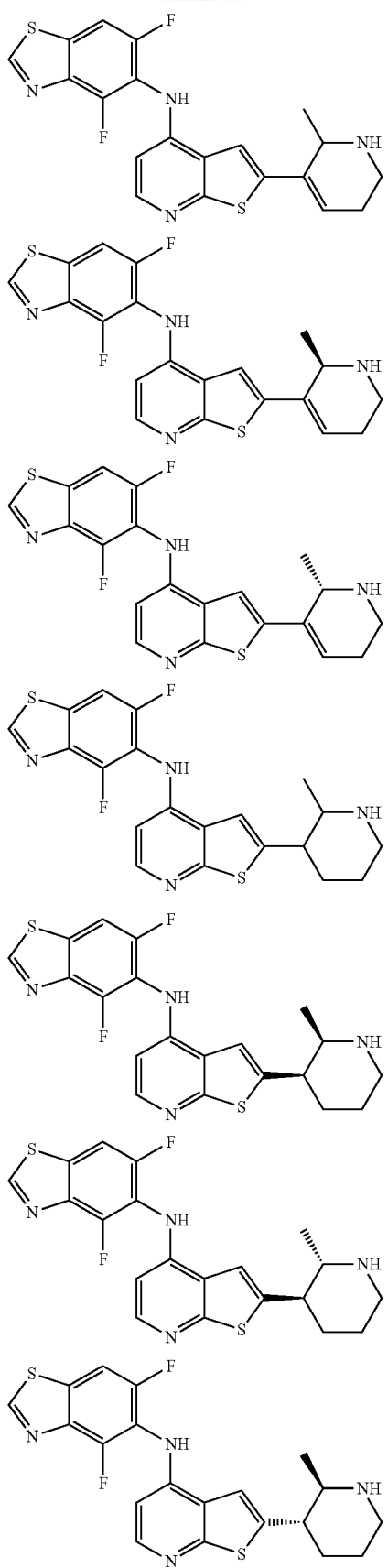
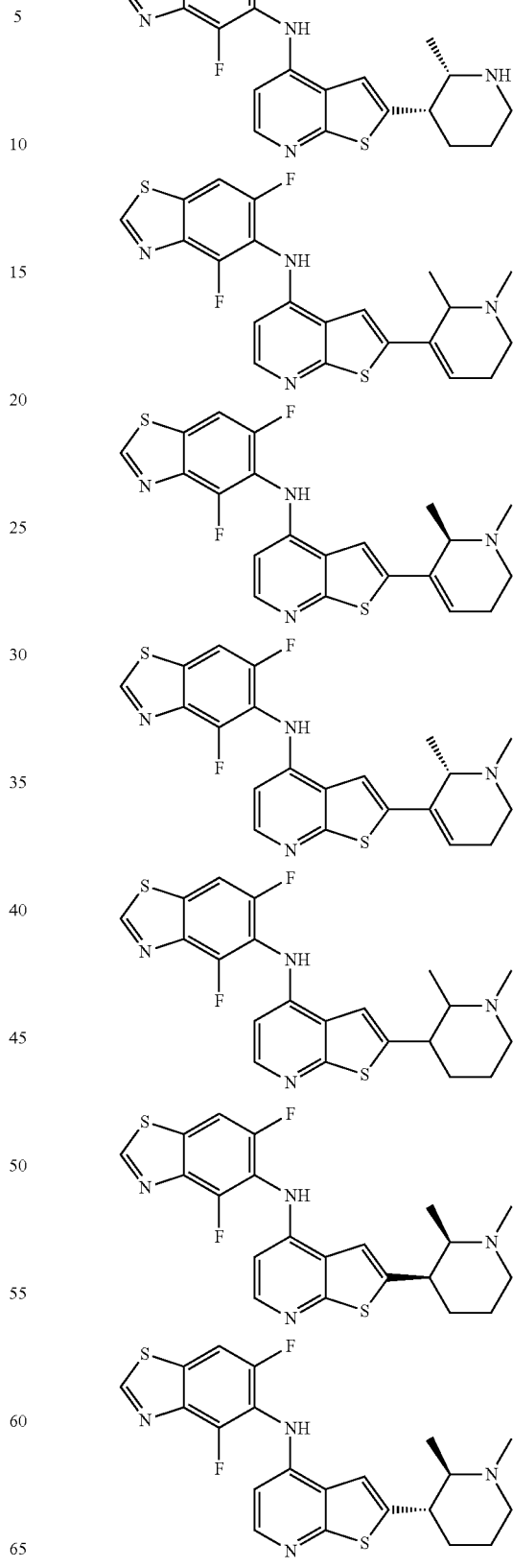

-continued
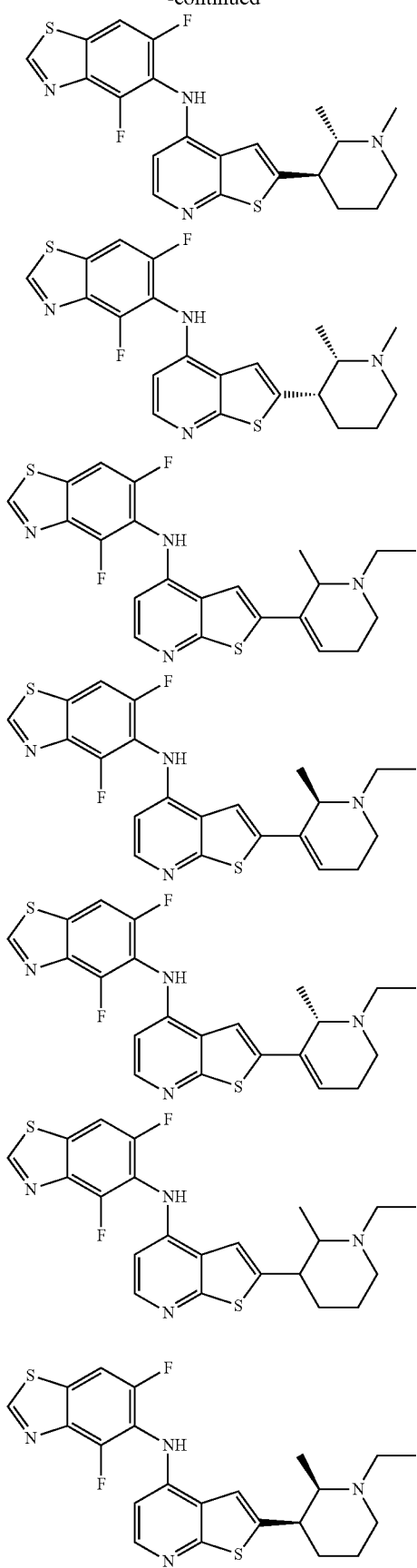
-continued
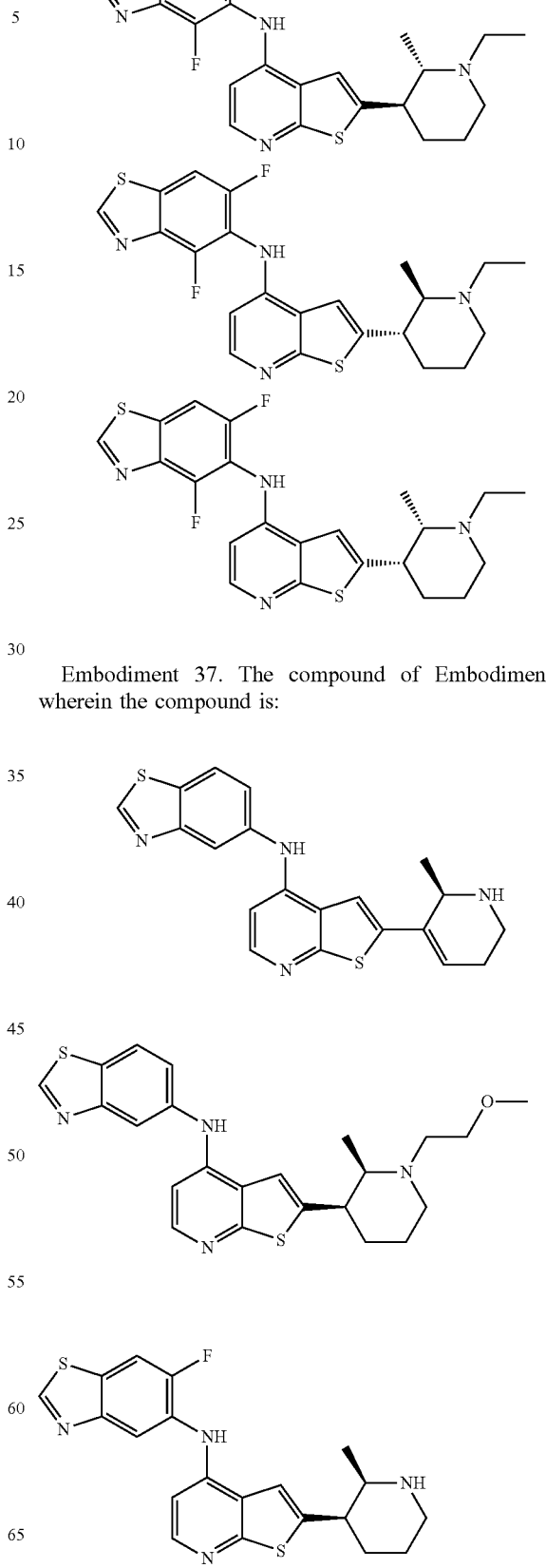
Embodiment 37. The compound of Embodiment 1, wherein the compound is:

-continued

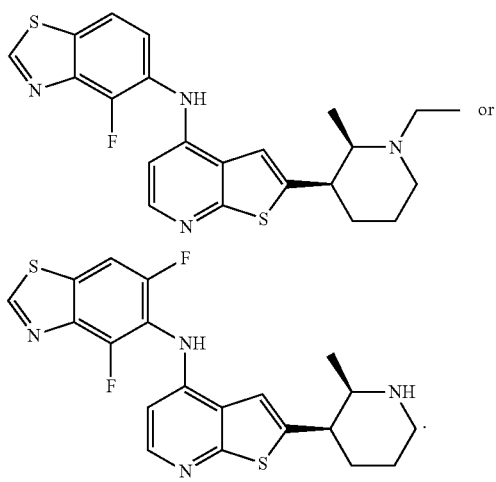

Embodiment 38. The compound of Embodiment 1, wherein the compound is

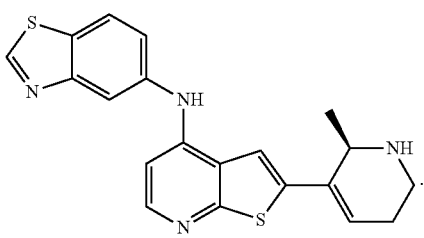 [SMILES: C[C@H]1NCCC=C1c1cc2c(Nc3ccc4scnc4c3)ccnc2s1]

Embodiment 39. The compound of Embodiment 1, wherein the compound is

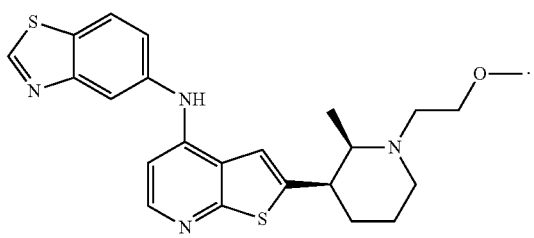

Embodiment 40. The compound of Embodiment 1, wherein the compound is

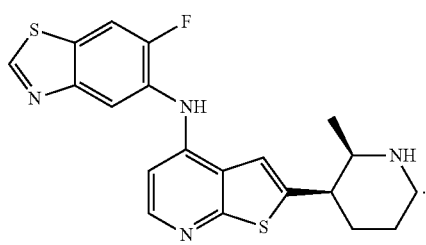 [SMILES: C[C@H]1NCCC[C@H]1c1cc2c(Nc3cc4ncsc4cc3F)ccnc2s1]

Embodiment 41. The compound of Embodiment 1, wherein the compound is

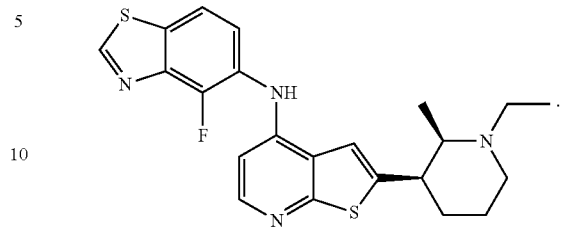

Embodiment 42. The compound of Embodiment 1, wherein the compound is

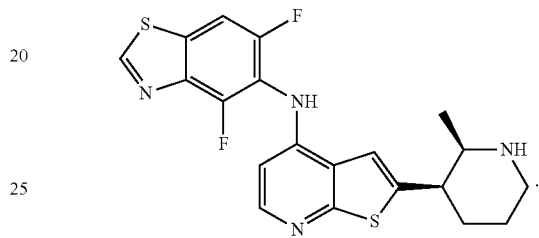

Embodiment 43. A composition comprising a compound of any one of Embodiments 1-42 and a pharmaceutically acceptable carrier or excipient.

Embodiment 44. A method of inhibiting RIPK2 in a biological sample or in a patient, comprising contacting the biological sample or administering to the patient a therapeutically effective amount of any one of Embodiments 1-42, or a composition thereof.

Embodiment 45. A method of treating a disorder mediated by RIPK2 in a patient, comprising administering to the patient a therapeutically effective amount of any one of Embodiments 1-42, or a composition thereof.

Embodiment 46. The method of Embodiment 45, wherein the disorder mediated by RIPK2 is an inflammatory disorder, an autoimmune disorder, or a disorder associated with NOD2 receptors.

Embodiment 47. The method of Embodiment 46, wherein the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

Embodiment 48. The method of Embodiments 46 or 47, wherein the inflammatory disorder is inflammatory bowel disease.

Embodiment 49. The compound of any one of Embodiments 1-42, or a composition thereof, for use in medicine.

Embodiment 50. Use of a compound of any one of Embodiments 1-42, or a composition thereof, for inhibiting RIPK2 in a biological sample or in a patient.

Embodiment 51. Use of a compound of any one of Embodiments 1-42, or a composition thereof, for treating a disorder mediated by RIPK2.

Embodiment 52. The use of Embodiment 51, wherein the disorder mediated by RIPK2 is an inflammatory disorder, an autoimmune disorder, or a disorder associated with NOD2 receptors.

Embodiment 53. The use of Embodiment 52, wherein the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

Embodiment 54. Use of a compound of any one of Embodiments 1-42, or a composition thereof, in the manufacture of a medicament for inhibiting RIPK2.

Embodiment 55. Use of a compound of any one of Embodiments 1-42, or a composition thereof, in the manufacture of a medicament for treating a disorder mediated by RIPK2.

Embodiment 56. The use of Embodiment 55, wherein the disorder mediated by RIPK2 is an inflammatory disorder, an autoimmune disorder, or a disorder associated with NOD2 receptors.

Embodiment 57. The use of Embodiment 56, wherein the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

Embodiment 58. The compound of any one of Embodiments 1-35, wherein p is 1, 2, or 3.

Embodiment 59. The compound of Embodiment 58, wherein p is 1.

Embodiment 60. The compound of Embodiment 58, wherein p is 2.

Embodiment 61. The compound of Embodiment 58, wherein p is 3.

Embodiment 62. The compound of Embodiment 29, wherein $R^2$ is $C_{1-6}$ aliphatic.

Embodiment 63. The compound of Embodiment 62, wherein $R^2$ is methyl or ethyl.

Embodiment 64. The compound of Embodiment 63, wherein $R^2$ is methyl.

Embodiment 65. A compound of formula I':

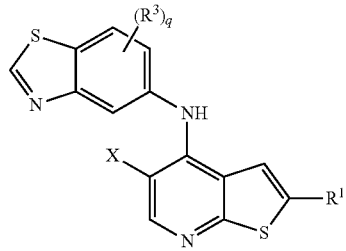

or a pharmaceutically acceptable salt thereof,
wherein:
$R^1$ is a 4- to 7-membered monocyclic saturated or partially unsaturated heterocyclic ring having 1 to 3 heteroatoms independently selected from nitrogen, oxygen, and sulfur; a 9- to 10-membered bicyclic heterocyclic ring having 1 to 3 heteroatoms independently selected from nitrogen, oxygen, and sulfur; or a 7- to 11-membered spirocyclic fused heterocyclic ring having 1 to 3 heteroatoms independently selected from nitrogen, oxygen, and sulfur, and wherein $R^1$ is substituted with $(R^2)_p$;

each $R^2$ is independently halogen, optionally substituted $C_{1-6}$ aliphatic, —OR, —N(R)$_2$, —C(O)R, —C(O)OR, —SO$_2$R, or an optionally substituted 3- to 7-membered saturated heterocyclic ring having 1 to 2 heteroatoms independently selected from nitrogen, oxygen, and sulfur;

each R is independently hydrogen, optionally substituted $C_{1-6}$ aliphatic, or an optionally substituted 4- to 6-membered saturated heterocyclic ring having 1 to 3 heteroatoms independently selected from nitrogen, oxygen, and sulfur; or two R groups on a nitrogen atom, together with the atoms to which they are attached, form a 4- to 6-membered heterocyclic ring having 1 or 2 additional heteroatoms independently selected from nitrogen, oxygen, or sulfur;

each $R^3$ is independently halogen, CN, —N(R)$_2$, —OR, or optionally substituted $C_{1-6}$ aliphatic;

X is hydrogen or halogen;

p is 0-4; and q is 0-4.

Embodiment 66. The compound of Embodiment 65, wherein $R^1$ is a 4- to 7-membered monocyclic saturated or partially unsaturated heterocyclic ring having 1 to 3 heteroatoms independently selected from nitrogen, oxygen, and sulfur, wherein $R^1$ is substituted with $(R^2)_p$.

Embodiment 67. The compound of Embodiments 65 or 66, wherein $R^1$ is

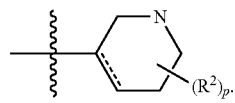

Embodiment 68. The compound of Embodiment 67, wherein $R^1$ is

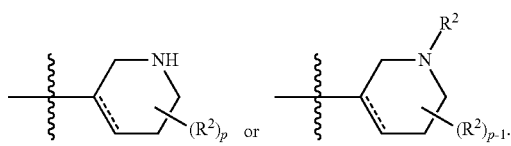

Embodiment 69. The compound of Embodiment 67, wherein $R^1$ is

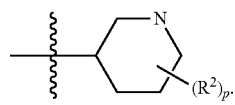

Embodiment 70. The compound of Embodiment 69, wherein $R^1$ is

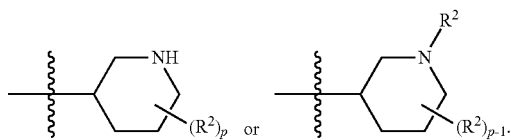

Embodiment 71. The compound of Embodiment 67, wherein $R^1$ is

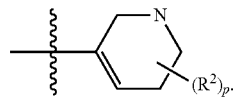

Embodiment 72. The compound of Embodiment 71, wherein R¹ is

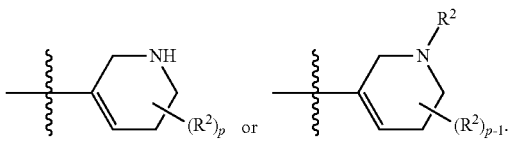

Embodiment 73. The compound of Embodiment 70, wherein R¹ is

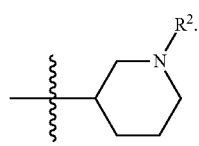

Embodiment 74. The compound of Embodiment 70, wherein R¹ is

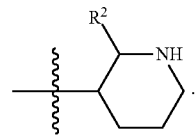

Embodiment 75. The compound of Embodiment 70, wherein R¹ is

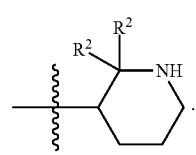

Embodiment 76. The compound of Embodiment 70, wherein R¹ is

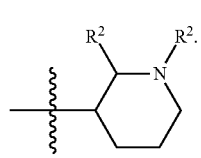

Embodiment 77. The compound of Embodiment 70, wherein R¹ is

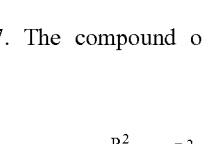

Embodiment 78. The compound of Embodiment 72, wherein R¹ is

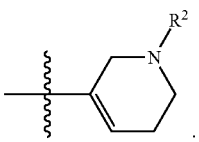

Embodiment 79. The compound of Embodiment 72, wherein R¹ is

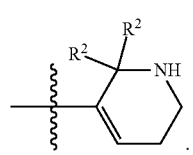

Embodiment 80. The compound of Embodiment 72, wherein R¹ is

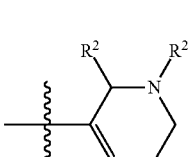

Embodiment 81. The compound of Embodiment 72, wherein R¹ is

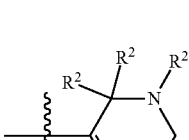

Embodiment 82. The compound of Embodiment 72, wherein R¹ is

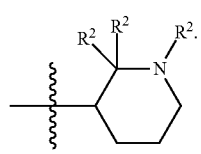

Embodiment 83. The compound of Embodiments 65 or 66, wherein R¹ is

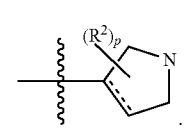

Embodiment 84. The compound of Embodiment 83, wherein R¹ is

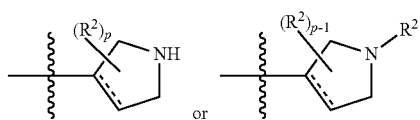

or

Embodiment 85. The compound of Embodiment 84, wherein R¹ is

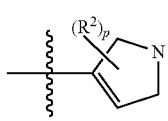

Embodiment 86. The compound of Embodiment 85, wherein R¹ is

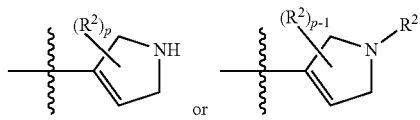

or

Embodiment 87. The compound of Embodiment 86, wherein R¹ is

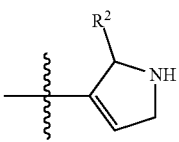

Embodiment 88. The compound of Embodiment 86, wherein R¹ is

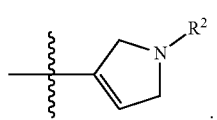

Embodiment 89. The compound of Embodiment 86, wherein R¹ is

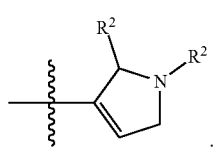

Embodiment 90. The compound of Embodiment 86, wherein R¹ is

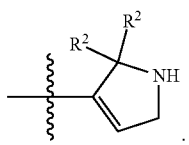

Embodiment 91. The compound of Embodiment 86, wherein R¹ is

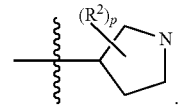

Embodiment 92. The compound of Embodiment 84, wherein R¹ is

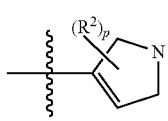

Embodiment 93. The compound of Embodiment 92, wherein R¹ is

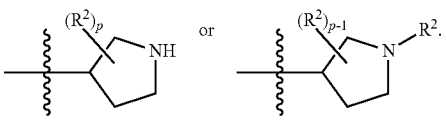

or

Embodiment 94. The compound of Embodiment 93, wherein R¹ is

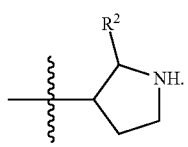

Embodiment 95. The compound of Embodiment 93, wherein R¹ is

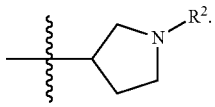

Embodiment 96. The compound of Embodiment 93, wherein R¹ is

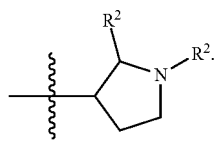

Embodiment 97. The compound of Embodiment 93, wherein R¹ is

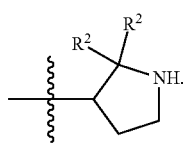

Embodiment 98. The compound of Embodiment 93, wherein R¹ is

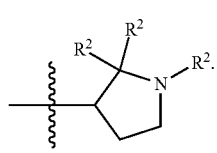

Embodiment 99. The compound of Embodiments 65 or 66, wherein R¹ is

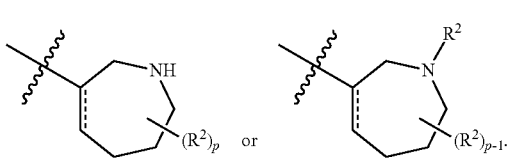

Embodiment 100. The compound of Embodiment 99, wherein R¹ is

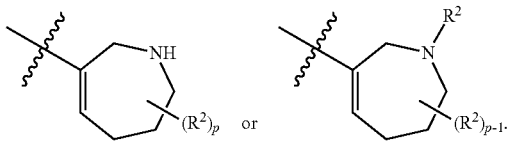

Embodiment 101. The compound of Embodiment 99, wherein R¹ is

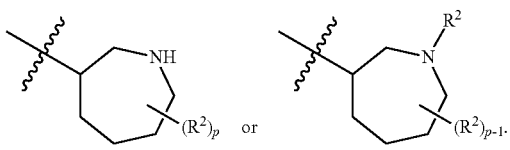

Embodiment 102. The compound of Embodiment 100, wherein R¹ is

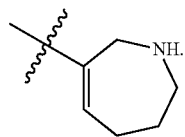 [SMILES: *C1=CCCCNC1]

Embodiment 103. The compound of Embodiment 100, wherein R¹ is

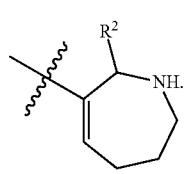

Embodiment 104. The compound of Embodiment 100, wherein R¹ is

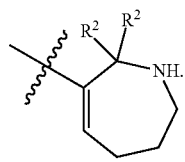

Embodiment 105. The compound of Embodiment 100, wherein R¹ is

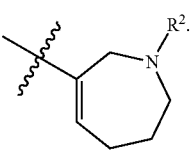

Embodiment 106. The compound of Embodiment 100, wherein R¹ is

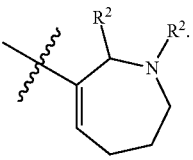

Embodiment 107. The compound of Embodiment 100, wherein R¹ is

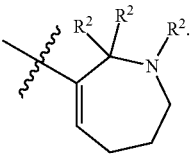

Embodiment 108. The compound of Embodiment 101, wherein $R^1$ is

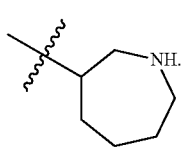 [SMILES: *C1CCCCNC1]

Embodiment 109. The compound of Embodiment 101, wherein $R^1$ is

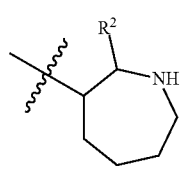

Embodiment 110. The compound of Embodiment 101, wherein $R^1$ is

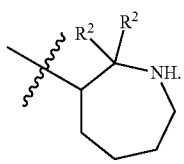

Embodiment 111. The compound of Embodiment 101, wherein $R^1$ is

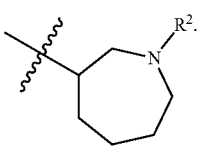

Embodiment 112. The compound of Embodiment 101, wherein $R^1$ is

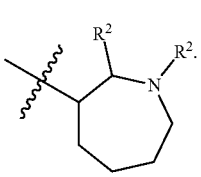

Embodiment 113. The compound of Embodiment 101, wherein $R^1$ is

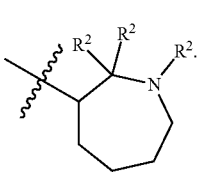

Embodiment 114. The compound of Embodiments 65 or 66, wherein $R^1$ is

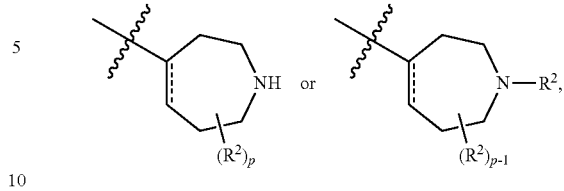

Embodiment 115. The compound of Embodiment 114, wherein $R^1$ is

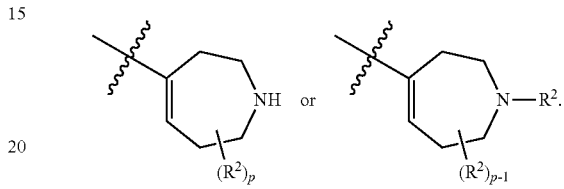

Embodiment 116. The compound of Embodiment 114, wherein $R^1$ is

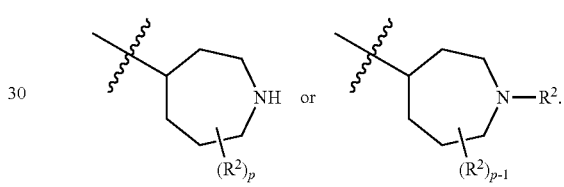

Embodiment 117. The compound of Embodiment 115, wherein $R^1$ is

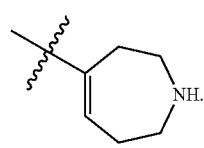 [SMILES: *C1=CCCNCC1]

Embodiment 118. The compound of Embodiment 115, wherein $R^1$ is

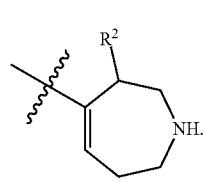

Embodiment 119. The compound of Embodiment 115, wherein $R^1$ is

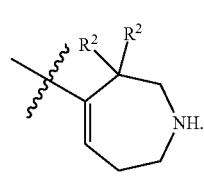

Embodiment 120. The compound of Embodiment 115, wherein $R^1$ is

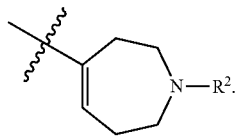

Embodiment 121. The compound of Embodiment 115, wherein $R^1$ is

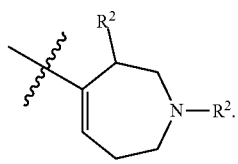

Embodiment 122. The compound of Embodiment 115, wherein $R^1$ is

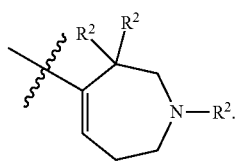

Embodiment 123. The compound of Embodiment 116, wherein $R^1$ is

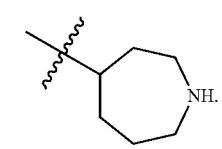 [SMILES: *C1CCCNCC1]

Embodiment 124. The compound of Embodiment 116, wherein $R^1$ is

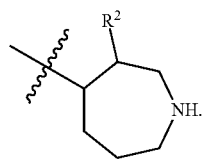

Embodiment 125. The compound of Embodiment 116, wherein $R^1$ is

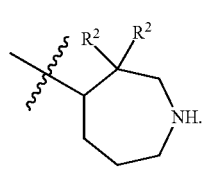

Embodiment 126. The compound of Embodiment 116, wherein $R^1$ is

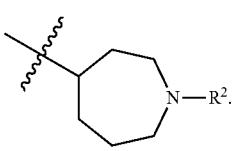

Embodiment 127. The compound of Embodiment 116, wherein $R^1$ is

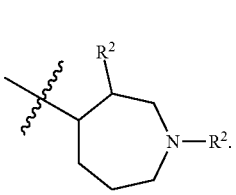

Embodiment 128. The compound of Embodiment 116, wherein $R^1$ is

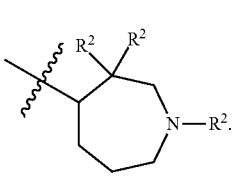

Embodiment 129. The compound of any one of Embodiments 65-128, wherein $R^2$ is optionally substituted $C_{1-6}$ aliphatic.

Embodiment 130. The compound of any one of Embodiments 65-70 or 74, wherein $R^1$ is

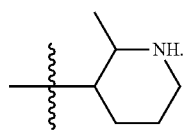

Embodiment 131. The compound of Embodiment 130, wherein $R^1$ is

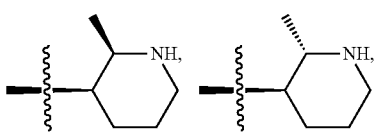

Embodiment 132. The compound of Embodiment 65, wherein R¹ is selected from
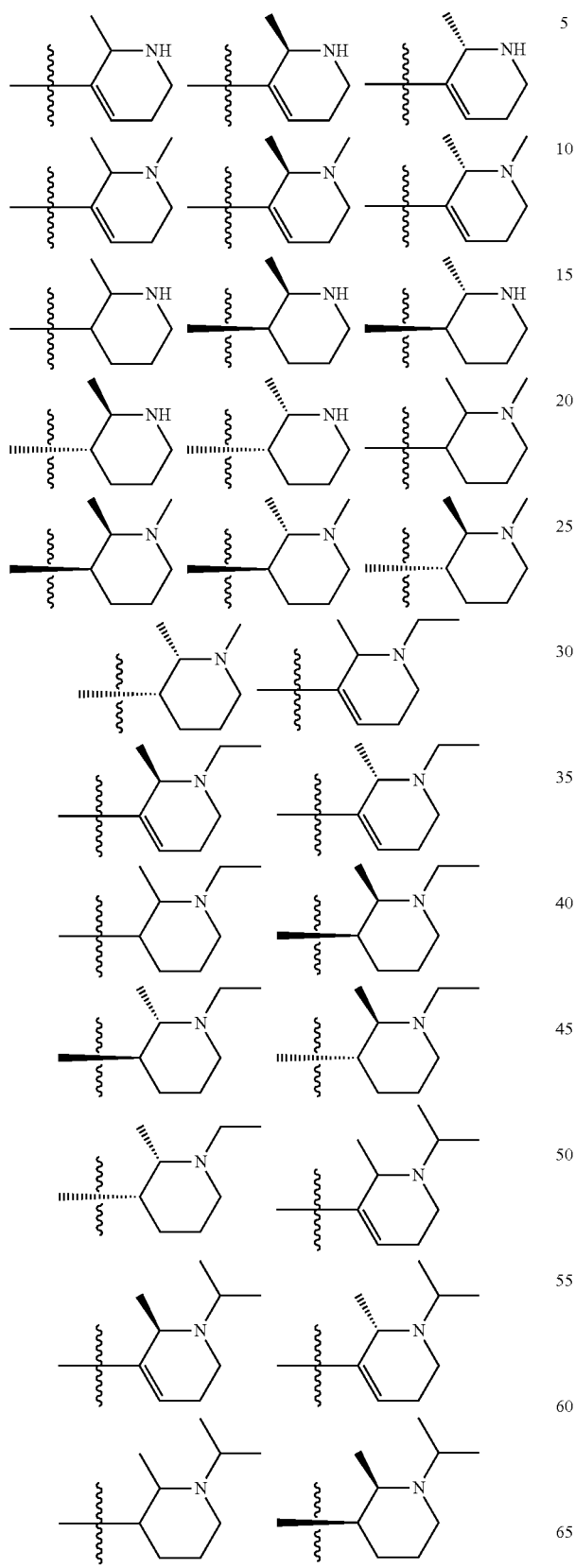
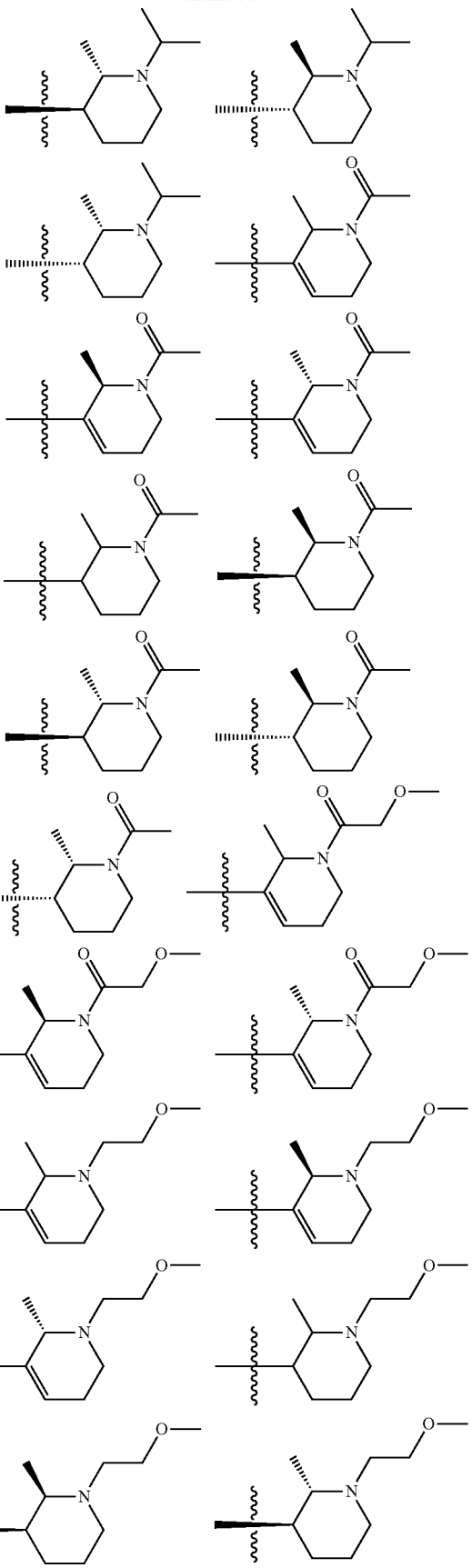

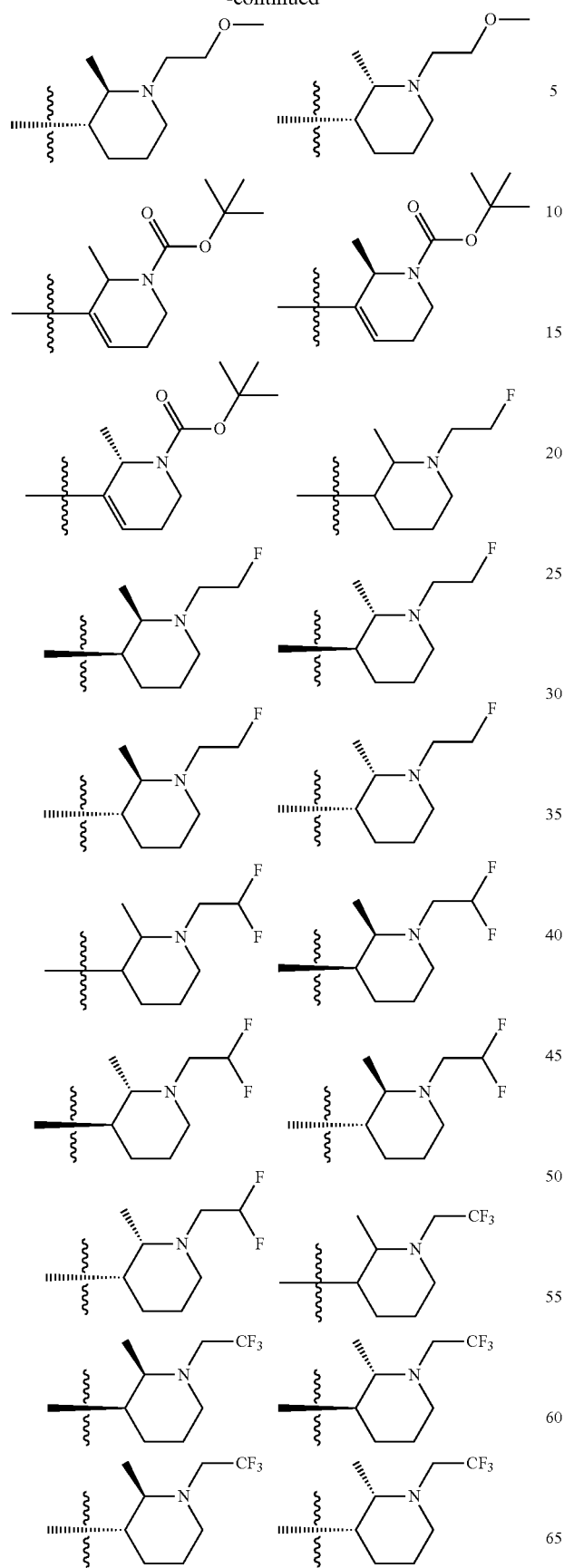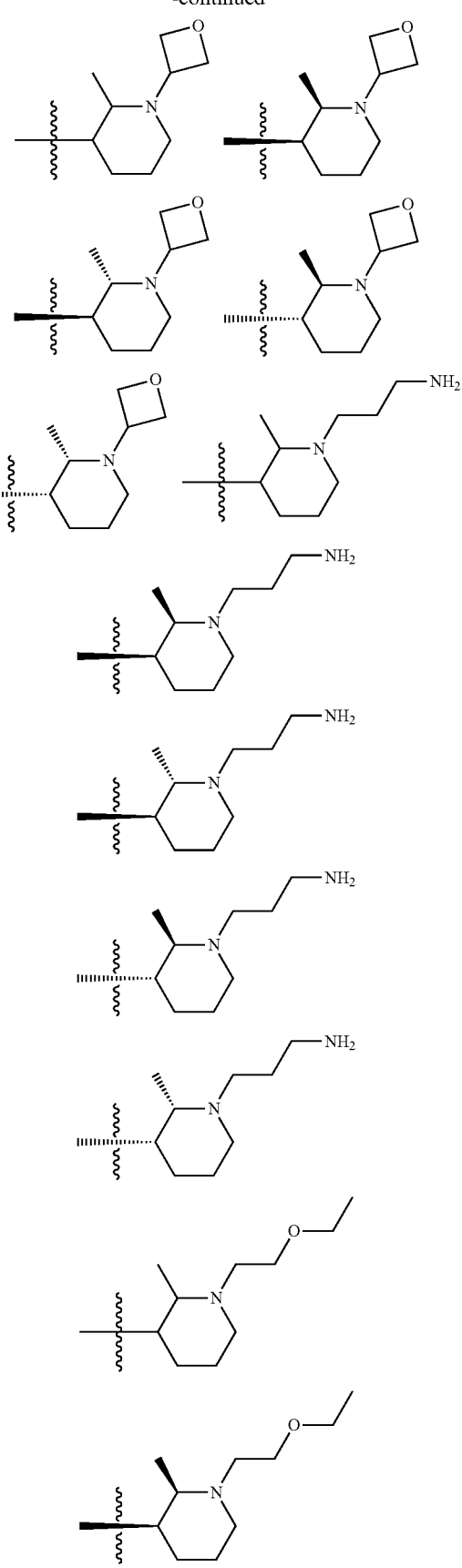

217
-continued
218
-continued
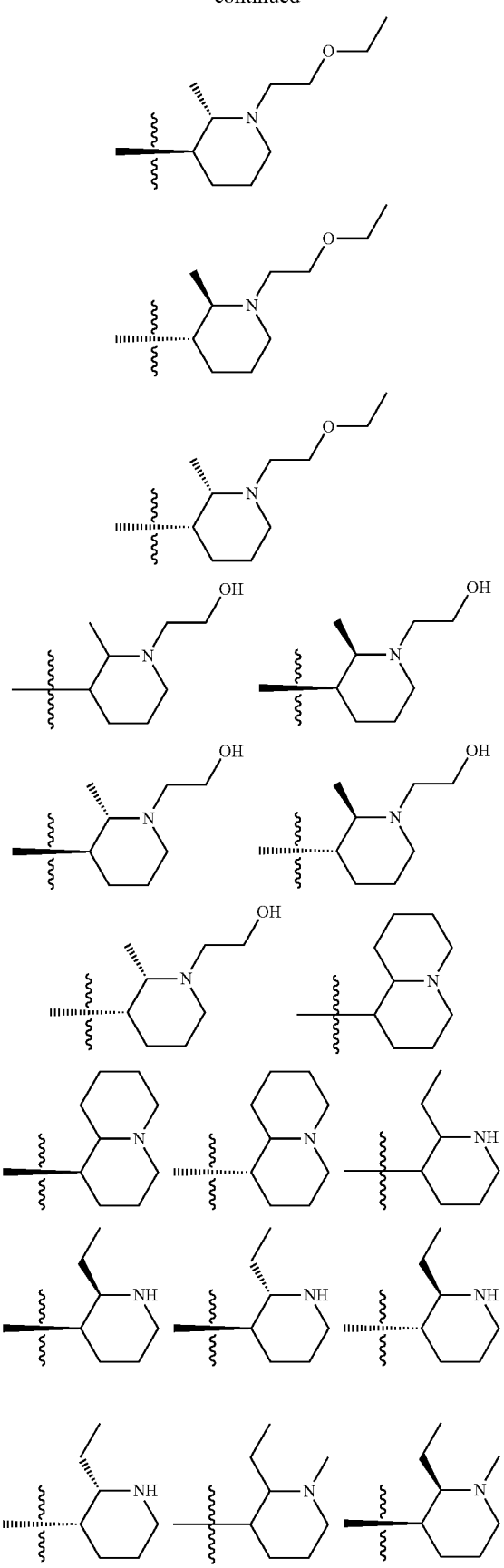
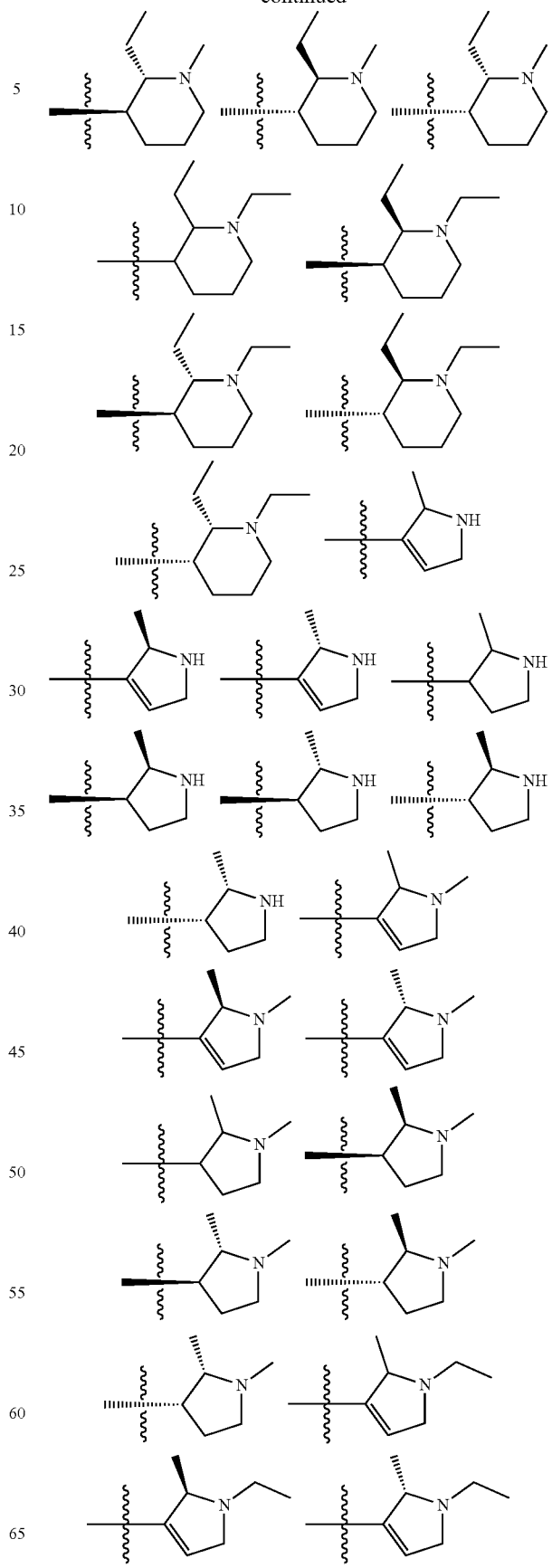

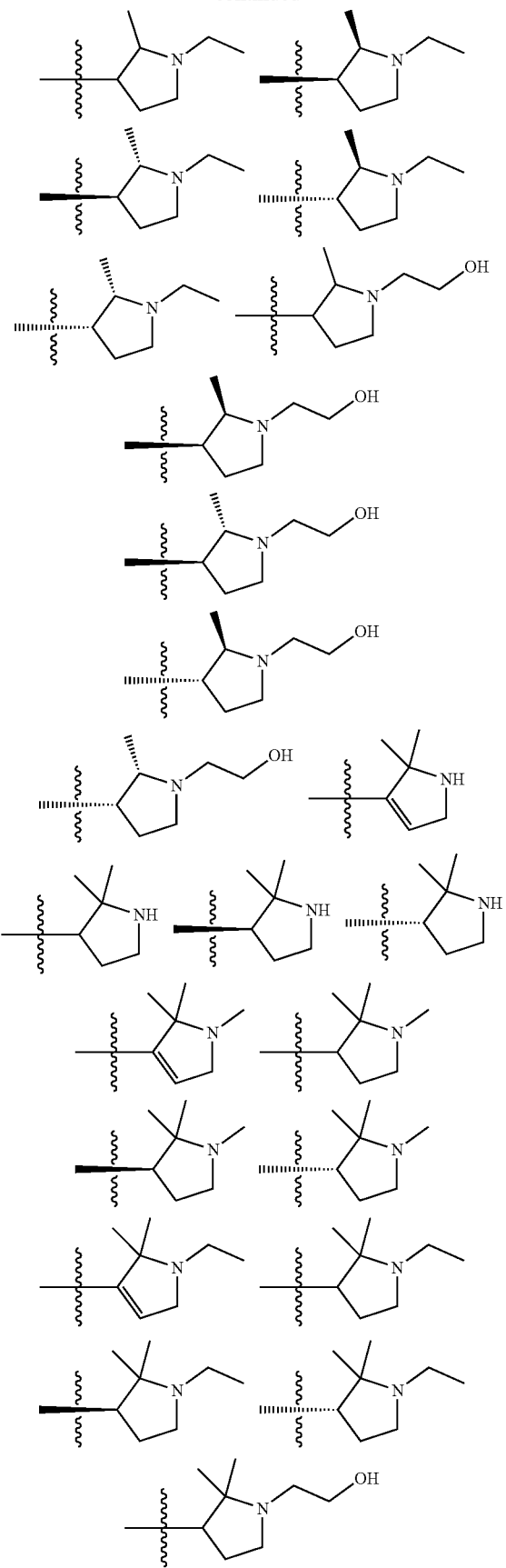
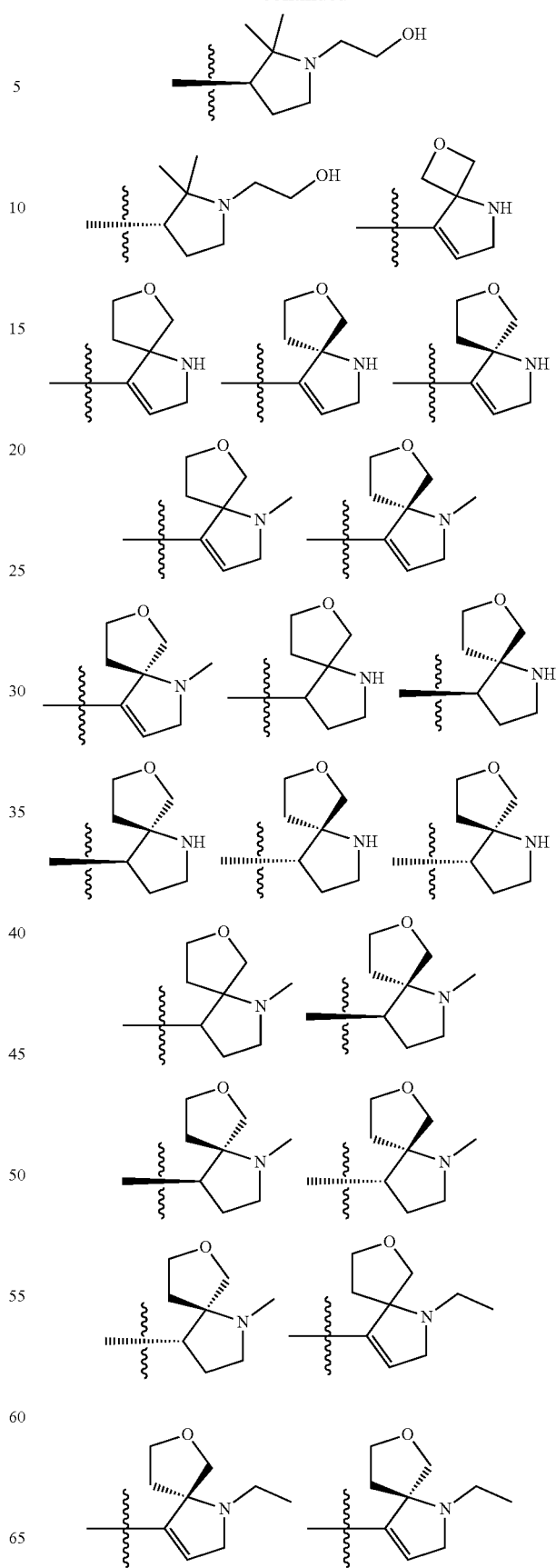

221
-continued
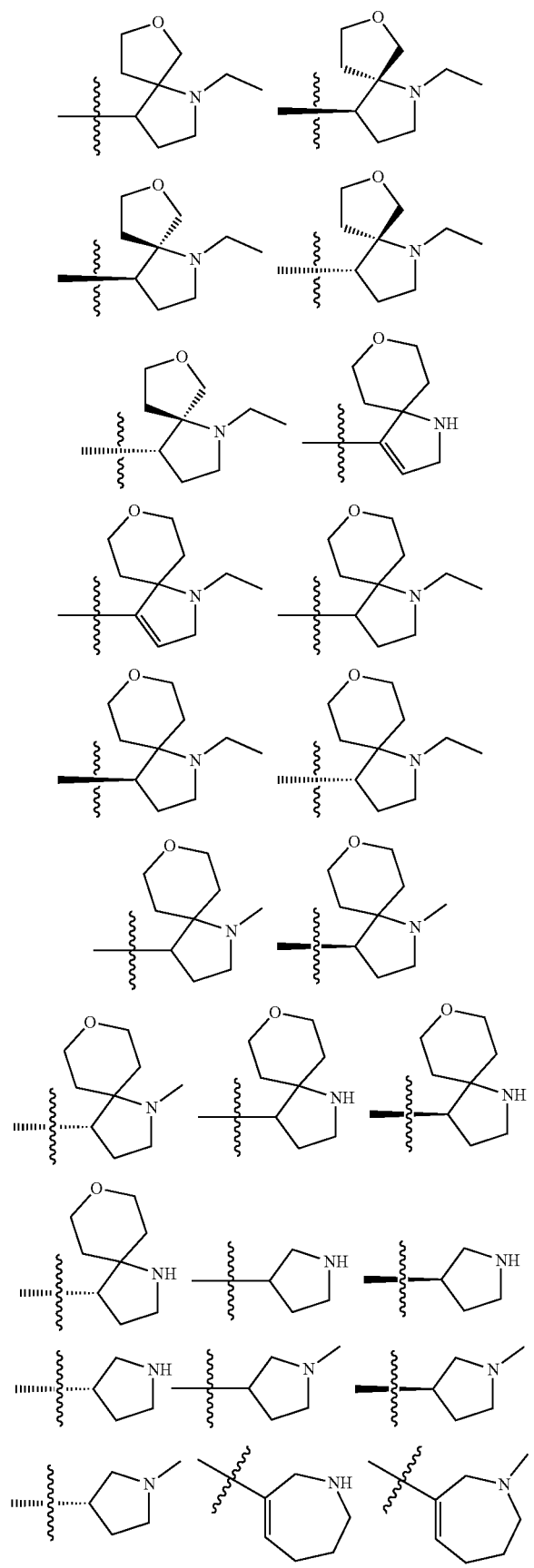
222
-continued
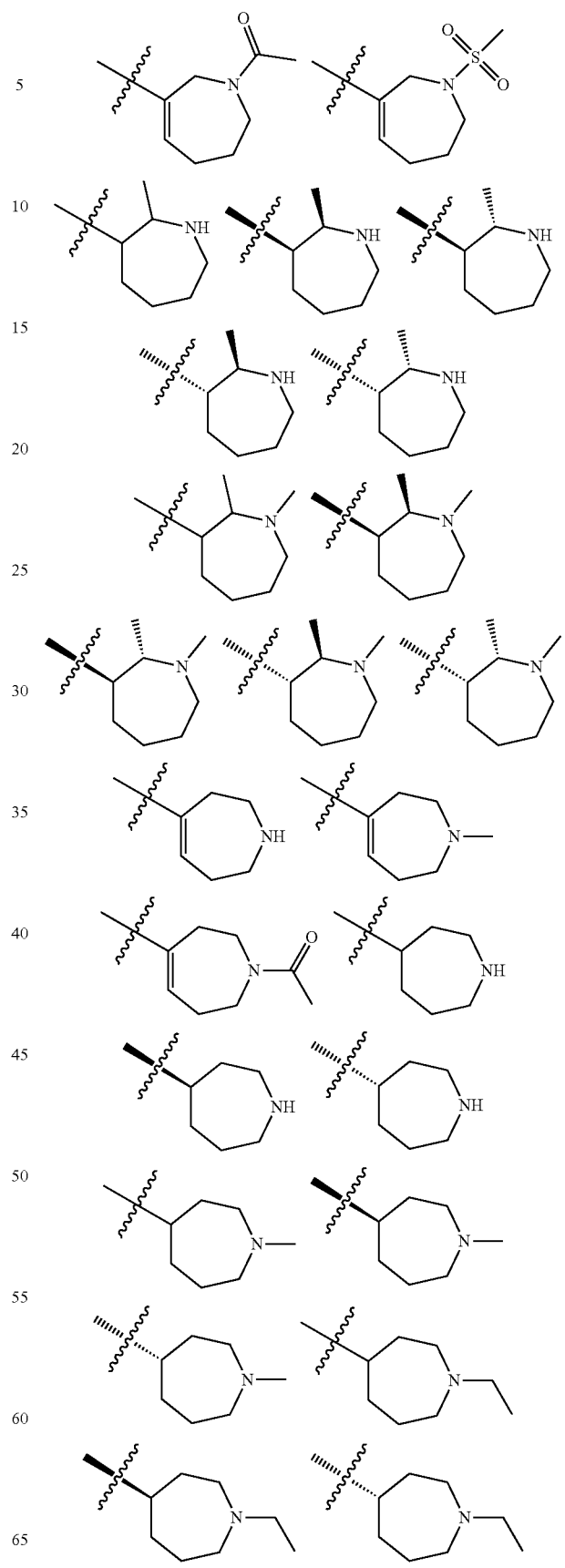

-continued

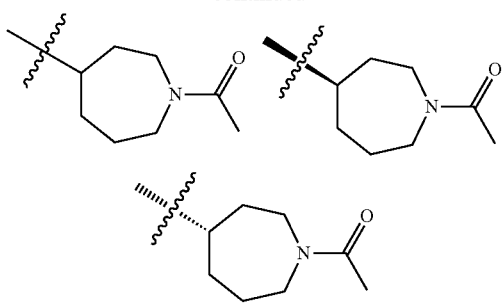

Embodiment 133. The compound of any one of Embodiments 65-132, wherein the compound is of Formula II':

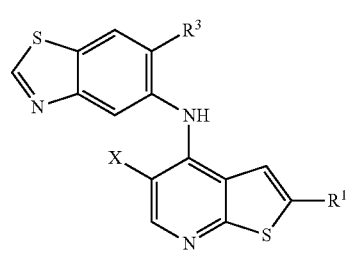

II' or a pharmaceutically acceptable salt thereof.

Embodiment 134. The compound of any one of Embodiments 65-132, wherein the compound is of Formula III':

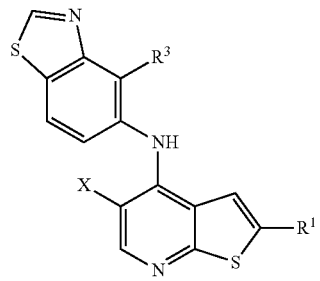

III' or a pharmaceutically acceptable salt thereof.

Embodiment 135. The compound of any one of Embodiments 65-132, wherein the compound is of Formula IV':

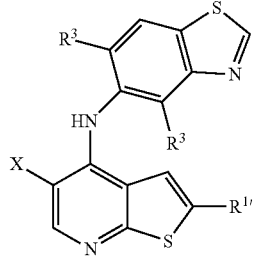

IV' or a pharmaceutically acceptable salt thereof.

Embodiment 136. The compound of Embodiment 65, wherein the compound is selected from:

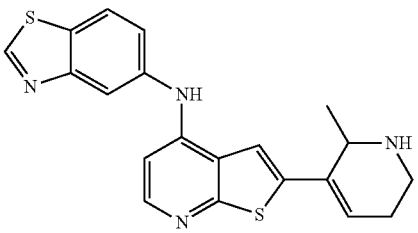

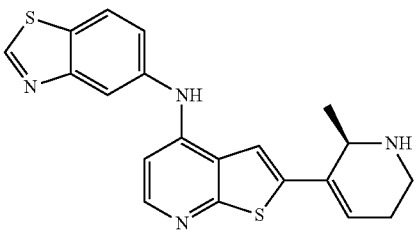

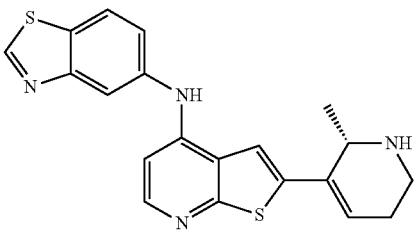

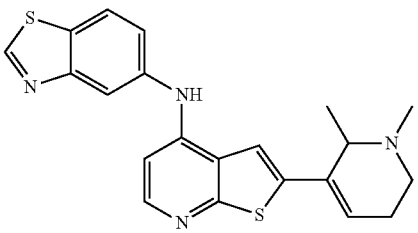

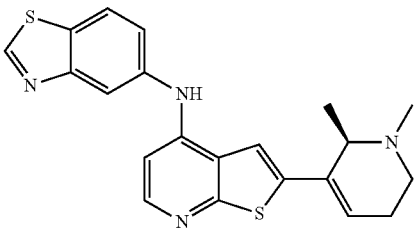

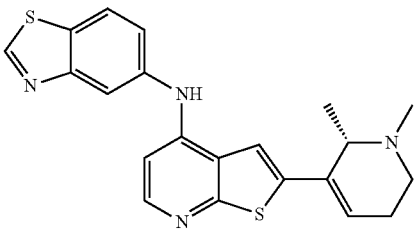

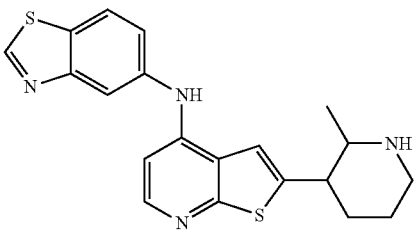

225
-continued
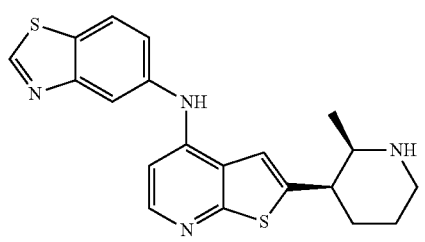
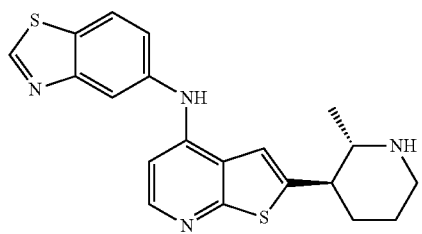
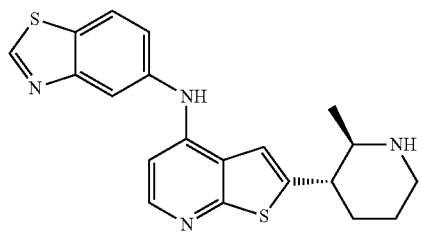
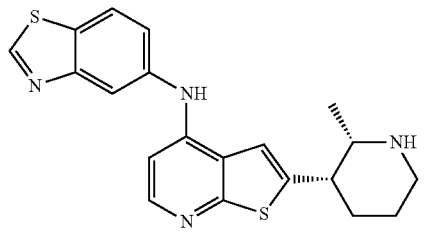
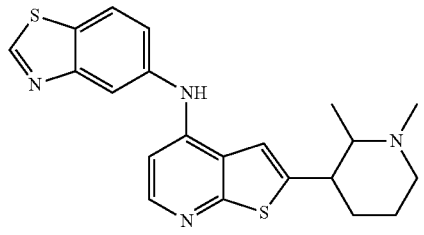
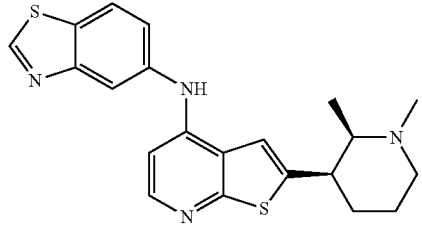
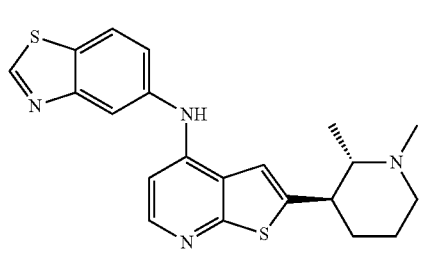
226
-continued
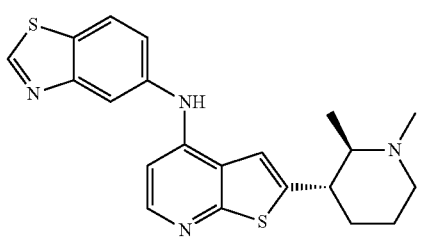
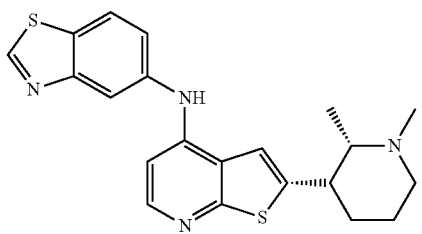
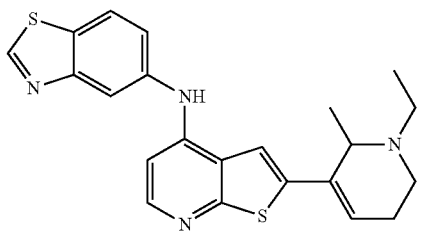
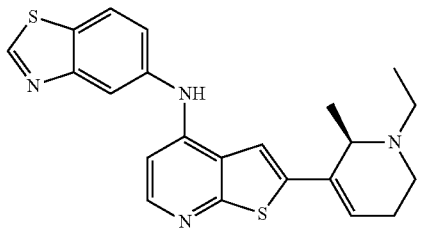
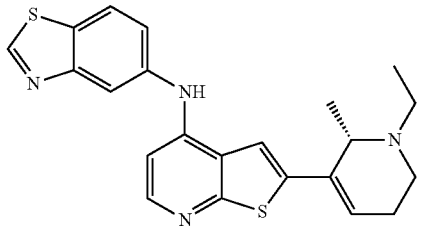
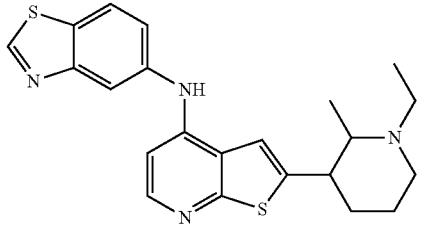
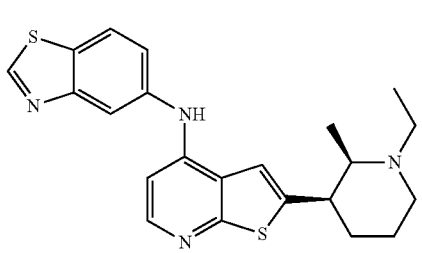

227
-continued
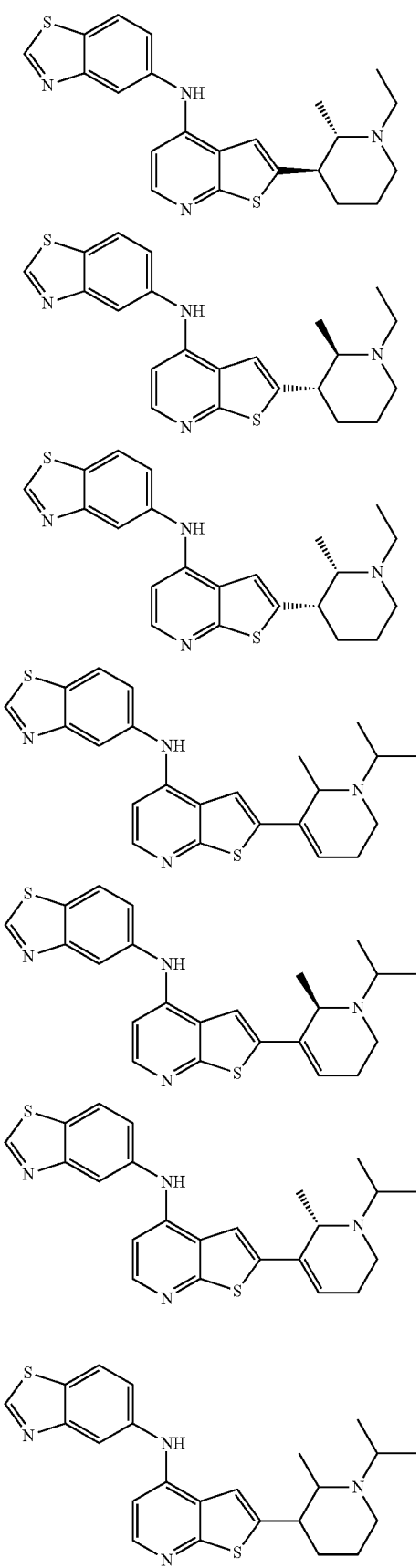
228
-continued
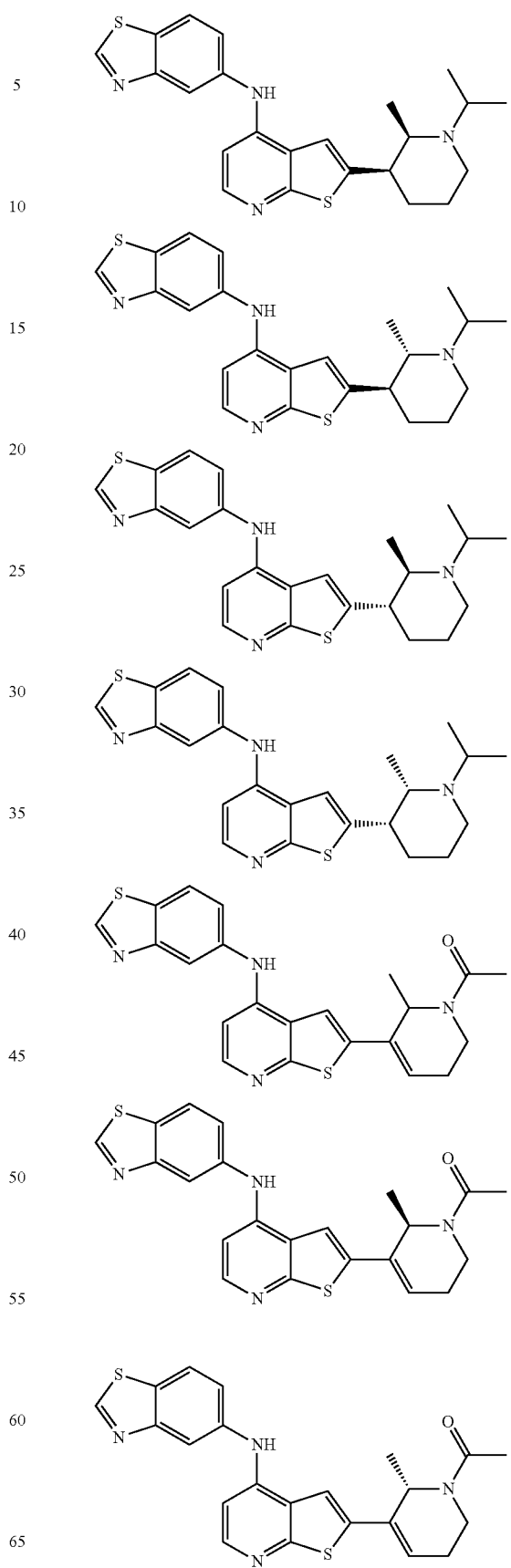

229
-continued
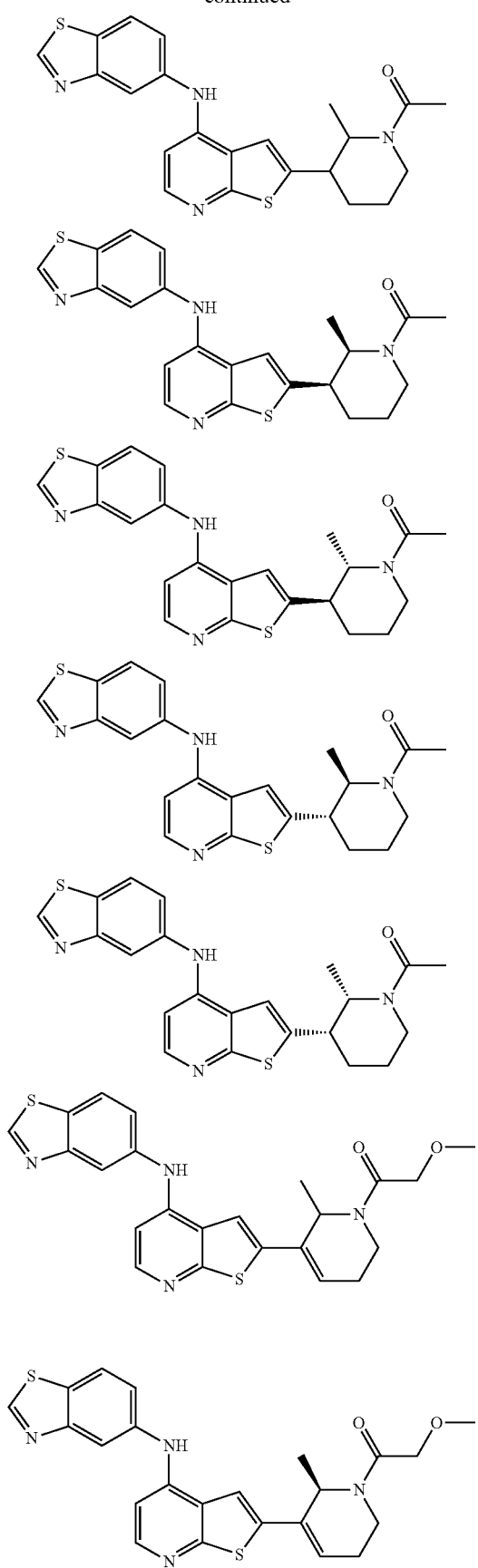
230
-continued
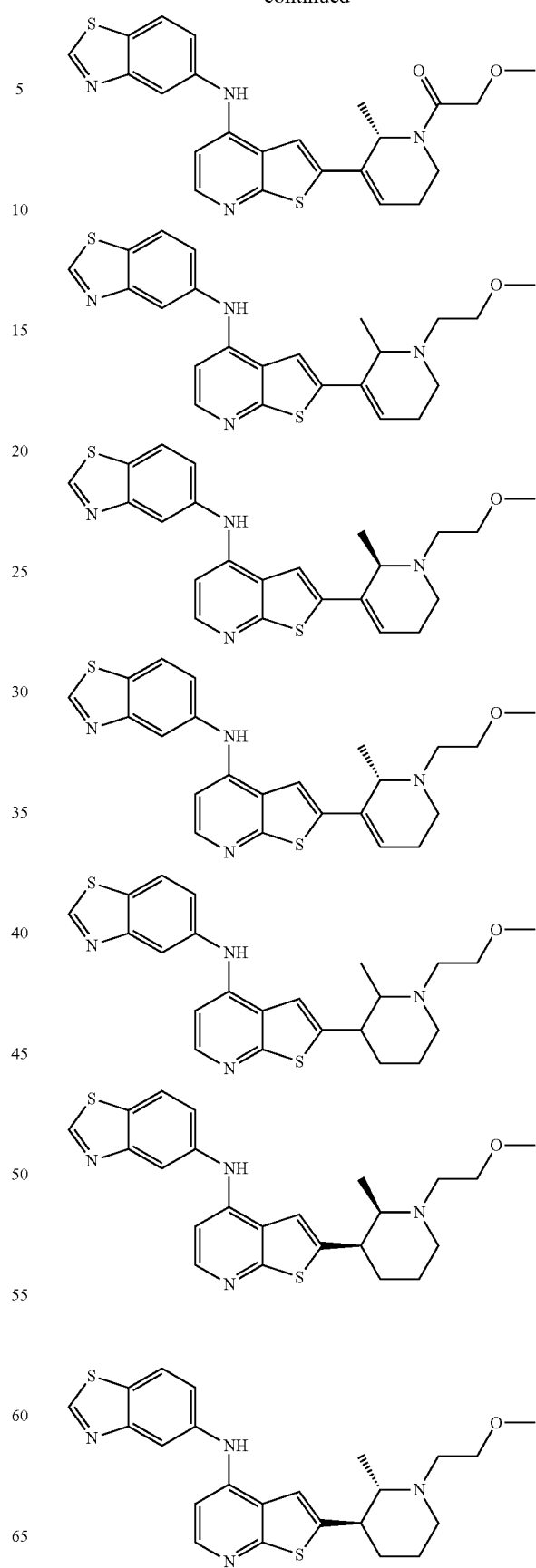

231
-continued
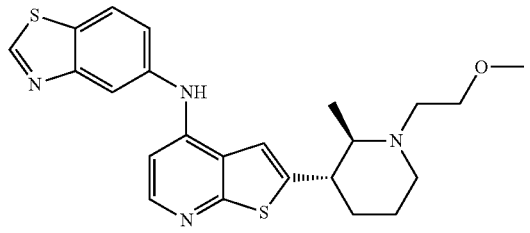
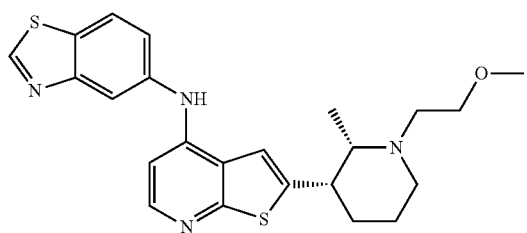
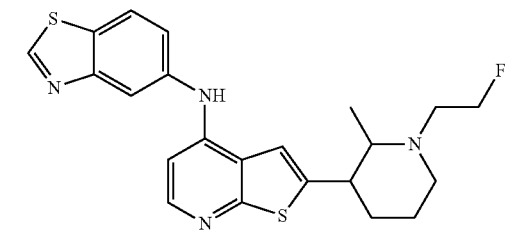
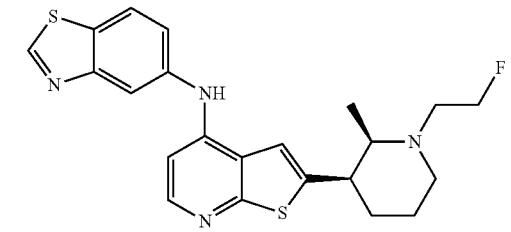
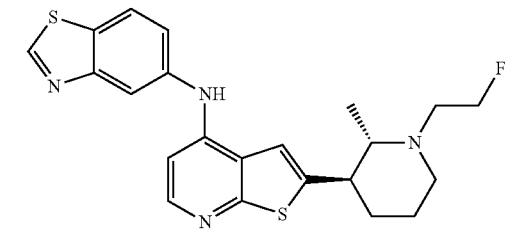
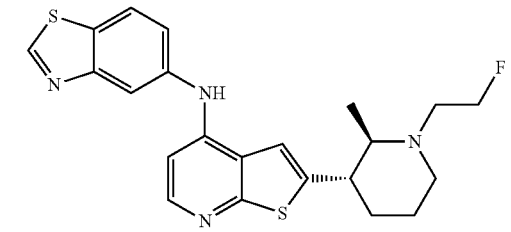
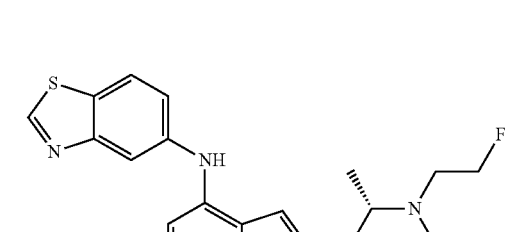
232
-continued
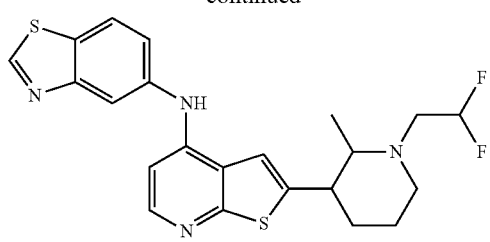
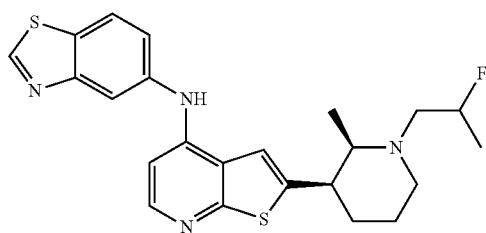
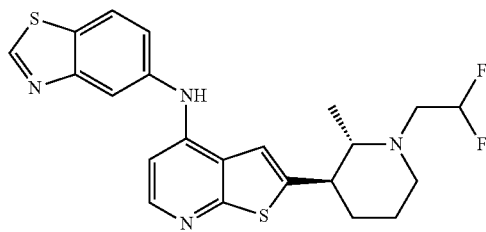
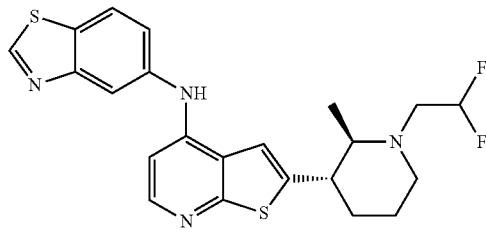
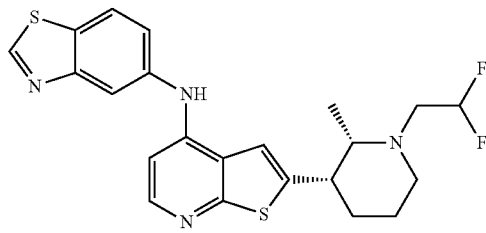
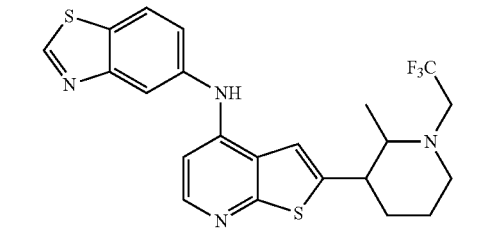
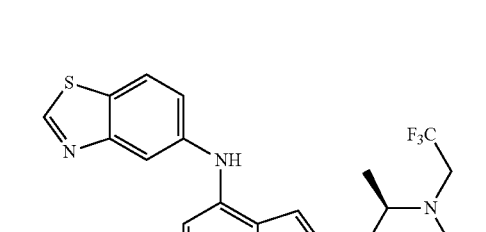

233
-continued
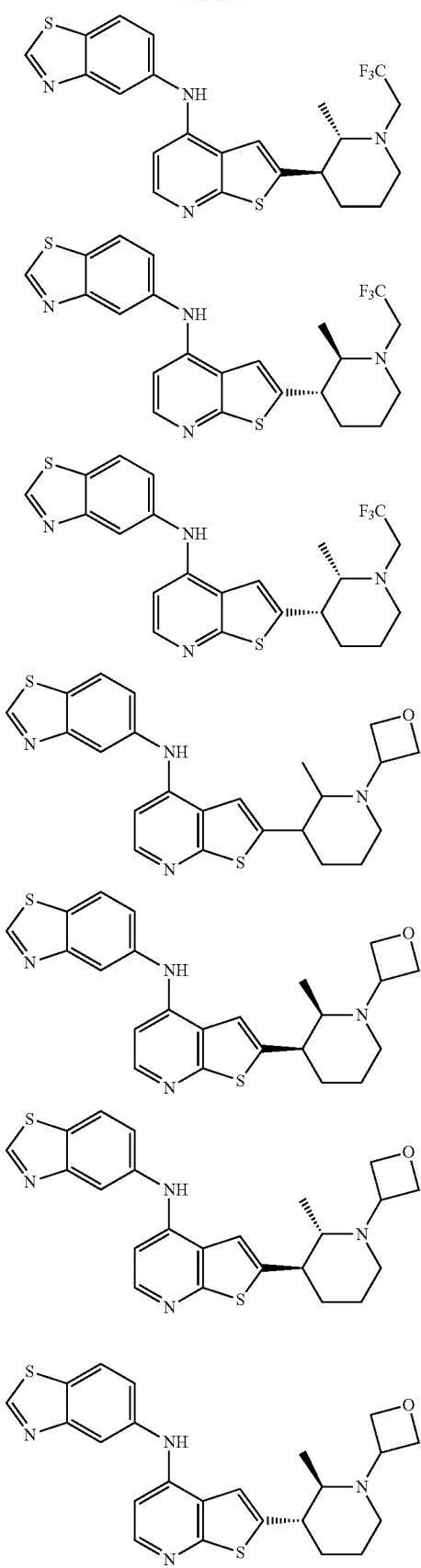
234
-continued
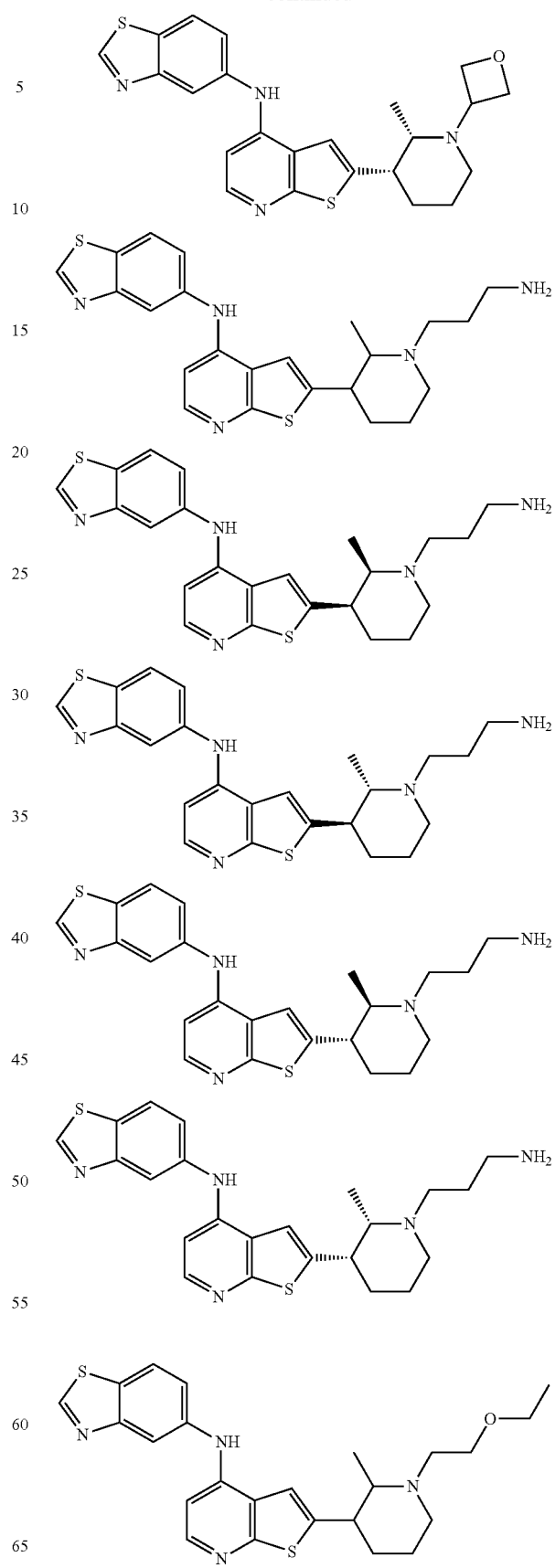

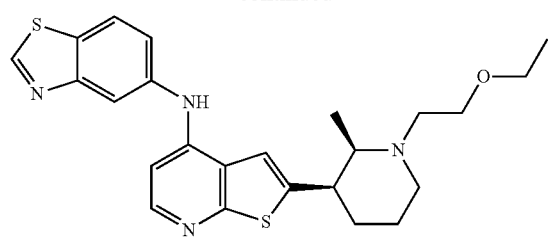
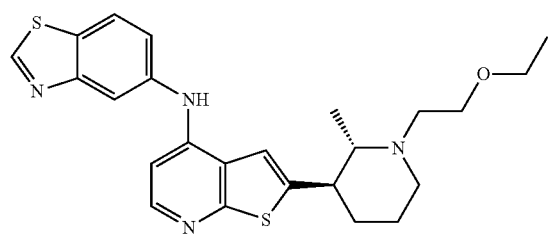
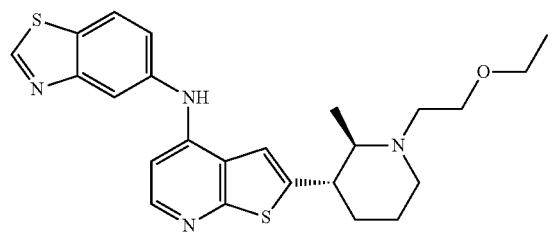
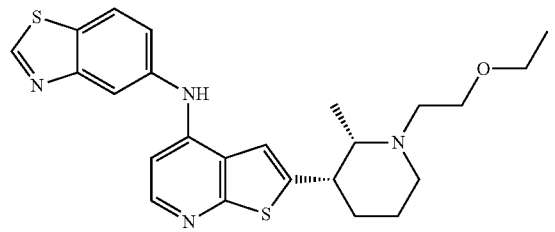
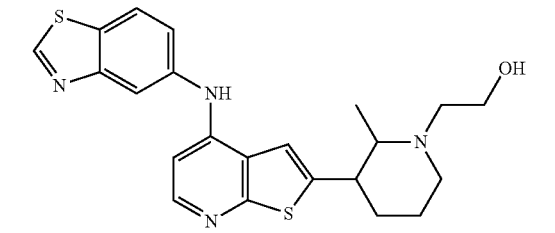
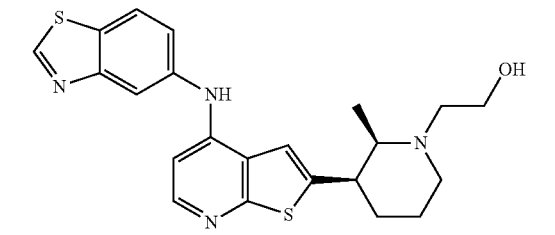
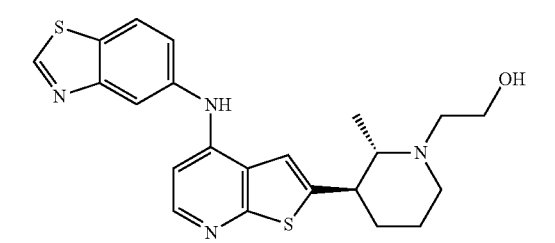
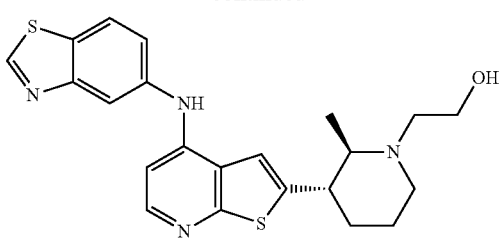
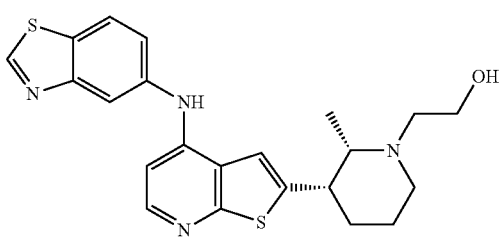
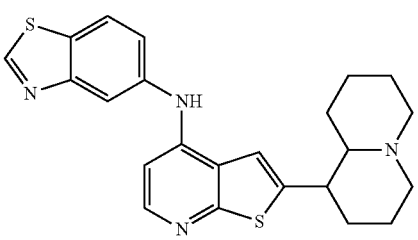
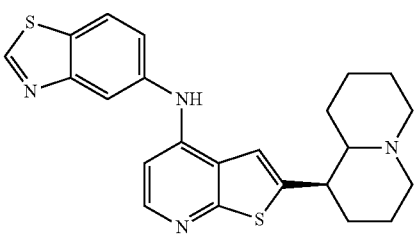
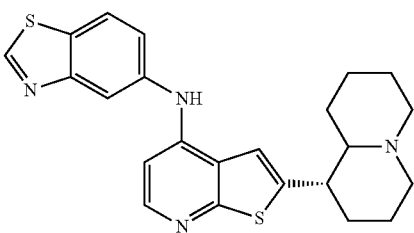
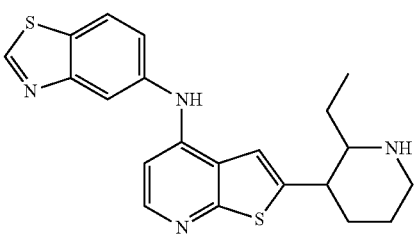
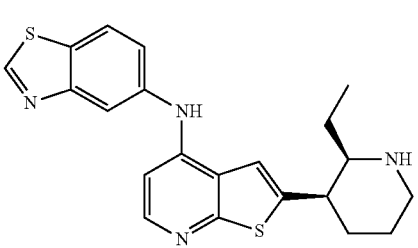

-continued
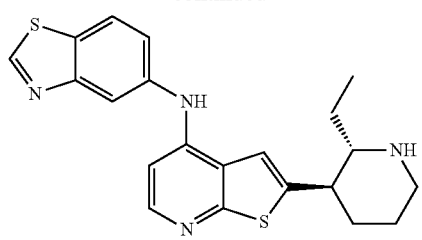
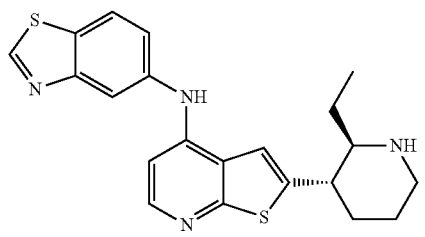
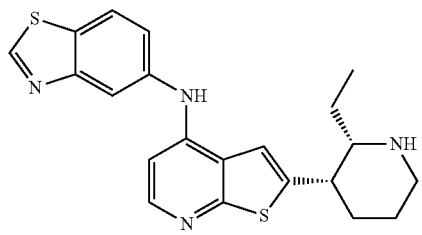
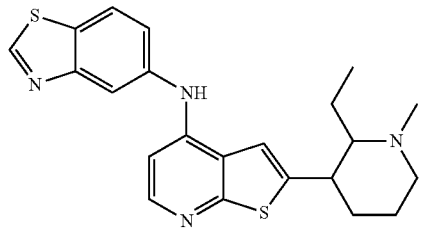
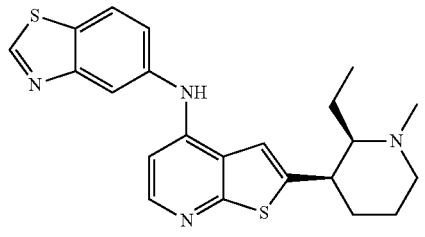
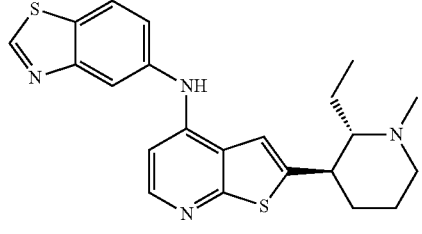
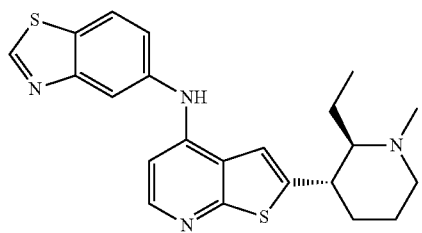
-continued
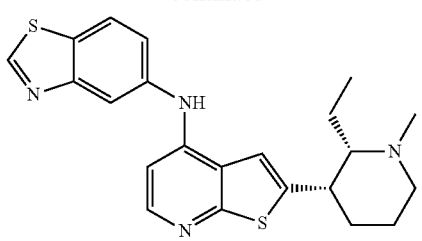
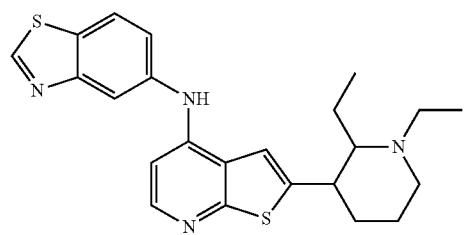
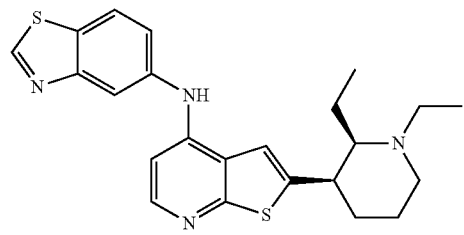
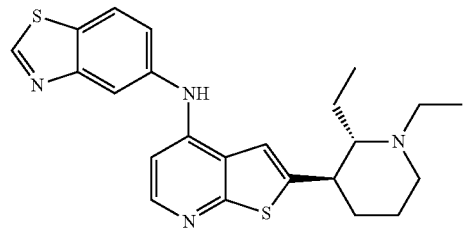
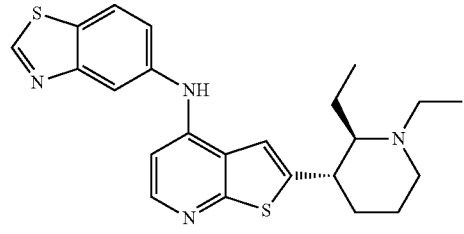
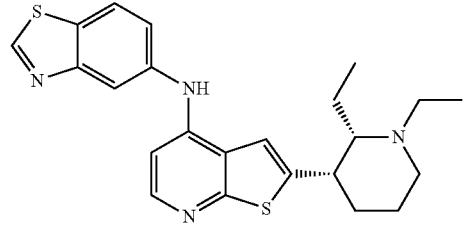

239
-continued
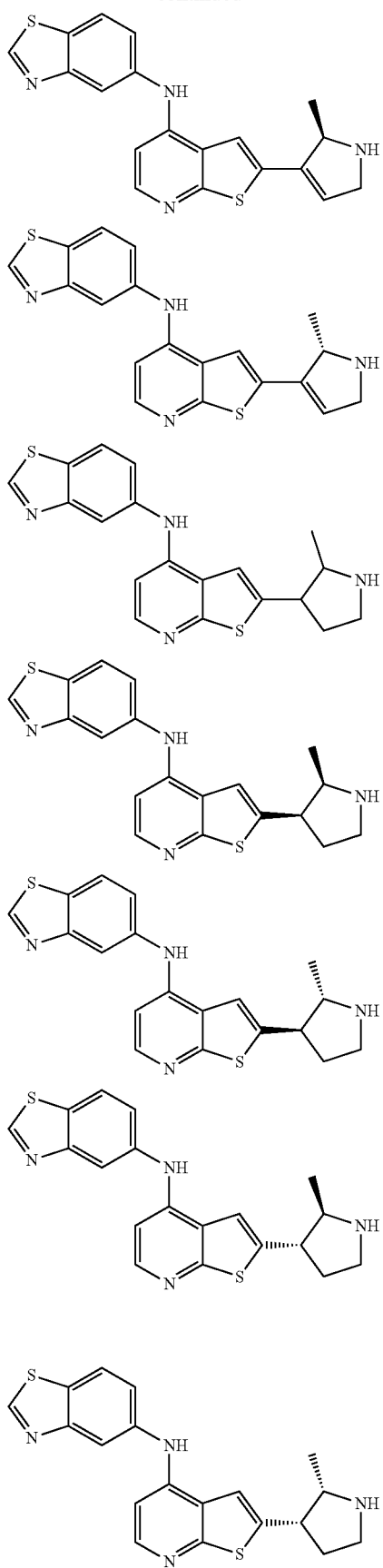
240
-continued
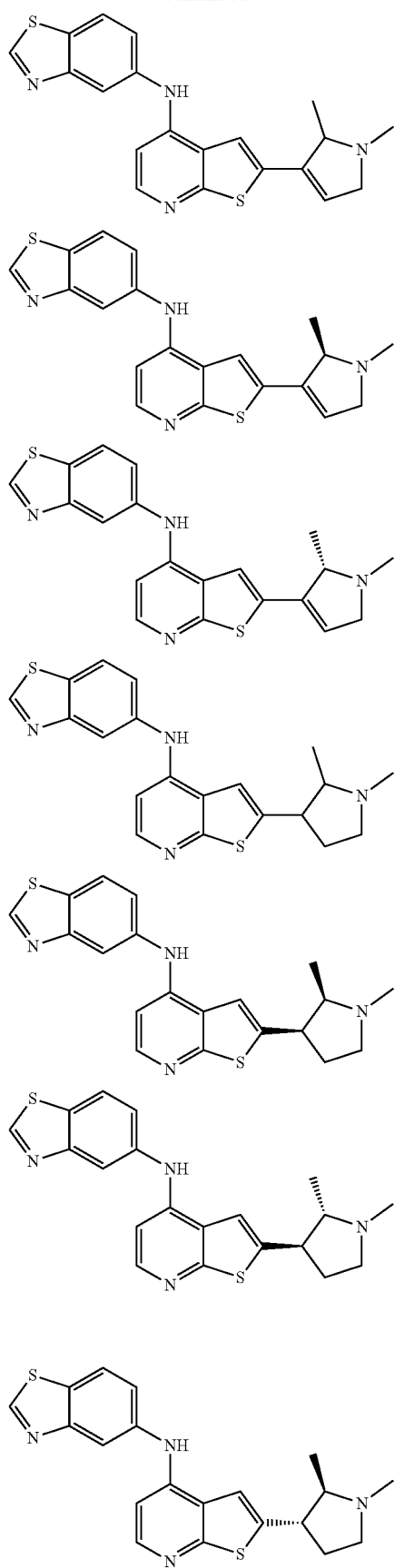

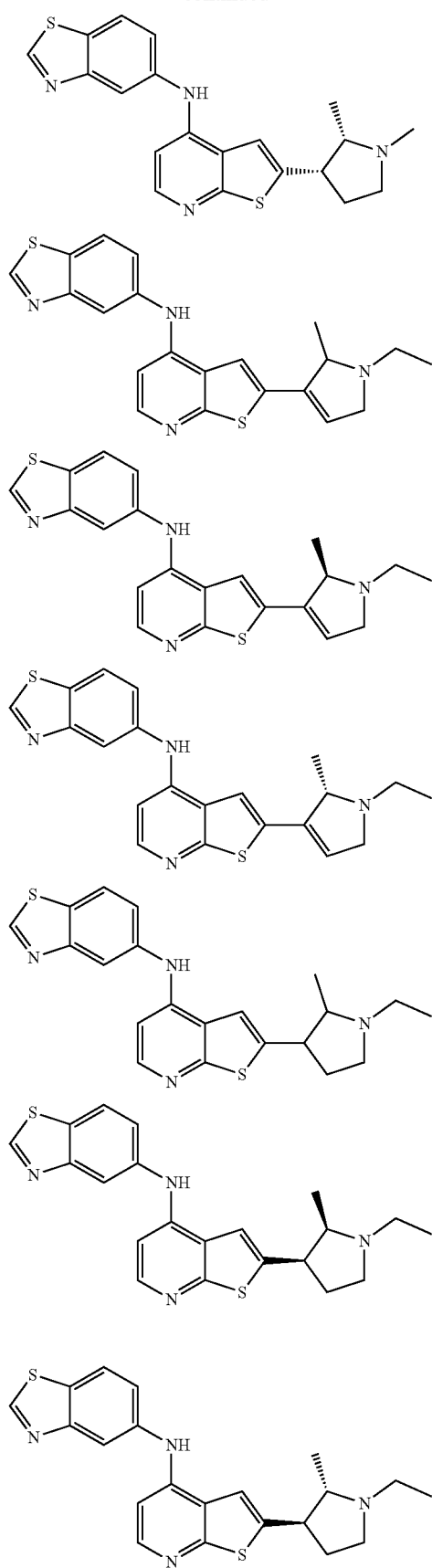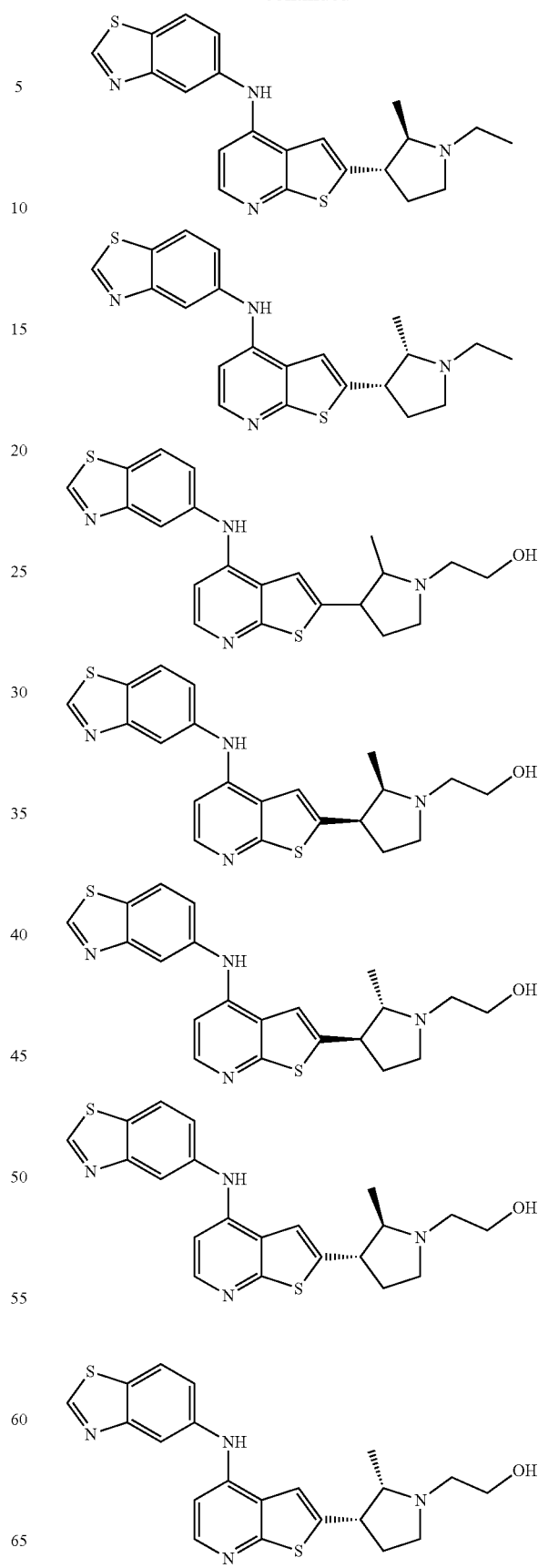

243
-continued
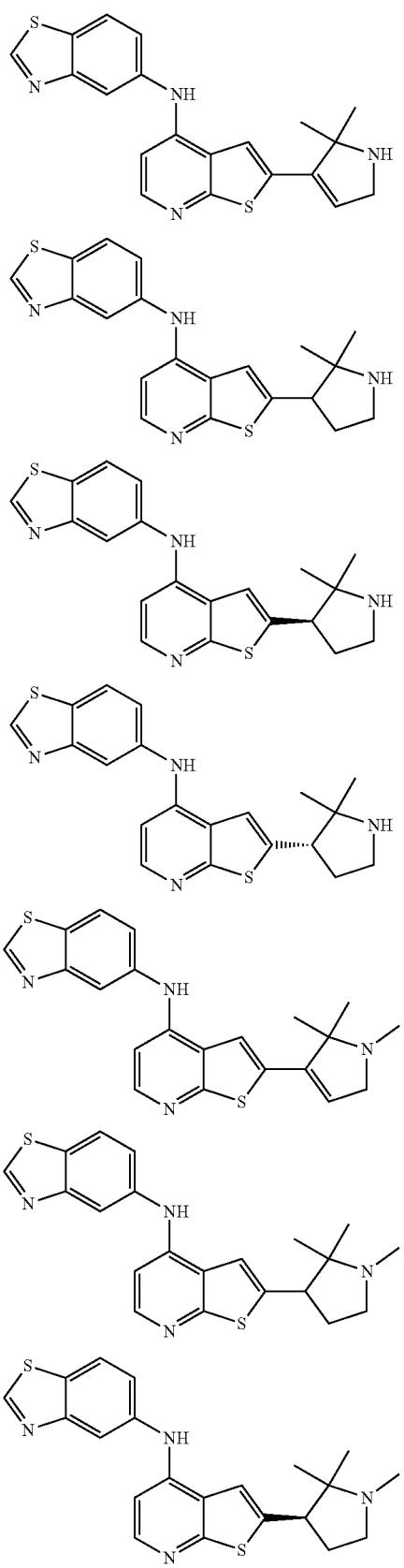
244
-continued
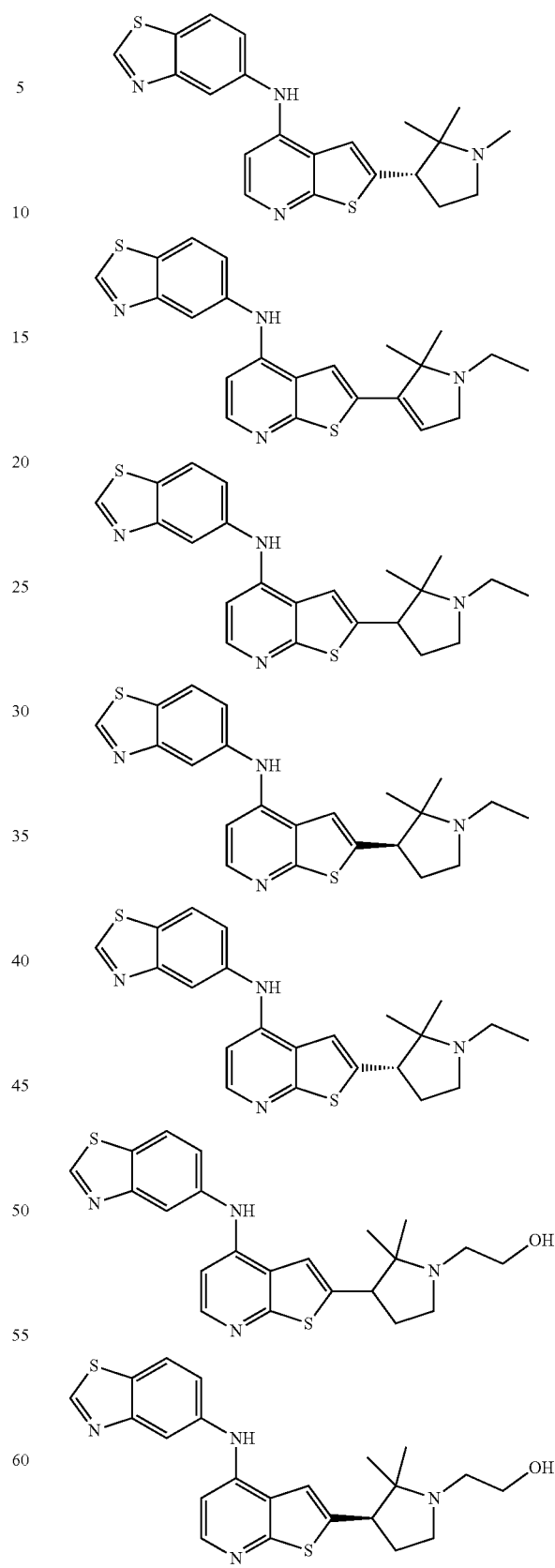

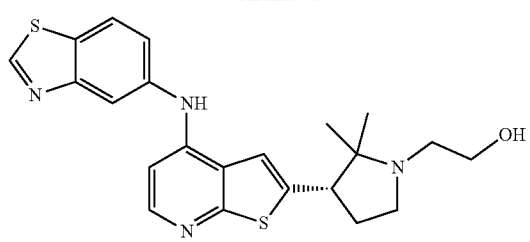
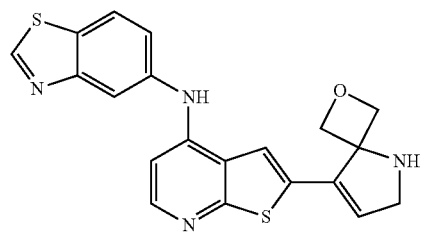
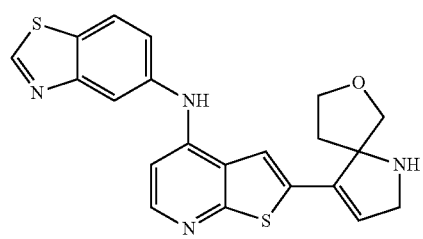
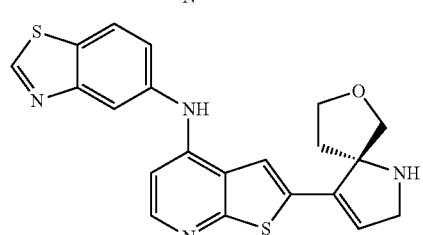
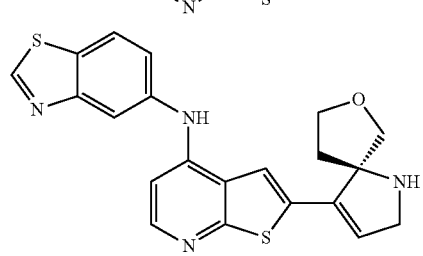
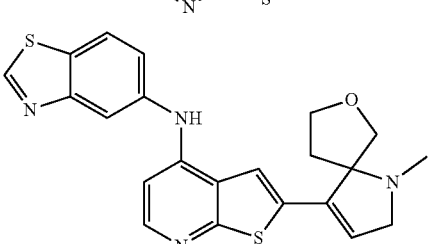
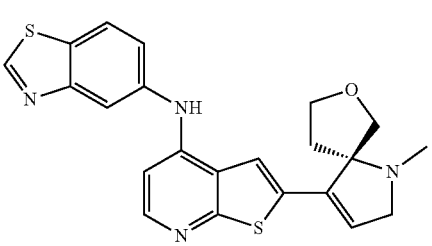
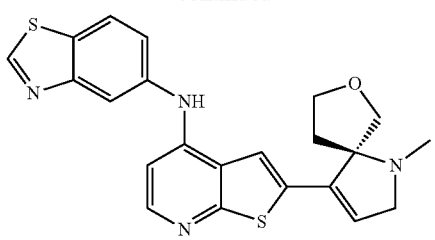
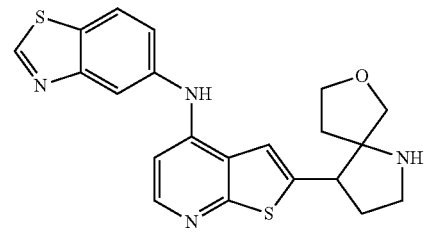
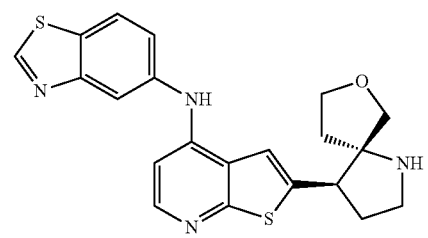
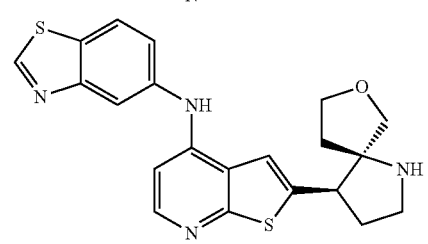
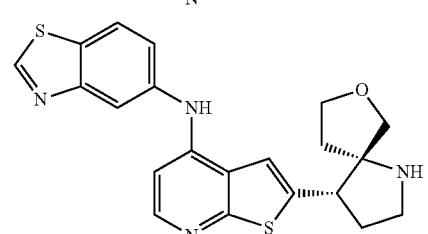
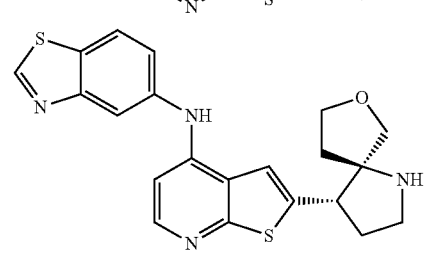
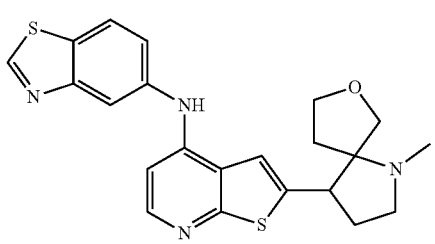

247
-continued
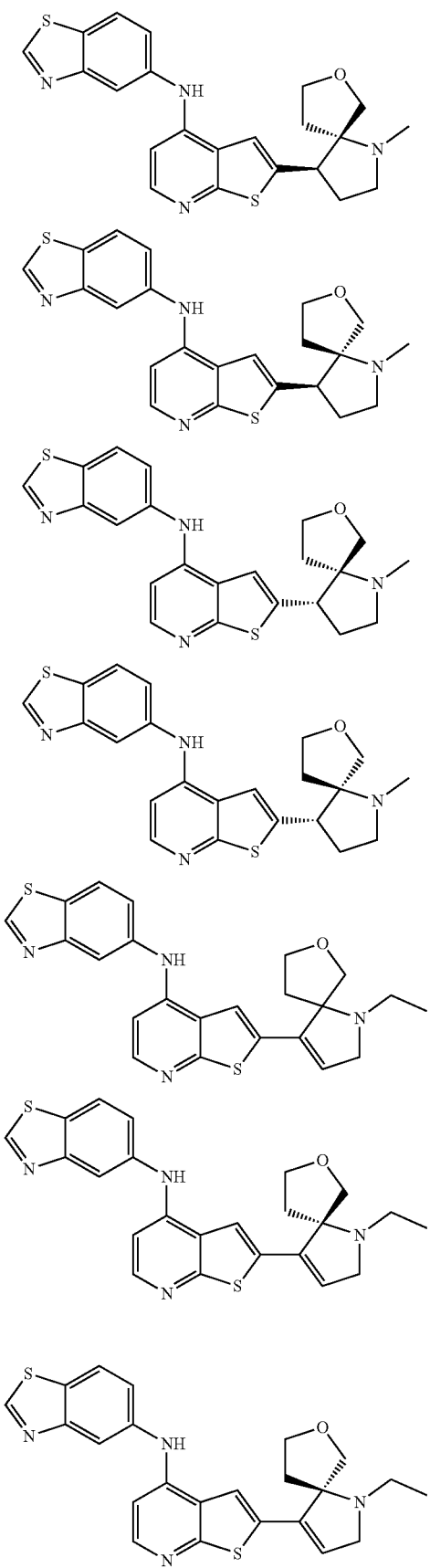
248
-continued
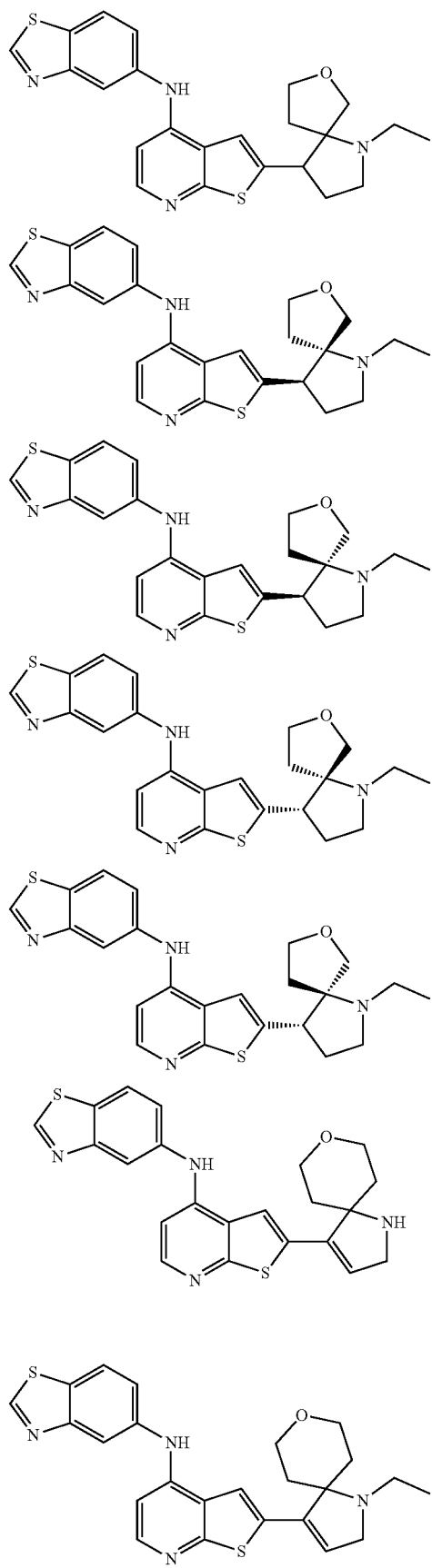

249
-continued
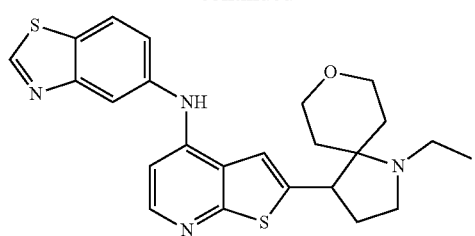
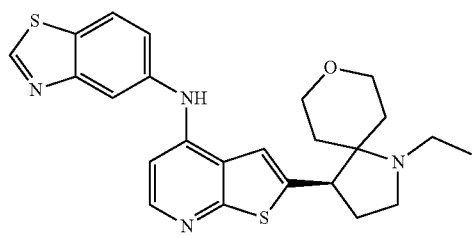
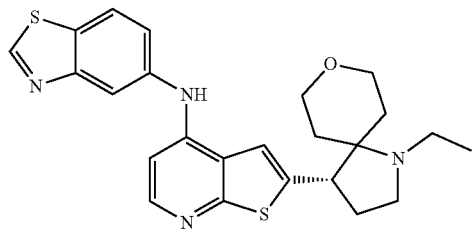
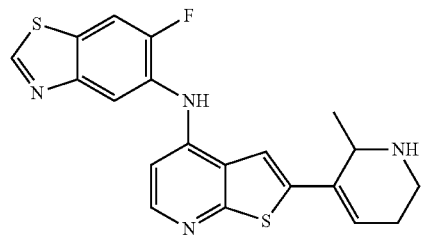
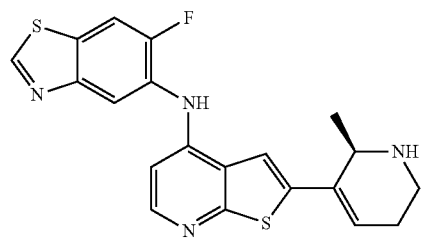
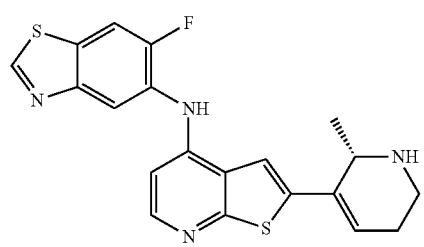
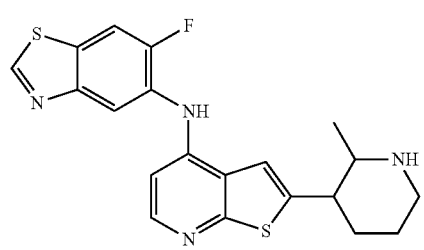
250
-continued
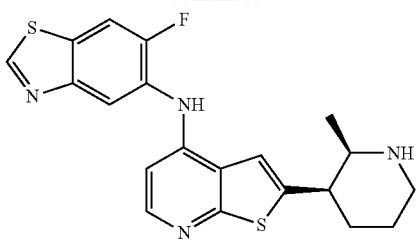
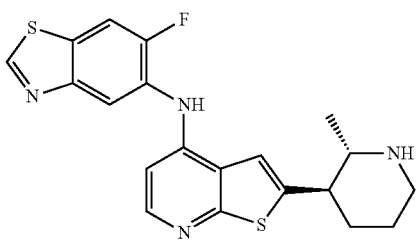
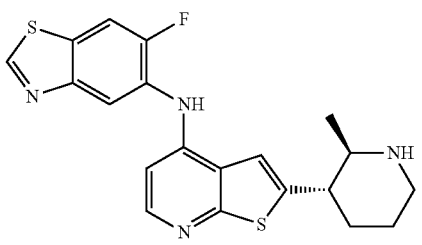
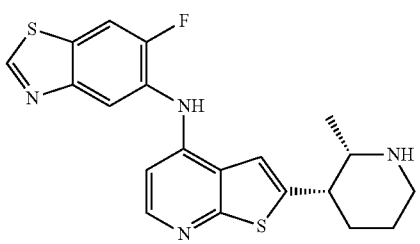
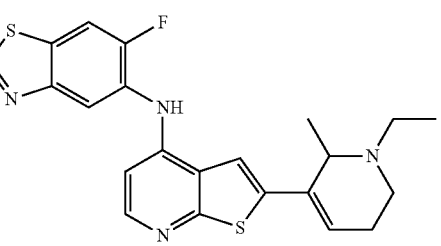
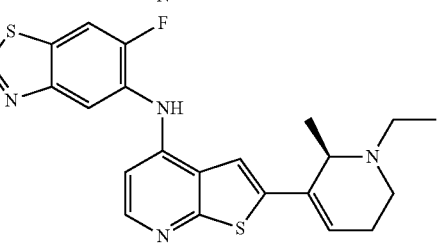
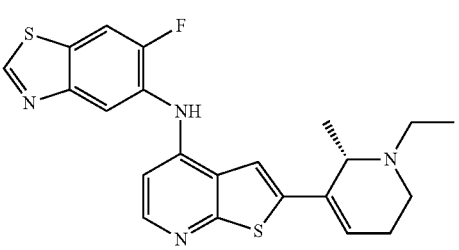

251
-continued
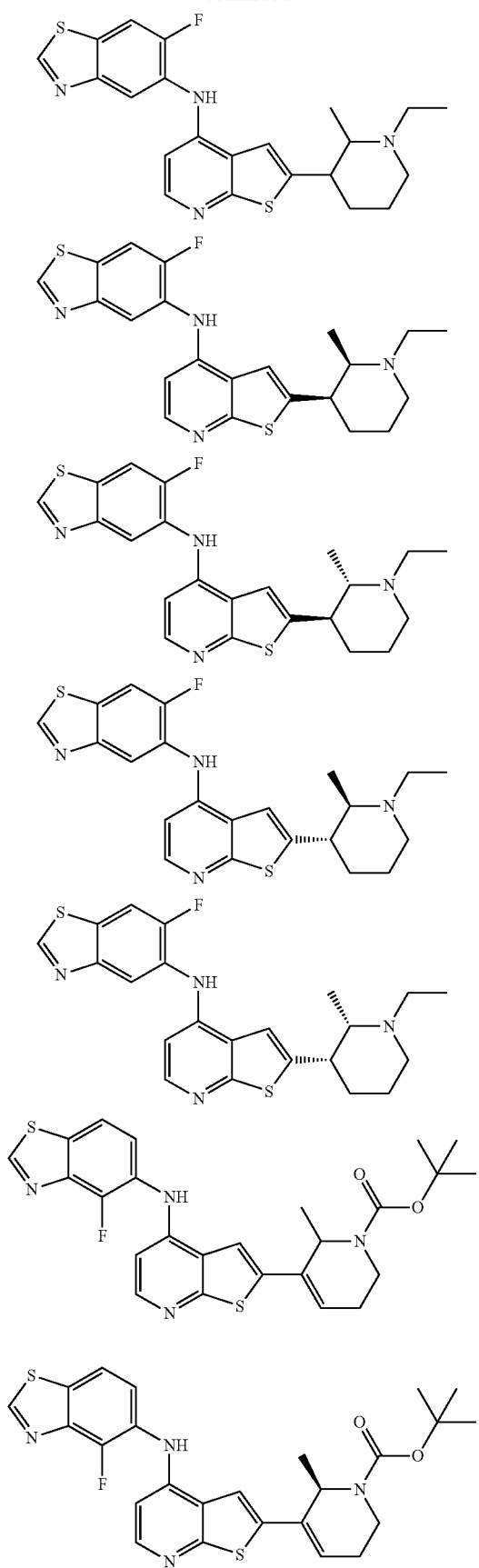
252
-continued
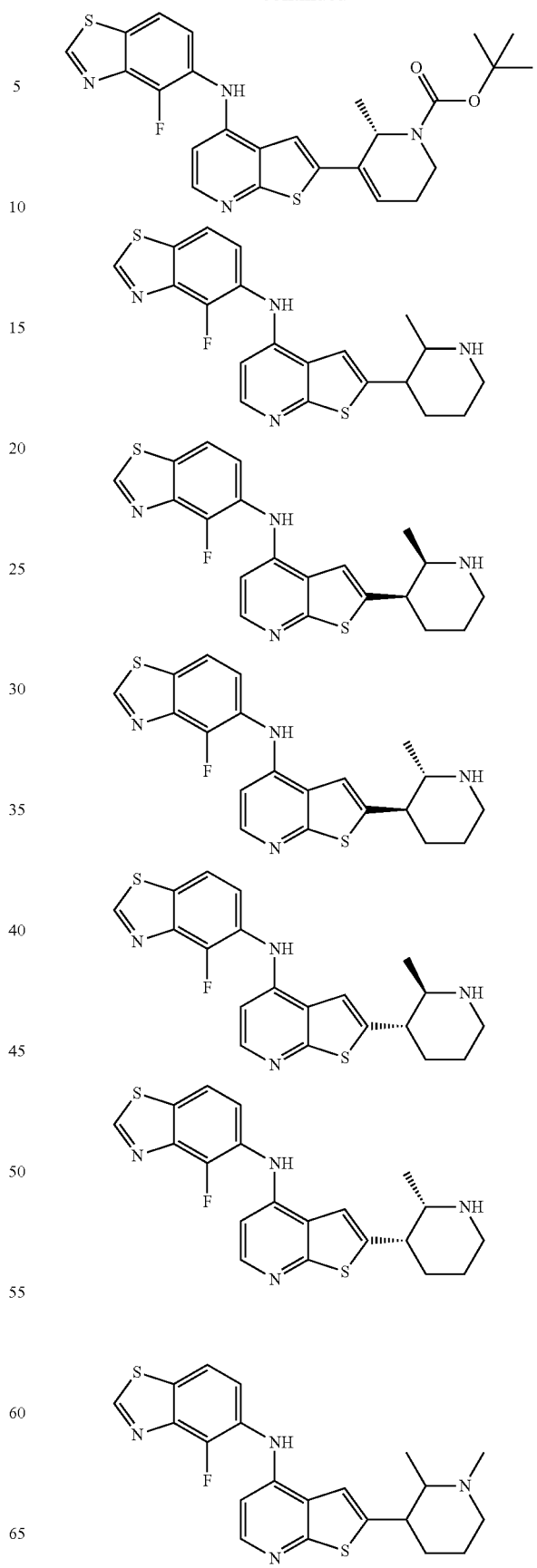

253
-continued
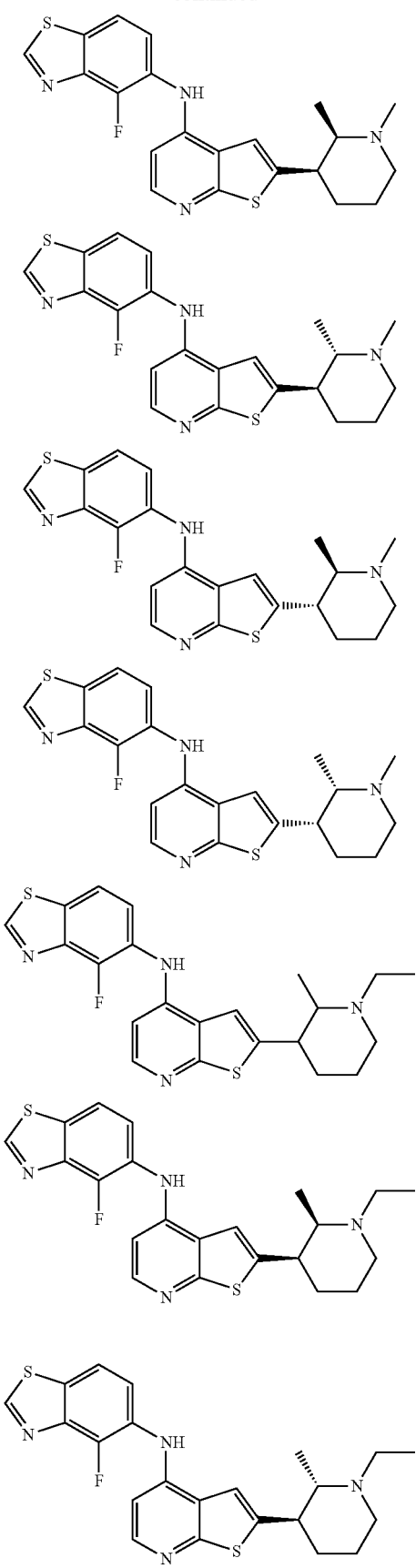
254
-continued
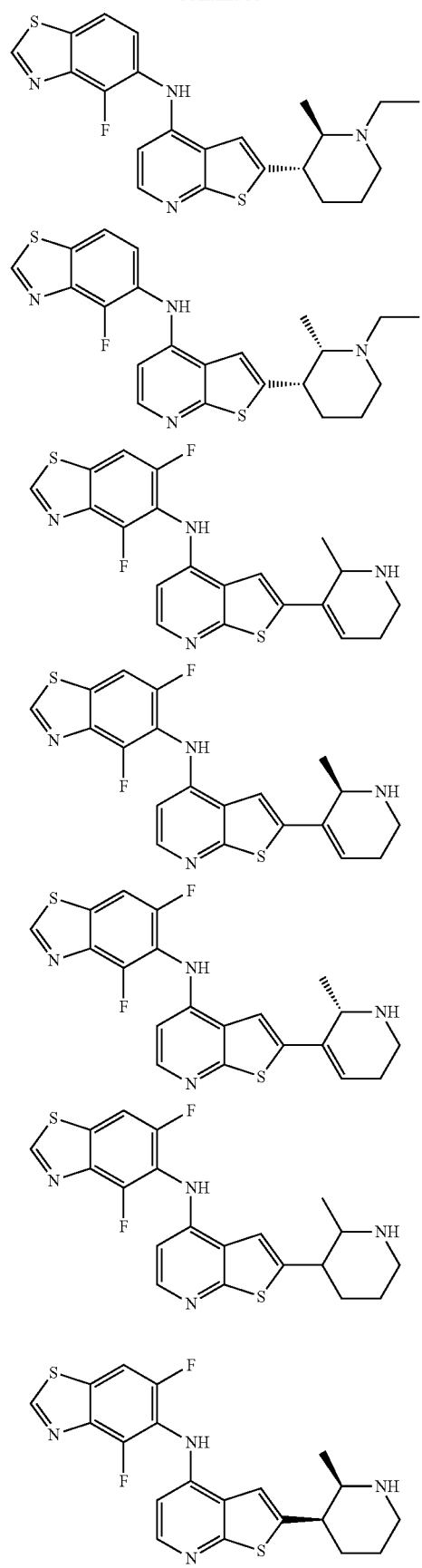

255
-continued
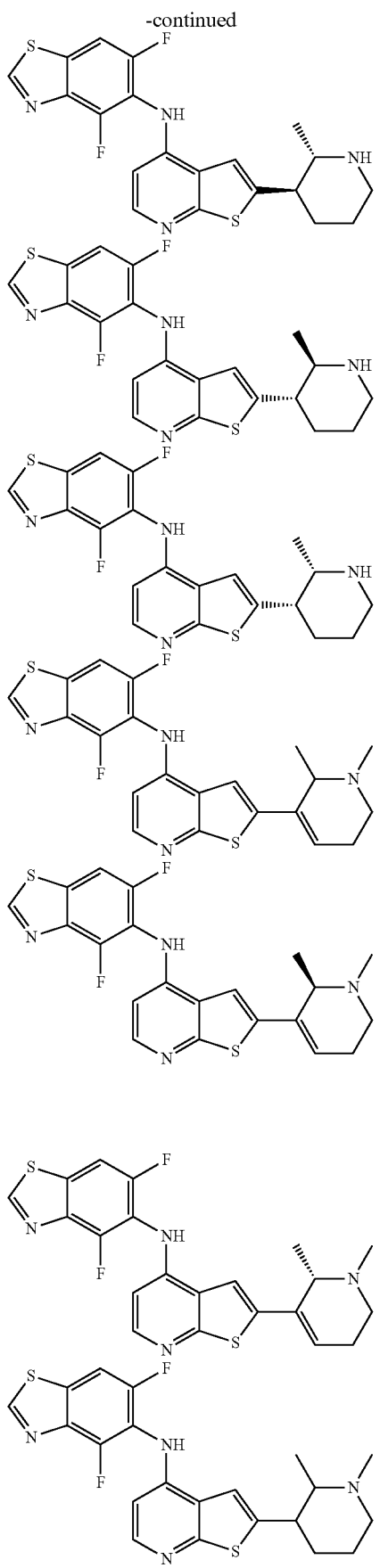
256
-continued
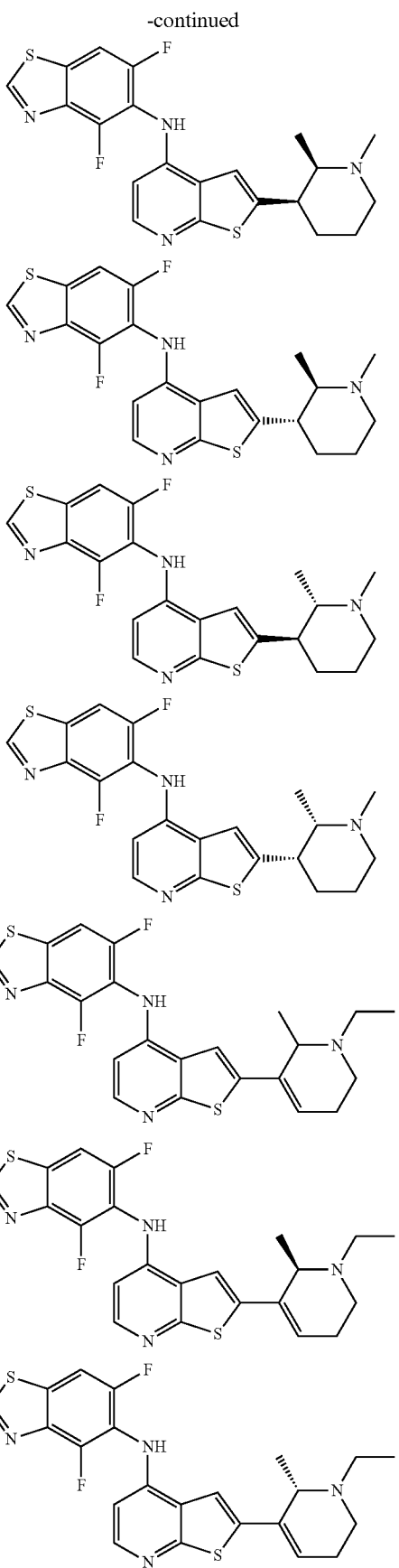

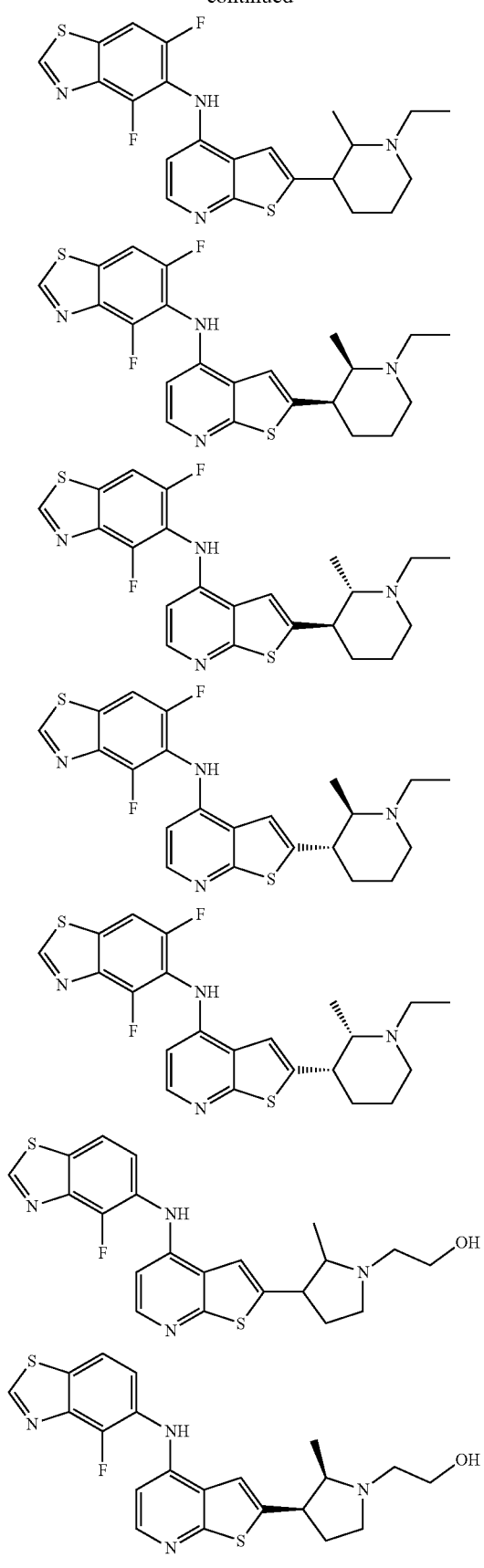
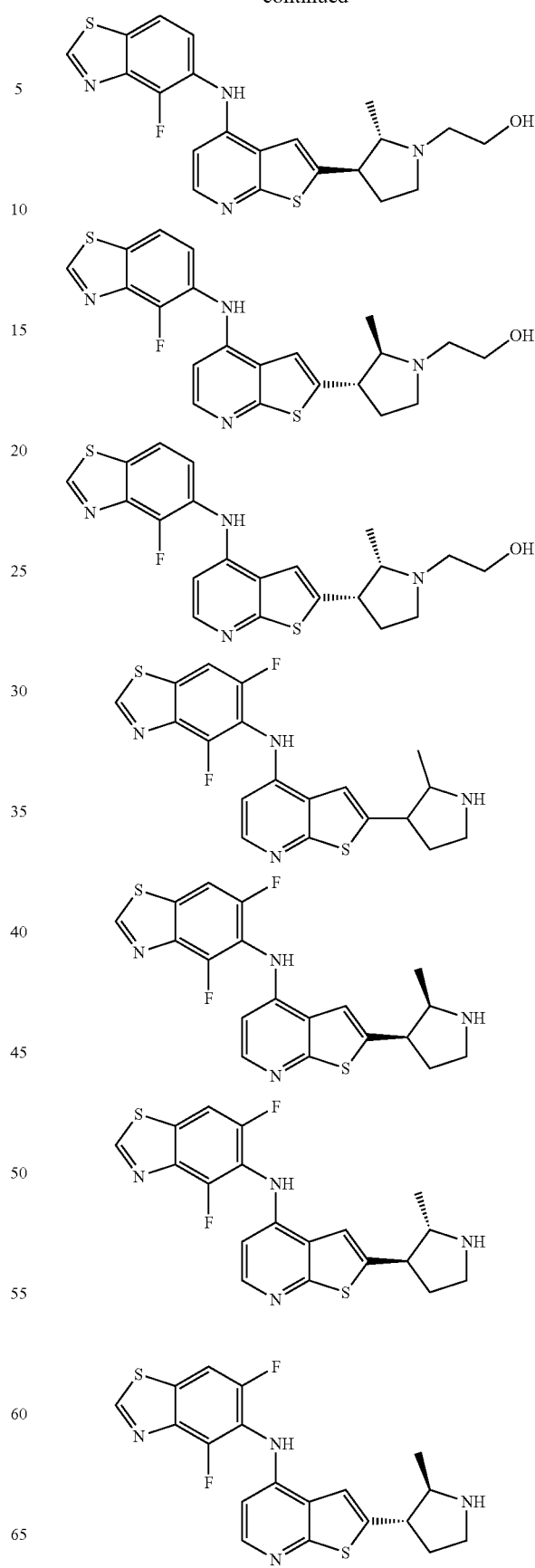

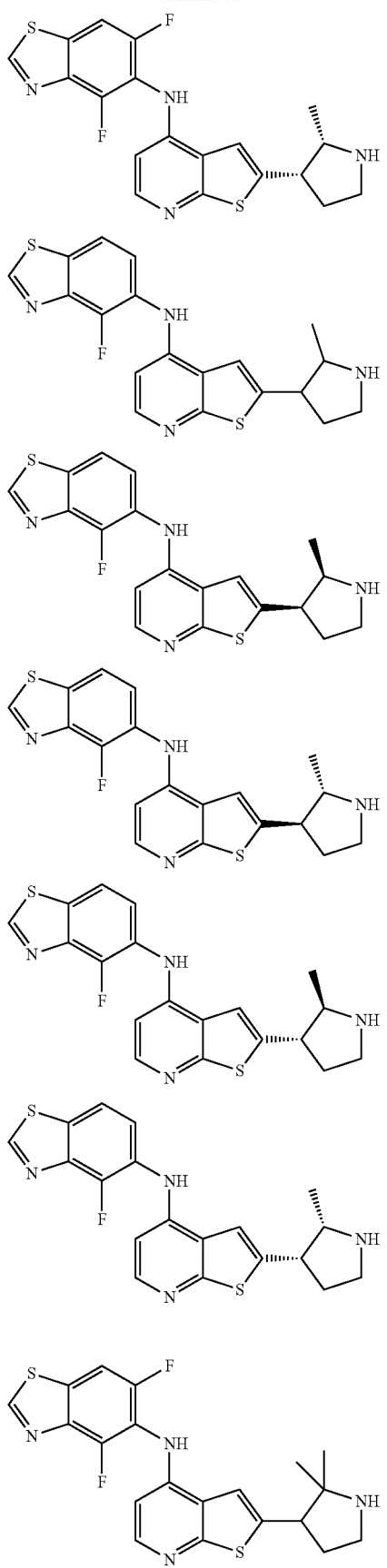
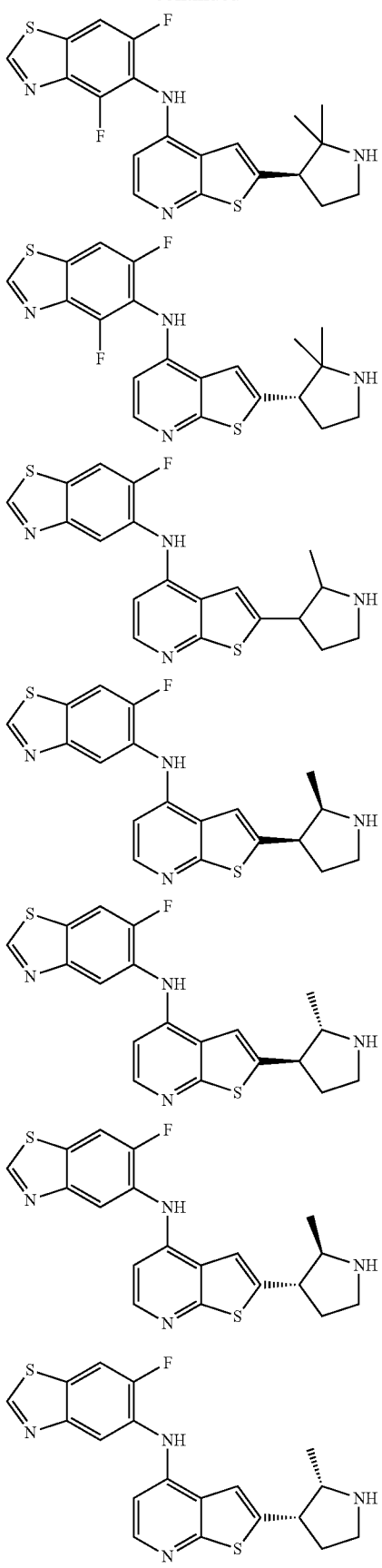

-continued
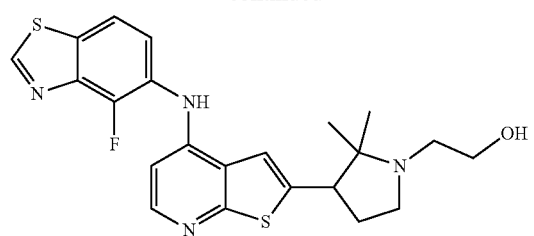
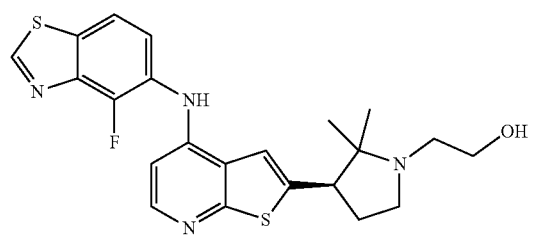
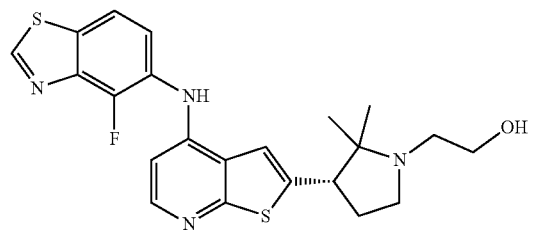
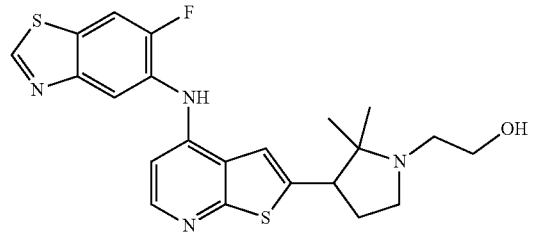
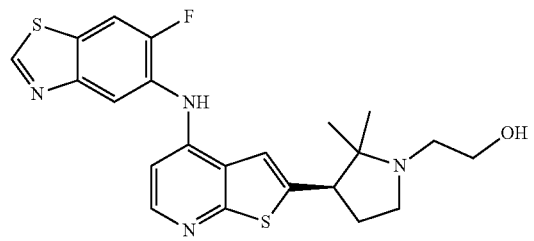
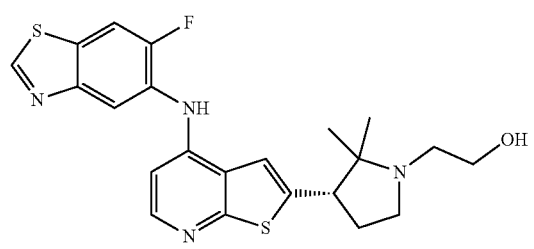
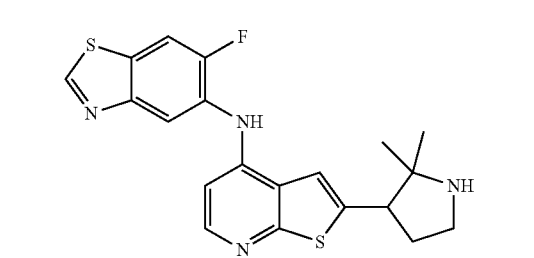
-continued
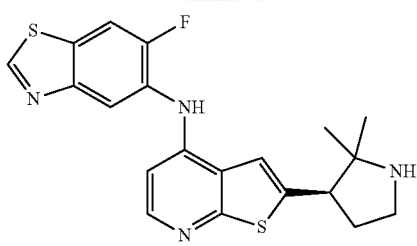
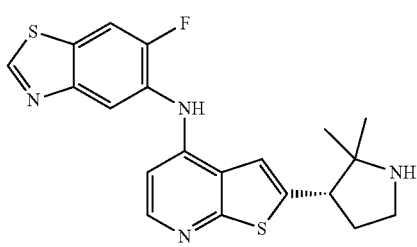
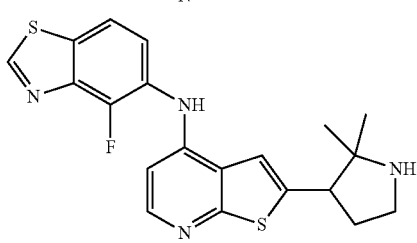
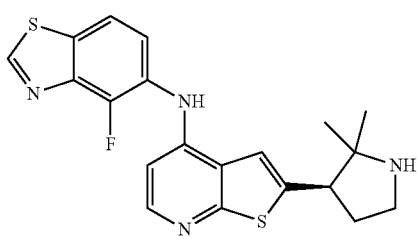
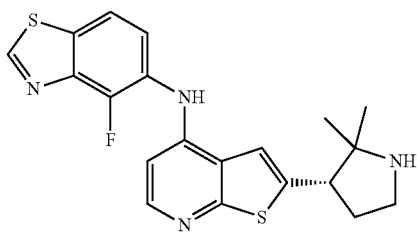
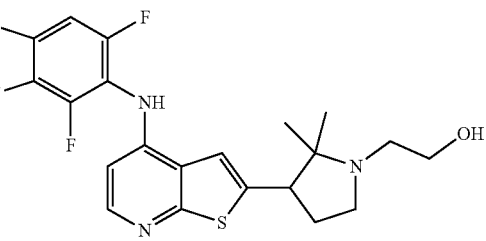
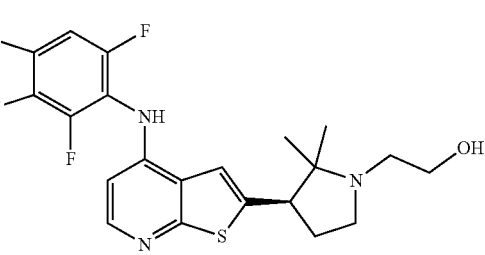

263
-continued
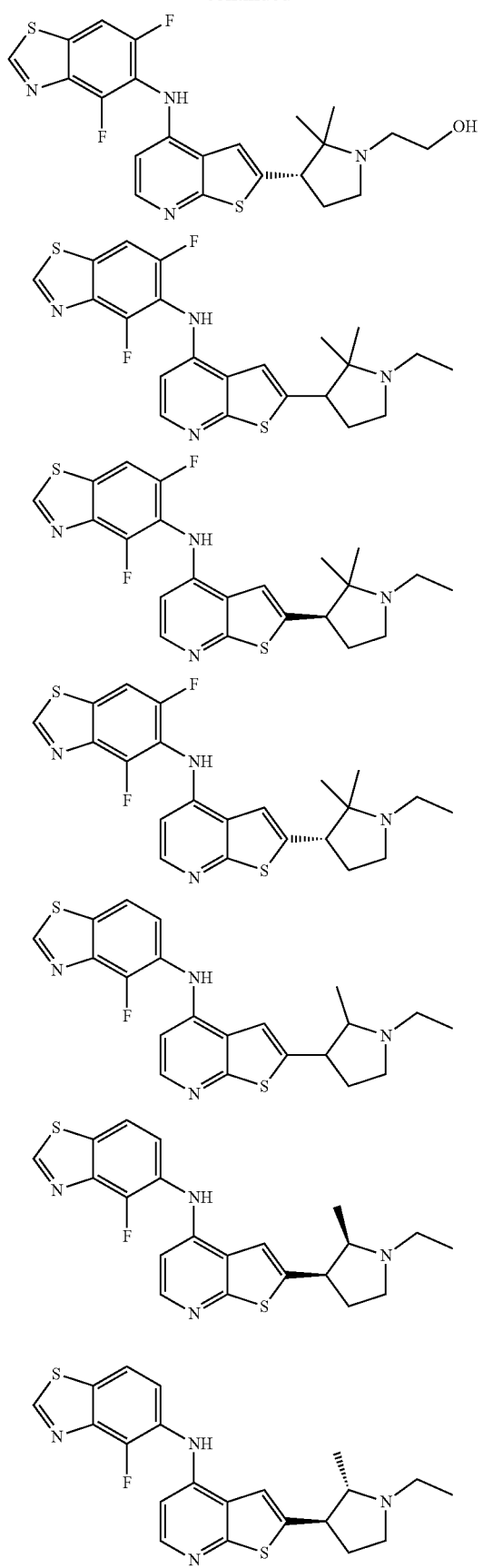
264
-continued
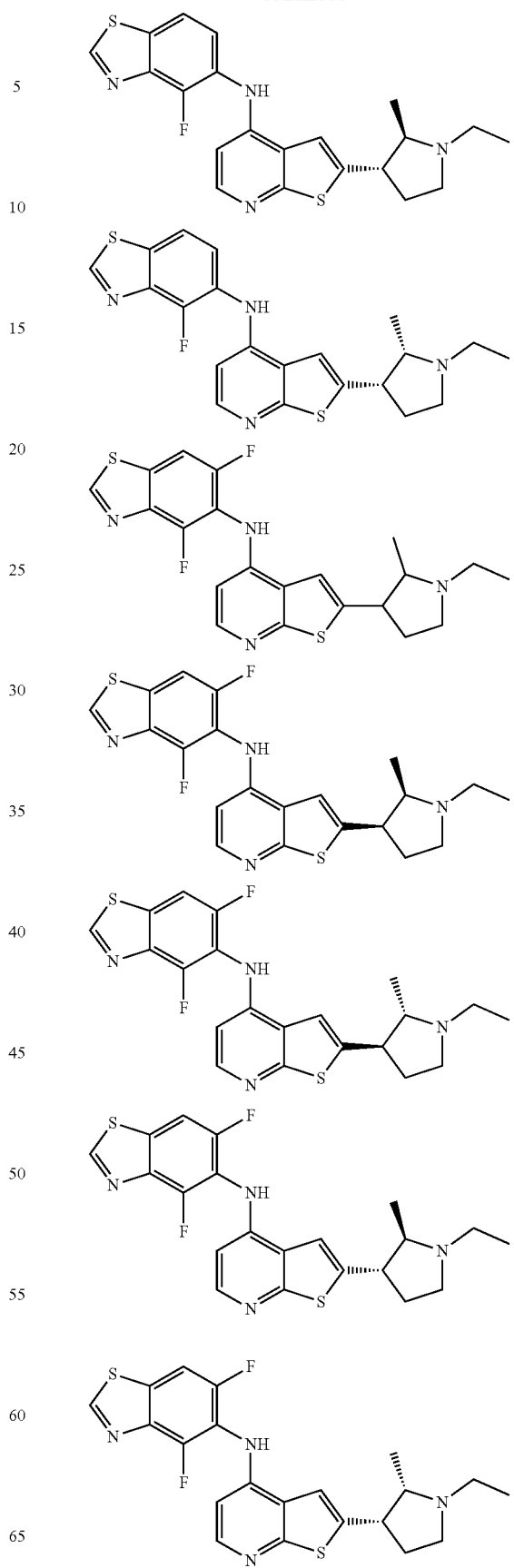

265
-continued
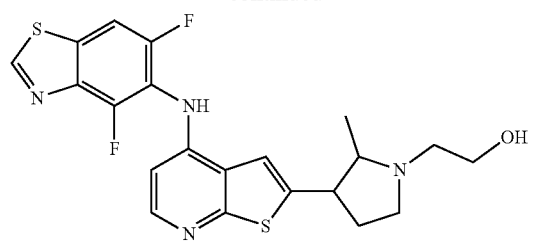
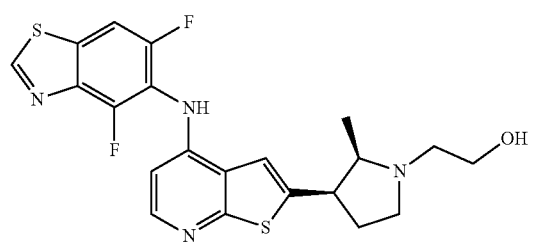
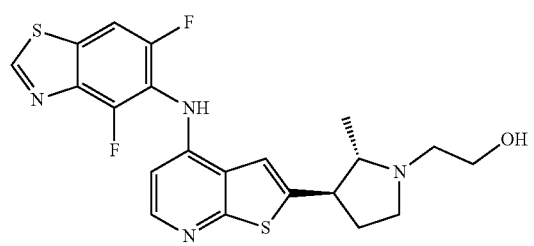
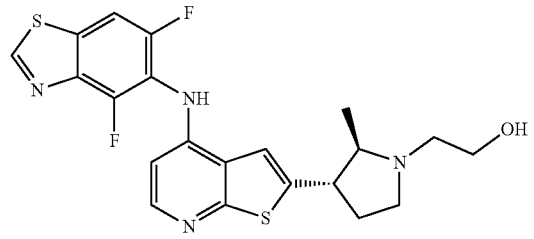
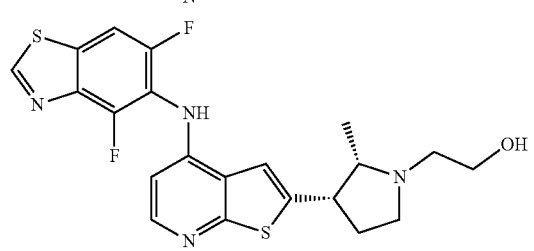
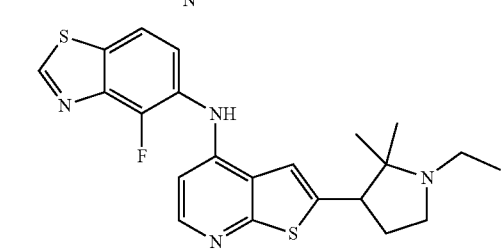
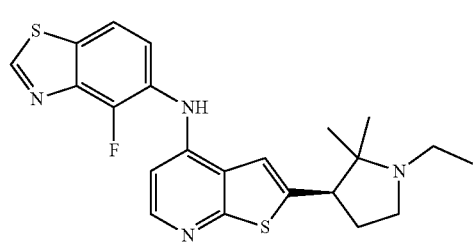
266
-continued
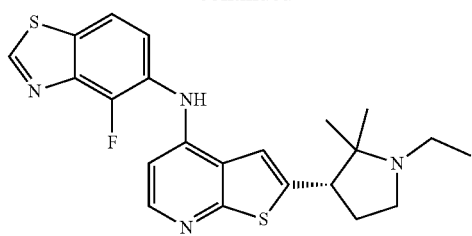
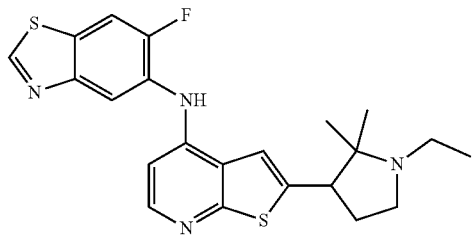
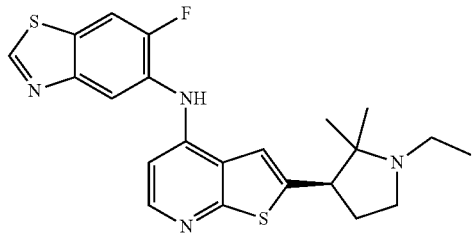
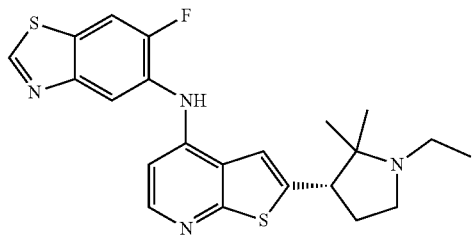
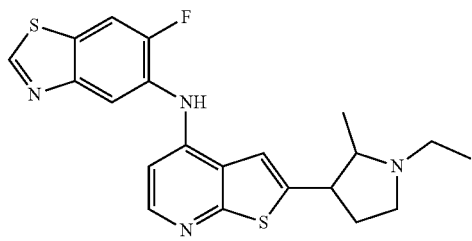
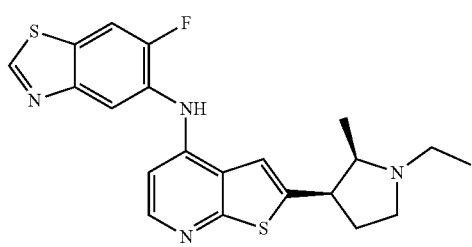
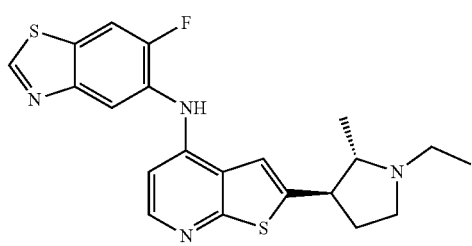

267
-continued
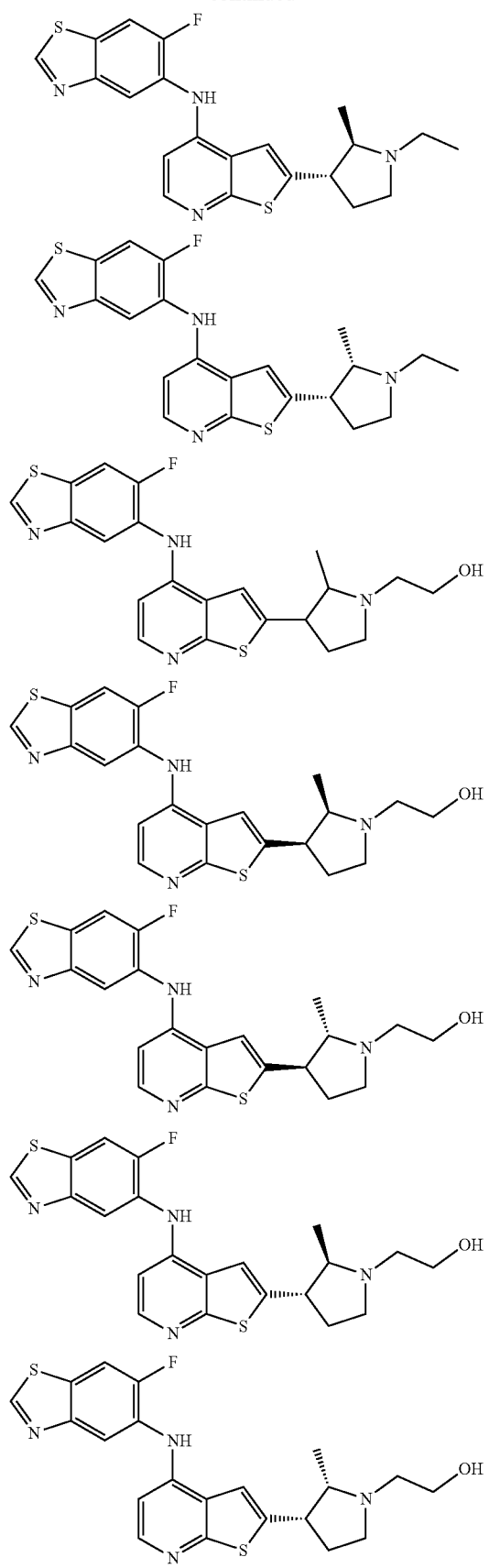
268
-continued
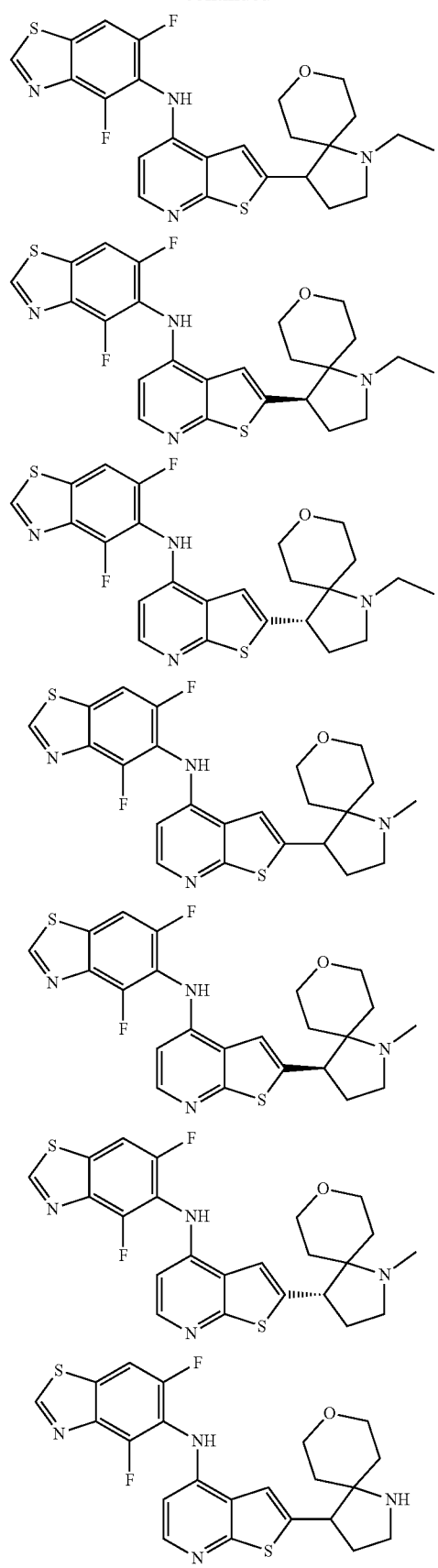

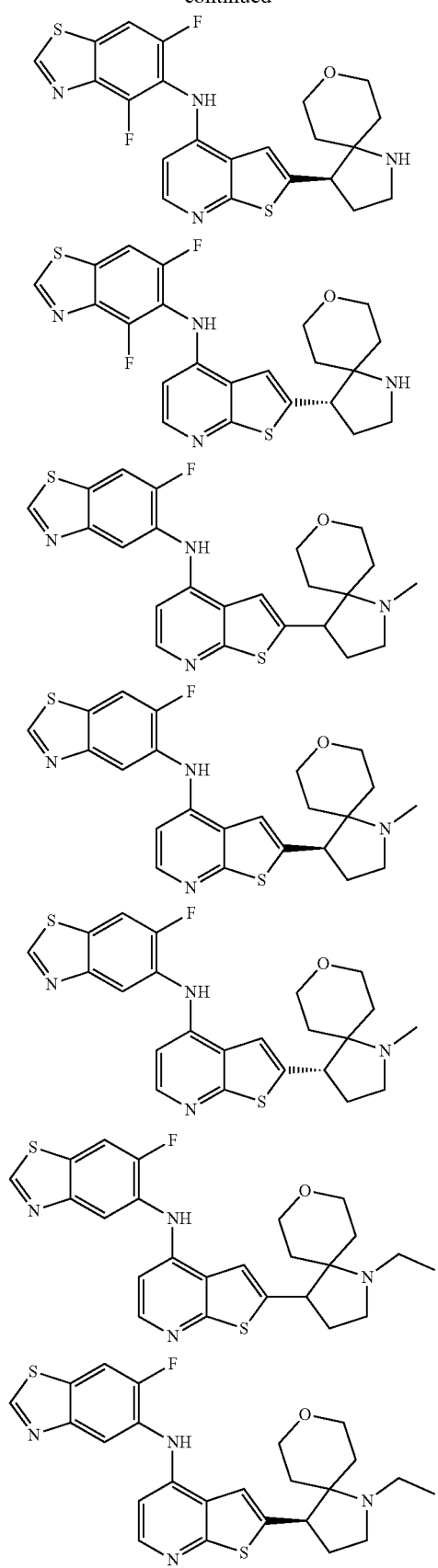
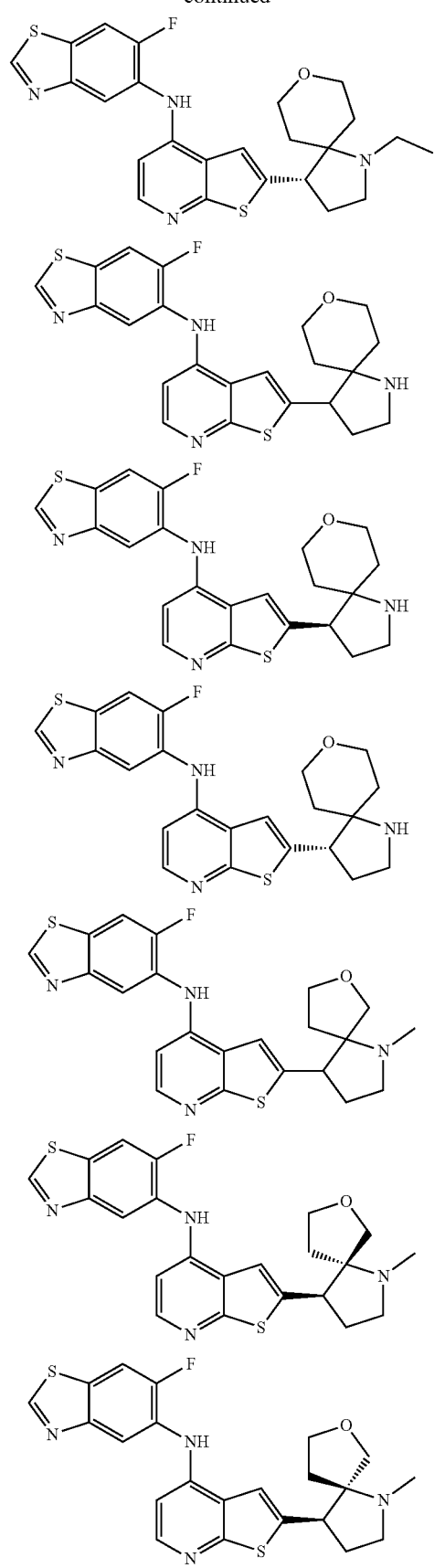

271
-continued
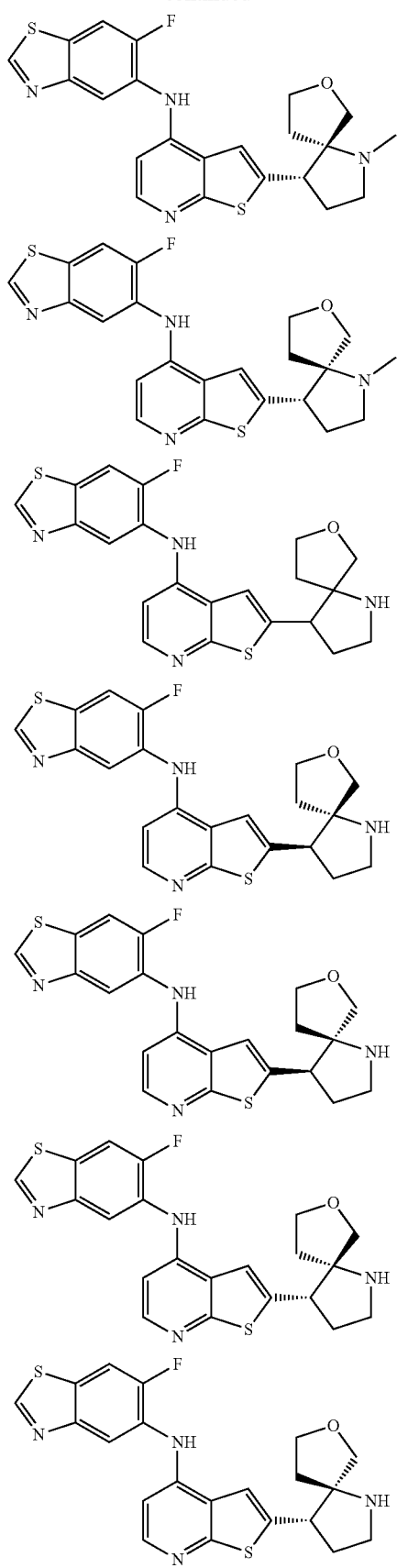
272
-continued
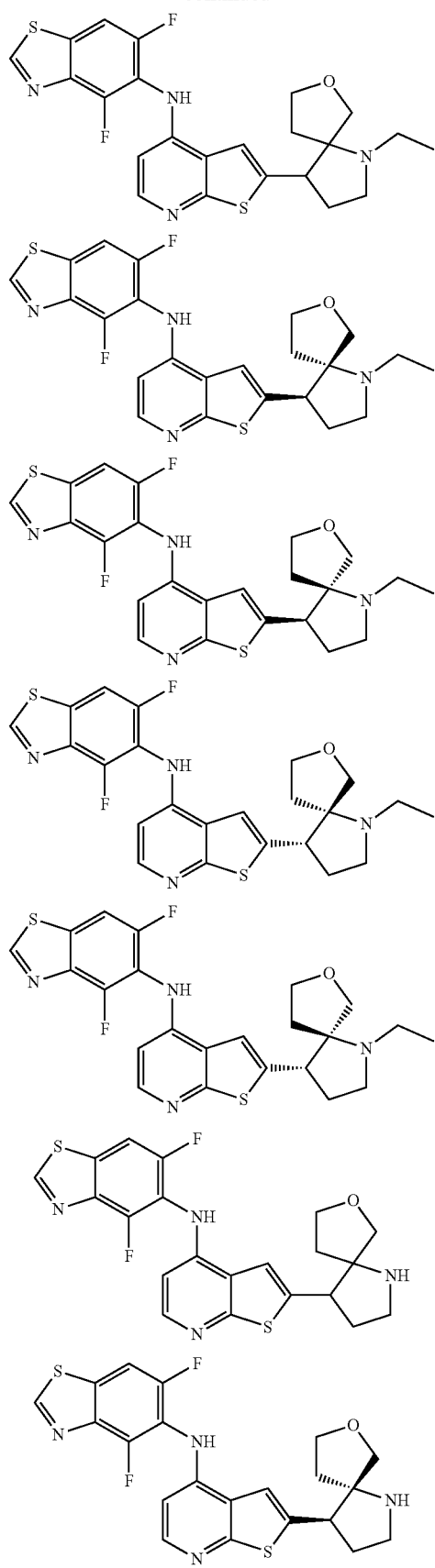

273
-continued
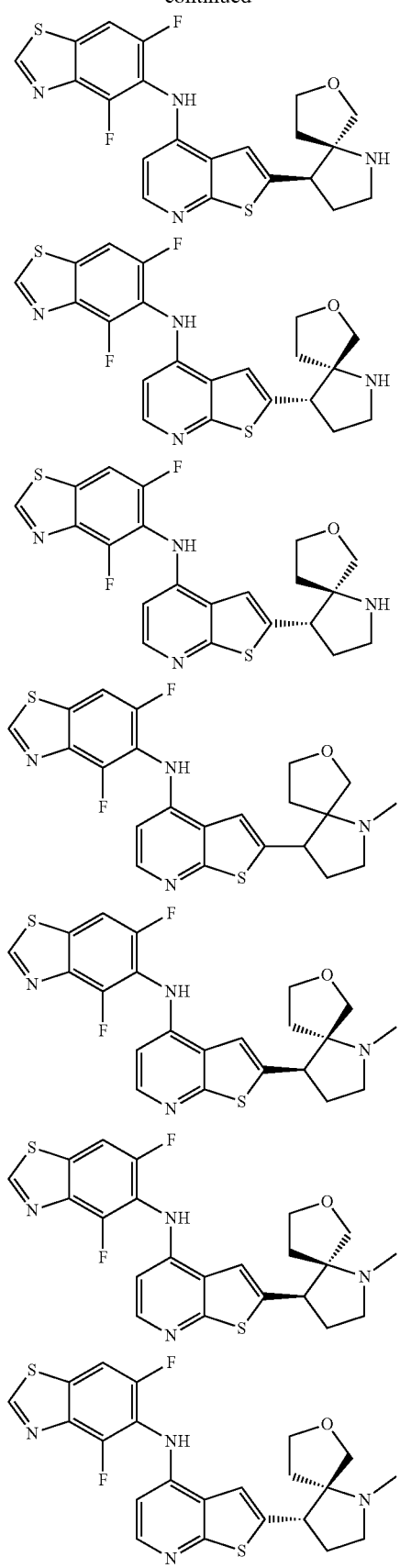
274
-continued
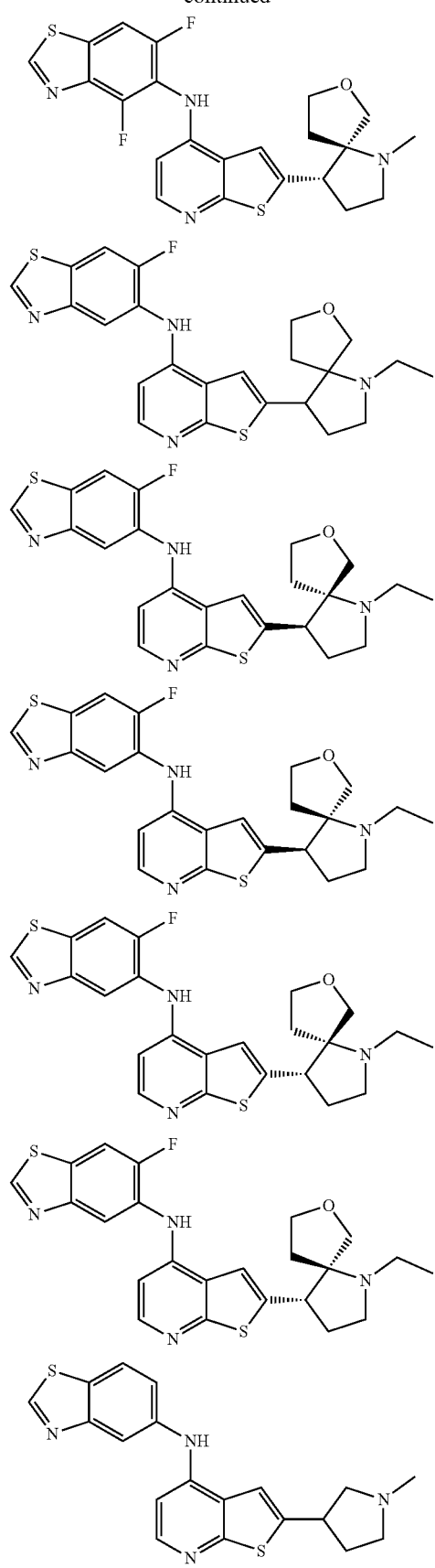

275
-continued
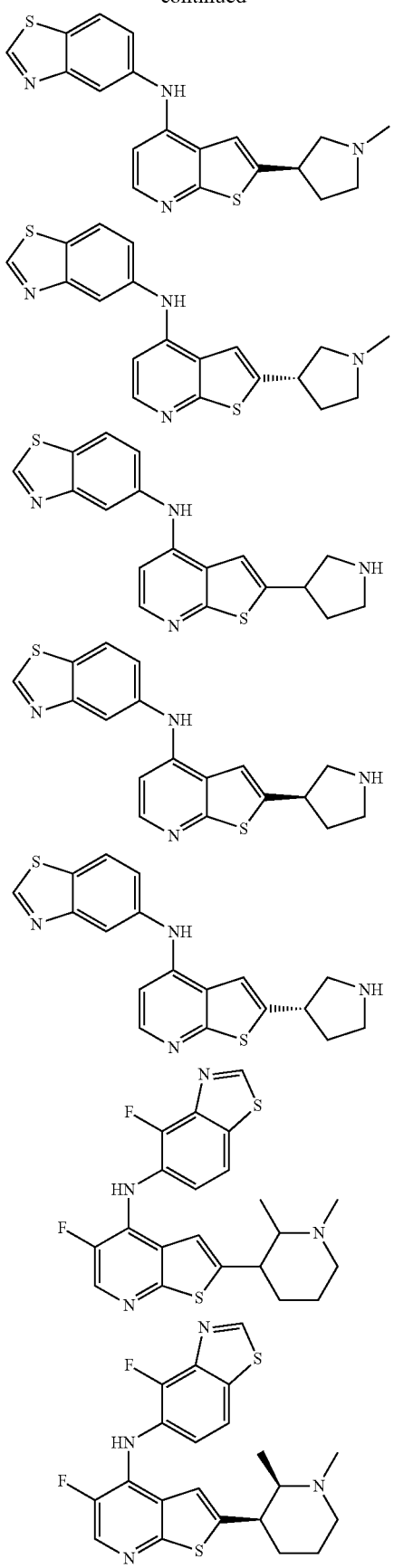
276
-continued
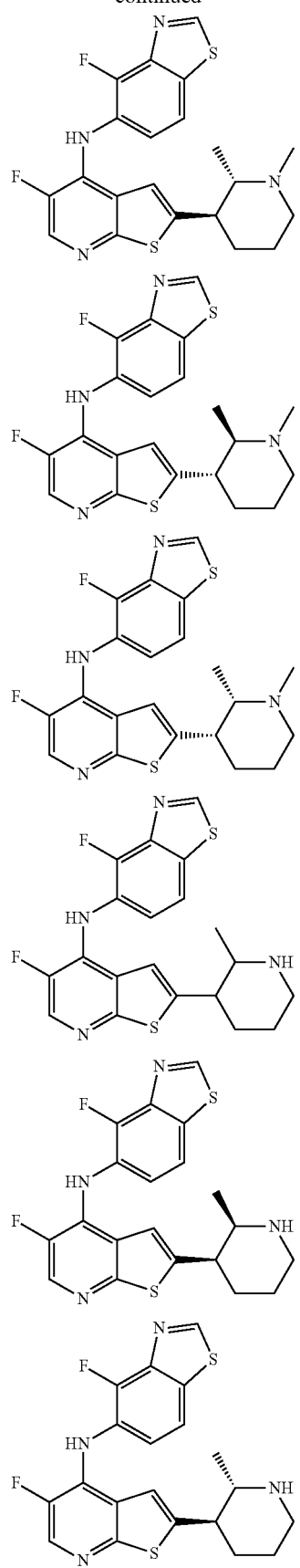

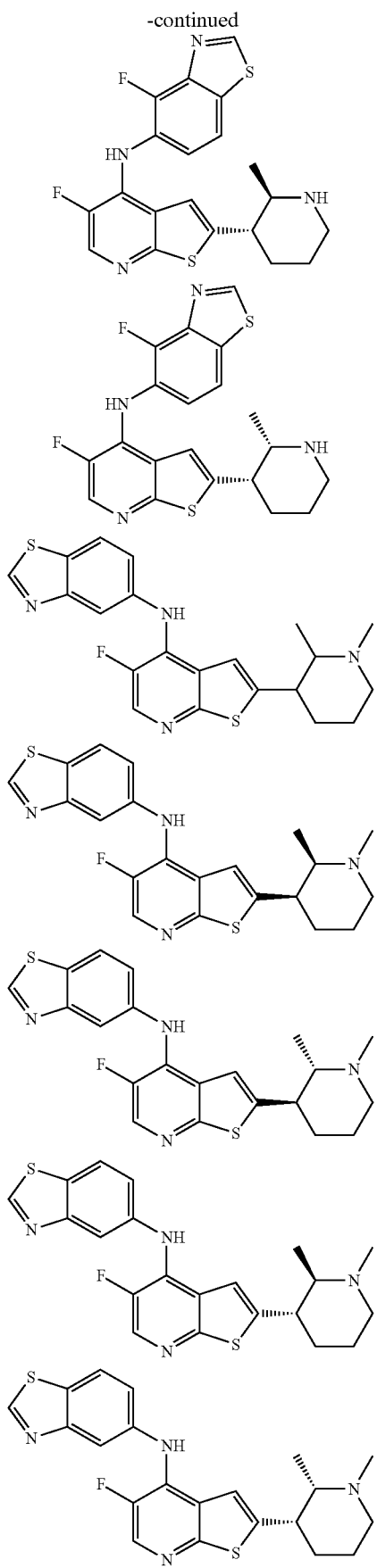
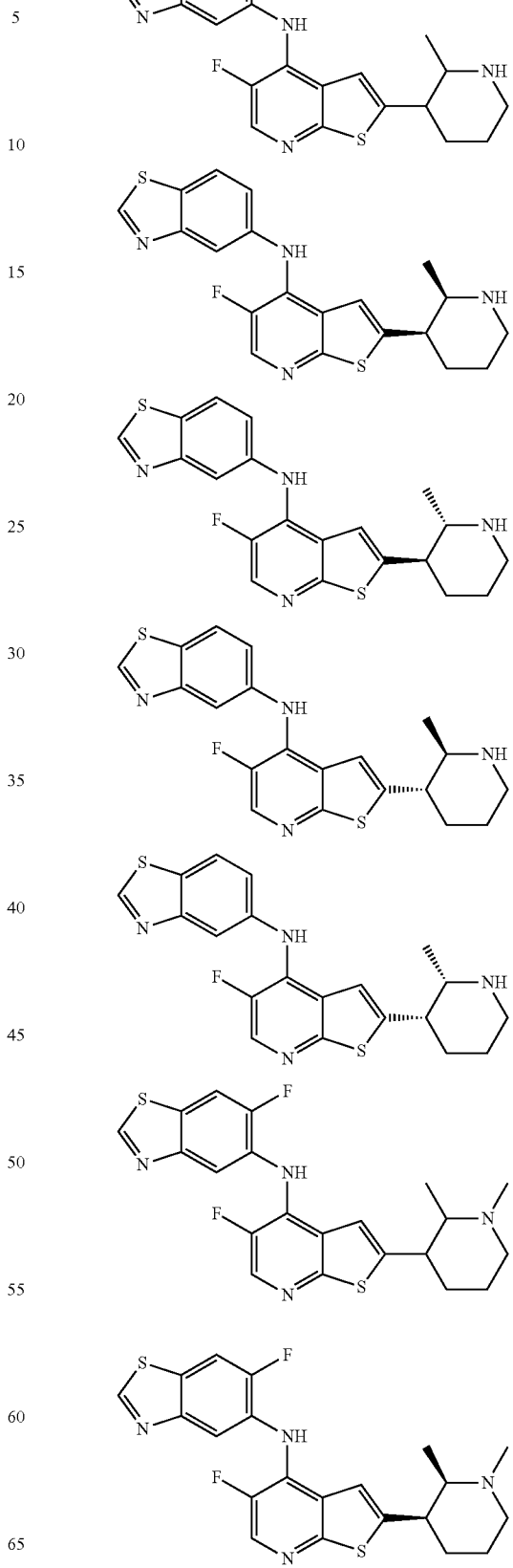

279
-continued
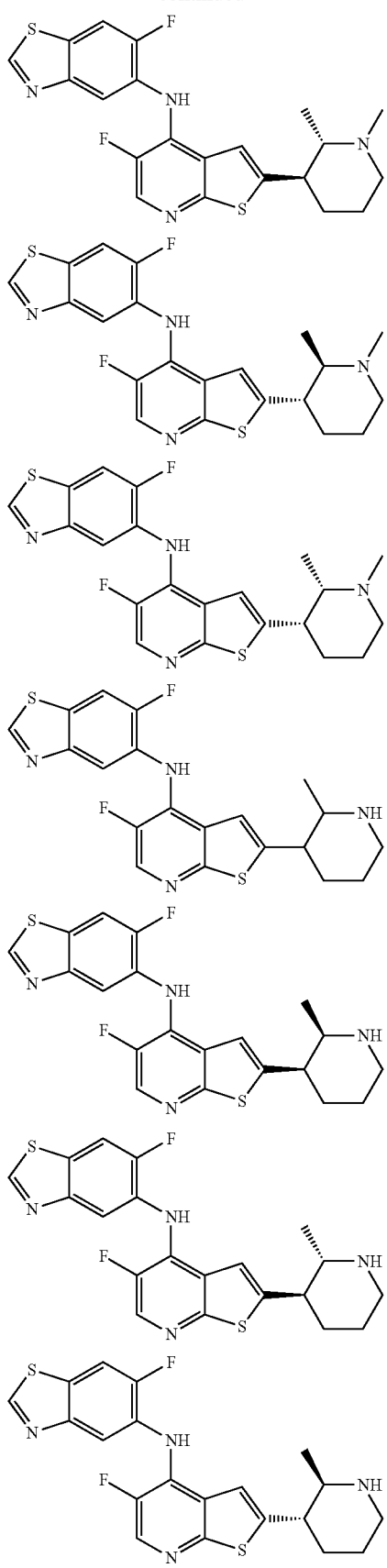
280
-continued
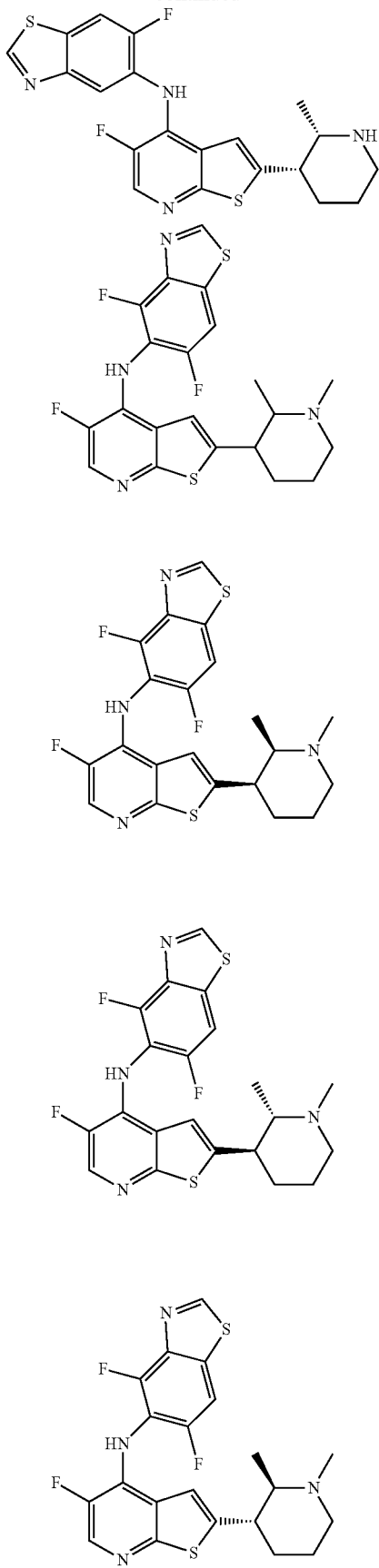

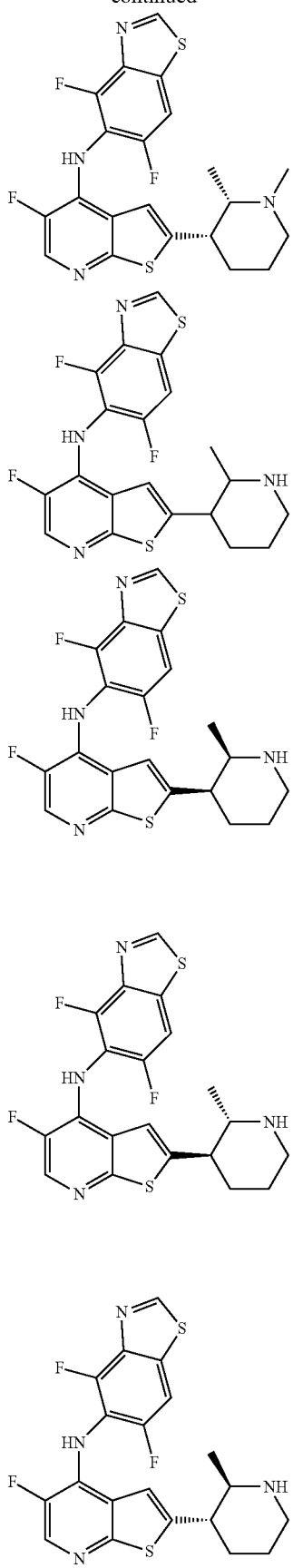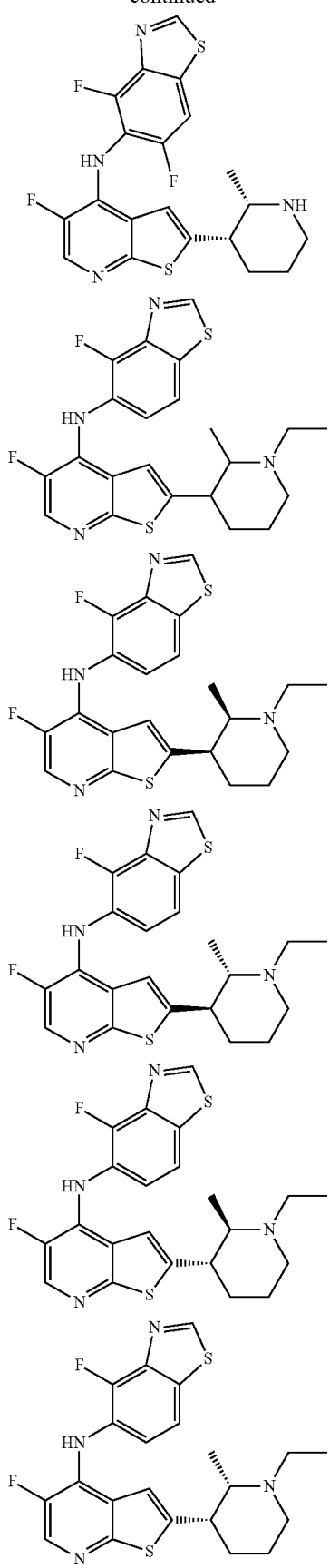

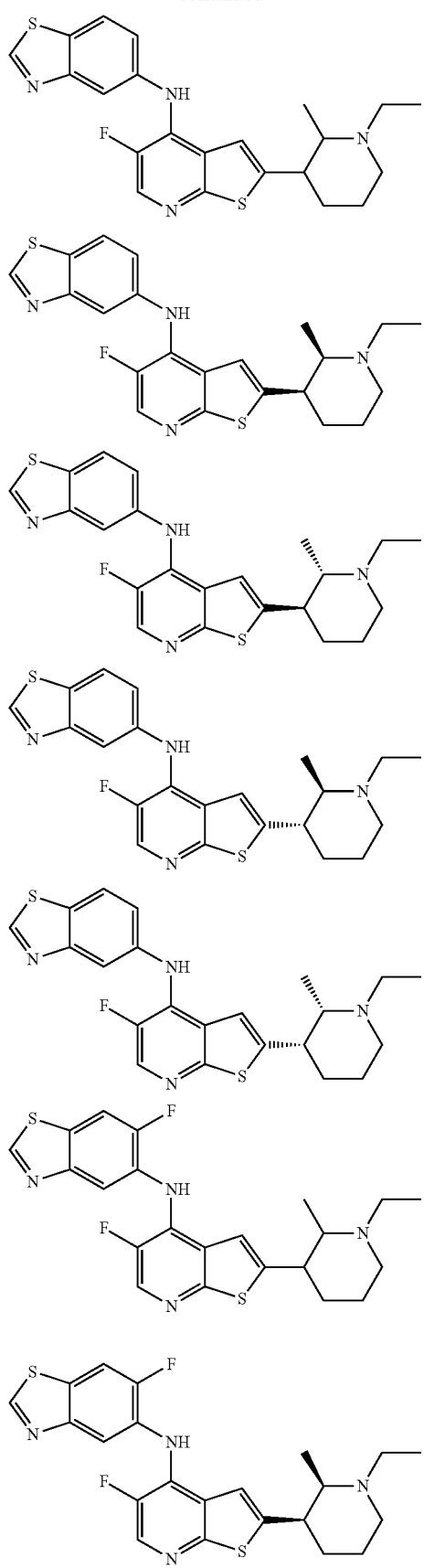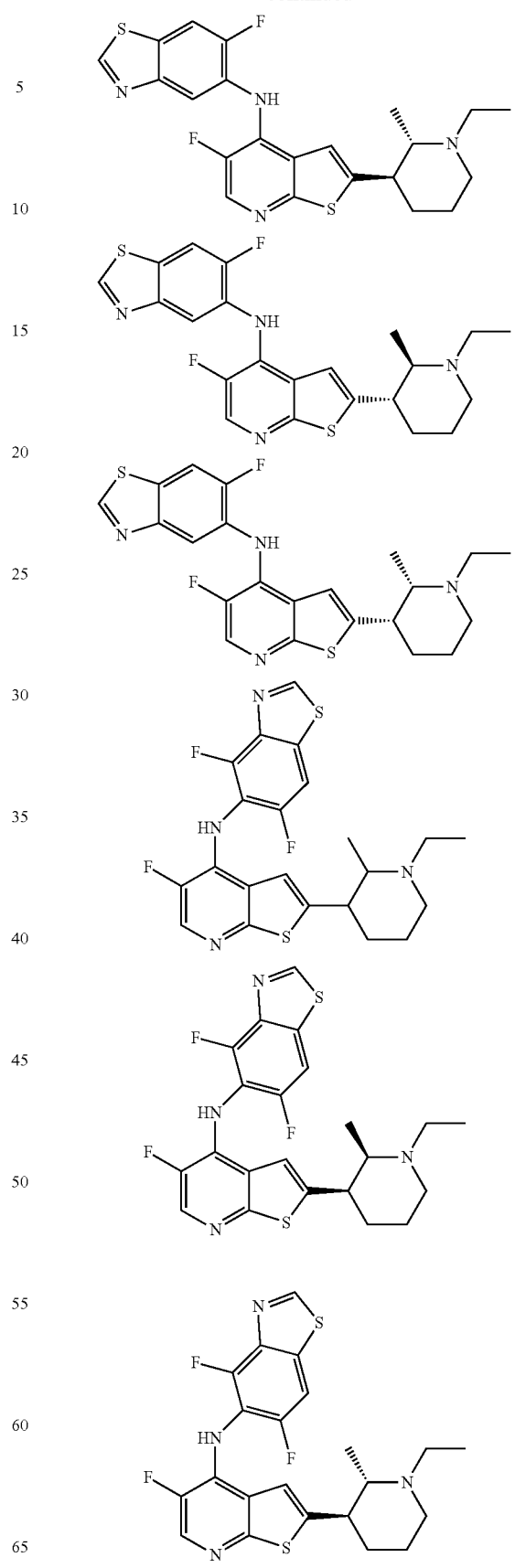

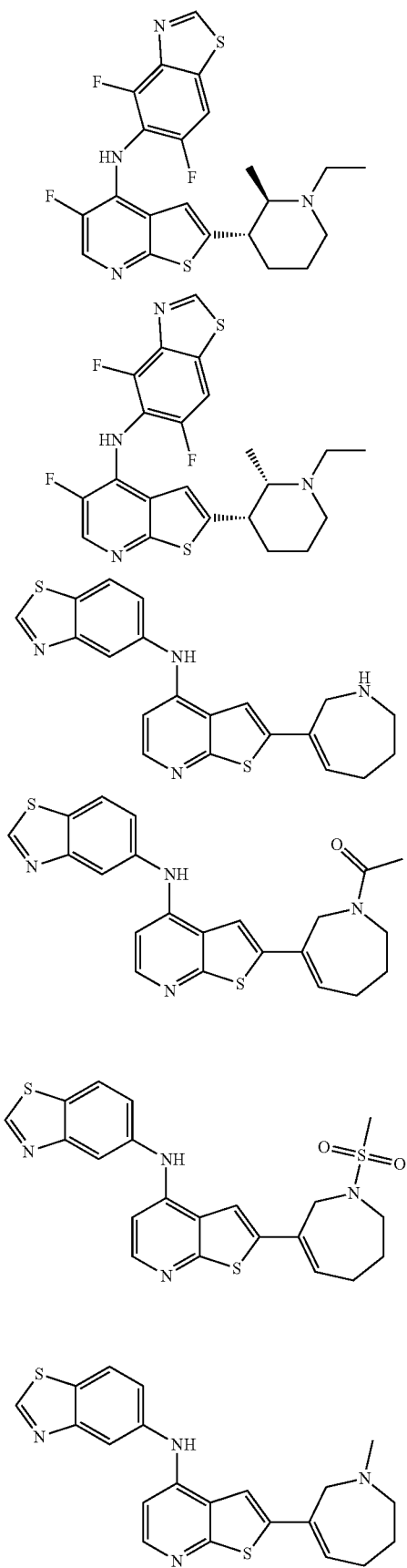
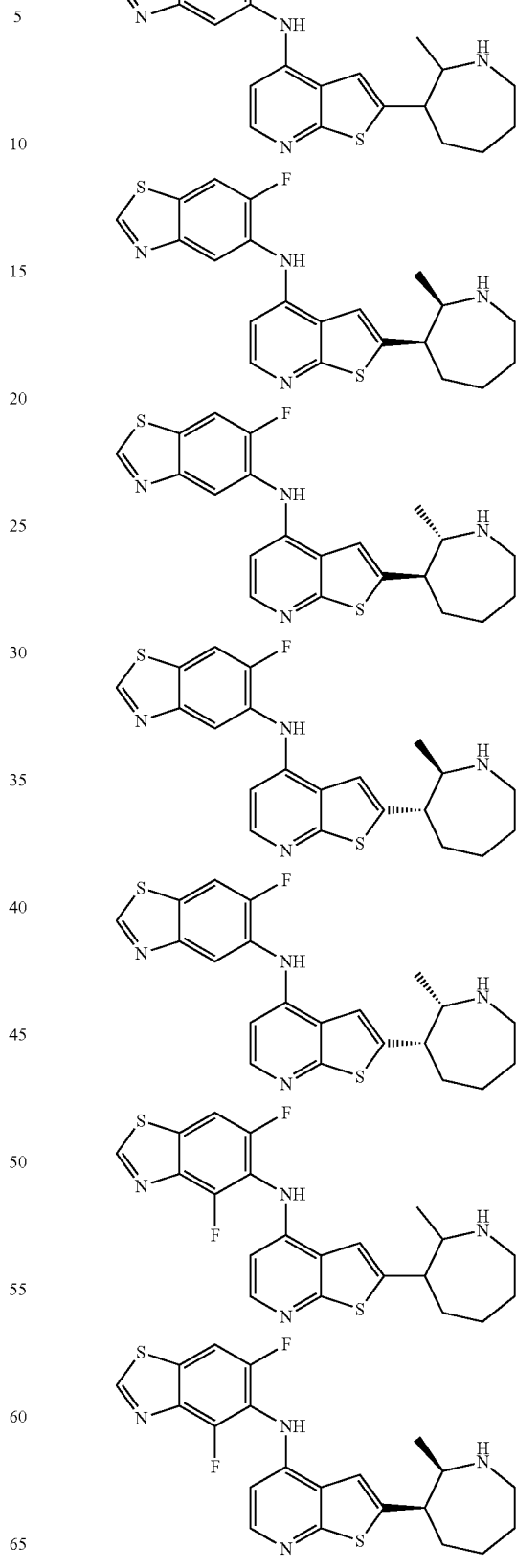

-continued
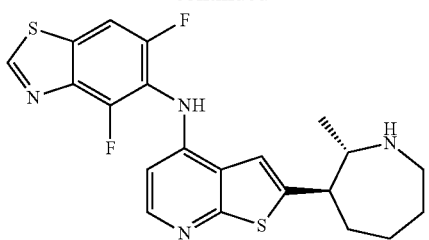
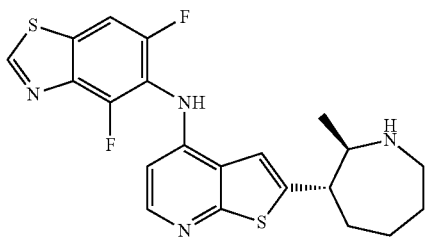
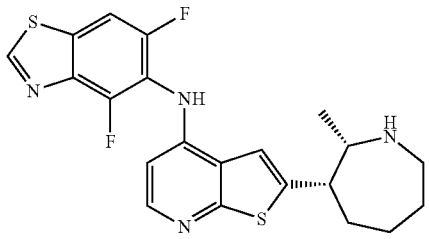
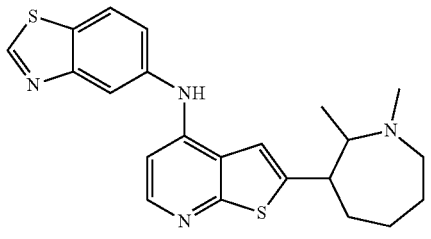
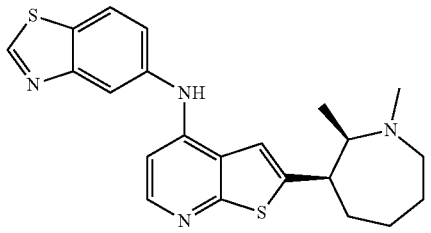
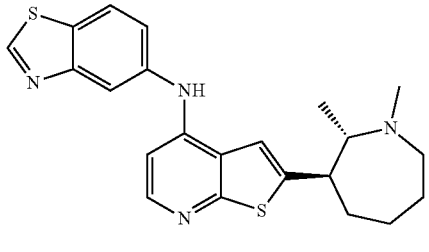
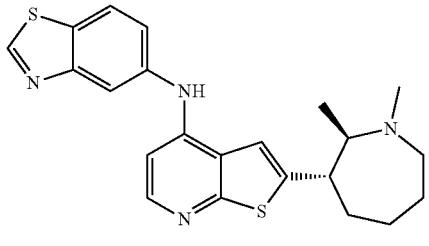
-continued
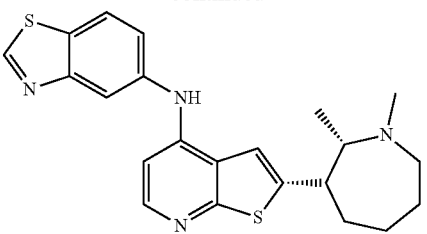
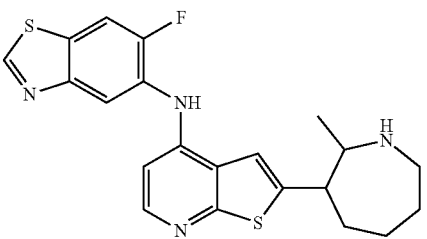
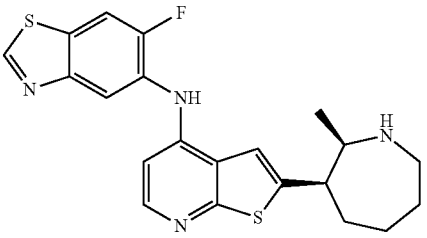
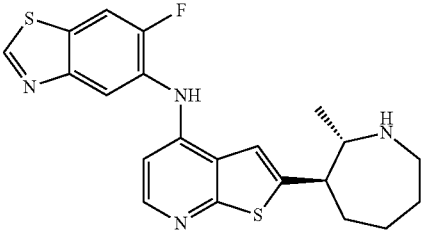
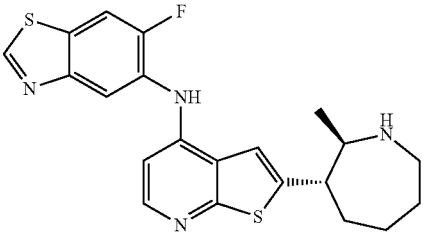
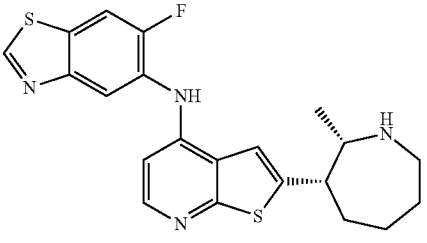
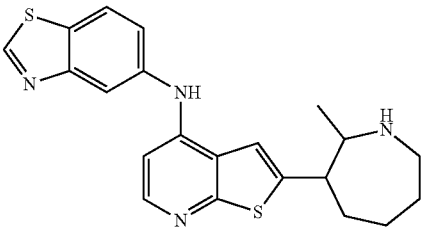

289
-continued
290
-continued
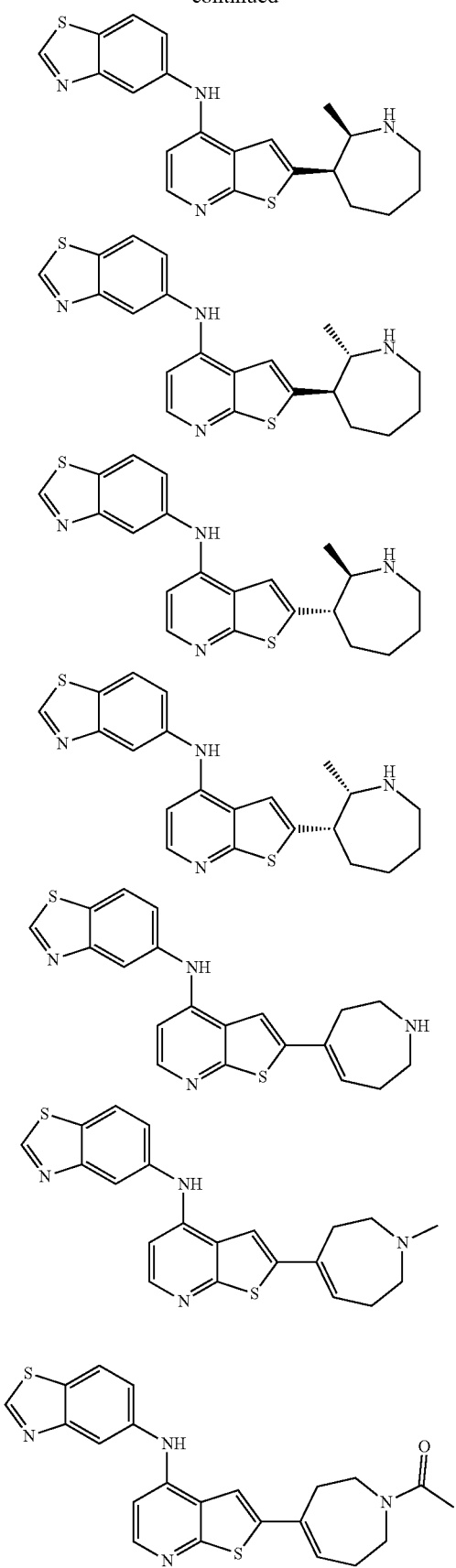
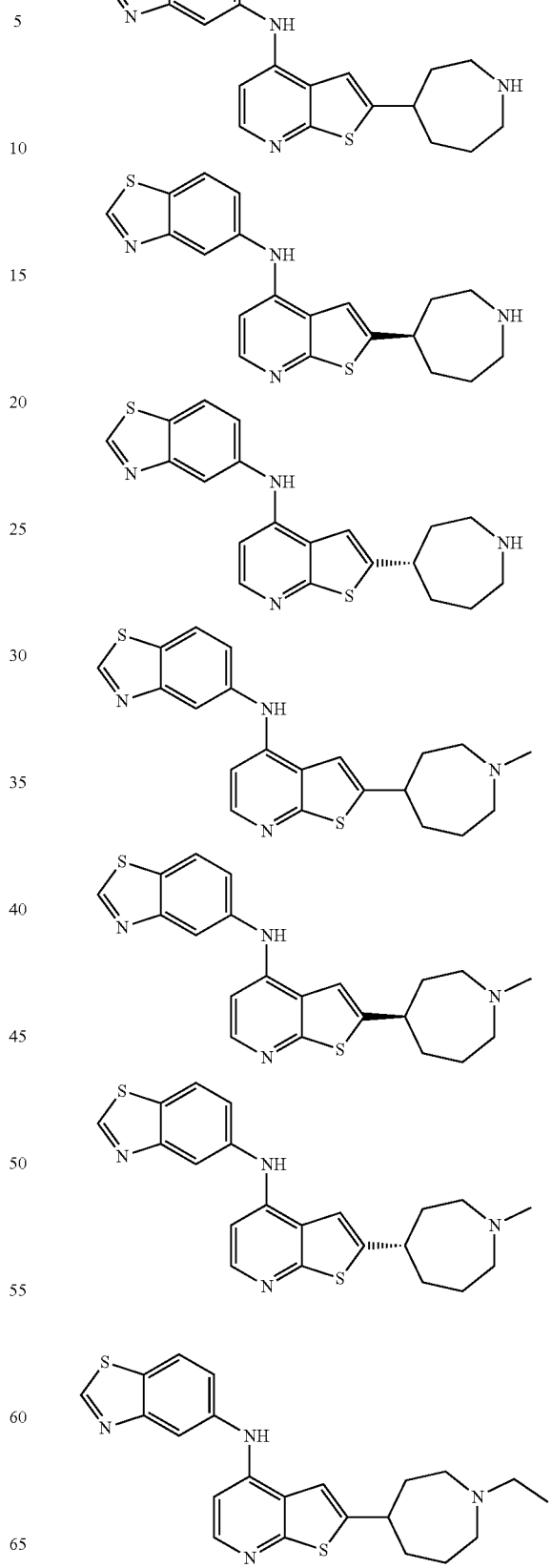

-continued

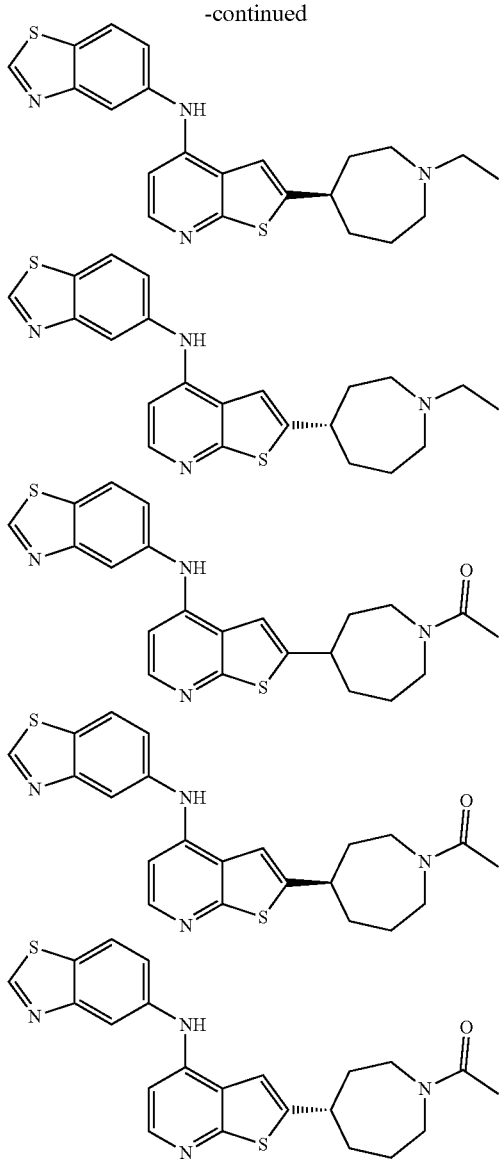

Embodiment 137. A composition comprising a compound of any one of Embodiments 65-136 and a pharmaceutically acceptable carrier or excipient.

Embodiment 138. A method of inhibiting RIPK2 in a biological sample or in a patient, comprising contacting the biological sample or administering to the patient a therapeutically effective amount of any one of Embodiments 65-136, or a composition thereof.

Embodiment 139. A method of treating a disorder mediated by RIPK2 in a patient, comprising administering to the patient a therapeutically effective amount of any one of Embodiments 65-136, or a composition thereof.

Embodiment 140. The method of Embodiment 139, wherein the disorder mediated by RIPK2 is an inflammatory disorder, an autoimmune disorder, or a disorder associated with NOD2 receptors.

Embodiment 141. The method of Embodiment 140, wherein the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

Embodiment 142. The method of Embodiments 140 or 141, wherein the inflammatory disorder is inflammatory bowel disease.

Embodiment 143. The compound of any one of Embodiments 65-136, or a composition thereof, for use in medicine.

Embodiment 144. Use of a compound of any one of Embodiments 65-136, or a composition thereof, for inhibiting RIPK2 in a biological sample or in a patient.

Embodiment 145. Use of a compound of any one of Embodiments 65-136, or a composition thereof, for treating a disorder mediated by RIPK2.

Embodiment 146. The use of Embodiment 145, wherein the disorder mediated by RIPK2 is an inflammatory disorder, an autoimmune disorder, or a disorder associated with NOD2 receptors.

Embodiment 147. The use of Embodiment 146, wherein the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

Embodiment 148. Use of a compound of any one of Embodiments 65-136, or a composition thereof, in the manufacture of a medicament for inhibiting RIPK2.

Embodiment 149. Use of a compound of any one of Embodiments 65-136, or a composition thereof, in the manufacture of a medicament for treating a disorder mediated by RIPK2.

Embodiment 150. The use of Embodiment 149, wherein the disorder mediated by RIPK2 is an inflammatory disorder, an autoimmune disorder, or a disorder associated with NOD2 receptors.

Embodiment 151. The use of Embodiment 150, wherein the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

Embodiment 152. The compound of any one of Embodiments 65-101, 103-107, 109-116, 118-122, and 124-129, wherein p is 1, 2, or 3.

Embodiment 153. The compound of Embodiment 152, wherein p is 1.

Embodiment 154. The compound of Embodiment 152, wherein p is 2.

Embodiment 155. The compound of Embodiment 152, wherein p is 3.

Embodiment 156. The compound of Embodiment 129, wherein $R^2$ is $C_{1-6}$ aliphatic.

Embodiment 157. The compound of Embodiment 156, wherein $R^2$ is methyl or ethyl.

Embodiment 158. The compound of Embodiment 157, wherein $R^2$ is methyl.

Embodiment 159. The compound of Embodiment 1 or Embodiment 65, wherein $R^1$ is a 4- to 7-membered monocyclic saturated or partially unsaturated heterocyclic ring having 1 to 3 heteroatoms independently selected from nitrogen, oxygen, and sulfur, wherein $R^1$ is substituted with $(R^2)_p$.

Embodiment 160. The compound of Embodiment 159, wherein $R^1$ is

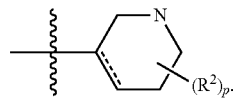

Embodiment 161. The compound of Embodiment 160, wherein $R^1$ is

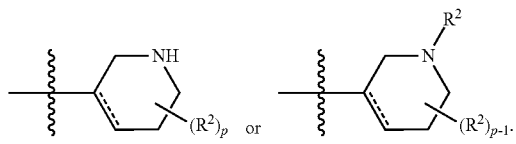

Embodiment 162. The compound of Embodiment 160, wherein $R^1$ is

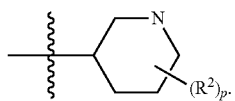

Embodiment 163. The compound of Embodiment 161 or Embodiment 162, wherein $R^1$ is

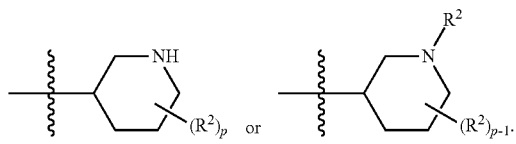

Embodiment 164. The compound of Embodiment 163, wherein $R^1$ is selected from

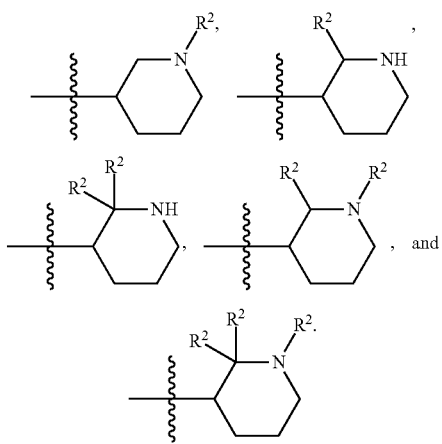

Embodiment 165. The compound of Embodiment 160, wherein $R^1$ is

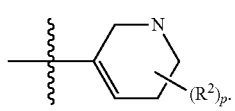

Embodiment 166. The compound of Embodiment 161 or Embodiment 165, wherein $R^1$ is

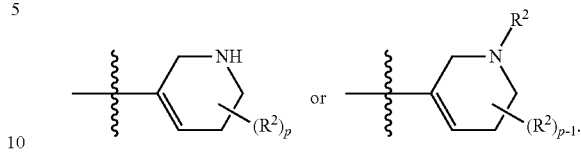

Embodiment 167. The compound of Embodiment 166, wherein $R^1$ is selected from

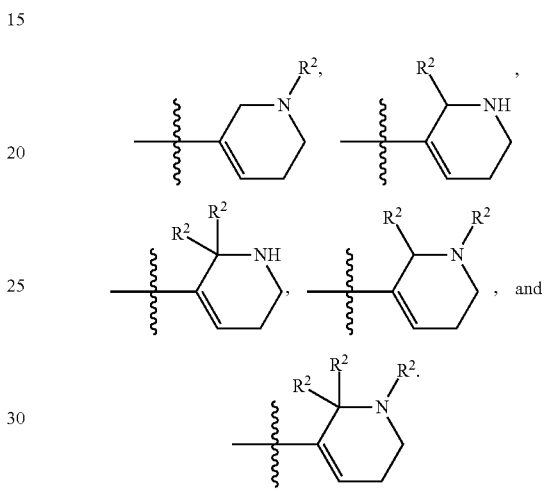

Embodiment 168. The compound of Embodiment 159, wherein $R^1$ is

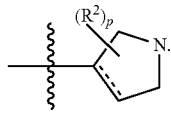

Embodiment 169. The compound of Embodiment 168, wherein $R^1$ is

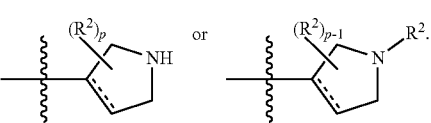

Embodiment 170. The compound of Embodiment 168, wherein $R^1$ is

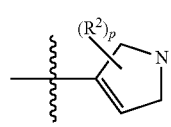

Embodiment 171. The compound of Embodiment 169 or Embodiment 170, wherein R¹ is

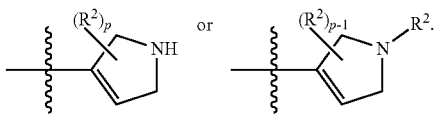

Embodiment 172. The compound of Embodiment 171, wherein R¹ is selected from

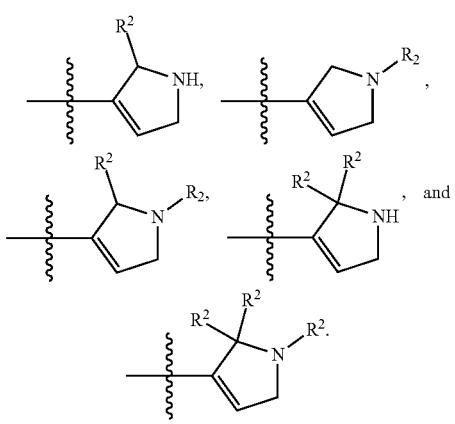

Embodiment 173. The compound of Embodiment 168, wherein R¹ is

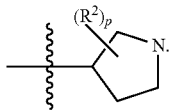

Embodiment 174. The compound of Embodiment 169 or Embodiment 173, wherein R¹ is

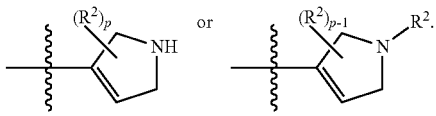

Embodiment 175. The compound of Embodiment 174, wherein R¹ is selected from

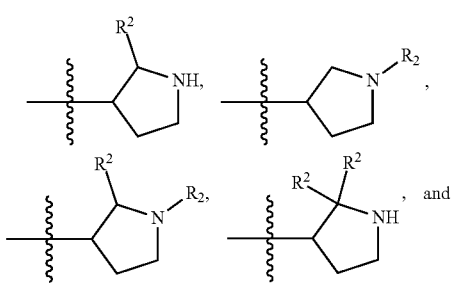

-continued

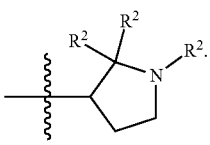

Embodiment 176. The compound of Embodiment 159, wherein R¹ is

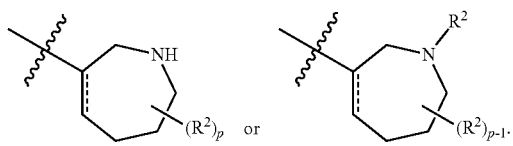

Embodiment 177. The compound of Embodiment 176, wherein R¹ is

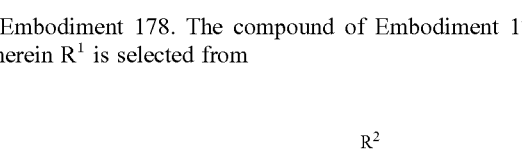

Embodiment 178. The compound of Embodiment 177, wherein R¹ is selected from

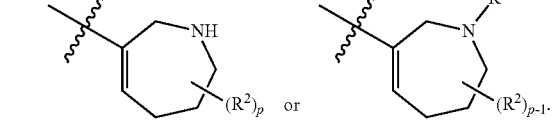

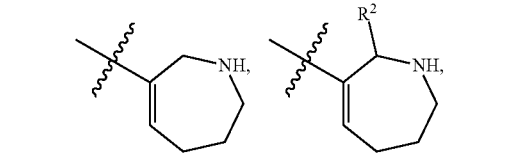

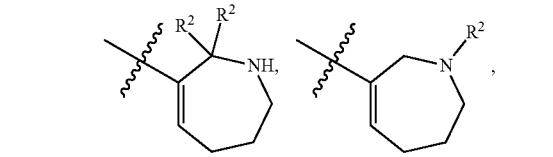

Embodiment 179. The compound of Embodiment 176, wherein R¹ is

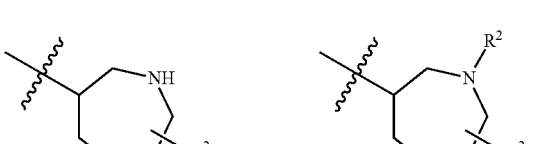

Embodiment 180. The compound of Embodiment 179, wherein R¹ is selected from

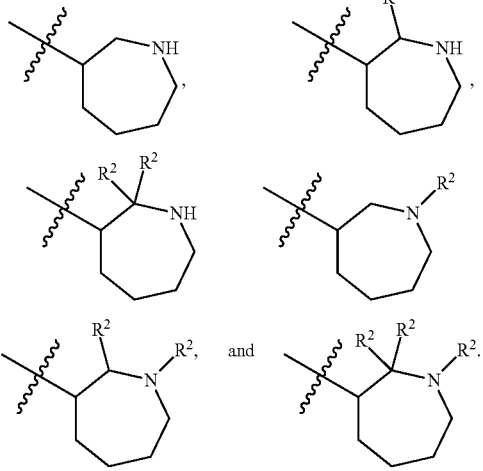

Embodiment 181. The compound of Embodiment 159, wherein R¹ is

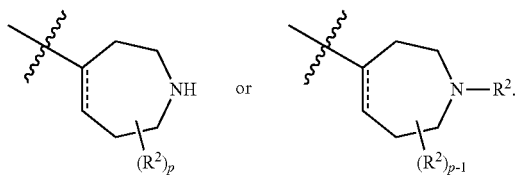

Embodiment 182. The compound of Embodiment 181, wherein R¹ is

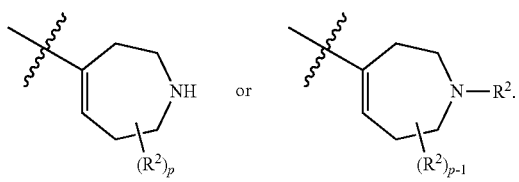

Embodiment 183. The compound of Embodiment 182, wherein R¹ is selected from

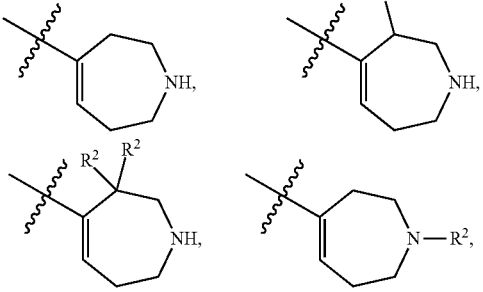

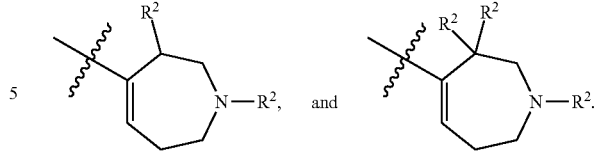

Embodiment 184. The compound of Embodiment 181, wherein R¹ is

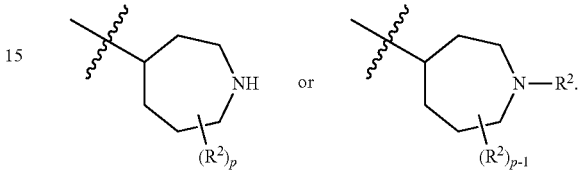

Embodiment 185. The compound of Embodiment 184, wherein R¹ is selected from

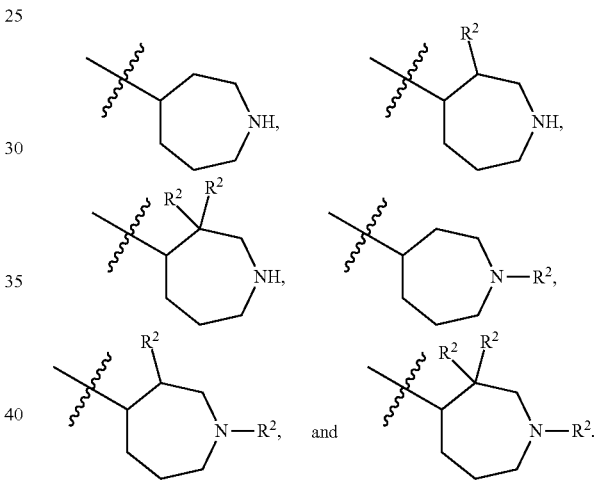

Embodiment 186. The compound of any one of Embodiments 159-185, wherein R² is optionally substituted $C_{1-6}$ aliphatic.

Embodiment 187. The compound of Embodiment 159, wherein R¹ is

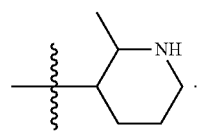

Embodiment 188. The compound of Embodiment 187, wherein R¹ is

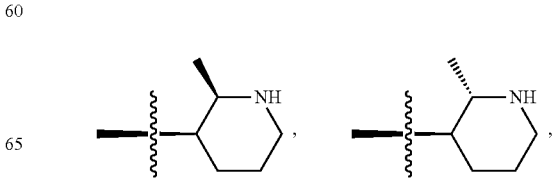

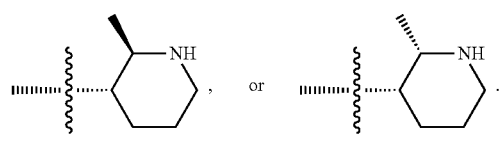
Embodiment 189. The compound of Embodiment 159, wherein R¹ is selected from
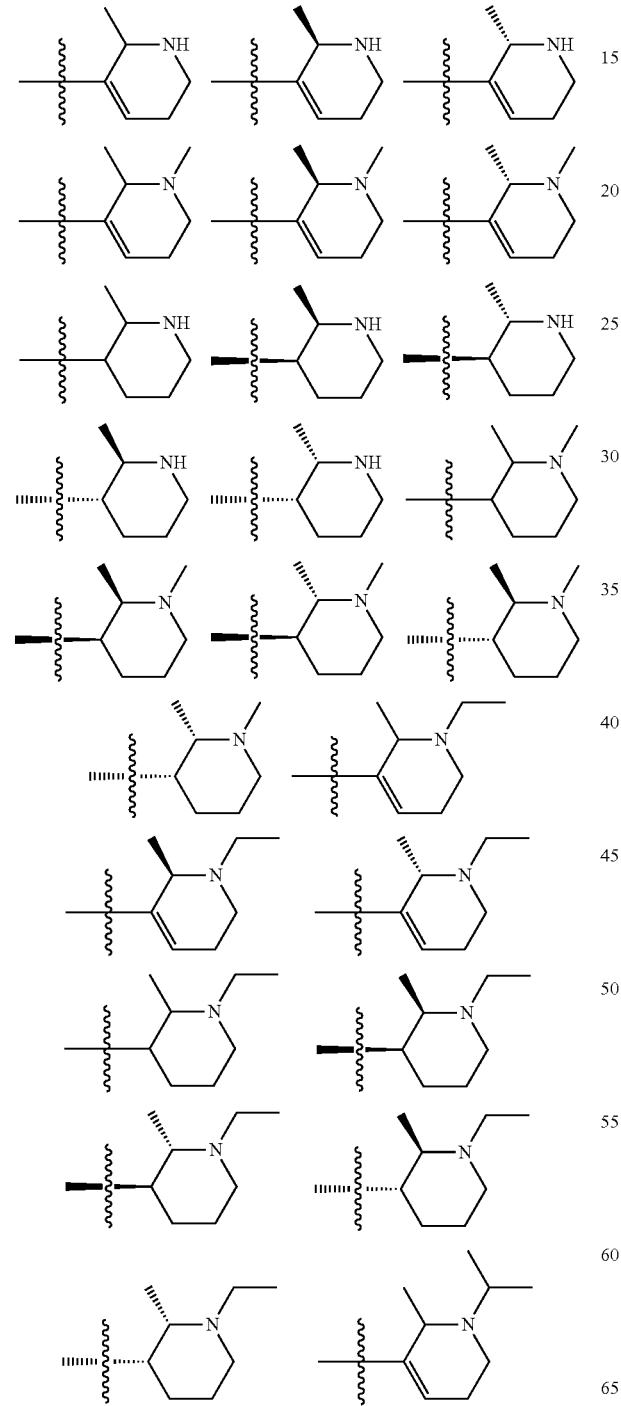
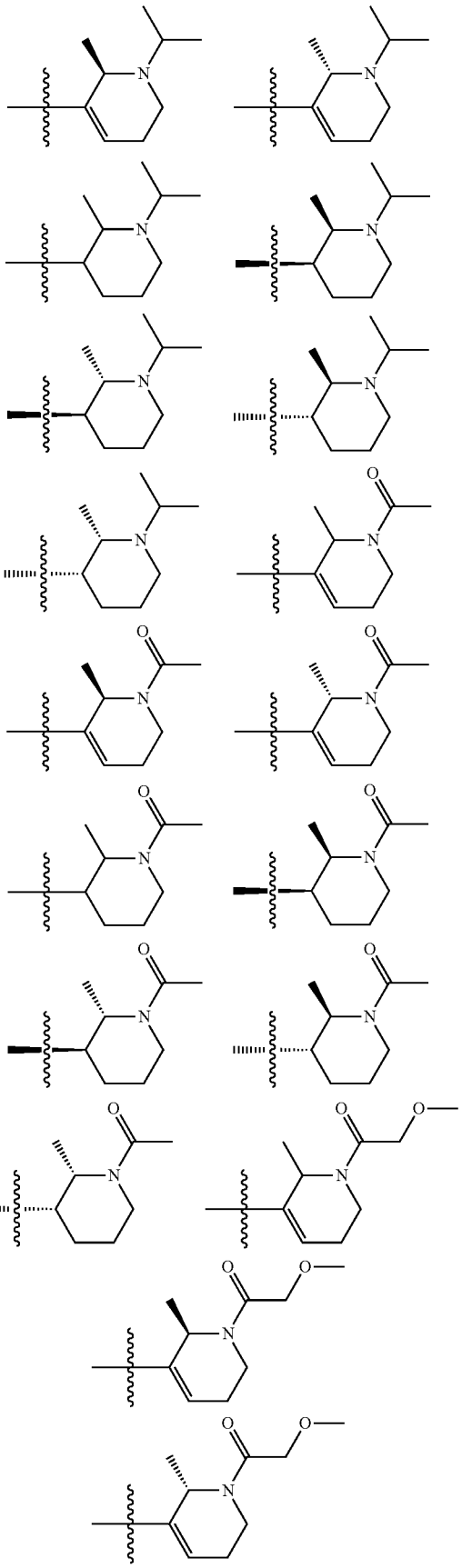

301
-continued
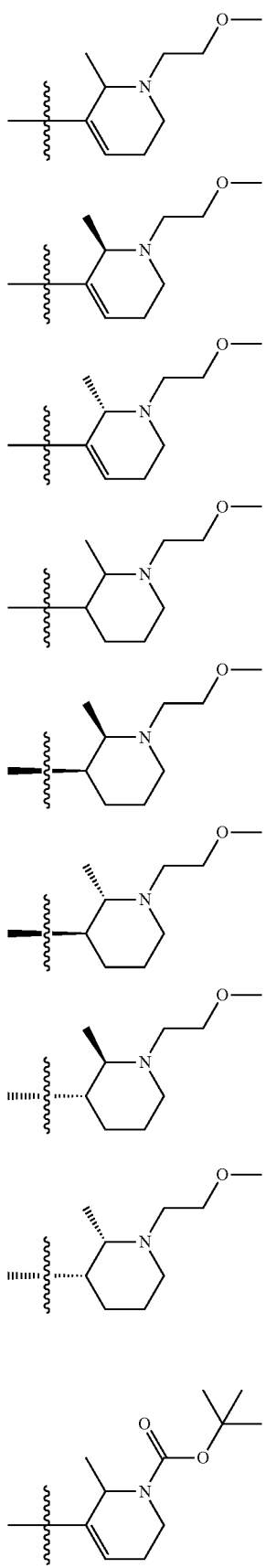
302
-continued
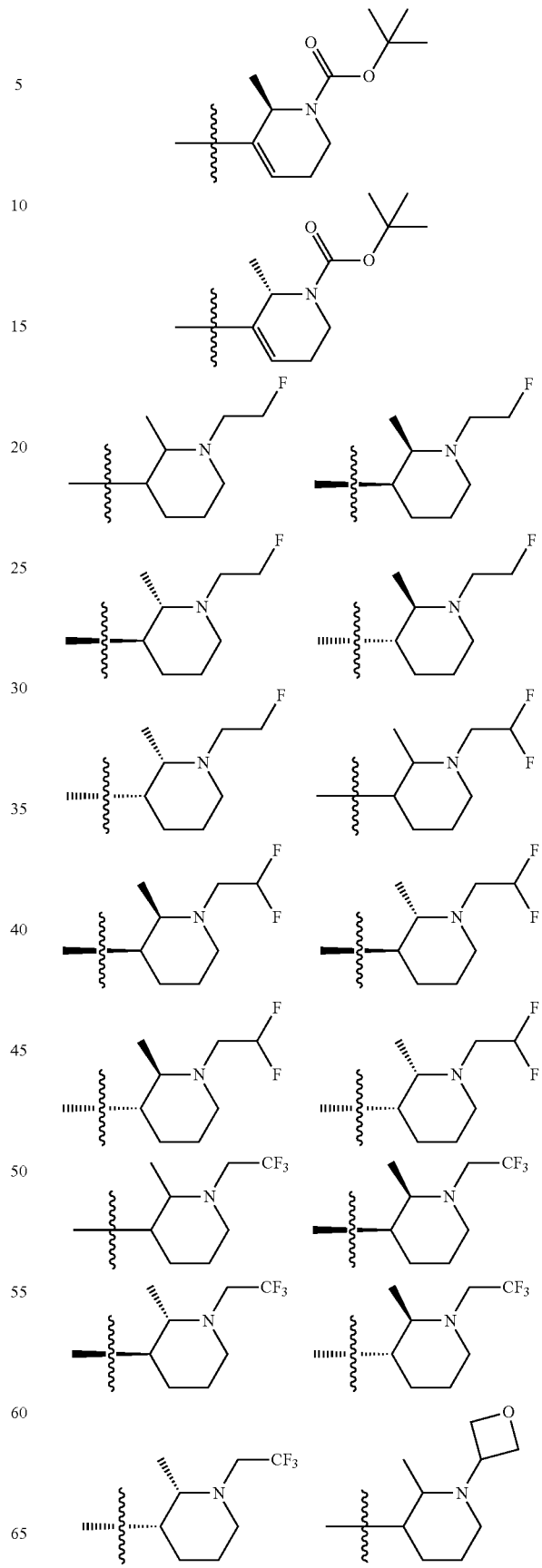

303
-continued
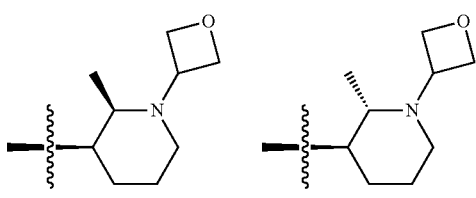
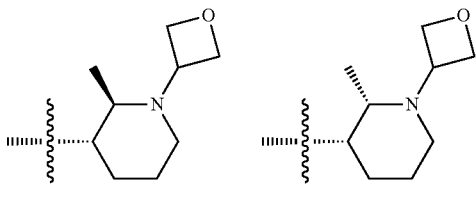
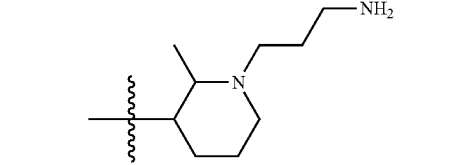
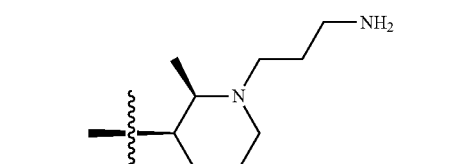
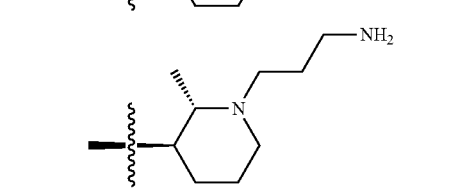
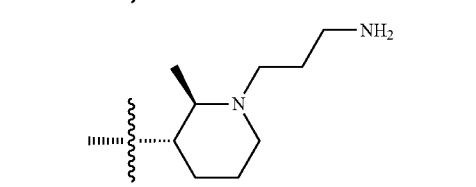
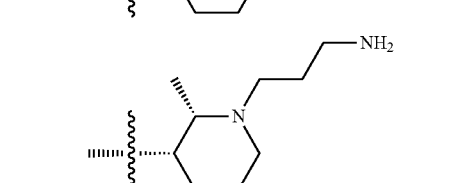
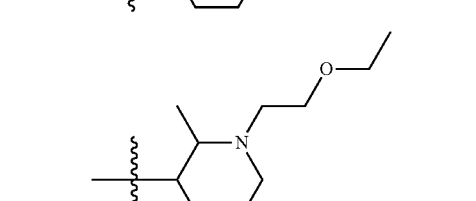
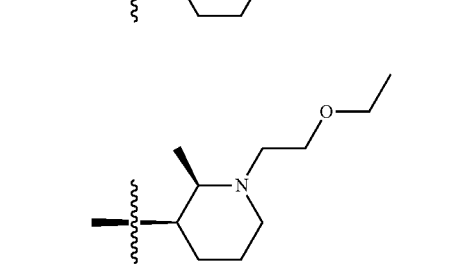
304
-continued
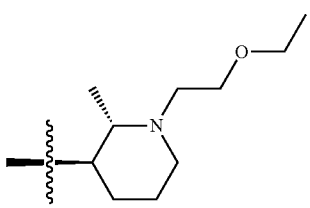
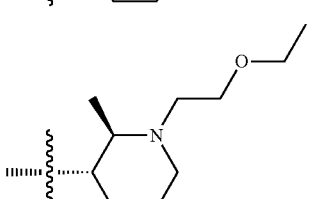
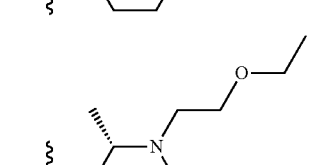
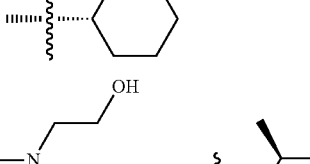
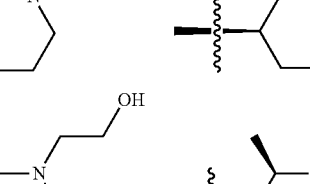
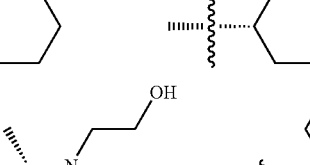
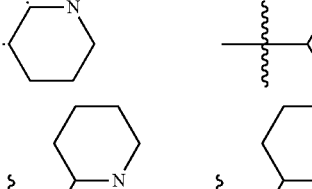
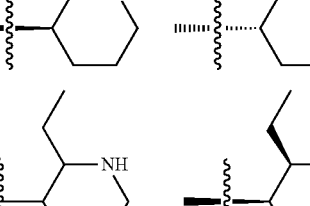
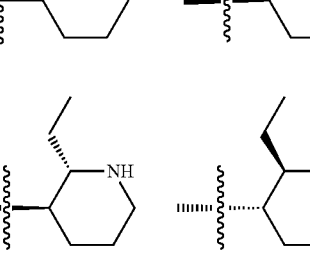

305
-continued
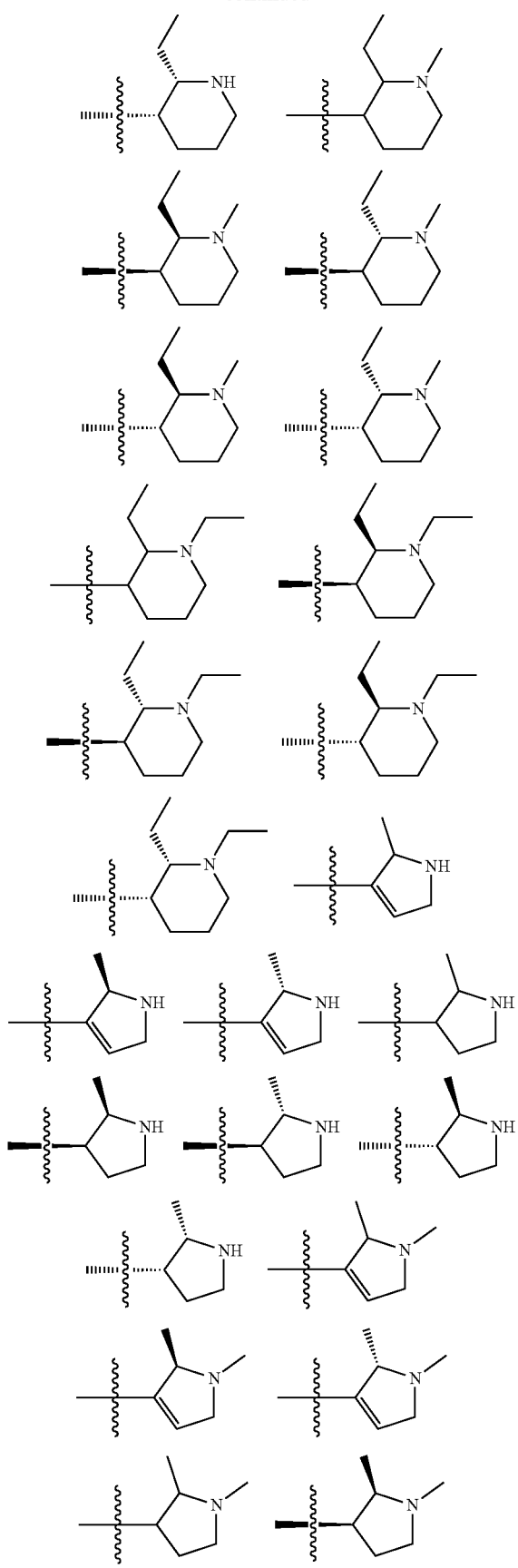
306
-continued
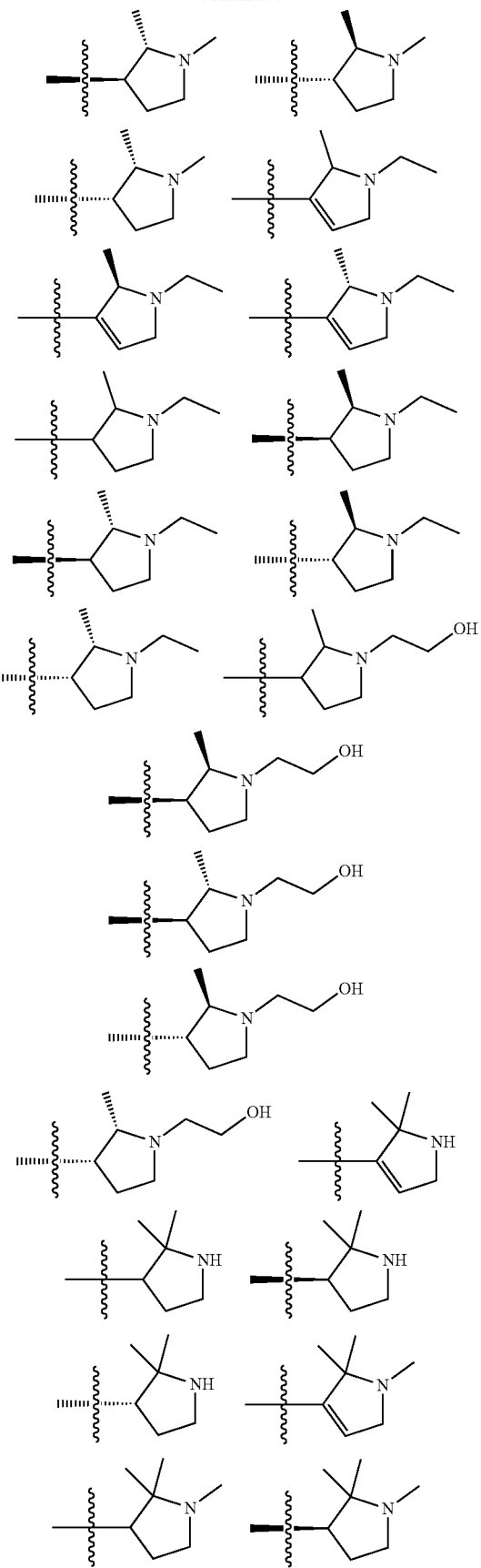

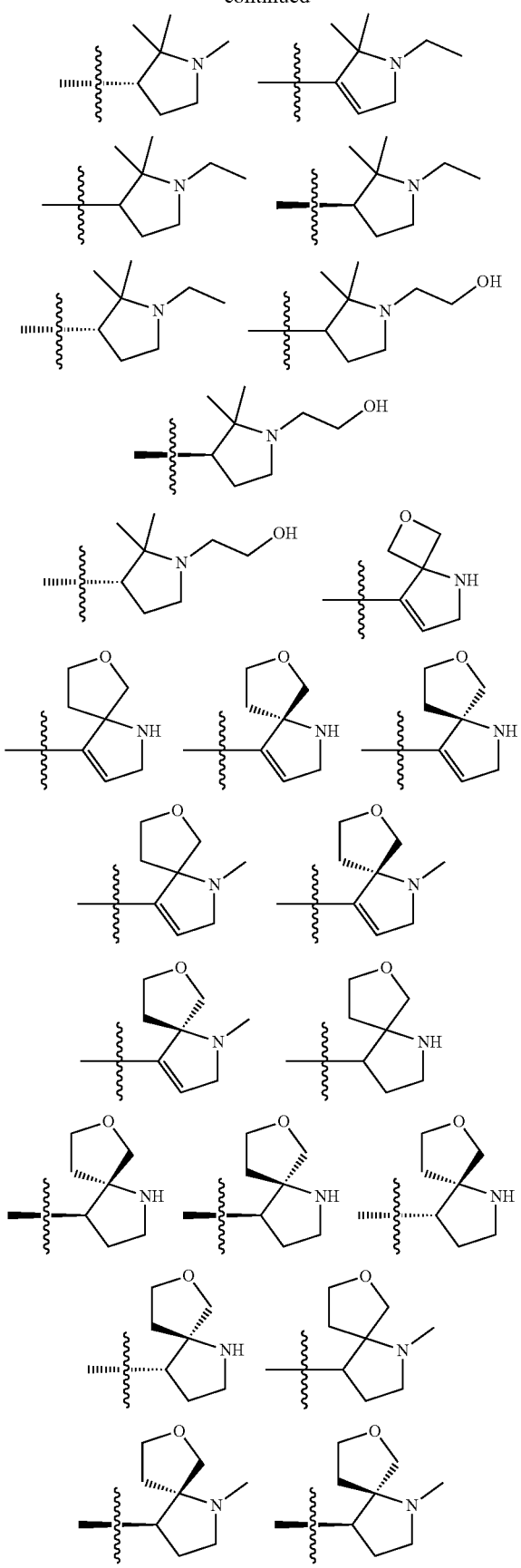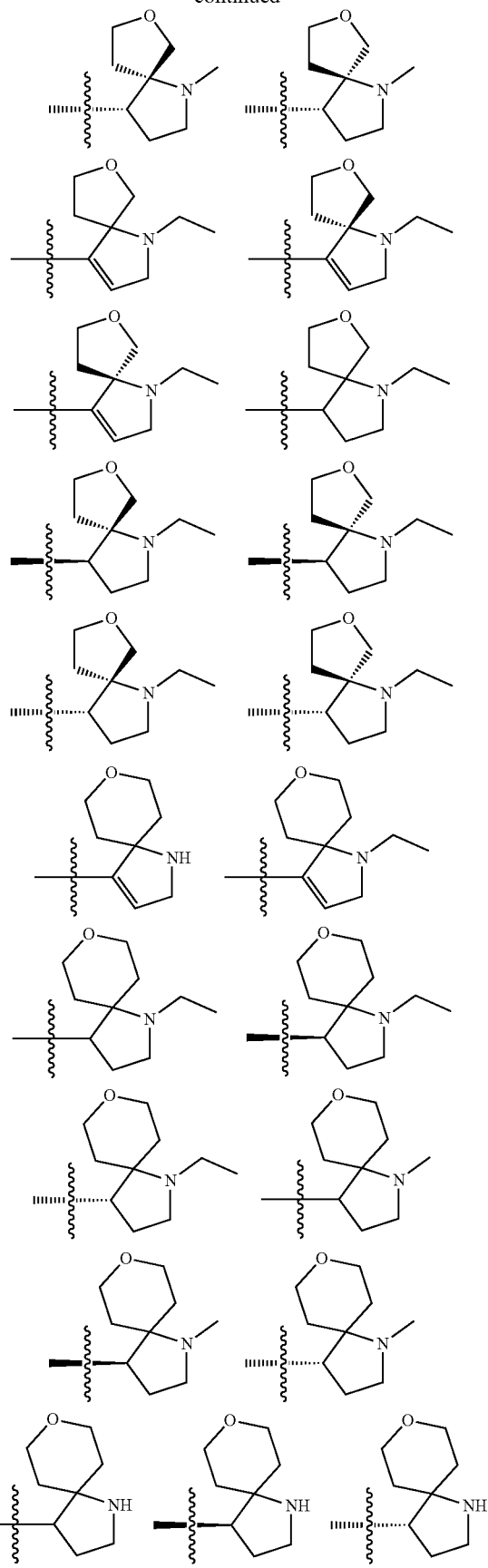

309
-continued
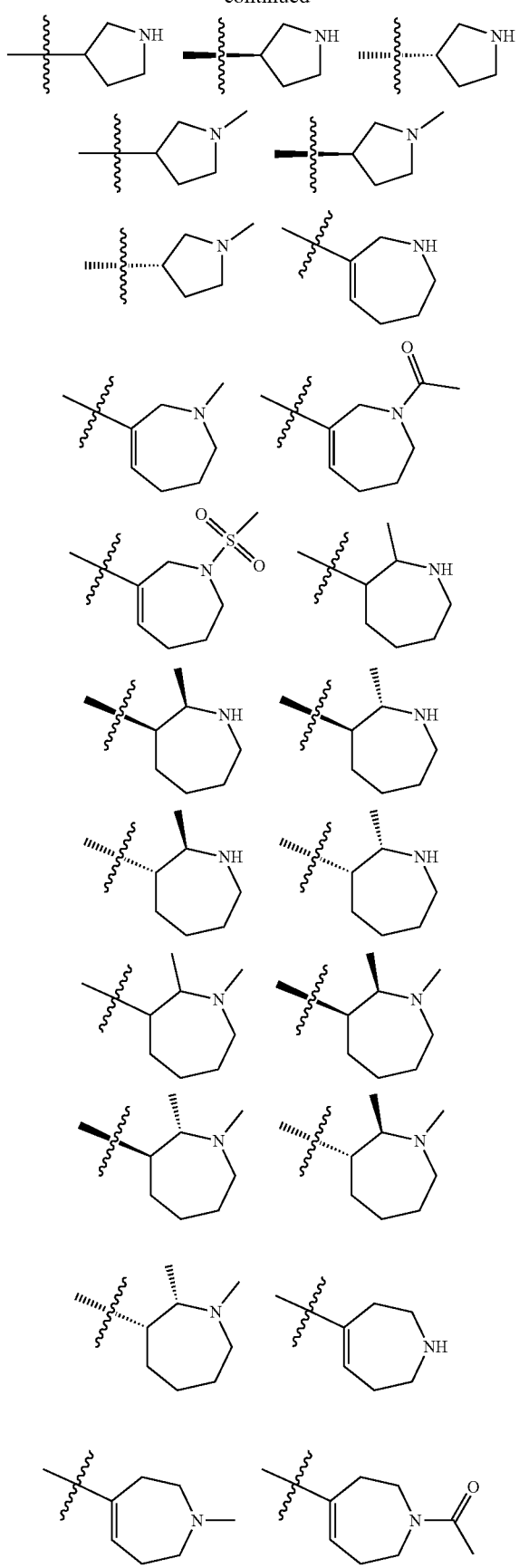
310
-continued
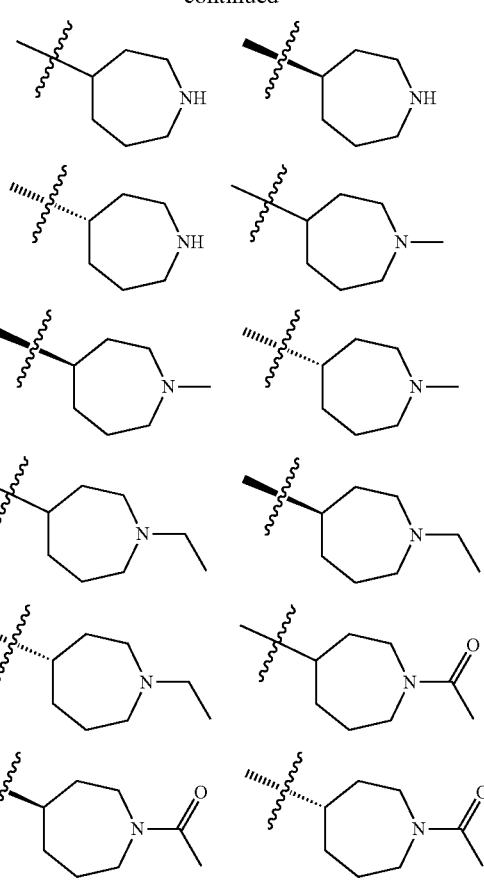
Embodiment 190. The compound of any one of Embodiments 159-189, wherein the compound is of Formula II or II':
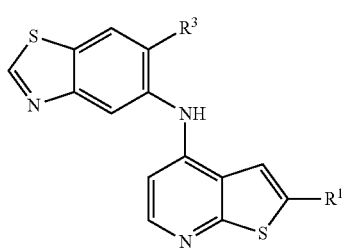
II
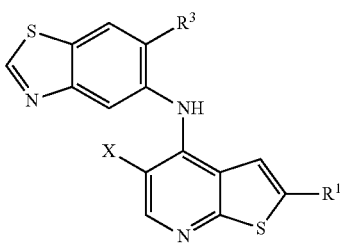
II'
or a pharmaceutically acceptable salt thereof.

Embodiment 191. The compound of any one of Embodiments 159-189, wherein the compound is of Formula III or III':

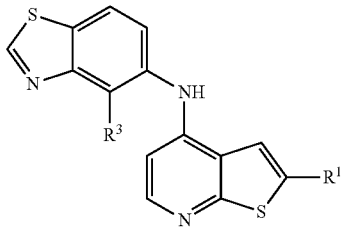

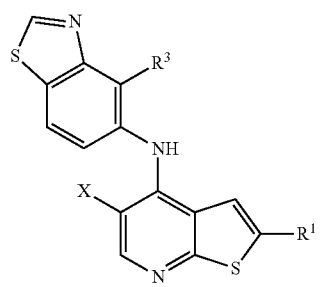

or a pharmaceutically acceptable salt thereof.

Embodiment 192. The compound of any one of Embodiments 159-189, wherein the compound is of Formula IV or IV':

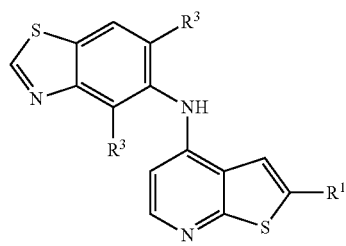

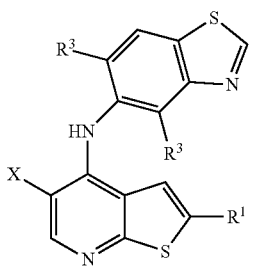

or a pharmaceutically acceptable salt thereof.

Embodiment 193. A composition comprising a compound of any one of Embodiments 159-192 and a pharmaceutically acceptable carrier or excipient.

Embodiment 194. A method of inhibiting RIPK2 in a biological sample or in a patient, comprising contacting the biological sample or administering to the patient a therapeutically effective amount of any one of Embodiments 159-192, or a composition thereof.

Embodiment 195. A method of treating a disorder mediated by RIPK2 in a patient, comprising administering to the patient a therapeutically effective amount of any one of Embodiments 159-192, or a composition thereof.

Embodiment 196. The method of Embodiment 195, wherein the disorder mediated by RIPK2 is an inflammatory disorder, an autoimmune disorder, or a disorder associated with NOD2 receptors.

Embodiment 197. The method of Embodiment 196, wherein the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

Embodiment 198. The method of Embodiments 196 or 197, wherein the inflammatory disorder is inflammatory bowel disease.

Embodiment 199. The compound of any one of Embodiments 159-192, or a composition thereof, for use in medicine.

Embodiment 200. Use of a compound of any one of Embodiments 159-192, or a composition thereof, for inhibiting RIPK2 in a biological sample or in a patient.

Embodiment 201. Use of a compound of any one of Embodiments 159-192, or a composition thereof, for treating a disorder mediated by RIPK2.

Embodiment 202. The use of Embodiment 201, wherein the disorder mediated by RIPK2 is an inflammatory disorder, an autoimmune disorder, or a disorder associated with NOD2 receptors.

Embodiment 203. The use of Embodiment 202, wherein the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

Embodiment 204. Use of a compound of any one of Embodiments 159-192, or a composition thereof, in the manufacture of a medicament for inhibiting RIPK2.

Embodiment 205. Use of a compound of any one of Embodiments 159-192, or a composition thereof, in the manufacture of a medicament for treating a disorder mediated by RIPK2.

Embodiment 206. The use of Embodiment 205, wherein the disorder mediated by RIPK2 is an inflammatory disorder, an autoimmune disorder, or a disorder associated with NOD2 receptors.

Embodiment 207. The use of Embodiment 206, wherein the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

Embodiment 208. The compound of any one of Embodiments 159-192, wherein p is 1, 2, or 3.

Embodiment 209. The compound of Embodiment 208, wherein p is 1.

Embodiment 210. The compound of Embodiment 208, wherein p is 2.

Embodiment 211. The compound of Embodiment 208, wherein p is 3.

Embodiment 212. The compound of Embodiment 186, wherein $R^2$ is $C_{1-6}$ aliphatic.

Embodiment 213. The compound of Embodiment 212, wherein $R^2$ is methyl or ethyl.

Embodiment 214. The compound of Embodiment 213, wherein $R^2$ is methyl.

EXEMPLIFICATION

The present teachings include descriptions provided in the Examples that are not intended to limit the scope of any claim. Unless specifically presented in the past tense, inclusion in the Examples is not intended to imply that the experiments were actually performed. The following non-limiting examples are provided to further illustrate the present teachings. Those of skill in the art, in light of the present application, will appreciate that many changes can be made in the specific embodiments that are provided herein and still obtain a like or similar result without departing from the spirit and scope of the present teachings.

| Table of Abbreviations | |
|---|---|
| Abbreviation | Definition |
| "ACN" or "MeCN" | Acetonitrile |
| "atm" | Atmospheres |
| "BINAP" | 2,2'-bis(diphenylphosphino)-1,1'-binaphthyl |
| "Boc" | tert-butyloxycarbonyl |
| "Bpin" | Bis(pinacolato)diboron |
| "BzCl" | Benzyl chloride |
| "Cbz" | Carboxybenzyl |
| "Comins' reagent" | N,N-bis(trifluoromethylsulfonyl)-5-chloro-2-pyridylamine |
| "dba" | dibenzylideneacetone |
| "DCM" | dichloromethane |
| "DEA" | Diethanolamine |
| "DIEA" | Diisopropylethylamine |
| "DMF" | Dimethylformamide |
| "dppf" | 1,1'-Bis(diphenylphosphino)ferrocene |
| "EA" or "EtOAc" | Ethyl Acetate |
| "ESI" | Electrospray ionization |
| "EtOH" | Ethanol |
| "G3-Brettphos Pd" | [(2-di-cyclohexylphosphino-3,6-dimethoxy-2',4',6'-triisopropyl-1,1'-biphenyl)-2-(2'-amino-1,1'-biphenyl)] palladium(II) methanesulfonate methanesulfonate |
| "h" | Hour or hours |
| "HATU" | 1-[bis(dimethylamino)methylene]-1H-1,2,3-triazolo[4,5-b]pyridinium 3-oxid hexafluorophosphate |
| "Het" | Heteroaryl |
| "HMDS" | Bis(trimethylsilyl)amide |
| "HPLC" | High pressure liquid chromatography |
| "Hz" | Hertz |
| "i-PrOH" | iso-propanol |
| "LCMS" | Liquid chromatography mass spectometry |
| "LDA" | Lithium diisopropylamide |
| "MeOH" | Methanol |
| "NMR" | Nuclear magnetic resonance |
| "OBD" | Optimum bed density |
| "PE" | Petroleum ether |
| "p-TSA" | p-toluenesolfuonic acid |
| "Py" | Pyridine |
| "Rockphos" | 2-di(tert-butyl)phosphino-2',4',6'-triisopropyl-3-methoxy-6-methylbiphenyl |
| "rt" | Room temperature |
| "SFC" | Supercritical fluid chromatography |
| "t-BuBrettphos" | 2-(di-tert-butylphosphino)-2',4',6'-triisopropyl-3,6-dimethoxy-1,1'-biphenyl |
| "TEA" | Triethylamine |
| "Tf" | Triflate (trifluoromethanesulfonate) |
| "TFA" | Trifluoroacetic acid |
| "THF" | Tetrahydrofuran |
| "THP" | Tetrahydropyran |
| "TLC" | Thin layer chromatography |
| "TMS" | Trimethysilyl |

SYNTHETIC EXAMPLES

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Synthesis of 4-chloro-2-iodothieno[2,3-b]pyridine

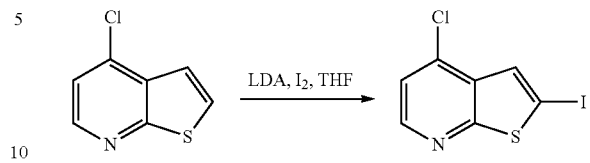

4-Chlorothieno[2,3-b]pyridine (290 mg, 1.710 mmol, 1.00 equiv) was dissolved in THF (8 mL) and lithium diisopropylamide (1.3 mL, 2.560 mmol, 1.50 equiv) was added dropwise at −78° C. under $N_2$ atmosphere. The resulting solution was stirred at −78° C. for 30 min, followed by the addition of diiodine (456 mg, 1.800 mmol, 1.05 equiv) in 5 ml THF at −78° C. The reaction temperature was allowed to warm to rt and stirred for 30 min. The reaction solution was quenched with $NH_4Cl$ (aq) (20 ml) and extracted with EA (4×50 ml). The combined organic phase was dried over $Na_2SO_4$, filtered and concentrated to give 4-chloro-2-iodo-thieno[2,3-b]pyridine (470 mg, 93%) as a yellow solid. LCMS (ESI, m/z): 296 [M+H]$^+$.

Example 1: Synthesis of N-(2-(2-methyl-1,2,5,6-tetrahydropyridin-3-yl)thieno[2,3-b]pyridin-4-yl)benzo[d]thiazol-5-amine

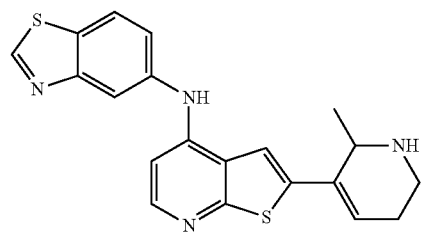 [SMILES: CC1NCCC=C1c1cc2c(Nc3ccc4scnc4c3)ccnc2s1]

Step 1

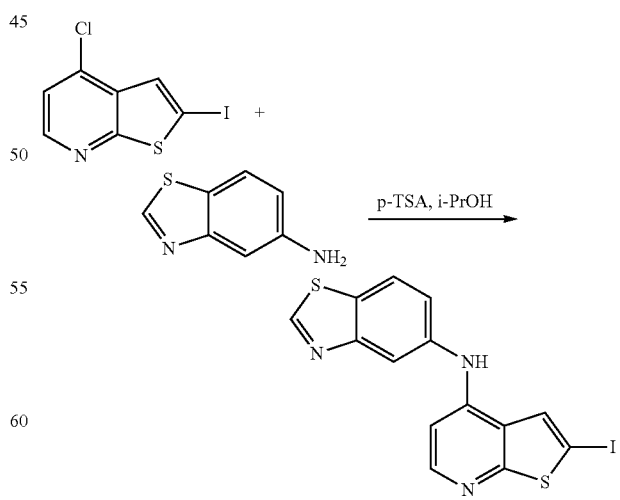

4-chloro-2-iodo-thieno[2,3-b]pyridine (250 mg, 0.850 mmol, 1.00 equiv) and 1,3-benzothiazol-5-amine (127 mg, 0.850 mmol, 1.00 equiv) and catalytic p-toluenesulfonic acid were dissolved in iso-propanol (10 mL). The resulting solution was refluxed overnight. The reaction mixture was filtered and the cake was dried to provide N-(2-iodothieno[2,3-b]pyridin-4-yl)benzo[d]thiazol-5-amine (250 mg, 72%) as a grey solid. LCMS (ESI, m/z): 410 [M+H]+.

Step 2

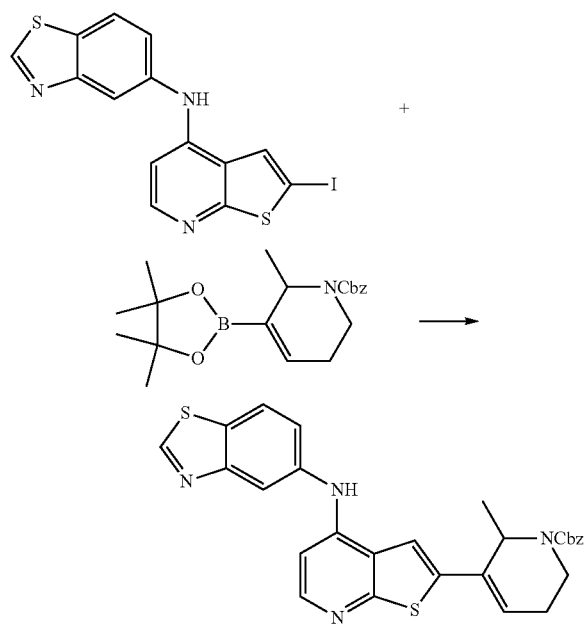

To a solution of N-(1,3-benzothiazol-5-yl)-2-iodo-thieno[2,3-b]pyridin-4-amine (500 mg, 1.22 mmol, 1.00 equiv) in 1,4-dioxane/H$_2$O (10 mL/2 ml), was added benzyl 6-methyl-5-(4,4,5,5-tetramethyl-1,3,2-dioxa-borolan-2-yl)-3,6-dihydro-2H-pyridine-1-carboxylate (436.45 mg, 1.22 mmol, 1.00 equiv), Pd(dppf)Cl$_2$ (26.82 mg, 0.037 mmol, 0.03 equiv) and Cs$_2$CO$_3$ (1.19 g, 3.66 mmol, 3.00 equiv). The mixture was stirred under nitrogen at 90° C. for 2 h. TLC showed complete consumption of starting material. The reaction mixture was diluted with EA and washed with water, the organic layer was dried over sodium sulphate and concentrated. The product was purified by silica gel flash chromatography (PE:EA=1:1) and benzyl 5-(4-(benzo[d]thiazol-5-ylamino)thieno[2,3-b]pyridin-2-yl)-6-methyl-3,6-dihydropyridine-1(2H)-carboxylate was obtained as yellow solid (Example 1, 400 mg, 0.78 mmol, 64% yield). LCMS (ESI, m/z): 513 [M+H]+.

Step 3

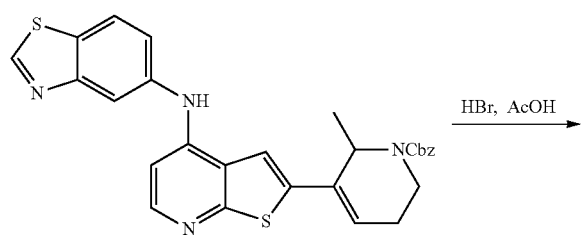

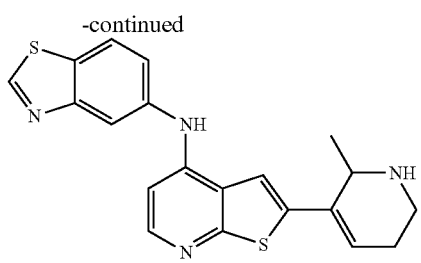

Benzyl 5-(4-(benzo[d]thiazol-5-ylamino)thieno[2,3-b]pyridin-2-yl)-6-methyl-3,6-dihydropyridine-1(2H)-carboxylate (500 mg, 1.22 mmol, 1.00 equiv) was dissolved by HBr (40% in AcOH). The reaction mixture was stirred at room temperature overnight. TLC showed the reaction was completed. The reaction mixture was concentrated to give the desired product N-(2-(2-methyl-1,2,5,6-tetrahydropyridin-3-yl)thieno[2,3-b]pyridin-4-yl)benzo[d]thiazol-5-amine (510 mg, crude). LCMS (ESI, m/z): 379 [M+H]+.

Example 2: Synthesis of N-(2-(1,2-dimethyl-1,2,5,6-tetrahydropyridin-3-yl)thieno[2,3-b]pyridin-4-yl)benzo-[d]thiazol-5-amine

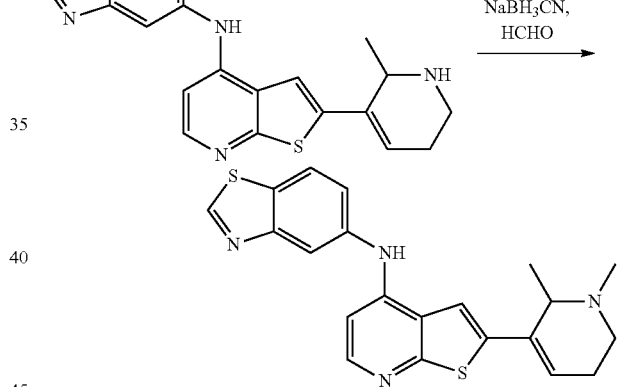

To a stirred solution of N-(2-(2-methyl-1,2,5,6-tetrahydropyridin-3-yl)thieno[2,3-b]pyridin-4-yl)benzo[d]thiazol-5-amine (Example 1, 200 mg, 0.530 mmol, 1.00 equiv) was added formaldehyde (0.3 mL, 10.890 mmol, 20.55 equiv) in methanol (5 mL). After 30 min, NaBH$_3$CN (40 mg, 0.630 mmol, 1.19 equiv) was added. The resulting solution was stirred at room temperature for 18 h. TLC showed the reaction was completed. The reaction mixture was diluted with DCM and washed with water. The organic layer was dried over Na$_2$SO$_4$, filtered and concentrated. The residue was purified by preparative HPLC to obtain N-(2-(1,2-dimethyl-1,2,5,6-tetrahydropyridin-3-yl)thieno[2,3-b]pyridin-4-yl)benzo[d]thiazol-5-amine (Example 2, 101.8 mg, 49%) as a yellow solid. $^1$H NMR (300 MHz, Methanol-d$_4$) δ 9.28 (s, 1H), 8.10-8.07 (m, 2H), 8.01 (d, 1H, J=1.8 Hz), 7.55-7.45 (m, 2H), 6.99 (d, J=5.7 Hz, 1H), 6.27 (t, J=4.1 Hz, 1H), 3.80-3.78 (m, 1H), 3.10-3.00 (m, 1H), 2.75-2.65 (m, 1H), 2.30 (s, 3H), 2.15-2.05 (m, 2H), 1.36 (d, J=6.6 Hz, 3H). LCMS (ESI, m/z): 393 [M+H]+. Separation conditions: Column: XBridge C18 OBD Prep Column 100 Å, 10 μm, 19 mm×250 mm; Mobile Phase A: Water (10 mmoL/L

Example 3: Synthesis of N-(2-(2-methylpiperidin-3-yl)thieno[2,3-b]pyridin-4-yl)benzo[d]thiazol-5-amine

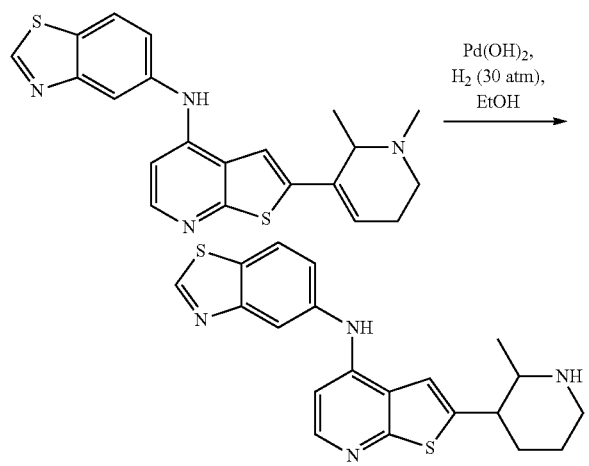

To a solution of N-(2-(2-methyl-1,2,5,6-tetrahydropyridin-3-yl)thieno[2,3-b]pyridin-4-yl)benzo[d]thiazol-5-amine (Example 1, 110 mg, 0.290 mmol, 1.00 equiv) in ethanol (10 mL) was added dry Pd(OH)$_2$/C (110 mg, 1.00 w/w). The resulting mixture was stirred at 65° C. overnight under an atmosphere of hydrogen (30 atm). LCMS showed the reaction was complete. The solid was filtered out. The filtrate was concentrated under reduced pressure and the residue was purified by preparative HPLC (Column: XBridge Shield RP18 OBD Column, 19×250 mm, 10 μm; Mobile Phase A: Water (10 mmol/L NH$_4$HCO$_3$), Mobile Phase B: ACN; Flow rate: 25 mL/min; Gradient: 35% B to 40% B in 15 min; 254/210 nm; Rt: 9.00; 14.10 min) to give the product N-(2-(2-methylpiperidin-3-yl)thieno[2,3-b]pyridin-4-yl)benzo[d]thiazol-5-amine (21.1 mg, 19%) as an off-white solid. $^1$H NMR (400 MHz, Methanol-d$_4$) δ 9.30 (s, 1H), 8.12-8.06 (m, 2H), 8.03 (s, 1H), 7.54 (dd, J=8.7, 2.1 Hz, 1H), 7.42 (d, J=10.7 Hz, 1H), 7.01 (d, J=5.8 Hz, 1H), 3.43-3.35 (m, 1H), 3.17-3.02 (m, 1H), 2.86-2.67 (m, 2H), 2.10-1.91 (m, 2H), 1.87-1.61 (m, 2H), 1.07 (d, J=6.7 Hz, 3H). LCMS (ESI, m/z): 381 [M+H]+.

Example 4: Synthesis of N-(2-(1,2-dimethylpiperidin-3-yl)thieno[2,3-b]pyridin-4-yl)benzo[d]thiazol-5-amine

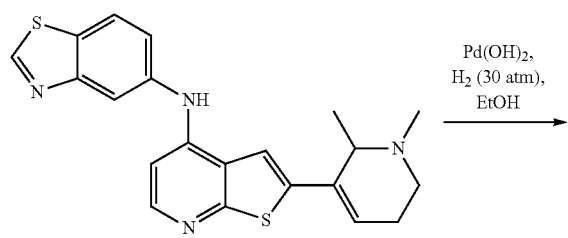

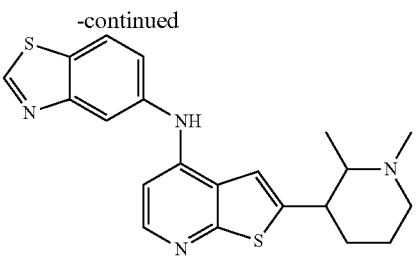

To a solution of N-(2-(1,2-dimethyl-1,2,5,6-tetrahydropyridin-3-yl)thieno[2,3-b]pyridin-4-yl)-benzo[d]thiazol-5-amine (Example 2, 200 mg, 0.510 mmol, 1.00 equiv) in ethanol (10 mL) was added dry Pd(OH)$_2$/C (200 mg, 1.00 w/w). The resulting mixture was stirred at 65° C. overnight under an atmosphere of hydrogen (30 atm.). LCMS showed the reaction was complete. The solid was filtered out. The filtrate was concentrated under reduced pressure and the residue was purified by preparative HPLC (Column: XBridge Shield RP18 OBD Column, 19×250 mm, 10 μm; Mobile Phase A: Water (10 mmol/L NH$_4$HCO$_3$), Mobile Phase B: ACN; Flow rate: 25 mL/min; Gradient: 45% B to 63% B in 8 min; 254/210 nm; Rt: 7 min) to give the desired product N-(2-(1,2-dimethylpiperidin-3-yl)thieno[2,3-b]pyridin-4-yl)benzo[d]thiazol-5-amine (Example 4, 120.7 mg, 60%) as a light-yellow solid. $^1$H NMR (400 MHz, Methanol-d$_4$) δ 9.38 (s, 1H), 8.27-8.25 (m, 2H), 8.14 (s, 1H), 7.78 (s, 1H), 7.58 (d, J=8.8 Hz, 1H), 7.03 (d, J=7.2 Hz, 1H), 4.15-4.00 (m, 1H), 3.85-3.70 (m, 1H), 3.58-3.20 (m, 2H), 2.95 (s, 3H), 2.30-1.95 (m, 4H), 1.28 (d, J=7.0 Hz, 3H). LCMS (ESI, m/z): 395 [M+H]+.

Chiral SFC separation: Column Lux Cellulose-4, 4.6×150 mm, 5 μm, co-solvent: EtOH (0.1% DEA), gradient (B %) 10-50 in 4.0 min, hold 2.0 min at 50% B, back pressure 1500.000 psi, 4 mL/min, 35° C., Rt=4.136 (Example 4a), 4.296 (Example 4b), 4.703 (Example 4c), and 5.218 (Example 4d).

Example 5: Synthesis of N-(2-(1-ethyl-2-methyl-1,2,5,6-tetrahydropyridin-3-yl)thieno[2,3-b]pyridin-4-yl)benzo-[d]thiazol-5-amine

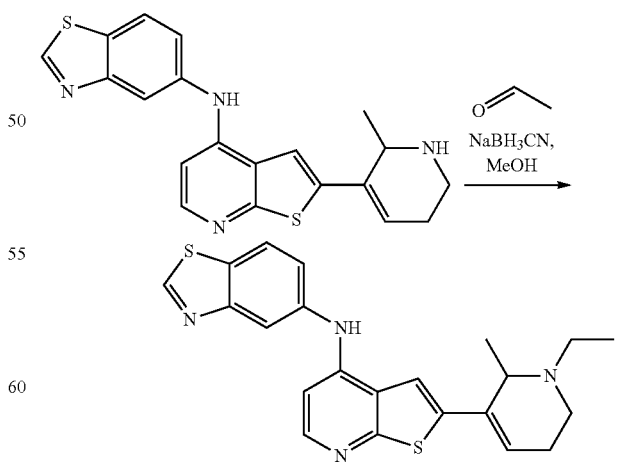

To a solution of N-(2-(2-methyl-1,2,5,6-tetrahydropyridin-3-yl)thieno[2,3-b]pyridin-4-yl)benzo-[d]thiazol-5-amine (Example 1, 80 mg, 0.210 mmol, 1.00 equiv) in methanol (5 mL) was added acetaldehyde (70 mg, 0.630 mmol, 3.00 equiv). 30 min later, NaBH₃CN (40 mg, 0.630 mmol, 3.00 equiv) was added and the reaction mixture was stirred overnight at room temperature. LCMS showed the reaction was complete. The reaction mixture was concentrated under reduced pressure and the residue was purified by flash chromatography on silica gel with EA/PE=1/1 to give the desired product N-(2-(1-ethyl-2-methyl-1,2,5,6-tetrahydropyridin-3-yl)thieno[2,3-b]pyridin-4-yl)benzo[d]thiazol-5-amine (20.4 mg, 19%) as a light-yellow solid. ¹H NMR (400 MHz, Methanol-d₄) δ 9.40 (s, 1H), 8.35-8.20 (m, 2H), 8.15 (d, J=2.4 Hz, 1H), 7.90 (s, 1H), 7.61 (d, J=8.7 Hz, 1H), 7.08 (d, J=6.8 Hz, 1H), 6.60-6.50 (m, 1H), 4.70-4.50 (m, 1H), 3.90-3.35 (m, 4H), 2.95-2.60 (m, 2H), 1.90-1.60 (t, 3H), 1.49 (d, J=7.3 Hz, 3H). LCMS (ESI, m/z): 407 [M+H]⁺.

Example 6: Synthesis of N-(2-(1-ethyl-2-methylpiperidin-3-yl)thieno[2,3-b]pyridin-4-yl)benzo[d]thiazol-5-amine

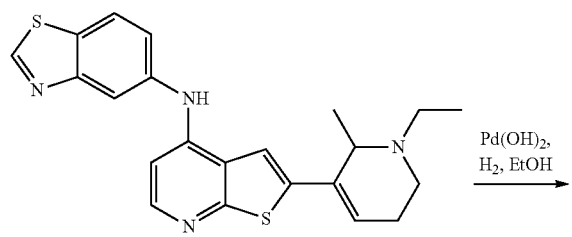

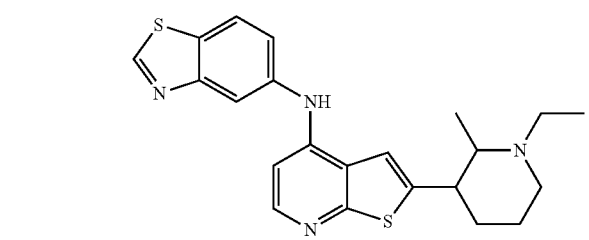

To a solution of N-(2-(1-ethyl-2-methyl-1,2,5,6-tetrahydropyridin-3-yl)thieno[2,3-b]pyridin-4-yl)benzo[d]thiazol-5-amine (Example 5, 60 mg, 0.150 mmol, 1.00 equiv) in ethanol (5 mL) was added dry Pd(OH)₂/C (60 mg, 1.00 w/w). The resulting mixture was stirred overnight at 65° C. under an atmosphere of H₂ (3 atm.). LCMS showed the reaction was complete. The solid was filtered out. The filtrate was concentrated under reduced pressure and the residue was purified by flash chromatography on silica gel to give the desired product N-(2-(1-ethyl-2-methylpiperidin-3-yl)thieno[2,3-b]pyridin-4-yl)benzo[d]-thiazol-5-amine (Example 6, 12.9 mg, 16%) as an off-white solid. ¹H NMR (400 MHz, Methanol-d₄) δ 9.37 (s, 1H), 8.30-8.20 (m, 2H), 8.12 (s, 1H), 7.75 (s, 1H), 7.57 (d, J=8.8 Hz, 1H), 7.04 (d, J=6.8 Hz, 1H), 4.15-3.90 (m, 1H), 3.80-3.60 (m, 1H), 3.50-3.40 (m, 1H), 3.31-3.17 (m, 3H), 2.30-2.10 (m, 3H), 2.09-1.90 (m, 1H), 1.44 (t, J=7.3 Hz, 3H), 1.27 (d, J=6.7 Hz, 3H). LCMS (ESI, m/z): 409 [M+H]⁺.

Example 7: Synthesis of N-(2-(1-isopropyl-2-methyl-1,2,5,6-tetrahydropyridin-3-yl)thieno[2,3-b]pyridin-4-yl)benzo[d]thiazol-5-amine

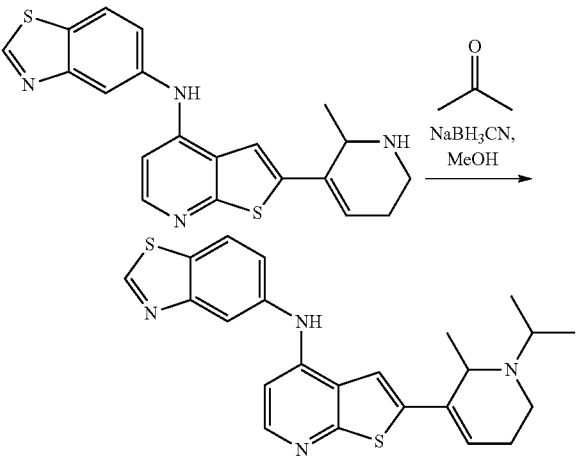

To a solution of N-(2-(2-methyl-1,2,5,6-tetrahydropyridin-3-yl)thieno[2,3-b]pyridin-4-yl)benzo[d]-thiazol-5-amine (Example 1, 60 mg, 0.160 mmol, 1.00 equiv) in methanol (5 mL) was added acetone (0.2 mL, 1.600 mmol, 10.00 equiv). After 30 minutes, NaBH₃CN (30 mg, 0.480 mmol, 3.00 equiv) was added to the reaction and stirred at 40° C. overnight. LCMS showed the reaction was complete. The reaction mixture was concentrated under reduced pressure and the residue was purified by flash chromatography on silica gel with EA/PE=1/1 to give the desired product N-(2-(1-isopropyl-2-methyl-1,2,5,6-tetrahydropyridin-3-yl)thieno[2,3-b]pyridin-4-yl)benzo[d]thiazol-5-amine (Example 7, 27 mg, 31%) as a light-yellow solid. ¹H NMR (400 MHz, Methanol-d₄) δ 9.38 (s, 1H), 8.27-8.25 (m, 2H), 8.15 (s, 1H), 7.95 (s, 1H), 7.59 (d, J=8.4 Hz, 1H), 7.07 (d, J=7.2 Hz, 1H), 6.65-6.50 (m, 1H), 4.80-4.65 (d, J=6.4 Hz, 1H), 3.90-3.30 (m, 3H), 2.90-2.60 (m, 2H), 1.60 (d, 3H), 1.54 (d, J=6.8 Hz, 6H). LCMS (ESI, m/z): 421 [M+H]+.

Example 8: Synthesis of N-(2-(1-isopropyl-2-methylpiperidin-3-yl)thieno[2,3-b]pyridin-4-yl)benzo[d]thiazol-5-amine

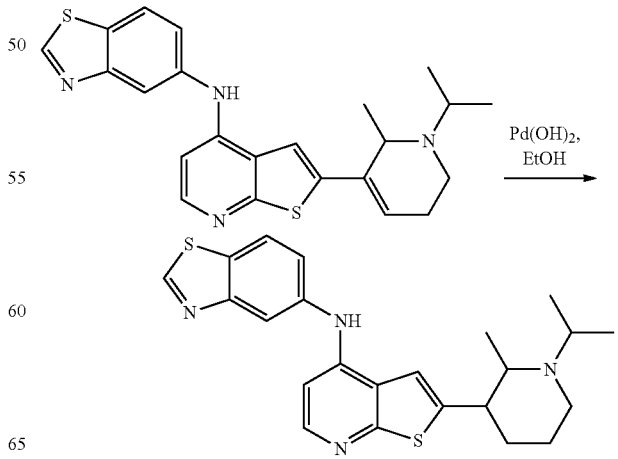

To a solution of the compound N-(2-(1-isopropyl-2-methyl-1,2,5,6-tetrahydropyridin-3-yl)-thieno[2,3-b]pyridin-4-yl)benzo[d]thiazol-5-amine (Example 7, 60 mg, 0.140 mmol, 1.00 equiv) in ethanol (10 mL) was added Pd(OH)$_2$/C (60 mg, 1.00 w/w). The resulting mixture was stirred for 15 h at 60° C. under H$_2$ atmosphere (1-3 atm.). TLC showed the reaction was complete. The solid was filtered out and the filtrate was concentrated. The residue was purified by preparative TLC (DCM/MeOH=5/1) and preparative HPLC (Column: Sunfire Prep C18 OBD Column, 10 μm, 19×250 mm; Mobile Phase A: Water (0.05% TFA), Mobile Phase B: ACN; Flow rate: 25 mL/min; Gradient: 30% B to 50% B in 8 min; 254/210 nm; Rt: 7.65 min) to afford N-(2-(1-isopropyl-2-methylpiperidin-3-yl)thieno[2,3-b]pyridin-4-yl)benzo[d]-thiazol-5-amine TFA salt (Example 8, 15.9 mg, 20%) as off-white solid. $^1$H NMR (400 MHz, Methanol-d$_4$) δ 9.41 (s, 1H), 8.33-8.26 (m, 2H), 8.16 (d, J=2.0 Hz, 1H), 7.83 (s, 1H), 7.61 (dd, J=8.6, 2.1 Hz, 1H), 7.07 (d, J=6.9 Hz, 1H), 4.25-4.15 (m, 1H), 3.84-3.75 (m, 1H), 3.70 (d, J=13.4 Hz, 1H), 3.54 (dq, J=11.0, 5.4, 4.5 Hz, 1H), 3.18 (t, J=12.6 Hz, 1H), 2.22 (t, J=10.5 Hz, 3H), 2.02 (q, J=18.0, 17.1 Hz, 1H), 1.50-1.40 (m, 6H), 1.31 (dd, J=7.2 Hz, 3H). LCMS (ESI, m/z): 423 [M+H]$^+$.

Example 9: Synthesis of 1-(5-(4-(benzo[d]thiazol-5-ylamino)thieno[2,3-b]pyridin-2-yl)-6-methyl-3,6-dihydropyridin-1(2H)-yl)ethan-1-one

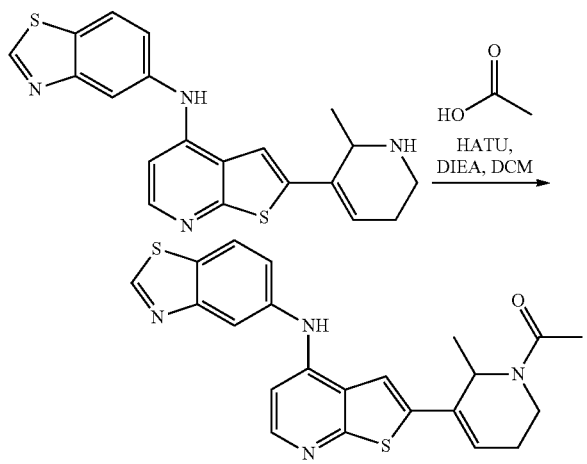

To a solution of N-(2-(2-methyl-1,2,5,6-tetrahydropyridin-3-yl)thieno[2,3-b]pyridin-4-yl)benzo-[d]thiazol-5-amine (Example 1, 80 mg, 0.210 mmol, 1.00 equiv), CH$_3$COOH (17 mg, 0.270 mmol, 1.30 equiv) and HATU (121 mg, 0.320 mmol, 1.50 equiv) in DCM (8 mL) was added DIEA (0.2 mL, 0.850 mmol, 4.00 equiv) dropwise at 0° C. The resulting mixture was stirred at room temperature until LCMS showed the reaction was completed. The mixture was diluted with water (10 mL) and extracted with DCM (3×20 mL). The combined organic layer was washed with brine (2×20 mL), dried and concentrated. The crude product was purified by preparative HPLC to give 1-(5-(4-(benzo[d]thiazol-5-ylamino)thieno[2,3-b]pyridin-2-yl)-6-methyl-3,6-dihydropyridin-1(2H)-yl)ethan-1-one (Example 9, 25.5 mg, yield 22%) as an off-white solid. $^1$H NMR (400 MHz, Methanol-d$_4$) δ 9.38 (s, 1H), 8.28-8.21 (m, 2H), 8.15 (d, J=2.4 Hz, 1H), 7.87-7.84 (m, 1H), 7.59 (dd, J=8.6, 2.5 Hz, 1H), 7.06-7.02 (m, 1H), 6.49-6.45 (m, 1H), 5.64-5.62 (m, 1H), 3.99-3.94 (m, 1H), 3.53-3.48 (m, 1H), 2.48-2.26 (m, 2H), 2.20 (s, 3H), 1.58-1.44 (m, 3H). LCMS (ESI, m/z): 421 [M+H]$^+$ Example 10: Synthesis of 1-(3-(4-(benzo[d]thiazol-5-ylamino)thieno[2,3-b]pyridin-2-yl)-2-methylpiperidin-1-yl)ethan-1-one

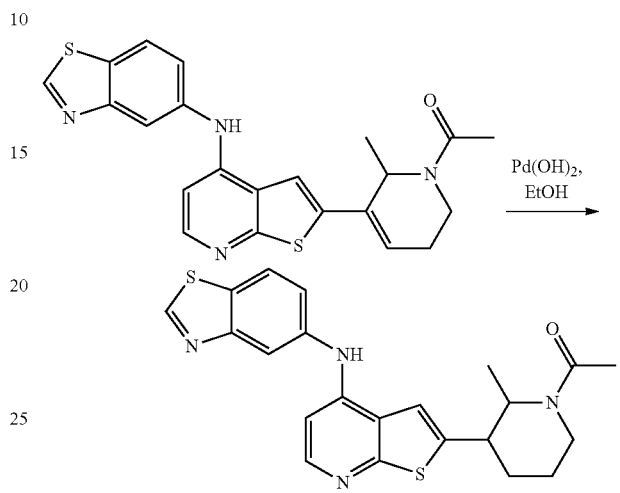

To a solution of the compound 1-(5-(4-(benzo[d]thiazol-5-ylamino)thieno[2,3-b]pyridin-2-yl)-6-methyl-3,6-dihydropyridin-1(2H)-yl)ethan-1-one (Example 9, 100 mg, 0.240 mmol, 1.00 equiv) in ethanol (8 mL) was added Pd(OH)$_2$/C (100 mg, 1.00 w/w). The resulting mixture was stirred for 15 h at 60° C. under H$_2$ atmosphere (1-3 atm.). TLC showed the reaction was complete. The solid was filtered out and the filtrate was concentrated. The residue was purified by preparative TLC and preparative HPLC (Column: Sunfire Prep C18 OBD Column, 10 μm, 19×250 mm; Mobile Phase A: Water (0.05% TFA), Mobile Phase B: ACN; Flow rate: 25 mL/min; Gradient: 30% B to 50% B in 8 min; 254/210 nm; Rt: 7.65 min) to afford 1-(3-(4-(benzo[d]thiazol-5-ylamino)thieno[2,3-b]pyridin-2-yl)-2-methylpiperidin-1-yl)ethan-1-one (Example 10, 9.7 mg, 8%) as a white solid. $^1$H NMR (400 MHz, Methanol-d$_4$) δ 9.41 (s, 1H), 8.35-8.20 (m, 2H), 8.17 (d, J=2.1 Hz, 1H), 7.75 (d, J=10.1 Hz, 1H), 7.68-7.56 (m, 1H), 7.05 (d, J=7.0 Hz, 1H), 5.30-5.10 (m, 1H), 4.60-4.35 (m, 1H), 3.86 (d, J=13.9 Hz, 1H), 3.60-3.30 (m, 1H), 2.31-2.09 (m, 5H), 2.05-1.95 (m, 1H), 1.78-1.65 (m, 1H), 1.45-1.00 (m, 3H). LCMS (ESI, m/z): 423 [M+H]$^+$.

Example 11: Synthesis of 1-(5-(4-(benzo[d]thiazol-5-ylamino)thieno[2,3-b]pyridin-2-yl)-6-methyl-3,6-dihydro-pyridin-1(2H)-yl)-2-methoxyethan-1-one

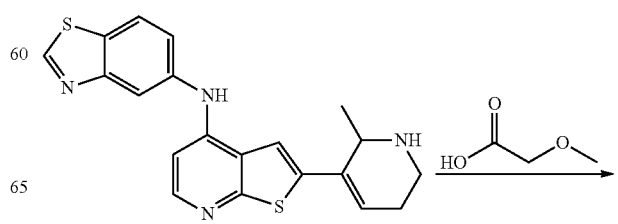

-continued

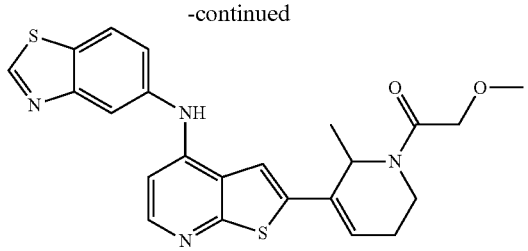

To a stirred solution of 2-methoxyacetic acid (21 mg, 0.240 mmol, 1.20 equiv) in DCM (5 mL) was added HATU (90 mg, 0.240 mmol, 1.20 equiv) and TEA (60 mg, 0.590 mmol, 3.00 equiv). The resulting mixture was stirred at room temperature for 30 min. Then N-(2-(2-methyl-1,2,5,6-tetrahydropyridin-3-yl)thieno[2,3-b]pyridin-4-yl)benzo[d]thiazol-5-amine (Example 1, 75 mg, 0.200 mmol, 1.00 equiv) was added and the resulting solution was stirred for 1 h. LCMS showed the reaction was complete. The reaction mixture was concentrated under reduced pressure. The crude product was purified by preparative HPLC using the following gradient conditions: Column: XBridge Shield RP18 OBD Column, 19×250 mm, 10 μm; Mobile Phase A: ACN, Mobile Phase B: Water (5 mmol/L TFA); Flow rate: 20 mL/min; Gradient: 35% B to 90% B in 7 min; 210/254 nm; Rt: 6.67 min. Purification resulted in 1-(5-(4-(benzo[d]thiazol-5-ylamino)-thieno[2,3-b]pyridin-2-yl)-6-methyl-3,6-dihydropyridin-1(2H)-yl)-2-methoxyethan-1-one (Example 11, 34 mg, 38%) as a white solid. $^1$H NMR (400 MHz, Methanol-$d_4$) δ 9.38 (s, 1H), 8.29-8.21 (m, 2H), 8.15 (s, 1H), 7.85 (s, 1H), 7.59 (d, J=8.0 Hz, 1H), 7.03 (d, J=6.8 Hz, 1H), 6.44 (s, 1H), 5.58 (d, J=4.0 Hz, 1H), 4.35-4.15 (m, 2H), 3.94-3.89 (m, 1H), 3.61-3.43 (m, 4H), 2.70-2.50 (m, 1H), 2.47-2.36 (m, 1H), 1.59-1.47 (m, 3H). LCMS (ESI, m/z): 451 [M+H]t.

Example 12: Synthesis of N-(2-(1-(2-methoxyethyl)-2-methyl-1,2,5,6-tetrahydropyridin-3-yl)thieno[2,3-b]pyridin-4-yl)benzo[d]thiazol-5-amine

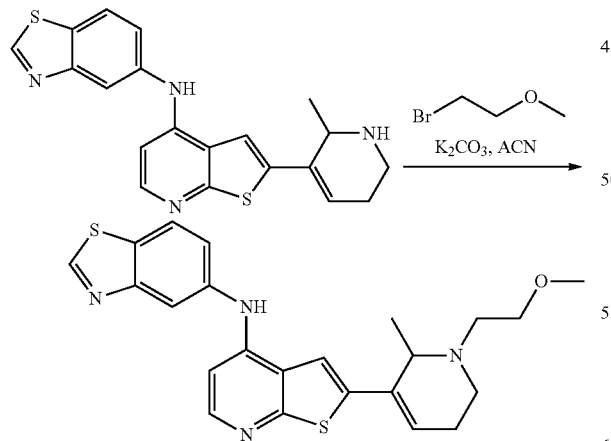

To a stirred mixture of N-(2-(2-methyl-1,2,5,6-tetrahydropyridin-3-yl)thieno[2,3-b]pyridin-4-yl)benzo[d]thiazol-5-amine (Example 1, 120 mg, 0.320 mmol, 1.00 equiv) and $K_2CO_3$ (134 mg, 1.270 mmol, 3.97 equiv) in MeCN (3 mL) was added 1-bromo-2-methoxy-ethane (48 mg, 0.340 mmol, 1.06 equiv) at rt and was heated at 80° C. for 3 hours. Then additional 1-bromo-2-methoxy-ethane (48 mg, 0.340 mmol, 1.06 equiv) was added and stirred for another 3 hours. LCMS showed the reaction was complete. The mixture was filtered and the filtrate was concentrated. The crude product was purified by preparative HPLC to afford the desired product N-(2-(1-(2-methoxyethyl)-2-methyl-1,2,5,6-tetrahydropyridin-3-yl)thieno[2,3-b]pyridin-4-yl)benzo[d]thiazol-5-amine (Example 12, 39.3 mg, 28%) as an off-white solid. $^1$H NMR (300 MHz, Methanol-$d_4$) δ 9.29 (s, 1H), 8.14-8.04 (m, 2H), 8.00 (s, 1H), 7.58-7.47 (m, 2H), 6.99 (d, J=5.7 Hz, 1H), 6.33-6.26 (m, 1H), 4.02-3.91 (m, 1H), 3.62 (t, J=5.7 Hz, 2H), 3.37 (s, 3H), 3.16-3.00 (m, 1H), 2.97-2.77 (m, 3H), 2.63-2.48 (m, 1H), 2.25-2.10 (m, 1H), 1.38 (d, J=6.7 Hz, 3H). LCMS (ESI, m/z): 437 [M+H]$^+$.

Chiral Separation

N-(2-(1-(2-methoxyethyl)-2-methyl-1,2,5,6-tetrahydropyridin-3-yl)thieno[2,3-b]pyridin-4-yl)-benzo[d]thiazol-5-amine (Example 12, 200 mg, 0.460 mmol) was purified by SFC using the following gradient conditions: Column: CHIRALPAK AS-H, 2×25 cm (5 μm); Mobile Phase A: $CO_2$: 60, Mobile Phase B: MeOH (2 mM $NH_3$-MeOH): 40; Flow rate: 40 mL/min; 220 nm; RT$^1$: 3.94 (Example 12a); RT$^2$: 6.39 (Example 12b). Then each product was further purified by preparative HPLC using the following gradient conditions: Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 10% B to 30% B in 10 min; 254/210 nm; Rt: 8.70 min. Purification resulted in Example 12a (61 mg, 30%, 100% ee) and Example 12b (55.3 mg, 27%, 99.1% ee) as light yellow solids.

Example 13: Synthesis of N-(2-(1-(2-methoxyethyl)-2-methylpiperidin-3-yl)thieno[2,3-b]pyridin-4-yl)benzo[d]thiazol-5-amine

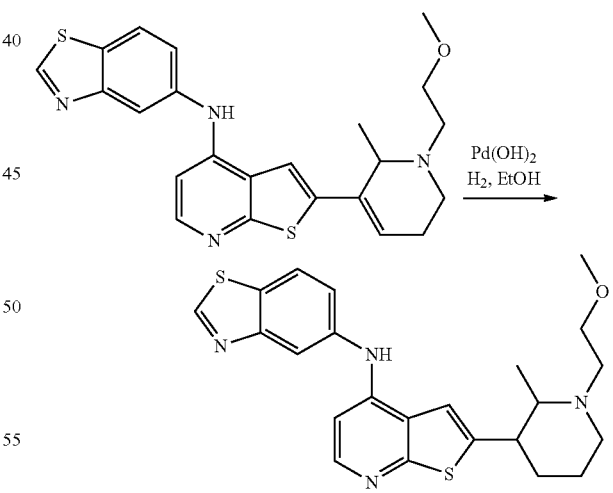

To a solution of N-(2-(1-(2-methoxyethyl)-2-methyl-1,2,5,6-tetrahydropyridin-3-yl)thieno[2,3-b]pyridin-4-yl)benzo[d]thiazol-5-amine (Example 12, 80 mg, 0.180 mmol, 1.00 equiv) in ethanol (8 mL) was added PdOH$_2$/C (80 mg, w/w=1/1). The mixture was stirred at 65° C. overnight under an atmosphere of hydrogen (1-3 atm.). LCMS showed the reaction was completed. The resulting mixture was passed through a celite pad and the filtrate was concentrated under reduced pressure. The residue was purified by preparative HPLC (Column: XBridge Shield RP18 OBD Column, 19×250 mm, 10 μm; Mobile Phase A: Water (10 mmol/L NH$_4$HCO$_3$), Mobile Phase B: ACN; Flow rate: 25 mL/min; Gradient: 29% B to 52% B in 16 min; 254/210 nm; Rt: 15.52 min) to provide N-(2-(1-(2-methoxy-ethyl)-2-methyl-piperidin-3-yl)thieno[2,3-b]pyridin-4-yl)benzo[d]thiazol-5-amine (Example 13, 15.3 mg, 18%) as an off-white solid. $^1$H NMR (400 MHz, Methanol-d$_4$) δ 9.30 (s, 1H), 8.14-8.07 (m, 2H), 8.02 (d, J=2.1 Hz, 1H), 7.54 (dd, J=8.6, 2.1 Hz, 1H), 7.40 (s, 1H), 7.01 (d, J=5.6 Hz, 1H), 4.65-4.55 (m, 1H), 3.60 (t, J=5.7 Hz, 2H), 3.50-3.43 (m, 1H), 3.40 (s, 3H), 2.77 (t, J=5.8 Hz, 2H), 2.70-2.60 (s, 2H), 1.97 (dd, J=12.3, 8.0 Hz, 2H), 1.90-1.70 (m, 2H), 0.93 (d, J=6.6 Hz, 3H). LCMS (ESI, m/z): 439 [M+H]$^+$ Example 14: Synthesis of N-(2-(1-(2-fluoroethyl)-2-methylpiperidin-3-yl)thieno[2,3-b]pyridin-4-yl)benzo[d]thiazol-5-amine

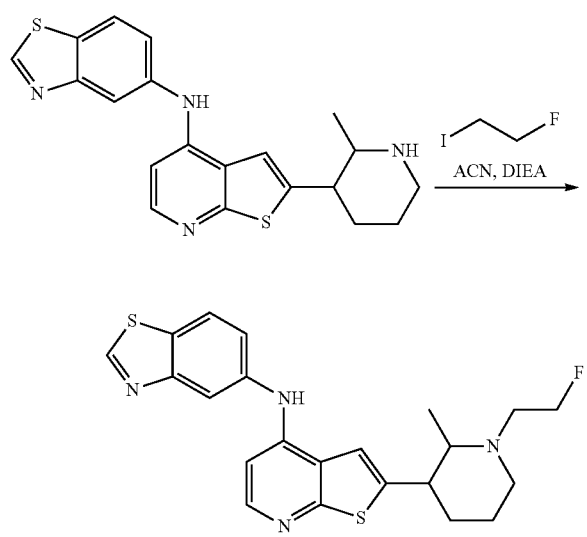

To a stirred solution of N-(2-(2-methylpiperidin-3-yl)thieno[2,3-b]pyridin-4-yl)benzo[d]thiazol-5-amine (Example 3, 80 mg, 0.210 mmol, 1.00 equiv) in MeCN (5 mL) was added 1-fluoro-2-iodoethane (55 mg, 0.320 mmol, 1.50 equiv) and DIEA (0.15 mL, 0.840 mmol, 4.00 equiv). The resulting solution was stirred at 80° C. for 48 h. LCMS showed the reaction was complete. The mixture was concentrated under reduced pressure. The crude product was purified by preparative HPLC using the following gradient conditions: Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 10% B to 40% B in 8 min; 254/210 nm; Rt: 7.68 min. Purification resulted in N-(2-(1-(2-fluoroethyl)-2-methylpiperidin-3-yl)thieno[2,3-b]pyridin-4-yl)benzo[d]thiazol-5-amine (Example 14, 20.2 mg, 22%) in TFA salt form as a yellow solid. $^1$H NMR (300 MHz, Methanol-d$_4$) δ 9.40 (s, 1H), 8.35-8.27 (m, 2H), 8.17 (d, J=2.4 Hz, 1H), 7.82 (s, 1H), 7.61 (dd, J=8.6, 2.1 Hz, 1H), 7.06 (dd, J=7.0, 1.6 Hz, 1H), 5.03 (t, J=4.4 Hz, 1H), 4.90-4.85 (m, 1H), 4.21-3.39 (m, 6H), 2.32-1.97 (m, 4H), 1.97-1.32 (m, 3H). LCMS (ESI, m/z): 427 [M+H]$^+$.

Example 15: Synthesis of N-(2-(1-(2,2-difluoroethyl)-2-methylpiperidin-3-yl)thieno[2,3-b]pyridin-4-yl)benzo-[d]thiazol-5-amine

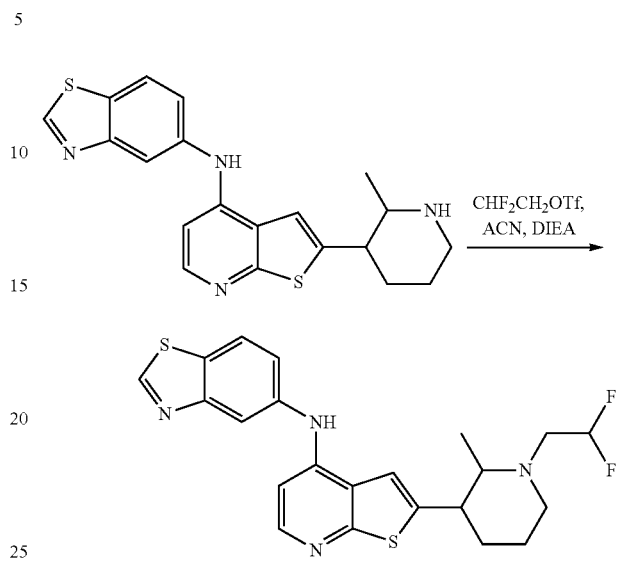

To a stirred solution of N-(2-(2-methylpiperidin-3-yl)thieno[2,3-b]pyridin-4-yl)benzo[d]thiazol-5-amine (Example 3, 80 mg, 0.210 mmol, 1.00 equiv) in MeCN (4 mL) was added 2,2-difluoroethyl trifluoro-methanesulfonate (45 mg, 0.210 mmol, 1.00 equiv) and DIEA (0.15 mL, 0.840 mmol, 4.00 equiv). The resulting solution was stirred at 80° C. for 48 h. LCMS showed the reaction was complete. The mixture was concentrated under reduced pressure. The crude product was purified by preparative HPLC using the following gradient conditions: Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 5% B to 30% B in 10 min; 254/210 nm; Rt: 9.52 min. Purification resulted in N-(2-(1-(2,2-difluoroethyl)-2-methylpiperidin-3-yl)thieno[2,3-b]pyridin-4-yl)benzo[d]thiazol-5-amine (Example 15, 15.5 mg, 16%) in TFA salt form as a white solid. $^1$H NMR (400 MHz, Methanol-d$_4$) δ 9.41 (s, 1H), 8.50-8.23 (m, 2H), 8.17 (s, 1H), 7.88 (s, 1H), 7.61 (d, J=8.0 Hz, 1H), 7.06 (d, J=6.8 Hz, 1H), 6.60-6.30 (m, 1H), 4.08-3.55 (m, 4H), 3.50-3.33 (m, 2H), 2.30-2.00 (m, 4H), 1.47-1.32 (m, 3H). LCMS (ESI, m/z): 445 [M+H]+.

Example 16: Synthesis of N-(2-(2-methyl-1-(2,2,2-trifluoroethyl)piperidin-3-yl)thieno[2,3-b]pyridin-4-yl)benzo[d]thiazol-5-amine

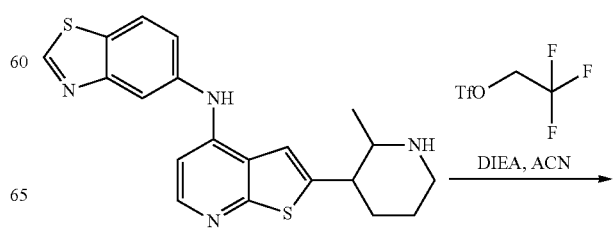

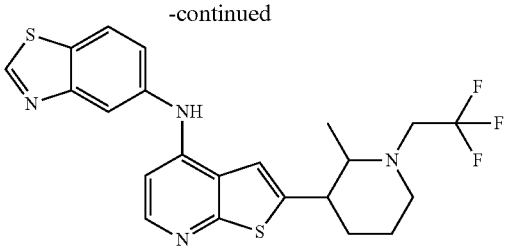

To the solution of N-(2-(2-methylpiperidin-3-yl)thieno[2,3-b]pyridin-4-yl)benzo[d]thiazol-5-amine (Example 3, 100 mg, 0.260 mmol, 1.00 equiv) and 2,2,2-trifluoroethyl trifluoromethanesulfonate (61 mg, 0.260 mmol, 1.00 equiv) in ACN (1 mL) was added DIEA (0.07 mL, 0.530 mmol, 2.00 equiv). The resulting mixture was stirred at 80° C. overnight. LCMS showed the reaction was complete. The reaction mixture was concentrated and the crude product was purified by preparative HPLC (Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 15% B to 45% B in 10 min; 254/210 nm; Rt: 8.63, 9.40 min) to give N-(2-(2-methyl-1-(2,2,2-trifluoroethyl)piperidin-3-yl)thieno[2,3-b]pyridin-4-yl)benzo[d]thiazol-5-amine (Example 16, 8.5 mg, 7%). $^1$H NMR (400 MHz, Methanol-$d_4$) δ 9.40 (s, 1H), 8.28 (d, J=8.6 Hz, 1H), 8.22 (d, J=7.0 Hz, 1H), 8.16 (d, J=2.0 Hz, 1H), 7.66 (s, 1H), 7.60 (dd, J=8.6, 2.1 Hz, 1H), 7.02 (d, J=7.0 Hz, 1H), 3.29-3.25 (m, 2H), 3.22-3.14 (m, 1H), 3.11-3.05 (m, 2H), 2.89-2.81 (m, 1H), 2.26-2.16 (m, 1H), 1.92-1.84 (m, 1H), 1.78-1.70 (m, 2H), 1.21 (d, J=6.3 Hz, 3H). LCMS (ESI, m/z): 463 [M+H]$^+$.

Example 17: Synthesis of N-(2-(2-methyl-1-(oxetan-3-yl)piperidin-3-yl)thieno[2,3-b]pyridin-4-yl)benzo[d]thiazol-5-amine

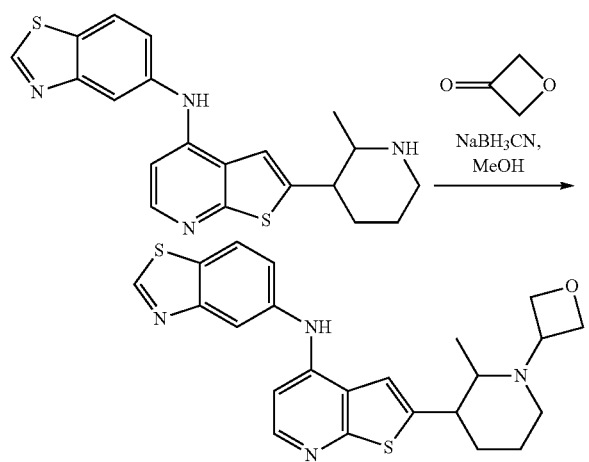

Into a 10-mL sealed tube was placed N-(2-(2-methylpiperidin-3-yl)thieno[2,3-b]pyridin-4-yl)benzo[d]thiazol-5-amine (Example 3, 50 mg, 0.130 mmol, 1.00 equiv), oxetan-3-one (10 mg, 0.140 mmol, 1.00 equiv) and methanol (2 mL). After stirring for 10 min, NaBH$_3$CN (25 mg, 0.400 mmol, 3.00 equiv) was added portion wise. The resulting solution was stirred for 1 h at 80° C. LCMS showed the reaction was complete. The resulting solution was concentrated. The crude product was purified by preparative HPLC using the following gradient conditions: Column: XBridge Prep C18 OBD Column, 5 μm, 19×150 mm; Mobile Phase A: Water (0.05% TFA), Mobile Phase B: ACN; Flow rate: 25 mL/min; Gradient: 10% B to 40% B in 7 min; 254/210 nm; Rt: 6.12 min. Purification gave N-(2-(2-methyl-1-(oxetan-3-yl)piperidin-3-yl)thieno[2,3-b]pyridin-4-yl)benzo[d]thiazol-5-amine (Example 17, 8.5 mg, 15%) as a light yellow solid. $^1$H NMR (400 MHz, Methanol-$d_4$) δ 9.40 (s, 1H), 8.28-8.24 (m, 2H), 8.16 (d, J=2.0 Hz, 1H), 7.82 (s, 1H), 7.61 (d, J=8.5, 1H), 7.05 (dd, J=7.0, 2.9 Hz, 1H), 5.02-4.93 (m, 4H), 4.74-4.67 (m, 1H), 4.06-3.87 (m, 2H), 3.67-3.54 (m, 1H), 3.33-3.26 (m, 1H), 2.22-1.98 (m, 4H), 1.23 (d, J=6.6 Hz, 3H). LCMS (ESI, m/z): 437 [M+H]$^+$.

Example 18: Synthesis of tert-butyl (3-(3-(4-(benzo[d]thiazol-5-ylamino)thieno[2,3-b]pyridin-2-yl)-2-methyl-piperidin-1-yl)propyl)carbamate

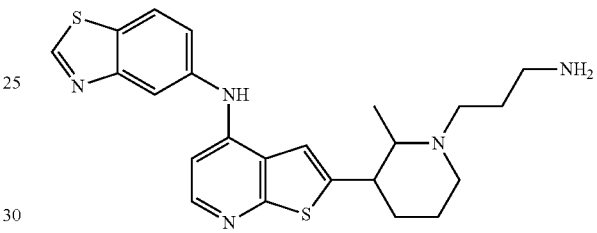

Step 1

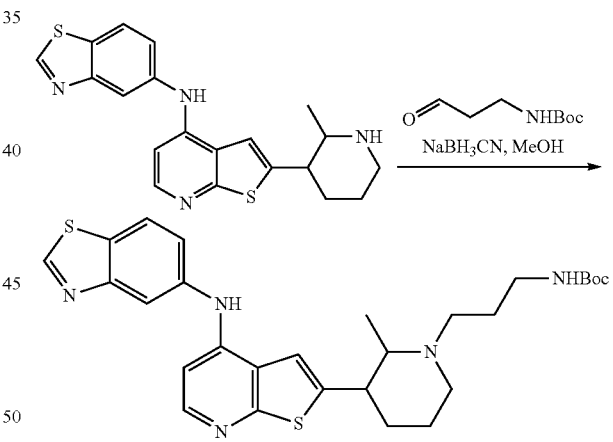

Into a 10-mL sealed tube was placed N-(2-(2-methylpiperidin-3-yl)thieno[2,3-b]pyridin-4-yl)benzo-[d]thiazol-5-amine (Example 3, 30 mg, 0.080 mmol, 1.00 equiv), tert-butyl N-(3-oxopropyl)carbamate (14 mg, 0.080 mmol, 1.00 equiv) and methanol (1 mL). After stirring for 10 min, NaBH$_3$CN (15 mg, 0.240 mmol, 3.00 equiv) was added portion wise. The resulting solution was stirred for 1 h at 80° C. LCMS showed the reaction was complete. The resulting solution was concentrated. The crude product was purified by preparative HPLC using the following gradient conditions: Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 20% B to 40% B in 7 min; 254/210 nm; Rt: 5.93 min. Purification gave the desired product tert-butyl (3-(3-(4-

(benzo[d]thiazol-5-ylamino)thieno-[2,3-b]pyridin-2-yl)-2-methyl-piperidin-1-yl)propyl)carbamate (Example 18-1, 7 mg, 35%) as a light yellow solid. ¹H NMR (400 MHz, Methanol-d₄) δ 9.41 (s, 1H), 8.29-8.26 (m, 2H), 8.16 (d, J=2.0 Hz, 1H), 7.81 (s, 1H), 7.64-7.57 (m, 1H), 7.06 (dd, J=7.0, 2.7 Hz, 1H), 4.10-3.35 (m, 4H), 3.22-3.14 (m, 4H), 2.35-1.91 (m, 6H), 1.52-1.44 (m, 9H), 1.28 (d, J=6.8 Hz, 3H). LCMS (ESI, m/z): 538 [M+H]⁺.

Step 2

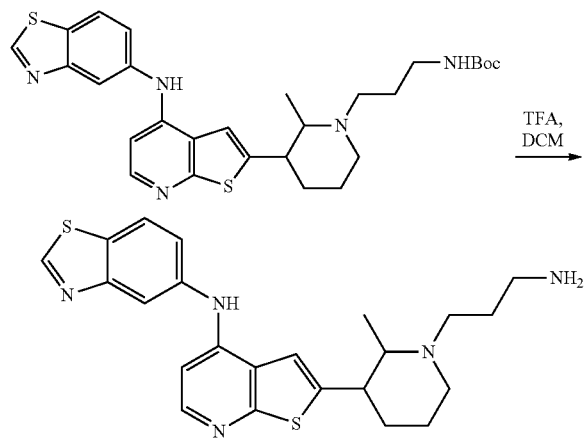

To a solution of tert-butyl (3-(3-(4-(benzo[d]thiazol-5-ylamino)thieno[2,3-b]pyridin-2-yl)-2-methylpiperidin-1-yl)propyl)carbamate (Example 18-1, 80 mg, 0.150 mmol, 1.00 equiv) in DCM (6 mL) was added TFA (2 mL). The resulting mixture was stirred for 30 min at room temperature. LCMS showed the reaction was complete. The solvent was removed under reduced pressure. The reaction mixture was purified by preparative HPLC using the following gradient conditions: Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 5% B to 25% B in 11 min; 254/210 nm; Rt: 10.83 min. Purification gave the desired product N-(2-(1-(3-aminopropyl)-2-methylpiperidin-3-yl)thieno[2,3-b]pyridin-4-yl)benzo[d]thiazol-5-amine (Example 18, 28.0 mg, 42%) as a white solid. ¹H NMR (400 MHz, Methanol-d₄) δ 9.40 (s, 1H), 8.28-8.24 (m, 2H), 8.17 (d, J=2.0 Hz, 1H), 7.83 (s, 1H), 7.58 (d, J=7.2 Hz, 1H), 7.05 (d, J=6.9 Hz, 1H), 4.22-3.41 (m, 4H), 3.41-3.35 (m, 2H), 3.15-3.07 (m, 2H), 2.39-1.95 (m, 6H), 1.45-1.25 (m, 3H). LCMS (ESI, m/z): 438 [M+H]⁺.

Example 19: Synthesis of N-(2-(1-(2-ethoxyethyl)-2-methylpiperidin-3-yl)thieno[2,3-b]pyridin-4-yl)benzo[d]thiazol-5-amine

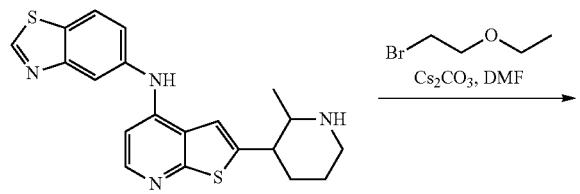

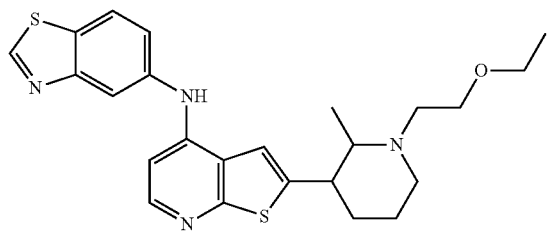

Into a 10-mL sealed tube was placed Cs₂CO₃ (129 mg, 0.395 mmol, 3.00 equiv), N-(2-(2-methyl-piperidin-3-yl)thieno[2,3-b]pyridin-4-yl)benzo[d]thiazol-5-amine (Example 3, 50 mg, 0.130 mmol, 1.00 equiv), 1-bromo-2-ethoxy-ethane (20 mg, 0.130 mmol, 1.00 equiv) and DMF (1 mL). The resulting solution was stirred for 1 h at 110° C. LCMS showed the reaction was complete. The mixture was purified by preparative HPLC using the following gradient conditions: Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 15% B to 27% B in 8 min; 254/210 nm; Rt: 5.3 min. Purification gave N-(2-(1-(2-ethoxyethyl)-2-methylpiperidin-3-yl)thieno[2,3-b]-pyridin-4-yl)benzo-[d]thiazol-5-amine (Example 19, 26.3 mg, 45%) as a light yellow solid. ¹H NMR (400 MHz, Methanol-d₄) δ 9.39 (s, 1H), 8.30-8.23 (m, 2H), 8.14 (d, J=2.1 Hz, 1H), 7.75 (d, J=6.1 Hz, 1H), 7.59 (dd, J=8.6, 2.1 Hz, 1H), 7.05 (dd, J=6.8, 2.6 Hz, 1H), 3.98-3.54 (m, 7H), 3.54-3.36 (m, 3H), 2.41-1.92 (m, 4H), 1.52-1.19 (m, 6H). LCMS (ESI, m/z): 453 [M+H]⁺.

Example 20: Synthesis of 2-(3-(4-(benzo[d]thiazol-5-ylamino)thieno[2,3-b]pyridin-2-yl)-2-methylpiperidin-1-yl)ethan-1-ol

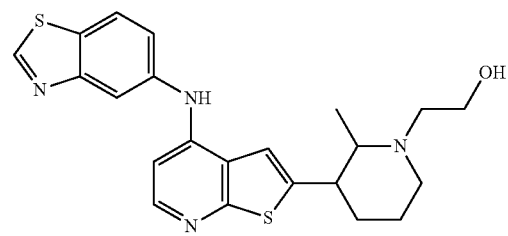 [SMILES: CC1C(c2cc3c(Nc4ccc5scnc5c4)ccnc3s2)CCCN1CCO]

Step 1

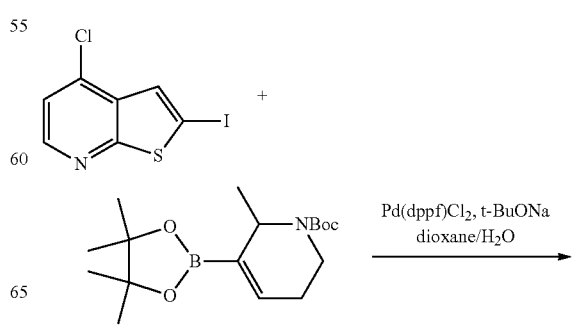

-continued

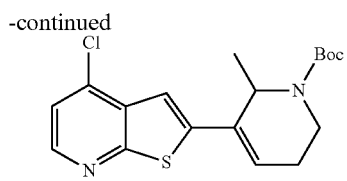

To a stirred solution of 4-chloro-2-iodo-thieno[2,3-b]pyridine (2.0 g, 6.770 mmol, 1.00 equiv) in 1,4-dioxane (30 mL) and water (5 mL) was added Pd(dppf)Cl₂ (0.5 g, 0.680 mmol, 0.10 equiv), t-BuONa (1.9 g, 20.300 mmol, 3.00 equiv) and tert-butyl 6-methyl-5-(4,4,5,5-tetramethyl-1,3,2-dioxaborolan-2-yl)-3,6-dihydro-2H-pyridine-1-carboxylate (2.2 g, 6.770 mmol, 1.00 equiv). The resulting mixture was stirred at 80° C. for 3 h. LCMS showed the reaction was complete. The reaction mixture was concentrated under reduced pressure. The crude product was purified by flash chromatography on silica gel with ethyl acetate/petroleum ether (1:10) to afford tert-butyl 5-(4-chlorothieno[2,3-b]pyridin-2-yl)-6-methyl-3,6-dihydropyridine-1(2H)-carboxylate (Example 20-1, 1.6 g, 65%) as a yellow solid. LCMS (ESI, m/z): 365 [M+H]⁺.

Step 2

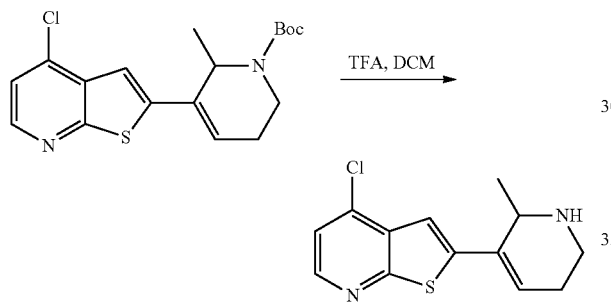

To a stirred solution tert-butyl 5-(4-chlorothieno[2,3-b]pyridin-2-yl)-6-methyl-3,6-dihydro-pyridine-1(2H)-carboxylate (Example 20-1, 1.6 g, 4.380 mmol, 1.00 equiv) in DCM (12 mL) was added TFA (6 mL). The resulting mixture was stirred at room temperature for 30 min. LCMS showed the reaction was complete. The solution was concentrated under reduced pressure to afford 4-chloro-2-(2-methyl-1,2,5,6-tetrahydropyridin-3-yl)thieno[2,3-b]pyridine (Example 20-2, 1.1 g, crude) in TFA salt form as a yellow oil. LCMS (ESI, m/z): 265 [M+H]⁺.

Step 3

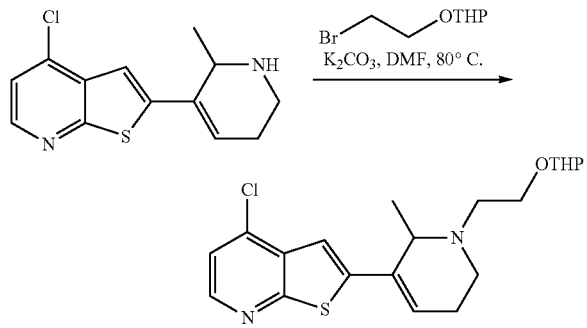

To a stirred solution of 4-chloro-2-(2-methyl-1,2,5,6-tetrahydropyridin-3-yl)thieno[2,3-b]pyridine (Example 20-2, 500 mg, 1.890 mmol, 1.00 equiv) in DMF (10 mL) was added 2-(2-bromoethoxy)tetrahydro-pyran (592 mg, 2.830 mmol, 1.50 equiv), K₂CO₃ (600 mg, 5.670 mmol, 3.00 equiv). The resulting solution was stirred at 80° C. overnight. LCMS showed the reaction was completed. The reaction mixture was concentrated under reduced pressure. The crude product was purified by flash chromatography on silica gel with ethyl acetate/petroleum ether (1:1) to afford 4-chloro-2-(2-methyl-1-(2-((tetrahydro-2H-pyran-2-yl)oxy)ethyl)-1,2,5,6-tetrahydropyridin-3-yl)thieno[2,3-b]pyridine (Example 20-3, 650 mg, 88%) as a yellow oil. LCMS (ESI, m/z): 393 [M+H]⁺.

Step 4

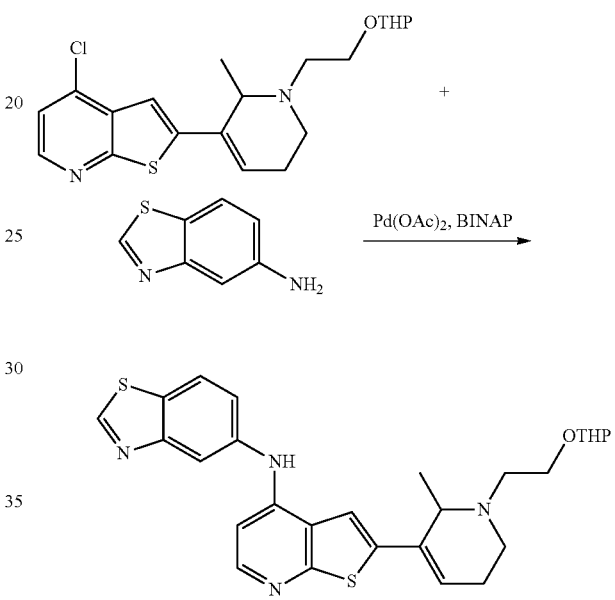

To a solution of 4-chloro-2-(2-methyl-1-(2-((tetrahydro-2H-pyran-2-yl)oxy)ethyl)-1,2,5,6-tetrahydropyridin-3-yl)thieno[2,3-b]pyridine (Example 20-3, 650 mg, 1.650 mmol, 1.00 equiv), 1,3-benzo-thiazol-5-amine (248 mg, 1.650 mmol, 1.00 equiv) and Cs₂CO₃ (1.6 g, 4.960 mmol, 3.00 equiv) in 1,4-dioxane (15 mL) was added Pd(OAc)₂ (37 mg, 0.170 mmol, 0.10 equiv) and BINAP (206 mg, 0.330 mmol, 0.20 equiv) under N₂ atmosphere. The resulting mixture was stirred at 90° C. for 3 h. TLC and LCMS showed the reaction was completed. The crude product was purified by flash chromatography on silica gel with ethyl acetate to afford N-(2-(2-methyl-1-(2-((tetrahydro-2H-pyran-2-yl)oxy)ethyl)-1,2,5,6-tetrahydropyridin-3-yl)thieno[2,3-b]pyridin-4-yl)benzo[d]thiazol-5-amine (Example 20-4, 300 mg, 36%) as a yellow solid. LCMS (ESI, m/z): 507 [M+H]⁺.

Step 5

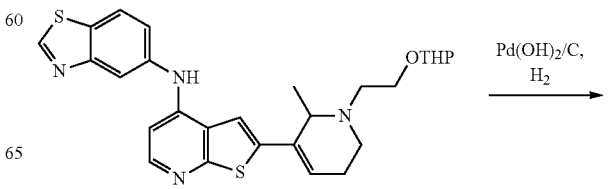

333
-continued

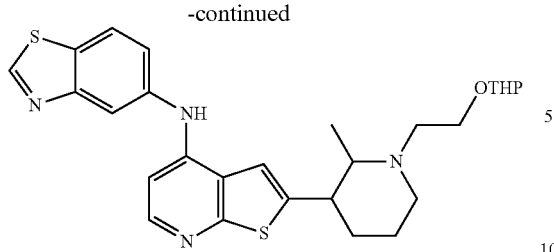

To a stirred solution of N-(2-(2-methyl-1-(2-((tetrahydro-2H-pyran-2-yl)oxy)ethyl)-1,2,5,6-tetrahydropyridin-3-yl)thieno[2,3]pyridin-4-yl)benzo[d]thiazol-5-amine (Example 20-4, 200 mg, 0.100 mmol, 1.00 equiv) in ethanol (15 mL) was added Pd(OH)$_2$/C (200 mg, 1.00 w/w). The resulting mixture was stirred at 65° C. under an atmosphere of hydrogen (2 atm.) overnight. LCMS showed the reaction was completed. The resulting mixture was filtered through celite and the filtrate was concentrated under reduced pressure. The crude product was purified by flash chromatography on silica gel with methanol/dichloromethane (1:15) to afford N-(2-(2-methyl-1-(2-((tetrahydro-2H-pyran-2-yl)oxy)-ethyl)piperidin-3-yl)thieno[2,3]pyridin-4-yl)benzo[d]thiazol-5-amine (Example 20-5, 60 mg, 30%). LCMS (ESI, m/z): 509 [M+H]$^+$.

Step 6

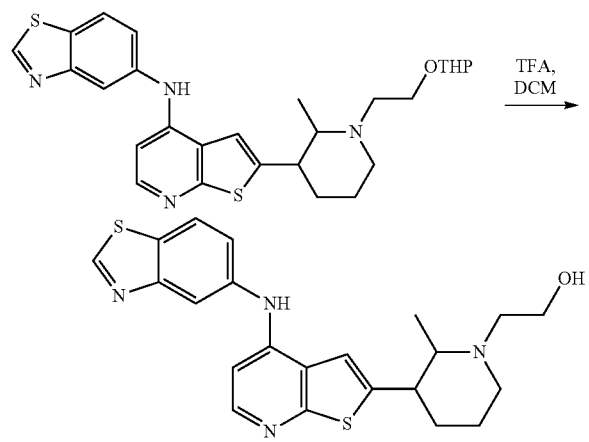

To a stirred solution of N-(2-(2-methyl-1-(2-((tetrahydro-2H-pyran-2-yl)oxy)ethyl)piperidin-3-yl)thieno[2,3]pyridin-4-yl)benzo[d]thiazol-5-amine (Example 20-5, 60 mg, 0.120 mmol, 1.00 equiv) in DCM (4 mL) was added TFA (2 ml). The resulting mixture was stirred at room temperature for 30 min. LCMS showed the reaction was complete. The reaction mixture was concentrated under reduced pressure. The crude product was purified by preparative HPLC using the following gradient conditions: Column: Sunfire Prep C18 OBD Column, 10 μm, 19×250 mm; Mobile Phase A: Water (0.05% TFA), Mobile Phase B: ACN; Flow rate: 25 mL/min; Gradient: 10% B to 30% B in 8 min; 254/210 nm; Rt: 7.65 min. Purification resulted 2-(3-(4-(benzo[d]thiazol-5-ylamino)thieno[2,3-b]pyridin-2-yl)-2-methylpiperidin-1-yl)ethan-1-ol (Example 20, 34.2 mg, 38%) as a white solid. $^1$H NMR (400 MHz, Methanol-d$_4$) δ 9.37 (s, 1H), 8.25-8.23 (m, 2H), 8.13 (d, J=1.6 Hz, 1H), 7.80 (d, J=3.2 Hz, 1H), 7.61-7.56 (m, 1H), 7.03 (d, J=8.0 Hz, 1H), 4.18-4.15 (m, 1H), 4.14-3.95 (m, 2H), 3.83-3.70 (m, 1H), 3.64-3.48 (m,

334

2H), 3.45-3.35 (m, 2H), 2.71-2.03 (m, 4H), 1.73-1.23 (m, 3H). LCMS (ESI, m/z): 425 [M+H]$^+$.

Example 21: Synthesis of N-(2-(octahydro-2H-quinolizin-1-yl)thieno[2,3-b]pyridin-4-yl)benzo[d]thiazol-5-amine

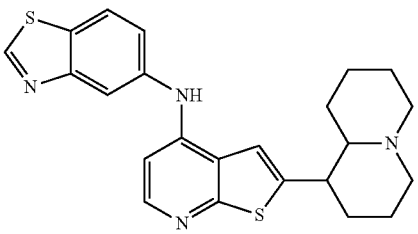 [SMILES: c1cc(Nc2ccc3scnc3c2)c2cc(C3CCCN4CCCCC34)sc2n1]

Step 1

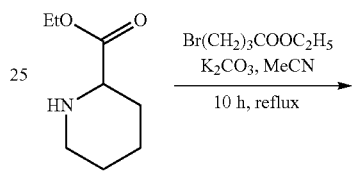

Ethyl piperidine-2-carboxylate (2.0 g, 12.739 mmol, 1.00 equiv), Br(CH$_2$)$_3$COOC$_2$H$_5$ (2.8 g, 14.508 mmol, 1.00 equiv) and K$_2$CO$_3$ (5.6 g, 40.580 mmol, 3.00 equiv) in MeCN (200 ml) were placed in a 100-ml round-bottom flask. The resulting solution was stirred at 60° C. for 10 h. LCMS showed the reaction was complete. The solid was filtered out and the filtrate was concentrated under reduced pressure to give the crude product ethyl 1-(4-ethoxy-4-oxobutyl)piperidine-2-carboxylate (Example 21-1), which was used directly for the next step without further purification. LCMS (ESI, m/z): 272 [M+H]$^+$.

Step 2

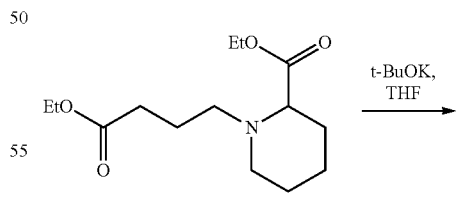

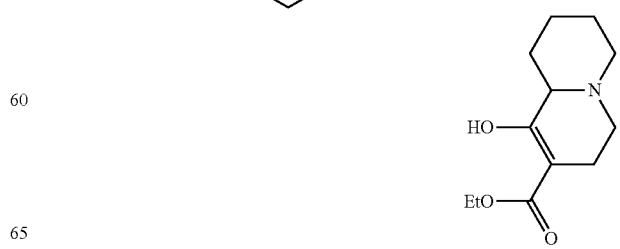

Ethyl 1-(4-ethoxy-4-oxo-butyl)piperidine-2-carboxylate (Example 21-1, crude, 1.8 g, 6.617 mmol, 1.00 equiv) and t-BuOK (2.5 g, 22.321 mmol, 3.00 equiv) in THF (10 ml) were placed in a 100-ml round-bottom flask. The resulting solution was stirred at 0° C. for 1 h. The reaction solution was allowed to warm up to room temperature slowly and stirred for 1 h. LCMS showed the reaction was complete. The resulting solution was quenched with water (100 mL) and extracted with ethyl acetate (3×100 mL). The combined organic layer was washed with sodium carbonate and brine, dried over Na$_2$SO$_4$ and concentrated under reduced pressure. The residue was purified by flash reverse chromatography (H$_2$O/ACN=5/1) to give the desired product ethyl 9-hydroxy-1,3,4,6,7,9a-hexahydro-2H-quinolizine-8-carboxylate (Example 21-2, 0.7 g, 47%) as a yellow oil. LCMS (ESI, m/z): 226 [M+H]$^+$.

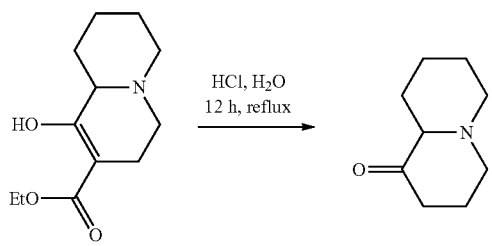 [SMILES: CCOC(=O)C1=C(O)C2CCCCN2CC1 ; O=C1CCCN2CCCCC12]

Step 3

Ethyl 9-hydroxy-1,3,4,6,7,9a-hexahydro-2H-quinolizine-8-carboxylate (Example 21-2, 700 mg, 3.097 mmol, 1.00 equiv) in hydrochloric acid (concentrated, 2 ml) and H$_2$O (2 ml) was placed in a 100-ml round-bottom flask. The resulting solution was stirred at 100° C. for 12 h. LCMS showed the reaction was complete. The solution was concentrated under reduced pressure to give the crude product hexahydro-2H-quinolizin-1(6H)-one (Example 21-3, 500 mg) as a brown oil. LCMS (ESI, m/z): 154 [M+H]$^+$.

Step 4

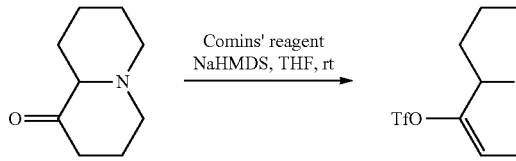

A solution of hexahydro-2H-quinolizin-1(6H)-one (Example 21-3, 350 mg, 2.272 mmol, 1.00 equiv) in THF (20 ml) was treated with NaHMDS (2 mol/mL in THF, 2 mL, 4.000 mmol, 1.75 equiv) at −78° C. for 0.5 h. Comins' reagent (896 mg, 2.286 mmol, 2.50 equiv) was added dropwise under N$_2$ atmosphere and the resulting mixture was stirred at room temperature for 1 h. LCMS showed the reaction was complete. The reaction was quenched with ice-water (50 mL). The aqueous layer was extracted with EA (3×50 mL). The combined organic extract was washed with saturated brine (50 mL), dried over Na$_2$SO$_4$, concentrated and purified by flash chromatography on silica gel (EA/PE=1/10) to give 1,3,4,6,7,9a-hexahydro-2H-quinolizin-9-yl trifluoromethanesulfonate (Example 21-4, 300 mg, 46%) as a yellow oil. LCMS (ESI, m/z): 286 [M+H]$^+$.

Step 5

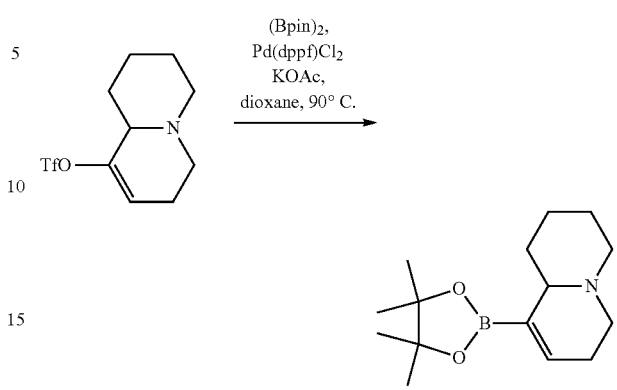

A solution of 1,3,4,6,7,9a-hexahydro-2H-quinolizin-9-yl trifluoromethanesulfonate (Example 21-4, 300 mg, 1.049 mmol, 1.00 equiv), (Bpin)$_2$ (346 mg, 1.362 mmol, 1.30 equiv), Pd(dppf)Cl$_2$ (38 mg, 0.052 mmol. 0.50 equiv) and potassium acetate (308 mg, 3.142 mmol, 3.00 equiv) in 1,4-dioxane (20 ml) was placed in a 100-ml round-bottom flask. The resulting solution was stirred at 90° C. for 2 h under N$_2$ atmosphere. LCMS showed the reaction was complete. The solution was diluted with 20 ml of water and extracted with ethyl acetate (3×20 mL). The combined organic layer was washed with sodium carbonate and brine, dried over Na$_2$SO$_4$, and concentrated under reduced pressure. The residue was purified by flash chromatography on silica gel (MeOH/DCM=1/10) to give the desired product 9-(4,4,5,5-tetramethyl-1,3,2-dioxaborolan-2-yl)-1,3,4,6,7,9a-hexahydro-2H-quinolizine (Example 21-5, 200 mg, 72%) as a brown oil. LCMS (ESI, m/z): 264 [M+H]$^+$ Step 6

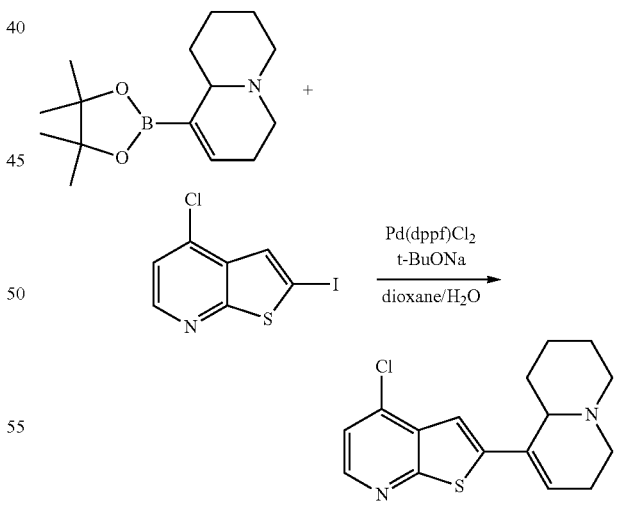

A mixture of 4-chloro-2-iodo-thieno[2,3-b]pyridine (1 g, 3.38 mmol) and 9-(4,4,5,5-tetramethyl-1,3,2-dioxaborolan-2-yl)-2,3,4,6,7,9a-hexahydro-1H-quinolizine (Example 21-5, 0.89 g, 3.38 mmol), Pd(dppf)Cl$_2$ (0.25 g, 0.3400 mmol), t-BuONa (0.97 g, 10.15 mmol) in 1,4-dioxane (20 mL) and water (2 mL) was placed in a 100 ml round-bottom flask. The flask was evacuated and flushed three times with nitrogen, followed by flushing with nitrogen. The resulting solution was stirred for 1 h at 90° C. in an oil bath. LCMS showed the reaction was complete. The mixture was diluted with 50 ml of water, then extracted with ethyl acetate. The organic layers were combined, washed with sodium carbonate, dried and concentrated under vacuum. The residue was purified by flash chromatography on silica gel (EA/PE=1/1) to give 4-chloro-2-(1,3,4,6,7,9a-hexahydro-2H-quinolizin-9-yl)thieno[2,3-b]pyridine (Example 21-6, 800 mg, 77% yield) as a light brown solid. LCMS (ESI, m/z): 305 [M+H]$^+$.

Step 7

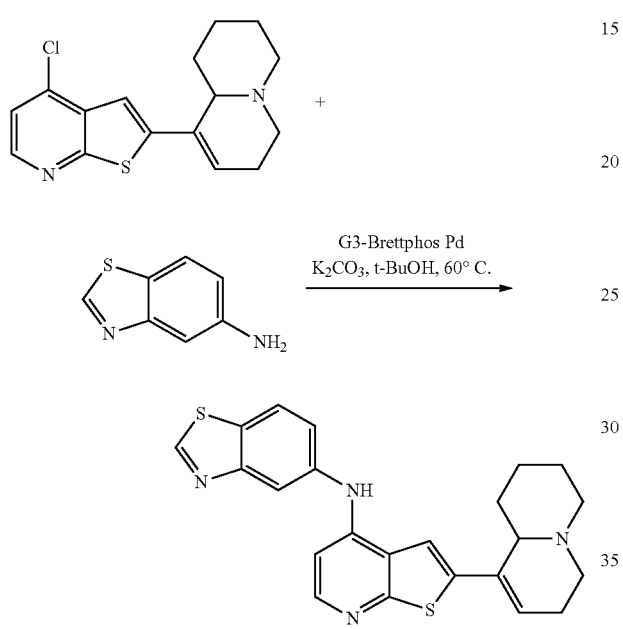

A solution of 4-chloro-2-(1,3,4,6,7,9a-hexahydro-2H-quinolizin-9-yl)thieno[2,3-b]pyridine (Example 21-6, 100 mg, 0.329 mmol, 1.00 equiv), benzo[d]thiazol-5-amine (55 mg, 0.294 mmol, 1.00 equiv), K$_2$CO$_3$(135 mg, 0.967 mmol, 3.00 equiv) and G3-Brettphos Pd (30 mg, 0.033 mmol, 0.10 equiv) in t-BuOH (5 ml) was placed in a 25-ml round-bottom flask. The resulting solution was stirred at 60° C. for 2 h under N$_2$ atmosphere. LCMS showed the reaction was complete. The residue was purified by flash chromatography on silica gel (MeOH/DCM=1/10) to give the desired product N-(2-(1,3,4,6,7,9a-hexahydro-2H-quinolizin-9-yl)thieno[2,3-b]pyridin-4-yl)benzo[d]thiazol-5-amine (Example 21-7, 60 mg, 36%) as a yellow oil. LCMS (ESI, m/z): 417 [M+H]$^+$.

Step 8

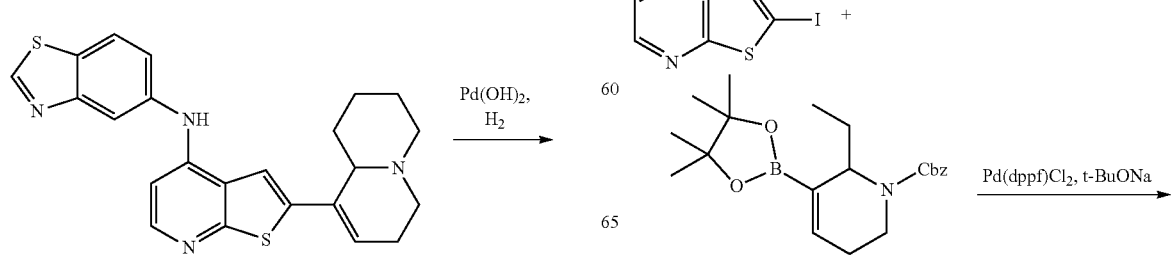

To a solution of N-(2-(1,3,4,6,7,9a-hexahydro-2H-quinolizin-9-yl)thieno[2,3-b]pyridin-4-yl)benzo[d]thiazol-5-amine (Example 21-7, 100.0 mg, 0.240 mmol, 1.00 equiv) was added Pd(OH)$_2$ (100 mg, 1.00 w/w) in ethanol (10 mL). The resulting solution was stirred at room temperature for 15 h under H$_2$ atmosphere. LCMS showed the reaction was complete. The solid was filtered out and the filtrate was concentrated under reduced pressure. The residue was purified by preparative HPLC (Column: XBridge Shield RP18 OBD Column, 19×250 mm, 10 μm; Mobile Phase A: Water (10 mmol/L NH$_4$HCO$_3$), Mobile Phase B: ACN; Flow rate: 25 mL/min; Gradient: 70% B to 90% B in 7 min; 254/210 nm; Rt: 6.95 min) to give the desired product N-(2-(octahydro-2H-quinolizin-1-yl)thieno[2,3-b]pyridin-4-yl)benzo[d]thiazol-5-amine (Example 21, 19.2 mg, 19%) as a white solid. $^1$H NMR (400 MHz, Methanol-d$_4$) δ 9.27 (s, 1H), 8.08-8.07 (m, 2H), 7.99 (s, 1H), 7.53-7.50 (m, 1H), 7.42 (s, 1H), 6.98 (d, J=5.6 Hz, 1H), 2.92-2.89 (m, 2H), 2.42-1.95 (m, 4H), 1.92-1.79 (m, 2H), 1.79-1.65 (m, 1H), 1.67-1.53 (m, 3H), 1.44-1.28 (m, 4H). LCMS (ESI, m/z): 421 [M+H]$^+$.

Example 22: Synthesis of N-(2-(2-ethylpiperidin-3-yl)thieno[2,3-b]pyridin-4-yl)benzo[d]thiazol-5-amine Step 1

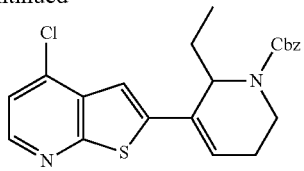

To a stirred solution of 4-chloro-2-iodo-thieno[2,3-b]pyridine (660 mg, 2.233 mmol, 1.00 equiv) in 1,4-dioxane (10 mL) and H₂O (1 mL) was added benzyl 6-ethyl-5-(4,4,5,5-tetramethyl-1,3,2-dioxaborolan-2-yl)-3,6-dihydropyridine-1(2H)-carboxylate (1.0 g, 2.693 mmol, 1.20 equiv), Pd(dppf)Cl₂ (175 mg, 0.224 mmol, 0.10 equiv) and t-BuONa (680 mg, 7.0833 mmol, 3.00 equiv). The reaction mixture was stirred at 80° C. for 4 h. LCMS showed the reaction was complete. The resulting mixture was diluted with water (25 mL) and extracted with EA (3×50 mL). The combined organic layer was dried over Na₂SO₄, filtered and concentrated under reduced pressure. The crude product was purified by silica chromatography (EA/PE=20/80) to obtain benzyl 5-(4-chlorothieno[2,3-b]pyridin-2-yl)-6-ethyl-3,6-dihydropyridine-1(2H)-carboxylate (Example 22-1, 330 mg, 36%) as a light yellow solid. LCMS (ESI, m/z): 413 [M+H]⁺.

Step 2

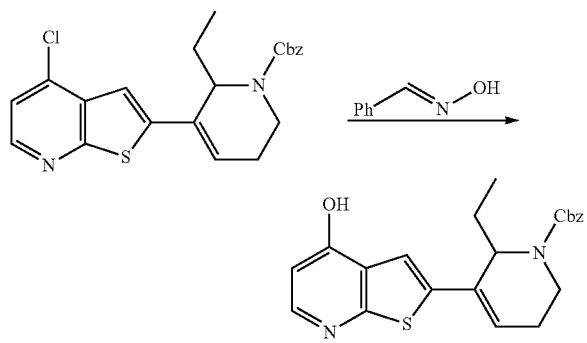

To a stirred solution of benzyl 5-(4-chlorothieno[2,3-b]pyridin-2-yl)-6-ethyl-3,6-dihydropyridine-1(2H)-carboxylate (Example 22-1, 330 mg, 0.799 mmol, 1.00 equiv) in DMF (5 mL) was added (E)-benzaldehyde oxime (290 mg, 2.397 mmol, 3.00 equiv), K₂CO₃ (330 mg, 2.397 mmol, 3.00 equiv) and Rockphos (33 mg, 0.040 mmol, 0.05 equiv). The reaction mixture was stirred at 80° C. for 20 h. LCMS showed the reaction was complete. The crude product was purified by silica gel flash chromatograph (MeOH/DCM=1/10) to obtain benzyl 6-ethyl-5-(4-hydroxythieno[2,3]pyridin-2-yl)-3,6-dihydropyridine-1(2H)-carboxylate (Example 22-2, 170 mg, 54%) as a light yellow oil. LCMS (ESI, m/z): 395 [M+H]⁺.

Step 3

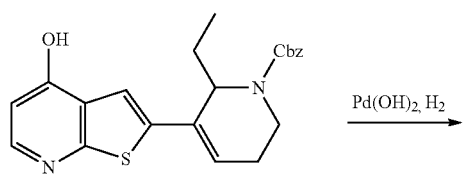

To a stirred solution benzyl 6-ethyl-5-(4-hydroxythieno[2,3-b]pyridin-2-yl)-3,6-dihydropyridine-1(2H)-carboxylate (Example 22-2, 150 mg, 0.380 mmol, 1.00 equiv) in EtOH (20 mL) was added Pd(OH)₂ (150 mg, 1.00 w/w). The mixture was stirred at 65° C. for 24 h under H₂ atmosphere (1-3 atm). LCMS showed the reaction was complete. Then the mixture was filtered and concentrated to obtain benzyl 2-ethyl-3-(4-hydroxythieno[2,3-b]pyridin-2-yl)piperidine-1-carboxylate (Example 22-3, 140 mg, crude) as a light yellow oil. LCMS (ESI, m/z): 397 [M+H]⁺.

Step 4

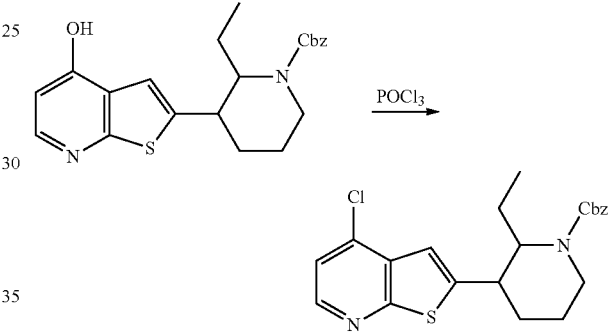

Benzyl 2-ethyl-3-(4-hydroxythieno[2,3-b]pyridin-2-yl)piperidine-1-carboxylate (Example 22-3, 160 mg, 0.404 mmol, 1.00 equiv) was dissolved in POCl₃ (4 mL, 1.21 mmol, 3.00 equiv). The resulting mixture was stirred at 75° C. for 3 h. LCMS showed the reaction was complete. The solvent was removed under reduced pressure and the residue was quenched with NaHCO₃(aq., 10 mL). The mixture was extracted with EA (3×50 mL). The combined organic layer was dried over Na₂SO₄, filtered and concentrated under reduced pressure. The crude product was purified by silica gel flash chromatography (EA/PE=75/25) to give benzyl 3-(4-chlorothieno[2,3-b]pyridin-2-yl)-2-ethyl-piperidine-1-carboxylate (Example 22-4, 80 mg, 48%) of as a light yellow solid. LCMS (ESI, m/z): 415 [M+H]⁺.

Step 5

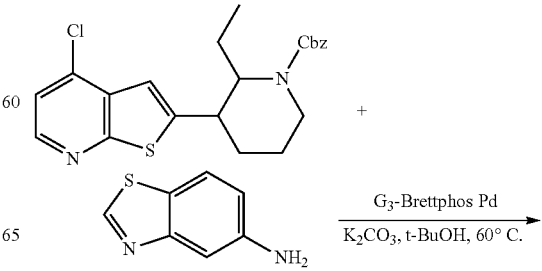

-continued

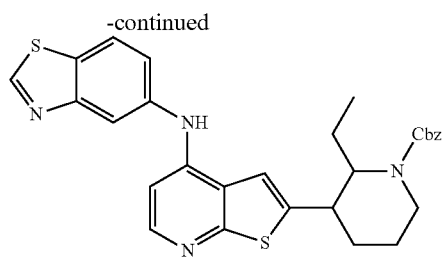

To a stirred solution of benzyl 3-(4-chlorothieno[2,3-b]pyridin-2-yl)-2-ethyl-piperidine-1-carboxylate (Example 22-4, 80 mg, 0.193 mmol, 1.00 equiv) in t-BuOH (3 mL) was added 1,3-benzothiazol-5-amine (29 mg, 0.193 mmol, 1.00 equiv), G3-Brettphos Pd (17.4 mg, 0.019 mmol, 0.10 equiv) and $K_2CO_3$ (80 mg, 0.578 mmol, 3.00 equiv). The resulting mixture was stirred at 60° C. for 2 h under $N_2$ atmosphere. LCMS showed the reaction was complete. The solvent was removed under reduced pressure and the residue was purified by silica column (MeOH/DCM=1/10) to obtain benzyl 3-(4-(benzo[d]thiazol-5-ylamino)thieno[2,3-b]pyridin-2-yl)-2-ethylpiperidine-1-carboxylate (Example 22-5, 50 mg, 50%) as a light yellow solid. LCMS (ESI, m/z): 529 $[M+H]^+$.

Step 6

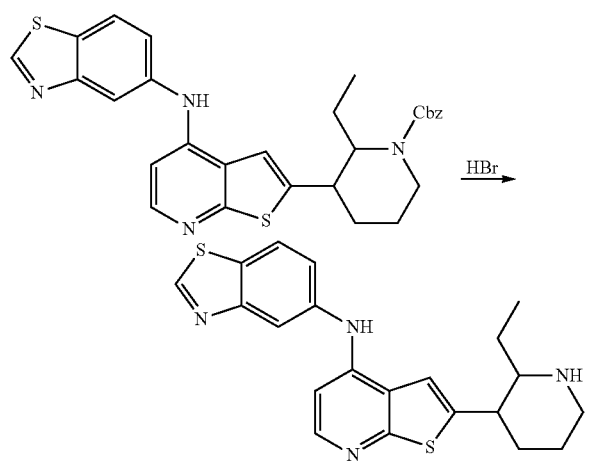

To a stirred solution of benzyl 3-(4-(benzo[d]thiazol-5-ylamino)thieno[2,3-b]pyridin-2-yl)-2-ethylpiperidine-1-carboxylate (Example 22-5, 50 mg, 0.095 mmol) in HBr (8 mL) and $H_2O$ (12 mL) at room temperature for 1.5 h. LCMS showed the reaction was complete. The solvent was removed under reduced pressure. The obtained orange sticky solid of crude N-(2-(2-ethylpiperidin-3-yl)thieno[2,3] pyridin-4-yl)benzo[d]thiazol-5-amine (Example 22) was further purified by preparative HPLC using the following gradient conditions: Column: XBridge Prep C18 OBD Column, 19×150 mm 5 μm; Mobile Phase A: Water (10 mmol/L $NH_4HCO_3$+0.1% $NH_3H_2O$), Mobile Phase B: ACN; Flow rate: 25 mL/min; Gradient: 30% B to 58% B in 7 min; 254 nm; Rt: 6.03/6.55 min. Purification gave Example 22a (6.4 mg, 17%). $^1$H NMR (400 MHz, Methanol-$d_4$) δ 9.30 (s, 1H), 8.14-8.07 (m, 2H), 8.03 (d, J=2.1 Hz, 1H), 7.55 (dd, J=8.6, 2.1 Hz, 1H), 7.46 (d, J=0.9 Hz, 1H), 7.02 (d, J=5.7 Hz, 1H), 3.45-3.38 (m, 1H), 3.12-3.03 (m, 1H), 2.97 (s, 1H), 2.85-2.76 (m, 1H), 2.08-2.00 (m, 2H), 2.04-1.93 (m, 1H), 1.64 (s, 1H), 1.53 (dq, J=15.0, 7.5 Hz, 1H), 1.31 (dq, J=14.4, 7.0 Hz, 1H), 0.93 (t, J=7.5 Hz, 3H). LCMS (ESI, m/z): 395 $[M+H]^+$; and Example 22b (3.2 mg, 9%). $^1$H NMR (400 MHz, Methanol-$d_4$) δ 9.30 (s, 1H), 8.05-8.15 (m, 2H), 8.02 (d, J=2.1 Hz, 1H), 7.54 (dd, J=8.6, 2.1 Hz, 1H), 7.41 (s, 1H), 7.02 (d, J=5.7 Hz, 1H), 3.20-3.10 (m, 1H), 2.90-2.76 (m, 2H), 2.71 (t, J=9.1 Hz, 1H), 2.16 (d, J=12.9 Hz, 1H), 1.88-1.56 (m, 4H), 1.34 (dt, J=14.1, 7.2 Hz, 1H), 0.94 (t, J=7.5 Hz, 3H). LCMS (ESI, m/z): 395 $[M+H]^+$.

Example 23: Synthesis of N-(2-(2-ethyl-1-methylpiperidin-3-yl)thieno[2,3-b]pyridin-4-yl)benzo[d]thiazol-5-amine

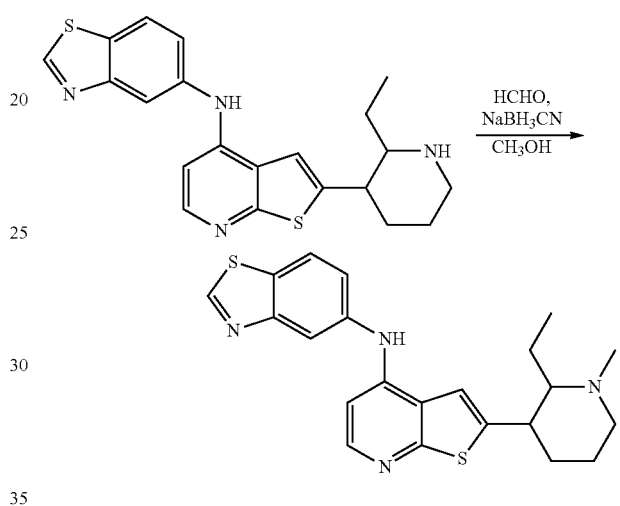

To a stirred solution of crude N-(2-(2-ethylpiperidin-3-yl)thieno[2,3-b]pyridin-4-yl)benzo[d]-thiazol-5-amine (Example 22, 80 mg, 0.203 mmol, 1.00 equiv) in MeOH (3 mL) was added TEA (cat.) to prepare the freebase, followed by addition of HCHO (12 mg, 0.406 mmol, 2.00 equiv). After acidifying with HOAc, $NaBH_3CN$ (25 mg, 0.406 mmol, 2.00 equiv) was added. The reaction mixture was stirred at rt for 1 h. LCMS showed the reaction was complete. The solvent was removed under reduced pressure and the crude product N-(2-(2-ethyl-1-methylpiperidin-3-yl)thieno[2,3-b]pyridin-4-yl)benzo[d]thiazol-5-amine (Example 23) was purified by preparative HPLC using the following gradient conditions: Column: XBridge Prep C18 OBD Column, 19×150 mm, 5 μm; Mobile Phase A: Water (10 mmol/L $NH_4HCO_3$+0.1% $NH_3H_2O$), Mobile Phase B: ACN; Flow rate: 25 mL/min; Gradient: 30% B to 52% B in 13 min; 254 nm; Rt: 9.40/11.92 min. Purification gave Example 23a (11.5 mg, 14%) as a white solid. $^1$H NMR (400 MHz, Methanol-$d_4$) δ 9.30 (s, 1H), 8.13-8.07 (m, 2H), 8.03 (d, J=2.1 Hz, 1H), 7.54 (dd, J=8.6, 2.1 Hz, 1H), 7.46 (d, J=1.0 Hz, 1H), 7.01 (d, J=5.7 Hz, 1H), 3.54-3.48 (m, 1H), 2.90-2.75 (m, 1H), 2.70-2.60 (m, 1H), 2.50-2.40 (m, 4H), 1.98-1.86 (m, 3H), 1.80-1.60 (s, 2H), 1.35-1.25 (m, 1H), 0.82 (t, J=7.5 Hz, 3H). LCMS (ESI, m/z): 409 $[M+H]^+$. As well as Example 23b (7.7 mg, 9%) as a white solid. $^1$H NMR (400 MHz, Methanol-$d_4$) δ 9.30 (s, 1H), 8.15-8.05 (m, 2H), 8.02 (d, J=2.1 Hz, 1H), 7.54 (dd, J=8.6, 2.1 Hz, 1H), 7.41 (s, 1H), 7.02 (d, J=5.7 Hz, 1H), 3.20-3.00 (m, 2H), 2.50-2.30 (m, 5H), 2.20-2.10 (m, 1H), 1.95-1.65 (m, 4H), 1.55-1.40 (m, 1H), 0.94 (t, J=7.5 Hz, 3H). LCMS (ESI, m/z): 409 $[M+H]^+$.

Example 24: Synthesis of N-(2-(1,2-diethylpiperidin-3-yl)thieno[2,3-b]pyridin-4-yl)benzo[d]thiazol-5-amine

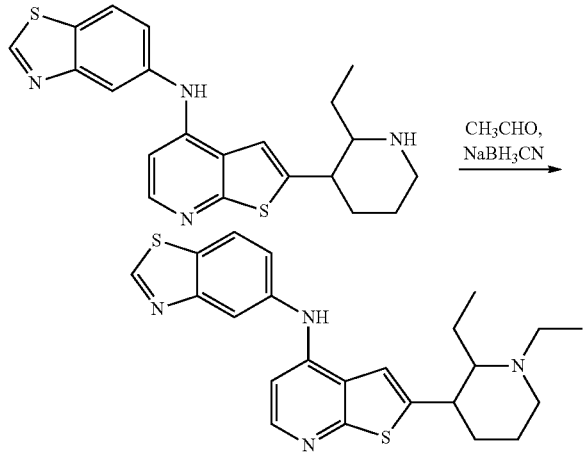

Into a 25-mL round-bottom flask was placed N-(2-(2-ethylpiperidin-3-yl)thieno[2,3-b]pyridin-4-yl)benzo[d]thiazol-5-amine (Example 22, 70 mg, 0.180 mmol, 1.00 equiv). Methanol (5 mL), 20 μL TEA (cat.) and CH$_3$CHO (16 mg, 0.350 mmol, 2.00 equiv) were added. The mixture was stirred for 10 min, then HOAc (50 μL) and NaBH$_3$CN (22 mg, 0.350 mmol, 2.00 equiv) were added. The resulting solution was stirred at room temperature for 20 min. LCMS showed the reaction was complete. The solvent was removed under reduced pressure and the crude product was purified by preparative HPLC using the following gradient conditions: Column: Atlantis HILIC OBD Column, 19×150 mm, 5 μm; Phase A: Water (0.05% TFA), Phase B: ACN; Flow Rate:25 mL/min; Wave Length: 254/210. Purification gave the desired product N-(2-(1,2-diethylpiperidin-3-yl)thieno[2,3-b]pyridin-4-yl)benzo[d]thiazol-5-amine (Example 24, 22 mg, 29%) as a light yellow solid. $^1$H NMR (400 MHz, Methanol-d$_4$) δ 9.41 (s, 1H), 8.39-8.21 (m, 2H), 8.15 (d, J=2.1 Hz, 1H), 7.81 (s, 1H), 7.60 (dd, J=8.5, 2.1 Hz, 1H), 7.06 (d, J=6.8 Hz, 1H), 3.80-3.45 (m, 3H), 3.44-25 (m, 3H), 2.53-1.92 (m, 5H), 1.88-1.58 (m, 1H), 1.44 (t, J=7.2 Hz, 3H), 1.06 (t, J=7.5 Hz, 3H). LCMS (ESI, m/z): 423 [M+H]$^+$.

Example 25: Synthesis of N-(2-(2-methyl-2,5-dihydro-1H-pyrrol-3-yl)thieno[2,3-b]pyridin-4-yl)benzo[d]thiazol-5-amine

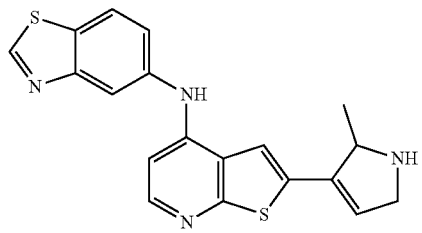 [SMILES: CC1NCC=C1c1cc2c(Nc3ccc4scnc4c3)ccnc2s1]

Step 1

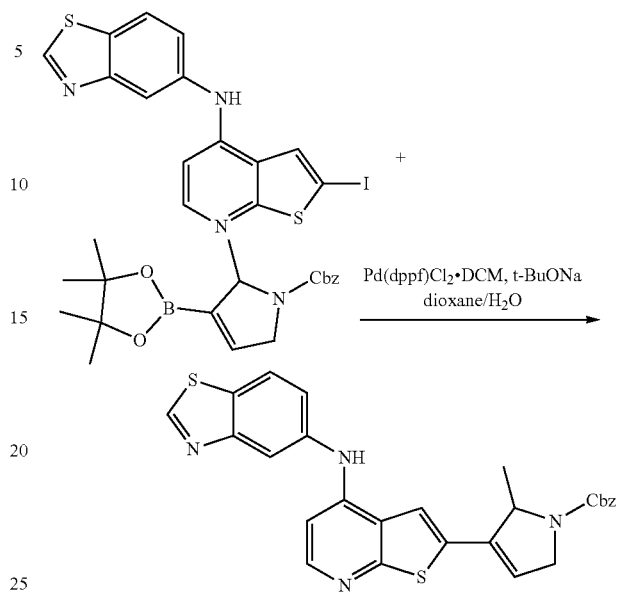

To a solution of N-(2-iodothieno[2,3-b]pyridin-4-yl)benzo[d]thiazol-5-amine (450 mg, 0.770 mmol, 1.00 equiv) in 1,4-dioxane (4 mL) and water (0.4 mL) was added benzyl 2-methyl-3-(4,4,5,5-tetramethyl-1,3,2-dioxaborolan-2-yl)-2,5-dihydro-1H-pyrrole-1-carboxylate (266 mg, 0.770 mmol, 1.00 equiv), Pd(dppf)Cl$_2$.CH$_2$Cl$_2$ (63 mg, 0.080 mmol, 0.10 equiv) and t-BuONa (223 mg, 2.320 mmol, 3.00 equiv). The resulting mixture was stirred for 15h at 80° C. TLC showed the reaction was complete. The solid was filtered out and the filtrate was concentrated. The residue was purified by silica gel flash chromatography (PE/EA=1/1) to afford benzyl 3-(4-(benzo[d]thiazol-5-ylamino)thieno[2,3-b]pyridin-2-yl)-2-methyl-2,5-dihydro-1H-pyrrole-1-carboxylate (Example 25-1, 260 mg, 68%) as a light yellow solid. LCMS (ESI, m/z): 499 [M+H]$^+$.

Step 2

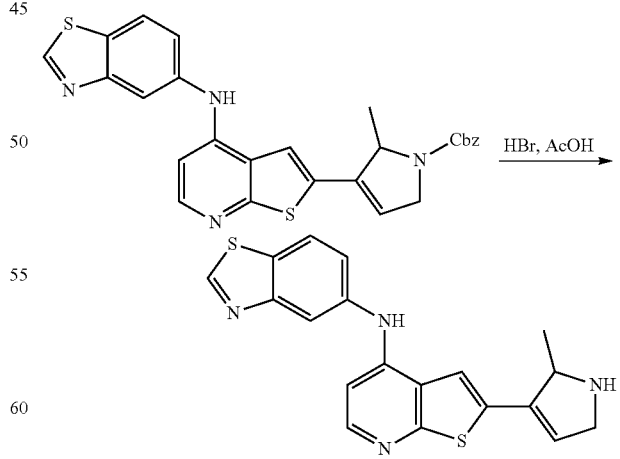

Benzyl 3-(4-(benzo[d]thiazol-5-ylamino)thieno[2,3-b]pyridin-2-yl)-2-methyl-2,5-dihydro-1H-pyrrole-1-carboxylate (Example 25-1, 540 mg, 1.080 mmol, 1.00 equiv) was dissolved in HBr (40% in AcOH, 5 mL). The resulting mixture was stirred for 1 h at room temperature. TLC showed the reaction was complete. The reaction mixture was quenched with saturated Na₂CO₃ (aq.) and extracted with EA. The combined organic layer was washed with brine and dried over Na₂SO₄, filtered and concentrated to afford 500 mg of the crude product. 80 mg of the crude product was purified by preparative HPLC (Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 9% B to 30% B in 7 min; 254 nm; Rt: 6.12 min) to afford N-(2-(2-methyl-2,5-dihydro-1H-pyrrol-3-yl)thieno[2,3-b]pyridin-4-yl)benzo[d]thiazol-5-amine (Example 25, 21.5 mg, 6%) as a white solid. ¹H NMR (400 MHz, Methanol-d₄) δ 9.39 (s, 1H), 8.27-8.20 (m, 2H), 8.16 (d, J=2.1 Hz, 1H), 7.91 (s, 1H), 7.61 (dd, J=8.5, 2.1 Hz, 1H), 7.07 (d, J=6.8 Hz, 1H), 6.42 (s, 1H), 5.14-5.01 (m, 1H), 4.47-4.21 (m, 2H), 1.74 (d, J=6.8 Hz, 3H). LCMS (ESI, m/z): 365 [M+H]⁺.

Example 26: Synthesis of N-(2-(2-methylpyrrolidin-3-yl)thieno[2,3-b]pyridin-4-yl)benzo[d]thiazol-5-amine

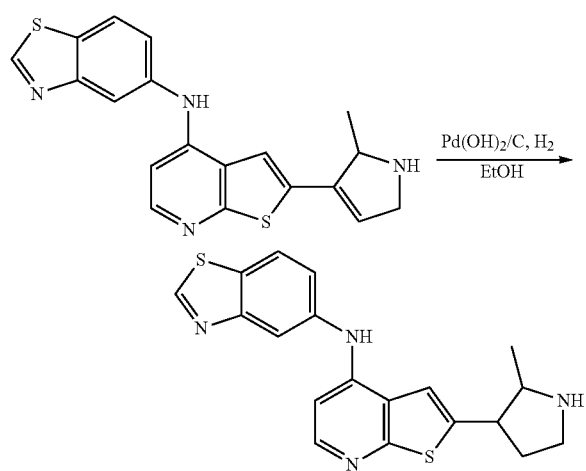

To a solution of the compound N-(2-(2-methyl-2,5-dihydro-1H-pyrrol-3-yl)thieno[2,3-b]pyridin-4-yl)benzo[d]thiazol-5-amine (Example 25, 110 mg, 0.300 mmol, 1.00 equiv) in ethanol (10 mL) was added Pd(OH)₂/C (110 mg, 1.00 w/w). The resulting mixture was stirred for 48 h at 60° C. under an atmosphere of hydrogen (1-3 atm.). TLC showed the reaction was complete. The solid was filtered out and the filtrate was concentrated. The residue was purified by preparative HPLC (Column: Sunfire Prep C18 OBD Column, 19×250 mm, 10 μm; Mobile Phase A: Water (0.05% TFA), Mobile Phase B: ACN; Flow rate: 25 mL/min; Gradient: 30% B to 50% B in 8 min; 254/210 nm; Rt: 7.65 min) to afford N-(2-(2-methylpyrrolidin-3-yl)thieno[2,3-b]pyridin-4-yl)benzo[d]thiazol-5-amine (Example 26, 22.2 mg, 21%) as a white solid. ¹H NMR (400 MHz, Methanol-d₄): δ 9.40 (s, 1H), 8.35-8.25 (m, 2H), 8.17 (s, 1H), 7.86 (s, 1H), 7.61 (d, J=8.6 Hz, 1H), 7.06 (d, J=6.9 Hz, 1H), 4.30-4.02 (m, 1H), 3.86-3.45 (m, 3H), 2.80-2.31 (m, 2H), 1.56 (d, J=6.4 Hz, 1H), 1.25 (d, J=6.9 Hz, 2H). LCMS (ESI, m/z): 367 [M+H]⁺.

Example 27: Synthesis of N-(2-(1,2-dimethyl-2,5-dihydro-1H-pyrrol-3-yl)thieno[2,3-b]pyridin-4-yl)benzo[d]thiazol-5-amine

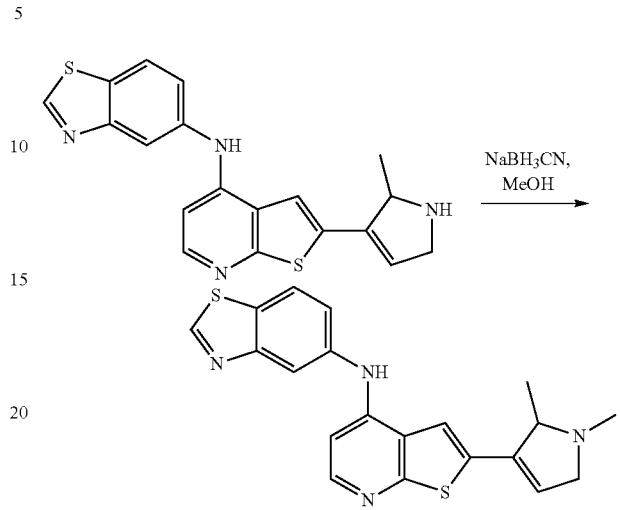

To a solution of N-(2-(2-methyl-2,5-dihydro-1H-pyrrol-3-yl)thieno[2,3-b)]pyridin-4-yl)benzo[d]-thiazol-5-amine (Example 25, 395 mg, 1.080 mmol, 1.00 equiv) in methanol (10 mL) was added AcOH (0.01 mL, 0.110 mmol, 0.10 equiv), HCHO (97 mg, 3.250 mmol, 3.00 equiv). The mixture was stirred for 10 min at 0° C. Then NaBH₃CN (204 mg, 3.250 mmol, 3.00 equiv) was added slowly. The resulting mixture was stirred for 1 h at room temperature. TLC showed the reaction was complete. The reaction mixture was quenched with water and extracted with EA. The organic layer was washed with brine, dried over Na₂SO₄, filtered and concentrated. The residue was purified by preparative HPLC (Column: XBridge Prep C18 OBD Column, 19×150 mm, 5 μm; Mobile Phase A: Water (0.05% TFA), Mobile Phase B: ACN; Flow rate: 25 mL/min; Gradient: 30% B to 45% B in 8 min; 254/220 nm; Rt: 6.75 min) to afford N-(2-(1,2-dimethyl-2,5-dihydro-1H-pyrrol-3-yl)thieno[2,3-b]pyridin-4-yl)benzo[d]thiazol-5-amine (Example 27, 33.6 mg, 8%) as a light yellow solid. ¹H NMR (400 MHz, Methanol-d₄) δ 9.40 (s, 1H), 8.33-8.25 (m, 2H), 8.17 (d, J=2.1 Hz, 1H), 7.92 (s, 1H), 7.61 (dd, J=8.5, 2.1 Hz, 1H), 7.07 (d, J=6.9 Hz, 1H), 6.45 (brs, 1H), 5.00-4.80 (m, 1H), 4.70-4.50 (m, 1H), 4.30-4.10 (m, 1H), 3.14 (s, 3H), 1.76 (d, J=6.6 Hz, 3H). LCMS (ESI, m/z): 379 [M+H]⁺.

Example 28: Synthesis of N-(2-(1,2-dimethylpyrrolidin-3-yl)thieno[2,3-b]pyridin-4-yl)benzo[d]thiazol-5-amine

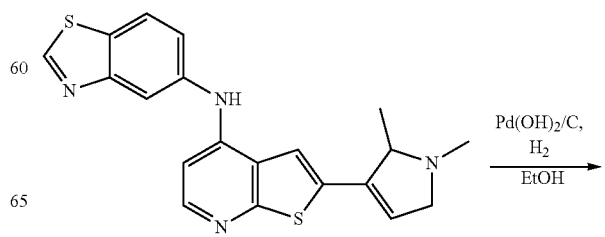

-continued

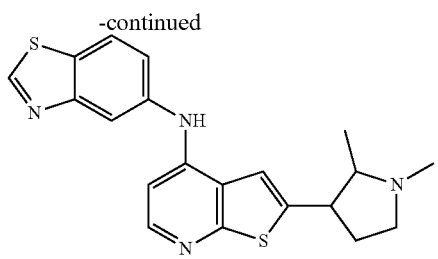

To a solution of N-(2-(1,2-dimethyl-2,5-dihydro-1H-pyrrol-3-yl)thieno[2,3-b]pyridin-4-yl)benzo[d]-thiazol-5-amine (Example 27, 80 mg, 0.210 mmol, 1.00 equiv) in ethanol (10 mL) was added Pd(OH)$_2$/C (80 mg, 1.00 w/w). The resulting mixture was stirred for 48 h at 60° C. under an atmosphere of hydrogen (1-3 atm.). TLC showed the reaction was complete. The solid was filtered out and the filtrate was concentrated. The residue was purified by preparative HPLC (Column: XBridge Prep C18 OBD Column, 19×150 mm 5 μm; Mobile Phase A: Water (0.05% TFA), Mobile Phase B: ACN; Flow rate: 25 mL/min; Gradient: 30% B to 50% B in 8 min; 254/220 nm; Rt: 7.65 min) to afford N-(2-(1,2-dimethylpyrrolidin-3-yl)thieno[2,3-b]-pyridin-4-yl)benzo[d]thiazol-5-amine (Example 28, 12.1 mg, 15%) as a white solid. $^1$H NMR (400 MHz, Methanol-d$_4$): δ 9.40 (s, 1H), 8.35-8.25 (m, 2H), 8.17 (d, J=1.9 Hz, 1H), 7.88 (t, J=4.3 Hz, 1H), 7.61 (d, J=8.6 Hz, 1H), 7.06 (d, J=6.9 Hz, 1H), 4.42-3.84 (m, 2H), 3.83-3.39 (m, 2H), 3.07 (s, 3H), 2.84-2.67 (m, 1H), 2.64-2.35 (m, 1H), 1.55 (d, J=6.3 Hz, 1H), 1.30 (d, J=6.7 Hz, 2H). LCMS (ESI, m/z): 381 [M+H]$^+$.

Example 29: Synthesis of N-(2-(1-ethyl-2-methyl-2,5-dihydro-1H-pyrrol-3-yl)thieno[2,3-b]pyridin-4-yl)benzo[d]thiazol-5-amine

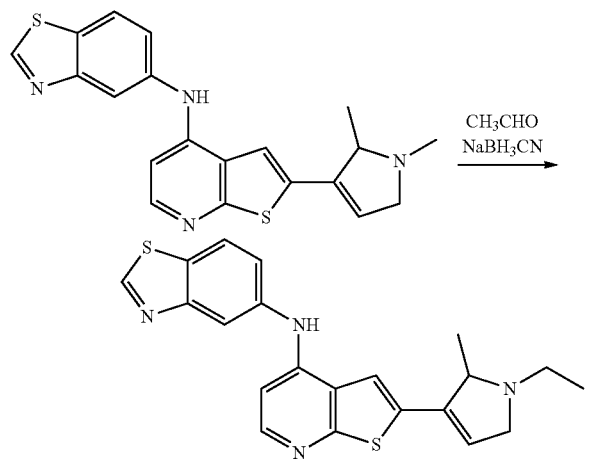

To a solution of N-(2-(2-methyl-2,5-dihydro-1H-pyrrol-3-yl)thieno[2,3-b]pyridin-4-yl)benzo[d]-thiazol-5-amine (Example 25, 120 mg, 0.328 mmol, 1.00 equiv) in MeOH (5 mL) was added CH$_3$CHO (29 mg, 0.658 mmol, 2.00 equiv). The resulting solution was stirred at room temperature for 30 min and NaBH$_3$CN (62 mg, 0.986 mmol, 3.00 equiv) was added. After stirring for 1 h, LCMS showed the reaction was complete. The reaction mixture was concentrated under reduced pressure. The crude product was purified by flash chromatography on silica gel (EA/PE=1/2) to afford N-(2-(1-ethyl-2-methyl-2,5-dihydro-1H-pyrrol-3-yl)thieno[2,3-b]pyridin-4-yl)benzo[d]thiazol-5-amine (Example 29, 100 mg, 78%) as a yellow oil. LCMS (ESI, m/z): 393 [M+H]$^+$.

Example 30: Synthesis of N-(2-(1-ethyl-2-methylpyrrolidin-3-yl)thieno[2,3-b]pyridin-4-yl)benzo[d]thiazol-5-amine

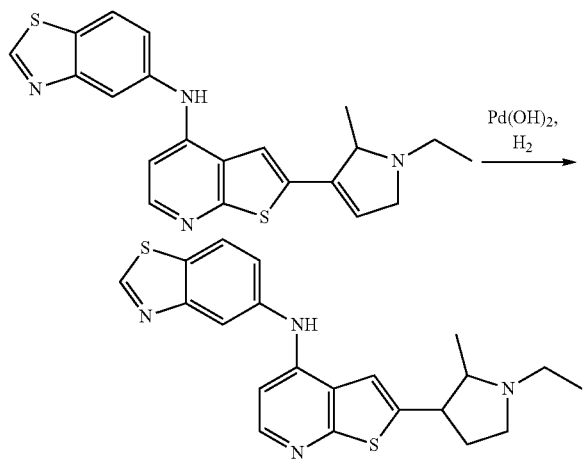

A solution of N-(2-(1-ethyl-2-methyl-2,5-dihydro-1H-pyrrol-3-yl)thieno[2,3-b]pyridin-4-yl)-benzo[d]thiazol-5-amine (Example 29, 100 mg, 0.254 mmol, 1.00 equiv) and Pd(OH)$_2$ (100 mg) in ethanol (10 mL) was stirred at room temperature for 3 h under H$_2$ atmosphere (1-3 atm.). LCMS showed the reaction was completed. The residue was purified by preparative HPLC (Column: Sunfire Prep C18 OBD Column, 10 μm, 19×250 mm; Mobile Phase A: Water (0.05% TFA), Mobile Phase B: ACN; Flow rate: 25 mL/min; Gradient: 10% B to 50% B in 8 min; 254/210 nm; Rt: 7.65 min) to give the desired product N-(2-(1-ethyl-2-methylpyrrolidin-3-yl)thieno[2,3-b]pyridin-4-yl)benzo[d]thiazol-5-amine (Example 30, 32.4 mg, 32%) as a yellow solid. $^1$H NMR (400 MHz, Methanol-d$_4$) δ 9.38 (s, 1H), 8.27-8.25 (m, 2H), 8.13 (s, 1H), 7.82 (s, 1H), 7.60-7.56 (m, 1H), 7.04 (d, J=8.0 Hz, 1H), 4.32-4.29 (m, 1H), 4.27-3.92 (m, 2H), 3.84-3.48 (m, 2H), 2.72-2.70 (m, 1H), 2.69-2.67 (m, 1H), 1.55 (d, J=4.0 Hz, 1H), 1.54-1.43 (m, 3H), 1.41-1.26 (m, 3H). LCMS (ESI, m/z): 395 [M+H]$^+$.

Example 31: Synthesis of 2-(3-(4-(benzo[d]thiazol-5-ylamino)thieno[2,3-b]pyridin-2-yl)-2-methylpyrrolidin-1-yl)ethan-1-ol

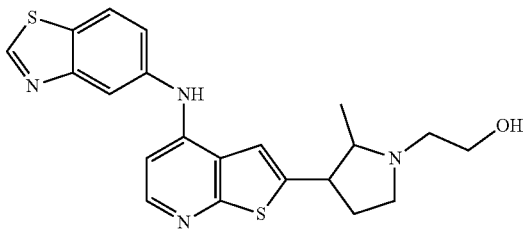 [SMILES: CC1C(c2cc3c(Nc4ccc5scnc5c4)ccnc3s2)CCN1CCO]

Step 1

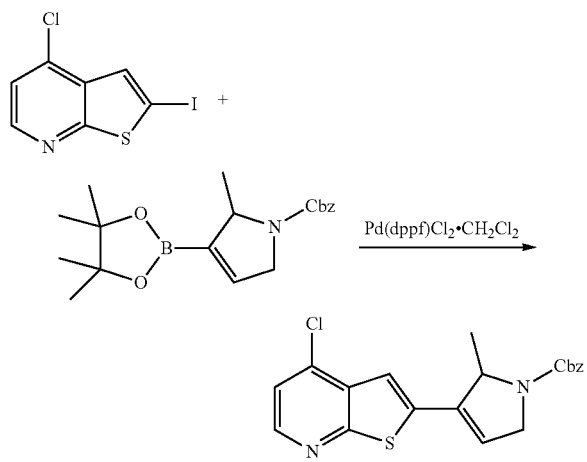

To a solution of 4-chloro-2-iodo-thieno[2,3-b]pyridine (2.0 g, 6.770 mmol, 1.00 equiv), t-BuONa (1.9 g, 20.300 mmol, 3.00 equiv) and benzyl 2-methyl-3-(4,4,5,5-tetramethyl-1,3,2-dioxa-borolan-2-yl)-2,5-dihydropyrrole-1-carboxylate (2.5 g, 7.440 mmol, 1.10 equiv) in 1,4-dioxane (30 mL) and water (3 mL) was added Pd(dppf)Cl$_2$—CH$_2$Cl$_2$ (552 mg, 0.680 mmol, 0.10 equiv). The resulting mixture was stirred at 80° C. for 3 h under nitrogen atmosphere. TLC showed the reaction was completed. The reaction mixture was concentrated and the residue was purified by flash chromatography on silica gel (PE/EA=3/1) to afford benzyl 3-(4-chlorothieno[2,3-b]pyridin-2-yl)-2-methyl-2,5-dihydro-1H-pyrrole-1-carboxylate (Example 31-1, 2.4 g, 91%) as a light-yellow solid. LCMS (ESI, m/z): 385 [M+H]$^+$.

Step 2

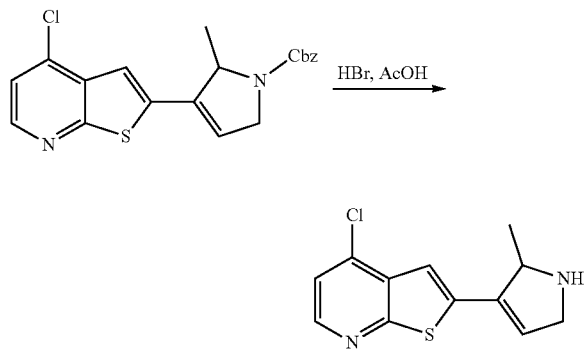

Benzyl 3-(4-chlorothieno[2,3-b)]pyridin-2-yl)-2-methyl-2,5-dihydro-1H-pyrrole-1-carboxylate (Example 31-1, 420 mg, 1.090 mmol, 1.00 equiv) was dissolved by HBr (40% in AcOH, 10 mL) and the resulting solution was stirred at room temperature for 30 min. LCMS showed the reaction was completed. The solvent was removed and gave 4-chloro-2-(2-methyl-2,5-dihydro-1H-pyrrol-3-yl)thieno[2,3-b]pyridine (Example 31-2, 273 mg, crude). LCMS (ESI, m/z): 251 [M+H]$^+$.

Step 3

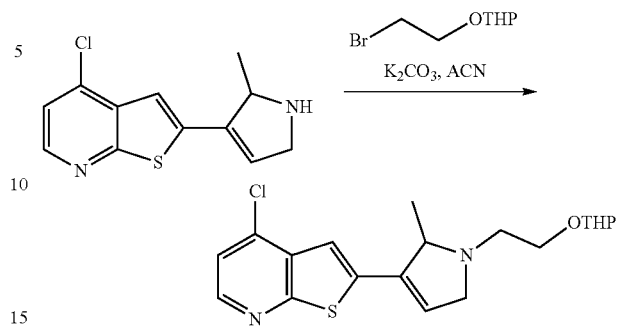

To a solution of 4-chloro-2-(2-methyl-2,5-dihydro-1H-pyrrol-3-yl)thieno[2,3-b]pyridine (Example 31-2, 350 mg, 1.400 mmol, 1.00 equiv) and K$_2$CO$_3$ (577 mg, 4.190 mmol, 3.00 equiv) in DMF (7 mL) was added 2-(2-bromoethoxy)tetrahydro-2H-pyran (437 mg, 2.090 mmol, 1.50 equiv). Then TEA was added to adjust pH to 8-9. The reaction mixture was stirred at 80° C. overnight. LCMS showed the reaction was complete. The resulting mixture was diluted with water and extracted with EA. The combined organic layer was concentrated under reduced pressure and the residue was purified by preparative TLC (PE:EA=1:1) to afford 4-chloro-2-(2-methyl-1-(2-((tetrahydro-2H-pyran-2-yl)oxy)ethyl)-2,5-dihydro-1H-pyrrol-3-yl)thieno[2,3-b]pyridine (Example 31-3, 30 mg, 6%). LCMS (ESI, m/z): 379 [M+H]$^+$.

Step 4

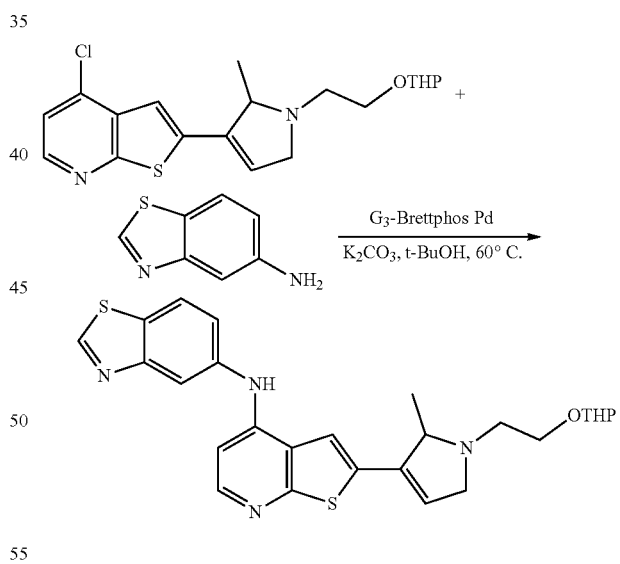

4-chloro-2-(2-methyl-1-(2-((tetrahydro-2H-pyran-2-yl)oxy)ethyl)-2,5-dihydro-1H-pyrrol-3-yl)thieno[2,3-b]pyridine (Example 31-3, 140 mg, 0.370 mmol, 1.00 equiv), benzo[d]thiazol-5-amine (83 mg, 0.550 mmol, 1.49 equiv), G3-BrettPhos Pd (33 mg, 0.040 mol, 0.10 equiv) and K$_2$CO$_3$ (143 mg, 1.110 mmol, 3.00 equiv) were dissolved in tert-butanol (10 mL) and the reaction mixture was stirred at 60° C. for 3 h under N$_2$ atmosphere. The solid was filtered out and the filtration was concentrated. The residue was purified by preparative TLC (MeOH:DCM=1:15) to give N-(2-(2-methyl-1-(2-((tetrahydro-2H-pyran-2-yl)oxy)ethyl)-2,5-dihydro-1H-pyrrol-3-yl)thieno[2,3]pyridin-4-yl)benzo[d]thi azol-5-amine (Example 31-4, 50 mg, 23%) as a light yellow solid. LCMS (ESI, m/z): 493 [M+H]$^+$.

Step 5

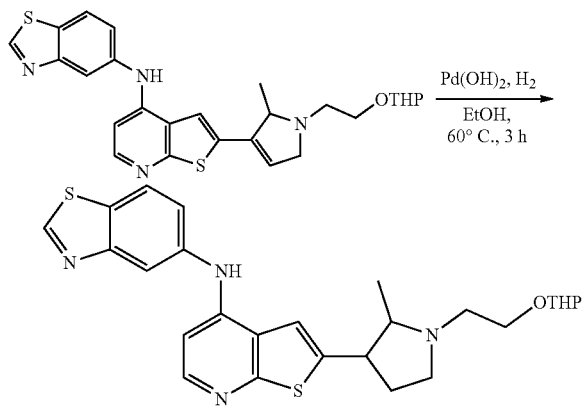

N-(2-(2-methyl-1-(2-((tetrahydro-2H-pyran-2-yl)oxy)ethyl)-2,5-dihydro-1H-pyrrol-3-yl)thieno-[2,3-b]pyridin-4-yl)benzo[d]thiazol-5-amine (Example 31-4, 50 mg, 0.10 mmol, 1.00 equiv) was dissolved in ethanol (50 mL), then 10% Pd(OH)$_2$ (50 mg, 1.00 w/w) was added. The resulting mixture was stirred at 60° C. under H$_2$ atmosphere (5 atm.) for 3 h. The solid was filtered out and the filtration was concentrated to N-(2-(2-methyl-1-(2-((tetrahydro-2H-pyran-2-yl)oxy)ethyl)pyrrolidin-3-yl)thieno[2,3]pyridin-4-yl)benzo[d]thiazol-5-amine (Example 31-5, 50 mg, crude) as a light yellow solid. LCMS (ESI, m/z): 495 [M+H]$^+$.

Step 6

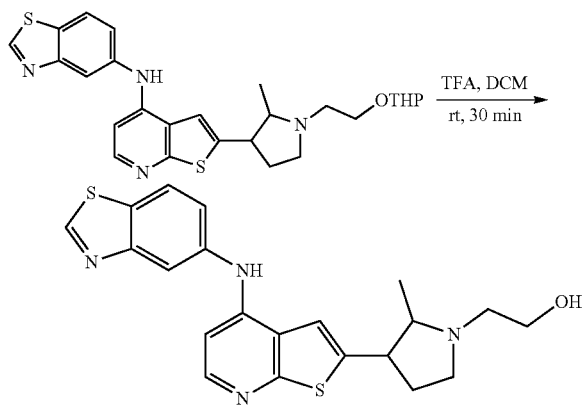

N-(2-(2-methyl-1-(2-((tetrahydro-2H-pyran-2-yl)oxy)ethyl)pyrrolidin-3-yl)thieno[2,3]pyridin-4-yl)benzo[d]thiazol-5-amine (Example 31-5, 50 mg, 0.100 mmol, 1.00 equiv) was dissolved in DCM (10 mL) and TFA (5 mL) was added. The resulting solution was stirred at rt for 30 min. LCMS showed the reaction was completed. The solvent was removed and the residue was purified by preparative HPLC (Separation condition: Column: Sunfire Prep C18 OBD Column, 10 μm, 19×250 mm; Mobile Phase A: Water (0.05% TFA), Mobile Phase B: ACN; Flow rate: 25 mL/min; Gradient: 10% B to 30% B in 9 min; 254/210 nm; Rt: 8.65 min.) to give 2-(3-(4-(benzo[d]thiazol-5-ylamino)thieno[2,3-b]pyridin-2-yl)-2-methylpyrrolidin-1-yl)ethan-1-ol (Example 31, 10.6 mg, 26%) as a light yellow solid. $^1$H NMR (400 MHz, Methanol-d$_4$) δ 9.36 (s, 1H), 8.23-8.21 (m, 2H), 8.09 (s, 1H), 7.78 (s, 1H), 7.56 (d, J=8.0 Hz, 2H), 7.03 (d, J=8.0 Hz, 1H), 4.28-4.13 (m, 1H), 3.93-3.85 (m, 3H), 3.70-3.31 (m, 4H), 2.80-2.50 (m, 2H), 1.56-1.20 (d, 3H). LCMS (ESI, m/z): 411 [M+H]$^+$.

Example 32: Synthesis of N-(2-(2,2-dimethyl-2,5-dihydro-1H-pyrrol-3-yl)thieno[2,3-b]pyridin-4-yl)benzo[d]thiazol-5-amine

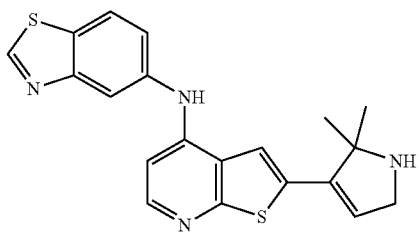 [SMILES: CC1(C)NCC=C1c1cc2c(Nc3ccc4scnc4c3)ccnc2s1]

Step 1

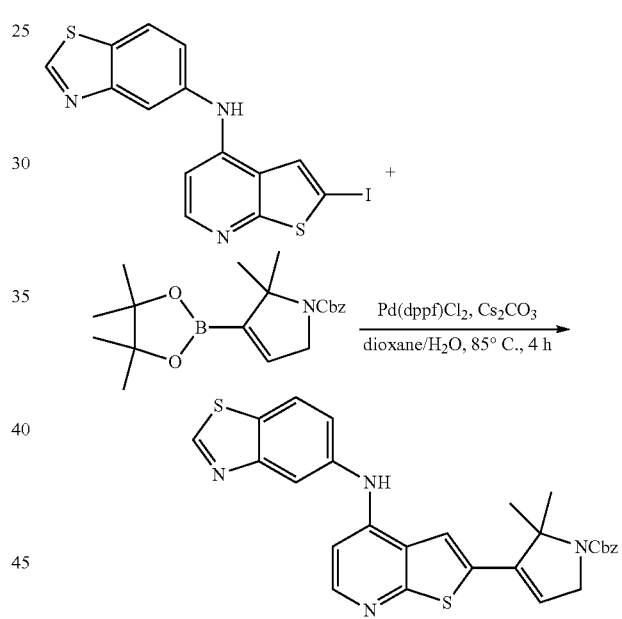

To a solution of benzyl 2,2-dimethyl-3-(4,4,5,5-tetramethyl-1,3,2-dioxaborolan-2-yl)-2,5-dihydro-1H-pyrrole-1-carboxylate (300 mg, 0.840 mmol, 1.00 equiv) in 1,4-dioxane (6 mL) and water (0.6 mL) were added N-(2-iodothieno[2,3-b]pyridin-4-yl)benzo[d]thiazol-5-amine (378 mg, 0.920 mmol, 1.10 equiv), Pd(dppf)Cl$_2$—CH$_2$Cl$_2$ (69 mg, 0.080 mmol, 0.10 equiv) and Cs$_2$CO$_3$ (1.6 g, 5.040 mmol, 6.00 equiv) under N$_2$ atmosphere. The reaction was stirred for 4 h at 85° C. LCMS showed the reaction was complete. The solution was concentrated, diluted with water (100 mL) and extracted with EA (3×100 mL). The combined organic layer was dried over Na$_2$SO$_4$, filtered and concentrated under reduced pressure. The residue was purified by preparative TLC (PE/EA=1/1) to give benzyl 3-(4-(benzo[d]-thiazol-5-ylamino)thieno[2,3-b]pyridin-2-yl)-2,2-dimethyl-2,5-dihydro-1H-pyrrole-1-carboxylate (Example 32-1, 100 mg, 23%) as a light yellow solid. LCMS (ESI, m/z): 513 [M+H]$^+$.

Step 2

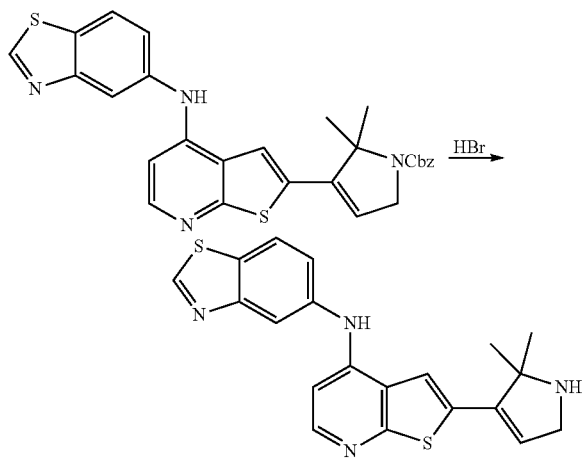

To a stirred solution of HBr (33% in AcOH) (1 mL) was added benzyl 3-(4-(benzo[d]thiazol-5-ylamino)thieno[2,3-b]pyridin-2-yl)-2,2-dimethyl-2,5-dihydro-1H-pyrrole-1-carboxylate (Example 32-1, 60 mg, 0.120 mmol, 1.00 equiv). The reaction solution was stirred for 1 h at room temperature. TLC showed the reaction was completed. The reaction solution was concentrated under vacuum and purified by preparative HPLC with the following conditions: Column, XBridge Prep C18 OBD Column; 5 μm, 19×150 mm; mobile phase, water (0.05% TFA) and ACN (30% up to 60% in 8 min); detector, 254/210 nm. The mixture was dried by lyophilization to give N-(2-(2,2-dimethyl-2,5-dihydro-1H-pyrrol-3-yl)thieno-[2,3-b]pyridin-4-yl)benzo[d]thiazol-5-amine (Example 32, 26.5 mg, 60%) as a light yellow solid. $^1$H NMR (300 MHz, Methanol-$d_4$) δ 9.39 (s, 1H), 8.29-8.25 (m, 2H), 8.15 (d, J=1.8 Hz, 1H), 7.99 (s, 1H), 7.59 (dd, J=8.4, 1.8 Hz, 1H), 7.05 (d, J=6.6 Hz, 1H), 6.41 (t, J=2.1 Hz, 1H), 4.26 (d, J=2.4 Hz, 2H), 1.87 (s, 6H). LCMS (ESI, m/z): 379 [M+H]$^+$.

Example 33: Synthesis of N-(2-(2,2-dimethylpyrrolidin-3-yl)thieno[2,3-b]pyridin-4-yl)benzo[d]thiazol-5-amine

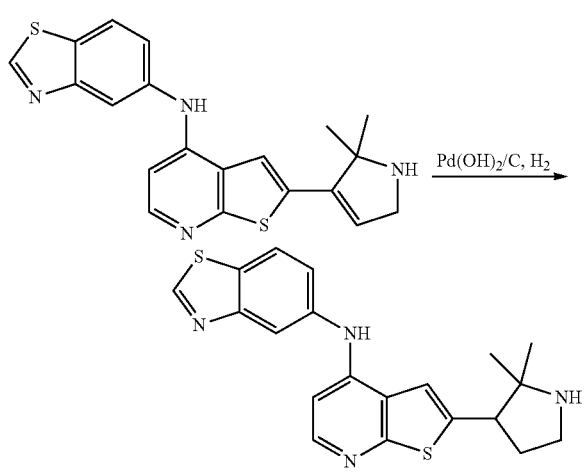

To the solution of N-(2-(2,2-dimethyl-2,5-dihydro-1H-pyrrol-3-yl)thieno[2,3-b]pyridin-4-yl)benzo[d]thiazol-5-amine (Example 32, 100 mg, 0.260 mmol, 1.00 equiv) in ethanol (15 mL) was added Pd(OH)$_2$/C (200 mg, 2.00 w/w) under a nitrogen atmosphere. The reaction solution was degassed and back filled with hydrogen. The reaction was stirred for 2 days at 60° C. under H$_2$ atmosphere (1-3 atm.). LCMS showed the reaction was completed. The resulting mixture was filtered through celite. The filtrate was concentrated and the residue purified by preparative TLC (PE/EA=1/1) and preparative HPLC with the following conditions: Column, XBridge Prep C18 OBD Column; 5 μm, 19×150 mm; mobile phase, Water (0.05% TFA) and ACN (15% up to 18% in 7 min); Detector, 254/210 nm. The mixture was dried by lyophilization to give N-(2-(2,2-dimethylpyrrolidin-3-yl)thieno[2,3-b]pyridin-4-yl)benzo[d]thiazol-5-amine (Example 33, 5.2 mg, 5%) as a light yellow semi-solid. $^1$H NMR (300 MHz, Methanol-$d_4$) δ 9.36 (s, 1H), 8.30-8.15 (m, 2H), 8.11 (d, J=1.8 Hz, 1H), 7.80 (s, 1H), 7.58 (dd, J=8.7, 2.1 Hz, 1H), 7.04 (d, J=6.6 Hz, 1H), 3.76-3.49 (m, 3H), 2.70-2.55 (m, 2H), 1.67 (s, 3H), 1.28 (s, 3H). LCMS (ESI, m/z): 381 [M+H]$^+$.

Example 34: Synthesis of N-(2-(1,2,2-trimethyl-2,5-dihydro-1H-pyrrol-3-yl)thieno[2,3-b]pyridin-4-yl)benzo[d]thiazol-5-amine

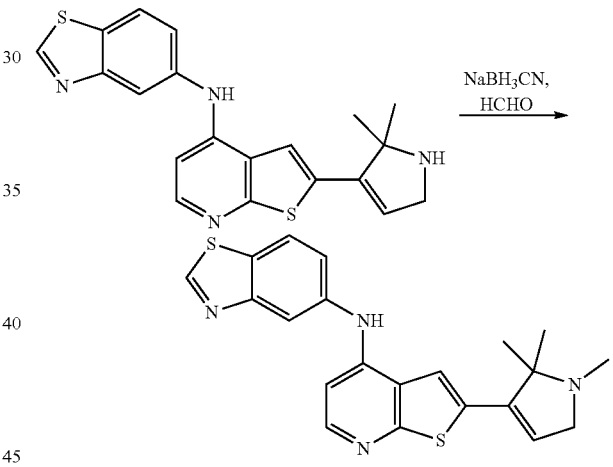

To a solution of N-(2-(2,2-dimethyl-2,5-dihydro-1H-pyrrol-3-yl)thieno[2,3-b]pyridin-4-yl)benzo[d]-thiazol-5-amine (Example 32, 200 mg, 0.530 mmol, 1.00 equiv) in methanol (10 mL) was added HCHO (64 mg, 0.790 mmol, 1.50 equiv) and stirred for 0.5 h at room temperature, followed by the addition of NaBH$_3$CN (100 mg, 1.590 mmol, 3.00 equiv). The reaction was stirred for 0.5 h at room temperature. LCMS showed the reaction was complete. The reaction mixture was quenched with water (100 mL) and extracted with EA (3×50 mL). The combined organic layer was washed with brine, dried over anhydrous Na$_2$SO$_4$, filtered and concentrated under reduced pressure. The residue was purified by preparative HPLC with the following conditions: Column, Sunfire Prep C18 OBD Column; 10 μm, 19×250 mm; mobile phase, water (0.05% TFA) and ACN (20% up to 40% in 8 min); detector, 254/210 nm. The mixture was dried by lyophilization to give the desired compound N-(2-(1,2,2-trimethyl-2,5-dihydro-1H-pyrrol-3-yl)thieno[2,3-b]pyridin-4-yl)benzo[d]thiazol-5-amine (Example 34, 22.8 mg, 11%) as a light yellow solid. $^1$H NMR (300 MHz, Methanol-$d_4$) δ 9.38 (s, 1H), 8.31-8.22 (m, 2H), 8.14 (d, J=1.8 Hz, 1H), 8.03 (s, 1H), 7.59 (dd, J=8.5, 2.1 Hz, 1H), 7.06 (d, J=6.9 Hz, 1H), 6.45 (t, J=2.4 Hz, 1H), 4.30 (s, 2H), 3.03 (s, 3H), 1.85 (s, 6H). LCMS (ESI, m/z): 393 [M+H]⁺.

Example 35: Synthesis of N-(2-(1,2,2-trimethylpyrrolidin-3-yl)thieno[2,3-b]pyridin-4-yl)benzo[d]thiazol-5-amine

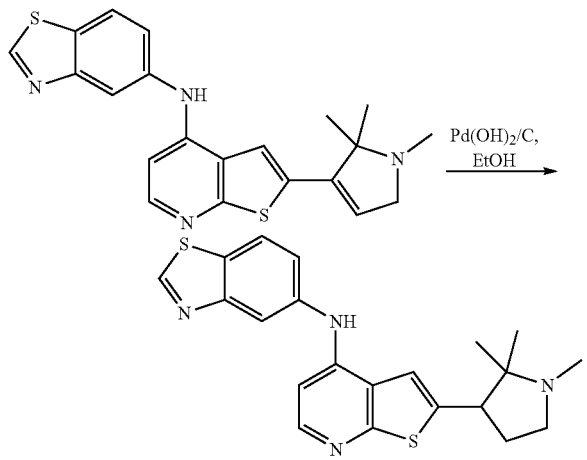

To a solution N-(2-(1,2,2-trimethyl-2,5-dihydro-1H-pyrrol-3-yl)thieno[2,3-b]pyridin-4-yl)benzo[d]-thiazol-5-amine (Example 34, 95 mg, 0.240 mmol, 1.00 equiv) in ethanol (20 mL), was added dry Pd(OH)₂ (95 mg, 1.00 w/w). The solution was degassed and back filled with hydrogen. The reaction was stirred for 72 h at 60° C. under H₂ atmosphere (1-3 atm.). LCMS showed the reaction was complete and the solid was filtered out. The filtrate was concentrated and purified by preparative HPLC with the following conditions: Column, XBridge BEH130 Prep C18 OBD Column; 5 μm, 19×150 mm; mobile phase, water (0.05% TFA) and ACN (15% up to 50% in 8 min); detector, 254/210 nm. The mixture was dried by lyophilization to give the desired compound N-(2-(1,2,2-trimethylpyrrolidin-3-yl)thieno[2,3-b]pyridin-4-yl)benzo[d]-thiazol-5-amine (Example 35, 26.3 mg, 28%) as a yellow semi-solid. ¹H NMR (400 MHz, Methanol-d₄) δ 9.38 (s, 1H), 8.35-8.20 (m, 2H), 8.16 (d, J=2.0 Hz, 1H), 7.87 (s, 1H), 7.61 (dd, J=8.4, 2.0 Hz, 1H), 7.07 (d, J=6.8 Hz, 1H), 3.95-3.80 (m, 1H), 3.79 (t, J=10.1 Hz, 1H), 3.55-3.40 (m, 1H), 2.94 (s, 3H), 2.71-2.59 (m, 2H), 1.62 (s, 3H), 1.22 (s, 3H). LCMS (ESI, m/z): 395 [M+H]⁺.

Example 36: Synthesis of N-(2-(1-ethyl-2,2-dimethyl-2,5-dihydro-1H-pyrrol-3-yl)thieno[2,3-b]pyridin-4-yl)benzo[d]thiazol-5-amine

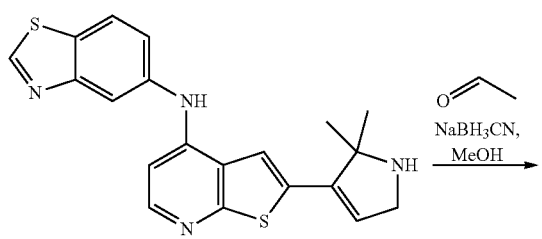

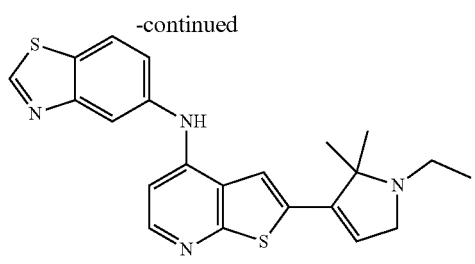

To a solution of N-(2-(2,2-dimethyl-2,5-dihydro-1H-pyrrol-3-yl)thieno[2,3-b]pyridin-4-yl)benzo-[d]thiazol-5-amine (Example 32, 50 mg 0.130 mmol, 1.00 equiv) in CH₃OH (5 mL) was added CH₃CHO (6 mg, 0.130 mmol, 1.00 equiv) and NaBH₃CN (25 mg, 0.390 mmol, 3.00 equiv). The resulting mixture was stirred for 1 h at room temperature. LCMS showed the reaction was complete. The resulting mixture was concentrated and the residue was purified by flash chromatography on silica gel (DCM:MeOH=15:1) to give the desired product N-(2-(1-ethyl-2,2-dimethyl-2,5-dihydro-1H-pyrrol-3-yl)thieno[2,3-b]pyridin-4-yl)benzo[d]thiazol-5-amine (Example 36, 20 mg, 37%) as a light yellow solid. LCMS (ESI, m/z): 407 [M+H]⁺.

Example 37: Synthesis of N-(2-(1-ethyl-2,2-dimethylpyrrolidin-3-yl)thieno[2,3-b]pyridin-4-yl)benzo[d]thiazol-5-amine

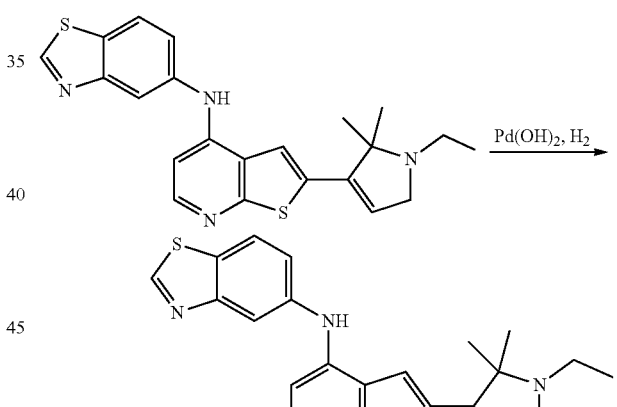

To a solution of N-(2-(1-ethyl-2,2-dimethyl-2,5-dihydro-1H-pyrrol-3-yl)thieno[2,3-b]pyridin-4-yl)benzo[d]thiazol-5-amine (Example 36, 20 mg, 0.050 mmol, 1.00 equiv) in ethanol (5 mL) was added Pd(OH)₂/C (20 mg, 1.00 w/w). The resulting mixture was stirred at 60° C. under an atmosphere of hydrogen (2-3 atm.) for 24 h. LCMS showed the reaction was complete. The solid was filtered out and the filtrate was concentrated under vacuum and the residue was purified by preparative HPLC using the following gradient conditions: Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 15% B to 27% B in 8 min; 254/210 nm; Rt: 5.3 min. Purification gave the desired product N-(2-(1-ethyl-2,2-dimethyl-pyrrolidin-3-yl)thieno[2,3-b]pyridin-4-yl)benzo[d]thiazol-5-amine (Example 37, 16.2 mg, 81%). ¹H NMR (400 MHz, Methanol-d₄) δ 9.39 (s, 1H), 8.31-8.23 (m, 2H), 8.13 (d, J=2.1 Hz, 1H), 7.86 (s, 1H), 7.59 (dd, J=8.5, 2.0 Hz, 1H), 7.07 (d, J=6.7 Hz, 1H), 3.97-3.90 (m, 1H), 3.79-3.69 (m, 1H), 3.53-3.42 (m, 1H), 3.18-3.06 (m, 2H), 2.73-2.60 (m, 2H), 1.66 (s, 3H), 1.45 (t, J=7.2 Hz, 3H), 1.24 (s, 3H). LCMS (ESI, m/z): 409 [M+H]⁺.

Example 38: Synthesis of 2-(3-(4-(benzo[d]thiazol-5-ylamino)thieno[2,3-b]pyridin-2-yl)-2,2-dimethylpyrrolidin-1-yl)ethan-1-ol

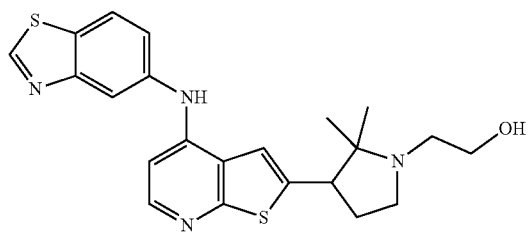 [SMILES: CC1(C)C(c2cc3c(Nc4ccc5scnc5c4)ccnc3s2)CCN1CCO]

Step 1

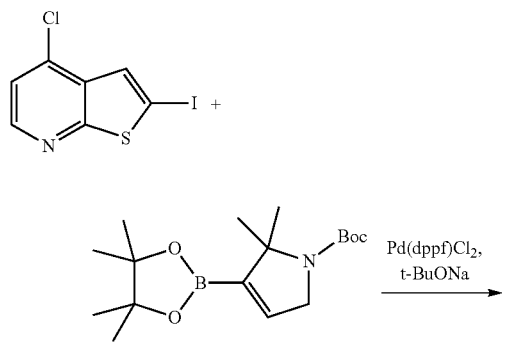

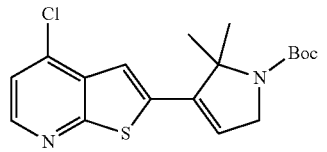

To a stirred solution of 4-chloro-2-iodothieno[2,3-b]pyridine (4.5 g, 15.227 mmol, 1.00 equiv) in 1,4-dioxane (30 mL) and H₂O (5 mL) was added tert-butyl 5,5-dimethyl-4-(4,4,5,5-tetramethyl-1,3,2-dioxa-borolan-2-yl)-2H-pyrrole-1-carboxylate (5.9 g, 18.270 mmol, 1.20 equiv), Pd(dppf)Cl₂ (1.1 g, 1.520 mmol, 0.10 equiv) and t-BuONa (4.4 g, 45.680 mmol, 3.00 equiv) at 70° C. for 4 h under N₂ atmosphere. TLC showed the reaction was complete. The reaction mixture was quenched with water and extracted with EA. The organic layer was washed with brine and concentrated. The residue was purified by flash chromatography (EA/PE=1/1) to afford the desired product tert-butyl 3-(4-chlorothieno[2,3-b]pyridin-2-yl)-2,2-dimethyl-2,5-dihydro-1H-pyrrole-1-carboxylate (Example 38-1, 4.4 g, 79%) as a light yellow solid. LCMS (ESI, m/z): 365 [M+H]⁺.

Step 2

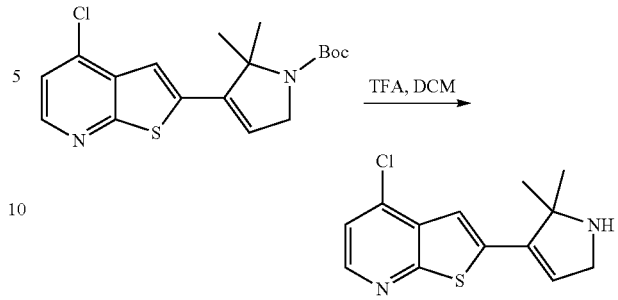

To a stirred solution of tert-butyl 3-(4-chlorothieno[2,3-b]pyridin-2-yl)-2,2-dimethyl-2,5-dihydro-1H-pyrrole-1-carboxylate (Example 38-1, 700 mg, 1.750 mmol, 1.00 equiv) was added DCM (4 mL) and TFA (2 mL). The resulting solution was stirred at rt overnight. TLC showed the reaction was completed. The reaction mixture was concentrated to give the crude product 4-chloro-2-(2,2-dimethyl-2,5-dihydro-1H-pyrrol-3-yl)thieno[2,3-b]pyridine (Example 38-2, 400 mg). LCMS (ESI, m/z): 265 [M+H]⁺.

Step 3

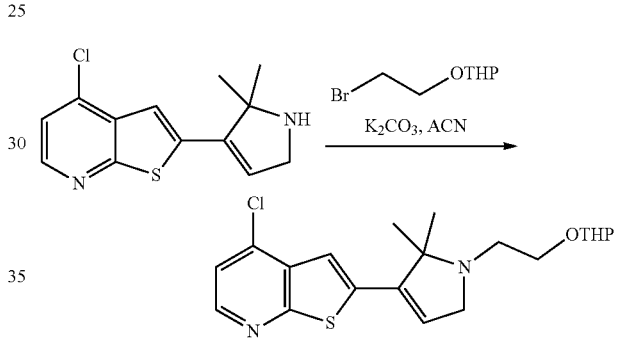

To a stirred solution of 4-chloro-2-(2,2-dimethyl-2,5-dihydro-1H-pyrrol-3-yl)thieno[2,3-b]pyridine (Example 38-2, 400 mg, 1.510 mmol, 1.00 equiv) in DMF (5 mL) was added 2-(2-bromoethoxy)tetrahydropyran (474 mg, 2.267 mmol, 1.50 equiv), K₂CO₃ (625 mg, 4.530 mmol, 3.00 equiv) and Et₃N (168 mg, 1.660 mmol, 1.10 equiv) at 80° C. overnight. TLC showed the reaction was complete. The reaction mixture was quenched with water and extracted with EA. The organic layer was washed with brine and concentrated. The residue was purified by flash chromatography (EA/PE=1/1) to afford the desired product 4-chloro-2-(2,2-dimethyl-1-(2-((tetrahydro-2H-pyran-2-yl)oxy)ethyl)-2,5-dihydro-1H-pyrrol-3-yl)thieno[2,3-b]pyridine (Example 38-3, 200 mg, 34%) as a light yellow oil. LCMS (ESI, m/z): 393 [M+H]⁺.

Step 4

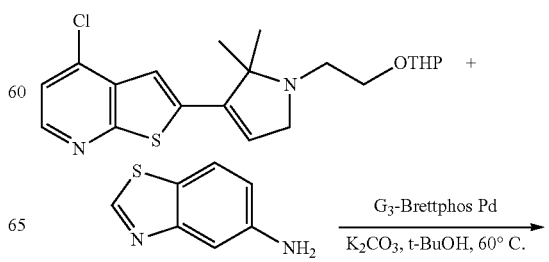

-continued

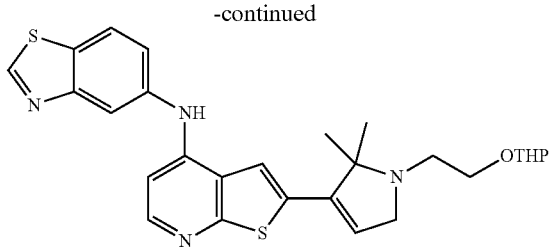

Into a 25-mL sealed tube purged and maintained under an inert atmosphere of nitrogen, was placed 4-chloro-2-(2,2-dimethyl-1-(2-((tetrahydro-2H-pyran-2-yl)oxy)ethyl)-2,5-dihydro-1H-pyrrol-3-yl)thieno-[2,3-b]pyridine (Example 38-3, 105 mg, 0.270 mmol, 1.00 equiv), benzo[d]thiazol-5-amine (40 mg, 0.270 mmol, 1.00 equiv), $K_2CO_3$ (111 mg, 0.800 mmol, 3.00 equiv), G3-brettphos Pd (24 mg, 0.030 mmol, 0.10 equiv) and tert-butanol (5 mL). The resulting solution was stirred for 2 h at 60° C. The solution was filtered and the filtrate was concentrated. The crude product was purified by silica gel flash chromatography (EA/PE=2/1) to give the desired product N-(2-(2,2-dimethyl-1-(2-((tetrahydro-2H-pyran-2-yl)oxy)-ethyl)-2,5-dihydro-1H-pyrrol-3-yl)thieno[2,3-b]pyridin-4-yl)benzo[d]thiazol-5-amine (Example 38-4, 65 mg, 48%) as an off-white solid. LCMS (ESI, m/z): 507 $[M+H]^+$.

Step 5

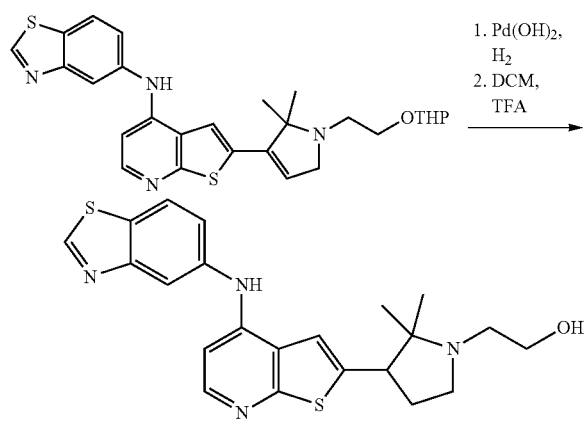

A mixture of N-(2-(2,2-dimethyl-1-(2-((tetrahydro-2H-pyran-2-yl)oxy)ethyl)-2,5-dihydro-1H-pyrrol-3-yl)thieno[2,3-b]pyridin-4-yl)benzo[d]thiazol-5-amine (Example 38-4, 25 mg, 0.049 mmol, 1.00 equiv) and $Pd(OH)_2/C$ (25 mg, 1.00 w/w) in EtOH (2 mL) was stirred overnight at 65° C. under $H_2$ atmosphere (1-3 atm.). LCMS showed the reaction was complete. The reaction mixture was filtered and the filtrate was concentrated. The crude product was dissolved with DCM (2 mL) and TFA (1 mL) was added. The resulting solution was stirred at rt for 30 min. TLC indicated the reaction was complete. The reaction mixture was concentrated and the crude product was purified by preparative HPLC (Column: Sunfire Prep C18 OBD Column, 10 μm, 19×250 mm; Mobile Phase A: Water (0.05% TFA), Mobile Phase B: ACN; Flow rate: 25 mL/min; Gradient: 10% B to 30% B in 9 min; 254/210 nm; Rt: 8.65 min) to give the desired product 2-(3-(4-(benzo[d]thiazol-5-ylamino)thieno [2,3-b]pyridin-2-yl)-2,2-dimethyl-pyrrolidin-1-yl)ethan-1-ol (Example 38, 7.4 mg, 36%) as an off-white solid. $^1H$ NMR (400 MHz, Methanol-$d_4$) δ 9.34 (s, 1H), 8.31-8.22 (m, 2H), 8.14 (d, J=2.1 Hz, 1H), 7.86 (s, 1H), 7.60 (dd, J=8.6, 2.1 Hz, 1H), 7.07 (d, J=6.6 Hz, 1H), 4.06-3.83 (m, 4H), 3.65-3.50 (m, 2H), 3.23-3.13 (m, 1H), 2.83-2.31 (m, 2H), 1.66 (s, 3H), 1.26 (s, 3H). LCMS (ESI, m/z): 425 $[M+H]^+$.

Example 39: Synthesis of N-(2-(2-oxa-5-azaspiro [3.4]oct-7-en-8-yl)thieno[2,3-b]pyridin-4-yl)benzo [d]thiazol-5-amine

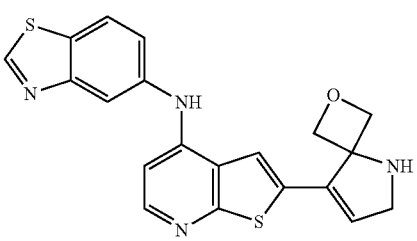 [SMILES: C1=C(c2cc3c(Nc4ccc5scnc5c4)ccnc3s2)C2(COC2)NC1]

Step 1

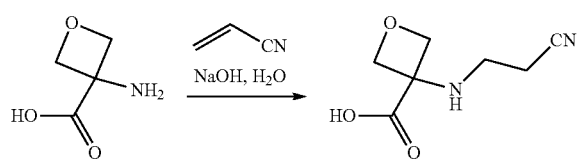

Into a 100-mL round-bottom flask was placed 3-aminooxetane-3-carboxylic acid (9.0 g, 76.860 mmol, 1.00 equiv), acrylonitrile (8.2 g, 153.710 mmol, 2.00 equiv), NaOH (3.4 g, 84.540 mmol, 1.20 equiv) and water (20 mL). The resulting mixture was stirred for 12 h at 60° C. LCMS showed the reaction was complete. The resulting mixture was concentrated under reduced pressure. The crude product 3-((2-cyanoethyl)amino)oxetane-3-carboxylic acid (Example 39-1) was used directly in the next step without further purification. LCMS (ESI, m/z): 171 $[M+H]^+$.

Step 2

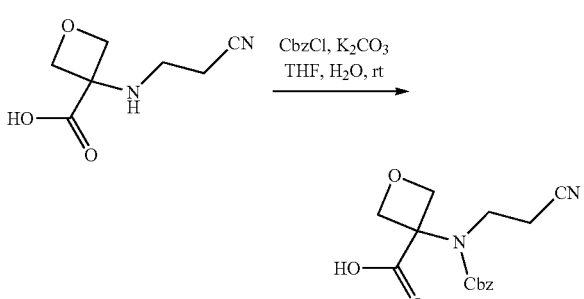

Into a 100-mL round-bottom flask was placed 3-(2-cyanoethylamino)oxetane-3-carboxylic acid (Example 39-1, 13.1 g, 76.980 mmol, 1.00 equiv), benzyl carbonochloridate (15.8 g, 92.380 mmol, 1.20 equiv), $K_2CO_3$ (16.3 g, 153.960 mmol, 2.00 equiv), THF (50 mL) and water (50 mL). The resulting mixture was stirred for 12 h at room temperature. LCMS showed the reaction was complete. The resulting mixture was concentrated. The crude material was purified by reverse flash chromatography. Purification gave the desired product 3-[benzyloxycarbonyl(2-cyanoethyl)amino]

oxetane-3-carboxylic acid (Example 39-2, 2.9 g, 12%) as a white solid. LCMS (ESI, m/z): 305 [M+H]⁺.

Step 3

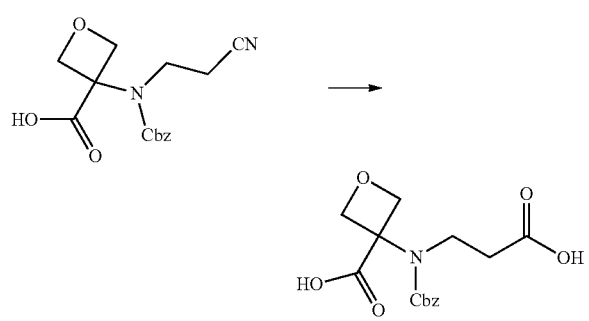

A mixture of 3-[benzyloxycarbonyl(2-cyanoethyl)amino]oxetane-3-carboxylic acid (Example 39-2, 22.0 g, 72.300 mmol, 1.00 equiv), KOH (20.3 g, 361.490 mmol, 5.00 equiv) and water (100 mL) was placed in a 100-ml round-bottom flask. The resulting mixture was stirred for 3 h at 100° C. LCMS showed the reaction was completed. The resulting mixture was concentrated. The crude material was purified by reverse flash chromatography to give the desired product 3-[benzyloxycarbonyl(2-carboxyethyl)amino]oxetane-3-carboxylic acid (Example 39-3, 17.0 g, 72%) as a white solid. LCMS (ESI, m/z): 324 [M+H]⁺.

Step 4

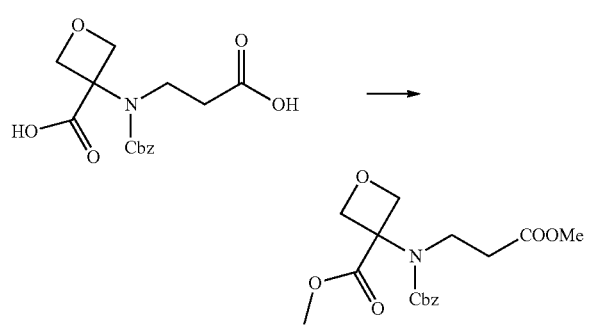

A mixture of 3-[benzyloxycarbonyl(2-carboxyethyl)amino]oxetane-3-carboxylic acid (Example 39-3, 16.0 g, 49.490 mmol, 1.0 equiv), iodomethane (15.4 g, 108.880 mmol, 2.20 equiv) and DMF (50 mL) was placed in a 100-ml round-bottom flask. The resulting mixture was stirred for 12 h at room temperature. LCMS showed the reaction was completed. The resulting mixture was concentrated. The crude material was purified by reverse flash chromatography to give the desired product methyl 3-[benzyloxycarbonyl-(3-methoxy-3-oxo-propyl)amino]oxetane-3-carboxylate (Example 39-4, 3.7 g, 21%) as a white solid. LCMS (ESI, m/z): 352 [M+H]⁺.

Step 5

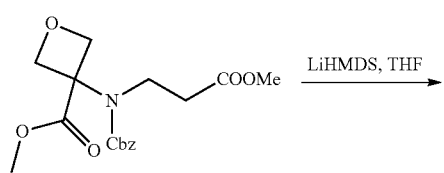

-continued

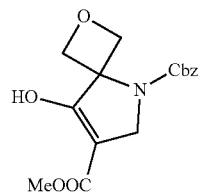

To a solution of methyl 3-[benzyloxycarbonyl-(3-methoxy-3-oxo-propyl)amino]oxetane-3-carboxylate (Example 39-4, 3.7 g, 10.530 mmol, 1.00 equiv) in THF (30 mL) was added LiHMDS (3.5 g, 21.06 mmol, 2.00 equiv) dropwise at −78° C. The resulting mixture was stirred for 1 h at 0° C. LCMS showed the reaction was completed. The resulting mixture was concentrated. The crude material was purified by reverse flash chromatography to give the desired product 5-benzyl 7-methyl 8-hydroxy-2-oxa-5-aza-spiro[3.4]oct-7-ene-5,7-dicarboxylate (Example 39-5, 3 g, 89%) as a white solid. LCMS (ESI, m/z): 320 [M+H]⁺.

Step 6

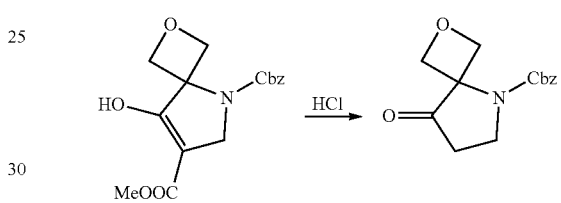

A mixture of O5-benzyl O7-methyl 8-hydroxy-2-oxa-5-azaspiro[3.4]oct-7-ene-5,7-dicarboxylate (Example 39-5, 3.7 g, 11.590 mmol, 1.00 equiv), HCl (12M in water, 3 mL) and water (50 mL) was placed in a 25-ml round-bottom flask. The resulting mixture was stirred for 12 h at 100° C. LCMS showed the reaction was complete. The resulting mixture was quenched with water (50 mL) and extracted with EA (3×50 mL). The combined organic layer was dried over Na₂SO₄, filtered and concentrated under reduced pressure. The crude material was purified by flash chromatography on silica gel (EA/PE=1/5) to give the desired product benzyl 8-oxo-2-oxa-5-azaspiro[3.4]octane-5-carboxylate (Example 39-6, 577 mg, 19%) as a brown oil. LCMS (ESI, m/z): 262 [M+H]⁺.

Step 7

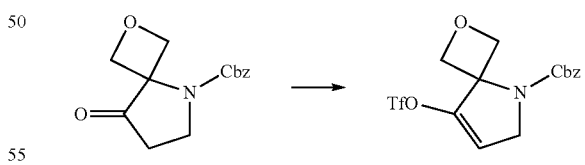

To a solution of benzyl 8-oxo-2-oxa-5-azaspiro[3.4]octane-5-carboxylate (Example 39-6, 100 mg, 0.190 mmol, 1.00 equiv) in DCM (2 mL) was added TFA (1.0 mL). The resulting mixture was stirred for 3 h at room temperature. LCMS showed the reaction was completed. The mixture was concentrated and the residue was purified by flash chromatography on silica gel (EA/PE=1/20) to afford the desired product benzyl 8-(trifluoromethylsulfonyloxy)-2-oxa-5-azaspiro-[3.4]oct-7-ene-5-carboxylate (Example 39-7, 66.5 mg, 44%) product as a semi-solid. LCMS (ESI, m/z): 394 [M+H]⁺.

Step 8

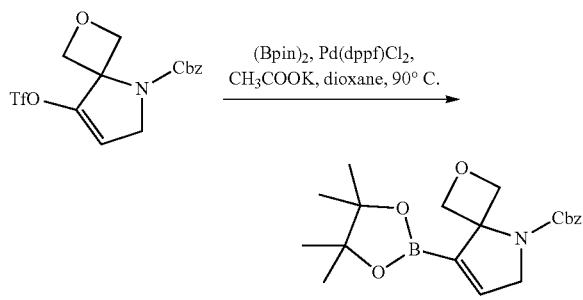

A mixture of 4,4,5,5-tetramethyl-2-(4,4,5,5-tetramethyl-1,3,2-dioxaborolan-2-yl)-1,3,2-dioxa-borolane (482 mg, 1.900 mmol, 1.20 equiv), benzyl 8-(trifluoromethylsulfonyloxy)-2-oxa-5-azaspiro-[3.4]oct-7-ene-5-carboxylate (Example 39-7, 622 mg, 1.580 mmol, 1.00 equiv), Pd(dppf)Cl$_2$ (116 mg, 0.160 mmol, 0.10 equiv), CH$_3$COOK (399 mg, 4.740 mmol, 3.00 equiv) and 1,4-dioxane (15 mL) was placed in a 100-ml round-bottom flask. The resulting mixture was stirred for 6 h at 90° C. under a nitrogen atmosphere. LCMS showed the reaction was complete. The mixture was concentrated. The crude product was purified by flash chromatography on silica gel (PE/EA=10/1) to afford the desired product benzyl 8-(4,4,5,5-tetramethyl-1,3,2-dioxaborolan-2-yl)-2-oxa-5-azaspiro[3.4]oct-7-ene-5-carboxylate (Example 39-8, 375 mg, 82%) as a yellow oil. LCMS (ESI, m/z): 372 [M+H]$^+$.

Step 9

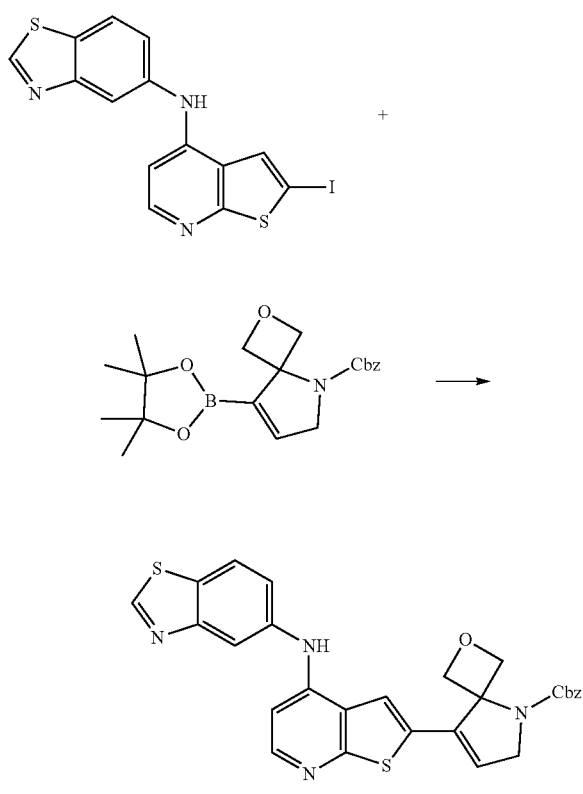

A mixture of benzyl 8-(4,4,5,5-tetramethyl-1,3,2-dioxaborolan-2-yl)-2-oxa-5-azaspiro[3.4]oct-7-ene-5-carboxylate (Example 39-8, 375 mg, 1.010 mmol, 1.00 equiv), N-(2-iodothieno[2,3-b]pyridin-4-yl)benzo[d]-thiazol-5-amine (409 mg, 1.000 mmol, 1.00 equiv), Pd(dppf)Cl$_2$ (73 mg, 0.100 mmol, 0.10 equiv), Cs$_2$CO$_3$ (977 mg, 3.000 mmol, 3.00 equiv), 1,4-dioxane (15 mL) and water (1.5 mL) was placed in a 50-ml round-bottom flask. The resulting mixture was stirred for 3 h at 90° C. under nitrogen atmosphere. LCMS showed the reaction was complete. The resulting mixture was quenched with water (20 mL) and extracted with EA (3×20 mL). The combined organic layers was dried over Na$_2$SO$_4$, filtered and concentrated under reduced pressure. The crude material was purified by flash chromatography on silica gel (DCM/MeOH=50/1) to afford the desired product benzyl 8-(4-(benzo-[d]thiazol-5-ylamino)thieno[2,3-b]pyridin-2-yl)-2-oxa-5-azaspiro[3.4]oct-7-ene-5-carboxylate (Example 39-9, 90 mg, 17%) as a yellow solid. LCMS (ESI, m/z): 527 [M+H]$^+$.

Step 10

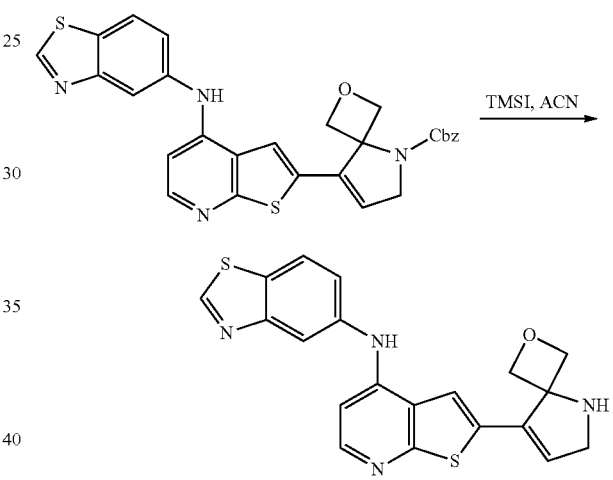

A mixture of benzyl 8-[4-(1,3-benzothiazol-5-ylamino)thieno[2,3-b]pyridin-2-yl]-2-oxa-5-azaspiro[3.4]oct-7-ene-5-carboxylate (Example 39-9, 70 mg, 0.130 mmol, 1.00 equiv), TMSI (70 mg, 0.870 mmol, 7.00 equiv) and ACN (15 mL) was placed in a 100-ml round-bottom flask. The resulting mixture was stirred for 16 h at room temperature. LCMS showed the reaction was complete. The mixture was quenched with TEA and concentrated under reduced pressure. The crude product was purified by preparative HPLC with the following conditions Column: XBridge Prep OBD C18 Column 30×150 mm; 5 μm; Mobile Phase A: Water (10 mmol/L NH$_4$HCO$_3$), Mobile Phase B: ACN; Flow rate: 60 mL/min; Gradient: 20% B to 38% B in 7.5 min; 210/254 nm; Rt: 7.15 min. Purification gave the desired product N-(2-(2-oxa-5-azaspiro[3.4]oct-7-en-8-yl)thieno[2,3-b]pyridin-4-yl)benzo[d]-thiazol-5-amine (Example 39, 19.6 mg, 38%) as a white solid. $^1$H NMR (400 MHz, Methanol-d$_4$) δ 9.32 (s, 1H), 8.14 (s, 1H), 8.12 (d, J=2.6 Hz, 1H), 8.05 (d, J=2.1 Hz, 1H), 7.78 (s, 1H), 7.56 (dd, J=8.6, 2.1 Hz, 1H), 7.03 (d, J=5.7 Hz, 1H), 6.00 (s, 1H), 4.48 (d, J=12.7 Hz, 1H), 4.08 (d, J=17.9 Hz, 1H), 3.74 (dd, J=17.9, 2.3 Hz, 1H), 3.57 (d, J=12.6 Hz, 1H), 2.37 (s, 1H), 1.70 (s, 1H). LCMS (ESI, m/z): 393 [M+H]$^+$.

Example 40: Synthesis of N-(2-(7-oxa-1-azaspiro[4.4]non-3-en-4-yl)thieno[2,3-b]pyridin-4-yl)benzo[d]thiazol-5-amine

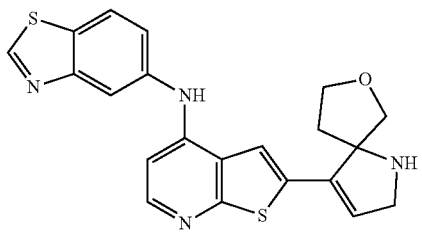 [SMILES: C1=C(c2cc3c(Nc4ccc5scnc5c4)ccnc3s2)C2(CCOC2)NC1]

Step 1

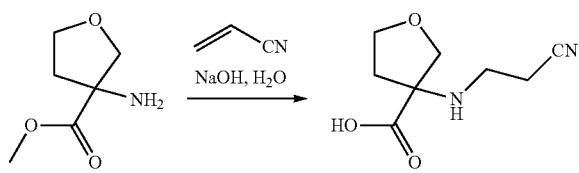

A mixture of methyl 3-aminotetrahydrofuran-3-carboxylate (15.0 g, 103.330 mmol, 1.00 equiv), prop-2-enenitrile (11.0 g, 206.670 mmol, 2.00 equiv) and NaOH (4.1 g, 103.330 mmol, 1.00 equiv) in water (33 mL) was placed in a 500-ml round-bottom flask. The resulting mixture was stirred for 12 h at 80° C. LCMS showed the reaction was completed. The mixture was concentrated to give 20 g of the crude product 3-((2-cyanoethyl)amino)tetrahydrofuran-3-carboxylic acid (Example 40-1), as a yellow solid. LCMS (ESI, m/z): 185 [M+H]⁺.

Step 2

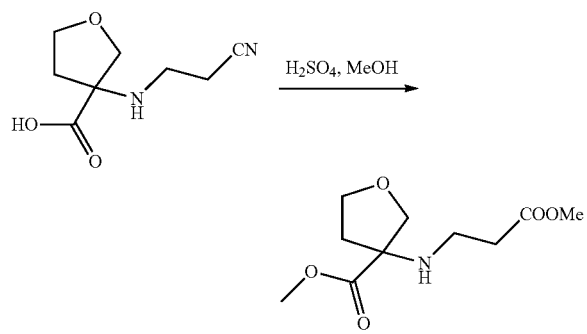

A mixture of 3-(2-cyanoethylamino)tetrahydrofuran-3-carboxylic acid (Example 40-1, 20 g, 108.580 mmol, 1.00 equiv), methanol (150 mL) and H₂SO₄ (30 mL) was placed in a 250-ml round-bottom flask. The resulting mixture was stirred for 12 h at 70° C. LCMS showed the reaction was completed. The mixture was quenched with NaHCO₃, extracted with DCM. The organic layer was washed with brine and concentrated. The residue was purified by flash chromatography (DCM/MeOH=10/1) to afford the desired product methyl 3-((3-methoxy-3-oxopropyl)amino)tetrahydrofuran-3-carboxylate (Example 40-2, 10.5 g, 44% for 2 steps) as a yellow oil. LCMS (ESI, m/z): 232 [M+H]⁺.

Step 3

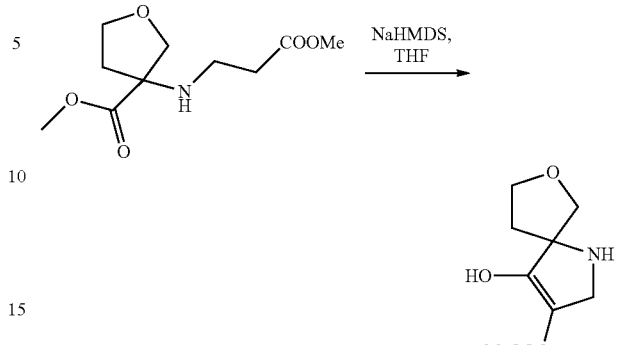

A mixture of methyl 3-[(3-methoxy-3-oxo-propyl)amino]tetrahydrofuran-3-carboxylate (Example 40-2, 10.5 g, 45.410 mmol, 1.00 equiv), LiHMDS (15.2 g, 90.810 mmol, 2.00 equiv) and THF (91 mL) was placed in a 500-ml round-bottom flask. The resulting mixture was stirred for 10 min at 0° C. TLC showed the reaction was complete. The mixture was quenched with HCl (1N, 136 mL) and extracted with DCM (3×200 mL). The combined organic phase was concentrated to give 15 g of the crude product methyl 4-hydroxy-7-oxa-1-azaspiro[4.4]non-3-ene-3-carboxylate (Example 40-3) as a brown oil. LCMS (ESI, m/z): 200 [M+H]⁺.

Step 4

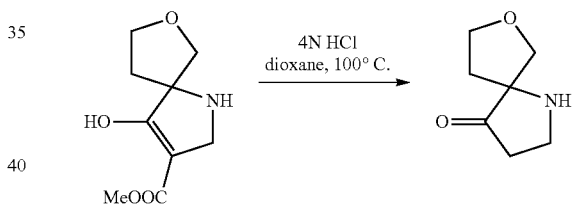

A mixture of methyl 4-hydroxy-7-oxa-1-azaspiro[4.4]non-3-ene-3-carboxylate (Example 40-3, 15.0 g, 75.300 mmol, 1.00 equiv) and HCl (4N in water, 95 mL) was placed in a 250-ml round-bottom flask. The resulting mixture was stirred for 12 h at 70° C. LCMS showed the reaction was complete, and the mixture was concentrated to give 11 g of the crude product 7-oxa-1-azaspiro[4.4]nonan-4-one (Example 40-4) as a yellow oil. LCMS (ESI, m/z): 142 [M+H]⁺.

Step 5

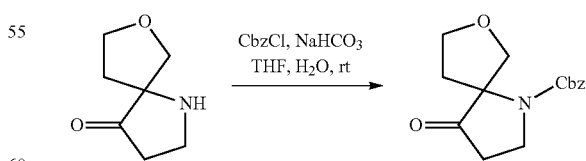

A mixture of 7-oxa-1-azaspiro[4.4]nonan-4-one (Example 40-4, 11.0 g, 77.920 mmol, 1.00 equiv), benzyl carbonochloridate (15.9 g, 93.500 mmol, 1.20 equiv), K₂CO₃ (24.8 g, 233.760 mmol, 3.00 equiv), THF (120 mL) and water (15 mL) was placed in a 100-ml round-bottom flask. The resulting mixture was stirred for 3 h at room temperature. LCMS showed the reaction was complete. The mixture was quenched with water and extracted with EA. The organic layer was washed with brine and concentrated. The residue was purified by flash chromatography (DCM/MeOH=80/1) to afford the desired product benzyl 4-oxo-7-oxa-1-azaspiro[4.4]nonane-1-carboxylate (Example 40-5, 4.5 g, 21%) as a yellow oil. LCMS (ESI, m/z): 276 [M+H]⁺.

Step 6

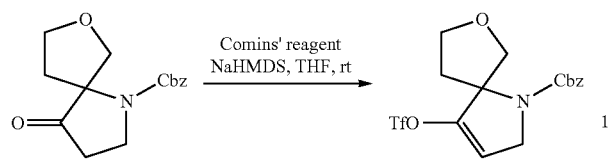

A mixture of benzyl 4-oxo-7-oxa-1-azaspiro[4.4]nonane-1-carboxylate (Example 40-5, 4.5 g, 16.160 mmol, 1.00 equiv), NaHMDS (3.8 g, 21.010 mmol, 1.30 equiv) and THF (80 mL) was placed in a 100-ml 3-necked round-bottom flask. The resulting mixture was stirred for min at −78° C. N-(5-chloro-2-pyridyl)-1,1,1-trifluoro-N-(trifluoromethylsulfonyl)methanesulfonamide (8.2 g, 21.010 mmol, 1.30 equiv) was added and the resulting mixture was stirred for 1 h at −78° C. Then the reaction temperature was allowed to warm up to room temperature and the mixture was stirred overnight. LCMS showed the reaction was complete. The mixture was quenched with water and extracted with EA. The organic layer was washed with brine and concentrated. The residue was purified by silica gel flash chromatography (PE/EA=40/1) to afford the desired product benzyl 4-(((trifluoro-methyl)sulfonyl)-oxy)-7-oxa-1-azaspiro[4.4]non-3-ene-1-carboxylate (Example 40-6, 6.6 g, 99%) as a yellow oil. LCMS (ESI, m/z): 408 [M+H]⁺.

Step 7

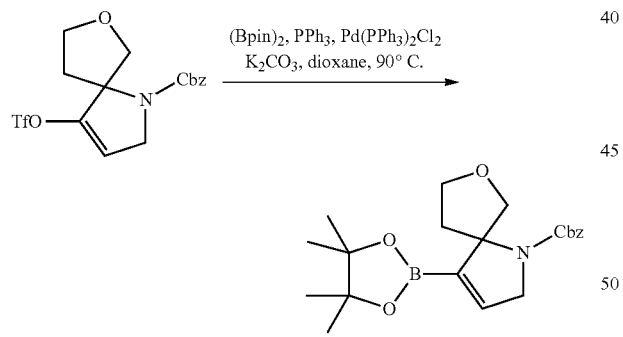

A mixture of benzyl 4-(((trifluoromethyl)sulfonyl)oxy)-7-oxa-1-azaspiro[4.4]non-3-ene-1-carboxylate (Example 40-6, 6.6 g, 16.200 mmol, 1.00 equiv), 4,4,5,5-tetramethyl-2-(4,4,5,5-tetramethyl-1,3,2-dioxaborolan-2-yl)-1,3,2-dioxaborolane (4.9 g, 19.440 mmol, 1.20 equiv), Pd(dppf)Cl₂ (1.2 g, 1.620 mmol, 0.10 equiv) and CH₃COOK (4.1 g, 48.610 mmol, 3.00 equiv) in 1,4-dioxane (80 mL) was placed in a 25-ml round-bottom flask. The resulting mixture was stirred for 3 h at 90° C. under nitrogen atmosphere. LCMS showed the reaction was complete. The reaction mixture was filtered and the filtrate was concentrated. The crude mixture was purified by silica gel flash chromatography (PE/EA=4/1) to afford the desired product benzyl 4-(4,4,5,5-tetramethyl-1,3,2-dioxaborolan-2-yl)-7-oxa-1-azaspiro[4.4]non-3-ene-1-carboxylate (Example 40-7, 2.6 g, 42%) as a yellow oil. LCMS (ESI, m/z): 386 [M+H]⁺.

Step 8

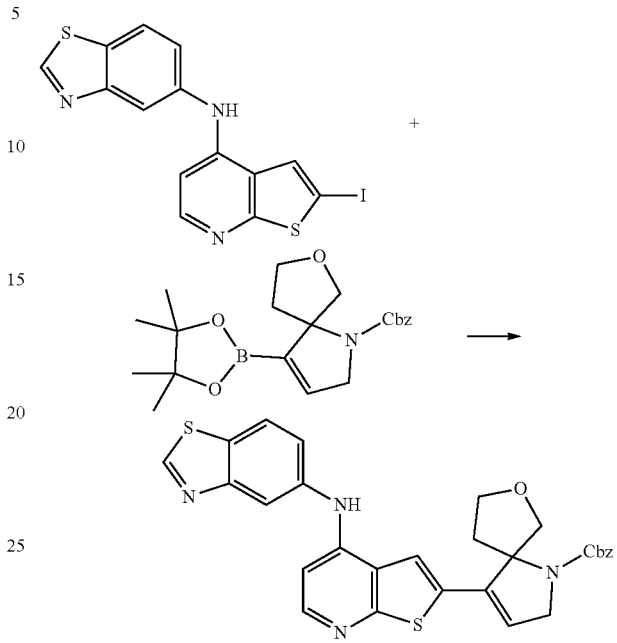

A mixture of N-(2-iodothieno[2,3-b]pyridin-4-yl)benzo[d]thiazol-5-amine (1.1 g, 2.600 mmol, 1.00 equiv), benzyl 4-(4,4,5,5-tetramethyl-1,3,2-dioxaborolan-2-yl)-7-oxa-1-azaspiro[4.4]non-3-ene-1-carboxylate (Example 40-7, 1.0 g, 2.600 mmol, 1.00 equiv), Pd(dppf)Cl₂ (190 mg, 0.2600 mmol, 0.10 equiv), Cs₂CO₃ (2.5 g, 7.790 mmol, 3.00 equiv), 1,4-dioxane (15 mL) and water (1.5 mL) was placed in a 100-ml round-bottom flask. The resulting mixture was stirred for 6 h at 90° C. under nitrogen atmosphere. LCMS showed the reaction was complete. The reaction mixture was filtered and the filtrate was concentrated. The residue was purified by silica gel flash chromatography on silica gel (EA/PE=1/1) to give the desired product benzyl 4-(4-(benzo[d]thiazol-5-ylamino)thieno[2,3-b]pyridin-2-yl)-7-oxa-1-azaspiro[4.4]non-3-ene-1-carboxylate (Example 40-8, 700 mg, 50%) as a yellow solid. LCMS (ESI, m/z): 541 [M+H]⁺.

Step 9

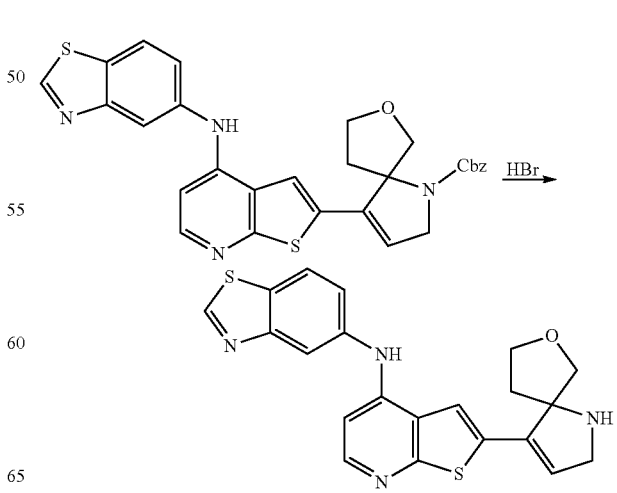

A mixture of benzyl 4-(4-(benzo[d]thiazol-5-ylamino) thieno[2,3-b]pyridin-2-yl)-7-oxa-1-azaspiro[4.4]non-3-ene-1-carboxylate (Example 40-8, 100 mg, 0.180 mmol, 1.00 equiv) and HBr (40% in water, 5 mL) was placed in a 100-ml round-bottom flask. The resulting mixture was stirred for 12 h at room temperature. LCMS showed the reaction was complete. The mixture was concentrated and the crude product was purified by preparative HPLC with the following conditions: Column: XBridge BEH130 Prep C18 OBD Column, 19×150 mm, 5 μm, 13 nm; Mobile Phase A: Water (10 mmol/L $NH_4HCO_3$), Mobile Phase B: ACN; Flow rate: 25 mL/min; Gradient: 30% B to 50% B in 10 min; 254/210 nm; Rt: 9.65 min. Purification gave the desired product N-(2-(7-oxa-1-azaspiro[4.4]non-3-en-4-yl)thieno[2,3-b]pyridin-4-yl)benzo[d]thiazol-5-amine (Example 40, 33.4 mg, 46%) as a white solid. $^1$H NMR (400 MHz, Methanol-$d_4$) δ 9.30 (s, 1H), 8.16-8.08 (m, 2H), 8.00 (d, J=2.1 Hz, 1H), 7.58-7.42 (m, 2H), 6.98 (d, J=5.7 Hz, 1H), 6.39 (t, J=2.3 Hz, 1H), 4.28 (d, J=9.6 Hz, 1H), 4.07 (td, J=8.5, 2.6 Hz, 1H), 3.92 (td, J=9.3, 6.3 Hz, 1H), 3.79 (d, J=2.4 Hz, 2H), 3.70 (d, J=9.7 Hz, 1H), 2.51 (dt, J=13.1, 9.2 Hz, 1H), 2.06 (ddd, J=13.0, 6.1, 2.6 Hz, 1H). LCMS (ESI, m/z): 407 [M+H]$^+$.

Example 41: Synthesis of N-(2-(1-methyl-7-oxa-1-azaspiro[4.4]non-3-en-4-yl)thieno[2,3-b]pyridin-4-yl)benzo[d]thiazol-5-amine

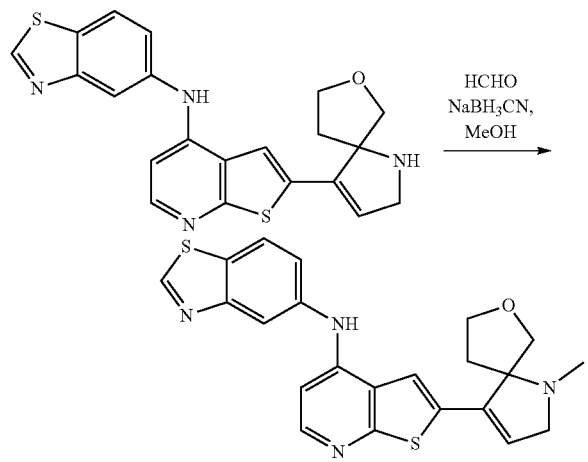

A mixture of N-(2-(7-oxa-1-azaspiro[4.4]non-3-en-4-yl) thieno[2,3-b]pyridin-4-yl)benzo[d]thiazol-5-amine (Example 40, 100 mg, 0.250 mmol, 1.00 equiv), TEA (0.1 mL, 0.740 mmol, 3.00 equiv), HCHO (74 mg, 2.460 mmol, 1.50 equiv), AcOH (0.14 mL, 2.460 mmol, 10.00 equiv) in methanol (5 mL) was stirred at 25° C. for 0.5 hours, followed by the addition of NaBH$_3$CN (46 mg, 0.740 mmol, 3.00 equiv). LCMS showed the reaction was complete. The reaction mixture was quenched with water (10 ml) and extracted with EA (3×10 ml). The combined organic layers was washed with brine, concentrated and purified by preparative HPLC to afford the desired product N-(2-(1-methyl-7-oxa-1-azaspiro[4.4]non-3-en-4-yl)thieno[2,3-b]pyridin-4-yl)benzo[d]thiazol-5-amine (Example 41, 26 mg, 25%) as a yellow solid. Column: XBridge BEH130 Prep C18 OBD Column, 19×150 mm, 5 μm, 13 nm; Mobile Phase A: Water (0.05% TFA), Mobile Phase B: ACN; Flow rate: 25 mL/min; Gradient: 10% B to 40% B in 7 min; 254/210 nm; Rt: 6.95 min. $^1$H NMR (400 MHz, Methanol-$d_4$) δ 9.41 (s, 1H), 8.30-8.27 (m, 2H), 8.15 (d, J=2.0 Hz, 1H), 7.88 (s, 1H), 7.60 (dd, J=8.5, 2.1 Hz, 1H), 7.06 (d, J=6.9 Hz, 1H), 6.69-6.24 (m, 1H), 4.49 (s, 1H), 4.40-4.28 (m, 2H), 4.22 (s, 1H), 4.13 (q, J=8.0 Hz, 1H), 3.14 (s, 3H), 2.91-2.58 (m, 2H). LCMS (ESI, m/z): 421 [M+H]$^+$.

Example 42: Synthesis of N-(2-(7-oxa-1-azaspiro [4.4]nonan-4-yl)thieno[2,3-b]pyridin-4-yl)benzo[d]thiazol-5-amine

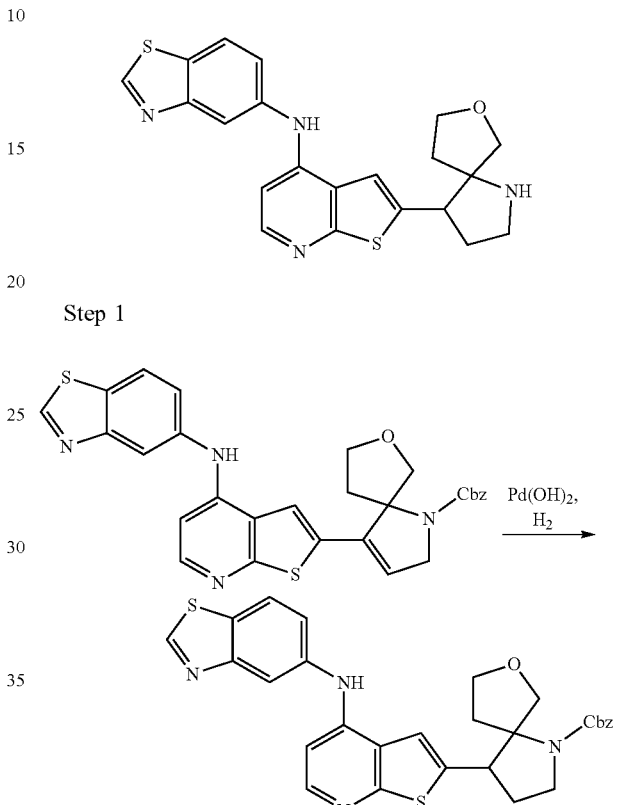

Step 1

A mixture benzyl 4-(4-(benzo[d]thiazol-5-ylamino)thieno [2,3-b]pyridin-2-yl)-7-oxa-1-azaspiro-[4.4]non-3-ene-1-carboxylate (Example 40-8, 200 mg, 0.370 mmol, 1.00 equiv) and Pd(OH)$_2$ (200 mg, 1.00 w/w) in ethanol (15 mL) was placed in a 25-ml round-bottom flask. The resulting mixture was stirred for 36 h under hydrogen atmosphere (1-3 atm.) at 60° C. LCMS showed the reaction was complete. The reaction mixture was filtered and the filtrate was concentrated. The crude residue was purified by silica gel flash chromatography (PE/EA=1/1) to afford the desired product benzyl 4-(4-(benzo[d]thiazol-5-yl-amino)thieno[2,3-b]pyridin-2-yl)-7-oxa-1-azaspiro[4.4]nonane-1-carboxylate (Example 42-1, 105 mg, 52%) as a yellow solid. LCMS (ESI, m/z): 543 [M+H]$^+$.

Step 2

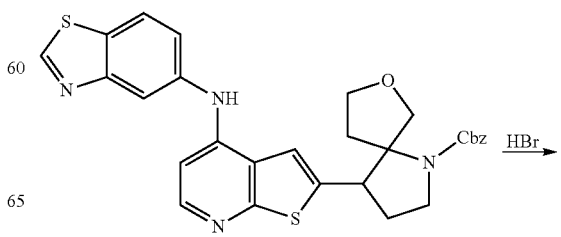

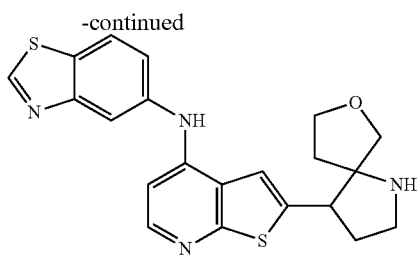

A solution of benzyl 4-(4-(benzo[d]thiazol-5-ylamino)thieno[2,3-b]pyridin-2-yl)-7-oxa-1-aza-spiro[4.4]nonane-1-carboxylate (Example 42-1, 105 mg, 0.190 mmol, 1.00 equiv) in HBr (40% in water, 5 mL) was placed in a 100-ml round-bottom flask. The resulting mixture was stirred for 4 h at room temperature. LCMS showed the reaction was completed and the mixture was concentrated. The crude product was purified by preparative HPLC (Column: XBridge Prep C18 OBD Column, 19×150 mm, 5 μm; Mobile Phase A: Water (10 mmol/L NH$_4$HCO$_3$), Mobile Phase B: ACN; Flow rate: 25 mL/min; Gradient: 20% B to 45% B in 9 min; 254/210 nm; Rt: 7.95 min) to give the desired product N-(2-(7-oxa-1-azaspiro[4.4]nonan-4-yl)thieno[2,3-b]pyridin-4-yl)benzo[d]thiazol-5-amine (Example 42, 34 mg, 44%) as a white solid. $^1$H NMR (400 MHz, Methanol-d$_4$) δ 9.30 (s, 1H), 8.17-8.08 (m, 2H), 8.03 (d, J=2.1 Hz, 1H), 7.54 (dd, J=8.5, 2.2 Hz, 1H), 7.48 (d, J=3.5 Hz, 1H), 7.02 (d, J=5.7 Hz, 1H), 4.01-3.73 (m, 3H), 3.70-3.45 (m, 2H), 3.41-3.28 (m, 1H), 3.30-3.01 (m, 1H), 2.60-1.62 (m, 4H). LCMS (ESI, m/z): 409 [M+H]$^+$.

Example 43: Synthesis of N-(2-(1-methyl-7-oxa-1-azaspiro[4.4]nonan-4-yl)thieno[2,3-b]pyridin-4-yl)benzo[d]thiazol-5-amine

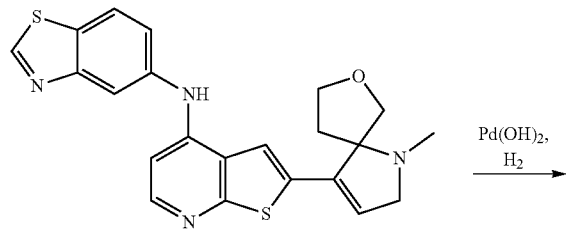

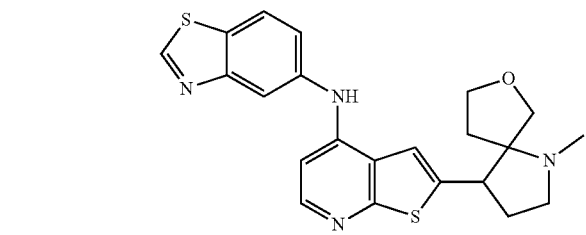

A mixture of N-(2-(1-methyl-7-oxa-1-azaspiro[4.4]non-3-en-4-yl)thieno[2,3-b]pyridin-4-yl)benzo[d]-thiazol-5-amine (Example 41, 50 mg, 0.120 mmol, 1.00 equiv) and Pd(OH)$_2$ (50 mg, 1.00 w/w) in ethanol (4 mL) was stirred at 60° C. for 12 hours under H$_2$ atmosphere (1-3 atm.). LCMS showed the reaction was completed. The reaction mixture was filtered with the aid of celite and the filtration was concentrated. The residue was purified by preparative HPLC to afford the desired product N-(2-(1-methyl-7-oxa-1-azaspiro-[4.4]nonan-4-yl)thieno[2,3-b]pyridin-4-yl)benzo[d]thiazol-5-amine (Example 43, 26.7 mg, 53%) as a yellow solid. Column: XBridge BEH130 Prep C18 OBD Column, 19×150 mm, 5 μm, 13 nm; Mobile Phase A: Water (0.05% TFA), Mobile Phase B: ACN; Flow rate: 25 mL/min; Gradient: 10% B to 40% B in 7 min; 254/210 nm; Rt: 6.95 min. $^1$H NMR (400 MHz, Methanol-d$_4$) δ 9.40 (s, 1H), 8.44-8.21 (m, 3H), 8.16 (d, J=2.0 Hz, 1H), 7.93 (s, 1H), 7.60 (dd, J=8.5, 2.1 Hz, 1H), 7.07 (d, J=6.9 Hz, 1H), 4.53-3.94 (m, 4H), 3.91-3.53 (m, 3H), 3.03 (d, J=5.4 Hz, 3H), 2.89-2.09 (m, 4H). LCMS (ESI, m/z): 423 [M+H]$^+$.

Example 44: Synthesis of N-(2-(1-ethyl-7-oxa-1-azaspiro[4.4]non-3-en-4-yl)thieno[2,3-b]pyridin-4-yl)benzo[d]thiazol-5-amine

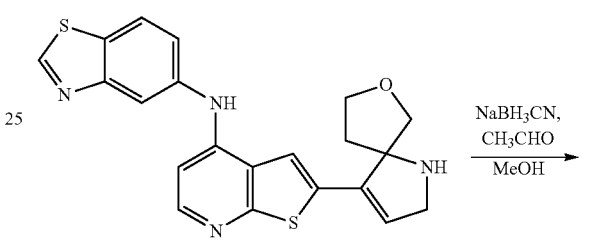

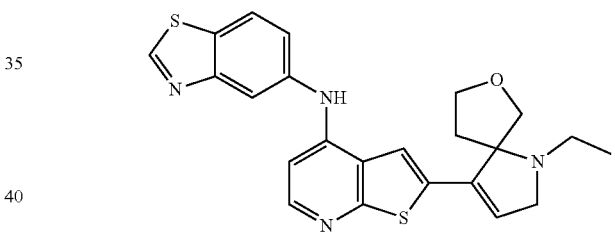

A mixture of N-(2-(7-oxa-1-azaspiro[4.4]non-3-en-4-yl)thieno[2,3-b]pyridin-4-yl)benzo[d]thiazol-5-amine (Example 40, 100 mg, 0.250 mmol, 1.00 equiv), TEA (0.1 mL, 0.740 mmol, 3.00 equiv), CH$_3$CHO (5M in THF, 0.5 mL) and AcOH (0.14 mL, 2.460 mmol, 10.00 equiv) in methanol (5 mL) was stirred at 25° C. for 0.5 hours, followed by the addition of NaBH$_3$CN (46 mg, 0.740 mmol, 3.00 equiv). LCMS showed the reaction was complete. The reaction mixture was quenched with water (10 ml) and extracted with EA (3×10 ml). The combined organic layer was washed with brine, concentrated and purified by preparative HPLC to afford the desired product N-(2-(1-ethyl-7-oxa-1-azaspiro[4.4]non-3-en-4-yl)thieno[2,3-b]pyridin-4-yl)-benzo[d]thiazol-5-amine (Example 44, 33.9 mg, 32%) as a yellow solid. Column: XBridge BEH130 Prep C18 OBD Column, 19×150 mm, 5 μm, 13 nm; Mobile Phase A: Water (0.05% TFA), Mobile Phase B: ACN; Flow rate: 25 mL/min; Gradient: 10% B to 35% B in 10 min; 254/210 nm; Rt: 9.56 min. $^1$H NMR (400 MHz, Methanol-d$_4$) δ 9.40 (s, 1H), 8.35-8.24 (m, 2H), 8.14 (d, J=2.1 Hz, 1H), 7.87 (s, 1H), 7.59 (dd, J=8.5, 2.1 Hz, 1H), 7.06 (d, J=6.9 Hz, 1H), 6.61 (s, 1H), 4.72-3.97 (m, 6H), 3.72-3.45 (m, 2H), 3.01-2.47 (m, 2H), 1.45 (t, J=7.2 Hz, 3H). LCMS (ESI, m/z): 435[M+H]$^+$.

Example 45: Synthesis of N-(2-(1-ethyl-7-oxa-1-azaspiro[4.4]nonan-4-yl)thieno[2,3-b]pyridin-4-yl)benzo[d]thiazol-5-amine

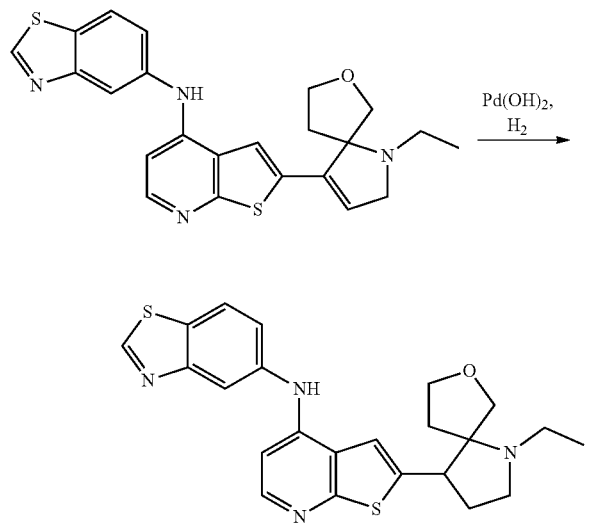

A mixture of N-(2-(1-ethyl-7-oxa-1-azaspiro[4.4]non-3-en-4-yl)thieno[2,3-b]pyridin-4-yl)benzo[d]-thiazol-5-amine (Example 44, 50 mg, 0.120 mmol, 1.00 equiv) and Pd(OH)$_2$ (50 mg, 1.00 w/w) in ethanol (4 mL) was stirred at 60° C. for 12 hours under H$_2$ atmosphere (1-3 atm.). LCMS showed the reaction was complete. The reaction mixture was filtered through celite and the filtrate was concentrated. The residue was purified by preparative HPLC to afford the desired product N-(2-(1-ethyl-7-oxa-1-azaspiro[4.4]nonan-4-yl)-thieno[2,3-b]pyridin-4-yl)benzo[d]thiazol-5-amine (Example 45, 16.2 mg, 50%) as a yellow solid. Column: Sunfire Prep C18 OBD Column, 10 μm, 19×250 mm; Mobile Phase A: Water (0.05% TFA), Mobile Phase B: ACN; Flow rate: 25 mL/min; Gradient: 15% B to 20% B in 8 min; 254/210 nm; Rt: 5.76 min. $^1$H NMR (400 MHz, Methanol-d$_4$) δ 9.40 (s, 1H), 8.35-8.24 (m, 2H), 8.16 (d, J=2.1 Hz, 1H), 7.93 (d, J=4.1 Hz, 1H), 7.60 (dd, J=8.6, 2.1 Hz, 1H), 7.07 (d, J=7.0 Hz, 1H), 4.51-3.80 (m, 5H), 3.69-3.42 (m, 4H), 2.90-2.08 (m, 4H), 1.58-1.25 (m, 3H). LCMS (ESI, m/z): 437 [M+H]$^+$.

Example 46: Synthesis of N-(2-(8-oxa-1-azaspiro[4.5]dec-3-en-4-yl)thieno[2,3-b]pyridin-4-yl)benzo[d]thiazol-5-amine

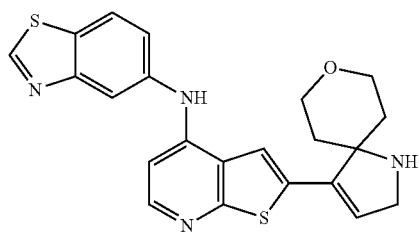 [SMILES: C1=C(c2cc3c(Nc4ccc5scnc5c4)ccnc3s2)C2(CCOCC2)NC1]

Step 1

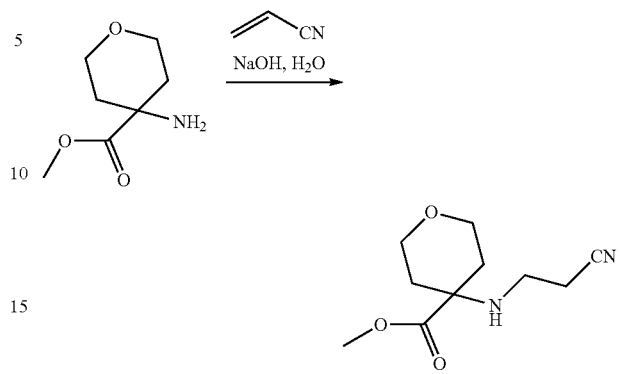

To a solution of methyl 4-aminotetrahydro-2H-pyran-4-carboxylate (2.0 g, 12.560 mmol, 1.00 equiv) in water (3 mL) was added NaOH (0.5 g, 12.560 mmol, 1.00 equiv) at 0° C., followed by dropwise addition of prop-2-enenitrile (0.7 mL, 12.560 mmol, 1.00 equiv). The reaction solution was stirred at 80° C. for 3 h. Then another portion of prop-2-enenitrile (0.7 mL, 12.560 mmol, 1.00 equiv) was added. The reaction mixture was stirred at 80° C. for 16 h. LCMS showed the reaction was complete. The resulting solution was concentrated. The crude product methyl 4-((2-cyanoethyl)-amino)tetrahydro-2H-pyran-4-carboxylate (Example 46-1) was used directly for the next step without further purification. LCMS (ESI, m/z): 213 [M+H]$^+$ Step 2

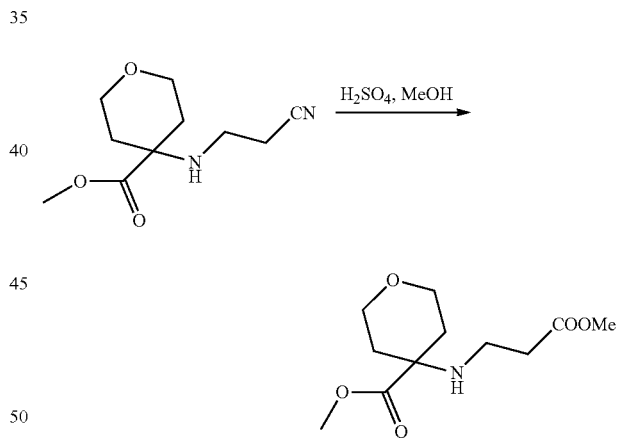

To a solution of methyl 4-((2-cyanoethyl)amino)tetrahydro-2H-pyran-4-carboxylate (Example 46-1, 2.2 g, 10.220 mmol, 1.00 equiv) in methanol (15 mL) was added H$_2$SO$_4$ (3.5 mL, 71.570 mmol, 7.00 equiv). The resulting solution was stirred at 75° C. for 16 h. LCMS showed the reaction was complete. The resulting mixture was quenched with NaHCO$_3$ (sat. aq., 60 mL) and extracted with DCM (3×50 mL). The combined organic lawyer was dried over Na$_2$SO$_4$, filtered and concentrated under reduced pressure. The crude product was purified by flash chromatography on silica gel with DCM/MeOH (10:1) to afford methyl 4-((3-methoxy-3-oxopropyl)amino)tetrahydro-2H-pyran-4-carboxylate (Example 46-2, 1.73 g, 69% yield) as an orange oil. LCMS (ESI, m/z): 246 [M+H]$^+$.

Step 3

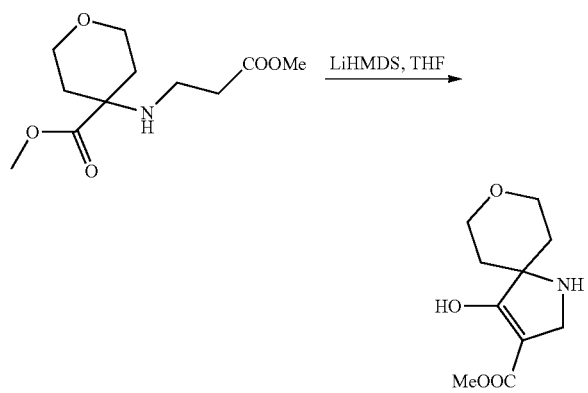

To a solution of methyl 4-((3-methoxy-3-oxopropyl)amino)tetrahydro-2H-pyran-4-carboxylate (Example 46-2, 1.7 g, 7.050 mmol, 1.00 equiv) in THF (15 mL) was added LiHMDS in THF (1 mol/mL, 14 mL, 14.100 mmol, 2.00 equiv) dropwise at 0° C. The reaction mixture was stirred at 0° C. for 10 min under nitrogen atmosphere. LCMS showed the reaction was complete. The resulting mixture was quenched with 1N HCl (50 mL), extracted with DCM (3×50 mL), dried over Na$_2$SO$_4$, filtered and concentrated under reduced pressure. The crude product methyl 4-hydroxy-8-oxa-1-azaspiro[4.5]dec-3-ene-3-carboxylate (Example 46-3) was used directly for the next step without further purification. LCMS (ESI, m/z): 214 [M+H]$^+$.

Step 4

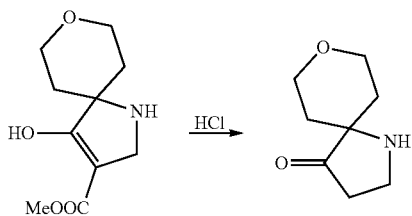 [SMILES: COC(=O)C1=C(O)C2(CCOCC2)NC1 ; Cl ; O=C1CCNC12CCOCC2]

To a solution of methyl 4-hydroxy-8-oxa-1-azaspiro[4.5]dec-3-ene-3-carboxylate (Example 46-3, crude, 1.5 g, 7.030 mmol, 1.00 equiv) in water (20 mL) was added hydrochloric acid (concentrated, 15 mL). The resulting solution was stirred at 70° C. for 16 h. LCMS showed the reaction was complete. The solvent was removed and the crude product 8-oxa-1-azaspiro[4.5]decan-4-one (Example 46-4) was used directly for the next step without further purification. LCMS (ESI, m/z): 156 [M+H]$^+$ Step 5

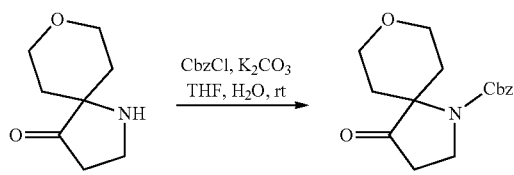 [SMILES: O=C1CCNC12CCOCC2 ; "CbzCl, K2CO3THF, H2O, rt" ; O=C(OCc1ccccc1)N1CCC(=O)C12CCOCC2]

To a solution of of 8-oxa-1-azaspiro[4.5]decan-4-one (Example 46-4, crude, 1.1 g, 7.020 mmol, 1.00 equiv) in THF/Water (15 mL/15 mL) was added K$_2$CO$_3$ (3.9 g, 28.090 mmol, 4.00 equiv) and benzyl carbonochloridate (1.4 g, 8.430 mmol, 1.20 equiv) and the resulting solution was stirred 30 min at room temperature. LCMS showed the reaction was complete. The reaction was quenched by water (30 mL) and extracted with EA (2×20 mL). The combined organic lawyer was dried over Na$_2$SO$_4$, filtered and concentrated under reduced pressure. The crude residue was purified by HPLC (0% ACN to 100% ACN) to afford benzyl 4-oxo-8-oxa-1-azaspiro[4.5]decane-1-carboxylate (Example 46-5, 1.03 g, 3.560 mmol, 50%) as a light yellow oil. LCMS (ESI, m/z): 290 [M+H]$^+$.

Step 6

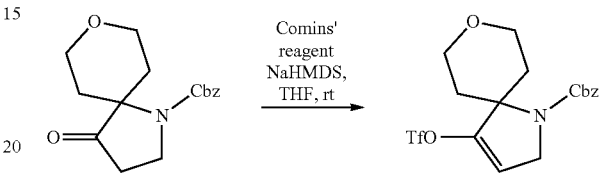

To a solution of benzyl 4-oxo-8-oxa-1-azaspiro[4.5]decane-1-carboxylate (Example 46-5, 1.0 g, 3.560 mmol, 1.00 equiv) in THF (5 mL) was added NaHMDS (2.5 M in THF, 2 mL, 4.500 mmol, 1.30 equiv) dropwise at −78° C. The resulting mixture was stirred at −78° C. for 0.5 h under nitrogen atmosphere. A solution of Comins' reagent (1.8 g, 4.500 mmol, 1.30 equiv) in THF (5 mL) was then added dropwise and stirred at −78° C. for 10 min. The reaction solution was allowed to warm up to room temperature and stirred for 16 h. LCMS showed the reaction was complete. The resulting mixture was quenched with NH$_4$Cl (sat. aq, 20 mL) and extracted with EA (3×10 mL). The combined organic layer was dried over Na$_2$SO$_4$, filtered and concentrated under reduced pressure. The crude product was purified by flash chromatography on silica gel (100% PE to 30% EtOAc) to afford benzyl 4-(((trifluoromethyl)-sulfonyl)oxy)-8-oxa-1-azaspiro[4.5]dec-3-ene-1-carboxylate (Example 46-6, 1.3 g, 3.080 mmol, 86% yield) as a light yellow oil. LCMS (ESI, m/z): 422 [M+H]$^+$.

Step 7

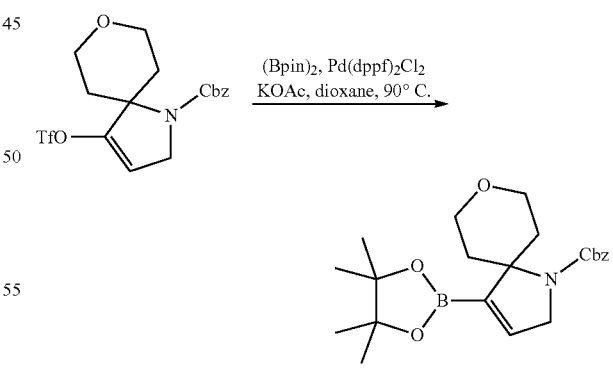

Into a 40-mL sealed tube purged and maintained under an inert atmosphere of nitrogen was placed benzyl 4-(((trifluoromethyl)sulfonyl)oxy)-8-oxa-1-azaspiro[4.5]dec-3-ene-1-carboxylate (Example 46-6, 1.3 g, 3.090 mmol, 1.00 equiv), 4,4,5,5-tetramethyl-2-(4,4,5,5-tetramethyl-1,3,2-dioxaborolan-2-yl)-1,3,2-dioxa-borolane (783 mg, 3.090 mmol, 1.00 equiv), KOAc (908 mg, 9.260 mmol, 3.00 equiv), Pd(dppf)Cl$_2$ (226 mg, 0.310 mmol, 0.10 equiv) and 1,4-dioxane (4 mL). The resulting solution was stirred for 5 h at 90° C. The resulting solution was concentrated. The residue was purified by flash chromatography on silica gel (PE:EA=8:1) to give 1.0 g (81%) of benzyl 4-(4,4,5,5-tetramethyl-1,3,2-dioxaborolan-2-yl)-8-oxa-1-azaspiro[4.5]dec-3-ene-1-carboxylate (Example 46-7) as a light yellow oil. LCMS (ESI, m/z): 400 [M+H]$^+$.

Step 8

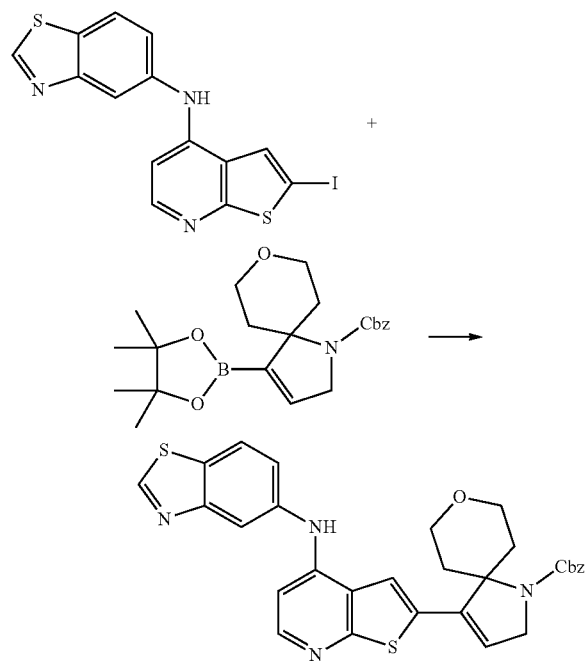

Into a 40-mL sealed tube purged and maintained inert atmosphere of nitrogen was placed N-(2-iodothieno[2,3-b]pyridin-4-yl)benzo[d]thiazol-5-amine (300 mg, 0.730 mmol, 1.00 equiv), benzyl 4-(4,4,5,5-tetramethyl-1,3,2-dioxaborolan-2-yl)-8-oxa-1-azaspiro[4.5]dec-3-ene-1-carboxylate (Example 46-7, 293 mg, 0.730 mmol, 1.00 equiv), Cs$_2$CO$_3$ (717 mg, 2.200 mmol, 3.00 equiv), Pd(dppf)Cl$_2$ (54 mg, 0.070 mmol, 0.10 equiv) and 1,4-dioxane/water (5 mL/1 mL). The resulting solution was stirred for 2 h at 90° C. LCMS showed the reaction was complete. The resulting solution was concentrated. The residue was purified by flash chromatography on silica gel (PE:EA=4:1) to give 210 mg (51%) of benzyl 4-(4-(benzo[d]thiazol-5-ylamino)thieno[2,3-b]pyridin-2-yl)-8-oxa-1-azaspiro[4.5]dec-3-ene-1-carboxylate (Example 46-8) as a light yellow oil. LCMS (ESI, m/z): 555 [M+H]$^+$.

Step 9

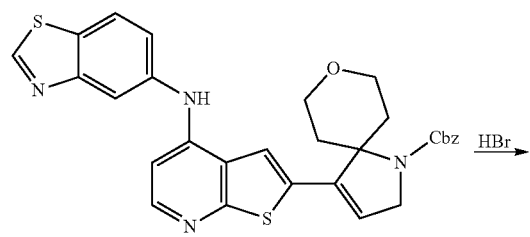

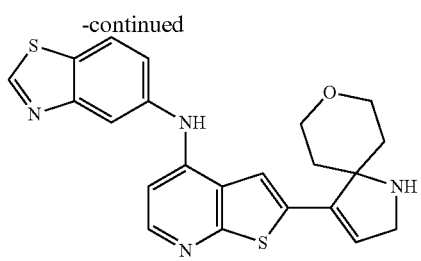

Into a 50-mL round-bottom flask was placed benzyl 4-(4-(benzo[d]thiazol-5-ylamino)thieno[2,3-b]pyridin-2-yl)-8-oxa-1-azaspiro[4.5]dec-3-ene-1-carboxylate (Example 46-8, 100 mg, 0.180 mmol, 1.00 equiv), HBr (~30% in water, 6 mL). The resulting mixture was stirred for 30 min at room temperature. LCMS showed the reaction was complete. The mixture was purified by preparative HPLC using the following gradient conditions: Column: Sunfire Prep C18 OBD Column, 10 μm, 19×250 mm; Mobile Phase A: water (0.05% TFA), Mobile Phase B: ACN; Flow rate: 25 mL/min; Gradient: 5% B to 30% B in 8 min; 254/210 nm; Rt: 6.95 min. Purification gave N-(2-(8-oxa-1-azaspiro[4.5]dec-3-en-4-yl)thieno[2,3-b]pyridin-4-yl)benzo[d]thiazol-5-amine (Example 46, 28.2 mg, 37%) as light yellow solid. $^1$H NMR (400 MHz, Methanol-d$_4$) δ 9.40 (s, 1H), 8.28-8.24 (m, 2H), 8.15 (d, J=2.1 Hz, 1H), 8.07 (s, 1H), 7.61 (d, J=8.6 Hz, 1H), 7.08 (d, J=6.8 Hz, 1H), 6.50 (t, J=2.5 Hz, 1H), 4.37 (d, J=2.5 Hz, 2H), 4.14 (dd, J=12.6, 5.4 Hz, 2H), 3.74 (dd, J=13.6, 11.7 Hz, 2H), 2.69 (td, J=14.0, 13.4, 5.6 Hz, 2H), 2.02 (d, J=14.8 Hz, 2H). LCMS (ESI, m/z): 421 [M+H]$^+$.

Example 47: Synthesis of N-(2-(1-ethyl-8-oxa-1-azaspiro[4.5]dec-3-en-4-yl)thieno[2,3-b]pyridin-4-yl)benzo[d]thiazol-5-amine

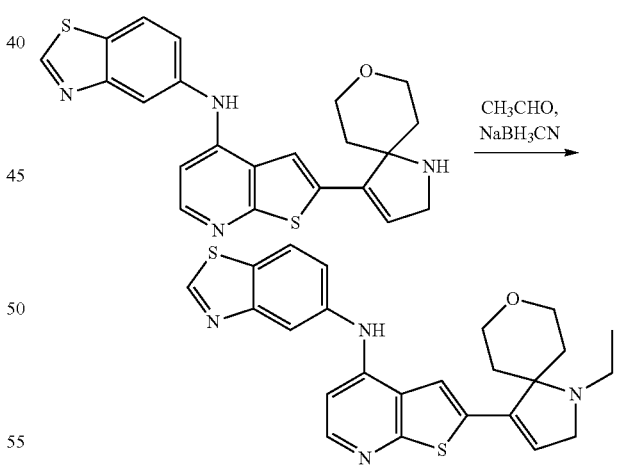

Into a 10-mL sealed tube was placed N-(2-(8-oxa-1-azaspiro[4.5]dec-3-en-4-yl)thieno[2,3-b]pyridin-4-yl)benzo[d]thiazol-5-amine (Example 46, 80 mg, 0.190 mmol, 1.00 equiv), CH$_3$CHO (17 mg, 0.380 mmol, 2.00 equiv) and methanol (2 mL). After stirring for 10 min, NaBH$_3$CN (23.9 mg, 0.380 mmol, 2.00 equiv) was added portion wise. The resulting solution was stirred for 1 h at room temperature. LCMS showed the reaction was complete. The resulting solution was concentrated. The residue was purified by preparative HPLC using the following gradient conditions:

Column: XBridge BEH130 Prep C18 OBD Column, 19×150 mm, 5 μm, 13 nm; Mobile Phase A: Water (10 mmol/L NH₄HCO₃), Mobile Phase B: ACN; Flow rate: 25 mL/min; Gradient: 30% B to 60% B in 7 min; 254/210 nm; Rt: 6.95 min. Purification gave N-(2-(1-ethyl-8-oxa-1-azaspiro[4.5]dec-3-en-4-yl)thieno[2,3-b]pyridin-4-yl)benzo[d]thiazol-5-amine (Example 47, 23.5 mg, 27%) as a light pink solid. $^1$H NMR (400 MHz, Methanol-$d_4$) δ 9.31 (s, 1H), 8.17-8.09 (m, 2H), 8.04 (d, J=2.1 Hz, 1H), 7.61 (s, 1H), 7.55 (dd, J=8.6, 2.1 Hz, 1H), 7.02 (d, J=5.7 Hz, 1H), 6.23 (s, 1H), 3.92-3.78 (m, 4H), 3.67 (s, 2H), 2.90-2.81 (m, 2H), 2.31-2.19 (m, 2H), 2.01-1.91 (m, 2H), 1.19 (t, J=7.1 Hz, 3H). LCMS (ESI, m/z): 449 [M+H]$^+$.

Example 48: Synthesis of N-(2-(1-ethyl-8-oxa-1-azaspiro[4.5]decan-4-yl)thieno[2,3-b]pyridin-4-yl)benzo[d]thiazol-5-amine

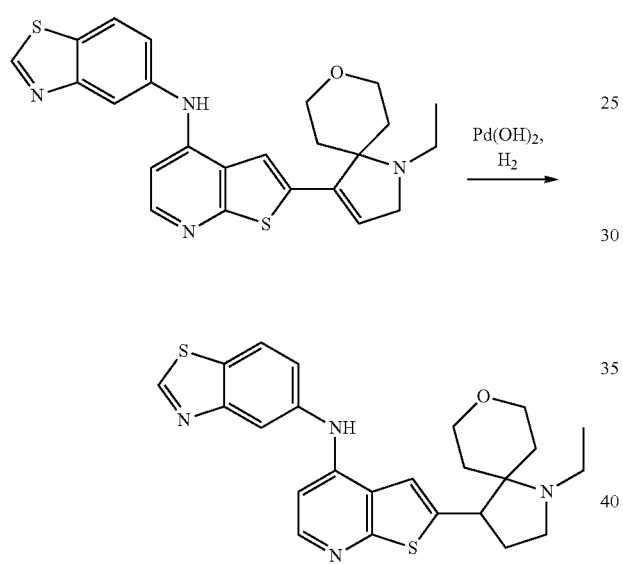

To a solution of N-(2-(1-ethyl-8-oxa-1-azaspiro[4.5]dec-3-en-4-yl)thieno[2,3-b]pyridin-4-yl)benzo-[d]thiazol-5-amine (Example 47, 30 mg, 0.070 mmol, 1.00 equiv) in ethanol (8 mL) was added Pd(OH)₂/C (30 mg, 1.00 w/w). The resulting mixture was degassed and back filled with hydrogen (1-3 atm). The reaction mixture was stirred for 1 h at 60° C. LCMS showed the reaction was completed. The solid was filtered out. The filtrate was concentrated. The crude product was purified by preparative HPLC using the following gradient conditions: Column: Sunfire Prep C18 OBD Column 10 μm, 19×250 mm; Mobile Phase A: Water (0.05% TFA), Mobile Phase B: ACN; Flow rate: 25 mL/min; Gradient: 12% B to 18% B in 13 min; 254/210 nm; Rt: 12.57 min. Purification gave N-(2-(1-ethyl-8-oxa-1-azaspiro-[4.5]-decan-4-yl)thieno[2,3-b]pyridin-4-yl)benzo[d]thiazol-5-amine (Example 48, 7.9 mg, 26%) as a white solid. $^1$H NMR (400 MHz, Methanol-$d_4$) δ 9.38 (s, 1H), 8.29-8.21 (m, 2H), 8.16-8.10 (m, 1H), 7.91-7.85 (m, 1H), 7.59 (dd, J=8.5, 2.1 Hz, 1H), 7.06 (d, J=6.5 Hz, 1H), 4.36-4.29 (m, 1H), 3.92-3.67 (m, 4H), 3.67-3.36 (m, 3H), 2.97-1.82 (m, 7H), 1.47 (s, 3H). LCMS (ESI, m/z): 451 [M+H]$^+$.

Example 49: Synthesis of 6-fluoro-N-(2-(2-methyl-1,2,5,6-tetrahydropyridin-3-yl)thieno[2,3-b]pyridin-4-yl)benzo[d]thiazol-5-amine

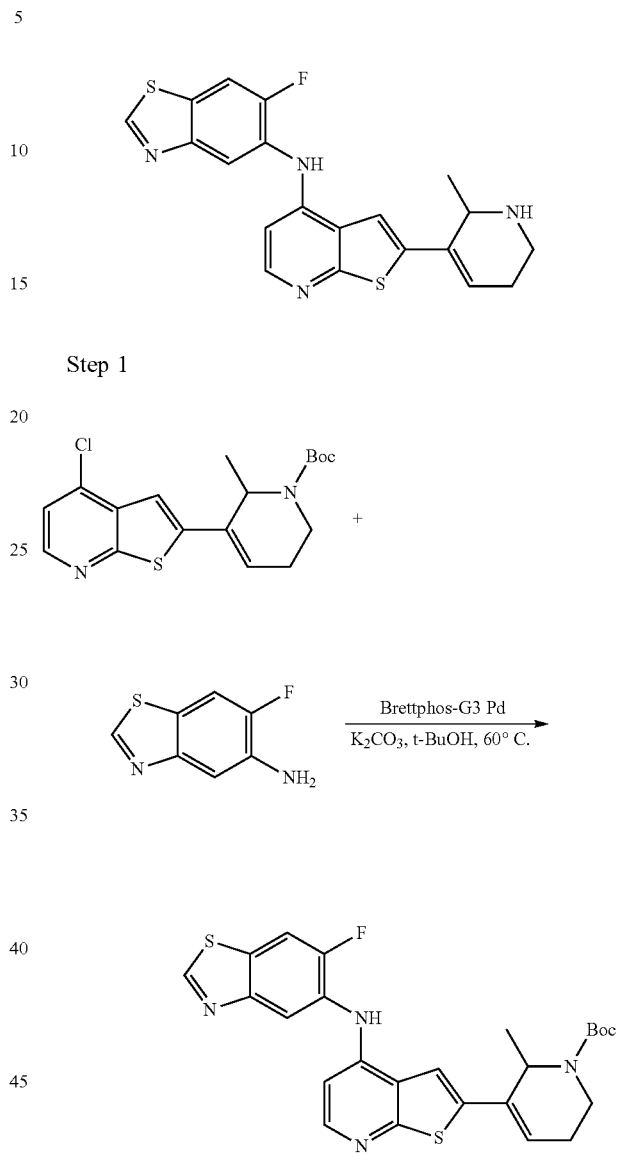

Step 1

To a solution of tert-butyl 5-(4-chlorothieno[2,3-b]pyridin-2-yl)-6-methyl-3,6-dihydropyridine-1(2H)-carboxylate (Example 20-1, 1.4 g, 3.790 mmol, 1.00 equiv), 6-fluorobenzo[d]thiazol-5-amine (701 mg, 4.170 mmol, 1.10 equiv) and K₂CO₃ (1.6 g, 11.370 mmol, 3.00 equiv) in t-BuOH (20 mL) was added Brettphos-G3 Pd (344 mg, 0.380 mmol, 0.10 equiv). The resulting mixture was stirred at 60° C. under an atmosphere of nitrogen for 3 h. LCMS showed the reaction was complete. The solid was filtered out. The filtrate was concentrated under reduced pressure and the residue was purified by by flash chromatography on silica gel with ethyl acetate/petroleum ether (1/1) to afford the desired product tert-butyl 5-(4-((6-fluorobenzo[d]thiazol-5-yl)amino)thieno[2,3-b]pyridin-2-yl)-6-methyl-3,6-dihydro-pyridine-1(2H)-carboxylate (Example 49-1, 1.68 g, 89%) as a light-yellow solid. LCMS (ESI, m/z): 497 [M+H]$^+$.

Step 2

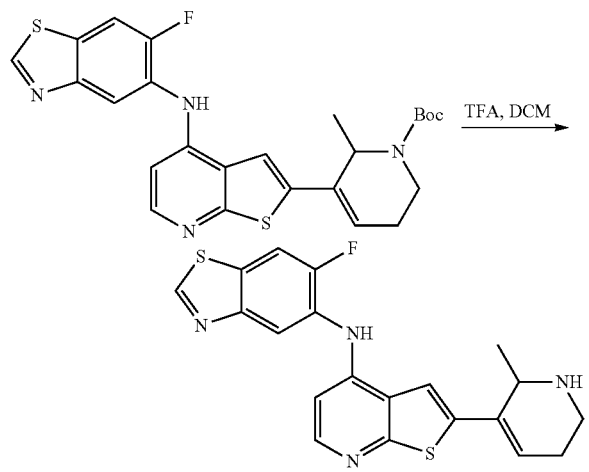

To a solution of tert-butyl 5-(4-(((6-fluorobenzo[d]thiazol-5-yl)amino)thieno[2,3-b]pyridin-2-yl)-6-methyl-3,6-dihydropyridine-1(2H)-carboxylate (Example 49-1, 1.0 g, 2.010 mmol, 1.00 equiv) in DCM (10 mL) was added TFA (2 mL). The resulting mixture was stirred at room temperature for 2 h. LCMS showed the reaction was completed. The reaction mixture was concentrated under reduced pressure to afford the desired product 6-fluoro-N-(2-(2-methyl-1,2,5,6-tetrahydropyridin-3-yl)thieno[2,3-b]pyridin-4-yl)benzo[d]thiazol-5-amine (Example 49, 750 mg, crude) as a light-yellow solid. LCMS (ESI, m/z): 397 [M+H]+.

Chiral Separation 6-fluoro-N-(2-(2-methyl-1,2,5,6-tetrahydropyridin-3-yl)thieno[2,3-b]pyridin-4-yl)benzo[d]thiazol-5-amine (Example 49, 770 mg, 1.940 mmol, 1.00 equiv) was separated by SFC using the following gradient conditions: Column: CHIRALPAK AD-H SFC, 5×25 cm, 5 μm; Mobile Phase A: CO$_2$: 50, Mobile Phase B: MeOH (2 mM NH$_3$-MeOH): 50; Flow rate: 200 mL/min; 220 nm; RT$^1$: 3.13 (Example 49a); RT$^2$: 5.76 (Example 49b). Then the respective fractions were combined and dried by lyophilization to give the desired products (Example 49a, 352 mg, 46%; Example 49b, 268 mg, 35%) as an off-white solid. $^1$H NMR (400 MHz, Methanol-d$_4$) δ 9.28 (s, 1H), 8.26 (d, J=7.2 Hz, 1H), 8.21 (dd, J=9.2, 4.4 Hz, 1H), 7.82 (s, 1H), 7.62 (t, J=9.6 Hz, 1H), 6.60-6.50 (m, 2H), 4.66 (d, J=7.2 Hz, 1H), 3.58-3.43 (m, 2H), 2.72-2.62 (m, 2H), 1.68 (d, J=6.8 Hz, 3H). LCMS (ESI, m/z): 397 [M+H]+.

Example 50: Synthesis of 6-fluoro-N-(2-((2R)-2-methylpiperidin-3-yl)thieno[2,3-b]pyridin-4-yl)benzo[d]thiazol-5-amine

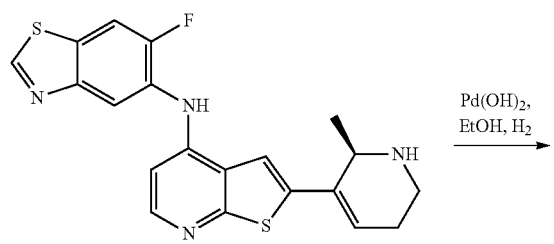

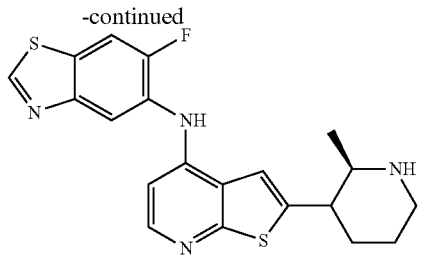

To a solution of 6-fluoro-N-(2-(2-methyl-1,2,5,6-tetrahydropyridin-3-yl)thieno[2,3-b]pyridin-4-yl)benzo[d]thiazol-5-amine (Example 49a, 250 mg, 0.630 mmol, 1.00 equiv) in ethanol (20 mL) was added dry Pd(OH)$_2$ (250 mg, 1.00 w/w). The resulting mixture was stirred at 65° C. under an atmosphere of hydrogen (1-3 atm.) for 4 days. LCMS showed the reaction was complete. The solid was filtered out. The filtration was concentrated under reduced pressure and the residue was purified by preparative TLC (MeOH:DCM=1:1) to give the desired product 6-fluoro-N-(2-((2R)-2-methylpiperidin-3-yl)thieno[2,3-b]pyridin-4-yl)benzo[d]thiazol-5-amine (Example 50, 60 mg, 24%) as an off-white solid. LCMS (ESI, m/z): 399 [M+H]+.

Chiral Separation

N-(6-fluoro-1,3-benzothiazol-5-yl)-2-(2-methyl-3-piperidyl)thieno[2,3-b]pyridin-4-amine (Example 50, 60 mg, 0.150 mmol, 1.00 equiv) was purified by SFC using the following gradient conditions: Column: CHIRALPAK IG, 20×250 mm, 5 μm; Mobile Phase A: Hex (8 mmol/L NH$_3$.MeOH)-HPLC, Mobile Phase B: EtOH-HPLC; Flow rate: 17 mL/min; Gradient: 50% B to 50% B in 12 min; 220/254 nm; RT$^1$: 9.922 to give the desired product (Example 50b, 24.8 mg, 41%, 99.1%) as an off-white solid. $^1$H NMR (400 MHz, Methanol-d$_4$) δ 9.31 (s, 1H), 8.31 (d, J=6.8 Hz, 1H), 8.25 (dd, J=9.2, 4.4 Hz, 1H), 7.83 (s, 1H), 7.65 (dd, J=10, 9.2 Hz, 1H), 6.57 (dd, J=6.8, 1.6 Hz, 1H), 4.14-4.06 (m, 1H), 3.79-3.72 (m, 1H), 3.37-3.30 (m, 2H), 3.15 (s, 1H), 2.30-2.14 (m, 3H), 2.10-1.90 (m, 1H), 1.33 (d, J=7.0 Hz, 3H). LCMS (ESI, m/z): 399 [M+H]+. Trace amounts of additional isomer Example 50a were detected.

Example 51: Synthesis of 6-fluoro-N-((2-((2S)-2-methylpiperidin-3-yl)thieno[2,3-b]pyridin-4-yl)benzo[d]thiazol-5-amine

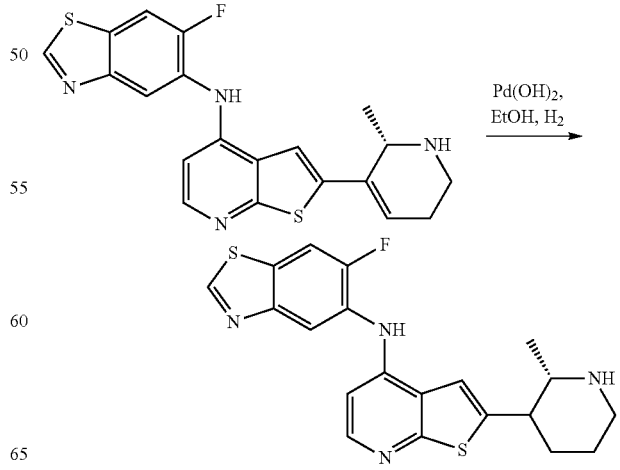

To a solution of 6-fluoro-N-(2-(2-methyl-1,2,5,6-tetrahydropyridin-3-yl)thieno[2,3-b]pyridin-4-yl)benzo[d]thiazol-5-amine (Example 49b, 240 mg, 0.610 mmol, 1.00 equiv) in ethanol (20 mL) was added dry Pd(OH)₂ (240 mg, 1.00 w/w). The resulting mixture was stirred at 65° C. under an atmosphere of hydrogen (1-3 atm) for 4 days. LCMS showed the reaction was complete. The solid was filtered out. The filtrate was concentrated under reduced pressure and the residue was purified by preparative TLC (MeOH:DCM=1:1) to give the desired product 6-fluoro-N-((2-((2S)-2-methylpiperidin-3-yl)thieno[2,3-b]pyridin-4-yl)benzo[d]thiazol-5-amine (Example 51, 90 mg, 37%) as an off-white solid. LCMS (ESI, m/z): 399 [M+H]⁺.

Chiral Separation 6-fluoro-N-(2-(2-methylpiperidin-3-yl)thieno[2,3-b]pyridin-4-yl)benzo[d]thiazol-5-amine (Example 51, 60 mg, 0.150 mmol, 1.00 equiv) was purified by SFC using the following gradient conditions: Column: CHIRALPAK IG, 20×250 mm, 5 μm; Mobile Phase A: Hex (8 mmol/L NH₃.MeOH)-HPLC, Mobile Phase B: EtOH-HPLC; Flow rate: 17 mL/min; Gradient: 50% B to 50% B in 12 min; 220/254 nm; RT¹: 9.922 to give the desired product (Example 51b, 33.2 mg, 41%, 98.6% ee) as an off-white solid. ¹H NMR (400 MHz, Methanol-d₄) δ 9.30 (s, 1H), 8.27 (d, J=6.8 Hz, 1H), 8.25 (dd, J=9.2, 4.2 Hz, 1H), 7.83 (s, 1H), 7.65 (dd, J=10.0, 9.2 Hz, 1H), 6.57 (dd, J=6.8, 1.6 Hz, 1H), 4.14-4.06 (m, 1H), 3.79-3.72 (m, 1H), 3.40-3.25 (m, 2H), 2.30-2.14 (m, 3H), 2.10-1.90 (m, 1H), 1.32 (d, J=7.6 Hz, 3H). LCMS (ESI, m/z): 399 [M+H]+. Trace amounts of additional isomer Example 51a were detected.

Example 52: Synthesis of N-(2-(1-ethyl-2-methyl-1,2,5,6-tetrahydropyridin-3-yl)thieno[2,3-b]pyridin-4-yl)-6-fluorobenzo[d]thiazol-5-amine

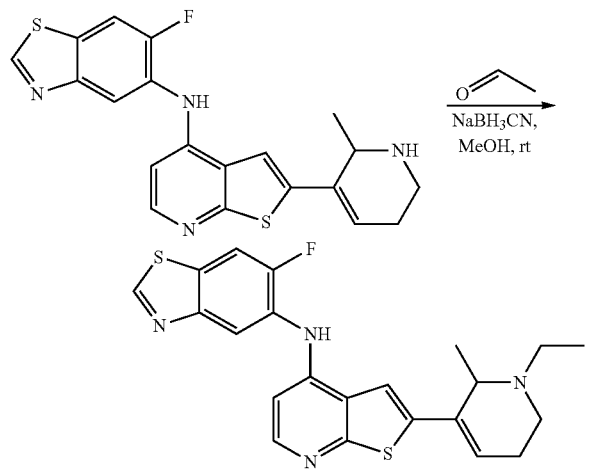

To a solution of 6-fluoro-N-(2-(2-methyl-1,2,5,6-tetrahydropyridin-3-yl)thieno[2,3-b]pyridin-4-yl)benzo[d]thiazol-5-amine (Example 49, 750 mg, 1.890 mmol, 1.00 equiv) in MeOH (10 mL) was added acetaldehyde (40% in water, 625 mg, 5.670 mmol, 3.00 equiv) and NaBH₃CN (357 mg, 5.670 mmol, 3.00 equiv). The resulting mixture was stirred for 2 h at room temperature. LCMS showed the reaction was complete. The reaction mixture was concentrated under reduced pressure and the residue was purified by flash chromatography on silica gel to give the desired product N-(2-(1-ethyl-2-methyl-1,2,5,6-tetrahydropyridin-3-yl) thieno[2,3-b]pyridin-4-yl)-6-fluorobenzo[d]thiazol-5-amine (Example 52, 680 mg, 85%) as a light-yellow solid. LCMS (ESI, m/z): 425 [M+H]⁺.

Chiral Separation

N-(2-(1-ethyl-2-methyl-1,2,5,6-tetrahydropyridin-3-yl)thieno[2,3-b)]pyridin-4-yl)-6-fluorobenzo-[d]thiazol-5-amine (Example 52, 680 mg, 1.640 mmol, 1.00 equiv) was separated by SFC using the following gradient conditions: Column: CHIRALPAK AS-H, 5×25 cm, 5 μm; Mobile Phase A: CO₂: 50, Mobile Phase B: EtOH (2 mmol NH₃-MeOH)-HPLC: 50; Flow rate: 150 mL/min; 220 nm; RT¹: 3.41; RT²: 4.90, to give the desired products (Example 52a, 236 mg, 33% and Example 52b, 250 mg, 35%)) as off-white solids. ¹H NMR (400 MHz, Methanol-d₄) δ 9.20 (s, 1H), 8.08-8.01 (m, 2H), 7.54 (t, J=9.6 Hz, 1H), 7.48 (s, 1H), 6.28 (s, 1H), 6.19 (d, J=6.4 Hz, 1H), 3.94 (d, J=7.2 Hz, 1H), 3.08-2.96 (m, 1H), 2.86 (dd, J=13.1, 6.8 Hz, 1H), 2.75-2.65 (m, 2H), 2.60-2.51 (m, 1H), 2.25-2.15 (m, 1H), 1.35 (d, J=6.6 Hz, 3H), 1.24 (t, J=7.2 Hz, 3H). LCMS (ESI, m/z): 425 [M+H]⁺.

Example 53: Synthesis of N-(2-((2R)-1-ethyl-2-methylpiperidin-3-yl)thieno[2,3-b]pyridin-4-yl)-6-fluorobenzo-[d]thiazol-5-amine

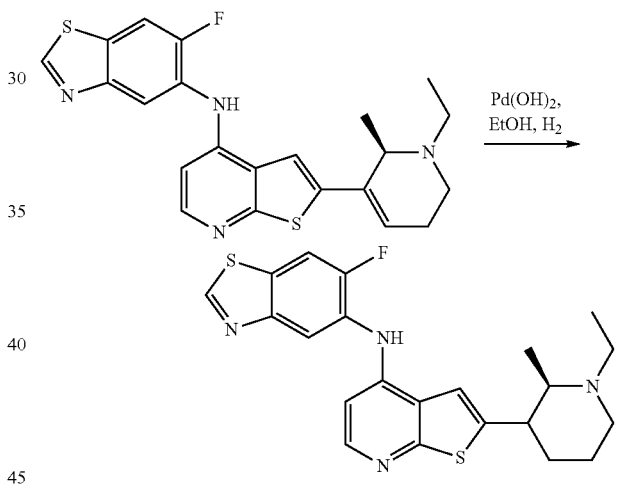

To a solution of N-(2-(1-ethyl-2-methyl-1,2,5,6-tetrahydropyridin-3-yl)thieno[2,3-b]pyridin-4-yl)-6-fluorobenzo[d]thiazol-5-amine (Example 52a, 220 mg, 0.520 mmol, 1.00 equiv) in ethanol (20 mL) was added dry Pd(OH)₂ (220 mg, 1.00 w/w). The resulting mixture was stirred at 60° C. under an atmosphere of hydrogen (1-3 atm.) for 4 days. LCMS showed the reaction was complete. The solid was filtered out. The filtrate was concentrated under reduced pressure and the residue was purified by preparative HPLC using the following gradient conditions: Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 8% B to 50% B in 7.5 min; 254/210 nm; Rt: 6.28 min to give the desired product N-(2-((2R)-1-ethyl-2-methylpiperidin-3-yl)thieno[2,3-b]pyridin-4-yl)-6-fluorobenzo[d]thiazol-5-amine (Example 53, 130 mg, 59%) as an off-white solid. LCMS (ESI, m/z): 427 [M+H]⁺.

Chiral Separation 2-(1-ethyl-2-methyl-3-piperidyl)-N-(6-fluoro-1,3-benzothiazol-5-yl)thieno[2,3-b]pyridin-4-amine (Example 53, 130 mg, 0.300 mmol, 1.00 equiv) was purified by SFC using the following gradient conditions: Column: CHIRALPAK IG-03, 2.0 cm I.D×25 cm L (5 μm); Mobile Phase A: Hex (8 mmol/L NH$_3$.MeOH)-HPLC, Mobile Phase B: EtOH-HPLC; Flow rate: 20 mL/min; Gradient: 30 B % to 30 B % in 16 min; 254/220 nm, to give the desired product (Example 53b; 53.0 mg, 40%) as a light-yellow solid. $^1$H NMR (400 MHz, Methanol-d$_4$) δ 9.33 (s, 1H), 8.34 (d, J=7.2 Hz, 1H), 8.25 (dd, J=9.2, 4.4 Hz, 1H), 7.92 (s, 1H), 7.66 (dd, J=10.0, 9.2 Hz, 1H), 6.60 (dd, J=7.2, 1.6 Hz, 1H), 4.20-3.90 (m, 2H), 3.49 (d, J=12.4 Hz, 1H), 3.30-3.17 (m, 3H), 2.30-2.24 (m, 4H), 1.48 (t, J=7.2 Hz, 3H), 1.28 (d, J=6.8 Hz, 3H). LCMS (ESI, m/z): 427 [M+H]+. Trace amounts of Example 53a were detected.

Example 54: Synthesis of N-(2-(1-ethyl-2-methylpiperidin-3-yl)thieno[2,3-b]pyridin-4-yl)-6-fluorobenzo[d]thiazol-5-amine

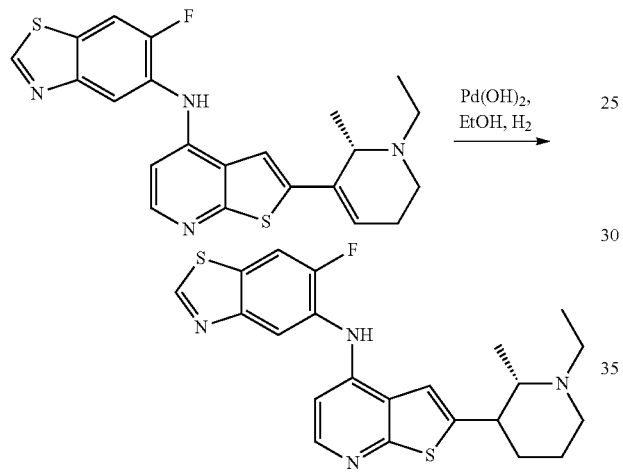

To a solution of N-(2-(1-ethyl-2-methyl-1,2,5,6-tetrahydropyridin-3-yl)thieno[2,3-b]pyridin-4-yl)-6-fluorobenzo[d]thiazol-5-amine (Example 52b, 240 mg, 0.570 mmol, 1.00 equiv) in ethanol (20 mL) was added dry Pd(OH)$_2$ (240 mg, 1.00 w/w). The resulting mixture was stirred at 60° C. under an atmosphere of hydrogen (1-3 atm.) for 4 days. LCMS showed the reaction was complete. The solid was filtered out. The filtration was concentrated under reduced pressure and the residue was purified by preparative HPLC using the following gradient conditions: Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 8% B to 50% B in 7.5 min; 254/210 nm; Rt: 6.28 min to give the desired product N-(2-(1-ethyl-2-methylpiperidin-3-yl)thieno[2,3-b]pyridin-4-yl)-6-fluorobenzo[d]thiazol-5-amine (Example 54, 120 mg, 50%) as an off-white solid. LCMS (ESI, m/z): 427 [M+H]+.

Chiral Separation 2-(1-ethyl-2-methyl-3-piperidyl)-N-(6-fluoro-1,3-benzothiazol-5-yl)thieno[2,3-b]pyridin-4-amine (Example 54, 120 mg, 0.282 mmol, 1.00 equiv) was purified by SFC using the following gradient conditions: Column: CHIRALPAK IG-03, 2.0 cm I.D×25 cm L (5 μm); Mobile Phase A: Hex (8 mmol/L NH$_3$.MeOH)-HPLC, Mobile Phase B: EtOH-HPLC; Flow rate: 20 mL/min; Gradient: 30% B to 30% B in 16 min; 254/220 nm to give the desired product (Example 54b; 53.0 mg, 40%, 99.3% ee) as a light-yellow solid. $^1$H NMR (400 MHz, Methanol-d$_4$) δ 9.32 (s, 1H), 8.34 (d, J=6.8 Hz, 1H), 8.24 (dd, J=8.8, 4.2 Hz, 1H), 7.93 (s, 1H), 7.66 (dd, J=10.0, 8.8 Hz, 1H), 6.60 (dd, J=6.8, 2 Hz, 1H), 4.20-3.90 (m, 1H), 3.49 (d, J=12.4 Hz, 1H), 3.40-3.15 (m, 3H), 2.27-2.22 (m, 4H), 1.48 (t, J=7.2 Hz, 3H), 1.28 (d, J=6.8 Hz, 3H). LCMS (ESI, m/z): 427 [M+H]+. Trace amounts of additional isomer Example 54a were detected.

Example 55: Synthesis of tert-butyl 5-(4-((4-fluorobenzo[d]thiazol-5-yl)amino)thieno[2,3-b]pyridin-2-yl)-6-methyl-3,6-dihydropyridine-1(2H)-carboxylate

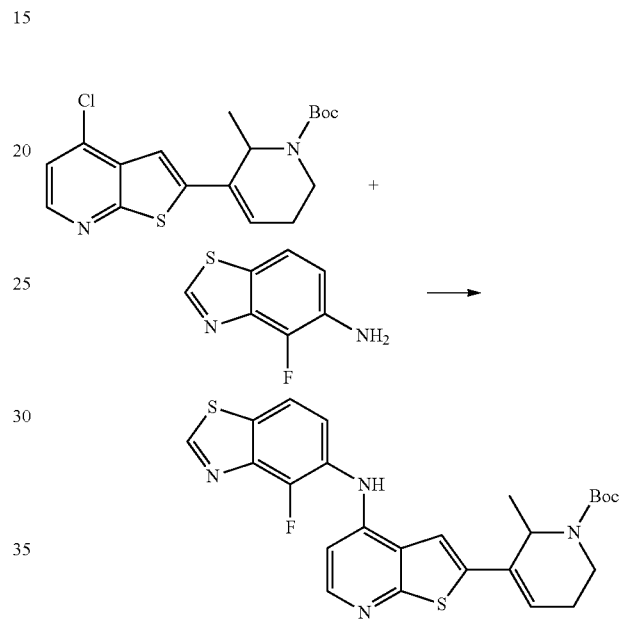

Into a 100-mL round-bottom flask purged with and maintained under inert atmosphere of nitrogen was placed tert-butyl 5-(4-chlorothieno[2,3-b]pyridin-2-yl)-6-methyl-3,6-dihydropyridine-1(2H)-carboxylate (Example 20-1, 2.7 g, 7.440 mmol, 1.00 equiv), 4-fluorobenzo[d]thiazol-5-amine (1.3 g, 7.440 mmol, 1.00 equiv), K$_2$CO$_3$ (3.1 g, 22.330 mmol, 3.00 equiv), G3-Brettphos Pd (0.7 g, 0.740 mmol, 0.10 equiv) and tert-butanol (25 mL). The resulting solution was stirred for 1 h at 60° C. LCMS showed the reaction was complete. The resulting solution was concentrated. The residue was purified by flash chromatography (PE:EA=1:1) to give tert-butyl 5-(4-((4-fluorobenzo[d]thiazol-5-yl)amino)thieno[2,3-b]pyridin-2-yl)-6-methyl-3,6-dihydropyridine-1(2H)-carboxylate (Example 55, 2.8 g, 77%) as a light yellow solid. LCMS (ESI, m/z): 497 [M+H]$^+$.

Chiral Separation tert-butyl 5-(4-((4-fluorobenzo[d]thiazol-5-yl)amino)thieno[2,3-b]pyridin-2-yl)-6-methyl-3,6-dihydropyridine-1(2H)-carboxylate (Example 55, 2.8 g, 5.74 mmol) was purified by SFC using the following gradient conditions: Column: CHIRAL ART Amylose-SA S-5 μm, 250×20 mm; Mobile Phase A: CO$_2$: 65, Mobile Phase B: EtOH (2 mM NH$_3$-MeOH): 35; Flow rate: 40 mL/min; 254 nm; RT$^1$: 6.86; RT$^2$: 9.45. Purification gave the desired isomers (Example 55a, 1.2 g, 42%; and Example 55b, 1.3 g) as light yellow solids. LCMS (ESI, m/z): 497 [M+H]$^+$.

Example 56: Synthesis of 4-fluoro-N-(2-(2-methylpiperidin-3-yl)thieno[2,3-b]pyridin-4-yl)benzo[d]thiazol-5-amine

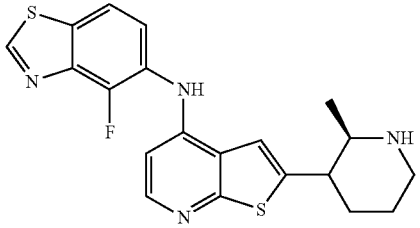 [SMILES: C[C@H]1NCCCC1c1cc2c(Nc3ccc4scnc4c3F)ccnc2s1]

Step 1

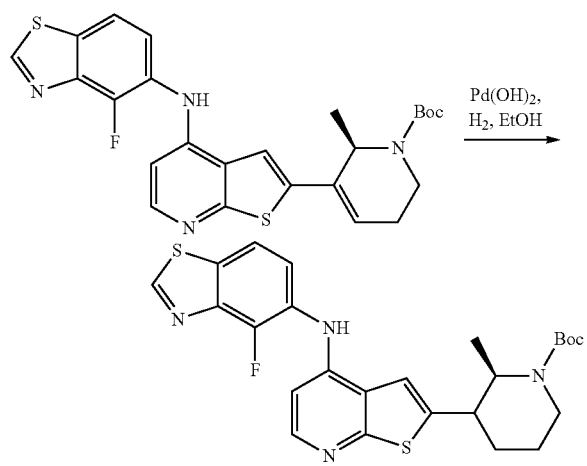

To a solution of tert-butyl 5-(4-((4-fluorobenzo[d]thiazol-5-yl)amino)thieno[2,3-b]pyridin-2-yl)-6-methyl-3,6-dihydropyridine-1(2H)-carboxylate (Example 55a, 1.2 g, 2.420 mmol, 1.00 equiv) in ethanol (35 mL) was added Pd(OH)$_2$/C (2.4 g, 1.00 w/w). The mixture was degassed and back filled with hydrogen (1-3 atm). The resulting solution was stirred for 16 h at 60° C. LCMS showed the reaction was complete. The solid was filtered out. The filtrate was concentrated. The residue was purified by preparative HPLC using the following gradient conditions: Column: Xselect CSH OBD Column 30×150 mm, 5 μm; Mobile Phase A: Water (0.05% TFA), Mobile Phase B: ACN; Flow rate: 60 mL/min; Gradient: 10% B to 30% B in 8 min; 254/210 nm; Rt: 7.65 min. Purification gave tert-butyl 3-(4-((4-fluorobenzo[d]thiazol-5-yl)amino)thieno[2,3-b]pyridin-2-yl)-2-methylpiperidine-1-carboxylate (Example 56-1, 620 mg, 51%) as a yellow solid. LCMS (ESI, m/z): 499 [M+H]$^+$.

Step 2

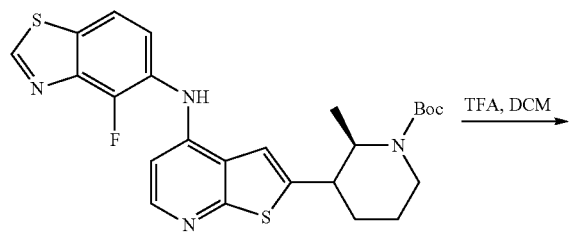

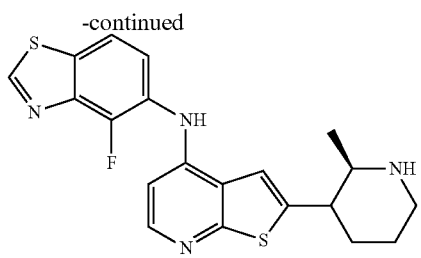

Into a 50 mL round bottom flask was placed tert-butyl 3-(4-((4-fluorobenzo[d]thiazol-5-yl)amino)thieno[2,3-b]pyridin-2-yl)-2-methylpiperidine-1-carboxylate (Example 56-1, 620 mg, 1.240 mmol, 1.00 equiv), TFA (7 mL) and DCM (14 mL). The resulting mixture was stirred for 30 min at room temperature. LCMS showed the reaction was complete. The mixture was concentrated to give 400 mg (crude) of 4-fluoro-N-(2-(2-methylpiperidin-3-yl)thieno[2,3-b]pyridin-4-yl)benzo[d]thiazol-5-amine (Example 56) as a light yellow solid. LCMS (ESI, m/z): 399 [M+H]$^+$.

Chiral Separation 4-fluoro-N-(2-(2-methylpiperidin-3-yl)thieno[2,3-b]pyridin-4-yl)benzo[d]thiazol-5-amine (Example 56, 100 mg, 0.250 mmol) was purified by Pre-SFC-HPLC using the following gradient conditions: Column: CHIRAL ART Cellulose-SB S-5 μm-02, 250*20 mm; Mobile Phase A: CO$_2$: 60, Mobile Phase B: EtOH (0.1% DEA)-HPLC: 40; Flow rate: 50 mL/min; 254 nm; RT[1]: 3.98 (Example 56a); RT2: 5.43 (Example 56b).

Example 56a was further purified by preparative HPLC using the following gradient conditions: Column: XBridge Shield RP18 OBD Column, 19×250 mm, 10 μm; Mobile Phase A: Water (0.05% TFA), Mobile Phase B: ACN; Flow rate: 25 mL/min; Gradient: 15% B to 28% B in 7 min; 254/210 nm; Rt: 5.43 min. Purification gave 49.2 mg (49%, 99.1% ee) of 4-fluoro-N-(2-((2R,3S)-2-methyl-piperidin-3-yl)thieno[2,3-b]pyridin-4-yl)benzo[d]thiazol-5-amine) (Example 56a) as a light yellow solid. $^1$H NMR (400 MHz, Methanol-d$_4$) δ 9.42 (s, 1H), 8.30 (d, J=6.9 Hz, 1H), 8.09 (dd, J=8.6, 1.2 Hz, 1H), 7.79 (s, 1H), 7.63 (dd, J=8.6, 6.6 Hz, 1H), 6.77 (dd, J=6.9, 2.3 Hz, 1H), 3.57-3.44 (m, 2H), 3.31-3.17 (m, 2H), 2.32 (d, J=10.4 Hz, 1H), 2.14 (d, J=11.6 Hz, 1H), 2.08-1.91 (m, 2H), 1.35 (d, J=6.4 Hz, 3H). LCMS (ESI, m/z): 399 [M+H]$^+$.

Example 56b was further purified by preparative HPLC using the following gradient conditions: Column: XBridge Shield RP18 OBD Column, 19×250 mm, 10 μm; Mobile Phase A: Water (0.05% TFA), Mobile Phase B: ACN; Flow rate: 25 mL/min; Gradient: 15% B to 35% B in 7 min; 254/210 nm; Rt: 4.78 min. Purification gave 10.4 mg (10%, 100% ee) of 4-fluoro-N-(2-((2R,3R)-2-methyl-piperidin-3-yl)thieno[2,3-b]pyridin-4-yl)benzo[d]thiazol-5-amine (Example 56b) as a light yellow solid. $^1$H NMR (400 MHz, Methanol-d$_4$) δ 9.41 (s, 1H), 8.27 (s, 1H), 8.07 (d, J=8.7 Hz, 1H), 7.76 (s, 1H), 7.63 (t, J=7.6 Hz, 1H), 6.75 (d, J=6.5 Hz, 1H), 4.11-4.02 (m, 1H), 3.68-3.60 (m, 1H), 3.38-3.33 (m, 2H), 2.29-2.14 (m, 4H), 1.32 (d, J=7.0 Hz, 3H). LCMS (ESI, m/z): 399 [M+H]$^+$.

Example 57: Synthesis of 4-fluoro-N-(2-(2-methylpiperidin-3-yl)thieno[2,3-b]pyridin-4-yl)benzo[d]thiazol-5-amine

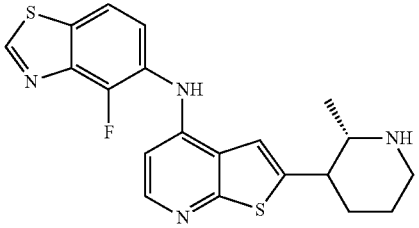 [SMILES: C[C@@H]1NCCCC1c1cc2c(Nc3ccc4scnc4c3F)ccnc2s1]

Step 1

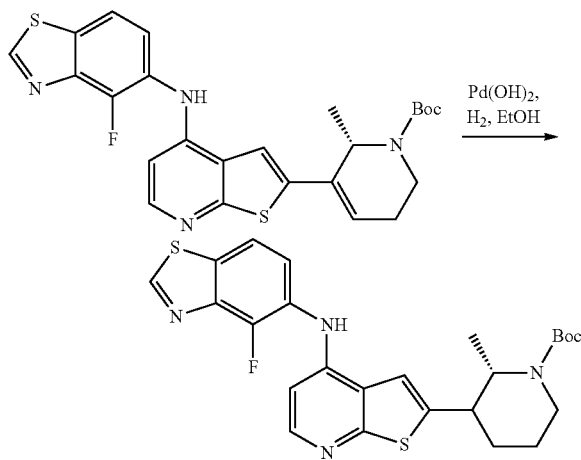

To a solution tert-butyl 5-(4-(((4-fluorobenzo[d]thiazol-5-yl)amino)thieno[2,3-b]pyridin-2-yl)-6-methyl-3,6-dihydropyridine-1(2H)-carboxylate (Example 55b, 1.3 g, 2.560 mmol, 1.00 equiv) in ethanol (35 mL) was added Pd(OH)$_2$/C (2.6 g, 2.00 w/w). The reaction mixture was degassed and back filled with hydrogen (1-3 atm). The resulting solution was stirred for 16 h at 60° C. LCMS showed the reaction was complete. The solid was filtered out. The filtrate was concentrated. The residue was purified by preparative HPLC using the following gradient conditions: Column: Xselect CSH OBD Column 30×150 mm, 5 µm; Mobile Phase A: Water (0.05% TFA), Mobile Phase B: ACN; Flow rate: 60 mL/min; Gradient: 20% B to 30% B in 8 min; 254/210 nm; Rt: 7.65 min. Purification gave tert-butyl 3-(4-((4-fluorobenzo[d]thiazol-5-yl)amino)thieno[2,3-b]pyridin-2-yl)-2-methyl-piperidine-1-carboxylate (Example 57-1, 620 mg, 48%) as a yellow solid. LCMS (ESI, m/z): 499 [M+H]$^+$.

Step 2

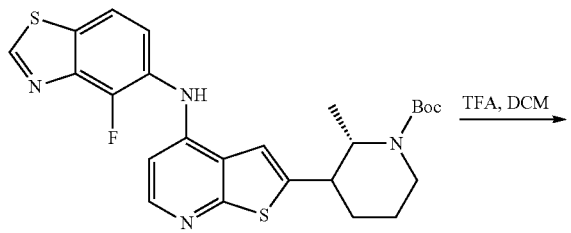

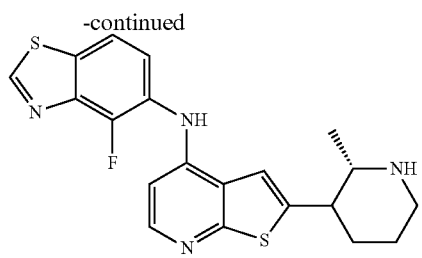

To a solution of tert-butyl 3-(4-((4-fluorobenzo[d]thiazol-5-yl)amino)thieno[2,3-b]pyridin-2-yl)-2-methylpiperidine-1-carboxylate (Example 57-1, 620 mg, 1.240 mmol, 1.00 equiv) in DCM (14 mL) was added TFA (7 mL). The resulting mixture was stirred for 30 min at room temperature. LCMS showed the reaction was complete. The mixture was purified by preparative HPLC using the following gradient conditions: Column: Xselect CSH OBD Column 30×150 mm, 5 µm; Mobile Phase A: Water (0.05% TFA), Mobile Phase B: ACN; Flow rate: 60 mL/min; Gradient: 20% B to 30% B in 8 min; 254/210 nm; Rt: 7.65 min. Purification gave 4-fluoro-N-(2-(2-methylpiperidin-3-yl)thieno-[2,3-b]pyridin-4-yl)benzo[d]thiazol-5-amine (Example 57, 400 mg, 77%) of as a light yellow solid. LCMS (ESI, m/z): 399 [M+H]$^+$.

Chiral Separation 4-fluoro-N-[2-(2-methyl-3-piperidyl)thieno[2,3-b]pyridin-4-yl]-1,3-benzothiazol-5-amine (Example 57, 100 mg, 0.250 mmol) was purified by Pre-SFC-HPLC using the following gradient conditions: Column: CHIRAL ART Cellulose-SB S-5 µm-02, 250×20 mm; Mobile Phase A: CO$_2$: 60, Mobile Phase B: EtOH (0.1% DEA)-HPLC: 40; Flow rate: 50 mL/min; 254 nm; RT$^1$: 3.98 (Example 57a); RT$^2$: 5.43 (Example 57b).

Example 57a was further purified by preparative HPLC using the following gradient conditions: Column: Xselect CSH OBD Column 30×150 mm, 5 µm; Mobile Phase A: Water (0.05% TFA), Mobile Phase B: ACN; Flow rate: 60 mL/min; Gradient: 5% B to 30% B in 7 min; 254/210 nm; Rt: 6.95 min. Purification gave 38.9 mg (39%, 99.3% ee) of 4-fluoro-N-(2-((2S,3R)-2-methylpiperidin-3-yl)thieno-[2,3-b]pyridin-4-yl)benzo[d]thiazol-5-amine (Example 57a) as a light yellow solid. $^1$H NMR (400 MHz, Methanol-d$_4$) δ 9.41 (s, 1H), 8.27 (d, J=6.6 Hz, 1H), 8.07 (dd, J=8.6, 1.1 Hz, 1H), 7.75 (s, 1H), 7.62 (dd, J=8.6, 6.7 Hz, 1H), 6.74 (dd, J=6.6, 2.2 Hz, 1H), 3.61-3.42 (m, 2H), 3.26-3.10 (m, 2H), 2.31 (d, J=11.3 Hz, 1H), 2.15 (d, J=12.9 Hz, 1H), 2.07-1.85 (m, 2H), 1.34 (d, J=6.4 Hz, 3H). LCMS (ESI, m/z): 399 [M+H]$^+$.

Example 57b was further purified by preparative HPLC using the following gradient conditions: Column: Xselect CSH OBD Column 30×150 mm, 5 µm; Mobile Phase A: Water (0.05% TFA), Mobile Phase B: ACN; Flow rate: 60 mL/min; Gradient: 5% B to 30% B in 8 min; 254/210 nm; Rt: 7.65 min. Purification gave 21.6 mg (21%, 91.9% ee) of 4-fluoro-N-(2-((2S,3S)-2-methylpiperidin-3-yl)thieno-[2,3-b]pyridin-4-yl)benzo[d]thiazol-5-amine (Example 57b) as light yellow solid. $^1$H NMR (400 MHz, Methanol-d$_4$) δ 9.41 (s, 1H), 8.27 (d, J=6.6 Hz, 1H), 8.07 (dd, J=8.6, 1.1 Hz, 1H), 7.75 (s, 1H), 7.62 (dd, J=8.6, 6.7 Hz, 1H), 6.74 (dd, J=6.6, 2.2 Hz, 1H), 4.13-4.02 (m, 1H), 3.67 (dd, J=10.7, 5.0 Hz, 1H), 3.34-3.27 (m, 2H), 2.34-2.14 (m, 3H), 2.05-1.84 (m, 1H), 1.32 (d, J=7.0 Hz, 3H). LCMS (ESI, m/z): 399 [M+H]$^+$.

Examples 58-61: Synthesis of N-(2-(1,2-dimethylpiperidin-3-yl)thieno[2,3-b]pyridin-4-yl)-4-fluorobenzo[d]thiazol-5-amine

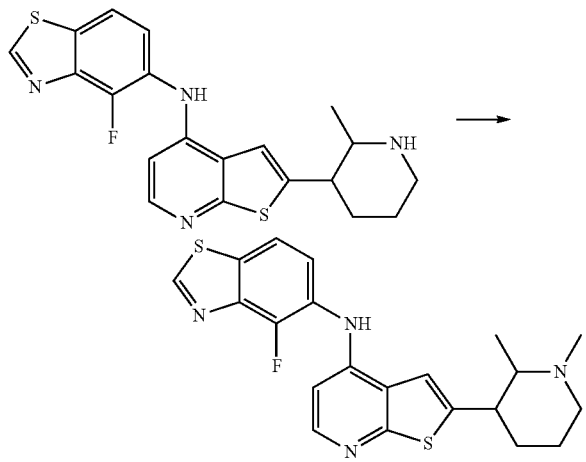

The following general procedure was used to prepare Examples 58, 59, 60, and 61. Into a 10-mL sealed tube was placed 4-fluoro-N-[2-(2-methyl-3-piperidyl)thieno[2,3-b]pyridin-4-yl]-1,3-benzothiazol-5-amine (60 mg, 0.150 mmol, 1.00 equiv), HCHO (10 mg, 0.320 mmol, 2.00 equiv) and ethanol (3 mL). After stirring for 10 min, NaBH$_3$CN (19 mg, 0.300 mmol, 2.00 equiv) was added portion wise and the resulting solution was stirred for 1 h at room temperature. LCMS showed the reaction was complete. The mixture was concentrated and the residue purified by preparative HPLC.

Example 58: N-(2-((2R,3S)-1,2-dimethylpiperidin-3-yl)thieno[2,3-b]pyridin-4-yl)-4-fluorobenzo[d]thiazol-5-amine Starting from Example 56a (60 mg, 0.150 mmol), following the general procedure above, the crude product was purified by preparative HPLC using the following gradient conditions: Column: XBridge Shield RP18 OBD Column, 19×250 mm, 10 μm; Mobile Phase A: Water (0.05% TFA), Mobile Phase B: ACN; Flow rate: 25 mL/min; Gradient: 15% B to 25% B in 8 min; 254/210 nm; Rt: 6.1 min. Purification gave 49.6 mg (80%, 100% ee) of N-(2-((2R,3S)-1,2-dimethylpiperidin-3-yl)thieno[2,3-b]pyridin-4-yl)-4-fluorobenzo[d]thiazol-5-amine (Example 58) as a light yellow solid. $^1$H NMR (400 MHz, Methanol-d$_4$) δ 9.42 (s, 1H), 8.30 (d, J=6.7 Hz, 1H), 8.09 (dd, J=8.6, 1.1 Hz, 1H), 7.76 (s, 1H), 7.63 (dd, J=8.6, 6.7 Hz, 1H), 6.77 (dd, J=6.8, 2.2 Hz, 1H), 3.73-3.63 (m, 1H), 3.57-3.49 (m, 1H), 3.45-3.37 (m, 2H), 3.05 (s, 3H), 2.35-2.27 (m, 1H), 2.20-2.10 (m, 1H), 2.08-1.93 (m, 2H), 1.42 (d, J=6.4 Hz, 3H). LCMS (ESI, m/z): 413 [M+H]t.

Example 59: N-(2-((2S,3R)-1,2-dimethylpiperidin-3-yl)thieno[2,3-b]pyridin-4-yl)-4-fluorobenzo[d]thiazol-5-amine Starting from Example 57a (60 mg, 0.150 mmol), following the general procedure above, the crude product was purified by preparative HPLC using the following gradient conditions: Column: XBridge Shield RP18 OBD Column, 19×250 mm, 10 μm; Mobile Phase A: IPA (0.1% TFA), Mobile Phase B: ACN; Flow rate: 25 mL/min; Gradient: 18% B to 31% B in 8 min; 254/210 nm; Rt: 5.82 min. Purification gave 43.9 mg (70%, 100% ee) of N-(2-((2S,3R)-1,2-dimethylpiperidin-3-yl)thieno[2,3-b]pyridin-4-yl)-4-fluorobenzo[d]thiazol-5-amine (Example 59) as a light yellow solid. $^1$H NMR (400 MHz, Methanol-d$_4$) δ 9.42 (s, 1H), 8.31 (d, J=7.0, 1H), 8.09 (d, J=8.7 Hz, 1H), 7.79-7.71 (m, 1H), 7.63 (dd, J=8.6, 6.6 Hz, 1H), 6.77 (dd, J=7.0, 2.2 Hz, 1H), 3.67-3.51 (m, 2H), 3.57-3.36 (m, 2H), 3.04 (s, 3H), 2.31-2.91 (m, 4H), 1.42 (d, J=6.3 Hz, 3H). LCMS (ESI, m/z): 413 [M+H]$^+$.

Example 60: N-(2-(1,2-dimethylpiperidin-3-yl)thieno[2,3-b]pyridin-4-yl)-4-fluorobenzo[d]thiazol-5-amine Starting from Example 56b (30 mg, 0.080 mmol), following the general procedure above, the crude product was purified by preparative HPLC using the following gradient conditions: Column: Xselect CSH OBD Column 30×150 mm, 5 μm; Mobile Phase A: Water (0.05% TFA), Mobile Phase B: ACN; Flow rate: 60 mL/min; Gradient: 5% B to 30% B in 8 min; 254/210 nm; Rt: 7.65 min. Purification gave 9.8 mg (32%, 100% ee) of N-(2-((2R,3R)-1,2-dimethylpiperidin-3-yl)thieno[2,3-b]pyridin-4-yl)-4-fluorobenzo[d]thiazol-5-amine (Example 60) as a light yellow solid. $^1$H NMR (400 MHz, Methanol-d$_4$) δ 9.41 (s, 1H), 8.27 (d, J=6.4 Hz, 1H), 8.10-8.03 (m, 1H), 7.75 (s, 1H), 7.62 (dd, J=8.6, 6.7 Hz, 1H), 6.74 (d, J=6.5 Hz, 1H), 4.08-4.01 (m, 1H), 3.75-3.67 (m, 1H), 3.33-3.15 (m, 2H), 2.95 (s, 3H), 2.21 (dt, J=9.4, 4.4 Hz, 3H), 2.06-1.98 (m, 1H), 1.28 (d, J=6.9 Hz, 3H). LCMS (ESI, m/z): 414 [M+H]$^+$.

Example 61: N-(2-((2S,3S)-1,2-dimethylpiperidin-3-yl)thieno[2,3-b]pyridin-4-yl)-4-fluorobenzo[d]thiazol-5-amine Starting from Example 57b (30 mg, 0.080 mmol), following the general procedure above, the crude product was purified by preparative HPLC using the following gradient conditions: Column: Sunfire Prep C18 OBD Column, 10 μm, 19×250 mm; Mobile Phase A: Water (0.05% TFA), Mobile Phase B: ACN; Flow rate: 25 mL/min; Gradient: 5% B to 30% B in 7 min; 254/210 nm; Rt: 6.95 min. Purification gave 9.9 mg (32%, 100% ee) of N-(2-((2S,3S)-1,2-dimethylpiperidin-3-yl)thieno[2,3-b]pyridin-4-yl)-4-fluorobenzo[d]thiazol-5-amine (Example 61) as a light yellow solid. $^1$H NMR (400 MHz, Methanol-d$_4$) δ 9.40 (s, 1H), 8.25 (d, J=6.3 Hz, 1H), 8.06 (d, J=8.6 Hz, 1H), 7.74 (s, 1H), 7.62 (dd, J=8.5, 6.8 Hz, 1H), 6.73 (d, J=6.6 Hz, 1H), 4.12-4.03 (m, 1H), 3.77-3.68 (m, 1H), 3.33-3.23 (m, 2H), 2.95 (s, 3H), 2.24-1.98 (m, 4H), 1.28 (d, J=6.9 Hz, 3H). LCMS (ESI, m/z): 413 [M+H]$^+$.

Examples 62-65: Synthesis of N-(2-(1-ethyl-2-methylpiperidin-3-yl)thieno[2,3-b]pyridin-4-yl)-4-fluorobenzo[d]thiazol-5-amine

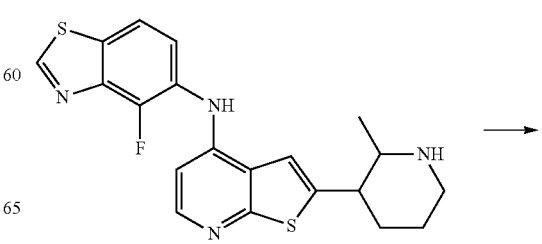

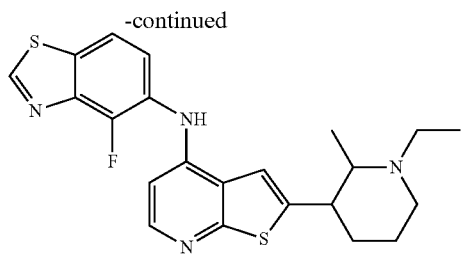

Into a 10-mL sealed tube was placed 4-fluoro-N-[2-(2-methyl-3-piperidyl)thieno[2,3-b]pyridin-4-yl]-1,3-benzothiazol-5-amine (1.00 equiv), CH₃CHO (2.00 equiv) and methanol (2 mL). After stirring for 10 min, NaBH₃CN (2.00 equiv) was added in portions and the resulting solution was stirred for 1 h at room temperature. LCMS showed the reaction was complete. The mixture was concentrated and the residue purified by preparative HPLC.

Example 62: N-(2-((2R,3S)-1-ethyl-2-methylpiperidin-3-yl)thieno[2,3-b]pyridin-4-yl)-4-fluorobenzo[d]thiazol-5-amine Starting from Example 56a (60 mg, 0.150 mmol), following the general procedure above, the crude product was purified by preparative HPLC using the following gradient conditions: Column: XBridge Shield RP18 OBD Column, 19×250 mm, 10 μm; Mobile Phase A: Water (0.05% TFA), Mobile Phase B: ACN; Flow rate: 25 mL/min; Gradient: 15% B to 25% B in 8 min; 254/210 nm; Rt: 6.38 min. Purification gave 44.4 mg (72%, 100% ee) of N-(2-((2R,3S)-1-ethyl-2-methylpiperidin-3-yl)thieno[2,3-b]pyridin-4-yl)-4-fluorobenzo[d]thiazol-5-amine (Example 62) as a light yellow solid. $^1$H NMR (400 MHz, Methanol-$d_4$) δ 9.41 (s, 1H), 8.30 (d, J=6.8 Hz, 1H), 8.09 (dd, J=8.6, 1.2 Hz, 1H), 7.80 (s, 1H), 7.64 (dd, J=8.6, 6.7 Hz, 1H), 6.77 (dd, J=6.9, 2.3 Hz, 1H), 3.68 (d, J=12.4 Hz, 1H), 3.62-3.50 (m, 1H), 3.50-3.43 (m, 1H), 3.43-3.35 (m, 3H), 2.29 (d, J=10.3 Hz, 1H), 2.17-2.04 (m, 3H), 1.46-1.38 (m, 6H). LCMS (ESI, m/z): 427 [M+H]⁺.

Example 63: N-((2-((2S,3R)-1-ethyl-2-methylpiperidin-3-yl)thieno[2,3-b]pyridin-4-yl)-4-fluorobenzo[d]thiazol-5-amine Starting from Example 57a (60 mg, 0.150 mmol), following the general procedure above, the crude product was purified by preparative HPLC using the following gradient conditions: Column: XBridge Shield RP18 OBD Column, 19×250 mm, 10 μm; Mobile Phase A: Water (0.05% TFA), Mobile Phase B: ACN; Flow rate: 25 mL/min; Gradient: 15% B to 40% B in 8 min; 254/210 nm; Rt: 6.13 min. Purification gave 57 mg (89%, 100% ee) of N-(2-((2S,3R)-1-ethyl-2-methylpiperidin-3-yl)thieno[2,3-b]pyridin-4-yl)-4-fluorobenzo[d]thiazol-5-amine (Example 63) as a light yellow solid. $^1$H NMR (400 MHz, Methanol-$d_4$) δ 9.42 (s, 1H), 8.30-8.26 (s, 1H), 8.12-8.05 (m, 1H), 7.79 (dd, J=12.3, 7.2 Hz, 1H), 7.63 (t, J=7.4 Hz, 1H), 6.81-6.74 (m, 1H), 3.68-3.35 (m, 6H), 2.29-1.97 (m, 4H), 1.46-1.38 (m, 6H). LCMS (ESI, m/z): 427 [M+H]⁺.

Example 64: N-(2-((2R,3R)-1-ethyl-2-methylpiperidin-3-yl)thieno[2,3-b]pyridin-4-yl)-4-fluorobenzo[d]thiazol-5-amine Starting from Example 56b (30 mg, 0.080 mmol), following the general procedure above, the crude product was purified by preparative HPLC using the following gradient conditions: Column: Xselect CSH OBD Column 30×150 mm, 5 μm; Mobile Phase A: Water (0.05% TFA), Mobile Phase B: ACN; Flow rate: 60 mL/min; Gradient: 5% B to 30% B in 8 min; 254/210 nm; Rt: 7.65 min. Purification gave 19.1 mg (62%, 100% ee) of N-(2-((2R,3R)-1-ethyl-2-methylpiperidin-3-yl)thieno[2,3-b]pyridin-4-yl)-4-fluorobenzo[d]thiazol-5-amine (Example 64) as a light yellow solid. $^1$H NMR (400 MHz, Methanol-$d_4$) δ 9.42 (s, 1H), 8.30 (d, J=6.8 Hz, 1H), 8.13-8.06 (m, 1H), 7.81 (d, J=7.4 Hz, 1H), 7.63 (dd, J=8.6, 6.6 Hz, 1H), 6.78 (d, J=6.3 Hz, 1H), 4.15-3.45 (m, 4H), 3.31-3.24 (m, 2H), 2.28-1.44 (m, 4H), 1.44 (t, J=7.2 Hz, 3H), 1.27 (d, J=6.9 Hz, 3H). LCMS (ESI, m/z): 427 [M+H]⁺.

Example 65: N-(2-((2S,3S)-1-ethyl-2-methylpiperidin-3-yl)thieno[2,3-b]pyridin-4-yl)-4-fluorobenzo[d]thiazol-5-amine Starting from Example 57b (30 mg, 0.080 mmol), following the general procedure above, the crude product was purified by preparative HPLC using the following gradient conditions: Column: Xselect CSH OBD Column 30×150 mm, 5 μm; Mobile Phase A: Water (0.05% TFA), Mobile Phase B: ACN; Flow rate: 60 mL/min; Gradient: 5% B to 30% B in 8 min; 254/210 nm; Rt: 7.65 min. Purification gave the desired product 9.4 mg (30%, 100% ee) of N-((2-((2S,3S)-1-ethyl-2-methylpiperidin-3-yl)thieno[2,3-b]pyridin-4-yl)-4-fluorobenzo[d]thiazol-5-amine (Example 65) as a light yellow solid. $^1$H NMR (400 MHz, Methanol-$d_4$) δ 9.41 (s, 1H), 8.26 (d, J=6.5 Hz, 1H), 8.07 (d, J=8.6 Hz, 1H), 7.76 (d, J=7.1 Hz, 1H), 7.62 (dd, J=8.5, 6.7 Hz, 1H), 6.78-6.70 (m, 1H), 4.10-3.41 (m, 3H), 3.31-3.17 (m, 3H), 2.23-2.03 (m, 4H), 1.44 (t, J=7.3 Hz, 3H), 1.27 (d, J=6.9 Hz, 3H). LCMS (ESI, m/z): 427 [M+H]⁺.

Example 66: Synthesis of 4,6-difluoro-N-(2-(2-methyl-1,2,5,6-tetrahydropyridin-3-yl)thieno[2,3-b]pyridin-4-yl)benzo-[d]thiazol-5-amine

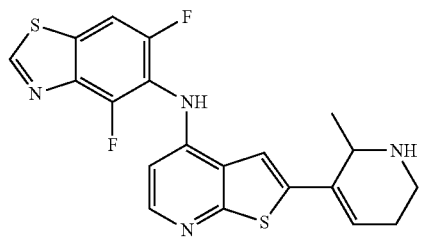 [SMILES: CC1NCCC=C1c1cc2c(Nc3c(F)cc4scnc4c3F)ccnc2s1]

Step 1

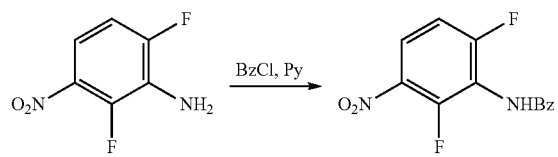

To a solution of 2,6-difluoro-3-nitroaniline (Example 66-1, 40 g, 229.75 mmol) in pyridine (100 mL) was added dropwise benzoyl chloride (32.03 mL, 275.7 mmol). The mixture was stirred at 50° C. overnight. LCMS showed the reaction was complete, and the mixture was quenched with water and extracted with EA. The organic layer was washed with 5% HCl(aq) and brine, concentrated. The residue was purified by silica gel column chromatography (PE/EA=8/1) to give N-(2,6-difluoro-3-nitrophenyl)benzamide (Example 66-2, 44 g, 68%) as a light-yellow solid.

Step 2

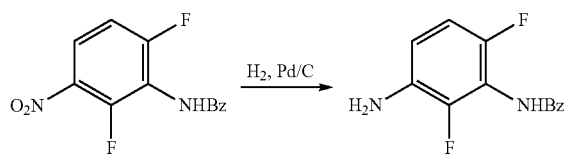

To a solution of N-(2,6-difluoro-3-nitrophenyl)benzamide (Example 66-2, 44 g, 158.3 mmol) in methanol (500 mL) was added Pd/C (2 g). Hydrogen gas was introduced to the mixture. The mixture was stirred 4 h at room temperature. LCMS showed the reaction was complete. The solids were filtered out. The filtrate was concentrate under vacuum to give N-(3-amino-2,6-difluoro-phenyl)benzamide (Example 66-3, 32 g, 81%) as an off-white solid.

Step 3

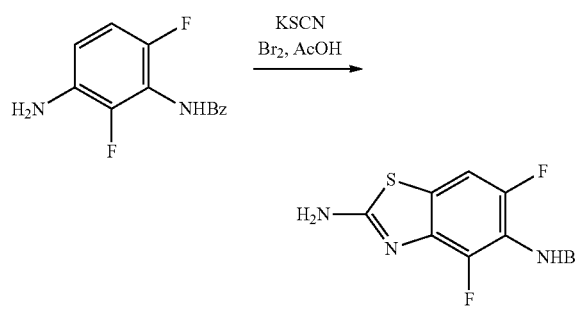

To a solution of N-(3-amino-2,6-difluoro-phenyl)benzamide (Example 66-3, 32 g, 129.0 mmol) and KSCN (31.26 g, 322.28 mmol) in acetic acid (800 mL) was added dropwise a solution of $Br_2$ (13.3 mL, 258.1 mmol) in acetic acid (100 mL). The mixture was stirred overnight at room temperature. LCMS showed the reaction was complete. The solid was collected by filtration and concentrated. The pH was adjusted to 10 with $NH_3 \cdot H_2O$, the solid was collected, washed with water and dried to give N-(2-amino-4,6-difluorobenzo[d]thiazol-5-yl)benzamide (Example 66-4, 26 g, 66%) as a light-yellow solid.

Step 4

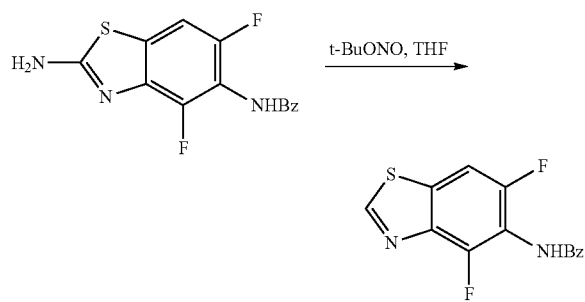

To a solution of N-(2-amino-4,6-difluorobenzo[d]thiazol-5-yl)benzamide (Example 66-4, 26 g, 85.25 mmol) in THF (400 mL) was added t-BuONO (13.49 g, 131.02 mmol). The mixture was stirred at 65° C. for 2 hours. LCMS showed the reaction was complete. The resulting solution was concentrated and purified by silica gel flash chromatography (PE: EA=2:1) to give N-(4,6-difluorobenzo[d]thiazol-5-yl)benzamide (Example 66-5, 21 g, 85%) as a red solid.

Step 5

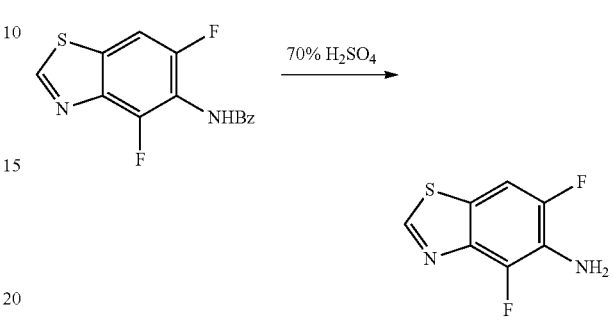

A solution of N-(4,6-difluorobenzo[d]thiazol-5-yl)benzamide (Example 66-5, 21. g, 72.4 mmol) in 70% $H_2SO_4$ (100. mL) was stirred at 100° C. for 2 hours. LCMS showed the reaction was complete. The pH was adjusted to 10 with sat. $Na_2CO_3$. The solid was collected, dried, then purified by silica gel flash chromatography (PE/EA=4/1) to afford 4,6-difluorobenzo-[d]thiazol-5-amine (Example 66-6, 11.4 g, 84%) as a light-yellow solid.

Step 6

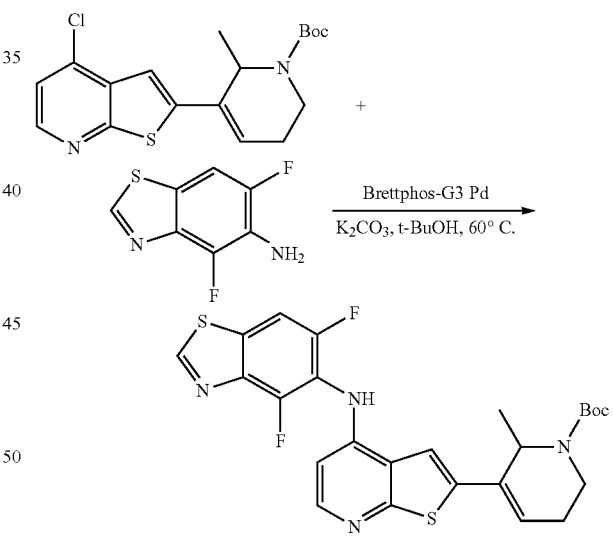

To a solution of tert-butyl 5-(4-chlorothieno[2,3-b]pyridin-2-yl)-6-methyl-3,6-dihydropyridine-1(2H)-carboxylate (Example 20-1, 7.0 g, 19.180 mmol, 1.00 equiv), 4,6-difluorobenzo[d]thiazol-5-amine (Example 66-6, 3.9 g, 21.100 mmol, 1.10 equiv) and $K_2CO_3$ (7.9 g, 57.550 mmol, 3.00 equiv) in tert-butanol (150 mL) was added BrettPhos-G3 Pd (1.7 g, 1.920 mmol, 0.10 equiv). The resulting mixture was stirred at 60° C. overnight under a nitrogen atmosphere. LCMS showed the reaction was complete. The solid was filtered out. The filtratre was concentrated under reduced pressure and the residue was purified by flash chromatography on silica gel with ethyl acetate/petroleum ether (1/1) to provide tert-butyl 5-(4-((4,6-difluorobenzo[d]

thiazol-5-yl)amino)thieno[2,3-b]pyridin-2-yl)-6-methyl-3,6-dihydropyridine-1(2H)-carboxylate (Example 66-7, 9.1 g, 93%) as a light-yellow solid. LCMS (ESI, m/z): 515 [M+H]$^+$.

Step 7

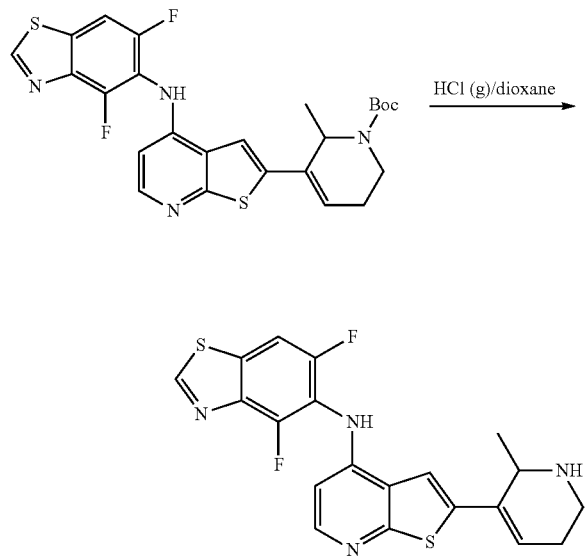

To a solution of tert-butyl 5-(4-((4,6-difluorobenzo[d]thiazol-5-yl)amino)thieno[2,3-b]pyridin-2-yl)-6-methyl-3,6-dihydropyridine-1(2H)-carboxylate (Example 66-7, 4.3 g, 8.320 mmol, 1.00 equiv) in 1,4-dioxane (30 mL) and methanol (1.5 mL) was added HCl(g) (4M in dioxane, 30 mL). The resulting mixture was stirred at room temperature for 1 h. LCMS showed the reaction was complete. The mixture was diluted with Et$_2$O. The solid was collected by filtration, washed with Et$_2$O and dried under reduced pressure to provide 4,6-difluoro-N-(2-(2-methyl-1,2,5,6-tetrahydropyridin-3-yl)thieno[2,3-b]pyridin-4-yl)benzo-[d]thiazol-5-amine (Example 66, 3.9 g, 96%) as a light-yellow solid. LCMS (ESI, m/z): 415 [M+H]$^+$.

Chiral Separation 4,6-difluoro-N-(2-(2-methyl-1,2,5,6-tetrahydropyridin-3-yl)thieno[2,3-b)]pyridin-4-yl)-benzo[d]thiazol-5-amine (Example 66, 790 mg, 1.910 mmol) was purified by SFC using the following gradient conditions: Column: CHIRALPAK AS-H, 5×25 cm, 5 µm; Mobile Phase A: CO$_2$: 50, Mobile Phase B: MeOH (2 mM NH$_3$-MeOH): 50; Flow rate: 180 mL/min; 220 nm; RT$^1$: 3.81 (Example 66a); RT$^2$: 5.2 (Example 66b) to provide (R)-4,6-difluoro-N-(2-(2-methyl-1,2,5,6-tetrahydropyridin-3-yl)thieno[2,3-b]pyridin-4-yl)benzo[d]thiazol-5-amine (Example 66a 29.8 mg, 4%, >99% ee) and (S)-4,6-difluoro-N-(2-(2-methyl-1,2,5,6-tetrahydropyridin-3-yl)thieno[2,3-b]pyridin-4-yl)-benzo[d]thiazol-5-amine (Example 66b 20.6 mg, 3%, >99% ee) as off-white solids. $^1$H NMR (400 MHz, Methanol-d$_4$) δ 9.32 (s, 1H), 8.10-8.04 (m, 1H), 7.94 (d, J=8.8 Hz, 1H), 7.54 (s, 1H), 6.34 (d, J=5.1 Hz, 2H), 4.09 (d, J=7.4 Hz, 1H), 3.16-3.08 (m, 1H), 2.96 (d, J=13.3 Hz, 1H), 2.50-2.20 (m, 2H), 1.47 (d, J=6.3 Hz, 3H). LCMS (ESI, m/z): 415 [M+H]$^+$.

Example 67: Synthesis of 4,6-difluoro-N-(2-((2R)-2-methyl-piperidin-3-yl)thieno[2,3-b]pyridin-4-yl)benzo[d]thiazol-5-amine

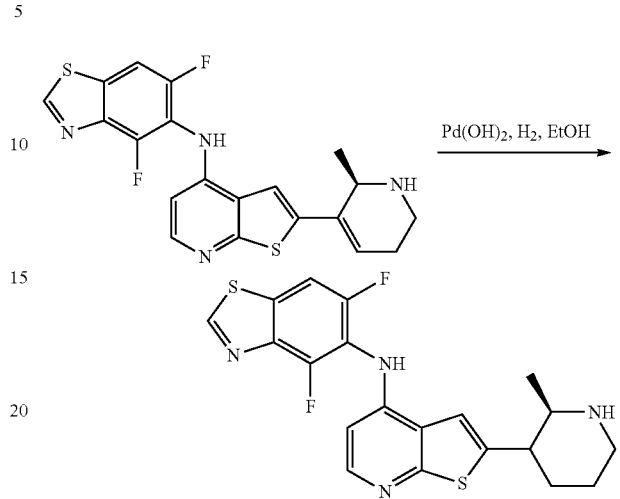

To a solution of (R)-4,6-difluoro-N-(2-(2-methylpiperidin-3-yl)thieno[2,3-b]pyridin-4-yl)benzo-[d]thiazol-5-amine (Example 66a, 310 mg, 0.750 mmol, 1.00 equiv) in ethanol (20 mL) was added Pd(OH)$_2$/C (310 mg, w/w=1/1). The mixture was stirred at 65° C. for 72 hours under an atmosphere of hydrogen (1-3 atm.). LCMS showed the desired product was formed. The resulting solution was filtered and the filtrate was concentrated under reduced pressure. The residue was purified by preparative HPLC using the following gradient conditions: Column: SunFire C18 OBD Prep Column, 100 Å, 5 µm, 19 mm×250 mm; Mobile Phase A: Water (0.05% TFA), Mobile Phase B: ACN; Flow rate: 25 mL/min; Gradient: 16% B to 18% B in 7.5 min; 254/210 nm; Rt: 6.38 min to provide 4,6-difluoro-N-(2-((2R)-2-methyl-piperidin-3-yl)thieno[2,3-b]pyridin-4-yl)benzo[d]thiazol-5-amine (Example 67, 100 mg, 32%) as an off-white solid. LCMS (ESI, m/z): 417[M+H]$^+$.

Chiral Separation 4,6-difluoro-N-(2-((2R)-2-methylpiperidin-3-yl)thieno[2,3-b]pyridin-4-yl)benzo[d]thiazol-5-amine (Example 67, 300 mg) was purified by preparative SFC using the following gradient conditions: Column: CHIRALPAK IG UL001, 20×250 mm, 5 µm; Mobile Phase A: Hex (8 mmol/L NH$_3$.MeOH)-HPLC, Mobile Phase B: EtOH-HPLC; Flow rate: 20 mL/min; Gradient: 50% B to 50% B in 12.5 min; 220/254 nm; RT$^1$: 6.535, 4,6-difluoro-N-(2-((2R,3S)-2-methylpiperidin-3-yl)thieno[2,3-b]pyridin-4-yl)benzo[d]thiazol-5-amine (Example 67a, 50 mg, 17%); RT$^2$: 9.344 4,6-difluoro-N-(2-((2R,3R)-2-methylpiperidin-3-yl)thieno[2,3-b]pyridin-4-yl)benzo[d]thiazol-5-amine (Example 67b, 191 mg, 65%) to give the desired products as off white solids. LCMS (ESI, m/z): 417 [M+H]$^+$.

Example 67a was further purified by preparative HPLC using the following gradient conditions: Column: Xselect CSH OBD Column 30×150 mm 5 µm; Mobile Phase A: Water (0.05% TFA), Mobile Phase B: ACN; Flow rate: 60 mL/min; Gradient: 20% B to 50% B in 8 min; 254/210 nm; Rt: 7.66 min to give the desired product 4,6-difluoro-N-(2-((2R,3S)-2-methylpiperidin-3-yl)thieno[2,3-b]pyridin-4-yl)benzo-[d]thiazol-5-amine (Example 67a, 82.2 mg, 82%) as a light-yellow solid. $^1$H NMR (300 MHz, Methanol-d$_4$) δ 9.36 (s, 1H), 8.29 (d, J=6.6 Hz, 1H), 8.04 (d, J=18 Hz, 1H), 7.78 (s, 1H), 6.65 (d, J=6.6 Hz, 1H), 3.50 (td, J=12.9, 6.7 Hz, 2H), 3.27 (s, 1H), 3.30-3.10 (m, 1H), 2.40-1.86 (m, 4H), 1.33 (d, J=6.6 Hz, 3H).

Example 67b was further purified by preparative HPLC using the following gradient conditions: Column: CHIRAL-PAK AD-3 3×100 mm, 3 μm; Co-Solvent: EtOH (0.1% DEA); Gradient (B %): 10% to 50% in 4.0 min, hold 2.0 min at 50%; Back Pressure (psi): 1500.000; Flow (ml/min): 2; Temperature: 35; Detector: 220 nm to give the desired product 4,6-difluoro-N-(2-((2R,3R)-2-methylpiperidin-3-yl)thieno[2,3-b]pyridin-4-yl)benzo-[d]thiazol-5-amine (Example 67b, 65 mg, 65%, >95% ee) as an off-white solid. $^1$H NMR (400 MHz, Methanol-$d_4$) δ 9.39 (s, 1H), 8.36 (d, J=6.9 Hz, 1H), 8.07 (dd, J=8.9, 1.8 Hz, 1H), 7.86 (s, 1H), 6.75 (d, J=6.9 Hz, 1H), 4.14-4.06 (m, 1H), 3.75 (m, 1H), 3.45-3.25 (m, 2H), 2.35-2.15 (m, 3H), 2.10-1.90 (m, 1H), 1.34 (d, J=7.0 Hz, 3H). LCMS (ESI, m/z): 417 [M+H]$^+$.

Example 68: Synthesis or 4,6-difluoro-N-[2-[(2S)-2-methyl-3-piperidyl]-thieno[2,3-b]pyridin-4-yl]-1,3-benzothiazol-5-amine

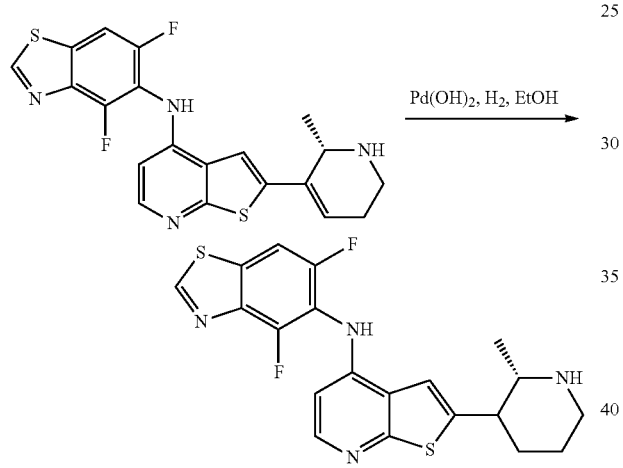

To a solution of (S)-4,6-difluoro-N-(2-(2-methylpiperidin-3-yl)thieno[2,3-b]pyridin-4-yl)benzo[d]-thiazol-5-amine (Example 66b, 330 mg, 0.800 mmol, 1.00 equiv) in ethanol (20 mL) was added Pd(OH)$_2$/C (330 mg, w/w=1/1). The mixture was stirred at 65° C. for 72 hours under an atmosphere of hydrogen (1-3 atm.). LCMS showed the reaction was complete. The resulting solution was filtered and the filtration was concentrated under reduced pressure. The residue was purified by preparative HPLC using the following gradient conditions: Column: SunFire C18 OBD Prep Column, 100 Å, 5 μm, 19 mm×250 mm; Mobile Phase A: Water (0.05% TFA), Mobile Phase B: ACN; Flow rate: 25 mL/min; Gradient: 16% B to 18% B in 7.5 min; 254/210 nm; Rt: 6.38 min to provide 4,6-difluoro-N-[2-[(2S)-2-methyl-3-piperidyl]-thieno[2,3-b]pyridin-4-yl]-1,3-benzothiazol-5-amine (Example 68, 110 mg, 33%) as an off-white solid. LCMS (ESI, m/z): 417 [M+H]$^+$.

Chiral Separation

Example 68 was purified by SFC (Column: CHIRALPAK AD-H SFC, 5×25 cm, 5 μm; Mobile Phase A: CO$_2$: 50, Mobile Phase B: EtOH (2 mM NH$_3$-MeOH): 50; Flow rate: 180 mL/min; 220 nm; RT$^1$: 4.2, Example 68a; RT$^2$: 6.0, Example 68b.

Example 68a was further purified via preparative HPLC (Column: XBridge Prep OBD C18 Column, 30×150 mm 5 μm; Mobile Phase A: Water (10 mmoL/L NH$_4$HCO$_3$+0.1% NH$_3$.H2O), Mobile Phase B: ACN; Flow rate: 60 mL/min; Gradient: 23 B to 43 B in 7 min; 254/210 nm; RT$^1$: 6.73). Purification yielded 4,6-difluoro-N-(2-((2S,3R)-2-methylpiperidin-3-yl)thieno[2,3-b]pyridin-4-yl)benzo[d]thiazol-5-amine (Example 68a, 23.3 mg, yield: 22%, 99% ee) as an off-white solid. $^1$H NMR (400 MHz, Methanol-$d_4$) δ 9.32 (s, 1H), 8.07 (d, J=5.7 Hz, 1H), 7.93 (dd, J=9.0, 1.8 Hz, 1H), 7.44 (s, 1H), 6.33 (dt, J=5.6, 1.9 Hz, 1H), 3.14 (d, J=12.6 Hz, 1H), 2.93-2.60 (m, 3H), 2.17 (d, J=12.9 Hz, 1H), 1.91-1.60 (m, 3H), 1.09 (d, J=6.2 Hz, 3H). LCMS (ESI, m/z): 417 [M+H]$^+$.

Example 68b was further purified via preparative HPLC, Column: CHIRALPAK AD-3 3*100 mm, 3 μm; Co-Solvent: EtOH (0.1% DEA); Gradient (B %): 10% to 50% in 4.0 min, hold 2.0 min at 50%; Back Pressure (psi): 1500.000; Flow (ml/min): 2; Temperature: 35; Detector: 220 nm to provide 4,6-difluoro-N-(2-((2S,3S)-2-methylpiperidin-3-yl)thieno[2,3-b]pyridin-4-yl)benzo[d]thiazol-5-amine (Example 68b, 6 mg, 5%, 99% ee). $^1$H NMR (400 MHz, Methanol-$d_4$) δ 9.37 (s, 1H), 8.30 (d, J=6.5 Hz, 1H), 8.02 (dd, J=8.9, 1.8 Hz, 1H), 7.80 (d, J=1.2 Hz, 1H), 6.64 (dd, J=6.6, 1.8 Hz, 1H), 4.14-4.03 (m, 1H), 3.73 (m, 1H), 3.35-3.25 (m, 2H), 2.31-2.14 (m, 3H), 2.05-1.90 (m, 1H), 1.34 (d, J=7.0 Hz, 3H). LCMS (ESI, m/z): 417 [M+H]$^+$.

Example 69: Synthesis of (R)—N-(2-(1,2-dimethyl-1,2,5,6-tetrahydropyridin-3-yl)thieno[2,3-b]pyridin-4-yl)-4,6-difluorobenzo[d]thiazol-5-amine

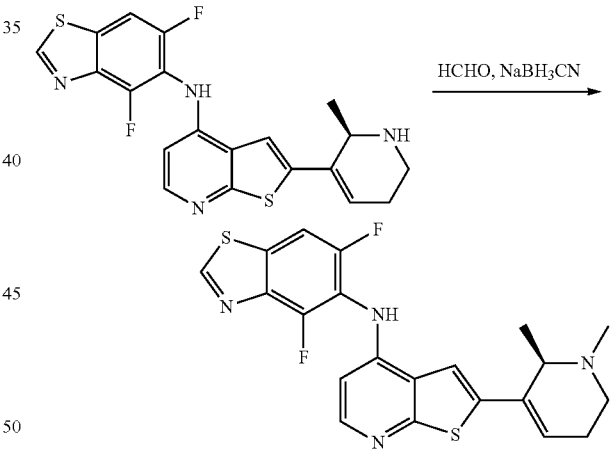

To a solution of (R)-4,6-difluoro-N-(2-(2-methyl-1,2,5,6-tetrahydropyridin-3-yl)thieno[2,3-b]pyridin-4-yl)benzo[d] thiazol-5-amine (Example 66a, 400 mg, 0.970 mmol, 1.00 equiv) in methanol (15 mL) was added HCHO (391 mg, 4.830 mmol, 5.00 equiv) and NaBH$_3$CN (182 mg, 2.900 mmol, 3.00 equiv). The resulting solution was stirred 1 hour at room temperature. LCMS showed the reaction was complete. The resulting solution was quenched with water and extracted with EA. The combined organic phase was dried over Na$_2$SO$_4$, filtered and concentrated. The residue was purified by preparative TLC with dichloromethane/methanol (1:1) to afford (R)—N-(2-(1,2-dimethyl-1,2, 5,6-tetrahydropyridin-3-yl)thieno[2,3-b]pyridin-4-yl)-4,6-difluorobenzo[d]thiazol-5-amine (Example 69, 320 mg, 78%). LCMS (ESI, m/z): 429 [M+H]$^+$

Example 70: Synthesis of N-(2-((2R)-1,2-dimethylpiperidin-3-yl)thieno[2,3-b]pyridin-4-yl)-4,6-difluorobenzo-[d]thiazol-5-amine

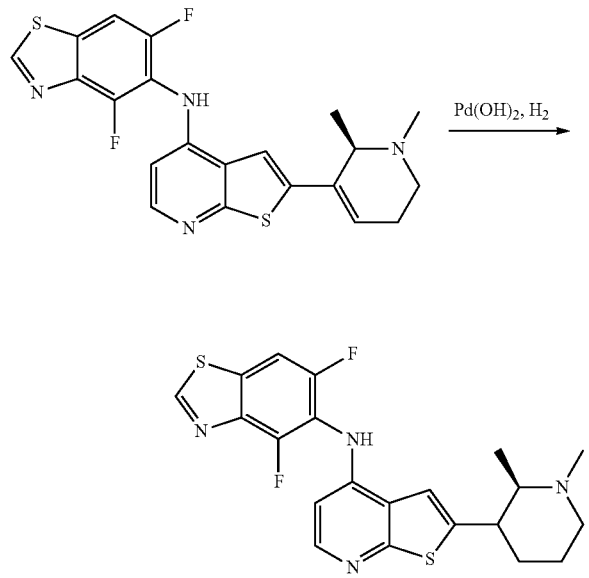

To a solution of (R)—N-(2-(1,2-dimethyl-1,2,5,6-tetrahydropyridin-3-yl)thieno[2,3-b]pyridin-4-yl)-4,6-difluorobenzo[d]thiazol-5-amine (Example 69, 320 mg, 0.750 mmol, 1.00 equiv) in ethanol (20 mL) was added Pd(OH)$_2$/C (320 mg, w/w=1/1). The resulting mixture was stirred at 60° C. overnight under an atmosphere of hydrogen (1-3 atm.). The reaction mixture was filtered and the filtration was concentrated. The residue was purified by preparative HPLC Column: Sunfire Prep C18 OBD Column, 10 μm, 19*250 mm; Mobile Phase A: Water (0.05% TFA), Mobile Phase B: ACN; Flow rate: 60 mL/min; Gradient: 30% B to 60% B in 8 min; 254/210 nm; Rt: 7.65 min to give N-(2-((2R)-1,2-dimethylpiperidin-3-yl)thieno[2,3-b]pyridin-4-yl)-4,6-difluorobenzo-[d]thiazol-5-amine (Example 70, 80 mg, 25%) as an off-white solid. LCMS (ESI, m/z): 431 [M+H]$^+$.

Chiral Separation

N-(2-((2R)-1,2-dimethylpiperidin-3-yl)thieno[2,3-b]pyridin-4-yl)-4,6-difluorobenzo-[d]thiazol-5-amine (Example 70, 80 mg, 0.190 mmol, 1.00 equiv) was purified by Chiral HPLC using the following gradient conditions: Column: CHIRALPAK IG UL001, 20×250 mm, 5 μm; Mobile Phase A: Hex (8 mmol/L NH$_3$-MeOH)-HPLC, Mobile Phase B: EtOH-HPLC; Flow rate: 20 mL/min; Gradient: 50% B to 50% B in 12.5 min; 220/254 nm; RT$^1$: 6.535, trace amounts of N-(2-((2R,3S)-1,2-dimethylpiperidin-3-yl)thieno[2,3-b]pyridin-4-yl)-4,6-difluorobenzo[d]thiazol-5-amine (Example 70a); RT$^2$: 9.344, N-(2-((2R,3R)-1,2-dimethylpiperidin-3-yl)thieno[2,3-b]pyridin-4-yl)-4,6-difluorobenzo[d]thiazol-5-amine (Example 70b, 50.3 mg, 62%) was isolated as an off-white solid. LCMS (ESI, m/z): 431 [M+H]$^+$. $^1$H NMR (400 MHz, Methanol-d$_4$) δ 9.38 (s, 1H), 8.34 (d, J=6.8 Hz, 1H), 8.06 (dd, J=8.9, 1.8 Hz, 1H), 7.83 (d, J=1.2 Hz, 1H), 6.72 (m, 1H), 4.15-4.05 (m, 1H), 3.90-3.75 (m, 1H), 3.40-3.20 (m, 2H), 2.95 (s, 3H), 2.30-2.00 (m, 4H), 1.39-1.20 (m, 3H). LCMS (ESI, m/z): 431 [M+H]$^+$.

Example 71: Synthesis of N-((2-((2S)-1,2-dimethylpiperidin-3-yl)thieno-[2,3-b]pyridin-4-yl)-4,6-difluorobenzo[d]thiazol-5-amine

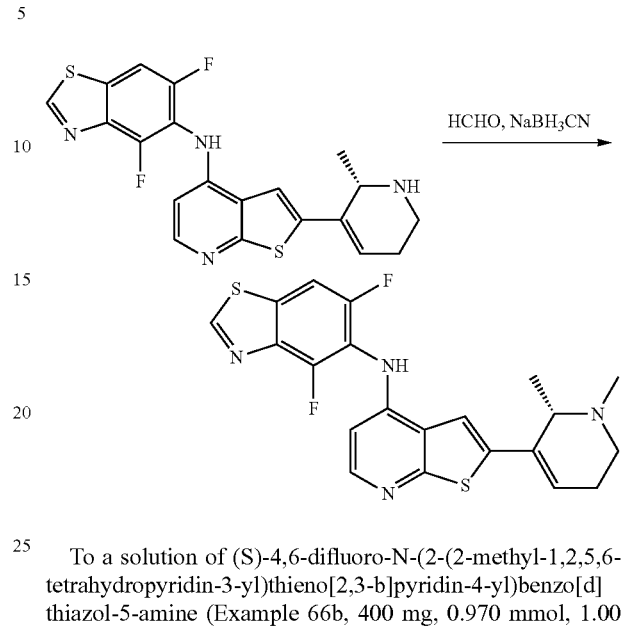

To a solution of (S)-4,6-difluoro-N-(2-(2-methyl-1,2,5,6-tetrahydropyridin-3-yl)thieno[2,3-b]pyridin-4-yl)benzo[d]thiazol-5-amine (Example 66b, 400 mg, 0.970 mmol, 1.00 equiv) in methanol (16 mL) was added HCHO (391 mg, 4.830 mmol, 5.00 equiv) and NaBH$_3$CN (182 mg, 2.90 mmol, 3.00 equiv). The resulting solution was stirred 1 hour at room temperature. The resulting mixture was quenched with water and extracted with EA. The combined organic phase was concentrated and the residue was purified by preparative TLC with dichloromethane:methanol (1:1) to afford N-((2-((2S)-1,2-dimethylpiperidin-3-yl)thieno-[2,3-b]pyridin-4-yl)-4,6-difluorobenzo[d]thiazol-5-amine (Example 71-1, 300 mg, 73%). LCMS (ESI, m/z): 429 [M+H]$^+$.

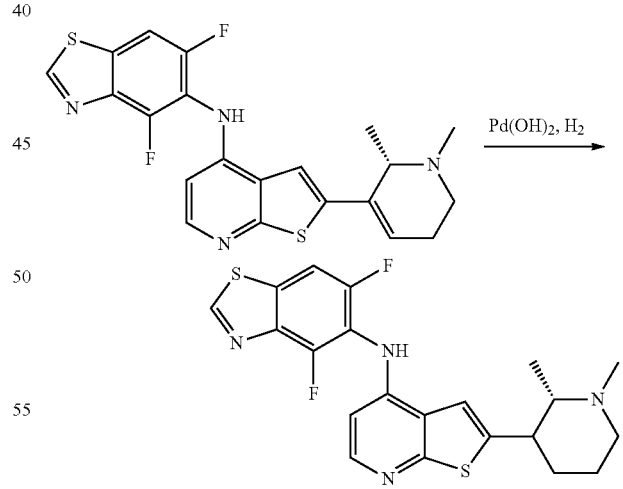

To a solution of N-((2-((2S)-1,2-dimethylpiperidin-3-yl)thieno[2,3-b]pyridin-4-yl)-4,6-difluoro-benzo[d]thiazol-5-amine (Example 71-1, 300 mg, 0.700 mmol, 1.00 equiv) in ethanol (20 mL) was added Pd(OH)$_2$/C (300 mg, w/w=1/1). The resulting mixture was stirred at 60° C. overnight under an atmosphere of hydrogen (1-3 atom.). The reaction mixture was filtered. The filtrate was concentrated and the residue was purified by preparative HPLC Column: Sunfire Prep C18 OBD Column, 10 μm, 19×250 mm; Mobile Phase A: Water (0.05% TFA), Mobile Phase B: ACN; Flow rate: 60 mL/min; Gradient: 30% B to 60% B in 8 min; 254/210 nm; Rt: 7.65 min to provide N-[2-[(2S)-1,2-dimethyl-3-piperidyl]-thieno-[2,3-b]pyridin-4-yl]-4,6-difluoro-1,3-benzothiazol-5-amine (Example 71, 90 mg, 30%) as an off-white solid. LCMS (ESI, m/z): 431 [M+H]$^+$.

Chiral Separation

N-[2-[(2S)-1,2-dimethyl-3-piperidyl]-thieno-[2,3-b]pyridin-4-yl]-4,6-difluoro-1,3-benzothiazol-5-amine (Example 71, 90 mg, 0.210 mmol, 1.00 equiv) was purified by Chiral HPLC using the following gradient conditions: Column: CHIRALPAK IG UL001, 20×250 mm, 5 μm; Mobile Phase A: Hex (8 mmol/L NH$_3$-MeOH), Mobile Phase B: EtOH-HPLC; Flow rate: 20 mL/min; Gradient: 50% B to 50% B in 12.5 min; 220/254 nm; RT$^1$: 6.535 trace N-(2-((2S,3R)-1,2-dimethylpiperidin-3-yl)thieno[2,3-b]pyridin-4-yl)-4,6-difluorobenzo[d]thiazol-5-amine (Example 71a); RT$^2$: 9.344, N-(2-((2S,3S)-1,2-dimethylpiperidin-3-yl)thieno[2,3-b]pyridin-4-yl)-4,6-difluorobenzo[d]thiazol-5-amine (Example 71b, 57.7 mg, 63%) as an off-white solid. [M+H]$^+$. $^1$H NMR (400 MHz, Methanol-d$_4$) δ 9.39 (s, 1H), 8.34 (d, J=6.7 Hz, 1H), 8.06 (d, J=9.0 Hz, 1H), 7.83 (s, 1H), 6.72 (d, J=6.8 Hz, 1H), 4.15-4.05 (m, 1H), 3.85-3.70 (m, 1H), 3.50-3.20 (m, 2H), 2.95 (s, 3H), 2.30-1.95 (m, 4H), 1.29 (d, J=7.0 Hz, 3H). LCMS (ESI, m/z): 431 [M+H]$^+$.

Example 72: Synthesis of N-(2-(1-ethyl-2-methyl-1,2,5,6-tetrahydropyridin-3-yl)thieno[2,3-b]pyridin-4-yl)-4,6-difluorobenzo[d]thiazol-5-amine

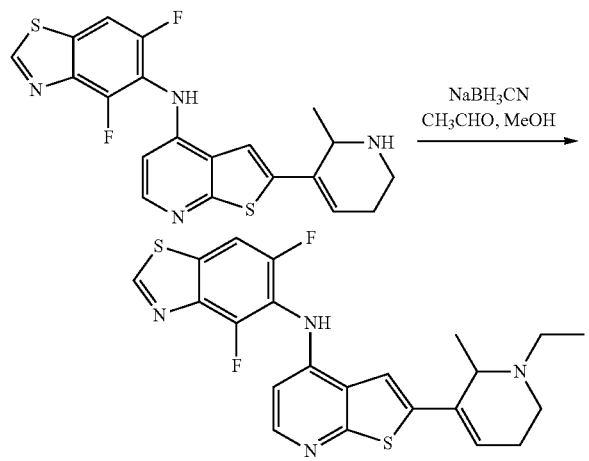

To a solution of 4,6-difluoro-N-(2-(2-methyl-1,2,5,6-tetrahydropyridin-3-yl)thieno[2,3-b]pyridin-4-yl)benzo[d]thiazol-5-amine (Example 66, 1.1 g, 2.650 mmol, 1.00 equiv) and CH$_3$CHO (875 mg, 7.951 mmol, 3.00 equiv) in methanol (15 mL) was added NaBH$_3$CN (510 mg, 7.951 mmol, 3.00 equiv). The resulting mixture was stirred for 1 h at room temperature. LCMS showed the reaction was completed. The reaction mixture was diluted with water (50 mL). The solid was collected by filtration, dried and purified by flash chromatography on silica gel with DCM/MeOH (8:1) to afford N-(4,6-difluorobenzo[d]thiazol-5-yl)-2-(1-ethyl-2-methyl-1,2,5,6-tetrahydropyridin-3-yl)thieno[2,3-b]pyridin-4-amine (Example 72, 1.1 g, 90%) as an off-white solid. LCMS (ESI, m/z): 443 [M+H]$^+$.

Chiral Separation

The mixture of the isomers (Example 72, 1.1 g, 2.365 mmol) was purified by SFC using the following gradient conditions: Column: CHIRALPAK AS-H SFC, 5×25 cm, 5 μm; Mobile Phase A: CO$_2$: 50, Mobile Phase B: MeOH (2 mMNH$_3$-MeOH): 50; Flow rate: 150 mL/min; 220 nm; RT$^1$: 4.09 (Example 72a); RT$^2$: 7.39 (Example 72b). Purification gave the Example 72a (60.2 mg, 6%, 100% ee) and Example 72b (57.0 mg, 6%, 100% ee) as off-white solids. $^1$H NMR (400 MHz, Methanol-d$_4$) δ 9.29 (s, 1H), 8.05 (d, J=5.7 Hz, 1H), 7.91 (dd, J=8.9, 1.8 Hz, 1H), 7.55 (s, 1H), 6.35-6.28 (m, 2H), 3.99-3.94 (m, 1H), 3.04-2.97 (m, 1H), 2.85-2.80 (m, 1H), 2.77-2.66 (m, 2H), 2.58-2.51 (m, 1H), 2.24-2.18 (m, 1H), 1.35 (d, J=6.6 Hz, 3H), 1.25 (t, J=7.2 Hz, 3H). LCMS (ESI, m/z): 443 [M+H]$^+$.

Example 73: Synthesis of N-(2-((2R)-1-ethyl-2-methylpiperidin-3-yl)thieno[2,3-b]-pyridin-4-yl)-4,6-difluorobenzo-[d]thiazol-5-amine

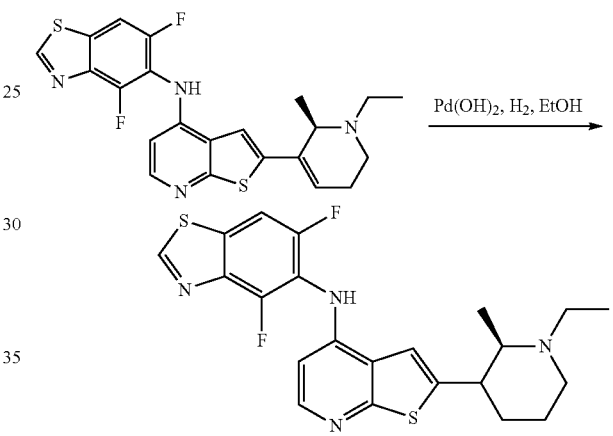

To a solution of (R)—N-(2-(1-ethyl-2-methyl-1,2,5,6-tetrahydropyridin-3-yl)thieno[2,3-b]-pyridin-4-yl)-4,6-difluorobenzo[d]thiazol-5-amine (Example 72a, 360 mg, 0.810 mmol, 1.00 equiv) in ethanol (30 mL) was added dry Pd(OH)$_2$ (360 mg, 1.00 w/w). The resulting mixture was stirred at 65° C. under an atmosphere of hydrogen (10 atm.) for 24 h. LCMS showed the reaction was completed. The resulting mixture was filtered with the aid of celite. The filtration was concentrated and the residue was purified by preparative TLC with DCM/MeOH (7:1) to give N-(2-((2R)-1-ethyl-2-methylpiperidin-3-yl)-thieno[2,3-b]-pyridin-4-yl)-4,6-difluorobenzo[d]thiazol-5-amine (Example 73, 140 mg, 39%) as an off-white solid. LCMS (ESI, m/z): 445 [M+H]$^+$.

Chiral Separation

N-(2-(1-ethyl-2-methylpiperidin-3-yl)thieno[2,3-b]pyridin-4-yl)-4,6-difluorobenzo[d]thiazol-5-amine (Example 73, 140 mg, 0.315 mmol) was purified by SFC using the following gradient conditions: Column: CHIRALPAK IG HPLC, 20×250 mm, 5 μm; Mobile Phase A: Hex (8 mmol/L NH$_3$.MeOH), Mobile Phase B: EtOH; Flow rate: 17 mL/min; Gradient: 50% B to 50% B in 13 min; 220/254 nm; RT$^1$: 9.434. Purification gave N-[2-((2R,3R)1-ethyl-2-methyl-3-piperidyl)thieno[2,3-b]pyridin-4-yl]-4,6-difluoro-1,3-benzothiazol-5-amine (Example 73b, 70 mg, 50%, 100% ee) as a white solid. $^1$H NMR (400 MHz, Methanol-d$_4$) δ 9.35 (s, 1H), 8.23 (d, J=6.2 Hz, 1H), 8.00 (dd, J=8.9, 1.8 Hz, 1H), 7.74 (s, 1H), 6.54 (d, J=6.3 Hz, 1H), 4.12-4.08

(m, 1H), 3.82-3.79 (m, 1H), 3.50-3.47 (m, 1H), 3.29-3.14 (m, 3H), 2.26-2.01 (m, 4H), 1.46 (t, J=7.3 Hz, 3H), 1.27 (d, J=6.9 Hz, 3H). LCMS (ESI, m/z): 445 [M+H]⁺. Trace amounts of additional isomer Example 73a were detected.

Example 74: Synthesis of N-[2-[(2S)-1-ethyl-2-methyl-3-piperidyl]thieno[2,3-b]pyridin-4-yl]-4,6-difluoro-1,3-benzothiazol-5-amine

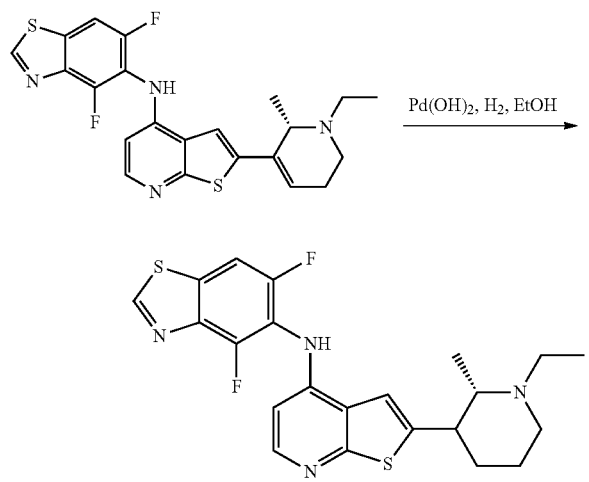

To a solution of (S)—N-(2-(1-ethyl-2-methyl-1,2,5,6-tetrahydropyridin-3-yl)thieno[2,3-b]pyridin-4-yl)-4,6-difluorobenzo[d]thiazol-5-amine (Example 72a, 370 mg, 0.835 mmol, 1.00 equiv) in ethanol (30 mL) was added dry Pd(OH)₂ (360 mg, 1.00 w/w). The resulting mixture was stirred at 65° C. under an atmosphere of hydrogen (10 atm.) for 24 h. LCMS showed the reaction was completed. The resulting mixture was filtered with the aid of celite. The filtration was concentrated and the residue was purified by preparative TLC with DCM/MeOH (8:1) to give N-[2-[(2S)-1-ethyl-2-methyl-3-piperidyl]-thieno[2,3-b]pyridin-4-yl]-4,6-difluoro-1,3-benzothiazol-5-amine (Example 74, 130 mg, 35%) as an off-white solid. LCMS (ESI, m/z): 445 [M+H]⁺.

Chiral Separation

Example 74 (130 mg, 0.293 mmol) was purified by SFC using the following gradient conditions: Column: CHIRALPAK IG HPLC, 20×250 mm, 5 μm; Mobile Phase A: Hex (8 mmol/L NH₃-MeOH), Mobile Phase B: EtOH; Flow rate: 17 mL/min; Gradient: 50% B to 50% B in 12 min; 220/254 nm; RT¹: 16.078. Purification gave N-(2-((2S,3S)-1-ethyl-2-methylpiperidin-3-yl)thieno[2,3-b]pyridin-4-yl)-4,6-difluorobenzo[d]thiazol-5-amine (Example 74b, 70 mg, 54%, 99.8% ee) as a white solid. LCMS (ESI, m/z): 445 [M+H]⁺. Analytic Conditions: Column: CHIRALPAK IG-3 0.46×5 cm, 3 μm; Mobile phase: Hex (0.2% DEA):EtOH=50:50; Flow (ml/min): 1; Temperature: 25; Detector: 254 nm. ¹H NMR (400 MHz, Methanol-d₄) δ 9.37 (s, 1H), 8.28 (d, J=6.5 Hz, 1H), 8.03 (dd, J=8.9, 1.8 Hz, 1H), 7.83 (s, 1H), 6.63 (d, J=6.5 Hz, 1H), 4.12-4.10 (m, 1H), 3.87-3.84 (m, 1H), 3.59-3.47 (m, 1H), 3.29-3.23 (m, 3H), 2.31-2.02 (m, 4H), 1.54-1.42 (t, J=7.3 Hz, 3H), 1.31-1.28 (d, J=6.9 Hz, 3H). LCMS (ESI, m/z): 445 [M+H]⁺. Trace amounts of additional isomer Example 74a were detected.

Example 75: Synthesis of 6-fluoro-N-(2-(2-methylpyrrolidin-3-yl)thieno[2,3-b]pyridin-4-yl)benzo[d]thiazol-5-amine

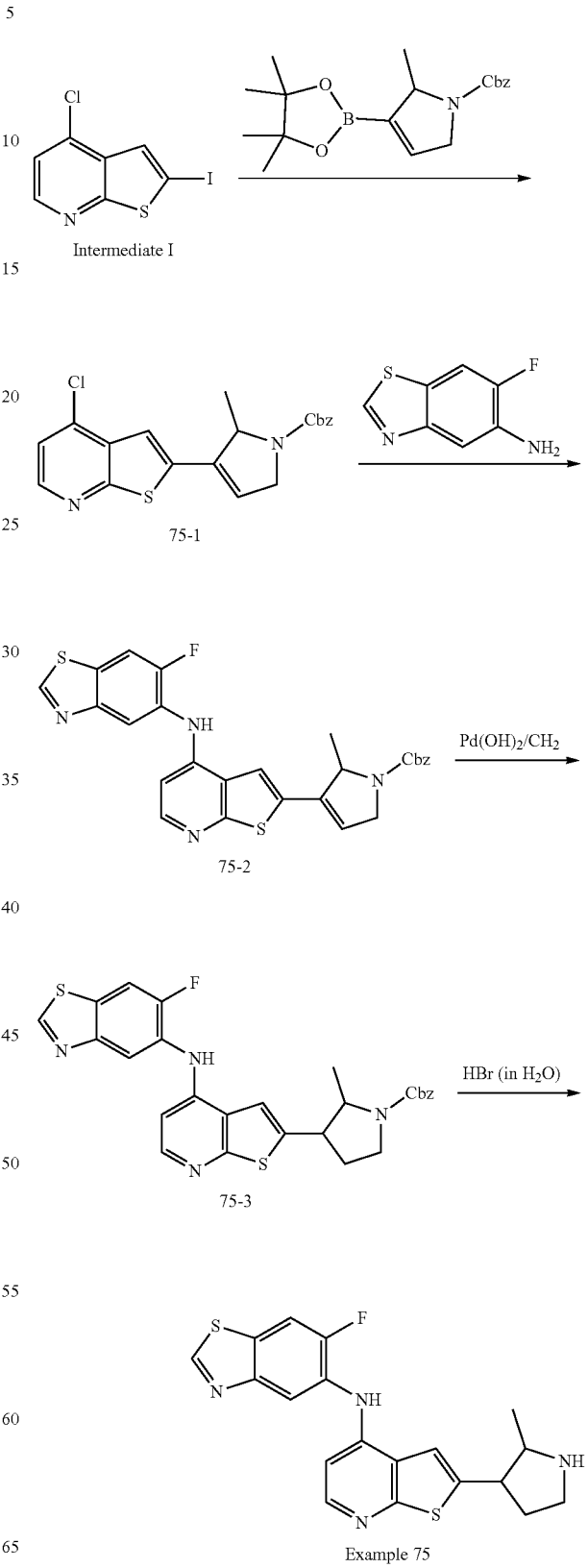

Synthesis of benzyl 3-(4-chlorothieno[2,3-b]pyridin-2-yl)-2-methyl-2,5-dihydro-1H-pyrrole-1-carboxylate

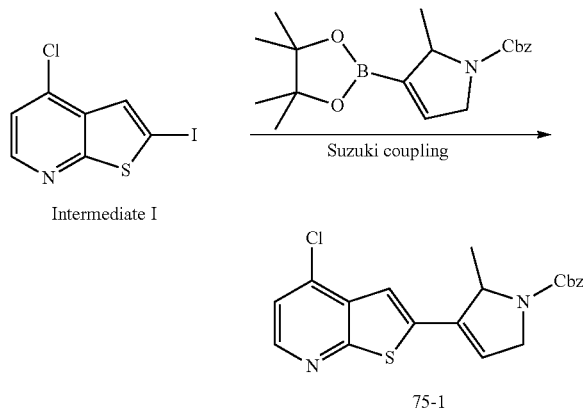

A solution of 4-chloro-2-iodo-thieno[2,3-b]pyridine (intermediate I, 1.9 g, 6.440 mmol, 1.00 equiv), benzyl-2-methyl-3-(4,4,5,5-tetramethyl-1,3,2-dioxaborolan-2-yl)-2,5-dihydro-pyrrole-1-carboxylate (2.2 g, 6.440 mmol, 1.00 equiv), Pd(dppf)Cl$_2$ (0.4 g, 0.644 mmol, 0.10 equiv) and t-BuONa (1.8 g, 19.320 mmol, 3.00 equiv) in 1,4-dioxane (20.0 mL) and water (2.0 mL) was placed in a 250-ml round-bottom flask. The flask was evacuated and flushed three times with nitrogen. The resulting solution was stirred at 70° C. for 2 h. LCMS showed the reaction was complete. The reaction mixture was filtered and concentrated under reduced pressure. The residue was applied onto silica gel and eluted with ethyl acetate/petroleum ether (1/4) to give the desired product benzyl 3-(4-chlorothieno[2,3-b]pyridin-2-yl)-2-methyl-2,5-dihydro-1H-pyrrole-1-carboxylate (75-1, 2.2 g, 89%) as a yellow oil. LCMS (ESI, m/z): 385 [M+H]$^+$.

Synthesis of benzyl 3-(4-((6-fluorobenzo[d]thiazol-5-yl)amino)thieno[2,3-b]pyridin-2-yl)-2-methyl-2,5-dihydro-1H-pyrrole-1-carboxylate

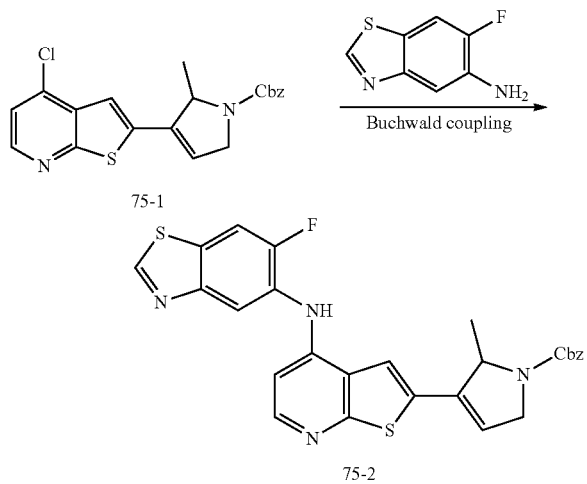

A solution of benzyl 3-(4-chlorothieno[2,3-b]pyridin-2-yl)-2-methyl-2,5-dihydropyrrole-1-carboxylate (75-1, 300 mg, 0.780 mmol, 1.00 equiv), 6-fluoro-1,3-benzothiazol-5-amine (131 mg, 0.780 mmol, 1.00 equiv), Cs$_2$CO$_3$ (762 mg, 2.340 mmol, 3.00 equiv), Pd(OAc)$_2$ (18 mg, 0.078 mmol, 0.10 equiv) and BINAP (97 mg, 0.390 mmol, 0.20 equiv) in 1,4-dioxane (10.0 mL) was placed in a 50-ml round-bottom flask. The flask was evacuated and flushed three times with nitrogen. The resulting solution was stirred at 90° C. for 15 h in an oil bath. LCMS showed the reaction was complete. The resulting mixture was filtered and concentrated under reduced pressure. The residue was applied onto silica gel and eluted with ethyl acetate/petroleum ether (1/5) to give the desired product benzyl 3-(4-((6-fluorobenzo[d]thiazol-5-yl)amino)thieno[2,3-b]pyridin-2-yl)-2-methyl-2,5-dihydro-1H-pyrrole-1-carboxylate (75-2, 170 mg, 42%) as a yellow oil. LCMS (ESI, m/z): 517 [M+H]$^+$.

Synthesis of benzyl 3-(4-((6-fluorobenzo[d]thiazol-5-yl)amino)thieno[2,3-b]pyridin-2-yl)-2-methylpyrrolidine-1-carboxylate

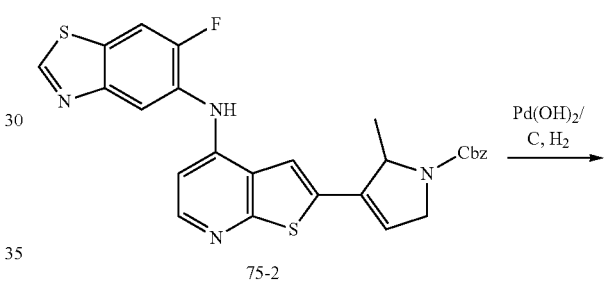

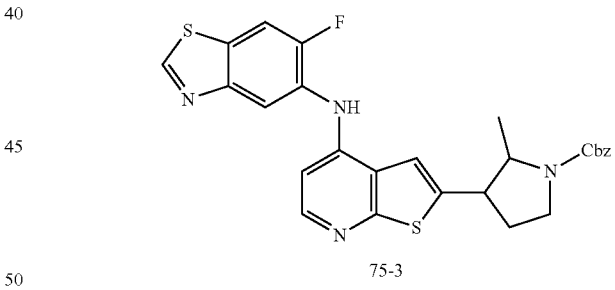

To a solution of benzyl 3-(4-((6-fluorobenzo[d]thiazol-5-yl)amino)thieno[2,3-b]pyridin-2-yl)-2-methyl-2,5-dihydro-1H-pyrrole-1-carboxylate (75-2, 170 mg, 0.330 mmol, 1.00 equiv) in ethanol (10.0 mL) was added Pd(OH)$_2$/C (170 mg, 1.00 w/w). The flask was evacuated and flushed three times with nitrogen, followed by flushing with hydrogen. The reaction mixture was stirred at 90° C. for 15 h in an oil bath under an atmosphere of hydrogen (balloon). LCMS showed the reaction was complete. The resulting mixture was filtered and concentrated under reduced pressure. Crude benzyl 3-(4-((6-fluorobenzo[d]thiazol-5-yl)amino)thieno[2,3-b]pyridin-2-yl)-2-methylpyrrolidine-1-carboxylate 75-3 was used in the next step without further purification. LCMS (ESI, m/z): 519 [M+H]$^+$.

Synthesis of 6-fluoro-N-(2-(2-methylpyrrolidin-3-yl)thieno[2,3-b]pyridin-4-yl)benzo[d]thiazol-5-amine

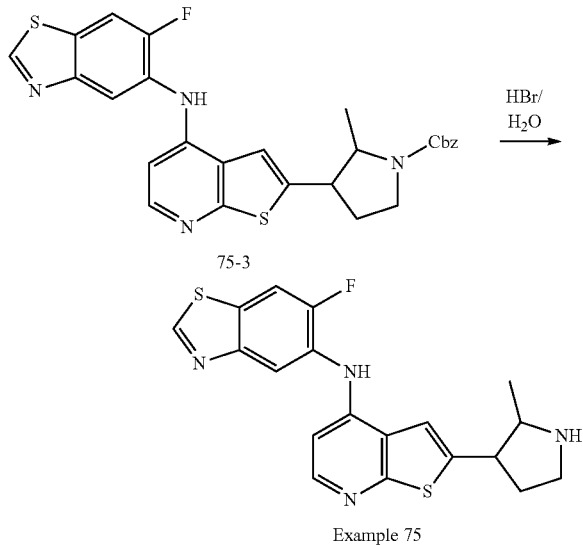

Example 75

A solution of benzyl 3-(4-((6-fluorobenzo[d]thiazol-5-yl)amino)thieno[2,3-b]pyridin-2-yl)-2-methylpyrrolidine-1-carboxylate (75-3, 105 mg, 0.200 mmol, 1.00 equiv) in HBr (40% in H$_2$O, 3.0 ml) was stirred at room temperature for 0.5 h. LCMS showed the reaction was complete. The resulting solution was purified by prep-HPLC (Column: X Bridge Prep C18 OBD 19×150 mm, 5 um; Mobile Phase A: Water (10 mmol/L NH$_4$HCO$_3$+0.1% NH$_3$.H$_2$O), Mobile Phase B: ACN; Flow rate: 25 mL/min; Gradient: 5% B to 52% B in 7.5 min; 254/210 nm; Rt: 7.17 min) to give the desired product 6-fluoro-N-(2-(2-methylpyrrolidin-3-yl)thieno[2,3-b]pyridin-4-yl)benzo[d]thiazol-5-amine (Example 75, 21 mg, 27%) as a colorless solid. $^1$H NMR (400 MHz, Methanol-d$_4$) δ 9.23 (s, 1H), 8.10-8.00 (m, 2H), 7.61-7.50 (m, 1H), 7.48-7.37 (m, 1H), 6.21 (dd, J=5.6, 1.6 Hz, 1H), 3.68 (q, J=7.2 Hz, 1H), 3.56-3.44 (m, 1H), 3.23-3.00 (m, 2H), 2.56-2.37 (m, 1H), 2.30-2.03 (m, 1H), 1.32 (d, J=6.2 Hz, 1H), 1.01 (d, J=6.7 Hz, 2H). LCMS (ESI, m/z): 385 [M+H]$^+$. Analytic Conditions: Column: XBridge BEH Shield RP18 Column 2.1×50 mm, 2.5 um; Mobile Phase A: Water+6.5 mM NH$_4$HCO$_3$ (pH=10), Mobile Phase B: Acetonitrile; Flow rate: 0.8000 mL/min; Gradient: 10% B to 95% B in 2.0 min; 254 nm; Rt: 1.378 min.

Chiral Separation:

The mixture of the isomers was separated by Chiral-HPLC (Column: CHIRALPAK IG, 2.0×25 cm (5 um); Mobile Phase A: Hex (8 mmol/L NH$_3$.MeOH), Mobile Phase B: EtOH; Flow rate: 20 mL/min; hold at 30% B for 23 min.

Example 75a

White solid. $^1$H NMR (400 MHz, Methanol-d$_4$) δ 9.37 (s, 1H), 8.33 (d, J=6.9 Hz, 1H), 8.26-8.14 (m, 2H), 7.95 (s, 1H), 6.81 (dd, J=7.0, 2.2 Hz, 1H), 3.88-3.49 (m, 4H), 2.80-2.68 (m, 1H), 2.46-2.33 (m, 1H), 1.58 (d, J=6.4 Hz, 3H). LCMS (ESI, m/z): 385 [M+H]$^+$. Chiral analytic conditions: Column: CHIRALCEL OD-3, 4.6×100 mm, 3 um; Mobile Phase: EtOH (0.1% DEA); Flow rate: 4.00 mL/min; Gradient: 10% B to 50% B in 4.0 min; 220 nm; Rt: 3.386 min.

Example 75b

White solid. $^1$H NMR (400 MHz, Methanol-d$_4$) δ 9.37 (s, 1H), 8.33 (d, J=7.0 Hz, 1H), 8.26-8.14 (m, 2H), 7.94 (s, 1H), 6.80 (dd, J=7.0, 2.2 Hz, 1H), 3.90-3.45 (m, 4H), 2.82-2.65 (m, 1H), 2.48-2.32 (m, 1H), 1.57 (d, J=6.4 Hz, 3H). LCMS (ESI, m/z): 385 [M+H]$^+$. Analytic Conditions: Column: Shim-pack XR-ODS 3.0×50 mm, 2.2 um; Mobile Phase A: Water/0.05% TFA, Mobile Phase B: Acetonitrile/0.05% TFA; Flow rate: 1.2000 mL/min; Gradient: 5% B to 100% B in 2.0 min; 254 nm; Rt: 1.283 min. Chiral analytic conditions: Column: CHIRALCEL OD-3, 4.6×100 mm, 3 um; Mobile Phase: EtOH (0.1% DEA); Flow rate: 4.00 mL/min; Gradient: 10% B to 50% B in 4.0 min; 220 nm; Rt: 3.224 min.

Example 75c

White solid. $^1$H NMR (400 MHz, Methanol-d$_4$) δ 9.37 (s, 1H), 8.33 (d, J=7.0 Hz, 1H), 8.26-8.17 (m, 2H), 7.95 (s, 1H), 6.80 (dd, J=6.9, 2.2 Hz, 1H), 4.28-4.19 (m, 1H), 4.12 (d, J=8.6 Hz, 1H), 3.79-3.67 (m, 1H), 3.57-3.47 (m, 1H), 2.77-2.65 (m, 1H), 2.63-2.51 (m, 1H), 1.25 (d, J=6.8 Hz, 3H). LCMS (ESI, m/z): 385 [M+H]$^+$. Chiral analytic conditions: Column: CHIRALCEL OD-3, 4.6×100 mm, 3 um; Mobile Phase: EtOH (0.1% DEA); Flow rate: 4.00 mL/min; Gradient: 10% B to 50% B in 4.0 min; 220 nm; Rt: 3.669 min.

Example 75d

White solid. $^1$H NMR (400 MHz, Methanol-d$_4$) δ 9.38 (s, 1H), 8.33 (d, J=7.0 Hz, 1H), 8.26-8.14 (m, 2H), 7.93 (d, J=1.1 Hz, 1H), 6.82 (dd, J=7.0, 2.2 Hz, 1H), 4.28-4.19 (m, 1H), 4.14-4.05 (m, 1H), 3.79-3.66 (m, 1H), 3.61-3.49 (m, 1H), 2.80-2.68 (m, 1H), 2.65-2.53 (m, 1H), 1.26 (d, J=6.9 Hz, 3H). LCMS (ESI, m/z): 385 [M+H]$^+$. Chiral analytic conditions: Column: CHIRALCEL OD-3, 4.6×100 mm, 3 um; Mobile Phase A: CO$_2$; Mobile Phase B: EtOH (0.1% DEA); Flow rate: 4.00 mL/min; Gradient: 10% B to 50% B in 4.0 min; 220 nm; Rt: 3.864 min.

Example 76: Synthesis of N-(2-(1-ethyl-2-methylpyrrolidin-3-yl)thieno[2,3-b]pyridin-4-yl)-6-fluorobenzo[d]thiazol-5-amine

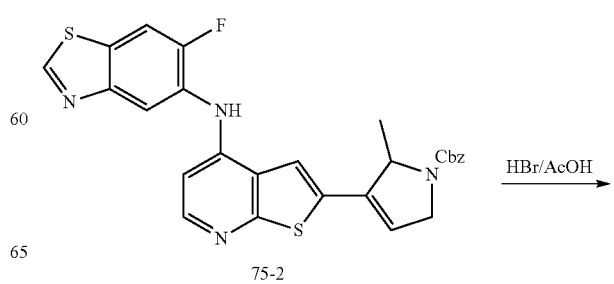

411

-continued

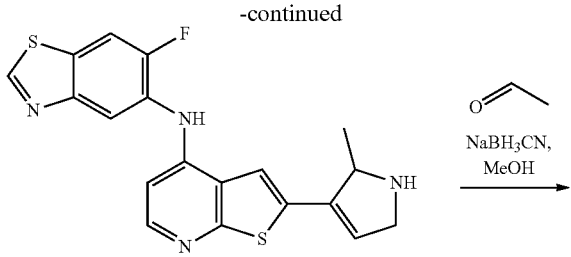
76-1

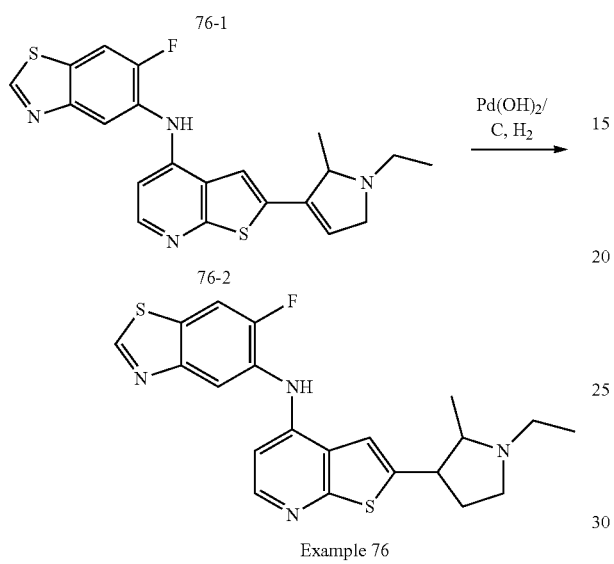

Synthesis of 6-fluoro-N-(2-(2-methyl-2,5-dihydro-1H-pyrrol-3-yl)thieno[2,3-b]pyridin-4-yl)benzo[d]thiazol-5-amine

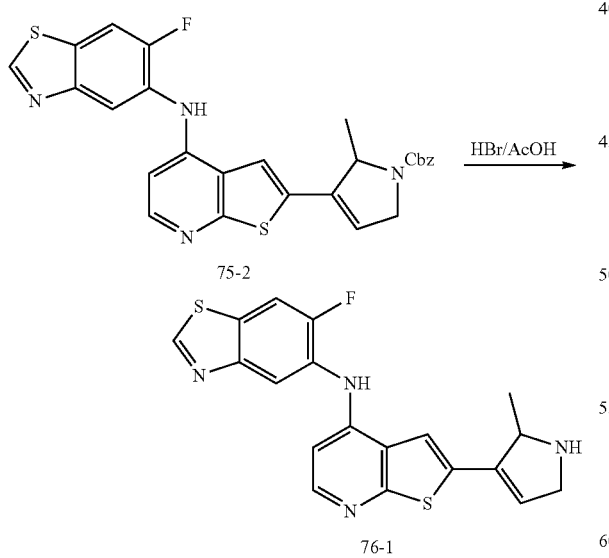

A solution of benzyl 3-(4-((6-fluorobenzo[d]thiazol-5-yl)amino)thieno[2,3-b]pyridin-2-yl)-2-methyl-2,5-dihydro-1H-pyrrole-1-carboxylate (75-2, 190 mg, 0.370 mmol, 1.00 equiv) in 40% HBr (6.0 mL, 0.370 mmol, 1.00 equiv) was stirred for 3 h at room temperature. To the resulting mixture

412 was added acetone (20.0 mL) and the precipitate was collected by filtration to afford 6-fluoro-N-(2-(2-methyl-2,5-dihydro-1H-pyrrol-3-yl)thieno[2,3-b]pyridin-4-yl)benzo[d]thiazol-5-amine (76-1, 100 mg, 71%). LCMS (ESI, m/z): 383 [M+H]$^+$.

Synthesis of N-(2-(1-ethyl-2-methyl-2,5-dihydro-1H-pyrrol-3-yl)thieno[2,3-b]pyridin-4-yl)-6-fluorobenzo[d]thiazol-5-amine

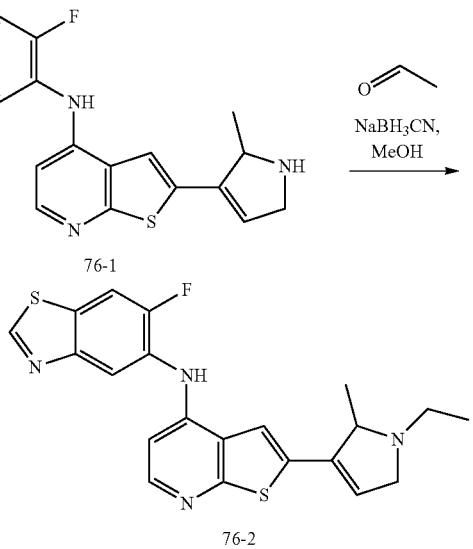

To a solution of 6-fluoro-N-(2-(2-methyl-2,5-dihydro-1H-pyrrol-3-yl)thieno[2,3-b]pyridin-4-yl)benzo[d]-thiazol-5-amine (76-1, 100 mg, 0.260 mmol, 1.00 equiv) in methanol (10.0 mL) was added CH$_3$CHO (144 mg, 1.310 mmol, 5.00 equiv) and NaBH$_3$CN (49 mg, 0.780 mmol, 3.00 equiv). The reaction mixture was stirred 1 h at RT under a nitrogen atmosphere. The resulting mixture was diluted with water (60 mL) and extracted with ethyl acetate (3×20 mL). The combined organic layer was washed with brine (2×100 mL), dried over anhydrous sodium sulfate, filtered and concentrated under reduced pressure. The crude product was purified by prep-TLC with dichloromethane/methanol (15:1) to afford N-(2-(1-ethyl-2-methyl-2,5-dihydro-1H-pyrrol-3-yl)thieno[2,3-b]pyridin-4-yl)-6-fluorobenzo[d]thiazol-5-amine (76-2, 60 mg, 56%). LCMS (ESI, m/z): 411 [M+H]$^+$.

Synthesis of N-(2-(1-ethyl-2-methylpyrrolidin-3-yl)thieno[2,3-b]pyridin-4-yl)-6-fluorobenzo[d]thiazol-5-amine

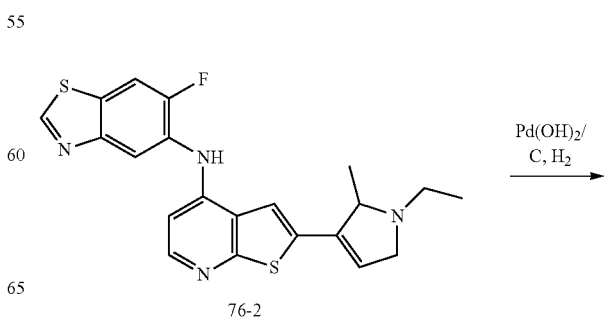

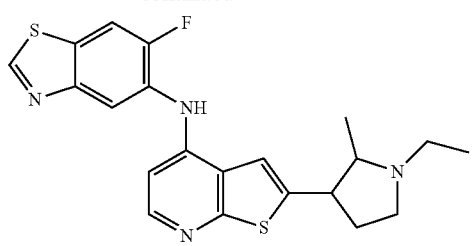

Example 76

To a solution of N-(2-(1-ethyl-2-methyl-2,5-dihydro-1H-pyrrol-3-yl)thieno[2,3-b]pyridin-4-yl)-6-fluorobenzo[d]thiazol-5-amine (76-2, 60 mg, 0.150 mmol, 1.00 equiv) in ethanol (10.0 mL) was added Pd(OH)$_2$/C (60 mg, 1.00 w/w). The reaction mixture was stirred overnight at 60° C. under an atmosphere of hydrogen (balloon). The resulting mixture was filtered and concentrated under reduced pressure. The crude product was purified by prep-HPLC. Column: Sunfire Prep C18 OBD, 19×250 mm, 10 um; Mobile Phase A: Water (0.05% TFA), Mobile Phase B: ACN; Flow rate: 25 mL/min; Gradient: 10% B to 50% B in 7 min; 254/210 nm; RT: 6.95 min. Purification resulted in N-(2-(1-ethyl-2-methylpyrrolidin-3-yl)thieno[2,3-b]pyridin-4-yl)-6-fluorobenzo[d]thiazol-5-amine (Example 76, 8.8 mg, 14%) as an off-white solid. $^1$H NMR (400 MHz, Methanol-d$_4$) δ 9.29 (s, 1H), 8.31-8.12 (m, 2H), 7.80 (s, 1H), 7.64 (t, J=9.6 Hz, 1H), 6.50 (d, J=5.9 Hz, 1H), 4.31-4.09 (m, 1H), 3.97-3.87 (m, 1H), 3.77-3.48 (m, 3H), 3.25-3.20 (m, 1H), 2.80-2.46 (m, 2H), 1.57 (d, J=6.0 Hz, 2H), 1.46 (t, J=7.2 Hz, 3H), 1.30 (d, J=4.6 Hz, 1H). LCMS (ESI, m/z): 413 [M+H]$^+$.

Example 77: Synthesis of 2-(3-(4-((6-fluorobenzo[d]thiazol-5-yl)amino)thieno[2,3-b]pyridin-2-yl)-2-methylpyrrolidin-1-yl)ethan-1-ol

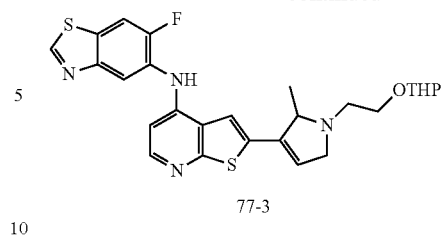

77-3

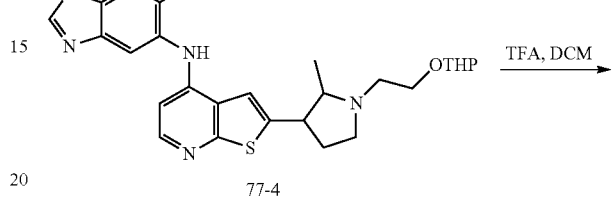

77-4

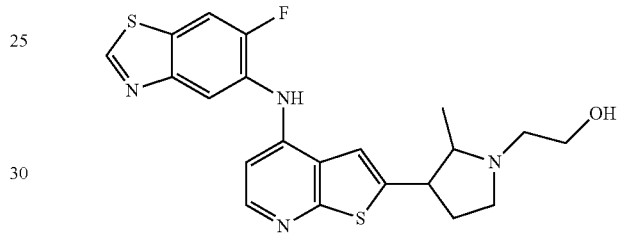

Example 77

Synthesis of 4-chloro-2-(2-methyl-2,5-dihydro-1H-pyrrol-3-yl)thieno[2,3-b]pyridine

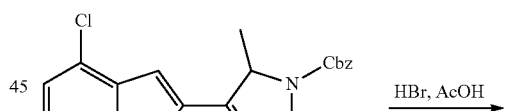

75-1

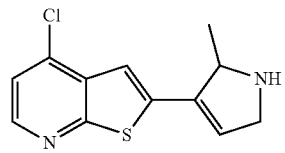

77-1

A solution of benzyl 3-(4-chlorothieno[2,3-b]pyridin-2-yl)-2-methyl-2,5-dihydro-1H-pyrrole-1-carboxylate (75-1, 340 mg, 0.880 mmol, 1.00 equiv) in HBr (40% in AcOH, 5.0 mL) was stirred for 1 h at room temperature under a nitrogen atmosphere. LCMS showed the reaction was complete. To the resulting mixture was added acetone (20.0 mL) and the precipitate was collected by filtration to afford 4-chloro-2-(2-methyl-2,5-dihydro-1H-pyrrol-3-yl)thieno[2,3-b]pyridine (77-1, 150 mg, 68%). LCMS (ESI, m/z): 251 [M+H]$^+$.

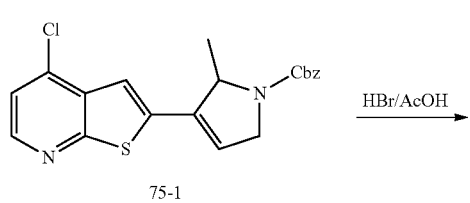

75-1

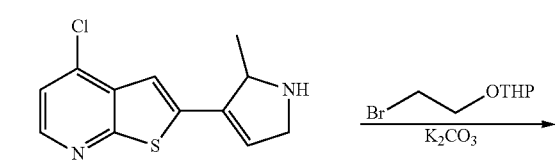

77-1

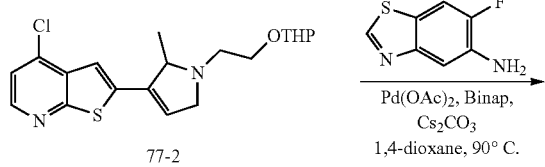

77-2

Synthesis of 4-chloro-2-(2-methyl-1-(2-((tetrahydro-2H-pyran-2-yl)oxy)ethyl)-2,5-dihydro-1H-pyrrol-3-yl)thieno[2,3]pyridine

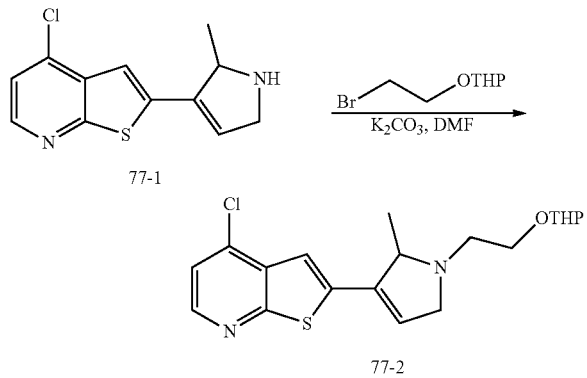

To a solution of 4-chloro-2-(2-methyl-2,5-dihydro-1H-pyrrol-3-yl)thieno[2,3-b]pyridine (77-1, 180 mg, 0.702 mmol, 1.00 equiv) in DMF (10.0 mL) was added K$_2$CO$_3$, (198 mg, 1.440 mmol, 2.00 equiv), and the pH was adjusted to 8-9 with Et$_3$N. After 5 min, 2-(2-bromo-ethoxy)tetrahydropyran (225 mg, 1.080 mmol, 1.50 equiv) was added. The reaction mixture was stirred at 80° C. overnight under a nitrogen atmosphere. The resulting mixture was diluted with water (50 mL) and extracted with ethyl acetate (3×20 mL). The combined organic layer was washed with brine (2×100 mL), dried over anhydrous sodium sulfate, filtered and concentrated under reduced pressure. The crude product was purified by prep-TLC with ethyl acetate/petroleum ether (1:1) to afford 4-chloro-2-(2-methyl-1-(2-((tetrahydro-2H-pyran-2-yl)oxy)ethyl)-2,5-dihydro-1H-pyrrol-3-yl)thieno[2,3-b]pyridine (77-2, 200 mg, 74%). LCMS (ESI, m/z): 379 [M+H]$^+$.

Synthesis of 6-fluoro-N-(2-(2-methyl-1-(2-((tetrahydro-2H-pyran-2-yl)oxy)ethyl)-2,5-dihydro-1H-pyrrol-3-yl)thieno[2,3-b]pyridin-4-yl)benzo[d]thiazol-5-amine

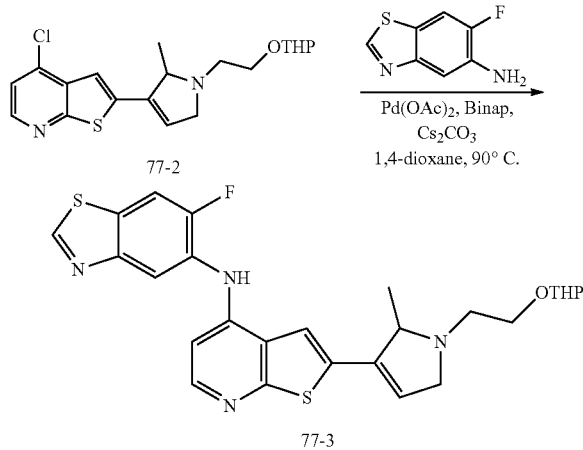

To a solution of 4-chloro-2-(2-methyl-1-(2-((tetrahydro-2H-pyran-2-yl)oxy)ethyl)-2,5-dihydro-1H-pyrrol-3-yl)thieno[2,3-b]pyridine (77-2, 150 mg, 0.400 mmol, 1.00 equiv) in 1,4-dioxane (6.0 mL) was added 6-fluoro-1,3-benzothiazol-5-amine (80 mg, 0.480 mmol, 1.20 equiv), Pd(OAc)$_2$ (9 mg, 0.040 mmol, 0.10 equiv), BINAP (49 mg, 0.080 mmol, 0.20 equiv) and Cs$_2$CO$_3$ (387 mg, 1.190 mmol, 3.00 equiv). The reaction mixture was stirred overnight at 90° C. under a nitrogen atmosphere. The resulting solution was diluted with ethyl acetate (30 mL). The resulting mixture was filtered and concentrated under reduced pressure. The crude product was purified by prep-TLC with ethyl acetate/petroleum ether (1:1) to afford 6-fluoro-N-(2-(2-methyl-1-(2-((tetrahydro-2H-pyran-2-yl)oxy)ethyl)-2,5-dihydro-1H-pyrrol-3-yl)-thieno[2,3-b]pyridin-4-yl)benzo[d]thiazol-5-amine (77-3, 120 mg, 59%). LCMS (ESI, m/z): 511 [M+H]$^+$.

Synthesis of 6-fluoro-N-(2-(2-methyl-1-(2-((tetrahydro-2H-pyran-2-yl)oxy)ethyl)pyrrolidin-3-yl)thieno[2,3-b]pyridin-4-yl)benzo[d]thiazol-5-amine

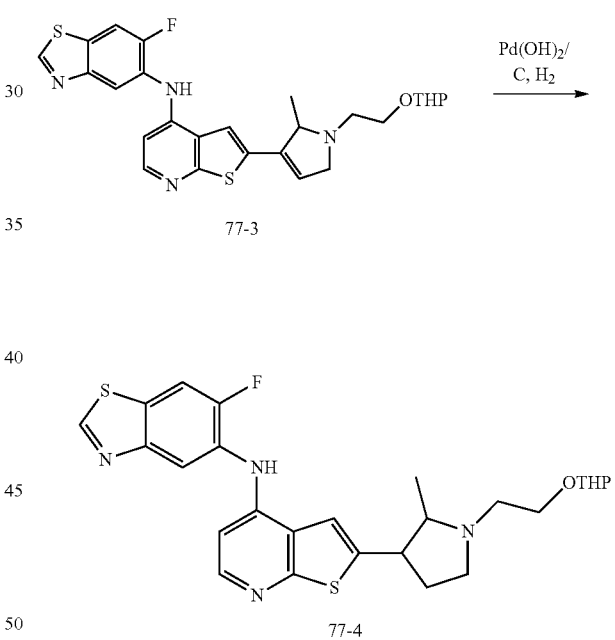

To a solution of 6-fluoro-N-(2-(2-methyl-1-(2-((tetrahydro-2H-pyran-2-yl)oxy)ethyl)-2,5-dihydro-1H-pyrrol-3-yl)thieno[2,3-b]pyridin-4-yl)benzo[d]thiazol-5-amine (77-3, 120 mg, 0.230 mmol, 1.00 equiv) in ethanol (20.0 mL) was added Pd(OH)$_2$/C (120 mg, 1.00 w/w). The reaction mixture was stirred overnight at 60° C. under an atmosphere of hydrogen (balloon). The resulting mixture was filtered and concentrated under reduced pressure. The crude product was purified by prep-TLC with dichloromethane/methanol (5:1) to afford 6-fluoro-N-(2-(2-methyl-1-(2-((tetrahydro-2H-pyran-2-yl)oxy)ethyl)pyrrolidin-3-yl)thieno[2,3-b]pyridin-4-yl)benzo[d]thiazol-5-amine (77-4, 60 mg, 50%). LCMS (ESI, m/z): 513 [M+H]$^+$.

417

Synthesis of 2-(3-(4-((6-fluorobenzo[d]thiazol-5-yl)amino)thieno[2,3-b]pyridin-2-yl)-2-methyl-pyrrolidin-1-yl)ethan-1-ol

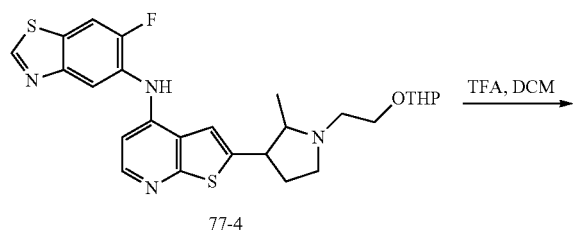

77-4

TFA, DCM
→

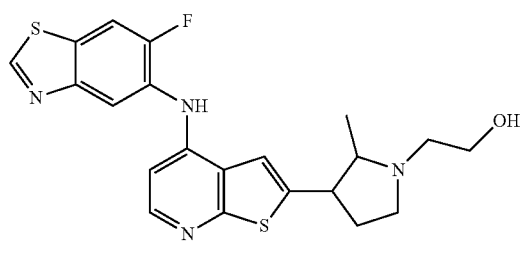

Example 77

To a solution 6-fluoro-N-(2-(2-methyl-1-(2-((tetrahydro-2H-pyran-2-yl)oxy)ethyl)pyrrolidin-3-yl)thieno[2,3-b]pyridin-4-yl)benzo[d]thiazol-5-amine (77-4, 60 mg, 0.120 mmol, 1.00 equiv) in DCM (5.0 mL) was added TFA (0.2 mL). The reaction mixture was stirred for 1 h at RT. The resulting solution was concentrated under reduced pressure and purified by prep-HPLC. Column: Xselect CSH OBD 30×150 mm, 5 um; Mobile Phase A: Water (0.05% TFA), Mobile Phase B: ACN; Flow rate: 60 mL/min; Gradient: 10% B to 30% B in 7 min; 254/210 nm; RT: 6.95 min. Purification resulted in 2-(3-(4-((6-fluorobenzo[d]thiazol-5-yl)amino)thieno[2,3-b]pyridin-2-yl)-2-methylpyrrolidin-1-yl)ethan-1-ol (Example 77, 17.5 mg, 35%) as an off-white solid. $^1$H NMR (400 MHz, Methanol-$d_4$) δ 9.29 (s, 1H), 8.35-8.03 (m, 2H), 7.79 (s, 1H), 7.63 (t, J=9.5 Hz, 1H), 6.49 (t, J=5.8 Hz, 1H), 4.27 (d, J=28.6 Hz, 1H), 3.95 (t, J=5.1 Hz, 3H), 3.83-3.38 (m, 4H), 2.82-2.39 (m, 2H), 1.59 (d, J=4.9 Hz, 1H), 1.31 (s, 2H). LCMS (ESI, m/z): 429 [M+H]$^+$.

Example 78: Synthesis of N-(2-(2,2-dimethylpyrrolidin-3-yl)thieno[2,3-b]pyridin-4-yl)-6-fluorobenzo[d]thiazol-5-amine

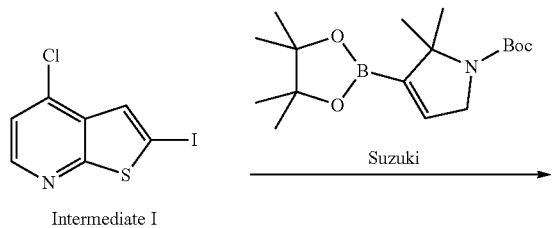

Intermediate I

Suzuki
→

-continued

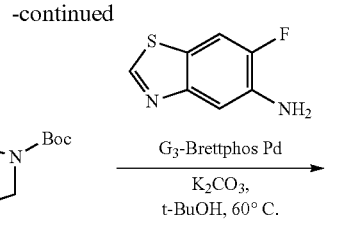

G$_3$-Brettphos Pd
K$_2$CO$_3$,
t-BuOH, 60° C.
→

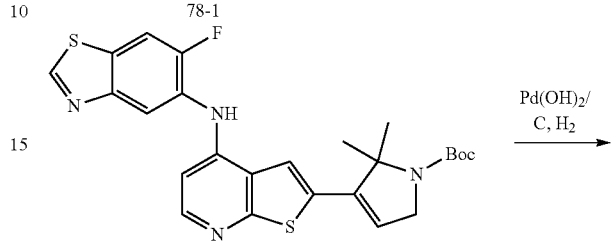

78-2

Pd(OH)$_2$/
C, H$_2$
→

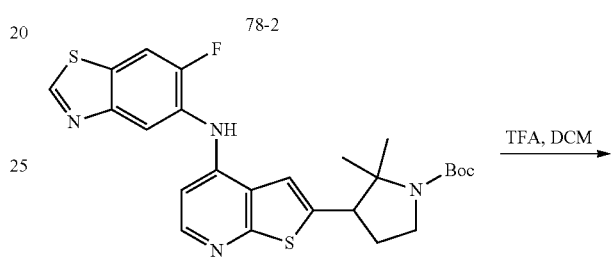

78-3

TFA, DCM
→

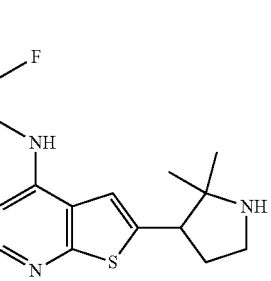

Example 78

Synthesis of tert-butyl 3-(4-chlorothieno[2,3-b]pyridin-2-yl)-2,2-dimethyl-2,5-dihydro-1H-pyrrole-1-carboxylate

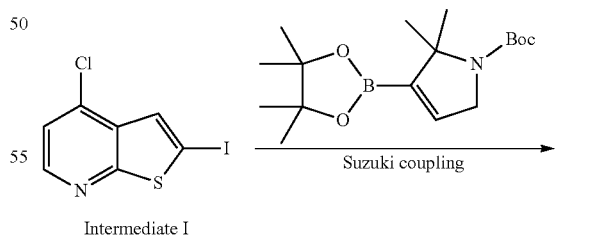

Intermediate I

Suzuki coupling
→

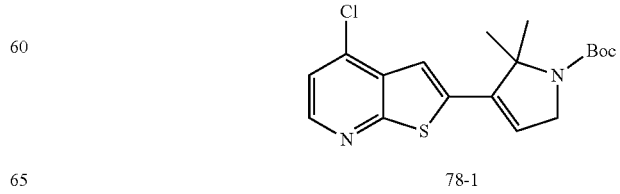

78-1

419

To a stirred solution of 4-chloro-2-iodo-thieno[2,3-b]pyridine (intermediate I, 2.5 g, 8.470 mmol, 1.00 equiv) in 1,4-dioxane (20.0 mL) and water (5.0 mL) were added Pd(dppf)Cl$_2$ (692 mg, 0.850 mmol, 0.10 equiv), t-BuONa (2.4 g, 25.410 mmol, 3.00 equiv) and tert-butyl 2,2-dimethyl-3-(4,4,5,5-tetramethyl-1,3,2-dioxaborolan-2-yl)-2,5-dihydro-1H-pyrrole-1-carboxylate (2.8 g, 8.470 mmol, 1.00 equiv) under a nitrogen atmosphere. The resulting mixture was stirred at 80° C. for 3 h. LCMS showed the reaction was complete. The reaction mixture was concentrated under reduced pressure and purified by flash chromatography on silica gel with ethyl acetate/petroleum ether (1:9) to afford tert-butyl 3-(4-chlorothieno[2,3-b]pyridin-2-yl)-2,2-dimethyl-2,5-dihydro-1H-pyrrole-1-carboxylate (78-1, 1.8 g, 58%) as a yellow solid. LCMS (ESI, m/z): 365 [M+H]$^+$.

Synthesis of tert-butyl 3-(4-((6-fluorobenzo[d]thiazol-5-yl)amino)thieno[2,3-b]pyridin-2-yl)-2,2-dimethyl-2,5-dihydro-1H-pyrrole-1-carboxylate

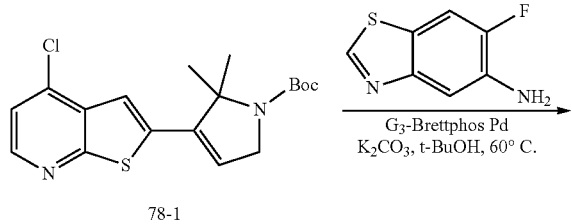

Into a 100-mL sealed tube purged and maintained with an inert atmosphere of nitrogen, was placed tert-butyl 3-(4-chlorothieno[2,3-b]pyridin-2-yl)-2,2-dimethyl-2,5-dihydro-1H-pyrrole-1-carboxylate (78-1, 300 mg, 0.820 mmol, 1.00 equiv), 6-fluoro-1,3-benzothiazol-5-amine (138 mg, 0.820 mmol, 1.00 equiv), K$_2$CO$_3$ (340 mg, 2.470 mmol, 3.00 equiv), G3-brettphos (74 mg, 0.080 mmol, 0.10 equiv) and tert-butanol (10.0 mL). The resulting solution was stirred for 4 h at 60° C. TLC showed the reaction was complete. The resulting mixture was concentrated under reduced pressure and purified by column chromatography on silica gel (DCM/MeOH=10/1) to give tert-butyl 3-(4-((6-fluorobenzo[d]thiazol-5-yl)amino)thieno[2,3-b]pyridin-2-yl)-2,2-dimethyl-2,5-dihydro-1H-pyrrole-1-carboxylate (78-2, 260 mg, 64%) as a yellow oil. LCMS (ESI, m/z): 497 [M+H]$^+$.

420

Synthesis of tert-butyl 3-(4-((6-fluorobenzo[d]thiazol-5-yl)amino)thieno[2,3-b]pyridin-2-yl)-2,2-dimethylpyrrolidine-1-carboxylate

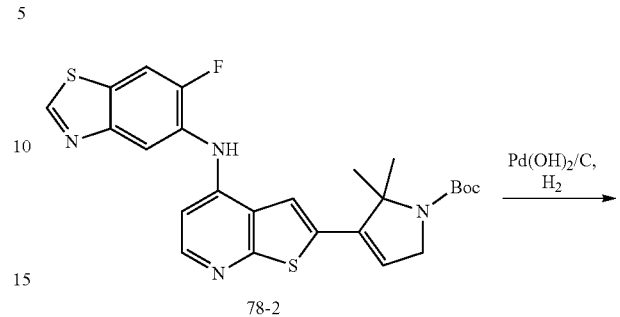

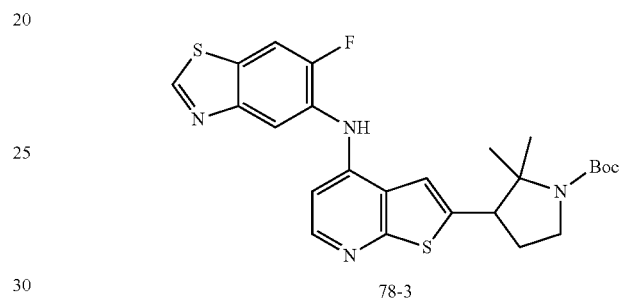

To a solution of tert-butyl 3-(4-((6-fluorobenzo[d]thiazol-5-yl)amino)thieno[2,3-b]pyridin-2-yl)-2,2-dimethyl-2,5-dihydro-1H-pyrrole-1-carboxylate (78-2, 260 mg, 0.520 mmol, 1.00 equiv) in ethanol (10.0 mL), was added 10% Pd(OH)$_2$/C (260 mg, 1.00 w/w) under a nitrogen atmosphere. The reaction solution was degassed and back-filled with hydrogen. The reaction was stirred for 7 days at 60° C. under H$_2$ atmosphere (balloon). LCMS showed the reaction was complete. The resulting mixture was filtered through a celite pad and the filtrate was concentrated under reduced pressure to give tert-butyl 3-(4-((6-fluorobenzo[d]thiazol-5-yl)amino)thieno[2,3-b]pyridin-2-yl)-2,2-dimethylpyrrolidine-1-carboxylate (78-3, 200 mg, crude) as a yellow oil. LCMS (ESI, m/z): 499 [M+H]$^+$.

Synthesis of N-(2-(2,2-dimethylpyrrolidin-3-yl)thieno[2,3-b]pyridin-4-yl)-6-fluorobenzo[d]-thiazol-5-amine

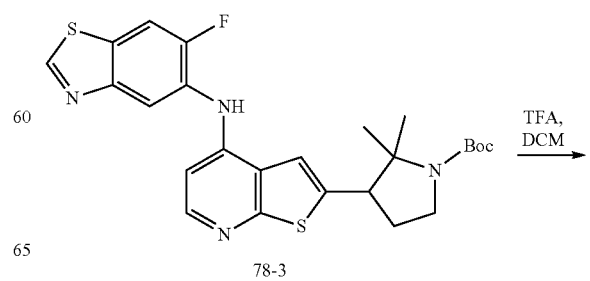

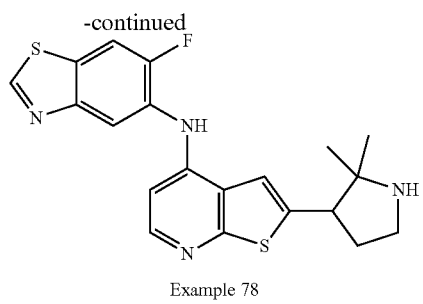

Example 78

To a stirred solution of tert-butyl 3-(4-((6-fluorobenzo[d]thiazol-5-yl)amino)thieno[2,3-b]pyridin-2-yl)-2,2-dimethylpyrrolidine-1-carboxylate (78-3, 85 mg, 0.170 mmol, 1.00 equiv) in DCM (4.0 mL) was added TFA (2.0 mL) at room temperature and stirred for 30 min. LCMS showed the reaction was complete. The resulting mixture was concentrated under reduced pressure and purified by preparative HPLC. Column: Sunfire Prep C18 OBD, 10 um, 19×250 mm; Mobile Phase A: Water (0.05% TFA), Mobile Phase B: ACN; Flow rate: 25 mL/min; Gradient: 5% B to 25% B in 7 min; 254/210 nm; Rt: 6.95 min. Purification resulted in N-(2-(2,2-dimethylpyrrolidin-3-yl)thieno[2,3-b]pyridin-4-yl)-6-fluorobenzo[d]-thiazol-5-amine (Example 78, 64.6 mg, 92%) as a white solid. $^1$H NMR (400 MHz, Methanol-d$_4$) δ 9.27 (s, 1H), 8.27 (d, J=7.2 Hz, 1H), 8.20 (dd, J=9.0, 4.2 Hz, 1H), 7.78 (s, 1H), 7.62 (dd, J=10.2, 9.0 Hz, 1H), 6.50 (dd, J=6.6, 1.7 Hz, 1H), 3.77-3.71 (m, 1H), 3.66-3.59 (m, 1H), 3.54-3.47 (m, 1H), 2.74-2.56 (m, 2H), 1.67 (s, 3H), 1.28 (s, 3H). LCMS (ESI, m/z): 399 [M+H]$^+$.

Chiral Separation

The mixture of isomers was separated by Chiral HPLC (Column: CHIRALPAK IG, 2.0×25 cm, 5 um; Mobile Phase A: Hex (8 mmol/L NH$_3$.MeOH), Mobile Phase B: EtOH; Flow rate: 20 mL/min; hold at 30% B for 17 min; 220/254 nm; RT: 10.39; RT2: 14.274; Injection Volume: 0.8 ml; Number Of Runs: 9) to give the desired products.

Peak 1—Example 78a (27.6 mg, 28%, 99.1% ee) as a white solid. LCMS (ESI, m/z): 399 [M+H]$^+$. $^1$H NMR (300 MHz, Methanol-d$_4$) δ 9.36 (s, 1H), 8.37 (d, J=6.3 Hz, 1H), 8.29-8.22 (m, 1H), 8.09 (s, 1H), 7.66 (t, J=9.6 Hz, 1H), 6.60 (d, J=6.2 Hz, 1H), 3.88-3.81 (m, 1H), 3.68-3.59 (m, 2H), 2.80-2.60 (m, 2H), 1.73 (s, 3H), 1.34 (s, 3H). Chiral analytic conditions: CHIRALPAK IG-3, 0.46×5 cm, 3 um; Mobile Phase: Hex (0.1% DEA):EtOH=70:30; Flow rate: 1 mL/min; 254 nm; RT: 2.435 min.

Peak 2—Example 78b (29.9 mg, 30%, 100% ee) as a white solid. LCMS (ESI, m/z): 399 [M+H]$^+$. $^1$H NMR (300 MHz, Methanol-d$_4$) δ 9.36 (s, 1H), 8.37 (d, J=6.3 Hz, 1H), 8.29-8.22 (m, 1H), 8.09 (s, 1H), 7.66 (t, J=9.6 Hz, 1H), 6.60 (d, J=6.2 Hz, 1H), 3.88-3.81 (m, 1H), 3.68-3.59 (m, 2H), 2.80-2.60 (m, 2H), 1.73 (s, 3H), 1.34 (s, 3H). Chiral Analytic Conditions: CHIRALPAK IG-3, 0.46×5 cm, 3 um; Mobile Phase: Hex (0.1% DEA):EtOH=70:30; Flow rate: 1 mL/min; 254 nm; RT: 3.000 min.

Example 79: Synthesis of N-(2-(1-ethyl-2,2-dimethylpyrrolidin-3-yl)thieno[2,3-b]pyridin-4-yl)-6-fluorobenzo[d]thiazol-5-amine

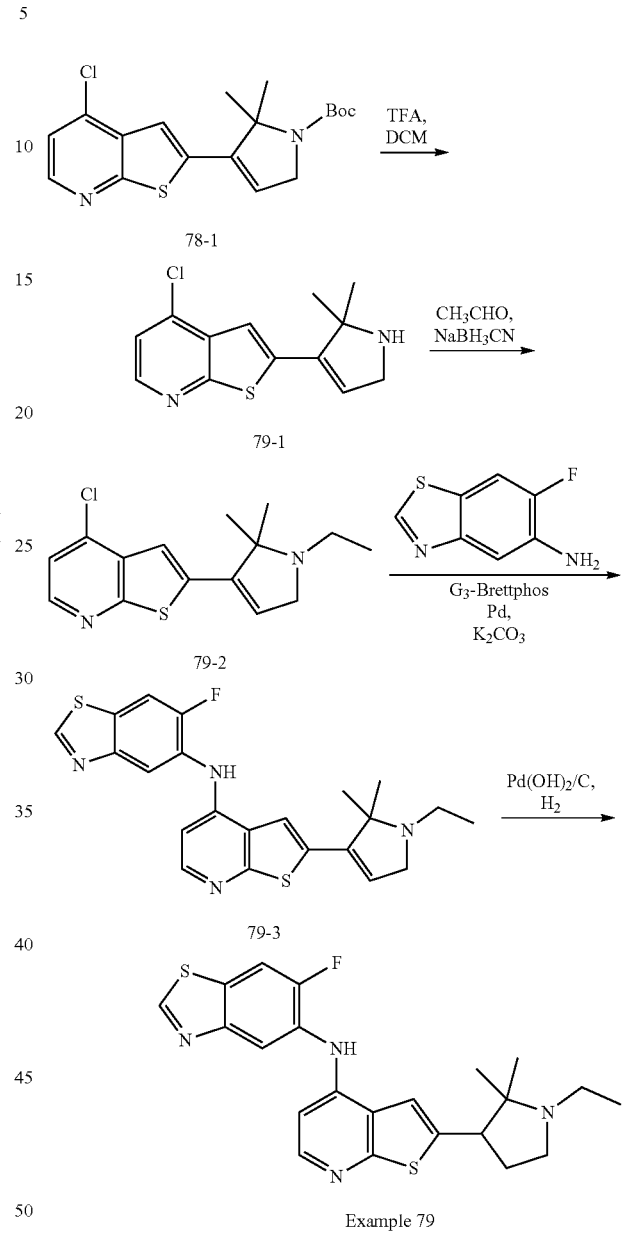

Example 79

Synthesis of 4-chloro-2-(2,2-dimethyl-2,5-dihydro-1H-pyrrol-3-yl)thieno[2,3-b]pyridine

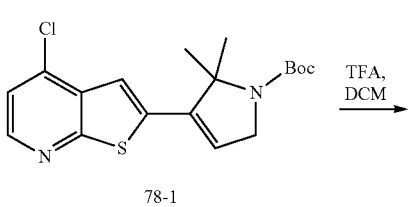

78-1

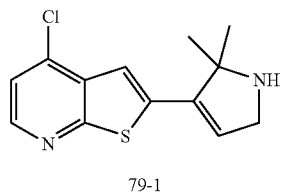

79-1

To a solution of tert-butyl 3-(4-chlorothieno[2,3-b]pyridin-2-yl)-2,2-dimethyl-2,5-dihydro-1H-pyrrole-1-carboxylate (78-1, 600 mg, 1.640 mmol, 1.00 equiv) in methanol (5.0 mL) was added HCl (4M in 1,4-dioxane, 1.5 mL). The resulting mixture was stirred at room temperature for 1 h. LCMS showed the reaction was complete. The resulting solution was concentrated under reduced pressure to afford 4-chloro-2-(5,5-dimethyl-1,2-dihydropyrrol-4-yl)thieno[2,3-b]pyridine (79-1, 450 mg, crude) in HCl salt form as a light yellow solid. LCMS (ESI, m/z): 265 [M+H]⁺.

Synthesis of 4-chloro-2-(1-ethyl-2,2-dimethyl-2,5-dihydro-1H-pyrrol-3-yl)thieno[2,3-b]pyridine

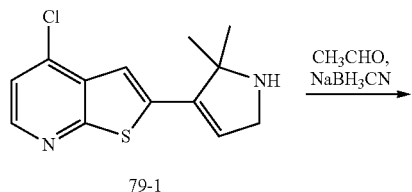

To a solution of 4-chloro-2-(2,2-dimethyl-2,5-dihydro-1H-pyrrol-3-yl)thieno[2,3-b]pyridine (79-1, 90 mg, 0.340 mmol, 1.00 equiv) in methanol (5.0 mL) was added acetaldehyde (75 mg, 0.680 mmol, 2.00 equiv). The resulting mixture was stirred for 0.5 h at RT and NaBH₃CN (66 mg, 1.020 mmol, 3.00 equiv) was added. The reaction mixture was stirred for 0.5 h at RT. LCMS showed the reaction was complete. The reaction mixture was quenched with water (50 mL) and extracted with ethyl acetate (3×50 mL). The combined organic layer was washed with brine and concentrated under reduced pressure. The residue was purified by prep-TLC (DCM/MeOH=10/1) to afford 4-chloro-2-(1-ethyl-2,2-dimethyl-2,5-dihydro-1H-pyrrol-3-yl)thieno[2,3-b]pyridine (79-2, 90 mg, 90%) as a light yellow oil. LCMS (ESI, m/z): 293 [M+H]⁺.

Synthesis of N-(2-(1-ethyl-2,2-dimethyl-2,5-dihydro-1H-pyrrol-3-yl)thieno[2,3-b]pyridin-4-yl)-6-fluorobenzo[d]thiazol-5-amine

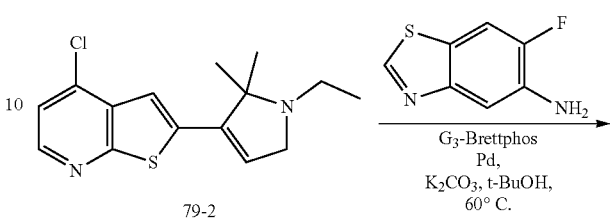

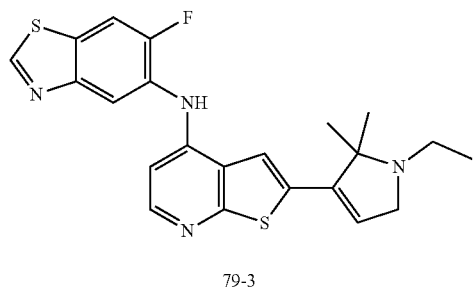

To a solution of 4-chloro-2-(1-ethyl-2,2-dimethyl-2,5-dihydro-1H-pyrrol-3-yl)thieno[2,3-b]pyridine (79-2, 90 mg, 0.310 mmol, 1.00 equiv) in tert-butanol (3.0 mL) was added K₂CO₃ (128 mg, 0.930 mmol, 3.00 equiv), 6-fluoro-1,3-benzothiazol-5-amine (57 mg, 0.341 mmol, 1.20 equiv) and G3-BrettPhos (56 mg, 0.062 mmol, 0.02 equiv) under a nitrogen atmosphere. The reaction mixture was stirred for 16 h at 60° C. TLC showed the reaction was complete. The resulting mixture was quenched with water (50 mL) and extracted with ethyl acetate (3×50 mL). The combined organic layer was washed with brine and concentrated under reduced pressure. The crude product was purified by prep-TLC (DCM/MeOH=8/1) to afford N-(2-(1-ethyl-2,2-dimethyl-2,5-dihydro-1H-pyrrol-3-yl)thieno[2,3-b]pyridin-4-yl)-6-fluorobenzo[d]thiazol-5-amine (79-3, 80 mg, 61%) as a light yellow solid. LCMS (ESI, m/z): 425 [M+H]⁺

Synthesis of N-(2-(1-ethyl-2,2-dimethylpyrrolidin-3-yl)thieno[2,3-b]pyridin-4-yl)-6-fluorobenzo[d]thiazol-5-amine

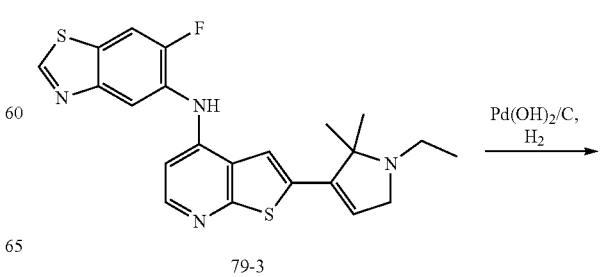

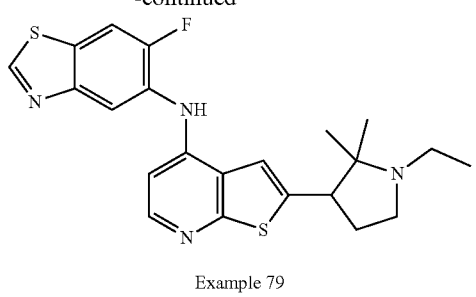

Example 79

To a solution of N-(2-(1-ethyl-2,2-dimethyl-2,5-dihydro-1H-pyrrol-3-yl)thieno[2,3-b]pyridin-4-yl)-6-fluorobenzo[d]thiazol-5-amine (79-3, 80 mg, 0.190 mmol, 1.00 equiv) in ethanol (20.0 mL) was added 10% Pd(OH)$_2$/C (80 mg, 1.00 w/w) under a nitrogen atmosphere. The resulting solution was degassed and back-filled with hydrogen 3 times. The reaction mixture was stirred for 90 h at 60° C. under H$_2$ (2 atm). LCMS showed the reaction was complete. The resulting mixture was filtered through a celite pad and the filtrate was concentrated under reduced pressure. The crude product was purified by preparative HPLC. Column: Sunfire Prep C18 OBD, 10 um, 19×250 mm; Mobile Phase A: Water (0.05% TFA), Mobile Phase B: ACN; Flow rate: 25 mL/min; Gradient: 5% B to 25% B in 7 min; 254/210 nm; Rt: 6.95 min. Purification resulted in N-(2-(1-ethyl-2,2-dimethylpyrrolidin-3-yl)thieno[2,3-b]pyridin-4-yl)-6-fluorobenzo[d]thiazol-5-amine (Example 79, 30.0 mg, 37%) as a white solid. $^1$H NMR (300 MHz, Methanol-d$_4$) δ 9.29 (s, 1H), 8.29 (d, J=6.3 Hz, 1H), 8.22 (dd, J=9.0, 4.2 Hz, 1H), 7.84 (s, 1H), 7.70-7.58 (m, 1H), 6.52 (d, J=6.6 Hz, 1H), 4.62-3.86 (m, 1H), 3.84-3.72 (m, 1H), 3.60-3.37 (m, 2H), 3.15-3.05 (m, 1H), 2.72-2.55 (m, 2H), 1.65 (s, 3H), 1.44 (t, J=7.2 Hz, 3H), 1.24 (s, 3H). LCMS (ESI, m/z): 427 [M+H]$^+$.

Example 80: Synthesis of 2-(3-(4-((6-fluorobenzo[d]thiazol-5-yl)amino)thieno[2,3-b]pyridin-2-yl)-2,2-dimethyl-pyrrolidin-1-yl)ethan-1-ol

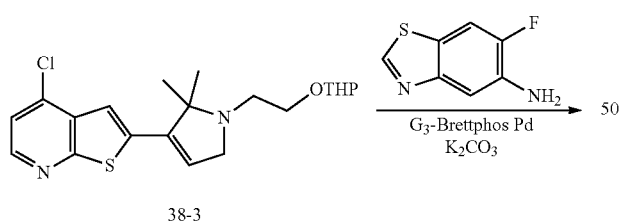

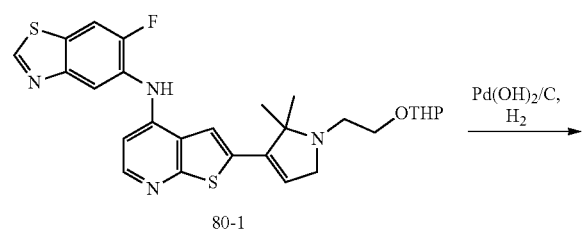

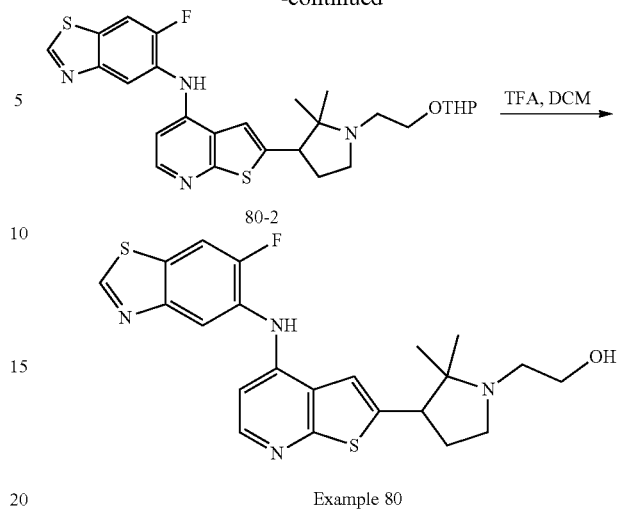

Example 80

Synthesis of N-(2-(2,2-dimethyl-1-(2-((tetrahydro-2H-pyran-2-yl)oxy)ethyl)-2,5-dihydro-1H-pyrrol-3-yl)thieno[2,3-b]pyridin-4-yl)-6-fluorobenzo[d]thiazol-5-amine

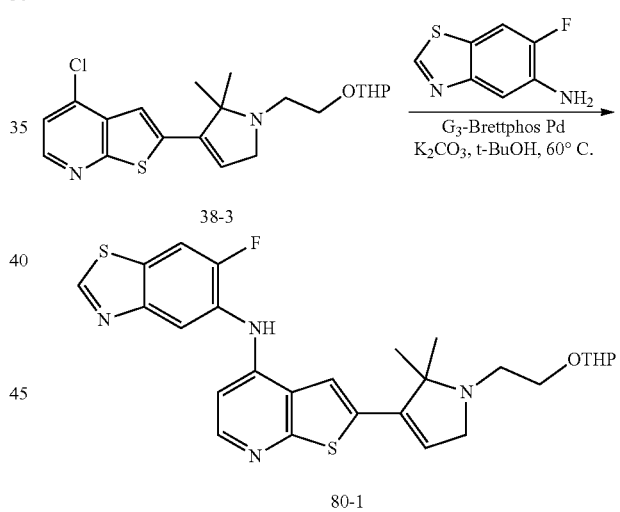

To a stirred solution of 4-chloro-2-(2,2-dimethyl-1-(2-((tetrahydro-2H-pyran-2-yl)oxy)ethyl)-2,5-dihydro-1H-pyrrol-3-yl)thieno[2,3-b]pyridine (38-3, 200 mg, 0.510 mmol, 1.00 equiv), 6-fluoro-1,3-benzothiazol-5-amine (86 mg, 0.510 mmol, 1.00 equiv) and K$_2$CO$_3$ (162 mg, 1.530 mmol, 3.00 equiv) in tert-butanol (10.0 mL) was added G3-Brettphos (46 mg, 0.050 mmol, 0.10 equiv) under a nitrogen atmosphere. The resulting mixture was stirred overnight at 60° C. LCMS showed the reaction was complete. The resulting mixture was filtered and concentrated under reduced pressure. The crude product was purified by flash chromatography on silica gel with ethyl acetate/petroleum ether (3:1) to afford N-(2-(2,2-dimethyl-1-(2-((tetrahydro-2H-pyran-2-yl)oxy)ethyl)-2,5-dihydro-1H-pyrrol-3-yl)thieno[2,3-b]pyridin-4-yl)-6-fluorobenzo[d]thiazol-5-amine (80-1, 130 mg, 48%). LCMS (ESI, m/z): 525 [M+H]$^+$.

Synthesis of N-(2-(2,2-dimethyl-1-(2-((tetrahydro-2H-pyran-2-yl)oxy)ethyl)pyrrolidin-3-yl)thieno[2,3-b]pyridin-4-yl)-6-fluorobenzo[d]thiazol-5-amine

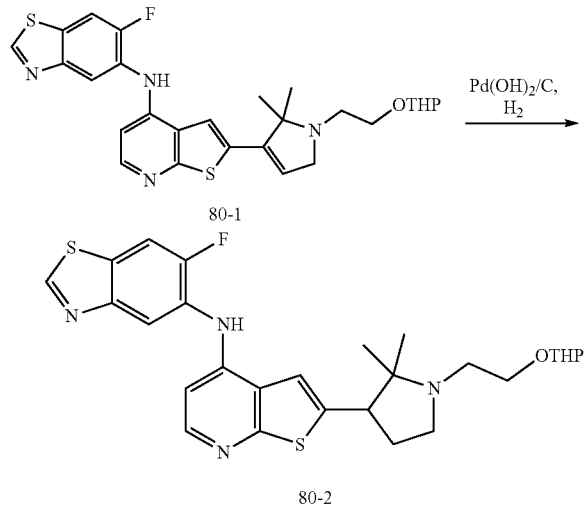

To a stirred solution of N-(2-(2,2-dimethyl-1-(2-((tetrahydro-2H-pyran-2-yl)oxy)ethyl)-2,5-dihydro-1H-pyrrol-3-yl)thieno[2,3-b]pyridin-4-yl)-6-fluorobenzo[d]thiazol-5-amine (80-1, 130 mg, 0.250 mmol, 1.00 equiv) in ethanol (25.0 mL) was added Pd(OH)$_2$/C (130 mg, 1.00 w/w). The resulting mixture was stirred at 60° C. under an atmosphere of hydrogen (2 atm) for 24 h. LCMS showed the reaction was complete. The resulting mixture was filtered through celite and concentrated under reduced pressure. The crude product was purified by flash chromatography on silica gel with DCM/MeOH (10:1) to afford N-(2-(2,2-dimethyl-1-(2-((tetrahydro-2H-pyran-2-yl)oxy)ethyl)pyrrolidin-3-yl)thieno[2,3-b]pyridin-4-yl)-6-fluorobenzo[d]thiazol-5-amine (80-2, 120 mg, 92%). LCMS (ESI, m/z): 527 [M+H]$^+$.

Synthesis of 2-(3-(4-((6-fluorobenzo[d]thiazol-5-yl)amino)thieno[2,3-b]pyridin-2-yl)-2,2-dimethylpyrrolidin-1-yl)ethan-1-ol

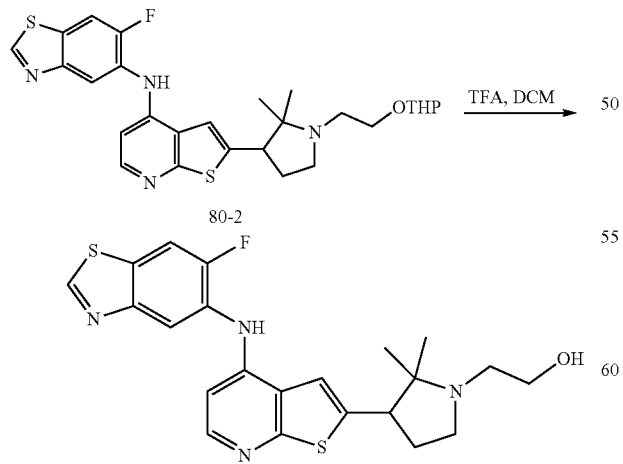

To a stirred solution of N-(2-(2,2-dimethyl-1-(2-((tetrahydro-2H-pyran-2-yl)oxy)ethyl)pyrrolidin-3-yl)thieno[2,3-b]pyridin-4-yl)-6-fluorobenzo[d]thiazol-5-amine (80-2, 120 mg, 0.230 mmol, 1.00 equiv) in DCM (4.0 mL) was added TFA (2.0 mL). The resulting mixture was stirred at RT for 30 min. LCMS showed the reaction was complete. The crude product was purified by preparative HPLC: Column: XBridge Prep C18 OBD, 19×150 mm, 5 um; Mobile Phase A: Water (10 mmol/L NH$_4$HCO$_3$+0.1% NH$_3$.H$_2$O), Mobile Phase B: ACN; Flow rate: 25 mL/min; Gradient: 15% B to 51% B in 7.5 min; 254/210 nm; RT: 7.62 min. Purification resulted in 2-(3-(4-((6-fluorobenzo[d]thiazol-5-yl)amino)thieno[2,3-b]pyridin-2-yl)-2,2-dimethylpyrrolidin-1-yl)ethan-1-ol (Example 80, 69.0 mg, 65%) as a white solid. $^1$H NMR (400 MHz, Methanol-d$_4$) δ 9.22 (s, 1H), 8.13-8.03 (m, 2H), 7.56 (t, J=9.6 Hz, 1H), 7.42 (s, 1H), 6.21 (d, J=5.6 Hz, 1H), 3.69 (t, J=6.3 Hz, 2H), 3.45-3.38 (m, 1H), 3.22-3.11 (m, 1H), 2.95-2.75 (m, 2H), 2.60-2.50 (m, 1H), 2.47-2.33 (m, 1H), 2.25-2.15 (m, 1H), 1.24 (s, 3H), 0.86 (s, 3H). LCMS (ESI, m/z): 443 [M+H]$^+$.

Example 81: Synthesis of N-(2-(7-oxa-1-azaspiro[4.4]nonan-4-yl)thieno[2,3-b]pyridin-4-yl)-6-fluorobenzo[d]thiazol-5-amine

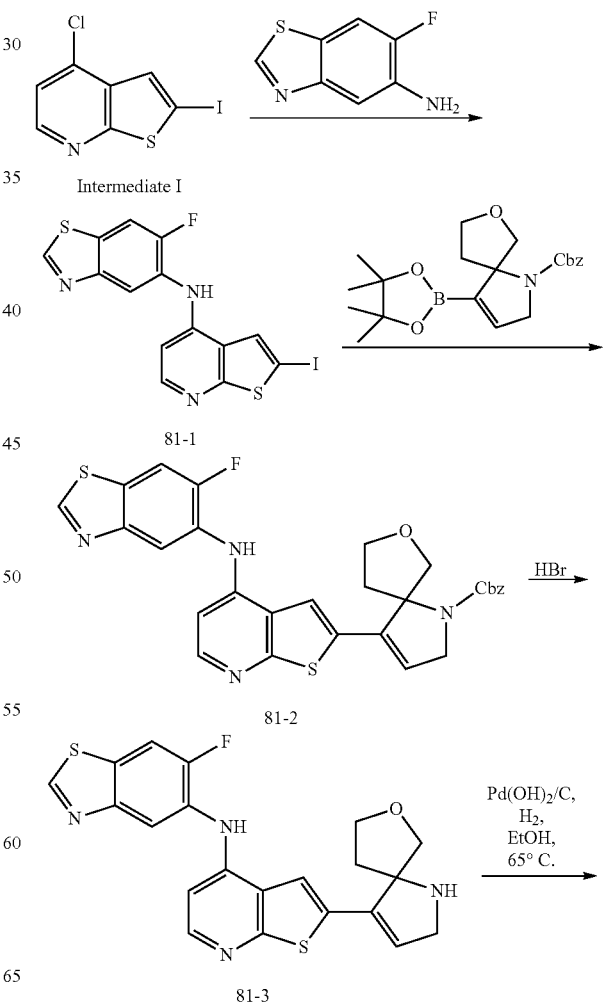

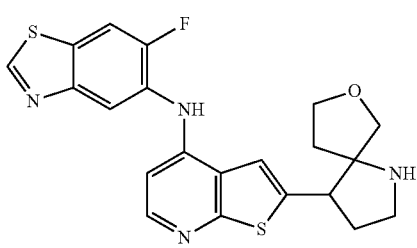

Example 81

6-Fluoro-N-(2-iodothieno[2,3-b]pyridin-4-yl)benzo[d]thiazol-5-amine (81-1) was prepared in a manner analogous to the synthesis of N-(2-iodothieno[2,3-b]pyridin-4-yl)benzo[d]thiazol-5-amine described in Example 1.

N-(2-(7-Oxa-1-azaspiro[4.4]non-3-en-4-yl)thieno[2,3-b]pyridin-4-yl)-6-fluorobenzo[d]thiazol-5-amine (81-3) was prepared from 6-fluoro-N-(2-iodothieno[2,3-b]pyridin-4-yl)benzo[d]thiazol-5-amine (81-1) in a manner analogous to the procedures described for Example 40.

To a solution of N-(2-(7-oxa-1-azaspiro[4.4]non-3-en-4-yl)thieno[2,3-b]pyridin-4-yl)-6-fluorobenzo[d]thiazol-5-amine (81-3, 100 mg, 0.240 mmol, 1.00 equiv) in ethanol (10.0 mL) was added dry Pd(OH)$_2$/C (100 mg, 1.00 w/w). The resulting mixture was stirred at 65° C. for 3 days under a hydrogen atmosphere (2 atm.). LCMS showed the reaction was complete. The resulting mixture was filtered and concentrated under reduced pressure. The residue was purified by Prep-HPLC using the following gradient conditions: Column: XBridge Prep C18 OBD, 19×150 mm, 5 um; Mobile Phase A: Water (10 mmoL/L NH$_4$HCO$_3$), Mobile Phase B: ACN; Flow rate: 25 mL/min; Gradient: 15% B to 48% B in 7.5 min; 254/210 nm; RT: 6.65. Purification resulted in N-(2-(7-oxa-1-azaspiro[4.4]nonan-4-yl)thieno[2,3-b]pyridin-4-yl)-6-fluorobenzo[d]thiazol-5-amine (Example 81, 25.8 mg, 25%) as a white solid. $^1$H NMR (400 MHz, Methanol-d$_4$) δ 9.22 (s, 1H), 8.12-8.03 (m, 2H), 7.56 (dd, J=10.2, 8.9 Hz, 1H), 7.44 (dd, J=1.8, 0.8 Hz, 1H), 6.23 (dd, J=5.6, 1.5 Hz, 1H), 3.99-3.72 (m, 3H), 3.64-3.49 (m, 2H), 3.28-3.01 (m, 2H), 2.55-2.40 (m, 1H), 2.31-2.03 (m, 2H), 1.90-1.65 (m, 1H). LCMS (ESI, m/z): 427 [M+H]$^+$.

Example 82: Synthesis of 6-fluoro-N-(2-(1-methyl-7-oxa-1-azaspiro[4.4]nonan-4-yl)thieno[2,3-b]pyridin-4-yl)benzo[d]thiazol-5-amine

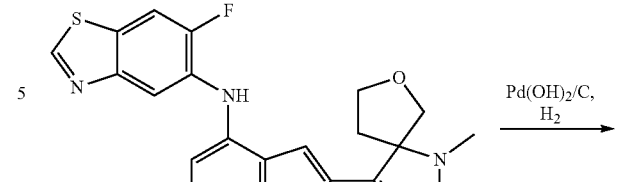

82-1

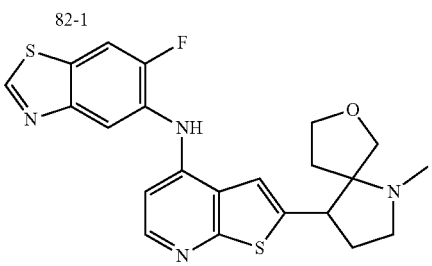

Example 82

6-Fluoro-N-(2-(1-methyl-7-oxa-1-azaspiro[4.4]non-3-en-4-yl)thieno[2,3-b]pyridin-4-yl)benzo[d]thiazol-5-amine (82-1) was prepared from N-(2-(7-oxa-1-azaspiro[4.4]non-3-en-4-yl)thieno[2,3-b]pyridin-4-yl)-6-fluorobenzo[d]thiazol-5-amine (81-3) in a manner analogous to the procedures described in Example 41.

To a solution of 6-fluoro-N-(2-(1-methyl-7-oxa-1-azaspiro[4.4]non-3-en-4-yl)thieno[2,3-b]pyridin-4-yl)benzo[d]thiazol-5-amine (82-1, 100 mg, 0.230 mmol, 1.00 equiv) in ethanol (10.0 mL) was added dry Pd(OH)$_2$/C (100 mg, 1.00 w/w). The resulting mixture was stirred for 3 days at 65° C. under a hydrogen atmosphere (2 atm). LCMS showed the reaction was complete. The resulting mixture was filtered and concentrated under reduce pressure and the residue was purified by Prep-HPLC. Column: XBridge Prep C18 OBD, 19×150 mm, 5 um; Mobile Phase A: Water (10 mmoL/L NH$_4$HCO$_3$), Mobile Phase B: ACN; Flow rate: 25 mL/min; Gradient: 25% B to 42% B in 10 min. Purification resulted in 6-fluoro-N-(2-(1-methyl-7-oxa-1-azaspiro[4.4]nonan-4-yl)thieno[2,3-b]pyridin-4-yl)benzo[d]thiazol-5-amine (Example 82, 21.2 mg, 21%) as a white solid. $^1$H NMR (400 MHz, Methanol-d$_4$) δ 9.22 (s, 1H), 8.12-8.02 (m, 2H), 7.56 (dd, J=10.2, 8.9 Hz, 1H), 7.43 (d, J=0.7 Hz, 1H), 6.21 (dd, J=5.6, 1.5 Hz, 1H), 4.01 (d, J=9.6 Hz, 1H), 3.93-3.88 (m, 1H), 3.69 (d, J=9.7 Hz, 1H), 3.63-3.57 (m, 2H), 2.98-2.90 (m, 1H), 2.89-2.81 (m, 1H), 2.44 (s, 3H), 2.41-2.32 (m, 1H), 2.18-2.08 (m, 1H), 2.02-1.90 (m, 1H), 1.87-1.78 (m, 1H). LCMS (ESI, m/z): 441 [M+H]$^+$.

Example 83: Synthesis of N-(2-(1-ethyl-7-oxa-1-azaspiro[4.4]nonan-4-yl)thieno[2,3-b]pyridin-4-yl)-6-fluorobenzo

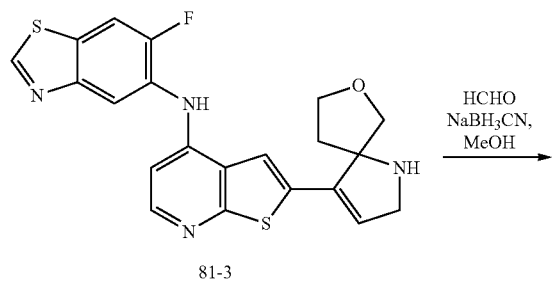

81-3

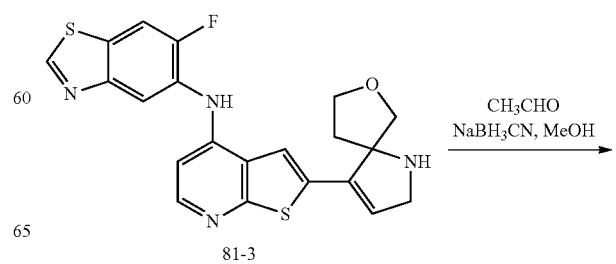

81-3

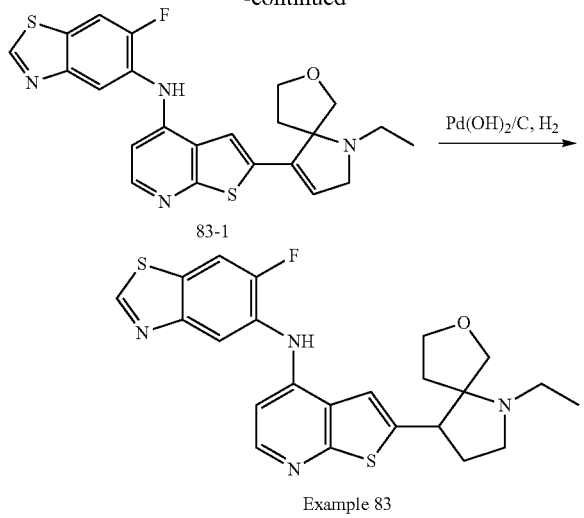

Example 83

N-(2-(1-Ethyl-7-oxa-1-azaspiro[4.4]non-3-en-4-yl)thieno[2,3-b]pyridin-4-yl)-6-fluorobenzo[d]thiazol-5-amine (83-1) was prepared from N-(2-(7-oxa-1-azaspiro[4.4]non-3-en-4-yl)thieno[2,3-b]pyridin-4-yl)-6-fluorobenzo[d]thiazol-5-amine (81-3) in a manner analogous to the procedures described in Example 44.

To a solution of N-(2-(1-ethyl-7-oxa-1-azaspiro[4.4]non-3-en-4-yl)thieno[2,3-b]pyridin-4-yl)-6-fluorobenzo[d]thiazol-5-amine (83-1, 60 mg, 0.131 mmol, 1.00 equiv) in ethanol (10.0 mL) was added Pd(OH)$_2$/C (60 mg, 1.00 w/w). The resulting mixture was stirred for 48 h at 60° C. under H$_2$ atmosphere (balloon). TLC showed the reaction was complete. The resulting mixture was filtered and concentrated under reduced pressure. The residue was purified by prep-TLC (DCM/MeOH=20/1) to afford 30 mg light yellow solid. The resulting solid was further purified by Prep-HPLC. Column: Sunfire Prep C18 OBD, 10 um, 19×250 mm; Mobile Phase A: Water (0.05% TFA), Mobile Phase B: ACN; Flow rate: 25 mL/min; Gradient: 20% B to 30% B in 10 min; to afford N-(2-(1-ethyl-7-oxa-1-azaspiro[4.4]nonan-4-yl)thieno[2,3-b]pyridin-4-yl)-6-fluorobenzo[d]thiazol-5-amine (Example 83, 16.8 mg, 28%) as a white solid. $^1$H NMR (400 MHz, Methanol-d$_4$) δ 9.30 (s, 1H), 8.33 (d, J=6.7 Hz, 1H), 8.24 (dd, J=9.0, 4.2 Hz, 1H), 7.93 (s, 1H), 7.65 (t, J=9.6 Hz, 1H), 6.57 (d, J=6.5 Hz, 1H), 4.62-3.80 (m, 5H), 3.72-3.42 (m, 4H), 2.90-1.91 (m, 4H), 1.45 (td, J=7.2, 3.7 Hz, 3H). LCMS (ESI, m/z): 455 [M+H]$^+$.

Example 84: Synthesis of N-(2-(8-oxa-1-azaspiro[4.5]decan-4-yl)thieno[2,3-b]pyridin-4-yl)-6-fluorobenzo[d]thiazol-5-amine

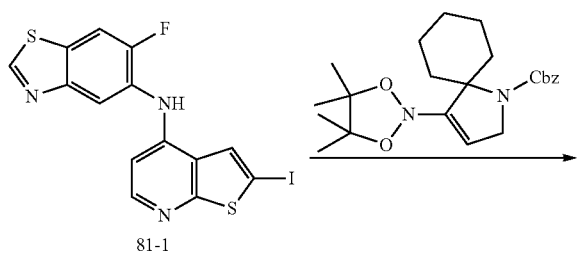

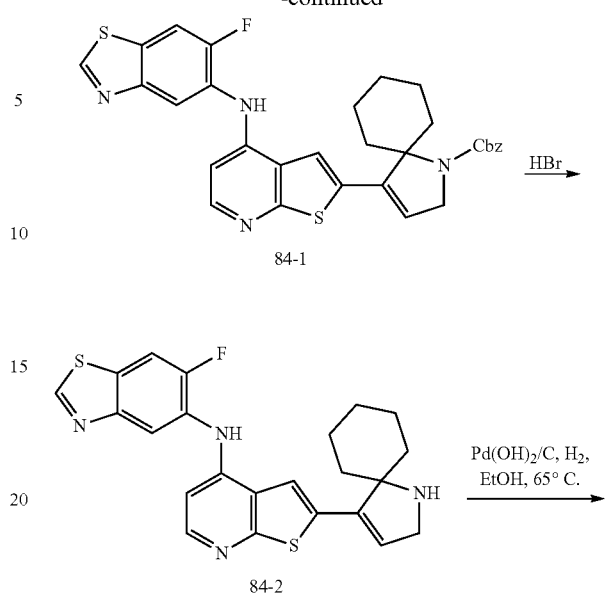

Example 84

N-(2-(8-Oxa-1-azaspiro[4.5]dec-3-en-4-yl)thieno[2,3-b]pyridin-4-yl)-6-fluorobenzo[d]thiazol-5-amine (84-2) was prepared from 6-fluoro-N-(2-iodothieno[2,3-b]pyridin-4-yl)benzo[d]thiazol-5-amine (81-1) in a manner analogous to the procedures described for Example 46.

To a solution of N-(2-(8-oxa-1-azaspiro[4.5]dec-3-en-4-yl)thieno[2,3-b]pyridin-4-yl)-6-fluorobenzo[d]thiazol-5-amine (84-2, 100 mg, 0.230 mmol, 1.00 equiv) in ethanol (10 mL) was added dry Pd(OH)$_2$/C (100 mg, 1.00 w/w). The resulting mixture was stirred for 24 h at 65° C. under a hydrogen atmosphere (2 atm). LCMS showed the reaction was complete. The resulting mixture was filtered, concentrated under reduce pressure, and purified by Prep-HPLC. Column: XBridge Prep C18 OBD, 19×150 mm, 5 um; Mobile Phase A: Water (10 mmoL/L NH$_4$HCO$_3$), Mobile Phase B: ACN; Flow rate: 25 mL/min; Gradient: 8% B to 55% B in 7.5 min; 254/210 nm; RT: 6.98. Purification resulted in N-(2-(8-oxa-1-azaspiro[4.5]decan-4-yl)thieno[2,3-b]pyridin-4-yl)-6-fluorobenzo[d]thiazol-5-amine (Example 84, 31.1 mg, 31%) as a white solid. $^1$H NMR (300 MHz, Methanol-d$_4$) δ 9.20 (s, 1H), 8.11-8.00 (m, 2H), 7.54 (dd, J=10.2, 8.9 Hz, 1H), 7.37 (d, J=0.8 Hz, 1H), 6.22 (dd, J=5.7, 1.4 Hz, 1H), 3.88-3.60 (m, 4H), 3.29-3.02 (m, 3H), 2.5-2.35 (m, 1H), 2.15-2.33 (m, 1H), 2.10-1.95 (m, 1H), 1.60-1.49 (m, 1H), 1.47-1.33 (m, 2H). LCMS (ESI, m/z): 441 [M+H]$^+$.

Example 85: Synthesis of 6-fluoro-N-(2-(1-methyl-8-oxa-1-azaspiro[4.5]decan-4-yl)thieno[2,3-b]pyridin-4-yl)benzo[d]thiazol-5-amine

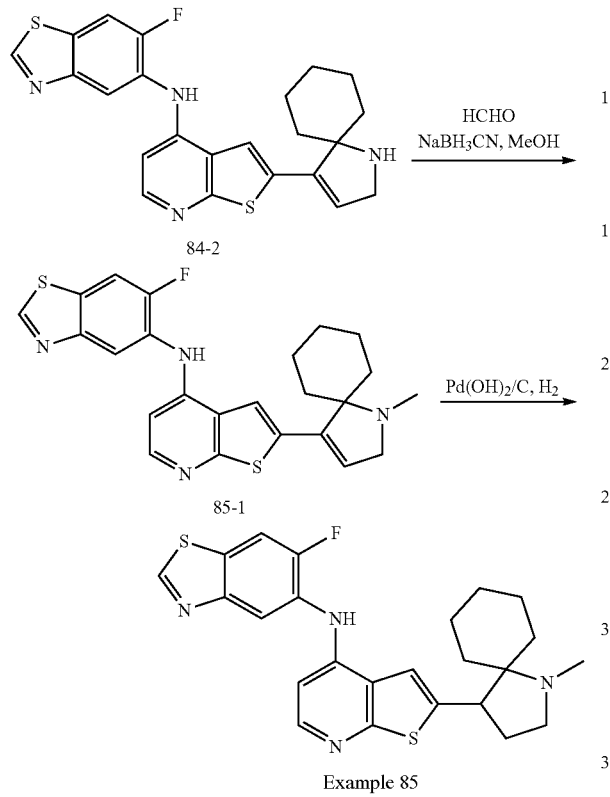

Example 86: Synthesis of N-(2-(1-ethyl-8-oxa-1-azaspiro[4.5]decan-4-yl)thieno[2,3-b]pyridin-4-yl)-6-fluorobenzo[d]thiazol-5-amine

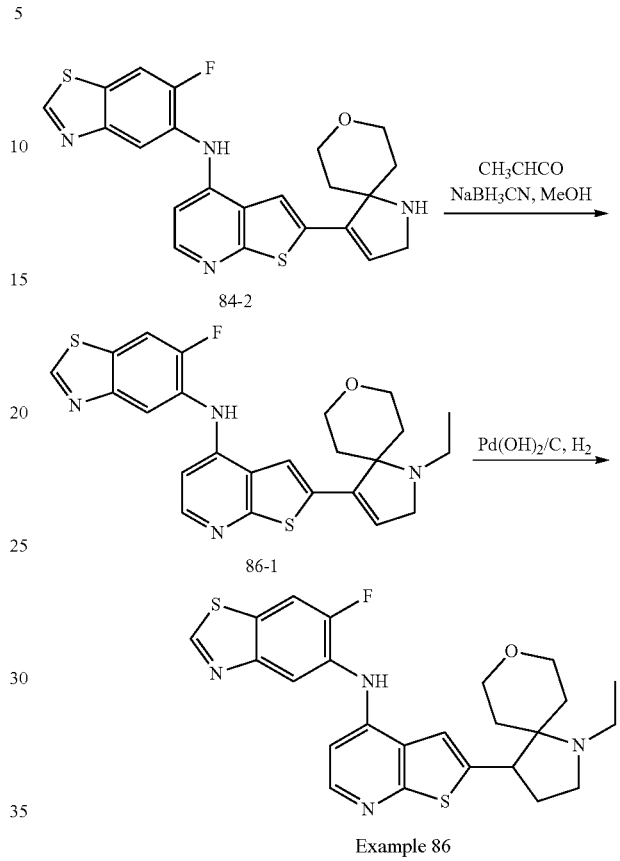

6-Fluoro-N-(2-(1-methyl-8-oxa-1-azaspiro[4.5]dec-3-en-4-yl)thieno[2,3-b]pyridin-4-yl)benzo[d]thiazol-5-amine (85-1) was prepared from N-(2-(8-oxa-1-azaspiro[4.5]dec-3-en-4-yl)thieno[2,3-b]pyridin-4-yl)-6-fluorobenzo[d]thiazol-5-amine (84-2) in a manner analogous to the procedures described for Example 41.

To a solution of 6-fluoro-N-(2-(1-methyl-8-oxa-1-azaspiro[4.5]dec-3-en-4-yl)thieno[2,3-b]pyridin-4-yl)benzo[d]thiazol-5-amine (85-1, 90 mg, 0.200 mmol, 1.00 equiv) in ethanol (20.0 mL) was added Pd(OH)$_2$/C (90 mg, 1.00 w/w). The reaction mixture was stirred at 60° C. overnight under an atmosphere of hydrogen (balloon). LCMS showed the reaction was complete. The resulting mixture was filtered and concentrated under reduced pressure. The crude product was purified by Prep-HPLC. Column: Xselect CSH OBD 30×150 mm, 5 um; Mobile Phase A: Water (0.05% TFA), Mobile Phase B: ACN; Flow rate: 60 mL/min; Gradient: 10% B to 40% B in 7 min; 254/210 nm; RT: 6.95 min. Purification resulted in 6-fluoro-N-(2-(1-methyl-8-oxa-1-azaspiro[4.5]decan-4-yl)thieno[2,3-b]pyridin-4-yl)benzo[d]thiazol-5-amine (Example 85, 41.9 mg, 46%) as an off-white solid. $^1$H NMR (400 MHz, Methanol-$d_4$) δ 9.30 (s, 1H), 8.32 (d, J=6.7 Hz, 1H), 8.23 (dd, J=9.0, 4.2 Hz, 1H), 7.94 (s, 1H), 7.65 (t, J=9.0 Hz, 1H), 6.57 (dd, J=6.7, 1.6 Hz, 1H), 4.42-4.24 (m, 1H), 4.09-3.80 (m, 4H), 3.68-3.45 (m, 2H), 3.02 (s, 3H), 2.97-2.82 (m, 1H), 2.59-2.50 (m, 1H), 2.28-2.20 (m, 1H), 2.14-2.00 (m, 2H), 1.94-1.80 (m, 1H). LCMS (ESI, m/z): 455 [M+H]$^+$.

N-(2-(1-ethyl-8-oxa-1-azaspiro[4.5]dec-3-en-4-yl)thieno[2,3-b]pyridin-4-yl)-6-fluorobenzo[d]thiazol-5-amine (86-1) was prepared from N-(2-(8-oxa-1-azaspiro[4.5]dec-3-en-4-yl)thieno[2,3-b]pyridin-4-yl)-6-fluorobenzo[d]thiazol-5-amine (84-2) in a manner analogous to the procedures described for Example 47.

To a solution of N-(2-(1-ethyl-8-oxa-1-azaspiro[4.5]dec-3-en-4-yl)thieno[2,3-b]pyridin-4-yl)-6-fluorobenzo[d]thiazol-5-amine (86-1, 100 mg, 0.211 mmol, 1.00 equiv) in ethanol (20.0 mL) was added Pd(OH)$_2$/C (100 mg, 1.00 w/w). The resulting mixture was stirred for 48 h at 60° C. under H$_2$ atmosphere (balloon). TLC showed the reaction was complete. The resulting mixture was filtered and concentrated under reduced pressure. The resulting solid was purified by Prep-HPLC. Column: Xselect CSH OBD 30×150 mm, 5 um; Mobile Phase A: Water (0.05% TFA), Mobile Phase B: ACN; Flow rate: 60 mL/min; Gradient: 10% B to 30% B in 7 min; to afford N-(2-(1-ethyl-8-oxa-1-azaspiro[4.5]decan-4-yl)thieno[2,3-b]pyridin-4-yl)-6-fluorobenzo[d]thiazol-5-amine (Example 86, 48.8 mg, 48%) as a white solid. $^1$H NMR (400 MHz, Methanol-$d_4$) δ 9.28 (s, 1H), 8.32-8.11 (m, 2H), 7.94-7.82 (m, 1H), 7.65-7.55 (m, 1H), 6.64-6.44 (m, 1H), 4.40-4.20 (m, 1H), 4.01-3.91 (m, 2H), 3.84-3.60 (m, 2H), 3.50-3.45 (m, 3H), 3.34-3.11 (m, 1H), 2.85-2.77 (m, 1H), 2.55-2.40 (m, 1H), 2.31-1.85 (m, 4H), 1.48 (t, J=7.0 Hz, 3H). LCMS (ESI, m/z): 469 [M+H]$^+$.

Example 87: Synthesis of 4-fluoro-N-(2-(2-methylpyrrolidin-3-yl)thieno[2,3-b]pyridin-4-yl)benzo[d]thiazol-5-amine

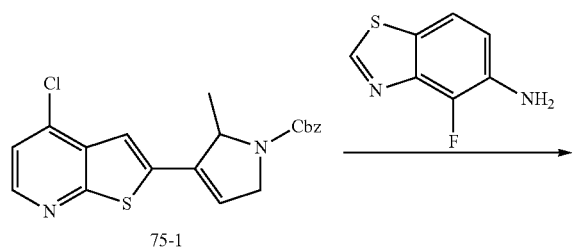

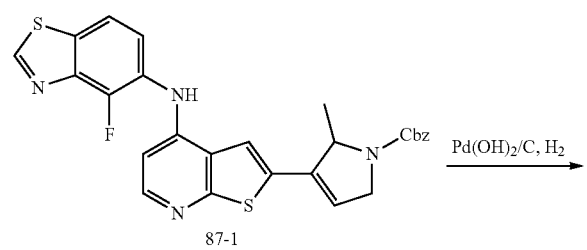

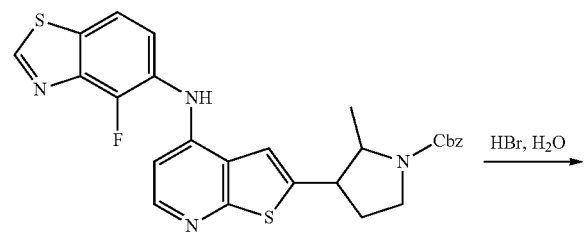

Synthesis of benzyl 3-(4-((4-fluorobenzo[d]thiazol-5-yl)amino)thieno[2,3-b]pyridin-2-yl)-2-methyl-2,5-dihydro-1H-pyrrole-1-carboxylate

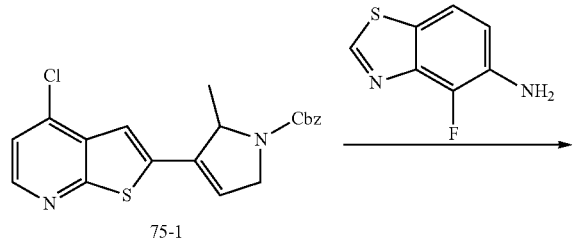

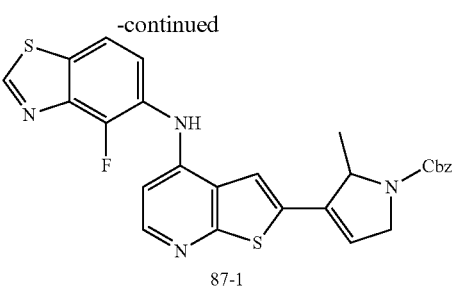

Benzyl 3-(4-chlorothieno[2,3-b]pyridin-2-yl)-2-methyl-2,5-dihydro-1H-pyrrole-1-carboxylate (75-1, 384 mg, 1.000 mmol, 1.00 equiv), 4-fluoro-1,3-benzothiazol-5-amine (184 mg, 1.100 mmol, 1.10 equiv), G3-BrettPhos (90 mg, 0.100 mmol, 0.10 equiv) and K₂CO₃ (386 mg, 2.990 mmol, 3.00 equiv) were dissolved in tert-butanol (10.0 mL). The resulting mixture was stirred at 60° C. overnight under N₂ atmosphere. LCMS showed the reaction was complete. The resulting mixture was filtered and concentrated under reduced pressure. The crude product was purified by prep-TLC (ethyl acetate:petroleum ether=1:1) to afford benzyl 3-(4-((4-fluorobenzo[d]thiazol-5-yl)amino)thieno[2,3-b]pyridin-2-yl)-2-methyl-2,5-dihydro-1H-pyrrole-1-carboxylate (87-1, 220 mg, 43%) as a light yellow solid. LCMS (ESI, m/z): 517 [M+H]⁺.

Synthesis of benzyl 3-(4-((4-fluorobenzo[d]thiazol-5-yl)amino)thieno[2,3-b]pyridin-2-yl)-2-methylpyrrolidine-1-carboxylate

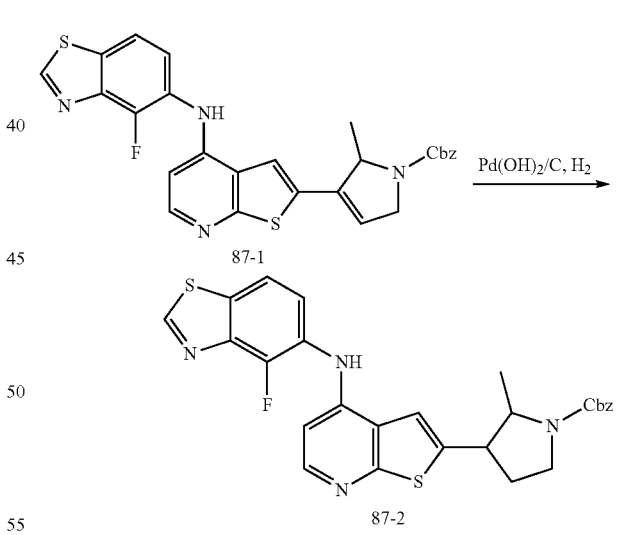

Benzyl 3-(4-((4-fluorobenzo[d]thiazol-5-yl)amino)thieno[2,3-b]pyridin-2-yl)-2-methyl-2,5-dihydro-1H-pyrrole-1-carboxylate (87-1, 220 mg, 0.430 mmol, 1.00 equiv) was dissolved in ethanol (42.0 mL), then Pd(OH)₂/C (212 mg, 1.00 w/w) was added. The reaction mixture was stirred at 60° C. overnight under H₂ (balloon). LCMS showed the reaction was complete. The resulting mixture was filtered and concentrated under reduced pressure. The crude product was purified by prep-TLC (ethyl acetate:petroleum ether=1:1) to afford benzyl 3-(4-((4-fluorobenzo[d]thiazol-5-yl)

amino)thieno[2,3-b]pyridin-2-yl)-2-methylpyrrolidine-1-carboxylate (87-2, 90 mg, 41%) as an off-white solid. LCMS (ESI, m/z): 519 [M+H]$^+$.

Synthesis of 4-fluoro-N-(2-(2-methylpyrrolidin-3-yl)thieno[2,3-b]pyridin-4-yl)benzo[d]-thiazol-5-amine

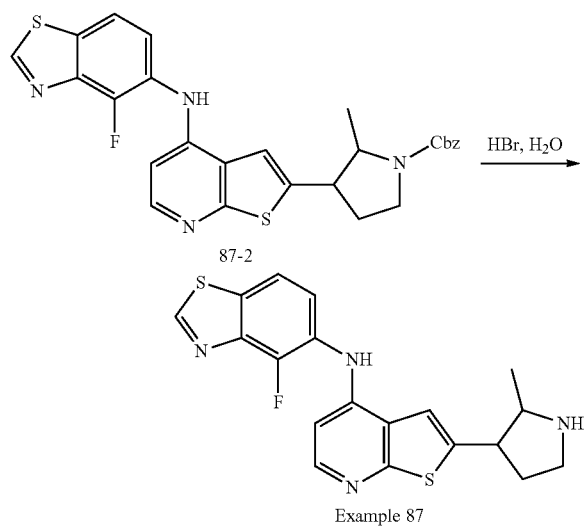 [SMILES: CC1C(c2cc3c(Nc4ccc5scnc5c4F)ccnc3s2)CCN1C(=O)OCc1ccccc1 ; CC1NCCC1c1cc2c(Nc3ccc4scnc4c3F)ccnc2s1]

Benzyl 3-(4-((4-fluorobenzo[d]thiazol-5-yl)amino)thieno[2,3-b]pyridin-2-yl)-2-methylpyrrolidine-1-carboxylate (87-2, 80 mg, 0.150 mmol, 1.00 equiv) was dissolved in hydrobromic acid (40% in water, 5.0 mL) and the reaction solution was stirred at RT for 30 min. LCMS showed the reaction was complete. The solvent was evaporated and the residue was purified by prep-HPLC. Column: Xselect CSH OBD 30×150 mm, 5 um; Mobile Phase A: Water (0.05% TFA), Mobile Phase B: ACN; Flow rate: 60 mL/min; Gradient: 5% B to 30% B in 8 min; to afford 4-fluoro-N-(2-(2-methylpyrrolidin-3-yl)thieno[2,3-b]pyridin-4-yl)benzo[d]thiazol-5-amine (Example 87, 41.3 mg, 70%) as a white solid. $^1$H NMR (300 MHz, Methanol-d) δ 9.41 (s, 1H), 8.29 (d, J=6.7 Hz, 1H), 8.13-8.02 (m, 1H), 7.84 (s, 1H), 7.63 (dd, J=8.6, 6.7 Hz, 1H), 6.76 (dd, J=6.8, 2.2 Hz, 1H), 4.33-3.45 (m, 4H), 2.84-2.23 (m, 2H), 1.56 (d, J=6.4 Hz, 1H), 1.25 (d, J=6.8 Hz, 2H). LCMS (ESI, m/z): 385 [M+H]$^+$.

Example 88: Synthesis of N-(2-(1-ethyl-2-methylpyrrolidin-3-yl)thieno[2,3-b]pyridin-4-yl)-4-fluorobenzo[d]thiazol-5-amine

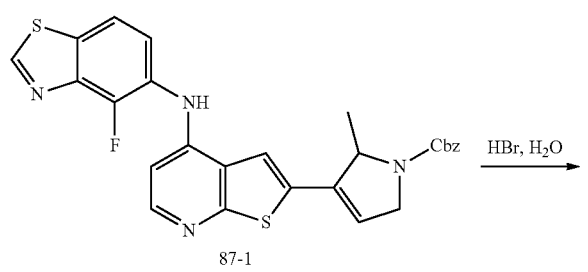

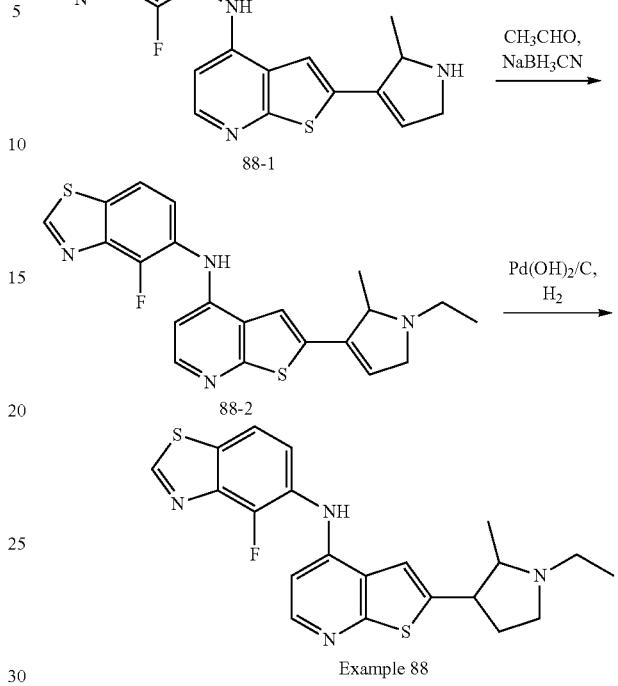

Synthesis of 4-fluoro-N-(2-(2-methyl-2,5-dihydro-1H-pyrrol-3-yl)thieno[2,3-b]pyridin-4-yl)benzo[d]thiazol-5-amine

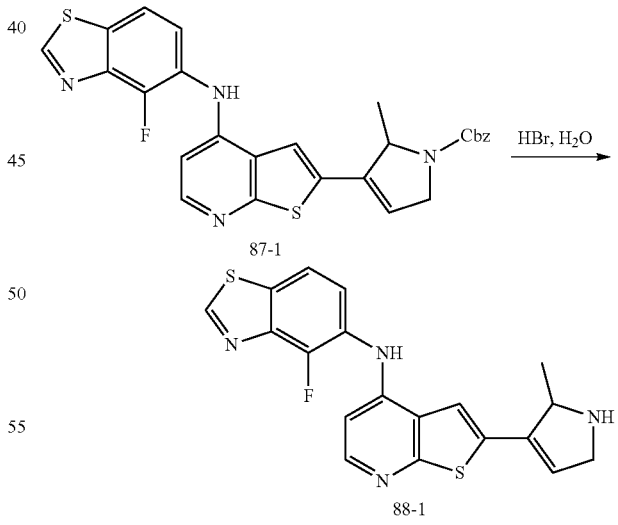

A solution of benzyl 3-(4-((4-fluorobenzo[d]thiazol-5-yl)amino)thieno[2,3-b]pyridin-2-yl)-2-methyl-2,5-dihydro-1H-pyrrole-1-carboxylate (87-1, 210 mg, 0.411 mmol, 1.00 equiv) in HBr (40% in H$_2$O, 10.0 mL) was stirred for 4 h at room temperature. TLC showed the reaction was complete. The resulting mixture was evaporated to dryness and washed with acetone to afford 4-fluoro-N-(2-(2-methyl-2,5-dihydro- 1H-pyrrol-3-yl)thieno[2,3-b]pyridin-4-yl)benzo[d]thiazol-5-amine (88-1, 220 mg, crude) as an off-white solid. LCMS (ESI, m/z): 382 [M+H]$^+$.

Synthesis of N-(2-(1-ethyl-2-methyl-2,5-dihydro-1H-pyrrol-3-yl)thieno[2,3-b]pyridin-4-yl)-4-fluorobenzo[d]thiazol-5-amine

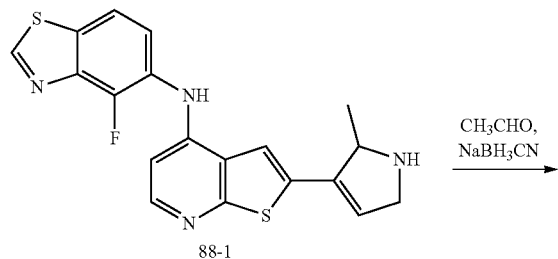

To a solution of 4-fluoro-N-(2-(2-methyl-2,5-dihydro-1H-pyrrol-3-yl)thieno[2,3-b]pyridin-4-yl)benzo[d]thiazol-5-amine (88-1, 190 mg, 0.412 mmol, 1.00 equiv) in methanol (10.0 mL) was added CH$_3$COOH (one drop), CH$_3$CHO (90 mg, 2.051 mmol, 5.00 equiv) and NaBH$_3$CN (77 mg, 1.232 mmol, 3.00 equiv). The resulting mixture was stirred for 1 h at RT. TLC showed the reaction was complete. The reaction mixture was quenched with NaHCO$_3$ (sat. aq, 100 ml), extracted with DCM (3×100 ml), dried over Na$_2$SO$_4$, filtered and evaporated to dryness. The residue was purified by prep-TLC (DCM/MeOH=8/1) to afford N-(2-(1-ethyl-2-methyl-2,5-dihydro-1H-pyrrol-3-yl)thieno[2,3-b]pyridin-4-yl)-4-fluorobenzo[d]thiazol-5-amine (88-2, 80 mg, 48%) as an off-white solid. LCMS (ESI, m/z): 411[M+H]$^+$.

Synthesis of N-(2-(1-ethyl-2-methylpyrrolidin-3-yl)thieno[2,3-b]pyridin-4-yl)-4-fluorobenzo[d]thiazol-5-amine

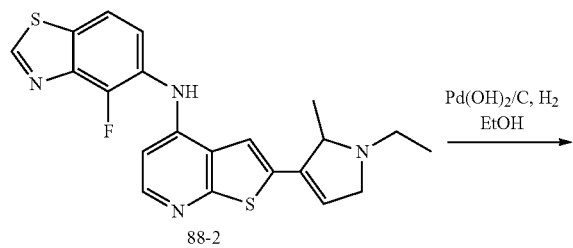

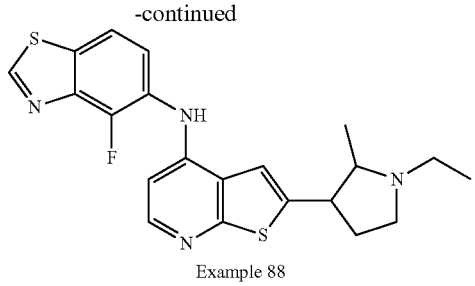

Example 88

To a solution of N-(2-(1-ethyl-2-methyl-2,5-dihydro-1H-pyrrol-3-yl)thieno[2,3-b]pyridin-4-yl)-4-fluorobenzo[d]thiazol-5-amine (88-2, 80 mg, 0.191 mmol, 1.00 equiv) in ethanol (20.0 mL) was added Pd(OH)$_2$/C (80 mg, 1.00 w/w). The resulting mixture was stirred for 48 h at 60° C. under H$_2$ atmosphere (balloon). LCMS showed the reaction was complete. The resulting mixture was filtered and concentrated under reduced pressure. The residue was purified by prep-TLC (DCM/MeOH=8/1) and prep-HPLC (Column: Xselect CSH OBD 30×150 mm, 5 um; Mobile Phase A: Water (0.05% TFA), Mobile Phase B: ACN; Flow rate: 60 mL/min; Gradient: 10% B to 30% B in 8 min) to afford N-(2-(1-ethyl-2-methylpyrrolidin-3-yl)thieno[2,3-b]pyridin-4-yl)-4-fluorobenzo[d]thiazol-5-amine (Example 88, 8.4 mg, 10%) as an off-white solid. $^1$H NMR (400 MHz, Methanol-d$_4$) δ 9.41 (s, 1H), 8.29 (d, J=6.7 Hz, 1H), 8.08 (d, J=8.5 Hz, 1H), 7.84 (s, 1H), 7.64 (dd, J=8.6, 6.6 Hz, 1H), 6.76 (dd, J=6.8, 2.2 Hz, 1H), 4.31-4.30 (m, 1H), 4.09-4.00 (m, 1H), 3.98-3.80 (m, 1H), 3.54-3.45 (m, 1H), 3.34-3.25 (m, 2H), 2.72-2.68 (m, 1H), 2.56-2.48 (m, 1H), 1.45 (t, J=6.4 Hz, 3H), 1.30 (d, J=6.9 Hz, 3H). LCMS (ESI, m/z): 413 [M+H]$^+$.

Example 89: Synthesis of 2-(3-(4-((4-fluorobenzo[d]thiazol-5-yl)amino)thieno[2,3-b]pyridin-2-yl)-2-methylpyrrolidin-1-yl)ethan-1-ol

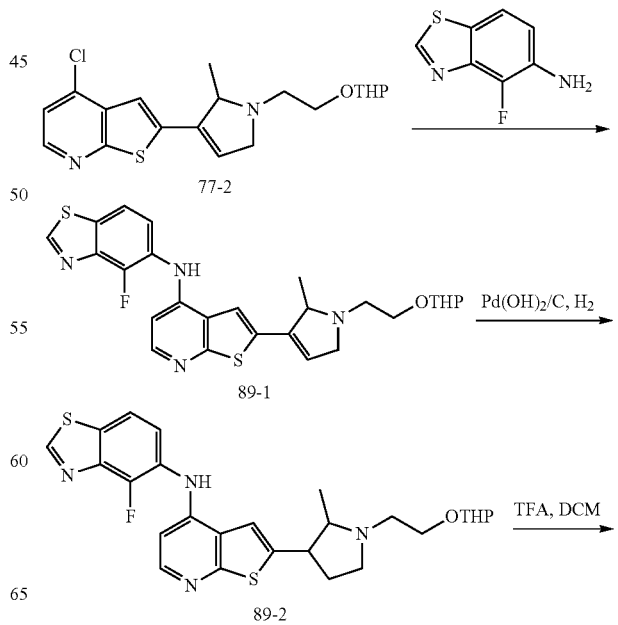

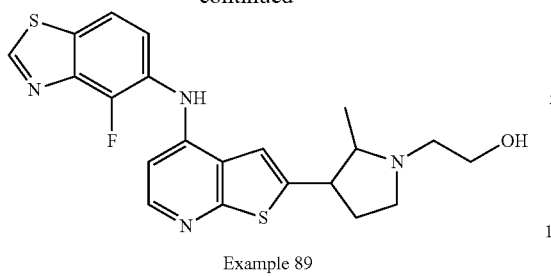

Example 89

Example 89 was prepared from 4-chloro-2-(2-methyl-1-(2-(((tetrahydro-2H-pyran-2-yl)oxy)ethyl)-2,5-dihydro-1H-pyrrol-3-yl)thieno[2,3-b]pyridine (77-2) in a manner analogous to the procedures described for Example 77 to afford 2-[3-[4-[(4-fluoro-1,3-benzothiazol-5-yl)amino]thieno[2,3-b]pyridin-2-yl]-2-methylpyrrolidin-1-yl]ethanol (Example 89) as a white solid. $^1$H NMR (400 MHz, Methanol-d) δ 9.41 (s, 1H), 8.29 (brs, 1H), 8.08 (d, J=8.6 Hz, 1H), 7.86 (s, 1H), 7.68-7.59 (m, 1H), 6.76 (d, J=6.6 Hz, 1H), 4.35-4.20 (m, 1H), 4.10-3.89 (m, 3H), 3.80-3.40 (m, 4H), 2.80-2.40 (m, 2H), 1.59 (d, J=2.4 Hz, 1H), 1.30 (brs, 2H). LCMS (ESI, m/z): 429 [M+H]$^+$.

Example 90: Synthesis of N-(2-(2,2-dimethylpyrrolidin-3-yl)thieno[2,3-b]pyridin-4-yl)-4-fluorobenzo[d]thiazol-5-amine

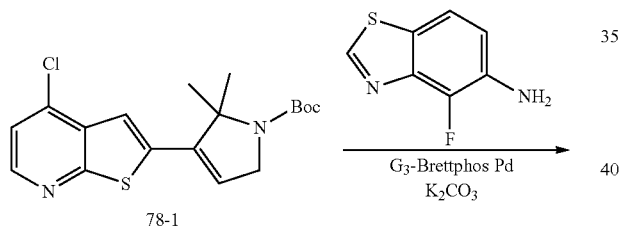

78-1

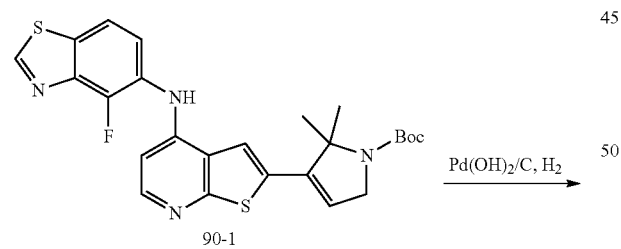

90-1

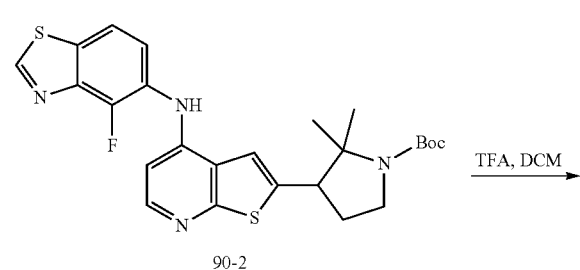

90-2

Synthesis of tert-butyl 3-(4-((4-fluorobenzo[d]thiazol-5-yl)amino)thieno[2,3-b]pyridin-2-yl)-2,2-dimethyl-2,5-dihydro-1H-pyrrole-1-carboxylate

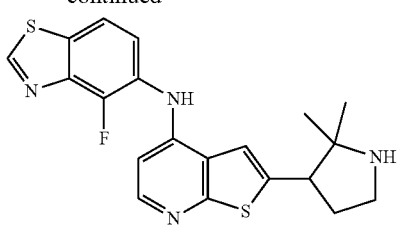

78-1

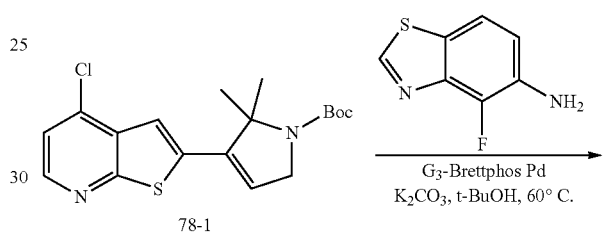

90-1

Into a 100-mL sealed tube purged and maintained with an inert atmosphere of nitrogen was placed tert-butyl 3-(4-chlorothieno[2,3-b]pyridin-2-yl)-2,2-dimethyl-2,5-dihydro-1H-pyrrole-1-carboxylate (78-1, 300 mg, 0.820 mmol, 1.00 equiv), 4-fluoro-1,3-benzothiazol-5-amine (138 mg, 0.820 mmol, 1.00 equiv), K$_2$CO$_3$ (340 mg, 2.470 mmol, 3.00 equiv), G3-brettphos (74 mg, 0.080 mmol, 0.10 equiv) and tert-butanol (10.0 mL). The resulting solution was stirred for 4 h at 60° C. The mixture was then concentrated under reduced pressure and the crude product was purified by column chromatography on silica gel (DCM/MeOH=10/1) to give tert-butyl 3-(4-((4-fluorobenzo[d]thiazol-5-yl)amino)thieno[2,3-b]pyridin-2-yl)-2,2-dimethyl-2,5-dihydro-1H-pyrrole-1-carboxylate (90-1, 280 mg, 69%) as a yellow oil. LCMS (ESI, m/z): 497 [M+H]$^+$.

Synthesis of tert-butyl 3-(4-((4-fluorobenzo[d]thi-azol-5-yl)amino)thieno[2,3-b]pyridin-2-yl)-2,2-dimethylpyrrolidine-1-carboxylate

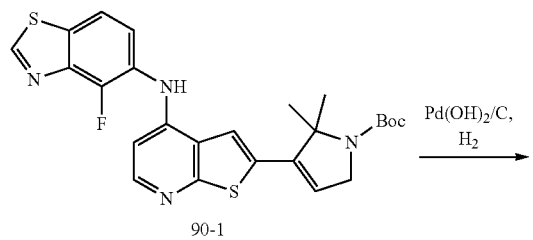

90-1

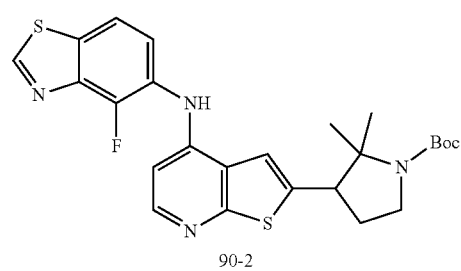

90-2

To a solution of tert-butyl 3-(4-((4-fluorobenzo[d]thiazol-5-yl)amino)thieno[2,3-b]pyridin-2-yl)-2,2-dimethyl-2,5-dihydro-1H-pyrrole-1-carboxylate (90-1, 260 mg, 0.520 mmol, 1.00 equiv) in ethanol (10.0 mL) was added 10% Pd(OH)$_2$/C (260 mg, 1.00 w/w) under a nitrogen atmosphere. The solution was degassed and back-filled with hydrogen. The reaction mixture was stirred for 7 days at 60° C. under H$_2$ atmosphere (2.0 atm.). LCMS showed the reaction was complete. The resulting mixture was filtered through celite and the filtrate was concentrated under reduced pressure to give tert-butyl 3-(4-((4-fluorobenzo[d]thiazol-5-yl)amino)thieno[2,3-b]pyridin-2-yl)-2,2-dimethylpyrrolidine-1-carboxylate (90-2, 200 mg, crude) as a yellow oil. LCMS (ESI, m/z): 499 [M+H]$^+$.

Synthesis of N-(2-(2,2-dimethylpyrrolidin-3-yl)thieno[2,3-b]pyridin-4-yl)-4-fluorobenzo[d]-thiazol-5-amine

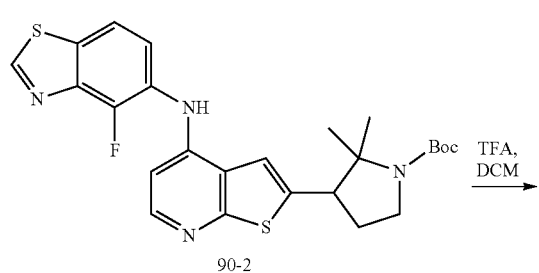

90-2

-continued

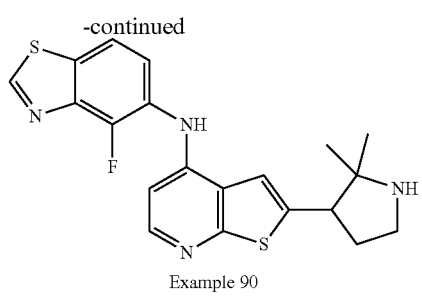

Example 90

To a stirred solution of tert-butyl 3-(4-((4-fluorobenzo[d]thiazol-5-yl)amino)thieno[2,3-b]pyridin-2-yl)-2,2-dimethylpyrrolidine-1-carboxylate (90-2, 85 mg, 0.170 mmol, 1.00 equiv) in DCM (4.0 mL) was added TFA (2.0 mL) at room temperature for 30 min. LCMS showed the reaction was complete. The resulting mixture was concentrated under reduced pressure. The residue was purified by preparative HPLC. Column: Sunfire Prep C18 OBD, 10 um, 19×250 mm; Mobile Phase A: Water (0.05% TFA), Mobile Phase B: ACN; Flow rate: 25 mL/min; Gradient: 5% B to 25% B in 7 min. Purification resulted in N-(2-(2,2-dimethylpyrrolidin-3-yl)thieno[2,3-b]pyridin-4-yl)-4-fluorobenzo[d]thiazol-5-amine (Example 90, 21.8 mg, 32%) as a white solid. $^1$H NMR (400 MHz, Methanol-d$_4$) δ 9.32 (s, 1H), 8.06 (d, J=5.7 Hz, 1H), 7.93 (dd, J=8.6, 1.2 Hz, 1H), 7.57 (dd, J=8.6, 6.8 Hz, 1H), 7.49 (d, J=1.0 Hz, 1H), 6.54 (dd, J=5.7, 2.2 Hz, 1H), 3.29-3.23 (m, 1H), 3.21-3.09 (m, 2H), 2.53-2.30 (m, 2H), 1.41 (s, 3H), 0.99 (s, 3H). LCMS (ESI, m/z): 399 [M+H]$^+$.

Example 91: Synthesis of N-(2-(1-ethyl-2,2-dimethylpyrrolidin-3-yl)thieno[2,3-b]pyridin-4-yl)-4-fluorobenzo[d]thiazol-5-amine

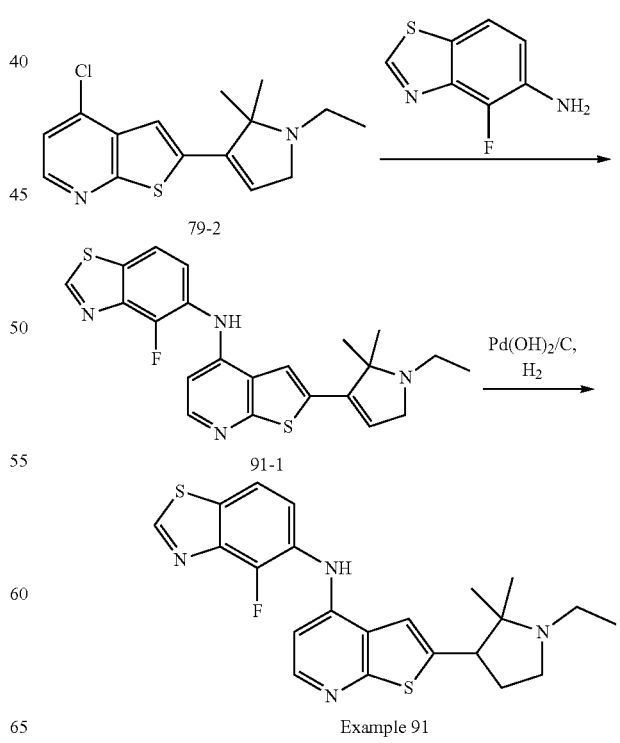

79-2

91-1

Example 91

Example 91 was prepared from 4-chloro-2-(1-ethyl-2,2-dimethyl-2,5-dihydro-1H-pyrrol-3-yl)thieno[2,3-b]pyridine (79-2) in a manner analogous to the procedures described for Example 79 to afford N-(2-(1-ethyl-2,2-dimethylpyrrolidin-3-yl)thieno[2,3-b]pyridin-4-yl)-4-fluorobenzo[d]thiazol-5-amine as a white solid. ¹H NMR (400 MHz, Methanol-d₄) δ 9.40 (s, 1H), 8.30 (d, J=6.8 Hz, 1H), 8.13-8.06 (m, 1H), 7.91 (s, 1H), 7.68-7.60 (m, 1H), 6.82-6.76 (m, 1H), 3.99-3.92 (m, 1H), 3.81-3.75 (m, 1H), 3.56-3.45 (m, 2H), 3.16-3.06 (m, 1H), 2.74-2.59 (m, 2H), 1.64 (s, 3H), 1.43 (t, J=7.3 Hz, 3H), 1.22 (s, 3H). LCMS (ESI, m/z): 427 [M+H]⁺.

Example 92: Synthesis of Synthesis of 2-(3-(4-((4-fluorobenzo[d]thiazol-5-yl)amino)thieno[2,3-b]pyridin-2-yl)-2,2-dimethylpyrrolidin-1-yl)ethan-1-ol

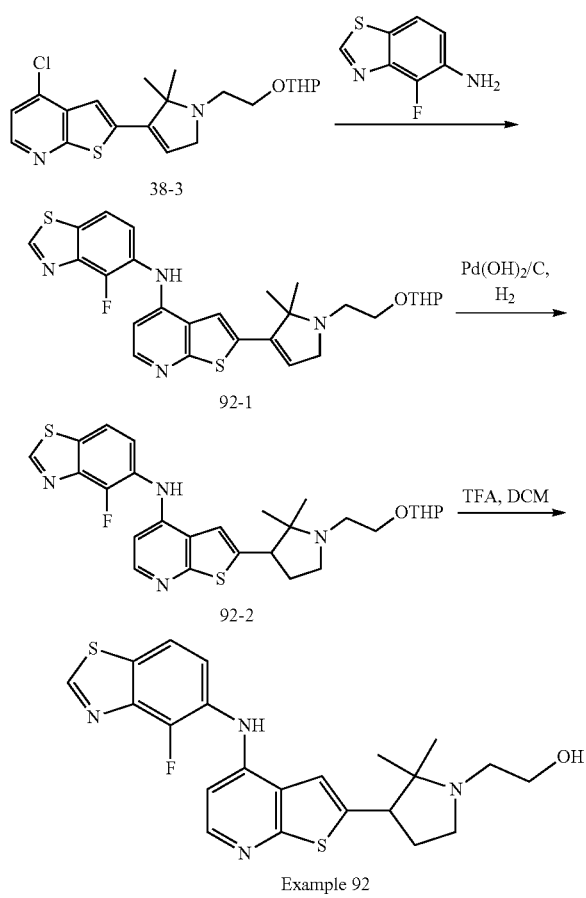

Example 92 was prepared from 4-chloro-2-(2,2-dimethyl-1-(2-((tetrahydro-2H-pyran-2-yl)oxy)ethyl)-2,5-dihydro-1H-pyrrol-3-yl)thieno[2,3-b]pyridine (38-3) in a manner analogous to the procedures described for Example 80 to afford 2-(3-(4-((4-fluorobenzo[d]thiazol-5-yl)amino)thieno[2,3-b]pyridin-2-yl)-2,2-dimethylpyrrolidin-1-yl)ethan-1-ol (Example 92) as a white solid. ¹H NMR (400 MHz, Methanol-d₄) δ 9.40 (s, 1H), 8.29 (d, J=6.7 Hz, 1H), 8.07 (dd, J=8.6, 1.2 Hz, 1H), 7.88 (s, 1H), 7.63 (dd, J=8.7, 6.7 Hz, 1H), 6.76 (dd, J=6.6, 2.2 Hz, 1H), 4.04-3.83 (m, 4H), 3.70-3.55 (m, 2H), 3.25-3.15 (m, 1H), 2.74-2.57 (m, 2H), 1.67 (s, 3H), 1.27 (s, 3H). LCMS (ESI, m/z): 443 [M+H]⁺.

Example 93: Synthesis of 4,6-difluoro-N-(2-(2-methylpyrrolidin-3-yl)thieno[2,3-b]pyridin-4-yl)benzo[d]thiazol-5-amine

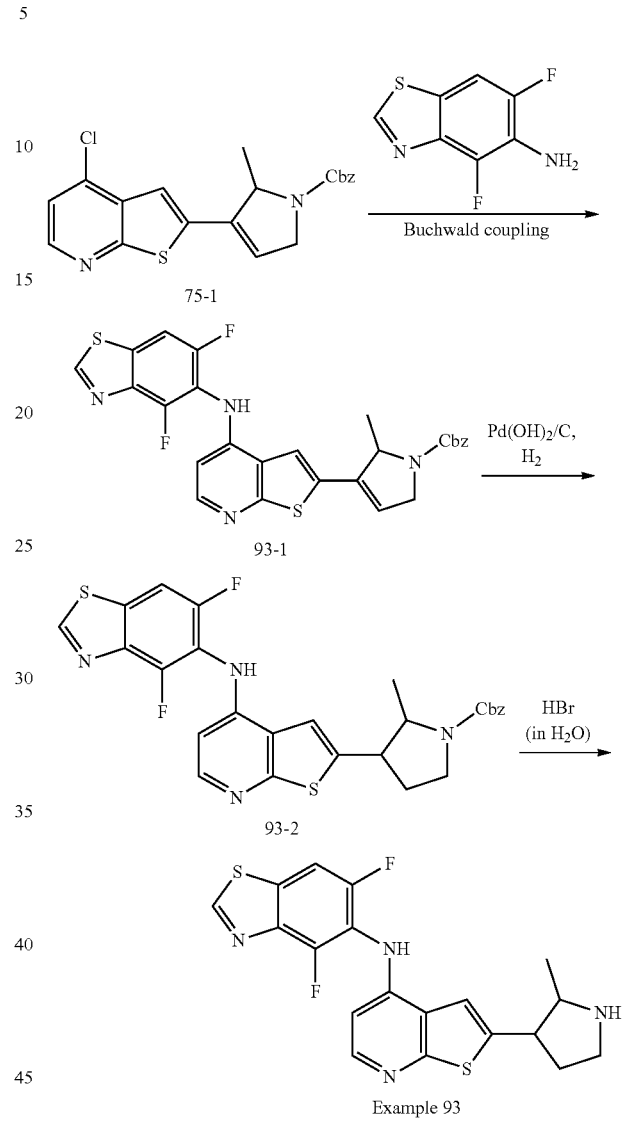

Synthesis of benzyl 3-(4-((4,6-difluorobenzo[d]thiazol-5-yl)amino)thieno[2,3-b]pyridin-2-yl)-2-methyl-2,5-dihydro-1H-pyrrole-1-carboxylate

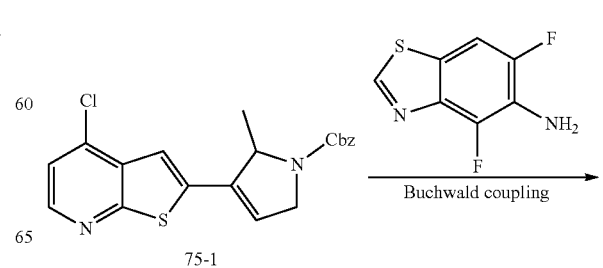

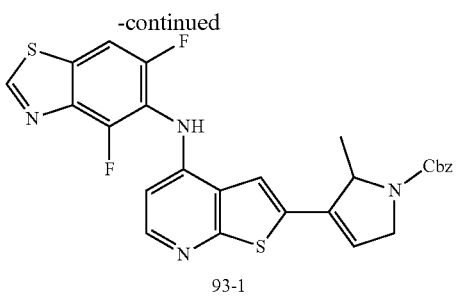

93-1

A solution of benzyl 3-(4-chlorothieno[2,3-b]pyridin-2-yl)-2-methyl-2,5-dihydro-1H-pyrrole-1-carboxylate (75-1, 300 mg, 0.781 mmol, 1.00 equiv), 4,6-difluoro-1,3-benzothiazol-5-amine (145 mg, 0.781 mmol, 1.00 equiv), G3-BrettPhos Pd (80 mg, 0.078 mmol, 0.10 equiv) and K₂CO₃ (247 mg, 2.343 mmol, 3.00 equiv) in t-BuOH (10.0 mL) was placed in a 50-ml round-bottom flask. The flask was evacuated and flushed three times with nitrogen. The resulting mixture was stirred at 90° C. for 2 h. LCMS showed the reaction was complete. The reaction was diluted with water (10.0 mL) and extracted with ethyl acetate (3×20.0 mL). The organic layers were combined, washed with sodium carbonate, dried over Na₂SO₄ and concentrated under reduced pressure. The residue was applied onto a silica gel column and eluted with ethyl acetate/petroleum ether (1/10) to give the desired product benzyl 3-(4-((4,6-difluorobenzo[d]thiazol-5-yl)amino)thieno[2,3-b]pyridin-2-yl)-2-methyl-2,5-dihydro-1H-pyrrole-1-carboxylate (93-1, 190 mg, 46%) as a yellow oil. LCMS (ESI, m/z): 535 [M+H]⁺.\

Synthesis of benzyl 3-(4-((4,6-difluorobenzo[d]thiazol-5-yl)amino)thieno[2,3-b]pyridin-2-yl)-2-methylpyrrolidine-1-carboxylate

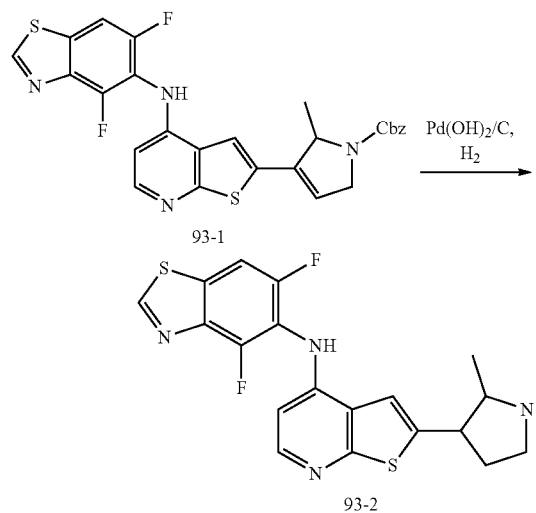

A solution of benzyl 3-(4-((4,6-difluorobenzo[d]thiazol-5-yl)amino)thieno[2,3-b]pyridin-2-yl)-2-methyl-2,5-dihydro-1H-pyrrole-1-carboxylate (93-1, 190 mg, 0.360 mmol, 1.00 equiv) and Pd(OH)₂/C (190 mg, 1.00 w/w) in ethanol (20.0 mL) was evacuated and flushed three times with hydrogen. The mixture was stirred at 60° C. for 15 h under an atmosphere of hydrogen (balloon). LCMS showed the reaction was complete. The resulting mixture was filtered and concentrated under reduced pressure to give the desired product 93-2, which was used in the next step without further purification. LCMS (ESI, m/z): 537 [M+H]⁺.

Synthesis of 4,6-difluoro-N-(2-(2-methylpyrrolidin-3-yl)thieno[2,3-b]pyridin-4-yl)benzo[d]thiazol-5-amine

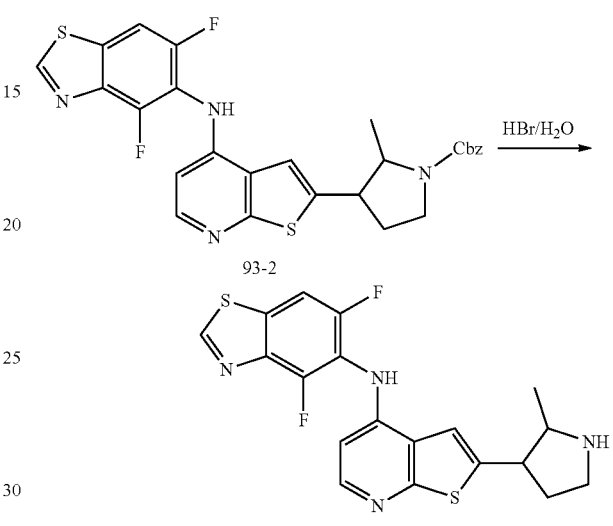

Example 93

A solution of benzyl 3-(4-((4,6-difluorobenzo[d]thiazol-5-yl)amino)thieno[2,3-b]pyridin-2-yl)-2-methylpyrrolidine-1-carboxylate (crude 93-2, 90 mg, 0.170 mmol, 1.00 equiv) in HBr (3.0 ml in H₂O) was stirred at RT for 0.5 h. LCMS showed the reaction was complete. The resulting mixture was purified by prep-HPLC (Column: XB ridge Prep OBD C18 30×150 mm, 5 um; Mobile Phase A: Water (10 mmol/L NH₄HCO₃), Mobile Phase B: ACN; Flow rate: 60 mL/min; Gradient: 10% B to 52% B in 7 min; 254/210 nm; Rt: 6.22 min) to give the desired product 4,6-difluoro-N-(2-(2-methylpyrrolidin-3-yl)thieno[2,3-b]pyridin-4-yl)benzo[d]thiazol-5-amine (Example 93, 30.0 mg, 45%) as a colorless solid. ¹H NMR (300 MHz, Methanol-d₄) δ 9.32 (s, 1H), 8.07 (dd, J=5.7, 1.6 Hz, 1H), 7.93 (dd, J=8.9, 1.8 Hz, 1H), 7.53-7.43 (m, 1H), 6.34 (d, J=5.3 Hz, 1H), 3.74-3.66 (m, 1H), 3.56-3.48 (m, 1H), 3.26-2.87 (m, 2H), 2.54-2.37 (m, 1H), 2.37-2.20 (m, 1H), 1.03 (d, J=6.7 Hz, 3H). LCMS (ESI, m/z): 403 [M+H]⁺.

Chiral Separation:

Column: CHIRALPAK IG, 2.0×25 cm (5 um); Mobile Phase A: Hex (8 mmol/L NH₃.MeOH), Mobile Phase B: EtOH; Flow rate: 20 mL/min; hold at 30% B for 18 min.

Example 93a

Light yellow solid. ¹H NMR (400 MHz, Methanol-d₄) δ 9.40 (s, 1H), 8.38 (d, J=6.9 Hz, 1H), 8.08 (dd, J=8.9, 1.7 Hz, 1H), 7.96-7.90 (m, 1H), 6.78 (d, J=7.1 Hz, 1H), 3.83-3.77 (m, 1H), 3.70-3.61 (m, 2H), 3.60-3.51 (m, 1H), 2.78-2.73 (m, 1H), 2.49-2.36 (m, 1H), 1.58 (d, J=6.5 Hz, 3H). LCMS (ESI, m/z): 403 [M+H]⁺. Chiral analytic conditions: Column: Reg-AD 0.46×10 cm, 5 um; Mobile Phase: Hex (0.1% DEA):EtOH=80:20; Flow rate: 1.00 mL/min; 254/210 nm; Rt: 6.367 min.

Example 93b

Light yellow solid. $^1$H NMR (400 MHz, Methanol-d$_4$) δ 9.39 (s, 1H), 8.38 (d, J=6.9 Hz, 1H), 8.08 (dd, J=8.9, 1.7 Hz, 1H), 8.00-7.95 (m, 2H), 6.77 (d, J=6.7 Hz, 1H), 3.87-3.78 (m, 1H), 3.76-3.60 (m, 2H), 3.61-3.49 (m, 1H), 2.78-2.73 (m, 1H), 2.50-2.35 (m, 1H), 1.58 (d, J=6.3 Hz, 3H). $^{19}$F NMR (376 MHz, Methanol-d$_4$) δ −122.08, −127.00. LCMS (ESI, m/z): 403 [M+H]$^+$. Chiral analytic Conditions: Column: Reg-AD 0.46×10 cm, 5 um; Mobile Phase: Hex (0.1% DEA):EtOH=80:20; Flow rate: 1.00 mL/min; 254/210 nm; Rt: 6.848 min.

Example 93c

Light yellow solid. $^1$H NMR (400 MHz, Methanol-d$_4$) δ 9.39 (s, 1H), 8.38 (d, J=6.9 Hz, 1H), 8.08 (dd, J=8.9, 1.8 Hz, 1H), 8.03-7.96 (m, 1H), 6.80-6.74 (m, 1H), 4.30-4.19 (m, 1H), 4.20-4.09 (m, 1H), 3.79-3.69 (m, 1H), 3.61-3.49 (m, 1H), 2.78-2.67 (m, 1H), 2.70-2.53 (m, 1H), 1.27 (d, J=6.9 Hz, 3H). LCMS (ESI, m/z): 403 [M+H]$^+$. Chiral analytic Conditions: Column: Reg-AD 0.46×10 cm, 5 um; Mobile Phase: Hex (0.1% DEA):EtOH=80:20; Flow rate: 1.00 mL/min; 254/210 nm; Rt: 7.676 min.

Example 93d

Light yellow solid. $^1$H NMR (400 MHz, Methanol-d$_4$) δ 9.39 (s, 1H), 8.38 (d, J=6.9 Hz, 1H), 8.08 (dd, J=8.9, 1.8 Hz, 1H), 8.00-7.95 (m, 1H), 6.80-6.73 (m, 1H), 4.30-4.18 (m, 1H), 4.19-4.08 (m, 1H), 3.79-3.68 (m, 1H), 3.60-3.49 (m, 1H), 2.78-2.67 (m, 1H), 2.67-2.53 (m, 1H), 1.26 (d, J=6.9 Hz, 3H). LCMS (ESI, m/z): 403 [M+H]$^+$. Chiral analytic Conditions: Column: Reg-AD 0.46×10 cm, 5 um; Mobile Phase: Hex (0.1% DEA):EtOH=80:20; Flow rate: 1.00 mL/min; 254/210 nm; Rt: 9.287 min.

Example 94: Synthesis of N-(2-(1-ethyl-2-methylpyrrolidin-3-yl)thieno[2,3-b]pyridin-4-yl)-4,6-difluorobenzo[d]thiazol-5-amine

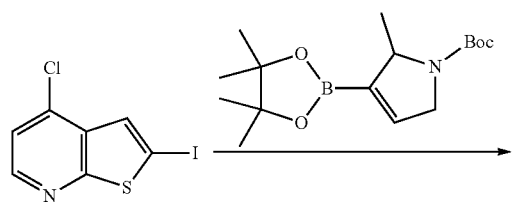

Intermediate I

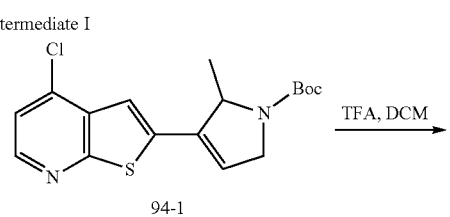

94-1

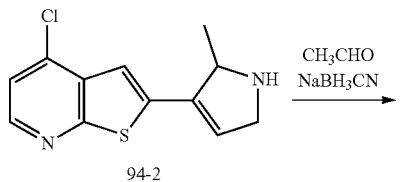

94-2

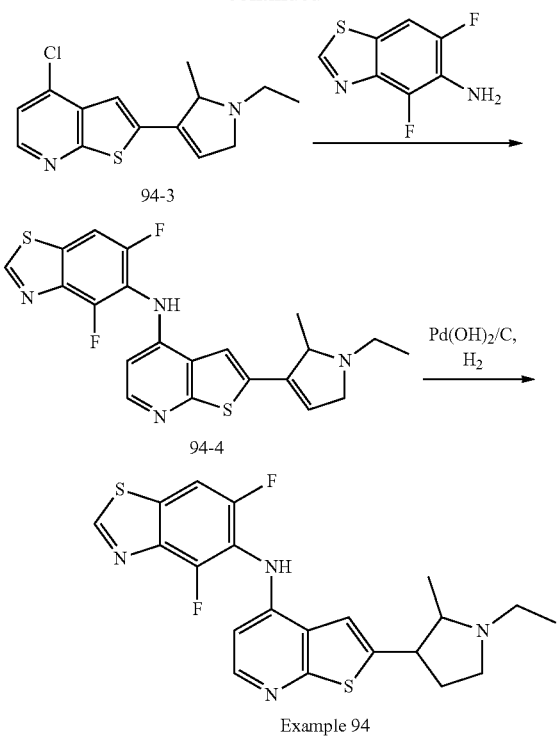

Example 94 tert-Butyl 3-(4-chlorothieno[2,3-b]pyridin-2-yl)-2-methyl-2,5-dihydro-1H-pyrrole-1-carboxylate (94-1) was prepared in a manner analogous to the procedure described in Example 78 for tert-butyl 3-(4-chlorothieno[2,3-b]pyridin-2-yl)-2,2-dimethyl-2,5-dihydro-1H-pyrrole-1-carboxylate (78-1).

Example 94 was prepared from tert-butyl 3-(4-chlorothieno[2,3-b]pyridin-2-yl)-2-methyl-2,5-dihydro-1H-pyrrole-1-carboxylate (94-1) in a manner analogous to the procedures described for Example 79 to afford N-(2-(1-ethyl-2-methylpyrrolidin-3-yl)thieno[2,3-b]pyridin-4-yl)-4,6-difluorobenzo[d]-thiazol-5-amine as an off-white solid. $^1$H NMR (400 MHz, Methanol-d$_4$) δ 9.37 (s, 1H), 8.31 (dd, J=6.7, 2.0 Hz, 1H), 8.04 (dd, J=8.9, 1.7 Hz, 1H), 7.85 (d, J=3.2 Hz, 1H), 6.66 (dq, J=6.5, 1.9 Hz, 1H), 4.20-4.01 (m, 1H), 4.02-3.81 (m, 1H), 3.75-3.45 (m, 3H), 3.23-3.15 (m, 1H), 2.78-2.68 (m, 1H), 2.62-2.36 (m, 1H), 1.58 (d, J=6.2 Hz, 2H), 1.46 (t, J=7.2 Hz, 3H), 1.26-1.15 (m, J=38.7 Hz, 1H). LCMS (ESI, m/z): 431 [M+H]$^+$.

Example 95: Synthesis of 2-(3-(4-((4,6-difluorobenzo[d]thiazol-5-yl)amino)thieno[2,3-b]pyridin-2-yl)-2-methyl-pyrrolidin-1-yl)ethan-1-ol

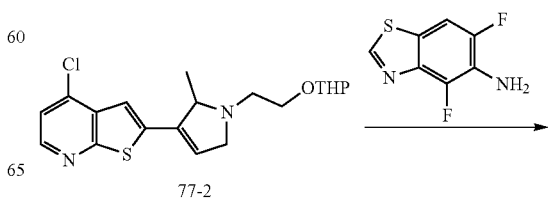

77-2

451

-continued

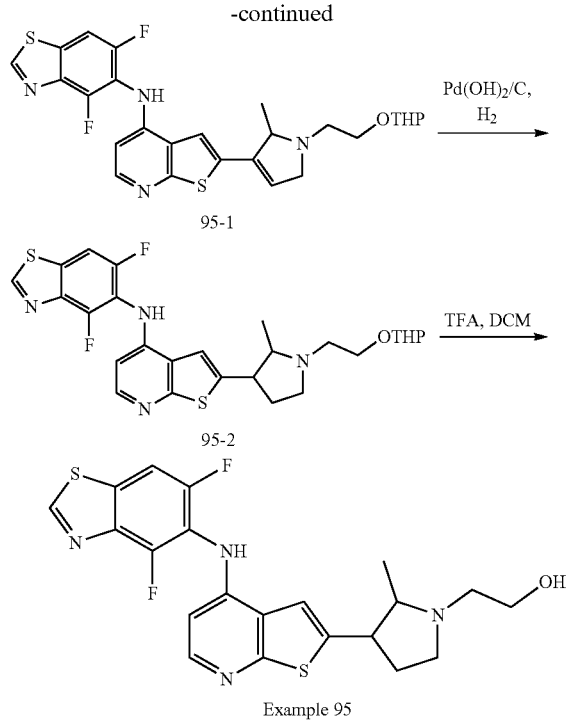

Example 95 was prepared from 4-chloro-2-(2-methyl-1-(2-((tetrahydro-2H-pyran-2-yl)oxy)ethyl)-2,5-dihydro-1H-pyrrol-3-yl)thieno[2,3-b]pyridine (77-2) in a manner analogous to the procedures described for Example 77 to afford the desired product 2-(3-(4-((4,6-difluorobenzo[d]thiazol-5-yl)amino)thieno[2,3-b]pyridin-2-yl)-2-methylpyrrolidin-1-yl)ethan-1-ol as a colorless solid. $^1$H NMR (400 MHz, Methanol-$d_4$) δ 9.38 (s, 1H), 8.33 (d, J=6.7 Hz, 1H), 8.05 (d, J=8.9 Hz, 1H), 7.85 (s, 1H), 6.70 (s, 1H), 4.37-4.19 (m, 1H), 3.95 (d, J=6.1 Hz, 3H), 3.81-3.58 (m, 2H), 3.54-3.40 (m, 2H), 2.87-2.33 (m, 2H), 1.59 (s, 1H), 1.31 (s, 2H). LCMS (ESI, m/z): 447 [M+H]$^+$.

Example 96: Synthesis of N-(2-(2,2-dimethylpyrrolidin-3-yl)thieno[2,3-b]pyridin-4-yl)-4,6-difluorobenzo[d]thiazol-5-amine

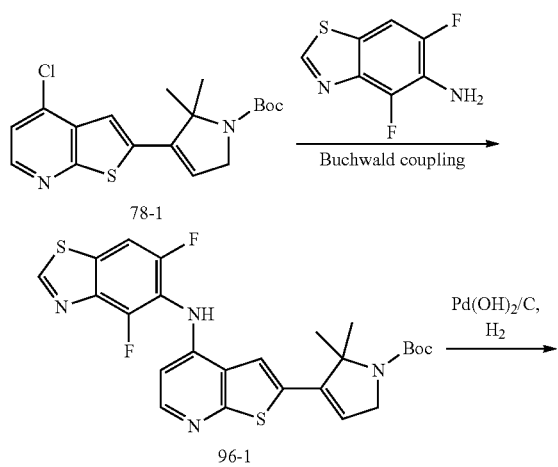

452

-continued

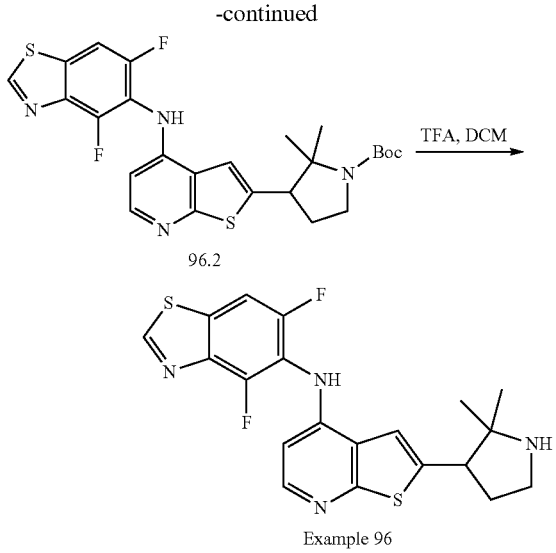

Synthesis of tert-butyl 3-(4-((4,6-difluorobenzo[d]thiazol-5-yl)amino)thieno[2,3-b]pyridin-2-yl)-2,2-dimethyl-2,5-dihydro-1H-pyrrole-1-carboxylate To a stirred solution of tert-butyl 3-(4-chlorothieno[2,3-b]pyridin-2-yl)-2,2-dimethyl-2,5-dihydro-1H-pyrrole-1-carboxylate (78-1, 150 mg, 0.411 mmol, 1.00 equiv) in t-BuOH (15.0 mL) was added 4,6-difluoro-1,3-benzothiazol-5-amine (76 mg, 0.411 mmol, 1.00 equiv), Brettphos-G3 Pd (37 mg, 0.0411 mmol, 0.10 equiv) and $K_2CO_3$ (170 mg, 1.233 mmol, 3.00 equiv). The resulting mixture was stirred at 60° C. for 8 h. LCMS showed the reaction was complete. The reaction mixture was concentrated to dryness under reduced pressure and purified by preparative TLC (petroleum ether:ethyl acetate=1:1) to afford tert-butyl 3-(4-((4,6-difluoro-benzo[d]thiazol-5-yl)amino)thieno[2,3-b]pyridin-2-yl)-2,2-dimethyl-2,5-dihydro-1H-pyrrole-1-carboxylate (96-1, 140 mg, 66%). LCMS (ESI, m/z): 515 [M+H]$^+$.

Synthesis of N-(2-(2,2-dimethylpyrrolidin-3-yl)thieno[2,3-b]pyridin-4-yl)-4,6-difluorobenzo[d]thiazol-5-amine

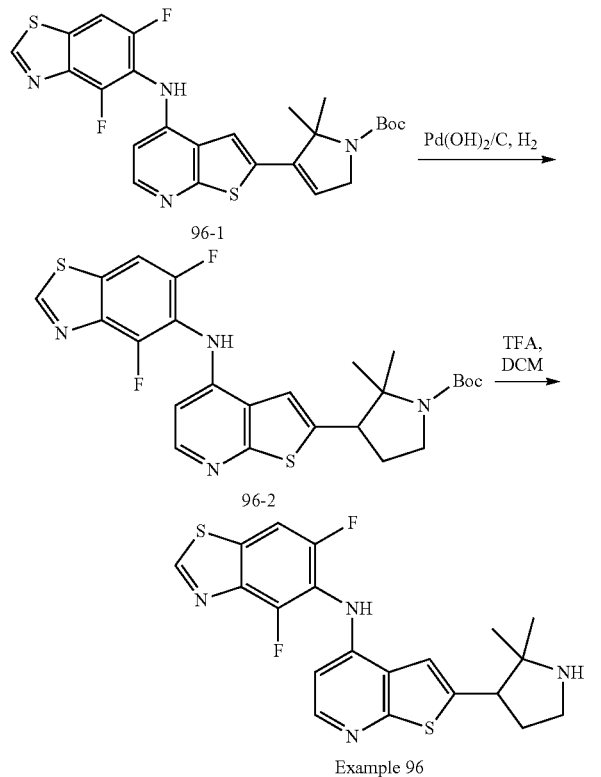

Example 96 was prepared following the procedures described for Example 90 to afford N-[2-(2,2-dimethylpyrrolidin-3-yl)thieno[2,3-b]pyridin-4-yl]-4,6-difluorobenzo[d]thiazol-5-amine (73.1 mg, 52%) in TFA salt form as a white solid. $^1$H NMR (400 MHz, Methanol-$d_4$) δ 9.36 (s, 1H), 8.33 (d, J=6.8 Hz, 1H), 8.04 (dd, J=9.0, 1.8 Hz, 1H), 7.88 (d, J=1.0 Hz, 1H), 6.70 (d, J=6.9 Hz, 1H), 3.77 (dd, J=11.6, 7.6 Hz, 1H), 3.68-3.59 (m, 1H), 3.58-3.46 (m, 1H), 2.79-2.55 (m, 2H), 1.68 (s, 3H), 1.30 (s, 3H). LCMS (ESI, m/z): 417 [M+H]$^+$.

Chiral Separation:
Column: Chiralpak ID-2, 2×25 cm, 5 um; Mobile Phase A: Hex (8 mmol/L NH$_3$.MeOH), Mobile Phase B: IPA; Flow rate: 18 mL/min; hold at 50% B for 21 min; 220/254 nm; RT1:10.822; RT2: 14.989; Injection Volumn: 0.6 ml; Number Of Runs: 10) to give the desired products.

Example 96a

White solid. LCMS (ESI, m/z): 417 [M+H]$^+$. $^1$H NMR (400 MHz, Methanol-$d_4$) δ 9.39 (s, 1H), 8.40 (d, J=6.9 Hz, 1H), 8.08 (dd, J=9.0 Hz, 1.7 Hz, 2H), 6.77 (d, J=6.8 Hz, 1H), 3.89-3.85 (m, 1H), 3.72-3.65 (m, 1H), 3.60-3.54 (m, 1H), 2.80-2.63 (m, 2H), 1.73 (s, 3H), 1.33 (s, 3H). Chiral analytic Conditions: Column: CHIRALPAK ID-3 4.6×50 mm, 3 um; Mobile Phase: Hex (0.1% DEA):IPA=50:50; Flow rate: 1 mL/min; 254 nm; RT1: 1.491 min.

Example 96b

White solid. LCMS (ESI, m/z): 417 [M+H]$^+$. $^1$H NMR (400 MHz, Methanol-$d_4$) δ 9.39 (s, 1H), 8.40 (d, J=6.9 Hz, 1H), 8.08 (dd, J=9.0 Hz, 1.7 Hz, 2H), 6.77 (d, J=6.8 Hz, 1H), 3.89-3.85 (m, 1H), 3.72-3.65 (m, 1H), 3.60-3.54 (m, 1H), 2.80-2.63 (m, 2H), 1.73 (s, 3H), 1.33 (s, 3H). Chiral analytic Conditions: Column: CHIRALPAK ID-3 4.6×50 mm, 3 um; Mobile Phase: Hex (0.1% DEA):IPA=50:50; Flow rate: 1 mL/min; 254 nm; RT: 2.087 min.

Example 97: Synthesis of N-(2-(1-ethyl-2,2-dimethylpyrrolidin-3-yl)thieno[2,3-b]pyridin-4-yl)-4,6-difluorobenzo[d]thiazol-5-amine

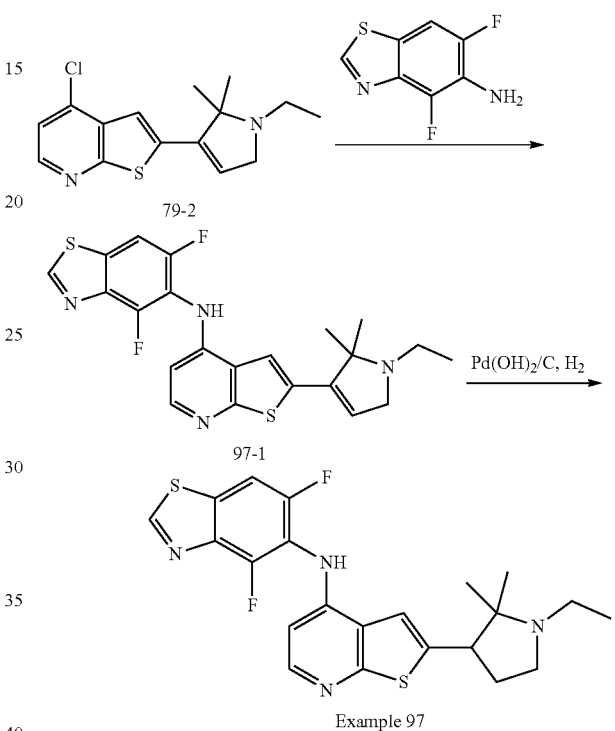

Example 97 was prepared from 4-chloro-2-(1-ethyl-2,2-dimethyl-2,5-dihydro-1H-pyrrol-3-yl)thieno[2,3-b]pyridine (79-2) in a manner analogous to the procedures described for Example 79 to afford N-(2-(1-ethyl-2,2-dimethylpyrrolidin-3-yl)thieno[2,3-b]pyridin-4-yl)-4,6-difluorobenzo[d]thiazol-5-amine as a white solid. $^1$H NMR (400 MHz, Methanol-$d_4$) δ 9.36 (s, 1H), 8.35-8.28 (m, 1H), 8.02 (t, J=8.0 Hz, 1H), 7.97-7.86 (m, 1H), 6.74-6.63 (m, 1H), 3.98-3.92 (m, 1H), 3.82-3.74 (m, 1H), 3.57-3.42 (m, 2H), 3.16-3.08 (m, 1H), 2.75-2.60 (m, 2H), 1.64 (s, 3H), 1.43 (t, J=7.2 Hz, 3H), 1.23 (s, 3H). LCMS (ESI, m/z): 445 [M+H]$^+$.

Example 98: Synthesis of 2-(3-(4-((4,6-difluorobenzo[d]thiazol-5-yl)amino)thieno[2,3-b]pyridin-2-yl)-2,2-dimethylpyrrolidin-1-yl)ethan-1-ol

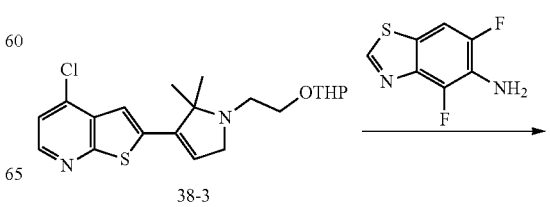

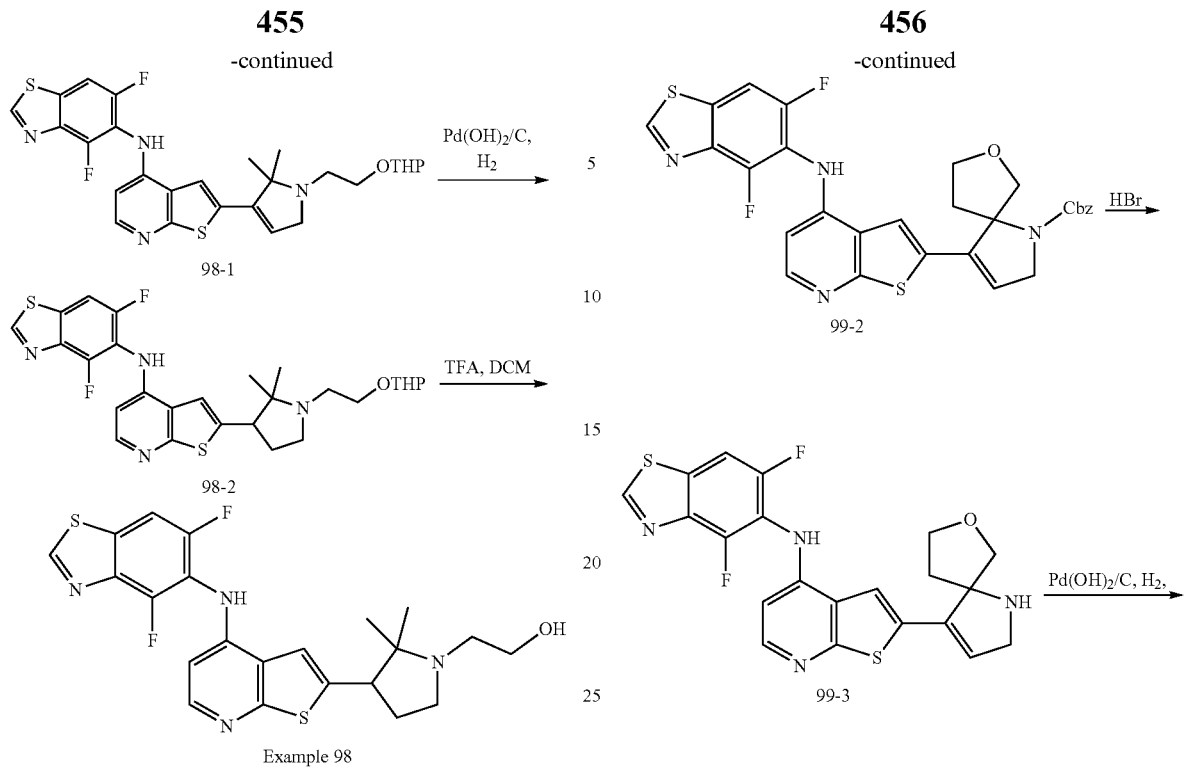

Example 98 was prepared from 4-chloro-2-(2,2-dimethyl-1-(2-((tetrahydro-2H-pyran-2-yl)oxy)ethyl)-2,5-dihydro-1H-pyrrol-3-yl)thieno[2,3-b]pyridine (38-3) in a manner analogous to the procedures described for Example 80 resulting in 2-(3-(4-((4,6-difluorobenzo[d]thiazol-5-yl)amino)thieno[2,3-b]pyridin-2-yl)-2,2-dimethylpyrrolidin-1-yl)ethan-1-ol as a white solid. $^1$H NMR (400 MHz, Methanol-$d_4$) δ 9.35 (s, 1H), 8.35-8.26 (m, 1H), 8.02 (d, J=8.8 Hz, 1H), 7.88 (d, J=6.0 Hz, 1H), 6.64 (d, J=6.4 Hz, 1H), 4.04-3.84 (m, 4H), 3.63-3.49 (m, 2H), 3.23-3.14 (m, 1H), 2.74-2.61 (m, 2H), 1.65 (s, 3H), 1.25 (s, 3H). LCMS (ESI, m/z): 461 [M+H]$^+$.

Example 99: Synthesis of N-(2-(7-oxa-1-azaspiro[4.4]nonan-4-yl)thieno[2,3-b]pyridin-4-yl)-4,6-difluorobenzo[d]thiazol-5-amine

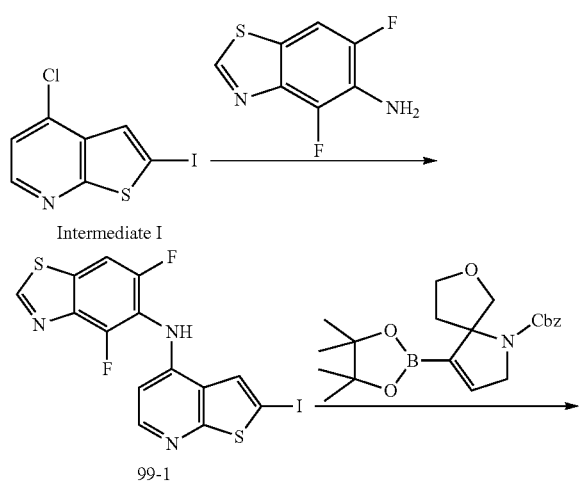

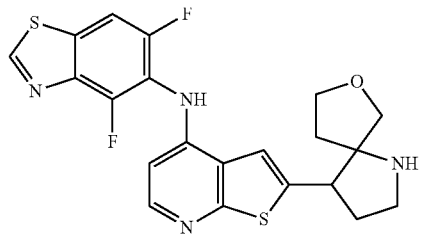

4,6-Difluoro-N-(2-iodothieno[2,3-b]pyridin-4-yl)benzo[d]thiazol-5-amine (99-1) was prepared in a manner analogous to N-(2-iodothieno[2,3-b]pyridin-4-yl)benzo[d]thiazol-5-amine described in Example 1.

N-(2-(7-Oxa-1-azaspiro[4.4]non-3-en-4-yl)thieno[2,3-b]pyridin-4-yl)-4,6-difluorobenzo[d]thiazol-5-amine (99-3) was prepared from 4,6-difluoro-N-(2-iodothieno[2,3-b]pyridin-4-yl)benzo[d]thiazol-5-amine (99-1) in a manner analogous to the procedures described for Example 40.

Example 99 was prepared from N-(2-(7-oxa-1-azaspiro[4.4]non-3-en-4-yl)thieno[2,3-b]pyridin-4-yl)-4,6-difluorobenzo[d]thiazol-5-amine (99-3) in a manner analogous to the procedures described for Example 81 resulting in N-(2-(7-oxa-1-azaspiro[4.4]nonan-4-yl)thieno[2,3-b]pyridin-4-yl)-4,6-difluorobenzo[d]thiazol-5-amine as an off-white solid. $^1$H NMR (400 MHz, Methanol-$d_4$) δ 9.37 (s, 1H), 8.31 (d, J=6.5 Hz, 1H), 8.03 (dd, J=8.9, 1.8 Hz, 1H), 7.88 (d, J=2.4 Hz, 1H), 6.66 (dt, J=6.6, 1.8 Hz, 1H), 4.25 (d, J=10.8 Hz, 1H), 4.13-3.96 (m, 3H), 3.92-3.81 (m, 1H), 3.75-3.54 (m, 2H), 2.83-2.75 (m, 1H), 2.65-2.51 (m, 2H), 2.21-2.14 (m, 1H). LCMS (ESI, m/z): 445 [M+H]$^+$.

Example 100: Synthesis of 4,6-difluoro-N-(2-(1-methyl-7-oxa-1-azaspiro[4.4]nonan-4-yl)thieno[2,3-b]pyridin-4-yl)benzo[d]thiazol-5-amine

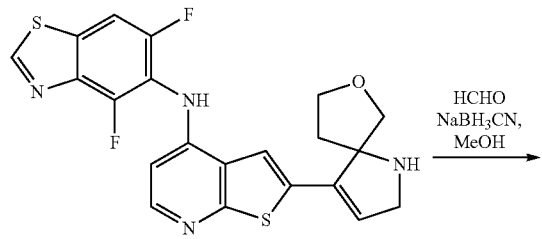

99-3

HCHO
NaBH₃CN,
MeOH

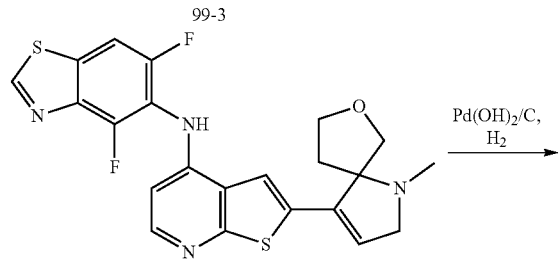

100-1

Pd(OH)₂/C,
H₂

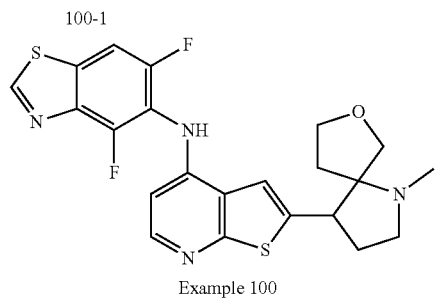

Example 100

Example 100 was prepared from N-(2-(7-oxa-1-azaspiro[4.4]non-3-en-4-yl)thieno[2,3-b]pyridin-4-yl)-4,6-difluorobenzo[d]thiazol-5-amine (99-3) in a manner analogous to the procedures described for Example 82 to afford 4,6-difluoro-N-(2-(1-methyl-7-oxa-1-azaspiro[4.4]nonan-4-yl)thieno[2,3-b]pyridin-4-yl)benzo[d]thiazol-5-amine (31.5 mg, 38%) as an off-white solid. ¹H NMR (400 MHz, Methanol-d₄) δ 9.38 (s, 1H), 8.36 (d, J=6.7 Hz, 1H), 8.05 (dd, J=9.0, 1.7 Hz, 1H), 7.97 (s, 1H), 6.72 (dt, J=6.8, 1.7 Hz, 1H), 4.52-4.05 (m, 3H), 3.97-3.50 (m, 3H), 3.03 (d, J=5.4 Hz, 3H), 2.80-2.47 (m, 3H), 2.45-2.17 (m, 1H). LCMS (ESI, m/z): 459 [M+H]⁺.

Example 101: Synthesis of N-(2-(1-ethyl-7-oxa-1-azaspiro[4.4]nonan-4-yl)thieno[2,3-b]pyridin-4-yl)-4,6-difluorobenzo[d]thiazol-5-amine

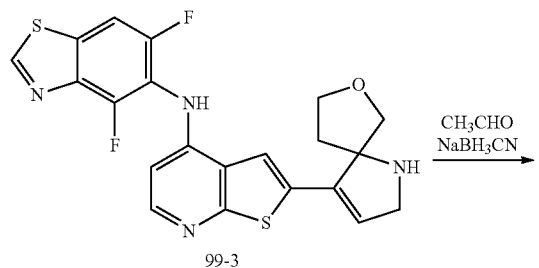

99-3

CH₃CHO
NaBH₃CN

-continued

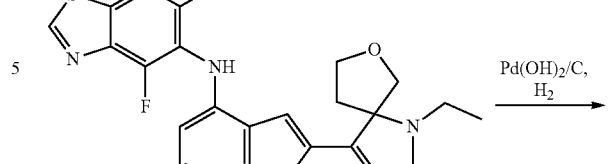

101-3

Pd(OH)₂/C,
H₂

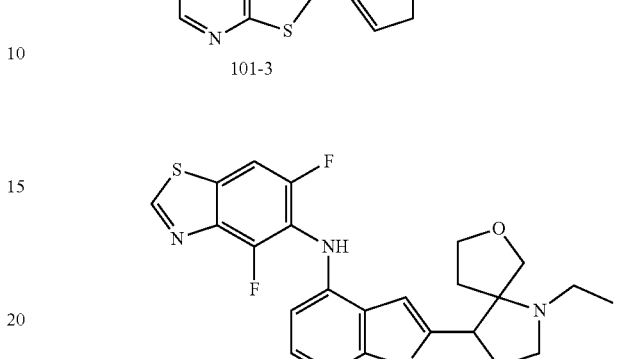

Example 101

Example 101 was prepared from N-(2-(7-oxa-1-azaspiro[4.4]non-3-en-4-yl)thieno[2,3-b]pyridin-4-yl)-4,6-difluorobenzo[d]thiazol-5-amine (99-3) in a manner analogous to the procedures described for Example 83 to afford N-(2-(1-ethyl-7-oxa-1-azaspiro[4.4]nonan-4-yl)thieno[2,3-b]pyridin-4-yl)-4,6-difluorobenzo[d]thiazol-5-amine as an off-white solid. ¹H NMR (400 MHz, Methanol-d₄) δ 9.36 (s, 1H), 8.29 (d, J=6.4 Hz, 1H), 8.02 (dd, J=9.0, 1.8 Hz, 1H), 7.88 (s, 1H), 6.62 (dt, J=6.4, 1.8 Hz, 1H), 4.47-4.28 (m, 1H), 4.23-3.84 (m, 4H), 3.78-3.41 (m, 4H), 2.82-2.19 (m, 4H), 1.47-1.42 (m, 3H). LCMS (ESI, m/z): 473[M+H]⁺.

Example 102: Synthesis of N-(2-(8-oxa-1-azaspiro[4.5]decan-4-yl)thieno[2,3-b]pyridin-4-yl)-4,6-difluorobenzo[d]thiazol-5-amine

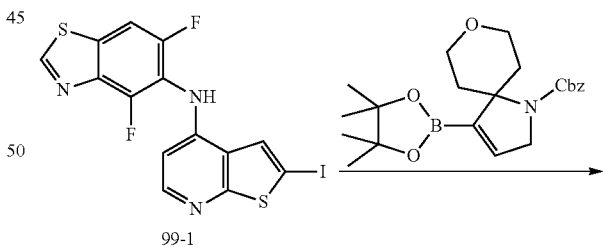

99-1

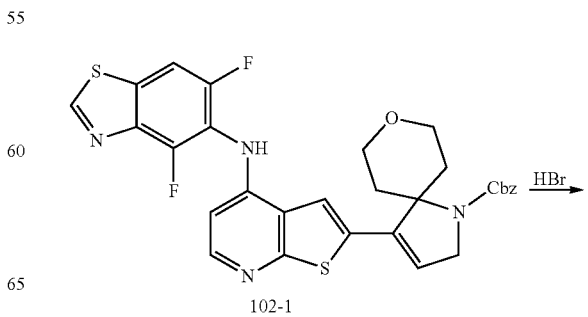

102-1

HBr

-continued

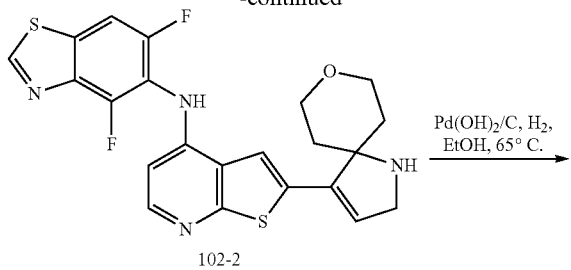
102-2

Pd(OH)₂/C, H₂,
EtOH, 65° C.

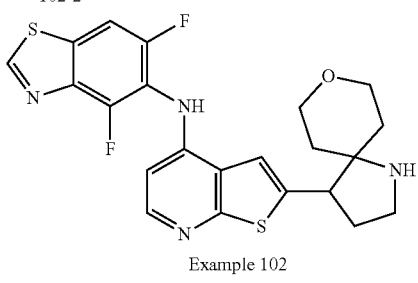
Example 102

N-(2-(8-Oxa-1-azaspiro[4.5]dec-3-en-4-yl)thieno[2,3-b]pyridin-4-yl)-4,6-difluorobenzo[d]thiazol-5-amine (102-2) was prepared following the procedures described for Example 46.

Example 102 was prepared from N-(2-(8-oxa-1-azaspiro[4.5]dec-3-en-4-yl)thieno[2,3-b]pyridin-4-yl)-4,6-difluorobenzo[d]thiazol-5-amine (102-2) in a manner analogous to the procedures described for Example 84 to afford N-(2-(8-oxa-1-azaspiro[4.5]decan-4-yl)thieno[2,3-b]pyridin-4-yl)-4,6-difluorobenzo[d]thiazol-5-amine as a white solid. ¹H NMR (400 MHz, Methanol-d₄) δ 9.34 (s, 1H), 8.11 (d, J=5.6 Hz, 1H), 8.01-7.90 (m, 1H), 7.53 (s, 1H), 6.41-6.35 (m, 1H), 3.93-3.68 (m, 4H), 3.31-3.08 (m, 3H), 2.58-2.42 (m, 1H), 2.39-2.25 (m, 1H), 2.19-2.05 (m, 1H), 1.65-1.55 (m, 1H), 1.52-1.38 (m, 2H). LCMS (ESI, m/z): 459 [M+H]+.

Example 103: Synthesis of 4,6-difluoro-N-(2-(1-methyl-8-oxa-1-azaspiro[4.5]decan-4-yl)thieno[2,3-b]pyridin-4-yl)benzo[d]thiazol-5-amine

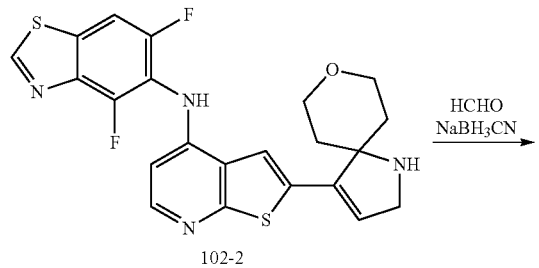
102-2

HCHO
NaBH₃CN

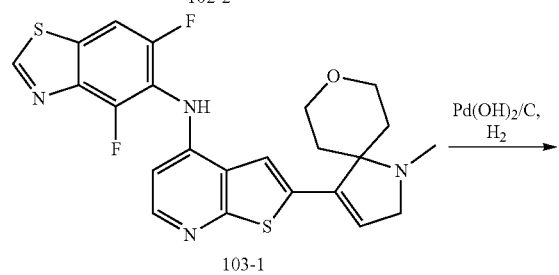
103-1

Pd(OH)₂/C,
H₂

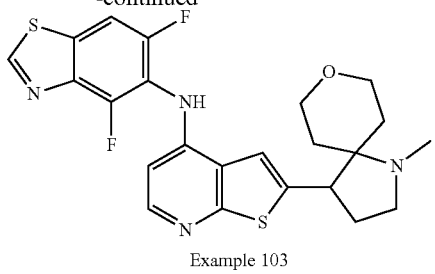
Example 103

Example 103 was prepared from N-(2-(8-oxa-1-azaspiro[4.5]dec-3-en-4-yl)thieno[2,3-b]pyridin-4-yl)-4,6-difluorobenzo[d]thiazol-5-amine (102-2) in a manner analogous to the procedures described for Example 85 to afford 4,6-difluoro-N-(2-(1-methyl-8-oxa-1-azaspiro[4.5]decan-4-yl)thieno[2,3-b]pyridin-4-yl)benzo[d]thiazol-5-amine (21.1 mg, 16%) as a white solid. ¹H NMR (400 MHz, Methanol-d₄) δ 9.33 (s, 1H), 8.06 (d, J=5.6 Hz, 1H), 7.98-7.91 (m, 1H), 7.46 (s, 1H), 6.36-6.30 (m, 1H), 4.08-3.95 (m, 2H), 3.85-3.74 (m, 2H), 3.64-3.54 (m, 1H), 3.33-3.25 (m, 1H), 2.78-2.67 (m, 1H), 2.59-2.45 (m, 1H), 2.41 (s, 3H), 2.07-1.97 (m, 1H), 1.90-1.75 (m, 2H), 1.55-1.30 (m, 2H). LCMS (ESI, m/z): 473 [M+H]+.

Example 104: Synthesis of N-(2-(1-ethyl-8-oxa-1-azaspiro[4.5]decan-4-yl)thieno[2,3-b]pyridin-4-yl)-4,6-difluorobenzo[d]thiazol-5-amine

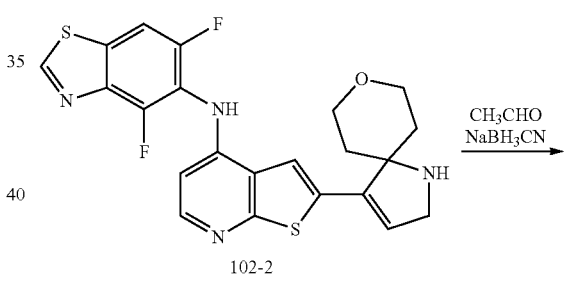
102-2

CH₃CHO
NaBH₃CN

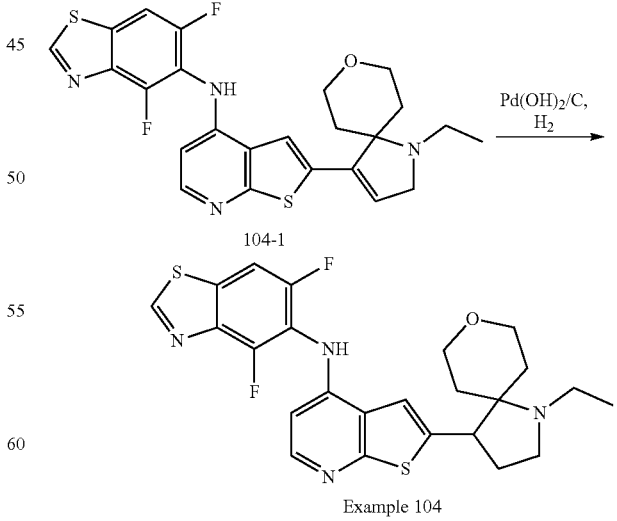
104-1

Pd(OH)₂/C,
H₂

Example 104

Example 104 was prepared from N-(2-(8-oxa-1-azaspiro[4.5]dec-3-en-4-yl)thieno[2,3-b]pyridin-4-yl)-4,6-difluorobenzo[d]thiazol-5-amine (102-2) in a manner analogous to the procedures described for Example 86 to afford N-(2-(1-ethyl-8-oxa-1-azaspiro[4.5]decan-4-yl)thieno[2,3-b]pyridin-4-yl)-4,6-difluorobenzo[d]thiazol-5-amine as a white solid. ¹H NMR (400 MHz, Methanol-d₄) δ 9.28 (s, 1H), 8.01 (d, J=5.6 Hz, 1H), 7.89 (d, J=8.5 Hz, 1H), 7.40 (s, 1H), 6.28 (d, J=5.4 Hz, 1H), 4.02-3.95 (m, 2H), 3.82-3.69 (m, 2H), 3.62-3.51 (m, 1H), 3.51-3.42 (m, 1H), 2.96-2.82 (m, 1H), 2.64-2.33 (m, 3H), 1.98-1.88 (m, 1H), 1.85-1.69 (m, 2H), 1.54-1.47 (m, 1H), 1.40-1.26 (m, 2H), 1.20 (t, J=7.1 Hz, 3H). LCMS (ESI, m/z): 487 [M+H]+.

Example 105: Synthesis of N-(2-(2,3,6,7-tetrahydro-1H-azepin-4-yl)thieno[2,3-b]pyridin-4-yl)benzo[d]thiazol-5-amine

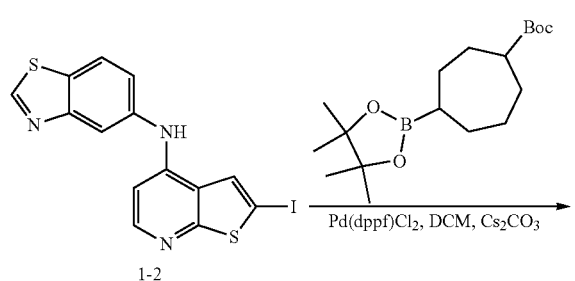

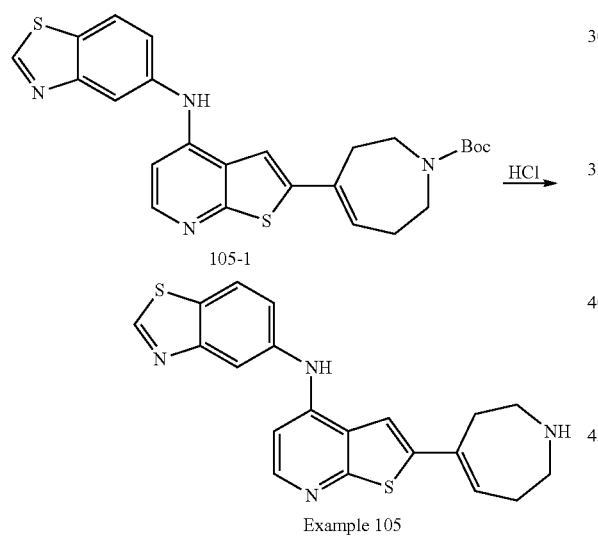

Synthesis of tert-butyl 4-(4-(benzo[d]thiazol-5-ylamino)thieno[2,3-b]pyridin-2-yl)-2,3,6,7-tetrahydro-1H-azepine-1-carboxylate

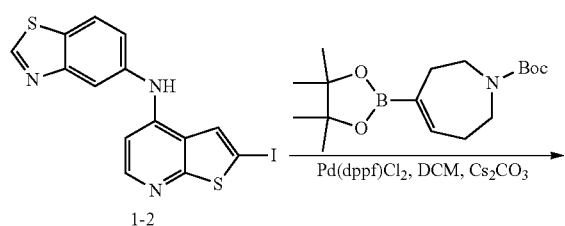

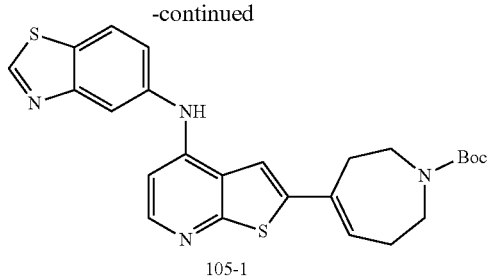

To a solution of N-(2-iodothieno[2,3-b]pyridin-4-yl)benzo[d]thiazol-5-amine (1-2, 844 mg, 2.100 mmol, 1.10 equiv), tert-butyl 4-(4,4,5,5-tetramethyl-1,3,2-dioxaborolan-2-yl)-2,3,6,7-tetrahydroazepine-1-carboxylate (600 mg, 1.860 mmol, 1.00 equiv) and Cs₂CO₃ (1.8 g, 5.570 mmol, 3.00 equiv) in 1,4-dioxane (5.0 mL) and water (0.5 mL) was added Pd(dppf)Cl₂.DCM (151 mg, 0.190 mmol, 0.10 equiv) under nitrogen atmosphere. The resulting mixture was stirred for 4 h at 70° C. LCMS showed the reaction was complete. The resulting mixture was filtered, concentrated, and purified by Prep-TLC with ethyl acetate/petroleum ether (1:1) to afford tert-butyl 4-(4-(benzo[d]thiazol-5-ylamino)thieno[2,3-b]pyridin-2-yl)-2,3,6,7-tetrahydro-1H-azepine-1-carboxylate (105-1, 650 mg, 73%) as a light yellow solid. LCMS (ESI, m/z): 479 [M+H]⁺.

Synthesis of N-(2-(2,3,6,7-tetrahydro-1H-azepin-4-yl)thieno[2,3-b]pyridin-4-yl)benzo[d]thiazol-5-amine

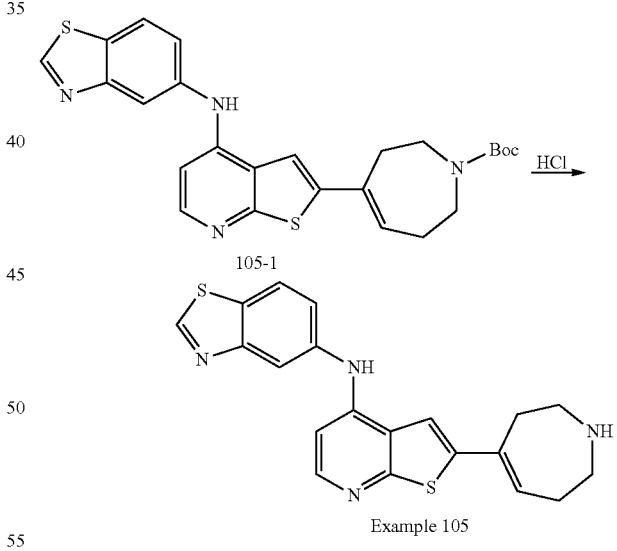

To a solution of the tert-butyl 4-[4-(1,3-benzothiazol-5-ylamino)thieno[2,3-b]pyridin-2-yl]-2,3,6,7-tetrahydroazepine-1-carboxylate (105-1, 80 mg, 0.170 mmol, 1.00 equiv) in 1,4-dioxane (3 mL) was added HCl (4M in 1,4-dioxane, 5 mL). The mixture was stirred at RT until LCMS showed the reaction was complete. The solid was collected by filtration and the crude product was purified by Prep-HPLC (Column: XBridge Shield RP 18 OBD 19×250 mm, 10 um; Mobile Phase A: Water (0.05% TFA), Mobile Phase B: ACN; Flow rate: 25 mL/min; Gradient: 45% B to 55% B in 8 min; 254/210 nm; Rt: 7 min) to afford N-(2-(2, 3,6,7-tetrahydro-1H-azepin-4-yl)thieno[2,3-b]pyridin-4-yl)benzo[d]thiazol-5-amine (Example 105, 37.9 mg, 45%) as a light yellow solid. ¹H NMR (400 MHz, Methanol-d₄) δ 9.37 (s, 1H), 8.28-8.20 (m, 2H), 8.14 (d, J=2.1 Hz, 1H), 7.98 (s, 1H), 7.60-7.57 (m, 1H), 7.05 (d, J=6.9 Hz, 1H), 6.61-6.42 (m, 1H), 4.03 (d, J=6.4 Hz, 1H), 3.53-3.46 (m, 2H), 3.38-3.35 (m, 1H), 3.15-3.05 (m, 2H), 2.79-2.66 (m, 1H), 2.14-2.03 (m, 1H). LCMS (ESI, m/z): 379 [M+H]⁺.

Example 106: Synthesis of N-(2-(1-methyl-2,3,6,7-tetrahydro-1H-azepin-4-yl)thieno[2,3-b]pyridin-4-yl)benzo[d]thiazol-5-amine

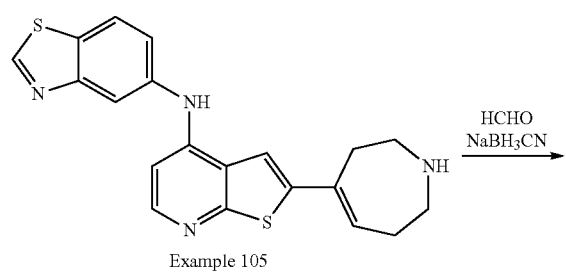

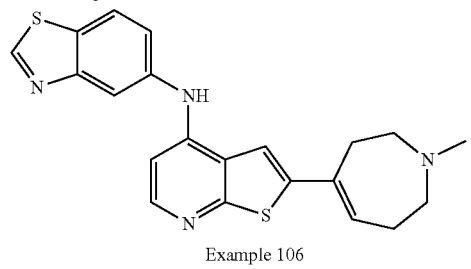

Example 106 was prepared from N-(2-(2,3,6,7-tetrahydro-1H-azepin-4-yl)thieno[2,3-b]pyridin-4-yl)benzo[d]thiazol-5-amine (Example 105) in a manner analogous to the procedures described for Example 2 to afford N-(2-(1-methyl-2,3,6,7-tetrahydro-1H-azepin-4-yl)thieno[2,3-b]pyridin-4-yl)benzo[d]thiazol-5-amine as a light yellow solid. ¹H NMR (400 MHz, Methanol-d₄) δ 9.28 (s, 1H), 8.10-8.06 (m, 2H), 8.01 (s, 1H), 7.63 (s, 1H), 7.52 (dd, J=8.6, 2.0 Hz, 1H), 6.98 (d, J=5.6 Hz, 1H), 6.33 (t, J=6.6 Hz, 1H), 3.35-3.31 (m, 2H), 2.89-2.84 (m, 4H), 2.38 (s, 3H), 1.88 (m, 2H). LCMS (ESI, m/z): 393 [M+H]⁺.

Example 107: Synthesis of 1-(4-(4-(benzo[d]thiazol-5-ylamino)thieno[2,3-b]pyridin-2-yl)-2,3,6,7-tetrahydro-1H-azepin-1-yl)ethan-1-one

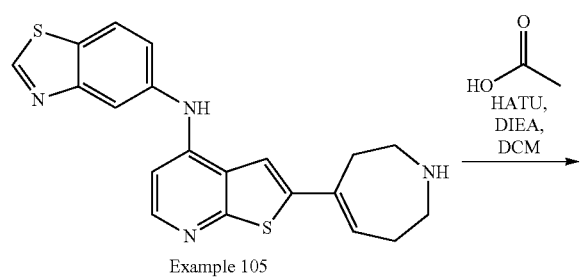

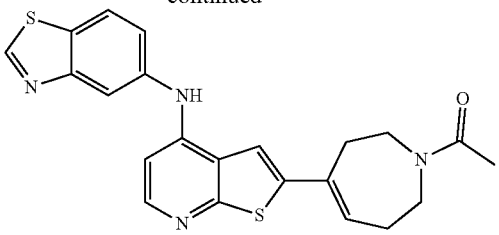

Example 107

Example 107 was prepared from N-(2-(2,3,6,7-tetrahydro-1H-azepin-4-yl)thieno[2,3-b]pyridin-4-yl)benzo[d]thiazol-5-amine (Example 105) in a manner analogous to the procedures described for Example 9 to afford 1-(4-(4-(benzo[d]thiazol-5-ylamino)thieno[2,3-b]pyridin-2-yl)-2,3,6,7-tetrahydro-1H-azepin-1-yl)ethan-1-one (43.4 mg, 22%) as a yellow solid. ¹H NMR (400 MHz, Methanol-d₄) δ 9.38 (s, 1H), 8.25 (d, J=8.4 Hz, 1H), 8.20 (dt, J=7.2, 2.3 Hz, 1H), 8.14 (d, J=2.2 Hz, 1H), 7.84-7.77 (m, 1H), 7.58 (dd, J=8.6, 2.2 Hz, 1H), 7.01 (dd, J=7.0, 2.4 Hz, 1H), 6.53 (t, J=5.6 Hz, 1H), 4.28 (t, J=6.7 Hz, 2H), 3.88-3.73 (m, 2H), 3.00-2.62 (m, 2H), 2.19 (s, 3H), 2.17-2.06 (m, 2H). LCMS (ESI, m/z): 421 [M+H]⁺.

Example 108: Synthesis of Synthesis of N-(2-(azepan-4-yl)thieno[2,3-b]pyridin-4-yl)benzo[d]thiazol-5-amine

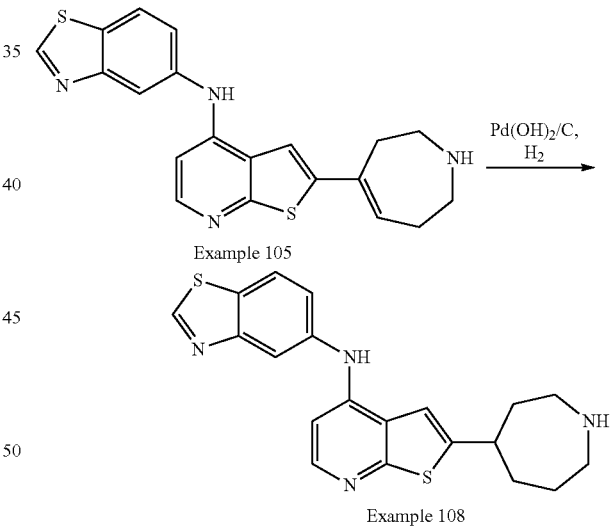

A mixture of N-(2-(2,3,6,7-tetrahydro-1H-azepin-4-yl)thieno[2,3-b]pyridin-4-yl)benzo[d]-thiazol-5-amine (Example 105, 500 mg, 1.320 mmol, 1.00 equiv) and Pd(OH)₂/C (500 mg, 3.570 mmol, 1.00 w/w) in ethanol (5 mL) was stirred at 25° C. for 2 h under H₂ atmosphere (1-3 atm). LCMS showed the reaction was complete. The reaction mixture was filtered through celite and concentrated under reduced pressure. The crude product was purified by flash chromatography (petroleum ether:ethyl acetate=3:1) to give the desired product N-(2-(azepan-4-yl)thieno[2,3-b]pyridin-4-yl)benzo[d]thiazol-5-amine (Example 108, 200 mg, 40%) as a yellow solid. ¹H NMR (400 MHz, Methanol-d₄) δ 9.41 (s, 1H), 8.35-8.22 (m, 2H), 8.16 (d, J=2.0 Hz, 1H), 7.73 (s, 1H), 7.68-7.56 (m, 1H), 7.05 (d, J=7.0 Hz, 1H), 3.58-3.37 (m, 5H), 2.60-2.36 (m, 2H), 2.33-2.13 (m, 2H), 2.13-1.92 (m, 2H). LCMS (ESI, m/z): 381 [M+H]$^+$.

Example 109: Synthesis of N-(2-(1-methylazepan-4-yl)thieno[2,3-b]pyridin-4-yl)benzo[d]thiazol-5-amine

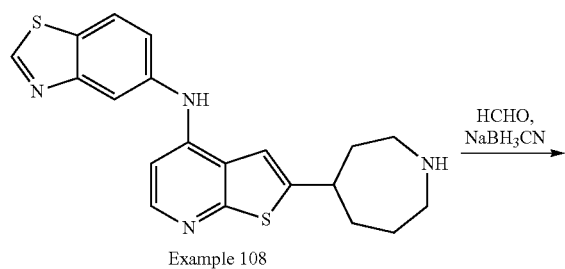

Example 109 was prepared from N-(2-(azepan-4-yl) thieno[2,3-b]pyridin-4-yl)benzo[d]thiazol-5-amine (Example 108) in a manner analogous to the procedures described for Example 2 to afford the desired product N-(2-(1-methylazepan-4-yl)thieno[2,3-b]pyridin-4-yl) benzo[d]thiazol-5-amine (7.9 mg, 15%) as a yellow oil. $^1$H NMR (400 MHz, Methanol-$d_4$) δ 9.41 (s, 1H), 8.28 (dd, J=13.0, 7.8 Hz, 2H), 8.16 (d, J=2.0 Hz, 1H), 7.73 (s, 1H), 7.60 (d, J=8.4 Hz, 1H), 7.05 (d, J=6.9 Hz, 1H), 3.74-3.59 (m, 2H), 3.57-3.42 (m, 2H), 3.40-3.25 (m, 2H), 3.00 (s, 3H), 2.57-2.35 (m, 2H), 2.28-2.12 (m, 2H), 2.11-1.93 (m, 2H). LCMS (ESI, m/z): 395 [M+H]$^+$.

Example 110: Synthesis of N-(2-(1-ethylazepan-4-yl)thieno[2,3-b]pyridin-4-yl)benzo[d]thiazol-5-amine

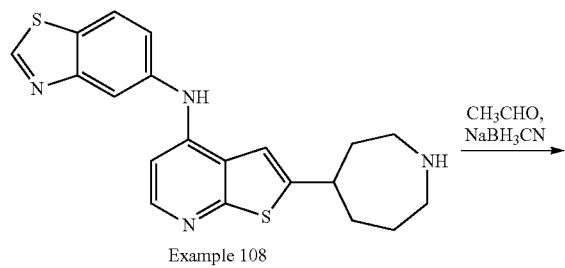

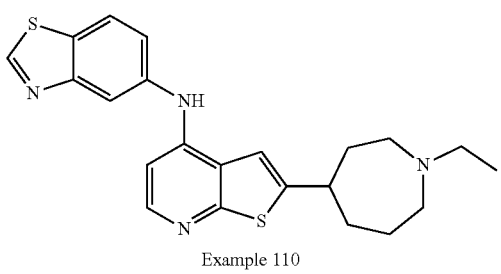

Example 110

Example 110 was prepared from N-(2-(azepan-4-yl) thieno[2,3-b]pyridin-4-yl)benzo[d]thiazol-5-amine (Example 108) in a manner analogous to the procedures described for Example 5 to afford the desired product N-(2-(1-ethylazepan-4-yl)thieno[2,3-b]pyridin-4-yl)benzo [d]thiazol-5-amine (30.7 mg, 28%) as a yellow oil. $^1$H NMR (400 MHz, Methanol-$d_4$) δ 9.41 (s, 1H), 8.36-8.22 (m, 2H), 8.16 (s, 1H), 7.72 (d, J=3.3 Hz, 1H), 7.60 (dd, J=8.6, 2.1 Hz, 1H), 7.05 (dd, J=7.0, 2.2 Hz, 1H), 3.95-3.38 (m, 7H), 2.72-1.72 (m, 6H), 1.58-1.30 (m, 3H). LCMS (ESI, m/z): 409 [M+H]$^+$.

Example 111: Synthesis of 1-(4-(4-(benzo[d]thiazol-5-ylamino)thieno[2,3-b]pyridin-2-yl)azepan-1-yl)ethan-1-one

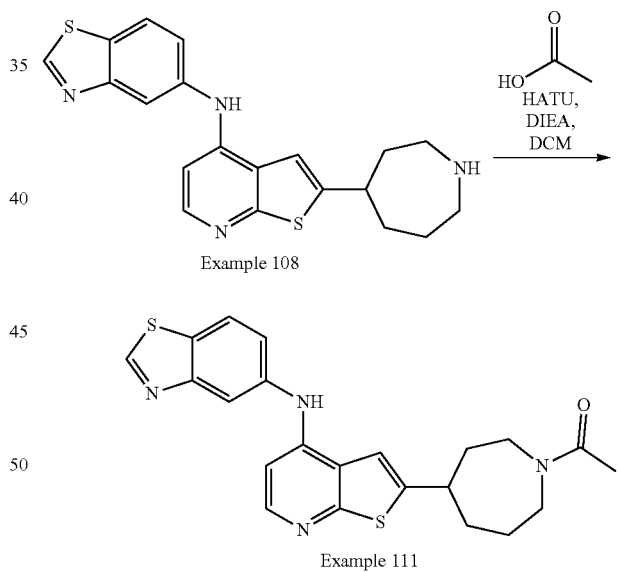

Example 111 was prepared from N-(2-(azepan-4-yl) thieno[2,3-b]pyridin-4-yl)benzo[d]thiazol-5-amine (Example 108) in a manner analogous to the procedures described for Example 9 to afford the desired product 1-(4-(4-(benzo[d]thiazol-5-ylamino)thieno[2,3-b]pyridin-2-yl)azepan-1-yl)ethan-1-one as a yellow oil. $^1$H NMR (400 MHz, Methanol-$d_4$) δ 9.41 (s, 1H), 8.30-8.22 (m, 2H), 8.16 (s, 1H), 7.70-7.60 (m, 1H), 7.05-7.04 (m, 1H), 4.00-3.82 (m, 1H), 3.73-3.50 (m, 3H), 3.28-3.25 (m, 1H), 2.35-2.26 (m, 2H), 2.20 (s, 3H), 1.98-1.83 (m, 4H). LCMS (ESI, m/z): 423 [M+H]$^+$

Example 112: Synthesis of N-(2-(2,5,6,7-tetrahydro-1H-azepin-3-yl)thieno[2,3-b]pyridin-4-yl)benzo[d]thiazol-5-amine

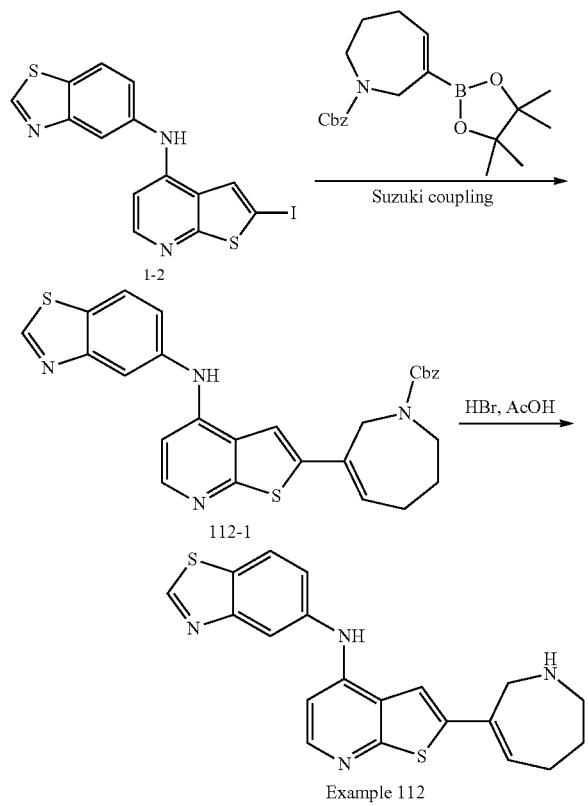

Synthesis of benzyl 6-(4-(benzo[d]thiazol-5-ylamino)thieno[2,3-b]pyridin-2-yl)-2,3,4,7-tetrahydro-1H-azepine-1-carboxylate

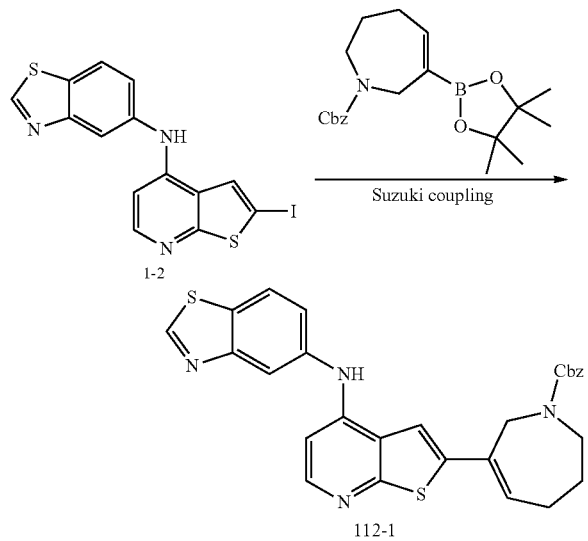

A mixture of N-(2-iodothieno[2,3-b]pyridin-4-yl)benzo[d]thiazol-5-amine (1-2, 500 mg, 0.730 mmol, 1.00 equiv), benzyl 6-(4,4,5,5-tetramethyl-1,3,2-dioxaborolan-2-yl)-2,3,4,7-tetra-hydroazepine-1-carboxylate (262 mg, 0.730 mmol 1.00 equiv), Pd(dppf)Cl$_2$ (26.8 mg, 0.040 mmol, 0.10 equiv), Cs$_2$CO$_3$ (716 mg, 2.20 mmol, 3.00 equiv) in 1,4-dioxane (4 mL) and water (1 mL) was stirred at 100° C. for 2 h under nitrogen atmosphere. LCMS showed the reaction was complete. The mixture was quenched with water (100 mL) and extracted with ethyl acetate (3×50 mL). The combined organic layer was washed with brine, concentrated and purified by flash chromatography on silica gel (petroleum ether/ethyl acetate=3/1) to afford the desired product benzyl 6-(4-(benzo[d]thiazol-5-ylamino)thieno[2,3-b]pyridin-2-yl)-2,3,4,7-tetrahydro-1H-azepine-1-carboxylate (112-1, 320 mg, 50%) as a brown solid. LCMS (ESI, m/z): 513 [M+H]$^+$.

Synthesis of N-(2-(2,5,6,7-tetrahydro-1H-azepin-3-yl)thieno[2,3-b]pyridin-4-yl)benzo[d]thiazol-5-amine

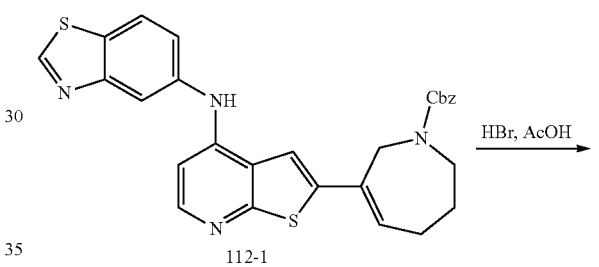

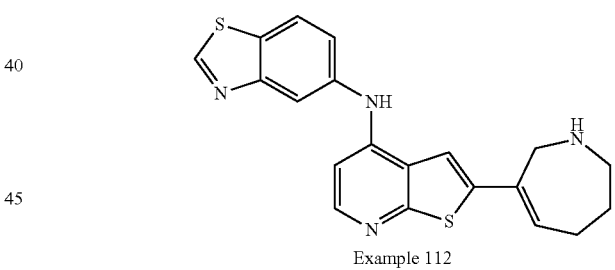

A mixture of benzyl 6-(4-(benzo[d]thiazol-5-ylamino)thieno[2,3-b]pyridin-2-yl)-2,3,4,7-tetrahydro-1H-azepine-1-carboxylate (112-1, 80 mg, 0.160 mmol 1.00 equiv) and HBr (30% in acetic acid, 4 mL) was stirred at 25° C. for 0.5 hours. LCMS showed the reaction was complete. The mixture was quenched with water (50 ml) and extracted with ethyl acetate (3×50 ml). The combined organic layer was washed with brine, concentrated and purified by Prep-HPLC to afford the desired product N-(2-(2,5,6,7-tetrahydro-1H-azepin-3-yl)thieno[2,3-b]pyridin-4-yl)benzo[d]thiazol-5-amine (Example 112, 24.9 mg, 41%) as a white solid. $^1$H NMR (400 MHz, Methanol-d$_4$) δ $^1$H NMR (400 MHz, Methanol-d$_4$) δ 9.31 (s, 1H), 8.10-8.07 (m, 2H), 8.05 (s, 1H), 7.57 (s, 1H), 7.54 (d, J=9.1 Hz, 1H), 7.01 (d, J=5.8 Hz, 1H), 6.58 (t, J=6.4 Hz, 1H), 3.98 (s, 2H), 3.20 (t, J=5.7 Hz, 2H), 2.56 (dd, J=11.0, 6.3 Hz, 2H), 1.85 (dt, J=10.1, 4.9 Hz, 2H). LCMS (ESI, m/z): 379 [M+H]$^+$.

Example 113: Synthesis of N-(2-(1-methyl-2,5,6,7-tetrahydro-1H-azepin-3-yl)thieno[2,3-b]pyridin-4-yl)benzo[d]thiazol-5-amine

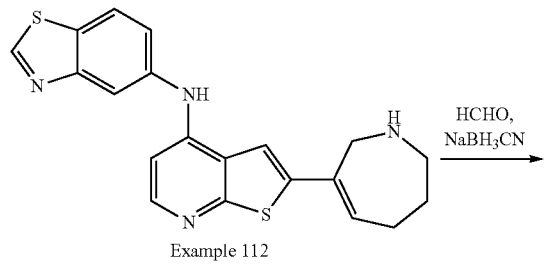

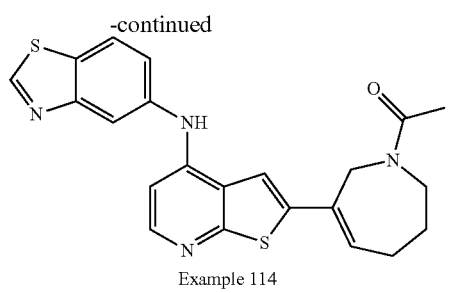

Example 114

Example 114 was prepared from N-(2-(2,5,6,7-tetrahydro-1H-azepin-3-yl)thieno[2,3-b]pyridin-4-yl)benzo[d]thiazol-5-amine (Example 112) in a manner analogous to the procedures described for Example 9 to afford product 1-(6-(4-(benzo[d]thiazol-5-ylamino)thieno[2,3-b]pyridin-2-yl)-2,3,4,7-tetrahydro-1H-azepin-1-yl)ethan-1-one (20.6 mg, 25%) as a white solid. $^1$H NMR (400 MHz, Methanol-$d_4$) δ 9.30 (s, 1H), 8.25-8.11 (m, 2H), 8.09 (s, 1H), 7.80 (s, 1H), 7.59 (s, 1H), 7.58-7.49 (m, 1H), 6.95-6.92 (m, 1H), 6.56-6.28 (m, 1H), 4.61-4.53 (m, 2H), 3.80-3.72 (m, 2H), 2.52-2.37 (m, 2H), 2.10-2.20 (m, 3H). 2.01-1.87 (m, 2H). LCMS (ESI, m/z): 421 [M+H]$^+$.

Example 115: Synthesis of N-(2-(2-methylazepan-3-yl)thieno[2,3-b]pyridin-4-yl)benzo[d]thiazol-5-amine Example 113 was prepared from N-(2-(2,5,6,7-tetrahydro-1H-azepin-3-yl)thieno[2,3-b]pyridin-4-yl)benzo[d]thiazol-5-amine (Example 112) in a manner analogous to the procedures described for Example 2 to afford the desired product N-(2-(1-methyl-2,5,6,7-tetrahydro-1H-azepin-3-yl)thieno[2,3-b]pyridin-4-yl)benzo[d]thiazol-5-amine as a white solid. $^1$H NMR (400 MHz, Methanol-$d_4$) δ 9.40 (s, 1H), 8.32-8.21 (m, 2H), 8.15 (d, J=2.1 Hz, 1H), 7.91 (s, 1H), 7.60 (d, J=8.6 Hz, 1H), 7.06 (d, J=6.6 Hz, 1H), 6.96 (t, J=6.6 Hz, 1H), 4.56-4.48 (s, 1H), 3.68-3.63 (s, 1H), 3.10 (s, 3H), 2.72 (q, J=5.5 Hz, 2H), 2.20-1.90 (s, 3H). $^{19}$F NMR (376 MHz, Methanol-$d_4$) δ −77.06. LCMS (ESI, m/z): 393 [M+H]$^+$.

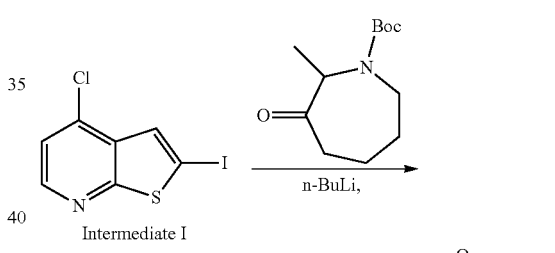

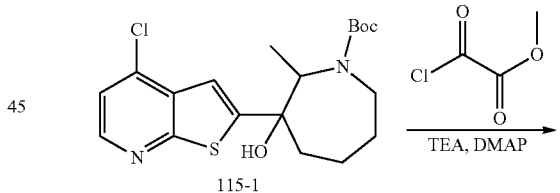

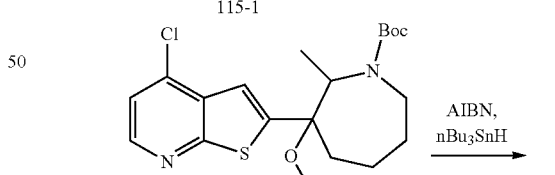

Example 114: Synthesis of 1-(6-(4-(benzo[d]thiazol-5-ylamino)thieno[2,3-b]pyridin-2-yl)-2,3,4,7-tetrahydro-1H-azepin-1-yl)ethan-1-one

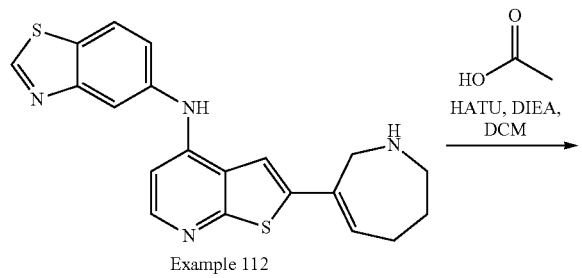

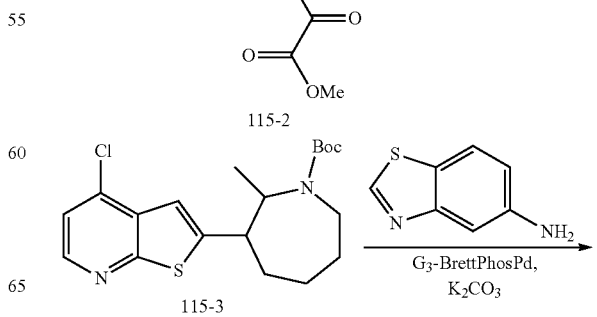

-continued

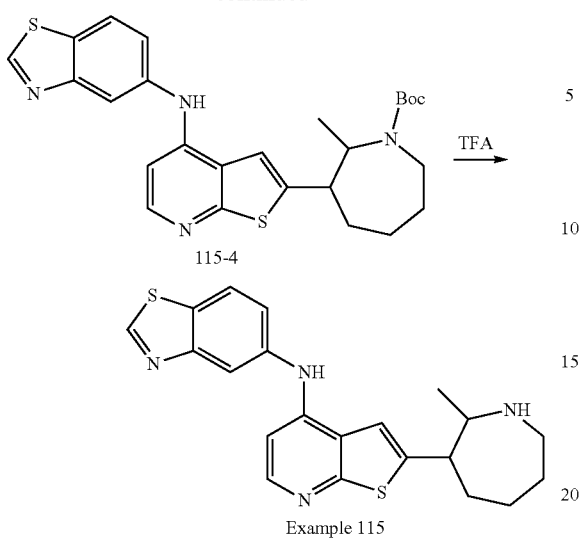

Example 115

Synthesis of tert-butyl 3-(4-chlorothieno[2,3-b]pyridin-2-yl)-3-hydroxy-2-methylazepane-1-carboxylate

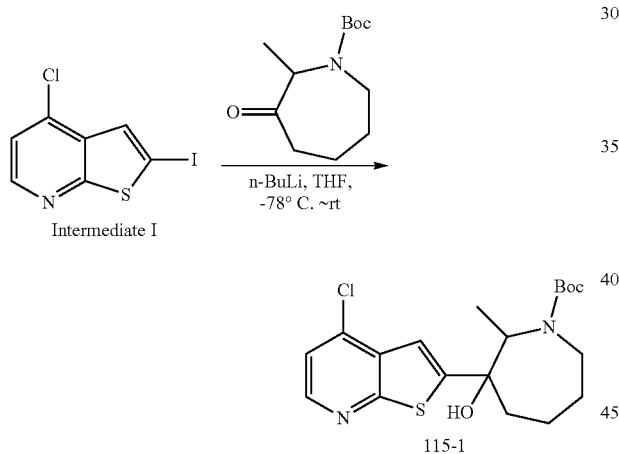

To a solution of 4-chloro-2-iodo-thieno[2,3-b]pyridine (intermediate I, 2.0 g, 6.770 mmol, 1.00 equiv) in THF (120.0 mL) was added n-BuLi (2.5 M in hexane, 7.6 mL, 6.770 mmol, 1.00 equiv) dropwise at −78° C. under nitrogen atmosphere. The resulting mixture was stirred at −78° C. for 1 h. A solution of tert-butyl 2-methyl-3-oxoazepane-1-carboxylate (5.2 g, 935.600 mmol, 2.00 equiv) in THF (20.0 mL) was added dropwise and the reaction solution was stirred at −78° C. for 1 h. LCMS showed the reaction was complete. The resulting mixture was quenched with NH₄Cl (sat. aq, 300.0 mL) and extracted with ethyl acetate (3×200.0 mL). The combined organic layer was dried over Na₂SO₄, filtered and concentrated under reduced pressure. The residue was purified by flash chromatography on silica gel with ethyl acetate/petroleum ether (1:15) to give tert-butyl 3-(4-chlorothieno[2,3-b]pyridin-2-yl)-3-hydroxy-2-methylazepane-1-carboxylate (115-1, 2.7 g, 97%) as a light yellow solid. LCMS (ESI, m/z): 397 [M+H]⁺.

Synthesis of 1-(tert-butoxycarbonyl)-3-(4-chlorothieno[2,3-b]pyridin-2-yl)-2-methylazepan-3-yl methyl oxalate

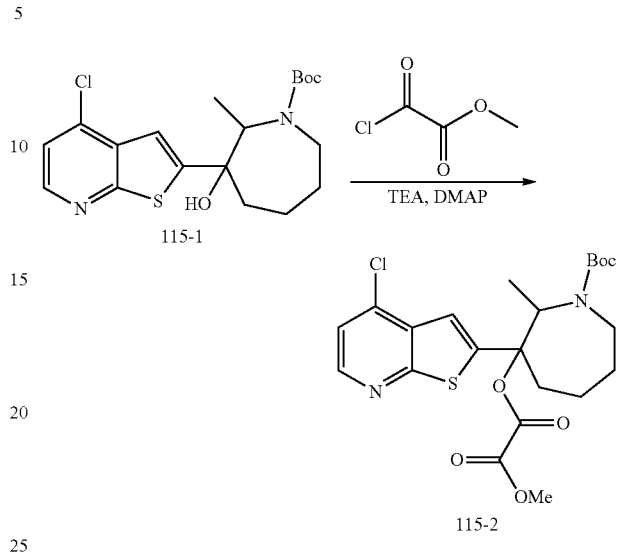

To a stirred solution of tert-butyl 3-(4-chlorothieno[2,3-b]pyridin-2-yl)-3-hydroxy-2-methylazepane-1-carboxylate (115-1, 5.6 g, 14.110 mmol, 1.00 equiv) in DCM (50.0 mL) was added methyl 2-chloro-2-oxo-acetate (3.4 g, 28.220 mmol, 2.00 equiv), TEA (5.9 mL, 42.320 mmol, 3.00 equiv) and DMAP (0.1 g, 0.710 mmol, 0.05 equiv) at RT. After stirring for 2 h, LCMS showed the reaction was complete. The reaction mixture was diluted with DCM and washed with NaHCO₃ and brine, dried over Na₂SO₄, filtered and concentrated under reduced pressure. The crude product was purified by flash chromatography on silica gel with petroleum ether/ethyl acetate (16:1) to give 1-(tert-butoxycarbonyl)-3-(4-chlorothieno[2,3-b]pyridin-2-yl)-2-methylazepan-3-yl methyl oxalate (115-2, 6.1 g, 51%) as a light yellow solid. LCMS (ESI, m/z): 483 [M+H]⁺.

Synthesis of tert-butyl 3-(4-chlorothieno[2,3-b]pyridin-2-yl)-2-methylazepane-1-carboxylate

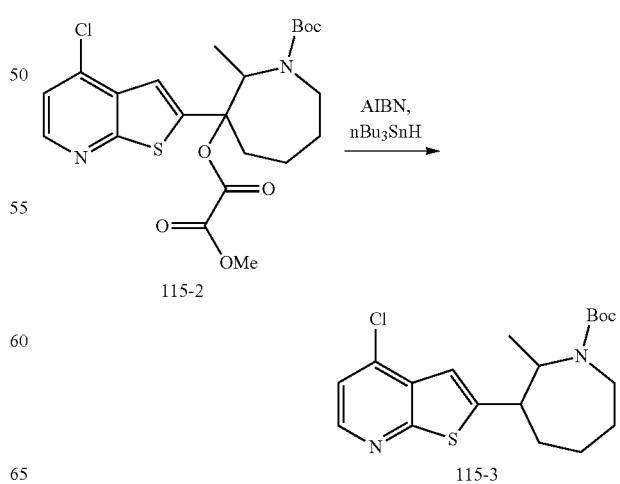

A solution of 1-(tert-butoxycarbonyl)-3-(4-chlorothieno[2,3-b]pyridin-2-yl)-2-methyl-azepan-3-yl methyl oxalate (115-2, 0.5 g, 1.040 mmol, 1.00 equiv) and tributyltin hydride (0.6 g, 2.070 mmol, 2.00 equiv) in toluene (20.0 mL) was degassed by bubbling with N₂ for 15 min. Then the resulting mixture was stirred at 90° C. and AIBN (0.2 g, 1.040 mmol, 0.25 equiv) was added every hour. After 2 h, LCMS showed the reaction was complete. The solvent was removed under reduced pressure. The residue was redissolved in DCM (100 mL), washed with KF (aq., 150 mL), dried over Na₂SO₄, filtered and concentrated under reduced pressure. The crude product was purified by flash chromatography on silica gel with petroleum ether/ethyl acetate (33:1) to give tert-butyl 3-(4-chlorothieno[2,3-b]pyridin-2-yl)-2-methylazepane-1-carboxylate (115-3, 205 mg, 59%) as a light yellow solid. LCMS (ESI, m/z): 381 [M+H]⁺.

Synthesis of tert-butyl 3-(4-(benzo[d]thiazol-5-ylamino)thieno[2,3-b]pyridin-2-yl)-2-methyl-azepane-1-carboxylate

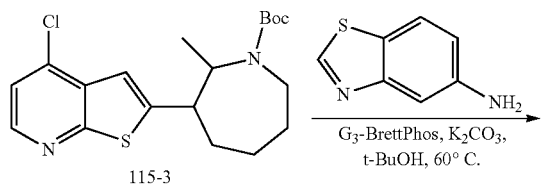

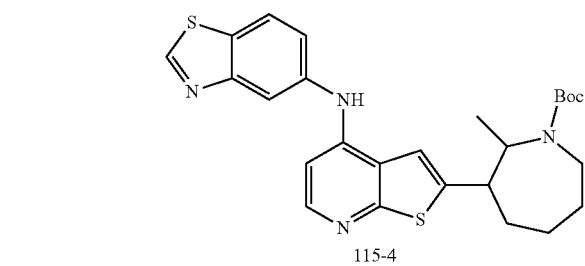

To a solution of tert-butyl 3-(4-chlorothieno[2,3-b]pyridin-2-yl)-2-methylazepane-1-carboxylate (115-3, 0.1 g, 0.360 mmol, 1.00 equiv), K₂CO₃ (0.3 g, 1.780 mmol, 5.00 equiv), 1,3-benzothiazol-5-amine (0.1 g, 0.360 mmol, 1.05 equiv) in tert-butanol (1.5 mL) was added G3-Brettphos (0.1 g, 0.360 mmol, 0.10 equiv) under N₂ atmosphere. The resulting mixture was stirred overnight at 65° C. TLC and LCMS showed the reaction was complete. The reaction mixture was filtered and concentrated under reduced pressure. The residue was purified by Prep-TLC with ethyl acetate to give tert-butyl 3-(4-(benzo[d]thiazol-5-ylamino)thieno[2,3-b]pyridin-2-yl)-2-methylazepane-1-carboxylate (115-4, 295 mg, 78%) as a light yellow solid. LCMS (ESI, m/z): 495 [M+H]⁺.

Synthesis of N-(2-(2-methylazepan-3-yl)thieno[2,3-b]pyridin-4-yl)benzo[d]thiazol-5-amine

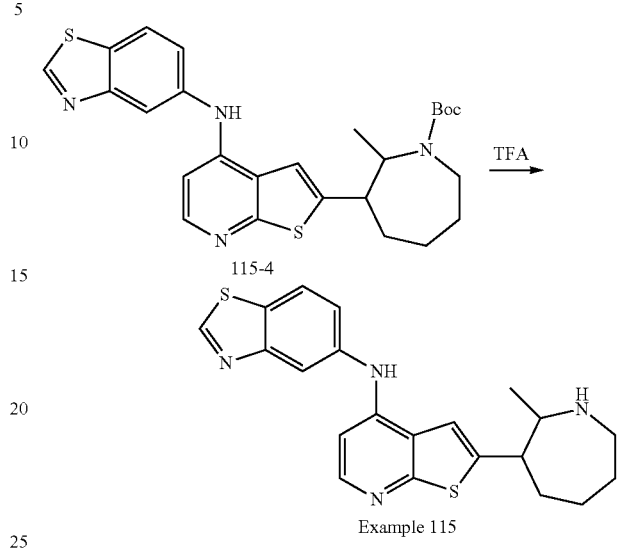

To a solution of tert-butyl 3-(4-(benzo[d]thiazol-5-ylamino)thieno[2,3-b]pyridin-2-yl)-2-methylazepane-1-carboxylate (115-4, 295 mg, 0.600 mmol, 1.00 equiv) in DCM (10.0 mL) was added TFA (5.0 mL). The resulting solution was stirred at room temperature for 30 min. LCMS showed the reaction was complete. The solvent was removed under reduced pressure and the crude product was purified by chiral HPLC (Column: Chiral pak IC, 2×25 cm, 5 um; Mobile Phase A: Hex (8 mmol/L NH₃.MeOH), Mobile Phase B: EtOH; Flow rate: 20 mL/min; hold at 30% B for 16 min; 220/254 nm).

Example 115a

White solid. ¹H NMR (400 MHz, Methanol-d₄) δ 9.30 (s, 1H), 8.14-8.08 (m, 2H), 8.02 (d, J=2.1 Hz, 1H), 7.54 (dd, J=8.6, 2.1 Hz, 1H), 7.40 (s, 1H), 7.01 (d, J=5.7 Hz, 1H), 3.27-3.14 (m, 1H), 3.14-3.03 (m, 1H), 3.01-2.84 (m, 2H), 2.15-2.06 (m, 1H), 2.06-1.89 (m, 2H), 1.89-1.69 (m, 3H), 1.17 (d, J=6.3 Hz, 3H). LCMS (ESI, m/z): 395 [M+H]⁺. Chiral Analytic Conditions: Column: Chiralpak IC-3 4.6×50 mm, 3 um; Mobile phase: Hex (0.1% DEA):EtOH=70:30; Flow rate: 1.00 mL/min; 254/210 nm; Rt: 1.916 min.

Example 115b

White solid. ¹H NMR (300 MHz, Methanol-d₄) δ 9.28 (s, 1H), 8.12-8.05 (m, 2H), 8.01 (s, 1H), 7.54 (d, J=2.1 Hz, 1H), 7.51 (s, 1H), 7.37 (s, 1H), 6.99 (s, 1H), 3.30-2.80 (m, 4H), 2.20-1.70 (m, 6H), 1.14 (d, J=6.2 Hz, 3H). LCMS (ESI, m/z): 393 [M−H]⁻. Chiral Analytic Conditions: Column: IC-3 4.6×50 mm, 3 um; Mobile Phase: Hex (0.1% DEA):EtOH=70:30; Flow rate: 1 mL/min; Rt: 2.089 min.

Example 115c

White solid. ¹H NMR (400 MHz, Methanol-d₄) δ 9.30 (s, 1H), 8.18-8.07 (m, 2H), 8.02 (d, J=2.1 Hz, 1H), 7.54 (dd, J=8.6, 2.1 Hz, 1H), 7.44 (s, 1H), 7.02 (d, J=5.7 Hz, 1H), 3.60-3.50 (m, 2H), 3.27-3.10 (m, 1H), 3.10-2.96 (m, 1H), 2.33-2.16 (m, 1H), 2.19-1.85 (m, 3H), 1.85-1.68 (m, 2H), 1.12 (d, J=6.6 Hz, 3H). LCMS (ESI, m/z): 395 [M+H]⁺. Chiral Analytic Conditions: Column: Chiralpak IC-3 4.6×50 mm, 3 um; Mobile phase: Hex (0.1% DEA):EtOH=70:30; Flow rate: 1.00 mL/min; 254/210 nm; Rt: 2.370 min.

Example 115d

White solid. ¹H NMR (300 MHz, Methanol-d₄) δ 9.28 (s, 1H), 8.10 (s, 1H), 8.08 (d, J=2.6 Hz, 1H), 8.01 (d, J=2.0 Hz, 1H), 7.52 (dd, J=8.4, 2.0 Hz, 1H), 7.39 (s, 1H), 6.99 (d, J=5.7 Hz, 1H), 3.49-3.38 (m, 2H), 3.20-3.04 (m, 1H), 3.01-2.81 (m, 1H), 2.27-2.13 (m, 1H), 2.09-1.82 (m, 3H), 1.80-1.62 (m, 2H), 1.05 (d, J=6.4 Hz, 3H). LCMS (ESI, m/z): 395 [M+H]⁺. Chiral analytic Conditions: Column: IC-3 4.6×50 mm, 3 um; Mobile Phase Hex (0.1% DEA):EtOH=70:30; Flow rate: 1 mL/min; Rt: 2.948 min.

Example 116: Synthesis of N-(2-(1,2-dimethylazepan-3-yl)thieno[2,3-b]pyridin-4-yl)benzo[d]thiazol-5-amine

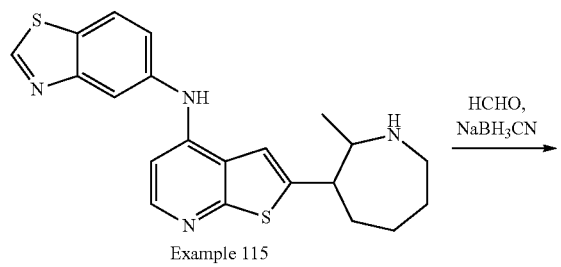

Example 115

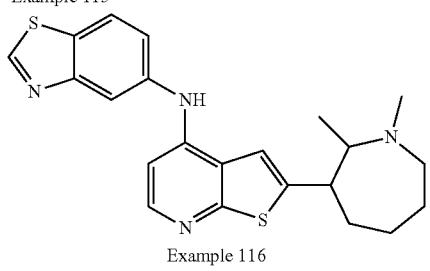

Example 116

Examples 116a-d were prepared from single enantiomers Examples 115a-d following the procedure described for Example 2.

Example 116a

White solid. ¹H NMR (400 MHz, Methanol-d₄) δ 9.30 (s, 1H), 8.15-8.06 (m, 2H), 8.02 (d, J=2.1 Hz, 1H), 7.54 (dd, J=8.6, 2.1 Hz, 1H), 7.38 (s, 1H), 7.01 (d, J=5.7 Hz, 1H), 3.22-3.00 (m, 3H), 2.87-2.76 (m, 1H), 2.52 (s, 3H), 2.19-2.06 (m, 1H), 2.05-1.90 (m, 2H), 1.90-1.80 (m, 1H), 1.79-1.58 (m, 2H), 1.13 (d, J=6.3 Hz, 3H). LCMS (ESI, m/z): 409 [M+H]⁺. Chiral Analytic Conditions: Column: Chiralpak IA-3 4.6×50 mm, 3 um; Mobile phase: Hex (0.1% DEA):EtOH=80:20; Flow rate: 1.00 mL/min; 254/210 nm; Rt: 2.837 min.

Example 116b

White solid. ¹H NMR (300 MHz, Methanol-d₄) δ 9.43 (s, 1H), 8.35-8.25 (m, 2H), 8.17 (d, J=2.0 Hz, 1H), 7.91 (d, J=7.6 Hz, 1H), 7.63 (dd, J=8.6, 2.1 Hz, 1H), 7.05 (d, J=7.0 Hz, 1H), 3.97-3.83 (m, 1H), 3.71-3.48 (m, 2H), 3.45-3.34 (m, 1H), 3.05 (d, J=38.3 Hz, 3H), 2.57-2.38 (m, 1H), 2.31-2.00 (m, 4H), 1.92-1.72 (m, 1H), 1.44 (d, J=6.6 Hz, 3H). LCMS (ESI, m/z): 409 [M+H]⁺. Chiral analytic Conditions: Column: CHIRALPAK AD 3 3×100 mm, 3 um; Mobile Phase A: CO₂, Mobile Phase B: MeOH (0.1% DEA); Flow rate: 2.00 mL/min; Gradient: 10% B to 50% B in 4 min; 254/210 nm; Rt: 4.157 min.

Example 116c

White solid. ¹H NMR (400 MHz, Methanol-d₄) δ 9.32 (s, 1H), 8.20-8.07 (m, 2H), 8.01 (d, J=2.1 Hz, 1H), 7.59-7.48 (m, 2H), 7.03 (d, J=5.7 Hz, 1H), 3.83 (s, 2H), 3.57-3.41 (m, 2H), 3.01 (s, 3H), 2.28 (d, J=9.8 Hz, 2H), 2.16-2.03 (m, 1H), 1.51-1.38 (m, 3H). LCMS (ESI, m/z): 409 [M+H]⁺. Chiral Analytic Conditions: Column: Chiralpak IA-3 4.6×50 mm, 3 um; Mobile phase: Hex (0.1% DEA):EtOH=80:20; Flow rate: 1.00 mL/min; 254/210 nm; Rt: 3.230 min.

Example 116d

White solid. ¹H NMR (400 MHz, Methanol-d₄) δ 9.40 (s, 1H), 8.35-8.25 (m, 2H), 8.15 (d, J=2.0 Hz, 1H), 7.85 (d, J=11.7 Hz, 1H), 7.60 (dd, J=9.0, 1.7 Hz, 1H), 7.05 (d, J=6.9 Hz, 1H), 4.21-3.82 (m, 2H), 3.78-3.43 (m, 3H), 3.15 (s, 1H), 2.97 (d, J=42.5 Hz, 2H), 2.38-2.24 (m, 2H), 2.22-1.94 (m, 4H), 1.53-1.44 (m, 3H). LCMS (ESI, m/z): 409 [M+H]⁺. Chiral analytic conditions: Column: CHIRALPAK AD 3 3×100 mm, 3 um; Mobile Phase A: CO₂, Mobile Phase B: MeOH (0.1% DEA); Flow rate: 2.00 mL/min; Gradient: 10% B to 50% B in 4 min; 254/210 nm; Rt: 3.561 min.

Example 117: Synthesis of 6-fluoro-N-(2-(2-methylazepan-3-yl)thieno[2,3-b]pyridin-4-yl)benzo[d]thiazol-5-amine

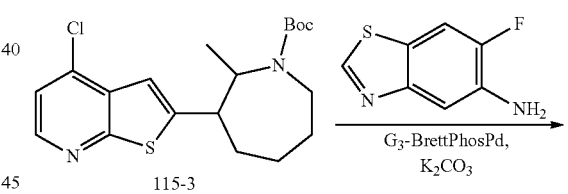

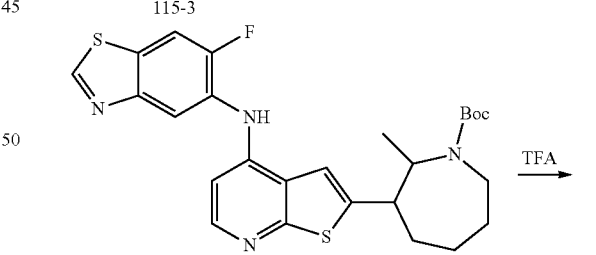

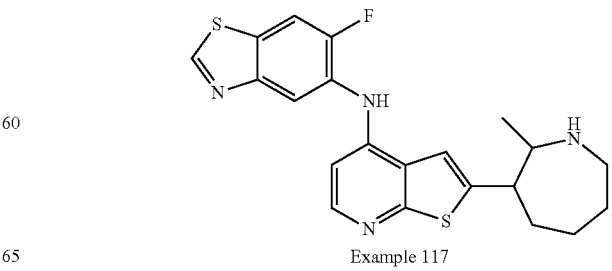

Example 117

Example 117 was prepared from tert-butyl 3-(4-chloro-thieno[2,3-b]pyridin-2-yl)-2-methylazepane-1-carboxylate (115-3) in a manner analogous to the procedures described for Example 115.

Isomers were separated by Prep Chiral-HPLC using the following condition: Column: CHIRALPAK IA, 2×25 cm, 5 um; Mobile Phase A: Hex (8 mmol/L NH$_3$.MeOH), Mobile Phase B: EtOH; Flow rate: 20 mL/min; hold at 30% B for 11.5 min.

Example 117a

White solid. $^1$H NMR (400 MHz, Methanol-d$_4$) δ 9.28 (s, 1H), 8.15-8.00 (m, 3H), 7.45 (s, 1H), 6.65 (dd, J=5.7, 2.1 Hz, 1H), 3.42 (ddd, J=34.6, 9.2, 4.6 Hz, 1H), 3.40-3.30 (m, 2H), 3.18 (dtd, J=18.8, 9.8, 9.1, 3.9 Hz, 2H), 2.22-1.75 (m, 6H), 1.31 (d, J=6.5 Hz, 3H). LCMS (ESI, m/z): 429 [M+H]$^+$. Chiral analytic conditions: CHIRALPAK IA-3, 0.46×50 cm, 3 um; Mobile Phase: Hex (0.1% DEA):EtOH=80:20; Flow rate: 1 mL/min; 254 nm; RT: 2.701 min.

Example 117b

White solid. $^1$H NMR (400 MHz, Methanol-d$_4$) δ 9.30 (s, 1H), 8.17 (d, J=5.9 Hz, 1H), 8.14-8.04 (m, 2H), 7.57 (s, 1H), 6.69 (d, J=5.8 Hz, 1H), 3.99-4.90 (m, 1H), 3.80-3.75 (m, 1H), 3.40-3.30 (m, 2H), 2.40-1.85 (m, 6H), 1.33 (d, J=7.0 Hz, 3H). $^{19}$F NMR (376 MHz, Methanol-d$_4$) δ −76.974, −124.840. LCMS (ESI, m/z): 429 [M+H]$^+$. Chiral analytic conditions: CHIRALPAK IA-3, 0.46×5 cm, 3 um; Mobile Phase: Hex (0.1% DEA): EtOH=80:20; Flow rate: 1 mL/min; 254 nm; RT: 4.696 min.

Example 117c

White solid. $^1$H NMR (400 MHz, Methanol-d$_4$) δ 9.27 (s, 1H), 8.15-7.99 (m, 3H), 7.38 (d, J=0.8 Hz, 1H), 6.62 (dd, J=5.7, 2.1 Hz, 1H), 3.48-3.36 (m, 2H), 3.18-3.08 (m, 1H), 2.94-2.83 (m, 1H), 2.27-2.12 (m, 1H), 2.08-1.82 (m, 3H), 1.76-1.63 (m, 2H), 1.03 (d, J=6.7 Hz, 1H). LCMS (ESI, m/z): 413 [M+H]$^+$. Chiral analytic Conditions: Column: DAICEL DCpak SFC-B 4.6×150 mm, 5 um; Mobile Phase A: CO$_2$, Mobile Phase B: MeOH (0.2% NH$_4$OH); Flow rate: 4.00 mL/min; Gradient: 10% B to 50% B in 4 min, and then hold at 50% B for 2 min; 254/210 nm; Rt: 3.283 min.

Example 117d

White solid. $^1$H NMR (400 MHz, Methanol-d$_4$) δ 9.28 (s, 1H), 8.15-8.01 (m, 3H), 7.39 (s, 1H), 6.63 (dd, J=5.7, 2.1 Hz, 1H), 3.26-3.17 (m, 1H), 3.17-3.07 (m, 1H), 3.03-2.89 (m, 2H), 2.25-2.07 (m, 1H), 2.06-1.92 (m, 2H), 1.89-1.71 (m, 3H), 1.19 (d, J=6.3 Hz, 3H). LCMS (ESI, m/z): 413 [M+H]$^+$. Chiral analytic Conditions: Column: DAICEL DCpak SFC-B 4.6×150 mm, 5 um; Mobile Phase A: CO$_2$, Mobile Phase B: MeOH (0.2% NH$_4$OH); Flow rate: 4.00 mL/min; isocratic elution at 50% B; 254/210 nm; Rt: 3.616 min.

Example 118: Synthesis of 4,6-difluoro-N-(2-(2-methylazepan-3-yl)thieno[2,3-b]pyridin-4-yl)benzo[d]thiazol-5-amine

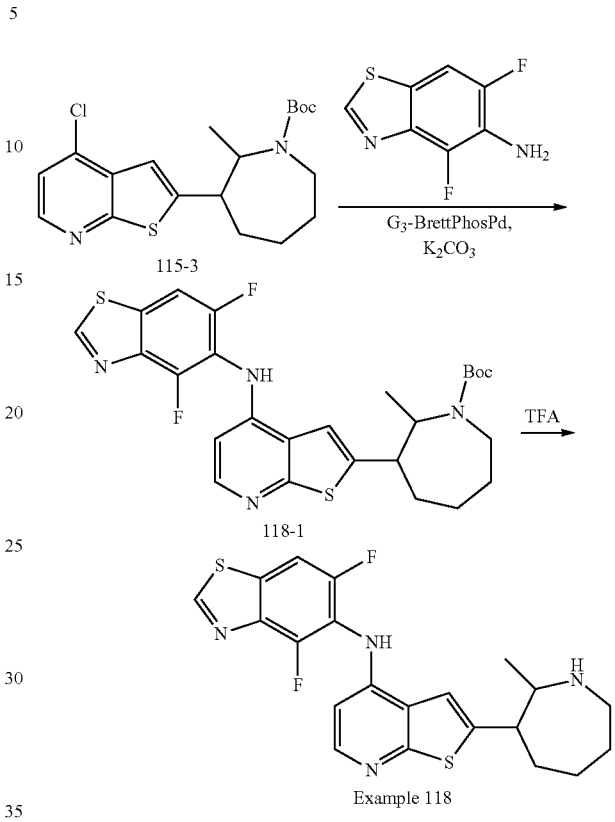

Example 118

Example 118 was prepared from tert-butyl 3-(4-chloro-thieno[2,3-b]pyridin-2-yl)-2-methylazepane-1-carboxylate (115-3) in a manner analogous to the procedures described for Example 115.

Isomers were separated by chiral HPLC: Column: (R,R)-WHELK-O1-Kromasil(02), 5×25 cm (5 um); Mobile Phase A: CO$_2$, Mobile Phase B: MeOH:ACN=2:8 (0.1% NH$_3$.H$_2$O); Flow rate: 40 mL/min; hold at 50% B for.

Example 118a

White solid. $^1$H NMR (400 MHz, Methanol-d$_4$) δ 9.31 (s, 1H), 8.05 (d, J=5.6 Hz, 1H), 7.92 (dd, J=9.0, 1.8 Hz, 1H), 7.42 (d, J=0.8 Hz, 1H), 6.35-6.28 (m, 1H), 3.47-3.35 (m, 2H), 3.19-3.08 (m, 1H), 2.93-2.82 (m, 1H), 2.28-2.16 (m, 1H), 2.10-1.85 (m, 3H), 1.76-1.63 (m, 2H), 1.04 (d, J=6.7 Hz, 3H). LCMS (ESI, m/z): 431 [M+H]$^+$. Chiral analytic conditions: Column: DAICEL DCpak SFC-B 4.6×150 mm, 5 um; Mobile Phase A: CO$_2$, Mobile Phase: MeOH (0.2% NH$_4$OH); Flow rate: 4.00 mL/min; Gradient: 10% B to 50% B in 4 min; 254/210 nm; Rt: 3.507 min.

Example 118b

White solid. $^1$H NMR (400 MHz, Methanol-d$_4$) δ 9.31 (s, 1H), 8.06 (d, J=5.6 Hz, 1H), 7.93 (dd, J=8.9, 1.8 Hz, 1H), 7.42 (s, 1H), 6.37-6.30 (m, 1H), 3.23-3.15 (m, 1H), 3.11-2.98 (m, 1H), 2.99-2.83 (m, 2H), 2.18-2.06 (m, 1H), 2.06-1.89 (m, 2H), 1.86-1.73 (m, 3H), 1.17 (d, J=6.3 Hz, 3H). LCMS (ESI, m/z): 431 [M+H]$^+$. Chiral Analytic Conditions: Column: DAICEL DCpak SFC-B, 4.6×150 mm, 5 um;

Mobile Phase A: CO₂, Mobile Phase B: MeOH (0.2% NH₄OH); Flow rate: 4.00 mL/min; Gradient: 10% B to 50% B in 4 min, and then hold at 50% B for 2 min; 254/210 nm; Rt: 3.841 min.

Example 118c

White solid. $^1$H NMR (400 MHz, Methanol-d$_4$) δ 9.31 (s, 1H), 8.07 (d, J=5.6 Hz, 1H), 7.93 (dd, J=8.9, 1.8 Hz, 1H), 7.44 (s, 1H), 6.34 (dt, J=5.7, 1.9 Hz, 1H), 3.26-3.08 (m, 2H), 3.00-2.85 (m, 2H), 2.16-1.94 (m, 3H), 1.91-1.74 (m, 3H), 1.20 (d, J=6.3 Hz, 3H). LCMS (ESI, m/z): 431 [M+H]⁺. Chiral analytic conditions: CHIRALPAK IA-3, 0.46×5 cm, 3 um; Mobile Phase: Hex (0.1% DEA):EtOH=80:20; Flow rate: 1 mL/min; 254 nm; RT: 2.529 min.

Example 118d

White solid. $^1$H NMR (400 MHz, Methanol-d$_4$) δ 9.32 (s, 1H), 8.07 (d, J=5.7 Hz, 1H), 7.97-7.90 (m, 1H), 7.45 (s, 1H), 6.33 (d, J=5.5 Hz, 1H), 3.50-3.40 (m, 2H), 3.20-3.10 (m, 1H), 3.00-2.90 (m, 1H), 2.25-2.15 (m, 1H), 2.10-1.85 (m, 3H), 1.80-1.65 (m, 2H), 1.09 (d, J=6.3 Hz, 3H). $^{19}$F NMR (376 MHz, Methanol-d$_4$) δ −76.940, −121.312, −127.896. LCMS (ESI, m/z): 431 [M+H]⁺. Chiral analytic conditions: CHIRALPAK IA-3, 0.46×5 cm, 3 um; Mobile Phase: Hex (0.1% DEA):EtOH=80:20; Flow rate: 1 mL/min; 254 nm; RT: 2.838 min.

Example 119: Synthesis of N-(5-fluoro-2-(2-methylpiperidin-3-yl)thieno[2,3-b]pyridin-4-yl)benzo[d]thiazol-5-amine

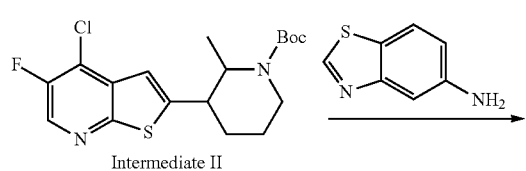

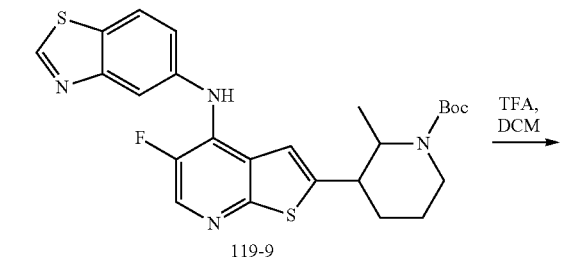

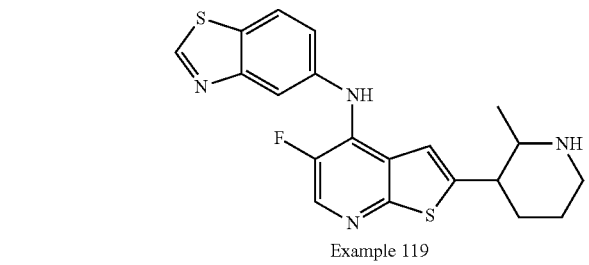

Synthesis of tert-butyl 3-(4-chloro-5-fluorothieno[2,3-b]pyridin-2-yl)-2-methyl-piperidine-1-carboxylate (Intermediate II)

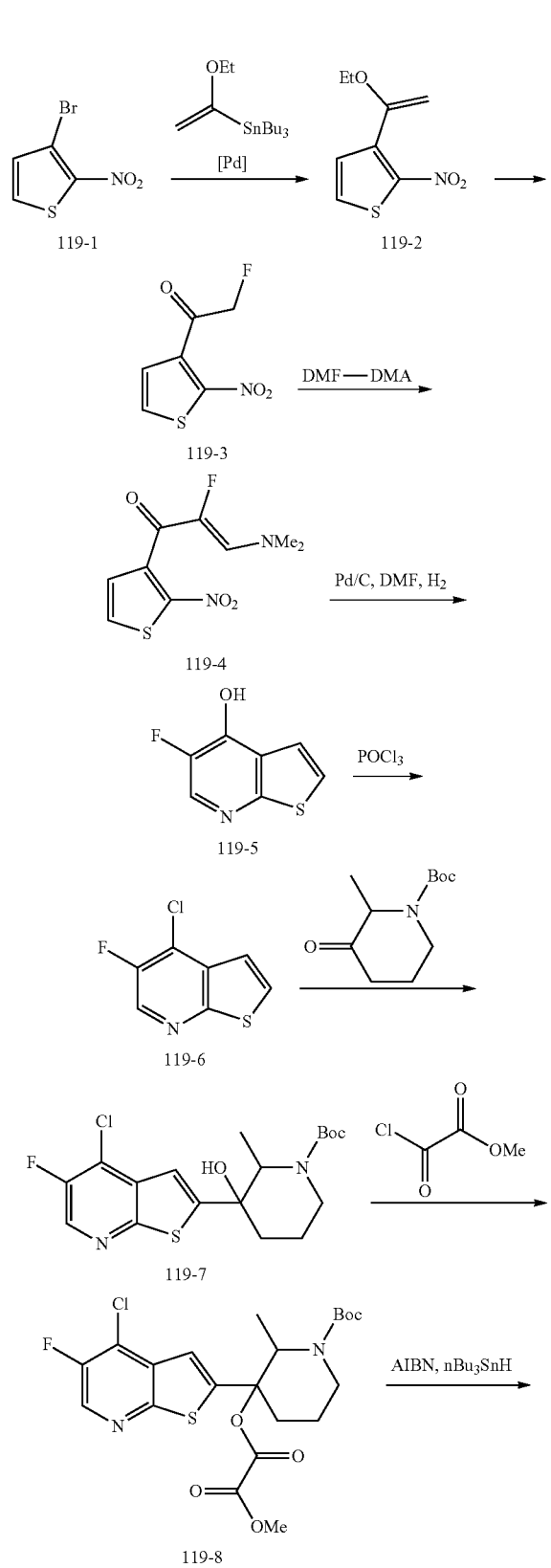

-continued

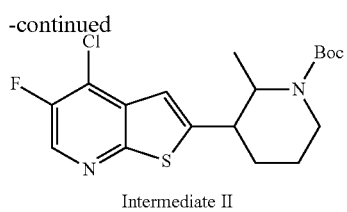

Intermediate II

Synthesis of 3-(1-ethoxyvinyl)-2-nitrothiophene

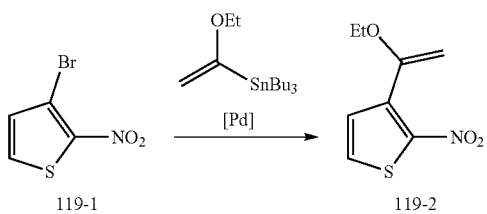

To a solution of 3-bromo-2-nitrothiophene (119-1, 14.6 g, 70.180 mmol, 1.00 equiv) in MeCN (500.0 mL) was added Pd(dppf)Cl$_2$ (5.1 g, 7.020 mmol, 0.10 equiv) and tributyl(1-ethoxyvinyl)stannane (27.0 mL, 77.200 mmol, 1.10 equiv). The reaction mixture was stirred at 65° C. for 2 h. LCMS showed the reaction was complete. 10% KF aqueous solution (500 mL) and celite was added and the solution was filtered and extracted with ethyl acetate (500 mL×3). The combined organic layer was washed with brine (500 mL), dried over anhydrous Na$_2$SO$_4$, filtered and concentrated under reduced pressure. The residue was purified by flash chromatography (SiO$_2$, petroleum ether/ethyl acetate=10:1) to give 3-(1-ethoxyvinyl)-2-nitro-thiophene (119-2, 10.9 g, 78%) as a light yellow oil. LCMS (ESI, m/z): 200 [M+H]$^+$.

Synthesis of 2-fluoro-1-(2-nitrothiophen-3-yl)ethan-1-one

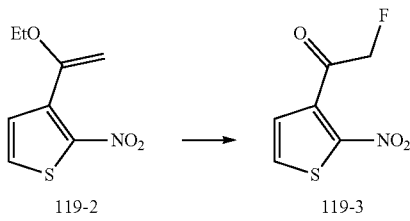

To a solution of Selectfluor (22.3 g, 62.920 mmol, 1.15 equiv) in MeCN (400.0 mL) was added 3-(1-ethoxyvinyl)-2-nitro-thiophene (119-2, 10.9 g, 54.710 mmol, 1.00 equiv) in an ice/water bath. The reaction mixture was stirred at RT for 3 hours. LCMS showed the reaction was complete. The reaction mixture was quenched with NaHCO$_3$ (aq., 200 mL) and extracted with ethyl acetate (200 mL×3). The combined organic layer was washed with brine (500 mL), dried over anhydrous Na$_2$SO$_4$, filtered and concentrated under reduced pressure. The residue was purified by flash chromatography (SiO$_2$, petroleum ether/ethyl acetate=4:1) to give 2-fluoro-1-(2-nitrothiophen-3-yl)ethan-1-one (119-3, 8.2 g, 79%) as a light yellow oil. LCMS (ESI, m/z): 190 [M+H]$^+$.

Synthesis of (Z)-3-(dimethylamino)-2-fluoro-1-(2-nitrothiophen-3-yl)prop-2-en-1-one

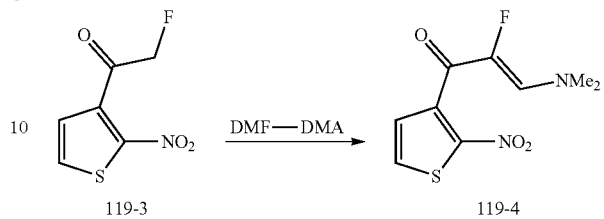

To a solution of 2-fluoro-1-(2-nitrothiophen-3-yl)ethan-1-one (119-3, 8.2 g, 43.350 mmol, 1.00 equiv) in toluene (50.0 mL) was added DMF-DMA (30.0 mL, 216.750 mmol, 5.00 equiv). The reaction mixture was stirred at 60° C. for 3 hours. LCMS showed the reaction was complete. The solvent was removed and the residue was purified by flash chromatography (SiO$_2$, petroleum ether/ethyl acetate=3:7) to give (Z)-3-(dimethylamino)-2-fluoro-1-(2-nitrothiophen-3-yl)prop-2-en-1-one (119-4, 6.6 g, 62%) as a light yellow oil. LCMS (ESI, m/z): 245 [M+H]$^+$.

Synthesis of 5-fluorothieno[2,3-b]pyridin-4-ol

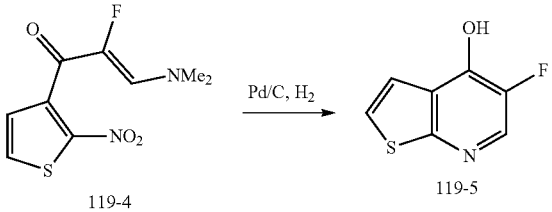 [SMILES: CN(C)/C=C(\F)C(=O)c1ccsc1[N+](=O)[O-] ; Oc1c(F)cnc2sccc12]

To a solution of (Z)-3-(dimethylamino)-2-fluoro-1-(2-nitrothiophen-3-yl)prop-2-en-1-one (119-4, 5.5 g, 22.52 mmol, 1.00 equiv) in methanol/THF=10:1 (100.0 mL) was added Pd/C (2.0 g, w/w=2.0:5.5) under hydrogen. The reaction mixture was stirred at RT for 12 hours. LCMS showed the reaction was complete. The reaction mixture was filtered through celite and the filtrate was concentrated under reduced pressure. The residue was purified by flash chromatography (SiO$_2$, petroleum ether/ethyl acetate=1:1) to give 5-fluorothieno[2,3-b]pyridin-4-ol (119-5, 4.6 g, 84%) as a light yellow oil. LCMS (ESI, m/z): 170 [M+H]$^+$.

Synthesis of 4-chloro-5-fluorothieno[2,3-b]pyridine

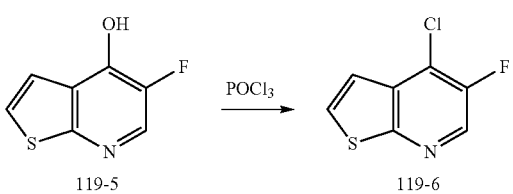

A solution of 5-fluorothieno[2,3-b]pyridin-4-ol (119-5, 4.6 g, 27.190 mmol, 1.00 equiv) in POCl$_3$ (8.0 mL) was stirred at 100° C. for 2 hours. LCMS showed the reaction was complete. The reaction mixture was cooled to 5° C. and quenched with iced water (200 mL). The pH value of the solution was adjusted to 10 with aq. Na₂CO₃ and then extracted with ethyl acetate (200 mL×3). The combined organic layer was washed with brine (500 mL), dried over anhydrous Na₂SO₄, filtered and concentrated under reduced pressure. The residue was purified by flash chromatography (SiO₂, petroleum ether/ethyl acetate=1:4) to give 4-chloro-5-fluorothieno[2,3-b]pyridine (119-6, 2.7 g, 53%) as a light yellow oil. LCMS (ESI, m/z): 188 [M+H]$^+$.

Synthesis of tert-butyl 3-(4-chloro-5-fluorothieno[2,3-b]pyridin-2-yl)-3-hydroxy-2-methyl-piperidine-1-carboxylate

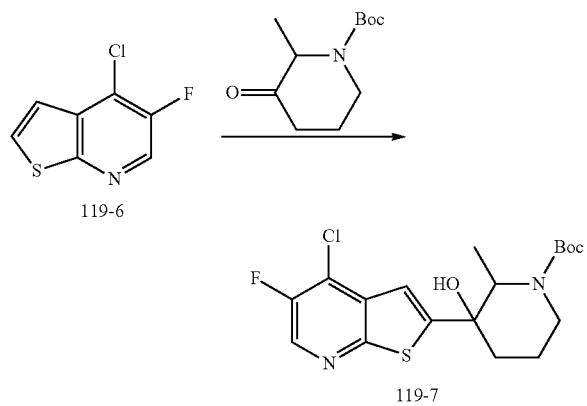

A solution of 4-chloro-5-fluorothieno[2,3-b]pyridine (119-6, 3.0 g, 15.990 mmol, 1.00 equiv) in THF (40.0 mL) was placed in a 100-mL round-bottom flask. The reaction solution was evacuated and flushed three times with nitrogen, and n-BuLi (2.5M in hexane, 9.0 mL, 22.500 mmol, 1.40 equiv) was added dropwise at −75° C. After stirring at −75° C. for 30 min, tert-butyl 2-methyl-3-oxo-piperidine-1-carboxylate (6.9 g, 31.200 mmol, 1.95 equiv) was added slowly. The reaction mixture was stirred at −75° C. for 10 min and continued to stir at RT for 3 h. LCMS showed the reaction was complete. The reaction solution was quenched with iced water (100 mL) and extracted with ethyl acetate (200 mL×3). The combined organic layer was washed with brine (500 mL), dried over anhydrous Na₂SO₄, filtered and concentrated under reduced pressure. The residue was purified by flash chromatography (SiO₂, petroleum ether/ethyl acetate=1:2) to give tert-butyl 3-(4-chloro-5-fluorothieno[2,3-b]pyridin-2-yl)-3-hydroxy-2-methylpiperidine-1-carboxylate (119-7, 2.1 g, 33%) as a light yellow solid. LCMS (ESI, m/z): 401 [M+H]$^+$.

Synthesis of 1-(tert-butoxycarbonyl)-3-(4-chloro-5-fluorothieno[2,3-b]pyridin-2-yl)-2-methylpiperidin-3-yl methyl oxalate

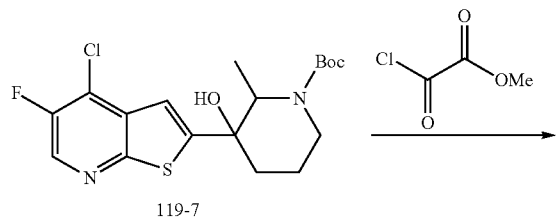

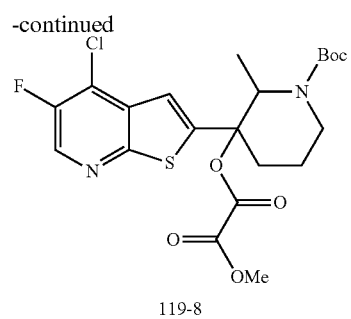

To a solution of tert-butyl 3-(4-chloro-5-fluorothieno[2,3-b]pyridin-2-yl)-3-hydroxy-2-methylpiperidine-1-carboxylate (119-7, 1.5 g, 3.620 mmol, 1.20 equiv) in DCM (20.0 mL) was added triethylamine (2.0 mL, 10.850 mmol, 3.00 equiv) and DMAP (44 mg, 0.360 mmol, 0.10 equiv). Methyl 2-chloro-2-oxo-acetate (1.0 mL, 4.340 mmol, 1.00 equiv) was added under cooling in an ice/water bath. The reaction mixture was stirred at RT for 2 h. LCMS showed the reaction was complete. The resulting solution was quenched with methanol (100 mL), filtered, and concentrated under reduced pressure. The residue was purified by flash chromatography (SiO₂, petroleum ether/ethyl acetate=5:1) to give 1-(tert-butoxycarbonyl)-3-(4-chloro-5-fluorothieno[2,3-b]pyridin-2-yl)-2-methylpiperidin-3-yl methyl oxalate (119-8, 1.6 g, 91%) as a light yellow oil. LCMS (ESI, m/z): 487 [M+H]$^+$.

Synthesis of tert-butyl 3-(4-chloro-5-fluorothieno[2,3-b]pyridin-2-yl)-2-methylpiperidine-1-carboxylate

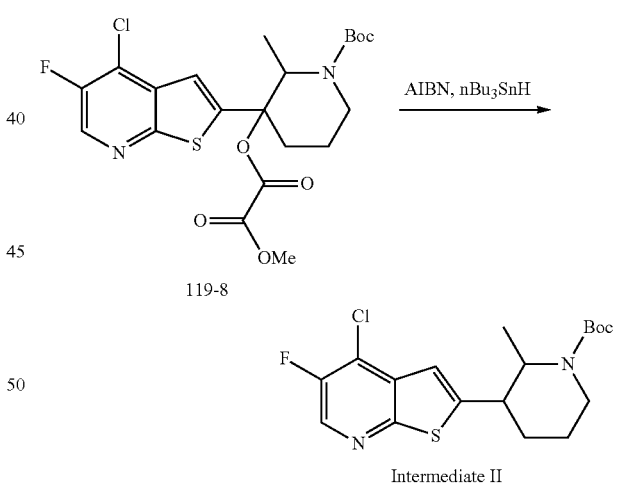

To a solution of 1-(tert-butoxycarbonyl)-3-(4-chloro-5-fluorothieno[2,3-b]pyridin-2-yl)-2-methylpiperidin-3-yl methyl oxalate (119-8, 900 mg, 1.890 mmol, 1.00 equiv) in toluene (10.0 mL) was added nBu₃SnH (60 mg, 3.670 mmol, 0.20 equiv) and AIBN (213 mg, 0.640 mmol, 0.50 equiv) under a nitrogen atmosphere at RT. The solution was degassed and back-filled with nitrogen 3 times. The reaction mixture was stirred at 90° C. for 2 h. LCMS showed 22% of the desired product was formed. The mixture was quenched with water (200 mL) and extracted with ethyl acetate (100 mL×3). The combined organic layer was washed with brine, dried over Na₂SO₄, filtered, and concentrated under reduced pressure. The residue was purified by Prep-TLC (petroleum ether/ethyl acetate=3/1) to afford tert-butyl 3-(4-chloro-5-fluorothieno[2,3-b]pyridin-2-yl)-2-methylpiperidine-1-carboxylate (intermediate II, 300 mg, 35%). LCMS (ESI, m/z): 385 [M+H]⁺.

Synthesis of tert-butyl 3-(4-(benzo[d]thiazol-5-ylamino)-5-fluorothieno[2,3-b]pyridin-2-yl)-2-methylpiperidine-1-carboxylate

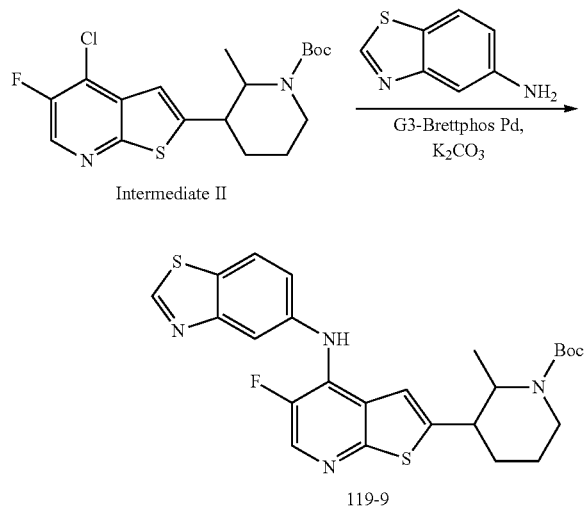

To a solution of tert-butyl 3-(4-chloro-5-fluorothieno[2,3-b]pyridin-2-yl)-2-methyl-piperidine-1-carboxylate (intermediate II, 220 mg, 0.570 mmol, 1.00 equiv) in tert-butanol (3.0 mL) was added 1,3-benzothiazol-5-amine (94 mg, 0.630 mmol, 1.50 equiv), K₂CO₃ (237 mg, 1.710 mmol, 3.00 equiv) and G3-Brettphos Pd precatalyst (78 mg, 0.090 mmol, 0.10 equiv) under a nitrogen atmosphere. The reaction was stirred for 3h at 60° C. LCMS showed the reaction was complete. The reaction mixture was filtered, concentrated under reduced pressure, and purified by Prep-TLC (petroleum ether/ethyl acetate=1/1) to afford tert-butyl 3-(4-(benzo[d]thiazol-5-ylamino)-5-fluorothieno[2,3-b]pyridin-2-yl)-2-methylpiperidine-1-carboxylate (119-9, 210 mg, 66%) as a yellow solid. LCMS (ESI, m/z): 499 [M+H]⁺.

Synthesis of N-(5-fluoro-2-(2-methylpiperidin-3-yl)thieno[2,3-b]pyridin-4-yl)benzo[d]thiazol-5-amine

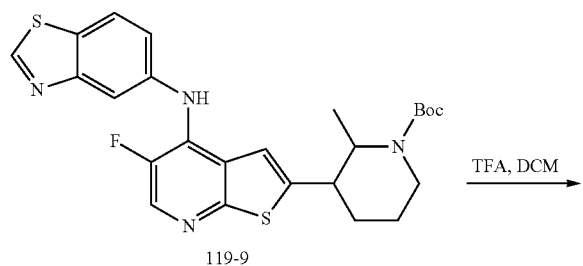

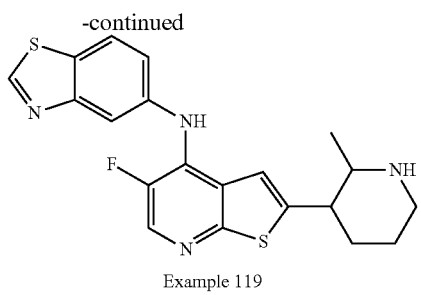

Example 119

To a solution tert-butyl 3-(4-(benzo[d]thiazol-5-ylamino)-5-fluorothieno[2,3-b]pyridin-2-yl)-2-methylpiperidine-1-carboxylate (119-9, 55 mg, 0.110 mmol, 1.00 equiv) in DCM (5.0 mL) was added TFA (1.0 mL). The reaction mixture was stirred at RT for 30 min. TLC showed the reaction was complete. The reaction mixture was concentrated under reduced pressure and the residue was purified by Prep-HPLC: Column: Sunfire prep C18 30×150, 5 um; Mobile Phase A: Water (0.05% TFA), Mobile Phase B: ACN; Flow rate: 60 mL/min; Gradient: 17% B to 27% B in 7 min; 254 nm; Rt: 6.13 min. The solution was lyophilized to give N-(5-fluoro-2-(2-methylpiperidin-3-yl)thieno[2,3-b]pyridin-4-yl)benzo[d]thiazol-5-amine (Example 119, 41.5 mg, 94%) as a yellow solid. ¹H NMR (400 MHz, Methanol-d₄) δ 9.31 (s, 1H), 8.44 (d, J=4.8 Hz, 1H), 8.08 (d, J=8.6 Hz, 1H), 7.81 (t, J=1.7 Hz, 1H), 7.38-7.26 (m, 1H), 6.82 (d, J=1.2 Hz, 1H), 3.94-3.83 (m, 1H), 3.52-3.43 (m, 1H), 3.22-3.11 (m, 2H), 2.07-1.84 (m, 4H), 1.18 (d, J=7.0 Hz, 3H). LCMS (ESI, m/z): 399 [M+H]⁺.
Chiral Separation Chiral HPLC (Column: CHIRAL ART Cellulose-SB S-5 um, 2×25 cm, 5 um; Mobile Phase A: Hex (8 mmol/L NH₃.MeOH), Mobile Phase B: IPA; Flow rate: 20 mL/min; hold at 30% B for 18 min.

Example 119a

Yellow solid. ¹H NMR (400 MHz, Methanol-d₄) δ 9.48 (s, 1H), 8.76 (d, J=6.5 Hz, 1H), 8.26 (d, J=8.6 Hz, 1H), 8.10 (d, J=2.0 Hz, 1H), 7.58 (d, J=10.6 Hz, 1H), 6.82 (s, 1H), 3.48-3.40 (m, 2H), 3.20-2.98 (m, 2H), 2.17-2.10 (m, 1H), 2.08-1.96 (m, 1H), 1.92-1.74 (m, 2H), 1.19 (d, J=6.4 Hz, 3H). LCMS (ESI, m/z): 399 [M+H]⁺. Chiral Analytic Conditions: Column: CHIRALPAK IE-3 4.6×50 mm, 3 um; Mobile Phase A: Hex (0.1% DEA), Mobile Phase B: EtOH; Flow rate: 1.00 mL/min; hold at 30% B for; 254 nm; Rt: 2.747 min.

Example 119b

Yellow solid. ¹H NMR (400 MHz, Methanol-d₄) δ 9.47 (s, 1H), 8.76 (d, J=6.4 Hz, 1H), 8.26 (d, J=8.5 Hz, 1H), 8.10 (d, J=2.0 Hz, 1H), 7.57 (d, J=6.5 Hz, 1H), 6.80 (s, 1H), 3.45-3.39 (m, 2H), 3.20-2.94 (m, 2H), 2.17-2.08 (m, 1H), 2.08-1.98 (m, 1H), 1.92-1.73 (m, 2H), 1.18 (d, J=6.4 Hz, 3H). LCMS (ESI, m/z): 399 [M+H]⁺. Chiral Analytic Conditions: Column: CHIRALPAK IE-3 4.6×50 mm, 3 um; Mobile Phase A: Hex (0.1% DEA), Mobile Phase B: EtOH; Flow rate: 1.00 mL/min; hold at 30% B for; 254 nm; Rt: 3.351 min.

Example 119c

Yellow solid. ¹H NMR (300 MHz, Methanol-d₄) δ 9.50 (s, 1H), 8.75 (d, J=6.6 Hz, 1H), 8.27 (d, J=8.6 Hz, 1H), 8.11 (s, 1H), 7.59 (d, J=8.5 Hz, 1H), 6.79 (s, 1H), 3.95-3.83 (m, 1H), 3.62-3.50 (m, 1H), 3.23-3.14 (m, 2H), 2.04-1.77 (m, 4H), 1.17 (d, J=7.0 Hz, 3H). LCMS (ESI, m/z): 399 [M+H]⁺. Chiral Analytic Conditions: Column: CHIRALPAK 4.6×50 mm, 3 um; Mobile Phase A: Hex (0.1% DEA), Mobile Phase B: EtOH; Flow rate: 1.00 mL/min; hold at 30% B for; 254 nm; Rt: 3.799 min.

Example 119d

Yellow solid. ¹H NMR (300 MHz, Methanol-d₄) δ 9.60 (s, 1H), 8.76 (d, J=6.6 Hz, 1H), 8.29 (d, J=8.6 Hz, 1H), 8.12 (s, 1H), 7.62 (d, J=8.6 Hz, 1H), 6.89 (s, 1H), 3.96-3.86 (m, 1H), 3.71-3.53 (m, 1H), 3.26-3.11 (m, 2H), 2.04-1.81 (m, 4H), 1.18 (d, J=7.0 Hz, 3H). LCMS (ESI, m/z): 399 [M+H]⁺. Chiral Analytic Conditions: Column: CHIRALPAK 4.6×50 mm, 3 um; Mobile Phase A: Hex (0.1% DEA), Mobile Phase B: EtOH; Flow rate: 1.00 mL/min; hold at 30% B for; 254 nm; Rt: 4.622 min.

Example 120: Synthesis of N-(2-(1,2-dimethylpiperidin-3-yl)-5-fluorothieno[2,3-b]pyridin-4-yl)benzo[d]-thiazol-5-amine

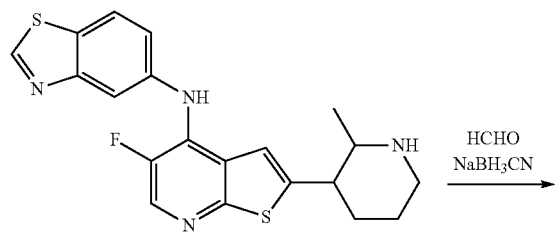

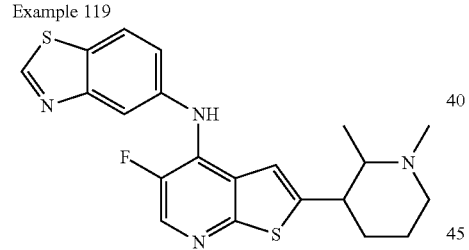

Example 120 was prepared from N-(5-fluoro-2-(2-methylpiperidin-3-yl)thieno[2,3-b]pyridin-4-yl)benzo[d]thiazol-5-amine (Example 119) in a manner analogous to the procedures described for Example 2.

Example 120a

Light yellow solid. ¹H NMR (400 MHz, Methanol-d₄) δ 9.45 (s, 1H), 8.75 (d, J=6.3 Hz, 1H), 8.24 (d, J=8.6 Hz, 1H), 8.08 (d, J=2.1 Hz, 1H), 7.56 (d, J=8.3 Hz, 1H), 6.84 (d, J=16.5 Hz, 1H), 3.60-3.53 (m, 1H), 3.51-3.39 (m, 1H), 3.28-3.10 (m, 2H), 2.97-2.85 (m, 3H), 2.18-2.08 (m, 1H), 2.09-1.77 (m, 3H), 1.30-1.10 (m, 3H). LCMS (ESI, m/z): 413 [M+H]⁺. Chiral Analytic Conditions: Column: Lux 3 um Cellulose-4 4.6×100 mm, 3 um; Mobile Phase A: CO₂, Mobile Phase B: MeOH (0.1% DEA); Flow rate: 4.00 mL/min; Gradient: 10% to 50% B in 4.0 min, and then hold at 50% B for 2.0 min; 220 nm; Rt: 4.166 min.

Example 120b

Light yellow solid. ¹H NMR (400 MHz, Methanol-d₄) δ 9.44 (s, 1H), 8.74 (d, J=6.3 Hz, 1H), 8.24 (d, J=8.6 Hz, 1H), 8.07 (s, 1H), 7.55 (d, J=8.5 Hz, 1H), 6.83 (d, J=16.4 Hz, 1H), 3.60-3.53 (m, 1H), 3.52-3.38 (m, 1H), 3.27-3.10 (m, 2H), 2.91 (s, 3H), 2.18-2.07 (m, 1H), 2.07-1.77 (m, 3H), 1.32-1.15 (m, 3H). LCMS (ESI, m/z): 413 [M+H]⁺. Chiral Analytic Conditions: Column: Lux 3 um Cellulose-4 4.6×100 mm, 3 um; Mobile Phase A: CO₂, Mobile Phase B: MeOH (0.1% DEA); Flow rate: 4.00 mL/min; Gradient: 10% to 50% B in 4.0 min, and then hold at 50% B for 2.0 min; 220 nm; Rt: 4.430 min.

Example 120c

White solid. ¹H NMR (400 MHz, Methanol-d₄) δ 9.33 (s, 1H), 8.48 (d, J=4.9 Hz, 1H), 8.11 (d, J=8.6 Hz, 1H), 7.84 (s, 1H), 7.40 (d, J=8.2 Hz, 1H), 6.85 (d, J=16.8 Hz, 1H), 3.95-3.87 (m, 1H), 3.60-3.47 (m, 1H), 3.31-3.22 (m, 1H), 3.21-3.08 (m, 1H), 2.86 (s, 3H), 2.08-1.99 (m, 1H), 1.98-1.81 (m, 3H), 1.32-1.12 (m, 3H). LCMS (ESI, m/z): 413 [M+H]⁺. Chiral Analytic Conditions: Column: Lux 3 um Cellulose-4 4.6×100 mm, 3 um; Mobile Phase A: CO₂, Mobile Phase B: MeOH (0.1% DEA); Flow rate: 4.00 mL/min; Gradient: 10% to 50% B in 4.0 min, and then hold at 50% B for 2.0 min; 220 nm; Rt: 4.707 min.

Example 120d

White solid. ¹H NMR (400 MHz, Methanol-d₄) δ 9.38 (s, 1H), 8.63 (d, J=5.8 Hz, 1H), 8.19 (d, J=8.6 Hz, 1H), 7.98 (s, 1H), 7.50 (d, J=7.8 Hz, 1H), 6.83 (d, J=26.9 Hz, 1H), 3.96-3.84 (m, 1H), 3.68-3.60 (m, 1H), 3.30-3.22 (m, 1H), 3.21-3.09 (m, 1H), 2.86 (s, 3H), 2.07-1.74 (m, 4H), 1.28-1.09 (m, 3H). LCMS (ESI, m/z): 413 [M+H]⁺. Chiral Analytic Conditions: Column: Lux 3 um Cellulose-4 4.6×100 mm, 3 um; Mobile Phase A: CO₂, Mobile Phase B: MeOH (0.1% DEA); Flow rate: 4.00 mL/min; Gradient: 10% to 50% B in 4.0 min, and then hold at 50% B for 2.0 min; 220 nm; Rt: 5.527 min.

Example 121: Synthesis of N-(2-(1-ethyl-2-methylpiperidin-3-yl)-5-fluorothieno[2,3-b]pyridin-4-yl)benzo[d]thiazol-5-amine

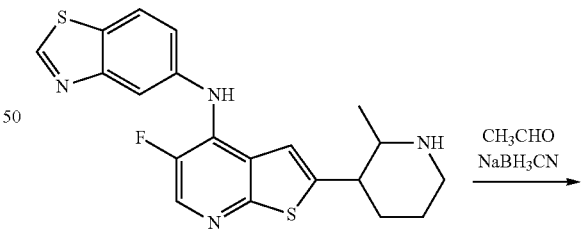

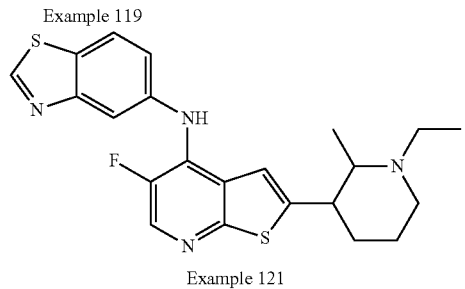

Example 121 was prepared from N-(5-fluoro-2-(2-methylpiperidin-3-yl)thieno[2,3-b]pyridin-4-yl)benzo[d]thiazol-5-amine (Example 119) in a manner analogous to the procedures described for Example 5 to give N-(1,3-benzothiazol-5-yl)-2-(1-ethyl-2-methyl-3-piperidyl)-5-fluoro-thieno[2,3-b]pyridin-4-amine as a white solid. ¹H NMR (400 MHz, Methanol-d₄) δ 9.25 (s, 1H), 8.27 (d, J=4.3 Hz, 1H), 7.99 (d, J=8.6 Hz, 1H), 7.69 (t, J=1.8 Hz, 1H), 7.29 (dt, J=8.7, 1.7 Hz, 1H), 6.77 (d, J=1.2 Hz, 1H), 3.25-3.18 (dt, J=8.8, 7.6 Hz, 2H), 2.60-2.40 (m, 4H), 1.82-1.60 (m, 4H), 1.07 (t, J=7.2 Hz, 3H), 0.79 (d, J=6.6 Hz, 3H). LCMS (ESI, m/z): 427 [M+H]⁺.

Example 122: Synthesis of 6-fluoro-N-(5-fluoro-2-(2-methylpiperidin-3-yl)thieno[2,3-b]pyridin-4-yl)benzo[d]thiazol-5-amine

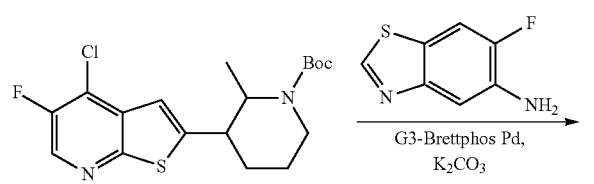

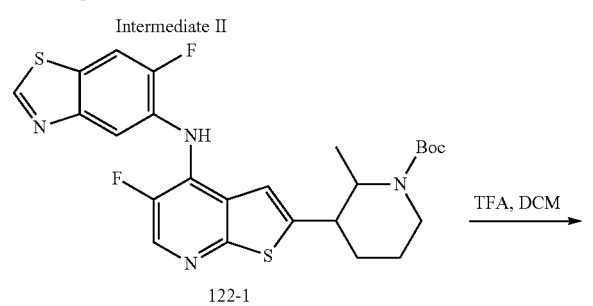

Example 122 was prepared from tert-butyl 3-(4-chloro-5-fluorothieno[2,3-b]pyridin-2-yl)-2-methylpiperidine-1-carboxylate (intermediate II) in a manner analogous to the procedures described for Example 119. The crude product was purified by chiral-SFC (Column: CHIRALPAK AD-H-TC001 SFC, 2×25 cm, 5 um; Mobile Phase A: CO₂, Mobile Phase B: MeOH (8 mmol/L NH₃.MeOH); Flow rate: 40 mL/min; isocratic elution at 35% B and preparative HPLC (Column: Sunfire prep C18, 30×150 mm, 5 um; Mobile Phase A: Water (0.05% HCl), Mobile Phase B: ACN; Flow rate: 60 mL/min; Gradient: 5% B to 29% B in 7 min.

Example 122a

White solid. ¹H NMR (400 MHz, Methanol-d₄) δ 9.18 (s, 1H), 8.23 (d, J=4.2 Hz, 1H), 8.02 (dd, J=8.9, 4.1 Hz, 1H), 7.50 (dd, J=10.5, 8.9 Hz, 1H), 6.43 (s, 1H), 3.10-3.02 (m, 1H), 2.76-2.57 (m, 2H), 2.48-2.37 (m, 1H), 2.03-1.95 (m, 1H), 1.77-1.70 (m, 1H), 1.65-1.48 (m, 2H), 0.85 (d, J=6.3 Hz, 3H). LCMS (ESI, m/z): 417 [M+H]⁺. Chiral Analytic Conditions: Column: CHIRALPAK IG-3 4.6×50 mm, 3 um; Mobile Phase A: Hex (0.1% DEA), Mobile Phase B: EtOH; Flow rate: 1.00 mL/min; isocratic elution at 20% B; 254 nm; Rt: 2.491 min.

Example 122b

White solid. ¹H NMR (400 MHz, Methanol-d₄) δ 9.18 (s, 1H), 8.23 (d, J=4.3 Hz, 1H), 8.02 (dd, J=8.9, 4.0 Hz, 1H), 7.50 (dd, J=10.4, 8.9 Hz, 1H), 6.43 (s, 1H), 3.09-3.01 (m, 1H), 2.73-2.55 (m, 2H), 2.47-2.36 (m, 1H), 2.02-1.92 (m, 1H), 1.76-1.69 (m, 1H), 1.63-1.51 (m, 2H), 0.85 (d, J=6.2 Hz, 3H). LCMS (ESI, m/z): 417 [M+H]⁺. Chiral Analytic Conditions: Column: CHIRALPAK IG-3 4.6×50 mm, 3 um; Mobile Phase A: Hex (0.1% DEA), Mobile Phase B: EtOH; Flow rate: 1.00 mL/min; isocratic elution at 20% B; 254 nm; Rt: 3.301 min.

Example 122c

Yellow solid. ¹H NMR (400 MHz, Methanol-d₄) δ 9.31 (s, 1H), 8.77 (d, J=6.2 Hz, 1H), 8.23 (dd, J=9.0, 4.2 Hz, 1H), 7.62 (dd, J=10.2, 9.0 Hz, 1H), 6.68 (s, 1H), 3.93-3.84 (m, 1H), 3.58-3.49 (m, 1H), 3.25-3.14 (m, 2H), 2.08-1.99 (m, 1H), 1.90-1.80 (m, 3H), 1.12 (d, J=7.0 Hz, 3H). LCMS (ESI, m/z): 417 [M+H]⁺. Chiral Analytic Conditions: Column: CHIRALPAK IG-3 4.6×50 mm, 3 um; Mobile Phase A: Hex (0.1% DEA), Mobile Phase B: EtOH; Flow rate: 1.00 mL/min; isocratic elution at 20% B; 254 nm; Rt: 4.175 min.

Example 122d

Yellow solid. ¹H NMR (400 MHz, Methanol-d₄) δ 9.32 (s, 1H), 8.81 (d, J=6.4 Hz, 1H), 8.24 (dd, J=9.0, 4.2 Hz, 1H), 7.63 (dd, J=10.2, 9.0 Hz, 1H), 6.73 (s, 1H), 3.95-3.84 (m, 1H), 3.60-3.53 (m, 1H), 3.25-3.15 (m, 2H), 2.09-1.98 (m, 1H), 1.94-1.82 (m, 3H), 1.13 (d, J=7.0 Hz, 3H). LCMS (ESI, m/z): 417 [M+H]⁺. Chiral Analytic Conditions: Column: CHIRALPAK IG-3 4.6×50 mm, 3 um; Mobile Phase A: Hex (0.1% DEA), Mobile Phase B: EtOH; Flow rate: 1.00 mL/min; isocratic elution at 20% B; 254 nm; Rt: 6.248 min.

Example 123: Synthesis of N-(2-(1,2-dimethylpiperidin-3-yl)-5-fluorothieno[2,3-b]pyridin-4-yl)-6-fluorobenzo[d]thiazol-5-amine

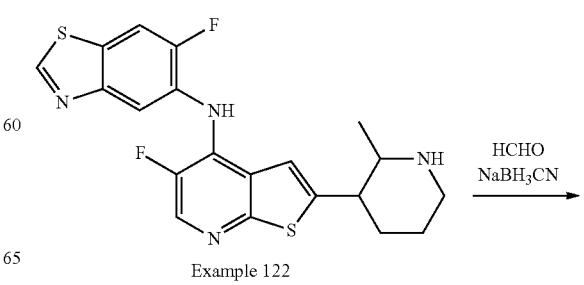

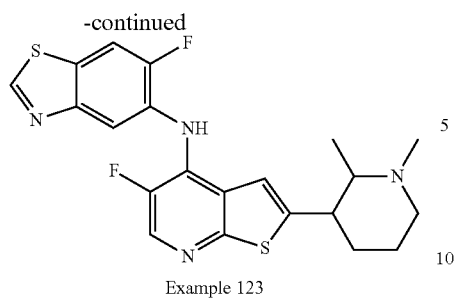

Example 123

Example 123 was prepared from 6-fluoro-N-(5-fluoro-2-(2-methylpiperidin-3-yl)thieno[2,3-b]pyridin-4-yl)benzo[d]thiazol-5-amine (Example 122) in a manner analogous to the procedures described for Example 2.

Example 123a

White solid. $^1$H NMR (400 MHz, Methanol-$d_4$) δ 9.20 (s, 1H), 8.32 (d, J=4.2 Hz, 1H), 8.04 (dd, J=8.9, 4.0 Hz, 1H), 7.52 (dd, J=10.5, 8.9 Hz, 1H), 6.53 (s, 1H), 3.59-3.51 (m, 1H), 3.29-3.13 (m, 2H), 2.95-2.85 (m, 4H), 2.11-1.99 (m, 2H), 1.94-1.75 (m, 2H), 1.19-1.02 (m, 3H). LCMS (ESI, m/z): 431 [M+H]$^+$. Chiral Analytic Conditions: Column: Lux 3 um Cellulose-4 4.6×100 mm, 3 um; Mobile Phase A: $CO_2$, Mobile Phase B: MeOH (0.1% DEA); Flow rate: 4.00 mL/min; Gradient: 10% to 50% B in 4.0 min, and then hold at 50% B for 2.0 min; 254 nm; Rt: 3.350 min.

Example 123b

White solid. $^1$H NMR (400 MHz, Methanol-$d_4$) δ 9.20 (s, 1H), 8.33 (d, J=4.2 Hz, 1H), 8.04 (dd, J=8.9, 4.1 Hz, 1H), 7.51 (dd, J=10.5, 8.9 Hz, 1H), 6.57 (s, 1H), 3.59-3.51 (m, 1H), 3.29-3.13 (m, 2H), 2.95-2.85 (m, 4H), 2.12-1.99 (m, 2H), 1.94-1.76 (m, 2H), 1.21-1.02 (m, 3H). LCMS (ESI, m/z): 431 [M+H]$^+$. Chiral Analytic Conditions: Column: Lux 3 um Cellulose-4 4.6×100 mm, 3 um; Mobile Phase A: $CO_2$, Mobile Phase B: MeOH (0.1% DEA); Flow rate: 4.00 mL/min; Gradient: 10% to 50% B in 4.0 min, and then hold at 50% B for 2.0 min; 254 nm; Rt: 3.597 min.

Example 123c

Yellow solid. $^1$H NMR (400 MHz, Methanol-$d_4$) δ 9.21 (s, 1H), 8.32 (d, J=4.4 Hz, 1H), 8.06 (dd, J=8.9, 4.0 Hz, 1H), 7.52 (dd, J=10.5, 8.9 Hz, 1H), 6.57 (s, 1H), 3.91-3.80 (m, 1H), 3.53-3.41 (m, 1H), 3.30-3.07 (m, 2H), 2.86 (s, 3H), 2.09-2.01 (m, 1H), 1.92-1.72 (m, 3H), 1.05 (d, J=6.9 Hz, 3H). LCMS (ESI, m/z): 431 [M+H]$^+$. Chiral Analytic Conditions: Column: Lux 3 um Cellulose-4 4.6×100 mm, 3 um; Mobile Phase A: $CO_2$, Mobile Phase B: MeOH (0.1% DEA); Flow rate: 4.00 mL/min; Gradient: 10% to 50% B in 4.0 min, and then hold at 50% B for 2.0 min; 254 nm; Rt: 3.862 min.

Example 123d

Yellow solid. $^1$H NMR (400 MHz, Methanol-$d_4$) δ 9.21 (s, 1H), 8.31 (d, J=4.3 Hz, 1H), 8.05 (dd, J=8.9, 4.1 Hz, 1H), 7.52 (dd, J=10.4, 8.9 Hz, 1H), 6.56 (s, 1H), 3.91-3.80 (m, 1H), 3.52-3.42 (m, 1H), 3.30-3.07 (m, 2H), 2.86 (s, 3H), 2.09-2.01 (m, 1H), 1.96-1.73 (m, 3H), 1.15-1.01 (m, 3H). LCMS (ESI, m/z): 431 [M+H]$^+$. Chiral Analytic Conditions: Column: Lux 3 um Cellulose-4 4.6×100 mm, 3 um; Mobile Phase A: $CO_2$, Mobile Phase B: MeOH (0.1% DEA); Flow rate: 4.00 mL/min; Gradient: 10% to 50% B in 4.0 min, and then hold at 50% B for 2.0 min; 254 nm; Rt: 4.275 min.

Example 124: Synthesis of 4-fluoro-N-(5-fluoro-2-(2-methylpiperidin-3-yl)thieno[2,3-b]pyridin-4-yl)benzo[d]thiazol-5-amine

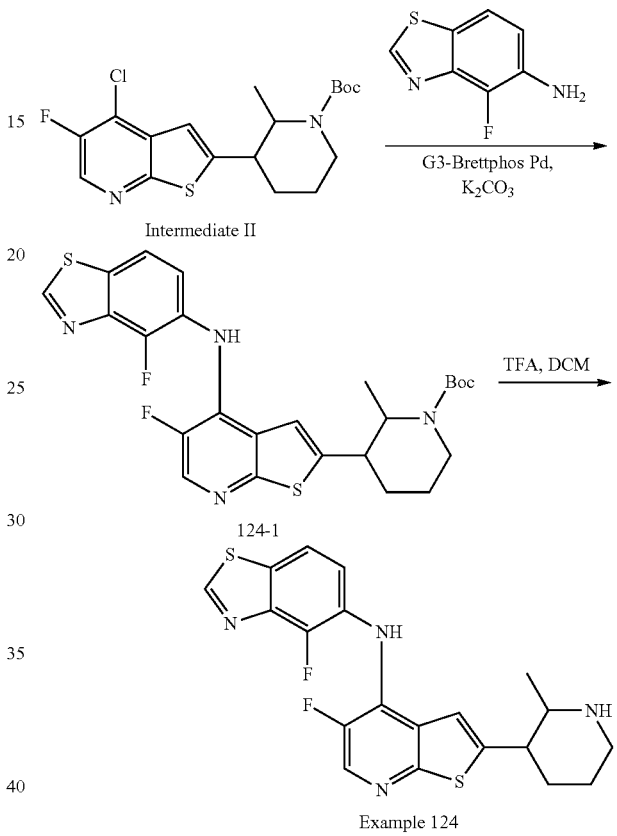

Example 124

Example 124 was prepared from tert-butyl 3-(4-chloro-5-fluorothieno[2,3-b]pyridin-2-yl)-2-methylpiperidine-1-carboxylate (intermediate II) in a manner analogous to the procedures described for Example 119. The crude product was purified by chiral HPLC (Column: CHIRALPAK IG, 2×25 cm, 5 um; Mobile Phase A: Hex (8 mmol/L $NH_3$.MeOH), Mobile Phase B: IPA; Flow rate: 20 mL/min; isocratic elution at 30% B in 24 min) and preparative HPLC (Column: XSelect CSH Prep C18 OBD, 19×250 mm, 5 um; Mobile Phase A: Water (0.05% HCl), Mobile Phase B: ACN; Flow rate: 25 mL/min; Gradient: 8% B to 38% B in 7 min)

Example 124a

White solid. $^1$H NMR (400 MHz, Methanol-$d_4$) δ 9.31 (s, 1H), 8.24 (d, J=4.4 Hz, 1H), 7.86 (dd, J=8.6, 1.2 Hz, 1H), 7.40 (t, J=8.1 Hz, 1H), 6.74 (s, 1H), 3.11-3.04 (m, 1H), 2.78-2.66 (m, 2H), 2.58-2.46 (m, 1H), 2.10-1.99 (m, 1H), 1.82-1.72 (m, 1H), 1.71-1.52 (m, 2H), 0.96 (d, J=6.2 Hz, 3H). LCMS (ESI, m/z): 417 [M+H]$^+$. Chiral Analytic Conditions: Column: CHIRALPAK IG-3 4.6×50 mm, 3 um; Mobile Phase A: Hex (0.1% DEA), Mobile Phase B: EtOH; Flow rate: 1.00 mL/min; isocratic elution at 50% B; 254 nm; Rt: 1.407 min.

Example 124b

White solid. $^1$H NMR (400 MHz, Methanol-d$_4$) δ 9.31 (s, 1H), 8.23 (d, J=4.4 Hz, 1H), 7.86 (d, J=8.6 Hz, 1H), 7.40 (t, J=8.1 Hz, 1H), 6.74 (s, 1H), 3.11-3.04 (m, 1H), 2.77-2.66 (m, 2H), 2.56-2.48 (m, 1H), 2.08-2.02 (m, 1H), 1.79-1.72 (m, 1H), 1.70-1.52 (m, 2H), 1.02-0.94 (m, 3H). LCMS (ESI, m/z): 417 [M+H]$^+$. Chiral Analytic Conditions: Column: CHIRALPAK IG-3 4.6×50 mm, 3 um; Mobile Phase A: Hex (0.1% DEA), Mobile Phase B: EtOH; Flow rate: 1.00 mL/min; isocratic elution at 50% B; 254 nm; Rt: 1.633 min.

Example 124c

White solid. $^1$H NMR (400 MHz, Methanol-d$_4$) δ 9.39 (s, 1H), 8.61 (d, J=6.0 Hz, 1H), 8.01 (d, J=9.8 Hz, 1H), 7.58 (t, J=7.7 Hz, 1H), 6.95 (s, 1H), 3.97-3.86 (m, 1H), 3.61-3.50 (m, 1H), 3.24-3.14 (m, 2H), 2.08-1.82 (m, 4H), 1.19 (d, J=7.0 Hz, 3H). LCMS (ESI, m/z): 417 [M+H]$^+$. Chiral Analytic Conditions: Column: CHIRALPAK IG-3 4.6×50 mm, 3 um; Mobile Phase A: Hex (0.1% DEA), Mobile Phase B: EtOH; Flow rate: 1.00 mL/min; isocratic elution at 50% B; 254 nm; Rt: 2.136 min.

Example 124d

White solid. $^1$H NMR (400 MHz, Methanol-d$_4$) δ 9.39 (s, 1H), 8.60 (d, J=5.9 Hz, 1H), 8.00 (dd, J=8.6, 1.2 Hz, 1H), 7.61-7.53 (m, 1H), 6.91 (s, 1H), 3.96-3.85 (m, 1H), 3.59-3.47 (m, 1H), 3.24-3.14 (m, 2H), 2.08-1.79 (m, 4H), 1.19 (d, J=7.0 Hz, 3H). LCMS (ESI, m/z): 417 [M+H]$^+$. Chiral Analytic Conditions: Column: CHIRALPAK IG-3 4.6×50 mm, 3 um; Mobile Phase A: Hex (0.1% DEA), Mobile Phase B: EtOH; Flow rate: 1.00 mL/min; isocratic elution at 50% B; 254 nm; Rt: 3.554 min.

Example 125: Synthesis of N-(2-(1,2-dimethylpiperidin-3-yl)-5-fluorothieno[2,3-b]pyridin-4-yl)-4-fluorobenzo[d]thiazol-5-amine

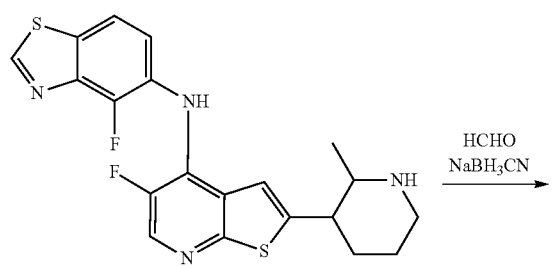

Example 125 was prepared from 4-fluoro-N-(5-fluoro-2-(2-methylpiperidin-3-yl)thieno[2,3-b]pyridin-4-yl)benzo[d]thiazol-5-amine (Example 124) in a manner analogous to the procedures described for Example 2.

Example 125a

Yellow solid. $^1$H NMR (400 MHz, Methanol-d$_4$) δ 9.41 (s, 1H), 8.76 (d, J=6.5 Hz, 1H), 8.05 (d, J=8.6 Hz, 1H), 7.63 (dd, J=8.6, 6.8 Hz, 1H), 7.03 (d, J=13.8 Hz, 1H), 3.61-3.54 (m, 1H), 3.51-3.37 (m, 1H), 3.29-3.15 (m, 1H), 2.92 (d, J=31.0 Hz, 3H), 2.20-2.11 (m, 1H), 2.09-1.82 (m, 3H), 1.24 (d, J=6.4 Hz, 3H). LCMS (ESI, m/z): 431 [M+H]$^+$. Chiral Analytic Conditions: Column: Lux 3 um Cellulose-4 4.6×100 mm, 3 um; Mobile Phase A: CO$_2$, Mobile Phase B: MeOH (0.1% DEA); Flow rate: 4.00 mL/min; Gradient: 10% to 50% in 4.0 min, and then hold at 50% B for 2.0 min; 220 nm; Rt: 4.069 min.

Example 125b

Yellow solid. $^1$H NMR (400 MHz, Methanol-d$_4$) δ 9.41 (s, 1H), 8.74 (d, J=6.4 Hz, 1H), 8.04 (d, J=8.6 Hz, 1H), 7.62 (dd, J=8.6, 6.8 Hz, 1H), 7.01 (d, J=13.4 Hz, 1H), 3.62-3.54 (m, 1H), 3.52-3.37 (m, 1H), 3.28-3.12 (m, 2H), 2.92 (d, J=31.7 Hz, 3H), 2.22-2.11 (m, 1H), 2.11-1.79 (m, 3H), 1.31-1.15 (m, 3H). LCMS (ESI, m/z): 431 [M+H]$^+$. Chiral Analytic Conditions: Column: Lux 3 um Cellulose-4 4.6×100 mm, 3 um; Mobile Phase A: CO$_2$, Mobile Phase B: MeOH (0.1% DEA); Flow rate: 4.00 mL/min; Gradient: 10% to 50% in 4.0 min, and then hold at 50% B for 2.0 min; 220 nm; Rt: 4.290 min.

Example 125c

White solid. $^1$H NMR (400 MHz, Methanol-d$_4$) δ 9.39 (s, 1H), 8.59 (d, J=5.8 Hz, 1H), 8.00 (d, J=8.9 Hz, 1H), 7.60-7.52 (m, 1H), 6.93 (d, J=18.5 Hz, 1H), 3.97-3.86 (m, 1H), 3.65-3.48 (m, 1H), 3.28-3.10 (m, 2H), 2.87 (s, 3H), 2.10-2.00 (m, 1H), 1.97-1.81 (m, 3H), 1.20 (d, J=6.9 Hz, 3H). LCMS (ESI, m/z): 431 [M+H]$^+$. Chiral Analytic Conditions: Column: Lux 3 um Cellulose-4 4.6×100 mm, 3 um; Mobile Phase A: CO$_2$, Mobile Phase B: MeOH (0.1% DEA); Flow rate: 4.00 mL/min; Gradient: 10% to 50% in 4.0 min, and then hold at 50% B for 2.0 min; 220 nm; Rt: 4.562 min.

Example 125d

White solid. $^1$H NMR (400 MHz, Methanol-d$_4$) δ 9.40 (s, 1H), 8.66-8.58 (m, 1H), 8.01 (d, J=8.3 Hz, 1H), 7.58 (d, J=7.1 Hz, 1H), 6.91 (s, 1H), 3.97-3.87 (m, 1H), 3.67-3.45 (m, 1H), 3.27-3.11 (m, 2H), 2.87 (s, 3H), 2.10-1.99 (m, 1H), 1.99-1.81 (m, 3H), 1.33-1.10 (m, 3H). LCMS (ESI, m/z): 431 [M+H]$^+$. Chiral Analytic Conditions: Column: Lux 3 um Cellulose-4 4.6×100 mm, 3 um; Mobile Phase A: CO$_2$, Mobile Phase B: MeOH (0.1% DEA); Flow rate: 4.00 mL/min; Gradient: 10% to 50% in 4.0 min, and then hold at 50% B for 2.0 min; 220 nm; Rt: 5.202 min.

Example 126: Synthesis of 4,6-difluoro-N-(5-fluoro-2-(2-methylpiperidin-3-yl)thieno[2,3-b]pyridin-4-yl)benzo[d]thiazol-5-amine

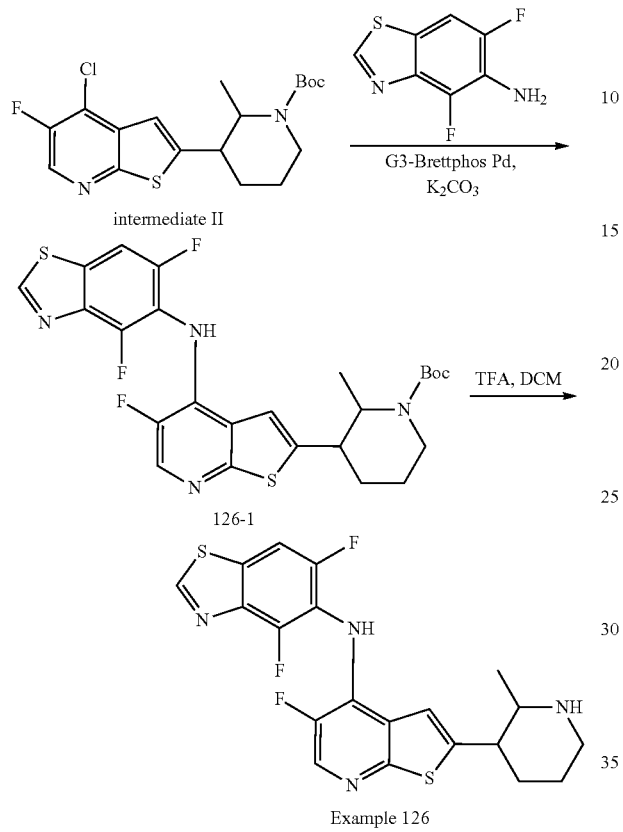

Example 126

Example 126 was prepared from tert-butyl 3-(4-chloro-5-fluorothieno[2,3-b]pyridin-2-yl)-2-methylpiperidine-1-carboxylate (intermediate II) in a manner analogous to the procedures described for Example 119. The crude product was purified by chiral HPLC (Column: Chiralpak ID-2, 2×25 cm, 5 um; Mobile Phase A: Hex (8 mmol/L NH$_3$.MeOH), Mobile Phase B: EtOH; Flow rate: 20 mL/min; isocratic elution at 30% B for 26 min.

Example 126a

White solid. $^1$H NMR (400 MHz, Methanol-d$_4$) δ 9.31 (s, 1H), 8.26 (d, J=4.7 Hz, 1H), 7.87 (dd, J=9.3, 1.8 Hz, 1H), 7.02 (s, 1H), 3.48-3.41 (m, 1H), 3.20-2.91 (m, 3H), 2.24-2.14 (m, 1H), 2.09-2.00 (m, 1H), 1.94-1.77 (m, 2H), 1.20 (d, J=6.5 Hz, 3H). LCMS (ESI, m/z): 435 [M+H]$^+$. Chiral Analytic Conditions: Column: CHIRALPAK ID-3 4.6×50 mm, 3 um; Mobile Phase A: Hex (0.1% DEA), Mobile Phase B: EtOH; Flow rate: 1.00 mL/min; isocratic elution at 30% B; 254 nm; Rt: 2.179 min.

Example 126b

White solid. $^1$H NMR (400 MHz, Methanol-d$_4$) δ 9.31 (s, 1H), 8.25 (d, J=4.7 Hz, 1H), 7.87 (dd, J=9.2, 1.8 Hz, 1H), 7.01 (s, 1H), 3.48-3.39 (m, 1H), 3.34-3.21 (m, 1H), 3.18-3.02 (m, 1H), 3.01-2.82 (m, 1H), 2.25-2.14 (m, 1H), 2.13-1.93 (m, 1H), 1.93-1.75 (m, 2H), 1.20 (d, J=6.5 Hz, 3H). LCMS (ESI, m/z): 435 [M+H]$^+$. Chiral Analytic Conditions: Column: CHIRALPAK ID-3 4.6×50 mm, 3 um; Mobile Phase A: Hex (0.1% DEA), Mobile Phase B: EtOH; Flow rate: 1.00 mL/min; isocratic elution at 30% B; 254 nm; Rt: 2.571 min.

Example 126c

White solid. $^1$H NMR (400 MHz, Methanol-d$_4$) δ 9.30 (s, 1H), 8.20 (d, J=4.8 Hz, 1H), 7.86 (dd, J=9.2, 1.8 Hz, 1H), 6.93 (s, 1H), 3.45-3.34 (m, 1H), 3.30-3.18 (m, 1H), 3.05-2.94 (m, 1H), 2.90-2.80 (m, 1H), 1.98-1.79 (m, 3H), 1.69-1.54 (m, 1H), 1.02 (d, J=6.8 Hz, 3H). LCMS (ESI, m/z): 435 [M+H]$^+$. Chiral Analytic Conditions: Column: CHIRALPAK ID-3 4.6×50 mm, 3 um; Mobile Phase A: Hex (0.1% DEA), Mobile Phase B: EtOH; Flow rate: 1.00 mL/min; isocratic elution at 30% B; 254 nm; Rt: 3.057 min.

Example 126d

White solid. $^1$H NMR (400 MHz, Methanol-d$_4$) δ 9.30 (s, 1H), 8.20 (d, J=4.7 Hz, 1H), 7.86 (dd, J=9.2, 1.8 Hz, 1H), 6.93 (s, 1H), 3.45-3.34 (m, 1H), 3.30-3.21 (m, 1H), 3.05-2.94 (m, 1H), 2.90-2.80 (m, 1H), 1.96-1.80 (m, 3H), 1.69-1.55 (m, 1H), 1.02 (d, J=6.8 Hz, 3H). LCMS (ESI, m/z): 435 [M+H]$^+$. Chiral Analytic Conditions: Column: CHIRALPAK ID-3 4.6×50 mm, 3 um; Mobile Phase A: Hex (0.1% DEA), Mobile Phase B: EtOH; Flow rate: 1.00 mL/min; isocratic elution at 30% B; 254 nm; Rt: 4.658 min.

Example 127: Synthesis of 4,6-difluoro-N-(5-fluoro-2-(2-methylpiperidin-3-yl)thieno[2,3-b]pyridin-4-yl)-benzo[d]thiazol-5-amine

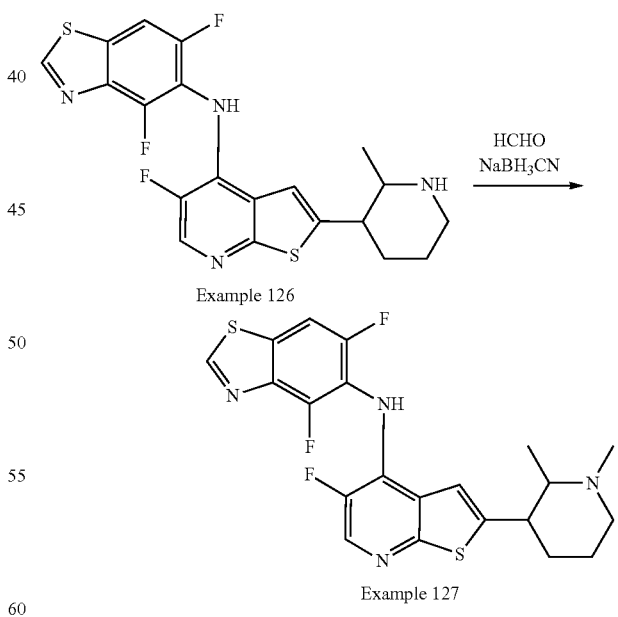

Example 127 was prepared from 4,6-difluoro-N-(5-fluoro-2-(2-methylpiperidin-3-yl)thieno[2,3-b]pyridin-4-yl)benzo[d]thiazol-5-amine (Example 126) in a manner analogous to the procedures described for Example 2. The crude product was purified by preparative HPLC (Column: XSelect CSH Prep C18 OBD, 19×250 mm, 5 um; Mobile Phase A: Water (0.05% HCl), Mobile Phase B: ACN; Flow rate: 25 mL/min; Gradient: 15% B to 36% B in 7 min.

Example 127a

Yellow solid. $^1$H NMR (400 MHz, Methanol-d$_4$) δ 9.38 (s, 1H), 8.75 (d, J=6.5 Hz, 1H), 8.01 (dd, J=9.0, 1.8 Hz, 1H), 7.29 (d, J=8.3 Hz, 1H), 3.67-3.42 (m, 2H), 3.30-3.23 (m, 2H), 2.95 (d, J=25.9 Hz, 3H), 2.25-2.15 (m, 1H), 2.12-1.84 (m, 3H), 1.28 (d, J=6.5 Hz, 3H). LCMS (ESI, m/z): 449 [M+H]$^+$. Chiral Analytic Conditions: Column: Lux 3 um Cellulose-4 4.6×100 mm, 3 um; Mobile Phase A: CO$_2$, Mobile Phase B: MeOH (0.1% DEA); Flow rate: 4.00 mL/min; Gradient: 10% B to 50% B in 4.0 min, and then hold at 50% B for 2.0 min; 254 nm; Rt: 3.403 min.

Example 127b

Yellow solid. $^1$H NMR (400 MHz, Methanol-d$_4$) δ 9.37 (s, 1H), 8.69 (d, J=6.3 Hz, 1H), 7.99 (dd, J=9.0, 1.7 Hz, 1H), 7.24 (s, 1H), 3.64-3.41 (m, 2H), 3.32-3.22 (m, 2H), 3.05-2.95 (m, 3H), 2.26-2.12 (m, 1H), 2.12-1.84 (m, 3H), 1.27 (dd, J=43.9, 6.4 Hz, 3H). LCMS (ESI, m/z): 449 [M+H]$^+$. Chiral Analytic Conditions: Column: Lux 3 um Cellulose-4 4.6×100 mm, 3 um; Mobile Phase A: CO$_2$, Mobile Phase B: MeOH (0.1% DEA); Flow rate: 4.00 mL/min; Gradient: 10% B to 50% B in 4.0 min, and then hold at 50% B for 2.0 min; 254 nm; Rt: 3.577 min.

Example 127c

White solid. $^1$H NMR (400 MHz, Methanol-d$_4$) δ 9.35 (s, 1H), 8.56 (d, J=6.0 Hz, 1H), 7.96 (dd, J=9.1, 1.8 Hz, 1H), 7.23 (d, J=16.5 Hz, 1H), 4.01-3.92 (m, 1H), 3.76-3.65 (m, 1H), 3.30-3.14 (m, 2H), 2.89 (s, 3H), 2.15-1.90 (m, 4H), 1.25 (dd, J=48.7, 6.9 Hz, 3H). LCMS (ESI, m/z): 449 [M+H]t. Chiral Analytic Conditions: Column: Lux 3 um Cellulose-4 4.6×100 mm, 3 um; Mobile Phase A: CO$_2$, Mobile Phase B: MeOH (0.1% DEA); Flow rate: 4.00 mL/min; Gradient: 10% B to 50% B in 4.0 min, and then hold at 50% B for 2.0 min; 254 nm; Rt: 3.861 min.

Example 127d

White solid. $^1$H NMR (400 MHz, Methanol-d$_4$) δ 9.35 (s, 1H), 8.56 (d, J=6.0 Hz, 1H), 7.96 (dd, J=9.1, 1.8 Hz, 1H), 7.24 (d, J=17.9 Hz, 1H), 4.02-3.93 (m, 1H), 3.75-3.66 (m, 1H), 3.31-3.13 (m, 2H), 2.89 (s, 3H), 2.13-1.93 (m, 4H), 1.34-1.15 (m, 3H). LCMS (ESI, m/z): 449 [M+H]$^+$. Chiral Analytic Conditions: Column: Lux 3 um Cellulose-4 4.6×100 mm, 3 um; Mobile Phase A: CO$_2$, Mobile Phase B: MeOH (0.1% DEA); Flow rate: 4.00 mL/min; Gradient: 10% B to 50% B in 4.0 min, and then hold at 50% B for 2.0 min; 254 nm; Rt: 4.226 min.

Example 128: Synthesis of N-(2-(1-methylpyrrolidin-3-yl)thieno[2,3-b]pyridin-4-yl)benzo-[d]thiazol-5-amine -continued

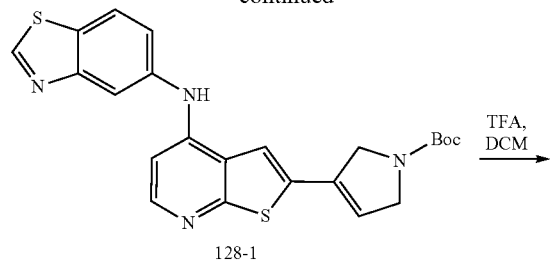

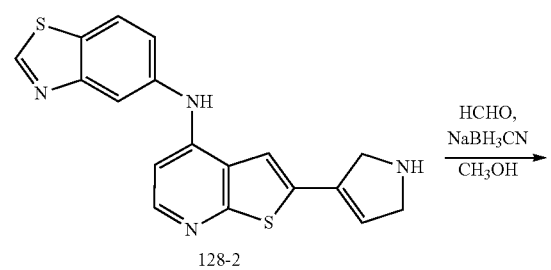

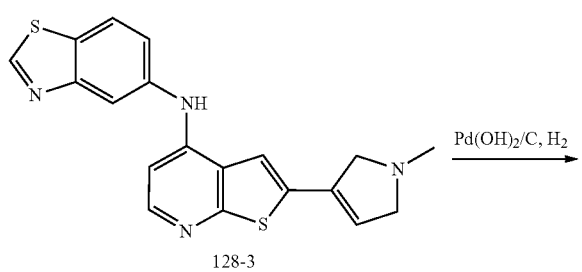

Example 128

Synthesis of tert-butyl 3-(4-(benzo[d]thiazol-5-ylamino)thieno[2,3-b]pyridin-2-yl)-2,5-dihydro-1H-pyrrole-1-carboxylate

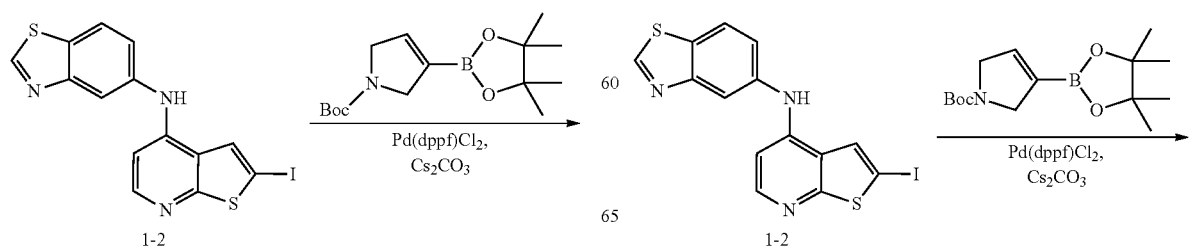

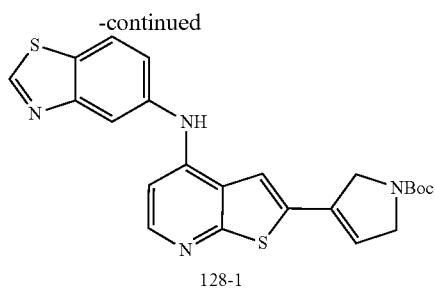

128-1

Into a 40-mL sealed tube purged and maintained with inert atmosphere of nitrogen was placed N-(1,3-benzothiazol-5-yl)-2-iodo-thieno[2,3-b]pyridin-4-amine (I-2, 1.0 g, 2.440 mmol, 1.00 equiv), tert-butyl 3-(4,4,5,5-tetramethyl-1,3,2-dioxaborolan-2-yl)-2,5-dihydropyrrole-1-carboxylate (0.7 g, 2.440 mmol, 1.00 equiv), $Cs_2CO_3$ (2.4 g, 7.330 mmol, 5.00 equiv) and $Pd(dppf)Cl_2$ (0.3 g, 0.370 mmol, 0.15 equiv) in 1,4-dioxane (5 mL) and water (0.5 mL). The resulting solution was stirred for 2 h at 90° C. The reaction solution was concentrated. The crude product was purified by flash chromatography (PE/EA=1/1) to give tert-butyl 3-(4-(benzo[d]thiazol-5-ylamino)thieno[2,3-b]pyridin-2-yl)-2,5-dihydro-1H-pyrrole-1-carboxylate (128-1, 900 mg, 82%) as a light yellow solid. LCMS (ESI, m/z): 451 $[M+H]^+$.

Synthesis of N-(2-(2,5-dihydro-1H-pyrrol-3-yl)thieno[2,3-b]pyridin-4-yl)benzo[d]thiazol-5-amine

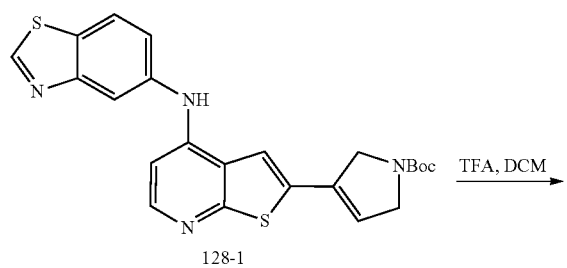

To a stirred solution of tert-butyl 3-(4-(benzo[d]thiazol-5-ylamino)thieno[2,3-b]pyridin-2-yl)-2,5-dihydro-1H-pyrrole-1-carboxylate (128-1, 100 mg, 0.220 mmol, 1.00 equiv) in DCM (2 mL) was added TFA (1 mL). The reaction was stirred for 15 min at room temperature. TLC showed the reaction was complete. The reaction solution was concentrated and purified by Prep HPLC with the following conditions: Column, XBridge Prep C18 OBD; 5 um, 19×150 mm; mobile phase, Water (0.05% TFA) and ACN (40% up to 60% in 10 min); Detector: 254/210 nm. The product was dried by lyophilization to give the desired compound N-(2-(2,5-dihydro-1H-pyrrol-3-yl)thieno[2,3-b]pyridin-4-yl)benzo[d]thiazol-5-amine (128-2, 57.2 mg, 74%) as a light yellow solid. $^1$H NMR (300 MHz, Methanol-$d_4$) δ 9.37 (s, 1H), 8.30-8.20 (dd, J=7.8, 4.5 Hz, 2H), 8.14 (d, J=1.8 Hz, 1H), 7.84 (s, 1H), 7.59 (dd, J=8.4, 2.1 Hz, 1H), 7.05 (d, J=7.2 Hz, 1H), 6.48-6.41 (m, 1H), 4.59 (q, J=2.4 Hz, 2H), 4.37 (q, J=2.5 Hz, 2H). LCMS (ESI, m/z): 351 $[M+H]^+$.

Synthesis of N-(2-(1-methyl-2,5-dihydro-1H-pyrrol-3-yl)thieno[2,3-b]pyridin-4-yl)benzo-[d]thiazol-5-amine

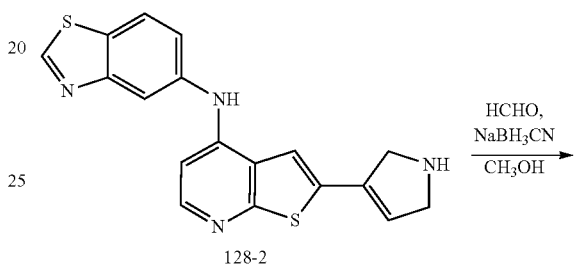

128-2

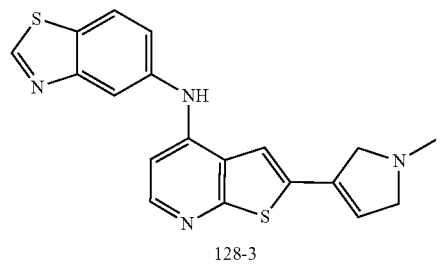

128-3

To a stirred solution of N-(2-(2,5-dihydro-1H-pyrrol-3-yl)thieno[2,3-b]pyridin-4-yl)-benzo[d]thiazol-5-amine (128-2, 60 mg, 0.170 mmol, 1.00 equiv) in methanol (2 mL) was added HCHO (21 mg, 0.260 mmol, 1.50 equiv). The reaction was stirred for 30 min at room temperature, followed by the addition of $NaBH_3CN$ (32 mg, 0.510 mmol, 3.00 equiv). The reaction was stirred for 5 min at room temperature. TLC showed the reaction was complete. The reaction solution was concentrated and extracted with EA (2×200 mL). The combined organic layer was washed with brine, dried over anhydrous $Na_2SO_4$, filtered, concentrated under reduced pressure. The residue was purified by Prep HPLC with the following conditions: Column, XBridge Prep C18 OBD; 5 um, 19×150 mm; mobile phase, Water (0.05 TFA) and ACN (30% up to 40% in 10 min); Detector: 254/210 nm. Then the product was dried by lyophilization to give the desired compound N-(2-(1-methyl-2,5-dihydro-1H-pyrrol-3-yl)thieno[2,3-b]pyridin-4-yl)benzo[d]thiazol-5-amine (128-3, 36.4 mg, 58%) as a light yellow solid. $^1$H NMR (300 MHz, Methanol-$d_4$) δ 9.37 (s, 1H), 8.29-8.20 (m, 2H), 8.13 (d, J=1.8 Hz, 1H), 7.80 (s, 1H), 7.58 (dd, J=8.4, 2.1 Hz, 1H), 7.04 (d, J=6.9 Hz, 1H), 6.42 (s, 1H), 4.69-4.46 (m, 4H), 3.18 (s, 3H). LCMS (ESI, m/z): 365 $[M+H]^+$.

501

Synthesis of N-(2-(1-methylpyrrolidin-3-yl)thieno[2,3-b]pyridin-4-yl)benzo[d]thiazol-5-amine

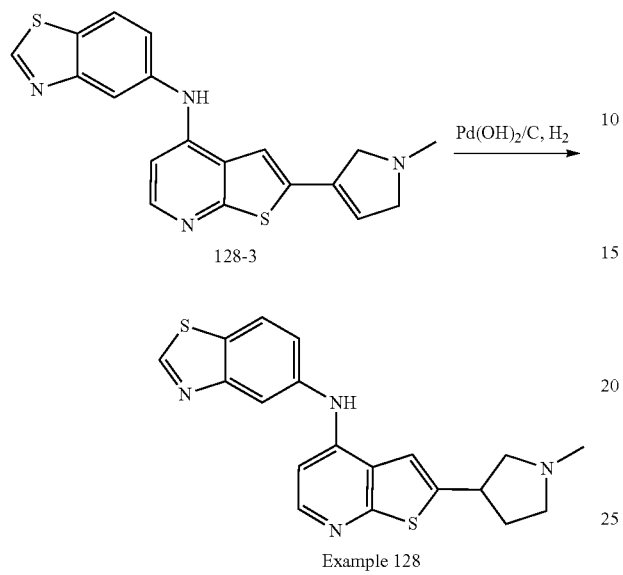

To a solution of N-(2-(1-methyl-2,5-dihydro-1H-pyrrol-3-yl)thieno[2,3-b)]pyridin-4-yl)benzo[d]thiazol-5-amine (128-3, 50 mg, 0.140 mmol, 1.00 equiv) in ethanol (5 mL) was added Pd(OH)$_2$/C (100 mg, 2.00 w/w) under nitrogen atmosphere. The reaction solution was degassed and back filled with hydrogen. The reaction was stirred for 48 h at 60° C. LCMS showed the reaction was complete. The resulting mixture was filtered through celite. The filtrate was concentrated and purified by Prep HPLC with the following conditions: Column, XBridge Prep C18 OBD; 5 um, 19×150 mm; mobile phase, Water (0.05% TFA) and ACN (7% up to 28% in 10 min); Detector: 254/210 nm. Then the mixture was dried by lyophilization to give N-(2-(1-methylpyrrolidin-3-yl)thieno[2,3-b]pyridin-4-yl)-benzo[d]-thiazol-5-amine (26.1 mg, 52%) as a light yellow solid. $^1$H NMR (300 MHz, Methanol-d$_4$) δ 9.38 (s, 1H), 8.30-8.20 (m, 2H), 8.13 (d, J=2.1 Hz, 1H), 7.80 (s, 1H), 7.58 (dd, J=8.7, 2.1 Hz, 1H), 7.04 (d, J=6.9 Hz, 1H), 4.44-3.63 (m, 5H), 3.07 (s, 3H), 2.83-2.75 (m, 1H), 2.52-2.44 (m, 1H). LCMS (ESI, m/z): 367 [M+H]$^+$.

Example 129: Synthesis of N-(2-(pyrrolidin-3-yl)thieno[2,3-b]pyridin-4-yl)benzo[d]thiazol-5-amine

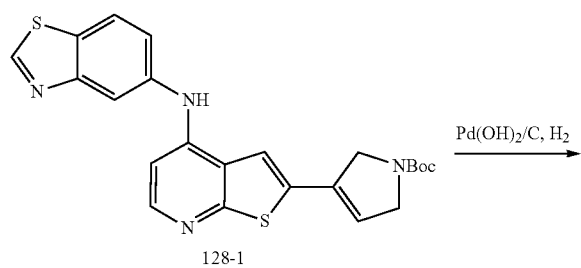

502

-continued

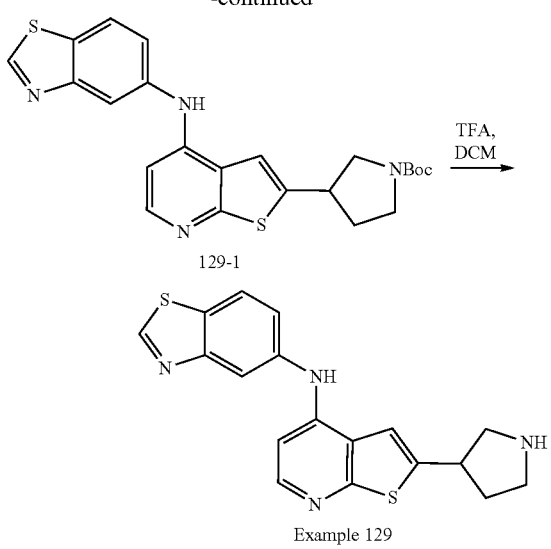

Synthesis of tert-butyl 3-(4-(benzo[d]thiazol-5-ylamino)thieno[2,3-b]pyridin-2-yl)pyrrolidine-1-carboxylate To a solution of tert-butyl 3-(4-(benzo[d]thiazol-5-ylamino)thieno[2,3-b]pyridin-2-yl)-2,5-dihydro-1H-pyrrole-1-carboxylate (128-1, 180 mg, 0.400 mmol, 1.00 equiv) in ethanol (6 mL) was added Pd(OH)$_2$/C (360 mg, 2.00 w/w). The flask was evacuated and flushed three times with nitrogen, followed by flushing with hydrogen. The mixture was stirred overnight at 60° C. under an atmosphere of hydrogen (1-3 atm). TLC showed the reaction was complete. The solid was filtered out and the filtrate was concentrated to give (52 mg, crude) tert-butyl 3-(4-(benzo[d]thiazol-5-ylamino)thieno[2,3-b]pyridin-2-yl)pyrrolidine-1-carboxylate (129-1) as an off-white solid. LCMS (ESI, m/z): 453 [M+H]$^+$.

Synthesis of N-(2-(pyrrolidin-3-yl)thieno[2,3-b]pyridin-4-yl)benzo[d]thiazol-5-amine

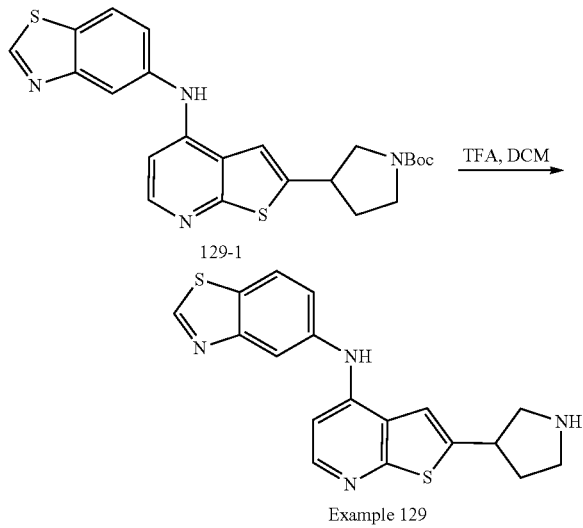

129-1

Example 129

To a stirred solution of tert-butyl 3-(4-(benzo[d]thiazol-5-ylamino)thieno[2,3-b]pyridin-2-yl)pyrrolidine-1-carboxylate (129-1, 52 mg, 0.110 mmol, 1.00 equiv) in DCM (2 mL) was added TFA (1 mL). The reaction was stirred for 15 min at room temperature. TLC showed the reaction was complete. The reaction solution was concentrated and the residue purified by Prep HPLC with the following conditions: Column, XBridge Prep C18 OBD; 5 um, 19×150 mm; mobile phase, Water (10 mmol/L $NH_4HCO_3$) and ACN (20% up to 40% in 10 min); Detector: 254/210 nm. Then the mixture was dried by lyophilization to give the desired compound N-(2-(pyrrolidin-3-yl)thieno[2,3-b]pyridin-4-yl)benzo[d]thiazol-5-amine (Example 129, 9.5 mg, 74%) as a light yellow solid. $^1$H NMR (300 MHz, Methanol-$d_4$) δ 9.28 (s, 1H), 8.15-8.05 (m, 2H), 8.00 (d, J=2.1 Hz, 1H), 7.52 (dd, J=8.7, 2.1 Hz, 1H), 7.44 (d, J=1.0 Hz, 1H), 6.99 (d, J=5.7 Hz, 1H), 3.69-3.61 (m, 1H), 3.44 (dd, J=11.1, 7.5 Hz, 1H), 3.25-3.07 (m, 2H), 2.99 (dd, J=11.1, 8.0 Hz, 1H), 2.45-2.36 (m, 1H), 2.12-2.02 (m, 1H). LCMS (ESI, m/z): 353 [M+H]$^+$.

Biological Activity

Biological Data:

All data was collected using a standard TR-FRET screening assay: LanthaScreen Tracer 199 at 50 nM, Eu-anti-His Antibody at 2 nM, 5 nM RIPK2 enzyme, and 1× Kinase Reaction Buffer. There was a 1 hour incubation prior to read. TR-FRET signal of the interaction (340Ex/665Em/615Em) was read at room temperature with standard setting. Background was subtracted of wells containing no enzyme. Percent inhibition was based on uninhibited controls log (inhibitor) vs. response. Variable slope equation was used with no constraints: Log Y=Bottom+(Top−Bottom)/(1+10^((Log IC50−X)*Hill Slope)).

Analytical Instrumentation:

NMR: Bruker UltraShield™-300 or Bruker Ascend™-400 spectrometers.

LCMS: Shimadzu LCMS-2020 or Agilent technologies 1260 Infinity-6120 Quadrupole LC/MS.

Purification:

TLC plates: Thin-layer chromatography with E. Merck silica gel 60 F254 pre-coated plates (0.25 mm).

Flash chromatography: Agela Technologies CHEETAH-MP200 CH16200 2T-A0099 or Biotage Isolera ISO-PSV ISPS 1832112.

Table 1 shows the activity of selected compounds of this invention in RIPK2 inhibition assays. The compound numbers correspond to the compound numbers above. Compounds having an activity designated as "++++" provided an $IC_{50}$ of ≤10.00 nM; compounds having an activity designated as "+++" provided an $IC_{50}$ of 10.01-20.00 nM; compounds having an activity designated as "++" provided an $IC_{50}$ of 20.01-50.00 nM; and compounds having an activity designated as "+" provided an $IC_{50}$ of ≥50.01 nM.

TABLE 1

| Example No. | Structure | $IC_{50}$ (nM) |
|---|---|---|
| 1 | 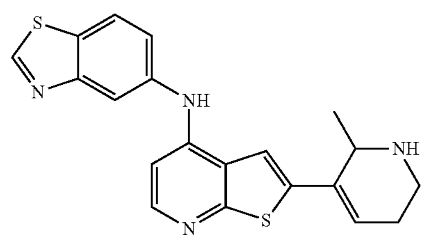 [SMILES: CC1NCCC=C1c1cc2c(Nc3ccc4scnc4c3)ccnc2s1] | ++++ |
| 2 | 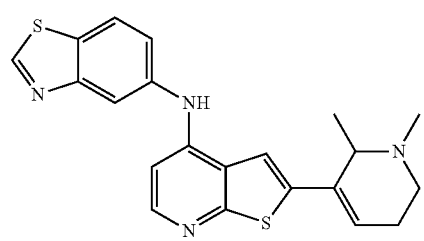 [SMILES: CC1C(c2cc3c(Nc4ccc5scnc5c4)ccnc3s2)=CCCN1C] | ++++ |

TABLE 1-continued

| Example No. | Structure | IC$_{50}$ (nM) |
|---|---|---|
| 3 | 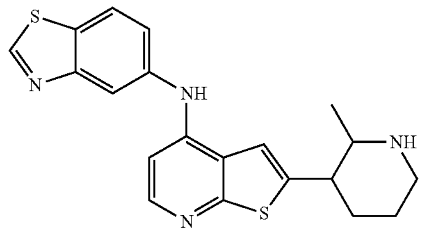 [SMILES: CC1NCCCC1c1cc2c(Nc3ccc4scnc4c3)ccnc2s1] | ++++ |
| 4 | 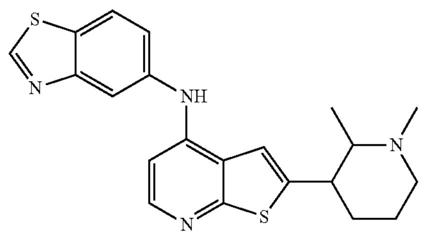 [SMILES: CC1C(c2cc3c(Nc4ccc5scnc5c4)ccnc3s2)CCCN1C] | ++++ |
| 4c | 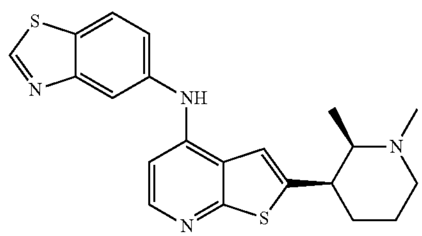 [SMILES: C[C@@H]1[C@H](c2cc3c(Nc4ccc5scnc5c4)ccnc3s2)CCCN1C] | ++++ |
| 4d | 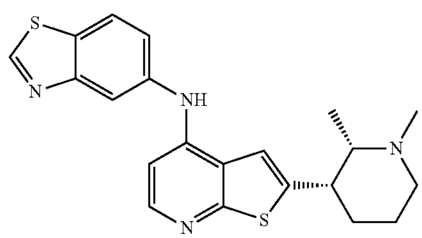 [SMILES: C[C@H]1[C@@H](c2cc3c(Nc4ccc5scnc5c4)ccnc3s2)CCCN1C] | ++++ |
| 5 | 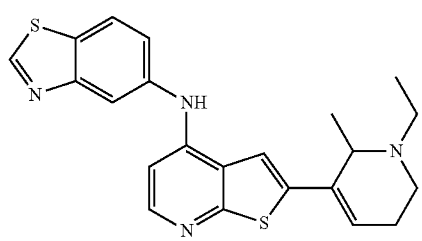 [SMILES: CCN1CCC=C(c2cc3c(Nc4ccc5scnc5c4)ccnc3s2)C1C] | ++++ |
| 6 | 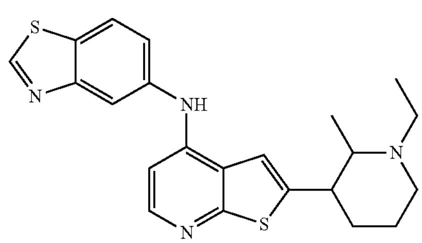 [SMILES: CCN1CCCC(c2cc3c(Nc4ccc5scnc5c4)ccnc3s2)C1C] | ++++ |

TABLE 1-continued

| Example No. | Structure | IC₅₀ (nM) |
|---|---|---|
| 7 | 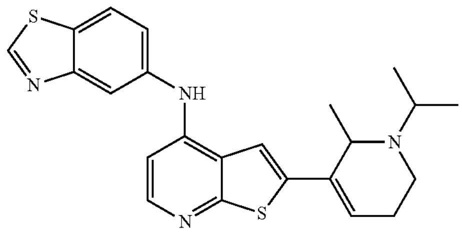 [SMILES: CC(C)N1CCC=C(c2cc3c(Nc4ccc5scnc5c4)ccnc3s2)C1C] | ++++ |
| 8 | 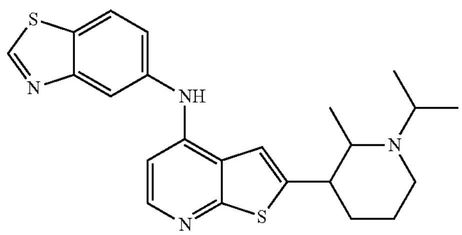 [SMILES: CC(C)N1CCCC(c2cc3c(Nc4ccc5scnc5c4)ccnc3s2)C1C] | ++++ |
| 9 | 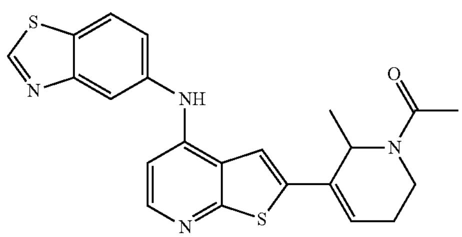 [SMILES: CC(=O)N1CCC=C(c2cc3c(Nc4ccc5scnc5c4)ccnc3s2)C1C] | +++ |
| 10 | 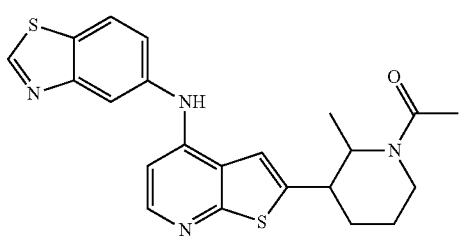 [SMILES: CC(=O)N1CCCC(c2cc3c(Nc4ccc5scnc5c4)ccnc3s2)C1C] | ++++ |
| 11 | 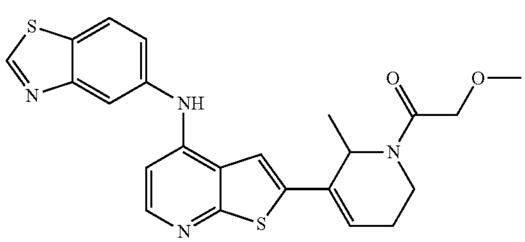 [SMILES: COCC(=O)N1CCC=C(c2cc3c(Nc4ccc5scnc5c4)ccnc3s2)C1C] | ++++ |
| 12 | 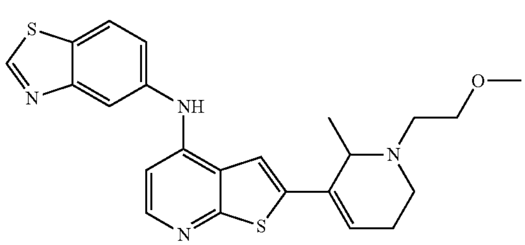 [SMILES: COCCN1CCC=C(c2cc3c(Nc4ccc5scnc5c4)ccnc3s2)C1C] | ++++ |

TABLE 1-continued

| Example No. | Structure | IC$_{50}$ (nM) |
|---|---|---|
| 12a | 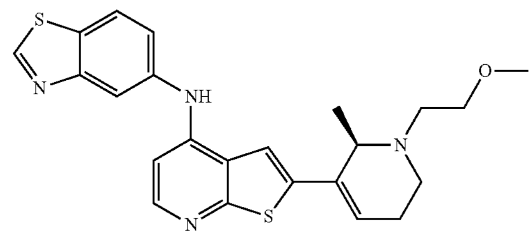 [SMILES: COCCN1CCC=C(c2cc3c(Nc4ccc5scnc5c4)ccnc3s2)[C@H]1C] | ++++ |
| 12b | 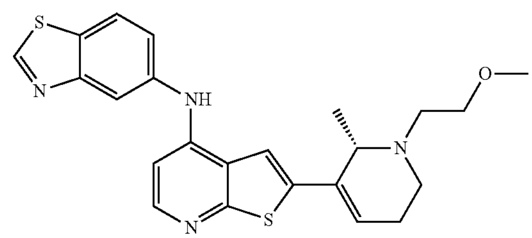 [SMILES: COCCN1CCC=C(c2cc3c(Nc4ccc5scnc5c4)ccnc3s2)[C@@H]1C] | ++++ |
| 13 | 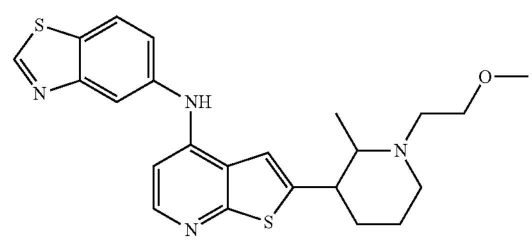 [SMILES: COCCN1CCCC(c2cc3c(Nc4ccc5scnc5c4)ccnc3s2)C1C] | ++++ |
| 14 | 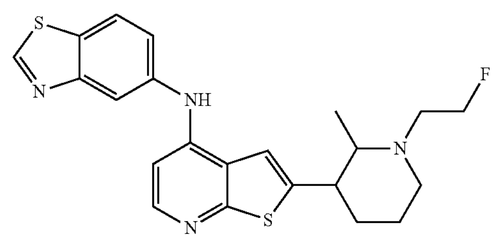 [SMILES: CC1C(c2cc3c(Nc4ccc5scnc5c4)ccnc3s2)CCCN1CCF] | ++++ |
| 15 | 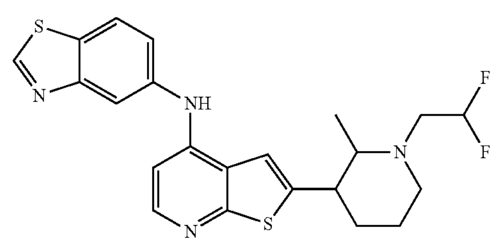 [SMILES: CC1C(c2cc3c(Nc4ccc5scnc5c4)ccnc3s2)CCCN1CC(F)F] | ++ |
| 17 | 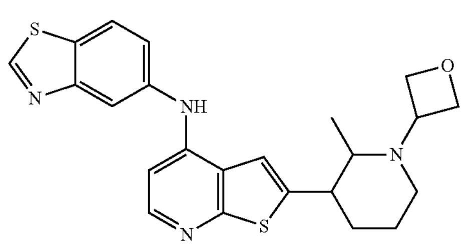 [SMILES: CC1C(c2cc3c(Nc4ccc5scnc5c4)ccnc3s2)CCCN1C1COC1] | +++ |

TABLE 1-continued

| Example No. | Structure | IC$_{50}$ (nM) |
|---|---|---|
| 18 | 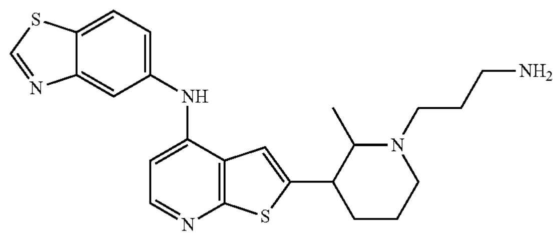 [SMILES: CC1C(c2cc3c(Nc4ccc5scnc5c4)ccnc3s2)CCCN1CCCN] | ++++ |
| 19 | 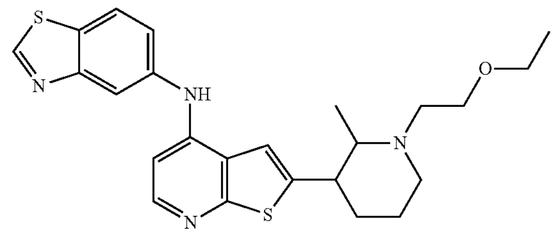 [SMILES: CCOCCN1CCCC(c2cc3c(Nc4ccc5scnc5c4)ccnc3s2)C1C] | +++ |
| 20 | 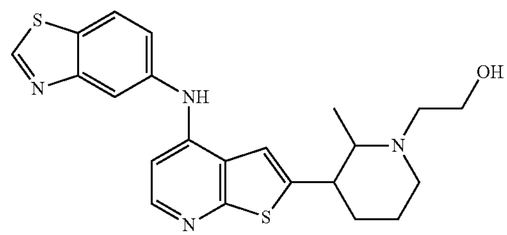 [SMILES: CC1C(c2cc3c(Nc4ccc5scnc5c4)ccnc3s2)CCCN1CCO] | ++++ |
| 21 | 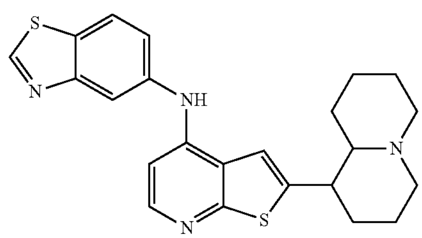 [SMILES: c1cc(Nc2ccc3scnc3c2)c2cc(C3CCCN4CCCCC34)sc2n1] | ++ |
| 23a | 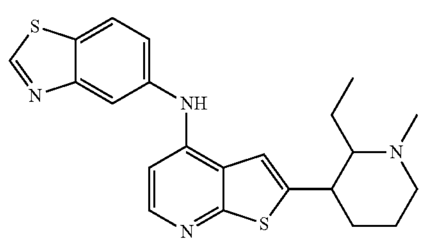 [SMILES: CCC1C(c2cc3c(Nc4ccc5scnc5c4)ccnc3s2)CCCN1C] | ++++ |
| 23b | 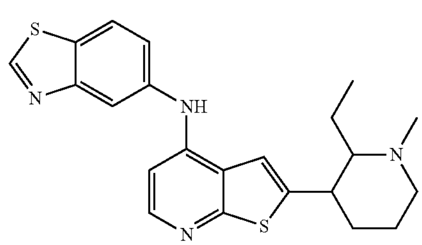 [SMILES: CCC1C(c2cc3c(Nc4ccc5scnc5c4)ccnc3s2)CCCN1C] | ++++ |

TABLE 1-continued

| Example No. | Structure | IC$_{50}$ (nM) |
|---|---|---|
| 24 | 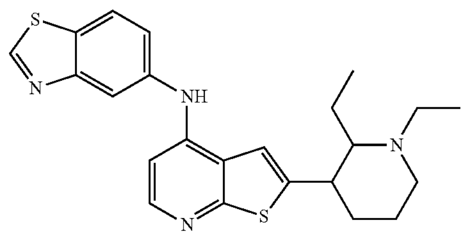 [SMILES: CCC1C(c2cc3c(Nc4ccc5scnc5c4)ccnc3s2)CCCN1CC] | +++ |
| 25 | 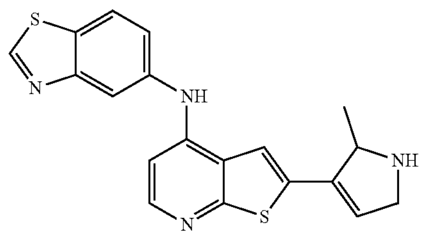 [SMILES: CC1NCC=C1c1cc2c(Nc3ccc4scnc4c3)ccnc2s1] | ++++ |
| 26 | 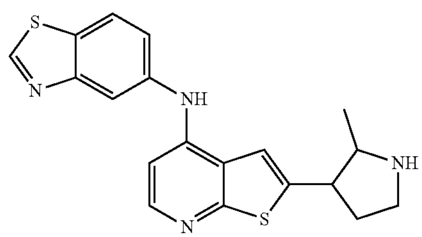 [SMILES: CC1NCCC1c1cc2c(Nc3ccc4scnc4c3)ccnc2s1] | ++++ |
| 27 | 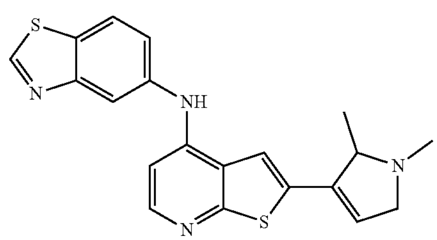 [SMILES: CC1C(c2cc3c(Nc4ccc5scnc5c4)ccnc3s2)=CCN1C] | ++++ |
| 28 | 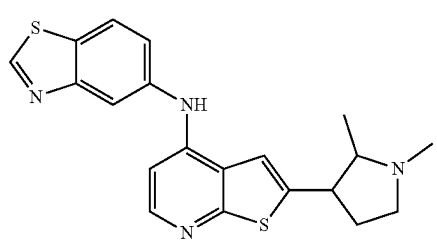 [SMILES: CC1C(c2cc3c(Nc4ccc5scnc5c4)ccnc3s2)CCN1C] | ++++ |
| 30 | 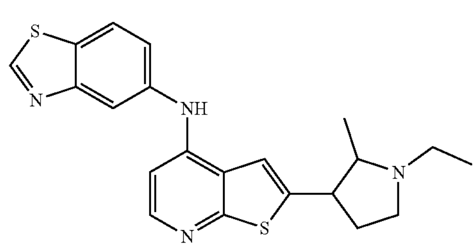 [SMILES: CCN1CCC(c2cc3c(Nc4ccc5scnc5c4)ccnc3s2)C1C] | ++++ |

TABLE 1-continued

| Example No. | Structure | IC$_{50}$ (nM) |
|---|---|---|
| 31 | 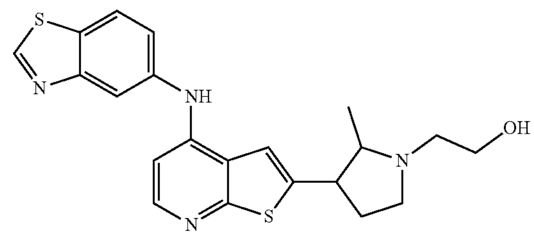 [SMILES: CC1C(c2cc3c(Nc4ccc5scnc5c4)ccnc3s2)CCN1CCO] | ++++ |
| 32 | 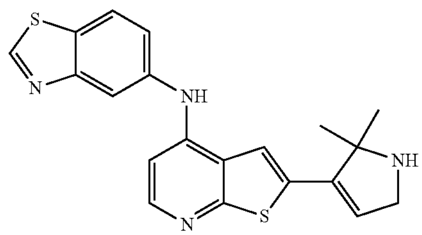 [SMILES: CC1(C)NCC=C1c1cc2c(Nc3ccc4scnc4c3)ccnc2s1] | ++++ |
| 33 | 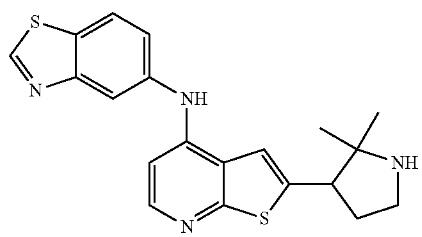 [SMILES: CC1(C)NCCC1c1cc2c(Nc3ccc4scnc4c3)ccnc2s1] | ++++ |
| 34 | 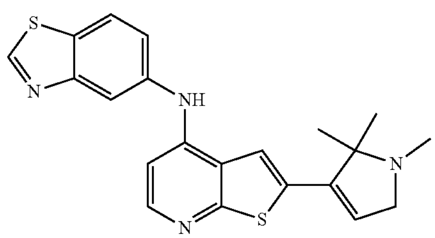 [SMILES: CN1CC=C(c2cc3c(Nc4ccc5scnc5c4)ccnc3s2)C1(C)C] | ++++ |
| 35 | 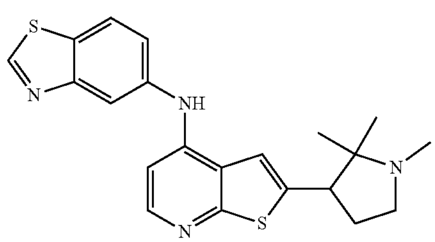 [SMILES: CN1CCC(c2cc3c(Nc4ccc5scnc5c4)ccnc3s2)C1(C)C] | +++ |
| 37 | 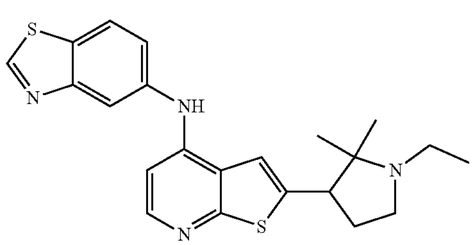 [SMILES: CCN1CCC(c2cc3c(Nc4ccc5scnc5c4)ccnc3s2)C1(C)C] | ++++ |

TABLE 1-continued

| Example No. | Structure | IC$_{50}$ (nM) |
|---|---|---|
| 38 | 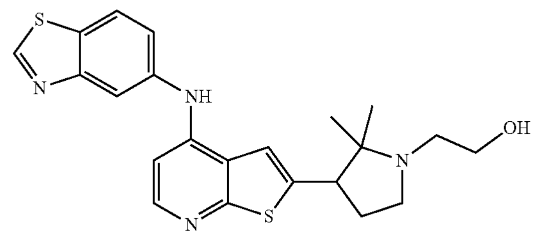 [SMILES: CC1(C)C(c2cc3c(Nc4ccc5scnc5c4)ccnc3s2)CCN1CCO] | ++++ |
| 39 | 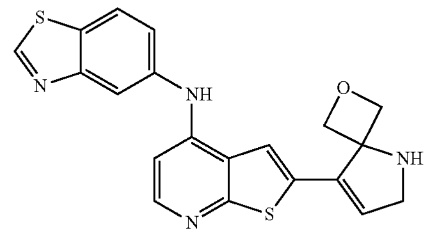 [SMILES: C1=C(c2cc3c(Nc4ccc5scnc5c4)ccnc3s2)C2(COC2)NC1] | ++++ |
| 40 | 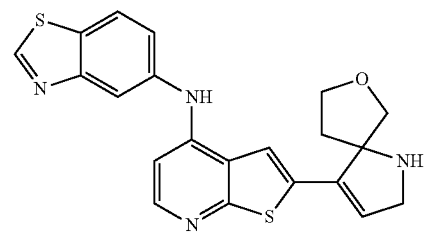 [SMILES: C1=C(c2cc3c(Nc4ccc5scnc5c4)ccnc3s2)C2(CCOC2)NC1] | ++++ |
| 41 | 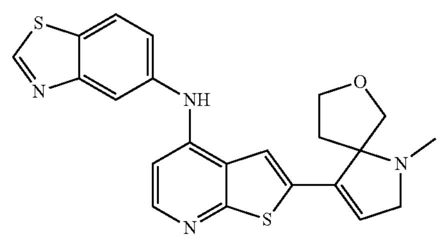 [SMILES: CN1CC=C(c2cc3c(Nc4ccc5scnc5c4)ccnc3s2)C12CCOC2] | +++ |
| 42 | 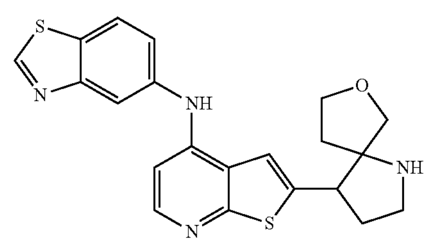 [SMILES: c1cc(Nc2ccc3scnc3c2)c2cc(C3CCNC34CCOC4)sc2n1] | +++ |
| 43 | 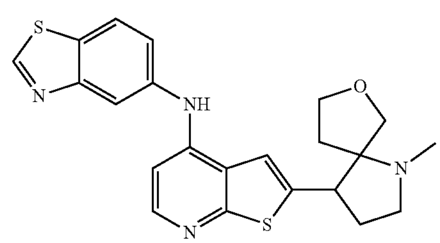 [SMILES: CN1CCC(c2cc3c(Nc4ccc5scnc5c4)ccnc3s2)C12CCOC2] | ++ |

TABLE 1-continued

| Example No. | Structure | IC$_{50}$ (nM) |
|---|---|---|
| 44 | 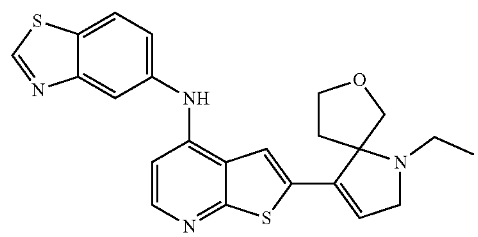 [SMILES: CCN1CC=C(c2cc3c(Nc4ccc5scnc5c4)ccnc3s2)C12CCOC2] | ++++ |
| 45 | 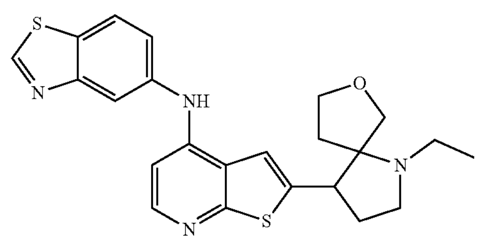 [SMILES: CCN1CCC(c2cc3c(Nc4ccc5scnc5c4)ccnc3s2)C12CCOC2] | +++ |
| 46 | 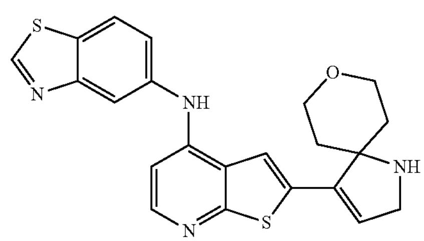 [SMILES: C1=C(c2cc3c(Nc4ccc5scnc5c4)ccnc3s2)C2(CCOCC2)NC1] | ++++ |
| 47 | 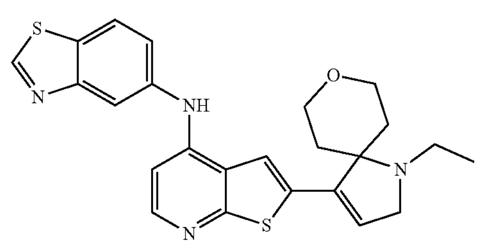 [SMILES: CCN1CC=C(c2cc3c(Nc4ccc5scnc5c4)ccnc3s2)C12CCOCC2] | ++++ |
| 48 | 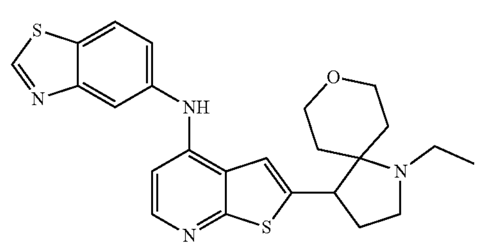 [SMILES: CCN1CCC(c2cc3c(Nc4ccc5scnc5c4)ccnc3s2)C12CCOCC2] | + |
| 49a | 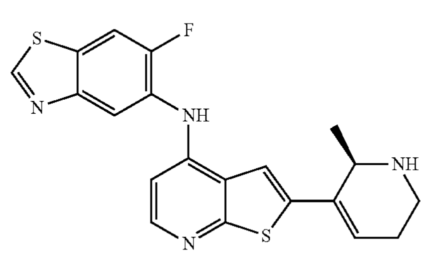 [SMILES: C[C@H]1NCCC=C1c1cc2c(Nc3cc4ncsc4cc3F)ccnc2s1] | +++ |

TABLE 1-continued

| Example No. | Structure | IC$_{50}$ (nM) |
|---|---|---|
| 49b | 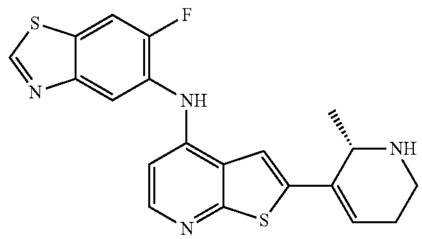 [SMILES: C[C@@H]1NCCC=C1c1cc2c(Nc3cc4ncsc4cc3F)ccnc2s1] | ++++ |
| 50b | 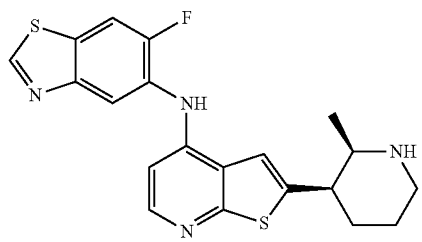 [SMILES: C[C@H]1NCCC[C@H]1c1cc2c(Nc3cc4ncsc4cc3F)ccnc2s1] | ++++ |
| 51b | 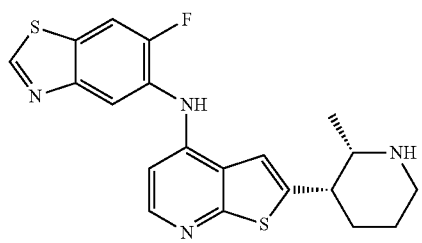 [SMILES: C[C@@H]1NCCC[C@@H]1c1cc2c(Nc3cc4ncsc4cc3F)ccnc2s1] | ++ |
| 52a | 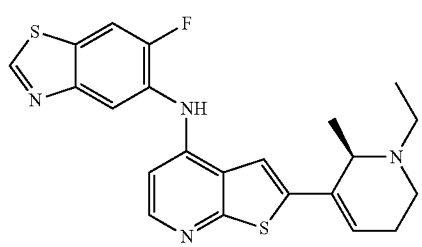 [SMILES: CCN1CCC=C(c2cc3c(Nc4cc5ncsc5cc4F)ccnc3s2)[C@H]1C] | +++ |
| 52b | 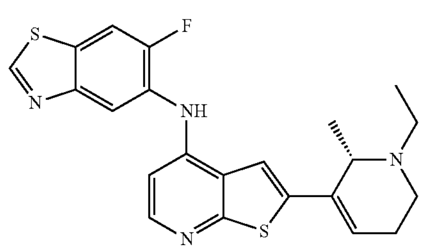 [SMILES: CCN1CCC=C(c2cc3c(Nc4cc5ncsc5cc4F)ccnc3s2)[C@@H]1C] | +++ |
| 53b | 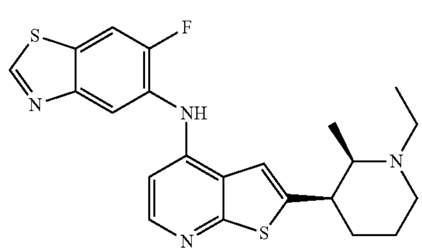 [SMILES: CCN1CCC[C@@H](c2cc3c(Nc4cc5ncsc5cc4F)ccnc3s2)[C@H]1C] | ++++ |

TABLE 1-continued

| Example No. | Structure | IC₅₀ (nM) |
|---|---|---|
| 54b | 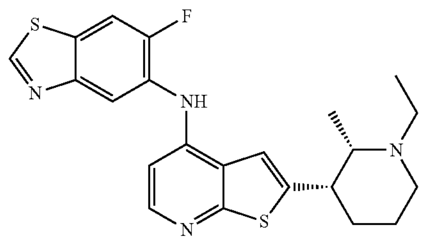 [SMILES: CCN1CCC[C@H](c2cc3c(Nc4cc5ncsc5cc4F)ccnc3s2)[C@@H]1C] | ++ |
| 56a | 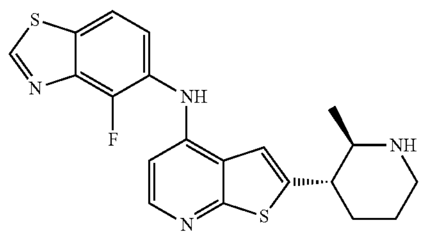 [SMILES: C[C@H]1NCCC[C@@H]1c1cc2c(Nc3ccc4scnc4c3F)ccnc2s1] | ++++ |
| 56b | 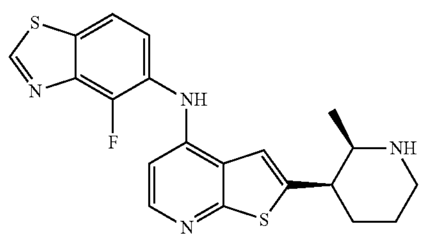 [SMILES: C[C@H]1NCCC[C@H]1c1cc2c(Nc3ccc4scnc4c3F)ccnc2s1] | ++++ |
| 57a | 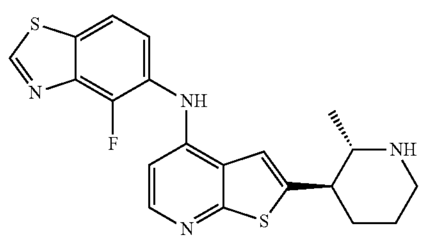 [SMILES: C[C@@H]1NCCC[C@H]1c1cc2c(Nc3ccc4scnc4c3F)ccnc2s1] | +++ |
| 57b | 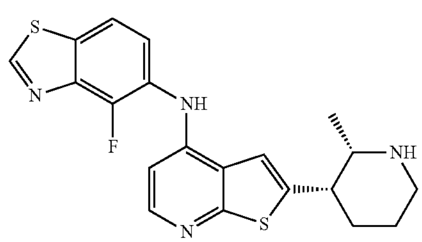 | ++++ |
| 58 | 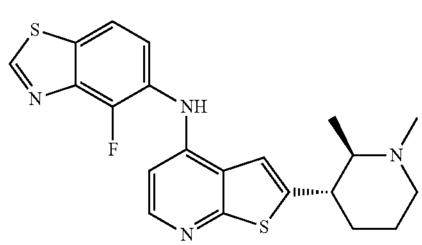 [SMILES: C[C@@H]1[C@@H](c2cc3c(Nc4ccc5scnc5c4F)ccnc3s2)CCCN1C] | ++++ |

TABLE 1-continued

| Example No. | Structure | IC$_{50}$ (nM) |
|---|---|---|
| 59 | 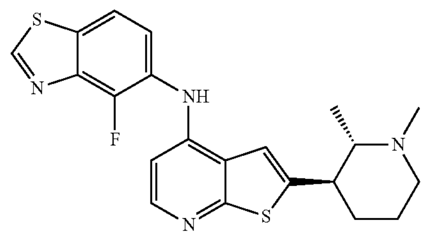 [SMILES: C[C@H]1[C@H](c2cc3c(Nc4ccc5scnc5c4F)ccnc3s2)CCCN1C] | ++++ |
| 60 | 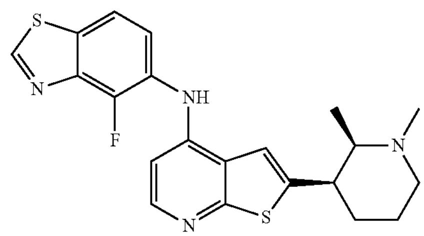 [SMILES: C[C@@H]1[C@H](c2cc3c(Nc4ccc5scnc5c4F)ccnc3s2)CCCN1C] | ++++ |
| 61 | 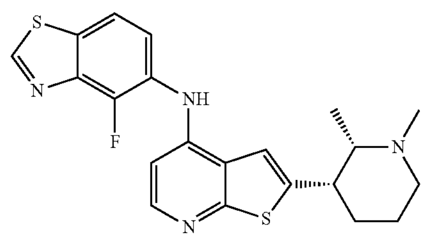 | ++++ |
| 62 | 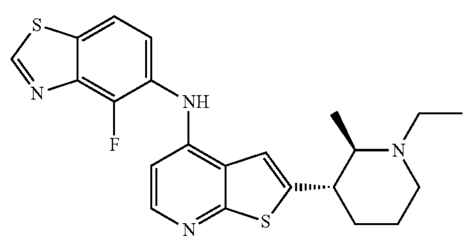 [SMILES: CCN1CCC[C@H](c2cc3c(Nc4ccc5scnc5c4F)ccnc3s2)[C@H]1C] | ++++ |
| 63 | 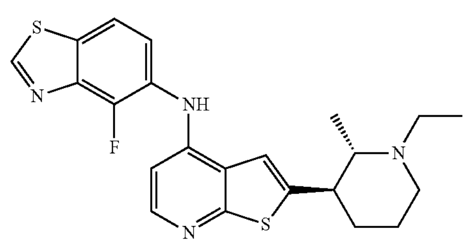 [SMILES: CCN1CCC[C@@H](c2cc3c(Nc4ccc5scnc5c4F)ccnc3s2)[C@@H]1C] | ++++ |
| 64 | 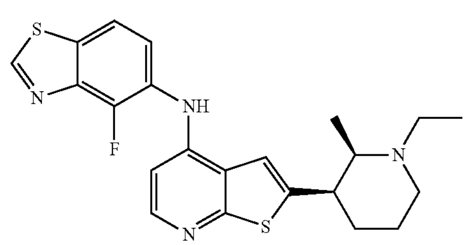 [SMILES: CCN1CCC[C@@H](c2cc3c(Nc4ccc5scnc5c4F)ccnc3s2)[C@H]1C] | ++++ |

TABLE 1-continued

| Example No. | Structure | IC$_{50}$ (nM) |
|---|---|---|
| 65 | 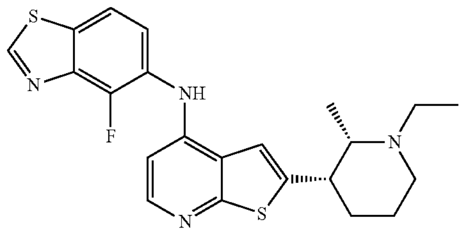 [SMILES: CCN1CCC[C@H](c2cc3c(Nc4ccc5scnc5c4F)ccnc3s2)[C@@H]1C] | ++++ |
| 66a | 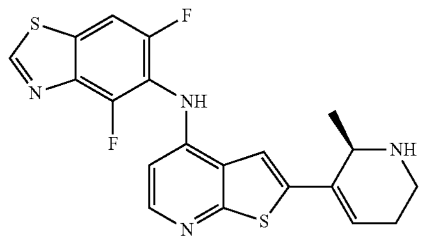 [SMILES: C[C@H]1NCCC=C1c1cc2c(Nc3c(F)cc4scnc4c3F)ccnc2s1] | ++++ |
| 66b | 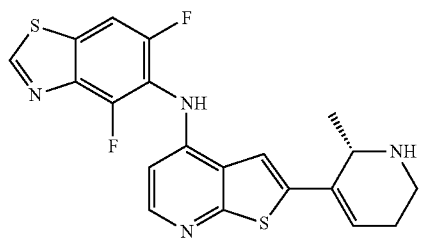 [SMILES: C[C@@H]1NCCC=C1c1cc2c(Nc3c(F)cc4scnc4c3F)ccnc2s1] | ++++ |
| 67a | 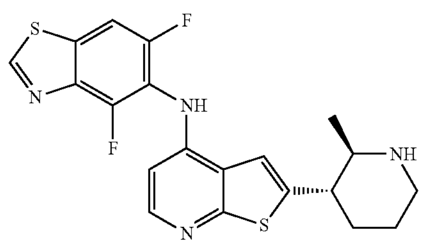 [SMILES: C[C@H]1NCCC[C@@H]1c1cc2c(Nc3c(F)cc4scnc4c3F)ccnc2s1] | ++++ |
| 67b | 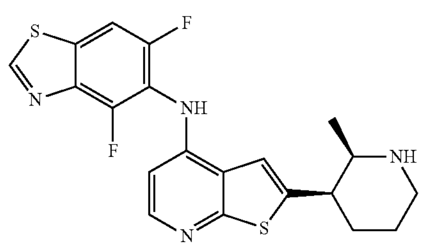 [SMILES: C[C@H]1NCCC[C@H]1c1cc2c(Nc3c(F)cc4scnc4c3F)ccnc2s1] | ++++ |
| 68a | 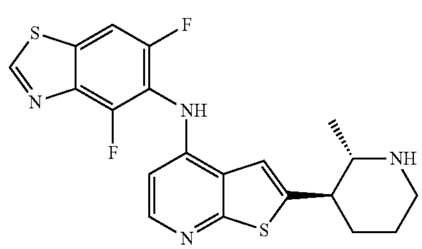 [SMILES: C[C@@H]1NCCC[C@H]1c1cc2c(Nc3c(F)cc4scnc4c3F)ccnc2s1] | +++ |

TABLE 1-continued

| Example No. | Structure | IC$_{50}$ (nM) |
|---|---|---|
| 68b | 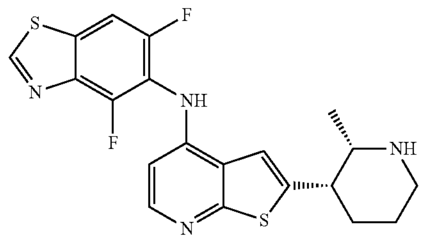 [SMILES: C[C@@H]1NCCC[C@@H]1c1cc2c(Nc3c(F)cc4scnc4c3F)ccnc2s1] | ++++ |
| 69 | 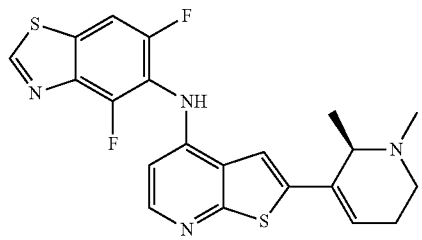 [SMILES: C[C@@H]1C(c2cc3c(Nc4c(F)cc5scnc5c4F)ccnc3s2)=CCCN1C] | ++++ |
| 70b | 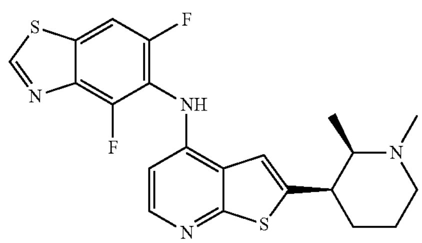 [SMILES: C[C@@H]1[C@H](c2cc3c(Nc4c(F)cc5scnc5c4F)ccnc3s2)CCCN1C] | ++++ |
| 71a | 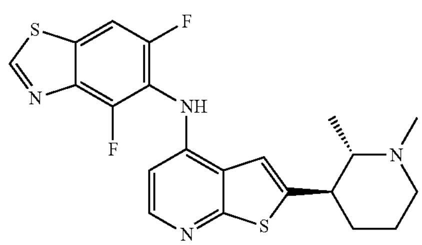 [SMILES: C[C@H]1[C@H](c2cc3c(Nc4c(F)cc5scnc5c4F)ccnc3s2)CCCN1C] | ++++ |
| 71b | 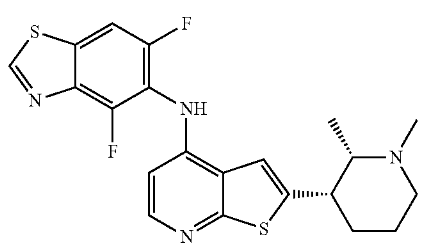 [SMILES: C[C@H]1[C@@H](c2cc3c(Nc4c(F)cc5scnc5c4F)ccnc3s2)CCCN1C] | ++++ |
| 72a | 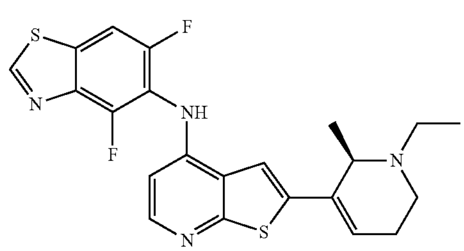 [SMILES: CCN1CCC=C(c2cc3c(Nc4c(F)cc5scnc5c4F)ccnc3s2)[C@H]1C] | ++++ |

TABLE 1-continued

| Example No. | Structure | IC$_{50}$ (nM) |
|---|---|---|
| 72b | 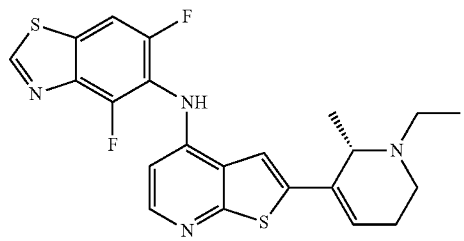 [SMILES: CCN1CCC=C(c2cc3c(Nc4c(F)cc5scnc5c4F)ccnc3s2)[C@@H]1C] | ++++ |
| 73b | 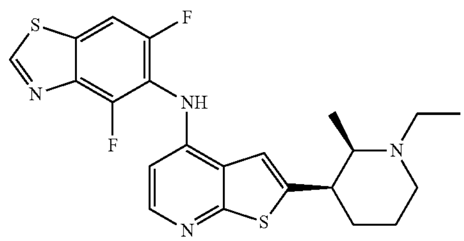 [SMILES: CCN1CCC[C@@H](c2cc3c(Nc4c(F)cc5scnc5c4F)ccnc3s2)[C@H]1C] | ++++ |
| 74b | 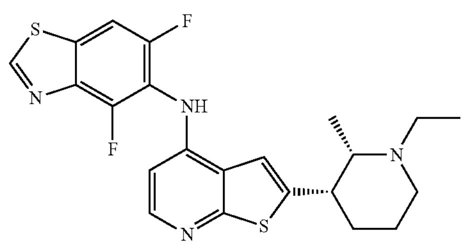 [SMILES: CCN1CCC[C@H](c2cc3c(Nc4c(F)cc5scnc5c4F)ccnc3s2)[C@@H]1C] | ++++ |
| 75 | (racemate) | ++++ |
| 75a | (Single enantiomer) | ++++ |
| 75b | (Single enantiomer) | ++++ |

TABLE 1-continued

| Example No. | Structure | IC$_{50}$ (nM) |
|---|---|---|
| 75c | Single enantiomer | ++++ |
| 75d | Single enantiomer | ++++ |
| 76 | Racemate | +++ |
| 77 | Racemate | +++ |
| 78a | Single enantiomer | ++++ |

TABLE 1-continued
| Example No. | Structure | IC$_{50}$ (nM) |
|---|---|---|
| 78b | 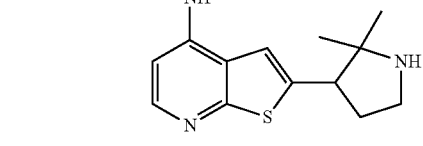 Single enantiomer | ++++ |
| 79 | 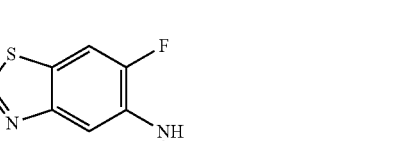 Racemate | ++ |
| 80 | 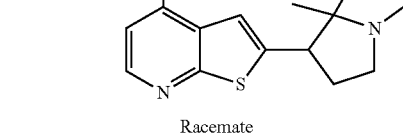 Racemate | ++ |
| 81 | 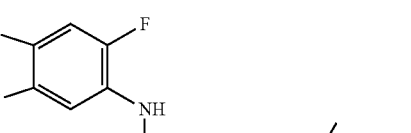 Racemate | + |
| 82 | 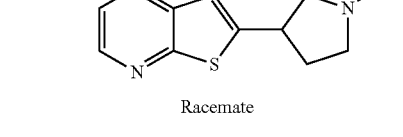 Racemate | + |

TABLE 1-continued

| Example No. | Structure | IC$_{50}$ (nM) |
|---|---|---|
| 83 | Racemate | + |
| 84 | Racemate | + |
| 85 | Racemate | + |
| 86 | Racemate | + |
| 87 | Racemate | ++++ |

TABLE 1-continued

| Example No. | Structure | IC$_{50}$ (nM) |
|---|---|---|
| 88 | Racemate | ++++ |
| 89 | Racemate | ++++ |
| 90 | Racemate | ++++ |
| 91 | Racemate | +++ |
| 92 | Racemate | ++++ |

TABLE 1-continued

| Example No. | Structure | IC$_{50}$ (nM) |
|---|---|---|
| 93 | Racemate | ++++ |
| 93a | Single enantiomer | ++++ |
| 93b | Single enantiomer | ++++ |
| 93c | Single enantiomer | ++++ |
| 93d | Single enantiomer | ++++ |

TABLE 1-continued

| Example No. | Structure | IC$_{50}$ (nM) |
|---|---|---|
| 94 | Racemate | ++++ |
| 95 | Racemate | +++ |
| 96 | Racemate | ++++ |
| 96a | Single enantiomer | ++++ |
| 96b | Single enantiomer | ++++ |

TABLE 1-continued

| Example No. | Structure | IC$_{50}$ (nM) |
|---|---|---|
| 97 | Racemate | ++++ |
| 98 | Racemate | ++++ |
| 99 | Racemate | +++ |
| 100 | Racemate | +++ |
| 101 | Racemate | ++ |

TABLE 1-continued
| Example No. | Structure | IC$_{50}$ (nM) |
|---|---|---|
| 102 | 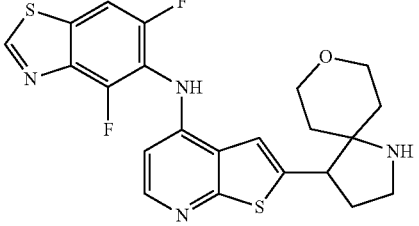 Racemate | +++ |
| 103 | 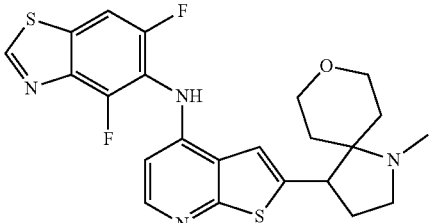 Racemate | ++ |
| 104 | 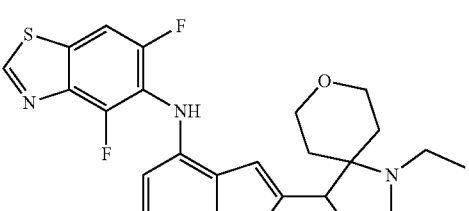 Racemate | + |
| 105 | 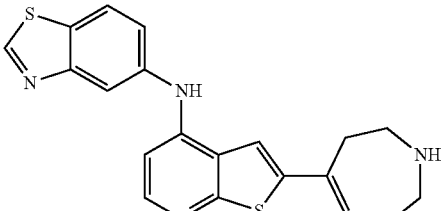 | ++++ |
| 106 | 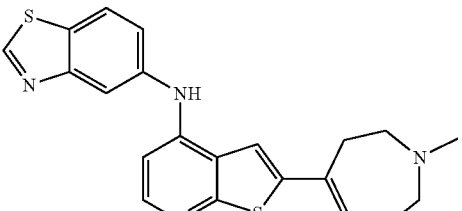 | ++++ |
| 107 | 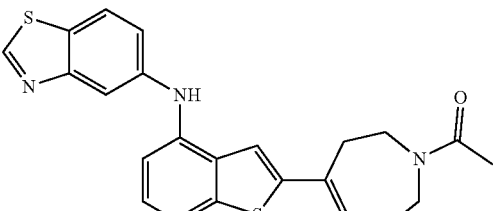 | ++++ |

TABLE 1-continued

| Example No. | Structure | IC$_{50}$ (nM) |
|---|---|---|
| 108 | Racemate | ++++ |
| 109 | Racemate | ++++ |
| 110 | Racemate | ++++ |
| 111 | Racemate | +++ |
| 112 | 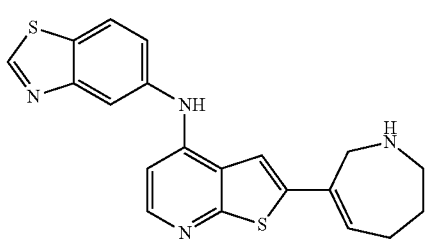 [SMILES: C1=C(c2cc3c(Nc4ccc5scnc5c4)ccnc3s2)CNCCC1] | ++++ |
| 113 | 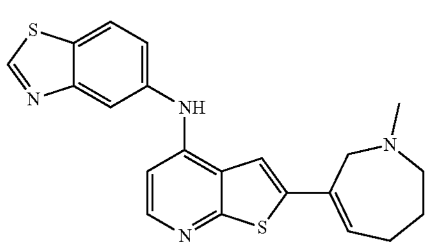 [SMILES: CN1CCCC=C(c2cc3c(Nc4ccc5scnc5c4)ccnc3s2)C1] | ++++ |

TABLE 1-continued

| Example No. | Structure | IC$_{50}$ (nM) |
|---|---|---|
| 114 | 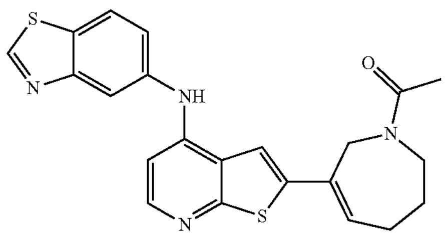 [SMILES: CC(=O)N1CCCC=C(c2cc3c(Nc4ccc5scnc5c4)ccnc3s2)C1] | ++++ |
| 115a | Single enantiomer | ++++ |
| 115b | Single enantiomer | ++++ |
| 115c | Single enantiomer | ++++ |
| 115d | Single enantiomer | ++++ |

TABLE 1-continued
| Example No. | Structure | IC$_{50}$ (nM) |
|---|---|---|
| 116a | 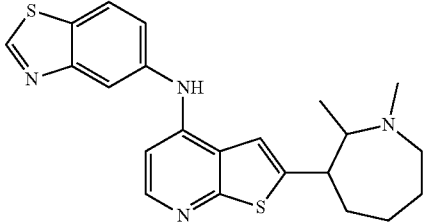<br>Single enantiomer | ++++ |
| 116b | 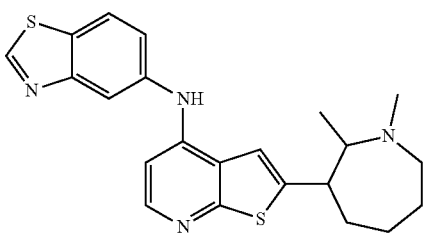<br>Single enantiomer | ++++ |
| 116c | 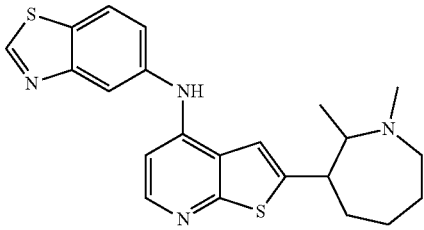<br>Single enantiomer | ++++ |
| 116d | 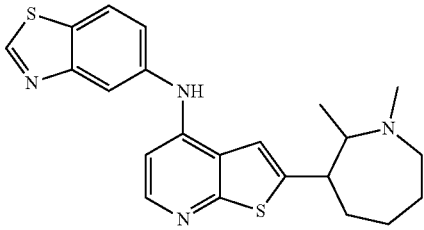<br>Single enantiomer | ++++ |
| 117a | 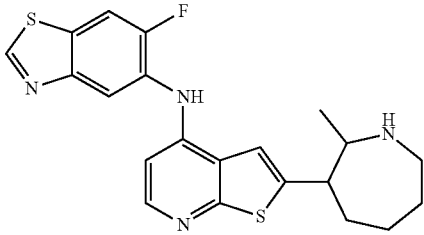<br>Single enantiomer | ++++ |

TABLE 1-continued

| Example No. | Structure | IC$_{50}$ (nM) |
|---|---|---|
| 117b | Single enantiomer | ++++ |
| 117c | Single enantiomer | ++++ |
| 117d | Single enantiomer | ++++ |
| 118b | Single enantiomer | ++++ |
| 118c | Single enantiomer | ++++ |

TABLE 1-continued

| Example No. | Structure | IC$_{50}$ (nM) |
|---|---|---|
| 118d | Single enantiomer | +++ |
| 119 | Racemate | ++ |
| 119b | Single enantiomer | ++++ |
| 119c | Single enantiomer | ++++ |
| 119d | Single enantiomer | + |

TABLE 1-continued
| Example No. | Structure | IC$_{50}$ (nM) |
|---|---|---|
| 120 | 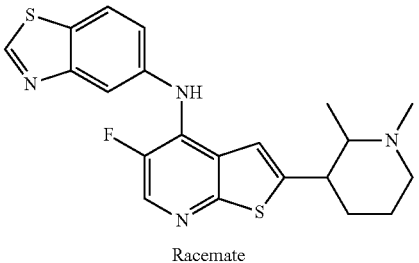 [SMILES: CC1C(c2cc3c(Nc4ccc5scnc5c4)c(F)cnc3s2)CCCN1C]<br>Racemate | ++++ |
| 120a | 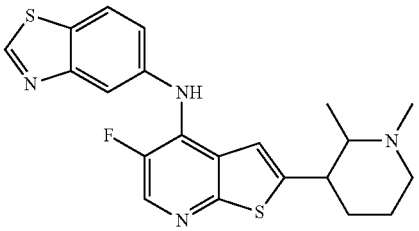<br>Single enantiomer | ++ |
| 120b | 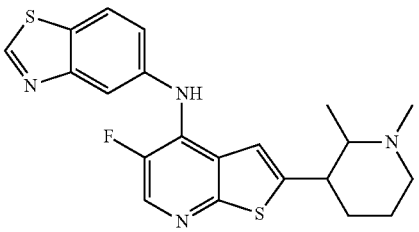<br>Single enantiomer | ++++ |
| 120c | 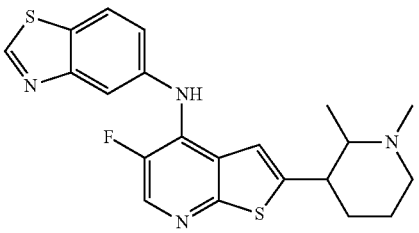<br>Single enantiomer | ++++ |
| 120d | 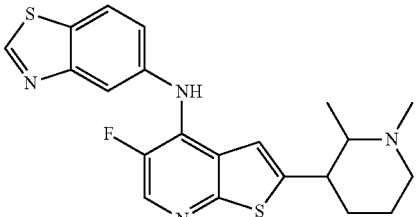<br>Single enantiomer | + |

TABLE 1-continued
| Example No. | Structure | IC$_{50}$ (nM) |
|---|---|---|
| 121 | 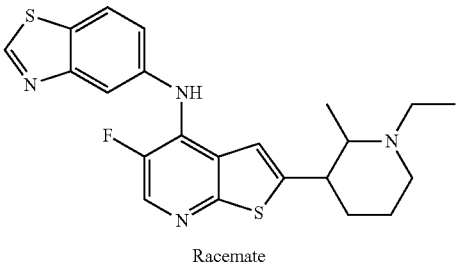 [SMILES: CCN1CCCC(c2cc3c(Nc4ccc5scnc5c4)c(F)cnc3s2)C1C] Racemate | ++++ |
| 122a | 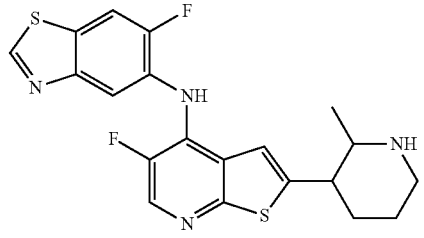 Single enantiomer | + |
| 122b | 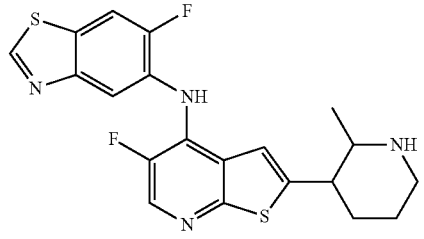 Single enantiomer | ++ |
| 122c | 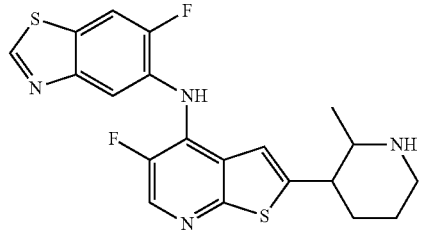 Single enantiomer | +++ |
| 122d | 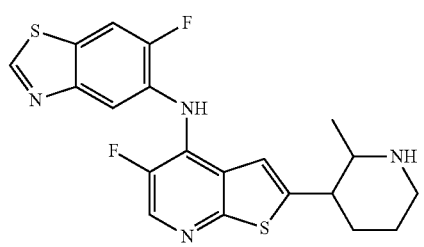 Single enantiomer | + |

TABLE 1-continued

| Example No. | Structure | IC$_{50}$ (nM) |
|---|---|---|
| 123a | Single enantiomer | + |
| 123b | Single enantiomer | + |
| 123c | Single enantiomer | + |
| 123d | Single enantiomer | ++ |
| 124a | Single enantiomer | + |

TABLE 1-continued

| Example No. | Structure | IC$_{50}$ (nM) |
|---|---|---|
| 124b | Single enantiomer | ++++ |
| 124c | Single enantiomer | ++++ |
| 124d | Single enantiomer | + |
| 125a | Single enantiomer | + |
| 125b | Single enantiomer | +++ |

TABLE 1-continued

| Example No. | Structure | IC$_{50}$ (nM) |
|---|---|---|
| 125c | Single enantiomer | ++++ |
| 125d | Single enantiomer | + |
| 126a | Single enantiomer | ++++ |
| 126b | Single enantiomer | ++++ |
| 126c | Single enantiomer | ++++ |

TABLE 1-continued

| Example No. | Structure | IC$_{50}$ (nM) |
|---|---|---|
| 126d | Single enantiomer | +++ |
| 127a | Single enantiomer | ++ |
| 127b | Single enantiomer | ++++ |
| 127c | Single enantiomer | ++++ |
| 127d | Single enantiomer | +++ |

The invention claimed is:
1. A compound of formula I':

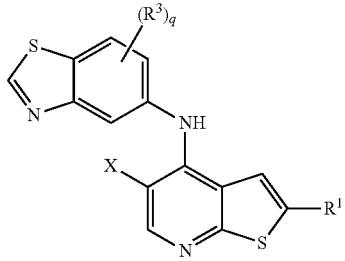

or a pharmaceutically acceptable salt thereof,
wherein:
$R^1$ is a 4- to 7-membered monocyclic saturated or partially unsaturated heterocyclic ring having 1 to 3 heteroatoms independently selected from nitrogen, oxygen, and sulfur; a 9- to 10-membered bicyclic heterocyclic ring having 1 to 3 heteroatoms independently selected from nitrogen, oxygen, and sulfur; or a 7- to 11-membered spirocyclic fused heterocyclic ring having 1 to 3 heteroatoms independently selected from nitrogen, oxygen, and sulfur, and wherein $R^1$ is substituted with $(R^2)_p$;
each $R^2$ is independently halogen, optionally substituted $C_{1-6}$ aliphatic, —OR, —N(R)$_2$, —C(O)R, —C(O)OR, —SO$_2$R, or an optionally substituted 3- to 7-membered saturated heterocyclic ring having 1 to 2 heteroatoms independently selected from nitrogen, oxygen, and sulfur;
each R is independently hydrogen, optionally substituted $C_{1-6}$ aliphatic, or an optionally substituted 4- to 6-membered saturated heterocyclic ring having 1 to 3 heteroatoms independently selected from nitrogen, oxygen, and sulfur; or
two R groups on a nitrogen atom, together with the atoms to which they are attached, form a 4- to 6-membered heterocyclic ring having 1 or 2 additional heteroatoms independently selected from nitrogen, oxygen, or sulfur;
each $R^3$ is independently halogen, CN, —N(R)$_2$, —OR, or optionally substituted $C_{1-6}$ aliphatic;
X is hydrogen or halogen;
p is 0-4; and
q is 0-4.

2. The compound of claim 1, wherein $R^1$ is a 4- to 7-membered monocyclic saturated or partially unsaturated heterocyclic ring having 1 to 3 heteroatoms independently selected from nitrogen, oxygen, and sulfur, wherein $R^1$ is substituted with $(R^2)_p$.

3. The compound of claim 2, wherein $R^1$ is selected from

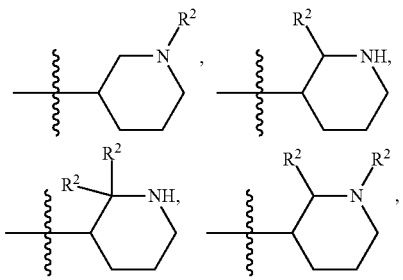

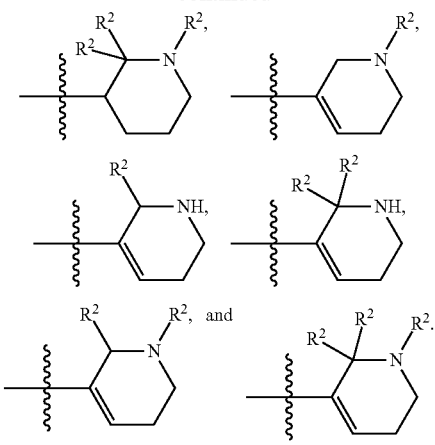

4. The compound of claim 2, wherein $R^1$ is selected from

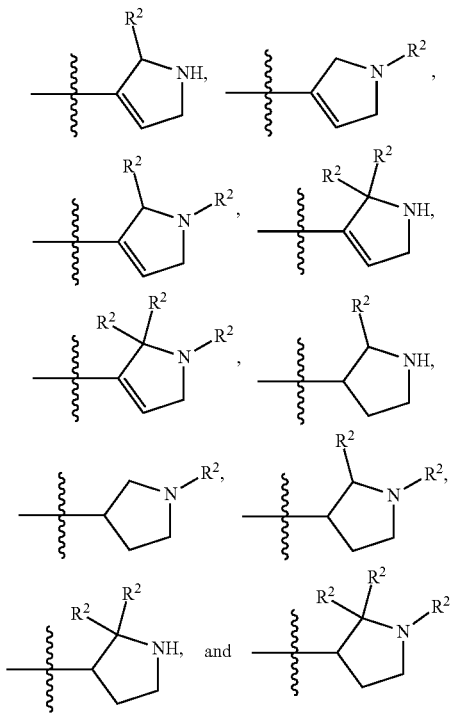

5. The compound of claim 2, wherein $R^1$ is selected from

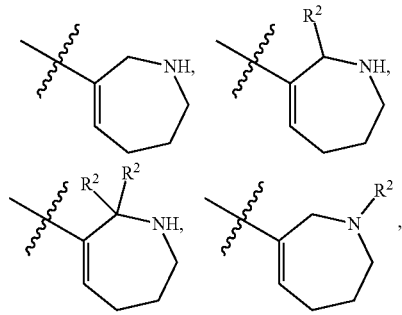

-continued
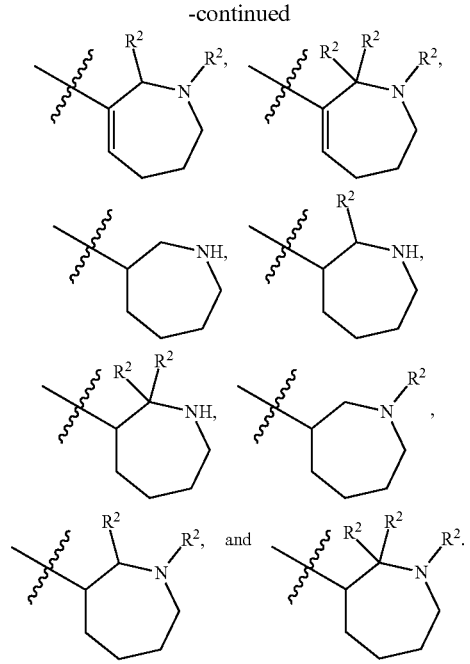
6. The compound of claim 2, wherein R¹ is selected from
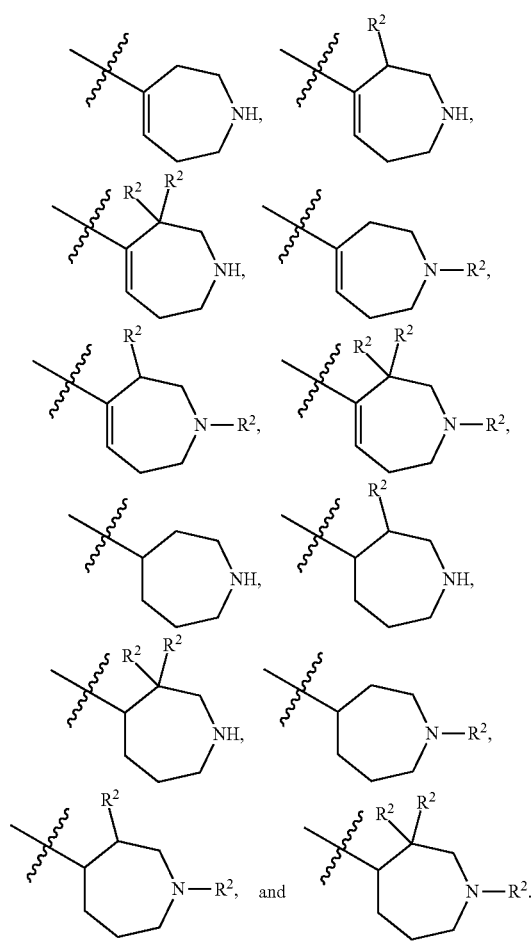
7. The compound of claim 1, wherein R² is optionally substituted $C_{1-6}$ aliphatic.
8. The compound of claim 1, wherein R¹ is selected from
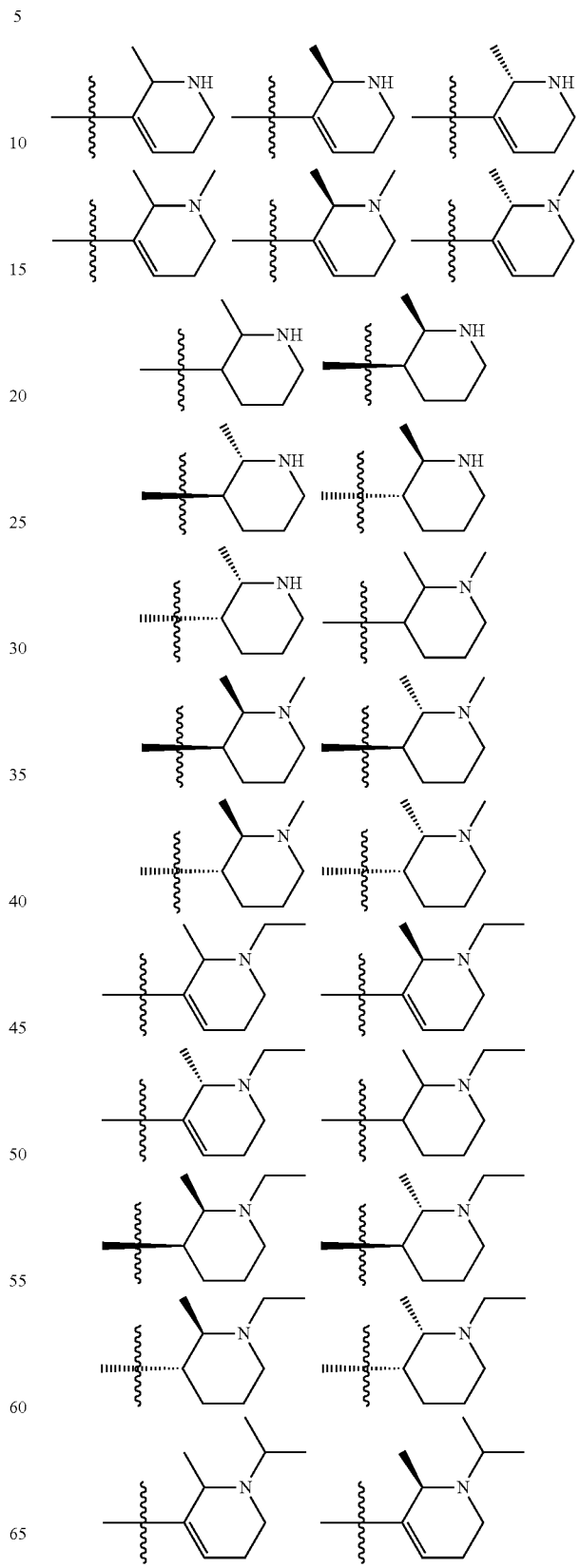

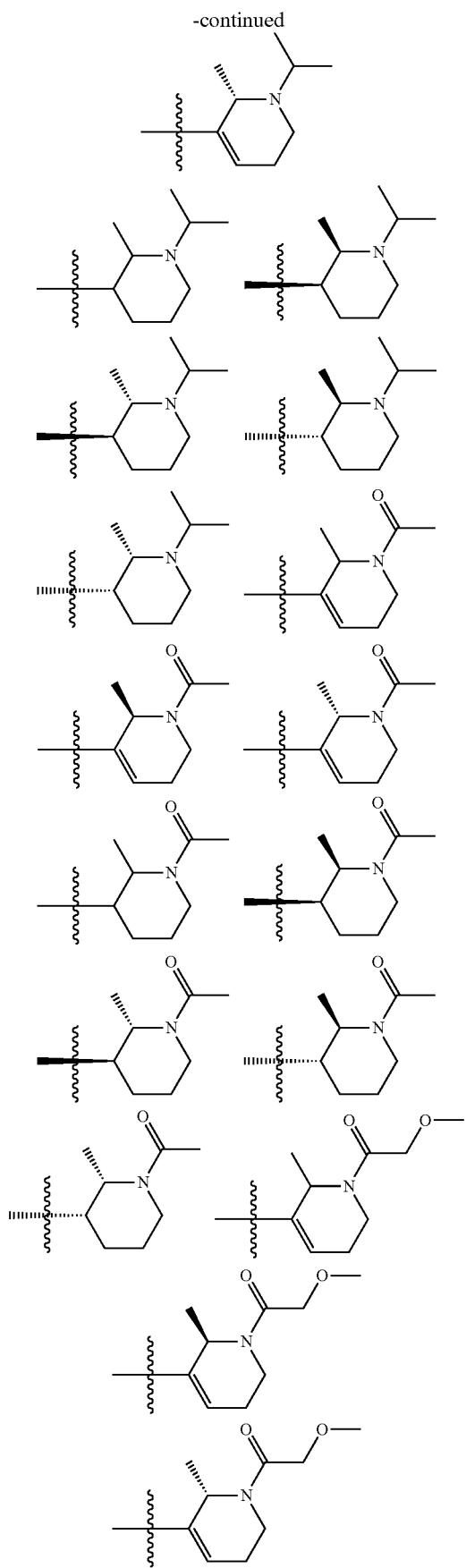
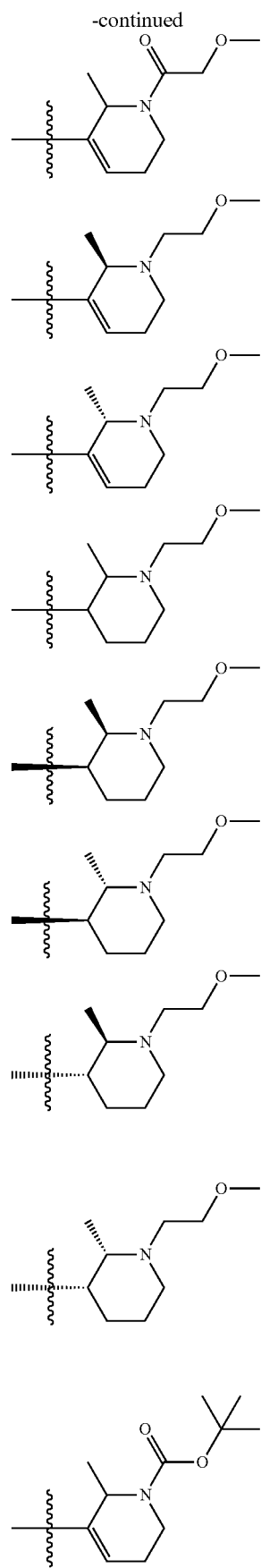

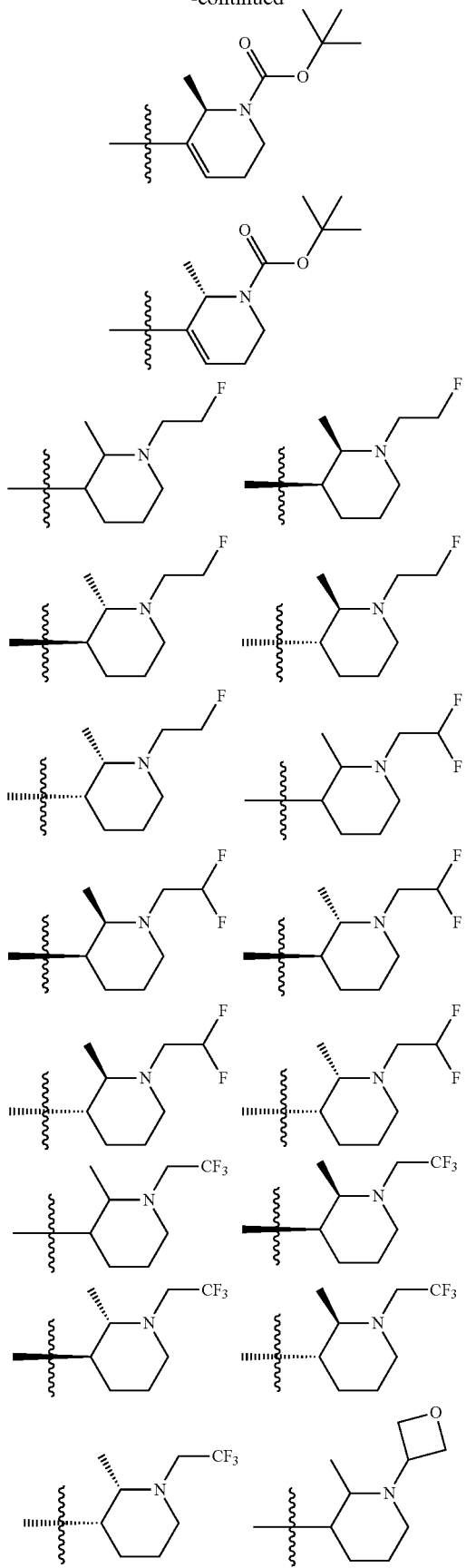
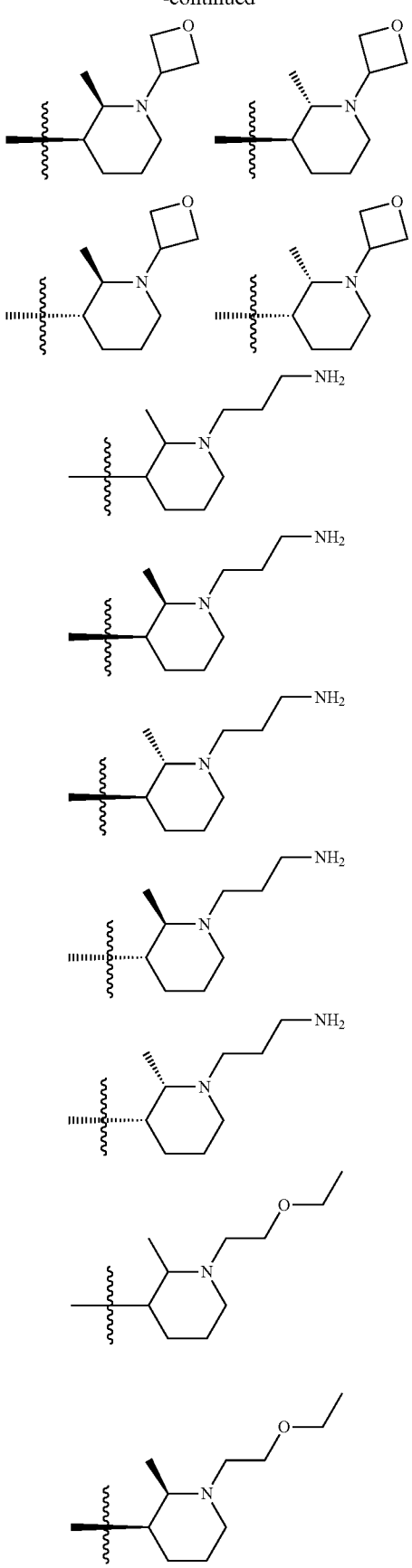

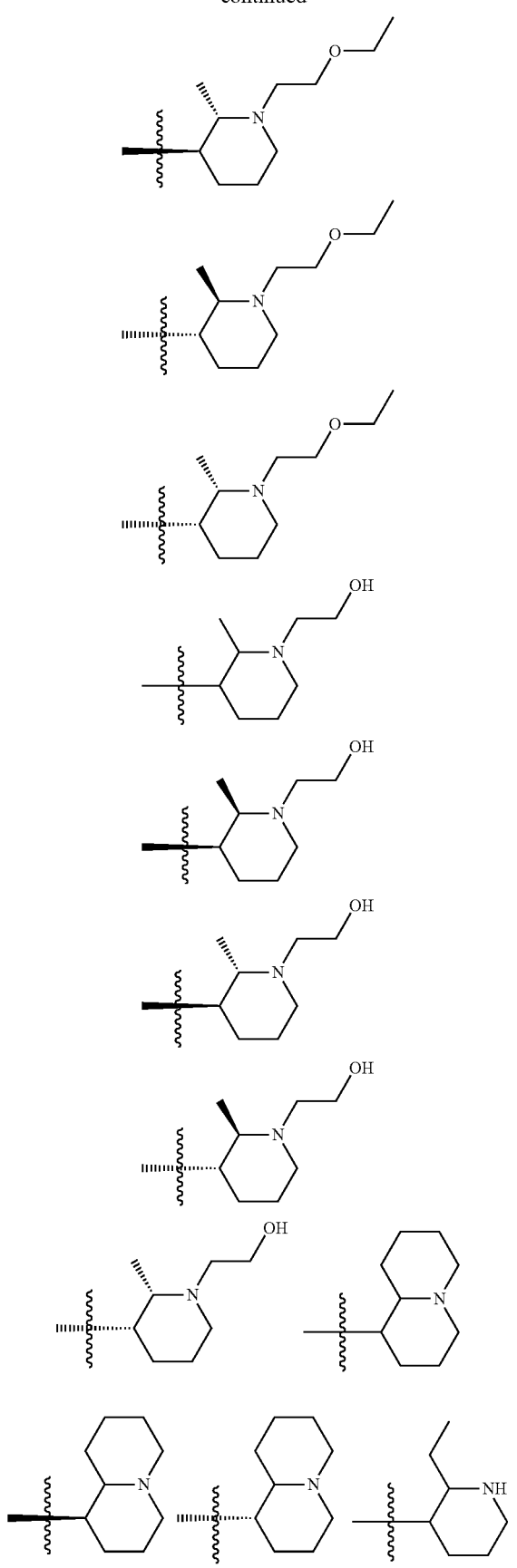
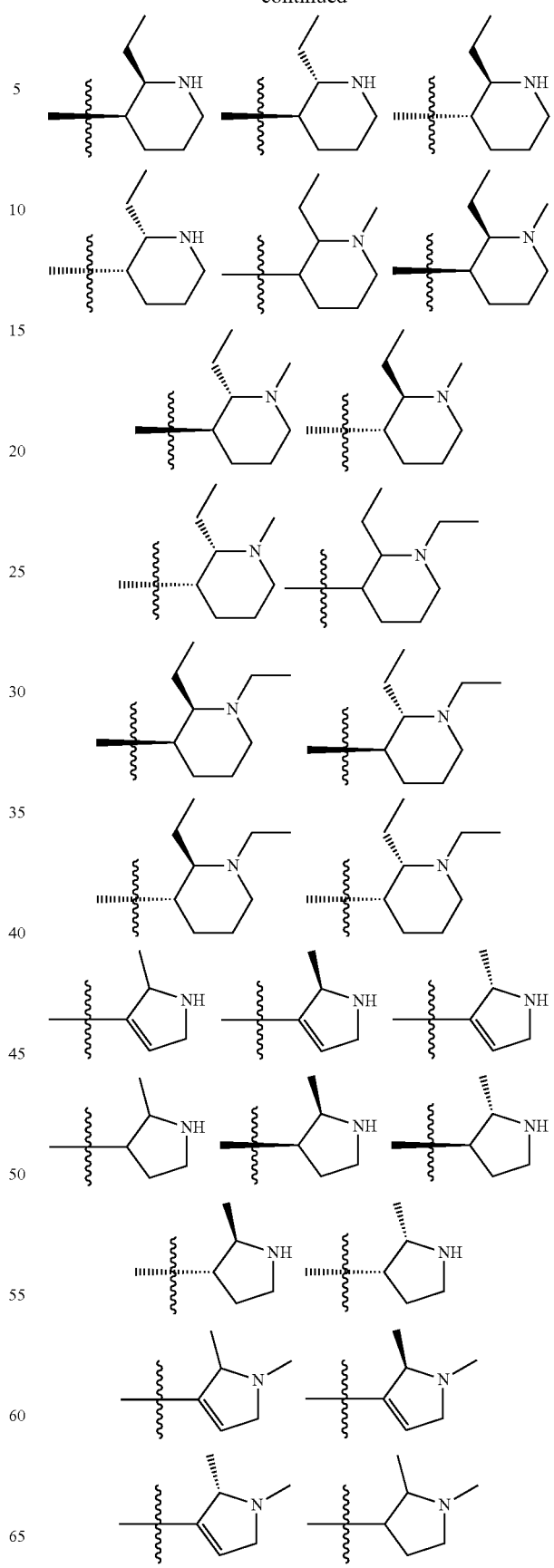

581
-continued
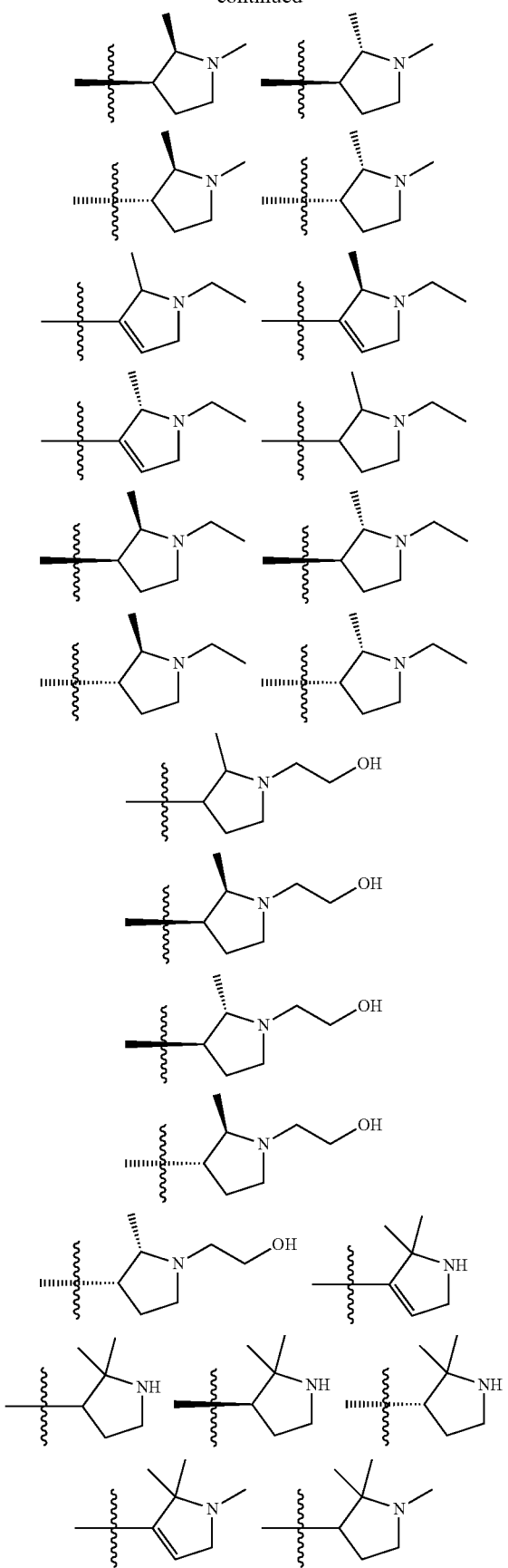
582
-continued
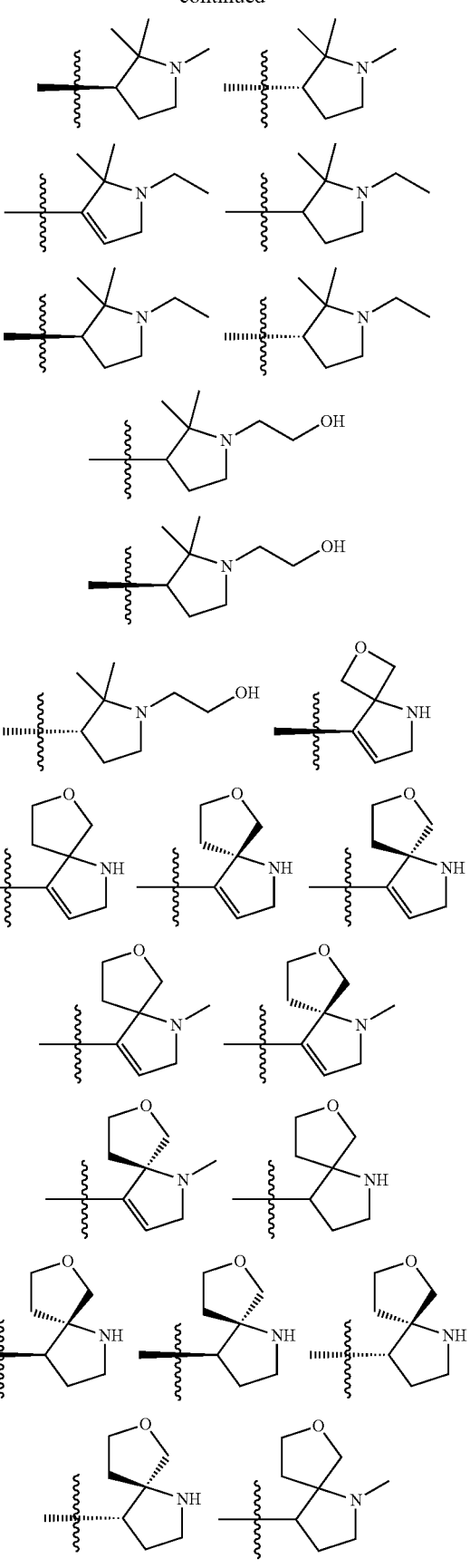

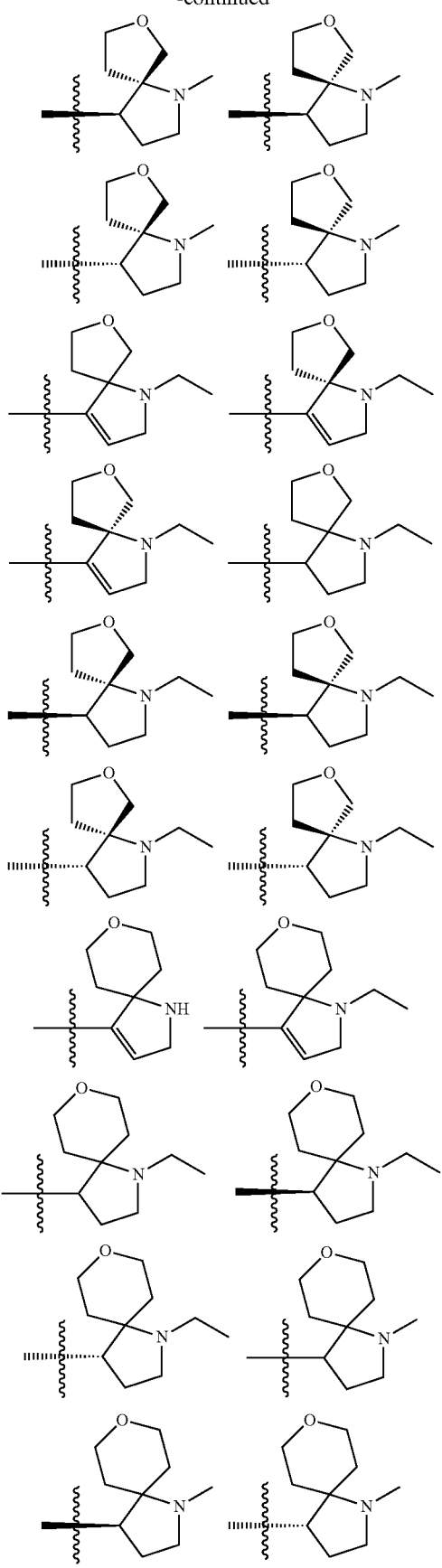
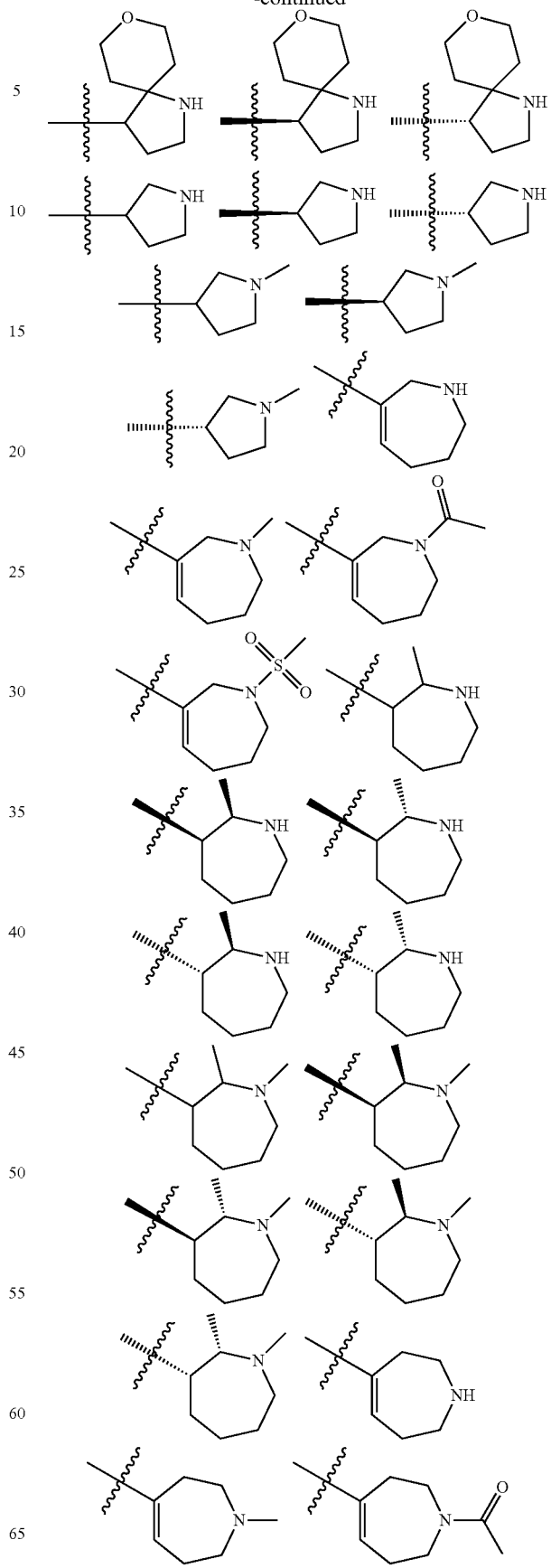

-continued

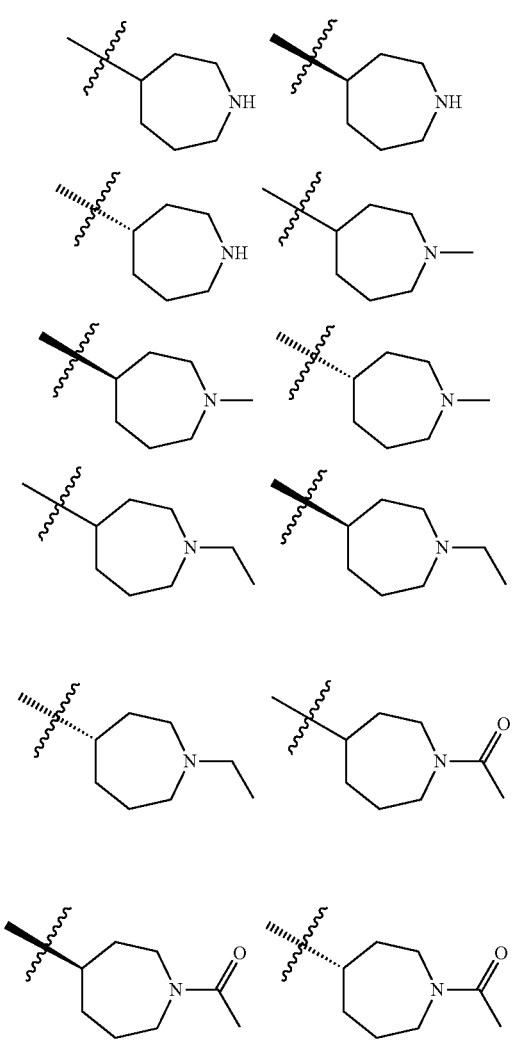

9. The compound of claim 1, wherein $R^3$ is

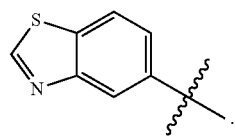 [SMILES: *c1ccc2scnc2c1 ; "."]

10. The compound of claim 1, wherein the compound is of Formula II or II':

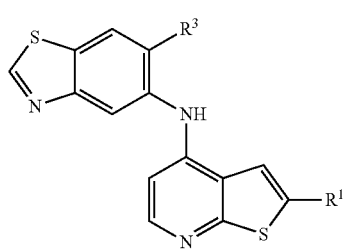
II

-continued

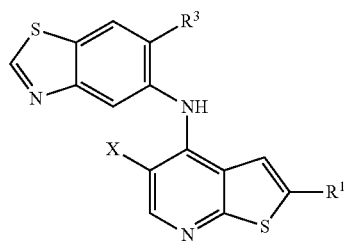
II' or a pharmaceutically acceptable salt thereof.

11. The compound of claim 1, wherein the compound is of Formula III or III':

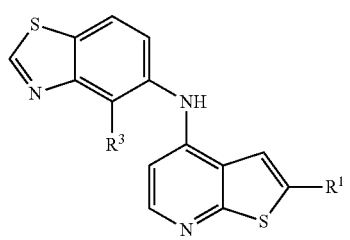
III

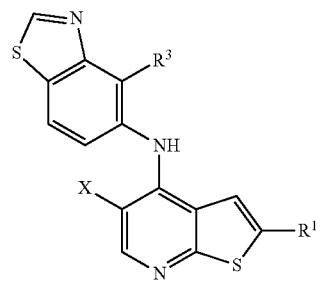
III' or a pharmaceutically acceptable salt thereof.

12. The compound of claim 1, wherein the compound is of Formula IV or IV':

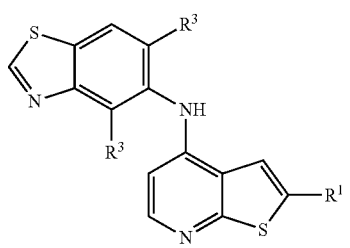
IV

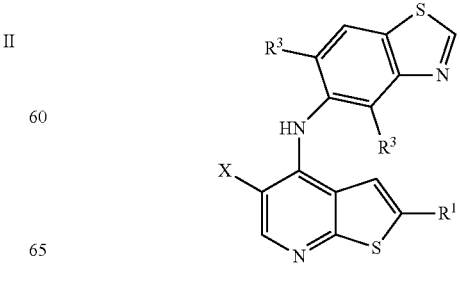
IV' or a pharmaceutically acceptable salt thereof.
13. The compound of claim 1, wherein R³ is halogen.
14. The compound of claim 1, wherein the compound is selected from:
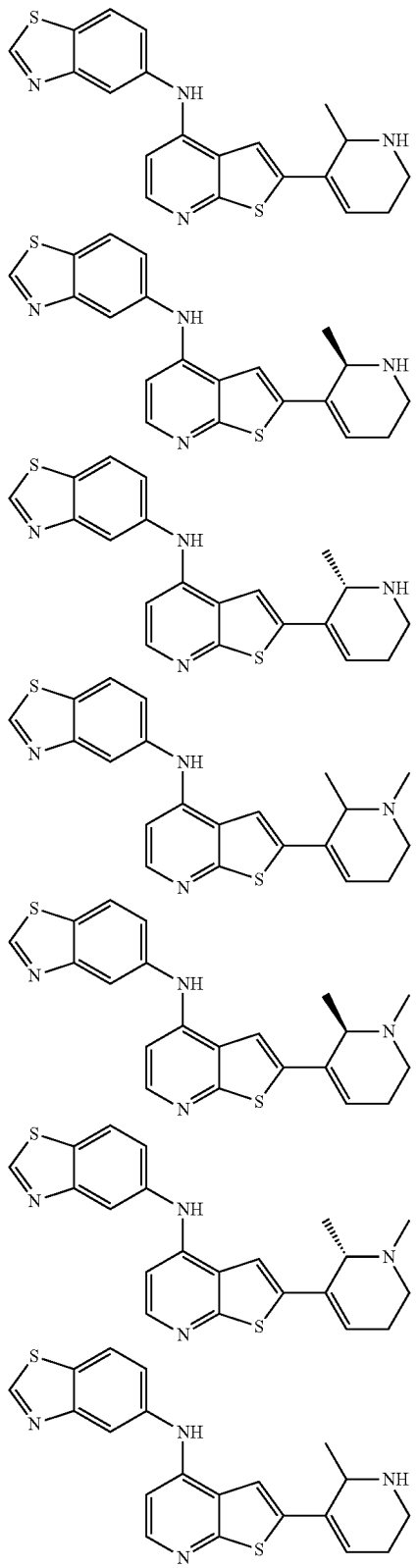
-continued
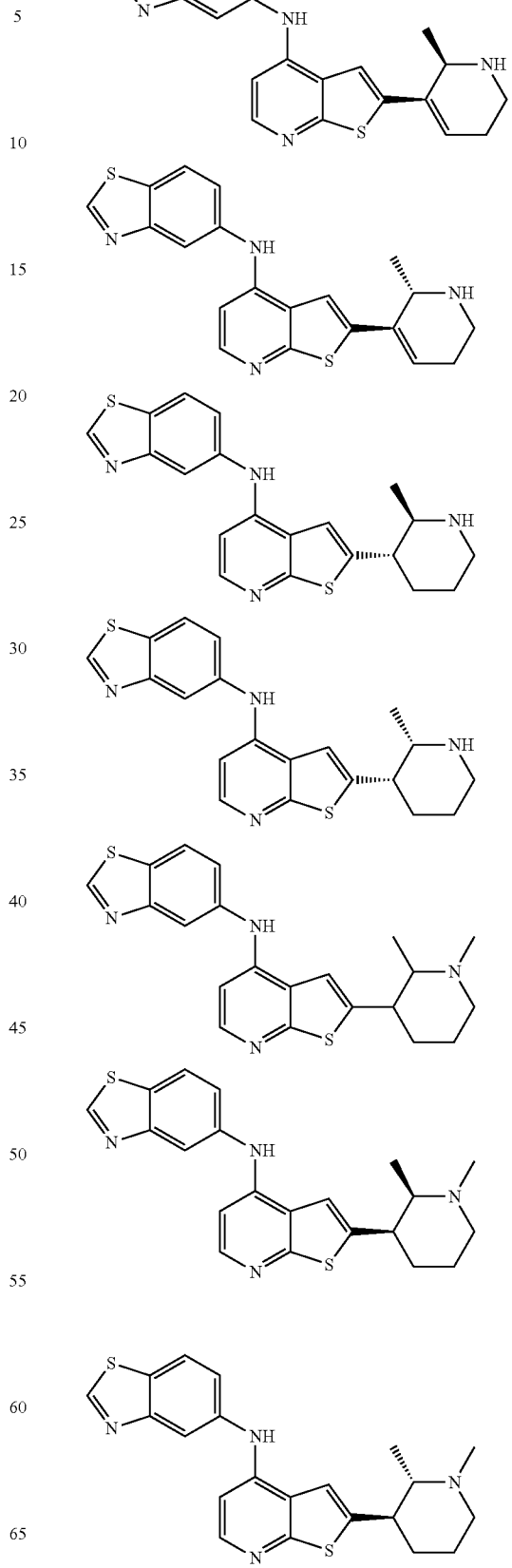

589
-continued
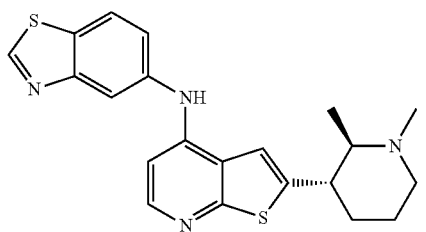
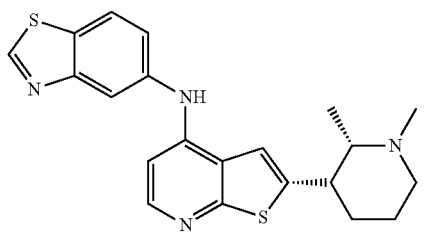
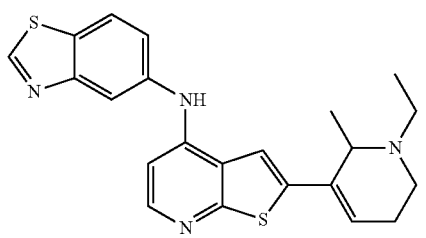
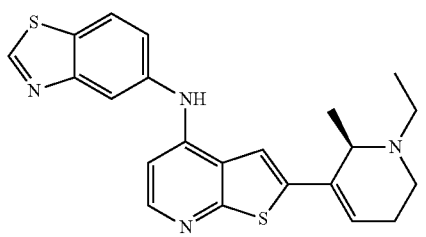
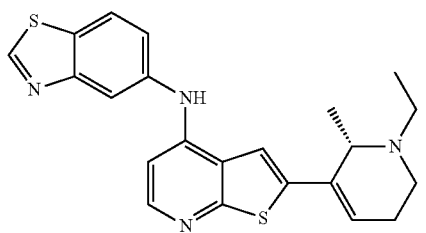
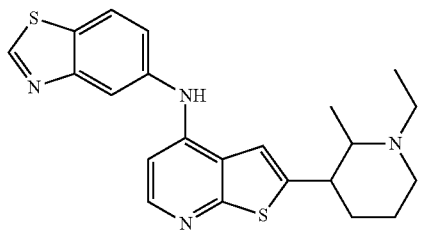
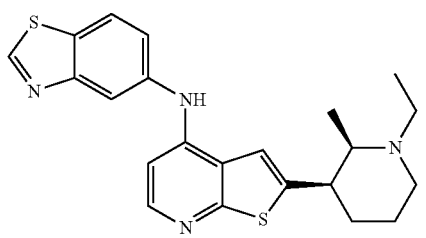
590
-continued
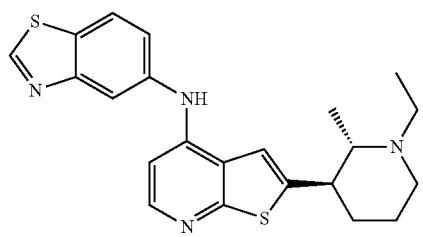
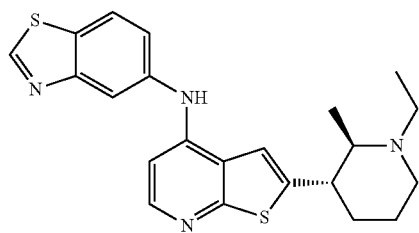
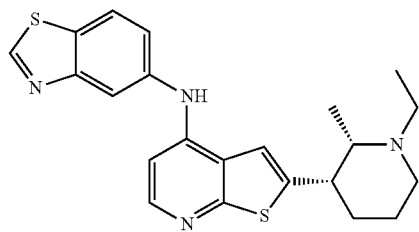
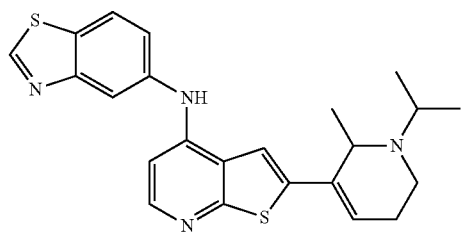
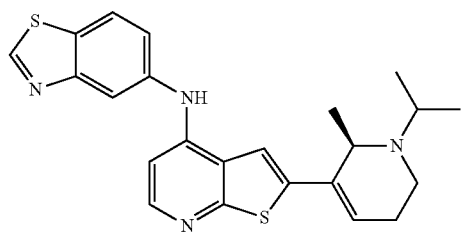
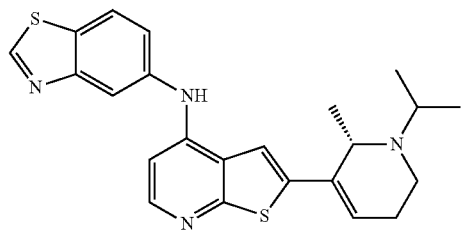
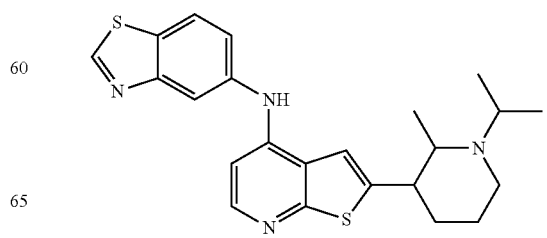

591
-continued
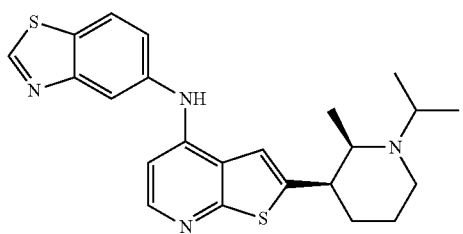
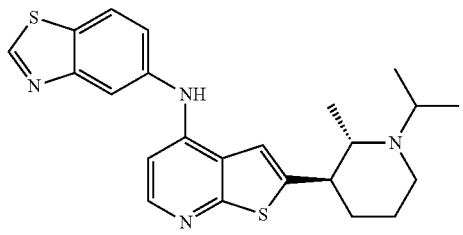
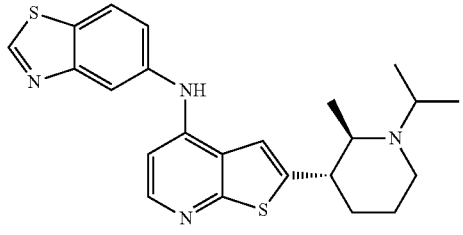
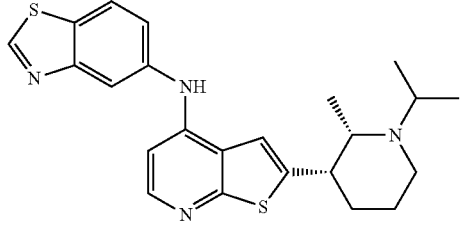
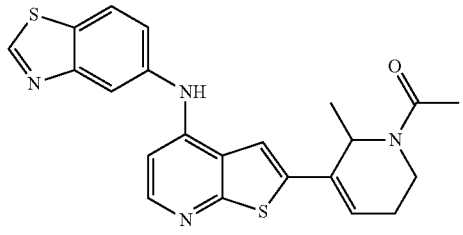
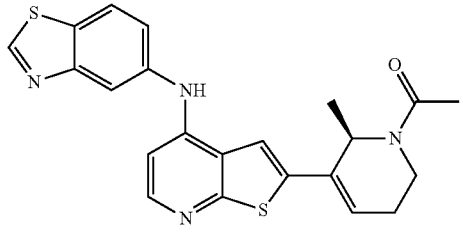
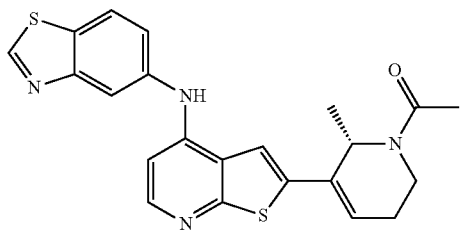
592
-continued
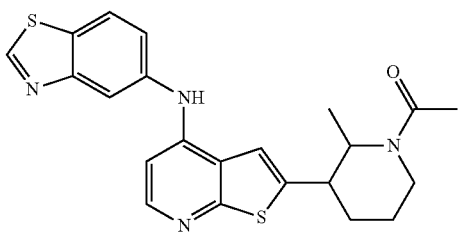
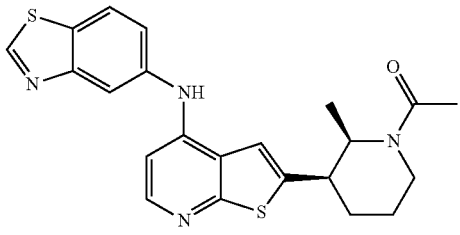
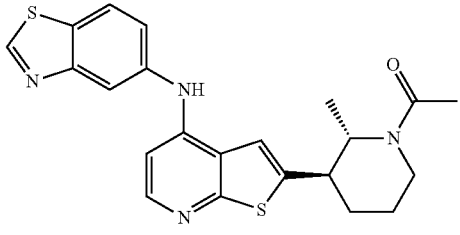
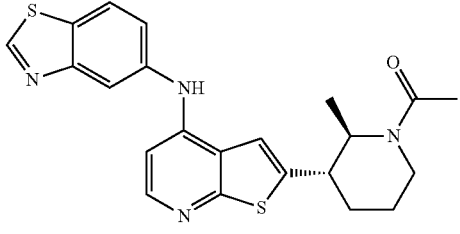
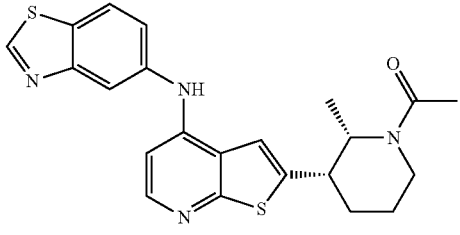
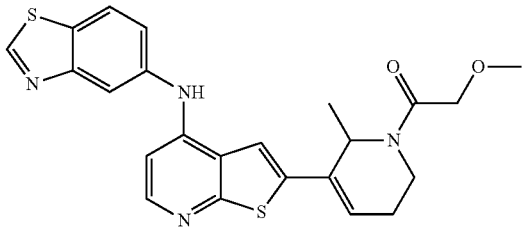
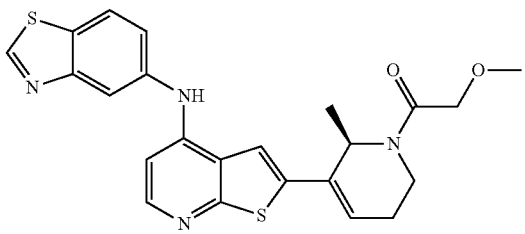

593
-continued
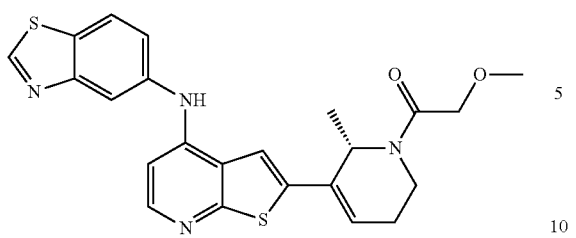
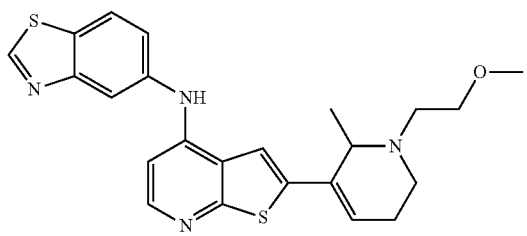
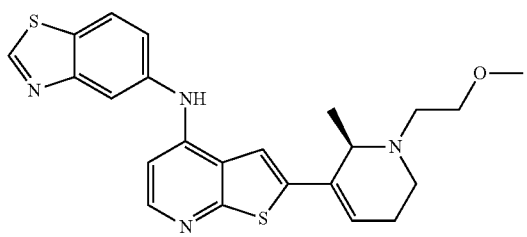
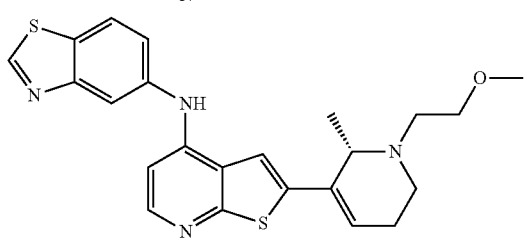
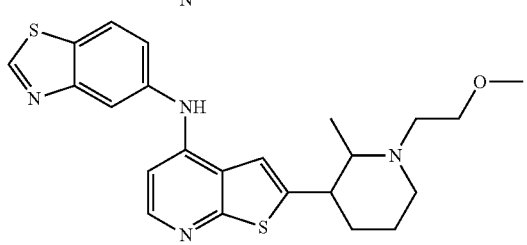
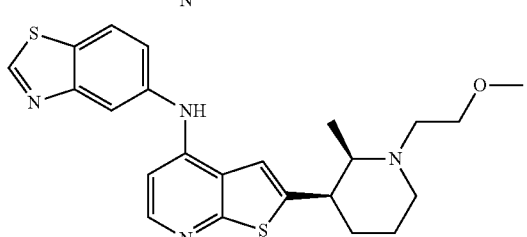
594
-continued
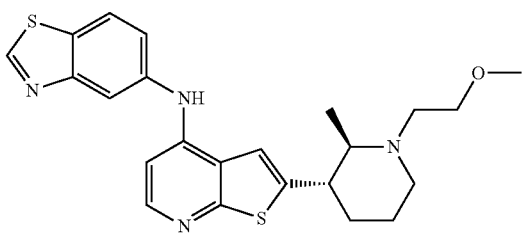
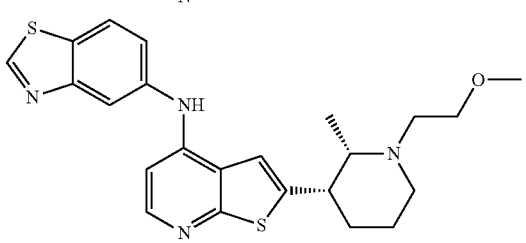
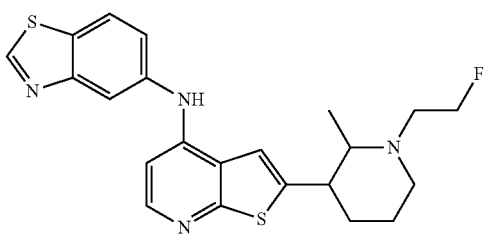
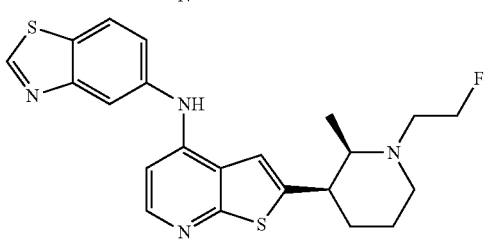
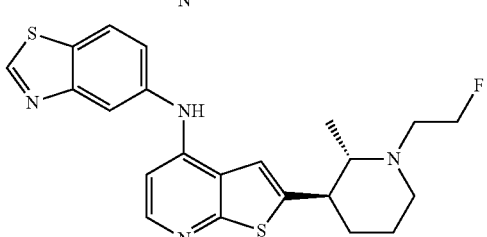
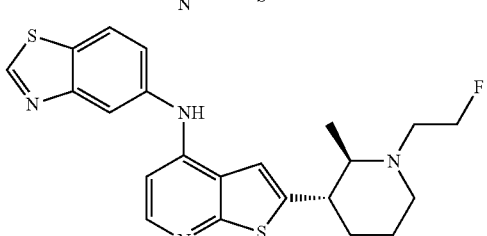
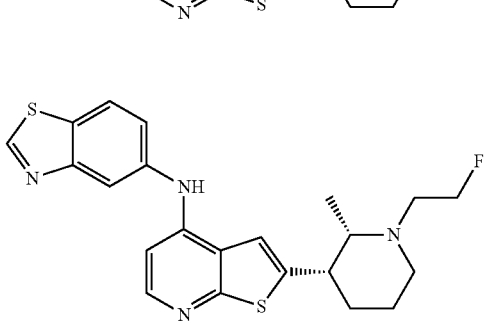

595
-continued
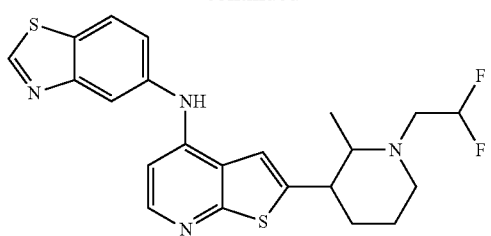
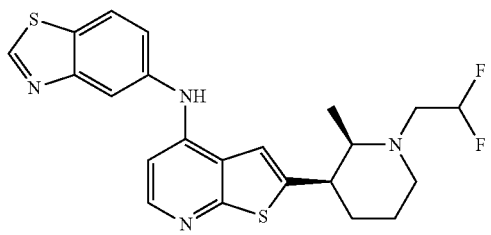
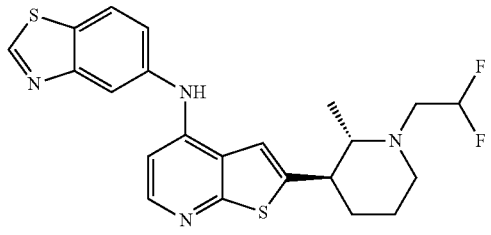
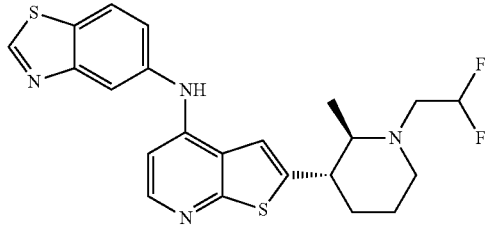
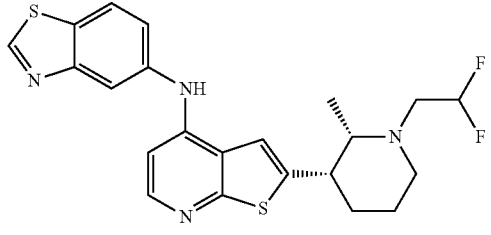
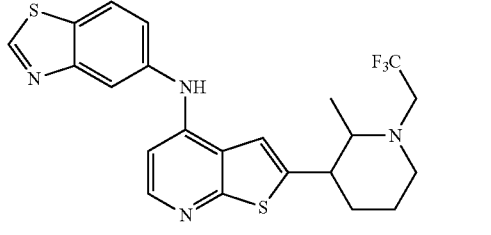
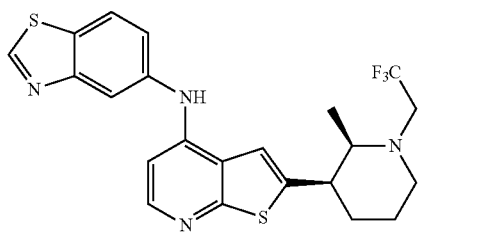
596
-continued
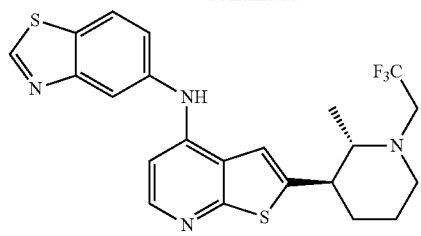
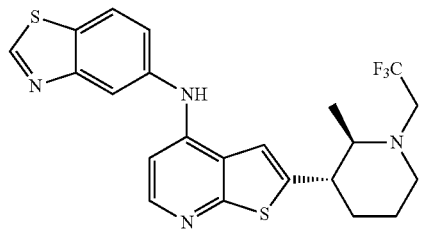
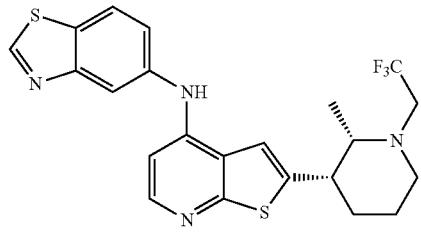
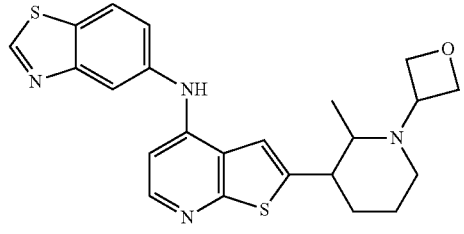
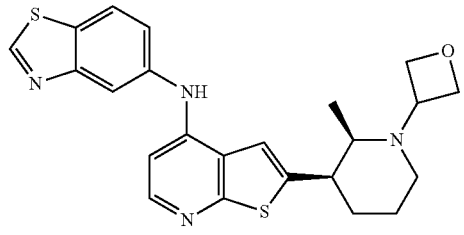
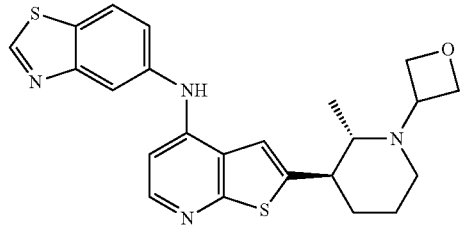
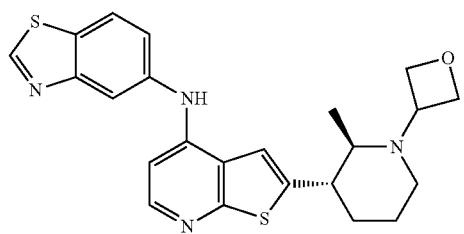

597
-continued
598
-continued
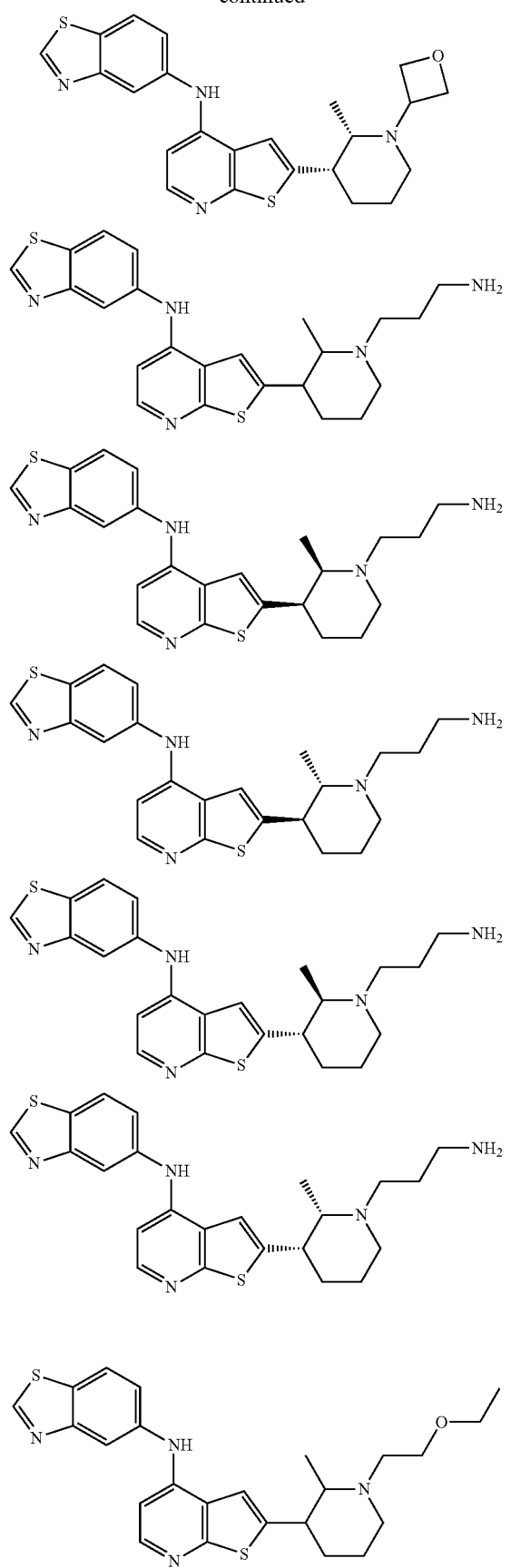
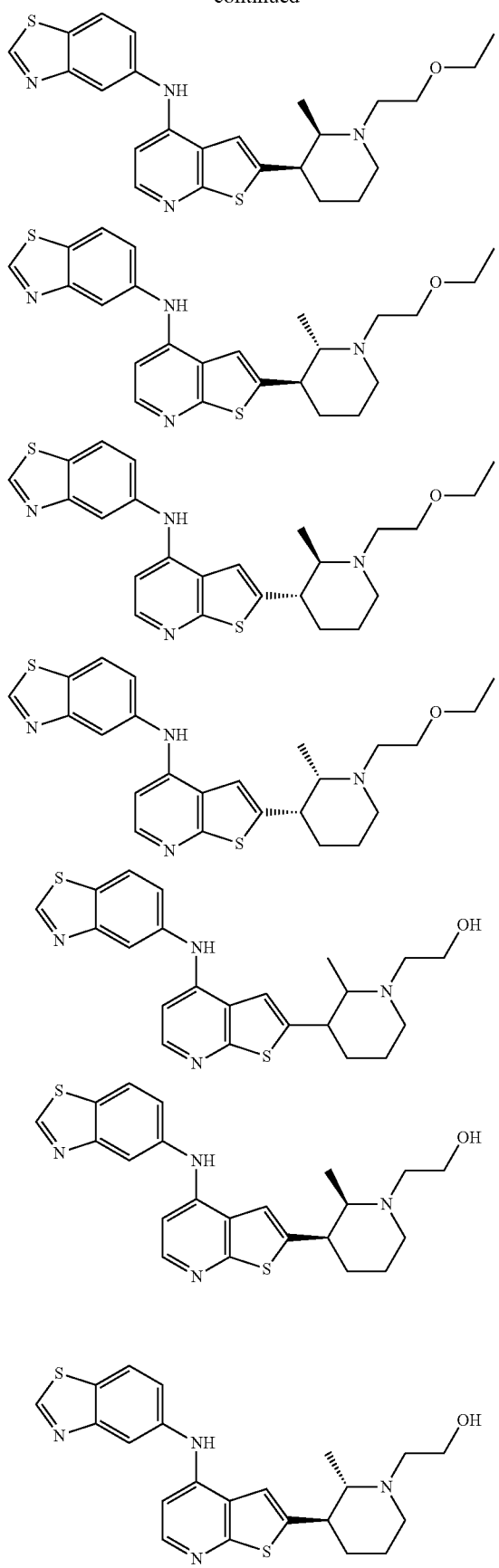

599
-continued
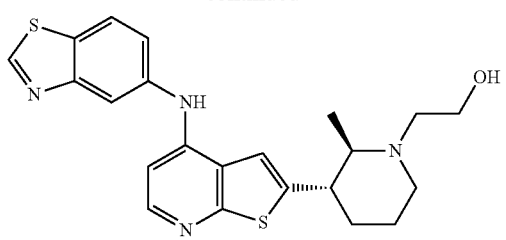
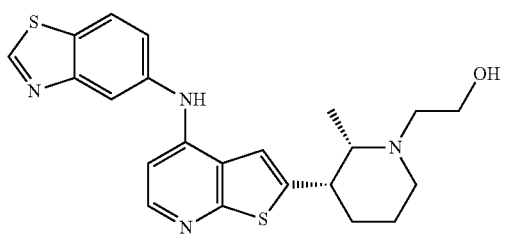
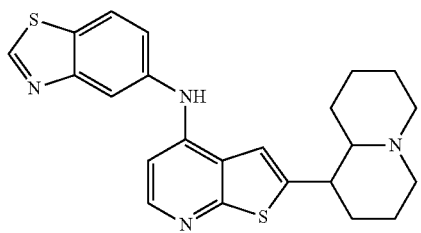
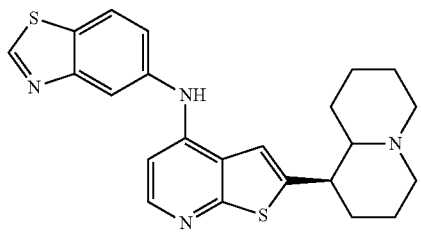
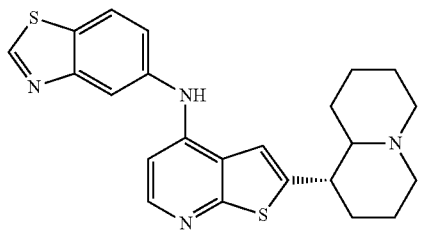
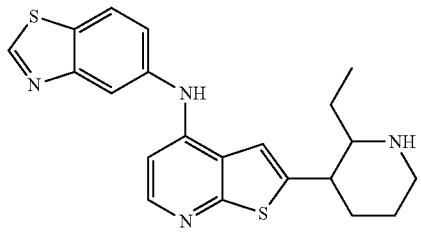
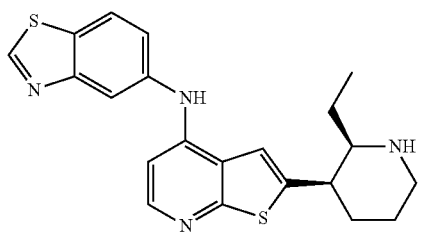
600
-continued
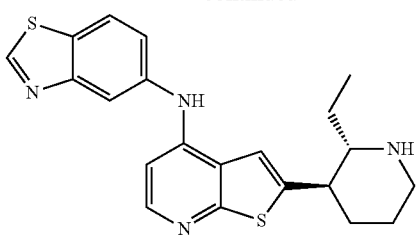
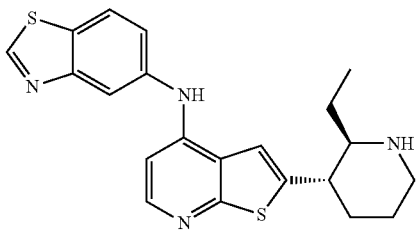
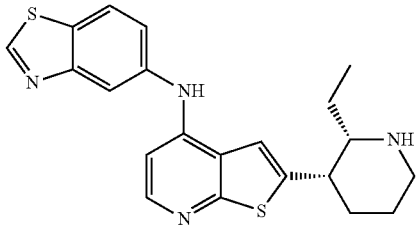
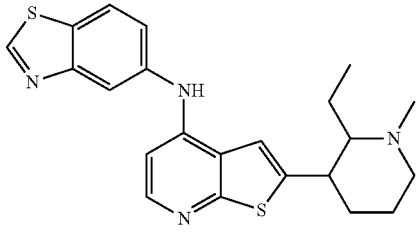
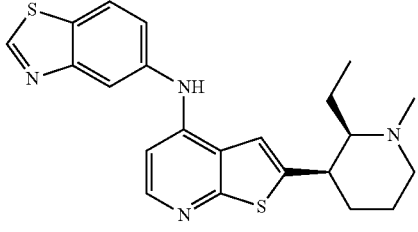
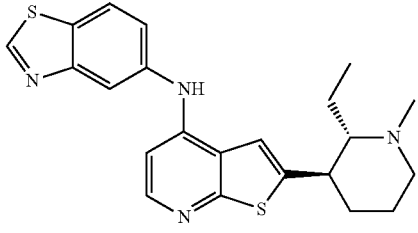

601
-continued
602
-continued
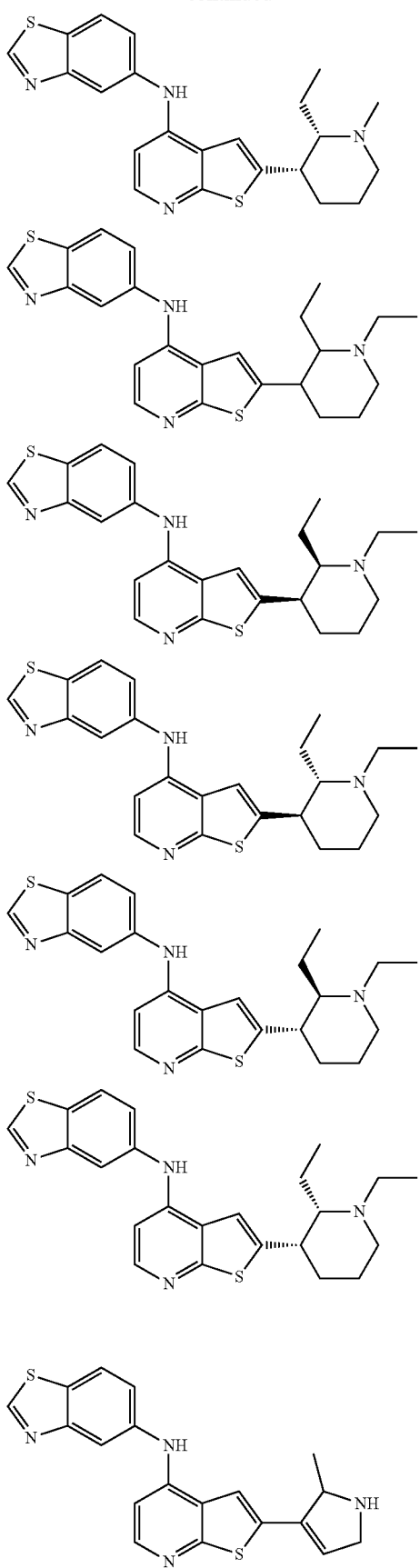
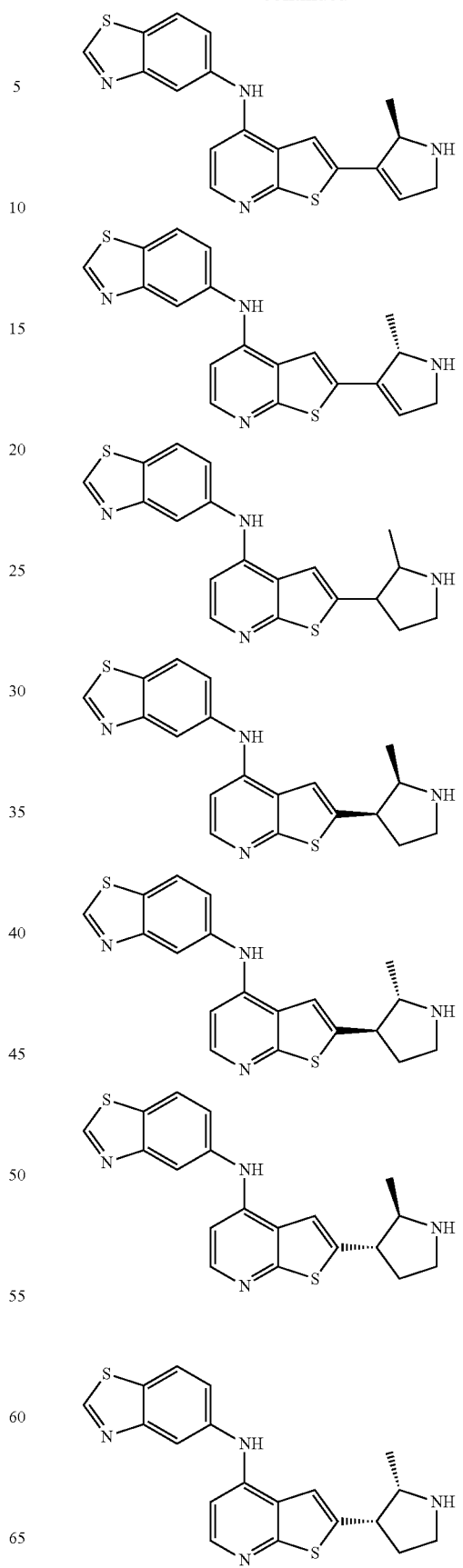

603
604
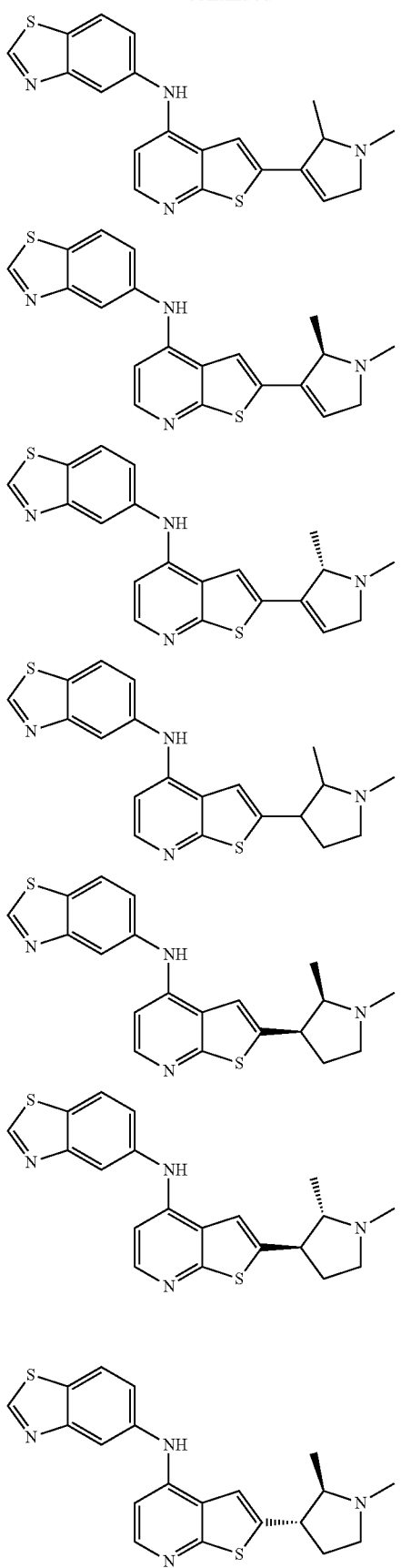
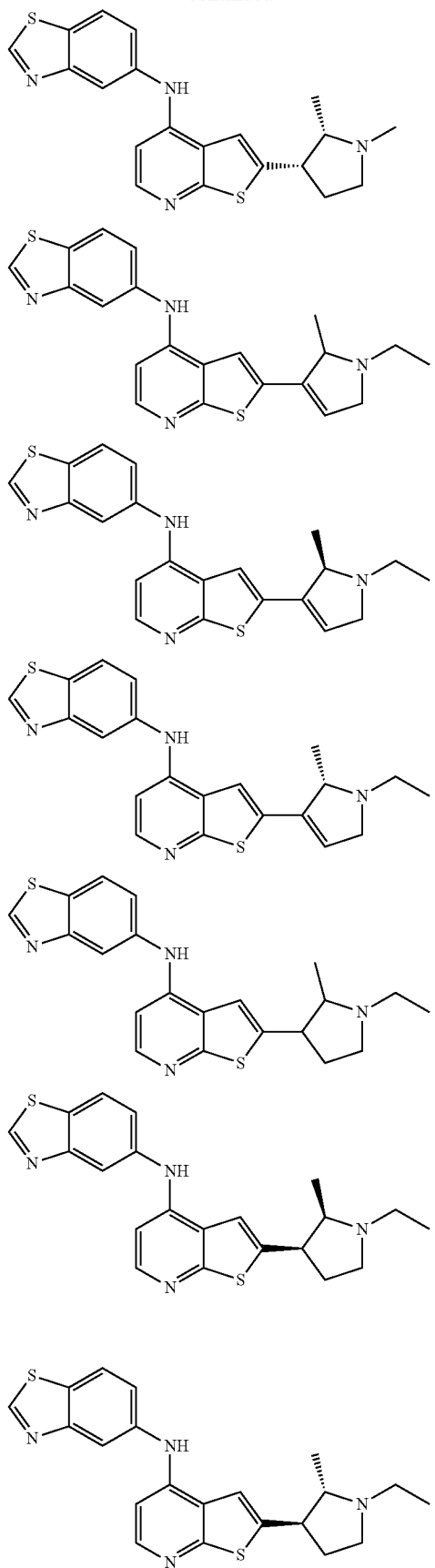

605
-continued
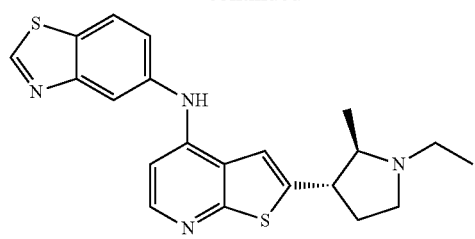
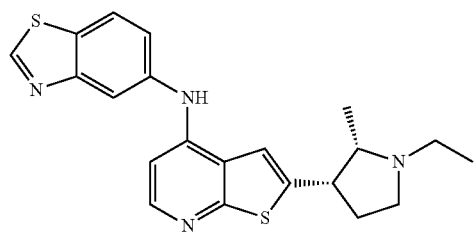
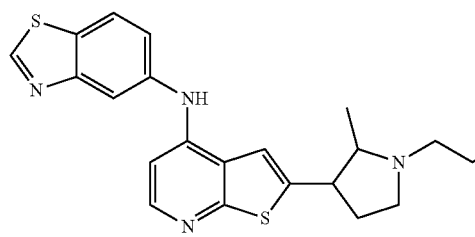
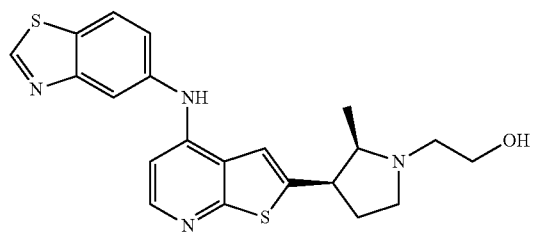
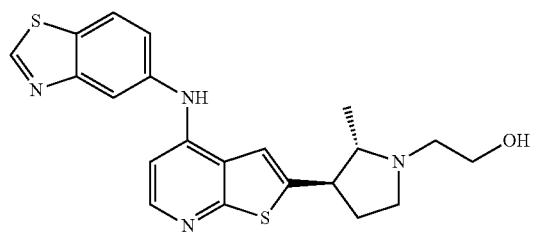
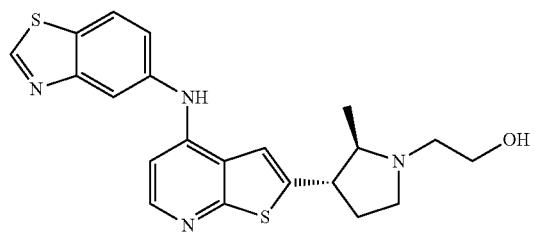
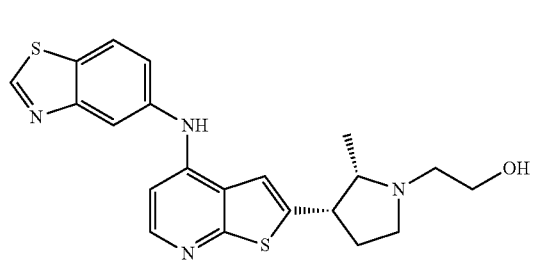
606
-continued
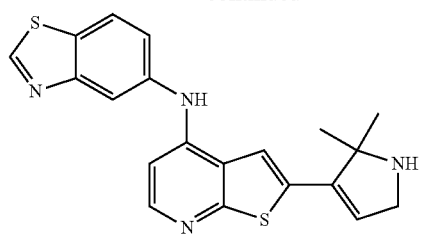
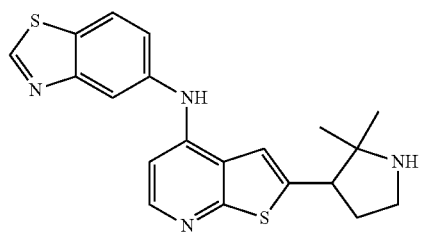
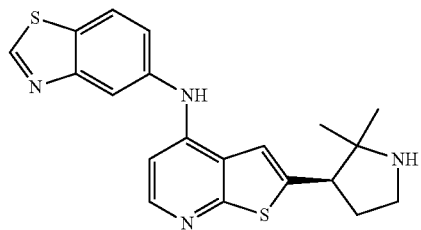
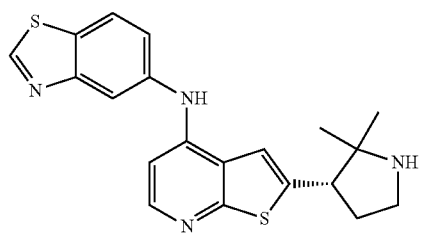
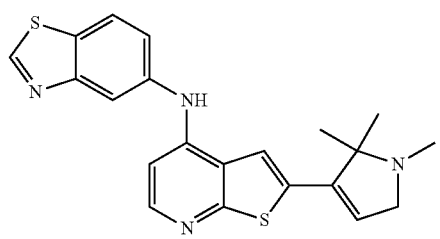
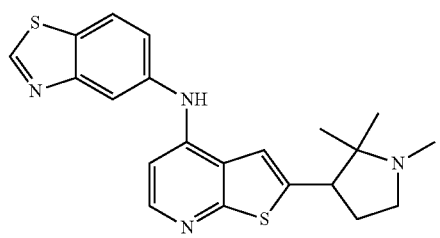
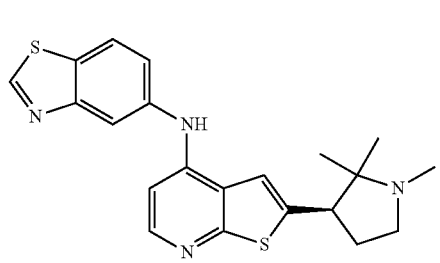

607
-continued
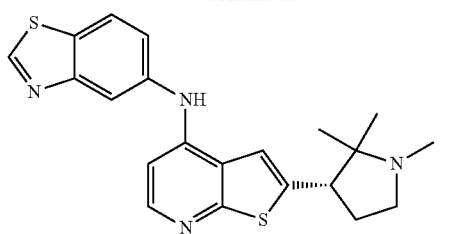
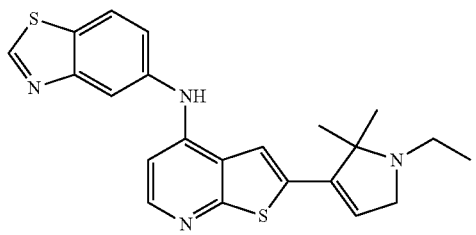
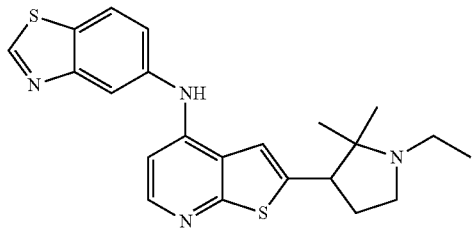
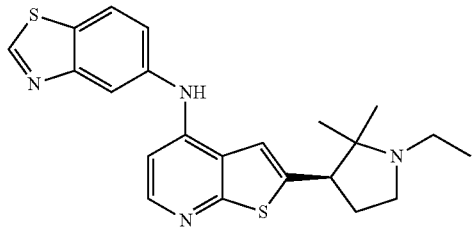
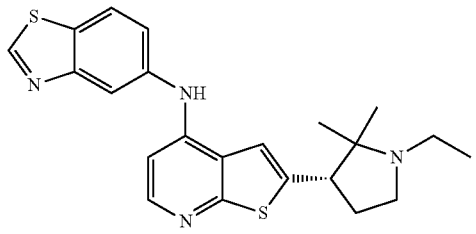
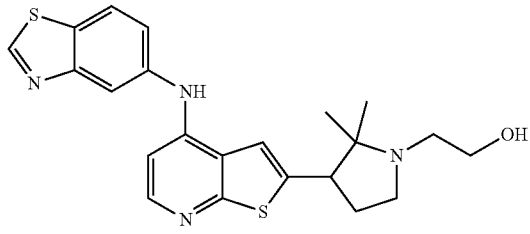
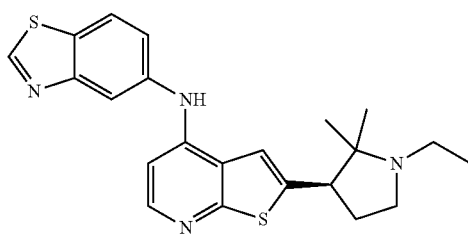
608
-continued
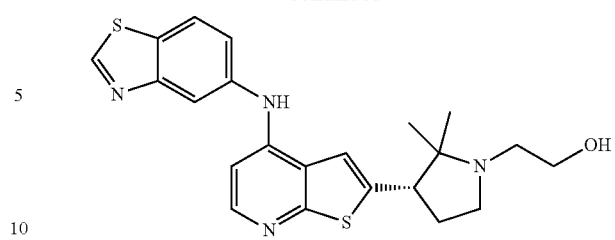
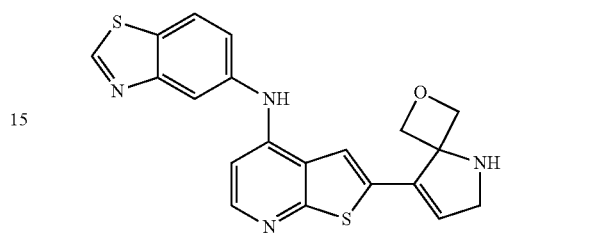
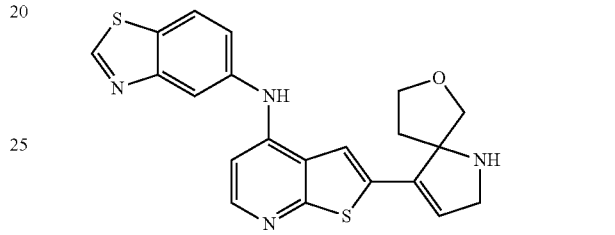
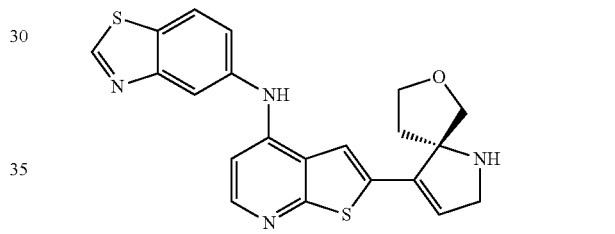
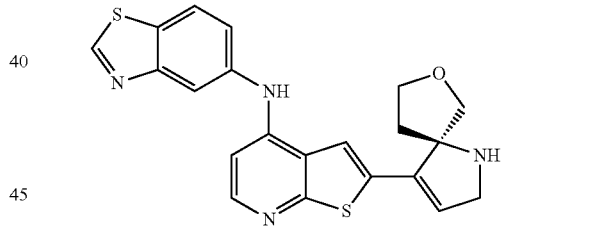
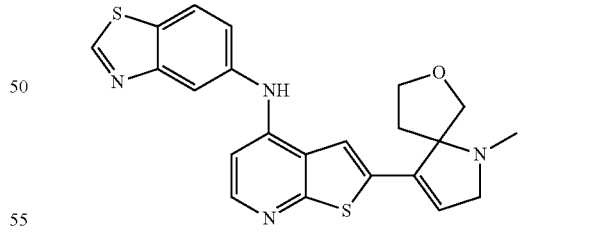
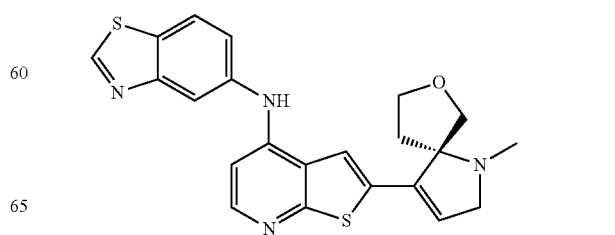

609
-continued
610
-continued
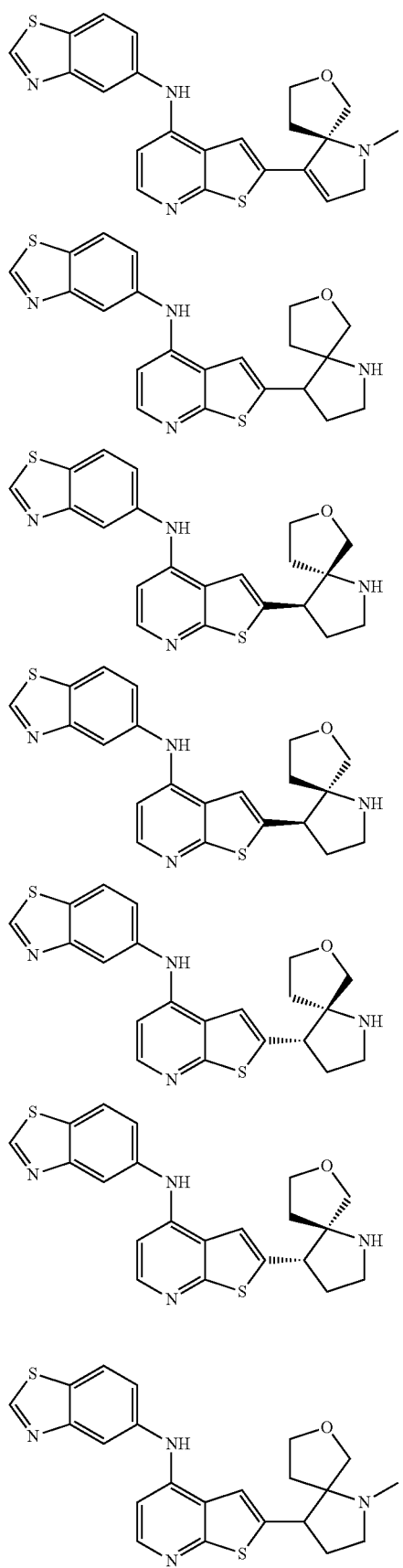
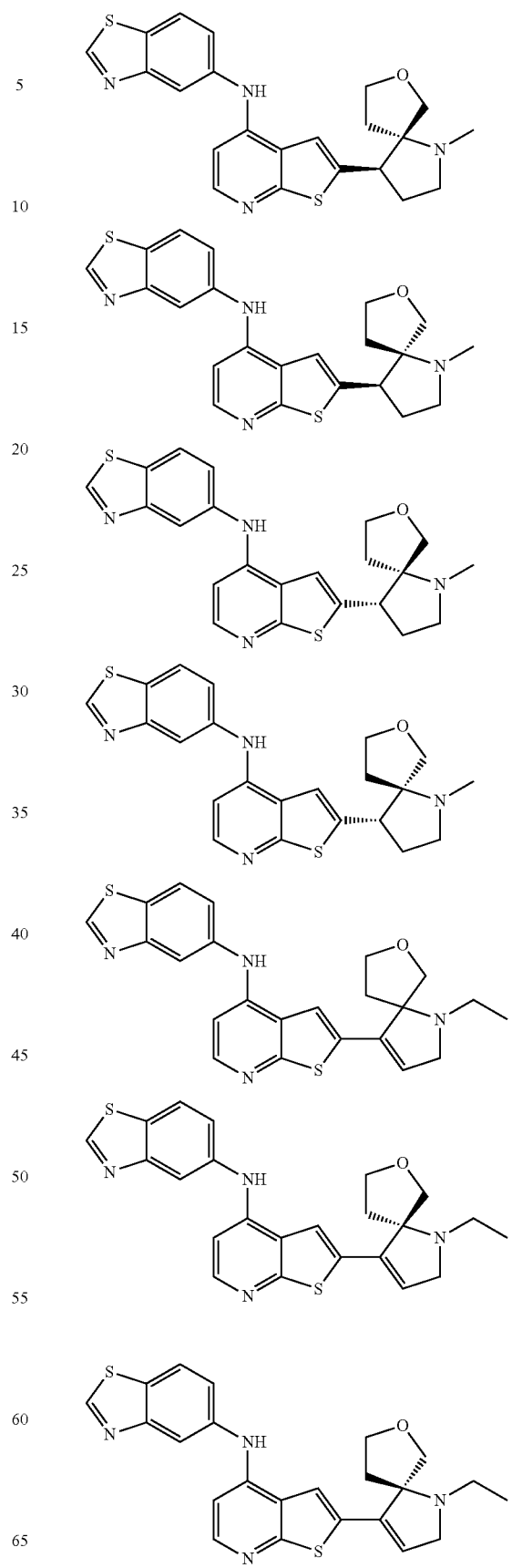

611
-continued
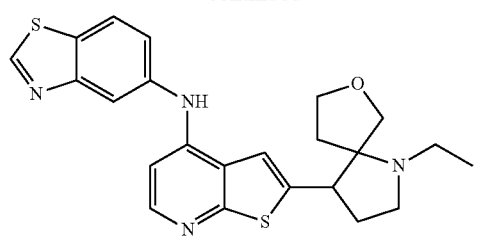
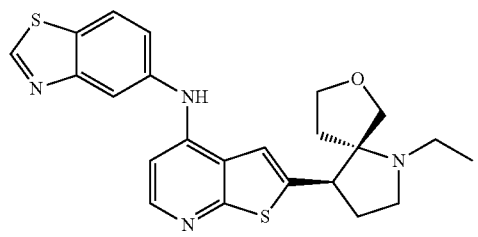
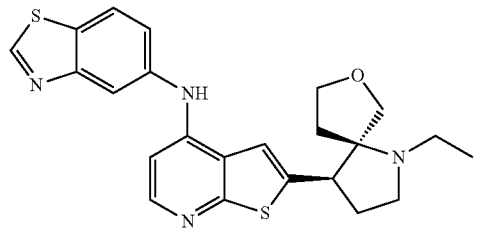
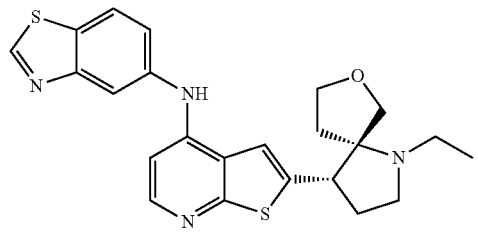
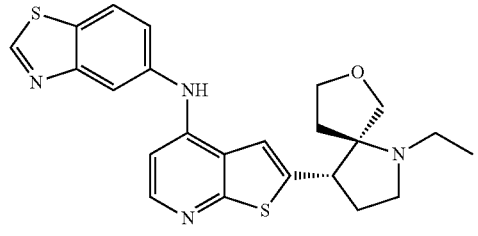
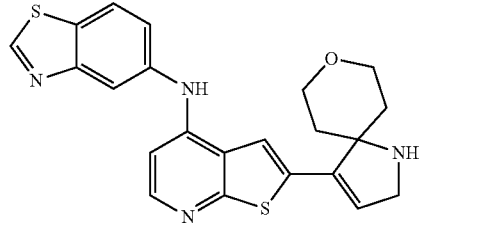
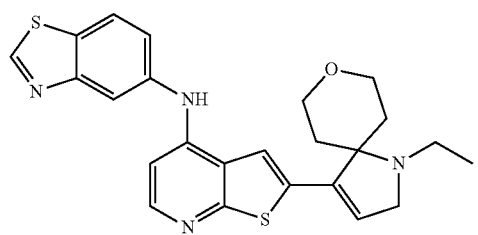
612
-continued
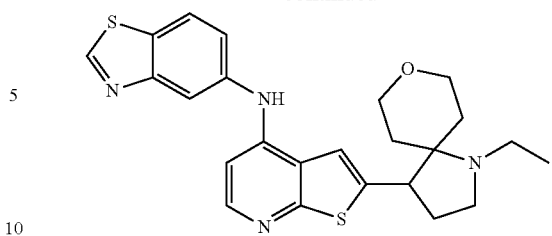
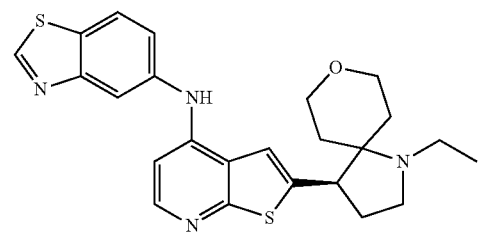
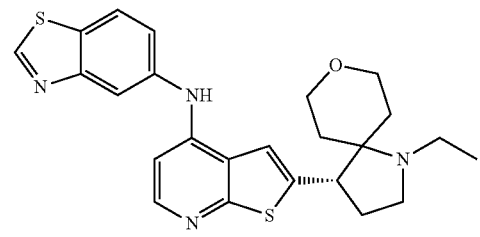
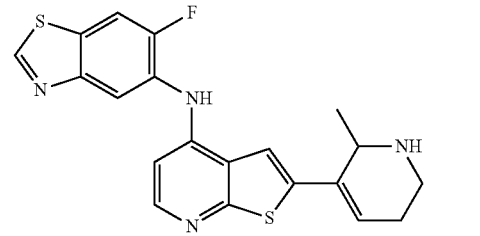
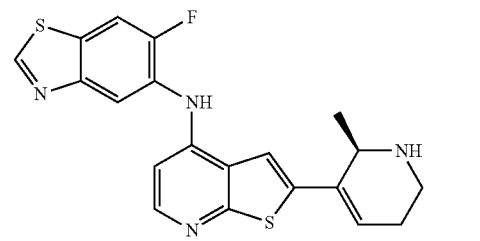
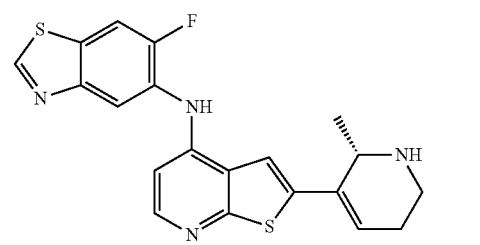
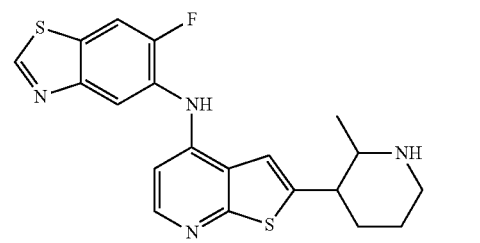

613
-continued
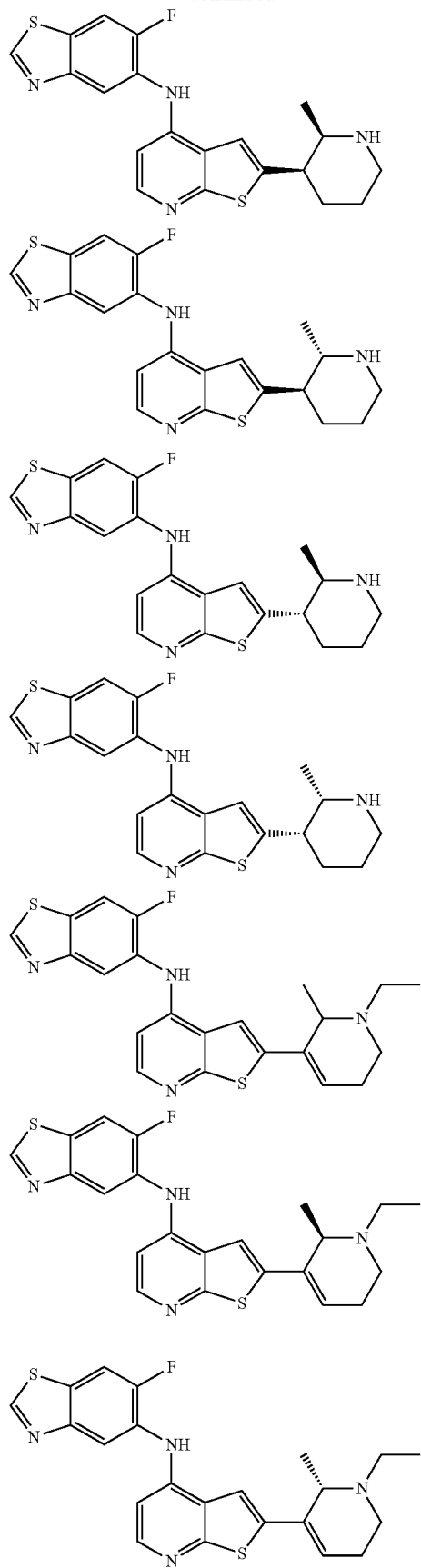
614
-continued
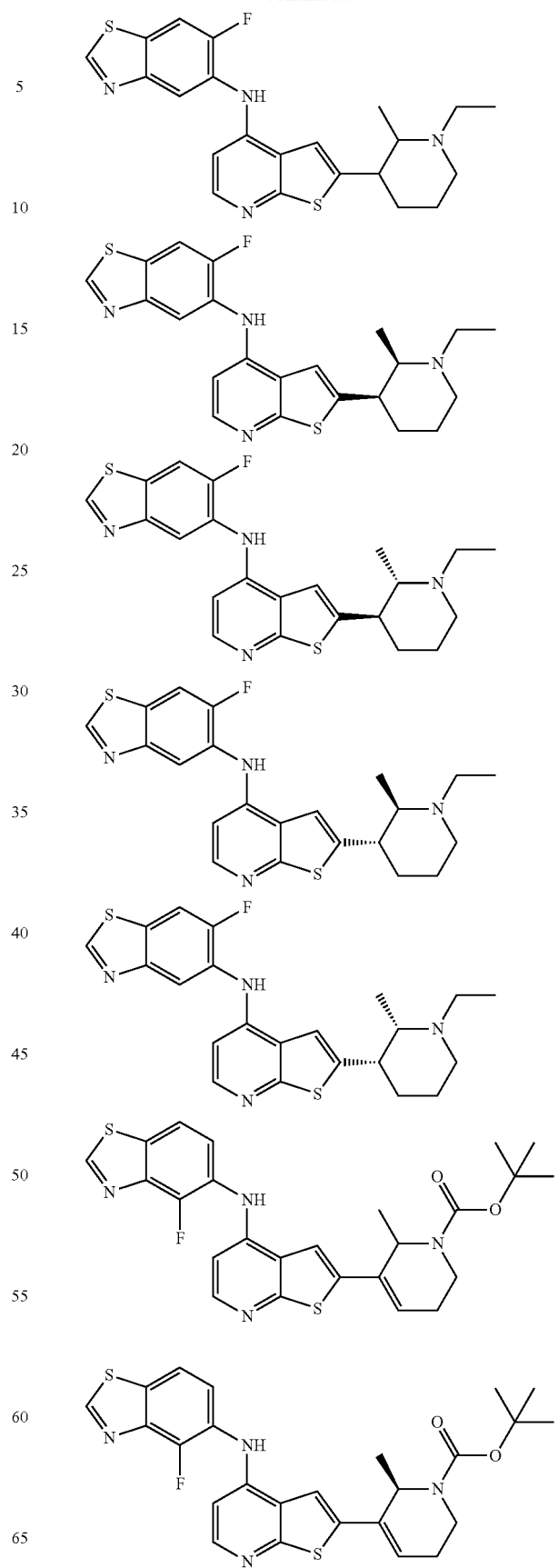

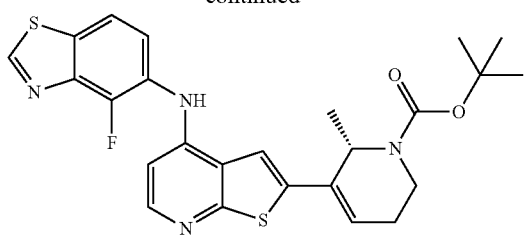
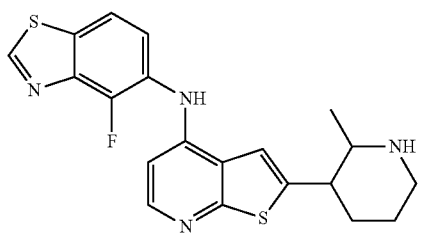
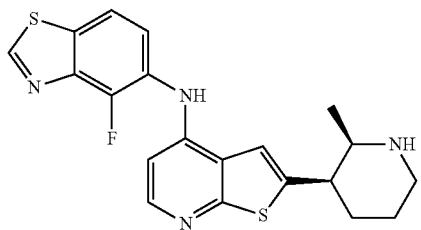
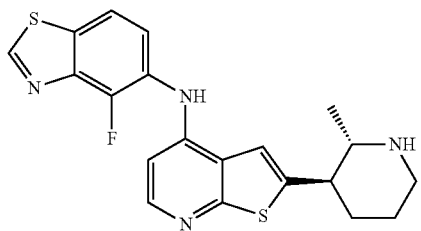
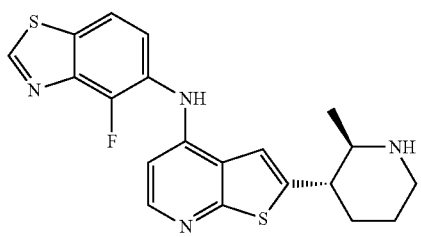
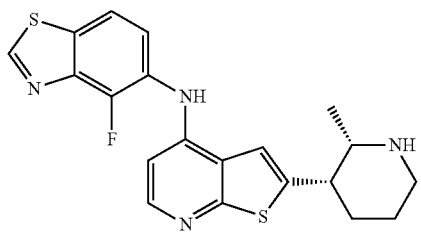
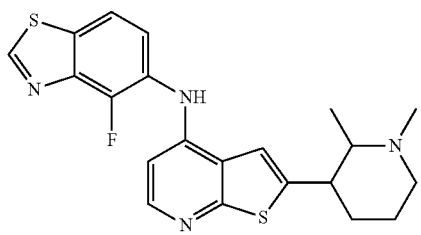
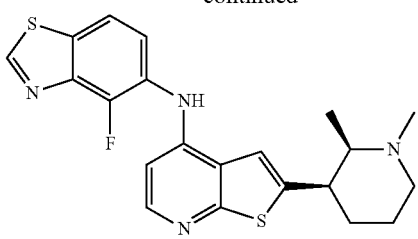
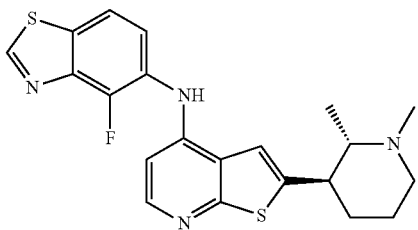
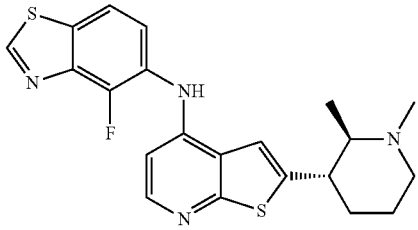
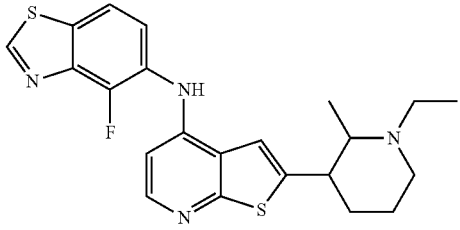
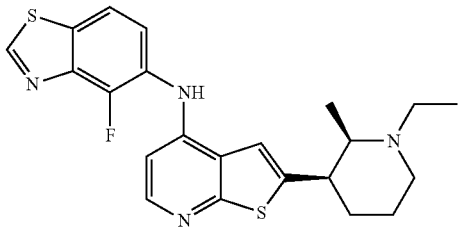
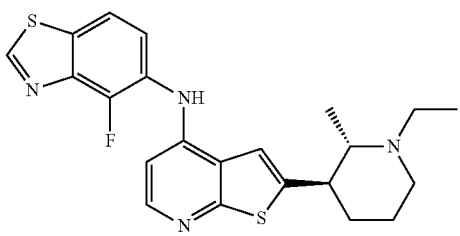

617
-continued
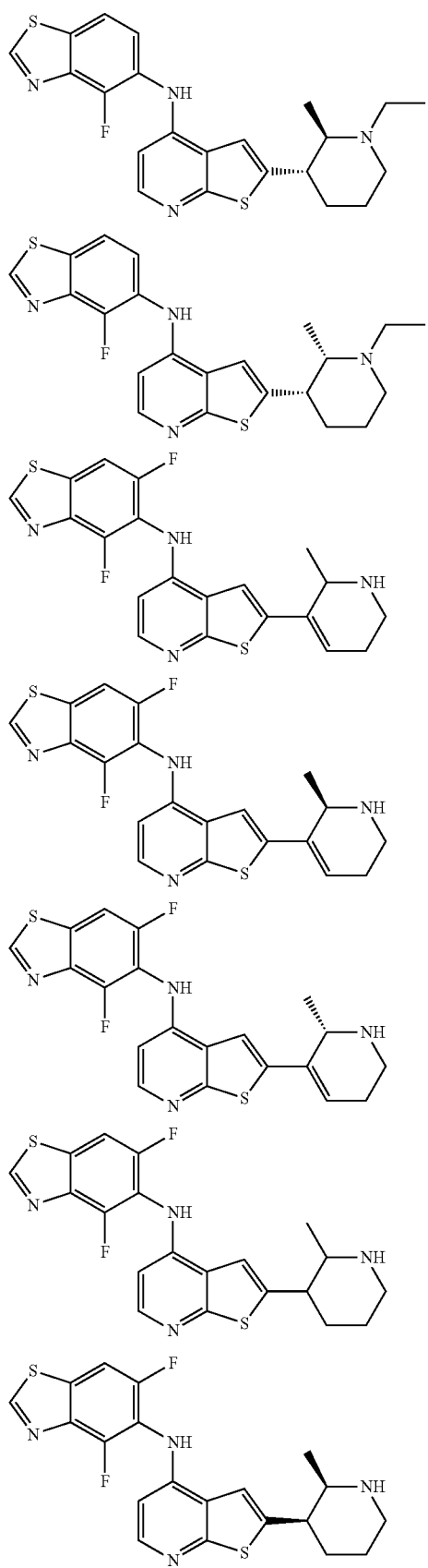
618
-continued
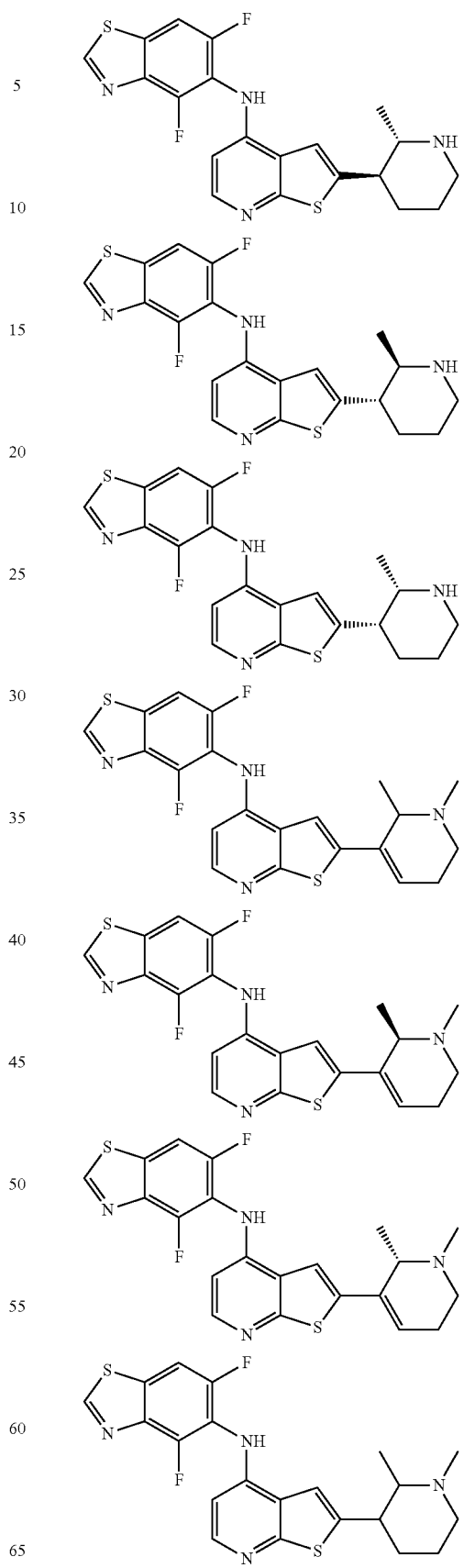

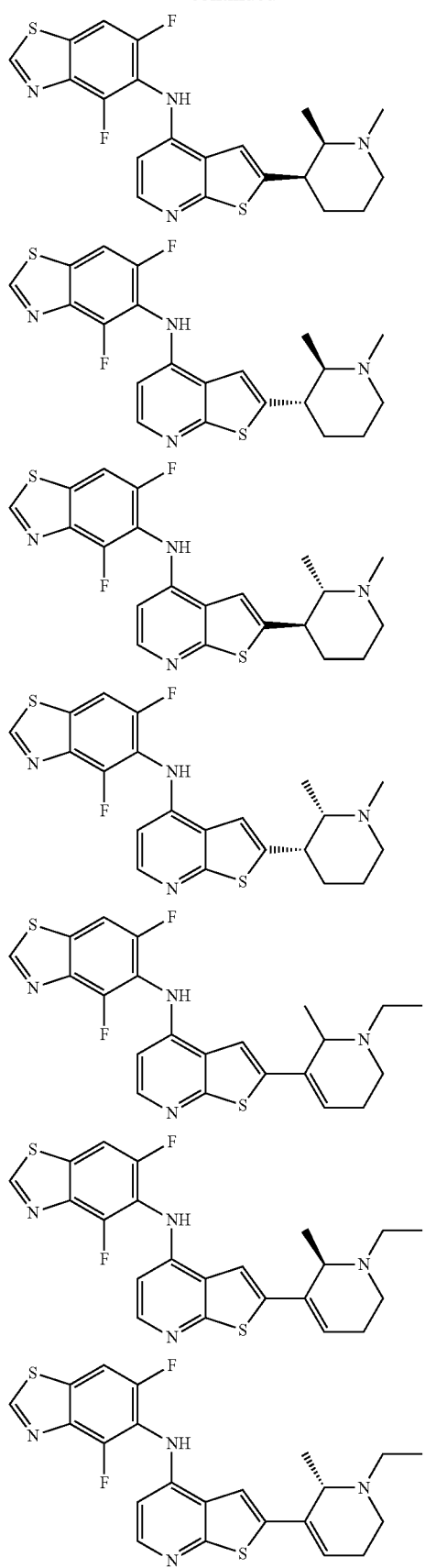
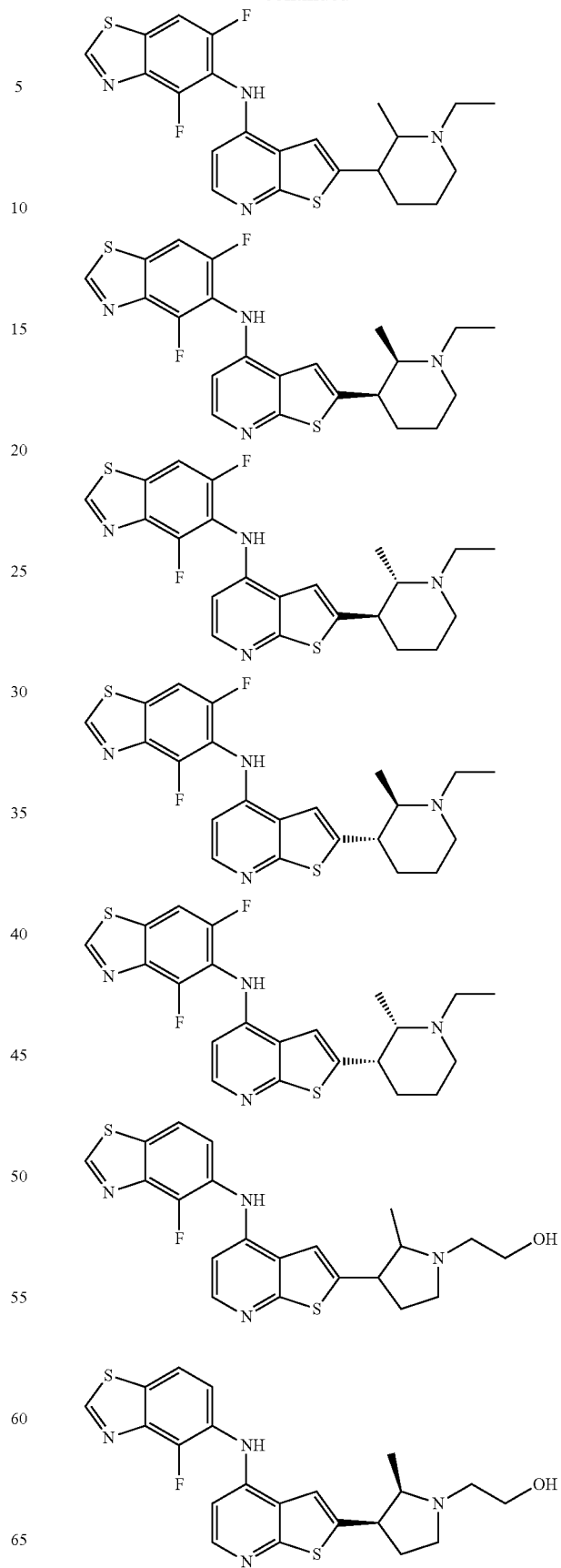

621
-continued
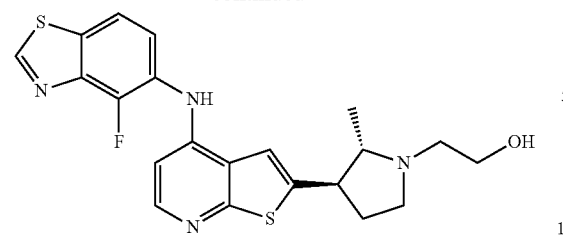
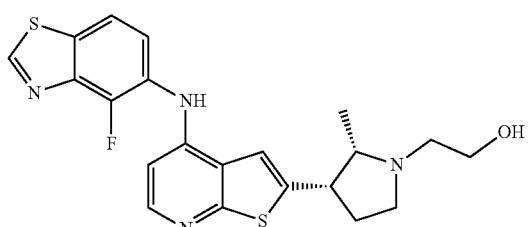
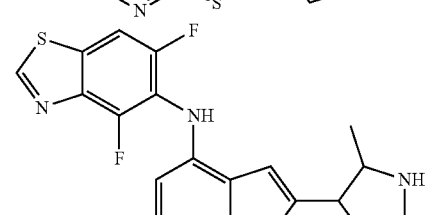
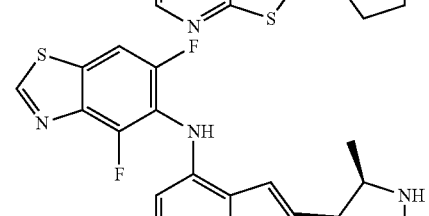
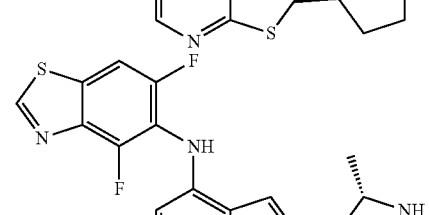
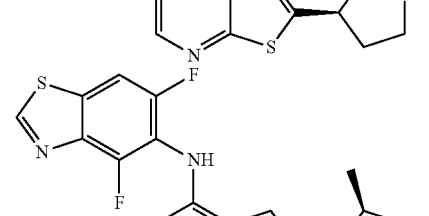
622
-continued
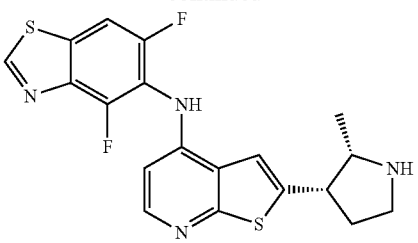
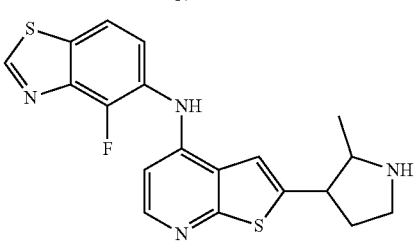
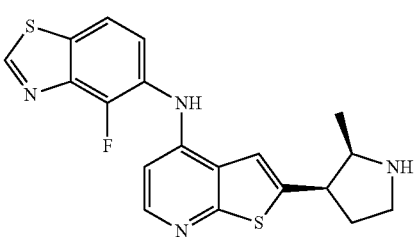
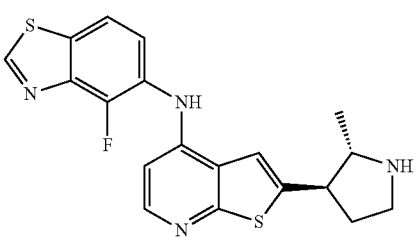
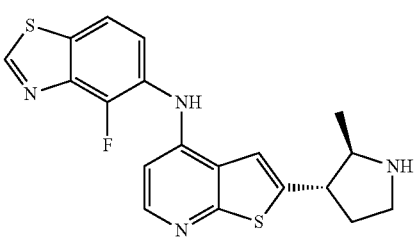
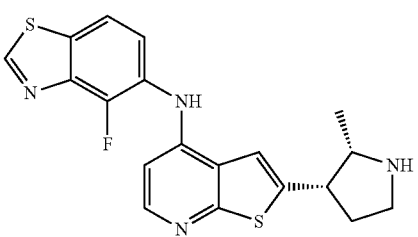
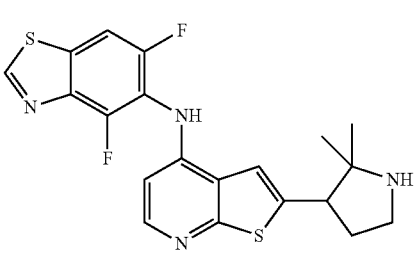

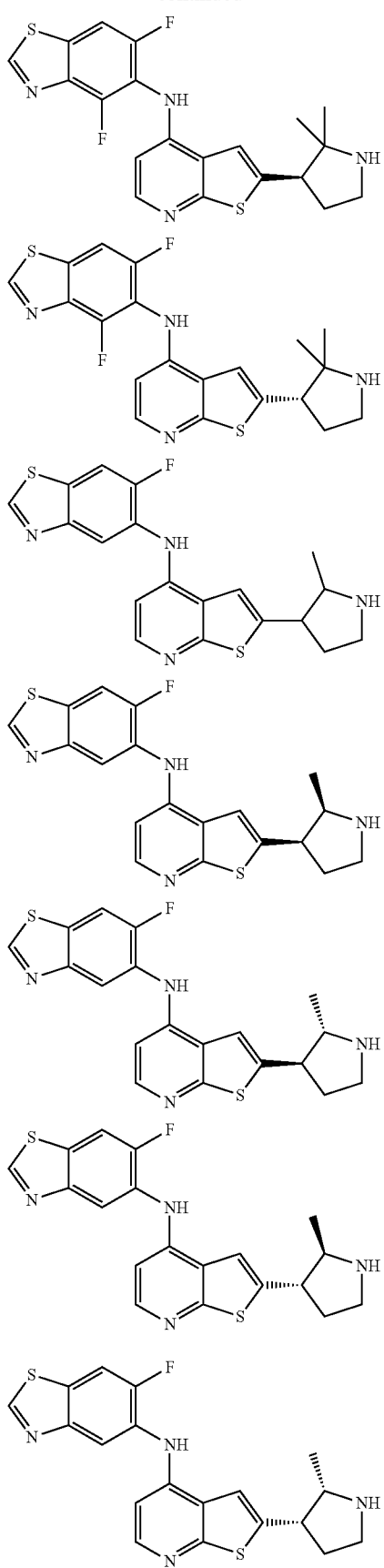
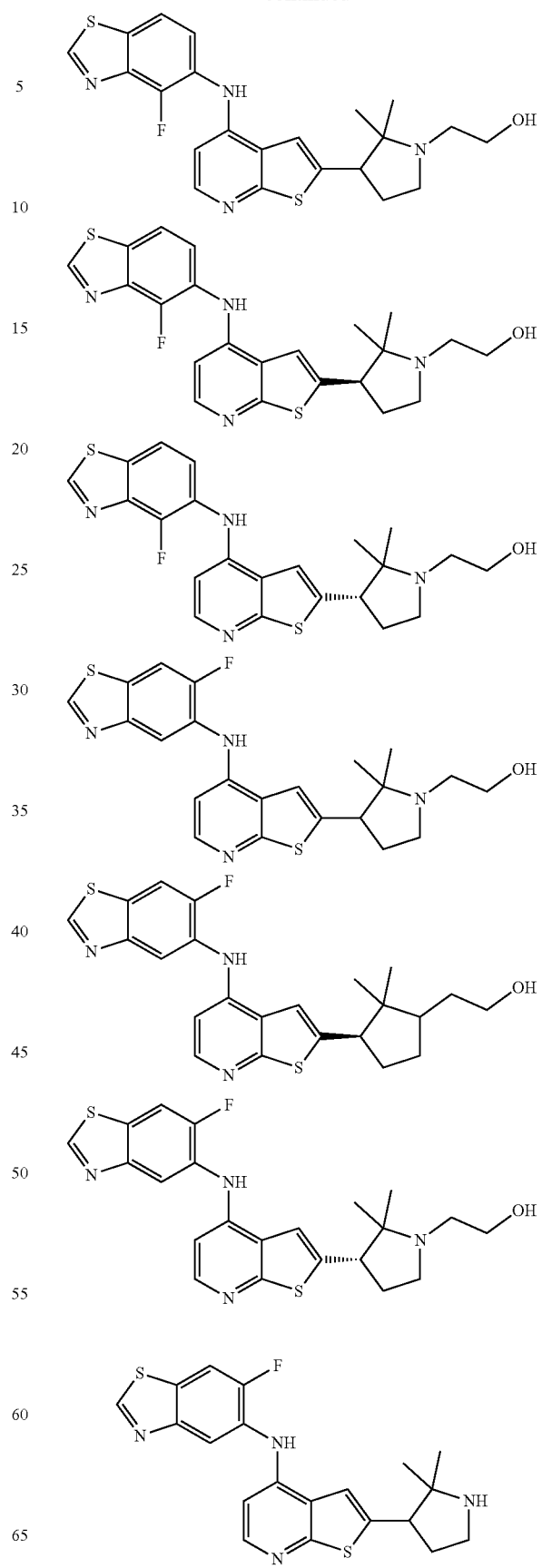

625
-continued
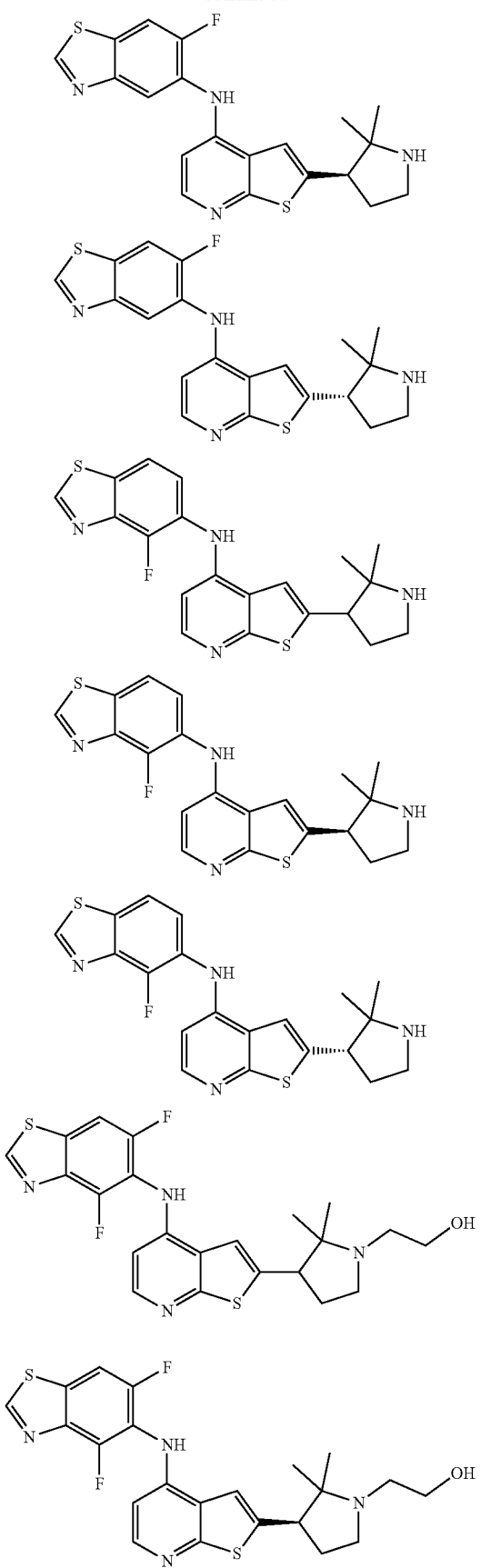
626
-continued
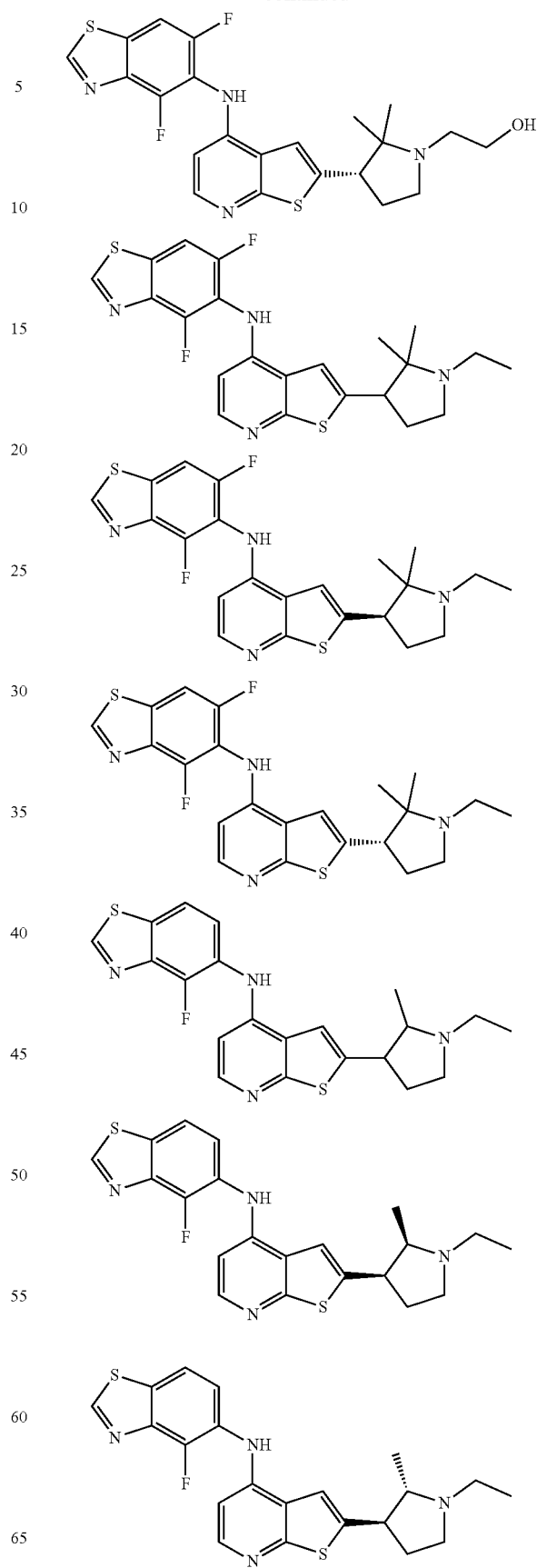

627
-continued
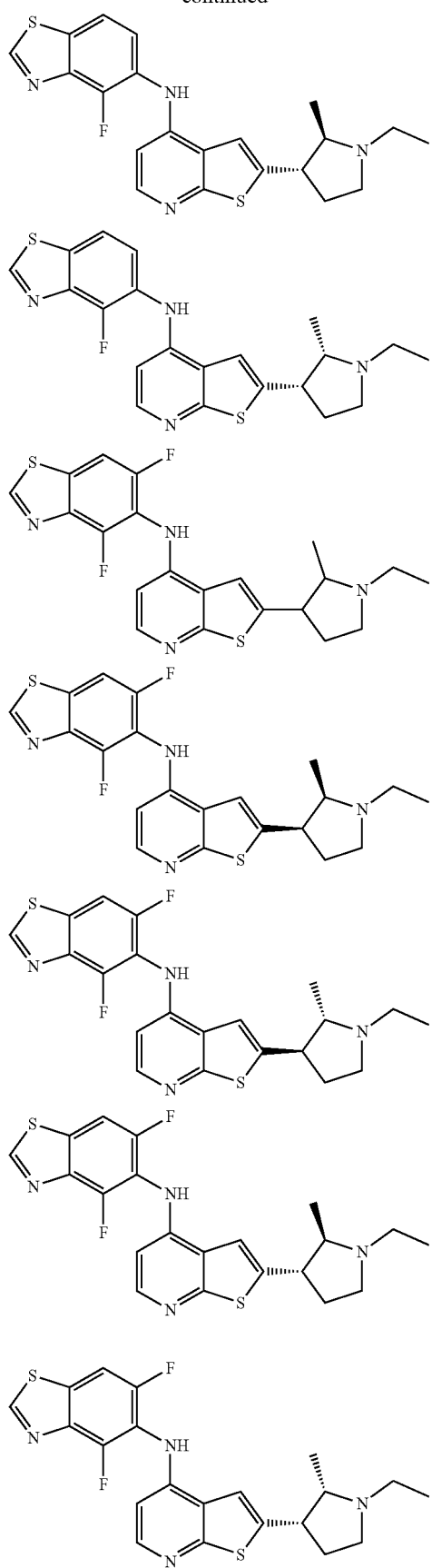
628
-continued
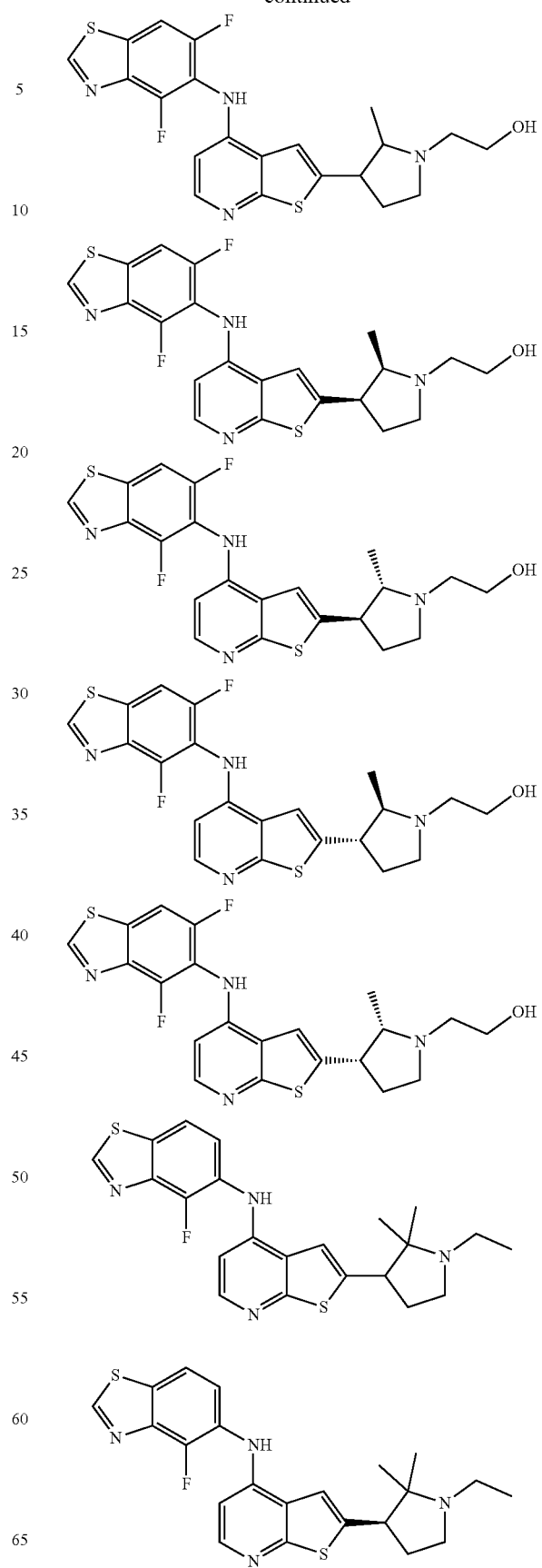

629
-continued
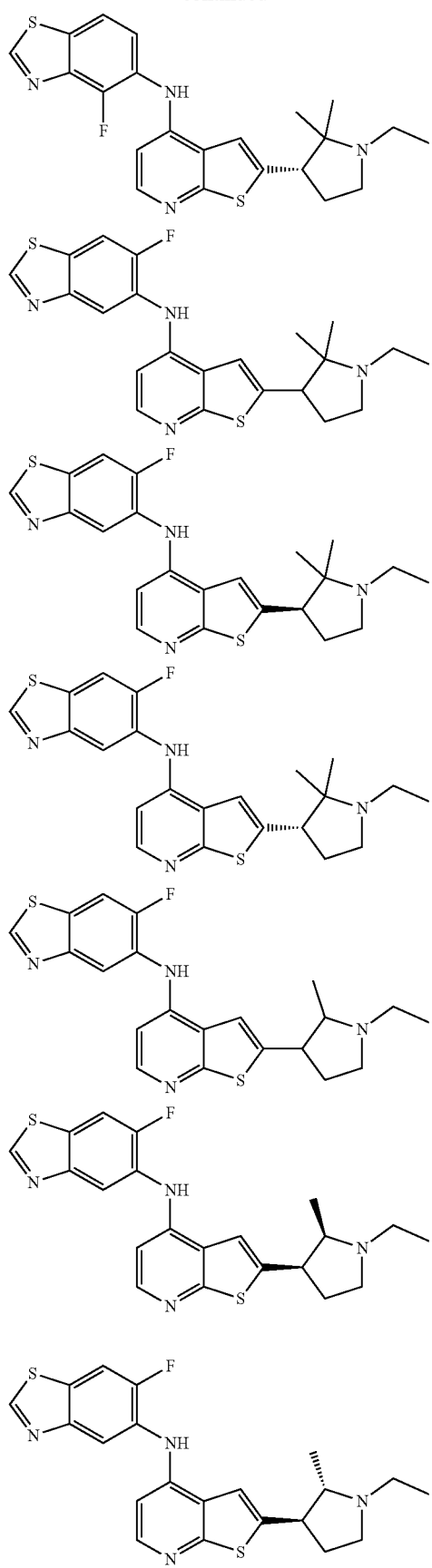
630
-continued
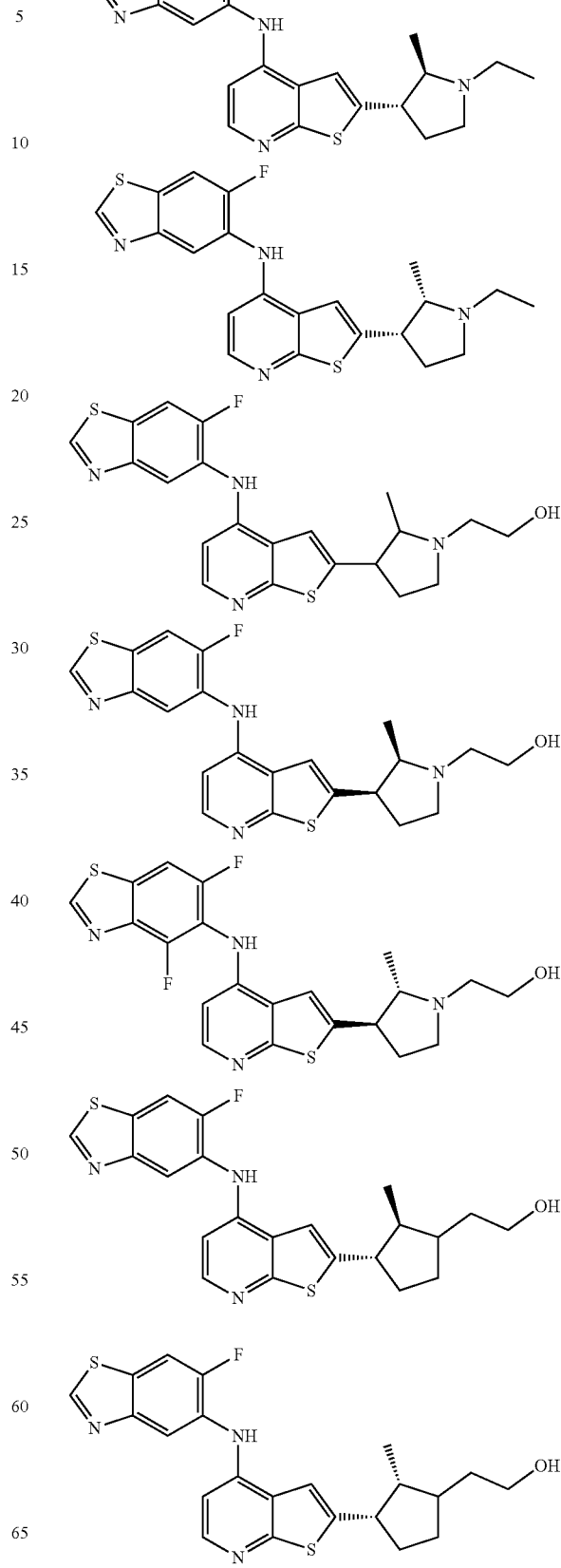

631
-continued
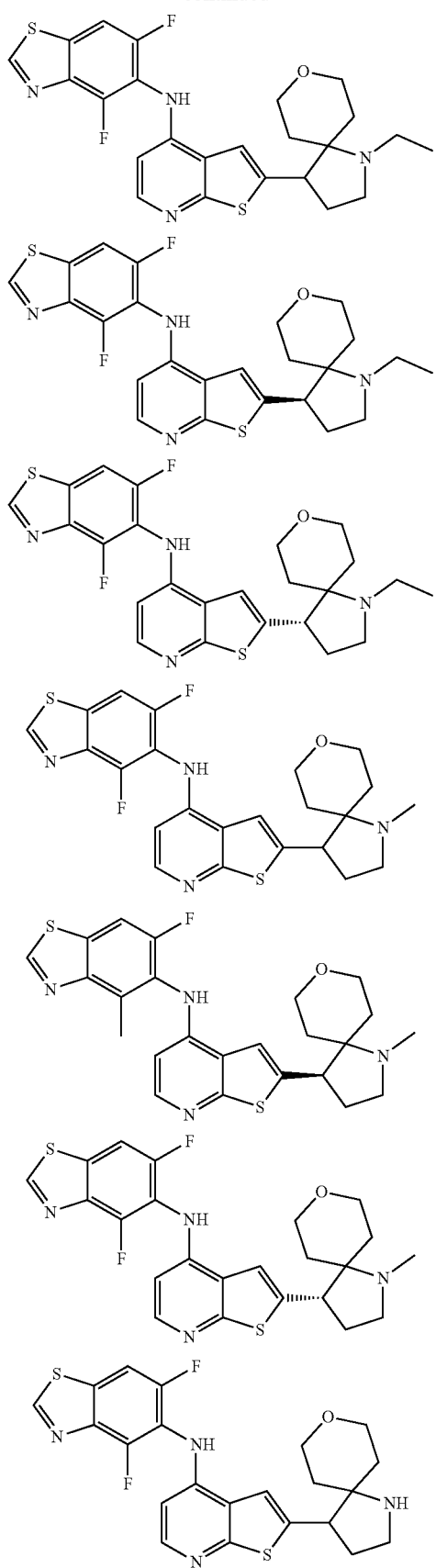
632
-continued
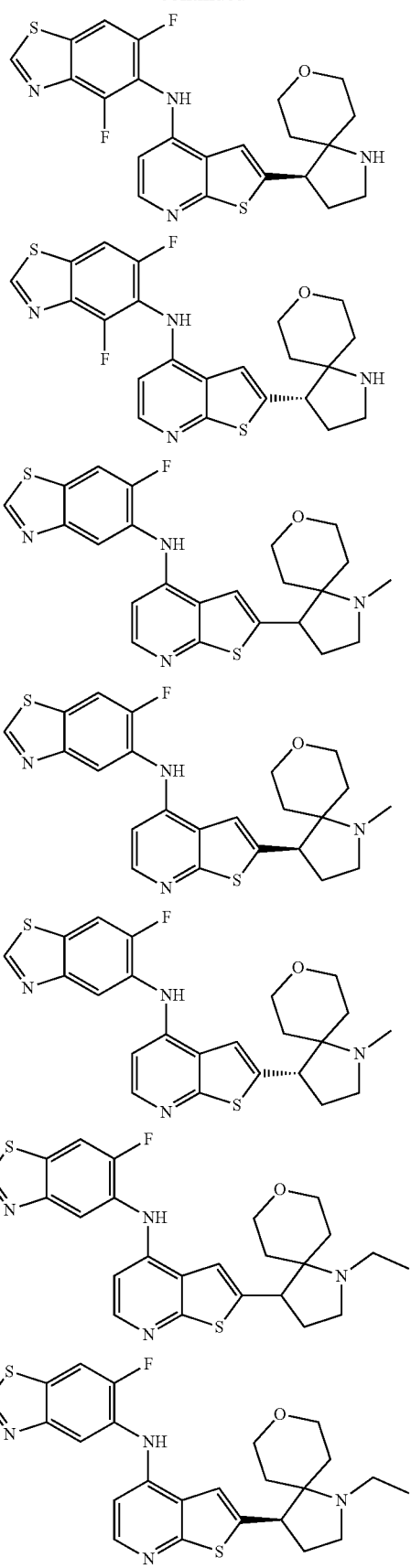

633
-continued
634
-continued
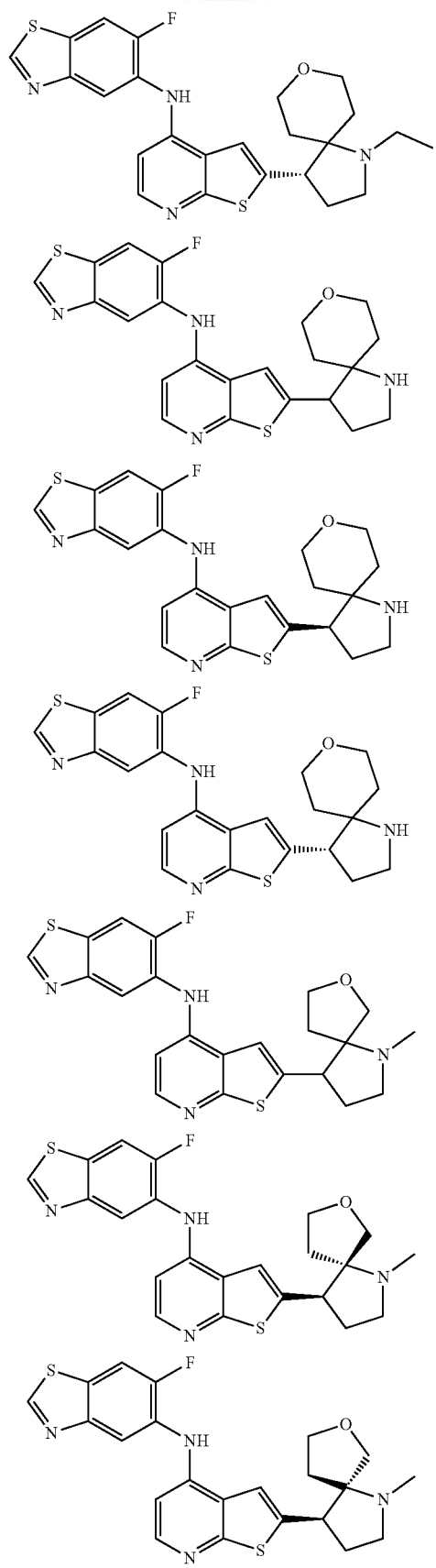
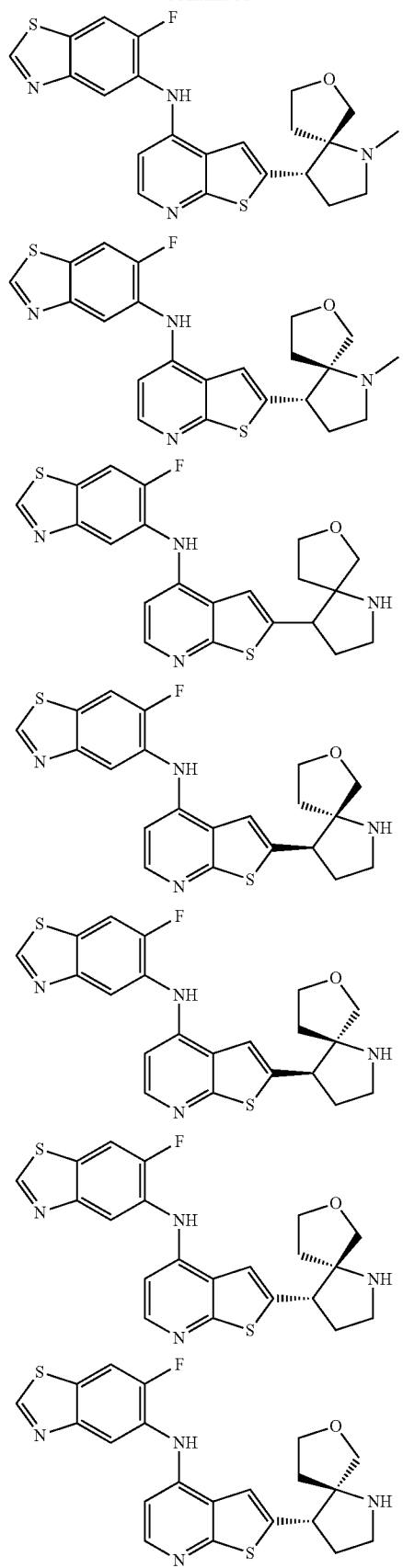

635
-continued
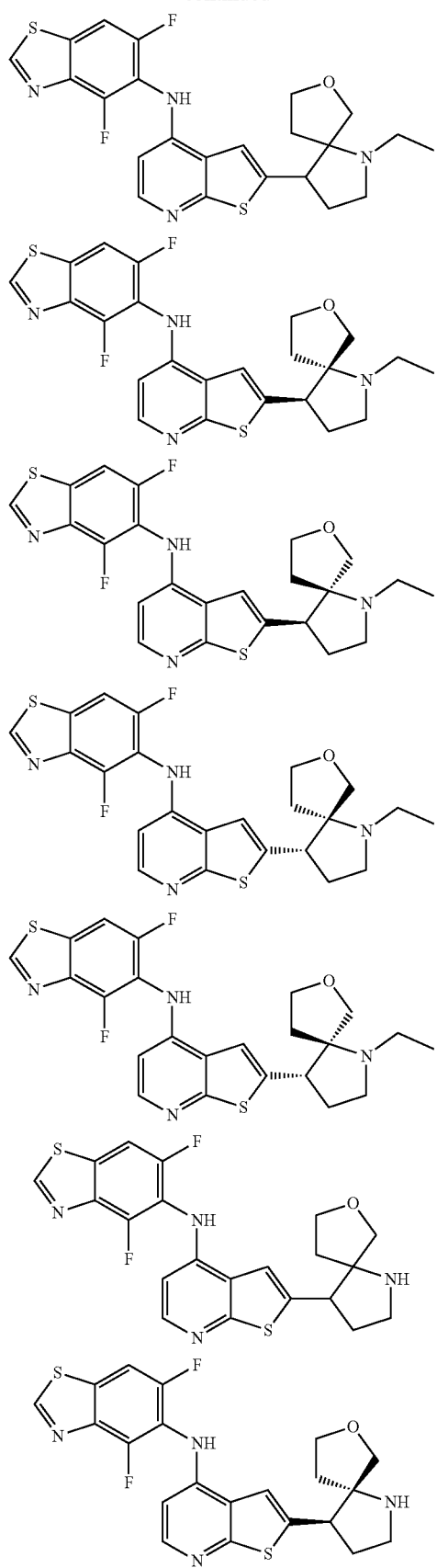
636
-continued
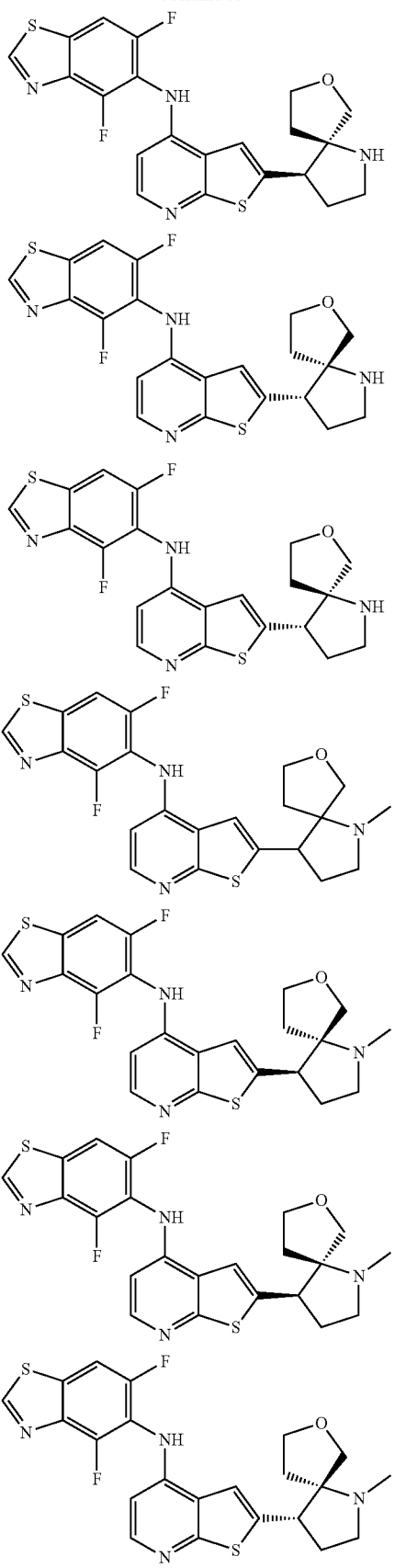

637
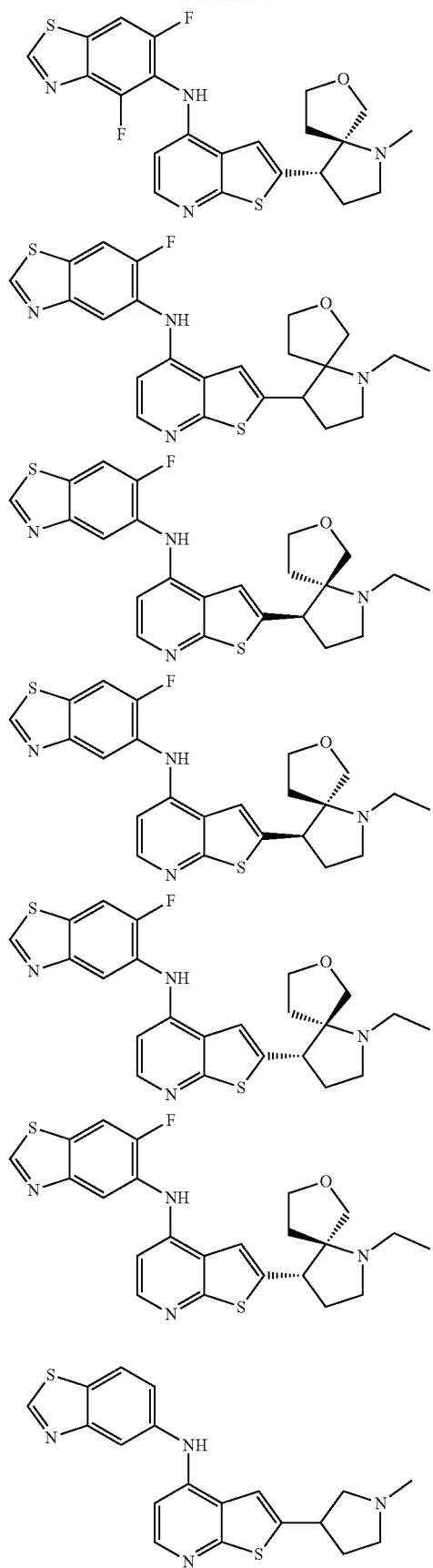
638
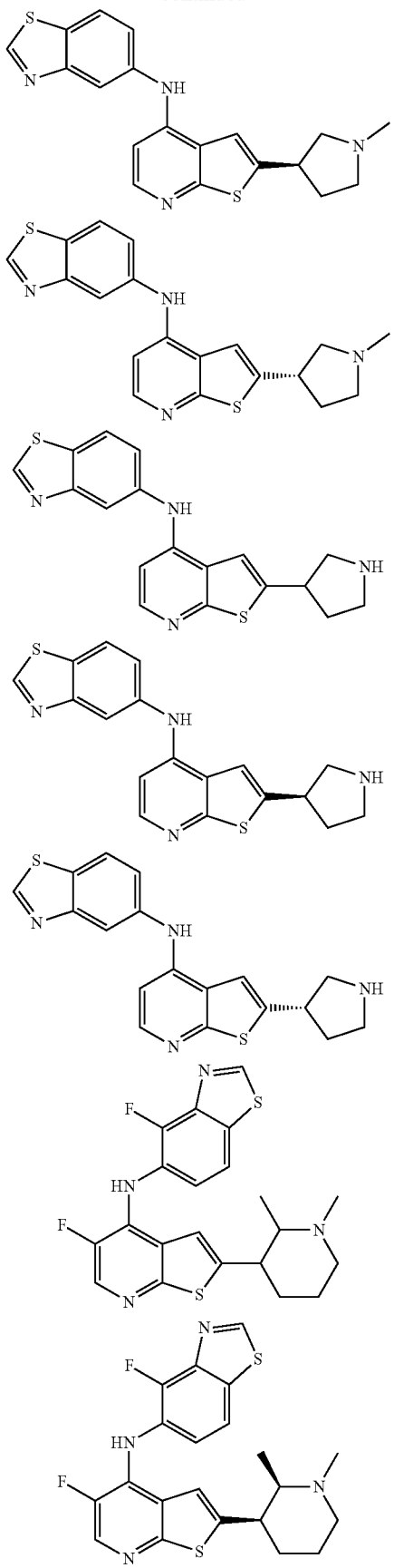

-continued
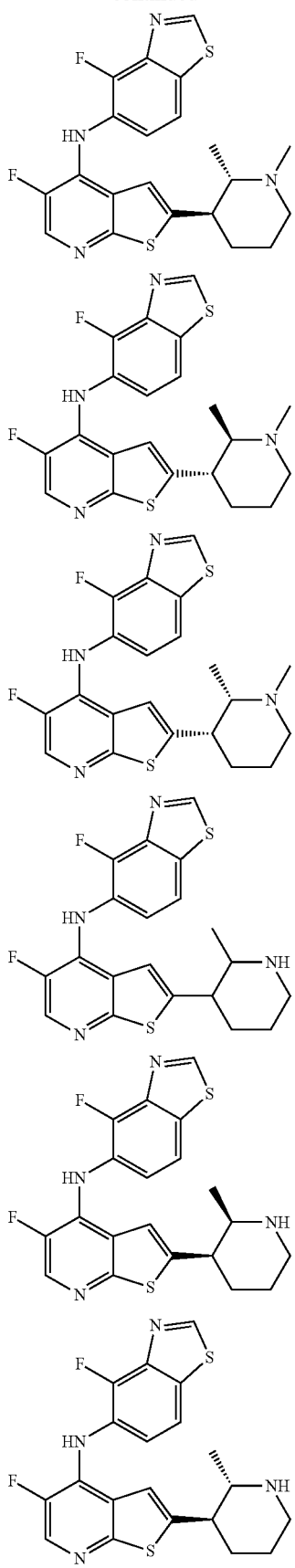
-continued
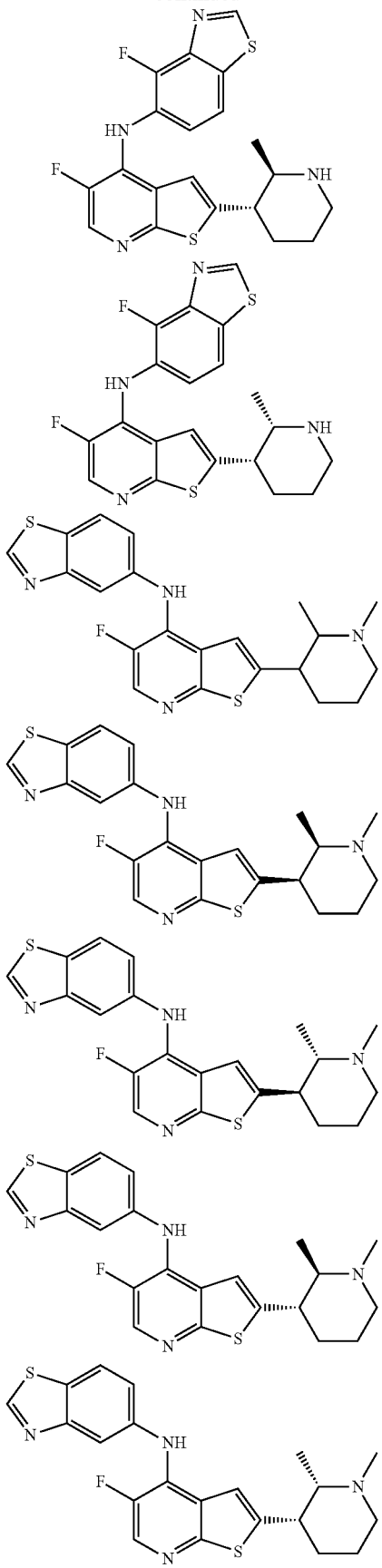

641
-continued
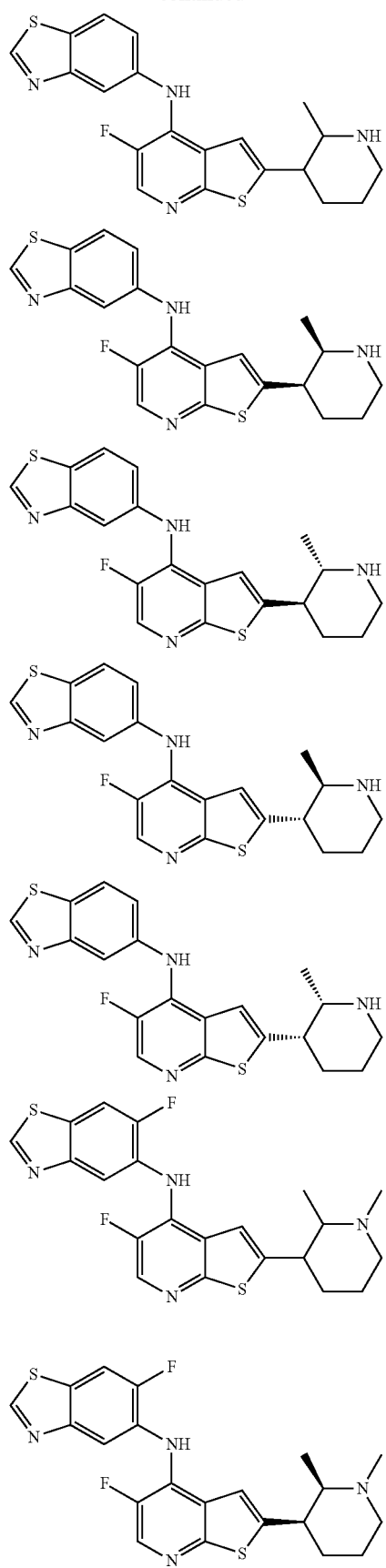
642
-continued
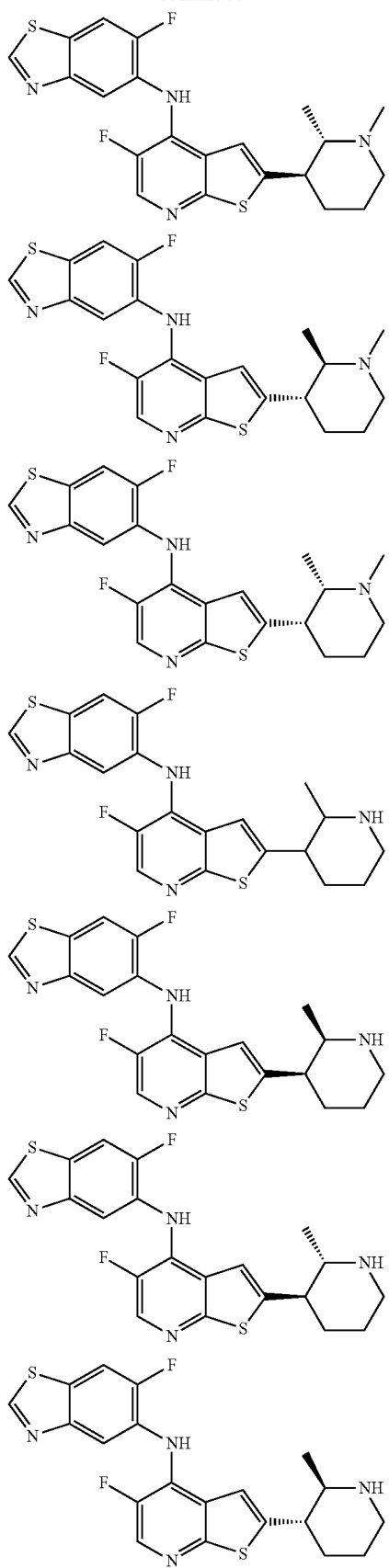

643
-continued
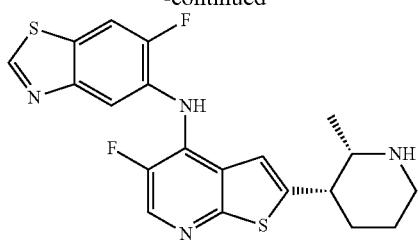
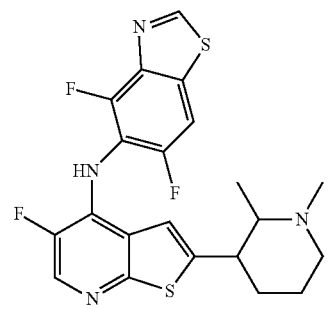
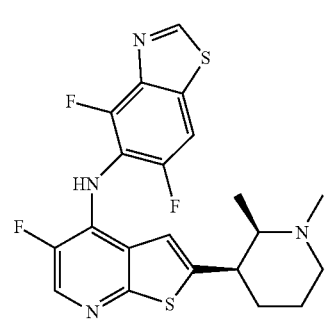
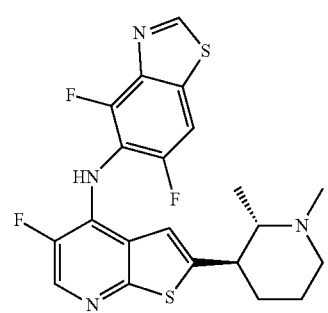
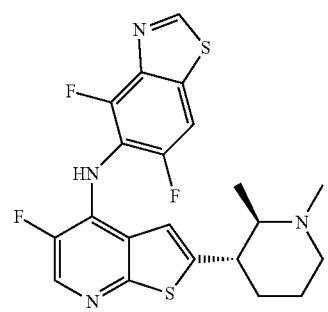
644
-continued
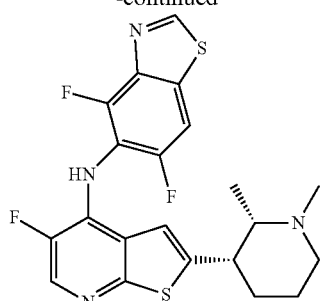
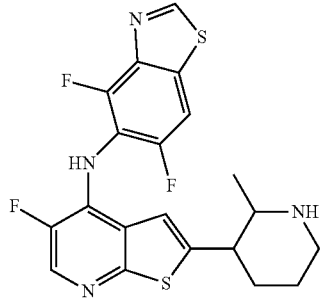
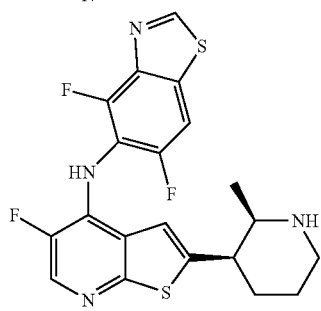
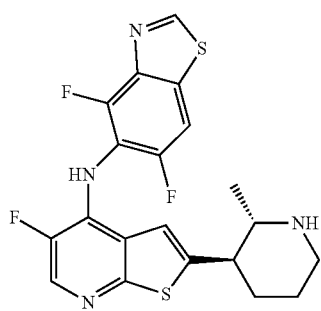
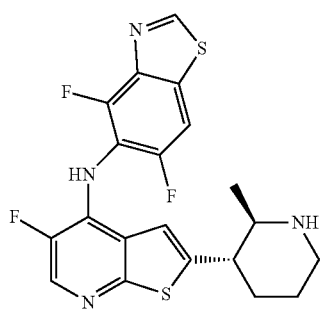

-continued
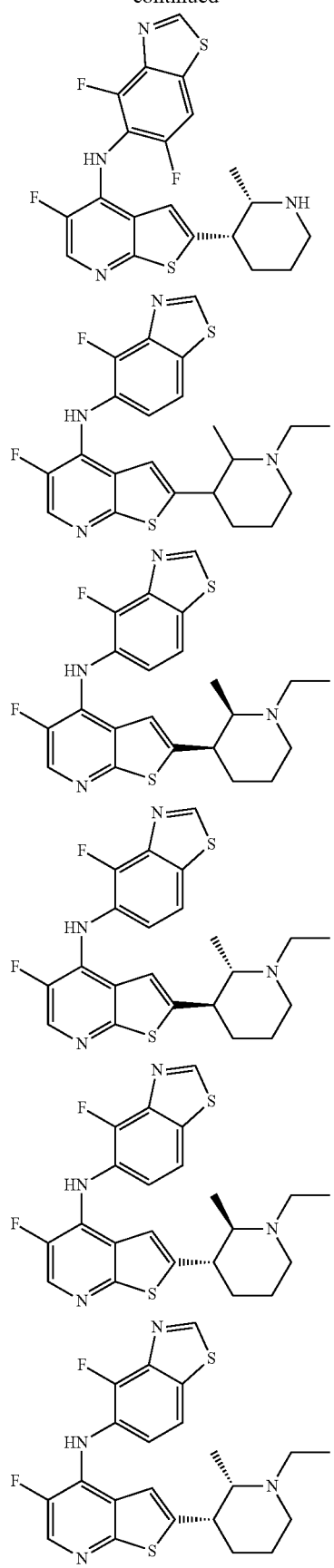
-continued
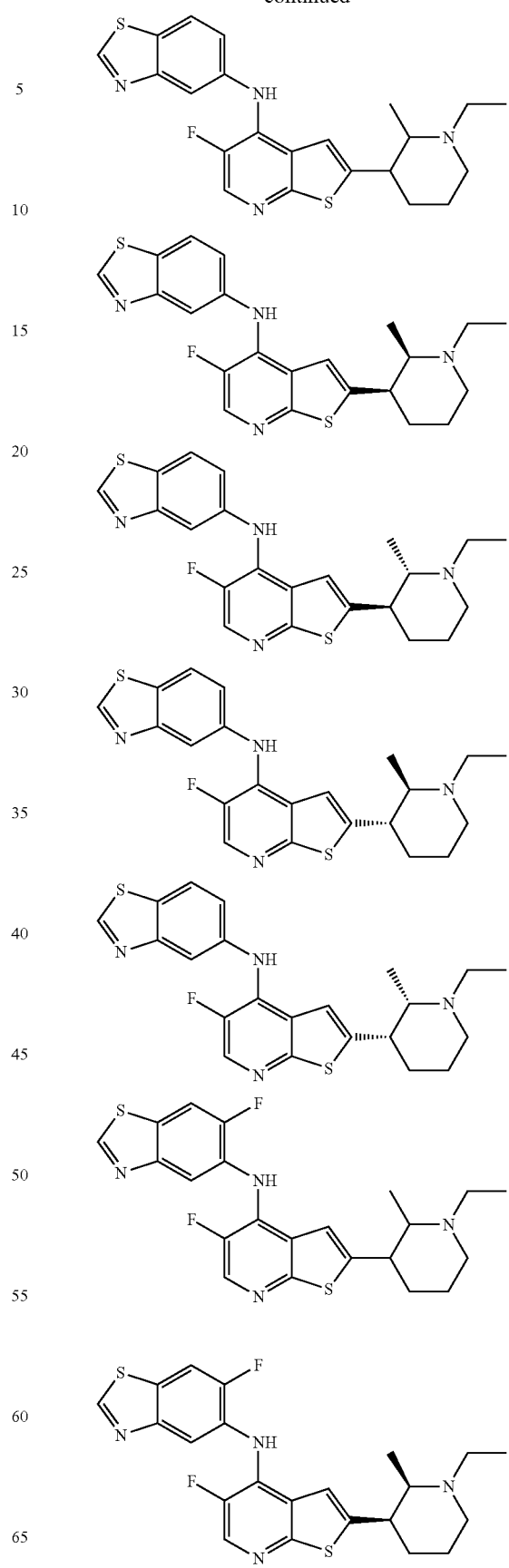

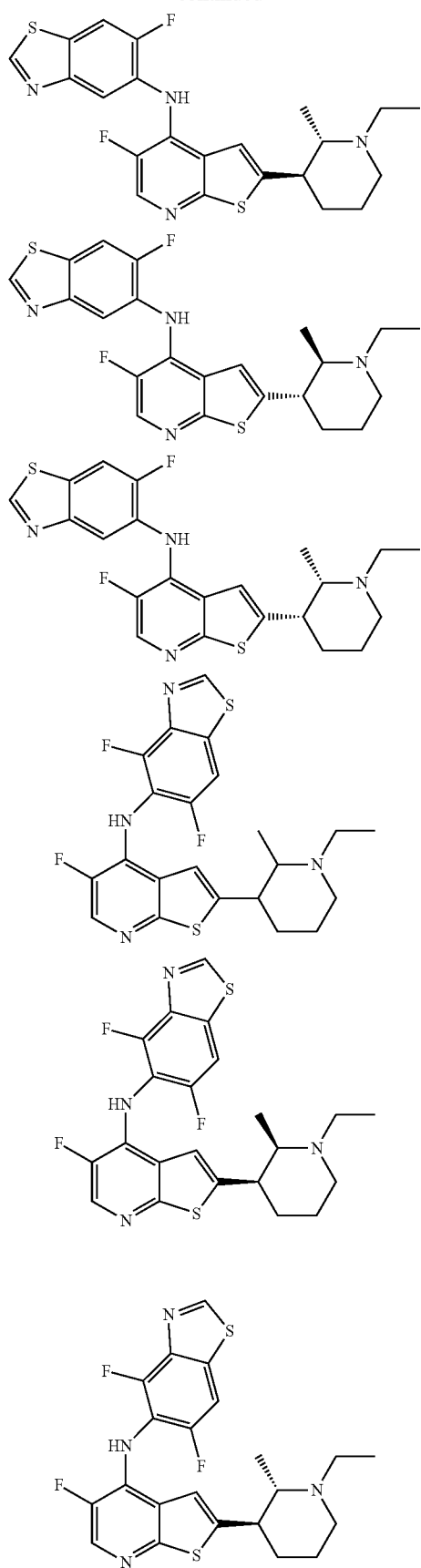
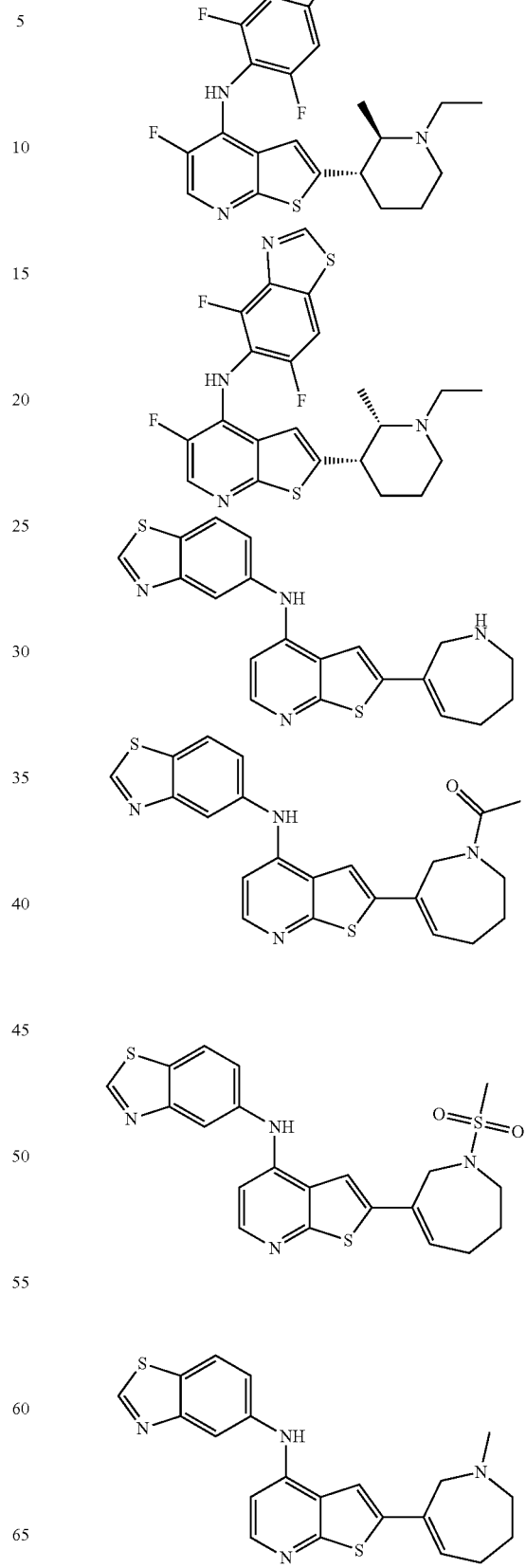

649
-continued
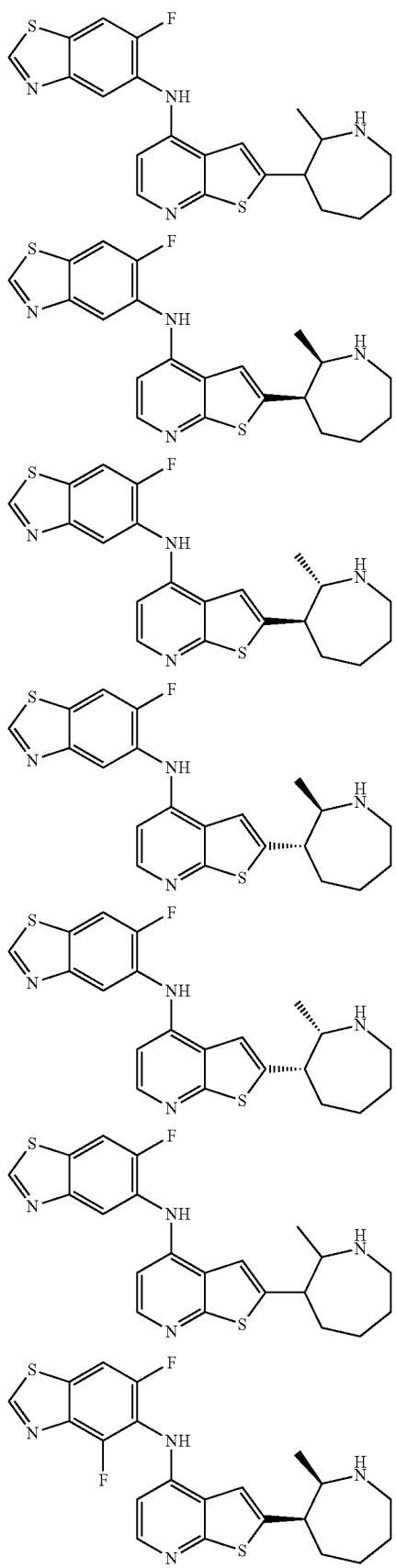
650
-continued
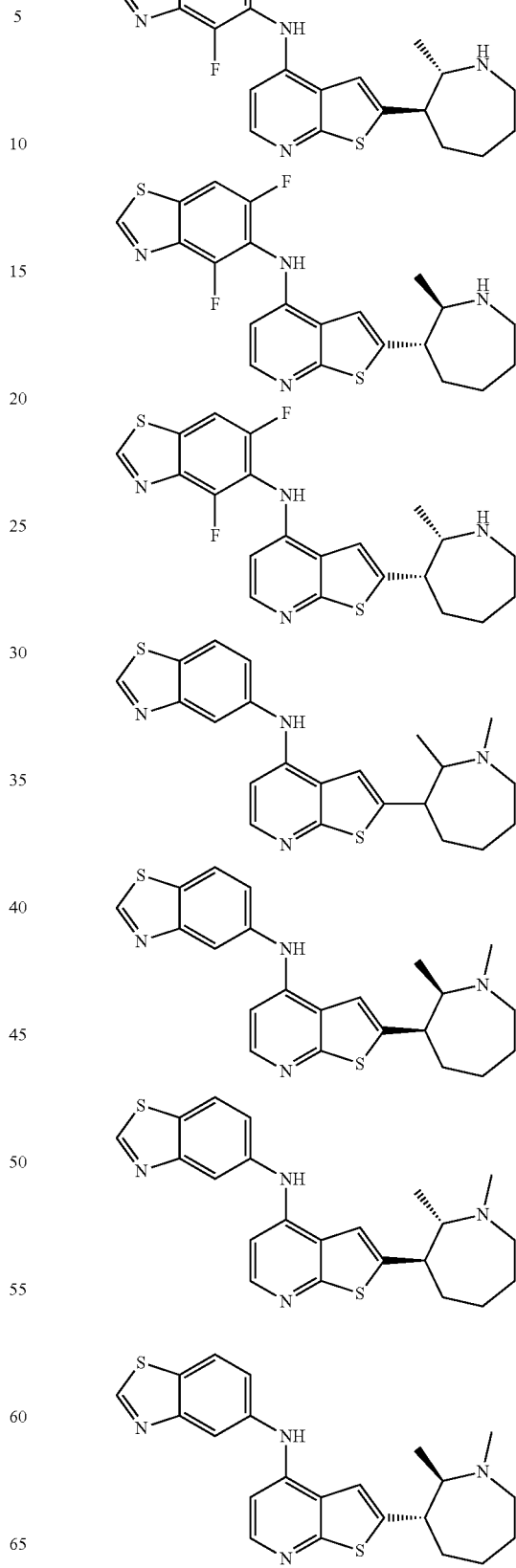

651
-continued
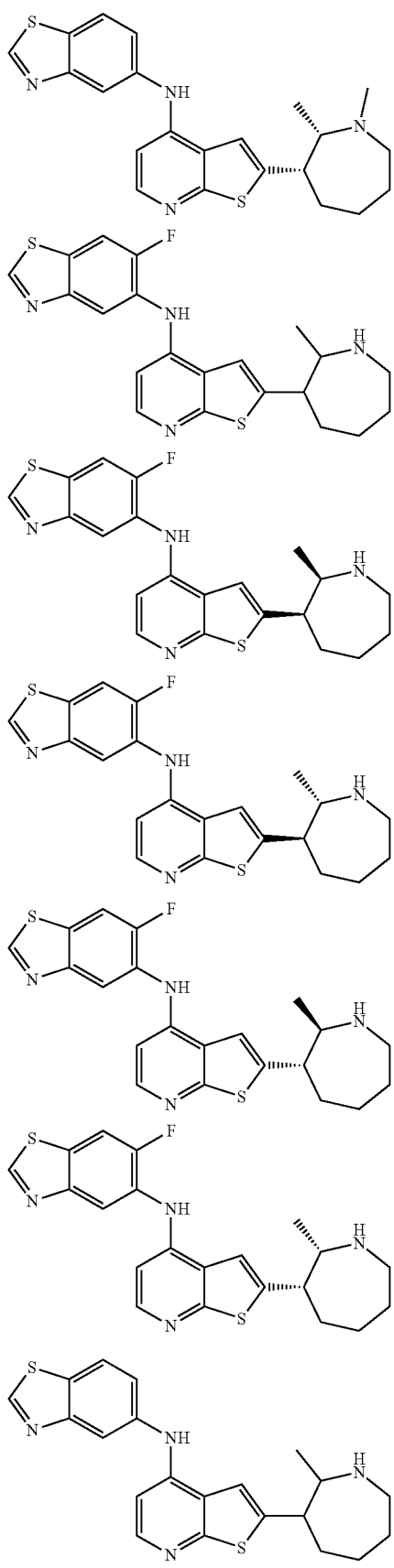
652
-continued
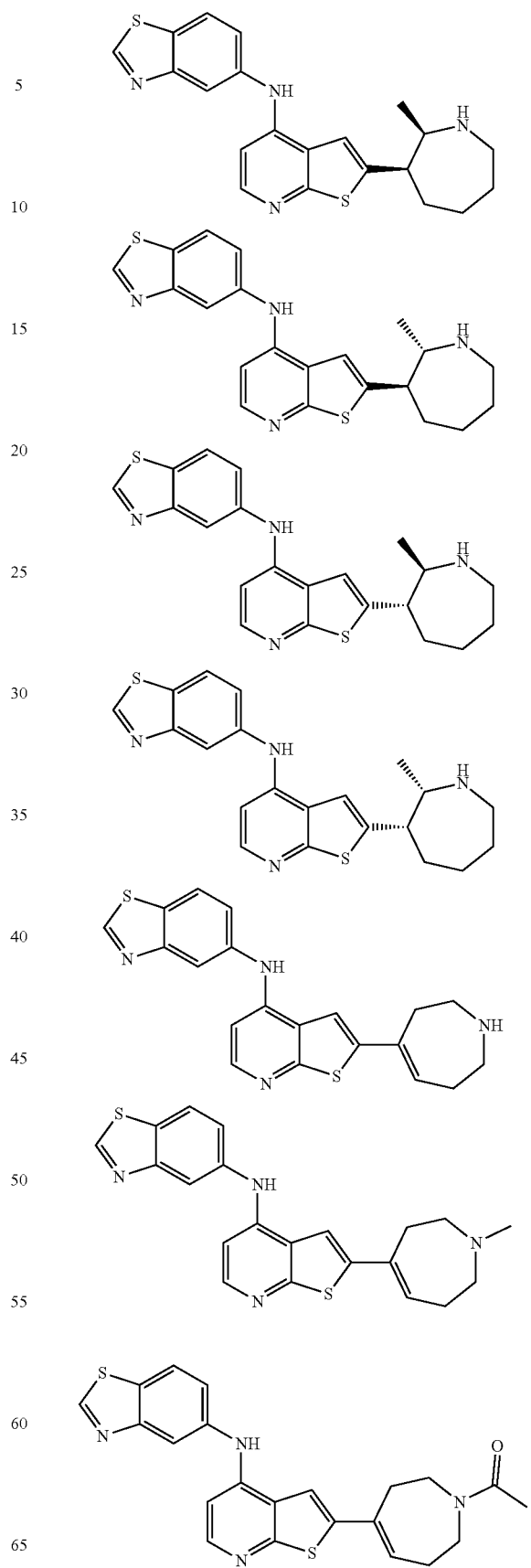

653
-continued

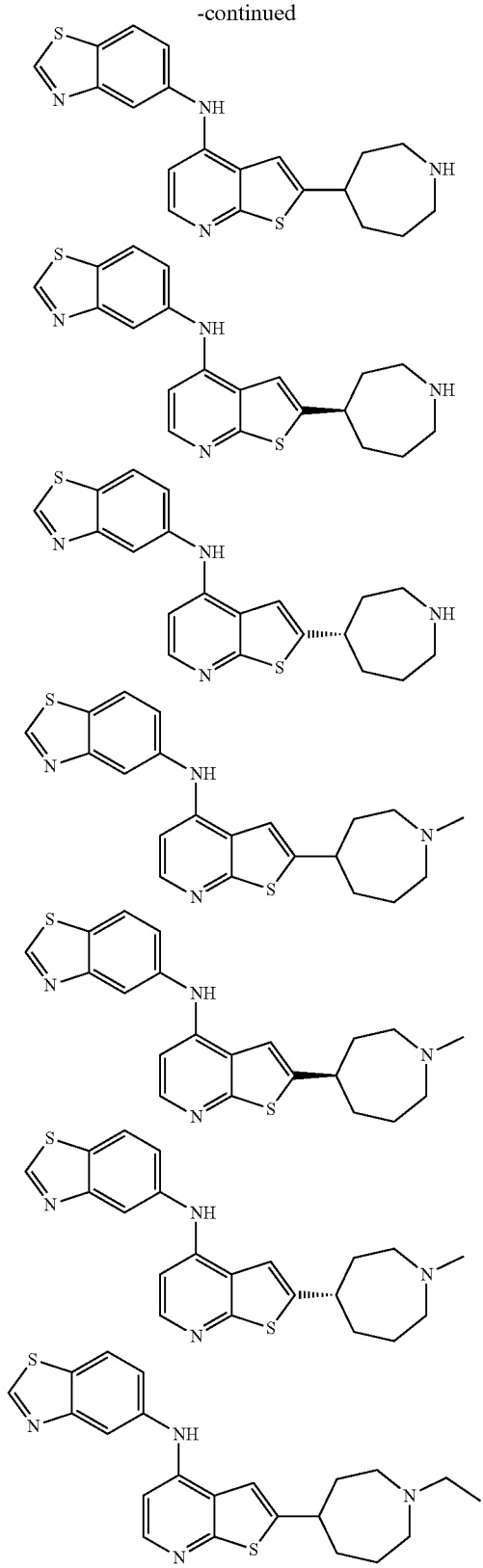

654
-continued

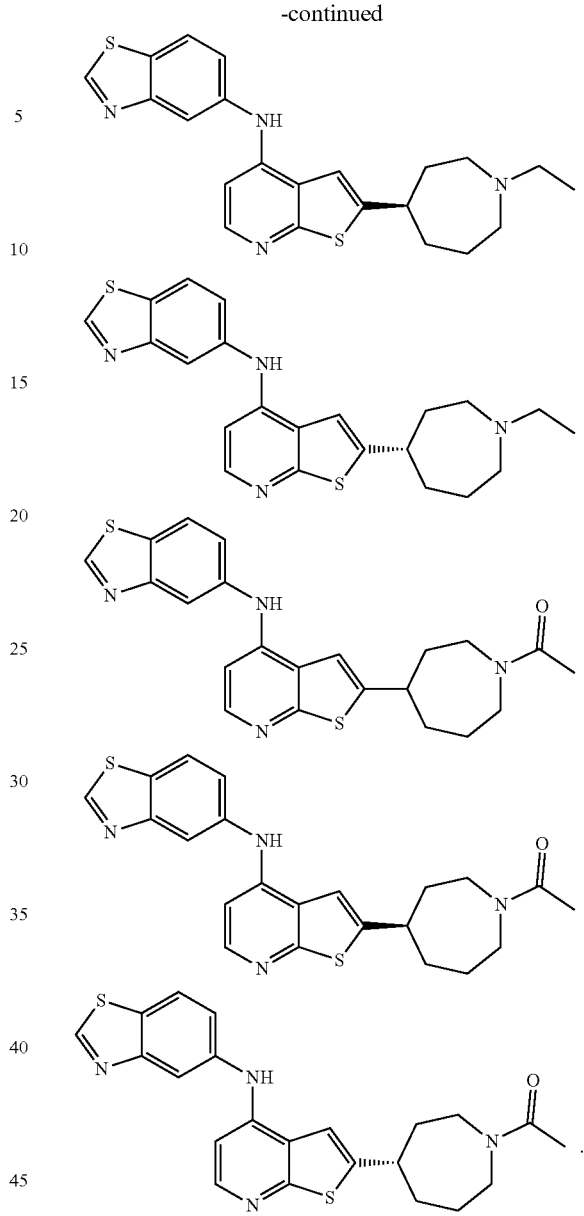

15. A composition comprising a compound of claim 1, and a pharmaceutically acceptable carrier or excipient.

16. A method of treating a disorder mediated by RIPK2 in a subject, the method comprising administering a compound of claim 1, and wherein the disorder mediated by RIPK2 is an inflammatory disorder, an autoimmune disorder, or a disorder associated with NOD2 receptors.

17. The method of claim 16, wherein the inflammatory disorder is selected from inflammatory bowel disease, sarcoidosis, inflammatory arthritis, Crohn's disease, peritonitis, multiple sclerosis, rheumatoid arthritis, and Wegener's granulomatosis.

* * * * *